(12) United States Patent
Bagdanoff et al.

(10) Patent No.: US 10,188,649 B2
(45) Date of Patent: *Jan. 29, 2019

(54) AMINOHETEROARYL BENZAMIDES AS KINASE INHIBITORS

(71) Applicant: Novartis AG, Basel (CH)

(72) Inventors: Jeffrey T. Bagdanoff, North Reading, MA (US); Yu Ding, Union City, CA (US); Wooseok Han, San Ramon, CA (US); Zilin Huang, Foster City, CA (US); Qun Jiang, Suzhou (JP); Xianming Jin, San Ramon, CA (US); Xiang Kou, Shanghai (CN); Patrick Lee, Walnut Creek, CA (US); Mika Lindvall, Oakland, CA (US); Zhongcheng Min, Shouzhou (CN); Yue Pan, Lexington, MA (US); Sabina Pecchi, Oakland, CA (US); Keith Bruce Pfister, San Ramon, CA (US); Daniel Poon, Piedmont, CA (US); Vivek Rauniyar, Cambridge, MA (US); Xiaojing Michael Wang, Livermore, CA (US); Qiong Zhang, Shanghai (CN); Jianguang Zhou, Shanghai (CN); Shejin Zhu, Dublin, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/672,568

(22) Filed: Aug. 9, 2017

(65) Prior Publication Data

US 2018/0028532 A1     Feb. 1, 2018

Related U.S. Application Data

(60) Continuation of application No. 14/964,057, filed on Dec. 9, 2015, now Pat. No. 9,763,937, which is a
(Continued)

(30) Foreign Application Priority Data

Oct. 11, 2014    (WO) ................ PCT/CN2014/088409

(51) Int. Cl.
| | |
|---|---|
| C07D 241/20 | (2006.01) |
| A61K 31/4965 | (2006.01) |
| A61K 31/497 | (2006.01) |
| A61K 31/4436 | (2006.01) |
| A61K 31/4439 | (2006.01) |
| A61K 31/4545 | (2006.01) |
| A61K 31/506 | (2006.01) |
| A61K 31/5377 | (2006.01) |
| A61K 31/5383 | (2006.01) |
| A61K 31/553 | (2006.01) |
| A61K 45/06 | (2006.01) |
| C07D 401/04 | (2006.01) |
| C07D 405/04 | (2006.01) |

(Continued)

(52) U.S. Cl.
CPC ............ *A61K 31/497* (2013.01); *A61K 31/44* (2013.01); *A61K 31/4433* (2013.01); *A61K 31/4436* (2013.01); *A61K 31/4439* (2013.01); *A61K 31/4545* (2013.01); *A61K 31/4965* (2013.01); *A61K 31/506* (2013.01); *A61K 31/5355* (2013.01); *A61K 31/5377* (2013.01); *A61K 31/5383* (2013.01); *A61K 31/553* (2013.01); *A61K 45/06* (2013.01); *C07D 213/73* (2013.01); *C07D 241/20* (2013.01); *C07D 401/04* (2013.01); *C07D 401/06* (2013.01); *C07D 401/12* (2013.01); *C07D 403/06* (2013.01); *C07D 405/04* (2013.01); *C07D 405/14* (2013.01); *C07D 409/04* (2013.01); *C07D 413/14* (2013.01); *C07D 498/04* (2013.01); *A61K 2121/00* (2013.01)

(58) Field of Classification Search
None
See application file for complete search history.

(56) References Cited

U.S. PATENT DOCUMENTS

| | | | |
|---|---|---|---|
| 9,242,996 B2 * | 1/2016 | Bagdanoff | ......... A61K 31/4436 |
| 9,763,937 B2 * | 9/2017 | Bagdanoff | ........... A61K 31/497 |

FOREIGN PATENT DOCUMENTS

| | | |
|---|---|---|
| WO | 2004016597 A2 | 2/2004 |
| WO | 2015051043 A1 | 4/2015 |
| WO | 2015/066188 A1 | 5/2015 |

* cited by examiner

*Primary Examiner* — Zinna Northington Davis
(74) *Attorney, Agent, or Firm* — Scott W. Reid

(57) ABSTRACT

The present invention provides a compound of Formula (I) or a salt thereof;

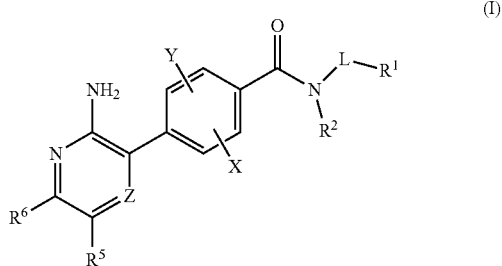

and therapeutic uses of these compounds. The present invention further provides pharmaceutical compositions comprising these compounds, and compositions comprising these compounds with a therapeutic co-agent.

4 Claims, 4 Drawing Sheets

Specification includes a Sequence Listing.

Related U.S. Application Data division of application No. 14/527,328, filed on Oct. 29, 2014, now Pat. No. 9,242,996.

(60) Provisional application No. 61/898,761, filed on Nov. 1, 2013.

(51) Int. Cl.
*C07D 405/14* (2006.01)
*C07D 409/04* (2006.01)
*C07D 413/14* (2006.01)
*C07D 498/04* (2006.01)
*C07D 213/73* (2006.01)
*C07D 401/06* (2006.01)
*C07D 401/12* (2006.01)
*C07D 403/06* (2006.01)
*A61K 31/44* (2006.01)
*A61K 31/4433* (2006.01)
*A61K 31/5355* (2006.01)

XRPD of HCl salt form of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide.

AMINOHETEROARYL BENZAMIDES AS KINASE INHIBITORS

CONTINUING DATA

This application is a continuation of U.S. patent application Ser. No. 14/964,057, filed Dec. 9, 2015, which is a divisional of U.S. patent application Ser. No. 14/527,328, filed Oct. 29, 2014, which claims priority under 35 U.S.C. § 119 to International Application No. PCT/CN2014/088409, filed Oct. 11, 2014, and claims benefit of U.S. Provisional Application No. 61/898,761, filed Nov. 1, 2013.

SEQUENCE LISTING

The instant application contains a Sequence Listing which has been submitted electronically in ASCII format and is hereby incorporated by reference in its entirety. Said ASCII copy, created on Dec. 4, 2014, is named PAT055069-USNPSL.txt and is 1,186 bytes in size.

BACKGROUND

Protein Kinases are involved in very complex signaling cascades that regulate most cellular functions, including survival and proliferation. These signaling pathways have been heavily studied, particularly in the context of disorders caused by dysregulated cellular function, such as cancer. The extracellular signal-regulated kinases (ERKs) are one class of signaling kinases that are involved in conveying extracellular signals into cells and subcellular organelles. ERK1 and 2 (ERK1/2) are kinases in the mitogen activated protein kinase (MAPK) pathway, and are also referred to as p42 and p44, respectively. ERK1 and ERK2 are present in relatively large quantities in cells ($\sim 10^7$ molecules per cell), and are involved in regulating a wide range of activities. Indeed, dysregulation of the ERK1/2 cascade is known to cause a variety of pathologies including neurodegenerative diseases, developmental diseases, diabetes and cancer. Wortzel and Seger, *Genes & Cancer*, 2:195-209 (2011), published online 9 May 2011.

The role of ERK1/2 in cancer is of special interest because activating mutations upstream of ERK1/2 in its signaling cascade are believed to be responsible for more than half of all cancers. Moreover, excessive ERK1/2 activity was also found in cancers where the upstream components were not mutated, suggesting that ERK1/2 signaling plays a role in carcinogenesis even in cancers without mutational activations. The ERK pathway has also been shown to control tumor cell migration and invasion, and thus may be associated with metastasis. See A. von Thun, et al., *ERK2 drives tumour cell migration in 3D microenvironments by suppressing expression of Rab17 and Liprin-β2, J. Cell Sciences*, online publication date 10 Feb. 2012. In addition, it has been reported that silencing either ERK1 or ERK2 using shRNA killed melanoma cells in culture, and also made melanoma cells more sensitive to inhibitors of BRAF. J. Qin, et al., *J. Translational Med.* 10:15 (2012). It is also reported that inhibitors of ERK1 and 2 are effective on tumor cells resistant to MEK inhibitors, and that inhibition of MEK and ERK simultaneously provides synergistic activity. *Molec. Cancer Therapeutics*, vol. 11, 1143 (May 2012).

Indazole derivatives acting as ERK inhibitors have been reported as therapeutics for treating cancers. WO2012/030685; WO2007/070398; WO2008/153858. Certain 2-amino pyridine/pyrimidine compounds with a biaryl linkage to a pyridone or similar ring have also been reported as inhibitors of ERK useful for treating cancer and hyperproliferative disorders: WO2013/130976. Other inhibitors of ERK have also been disclosed as therapeutic agents, see e.g., WO2004/016597. Because of their therapeutic value, new inhibitors of ERK1 and/or ERK2 are needed to treat disorders associated with undesired levels of ERK1/2 activity. The current invention provides novel compounds that inhibit ERK1 or ERK2 or both, for use to treat diseases such as cancer that are associated with excessive activity of ERK1 and/or ERK2.

SUMMARY OF THE INVENTION

In one aspect, the invention provides a compound of the formula (I):

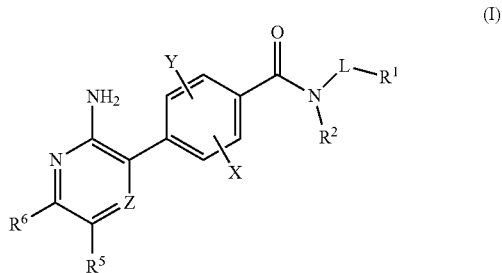

or a pharmaceutically acceptable salt thereof, wherein:

$R^1$ is an optionally substituted group selected from $C_{3-8}$ cycloalkyl, 5-8 membered heterocyclyl containing 1-2 heteroatoms selected from N, O and S as ring members, phenyl, —$SO_2$-phenyl, —C(O)-phenyl, —$C(R^8)_2$-phenyl, and 5-6 membered heteroaryl ring, wherein said heterocyclyl and heteroaryl contain 1-2 heteroatoms selected from N, O and S as ring members, and wherein the optional substituents for $R^1$ are 1-3 groups independently selected from D, halo, hydroxy, amino, —$N(R^8)_2$, CN, $C_{1-4}$ alkyl, $C_{1-4}$ alkoxy, —$S(C_{1-4}$ alkyl), $C_{1-4}$ haloalkyl, $C_{1-4}$ haloalkoxy, $C_{3-6}$ cycloalkyl, 3-6 membered heterocyclyl containing 1-2 heteroatoms selected from N, O and S, oxo (except on aromatic rings), CN, $COOR^8$, $CON(R^8)_2$, —$NR^8$—$C(O)R^8$, —$NR^8$—$C(O)OR^8$, —$SO_2R^8$, —$NR^8$—$SO_2R^8$, and $SO_2N(R^8)_2$, where each $R^8$ is independently H or $C_{1-4}$ alkyl;

L is a bond, or L can be a $C_{1-4}$ alkylene, $C_{2-4}$ alkenylene, $C_{1-4}$ alkynylene, $C_{3-6}$ cycloalkyl or a 4-7 membered heterocycloyl containing 1-2 heteroatoms selected from N, O and S as ring members, wherein L is optionally substituted with 1-3 groups independently selected from $R^{11}$, D, OH, $NH_2$, —$NHR^{11}$, $NHC(=O)R^{11}$, —$NHC(=O)$—$OR^{11}$, —$NHC(=O)$—$NH_2$, —$NHC(=O)$—$NHR^{11}$, —$N(R^{11})_2$, CN, halo, $N_3$, $CON(R^7)_2$, and $COOR^7$; where each $R^{11}$ is independently $C_{1-4}$ alkyl, which may be substituted with up to three groups independently selected from D, halo, OH, $NH_2$, —NHMe, —$NMe_2$, —$OP(O)(OH)_2$ and O—$C_{1-4}$ alkyl;

X and Y are independently selected from H, D, halo, CN, amino, hydroxy, $C_{1-4}$ alkyl, $C_{1-4}$ haloalkyl, $C_{1-4}$ alkoxy, and $C_{1-4}$ haloalkoxy;

$R^2$ is H, $C_{1-4}$ alkyl, or aryl-$C_{1-2}$-alkyl-, wherein the aryl and $C_{1-4}$ alkyl are optionally substituted with halo, CN, $C_{1-4}$ alkyl, $C_{1-4}$ haloalkyl, $C_{3-6}$ cycloalkyl, $C_{1-4}$ alkoxy, $C_{1-4}$ haloalkoxy, or $C_{1-4}$ alkylsulfonyl;

or R² can cyclize with X to form a 5-7 membered heterocyclic ring containing 1-2 heteroatoms selected from N, O and S fused to the phenyl ring to which X is attached, or R² can cyclize with L to form a 5-7 membered heterocyclic ring containing 1-2 heteroatoms selected from N, O and S, wherein the optional heterocyclic ring formed by R² cyclizing with X, or by R² cyclizing with L, can be optionally substituted with one or two groups independently selected from CN, halo, $C_{1-4}$ alkyl, $C_{1-4}$ alkoxy, $C_{1-4}$ haloalkyl, $C_{1-4}$ haloalkoxy, oxo, CN, $COOR^7$, $CON(R^7)_2$, and $—SO_2R^7$;

each $R^7$ is independently H or $C_{1-4}$ alkyl;

Z is N or $CR^4$;

$R^4$ is H, D, halo, $C_{1-4}$ alkyl, $C_{1-4}$ haloalkyl, or $C_{1-4}$ alkoxy;

$R^5$ is selected from $—C(O)—R^{5a}$ and $R^{5a}$; wherein $R^{5a}$ is an optionally substituted $C_{3-8}$ cycloalkyl, $C_{3-8}$ cycloalkenyl, saturated or unsaturated 3-8 membered heterocyclic ring containing 1-2 heteroatoms selected from N, O and S, phenyl, or 5-6 membered heteroaryl ring containing 1-3 heteroatoms selected from N, O and S, wherein the optional substituents for $R^5$ are 1-4 groups independently selected from D, halo, hydroxy, amino, CN, $C_{1-4}$ alkyl, $C_{1-4}$ alkoxy, $C_{1-4}$ haloalkyl, $C_{1-4}$ hydroxyalkyl, $C_{1-4}$ haloalkoxy, $C_{3-6}$ cycloalkyl, 3-6 membered heterocyclyl containing 1-2 heteroatoms selected from N, O and S, oxo (except on aromatic rings), CN, $—COOR^9$, $—C(O)R^9$, $CON(R^9)_2$, $—NR^9C(O)R^9$, $—NR^9CO_2R^9$, $—SO_2R^9$, $—NR^9SO_2R^9$, and $—SO_2N(R^9)_2$, where each $R^9$ is independently H or $C_{1-4}$ alkyl optionally substituted with 1-3 groups independently selected from D, halo, OH, $NH_2$, NHMe and $NMe_2$; and two substituents on the same or adjacent carbon atoms of $R^5$ can optionally be taken together to form a 5-6 membered ring that can be saturated or aromatic and contains 1-2 heteroatoms selected from N, O and S and can optionally be substituted with 1-2 groups independently selected from D, Me, halo, OH, oxo, $O(C_{1-4}$ alkyl), $NH_2$, $C_{1-4}$ alkylamino, di($C_{1-4}$alkyl) amino; and $R^6$ is H, D, halo, $C_{1-4}$ alkyl, or $C_{1-4}$ haloalkyl;

including the pharmaceutically acceptable salts of these compounds, for example a HCl salt form, and isotopically enriched versions of the compounds and salts, especially deuterated versions of the compounds, and salts thereof. These compounds are inhibitors of ERK1 and/or ERK2, and are accordingly useful to treat conditions associated with excessive or undesired levels of activity of ERK1 and/or ERK2, particularly cancers that respond to inhibitors of ERK1 and/or ERK2.

In another aspect, the invention provides pharmaceutical compositions comprising a compound of Formula (I), or any of the sub-classes thereof that are described herein, admixed with at least one pharmaceutically acceptable carrier or excipient, optionally admixed with two or more pharmaceutically acceptable carriers or excipients. These compositions are also useful to treat conditions associated with excessive or undesired levels of activity of ERK1 and/or ERK2, particularly cancers that respond to inhibitors of ERK1 and/or ERK2. The compositions may also comprise one or more co-therapeutic agents, such as those described herein, to enhance treatment of the treated condition or of associated symptoms of the condition.

In another aspect, the invention provides a method to treat a condition characterized by excessive or undesired levels of activity of one or both of ERK1 and ERK2, wherein the method comprises administering to a subject in need of such treatment an effective amount of a compound of Formula (I) or any subgenus thereof as described herein, or a pharmaceutical composition comprising such compound. The subject can be a mammal, and is preferably a human, and is typically a subject diagnosed with a condition associated with excessive activity of ERK1 and/or ERK2. Conditions treatable by the compounds and methods described herein include various forms of cancer that are responsive to ERK1/2 inhibitors, such as solid tumors, adenoma, bladder cancer, brain cancer, breast cancer, cervical cancer, colorectal cancer, colon cancer, epidermal carcinoma, follicular carcinoma, genitourinary cancers, glioblastoma, head and neck cancers, Hodgkin's disease, non-Hodgkin's lymphoma, hepatoma, kidney cancer, lung cancers such as small cell or non-small cell lung cancer, leukemias such as AML or CML, multiple myeloma, lymphoid disorders, skin cancers including melanoma, neuroblastoma, ovarian cancer, pancreatic cancer, prostate cancer, rectal cancer, sarcoma, testicular cancer, and thyroid cancer. The compounds are especially indicated for use to treat melanoma, ovarian cancer, thyroid cancer, colon cancer, lung cancer, pancreatic cancer, cervical cancer, head and neck cancer, and leukemias including chronic myelomonocytic leukemia (CMML), AML and CML. Indications of special interest for use of the compounds of the invention include cancers where BRAF mutations like V600E are present, e.g., melanoma, ovarian cancer, thyroid cancer, colorectal cancer and lung cancer; breast cancer where the MAPK and/or PI3K pathway is dysregulated; cancers associated with KRAS mutations such as lung cancer, pancreatic cancer, and colorectal cancer; cancers having ERK2 mutations such as cervical or head and neck cancers; leukemia, especially when exhibiting NF-1 mutations; and non-small cell lung cancer wherein EGFR is mutated.

In one aspect, the invention provides compounds of Formula (I) and the subgenera of Formula (I) described herein, as well as pharmaceutically acceptable salts of these compounds, and all stereoisomers (including diastereoisomers and enantiomers), tautomers and isotopically enriched versions thereof (including deuterium substitutions). Compounds of the present invention also comprise polymorphs of compounds of Formula I (or subformulae thereof) and salts thereof. These compounds can be for use to treat conditions responsive to an ERK1/2 inhibitor, such as those described herein, and for use in the preparation of a medicament for treating these disorders, and can be used in combination with co-therapeutic agents for treating these disorders. The pharmaceutical compositions and methods described herein can also be used with or formulated with a co-therapeutic agent; for example, compounds of Formula I and sub-formulae thereof can be used with or formulated with inhibitors of B-RAF and other therapeutic agents as further described herein.

In another aspect, the invention provides methods of making the compounds of Formula I as well as key intermediate compounds useful for making the compounds of the invention.

pyrazin-2-yl)-N-((S)-1-(3-bromo-5-fluorophenyl)-2-(methylamino)ethyl)-2-fluorobenzamide.

Figure 3:
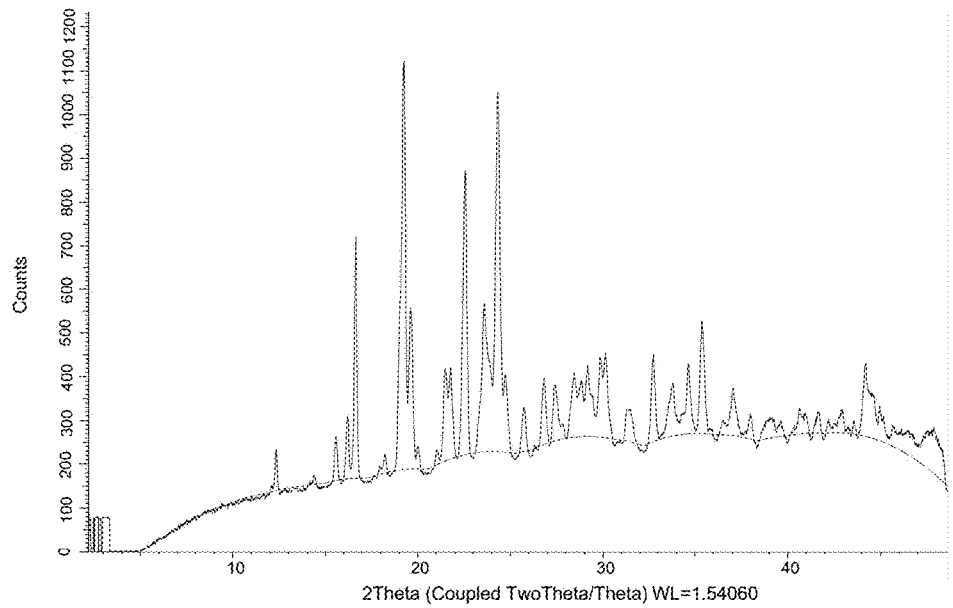

FIG. 3 shows the X-ray powder diffraction pattern of the HCl salt form of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide.

Figure 4:
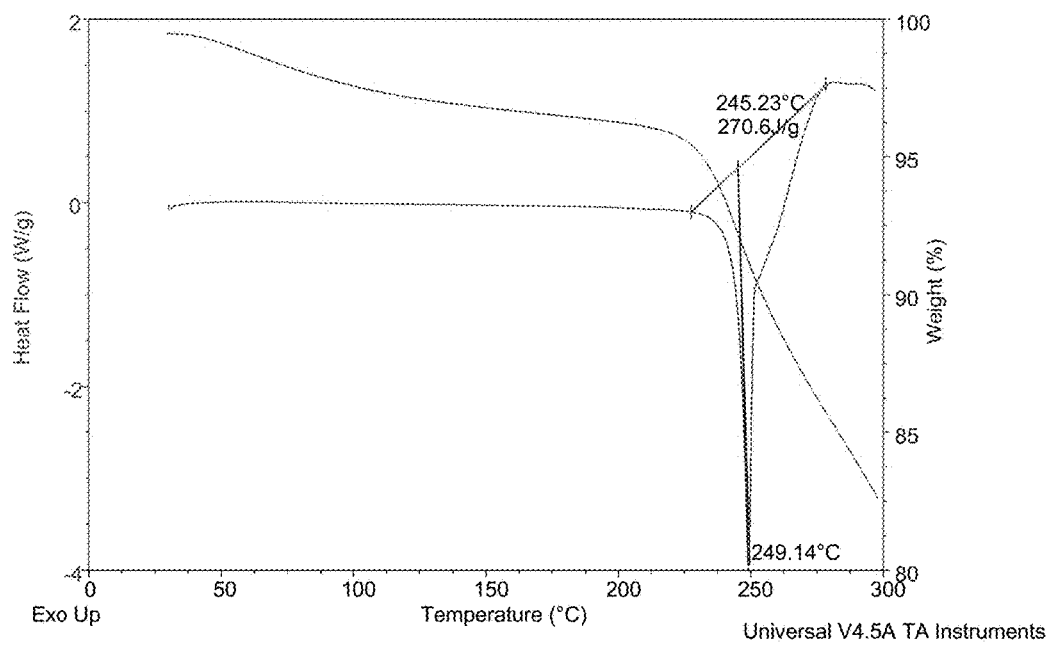

FIG. 4 is a DSC/TGA thermograph of the HCl salt form of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide.

DETAILED DESCRIPTION

The following definitions apply unless otherwise provided or apparent from context:

As used herein, the term "halogen" (or halo) refers to fluorine, bromine, chlorine or iodine. Halogen-substituted groups and moieties, such as alkyl substituted by halogen (haloalkyl) can be mono-, poly- or per-halogenated. Chloro and fluoro are preferred halo substituents on alkyl or cycloalkyl groups, unless otherwise specified; fluoro, chloro, and bromo are often preferred on aryl or heteroaryl groups, unless otherwise specified.

As used herein, the term "hetero atoms" refers to nitrogen (N), oxygen (O) or sulfur (S) atoms, in particular nitrogen or oxygen, unless otherwise provided.

As used herein the term "optionally substituted" indicates that a group being described can be unsubstituted or it can be substituted. Substituted groups are not intended to encompass numbers, placement or selections of substituent groups that would result in a compound that is not expected to be stable in water at room temperature for at least long enough to be administered as a pharmaceutical agent. When multiple substituents are present, the substituents are selected independently unless otherwise indicated, so where 2 or 3 substituents are present, for example, those substituents may be the same or different.

As used herein, the term "alkyl" refers to a fully saturated branched or unbranched hydrocarbon moiety having up to 10 carbon atoms. Unless otherwise provided, alkyl refers to hydrocarbon moieties having 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

A substituted alkyl is an alkyl group containing one or more substituents in place of hydrogen atoms of the unsubstituted alkyl, such as one, two or three substituents, or 1-4 substituents, up to the number of hydrogens present on the unsubstituted alkyl group. Suitable substituents for alkyl groups, if not otherwise specified, may be selected from halogen, D, CN, oxo, hydroxy, substituted or unsubstituted $C_{1-4}$ alkoxy, substituted or unsubstituted $C_{3-6}$ cycloalkyl, substituted or unsubstituted 3-7 membered heterocycloalkyl containing 1 or 2 heteroatoms selected from N, O and S as ring members, substituted or unsubstituted phenyl, amino, ($C_{1-4}$ alkyl)amino, di($C_{1-4}$alkyl)amino, $C_{1-4}$ alkylthio, $C_{1-4}$ alkylsulfonyl, —C(=O)—$C_{1-4}$ alkyl, COOH, COO($C_{1-4}$alkyl), —O(C=O)—$C_{1-4}$ alkyl, —NHC(=O) $C_{1-4}$alkyl and —NHC(=O)O$C_{1-4}$alkyl groups; wherein the substituents for substituted $C_{1-4}$alkoxy, substituted $C_{3-6}$ cycloalkyl, 3-7 membered heterocycloalkyl, and substituted phenyl are up to three groups independently selected from halo, $C_{1-4}$ alkyl, $C_{1-4}$ haloalkyl, D, $C_{1-4}$alkoxy, amino, $C_{1-4}$ alkylamino, di($C_{1-4}$alkyl)amino, hydroxy, and CN. Preferred substituents for alkyl groups, unless otherwise specified, include halogen, CN, oxo, hydroxy, $C_{1-4}$alkoxy, $C_{3-6}$ cycloalkyl, phenyl, amino, ($C_{1-4}$ alkyl)amino, di($C_{1-4}$ alkyl) amino, $C_{1-4}$ alkylthio, $C_{1-4}$ alkylsulfonyl, —C(=O)$C_{1-4}$ alkyl, COOH, —COO($C_{1-4}$ alkyl), —O(C=O)—$C_{1-4}$alkyl, —NHC(=O)$C_{1-4}$alkyl and —NHC(=O)O $C_{1-4}$ alkyl groups.

As used herein, the term "alkylene" refers to a divalent alkyl group having 1 to 10 carbon atoms, and two open valences to attach to other molecular components. The two molecular components attached to an alkylene can be on the same carbon atom or on different carbon atoms; thus for example propylene is a 3-carbon alkylene that can be 1,1-disubstituted, 1,2-disubstituted or 1,3-disubstituted. Unless otherwise provided, alkylene refers to moieties having 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable and preferred substituents are selected from the substituents described as suitable and preferred for alkyl groups.

Similarly, "alkenylene" and "alkynylene" refer to alkylene groups having a double bond or a triple bond, respectively; they are typically 2-6 and often 2-4 carbon atoms in length, and can be substituted as explained for alkylene groups generally.

As used herein, the term "haloalkyl" refers to an alkyl as defined herein, which is substituted by one or more halo groups as defined herein. Unless otherwise specified, the alkyl portion of the haloalkyl has 1-4 carbon atoms. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl. Preferred haloalkyl groups, unless specified otherwise, include monofluoro-, difluoro- and trifluoro-substituted methyl and ethyl groups, e.g. $CF_3$, $CF_2H$, $CFH_2$, and $CH_2CF_3$.

As used herein, the term "alkoxy" refers to alkyl-O, wherein alkyl is as defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable and preferred substituents are selected from the substituents listed above for alkyl groups, except that hydroxyl and amino are not normally present on the carbon that is directly attached to the oxygen of the substituted 'alkyl-O' group.

As used herein, the term "haloalkoxy" refers to haloalkyl-O, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyloxy groups have 1-4 carbon atoms, and up to three halogens, e.g., monofluoro, difluoro and trifluoro substituted methoxy groups and ethoxy groups.

Similarly, each alkyl part of other groups like "alkylaminocarbonyl", "alkoxyalkyl", "alkoxycarbonyl", "alkoxycarbonylalkyl", "alkylsulfonyl", "alkylsulfoxyl", "alkylamino", "haloalkyl" shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted, suitable substituents are selected from the suitable or preferred substituents named above for alkyl groups unless otherwise specified.

As used herein, the term "cycloalkyl" refers to saturated or unsaturated non-aromatic monocyclic, bicyclic, tricyclic or spirocyclic hydrocarbon groups of 3-12 carbon atoms: the cycloalkyl group may be unsaturated, and may be fused to another ring that can be saturated, unsaturated or aromatic, provided the ring atom of the cycloalkyl group that is connected to the molecular formula of interest is not an aromatic ring atom. Unless otherwise provided, cycloalkyl refers to cyclic hydrocarbon groups having between 3 and 9 ring carbon atoms or between 3 and 7 ring carbon atoms. Preferably, cycloalkyl groups, unless otherwise specified, are saturated monocyclic rings having 3-7 ring atoms, e.g., cyclopropyl, cyclobutyl, cyclopentyl, cyclohexyl or cycloheptyl.

A substituted cycloalkyl is a cycloalkyl group substituted by 1-3 (one, two, three), or more than three substituents, up to the number of hydrogens on the unsubstituted group. Typically, a substituted cycloalkyl will have 1-4 or 1-2 substituents. Suitable substituents, unless otherwise specified, are independently selected from the group consisting of halogen, hydroxyl, thiol, cyano, nitro, oxo, $C_{1-4}$-alkylimino, $C_{1-4}$-alkoximino, hydroxyimino, $C_{1-4}$-alkyl, $C_{2-4}$-alkenyl, $C_{2-4}$-alkynyl, $C_{1-4}$-alkoxy, $C_{1-4}$-thioalkyl, $C_{2-4}$-alkenyloxy, $C_{2-4}$-alkynyloxy, $C_{1-4}$-alkylcarbonyl, carboxy, $C_{1-4}$-alkoxycarbonyl, amino, $C_{1-4}$-alkylamino, di-$C_{1-4}$-alkylamino, $C_{1-4}$-alkylaminocarbonyl, $C_{1-4}$-alkylaminocarbonyl, $C_{1-4}$-alkylcarbonylamino, $C_{1-4}$-alkylcarbonyl($C_{1-4}$-alkyl)amino, $C_{1-4}$-alkylsulfonyl, $C_{1-4}$-alkylsulfamoyl, and $C_{1-4}$-alkylaminosulfonyl, where each of the aforementioned hydrocarbon groups (e.g., alkyl, alkenyl, alkynyl, alkoxy residues) may be further substituted by one or more groups independently selected at each occurrence from the list of substituents for 'alkyl' groups herein. Preferred substituents for a cycloalkyl, unless otherwise specified, include $C_{1-4}$ alkyl and the substituent groups listed above as preferred substituents for alkyl groups.

Exemplary monocyclic hydrocarbon groups include, but are not limited to, cyclopropyl, cyclobutyl, cyclopentyl, cyclopentenyl, cyclohexyl and cyclohexenyl and the like.

Similarly, each cycloalkyl part of other groups like "cycloalkyloxy", "cycloalkoxyalkyl", "cycloalkoxycarbonyl", "cycloalkoxy-carbonylalkyl", "cycloalkylsulfonyl", "halocycloalkyl" shall have the same meaning as described in the above definition of "cycloalkyl". When used in these terms, the cycloalkyl is typically a monocyclic 3-7 carbon ring that is unsubstituted or is substituted with 1-4 groups, commonly 1-2 groups. When (optionally) substituted, the substituents are typically selected from $C_{1-4}$ alkyl and those groups set forth above as suitable or preferred substituents for alkyl groups, unless otherwise specified.

As used herein, the term "aryl" refers to an aromatic hydrocarbon group having 6-14 carbon atoms in the ring portion. Typically, aryl is monocyclic, bicyclic or tricyclic aryl having 6-14 carbon atoms, often 6-10 carbon atoms, e.g., phenyl or naphthyl. Phenyl is sometimes preferred. Furthermore, the term "aryl" as used herein, refers to an aromatic substituent which can be a single aromatic ring, or multiple aromatic rings that are fused together. Non-limiting examples include phenyl, naphthyl and 1,2,3,4-tetrahydronaphthyl, provided the tetrahydronaphthyl is connected to the formula being described through a carbon of the aromatic ring of the tetrahydronaphthyl group.

A substituted aryl is an aryl group substituted by 1-5 (such as one, or two, or three) substituents independently selected from the group consisting of hydroxyl, thiol, cyano, nitro, $C_{1-4}$-alkyl, $C_{2-4}$-alkenyl, $C_{2-4}$-alkynyl, $C_{1-4}$-alkoxy, $C_{1-4}$-thioalkyl, $C_{2-4}$-alkenyloxy, $C_{2-4}$-alkynyloxy, halogen, $C_{1-4}$-alkylcarbonyl, carboxy, $C_{1-4}$-alkoxycarbonyl, amino, $C_{1-4}$-alkylamino, di-$C_{1-4}$-alkylamino, $C_{1-4}$-alkylaminocarbonyl, di-$C_{1-4}$-alkylaminocarbonyl, $C_{1-4}$-alkylcarbonylamino, $C_{1-4}$-alkylcarbonyl($C_{1-4}$-alkyl)amino, $C_{1-4}$-alkylsulfonyl, sulfamoyl, $C_{1-4}$-alkylsulfamoyl, and $C_{1-4}$-alkylaminosulfonyl where each of the afore-mentioned hydrocarbon groups (e.g., alkyl, alkenyl, alkynyl, alkoxy residues) may be further substituted by one or more groups independently selected at each occurrence from the groups listed above as suitable substituents for alkyl groups. Preferred substituents for a substituted aryl group, unless otherwise specified, are $C_{1-4}$ alkyl, halogen, CN, hydroxy, substituted or unsubstituted $C_{1-4}$ alkyl, substituted or unsubstituted $C_{1-4}$ alkoxy, substituted or unsubstituted $C_{3-6}$ cycloalkyl, substituted or unsubstituted 3-6 membered heterocycloalkyl containing 1-2 heteroatoms selected from N, O and S as ring members, amino, ($C_{1-4}$ alkyl)amino, di($C_{1-4}$ alkyl)amino, $C_{1-4}$ alkylthio, $C_{1-4}$ alkylsulfonyl, —C(=O)$C_{1-4}$ alkyl, COOH, COO($C_{1-4}$ alkyl), —O(C=O)—$C_{1-4}$ alkyl, —NHC(=O) $C_{1-4}$ alkyl and —NHC(=O)O $C_{1-4}$ alkyl groups; wherein the substituents for substituted C1-4 alkoxy, substituted $C_{3-6}$ cycloalkyl, 3-6 membered heterocycloalkyl, and substituted alkyl are up to three groups independently selected from halo, oxo, $C_{1-4}$ alkyl, $C_{1-4}$ haloalkyl, $C_{1-4}$ alkoxy, amino, hydroxy, and CN.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" or "heterocycloalkyl" refers to a heterocyclic radical that is saturated or partially unsaturated but not aromatic, and can be a monocyclic or a polycyclic ring, including a fused or bridged bicyclic, tricyclic or spirocyclic ring system. A heterocycle or heterocyclyl contains at least one non-carbon atom as a ring member, typically N, O or S unless otherwise specified. Unless otherwise specified, a heterocyclyl group has 3 to 10, and preferably 4 to 7 ring atoms; wherein one or more, preferably one to four, especially one or two ring atoms are heteroatoms independently selected from O, S and N (the remaining ring atoms therefore being carbon). An unsaturated heterocyclyl can have one or two double bonds, but is not aromatic. Preferably, unless described as unsaturated, the heterocyclyl groups in the compounds of the invention are saturated single rings. Even though described at times as, e.g., a $C_{5-6}$ atom group, a heterocycle contains at least one heteroatom as a ring atom and has the total number of ring atoms stated, e.g. 5 or 6 in this example; so a $C_{5-6}$ heterocyclyl group refers to a 5-6 membered heterocyclic ring wherein at least one ring member is a heteroatom. Preferably, a heterocyclyl group has one or two heteroatoms as ring atoms, and preferably the heteroatoms are not directly connected to each other. The bonding ring (i.e. the ring connecting to the Formula of interest) preferably has 4 to 7 ring atoms. The heterocyclic group can be fused to an aromatic ring, provided the atom of the heterocyclic group attached to the Formula of interest is not aromatic. The heterocyclic group can be attached to the Formula of interest via a heteroatom (typically nitrogen) or a carbon atom of the heterocyclic group. The heterocyclyl can comprise fused or bridged rings as well as spirocyclic ring systems (e.g., 2-oxa-6-azaspiro[3.3]heptane), and only one ring of a polycyclic heterocyclic group needs to contain a heteroatom as a ring atom. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclyl group independently substituted by 1-5 (such as one, or two, or three) substituents selected from the substituents described above as suitable or preferred for a cycloalkyl group, unless otherwise specified.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

A "cyclic ether" as used herein refers to a heterocyclic ring containing O as a ring atom, typically a 4-8 membered ring, e.g., oxetane, tetrahydrofuran or tetrahydropyran. A cyclic ether of 5-8 members can contain two non-adjacent oxygen atoms as ring members, e.g., dioxane and dioxolane. These rings can be substituted as for heterocyclic rings; preferred substituents if not otherwise specified include $C_{1-4}$ alkyl (e.g., methyl, ethyl), CN, OH, $NH_2$, NHR, $NR_2$, COOH, COOR, $CONR_2$, and OR, where each R is independently $C_{1-4}$ alkyl. Typically, for stability reasons, OH, $NH_2$, NHR, and $NR_2$ substituents are not attached at a ring carbon directly bonded to an oxygen atom in the ring.

As used herein, the term "heteroaryl" refers to a 5-14 membered monocyclic- or bicyclic- or tricyclic-aromatic ring system, having 1 to 8 heteroatoms as ring members; the heteroatoms are selected from N, O and S. Typically, the heteroaryl is a 5-10 membered ring system, e.g., a 5-6 membered monocyclic or an 8-10 membered bicyclic group. Typical heteroaryl groups include 2- or 3-thienyl, 2- or 3-furyl, 2- or 3-pyrrolyl, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2,3-triazolyl), 1- or 2- or 3-tetrazolyl, 2-, 3-, or 4-pyridyl, 3- or 4-pyridazinyl, 2-pyrazinyl, and 2-, 4-, or 5-pyrimidinyl.

The term "heteroaryl" also refers to a group in which a heteroaromatic ring is fused to one or more aryl, cycloalkyl, or heterocyclyl rings, where the radical or point of attachment to the Formula of interest is on a heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, and 2-, 3-, 4-, 5-, 6-, or 7-indazolyl.

A substituted heteroaryl is a heteroaryl group having one or more substituents on the heteroaryl ring replacing a hydrogen atom that would be on the unsubstituted heteroaryl, typically 1, 2 or 3 substituents, selected from the substituents described above as suitable or preferred for an aryl group, unless otherwise specified.

Similarly, each heteroaryl part of other groups like "heteroaryloxy", "heteroaryloxyalkyl", "heteroaryloxycarbonyl" shall have the same meaning as described in the above-mentioned definition of "heteroaryl".

Various embodiments of the invention are described herein. It will be recognized that features specified in each embodiment may be combined with other specified features to provide further embodiments of the present invention. The following enumerated embodiments are representative of the invention.

Embodiment 1. A compound of formula (I):

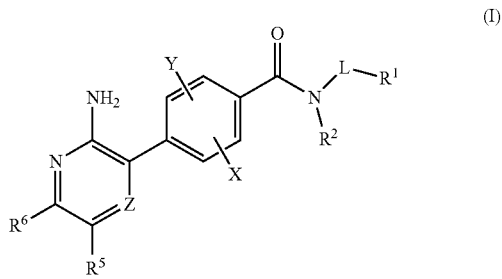

or a pharmaceutically acceptable salt thereof, wherein:

$R^1$ is an optionally substituted group selected from $C_{3-8}$ cycloalkyl, 5-8 membered heterocyclyl containing 1-2 heteroatoms selected from N, O and S as ring members, phenyl, —$SO_2$-phenyl, —C(O)-phenyl, —$C(R^8)_2$-phenyl, and 5-6 membered heteroaryl ring, wherein said heterocyclyl and heteroaryl contain 1-2 heteroatoms selected from N, O and S as ring members, and wherein the optional substituents for $R^1$ are 1-3 groups independently selected from D, halo, hydroxy, amino, —$N(R^8)_2$, CN, $C_{1-4}$ alkyl, $C_{1-4}$ alkoxy, —$S(C_{1-4}$ alkyl), $C_{1-4}$ haloalkyl, $C_{1-4}$ haloalkoxy, $C_{3-6}$ cycloalkyl, 3-6 membered heterocyclyl containing 1-2 heteroatoms selected from N, O and S, oxo (except on aromatic rings), CN, $COOR^8$, $CON(R^8)_2$, —$NR^8$—$C(O)R^8$, —$NR^8$—$C(O)OR^8$—$SO_2R^8$, —$NR^8SO_2R^8$, and $SO_2N(R^8)_2$, where each $R^8$ is independently H or $C_{1-4}$ alkyl;

L is a bond, or L can be a $C_{1-4}$ alkylene, $C_{2-4}$ alkenylene, $C_{1-4}$ alkynylene, $C_{3-6}$ cycloalkyl or a 4-7 membered heterocycloyl containing 1-2 heteroatoms selected from N, O and S as ring members, wherein L is optionally substituted with 1-3 groups independently selected from $R^{11}$, D, OH, $NH_2$, —$NHR^{11}$, —$NHC(=O)R^{11}$, —$NHC(=O)$—$OR^{11}$, —$NHC(=O)$—$NH_2$, —$NHC(=O)$—$NHR^{11}$, —$N(R^{11})_2$, CN, halo, $N_3$, $CON(R^7)_2$, and $COOR^7$; where each $R^{11}$ is independently $C_{1-4}$ alkyl, which may be substituted with up to three groups independently selected from D, halo, OH, $NH_2$, —$NHMe$, —$NMe_2$, —$OP(O)(OH)_2$ and O—$C_{1-4}$ alkyl;

X and Y are independently selected from H, D, halo, CN, amino, hydroxy, $C_{1-4}$ alkyl, $C_{1-4}$ haloalkyl, $C_{1-4}$ alkoxy, and $C_{1-4}$ haloalkoxy;

$R^2$ is H, $C_{1-4}$ alkyl, or aryl-$C_{1-2}$-alkyl-, wherein the aryl and $C_{1-4}$ alkyl are optionally substituted with halo, CN, $C_{1-4}$ alkyl, $C_{1-4}$ haloalkyl, $C_{3-6}$ cycloalkyl, $C_{1-4}$ alkoxy, $C_{1-4}$ haloalkoxy, or $C_{1-4}$ alkylsulfonyl;

or $R^2$ can cyclize with X to form a 5-7 membered heterocyclic ring containing 1-2 heteroatoms selected from N, O and S fused to the phenyl ring to which X is attached, or $R^2$ can cyclize with L to form a 5-7 membered heterocyclic ring containing 1-2 heteroatoms selected from N, O and S, wherein the optional heterocyclic ring formed by $R^2$ cyclizing with X, or by $R^2$ cyclizing with L, can be optionally substituted with one or two groups independently selected from CN, halo, $C_{1-4}$ alkyl, $C_{1-4}$ alkoxy, $C_{1-4}$ haloalkyl, $C_{1-4}$ haloalkoxy, oxo, CN, $COOR^7$, $CON(R^7)_2$, and $-SO_2R^7$;

each $R^7$ is independently H or $C_{1-4}$ alkyl;

Z is N or $CR^4$;

$R^4$ is H, D, halo, $C_{1-4}$ alkyl, $C_{1-4}$ haloalkyl, or $C_{1-4}$ alkoxy;

$R^5$ is selected from $-C(O)R^{5a}$ and $R^{5a}$; wherein $R^{5a}$ is an optionally substituted $C_{3-8}$ cycloalkyl, $C_{3-8}$ cycloalkenyl, saturated or unsaturated 3-8 membered heterocyclic ring containing 1-2 heteroatoms selected from N, O and S, phenyl, or 5-6 membered heteroaryl ring containing 1-3 heteroatoms selected from N, O and S, wherein the optional substituents for $R^5$ are 1-4 groups independently selected from D, halo, hydroxy, amino, CN, $C_{1-4}$ alkyl, $C_{1-4}$ alkoxy, $C_{1-4}$ haloalkyl, $C_{1-4}$ hydroxyalkyl, $C_{1-4}$ haloalkoxy, $C_{3-6}$ cycloalkyl, 3-6 membered heterocyclyl containing 1-2 heteroatoms selected from N, O and S, oxo (except on aromatic rings), CN, $-COOR^9$, $-C(O)R^9$, $CON(R^9)_2$, $-NR^9C(O)R^9$, $-NR^9CO_2R^9$, $-SO_2R^9$, $-NR^9SO_2R^9$, and $-SO_2N(R^9)_2$, where each $R^9$ is independently H or $C_{1-4}$ alkyl optionally substituted with 1-3 groups independently selected from D, halo, OH, $NH_2$, NHMe and $NMe_2$; and two substituents on the same or adjacent carbon atoms of $R^5$ can optionally be taken together to form a 5-6 membered ring that can be saturated or aromatic and contains 1-2 heteroatoms selected from N, O and S and can optionally be substituted with 1-2 groups independently selected from D, Me, halo, OH, oxo, $O(C_{1-4}$ alkyl), $NH_2$, $C_{1-4}$ alkylamino, di($C_{1-4}$alkyl) amino; and $R^6$ is H, D, halo, $C_{1-4}$ alkyl, or $C_{1-4}$ haloalkyl.

Embodiment 2. The compound according to embodiment 1 or a pharmaceutically acceptable salt thereof, wherein Z is N.

Embodiment 3. The compound of embodiment 1 or a pharmaceutically acceptable salt thereof, wherein Z is CH.

Embodiment 4. The compound according to any of embodiments 1-3 or a pharmaceutically acceptable salt thereof, wherein $R^2$ is H or Me.

Embodiment 5. The compound according to any one of embodiments 1 to 4 or a pharmaceutically acceptable salt thereof, wherein $R^6$ is H.

Embodiment 6. The compound according to any one of embodiments 1 to 5 or a pharmaceutically acceptable salt thereof, wherein $R^5$ is selected from $-C(O)R^{5a}$ and $R^{5a}$; wherein $R^{5a}$ is selected from $C_{3-8}$ cycloalkyl, 5-8 membered heterocyclyl containing 1-2 heteroatoms selected from N, O and S, phenyl, and 5-6 membered heteroaryl, and is optionally substituted with 1-3 groups independently selected from D, halo, CN, hydroxy, $C_{1-4}$ alkoxy, $C_{1-4}$ alkyl, $C_{1-4}$ haloalkyl, $C_{1-4}$ hydroxyalkyl, $C_{1-4}$ haloalkoxy, $-SO_2R'$, $-N(R')_2$, $-NR'-C(O)-R'$, and $-SO_2NR'_2$, where each R' is independently H or $C_{1-4}$ alkyl.

Embodiment 7. The compound according to any of embodiments 1-6, wherein $R^5$ is selected from $-C(O)-R^{5a}$ and $R^{5a}$; wherein $R^{5a}$ is selected from phenyl, pyridine, pyridone, pyrazine, pyridazine, pyrazole, triazole, tetrazole, thiazole, oxazole, imidazole, isothiazole, isoxazole, furan, and thiophene, each of which is optionally substituted with one or two groups independently selected from halo, D, CN, $C_{1-4}$ alkyl, $C_{1-4}$ alkoxy, $C_{1-4}$ haloalkyl, $C_{1-4}$ hydroxyalkyl, $C_{1-4}$ haloalkoxy, CN, $COOR^9$, $CON(R^9)_2$, and $-SO_2R^9$, where each $R^9$ is independently H or $C_{1-4}$ alkyl.

Embodiment 8. The compound of embodiment 3 or a pharmaceutically acceptable salt thereof, wherein $R^5$ is selected from $-C(O)-R^{5a}$ and $R^{5a}$; wherein $R^{5a}$ is $C_{5-6}$ heteroaryl containing at least one N as a ring member, which is optionally substituted with 1-2 groups independently selected from halo, CN, $C_{1-4}$ alkyl, $C_{1-4}$ haloalkyl, $C_{1-4}$ hydroxyalkyl, $C_{1-4}$ alkoxy, and $C_{1-4}$ haloalkoxy.

Embodiment 9. The compound of embodiment 8 or a pharmaceutically acceptable salt thereof, wherein $R^5$ is selected from $-C(O)R^{5a}$ and $R^{5a}$; wherein $R^{5a}$ is pyrazole or triazole and is optionally substituted with 1-2 groups independently selected from halo, CN, $C_{1-4}$ alkyl, $C_{1-4}$ haloalkyl, $C_{1-4}$ hydroxyalkyl, $C_{1-4}$ alkoxy, and $C_{1-4}$ haloalkoxy.

Embodiment 10. The compound according to any of embodiments 1-6, wherein $R^5$ is selected from $-C(O)-R^{5a}$ and $R^{5a}$; wherein $R^{5a}$ is selected from cyclobutyl, cyclopentyl, cyclohexyl, cyclohexenyl, tetrahydropyran, dihydropyran, tetrahydrofuran, oxetane, azetidine, pyrrolidine, piperidine, piperazine, morpholine, tetrahydrothiopyran (thiacyclohexane), and tetrahydrothiofuran (thiacyclopentane), each of which is optionally substituted with 1-3 groups independently selected from halo, D, CN, $N(R^9)_2$, hydroxy, $C_{1-4}$alkyl, $C_{1-4}$ alkoxy, $C_{1-4}$ haloalkyl, $C_{1-4}$ hydroxyalkyl, $C_{1-4}$ haloalkoxy, oxo, CN, $COOR^9$, $CON(R^9)_2$, $-NHC(O)R^9$, $-NHCOOR^9$, $-NHSO_2R^9$, and $-SO_2R^9$, where each $R^9$ is independently H or $C_{1-4}$ alkyl.

Embodiment 11. The compound of any of embodiments 1-10, wherein $R^1$ is phenyl and is optionally substituted with up to three groups independently selected from halo, D, CN, $C_{1-4}$ alkoxy, $C_{1-4}$ alkyl, $C_{1-4}$ haloalkyl, $C_{1-4}$ haloalkoxy, SR', $-SO_2R'$, $-N(R')_2$, $-NR'-C(O)-R'$, and $-SO_2NR'_2$, where each R' is independently H, $C_{1-4}$ alkyl or $C_{1-4}$ haloalkyl.

Embodiment 12. The compound of any of embodiments 1-10, wherein $R^1$ is thiophene, thiazole, pyridine, pyrimidine, pyrazine or pyridazine, and is optionally substituted with up to three groups independently selected from halo, CN, $C_{1-4}$ alkoxy, $C_{1-4}$ alkyl, $C_{1-4}$ haloalkyl, $C_{1-4}$ haloalkoxy, $-SO_2R'$, $-N(R')_2$, $-NR'-C(O)-R'$, and $-SO_2NR'_2$, where each R' is independently H or C1-4 alkyl.

Embodiment 13. The compound according to any of embodiments 1 to 12 or a pharmaceutically acceptable salt thereof, wherein L is selected from the group consisting of: cyclopropane-1,1-diyl; cyclopropane-1,2-diyl; and $-CHR''$, wherein R'' is H, D, or C1-2 alkyl optionally substituted with up to three groups independently selected from D, hydroxy, halo, amino, $C_{1-2}$ alkylamino, di($C_{1-2}$alkyl)amino, and $C_{1-2}$ alkoxy.

Embodiment 14. The compound of embodiment 13, wherein L is:

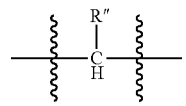

wherein R'' is methyl or ethyl, and is optionally substituted with fluoro, amino, hydroxy, methylamino, ethylamino, dimethylamino, $-OP(O)(OH)_2$, methoxy or ethoxy.

Embodiment 15. The compound according to any of embodiments 1 to 14 or a pharmaceutically acceptable salt thereof, wherein R2 and L are linked together to form a heterocyclic group selected from morpholine, piperidine, thiomorpholine, piperazine, and pyrrolidine that is attached to R1 and is also optionally substituted with one or two groups independently selected from $C_{1-4}$ alkyl, $C_{1-4}$ alkoxy, oxo, CN, $COOR^7$, $CON(R^7)_2$, and $—SO_2R^7$, where each $R^7$ is independently H or $C_{1-4}$ alkyl.

Embodiment 16. The compound of any of embodiments 1-15, wherein Y is H, methyl, or halo.

Embodiment 17. The compound of any of embodiments 1-16, wherein X is H, or $R^2$ cyclizes with X to form a 5-7 membered heterocyclic ring fused to the phenyl ring to which X is attached, wherein the 5-7 membered ring is optionally substituted as described in Embodiment 1.

Embodiment 18. The compound of embodiment 1, which is of the Formula IA:

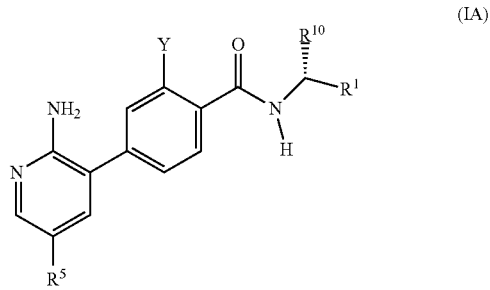

(IA)

wherein $R^5$ is pyrazole, imidazole, isoxazole, isothiazole, oxazole, triazole, or thiazole, which can be substituted with up to two groups independently selected from D, F, Cl, CN, Me, OMe, Et, iPr, OEt, and $CF_3$;
Y is H, F, Cl, or Me;
$R^{10}$ is H or $—CH_2R^*$, where $R^*$ is H, —OH, F, $—NH_2$, —NHMe, $—NMe_2$, $—OP(O)(OH)_2$ or —OMe; and
$R^1$ is phenyl or thienyl, optionally substituted with 1-2 groups independently selected from halo, CN, $C_{1-4}$ alkyl, $C_{1-4}$ alkoxy, $C_{1-4}$ haloalkyl, $C_{1-4}$ haloalkoxy, CN, $COOR^8$, $CON(R^8)_2$, —SMe, and $—SO_2R^8$, where each $R^8$ is independently H or $C_{1-4}$ alkyl;
or a pharmaceutically acceptable salt thereof.

Embodiment 19. The compound of embodiment 1, which is of the Formula IB:

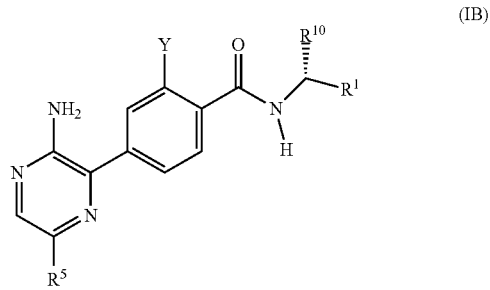

(IB)

wherein $R^5$ is a 4-7 membered cyclic ether or $C_{5-6}$ cycloalkyl, and $R^5$ can be substituted with up to four groups independently selected from D, F, Cl, CN, amino, NHMe, $NMe_2$, $—CH_2OH$, —NHC(O)Me, —NHCOOMe, $—NHSO_2Me$, Me, OMe, OH, oxo, Et, iPr, OEt, CN, and $CF_3$;
Y is H, F, Cl, or Me;
$R^{10}$ is H or $—CH_2R^*$, where $R^*$ is H, —OH, F, $—NH_2$, —NHMe, $—NMe_2$, $—OP(O)(OH)_2$ or —OMe; and
$R^1$ is phenyl, optionally substituted with 1-2 groups independently selected from halo, CN, $C_{1-4}$ alkyl, $C_{1-4}$ alkoxy, $C_{1-4}$ haloalkyl, $C_{1-4}$ haloalkoxy, CN, $COOR^8$, $CON(R^8)_2$, and $SO_2R^8$, where each $R^8$ is independently H or $C_{1-4}$ alkyl;
or a pharmaceutically acceptable salt thereof.

Embodiment 20. The compound of any one of embodiments 1-6 or 19, wherein $R^5$ is cyclohexyl substituted with 1-3 groups independently selected from D, F, Cl, CN, amino, NHMe, $NMe_2$, Me, $NHSO_2Me$, NHCOMe, OMe, OH, Et, CN, $—CH_2OH$, and $CF_3$.

In an alternative to embodiment 20, the compound of any one of embodiments 1-6 or 19 wherein $R^5$ is tetrahydropyranyl, especially 4-tetryandropyranyl.

In another alternative, the compound of any of embodiments 1-6 or 19, wherein R5 is selected from:

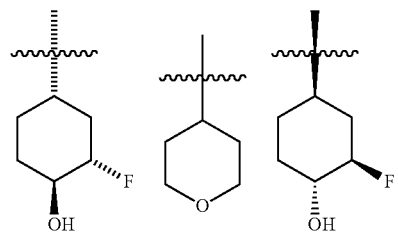

Embodiment 21. The compound of any one of embodiments 1-20, wherein $R^1$ is phenyl substituted with 0, 1 or 2 groups independently selected from F, Cl, Br, I, SMe, $SO_2Me$, and CH3.

Embodiment 22. The compound of embodiment 1, which is selected from the group consisting of the compounds of Examples 1-452 and pharmaceutically acceptable salts thereof.

Embodiment 23. A pharmaceutical composition comprising a compound according to any one of embodiments 1-22 admixed with at least one pharmaceutically acceptable excipient.

Embodiment 24. The pharmaceutical composition of embodiment 23, further comprising a therapeutic co-agent.

Embodiment 25. The pharmaceutical composition of embodiment 24, wherein the therapeutic co-agent is selected from anticancer compounds, analgesics, and anti-inflammatory compounds.

Embodiment 26. A method to treat cancer, comprising administering to a subject in need of such treatment a therapeutically effective amount of a compound according to any of embodiments 1-20 or a pharmaceutical composition of any of embodiments 23-25.

Embodiment 27. The method of embodiment 26, wherein the cancer is selected from adenoma, bladder cancer, brain cancer, breast cancer, cervical cancer, colorectal cancer, colon cancer, epidermal carcinoma, follicular carcinoma, genitourinary cancers, glioblastoma, head and neck cancers, Hodgkin's disease, non-Hodgkin's lymphoma, hepatoma, head and neck cancers, kidney cancer, lung cancers such as small cell or non-small cell lung cancer, leukemias such as AML or CML, multiple myeloma, lymphoid disorders, skin cancers including melanoma, neuroblastoma, ovarian cancer, pancreatic cancer, prostate cancer, rectal cancer, sarcoma, testicular cancer, and thyroid cancer.

Embodiment 28. A compound according to any one of embodiments 1-22 for use as a medicament.

Embodiment 29. Use of a compound according to any one of embodiments 1 to 22 or a pharmaceutically acceptable salt thereof in the manufacture of a medicament for the treatment of cancer; or use of a compound according to any one of embodiments 1 to 22 or a pharmaceutically acceptable salt thereof in medicine, especially for treatment of a cancer such as those named in embodiment 27.

Embodiment 30. A method of synthesizing a compound of the invention. For example, a method for synthesizing 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide comprising:

(a). reacting 5-((1S,3S,4S)-4-((tert-butyldimethylsilyl)oxy)-3-fluorocyclohexyl)pyrazin-2-amine with tert-butyl 2-fluoro-4-(4,4,5,5-tetramethyl-1,3,2-dioxaborolan-2-yl)benzoate in the presence of Pd(dppf)Cl$_2$, DCM, Na$_2$CO$_3$ and DME to form tert-butyl 4-(3-amino-6-((1S,3S,4S)-4-((tert-butyldimethylsilyl)oxy)-3-fluorocyclohexyl)pyrazin-2-yl)-2-fluorobenzoate;

(b). reacting tert-butyl 4-(3-amino-6-((1S,3S,4S)-4-((tert-butyldimethylsilyl)oxy)-3-fluorocyclohexyl)pyrazin-2-yl)-2-fluorobenzoate in the presence of HCl, ETOH and NaOH to form 4-(3-amino-6-((1S,3S,4S)-3-fluoro-4-hydroxycyclohexyl)pyrazin-2-yl)-2-fluorobenzoic acid;

(c). reacting 4-(3-amino-6-((1S,3S,4S)-3-fluoro-4-hydroxycyclohexyl)pyrazin-2-yl)-2-fluorobenzoic acid with (S)-N-(2-amino-2-(3-bromo-5-fluorophenyl)ethyl)-N-methyl-2-nitrobenzenesulfonamide hydrochloride in the presence of EDCI and HOAT to give 4-(3-amino-6-((1S,3S,4S)-3-fluoro-4-hydroxycyclohexyl)pyrazin-2-yl)-N-((S)-1-(3-bromo-5-fluorophenyl)-2-(N-methyl-2-nitrophenylsulfonamido)ethyl)-2-fluorobenzamide; and (d). reacting 4-(3-amino-6-((1S,3S,4S)-3-fluoro-4-hydroxycyclohexyl)pyrazin-2-yl)-N-((S)-1-(3-bromo-5-fluorophenyl)-2-(N-methyl-2-nitrophenylsulfonamido)ethyl)-2-fluorobenzamide in the presence of LiOH, DMF and 4-mercaptobenzoic acid to give 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide.

Embodiment 31. The invention provides a high crystallinity HCl salt of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide in that said form has at least one of the following characteristics:

a) A X-ray powder diffraction pattern with two or more peaks (preferably three peaks, preferable all peaks) at degrees 2-theta (wherein the angle variation is +/−0.3, 0.2 or 0.1 degrees) as shown in Example 184;

b) A X-ray powder diffraction pattern with peaks substantially the same as depicted in the FIG. 3; or c) A thermal gravimetric analysis curve substantially in accordance with that shown in FIG. 4.

In some embodiments of Formula I or IA or IB, Y is H or halo, particularly F or Cl. Halo, especially F, is preferred. Y may be positioned 'ortho' to the carbonyl depicted in these Formulas.

In many embodiments of the compounds described above, X is H. In other embodiments, X is a group ortho to the carbonyl shown in Formula I, such as F, Me or Cl, and in some such embodiments, X is a group that, taken together with R$^2$ as described herein, forms a ring fused to the phenyl ring shown in Formula I. This fused ring is typically a 5, 6 or 7 atom ring, and may contain, in addition to the N to which R$^2$ is attached, an additional N, O or S as a ring member. The fused ring can be substituted or unsubstituted; when substituted, it can have one or two substituents as described for Formula (I), with halo, C$_{1-4}$alkyl, oxo, and hydroxy as preferred substituents unless otherwise specified.

In some embodiments of the compounds of Formula I and other embodiments described above, R$^2$ is H or Me, and is preferably H. In alternative embodiments, R$^2$ and X taken together form a 5-7 membered heterocyclic ring as described for Formula I above, in which case X is attached to the phenyl ring at a position ortho to the carbonyl group depicted in Formula I.

In certain of the foregoing embodiments, L is a C$_{1-4}$ alkylene, which may be straight chain or branched, and can be unsubstituted or substituted with 1-3 groups as described for Formula I. In some embodiments, L is a group of the formula —CH(R$^L$) where R$^L$ is a C$_{1-3}$ alkyl or a C$_{1-2}$ alkyl and is optionally substituted with 1-3 groups as described for Formula I. Preferably, L is C$_{1-2}$ alkyl and is substituted by 1 or 2 groups independently selected from hydroxy, halo, amino, OMe, —NHMe, —OP(O)(OH)$_2$ and —NMe$_2$. In some embodiments, particularly where R$^1$ is an aryl or heteroaryl group, L is —CH$_2$— or a substituted alkylene of the formula —CH(CH$_2$R*)— where R* is H, Me, OH, F, NH$_2$, NHMe, —OP(O)(OH)$_2$ or OMe. In other embodiments, L is CH$_2$CH$_2$—. When L is substituted, it is often substituted with methyl, hydroxymethyl, aminomethyl, methylamino, methylaminomethyl, fluoromethyl, or methoxymethyl.

In embodiments where L is substituted alkylene (e.g., a group of formula —CHR" as described herein), L contains a chiral center; in certain of these embodiments, L has this stereochemistry:

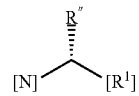

where [N] and [R$^1$] indicate the positions where —CH(R")— is connected to NR$^2$ and R$^1$, respectively. Preferably, R" is —CH$_3$, —CH$_2$OH, —CH$_2$NH$_2$, —CH$_2$NHMe, —CH$_2$NMe$_2$, —CH$_2$F, —CH$_2$OMe, —CH(OH)Me, —CH$_2$OP(O)(OH)$_2$ or —CH(OH)CH$_2$OH. In some embodiments, the compound of Formula (I) comprises L having the chiral configuration shown in excess over its enantiomer, so the compound is optically active. Preferably, such compounds of the invention are substantially free of the opposite enantiomer, i.e., at least 95% of the compound has the chirality shown above.

In some embodiments of the foregoing compounds, R$^1$ is aryl or heteroaryl, optionally substituted as described below, and commonly R$^1$ is an optionally substituted group selected from phenyl, thienyl, thiazolyl, pyridinyl, pyridazinyl, pyrazinyl, and pyrimidinyl. Substituted phenyl is preferred for R$^1$.

R$^1$ is often substituted with at least one group selected from those described for the embodiments described above. In some embodiments, R$^1$ is phenyl, 3-thienyl, 2-thiazolyl, 2-pyridinyl, or 3-pyridinyl that is unsubstituted or is substituted with 1-2 groups independently selected from halo (F, Cl, Br or I), methyl, methoxy, SMe, methylsulfonyl, cyano, and cyclopropyl. In some embodiments, R$^1$ is phenyl and is substituted in at least one position 'meta' to [L] (the position of R$^1$ that is attached to L) with F, Cl, Br, I, SMe, CH$_2$F, CHF$_2$, or methylsulfonyl.

In some embodiments, the —C(=O)—NR²-L-R¹ portion of the structure in Formula (I) has the following formula, where W¹ and W² are selected independently:

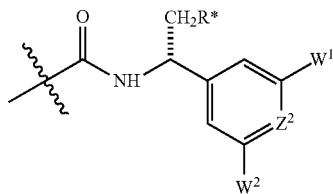

R* = H, OH, NH₂, NHMe, NMe₂, OMe, F, —OP(O)(OH)₂  Z² = CH W¹, W² = H, F, Cl, CN, —SO₂Me, Me, OMe, Br, I, CH₂F, CF₂H, SMe

In these embodiments, at least one of W¹ and W² is typically other than H, and preferably at least one of W¹ and W² is halo, particularly Cl, Br or I.

In some embodiments of the compounds of the invention, R⁶ is H or Me; often R⁶ is H.

In some embodiments of any of the compounds described above, Z is N. In alternative embodiments of any of the compounds described above, Z is CR⁴, preferably CH.

In some embodiments, R⁵ is a 5-6 membered heteroaryl ring or phenyl, and may be substituted as described for Formula I above. In such embodiments, R⁵ can be phenyl, pyridyl, pyridazinyl, or pyrimidinyl, optionally substituted as described above. In other such embodiments, R⁵ is a nitrogen-containing 5-membered heteroaryl ring, such as pyrazole, imidazole, isoxazole, oxazole, thiazole, triazole, tetrazole, isothiazole, pyrrole, and the like, optionally substituted as described above; in these embodiments, Z is preferably CH. Pyrazoles, triazoles, and imidazoles are sometimes preferred options for R⁵.

In the embodiments wherein R⁵ is heteroaryl, R⁵ may be unsubstituted or it may be substituted with 1-3 groups independently selected from Me, Et, isopropyl, propyl, butyl, t-butyl, sec-butyl, isobutyl, CF₃, CN, Cl and F.

Some preferred embodiments of these R⁵ groups include:

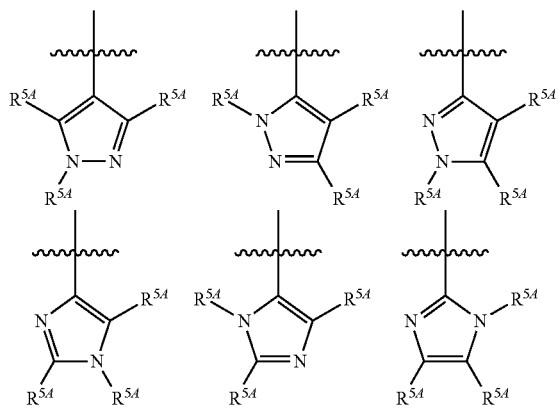

where each R⁵ᴬ is independently selected from H, Me, Et, propyl, and isopropyl. Preferably, no more than one or two of the R⁵ᵃ groups on R⁵ are other than H, and in most embodiments, R⁵ᴬ on N in these groups is methyl, ethyl, or isopropyl. Specific suitable groups include 1-methyl-4-pyrazole, 1-ethyl-4-pyrazole, 1-isopropyl-4-pyrazole, and 3-pyrazole and its tautomer; 1-methylimidazol-2-yl, 1-methylimidazol-4-yl, 1-methylimidazol-5-yl; and methyl-substituted versions of these.

In other embodiments, R⁵ is a non-aromatic cycloalkyl or heterocyclic group such as cyclohexyl, cyclopentyl, tetrahydropyranyl (e.g., 4-tetrahydropyranyl), 3-oxetanyl, 3- or 4-piperidinyl, 4- or 3-piperidin-2-onyl, 3- or 4-thiacyclopentane, 3-thiacyclohexane, 3-tetrahydrofuran, and the like. In these embodiments, a ring sulfur can be oxidized to sulfoxide or sulfone oxidation state, and each of these rings may be substituted with 1-3 groups, typically 1-2 groups, selected from oxo, Me, Et, isopropyl, CF₃, CN, Cl and F. Some preferred examples of these embodiments include:

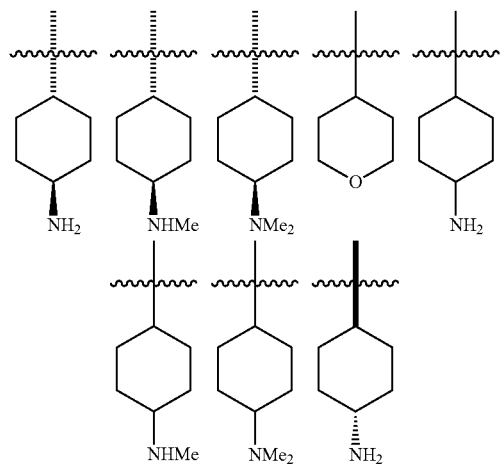

The 1,4-disubstituted cyclohexyl embodiments can have either a cis or trans relative stereochemistry between the groups attached at positions 1 and 4; in some embodiments, a trans relative orientation between these groups is preferred. Suitable cycloalkyl and heterocyclyl embodiments of R⁵ include:

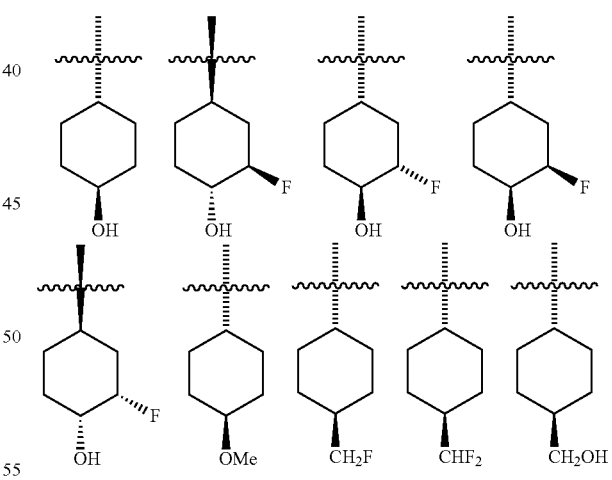

Preferred embodiments of R⁵ include these:

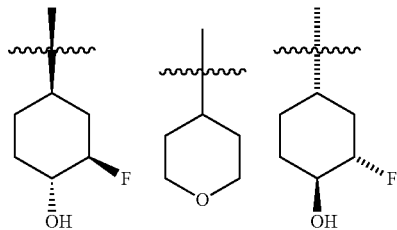

Where R⁵ is heterocyclic or cycloalkyl and is substituted, it frequently will contain at least one chiral center. In these chiral compounds, both R and S isomers can be used individually, as well as mixtures of R and S, including a racemic mixture. The compounds of the invention can also include atropisomers where rotation about an heteroaryl-aryl (heteroaryl) bond is hindered by the presence of substituent groups; in these situations, each atropisomer is included. Where one isomer (enantiomer, diastereomer, atropisomer, or geometric isomer) has higher intrinsic activity as an inhibitor of ERK1 or ERK2 than its opposite isomer, the more active isomer is typically preferred.

As used herein, the term "optical isomer" or "stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. The invention includes enantiomers, diastereomers or racemates of the compounds. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R-S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a di-substituted cycloalkyl, the cycloalkyl substituent may have a cis- or trans-configuration, unless otherwise specified. All tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, adipate, aluminum, ascorbate, aspartate, benzoate, besylate, bromide/hydrobromide, bicarbonate/carbonate, bisulfate/sulfate, camphorsulfonate, caproate, chloride/hydrochloride, chloroprocaine, chlortheophyllonate, citrate, edetate, calcium edetate, ethandisulfonate, ethylsulfonate, ethylene diamine, fumarate, galactarate (mucate), gluceptate, gluconate, glucuronate, glutamate, glycolate, hexyl resorcinate, hippurate, hydroiodide/iodide, hydroxynapthoate (xinafoate), isethionate, lactate, lactobionate, laurylsulfate, lithium, malate, maleate, malonate, mandelate, mesylate, methylsulphate, naphthoate, napsylate, nicotinate, nitrate, octadecanoate, oleate, oxalate, palmitate, pamoate, pantothenate, phosphate/hydrogen phosphate/dihydrogen phosphate, polygalacturonate, procaine, propionate, salicylate, sebacate, stearate, subacetate, succinate, sulfate, sulfosalicylate, tannate, tartrate, bitartrate, tosylate, triphenylacetate, and trifluoroacetate salts. Lists of additional suitable salts can be found, e.g., in Remington's Pharmaceutical Sciences, 20th ed., Mack Publishing Company, Easton, Pa., (1985); and in Handbook of Pharmaceutical Salts: Properties, Selection, and Use, by Stahl and Wermuth (Wiley-VCH, Weinheim, Germany, 2002).

In one embodiment, the present invention provides 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another embodiment, the present invention provides 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide in hydrochloride salt form.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is intended to represent unlabeled forms (i.e., compounds wherein all atoms are present at natural isotopic abundances, and not isotopically enriched) as well as isotopically enriched or labeled forms of the compounds. Isotopically enriched or labeled compounds have structures depicted by the formulas given herein except that at least one atom of the compound is replaced by an atom of the same element but having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}F$, $^{32}F$, $^{35}S$, $^{36}Cl$, $^{125}I$ respectively. The invention includes various isotopically labeled compounds as defined herein, for example those in which radioactive isotopes, such as $^3H$ and $^{14}C$, or those in which non-radioactive isotopes, such as $^2H$ and $^{13}C$, are present at levels significantly above the natural abundance for these isotopes. These isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I) if it is incorporated at substantially above the level of natural isotopic abundance. The invention includes isotopically enriched versions of the compounds, e.g., deuterated versions as well as non-deuterated versions. Deuterated versions may be deuterated at a single site, or at multiple sites.

The degree of incorporation of such an isotope in an isotopically-enriched compound, particularly deuterium, may be defined by the isotopic enrichment factor. The term "isotopic enrichment factor" as used herein means the ratio between the isotopic abundance of a specified isotope in a sample, and the natural abundance of the isotope in a non-enriched sample. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, e.g., compounds of formula (I) that contain groups capable of acting as donors and/or acceptors for hydrogen bonds, may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, REMINGTON'S PHARMACEUTICAL SCIENCES, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by a kinase such as ERK1/2 or (ii) associated with activity of a kinase such as ERK1/2, or (iii) characterized by activity (normal or abnormal) of ERK1/2; or (2) reduce or inhibit the activity of ERK1/2 or (3) reduce or inhibit the expression of ERK1/2.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of ERK1/2, or at least partially reduce or inhibit the expression of ERK1/2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, activity, effect, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to delaying the development or progression of the disease or disorder.

As used herein, a subject is "in need of" a treatment if such subject would be expected to benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95 enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with carbon-carbon double bonds may, where possible, be present in cis-(Z)- or trans-(E)-form, and both are included in the invention unless otherwise indicated.

Accordingly, as used herein a compound of the present invention can be in the form of one of the possible isomers, rotamers, atropisomers, or tautomers or as a mixture thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The compounds of formula (I) can be prepared according to the Schemes and examples provided herein. The Schemes in some instances illustrate preparation of compounds wherein L is methylene or a substituted alkylene group, but methods for preparing suitable benzamides where L is a bond or other options encompassed by Formula (I) are readily apparent to the skilled person in view of the many known methods for making the requisite benzamide intermediates, so these methods are equally applicable to preparation of compounds with other embodiments of L.

Scheme A.

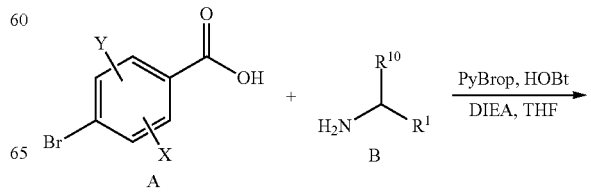

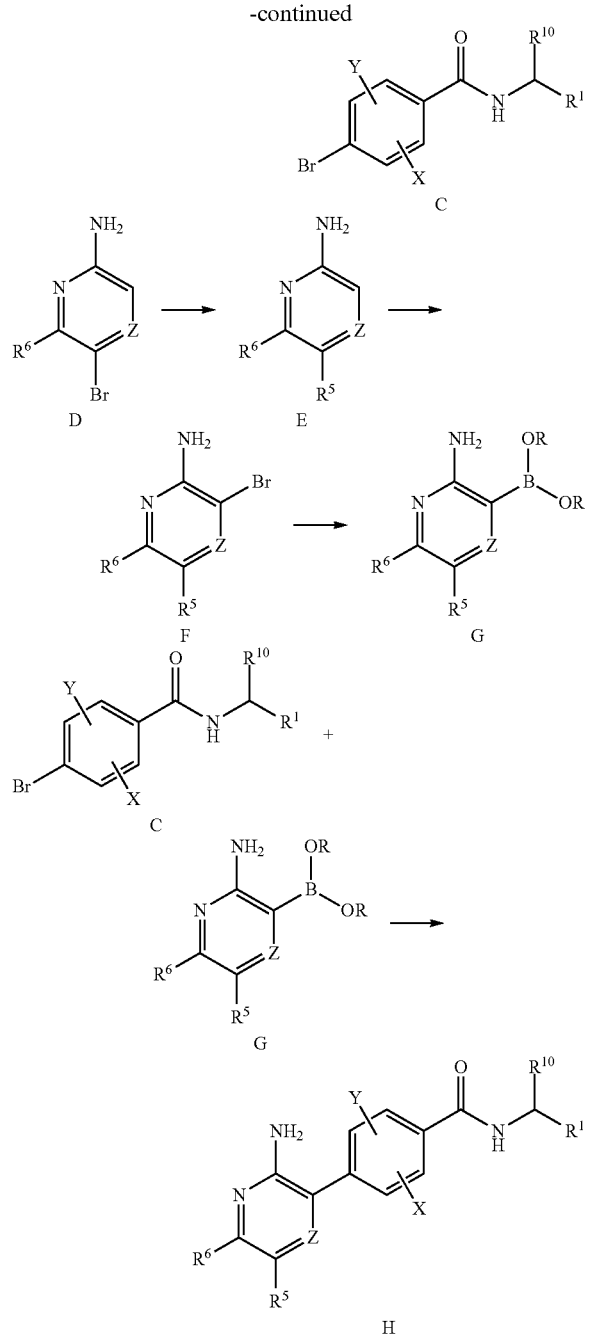

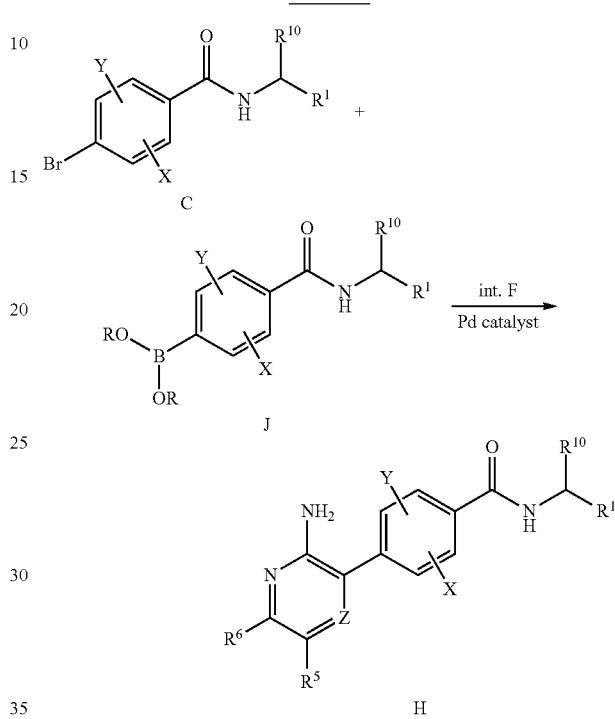

Alternatively, as shown in Scheme B, compound C can be converted to an arylboronic acid or ester, and can be coupled to heteroaryl bromide F, again using known palladium catalyzed coupling conditions, to provide compounds of the invention.

Precursors A and B can be coupled using known peptide bond formation conditions to provide intermediate C. Intermediate C can be coupled with a heteroaryl boronic acid such as intermediate G under well-known palladium-assisted conditions to form products of formula H, which are compounds of Formula (I). The requisite aminopyridine/pyrazine compounds (G) for coupling with Compound C can be prepared from bromopyridine/pyrazines by introducing a desired $R^5$ group using palladium chemistry (see intermediate E above), then brominating adjacent to the amino group and converting to the boronic acid or ester (G). Scheme C illustrates application of this sequence, including hydrogenation of an olefin to arrive at a compound of formula G, where $R^5$ is a tetrahydropyran.

Intermediate F can be prepared by methods known in the art and methods disclosed herein. Numerous compounds of Formula F can be synthesized from known amino-bromo-pyridines and -pyrazines as illustrated in Scheme C. Various aryl, heteroaryl, and vinyl boronic acid esters can be coupled to the bromopyridine or bromopyrazine using palladium catalysts as is known in the art, to introduce a desired $R^5$ group. This method is especially useful to introduce aryl or heteroaryl groups as $R^5$ in Formula (I). Where the initial coupling product introduces a partially unsaturated group at the $R^5$ position, as illustrated in Scheme C, the unsaturation can be reduced by conventional methods to provide compounds having a saturated group (e.g., heterocyclyl or cycloalkyl) as $R^5$. This option is illustrated in Scheme C, where preparation of a compound having 4-tetrahydropyranyl as $R^5$ is shown.

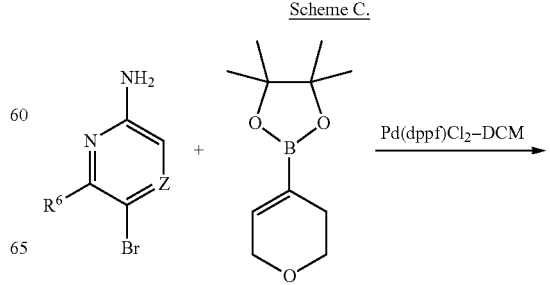

-continued

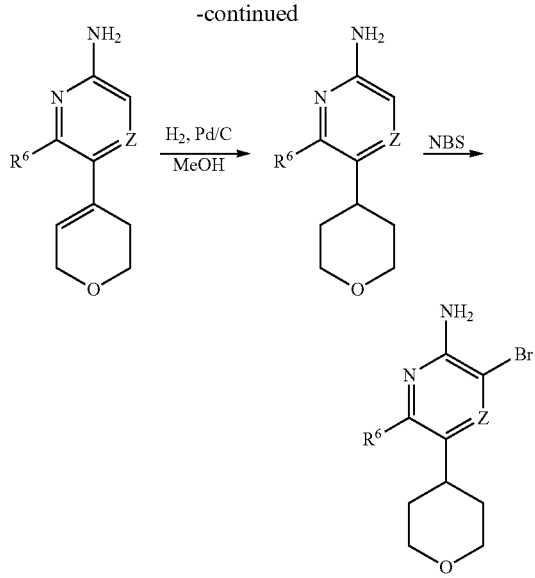

Scheme D illustrates another synthesis route, where the group corresponding to $R^5$ in Formula (I) is attached after the pyridine or pyrimidine is coupled to the benzamide portion. The method allows incorporation of a wide array of aryl, heteroaryl or vinylic (unsaturated) $R^5$ groups, and as illustrated herein, a vinylic $R^5$ group can be reduced after the coupling reaction to provide a saturated $R^5$ group. Again, the route is depicted with a benzylic group on the amide nitrogen, corresponding to L=optionally substituted alkylene, and $R^1$=optionally substituted phenyl, but due to the wide availability of starting materials and methods for making the amide intermediates, it is equally applicable for synthesis of compounds with other L and $R^1$ groups. Once the heteroaryl group is coupled to the benzamide phenyl ring, $R^5$ can be attached by palladium coupling, where the boronic acid/ester can be on $R^5$ or on the aminopyridine/aminopyrazine ring. $R^{1*}$ in this scheme represents optional substituents on the phenyl group, selected to correspond to substituents on $R^1$ in Formula (I).

Scheme D.

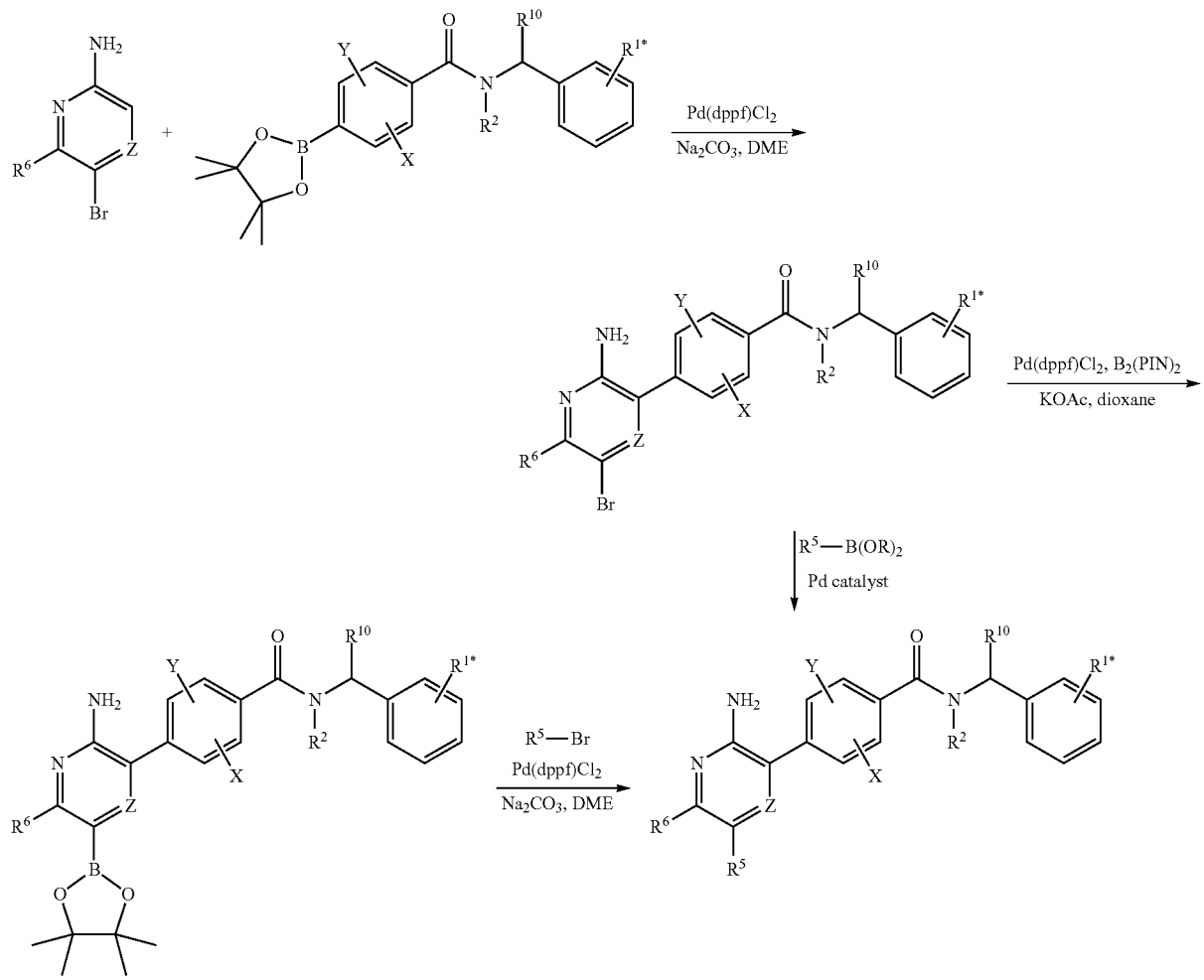

Scheme E illustrates a method to make compounds of Formula (I) starting from a 3-bromo-2-aminopyridine or a corresponding pyrazine, and a benzoate ester substituted with a boronic acid or ester. After coupling to form a biaryl group, the aminopyridine can be brominated readily under mild conditions, and the desired amide group can be prepared. $R^5$ can be introduced by palladium-catalyzed replacement of Br from the pyridine ring. Here again, the boronic acid ester can be on either the aminopyridine ring, or on the aryl, heteroaryl or vinylic $R^5$ group.

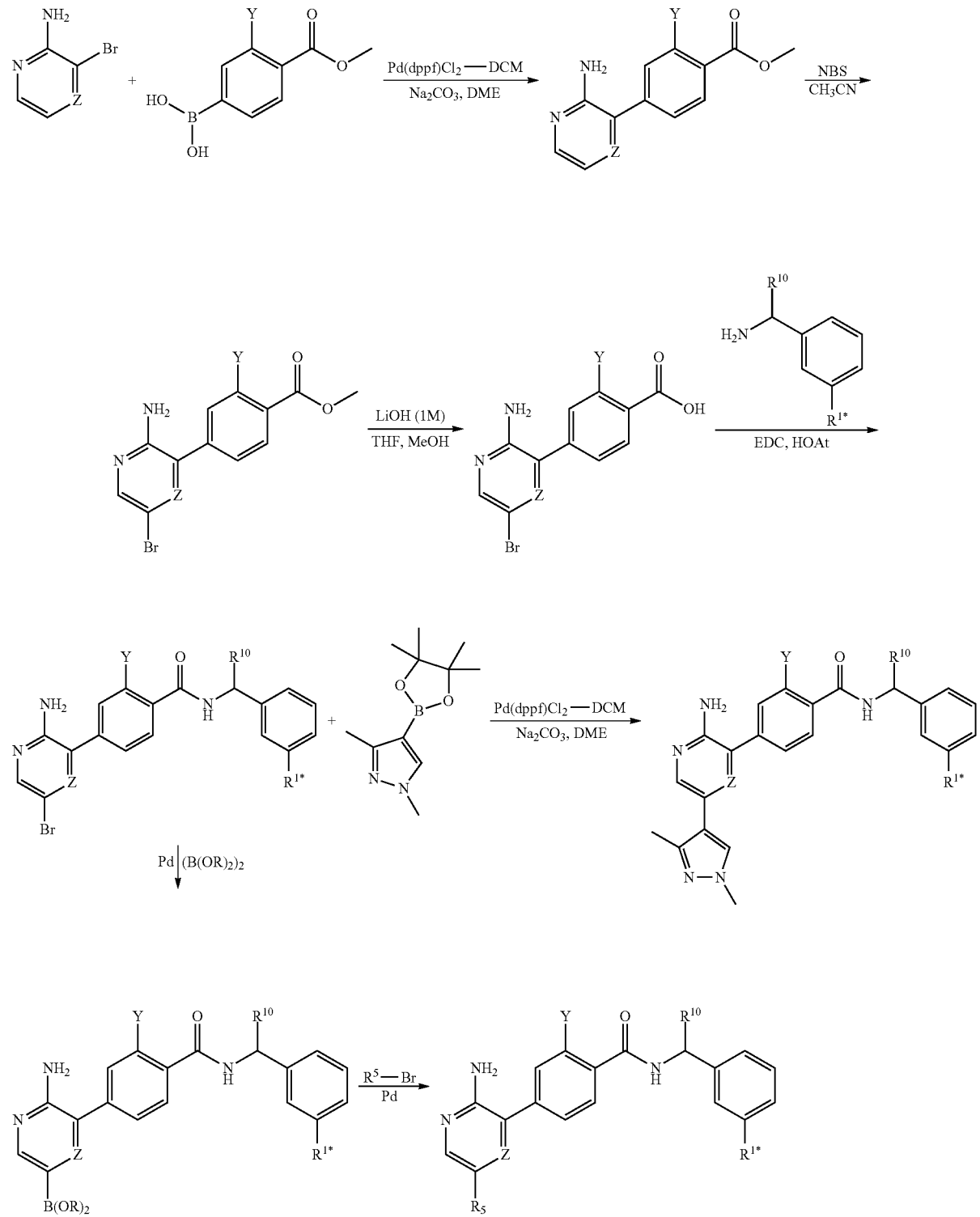

Scheme E.

The invention further includes any variant of the present processes in which an intermediate obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can be interconverted according to methods generally known to those skilled in the art.

In another aspect, the invention provides intermediates useful for the synthesis of the compounds of Formula (I), including compounds of Formula (II):

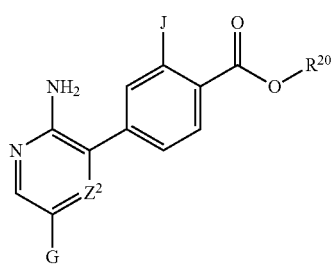

wherein $Z^2$ is CH or N;
G is Br or —B(OR$^{21}$)$_2$;
  where each $R^{21}$ is H or $C_{1-4}$ alkyl, or two $R^{21}$ taken together with the linkage —O—B—O— to which they are attached form a cyclic borate ester;
J is H, F, Cl or Me; and
$R^{20}$ is H or $C_{1-6}$ alkyl.

In some embodiments, J is advantageously fluoro (F), and in other embodiments J is Cl. In some embodiments G is a cyclic borate ester group such as 4,4,5,5-tetramethyl-1,3,2-dioxaborolan-2-yl or 1,3,2-dioxaborolan-2-yl.

In another aspect, the present invention provides a pharmaceutical composition comprising a compound of the present invention, or a pharmaceutically acceptable salt thereof, and at least one pharmaceutically acceptable carrier or excipient. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). Pills or tablets may be either film coated or enteric coated according to methods known in the art. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions comprising compounds of the invention are tablets or gelatin capsules comprising a compound of Formula (I) as an active ingredient together with one or more of the following excipients:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Selection of suitable capsules for encapsulation and of suitable excipients for formulating the compound of Formula I to make oral dosage forms is within the ordinary level of skill. Tablets may be either film coated or enteric coated using methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets, including the ones listed above. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil, to form a solution, emulsion or dispersion inside the soft capsule.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, where it is desirable to minimize exposure of the compound to water prior to administration. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. they modulate or inhibit activity of ERK1 and/or ERK2, as indicated by test data provided in the following sections, and are therefore indicated for therapy as described herein, or for use as research chemicals, e.g. as tool compounds to further the understanding of the effects of EKR1/2 inhibition or inhibition of a biochemical pathway (MAPK).

Thus, as a further embodiment, the present invention provides the use of a compound of formula (I) or any of the embodiments within the scope of Formula (I) as described herein, in therapy, or for the manufacture of a medicament. In a further embodiment, the therapy or medicament is for a disease which may be treated by inhibition of ERK1 and/or ERK2. In another embodiment, the compounds of the invention are useful to treat cancers, including but not limited to those mentioned herein.

In another embodiment, the invention provides a method of treating a disease which is treatable by inhibition of ERK1 and/or ERK2, comprising administration of a therapeutically effective amount of a compound of formula (I) or (IA) or any of the embodiments of the invention as described herein. In a further embodiment, the disease is selected from the afore-mentioned lists of suitable conditions. The method typically comprises administering an effective amount of a compound as described herein or a pharmaceutical composition comprising such compound to a subject in need of such treatment. The compound may be administered by any suitable method such as those described herein, and the administration may be repeated at intervals selected by a treating physician. The invention thus provides a compound of Formula I and IA or any subgenus thereof as described herein for use to treat a condition mediated by or associated with excessive or undesired levels of ERK1/2 activity, including those mentioned above.

Thus, as a further embodiment, the present invention provides the use of a compound of formula (I), or any of the embodiments of such compounds described herein, for the manufacture of a medicament. In a further embodiment, the medicament is for treatment of a disease which may be treated by inhibition of ERK1 and/or ERK2. In another embodiment, the disease is a cancer, e.g., a cancer selected from the aforementioned list, suitably.

In some embodiments, the compounds are used in combination with one or more co-therapeutic agents. Suitable co-therapeutic agents include anticancer agents, analgesics, anti-inflammatory agents, and the like. In some embodiments, the compositions include a co-therapeutic agent that acts on the RAF pathway, such as a B-RAF inhibitor or a C-Raf inhibitor.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by ERK1 and/or ERK2, wherein the medicament is prepared for administration with another therapeutic agent. The invention also provides the use of another co-therapeutic agent for treating a disease or condition, wherein the co-agent is administered with a compound of formula (I).

The invention also provides a compound of formula (I) for use in a method of treating a disease or condition mediated by ERK1 and/or ERK2, wherein the compound of formula (I) is prepared for administration with another therapeutic agent. The invention also provides another therapeutic co-agent for use in a method of treating a disease or condition mediated by ERK1 and/or ERK2, wherein the other therapeutic co-agent is prepared for administration with a compound of formula (I). The invention also provides a compound of formula (I) for use in a method of treating a disease or condition mediated by ERK1 and/or ERK2, wherein the compound of formula (I) is administered with another therapeutic co-agent. The invention also provides another co-therapeutic agent for use in a method of treating a disease or condition mediated by ERK1 and/or ERK2, wherein the other therapeutic co-agent is administered with a compound of formula (I).

The invention also provides the use of a compound of formula (I) for treating a disease or condition mediated by ERK1 and/or ERK2, wherein the patient is one treated previously or subsequently (e.g. within 24 hours) with another therapeutic agent. The invention also provides the use of a co-therapeutic agent for treating a disease or condition mediated by ERK1 and/or ERK2, wherein the patient has previously (e.g. within 24 hours) been treated with a compound of formula (I).

In one embodiment, the other therapeutic agent (co-therapeutic agent or just co-agent) is a compound useful for treating a cancer, and is typically an FDA approved drug approved for treating at least one type of cancer. Suitable co-therapeutic agents include erlotinib, bortezomib, fulvestrant, sunitib imatinib mesylate, letrozole, finasunate, platins such as oxaliplatin, carboplatin, and cisplatin, finasunate, fluorouracil, rapamycin, leucovorin, lapatinib, lonafamib, sorafenib, gefitinib, capmtothecin, topotecan, bryostatin, adezelesin, anthracyclin, carzelesin, bizelesin, dolastatin, auristatins, duocarmycin, eleutherobin, taxols such as paclitaxel or docetaxel, cyclophasphamide, doxorubicin, vincristine, prednisone or prednisolone, other alkylating agents such as mechlorethamine, chlorambucil, and ifosfamide, antimetabolites such as azathioprine or mercaptopurine, other microtubule inhibitors (vinca alkaloids like vincristine, vinblastine, vinorelbine and vindesine, as well as taxanes), podophyllotoxins (etoposide, teniposide, etoposide phosphate, and epipodophyllotoxins), topoisomerase inhibitors, other cytotoxins such as actinomycin, daunorubicin, valrubicin, idarubicin, edrecolomab, epirubicin, bleomycin, plicamycin, mitomycin, as well as other anticancer antibodies (cetuximab, bevacizumab, ibritumomab, abagovomab, adecatumumab, afutuzumab, alacizumab, alemtuzumab, anatumomab, apolizumab, bavituximab, belimumab, bivatuzumab mertansine, blinatumomab, brentuximab vedotin, cantuzumab mertansine, catumazomab, cetuximab, citatuzumab bogatox, cixutumumab, clivatuzumab tetraxetan, conatumumab, dacetuzumab, daclizumab, detumomab, ecromeximab, edrecolomab, elotuzumab, epratuzumab, ertumaxomab, etaracizumab, farletuzumab, figitumumab, fresolimumab, galiximab, gembatumumab vedotin, gemtuzumab, ibritumomab tiuxetan, inotuzumab ozogamicin, intetumumab, ipilimumab, iratumumab, labetuzumab, lexatumumab, lintuzumab, lucatumumab, lumilisimab, mapatumumab, matuzumab, milatuzumab, mitumomab, nacolomab tafenatox, naptumomab estafenatox, necitumumab, nimotuzumab, ofatumumab, olaratumab, oportuzumab monatox, oregovomab, panitumumab, pemtumomab, pertuzumab, pintumomab, pritumumab, ramucirumab, rilotumumab, robatumumab, rituximab, sibrotuzumab, tacatuzumab tetraxetan, taplitumomab paptox, tenatumomab, ticilimumab, tigatuzumab, tositumomab or $^{131}$I-tositumomab, trastuzumab, tremelimumab, tuocotuzumab celmoleukin, veltuzumab, visilizumab, volocixumab, votumumab, zalutumumab, zanolimumab, IGN-101, MDX-010, ABX-EGR, EMD72000, ior-t1, MDX-220, MRA, H-11 scFv, huJ591, TriGem, TriAb, R3, MT-201, G-250, ACA-125, Onyvax-105, CD:-960, Cea-Vac, BrevaRex AR54, IMC-1C11, GlioMab-H, ING-1, anti-LCG MAbs, MT-103, KSB-303, Therex, KW2871, anti-HMI.24, Anti-PTHrP, 2C4 antibody, SGN-30, TRAIL-RI MAb, Prostate Cancer antibody, H22xKi-r, ABX-Mai, Imuteran, Monopharm-C), and antibody-drug conjugates comprising any of the above agents (especially auristatins MMAE and MMAF, maytansinoids like DM-1, calicheamycins, or various cytotoxins). Preferred co-therapeutics, unless otherwise specified, include vemurafinib, debrafinib, LGX818, trametinib, MEK162, LEE011, PD-0332991, panobinostat, verinostat, romidepsin, cetuximab, gefitinib, erlotinib, lapatinib, panitumumab, vandetanib, INC280, everolimus, simolimus, BMK120, BYL719, and CLR457.

The pharmaceutical composition or combination of the present invention can be in unit dosage of about 1-2000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease being treated and the severity thereof. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more co-therapeutic agents, also referred to herein as co-agent(s). The compound of the present invention may be administered separately, by the same or different route of administration, or together in the same pharmaceutical composition as the co-agent(s).

In one embodiment, the invention provides a product comprising a compound of formula (I) and at least one other therapeutic co-agent as a combined preparation for simultaneous, separate or sequential use in therapy. In one embodiment, the therapy is the treatment of a disease or condition mediated by ERK1 and/or ERK2, such as cancer. Products provided as a combined preparation include a composition comprising the compound of formula (I) and the other therapeutic co-agent(s) together in the same pharmaceutical composition, or the compound of formula (I) and the other therapeutic co-agent(s) in separate form, e.g. in the form of a kit.

In one embodiment, the invention provides a pharmaceutical composition comprising a compound of formula (I) and another therapeutic co-agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by ERK1 and/or ERK2, wherein the medicament is prepared for administration with another therapeutic agent. The invention also provides the use of another therapeutic co-agent for treating a disease or condition, wherein the medicament is administered with a compound of formula (I). Suitable co-therapeutic agents for use with the compounds of the invention are typically selected based on the condition for treatment. For example, in the treatment of melanoma, the co-therapeutic agent may be selected from Aldesleukin, Dabrafenib, Dacarbazine, DTIC-Dome (Dacarbazine), Intron A (Recombinant Interferon Alfa-2b), Ipilimumab, Mekinist (Trametinib), Peginterferon Alfa-2b, PEG-Intron (Peginterferon Alfa-2b), Proleukin (Aldesleukin), Recombinant Interferon Alfa-2b, Sylatron (Peginterferon Alfa-2b), Tafinlar (Dabrafenib), Trametinib, Vemurafenib, Yervoy (Ipilimumab), and Zelboraf (Vemurafenib). For the treatment of ovarian cancer, the co-therapeutic agent may be selected from Adriamycin PFS (Doxorubicin Hydrochloride), Adriamycin RDF (Doxorubicin Hydrochloride), Carboplatin, Clafen (Cyclophosphamide), Cisplatin, Cyclophosphamide, Cytoxan (Cyclophosphamide), Doxorubicin Hydrochloride, Dox-SL (Doxorubicin Hydrochloride Liposome), DOXIL (Doxorubicin Hydrochloride Liposome), Doxorubicin Hydrochloride Liposome, Evacet (Doxorubicin Hydrochloride Liposome), Gemcitabine Hydrochloride, Gemzar (Gemcitabine Hydrochloride), Hycamtin (Topotecan Hydrochloride), LipoDox (Doxorubicin Hydrochloride Liposome), Neosar (Cyclophosphamide), Paclitaxel, Paraplat (Carboplatin), Paraplatin (Carboplatin), Platinol (Cisplatin), Platinol-AQ (Cisplatin), Taxol (Paclitaxel), and Topotecan Hydrochloride. For the treatment of thyroid cancer, the co-therapeutic agent may be selected from Adriamycin PFS (Doxorubicin Hydrochloride), Adriamycin RDF (Doxorubicin Hydrochloride), Cabozantinib-S-Malate, Caprelsa (Vandetanib), Cometriq (Cabozantinib-S-Malate), Doxorubicin Hydrochloride, and Vandetanib. For the treatment of colon cancer, the co-therapeutic may be selected from Adrucil (Fluorouracil), Avastin (Bevacizumab), Bevacizumab, Camptosar (Irinotecan Hydrochloride), Capecitabine, Cetuximab, Efudex (Fluorouracil), Eloxatin (Oxaliplatin), Erbitux (Cetuximab), Fluoroplex (Fluorouracil), Fluorouracil, Irinotecan Hydrochloride, Leucovorin Calcium, Oxaliplatin, Panitumumab, Regorafenib, Stivarga (Regorafenib), Vectibix (Panitumumab), Wellcovorin (Leucovorin Calcium), Xeloda (Capecitabine), Zaltrap (Ziv-Aflibercept), and Ziv-Aflibercept. For the treatment of lung cancer, the co-therapeutic may be selected from Abitrexate (Methotrexate), Abraxane (Paclitaxel Albumin-stabilized Nanoparticle Formulation), Afatinib Dimaleate, Alimta (Pemetrexed Disodium), Avastin (Bevacizumab), Bevacizumab, Carboplatin, Cisplatin, Crizotinib, Erlotinib Hydrochloride, Folex (Methotrexate), Folex PFS (Methotrexate), Gefitinib, Gilotrif (Afatinib Dimaleate), Gemcitabine Hydrochloride, Gemzar (Gemcitabine Hydrochlorde), Iressa (Gefitinib), Methotrexate, Methotrexate LPF (Methotrexate), Mexate (Methotrexate), Mexate-AQ (Methotrexate), Paclitaxel, Paclitaxel Albumin-stabilized Nanoparticle Formulation, Paraplat (Carboplatin), Paraplatin (Carboplatin), Pemetrexed Disodium, Platinol (Cisplatin), Platinol-AQ (Cisplatin), Tarceva (Erlotinib Hydrochloride), Taxol (Paclitaxel), and, Xalkori (Crizotinib). For the treatment of pancreatic cancer, the co-therapeutic agent can be selected from Adrucil (Fluorouracil), Efudex (Fluorouracil), Erlotinib Hydrochloride, Fluoroplex (Fluorouracil), Fluorouracil, Gemcitabine Hydrochloride, Gemzar (Gemcitabine Hydrochloride), Mitomycin C, Mitozytrex (Mitomycin C), Mutamycin (Mitomycin) and Tarceva (Erlotinib Hydrochloride. For the treatment of cervical cancer, the co-therapeutic agent may be selected from Blenoxane (Bleomycin), Bleomycin, Cisplatin, Hycamtin (Topotecan Hydrochloride), Platinol (Cisplatin), Platinol-AQ (Cisplatin), and Topotecan Hydrochloride. For the treatment of head and neck cancer, the co-therapeutic agent may be selected from Abitrexate (Methotrexate), Adrucil (Fluorouracil), Blenoxane (Bleomycin), Bleomycin, Cetuximab, Cisplatin, Docetaxel, Efudex (Fluorouracil), Erbitux (Cetuximab), Fluoroplex (Fluorouracil), Fluorouracil, Folex (Methotrexate), Folex PFS (Methotrexate), Methotrexate, Methotrexate LPF (Methotrexate), Mexate (Methotrexate), Mexate-AQ (Methotrexate), Platinol (Cisplatin), Platinol-AQ (Cisplatin), and Taxotere (Docetaxel). For the treatment of leukemia, including CMML, the co-therapeutic agent can be selected from Bosulif (Bosutinib), Bosutinib, Clafen (Cyclophosphamide), Cyclophosphamide, Cytarabine, Cytosar-U (Cytarabine), Cytoxan (Cyclophosphamide), Dasatinib, Gleevec (Imatinib Mesylate), Iclusig (Ponatinib Hydrochloride), Imatinib Mesylate, Neosar (Cyclophosphamide), Nilotinib, Omacetaxine Mepesuccinate, Ponatinib Hydrochloride, Sprycel (Dasatinib), Synribo (Omacetaxine Mepesuccinate), Tarabine PFS (Cytarabine), and Tasigna (Nilotinib).

The invention also provides a compound of formula (I) for use in a method of treating a disease or condition mediated by ERK1 and/or ERK2, wherein the compound of formula (I) is prepared for administration with another therapeutic agent. The invention also provides another therapeutic co-agent for use in a method of treating a disease or condition mediated by ERK1 and/or ERK2, wherein the other therapeutic co-agent is prepared for administration with a compound of formula (I). The invention also provides a compound of formula (I) for use in a method of treating a disease or condition mediated by ERK1 and/or ERK2, wherein the compound of formula (I) is administered with another therapeutic co-agent. The invention also provides another therapeutic co-agent for use in a method of treating a disease or condition mediated by ERK1 and/or ERK2, wherein the other therapeutic co-agent is administered with a compound of formula (I).

The invention also provides the use of a compound of formula (I) for treating a disease or condition mediated by ERK1 and/or ERK2, wherein the patient has previously (e.g. within 24 hours) been treated with another therapeutic agent. The invention also provides the use of another therapeutic agent for treating a disease or condition mediated by ERK1 and/or ERK2, wherein the patient has previously (e.g. within 24 hours) been treated with a compound of formula (I).

Specific individual combinations which may provide particular treatment benefits include a compound of the invention with at least one compound selected from inhibitors of BRAF, MEK, CDK4/6, SHP-2, HDAC, EGFR, MET, mTOR, PI3K, and AKT. Examples of these inhibitors include vemurafinib, debrafinib, LGX818, trametinib, MEK162, LEE011, PD-0332991, panobinostat, verinostat, romidepsin, cetuximab, gefitinib, erlotinib, lapatinib, panitumumab, vandetanib, INC280, everolimus, simolimus, BMK120, BYL719, and CLR457.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, METHODS OF ORGANIC SYNTHESIS, THIEME, Volume 21). Further, the compounds of the present invention can be produced by organic synthesis methods known to one of ordinary skill in the art in view of the following examples.

The compounds and/or intermediates were characterized by high performance liquid chromatography (HPLC) using a Waters Millennium chromatography system with a 2695 Separation Module (Milford, Mass.). The analytical columns were reversed phase Phenomenex Luna C18-5µ, 4.6× 50 mm, from Alltech (Deerfield, Ill.). A gradient elution was used (flow 2.5 mL/min), starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

Mass spectrometric analysis was performed on a Waters System (Waters Acquity UPLC and a Waters SQD mass spectrometer detector; Column: Phenomenex Kinetex 2.6 um C18, column size 4.6×50 mm; column temperature 50° C. gradient: 2-98% acetonitrile in water with 0.1% TFA over a 1.5 min period; flow rate 1.2 mL/min (or Polar gradient 1-30% over 1.3 min, NonPolar gradient 55-98% over 1.3 min); Mass Spectrometer molecular weight scan range 150-850; or 150-1900. cone Voltage 20 V. All masses were reported as those of the protonated parent ions, unless otherwise indicated. Nuclear magnetic resonance (NMR) analysis was performed on selected compounds, using a Varian 400 MHz NMR (Palo Alto, Calif.). The spectral reference was either TMS or the known chemical shift of the solvent.

X-ray Powder Diffraction (XRPD) was performed as follows:

X-ray powder diffraction patterns were determined under the following conditions:
Instrument: Bruker D8 Discovery -continued Irradiation: CuK1α (40 kV, 40 mA)
CuK1 = 1.540598 Å
Scan range 3°-40° (2-theta value)
Scan type: 2-theta scan/detector scan (HI-STAR detector)
Step time 60 seconds per frame
Step size 0.02 degrees As will be appreciated by the skilled person, the relative intensities of the various peaks within the "Table for FIG. 3" may vary due to a number of factors such as orientation effects of crystals in the X-ray beam or the purity of the material being analysed or the degree of crystallinity of the sample. The peak positions may also shift for variations in sample height but the peak positions will remain substantially as defined in the "table for FIG. 3". The skilled person will also appreciate that measurements using a different wavelength will result in different shifts according to the Bragg equation $n\lambda=2d \sin \theta$. Such alternative XRPD patterns generated by use of alternative wavelengths are nevertheless representations of the same material.

Differential Scanning calorimetry/Thermogravimetric Analysis (DSC/TGA) was performed as follows:

Instrument: TA DSC Q2000/TGA Q5000
Temperature Range: room temperature to 300° C.
Scan Rate: 10°/min
Nitrogen Flow: 50 ml/min As will be understood by persons skilled in the art, slight variations in observed peaks are expected based on the specific spectrometer employed and the analyst's sample preparation technique. Some margin of error is present in each of the peak assignments (+/−cm$^{-1}$).

Abbreviations used herein have their ordinary meaning in the art unless otherwise indicated or defined in the following list:
ATP adenosine 5'-triphosphate
BINAP racemic 2,2'-bis(diphenylphosphino)-1,1'-binaphthyl
BOC tertiary butoxycarbonyl
br broad
BSA bovine serum albumin
d doublet
dd doublet of doublets
DCM dichloromethane
DIEA diethylisopropylamine
DME 1,4-dimethoxyethane
DMF N,N-dimethylformamide
DMSO dimethylsulfoxide
DTT dithiothreitol
EDTA ethylenediamine tetraacetic acid
ESI electrospray ionization
EtOAc ethyl acetate
FCC flash column chromatography
h hour(s)
HBTU 1-[bis(dimethylamino)methylene]-1H-benzotriazolium hexafluorophosphate(1-) 3-oxide
HOBt 1-hydroxy-7-azabenzotriazole
HPLC high pressure liquid chromatography
IR infrared spectroscopy
LCMS liquid chromatography and mass spectrometry
MeOH methanol
MS mass spectrometry
MW microwave
m multiplet min minutes
mL milliliter(s)
m/z mass to charge ratio
NMR nuclear magnetic resonance
ppm parts per million
PyBOP benzotriazol-1-yloxytripyrrolidinophosphonium hexafluorophosphate
rac racemic
rt room temperature
s singlet
t triplet
TFA trifluoroacetic acid
THF tetrahydrofuran
Tris.HCl aminotris(hydroxymethyl)methane hydrochloride

EXAMPLES

The following examples illustrate certain embodiments of the invention and how to make and use them, they are not intended to limit the scope of the invention.

Method 1

Example 1

Synthesis of (S)-4-(3-amino-6-(tetrahydro-2H-pyran-4-yl)pyrazin-2-yl)-N-(2-hydroxy-1-phenyl-ethyl)benzamide

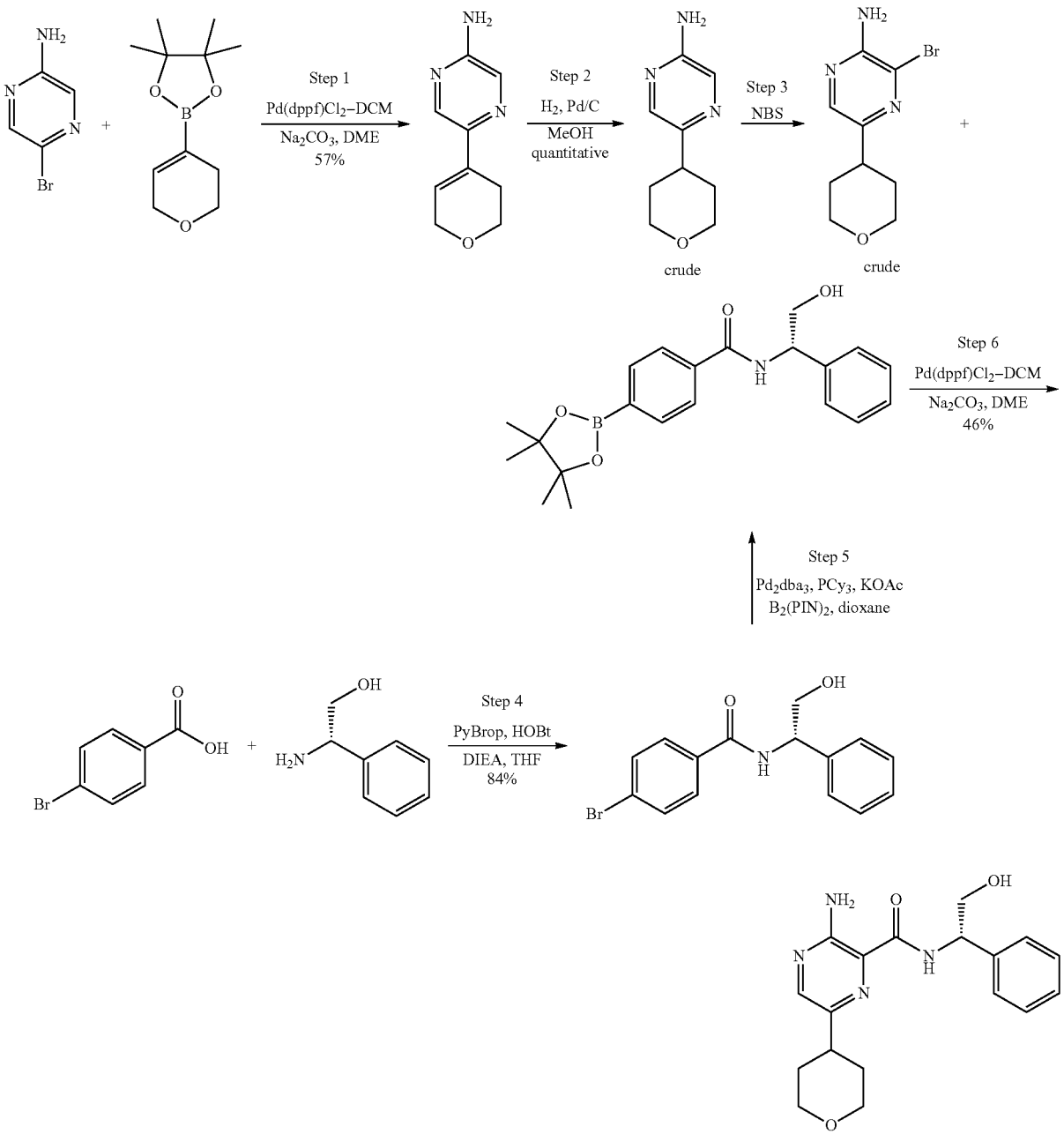

Scheme 1

Step 1.
5-(3,6-dihydro-2H-pyran-4-yl)pyrazin-2-amine

To a solution of boronic ester (6.64 g, 31.6 mmol), 5-bromopyrazin-2-amine (5 g, 28.7 mmol), and PdCl$_2$(dppf) (2.1 g, 2.87 mmol) was added DME (71.8 mL) and 2 M Na$_2$CO$_3$ solution (24 mL). The reaction mixture was heated at 90° C. for 15 h. The reaction mixture was worked up with EtOAc. The organic layer was washed with water and brine, dried over anhydrous sodium sulfate, filtered off, and concentrated in vacuo. The crude product was purified by flash chromatography (gradient EtOAc in heptanes) yielding 5-(3,6-dihydro-2H-pyran-4-yl)pyrazin-2-amine in 57% yield. LCMS (m/z): 178.1 (MH$^+$), 0.34 min; 1H NMR (400 MHz, CDCl$_3$) δ ppm 8.17-8.03 (m, 1 H), 8.04-7.88 (m, 1 H), 6.57-6.41 (m, 1 H), 4.68-4.42 (m, 2 H), 4.42-4.29 (m, 2 H), 4.06-3.84 (m, 2 H), 2.68-2.47 (m, 2 H).

Step 2.
5-(tetrahydro-2H-pyran-4-yl)pyrazin-2-amine

A solution of 5-(3,6-dihydro-2H-pyran-4-yl)pyrazin-2-amine (2.7 g, 15.24 mmol) and PdC (10%, Degussa type) (1.6 g, 1.5 mmol) in MeOH (50 mL) was degassed by N$_2$ stream for 15 min. After equipped with hydrogen gas balloon, the reaction mixture was stirred for 15 h at room temperature. The crude product was filtered off through celite pad and washed with EtOAc. The volatile material was concentrated in vacuo yielding 5-(tetrahydro-2H-pyran-4-yl)pyrazin-2-amine and was used for the next step. LCMS (m/z): 180.3 (MH$^+$), 0.28 min.

Step 3. 3-bromo-5-(tetrahydro-2H-pyran-4-yl)pyrazin-2-amine

To an ice cold solution of 5-(tetrahydro-2H-pyran-4-yl)pyrazin-2-amine (2.8 g, 15.6 mmol) in CH$_3$CN (52 mL) was added NBS (2.78 g, 15.62 mmol) in two portions at 0° C. The reaction mixture was stirred at 0° C. for 1 h. The reaction mixture was diluted with ethyl acetate and was washed with saturated sodium carbonate solution, water, brine, dried and concentrated. The crude 3-bromo-5-(tetrahydro-2H-pyran-4-yl)pyrazin-2-amine (3.9 g, 97%) was used for the next step without further purification. LCMS (m/z): 258/260 (MH$^+$), 0.52 min; 1H NMR (400 MHz, CDCl$_3$) δ ppm 7.83 (s, 1H), 4.90 (br. s., 2H), 4.14-4.02 (m, 2H), 3.59-3.43 (m, 2H), 2.83 (d, J=5.5 Hz, 1H), 1.91-1.77 (m, 4H).

Step 4. (S)-4-bromo-N-(2-hydroxy-1-phenylethyl)benzamide

To a solution of 4-bromobenzoic acid (892 mg, 4.44 mmol) in THF (9.9 mL) was added (S)-2-amino-2-phenylethanol (609 mg, 4.44 mmol), DIEA (1.9 mL, 11.1 mmol), PyBroP (2.5 g, 5.32 mmol), and HOBT (815 mg, 5.32 mmol). The reaction mixture was stirred at room temperature for 20 h. The reaction mixture was extracted with EtOAc. The organic layer was washed with water and brine. After dried over anhydrous sodium sulfate, filtered and concentrated in vacuo, the crude product was purified by flash chromatography (gradient EtOAc in DCM) yielding (S)-4-bromo-N-(2-hydroxy-1-phenylethyl)benzamide (850 mg, 60%). LCMS (m/z): 338.1 (MH$^+$), 0.61 min.

Step 5. (S)-N-(2-hydroxy-1-phenylethyl)-4-(4,4,5,5-tetramethyl-1,3,2-dioxaborolan-2-yl)benzamide To a solution of (S)-4-bromo-N-(2-hydroxy-1-phenylethyl)benzamide,4,4,4',4',5,5,5',5'-octamethyl-2,2'-bi(1,3,2-dioxaborolane) (B$_2$(PIN)$_2$) (238 mg, 0.937 mmol), Pd$_2$(dba)$_3$ (21.45 mg, 0.023 mmol), tricyclohexylphosphine (19.71 mg, 0.070 mmol) in dioxane (1.562 mL) was added potassium acetate (138 mg, 1.405 mmol). The reaction mixture was degassed by N$_2$ stream for 15 min. The reaction mixture was heated at 100° C. overnight. After diluted with EtOAc, the reaction mixture was filtered through Celite. After concentrated, (S)-N-(2-hydroxy-1-phenylethyl)-4-(4,4,5,5-tetramethyl-1,3,2-dioxaborolan-2-yl)benzamide was used for the next step without further purification. LCMS (m/z): 368.3 (MH$^+$), 0.88 min (for boronic ester) and 286.1 (MH$^+$), 0.49 min (for the corresponding boronic acid).

Step 6. (S)-4-(3-amino-6-(tetrahydro-2H-pyran-4-yl)pyrazin-2-yl)-N-(2-hydroxy-1-phenylethyl)benzamide To a solution of 3-bromo-5-(tetrahydro-2H-pyran-4-yl)pyrazin-2-amine (154 mg, 0.418 mmol), (S)-N-(2-hydroxy-1-phenylethyl)-4-(4,4,5,5-tetramethyl-1,3,2-dioxaborolan-2-yl)benzamide (90 mg, 0.349 mmol), and PdCl$_2$(dppf) (25.5 mg, 0.035 mmol) was added dioxane (2.3 mL) and 2 M Na$_2$CO$_3$ solution (1.163 mL). The reaction mixture was heated at the microwave synthesizer (120° C., 10 min). The reaction mixture was worked up with EtOAc. The organic layer was washed with water and brine, dried over anhydrous sodium sulfate, filtered off, and concentrated in vacuo. The crude product was purified by prep HPLC. The pure fractions were combined, free-based with sodium carbonate solution, and extracted with EtOAc. The organic layer was dried over anhydrous sodium sulfate, filtered off, and dried in vacuo. The pure solid was dissolved in MeCN/water (1:1, 6 mL) and lyophilized yielding (S)-4-(3-amino-6-(tetrahydro-2H-pyran-4-yl)pyrazin-2-yl)-N-(2-hydroxy-1-phenylethyl)benzamide as free base (46%). LCMS (m/z): 419.2 (MH$^+$), 0.58 min; 1H NMR (400 MHz, DMSO-d6) δ ppm 8.74 (d, J=12 Hz, 1 H), 7.99 (d, J=8 Hz, 2 H), 7.88 (s, 1 H), 7.79 (d, J=12 Hz, 2 H), 7.37 (d, J=8 Hz, 2 H), 7.29 (m, 2 H), 7.22 (m, 1 H), 5.99 (bs, 1 H), 5.07 (m, 1 H), 3.91 (m, 2 H), 3.67 (m, 2 H), 3.41 (m, 2 H), 2.82 (m, 1 H), 1.72 (m, 4 H).

Synthesis of 3-fluoro-4-(3-(methylsulfonyl)benzylcarbamoyl)phenylboronic acid

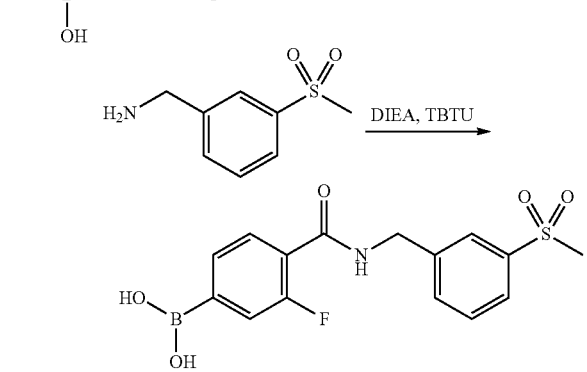

Scheme 2

A mixture of 4-borono-2-fluorobenzoic acid (218 mg, 1.2 mmol), (3-(methylsulfonyl)phenyl)-methanamine (200 mg, 1.08 mmol), DIEA (0.754 mL, 4.32 mmol) and TBTU (381 mg, 1.2 mmol) in DMF (2 mL) was stirred at room temperature for 2 days, then the reaction mixture was diluted with water (10 mL), and product precipitated out as gum, and the supernatant was separated via centrifugation, and the gummy residue was sonicated with water (3 mL), and the gummy residue was further dried under high vacuum yielding 3-fluoro-4-(3-(methylsulfonyl)benzylcarbamoyl)-phenylboronic acid (335 mg, 88%) as white foam. LCMS (m/z): 352.1 (MH$^+$), 0.51 min.

Synthesis of (+/−)-(3-fluoro-4-((2,2,2-trifluoro-1-phenylethyl)carbamoyl)phenyl)boronic acid Scheme 3

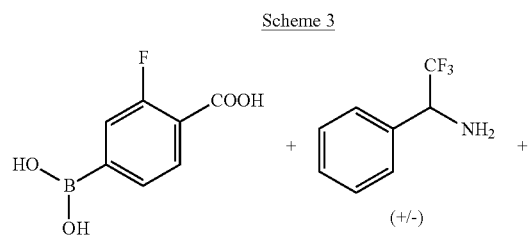

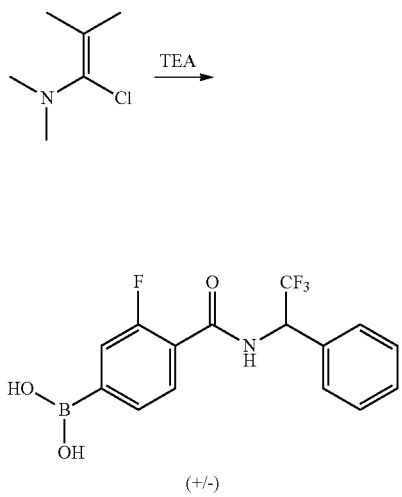

A mixture of 4-borono-2-fluorobenzoic acid (54 mg, 0.294 mmol) in DCM (1468 μL) was cooled to 0° C. Then ghosez reagent N,N,3-trimethylbut-2-en-2-amine (65.8 μL, 0.587 mmol) was added and the whole mixture was stirred at rt for 20 min. The mixture was added into a mixture of TEA (246 μL, 1.762 mmol), 2,2,2-trifluoro-1-phenylethanamine (59.1 mg, 0.338 mmol) and DCM (1468 μL). The reaction was stirred at room temperature for 2 h. To the reaction mixture was added EtOAc, and washed with sat. sodium bicarbonate, water, and dried over Na$_2$SO$_4$. Filtered and concentrated to provide the crude product which was taken to the next step without further purification. LCMS (m/z): 342.2 (MH$^+$), 0.84 min.

Synthesis of (R)-1-(2-fluorophenylsulfonyl)piperidin-3-amine

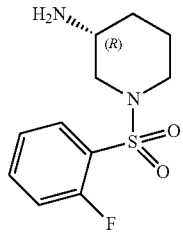

(R)-3-Boc-aminopiperidine (1.05 g, 5.25 mmol) was dissolved in DCM (10 mL) and then triethylamine (1.10 mL, 7.89 mmol) was added. To this solution at room temperature was added 2-fluorobenzenesulfonylchloride (1.127 g, 5.79 mmol). After 2 h, reaction was deemed complete by LCMS and diluted with water and extracted with DCM (30 mL), and the organic layer was separated and dried over magnesium sulfate, filtered and concentrated and taken to the next step as such. The crude product from above was dissolved in DCM (25 mL) and TFA (10 mL) added in one portion. Reaction mixture followed by LCMS. After 1 h, TFA was stripped in vacuo and then the residue suspended in 3N HCl and washed with ether. The aq. layer was basified and extracted with DCM and the DCM layer separated and dried over magnesium sulfate, filtered and concentrated in vacuo to give 873 mg of (R)-1-((2-fluorophenyl)sulfonyl)piperidin-3-amine as the desired product as free base. LCMS (m/z): 255.5 (MH$^+$), 0.49 min.

Synthesis of (R)-1-(phenylsulfonyl)piperidin-3-amine

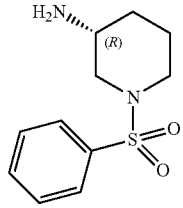

(R)-3-Boc-aminopiperidine (0.843 g, 4.21 mmol) was dissolved in DCM (10 mL) and then triethylamine (0.88 mL, 6.31 mmol) was added. To this solution at room temperature was added benzenesulfonylchloride (0.818 g, 4.63 mmol). After 2 h, reaction was deemed complete by LCMS and diluted with water and extracted with DCM (30 mL), and the organic layer was separated and dried over magnesium sulfate, filtered and concentrated and taken to the next step as such. The crude product from above was dissolved in DCM (25 mL) and TFA (10 mL) added in one portion. Reaction mixture followed by LCMS. After 3 h, complete Boc-deprotection was observed. At this stage, TFA was stripped in vacuo and then the residue suspended in 3N HCl and washed with ether. The aq. layer was basified and extracted with DCM and the DCM layer separated and dried over magnesium sulfate, filtered and concentrated in vacuo to give 850 mg of (R)-1-(phenylsulfonyl)piperidin-3-amine as the desired product as free base. LCMS (m/z): 241.4 (MH$^+$), 0.43 min.

Synthesis of (R)-3-fluoro-4-(1-(2-fluorophenylsulfonyl)piperidin-3-yl)carbamoyl)phenyl)boronic acid

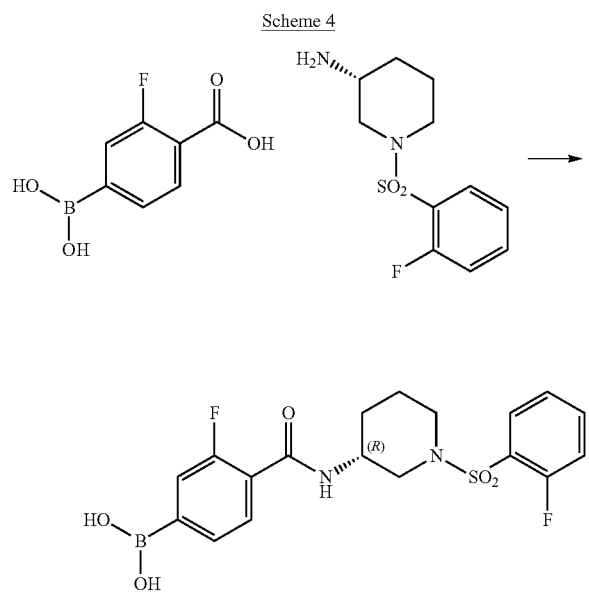

To a solution of 4-borono-2-fluorobenzoic acid (160 mg, 0.870 mmol), (R)-1-(2-fluorophenylsulfonyl)piperidin-3-amine (225 mg, 0.870 mmol), and DIEA (456 µL, 2.61 mmol) in THF (1450 µL) and DMF (1450 µL) was added HOAt (237 mg, 1.740 mmol) and EDC (417 mg, 2.175 mmol). After 3 h stirring at room temperature, the reaction mixture was extracted with EtOAc. The organic layer was washed with NaHCO$_3$, water and brine, dried over anhydrous sodium sulfate, filtered off, and concentrated in vacuo yielding (R)-3-fluoro-4-(1-(2-fluorophenylsulfonyl)piperidin-3-ylcarbamoyl)phenylboronic acid, which was used in next step reaction without purification. LCMS (m/z): 425.2 (MH$^+$), 0.72 min.

Synthesis of 4-(2,2-difluoro-1-phenylethylcarbamoyl)-3-fluorophenylboronic acid

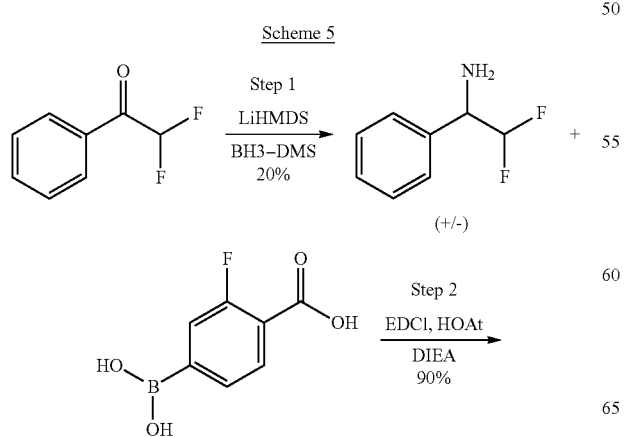

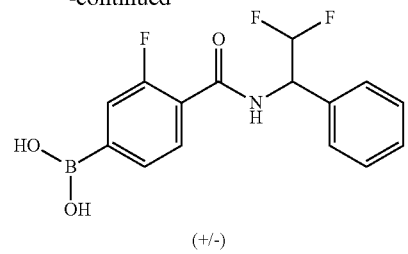

Step 1. 2,2-difluoro-1-phenylethanamine

To a solution of 2,2-difluoro-1-phenylethanone (1 g, 6.4 mmol) in toluene (32 mL) at room temperature was added LiHMDS (1M in THF) (7.05 mL, 7.05 mmol). The reaction mixture was stirred for 30 min, followed by addition of BH$_3$-DMS (1.216 mL, 12.81 mmol). The reaction mixture was stirred for 1 h. After cooling at 0° C., aqueous 2 N NaOH solution was carefully added over 5 min (Caution! gas evolution). The reaction was stirred for 1 h. The layer was separated and washed with water and brine. After dried over sodium sulfate, HCl in MeOH (7.17 mL, 8.97 mmol) was added to form a white precipitate. The precipitate was filtered off, washed with ether, and dried in vacuo yielding 2,2-difluoro-1-phenylethanamine (21%). 1H NMR (400 MHz, CDCl$_3$) δ ppm 7.49 (s, 5 H), 6.52-6.07 (m, 1 H), 4.78-4.69 (m, 2 H).

Step 2. 4-(2,2-difluoro-1-phenylethylcarbamoyl)-3-fluorophenylboronic acid

To a solution of 4-borono-2-fluorobenzoic acid (200 mg, 1.087 mmol), 2,2-difluoro-1-phenylethanamine (232 mg, 1.196 mmol), and DIEA (0.570 mL, 3.26 mmol) in THF (3.866 mL) and DMF (0.483 mL) was added HOAt (296 mg, 2.175 mmol) and EDC (521 mg, 2.72 mmol). After 3 h stirring at room temperature, 10% citric acid solution was added (pH~3) and extracted with 2-methyl THF and EtOAc (1:1). The organic layers were dried over anhydrous Na$_2$SO$_4$, filtered, and concentrated. The crude 4-(2,2-difluoro-1-phenylethylcarbamoyl)-3-fluorophenylboronic acid was obtained (90%) and used for the next step without purification. LCMS (m/z): 375.3 (MH$^+$), 0.48 min.

Synthesis of 4-benzyl-8-(4,4,5,5-tetramethyl-1,3,2-dioxaborolan-2-yl)-3,4-dihydrobenzo[f][1,4]oxazepin-5(2H)-one

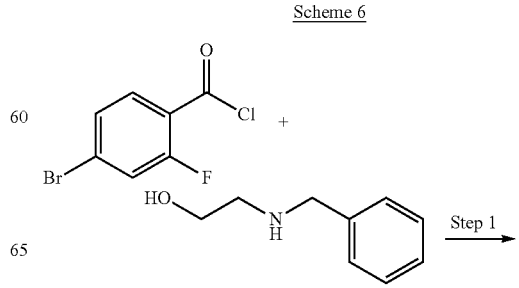

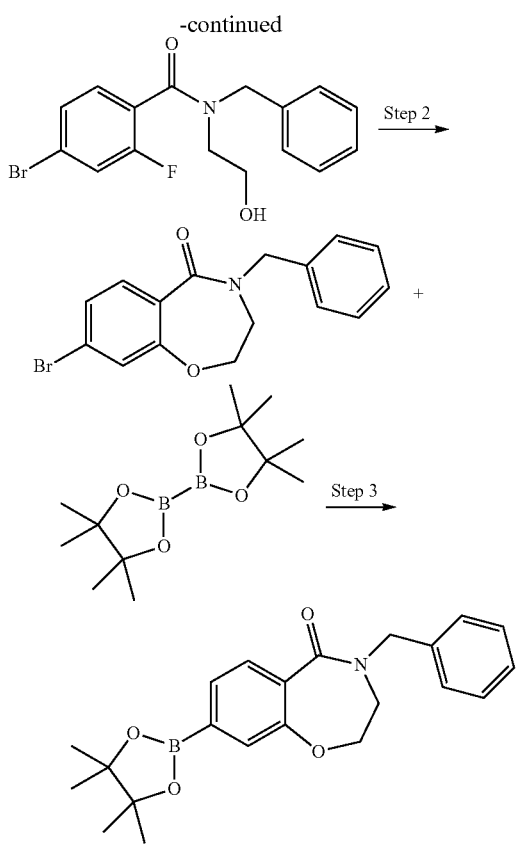

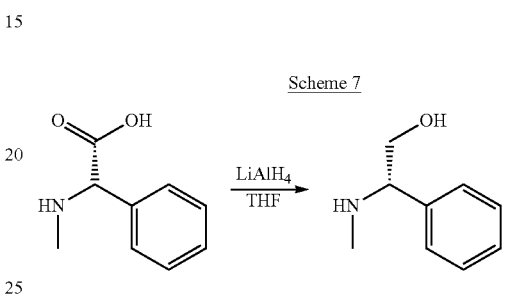

Step 1. N-benzyl-4-bromo-2-fluoro-N-(2-hydroxyethyl)benzamide

To a solution of 4-bromo-2-fluorobenzoyl chloride (1 g, 4.21 mmol) in THF (14.04 mL) was added DIEA (1.103 mL, 6.32 mmol) and 2-(benzylamino)ethanol (0.764 g, 5.05 mmol) at room temperature. The reaction mixture was stirred for overnight. The reaction mixture was extracted with EtOAc. The organic layer was washed with water and brine. After dried over anhydrous sodium sulfate, filtered and concentrated in vacuo, the crude N-benzyl-4-bromo-2-fluoro-N-(2-hydroxyethyl)benzamide was used for the next step (83%). LCMS (m/z): 352/354 (MH$^+$), 0.83 min.

Step 2. 4-benzyl-8-bromo-3,4-dihydrobenzo[f][1,4]oxazepin-5(2H)-one

To a solution of N-benzyl-4-bromo-2-fluoro-N-(2-hydroxyethyl)benzamide (494 mg, 1.403 mmol) in DMF (14.00 mL) was added NaH (60% in oil) (61.7 mg, 1.543 mmol) slowly. After H$_2$ gas evolved, the reaction mixture was heated at 90° C. for 24 h. After quenched with water, the reaction mixture was extracted with EtOAc. The organic layer was washed with water and brine. After drying over anhydrous sodium sulfate and filtration, the organic layer was evaporated in vacuo. The oily crude 4-benzyl-8-bromo-3,4-dihydrobenzo[f][1,4]oxazepin-5(2H)-one was purified by flash chromatography (gradient EtOAc in heptane) in 84% yield. LCMS (m/z): 332.1/334.1 (MH$^+$), 0.94 min.

Step 3. 4-benzyl-8-(4,4,5,5-tetramethyl-1,3,2-dioxaborolan-2-yl)-3,4-dihydrobenzo[f][1,4]oxazepin-5(2H)-one To a solution of 4-benzyl-8-bromo-3,4-dihydrobenzo[f][1,4]oxazepin-5(2H)-one (111.3 mg, 0.335 mmol), B$_2$(PIN)$_2$ (170 mg, 0.670 mmol), Pd$_2$(dba)$_3$ (15.34 mg, 0.017 mmol), tricyclohexylphosphine (14.09 mg, 0.050 mmol) in dioxane (3.35 mL) was added potassium acetate (99 mg, 1.005 mmol) just right after degassing. The reaction mixture was heated at 100° C. overnight. After diluted with EtOAc, the reaction mixture was filtered through Celite. After concentrated, the crude 4-benzyl-8-(4,4,5,5-tetramethyl-1,3,2-dioxaborolan-2-yl)-3,4-dihydrobenzo[f][1,4]oxazepin-5(2H)-one was obtained (>99%) and used for the next step without further purification. LCMS (m/z): 298.1 (MH$^+$ for boronic acid), 0.63 min and 380.2 (MH$^+$), 1.05 min.

Synthesis of (S)-2-(methylamino)-2-phenylethanol

Scheme 7

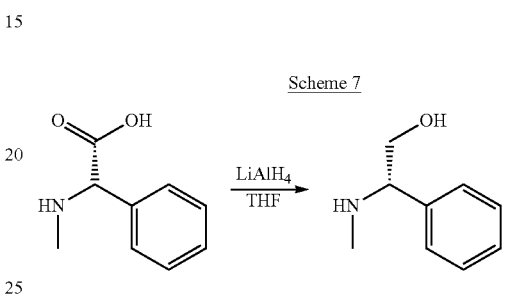

To a suspension of LiAlH$_4$ (0.689 g, 18.16 mmol) in THF (20.18 mL) was added (S)-2-(methylamino)-2-phenylacetic acid (1 g, 6.05 mmol) in THF (20 mL) slowly over 10 min at 0° C. The reaction mixture was stirred at room temperature for overnight. After quenched with water (0.7 mL), NaOH (2.1 mL), water (0.7 mL). The reaction mixture was filtered off. The filtrate was extracted with EtOAc 3 times. The combined organic layer was washed with water and brine, dried over anhydrous sodium sulfate, filtered off, and concentrated in vacuo. The crude product was purified by flash chromatography (10% methanol in DCM) yielding (S)-2-(methylamino)-2-phenylethanol as a colorless oil in 55% yield. LCMS (m/z): 152.1 (MH$^+$), 0.31 min; $^1$H NMR (400 MHz, CDCl$_3$) δ 7.40-7.33 (m, 2 H), 7.32-7.27 (m, 3 H), 3.77-3.69 (m, 1 H), 3.69-3.63 (m, 1 H), 3.58 (d, J=9.8 Hz, 1 H), 2.36 (s, 3 H).

Synthesis of (S)-4-phenyloxazolidine

Scheme 8

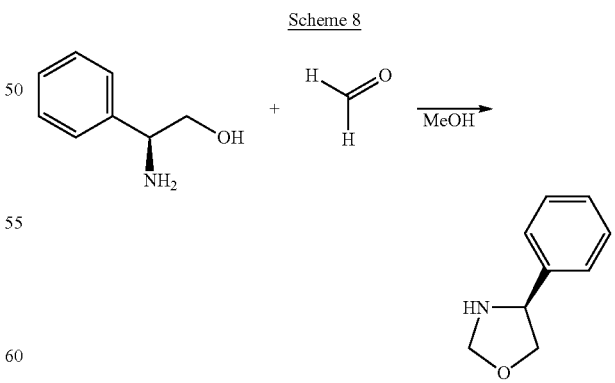

To a solution of (S)-2-amino-2-phenylethanol (1.5 g, 10.93 mmol) in methanol (36.4 mL) was added formaldehyde (1.065 g, 13.12 mmol) at room temperature. The reaction mixture was stirred at room temperature for 2 days. The reaction mixture was concentrated to dryness. The crude material was purified by flash chromatography (0-50% EtOAc/heptanes) to give (S)-4-phenyloxazolidine in 40% yield. LCMS (m/z): 150.1 (MH+), 0.31 min.

Synthesis of (S)-tert-butyl (2-amino-2-(3-chlorophenyl)ethyl)carbamate

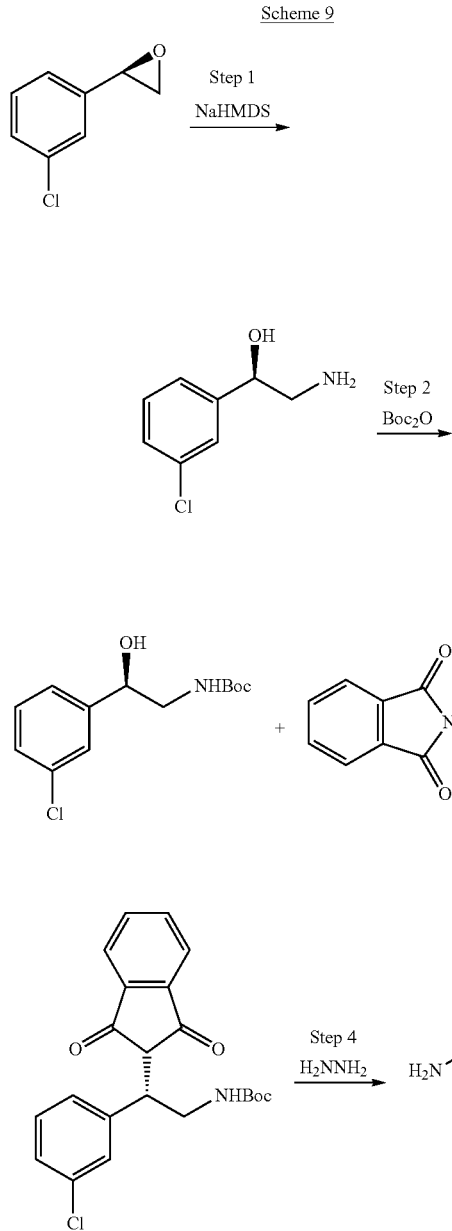

Scheme 9

Step 1. (R)-2-amino-1-(3-chlorophenyl)ethanol

To a solution of (R)-2-(3-chlorophenyl)oxirane (13 g, 84 mmol) in THF (84 mL) was added NaHMDS (1 M in THF) (252 mL, 252 mmol) slowly at 0° C. The reaction mixture was warmed up to room temperature and stirred for overnight. To the reaction mixture, water (33 mL, 2.5 mL/g) added. After stirring for 5 h at room temperature, solvent was removed in vacuo to about ¼ and partitioned by DCM. The bottom layer is a little cloudy and the top layer was a brown solution. Both layers were concentrated, which contained the desired (R)-2-amino-1-(3-chlorophenyl)ethanol (14 g, 97%). The combined products were used in next step without further purification. LCMS (m/z): 172.1 (MH+), 0.37 min.

Step 2. (R)-tert-butyl (2-(3-chlorophenyl)-2-hydroxyethyl)carbamate

To a solution of (R)-2-amino-1-(3-chlorophenyl)ethanol (14 g, 82 mmol) in THF (272 mL) was added di-tert-butyl dicarbonate (24.92 g, 114 mmol). The mixture was stirred at room temperature for overnight. The reaction mixture was diluted with DCM and then washed with saturated sodium bicarbonate solution. The separated organic layer was then dried over anhydrous sodium sulfate, filtered off, and concentrated in vacuo. The crude product was purified by flash chromatography (0 to 50% ethyl acetate in heptane) yielding (R)-tert-butyl (2-(3-chlorophenyl)-2-hydroxyethyl)carbamate (49.2%). LCMS (m/z): 216 (MH+-tBu), 0.85 min; 1H NMR (400 MHz, CD$_3$OD) δ ppm 1.40 (s, 9 H) 3.18 (s, 1 H) 3.26 (d, J=4.70 Hz, 1 H) 4.69 (br. s., 1 H) 7.20-7.34 (m, 3 H) 7.35-7.41 (m, 1 H).

Step 3. (S)-tert-butyl (2-(3-chlorophenyl)-2-(1,3-dioxoisoindolin-2-yl)ethyl)carbamate To a solution of (R)-tert-butyl (2-(3-chlorophenyl)-2-hydroxyethyl)carbamate (8.12 g, 29.9 mmol) in THF (100 mL) was added phthalimide (6.16 g, 41.8 mmol) and polymer-bound triphenylphosphine (3 mmol of PPh$_3$/1 g of resin, 9.8 g). DTBAD (7.09 g, 30.8 mmol) in THF (20 mL) was added slowly at room temperature to the reaction mixture, which was then stirred at room temperature overnight. The reaction mixture was filtered through Celite and washed with EtOAc. The resulting filtrate was washed with Na$_2$CO$_3$ solution, water and brine, dried over anhydrous sodium sulfate, filtered off, and concentrated in vacuo. The crude material was purified by flash chromatography (0-30% EtOAc/heptane) yielding (S)-tert-butyl (2-(3-chlorophenyl)-2-(1,3-dioxoisoindolin-2-yl)ethyl)carbamate (58.4%). LCMS (m/z): 301.1 (MH+-Boc), 1.06 min.

Step 4. (S)-tert-butyl (2-amino-2-(3-chlorophenyl)ethyl)carbamate

To a solution of (S)-tert-butyl (2-(3-chlorophenyl)-2-(1,3-dioxoisoindolin-2-yl)ethyl)carbamate (5.0 g, 12.47 mmol) in ethanol (41.6 mL) was added hydrazine hydrate (6.06 mL, 125 mmol). The reaction mixture was heated at 60° C. for 2 h. The reaction mixture was filtered through Celite pad. The filtrate was concentrated and the residue was diluted with DCM and filtered off through Celite. The same process was repeated until no white precipitate was shown. To remove the white side product completely, the product was dissolved in 1N HCl (30 mL), washed with EtOAc, and the aqueous phase was neutralized to pH 7 then back-extracted by EtOAc. The organic was dried over anhydrous sodium sulfate, filtered off, and concentrated in vacuo yielding (S)-tert-butyl (2-amino-2-(3-chlorophenyl)ethyl)carbamate (89%). LCMS (m/z): 271.1 (MH+), 0.58 min.

TABLE 1

Aryl halides or the corresponding boronic esters/acids obtained from amide bond formation and/or boronic ester formation

| Structure | Name | MH+ | R$_t$ (min) | NMR |
|---|---|---|---|---|
| [structure] | (S)-4-bromo-2-fluoro-N-(2-hydroxy-1-phenylethyl)benzamide | 338 | 0.76 | N/A |
| [structure] | (S)-2-fluoro-N-(2-hydroxy-1-phenylethyl)-4-(4,4,5,5-tetramethyl-1,3,2-dioxaborolan-2-yl)benzamide | 304 (for boronic acid) | 0.51 | N/A |
| [structure] | (S)-4-bromo-N-(2-hydroxy-1-phenylethyl)benzamide | 321.9 | 0.75 | 1H NMR (400 MHz, CDCl$_3$) δ ppm 7.70 (d, J = 8.2 Hz, 2H) 7.56-7.62 (m, 2H) 7.30-7.44 (m, 5H) 6.82 (d, J = 5.9 Hz, 1H, NH?) 5.27 (dt, J = 7.0, 4.7 Hz, 1 H) 4.03 (t, J = 5.1 Hz, 2H) 2.38 (t, J = 5.9 Hz, 1H) |
| [structure] | N-(3-(methylsulfonyl)benzyl)-4-(4,4,5,5-tetramethyl-1,3,2-dioxaborolan-2-yl)benzamide | 416.2 | 0.86 | N/A |
| [structure] | (S)-4-bromo-N-(1-(3-chlorophenyl)-2-hydroxyethyl)-2-fluorobenzamide | 372/374 | 0.89 | N/A |
| [structure] | (S)-(4-((1-(3-chlorophenyl)-2-hydroxyethyl)carbamoyl)-3-fluorophenyl)boronic acid | 420/422 | 0.96 | N/A |
| [structure] | (S)-4-bromo-N-(2-hydroxy-1-phenylethyl)-2-methylbenzamide | 334 | 0.76 | N/A |

TABLE 1-continued

Aryl halides or the corresponding boronic esters/acids obtained from amide bond formation and/or boronic ester formation

| Structure | Name | MH+ | R*t* (min) | NMR |
|---|---|---|---|---|
| 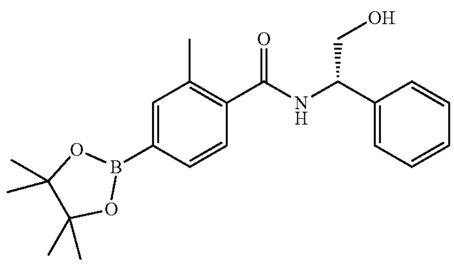 [SMILES: Cc1cc(B2OC(C)(C)C(C)(C)O2)ccc1C(=O)N[C@H](CO)c1ccccc1] | (S)-N-(2-hydroxy-1-phenylethyl)-2-methyl-4-(4,4,5,5-tetramethyl-1,3,2-dioxaborolan-2-yl)benzamide | 382.2 | 0.91 | N/A |
| 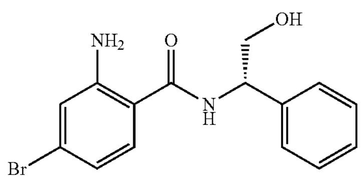 [SMILES: Nc1cc(Br)ccc1C(=O)N[C@H](CO)c1ccccc1] | (S)-2-amino-4-bromo-N-(2-hydroxy-1-phenylethyl) benzamide | 337.0 | 0.71 | 1H NMR (400 MHz, DMSO-d6) δ ppm 8.51 (d, J = 7.8 Hz, 1H) 7.60 (d, J = 8.2, 2H) 7.15-7.45 (m, 5H) 6.90 (d, J = 2.0 Hz, 1H) 6.70 (dd, J = 8.2, 2.0 Hz, 1H) 6.56 (bs, 2H, NH2) 4.83-5.01 (m, 1H) 4.92 (m, 1H, OH) 3.53-3.76 (m, 2H) |
| 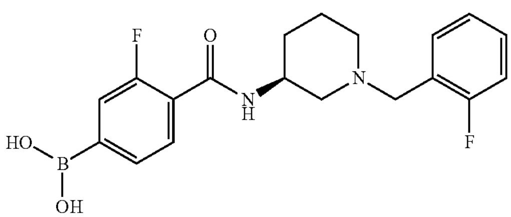 [SMILES: O=C(N[C@H]1CCCN(Cc2ccccc2F)C1)c1ccc(B(O)O)cc1F] | (S)-3-fluoro-4-(1-(2-fluorobenzyl)piperidin-3-ylcarbamoyl) phenylboronic acid | 375.3 | 0.48 | N/A |
| 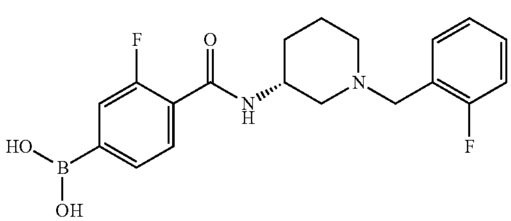 [SMILES: O=C(N[C@@H]1CCCN(Cc2ccccc2F)C1)c1ccc(B(O)O)cc1F] | (R)-3-fluoro-4-(1-(2-fluorobenzyl)piperidin-3-ylcarbamoyl) phenylboronic acid | 375.3 | 0.48 | N/A |
| 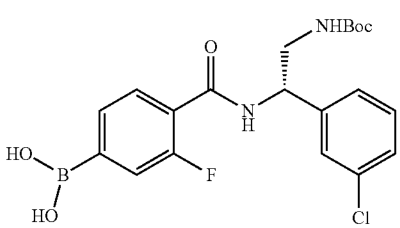 [SMILES: CC(C)(C)OC(=O)NC[C@@H](NC(=O)c1ccc(B(O)O)cc1F)c1cccc(Cl)c1] | (S)-(4-((2-((tert-butoxycarbonyl) amino)-1-(3-chlorophenyl)ethyl) carbamoyl)-3-fluorophenyl)boronic acid | 437.1 | 0.86 | N/A |

Example 2

Synthesis of (S)-4-(2-amino-5-(piperidin-4-yl)pyridin-3-yl)-2-fluoro-N-(2-hydroxy-1-phenylethyl)benzamide Scheme 10

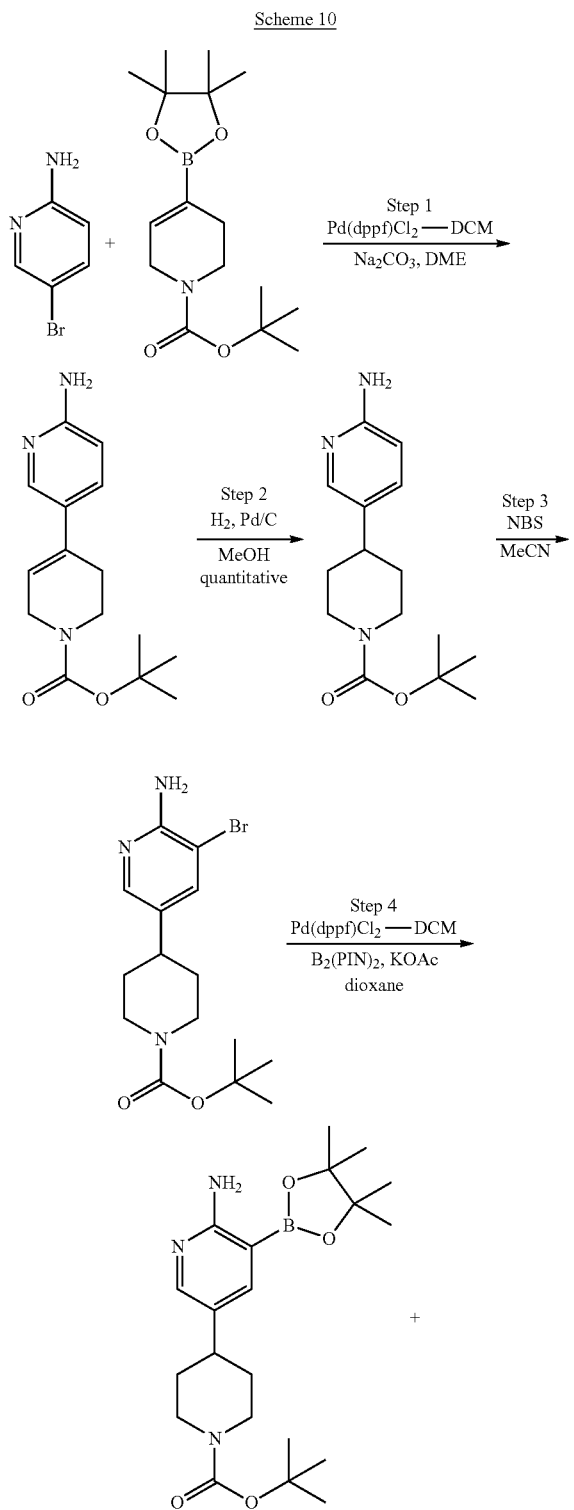

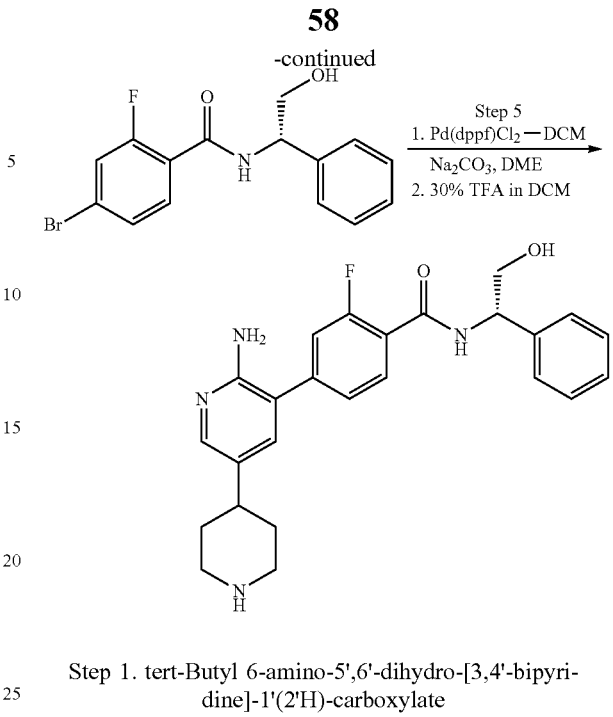

Step 1. tert-Butyl 6-amino-5',6'-dihydro-[3,4'-bipyridine]-1'(2'H)-carboxylate To a solution of 5-bromopyridin-2-amine (0.84 g, 4.85 mmol) in DME (10 mL) was added N-Boc-5,6-dihydropyridine-1(2H)-carboxylate (1 g, 3.23 mmol), and sodium carbonate (4.85 mL, 9.70 mmol). The mixture was purged with nitrogen for 5 min, and followed by the addition of $PdCl_2$(dppf)-$CH_2Cl_2$ (0.26 g, 0.32 mmol). The resulting mixture was heated to 120° C. in an oil bath for 2 h. The reaction mixture was diluted with ethyl acetate, washed with water, brine, dried and was concentrated. The residue was purified by flash column chromatography on silica gel (ISCO) eluting with 0-90% ethyl acetate in heptane to give tert-butyl 6-amino-5',6'-dihydro-[3,4'-bipyridine]-1'(2'H)-carboxylate (560 mg, 63%) as brown color solid. LCMS (m/z): 276 (MH+), 0.59 min.

Step 2. tert-Butyl 4-(6-aminopyridin-3-yl)piperidine-1-carboxylate

A suspension of tert-butyl 6-amino-5',6'-bipyridine]-1'(2'H)-carboxylate (560 mg, 2.03 mmol), 5% Pd/C (1082 mg, 0.5 mmol) in methanol (30 mL) was purged with nitrogen for 2 min. The reaction mixture was stirred under hydrogen at ambient temperature for 16 h. The reaction mixture was diluted with dichloromethane (50 mL) and was filtered through Celite pad. The filtrate was concentrated and the residue was purified by flash column chromatography on silica gel (ISCO) eluting with 0-90% ethyl acetate in heptane to give tert-butyl 4-(6-aminopyridin-3-yl)piperidine-1-carboxylate (180 mg, 31.9%) as yellow color solid. LCMS (m/z): 278 (MH+), 0.57 min.

Step 3. tert-butyl 4-(6-amino-5-bromopyridin-3-yl)piperidine-1-carboxylate

To an ice cold solution of tert-butyl 4-(6-amino-5-bromopyridin-3-yl)piperidine-1-carboxylate (180 mg, 0.65 mmol) in DCM (18 mL) was added NBS (116 mg, 0.65 mmol) in two portions. The reaction mixture was stirred at 0° C. in an ice bath for 30 min. The reaction solution was diluted with ethyl acetate, washed with water, saturated aqueous sodium bicarbonate, brine, dried over sodium sulfate and concentrated. The resulting residue was purified by flash column chromatography on silica gel (ISCO) eluting with 0-100% ethyl acetate in heptane to give tert-butyl 4-(6-amino-5-bromopyridin-3-yl)piperidine-1-carboxylate (180 mg, 78%) as yellow color oil. LCMS (m/z): 300/302 (MH+), 0.67 min.

Step 4. tert-butyl 4-(6-amino-5-(4,4,5,5-tetramethyl-1,3,2-dioxaborolan-2-yl)pyridin-3-yl)piperidine-1-carboxylate To a suspension of tert-butyl 4-(6-amino-5-bromopyridin-3-yl)piperidine-1-carboxylate (180 mg, 0.50 mmol) in 1,4-dioxane (8 mL) was added bis(pinacolato)diboron (385 mg, 1.51 mmol) and potassium acetate (248 mg, 2.53 mmol). The mixture was purged with nitrogen for 3 min, then PdCl$_2$(dppf)-CH$_2$Cl$_2$ Adduct (49.5 mg, 0.061 mmol) was added. The reaction mixture was heated to 110° C. in an oil bath for 20 h and filtered through neutral alumina (1 g). The filtrate was concentrated to give crude tert-butyl 4-(6-amino-5-(4,4,5,5-tetramethyl-1,3,2-dioxaborolan-2-yl)pyridin-3-yl)piperidine-1-carboxylate, which was used directly in next step without any purification. LCMS (m/z): 322 (MH+ for boronic acid), 0.60 min.

Step 5. (S)-4-(2-Amino-5-(piperidin-4-yl)pyridin-3-yl)-2-fluoro-N-(2-hydroxy-1-phenylethyl)benzamide To a suspension of (S)-4-bromo-2-fluoro-N-(2-hydroxy-1-phenylethyl)benzamide (67.1 mg, 0.20 mmol) in DME (5 mL) was added tert-butyl 4-(6-amino-5-(4,4,5,5-tetramethyl-1,3,2-dioxaborolan-2-yl)pyridin-3-yl)piperidine-1-carboxylate (40 mg, 0.099 mmol) and sodium carbonate (0.24 mL, 0.49 mmol). The mixture was purged with nitrogen for 10 min, then PdCl$_2$(dppf)-CH$_2$Cl$_2$ Adduct (12.15 mg, 0.015 mmol) was added. The reaction mixture was heated to 120° C. in an oil bath for 3 h. The reaction mixture was diluted with ethyl acetate. The organic solution was washed with water, brine, dried over sodium sulfate and concentrated. The resulting residue was treated with 30% TFA in DCM (20 mL) for 15 min. The reaction mixture was concentrated and the crude product was purified by HPLC to give (S)-4-(2-amino-5-(piperidin-4-yl)pyridin-3-yl)-2-fluoro-N-(2-hydroxy-1-phenylethyl)benzamide (9 mg, 20.8%) as TFA salt. LCMS (m/z): 435 (MH+), 0.44 min; $^1$H NMR (300 MHz, CD$_3$OD) δ ppm 8.63 (br. s., 1 H) 7.90 (t, J=7.77 Hz, 1 H) 7.84 (s, 2 H) 7.47-7.24 (m, 7 H), 5.27-5.17 (m, 1 H) 3.93-3.79 (m, 2 H) 3.52 (d, J=12.60 Hz, 2 H) 3.21-3.05 (m, 2 H) 2.96 (t, J=12.31 Hz, 1 H) 2.15 (d, J=14.07 Hz, 2 H) 1.96-1.78 (m, 2 H).

Synthesis of 3-bromo-5-(1-(methylsulfonyl)piperidin-4-yl)pyrazin-2-amine and methyl 4-(5-amino-6-bromopyrazin-2-yl)piperidine-1-carboxylate Scheme 11

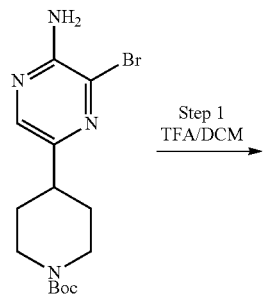

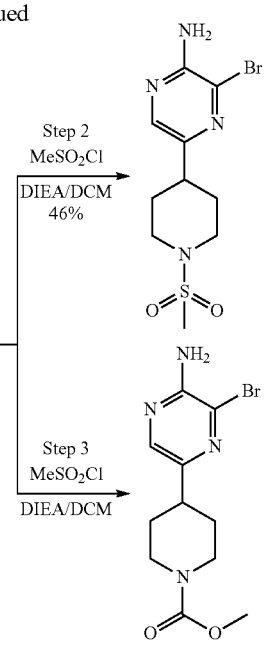

Following Step 1 to 3 in Scheme 10, using 5-bromopyrazin-2-amine and N-Boc-5,6-dihydropyridine-1(2H)-carboxylate, tert-butyl 4-(5-amino-6-bromopyrazin-2-yl)piperidine-1-carboxylate was obtained. LCMS (m/z): 301.0/303.0 (MH+-$^t$Bu), 0.875 min.

Step 1. 3-bromo-5-(piperidin-4-yl)pyrazin-2-amine

To a solution of tert-butyl 4-(5-amino-6-bromopyrazin-2-yl)piperidine-1-carboxylate (70 mg, 0.196 mmol) in DCM (4 mL) was added TFA (1 mL, 12.98 mmol). The reaction mixture was stirred at room temperature for 45 min. After toluene was added, the volatile materials were evaporated yielding 3-bromo-5-(piperidin-4-yl)pyrazin-2-amine. The crude product was used directly for the next reaction (99%). LCMS (m/z): 257.0/259.0 (MH+), 0.329 min.

Step 2. 3-bromo-5-(1-(methylsulfonyl)piperidin-4-yl)pyrazin-2-amine

To 3-bromo-5-(piperidin-4-yl)pyrazin-2-amine (50 mg, 0.194 mmol) in DCM (2 mL) in ice bath was added DIEA (340 µl, 1.945 mmol) and methanesulfonyl chloride (16.67 µl, 0.214 mmol). The reaction mixture was stirred for 60 min. The reaction mixture was extracted with DCM. The organic layer was washed with brine, dried over sodium sulfate, filtered and evaporated in vacuo. (30 mg, 46%). LCMS (m/z): 335.2/337.2 (MH+), 0.572 min.

Step 3. methyl 4-(5-amino-6-bromopyrazin-2-yl)piperidine-1-carboxylate

To a solution of 3-bromo-5-(piperidin-4-yl)pyrazin-2-amine (60 mg, 0.233 mmol) in DCM (2 mL) in ice bath was added DIEA (408 µl, 2.333 mmol) and methyl chloroformate (18.07 µl, 0.233 mmol). The reaction mixture was stirred under ice bath for 30 min. The reaction mixture was partitioned between DCM and water. The organic layer was separated and washed with brine, dried over sodium sulfate, filtered off, and evaporated in vacuo. The crude methyl 4-(5-amino-6-bromopyrazin-2-yl)piperidine-1-carboxylate was used for next step. LCMS (m/z): 315.0/317.0 (MH+), 0.647 min.

Example 3

Synthesis of 4-(2-amino-5-(tetrahydro-2H-pyran-4-yl)pyridin-3-yl)-2-fluoro-N-methyl-N-(pyrimidin-2-ylmethyl)benzamide

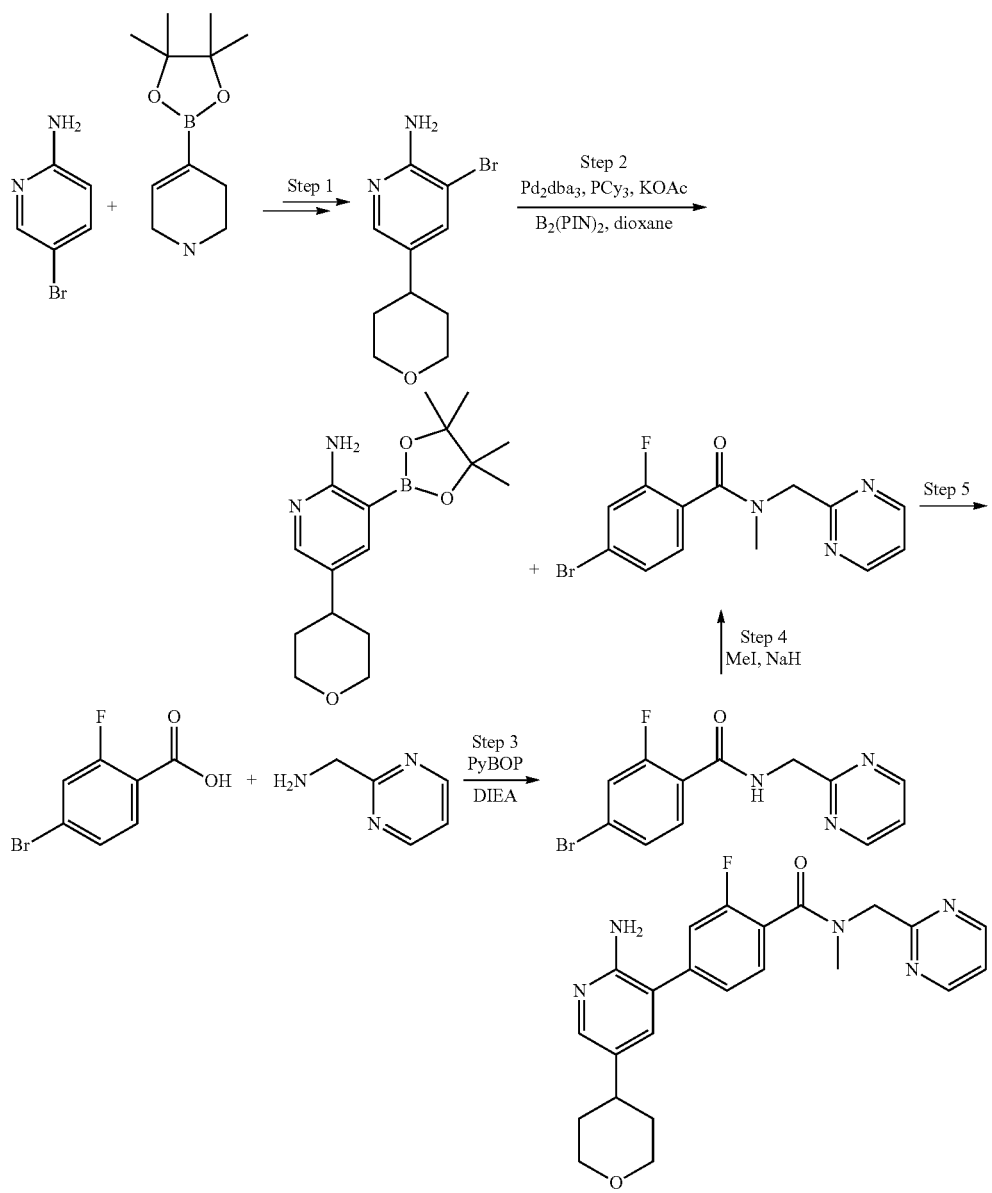

Scheme 12

Step 1. 3-bromo-5-(tetrahydro-2H-pyran-4-yl)pyridin-2-amine

Following Step 1 to 3 in Scheme 10, using 5-bromopyridin-2-amine, 3-bromo-5-(tetrahydro-2H-pyran-4-yl)pyridin-2-amine was obtained. LCMS (m/z): 257/259 (MH+), 0.38 min.

Step 2. 5-(tetrahydro-2H-pyran-4-yl)-3-(4,4,5,5-tetramethyl-1,3,2-dioxaborolan-2-yl)pyridin-2-amine Following Step 4 in Scheme 10, using 3-bromo-5-(tetrahydro-2H-pyran-4-yl)pyridin-2-amine was obtained, 5-(tetrahydro-2H-pyran-4-yl)-3-(4,4,5,5-tetramethyl-1,3,2-dioxaborolan-2-yl)pyridin-2-amine was obtained. LCMS (m/z): 233 (MH+), 0.36 min.

Step 3. 4-bromo-2-fluoro-N-(pyrimidin-2-ylmethyl)benzamide

To a flask was charged with 4-bromo-2-fluorobenzoic acid (180 mg, 0.821 mmol), pyrimidin-2-ylmethanamine (89.6 mg, 0.821 mmol), DIEA (0.358 mL, 2.05 mmol) in DMF (3 mL), and to the resulting solution was added PyBOP (513 mg, 0.915 mmol) and the resulting mixture was stirred at room temperature overnight, then was concentrated under reduced pressure and the residue was diluted with EtOAc (20 mL), washed with water (3×10 mL), brine (10 mL) and dried (Na$_2$SO$_4$), concentrated and the residue was purified by flash chromatography on silica gel eluted with gradient EtOAc/heptane (0-100%) and 4-bromo-2-fluoro-N-(pyrimidin-2-ylmethyl)benzamide (74.5 mg, 29.3%) was obtained as light color solid. LCMS (m/z): 310.0/312.0 (MH$^+$), 0.64 min.

Step 4. 4-bromo-2-fluoro-N-methyl-N-(pyrimidin-2-ylmethyl)benzamide

To a flask was charged with 4-bromo-2-fluoro-N-(pyrimidin-2-ylmethyl)benzamide (74.5 mg, 0.24 mmol), NaH (60% dispersion in mineral oil, 11.5 mg, 0.288 mmol) in DMF (2 mL), to the slurry was added iodomethane (20 µl, 0.312 mmol) and to the resulting mixture was stirred at room temperature for 10 min, then was quenched by water (20 µl), concentrated and the crude residue was dissolved in EtOAc, washed with water, and brine, dried (Na$_2$SO$_4$), concentrated and 4-bromo-2-fluoro-N-methyl-N-(pyrimidin-2-ylmethyl)benzamide was obtained as oil (55.3 mg, 71%). LCMS (m/z): 324.1/326.1 (MH$^+$), 0.66 min.

Step 5. 4-(2-amino-5-(tetrahydro-2H-pyran-4-yl)pyridin-3-yl)-2-fluoro-N-methyl-N-(pyrimidin-2-ylmethyl)benzamide To a microwave reactor vial was charged with 5-(tetrahydro-2H-pyran-4-yl)-3-(4,4,5,5-tetramethyl-1,3,2-dioxaborolan-2-yl)pyridin-2-amine (39.4 mg, 0.13 mmol), 4-bromo-2-fluoro-N-methyl-N-(pyrimidin-2-ylmethyl)benzamide (28 mg, 0.086 mmol), aqueous Na$_2$CO$_3$ (2 M, 0.26 mL) in DME (1.5 mL), and the mixture was purged with Argon followed by addition of tetrakis(triphenylphosphin) palladium (10 mg, 8.6 mmol), and final purge, then sealed and heated at 115° C. for 15 min in microwave synthesizer. The DME layer was collected, concentrated and the residue was subjected to prep HPLC purification and fractions containing final product were combined, frozen, lyophilized and TFA salt of 4-(2-amino-5-(tetrahydro-2H-pyran-4-yl)pyridin-3-yl)-2-fluoro-N-methyl-N-(pyrimidin-2-ylmethyl)benzamid was obtained as white powder. LCMS (m/z): 422.2 (MH$^+$), 0.49 min; $^1$H NMR (400 MHz, CD$_3$OD) δ 8.81 (d, J=4.9 Hz, 1H), 8.77 (d, J=4.9 Hz, 1H), 7.95 (d, J=2.2 Hz, 1H), 7.88 (d, J=2.2 Hz, 1H), 7.80 (dd, J=2.2, 0.6 Hz, 1H), 7.76 (dd, J=2.2, 0.6 Hz, 1H), 7.62-7.70 (m, 1H), 7.51-7.58 (m, 1H), 7.45 (s, 1H), 7.38-7.43 (m, 1H), 7.35 (dd, J=10.0, 1.5 Hz, 1H), 7.28 (dd, J=7.8, 1.6 Hz, 1H), 4.99 (s, 1H), 4.74 (s, 1H), 3.98-4.10 (m, 2H), 3.54 (tdd, J=11.5, 8.8, 2.7 Hz, 2H), 3.15-3.24 (m, 3H), 2.78-2.93 (m, 1H), 1.65-1.89 (m, 4H).

Synthesis of 4-(6-Amino-5-bromopyridin-3-yl)tetrahydro-2H-thiopyran 1,1-dioxide and 4-(6-Amino-5-(4,4,5,5-tetramethyl-1,3,2-dioxaborolan-2-yl)pyridin-3-yl)tetrahydro-2H-thiopyran 1,1-dioxide

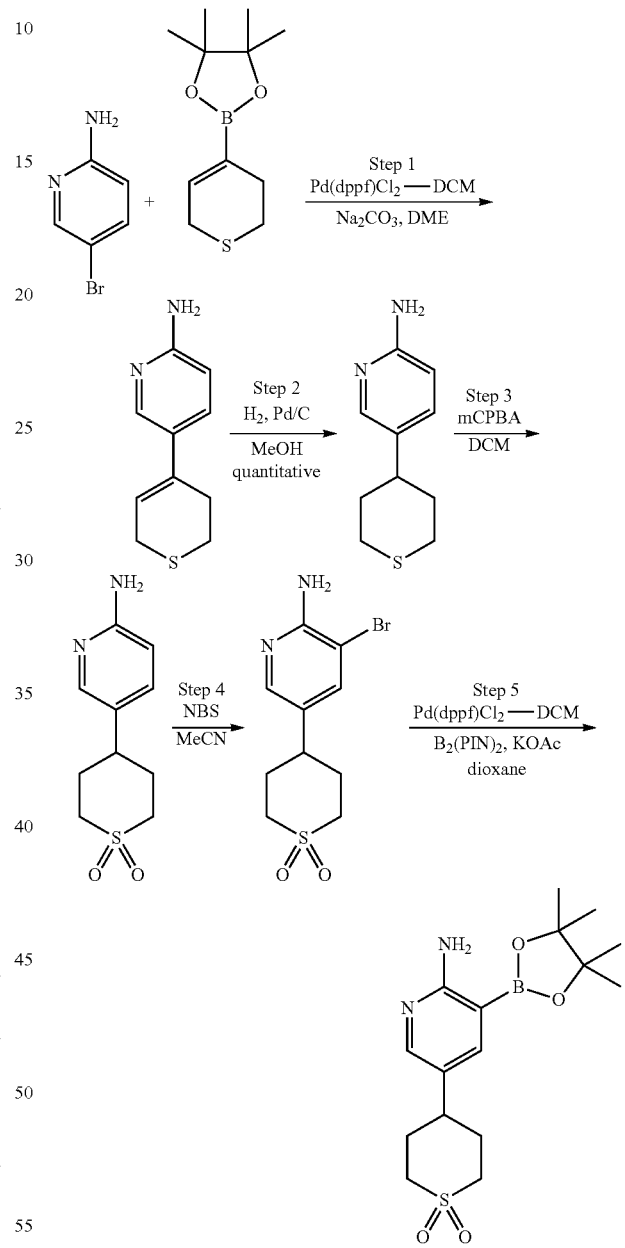

Scheme 13

Step 1. 5-(3,6-Dihydro-2H-thiopyran-4-yl)pyridin-2-amine

To a solution of 5-bromopyridin-2-amine (344 mg, 1.99 mmol) in DME (6 mL) was added 2-(3,6-dihydro-2H-thiopyran-4-yl)-4,4,5,5-tetramethyl-1,3,2-dioxaborolane (300 mg, 1.33 mmol), and sodium carbonate (1.99 mL, 3.98 mmol). The mixture was purged with nitrogen for 5 min, and followed by the addition of PdCl$_2$(dppf)-CH$_2$Cl$_2$ (108 mg, 0.13 mmol). The resulting mixture was heated to 115° C. in an oil bath for 5 h. The reaction mixture was diluted with ethyl acetate, washed with water, brine, dried and was concentrated. The residue was purified by flash column chromatography on silica gel (ISCO) eluting with 0-90% ethyl acetate in heptane to give Fractions were combined and concentrated to give 5-(3,6-dihydro-2H-thiopyran-4-yl) pyridin-2-amine (120 mg, 47%) as brown color solid. LCMS (m/z): 193 (MH+), 0.44 min.

Step 2.
5-(Tetrahydro-2H-thiopyran-4-yl)pyridin-2-amine

A suspension of 5-(3,6-dihydro-2H-thiopyran-4-yl)pyridin-2-amine (260 mg, 1.35 mmol), Pd/C (36 mg, 0.33 mmol) in methanol (16 mL) was stirred under hydrogen at ambient temperature for 16 h. The reaction mixture was diluted with DCM (80 mL), and was filtered through Celite. The filtrate was concentrated to give 5-(tetrahydro-2H-thiopyran-4-yl) pyridin-2-amine (240 mg, 91% yield) as yellow color solid. LCMS (m/z): 195 (MH+), 0.46 min.

Step 3.
4-(6-Aminopyridin-3-yl)tetrahydro-2H-thiopyran 1,1-dioxide

To an ice cooled solution of 5-(tetrahydro-2H-thiopyran-4-yl)pyridin-2-amine (290 mg, 1.49 mmol) in DCM (15 mL) was added 3-chlorobenzoperoxoic acid (592 mg, 3.43 mmol). The resulting solution was stirred at ambient temperature for 4 h. The reaction mixture was diluted with ethyl acetate. The resulting solution was washed with water, saturated aqueous sodium bicarbonate, dried over sodium sulfate and concentrated. The residue was purified by flash column chromatography on silica gel (ISCO) eluting with 0-100% ethyl acetate in heptane to give 4-(6-aminopyridin-3-yl)tetrahydro-2H-thiopyran 1,1-dioxide (140 mg, 41.4%) as white color solid. LCMS (m/z): 227 (MH+), 0.25 min.

Step 4. 4-(6-Amino-5-bromopyridin-3-yl)tetrahydro-2H-thiopyran 1,1-dioxide

To an ice cold solution of 4-(6-aminopyridin-3-yl)tetrahydro-2H-thiopyran 1,1-dioxide (140 mg, 0.62 mmol) in DCM (15 mL) was added NBS (110 mg, 0.62 mmol) in two portions. The reaction mixture was stirred at 0° C. for 20 min. The reaction solution was diluted with ethyl acetate, washed with water, saturated aqueous sodium bicarbonate solution, brine, dried over sodium sulfate and concentrated to give 4-(6-amino-5-bromopyridin-3-yl)tetrahydro-2H-thiopyran 1,1-dioxide (190 mg, 0.62 mmol). LCMS (m/z): 305/307 (MH+), 0.33 min.

Step 5. 4-(6-Amino-5-(4,4,5,5-tetramethyl-1,3,2-dioxaborolan-2-yl)pyridin-3-yl)tetrahydro-2H-thiopyran 1,1-dioxide To a suspension of 4-(6-amino-5-bromopyridin-3-yl)tetrahydro-2H-thiopyran 1,1-dioxide (190 mg, 0.62 mmol) in 1,4-dioxane (7 mL) was added bis(pinacolato)diboron (474 mg, 1.86 mmol) and potassium acetate (305 mg, 3.11 mmol), and followed by the addition of PdCl₂(dppf)-CH₂Cl₂ (61.0 mg, 0.075 mmol) was added. The reaction mixture was heated to 100° C. in an oil bath for 16 h. The reaction mixture was diluted with ethyl acetate and was filtered through neutral alumina (5 g). The filtrate was refiltered again through Celite. The filtrate was concentrated and the residue was triturated with heptane, and filtered to give 4-(6-amino-5-(4,4,5,5-tetramethyl-1,3,2-dioxaborolan-2-yl) pyridin-3-yl)tetrahydro-2H-thiopyran 1,1-dioxide (140 mg, 64% yield). LCMS (m/z): 271 (MH+), 0.15 min.

Synthesis of methyl 3-(6-amino-5-bromopyridin-3-yl)pyrrolidine-1-carboxylate

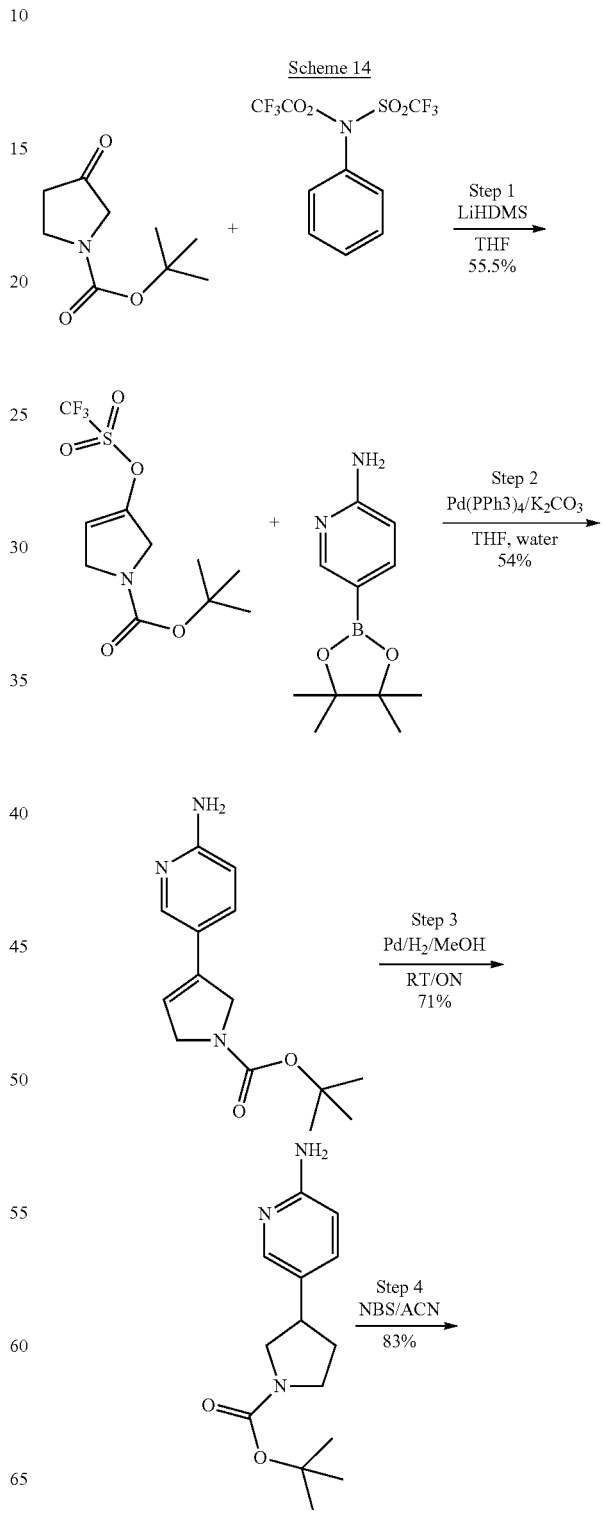

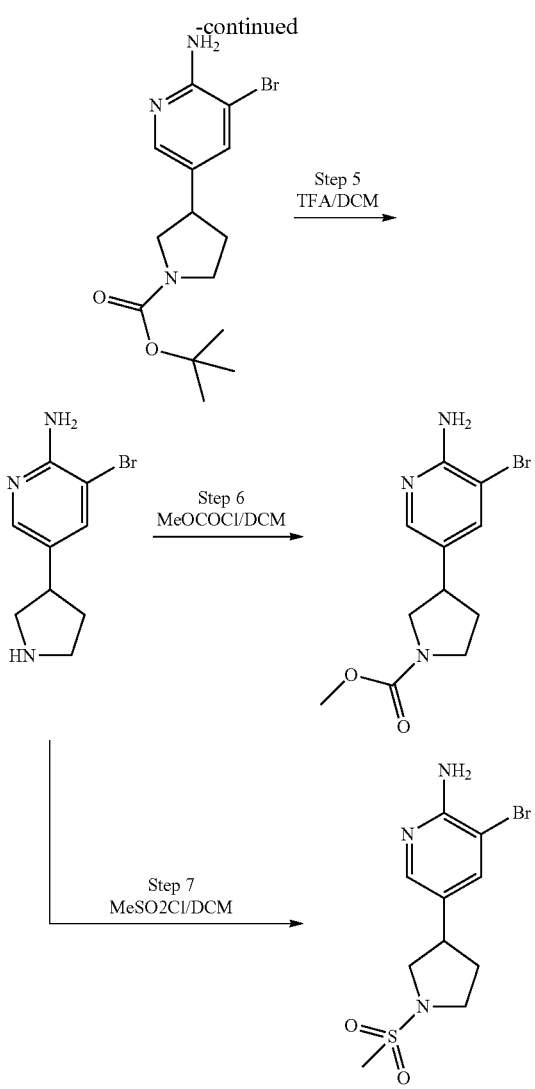

Step 1. tert-butyl 3-(((trifluoromethyl)sulfonyl)oxy)-2,5-dihydro-1H-pyrrole-1-carboxylate To an oven dried flask under $N_2$ was added tert-butyl 3-oxopyrrolidine-1-carboxylate (2 g, 10.8 mmol) and THF (16 mL). The solution was cooled in acetone ice bath (−78° C.). To that was added lithium bis(trimethylsilyl)amide (12.96 mL, 12.96 mmol) (1 M solution in THF). The reaction mixture was stirred at −78° C. for 15 min then added dropwise a solution of 1,1,1-trifluoro-N-phenyl-N-((trifluoromethyl)sulfonyl) methanesulfonamide (4.05 g, 11.34 mmol) in THF (16 mL). The reaction mixture was stirred for 30 min then warmed to 0° C. and stirred for 1.5 h. The reaction mixture was quenched with satd. sodium bicarbonate solution and then extracted with ethyl acetate. The combined extracts were washed with brine, dried over sodium sulfate, filtered and evaporated. The crude product was purified by ISCO column (0-30% EtOAc/heptane) providing tert-butyl 3-(((trifluoromethyl)sulfonyl)oxy)-2,5-dihydro-1H-pyrrole-1-carboxylate (1.9 g, 55.5%).

Step 2. tert-butyl 3-(6-aminopyridin-3-yl)-2,5-dihydro-1H-pyrrole-1-carboxylate A solution of tert-butyl 3-(((trifluoromethyl)sulfonyl)oxy)-2,5-dihydro-1H-pyrrole-1-carboxylate (400 mg, 0.882 mmol) in THF (10 mL) was purged with $N_2$ for 5 min and then was added potassium carbonate (610 mg, 4.41 mmol), 5-(4,4,5,5-tetramethyl-1,3,2-dioxaborolan-2-yl)pyridin-2-amine (233 mg, 1.059 mmol), Pd(PPh$_3$)$_4$ (10.20 mg, 8.82 µmol) and water (0.1 mL). The reaction mixture was heated and stirred at 70° C. overnight. The reaction mixture was poured to saturated sodium bicarbonate solution and extracted with ethyl ether. The organic layer was separated, washed with brine, dried over sodium sulfate, filtered and evaporated. The crude product was purified by flash chromatography (0-10% MeOH/DCM) to yield the desired product (180 mg, 54.6%). LCMS (m/z): 262.2 (MH$^+$), 0.598 min.

Step 3. tert-butyl 3-(6-aminopyridin-3-yl)pyrrolidine-1-carboxylate

To tert-butyl 3-(6-aminopyridin-3-yl)-2,5-dihydro-1H-pyrrole-1-carboxylate (180 mg, 0.482 mmol) in MeOH (10 mL) under $N_2$ atmosphere was added PdC (103 mg, 0.096 mmol). The reaction mixture was stirred at room temperature under $H_2$ balloon. After 2 h, the reaction mixture was filtered through Celite pad, washed with methanol and evaporated to provide desired product, which proceeded for next step without purification (150 mg, 71%). LCMS (m/z): 264.2 (MH$^+$), 0.565 min.

Step 4. tert-butyl 3-(6-amino-5-bromopyridin-3-yl)pyrrolidine-1-carboxylate

To tert-butyl 3-(6-aminopyridin-3-yl)pyrrolidine-1-carboxylate (60 mg, 0.228 mmol) in Acetonitrile (4 mL) in ice bath was added NBS (36.5 mg, 0.205 mmol) and stirred. LCMS after 30 min showed ~1:1 mixture of starting material and desired product. To this added 12 mg (0.3 equiv.) of NBS and stirred 30 min. LCMS shows complete reaction. To the reaction mixture was added aqueous saturated NaHCO$_3$ stirred 10 min and extracted with ethyl acetate. The combined extracts were dried over sodium sulfate, filtered off, and evaporated. The crude product was used for next step without purification (65 mg, 83%). LCMS (m/z): 342.1/344.1 (MH$^+$), 0.624 min.

Step 5. 3-bromo-5-(pyrrolidin-3-yl)pyridin-2-amine

To tert-butyl 3-(6-amino-5-bromopyridin-3-yl)pyrrolidine-1-carboxylate (65 mg, 0.171 mmol) in DCM (2.4 mL) was added TFA (0.6 mL, 7.79 mmol). The reaction mixture was stirred at room temperature for 45 min. The reaction mixture was evaporated in vacuo after dilution with toluene. The crude product was used for next step without purification. The crude yield was quantitative. LCMS (m/z): 242.1/244.1 (MH$^+$), 0.214 min.

Step 6. methyl 3-(6-amino-5-bromopyridin-3-yl)pyrrolidine-1-carboxylate

To 3-bromo-5-(pyrrolidin-3-yl)pyridin-2-amine, (20 mg, 0.083 mmol) in DCM in ice bath was added DIEA (43.3 µl, 0.248 mmol) and methyl chloroformate (6.40 µl, 0.083 mmol). The reaction mixture was stirred in ice bath for 30 min. The reaction mixture was partitioned between DCM and water. The DCM layer was separated and washed with brine, dried over sodium sulfate, filtered off, and evaporated. The crude product was used for next step without purification. LCMS (m/z): 300.0, 302.0 (MH$^+$), 0.421 min.

Step 7. 3-bromo-5-(1-(methylsulfonyl)pyrrolidin-3-yl)pyridin-2-amine

To 3-bromo-5-(pyrrolidin-3-yl)pyridin-2-amine (20 mg, 0.083 mmol) in DCM in ice bath was added DIEA (57.7 μl, 0.330 mmol) and methanesulfonyl chloride (7.08 μl, 0.091 mmol). The reaction mixture was stirred in ice bath 30 min. The reaction mixture was partitioned between DCM and water. The DCM layer was separated and washed with brine, dried over sodium sulfate, filtered and evaporated. The crude product was used for next step without purification. LCMS (m/z): 320.0/322.0 (MH+), 0.363 min.

Examples 4, 5, and 6

Synthesis of 4-(2-amino-5-(1,1-dioxidotetrahydrothiophen-3-yl)pyridin-3-yl)-N-benzyl-2-fluorobenzamide, (S)-4-(2-amino-5-(1,1-dioxidotetrahydrothiophen-3-yl)pyridin-3-yl)-N-benzyl-2-fluorobenzamide, and (R)-4-(2-amino-5-(1,1-dioxidotetrahydrothiophen-3-yl)pyridin-3-yl)-N-benzyl-2-fluorobenzamide

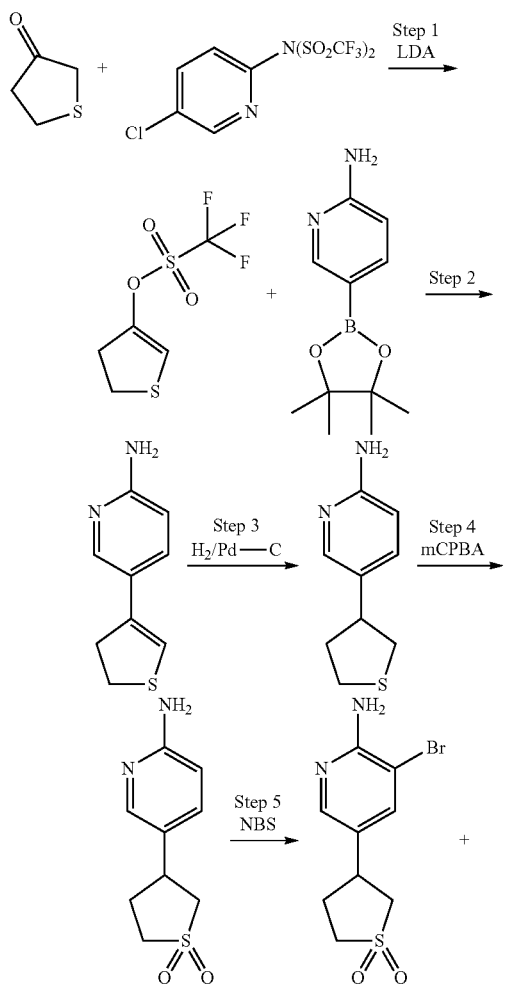

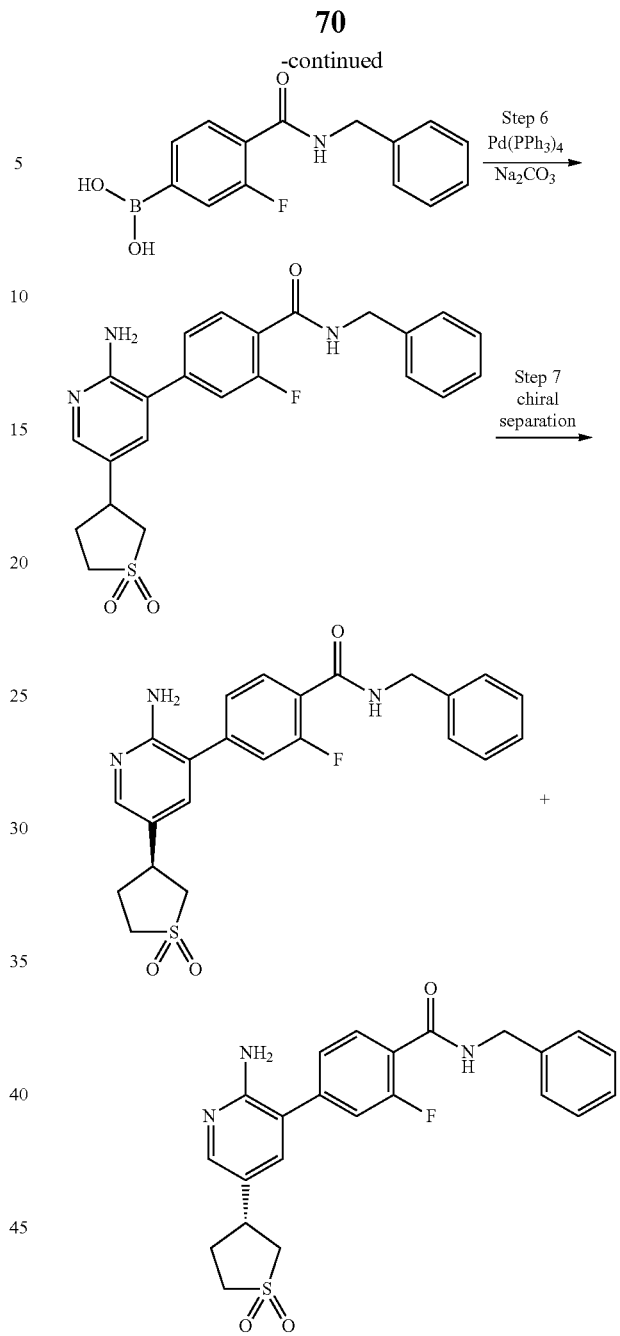

Step 1. 4,5-dihydrothiophen-3-yl trifluoromethanesulfonate

To freshly prepared LDA (10.5 mmol in 40 mL THF) between −75 to −65° C. was dropwise added dihydrothiophene-3-(2H)-one/THF solution (1.02 g/2 mL THF, 10 mmol) over 3 min, then the resulting reaction mixture was stirred at −75° C. for 3 h, followed by dropwise addition of N-(5-chloropyridin-2-yl)-1,1,1-trifluoro-N-(trifluoromethylsulfonyl)methanesulfonamide/THF (4.12 g, 10.5 mmol in 5 mL THF) over 10 min, then the reaction mixture was stirred at −75° C. for at least 1 h, then with temperature gradually warm up to room temperature overnight. The reaction mixture was concentrated, and the residue was partitioned between Et₂O/H₂O (100 mL/50 mL); the ether layer was sequentially washed with water (2×50 mL), 3 M sodium acetate pH 4.8 buffer (2×50 mL), 3M NaOH (2×50 mL), and dried over magnesium sulfate, concentrated and a brown oil was obtained as crude product (2.05 g) which was further purified by flash chromatography on silica gel eluted with gradient EtOAc/heptane (0-15%) and desired product (0.9 g, 38.5% yield) was obtained as colorless oil.

Step 2. 5-(4,5-dihydrothiophen-3-yl)pyridin-2-amine

To a vial was charged with all reagents: 4,5-dihydrothiophen-3-yl trifluoromethanesulfonate (900 mg, 3.84 mmol), 5-(4,4,5,5-tetramethyl-1,3,2-dioxaborolan-2-yl)pyridin-2-amine (1.69 g, 7.69 mmol), $K_3PO_4$ (2.45 g, 11.5 mmol), and $PdCl_2(dppf)$-$CH_2Cl_2$ adduct (314 mg, 0.384 mmol) and DME (16 mL), and the mixture was purged with Argon, then sealed and heated at 90° C. via external oil bath overnight. The reaction mixture was cooled down to room temperature, and the precipitates in the reaction mixture was removed by filtration, and the filtrate was concentrated under reduced pressure and a black residue was obtained as crude product. The crude product was dissolved in EtOAc (30 mL), washed with water (20 mL), and the slug between the two layers was removed by filtration. The EtOAc layer was collected, stripped with 1N HCl (2×20 mL) and the aqueous layers were combined, scrubbed with EtOAc (20 mL), basified with aqueous NaOH (3 g in 10 mL water), extracted with EtOAc (2×30 mL), and the obtained EtOAc extracts were combined, washed with brine (30 mL), dried ($Na_2SO_4$), concentrated and desired product was obtained as light color solid. LCMS (m/z): 179.0 (MH$^+$), 0.41, 0.43 min (for regioisomers).

Step 3. 5-(tetrahydrothiophen-3-yl)pyridin-2-amine 5-(4,5-dihydrothiophen-3-yl)pyridin-2-amine (0.78 g, 4.38 mmol) was dissolved in ethanol (30 mL), to it was added PdC(Deggussa, 10%, 0.233 g) and the mixture was stirred under $H_2$ balloon overnight. The reaction was not complete by LCMS. The PdC catalyst was removed by filtering through a Celite pad, and to the filtrate was added new PdC catalyst (0.24 g), and the mixture was stirred under $H_2$ balloon under same condition for another 6 h. The reaction mixture was filtered off through Celite pad, and the filtrate was concentrated under reduced pressure yielding 5-(tetrahydrothiophen-3-yl)pyridin-2-amine (0.661 g, 84%) as colorless oil. LCMS (m/z): 181.2 (MH$^+$), 0.39 min.

Step 4. 3-(6-aminopyridin-3-yl)tetrahydrothiophene 1,1-dioxide 5-(tetrahydrothiophen-3-yl)pyridin-2-amine (0.33 g, 1.831 mmol) was dissolved in $CH_2Cl_2$ (15 mL), to it was added mCPBA (70%, 0.903 g, 3.66 mmol) and the mixture was stirred at room temperature for 10 min and the reaction mixture was concentrated under reduced pressure and the residue was partitioned between EtOAc/sat. NaHCO$_3$ (30 mL/20 mL), the EtOAc layer was washed with sat. $Na_2CO_3$ (20 mL), brine (20 mL), dried ($Na_2SO_4$), filtered off, and concentrated in vacuo yielding 3-(6-aminopyridin-3-yl)tetrahydrothiophene 1,1-dioxide as light brown oil (96 mg, 25%). LCMS (m/z): 197.1 (MH$^+$), 0.21 min.

Step 5. 3-(6-amino-5-bromopyridin-3-yl)tetrahydrothiophene 1,1-dioxide 3-(6-aminopyridin-3-yl)tetrahydrothiophene 1,1-dioxide (96 mg, 0.452 mmol) was dissolved in acetonitrile (5 mL) and the solution was cooled to 0° C., to it was added NBS (80 mg, 0.452 mmol) and the mixture was stirred at 0° C. for 40 min. The reaction mixture was concentrated under reduced pressure and the residue was partitioned between EtOAc/sat. NaHCO$_3$ (30 mL/20 mL), the EtOAc layer was washed with sat. $Na_2CO_3$ (20 mL), brine (20 mL), dried ($Na_2SO_4$), filtered off and concentrated in vacuo yielding 3-(6-amino-5-bromopyridin-3-yl)tetrahydrothiophene 1,1-dioxide as light brown oil (50 mg, 38% yield). LCMS (m/z): 293.0/291.0 (MH$^+$), 0.29 min.

Step 6. 4-(2-amino-5-(1,1-dioxidotetrahydrothiophen-3-yl)pyridin-3-yl)-N-benzyl-2-fluorobenzamide To a microwave reactor was charged with 3-(6-amino-5-bromopyridin-3-yl)tetrahydrothiophene 1,1-dioxide (50 mg, 0.172 mmol), 4-(benzylcarbamoyl)-3-fluorophenylboronic acid (94 mg, 0.343 mmol), 2 M aqueous $Na_2CO_3$ (0.34 mL) and PdCl$_2$(dppf)-DCM adduct (14 mg) and DME (3 mL) were charged in a microwave vial and the mixture was purged with Argon, sealed and heated at 105° C. for 20 min. The DME layer of the reaction mixture was collected, concentrated under reduced pressure and the residue was redissolved in EtOAc (5 mL). The EtOAc solution was stripped with 1N HCl (4×1 mL) and the aqueous layers were combined, scrubbed with EtOAc (2×1 mL), then concentrated under reduced pressure and the residue was partitioned between EtOAc/sat. Na$_2$CO$_3$ (5 mL/1 mL), and the EtOAc extract was washed with sat. Na$_2$CO$_3$ (2×1 mL), brine (1 mL), dried (Na$_2$SO$_4$), concentrated and the residue was redissolved in acetonitrile/water (6 mL/6 mL), frozen and lyophilized yielding racemic 4-(2-amino-5-(1,1-dioxidotetrahydrothiophen-3-yl)pyridin-3-yl)-N-benzyl-2-fluorobenzamidein as light yellow powder. LCMS (m/z): 440.2 (MH$^+$), 0.60 min; $^1$H NMR (CD$_3$OD) δ ppm 7.97 (d, J=2.0 Hz, 1H), 7.84 (t, J=7.8 Hz, 1H), 7.50 (d, J=2.3 Hz, 1H), 7.31-7.44 (m, 6H), 7.22-7.30 (m, 1H), 4.61 (s, 2H), 3.55-3.70 (m, 1H), 3.47 (dd, J=13.3, 7.0 Hz, 1H), 3.33-3.39 (m, 1H), 3.08-3.25 (m, 2H), 2.53 (ddd, J=13.1, 7.4, 5.7 Hz, 1H), 2.18-2.40 (m, 1H). The racemic product was further resolved by chiral SFC (ChiralPak 5mic OJ column, 4.6× 100 (mm), 5 mL/min, MeOH+0.1% DEA=50%) to afford (S)-4-(2-amino-5-(1,1-dioxidotetrahydrothiophen-3-yl)pyridin-3-yl)-N-benzyl-2-fluorobenzamide (Rt=1.7 min) and (R)-4-(2-amino-5-(1,1-dioxidotetrahydrothiophen-3-yl)pyridin-3-yl)-N-benzyl-2-fluorobenzamide (Rt=2.22 min). The absolute stereochemistry was arbitrarily assigned.

Example 7

Synthesis of 4-(2-amino-5-((3R,5S)-5-(hydroxymethyl)pyrrolidin-3-yl)pyridin-3-yl)-N-((S)-1-(3-chlorophenyl)-2-hydroxyethyl)-2-fluorobenzamide

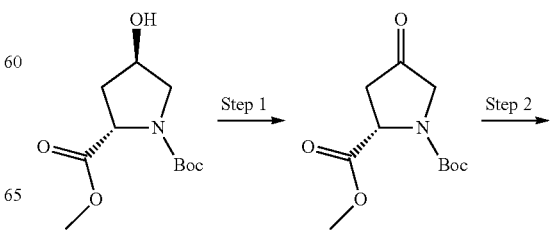

Scheme 16

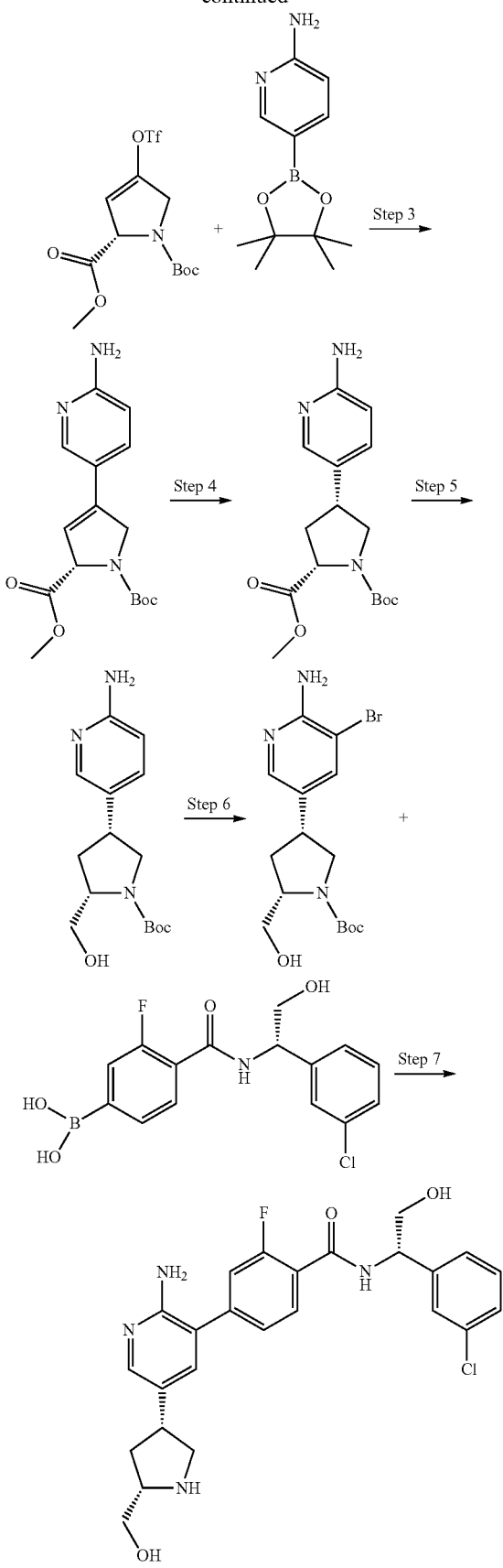

Step 1. (S)-1-tert-butyl 2-methyl 4-oxopyrrolidine-1,2-dicarboxylate

A solution of (2S,4R)-1-tert-butyl 2-methyl 4-hydroxypyrrolidine-1,2-dicarboxylate (10 g, 40.8 mmol) in DCM (100 mL) was cooled to 0° C., then treated portion wise with Dess-Martin periodinane (17.29 g, 40.8 mmol) over 20 min. The reaction was maintained at 0° C. for 1 h, and then the cold bath was removed. After another 3 h at room temperature, the reaction was treated with 300 mL of 1:1 sat. aq. $Na_2SO_3$:sat. aq. $NaHCO_3$. The reaction was stirred vigorously overnight at room temperature, then the layers were separated. The organics were washed with water and brine, then dried over magnesium sulfate and concentrated. The resulting mixture was slurried in DCM (20 mL) then filtered over Celite. The organics were concentrated. The crude oil was further purified by direct filtration from grained solids to provide (S)-1-tert-butyl 2-methyl 4-oxopyrrolidine-1,2-dicarboxylate (8.53 g, 87% yield). LCMS (m/z): 244.3 (MH+), 0.42 min.

Step 2. 1-tert-butyl 2-methyl 4-(((trifluoromethyl)sulfonyl)oxy)-1H-pyrrole-1,2(2H,5H)-dicarboxylate A solution of (S)-1-tert-butyl 2-methyl 4-oxopyrrolidine-1,2-dicarboxylate (2.9 g, 11.92 mmol) in THF (30 mL) was cooled to −78° C., then treated with 1.0 M LiHMDS in THF (14.31 mL, 14.31 mmol). The reaction was maintained at −78° C. for 1 h, then treated with a solution of N-(5-chloropyridin-2-yl)-1,1,1-trifluoro-N-((trifluoromethyl)sulfonyl)methanesulfonamide (5.62 g, 14.31 mmol) in THF (15 mL). The reaction was maintained at −78° C. for 1 h, and then placed in a −30° C. refrigerator overnight. At completion, the reaction was quenched with water, and diluted with ether. The organics were washed with 1N aqueous solution. NaOH (40 mL), then dried over magnesium sulfate and concentrated. The residue was dissolved in chloroform (40 mL) and cooled to 0° C. for 30 min. The resulting slurry was concentrated to ~8 mL total volume, then the viscous material was filtered and concentrated to provide (S)-1-tert-butyl 2-methyl 4-(((trifluoromethyl)sulfonyl)oxy)-1H-pyrrole-1,2(2H,5H)-dicarboxylate (4.4 g, 98% yield). LCMS (m/z): 376.4 (MH+), 0.64 min.

Step 3. (S)-1-tert-butyl 2-methyl 4-(6-aminopyridin-3-yl)-1H-pyrrole-1,2(2H,5H)-dicarboxylate A mixture of (S)-1-tert-butyl 2-methyl 4-(((trifluoromethyl)sulfonyl)oxy)-1H-pyrrole-1,2(2H,5H)-dicarboxylate (1.55 g, 4.13 mmol), 5-(4,4,5,5-tetramethyl-1,3,2-dioxaborolan-2-yl)pyridin-2-amine (1.00 g, 4.54 mmol), Pd(PPh3)4 (0.239 g, 0.21 mmol) and $Cs_2CO_3$ (3.36 g, 10.32 mmol) in THF (10 mL) and water (2 mL) was microwave heated to 100° C. for 10 min. The reaction was then diluted with ethyl acetate (50 mL) and water (25 mL). The layers were separated and the organics were washed with water (25 mL) and brine (25 mL), dried over magnesium sulfate and concentrated, then purified by flash chromatography [0-8% methanol/DCM eluent] to provide (S)-1-tert-butyl 2-methyl 4-(6-aminopyridin-3-yl)-1H-pyrrole-1,2(2H,5H)-dicarboxylate (0.955 g, 72% yield). LCMS (m/z): 320.4 (MH+), 0.50 min.

Step 4. (2S,4R)-1-tert-butyl 2-methyl 4-(6-aminopyridin-3-yl)pyrrolidine-1,2-dicarboxylate A degassed solution of (S)-1-tert-butyl 2-methyl 4-(6-aminopyridin-3-yl)-1H-pyrrole-1,2(2H,5H)-dicarboxylate (0.955 g, 2.99 mmol) in methanol (30 mL) was treated with 10% Pd/C (0.183 g, 0.172 mmol), then maintained under an atmosphere of hydrogen for 3 h. At completion, the reaction then filtered over a pad of Celite and concentrated to provide (2S,4R)-1-tert-butyl 2-methyl 4-(6-aminopyridin-3-yl)pyrrolidine-1,2-dicarboxylate (0.95 g. 99% yield). LCMS (m/z): 322.5 (MH+), 0.52 min.

Step 5. (2S,4R)-tert-butyl 4-(6-aminopyridin-3-yl)-2-(hydroxymethyl)pyrrolidine-1-carboxylate To a solution of (2S,4R)-1-tert-butyl 2-methyl 4-(6-aminopyridin-3-yl)pyrrolidine-1,2-dicarboxylate (250 mg, 0.778 mmol) in 2-methyl THF (18 mL) was added LiAlH$_4$ (59 mg, 1.56 mmol). After 15 min, the reaction was quenched by the sequential addition of water (60 μL), 1 N NaOH aqueous solution (60 μL) and water (60 μL). The mixture was stirred vigorously for 5 min, and then filtered over Celite, rinsing with 2-methyl THF. The organics were concentrated to provide (2S,4R)-tert-butyl 4-(6-aminopyridin-3-yl)-2-(hydroxymethyl)pyrrolidine-1-carboxylate (230 mg, 100% yield). LCMS (m/z): 294.1 (MH+), 0.49 min.

Step 6. (2S,4R)-tert-butyl 4-(6-amino-5-bromopyridin-3-yl)-2-(hydroxymethyl)pyrrolidine-1-carboxylate A solution of (2S,4R)-tert-butyl 4-(6-aminopyridin-3-yl)-2-(hydroxymethyl)pyrrolidine-1-carboxylate (230 mg, 0.784 mmol) in MeCN (10 mL) was treated with NBS (147 mg, 0.823 mmol). After 10 min, the reaction was complete. The reaction was treated with 10 mL 1:1 sat. aq. NaHCO$_3$: sat.aq. Na$_2$S$_2$O$_3$ and the mixture was stirred vigorously for 10 min. The mixture was diluted with ethyl acetate (30 mL) and the layers were separated. The organics were washed with brine, dried over magnesium sulfate and concentrated to provide (2S,4R)-tert-butyl 4-(6-amino-5-bromopyridin-3-yl)-2-(hydroxymethyl)pyrrolidine-1-carboxylate (290 mg, 100% yield). LCMS (m/z): 372.1/374.0 (MH+), 0.55 min.

Step 7. 4-(2-amino-5-((3R,5S)-5-(hydroxymethyl)pyrrolidin-3-yl)pyridin-3-yl)-N-((S)-1-(3-chlorophenyl)-2-hydroxyethyl)-2-fluorobenzamide Following Step 5 in Scheme 10, using (2S, 4R)-tert-butyl 4-(6-amino-5-bromopyridin-3-yl)-2-(hydroxymethyl)pyrrolidine-1-carboxylate and (S)-(4-(((1-(3-chlorophenyl)-2-hydroxyethyl)carbamoyl)-3-fluorophenyl)boronic acid, (2S,4R)-tert-butyl 4-(6-amino-5-(4-(((S)-1-(3-chlorophenyl)-2-hydroxyethyl)carbamoyl)-3-fluorophenyl)pyridin-3-yl)-2-(hydroxymethyl)pyrrolidine-1-carboxylate was obtained as TFA salt (30 mg, 35% yield. LCMS (m/z): 585.3, 587.3 (MH+), 0.74 min. Then, a solution of (2S,4R)-tert-butyl 4-(6-amino-5-(4-(((S)-1-(3-chlorophenyl)-2-hydroxyethyl)carbamoyl)-3-fluorophenyl)pyridin-3-yl)-2-(hydroxymethyl)pyrrolidine-1-carboxylate-TFA was dissolved in DCM (2 mL) and treated with TFA (2.0 mL). After 30 min, the reaction was concentrated, and then purified by reverse phase prep HPLC yielding 4-(2-amino-5-((3R,5S)-5-(hydroxymethyl)pyrrolidin-3-yl)pyridin-3-yl)-N-((S)-1-(3-chlorophenyl)-2-hydroxyethyl)-2-fluorobenzamide as the bis-TFA salt (15.0 mg, 54% yield). LCMS (m/z): 485.2, 487.2 (MH+), 0.51 min; $^1$H NMR (400 MHz, CD$_3$OD) δ ppm 8.59 (dd, J=4.50, 7.24 Hz, 1H), 7.87-7.77 (m, 4H), 7.39-7.31 (m, 3H), 7.29-7.24 (m, 2H), 7.24-7.16 (m, 1H), 5.15-5.05 (m, 1H), 3.87-3.71 (m, 5H), 3.70-3.60 (m, 2H), 3.59-3.46 (m, 1H), 2.41 (td, J=6.46, 12.91 Hz, 1H), 1.98-1.82 (m, 1H), 1.29-1.16 (m, 1H).

Example 8

Synthesis of 4-(2-amino-5-((7R,8aS)-4-oxohexahydro-1H-pyrrolo[2,1-c][1,4]oxazin-7-yl)pyridin-3-yl)-N-((S)-1-(3-chlorophenyl)-2-hydroxyethyl)-2-fluorobenzamide Scheme 17

A solution of 4-(2-amino-5-((3R,5S)-5-(hydroxymethyl)pyrrolidin-3-yl)pyridin-3-yl)-N-((S)-1-(3-chlorophenyl)-2-hydroxyethyl)-2-fluorobenzamide (45 mg, 0.063 mmol) (see Example 7) and chloroacetic acid (7.2 mg, 0.076 mmol) in THF (2.5 mL) was treated with HATU (36 mg, 0.095 mmol) and DIEA (55 μL, 0.316 mmol). The reaction was maintained at room temperature for 1 h. The reaction mixture was then treated directly with NaH (15.2 mg, 0.631 mmol). After 15 min, the reaction was quenched with water (2 mL) and the reaction mixture was extracted with ethyl acetate (10 mL). The organics were washed with brine, then dried over Na$_2$SO$_4$, concentrated, then purified by reverse phase prep HPLC yielding 4-(2-amino-5-((7R,8aS)-4-oxohexahydro-1H-pyrrolo[2,1-c][1,4]oxazin-7-yl)pyridin-3-yl)-N-((S)-1-(3-chlorophenyl)-2-hydroxyethyl)-2-fluorobenzamide (13.0 mg, 39% yield). LCMS (m/z): 525.2, 527.2 (MH+), 0.59 min; $^1$H NMR (400 MHz, CD$_3$OD) δ ppm 8.61 (dd, J=4.30, 7.04 Hz, 1H), 7.91 (d, J=1.96 Hz, 1H), 7.84-7.76 (m, 2H), 7.40-7.31 (m, 3H), 7.30-7.24 (m, 2H), 7.24-7.16 (m, 1H), 5.16-5.05 (m, 1H), 4.18-4.08 (m, 2H), 3.99-3.85 (m, 2H), 3.85-3.70 (m, 3H), 3.53-3.42 (m, 2H), 3.39-3.29 (m, 1H), 2.34-2.19 (m, 1H), 1.67 (q, J=11.48 Hz, 1H).

Example 9

Synthesis of 4-(2-amino-5-((6R,7aS)-3-oxohexahydropyrrolo[1,2-c]oxazol-6-yl)pyridin-3-yl)-N-((S)-1-(3-chlorophenyl)-2-hydroxyethyl)-2-fluorobenzamide

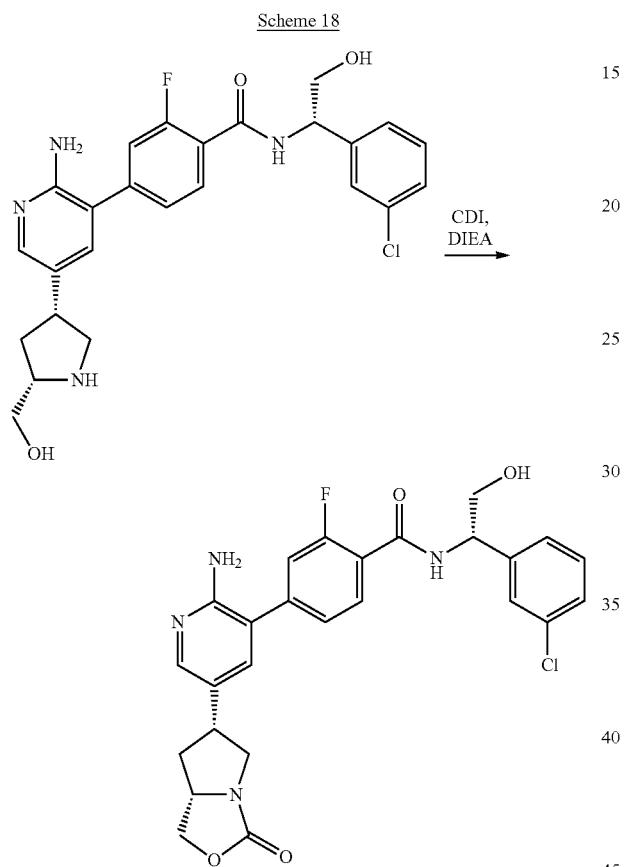

A solution of 4-(2-amino-5-((3R,5S)-5-(hydroxymethyl)pyrrolidin-3-yl)pyridin-3-yl)-N-((S)-1-(3-chlorophenyl)-2-hydroxyethyl)-2-fluorobenzamide (20 mg, 0.041 mmol) (Example 7) and DIEA (72 µL, 0.412 mmol) in acetonitrile (0.5 mL) was treated with carbonyldiimidazole (8.0 mg, 0.049 mmol). After 1 h, the starting material was completely consumed. The reaction mixture was quenched with 1.0 N aqueous NaOH solution (1.0 mL) and the mixture was stirred vigorously for 5 min, then, diluted with DCM (10 mL). The organics were washed with brine (2 mL) and dried over $Na_2SO_4$ and concentrated. The crude material was purified by reverse phase prep HPLC yielding 4-(2-amino-5-((6R,7aS)-3-oxohexahydropyrrolo[1,2-c]oxazol-6-yl)pyridin-3-yl)-N-((S)-1-(3-chlorophenyl)-2-hydroxyethyl)-2-fluorobenzamide (2.0 mg, 7% yield). LCMS (m/z): 511.3, 513.3 (MH$^+$), 0.61 min; $^1$H NMR (400 MHz, CD$_3$OD) δ ppm 7.92-7.84 (m, 2H), 7.46 (s, 1H), 7.44-7.40 (m, 1H), 7.38-7.35 (m, 1H), 7.34-7.28 (m, 1H), 5.19 (t, J=5.87 Hz, 1H), 4.61-4.56 (m, 1H), 4.34 (dd, J=3.52, 9.00 Hz, 1H), 4.24-4.15 (m, 1H), 3.92-3.80 (m, 1H), 3.74-3.62 (m, 1H), 2.41 (td, J=5.72, 11.64 Hz, 1H), 1.84-1.71 (m, 1H).

Example 10

Synthesis of 4-(2-amino-5-((6R,7aS)-3-iminohexahydropyrrolo[1,2-c]oxazol-6-yl)pyridin-3-yl)-N-((S)-1-(3-chlorophenyl)-2-hydroxyethyl)-2-fluorobenzamide

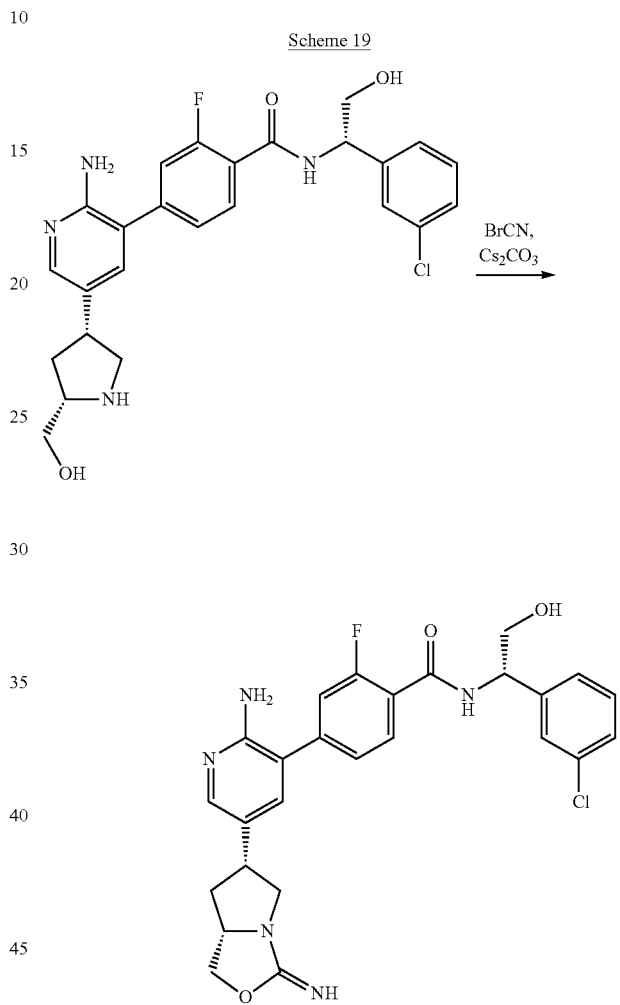

A room temperature mixture of 4-(2-amino-5-((3R,5S)-5-(hydroxymethyl)pyrrolidin-3-yl)pyridin-3-yl)-N-((S)-1-(3-chlorophenyl)-2-hydroxyethyl)-2-fluorobenzamide (12.5 mg, 0.026 mmol) (Example 7) and cesium carbonate (33.6 mg, 0.103 mmol) in ethanol (0.75 mL) was treated with cyanogen bromide (6.2 µL, 0.031 mmol). After 1 h, the reaction was diluted with water (1.0 mL) and extracted into ethyl acetate (10 mL). The organics were washed with brine (2 mL), then dried over $Na_2SO_4$ and concentrate and purified by reverse phase prep HPLC yielding 4-(2-amino-5-((6R,7aS)-3-iminohexahydropyrrolo[1,2-c]oxazol-6-yl)pyridin-3-yl)-N-((S)-1-(3-chlorophenyl)-2-hydroxyethyl)-2-fluorobenzamide. LCMS (m/z): 510.1, 512.1 (MH$^+$), 0.52 min. $^1$H NMR (400 MHz, CD$_3$OD) δ ppm 8.63-8.54 (m, 1H), 7.92-7.85 (m, 2H), 7.80 (t, J=7.83 Hz, 1H), 7.40-7.31 (m, 3H), 7.29-7.24 (m, 2H), 7.24-7.16 (m, 1H), 5.14-5.06 (m, 1H), 4.97-4.88 (m, 1H), 4.61-4.49 (m, 2H), 3.88-3.70 (m, 4H), 3.32 (s, 1H), 2.41-2.31 (m, 1H), 2.02-1.89 (m, 1H).

Example 11

4-(2-amino-54(6R,7aS)-3-thioxohexahydropyrrolo[1,2-c]oxazol-6-yl)pyridin-3-yl)-N-((S)-1-(3-chlorophenyl)-2-hydroxyethyl)-2-fluorobenzamide

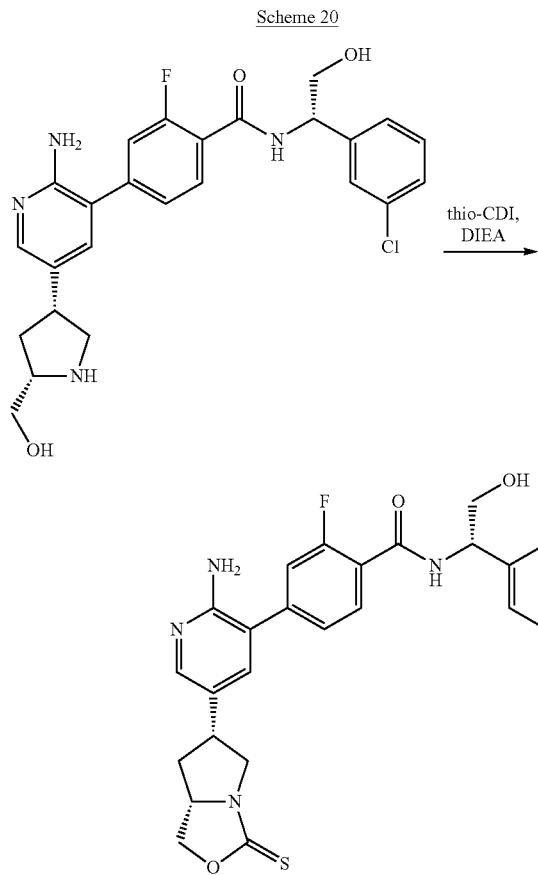

Scheme 20

To a solution of (2S,4R)-tert-butyl 4-(6-amino-5-(4-(((S)-1-(3-chlorophenyl)-2-hydroxyethyl)carbamoyl)-3-fluorophenyl)pyridin-3-yl)-2-(hydroxymethyl)pyrrolidine-1-carboxylate (45 mg, 0.063 mmol) (see Example 7) in acetonitrile (0.75 mL) and DMF (0.5 mL) was added DIEA (42 µL, 0.240 mmol) and thiocarbonyl diimidazole (15.6 mg, 0.088 mmol). After 2 h, the reaction was quenched with 1 N aqueous solution. NaOH (1 mL) and stirred vigorously to effect decomposition of a mixed thiocarbamate byproduct. The reaction was then diluted with ethyl acetate (10 mL), washed with water (5 mL) and brine (5 mL), then dried over sodium sulfate and concentrated. The crude material was purified by reverse phase prep HPLC yielding 4-(2-amino-5-((6R,7aS)-3-thioxohexahydropyrrolo[1,2-c]oxazol-6-yl)pyridin-3-yl)-N-((S)-1-(3-chlorophenyl)-2-hydroxyethyl)-2-fluorobenzamide (3.2 mg, 11% yield). LCMS (m/z): 527.3, 529.3 (MH$^+$), 0.67 min; $^1$H NMR (400 MHz, CD$_3$OD) δ ppm 8.64 (dd, J=3.91, 7.04 Hz, 1H), 7.85 (d, J=1.96 Hz, 2H), 7.83-7.77 (m, 3H), 7.39-7.32 (m, 5H), 7.30-7.26 (m, 3H), 7.25-7.19 (m, 2H), 5.15-5.07 (m, 2H), 4.73-4.69 (m, 2H), 4.45-4.35 (m, 3H), 3.85-3.65 (m, 8H), 2.38 (td, J=5.58, 11.54 Hz, 2H), 1.80-1.70 (m, 1H).

Synthesis of 5-morpholino-3-(4,4,5,5-tetramethyl-1,3,2-dioxaborolan-2-yl)pyridin-2-amine

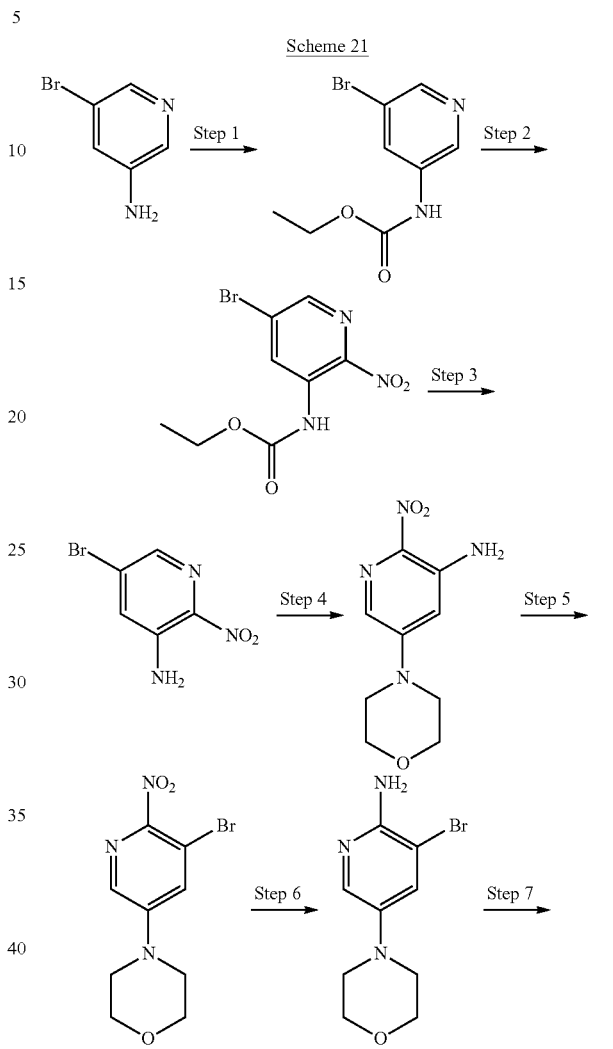

Scheme 21

Step 1. Ethyl (5-bromopyridin-3-yl)carbamate 5-bromopyridin-3-amine (20 g, 116 mmol) was dissolved in DCM (500 mL) and pyridine (28.0 mL, 347 mmol) was added, followed by ethyl chloroformate (11.44 mL, 119 mmol) dropwise. The reaction mixture was stirred for 1.5 h at room temperature. The reaction mixture was diluted with DCM. The two phases were separated and the organic phase was washed with 10% CuSO$_4$ solution (2×) sat. NaHCO$_3$ solution (1×) Brine (1×) dried (Na₂SO₄) and evaporated. The residue was triturated with diethyl ether filtered and dried obtaining ethyl (5-bromopyridin-3-yl)carbamate (21.58 g, 76%) as a white solid. LCMS (m/z): 247.0 (MH⁺), 0.58 min; 1H NMR (400 MHz, CDCl₃) δ ppm 8.62-8.15 (m, 3 H) 7.00 (br. s., 1 H) 4.27 (q, J=7.0 Hz, 2 H) 1.34 (t, J=7.0 Hz, 3 H).

Step 2. Ethyl (5-bromo-2-nitropyridin-3-yl)carbamate

To a mixture of concentrated H₂SO₄ (60 mL, 1126 mmol) and fuming HNO₃ (40 mL, 895 mmol), ethyl (5-bromopyridin-3-yl)carbamate (21.5 g, 88 mmol) was added portionwise at 0° C. After stirring at 0° C. for 5 min, the mixture was stirred at rt overnight and poured onto ice water. A crash out formed and was filtered off and washed thoroughly with water and dried. Ethyl (5-bromo-2-nitropyridin-3-yl)carbamate (21.26 g, 84%) was thus obtained as a white solid. LCMS (m/z): 290.1 (MH⁺), 0.76 min. 1H NMR (400 MHz, CDCl₃) δ ppm 9.63 (br. s., 1 H) 9.33 (d, J=2.0 Hz, 1 H) 8.28 (d, J=2.0 Hz, 1 H) 4.32 (q, J=7.3 Hz, 3 H) 1.68 (br. s., 2 H) 1.38 (t, J=7.0 Hz, 4 H).

Step 3. 5-Bromo-2-nitropyridin-3-amine

Ethyl (5-bromopyridin-3-yl)carbamate (8 g, 27.6 mmol) was dissolved in EtOH (250 mL) and the solution was cooled down to 5° C. with an ice bath. Cold 1M KOH (130 mL, 130 mmol) was added dropwise, maintaining below 5° C. The reaction mixture was stirred at room temperature overnight, concentrated under reduced pressure. Upon concentration a crash out forms, which was filtered off washed with water and dried affording 5-bromo-2-nitropyridin-3-amine (5.02 g, 83%). LCMS (m/z): 220.1 (MH⁺), 0.46 min; 1H NMR (400 MHz, CDCl₃) δ ppm 7.97 (d, J=1.6 Hz, 1 H) 7.50 (d, J=2.0 Hz, 1 H) 6.03 (br. s., 2 H).

Step 4. 5-morpholino-2-nitropyridin-3-amine

5-Bromo-2-nitropyridin-3-amine (2.32 g, 10.6 mmol) was suspended in morpholine (5 mL, 57.4 mmol) and the solution was heated at 140° C. for 1 h. The reaction mixture was cooled to room temperature and the solid crash out was triturated with water and filtered. The solid this obtained was washed with water, EtOH, and dried, obtaining 5-morpholino-2-nitropyridin-3-amine (2.0 g, 8.92 mmol, 84%) as a bright yellow powder. Depending on the outcome of the previous step, this solid may still contain the ethoxy derivative from the previous step, and the two compounds can be separated by column chromatography on silica gel (analogix, 20% EtOAc in heptane for 2 min, to 100% EtOAc to 15 min, then 100% EtOAc to 20 min). LCMS (m/z): 225.1 (MH⁺), 0.43 min; 1H NMR (400 MHz, CDCl₃) δ ppm 10.54 (s, 1 H) 8.57 (d, J=2.7 Hz, 1 H) 7.85 (d, J=2.7 Hz, 1 H) 7.70 (d, J=2.3 Hz, 1 H) 6.32 (d, J=2.3 Hz, 1 H) 6.00 (br. s., 1 H) 3.93-3.83 (m, 7 H) 3.83-3.74 (m, 3 H) 3.63-3.55 (m, 3 H) 3.51-3.43 (m, 3 H) 3.41-3.31 (m, 4 H).

Step 5. 4-(5-bromo-6-nitropyridin-3-yl)morpholine

A three neck round bottom flask equipped with a magnetic stir bar, a dropping funnel and a thermometer, was charged with CuBr (629 mg, 4.4 mmol) and HBr (25 mL). The solution was cooled to −5° C. (ice salt bath). Solid 5-morpholino-2-nitropyridin-3-amine (983 mg, 4.4 mmol) was slowly added, followed by the slow addition of a NaNO₂ (333 mg, 4.8 mmol) solution in H₂O (25 mL) via the dropping funnel, ensuring that the temperature did not rise above 0° C. The reaction mixture was stirred at −5° C. for 1 h, warmed to room temperature and stirred an additional 1.5 h. The reaction was deemed complete by LCMS and the mixture was cooled again to 0° C., quenched with 6 N NaOH to pH 12, diluted with water and extracted with EtOAc. EtOAc was washed with water (×2), brine (×1) dried and concentrated. The residue was azeotroped with EtOH dried under high vacuum, obtaining 4-(5-bromo-6-nitropyridin-3-yl)morpholine (1.21 g, 4.20 mmol, 96% yield) as a light yellow solid. LCMS (m/z): 288.2 (MH⁺), 0.65 min. 1H NMR (400 MHz, CDCl₃) δ ppm 8.08-7.99 (d, J=2.3 Hz, 1 H) 7.41 (d, J=2.3 Hz, 1 H) 3.98-3.81 (m, 4 H) 3.45-3.30 (m, 4 H).

Step 6. 3-bromo-5-morpholinopyridin-2-amine 4-(5-Bromo-6-nitropyridin-3-yl)morpholine (95 mg, 0.33 mmol) was dissolved in EtOH (12 mL) and water (3.0 mL) was added, followed by SnCl₂ (313 mg, 1.65 mmol). The reaction mixture was heated to 80° C. for 2 h, cooled to room temperature and diluted with DCM. The two phases were separated, the organic phase was washed with water. The water phase was back extracted with DCM. The pH was adjusted to 12 with 6N NaOH and the mixture was further extracted with DCM. The organic extracts were combined, dried (Na₂SO₄) and evaporated under reduced pressure obtaining the desired 3-bromo-5-morpholinopyridin-2-amine (71.5 mg, 84%). LCMS (m/z): 260.0 (MH⁺), 0.37 min.
Alternate Method To a solution of 4-(5-Bromo-6-nitropyridin-3-yl)morpholine (2 g, 6.9 mmol) in MeOH (150 mL) in a round bottom flask was added Zn dust (4.54 g, 69.4 mmol). The reaction mixture was cooled to 0° C. Solid NH₄Cl (3.71 g, 69.4 mmol) was added in portions, over 5 min. The heterogeneous reaction mixture was stirred at room temperature for 2 h, filtered through a plug of Celite washing the filter cake with methanol and ethanol. The filtrate was concentrated to a brownish solid which was purified by flash column chromatography on silica gel (ISCO, 80 g column, 0-70% EtOAc/heptane in 15 min and 70% EtOAc to 25 min), obtaining 3-bromo-5-morpholinopyridin-2-amine (936 mg, 52.2%) as a slightly off white solid. LCMS (m/z): 258.2 (MH⁺), 0.35 min; 1H NMR (400 MHz, CDCl₃) δ ppm 7.75 (d, J=2.3 Hz, 1 H) 7.40-7.30 (m, 1 H) 4.66 (br. s., 2 H) 3.91-3.74 (m, 4 H) 3.07-2.90 (m, 4 H).

Step 7. 5-Morpholino-3-(4,4,5,5-tetramethyl-1,3,2-dioxaborolan-2-yl)pyridin-2-amine 3-bromo-5-morpholinopyridin-2-amine (36 mg, 0.14 mmol), bis(pinacolato)diboron (70.8 mg, 0.28 mmol), potassium acetate (41.1 mg, 0.42 mmol) and tricyclohexylphosphine (5.9 mg, 0.021 mmol) were dissolved in 1,4-dioxane (1.5 mL) in a pressure vessel. The mixture was sparged with N₂ for 5 min and palladium diacetate (3.1 mg, 0.014 mmol) was added. The reaction mixture was heated to 110° C. for 16 h, cooled to room temperature and diluted with ethyl acetate. SyliaBondDMT was added, the mixture was stirred for 1 h, filtered over a Celite pad and concentrated, obtaining 21.3 mg of a solid which contains the desired 5-morpholino-3-(4,4,5,5-tetramethyl-1,3,2-dioxaborolan-2-yl)pyridin-2-amine. This solid was used in the next step without further purification. LCMS (m/z): 224.0 (MH⁺), 0.33 min (for boronic acid).

Synthesis of 3-bromo-5-((2R,4R)-2-methyltetrahydro-2H-pyran-4-yl)pyrazin-2-amine and 3-bromo-5-((2S,4S)-2-methyltetrahydro-2H-pyran-4-yl)pyrazin-2-amine

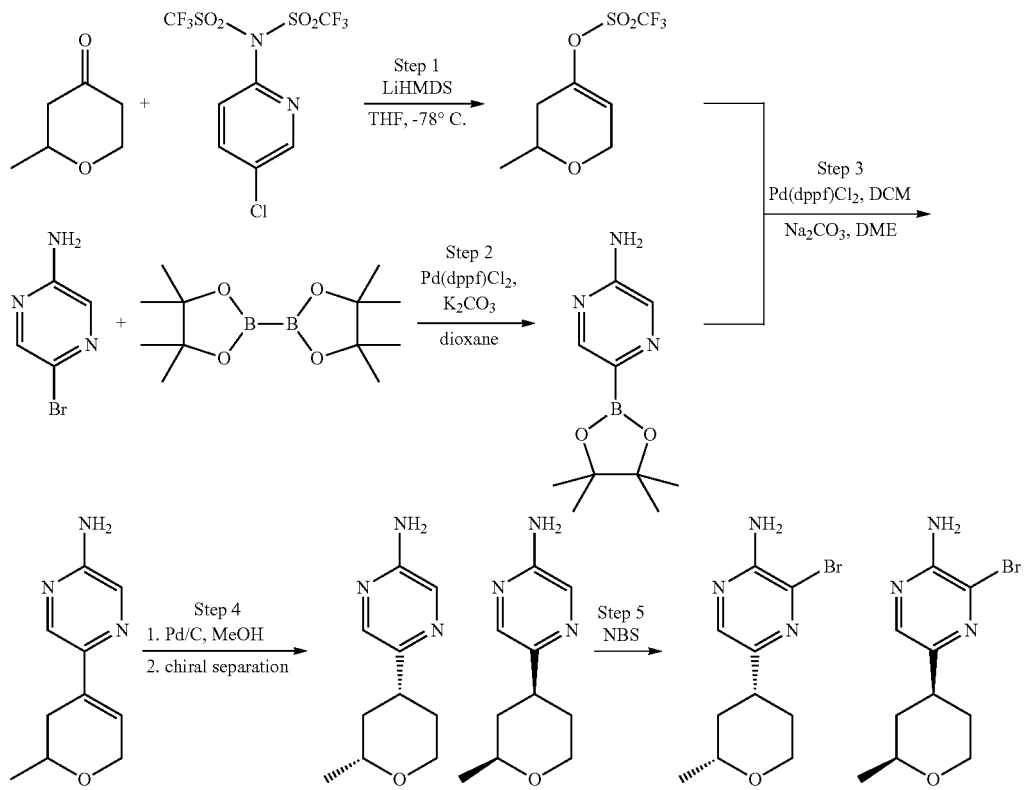

Scheme 22

Step 1. 2-methyl-3,6-dihydro-2H-pyran-4-yl trifluoromethanesulfonate

To a solution of 2-methyldihydro-2H-pyran-4(3H)-one (2 g, 17.52 mmol) in THF (8.76 mL) was added LiHMDS (18.40 mL, 18.40 mmol) dropwise at −78° C. The reaction mixture was stirred at −78° C. for 1.5 h, then N-(5-chloropyridin-2-yl)-1,1,1-trifluoro-N-((trifluoromethyl)sulfonyl)methanesulfonamide (7.22 g, 18.40 mmol) in THF (17 mL) was added at −78° C. The mixture was stirred at −78° C. for 1 h, and then allowed to warm up to room temperature, and stirred overnight. The reaction was monitored by TLC. After quenched with sat NaHCO₃, The reaction mixture was extracted with EtOAc 3 times. The combined organic layers were washed with water, brine, and dried over anhydrous sodium sulfate. Filtered and concentrated in vacuo. The desire compound (4.2 g, 17.06 mmol) was obtained as a brown oil by flash column chromatography eluting with 30% EtOAc in heptane.

Step 2. 5-(4,4,5,5-tetramethyl-1,3,2-dioxaborolan-2-yl)pyrazin-2-amine

To a solution of 5-bromopyrazin-2-amine (1 g, 5.75 mmol), bis(pinacolato)diboron (2.92 g, 11.49 mmol), and PdCl₂(dppf)CH₂Cl₂ adduct (0.469 g, 0.575 mmol) in dioxane (16.42 mL) was added potassium acetate (1.692 g, 17.24 mmol) just right after degassing. The reaction mixture was heated in microwave at 120° C. for 20 min. Diluted with EtOAc, and the reaction mixture was filtered through Celite. Concentrated, and the crude product was used for next step without further purification. LCMS (m/z): 140 (MH⁺ for boronic acid), 0.12 min.

Step 3. 5-(2-methyl-3,6-dihydro-2H-pyran-4-yl)pyrazin-2-amine

To a solution of 2-methyl-3,6-dihydro-2H-pyran-4-yl trifluoromethanesulfonate (0.637 g, 2.88 mmol), 5-(4,4,5,5-tetramethyl-1,3,2-dioxaborolan-2-yl)pyrazin-2-amine (0.914 g, 3.74 mmol), and PdCl₂(dppf)-CH₂Cl₂ adduct (0.235 g, 0.288 mmol) in DME (9.82 mL) was added 2M Na₂CO₃ (3.27 mL). The reaction mixture was heated at microwave synthesizer (120° C., 10 min). Ethyl acetated was added, and washed with sat NaHCO₃, and water. Then the desired compound was extracted to 1N HCl aqueous layer, and washed with EtOAc. Basified with 2N NaOH, and the product was extracted to EtOAc layer. EtOAc organic layer was washed with water and dried over Na₂SO₄. Filtered and concentrated to provide 250 mg of desired compound. LCMS (m/z): 192.2 (MH⁺), 0.40 min.

Step 4. 5-((2R,4R)-2-methyltetrahydro-2H-pyran-4-yl)pyrazin-2-amine

To a solution of 5-(2-methyl-3,6-dihydro-2H-pyran-4-yl)pyrazin-2-amine (250 mg, 1.307 mmol) in MeOH (13.100 mL) was added Pd/C (278 mg, 0.261 mmol). The solution was degassed by $N_2$ stream for 10 min. After flushed by $H_2$ gas, hydrogen balloon was equipped. The reaction mixture was stirred for 25 h. After filtered through Celite, the volatile material was removed to give the crude product, which was purified with flash chromatography eluting with 0-10% of MeOH in DCM to provide 180 mg of diastereomers. Then chiral separation (ChiralPak 5mic AD column, 4.6×100 (mm), 5 mL/min, EtOH+0.1% DEA=15%) provided 40 mg of 5-((2R,4R)-2-methyltetrahydro-2H-pyran-4-yl)pyrazin-2-amine (Rt=1.32 min; LCMS (m/z): 194.2 (MH$^+$), 0.44 min) in 22% yield and 30 mg of desired 5-((2S,4S)-2-methyltetrahydro-2H-pyran-4-yl)pyrazin-2-amine (Rt=1.83 min; LCMS (m/z): 194.2 (MH$^+$), 0.44 min) in 16% yield.

Step 5. 3-bromo-5-((2R,4R)-2-methyltetrahydro-2H-pyran-4-yl)pyrazin-2-amine and 3-bromo-5-((2S,4S)-2-methyltetrahydro-2H-pyran-4-yl)pyrazin-2-amine To a solution of 5-((2R,4R)-2-methyltetrahydro-2H-pyran-4-yl)pyrazin-2-amine (40 mg, 0.207 mmol) in acetonitrile (3 mL) was added NBS (35.0 mg, 0.197 mmol) at 0° C. The reaction mixture was stirred at 0° C. for 15 min. After quenched with $NaHCO_3$, the reaction mixture was extracted with EtOAc three times. The organic layers were combined and washed with water, and brine. Dried over $Na_2SO_4$, filtered and concentrated to afford 47 mg of 3-bromo-5-((2R,4R)-2-methyltetrahydro-2H-pyran-4-yl)pyrazin-2-amine, which was used as it was. LCMS (m/z): 274 (MH$^+$), 0.64 min. For 5-((2S,4S)-2-methyltetrahydro-2H-pyran-4-yl)pyrazin-2-amine, following the above method, 3-bromo-5-((2S,4S)-2-methyltetrahydro-2H-pyran-4-yl)pyrazin-2-amine was obtained. LCMS (m/z): 274 (MH$^+$), 0.65 min. The absolute stereochemistry of the products were assigned arbitrarily.

Synthesis of 3-bromo-5-cyclopropylpyrazin-2-amine

Step 1. 5-cyclopropylpyrazin-2-amine

To a microwave vial was charged with 5-bromopyrazin-2-amine (400 mg, 2.3 mmol), 2-cyclopropyl-4,4,5,5-tetramethyl-1,3,2-dioxaborolane (1.16 g, 6.9 mmol), KOt-Bu (1M in t-BuOH, 9.2 mL), 1,4-dioxane (10 mL), and water (0.10 mL), and the mixture was purged with Argon, followed by addition of Palladium tetrakis (266 mg, 0.23 mmol) and final Argon purge, then the mixture was sealed and heated at 150° C. via microwave reactor for 20 min. To the reaction mixture was added 2nd portion of PalladiumTetrakis (266 mg) and the reaction was heated at 160° C. via microwave reactor for 20 min. The reaction mixture was filtered through a thin layer of Celite, and the filtrate was concentrated. The residue was triturated with EtOAc (6 mL), and the precipitates were removed via centrifugation and filtration. The EtOAc supernatant was back extracted with aqueous TFA solution (3×3 mL, TFA/water1 mL/10 mL). The TFA solutions were combined, diluted with acetonitrile (10 mL), frozen and lyophilized to afford 5-cyclopropylpyrazin-2-amine in a yellow powder. The product after lyophilization was transferred to a vial, basified to pH>12 with sat. $Na_2CO_3$ (3 mL), extracted with EtOAc (4×6 mL), and the EtOAc extracts were combined, and concentrated and further dried under high vacuum, and final 5-cyclopropylpyrazin-2-amine free base was obtained (79 mg, 25.4% yield). LCMS (m/z): 136.1 (MH$^+$), 0.30 min. 1H NMR (CD$_3$OD) δ ppm 8.29 (d, J=1.2 Hz, 1H), 7.70 (d, J=1.6 Hz, 1H), 2.00-2.08 (m, 1H), 0.94-1.00 (m, 2H), 0.87-0.93 (m, 2H).

Step 2. 3-bromo-5-cyclopropylpyrazin-2-amine

A solution of 5-cyclopropylpyrazin-2-amine (79 mg, 0.584 mmol) in acetonitrile (10 mL) was cooled down to 0° C., and treated with gradual addition of NBS (140 mg, 1.46 mmol) over the course of 1 hour while closely monitoring reaction progress by LCMS. The reaction mixture was concentrated and the residue was triturated with EtOAc (2×5 mL) and the EtOAc supernatants were separated via centrifugation, combined and washed with 1N NaOH (3×1 mL) and the EtOAc layer was dried (over $Na_2SO_4$), concentrated and a crude brown reside was obtained. The crude product was further purified by flash chromatography on silica gel eluted with gradient EtOAc/CH$_2$Cl$_2$ (0-30%) to afford 3-bromo-5-cyclopropylpyrazin-2-amine in colorless solid (38.2 mg, 38.5% yield). LCMS (m/z): 214.0/216.0 (MH$^+$), 0.64 min.

Synthesis of 3'-methyl-5-(4,4,5,5-tetramethyl-1,3,2-dioxaborolan-2-yl)-[3,4'-bipyridin]-6-amine Scheme 23

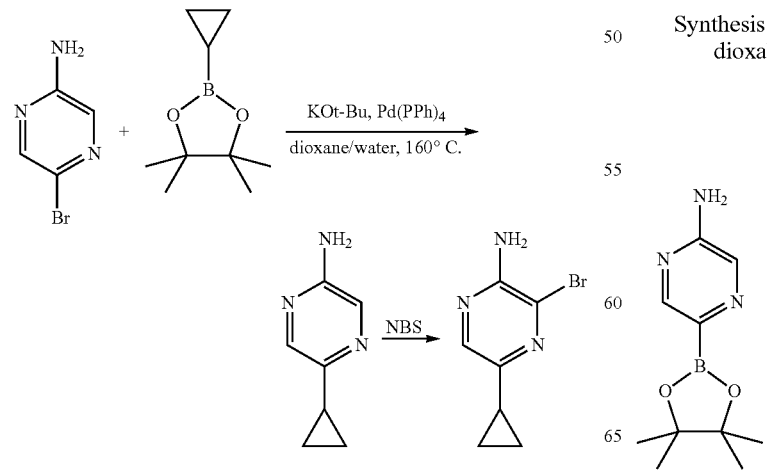

Scheme 24

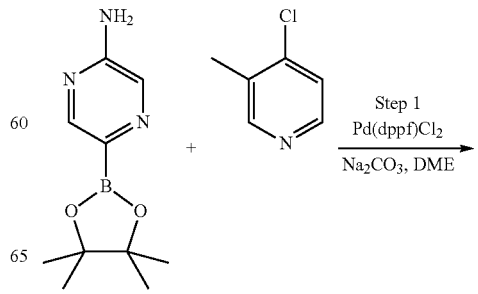

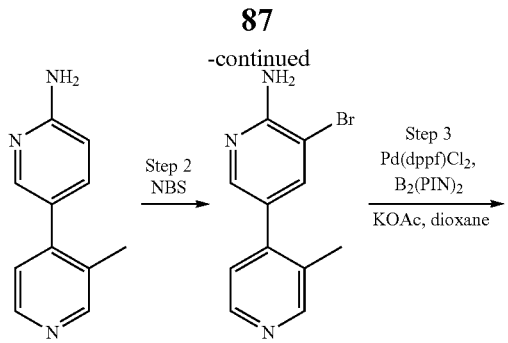

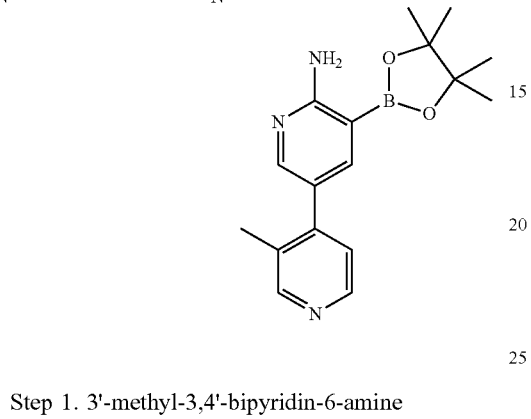

Step 1. 3'-methyl-3,4'-bipyridin-6-amine

To a solution of (2 g, 9.09 mmol) in DME (45.4 mL) was added 4-chloro-3-methylpyridine (1.739 g, 13.63 mmol), and PdCl$_2$(dppf)-CH$_2$Cl$_2$ Adduct (0.742 g, 0.909 mmol) and 2 M Na$_2$CO$_3$ (15.15 mL), mixture was purged with nitrogen for 5 min, The reaction mixture in sealed glass bomb was heated to 120° C. overnight. The reaction mixture was extracted by EtOAc, the organic layers and washed with brine water The organic was dried by Na$_2$SO$_4$ anhydrous, filtered and concentrated to yield crude product. The crude material was purified by flash chromatography (0-100% EtOAc/heptane) to yield 3'-methyl-3,4'-bipyridin-6-amine (255 mg, 1.377 mmol, 15.15% yield). LCMS (m/z): 406.3 (MH$^+$), 0.47 min

Step 2. 5-bromo-3'-methyl-3,4'-bipyridin-6-amine

To an ice cold solution of 3'-methyl-3,4'-bipyridin-6-amine (250 mg, 1.350 mmol) in DCM (4499 μL) was added NBS (264 mg, 1.485 mmol) in two portions. The reaction mixture was stirred at 0° C. for 2 h. Reaction mixture was diluted with ethyl acetate, and was washed with water, brine, dried and concentrated. Residue was treated heptane, the solid filtered to give 5-bromo-3'-methyl-3,4'-bipyridin-6-amine (350 mg, 1.325 mmol, 98 yield) as brown color solid, used in next step reaction without purification. LCMS (m/z): 264.4/266.4 (MH$^+$), 0.32 min; $^1$H NMR (400 MHz, CDCl$_3$) δ ppm 8.51 (s, 1 H), 8.47 (d, J=5.1 Hz, 1 H), 8.04 (d, J=2.0 Hz, 1 H), 7.69 (d, J=2.0 Hz, 1 H), 7.12 (d, J=5.1 Hz, 1 H), 5.06 (br. s., 2 H), 2.32 (s, 3 H).

Step 3. 3'-methyl-5-(4,4,5,5-tetramethyl-1,3,2-dioxaborolan-2-yl)-3,4'-bipyridin-6-amine To a suspension of (5-bromo-3'-methyl-3,4'-bipyridin-6-amine (100 mg, 0.379 mmol) in 1,4-dioxane (947 μL) was added bispinB (288 mg, 1.136 mmol) and potassium acetate, (186 mg, 1.893 mmol). Mixture was purged with nitrogen for 3 min, then PdCl$_2$(dppf)CH$_2$Cl$_2$ adduct (30.9 mg, 0.038 mmol) was added. The reaction mixture was heated to 120° C. in microwave for 10 min, Formation of desired product was confirmed. still some starting material left, resubmitted for microwave 120° C. for 10 min. The reaction mixture was filtered through filter and rinsed with dioxane (0.7 mL), the filtrate solution was used in next step reaction without purification. LCMS (m/z): 230.1 (MH$^+$ for boronic acid), 0.22 min.

Synthesis of 1-(4-(5-amino-6-bromopyrazin-2-yl)piperidin-1-yl)ethanone

Scheme 25

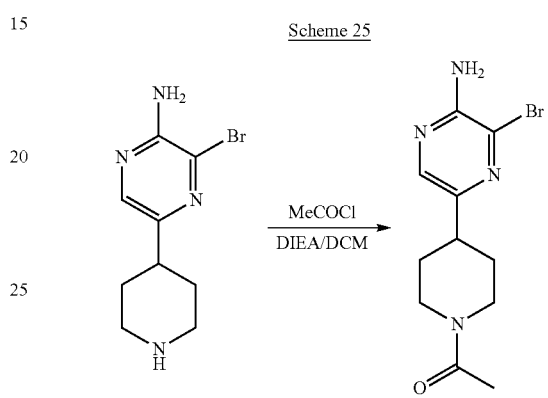

To 3-bromo-5-(piperidin-4-yl)pyrazin-2-amine (50 mg, 0.194 mmol) in DCM (4 mL) in ice bath was added DIEA (0.136 mL, 0.778 mmol) and acetyl chloride (0.017 mL, 0.233 mmol). The reaction mixture was stirred at in ice bath 30 min. The reaction mixture was partitioned between DCM and water. The DCM layer was separated and washed with brine. Dried over sodium sulfate, filtered and evaporated. Proceed for next step. LCMS (m/z): 299.1/301.1 (MH$^+$), 0.508 min. 1H NMR (400 MHz, CD$_3$OD) δ ppm 7.81-7.69 (m, 2 H), 7.62-7.45 (m, 2 H), 7.37-7.09 (m, 6 H), 6.5 (dd, J=8.61, 2.35 Hz, 1 H), 6.50 (dd, J=13.50, 2.15 Hz, 1 H), 5.17-5.01 (m, 1 H), 4.55 (d, J=13.30 Hz, 1 H), 3.94 (d, J=13.69 Hz, 1 H), 3.83-3.63 (m, 2 H), 2.88 (tt, J=11.84, 3.62 Hz, 1 H), 2.67 (td, J=12.91, 2.35 Hz, 1 H), 2.03 (s, 3 H), 1.96-1.79 (m, 2 H), 1.78-1.50 (m, 2 H).

Synthesis of 3-bromo-5-(1-methyl-1H-pyrazol-4-yl)pyridin-2-amine

Scheme 26

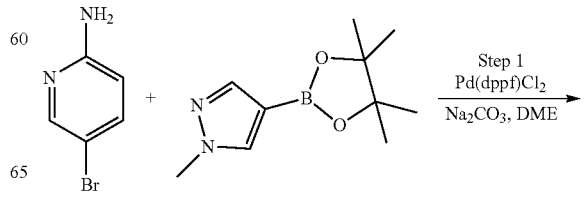

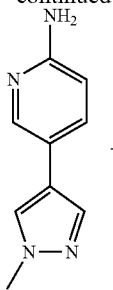 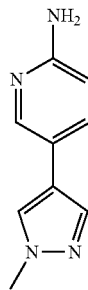 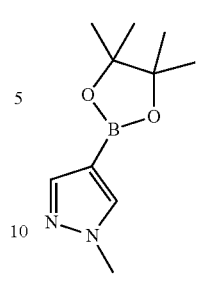 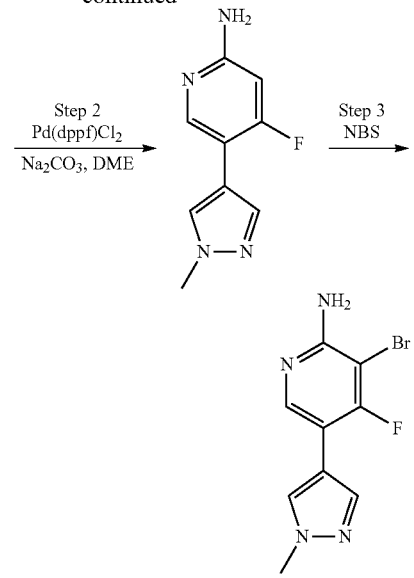

Step 1.
5-(1-methyl-1H-pyrazol-4-yl)pyridin-2-amine

To a microwave vial was charged 5-bromopyridin-2-amine (500 mg, 2.89 mmol), 1-methyl-4-(4,4,5,5-tetramethyl-1,3,2-dioxaborolan-2-yl)-1H-pyrazole (1.2 g, 5.78 mmol), aqueous $Na_2CO_3$ (2 M, 5.78 mL), $PdCl_2(dppf)$ $CH_2Cl_2$ (0.236 g) and DME (15 mL), and the reaction mixture was purged with Argon for 5 min, sealed and heated with microwave reactor at 115° C. for 20 min. The DME layer of reaction mixture was collected, concentrated and the residue was subjected to flash column chromatography on silica gel eluted with gradient Methanol/$CH_2Cl_2$ and 5-O-methyl-1H-pyrazol-4-yl)pyridin-2-amine was obtained as light brown solid (383 mg, 76% yield). LCMS (m/z): 175.2 (MH$^+$), 0.34 min.

Step 2. 3-bromo-5-(1-methyl-1H-pyrazol-4-yl)pyridin-2-amine

To 5-(1-methyl-1H-pyrazol-4-yl)pyridin-2-amine (380 mg, 2.18 mmol) acetonitrile (30 mL) solution at 0° C. was added NBS (388 mg, 2.18 mmol) and the reaction mixture was stirred at 0° C. for 30 min, then at room temperature for additional 40 min. The reaction mixture was then concentrated, redissolved in methanol, to it was added solid LiOH (80 mg), sonicated and concentrated, the residue was triturated with water (2×5 mL), and the supernatants were discarded. the residue was dried under high vacuum, then triturated with EtOAc (2×8 mL), and the supernatants were collected, combined, and concentrated and the light brown residue was obtained as crude 3-bromo-5-(1-methyl-1H-pyrazol-4-yl)pyridin-2-amine. LCMS (m/z): 253.0/255.0 (MH$^+$), 0.38 min.

Synthesis of (S)-4-(2-amino-4-fluoro-5-(1-methyl-1H-pyrazol-4-yl)pyridin-3-yl)-2-fluoro-N-(2-hydroxy-1-phenylethyl)benzamide

Scheme 27

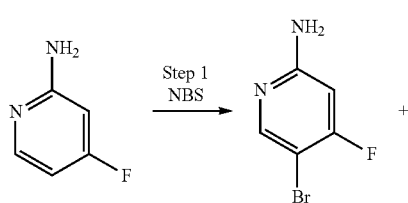

Step 1. 5-bromo-4-fluoropyridin-2-amine

To a solution of 4-fluoropyridin-2-amine (400 mg, 3.57 mmol) in acetonitrile (35.7 mL) was added NBS (648 mg, 3.64 mmol) in three portions at 0° C. The reaction mixture was stirred at 0° C. for 20 min. LCMS showed the reaction complete. After quenched with sat $Na_2S_2O_3$ and $NaHCO_3$, stirred for 30 min. The reaction mixture was extracted with EtOAc 3 times. Washed by sat $NaHCO_3$, water and brine. Dried and concentrated. The crude material was triturated with ether and taken to the next step without further purification. LCMS (m/z): 192.9 (MH$^+$), 0.32 min.

Step 2. 4-fluoro-5-(1-methyl-1H-pyrazol-4-yl)pyridin-2-amine

To the reaction mixture of 5-bromo-4-fluoropyridin-2-amine (369 mg, 1.932 mmol), 1-methyl-4-(4,4,5,5-tetramethyl-1,3,2-dioxaborolan-2-yl)-1H-pyrazole (603 mg, 2.90 mmol), $PdCl_2(dppf)DCM$ (141 mg, 0.193 mmol) and DME (9.660 μL), 2M $Na_2CO_3$ (3.220 mL) was added. The reaction mixture was heated at microwave synthesizer (120° C., 12 min). To the reaction mixture, anhydrous sodium sulfate was added, filtered, and concentrated. The crude product was purified by flash chromatography eluting with 0-100% EtOAc (containing 10% of MeOH/heptane to provide 280 mg of desired product in 75% yield. LCMS (m/z): 193.1 (MH$^+$), 0.35 min.

Step 3. 3-bromo-4-fluoro-5-(1-methyl-1H-pyrazol-4-yl)pyridin-2-amine

To a solution of 4-fluoro-5-(1-methyl-1H-pyrazol-4-yl)pyridin-2-amine (150 mg, 0.780 mmol) in acetonitrile (7.805 mL) was added NBS (142 mg, 0.796 mmol) in three portions at 0° C. The reaction mixture was stirred at 0° C. for 20 min. LCMS showed the reaction complete. After quenched with sat $Na_2SO_3$ and $NaHCO_3$, stirred for 30 min. The reaction mixture was extracted with EtOAc 3 times. Filtered out solid. The solid was not the desired product. The EtOAc layers were washed by sat $NaHCO_3$, water and brine. Dried and concentrated. The crude material was purified with flash chromatography eluting with 0-100% EtOAc (containing 10% MeOH/heptane to provide 30 mg of desired product. LCMS (m/z): 273.1 (MH$^+$), 0.46 min.

Synthesis of (+/−)-(1S,3R)-3-(5-amino-6-bromopyrazin-2-yl)cyclopentanol, (+/−)-(1R,3R)-3-(5-amino-6-bromopyrazin-2-yl)cyclopentanol, and (+/−)-3-bromo-5-((1R,3R)-3-methoxycyclopentyl)pyrazin-2-amine

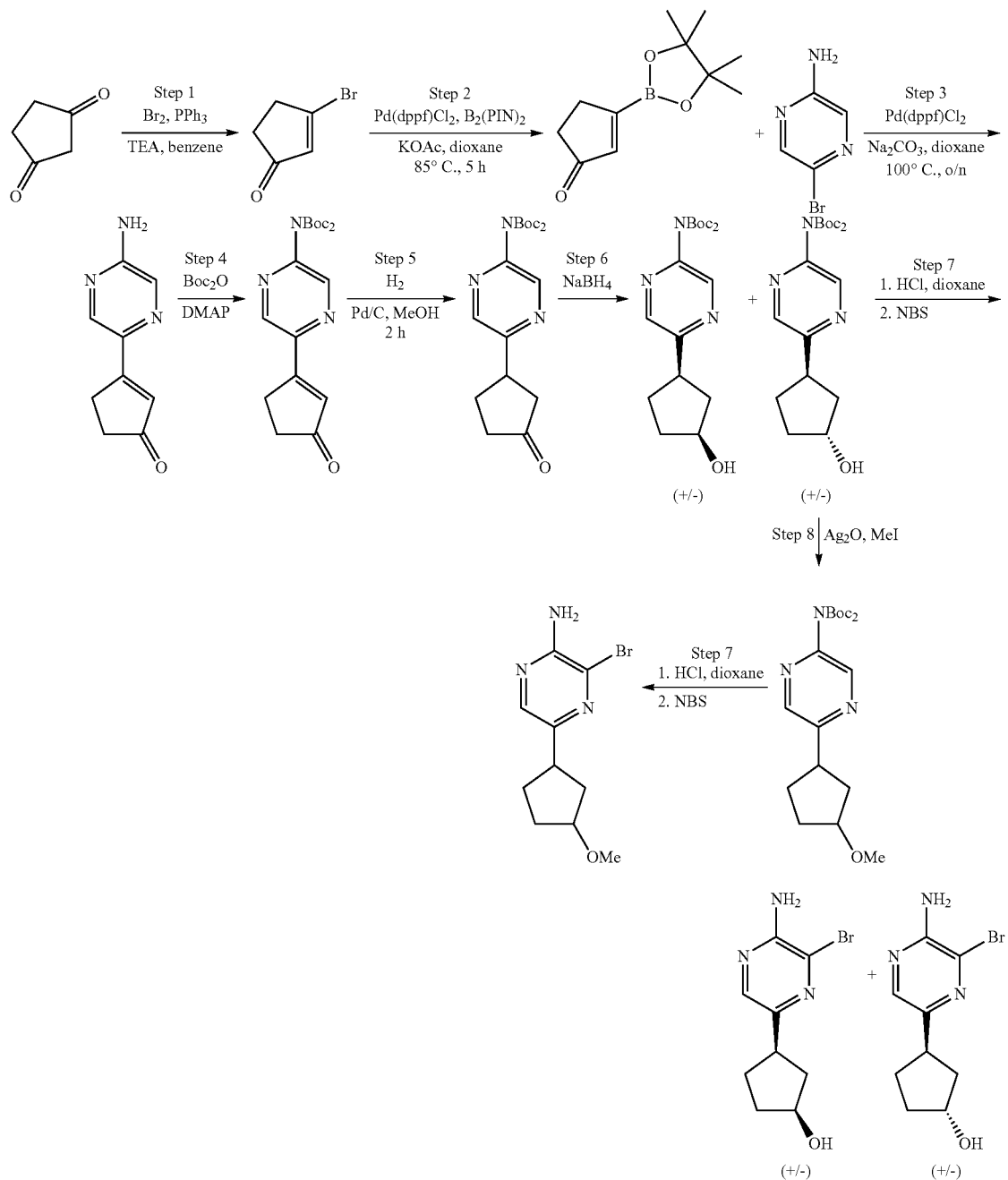

Scheme 28

Step 1. 3-bromocyclopent-2-enone

To a solution of PPh$_3$ (44.1 g, 168 mmol) in benzene (510 mL), Br$_2$ (8.67 mL, 168 mmol) was added dropwise at 0° C., the solution turned to yellow suspension, then TEA (23.44 mL, 168 mmol) was added slowly. To the mixture was added cyclopentane-1,3-dione (15 g, 153 mmol) in benzene (100 mL). The reaction mixture was stirred at room temperature for overnight. Ether 200 mL was added, the reaction mixture was then filtered. The filtrate was concentrated, the residue was treated with Et$_2$O, the solid was filtered, repeated one more time. The crude product was used in next step reaction. LCMS (m/z): 160.9 (MH$^+$), 0.35 min.

Step 2. 3-(4,4,5,5-tetramethyl-1,3,2-dioxaborolan-2-yl)cyclopent-2-enone

To a solution of 3-bromocyclopent-2-enone (13 g, 81 mmol) in dioxane (161 mL) was added $B_2(PIN)_2$ (41.0 g, 161 mmol) and $PdCl_2(dppf)CH_2Cl_2$ (2.95 g, 4.04 mmol). The reaction mixture was degassed for 15 min by $N_2$ bubbling. Then KOAc (23.77 g, 242 mmol) was added. The reaction mixture was heated at 90° C. overnight. After cooling down, the reaction mixture was filtered off through a frit glass filter and rinsed with dioxane (160 mL), the filtrate was concentrated in vacuo yielding crude 3-(4,4,5,5-tetramethyl-1,3,2-dioxaborolan-2-yl)cyclopent-2-enone, which was used for the next step without purification. LCMS (m/z): 126.9 ($MH^+$), 0.17 min.

Step 3. 3-(5-aminopyrazin-2-yl)cyclopent-2-enone

To 3-(4,4,5,5-tetramethyl-1,3,2-dioxaborolan-2-yl)cyclopent-2-enone (2.99 g, 14.37 mmol) (the filtrate from last step) was added 2-amino-5 bromopyrazine (2.5 g, 14.37 mmol), $PdCl_2(dppf)$-$CH_2Cl_2$ (1.173 g, 1.437 mmol), $Na_2CO_3$ (7.61 g, 71.8 mmol) and water (17.96 mL) the reaction mixture was stirred at 100° C. oil bath for overnight, filtered through Celite. The reaction mixture was then extracted by EtOAc. The organic was then used 3N HCl (20 mL) washed 2 times, and water 50 mL once, the AQ was then neutralized by NaOH to pH=8, the reaction mixture was then extracted by $CHCl_3$/IPA (7:3) 3 times, the organic was dried and concentrated and used as it. LCMS (m/z): 176.1 ($MH^+$), 0.32 min.

Step 4. N,N-di-tert-butyl (5-(3-oxocyclopent-1-en-1-yl)pyrazin-2-yl)carbamate To a solution of 3-(5-aminopyrazin-2-yl)cyclopent-2-enone (500 mg, 2.85 mmol) in DCM (9.5 mL) was added $Boc_2O$ (1988 µl, 8.56 mmol) and DMAP (523 mg, 4.28 mmol), the reaction mixture is dark solution, the reaction mixture was stirred at room temperature for 5 h. The reaction mixture was concentrated and purified by flash chromatography (0-40% EtOAc/heptane) to give N,N-di-tert-butyl (5-(3-oxocyclopent-1-en-1-yl)pyrazin-2-yl)carbamate in 47% yield. LCMS (m/z): 376.2 ($MH^+$) 0.96 min. $^1H$ NMR (400 MHz $CDCl_3$) δ ppm 8.77 (d, J=1.2 Hz, 1 H), 8.72 (d, J=1.2 Hz, 1 H), 6.89 (s, 1 H), 3.15 (td, J=2.3, 4.7 Hz, 2 H), 2.64 (td, J=2.4, 5.0 Hz, 2 H), 1.45-1.37 (m, 18 H).

Step 5. (+/−)-N,N-Di-tert-butyl (5-(3-oxocyclopentyl)pyrazin-2-yl)carbamate

N,N-di-tert-butyl (5-(3-oxocyclopent-1-en-1-yl)pyrazin-2-yl)carbamate (600 mg, 1.598 mmol) in methanol was purged by $N_2$ for 10 min, the Pd/C (170 mg, 0.160 mmol) was added, the reaction mixture was purged by $N_2$ for another 5 min, the reaction mixture was then charged with hydrogen balloon and stirred at room temperature for 2 h. Filtered through Celite, the filtrated was concentrated, the crude material was used in next step reaction without purification. LCMS (m/z): 378.1 ($MH^+$), 0.83 min.

Step 6. (+/−)-N,N-Di-tert-butyl (5-((1R,3R)-3-hydroxycyclopentyl)pyrazin-2-yl)carbamate and (+/−)-N,N-Di-tert-butyl (5-((1R,3S)-3-hydroxycyclopentyl)pyrazin-2-yl)carbamate (+/−)-N,N-Di-tert-butyl (5-(3-oxocyclopentyl)pyrazin-2-yl)carbamate (600 mg, 1.590 mmol) was dissolved in methanol (5299 µl), then $NaBH_4$ (90 mg, 2.385 mmol) was added, the reaction mixture was stirred at room temperature for 30 min, sat. $NH_4Cl$ added, the reaction mixture was then concentrated to remove methanol. Extracted by EtOAc, the organic was washed by sat. $NaHCO_3$ solution, water and brine, dried over anhydrous $Na_2SO_4$, concentrated to yield the crude product. The crude product was purified by flash chromatography to give (+/−)-N,N-Di-tert-butyl (5-((1R,3R)-3-hydroxycyclopentyl)pyrazin-2-yl)carbamate (24.9%). LCMS (m/z): 280.1 ($MH^+$), 0.86 min. $^1H$ NMR (400 MHz, $CDCl_3$) δ ppm 8.50-8.43 (m, 1 H), 8.43-8.33 (m, 1 H), 4.40 (br. s., 1 H), 3.58-3.45 (m, 1 H), 2.36-2.17 (m, 2 H), 2.02-1.75 (m, 5 H), 1.50-1.39 (m, 18 H). (+/−)-N,N-Di-tert-butyl (5-((1R,3S)-3-hydroxycyclopentyl)pyrazin-2-yl)carbamate (4%), LCMS (m/z): 380.1 ($MH^+$), 0.85 min. $^1H$ NMR (400 MHz, $CDCl_3$) δ ppm 8.43 (d, J=1.2 Hz, 1 H), 8.36-8.32 (m, 1 H), 4.59 (d, J=2.7 Hz, 1 H), 3.69-3.57 (m, 1 H), 2.37-2.13 (m, 2 H), 2.13-2.01 (m, 2 H), 1.93-1.68 (m, 2 H), 1.49-1.39 (m, 18 H).

Step 7. (+/−)-(1S,3R)-3-(5-amino-6-bromopyrazin-2-yl)cyclopentanol

N,N-Di-tert-butyl (5-((1R,3S)-3-hydroxycyclopentyl)pyrazin-2-yl)carbamate (35 mg, 0.092 mmol) in DCM (461 µl) was added HCl (922 µl, 3.69 mmol), the reaction mixture was stirred at room temperature overnight and concentrated to dryness yielding HCl salt. The crude product was used in next step reaction without purification. LCMS (m/z): 180.1 ($MH^+$), 0.22 min. (+/−)-(1S,3R)-3-(5-aminopyrazin-2-yl)cyclopentanol (15 mg, 0.084 mmol) was dissolved in acetonitrile (2 mL), then NBS (16.39 mg, 0.092 mmol) was added, the reaction mixture was stirred at room temperature for 30 min, water was added, the reaction mixture was then extracted by EtOAc, the organic was dried and concentrated, the crude material was used in next step reaction. LCMS (m/z): 258.1/260.2 ($MH^+$), 0.45 min. Following the above method, using (+/−)-N,N-Di-tert-butyl (5-((1R,3S)-3-hydroxycyclopentyl)pyrazin-2-yl)carbamate, (+/−)-(1R,3R)-3-(5-amino-6-bromopyrazin-2-yl)cyclopentanol was obtained. LCMS (m/z): 258.1/260.1 ($MH^+$), 0.50 min.

Step 8. N,N-Di-tert-butyl (5-(3-methoxycyclopentyl)pyrazin-2-yl)carbamate

To a solution of diastereomeric mixture of N,N-Di-tert-butyl (5-(3-hydroxycyclopentyl)pyrazin-2-yl)carbamate (50 mg, 0.132 mmol) in MeI (2.635 mL) was added silver oxide (305 mg, 1.318 mmol), the reaction mixture was capped in a reaction vial and stirred at room temperature overnight. 10 equiv. of silver oxide and 2 mL of MeI was added, the reaction mixture was stirred at room temperature for another day. The reaction mixture was filtered through Celite pad and washed with EtOAc and methanol. After the filtrate was concentrated, the crude product was purified by flash chromatography (0-40% EtOAc/heptane) yielding N,N-Di-tert-butyl (54(1R,3R)-3-methoxycyclopentyl)pyrazin-2-yl)carbamate (25 mg). LCMS (m/z): 394.1 ($MH^+$), 1.06 min.

Example 12

Synthesis of (+/−)-4-(3-amino-6-((1S,3R)-3-hydroxycyclohexyl)pyrazin-2-yl)-N-benzyl-2-fluorobenzamide

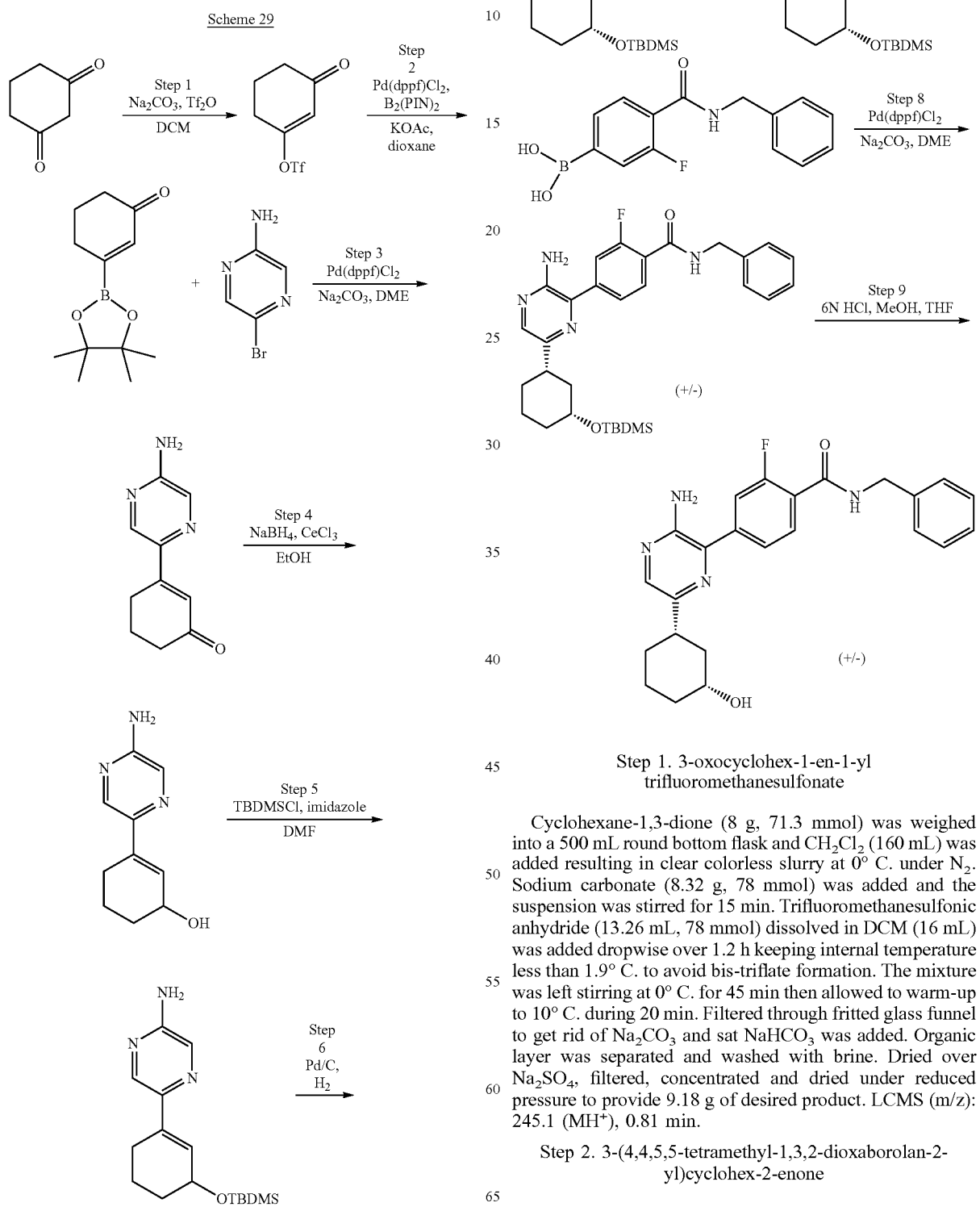

Step 1. 3-oxocyclohex-1-en-1-yl trifluoromethanesulfonate

Cyclohexane-1,3-dione (8 g, 71.3 mmol) was weighed into a 500 mL round bottom flask and $CH_2Cl_2$ (160 mL) was added resulting in clear colorless slurry at 0° C. under $N_2$. Sodium carbonate (8.32 g, 78 mmol) was added and the suspension was stirred for 15 min. Trifluoromethanesulfonic anhydride (13.26 mL, 78 mmol) dissolved in DCM (16 mL) was added dropwise over 1.2 h keeping internal temperature less than 1.9° C. to avoid bis-triflate formation. The mixture was left stirring at 0° C. for 45 min then allowed to warm-up to 10° C. during 20 min. Filtered through fritted glass funnel to get rid of $Na_2CO_3$ and sat $NaHCO_3$ was added. Organic layer was separated and washed with brine. Dried over $Na_2SO_4$, filtered, concentrated and dried under reduced pressure to provide 9.18 g of desired product. LCMS (m/z): 245.1 ($MH^+$), 0.81 min.

Step 2. 3-(4,4,5,5-tetramethyl-1,3,2-dioxaborolan-2-yl)cyclohex-2-enone

To a mixture of 4,4,4',4',5,5,5',5'-octamethyl-2,2'-bi(1,3,2-dioxaborolane) (19.09 g, 75 mmol) and potassium acetate (11.07 g, 113 mmol) was added 3-oxocyclohex-1-en-1-yl trifluoromethanesulfonate (9.18 g, 37.6 mmol) as a solution in dioxane (44.6 mL). Argon was bubbled through for 15 min, then Pd(dppf)Cl$_2$-DCM (0.824 g, 1.128 mmol) was added. The whole reaction mixture was heated at 100° C. overnight. Filtered the solution through Celite and all the solvent was evaporated. Dried under high vacuum to provide quantitative product which was used as it was. LCMS (m/z): 141 (MH$^+$ for boronic acid), 0.43 min.

Step 3. 3-(5-aminopyrazin-2-yl)cyclohex-2-enone

Into a 500 mL glass weighed 3-(4,4,5,5-tetramethyl-1,3,2-dioxaborolan-2-yl)cyclohex-2-enone (4.1 g, 18.46 mmol), 5-bromopyridin-2-amine (4.15 g, 24.00 mmol) was added as a solution in dioxane (69.2 mL), followed by sat Na$_2$CO$_3$ (23.08 mL) and Pd(dppf)Cl$_2$-DCM (1.350 g, 1.846 mmol). The whole mixture was then degassed by bubbling Ar through for 15 min and refluxed overnight. EtOAc and water was added, and stirred for 30 min. Organic was separated and the aqueous layer was extracted with EtOAc three times. Organic layers were combined and dried over Na$_2$SO$_4$, filtered and concentrated. Purified with flash chromatography eluting with 0-100% EtOAc (containing 10% of MeOH)/heptane to provide 2 g of desired product. LCMS (m/z): 190 (MH$^+$), 0.42 min.

Step 4. 3-(5-aminopyrazin-2-yl)cyclohex-2-enol

To a solution of 3-(5-aminopyrazin-2-yl)cyclohex-2-enone (150 mg, 0.793 mmol) in ethanol (2643 µL) was added cerium (III) chloride (293 mg, 1.189 mmol) at room temperature. The reaction mixture was stirred at room temperature for 1 h until all the materials were dissolved. The reaction mixture was then cooled to 0° C. and sodium borohydride (45.0 mg, 1.189 mmol) was added in portions. The reaction mixture was stirred upon warming up to room temperature for 2 h. The reaction mixture was cooled to 0° C. and 2 mL of water was slowly added until the bubbles clearly showed up and then disappeared, Continued to stir for 30 min. Then, sodium sulfate was added and stirred for 30 min. Filtered and dried under high vacuum to provide 149 mg of desired product. LCMS (m/z): 192.1 (MH$^+$), 0.46 min.

Step 5. 5-(3-((tert-butyldimethylsilyl)oxy)cyclohex-1-en-1-yl)pyrazin-2-amine

To a solution of 3-(5-aminopyrazin-2-yl)cyclohex-2-enol (149 mg, 0.779 mmol) in DMF (5.5 mL) at 0° C. were added tert-butylchlorodimethylsilane (294 mg, 1.95 mmol)) and 1H-imidazole (212 mg, 3.12 mmol). The reaction mixture was stirred at room temperature overnight. After quenched with sat NaHCO$_3$, the reaction mixture was extracted with EtOAc 3 times. The combined organic layers were dried over anhydrous sodium sulfate. Filtered and concentrated in vacuo. The crude product was purified with flash chromatography eluting with 0-100% of EtOAc/heptane to provide 238 mg of crude product which was used as it was. LCMS (m/z): 306.9 (MH$^+$), 1.04 min.

Step 6. 5-((1R,3S)-3-((tert-butyldimethylsilyl)oxy)cyclohexyl)pyrazin-2-amine

A mixture of 5-(3-((tert-butyldimethylsilyl)oxy)cyclohex-1-en-1-yl)pyrazin-2-amine (238 mg, 0.779 mmol) and Pd/C (10%) (50 mg, 0.779 mmol) in MeOH (7.79 mL) was stirred under H$_2$ atmosphere for 3 h. LCMS indicated about 60% conversion. More Pd/C (20 mg) was added, and stirred about another 4 h. LCMS indicated still little amount of starting material left. More Pd/C (20 mg) was added and stirred overnight. Catalyst was filtered out and solvent was evaporated. The residue was purified with flash chromatography eluting with 0-100% of EtOAc/heptane to provide 110 mg of desired cis racemate compound. LCMS (m/z): 308.4 (MH$^+$), 1.01 min.

Step 7. 3-bromo-5-(3-((tert-butyldimethylsilyl)oxy)cyclohexyl)pyrazin-2-amine

To a solution of 5-((1R,3S)-3-((tert-butyldimethylsilyl)oxy)cyclohexyl)pyrazin-2-amine (110 mg, 0.358 mmol) in acetonitrile (5.50 mL) was added NBS (66.9 mg, 0.376 mmol) at 0° C. The reaction mixture was stirred at 0° C. for 15 min. After quenched with sat sodium thiosulfate and sat NaHCO$_3$, extracted with EtOAc three times. The organic layers were combined and washed with brine, dried over Na$_2$SO$_4$, filtered and concentrated to afford 138 mg of desired cis racemate compound, which was used as it was. LCMS (m/z): 388 (MH$^+$), 0.72 min.

Step 8. 4-(3-amino-6-(3-((tert-butyldimethylsilyl)oxy)cyclohexyl)pyrazin-2-yl)-N-benzyl-2-fluorobenzamide To 3-bromo-5-(3-((tert-butyldimethylsilyl)oxy)cyclohexyl)pyrazin-2-amine (68 mg, 0.176 mmol) in 2 mL MW vial was added (4-(benzylcarbamoyl)-3-fluorophenyl)boronic acid (72.1 mg, 0.264 mmol), PdCl$_2$(dppf)-DCM (12.88 mg, 0.018 mmol), DME (1.32 mL) and 2M Na$_2$CO$_3$ solution (0.44 mL). The reaction mixture was heated at microwave synthesizer (12 min, 120° C.). The reaction mixture was diluted with EtOAc and washed with water three times, dried over Na$_2$SO$_4$, filtered and concentrated. The crude product was purified by flash chromatography eluting with 0-100% of EtOAc (containing 10% of MeOH)/heptane to provide 60 mg of crude cis racemate compound which was taken to the next reaction without further purification. LCMS (m/z): 535.4 (MH$^+$), 1.31 min.

Step 9. 4-(3-amino-6-((1R,3S)-3-hydroxycyclohexyl)pyrazin-2-yl)-N-benzyl-2-fluorobenzamide A mixture of 4-(3-amino-6-(3-((tert-butyldimethylsilyl)oxy)cyclohexyl)pyrazin-2-yl)-N-benzyl-2-fluorobenzamide (61 mg, 0.114 mmol) in 6N HCl (0.29 mL), THF (0.57 mL) and MeOH (0.285 mL) was stirred for 2 h. Solid sodium bicarbonate was added to neutralize the reaction mixture. Solvent was evaporated and 25% of the residue was dissolved in DMSO, and purified with auto-prep to provide 15 mg of desired cis racemate compound as a TFA salt. LCMS (m/z): 421.3 (MH$^+$), 0.74 min. 1H NMR (400 MHz, MeOD-d4) δ ppm 7.82-7.69 (m, 2 H) 7.62-7.45 (m, 2 H) 7.37-7.12 (m, 5 H) 4.52 (s, 2 H) 3.66-3.52 (m, 1 H) 2.75-2.60 (m, 1 H) 2.11-2.01 (m, 1 H) 1.97-1.70 (m, 3 H) 1.52-1.29 (m, 3 H) 1.24-1.08 (m, 1 H).

Synthesis of (+/−)-3-bromo-5-((1R,3S)-3-methoxy-cyclohexyl)pyrazin-2-amine

Scheme 30

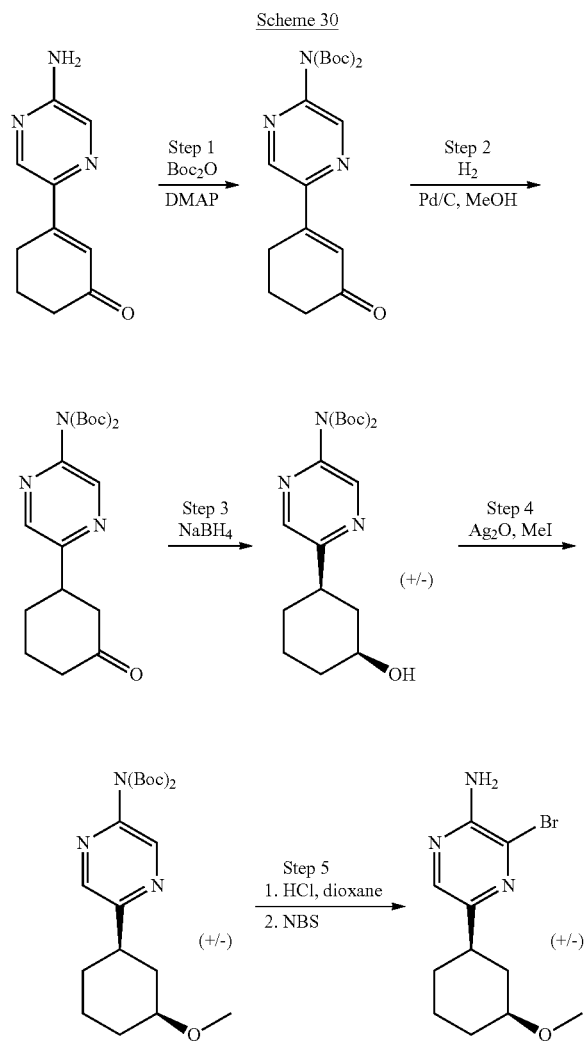

Step 1. (+/−)-N,N-di-Boc-3-(5-aminopyrazin-2-yl)cyclohex-2-enone

To 3-(5-aminopyrazin-2-yl)cyclohex-2-enone (1.3 g, 6.87 mmol) in DCM (34.0 mL) was added di-tert-butyl dicarbonate (4.50 g, 20.61 mmol) and N,N-dimethylpyridin-4-amine (0.084 g, 0.69 mmol) and the mixture was stirred at room temperature overnight. The reaction mixture was diluted with DCM and then washed with sat sodium bicarbonate solution. The separated organic layer was then dried with sodium sulfate and concentrated. The crude product was purified by flash chromatography (0 to 50% ethyl acetate in heptane) yielding 1.3 g of (+/−)-N,N-di-Boc-3-(5-aminopyrazin-2-yl)cyclohex-2-enone. LCMS (m/z): 390.3 (MH$^+$), 1.02 min.

Step 2. (+/−)-N,N-di-Boc-3-(5-aminopyrazin-2-yl)cyclohexanone

A mixture of (+/−)-N,N-di-Boc-3-(5-aminopyrazin-2-yl)cyclohex-2-enone (1.3 g, 3.34 mmol) and Pd/C (10%) (400 mg, 10.57 mmol) in MeOH (33.4 mL) was stirred under H$_2$ atmosphere overnight. The reaction mixture was filtered through Celite, and washed well with MeOH and EtOAc. The filtrate was evaporated yielding (+/−)-N,N-di-Boc-3-(5-aminopyrazin-2-yl)cyclohexanone which was used for the next step without further purification. LCMS (m/z): 392.9 (MH$^+$), 0.97 min.

Step 3. (+/−)-N,N-di-Boc-(1S,3R)-3-(5-aminopyrazin-2-yl)cyclohexanol (+/−)-N,N-di-Boc-3-(5-aminopyrazin-2-yl)cyclohexanone (600 mg, 1.533 mmol) was dissolved in EtOH (17.2 mL), then NaBH$_4$ (87 mg, 2.299 mmol) was added. The reaction mixture was stirred at room temperature for 30 min. After water added to quench the reaction, the reaction mixture was concentrated to remove methanol and extracted by EtOAc, and the organic layer was washed by NaHCO$_3$ solution, water and brine, dried over anhydrous Na$_2$SO$_4$, and concentrated yielding the crude (+/−)-N,N-di-Boc-(1S,3R)-3-(5-aminopyrazin-2-yl)cyclohexanol (containing 5% trans isomer) which was taken to the next step without further purification. LCMS (m/z): 394.2 (MH$^+$), 0.89 min.

Step 4. (+/−)-N,N-di-Boc-5-((1R,3S)-3-methoxycyclohexyl)pyrazin-2-amine

A mixture of (+/−)-N,N-di-Boc-(1S,3R)-3-(5-aminopyrazin-2-yl)cyclohexanol (350 mg, 0.89 mmol), silver oxide (2.06 g, 8.9 mmol), acetonitrile (2.224 mL) and methyl iodide (55.6 µL, 0.890 mmol) was stirred overnight. After EtOAc was added, the reaction mixture was filtered off. After volatile material was evaporated, the crude product was purified by flash chromatography (0-100% EtOAc in heptane) yielding 184 mg of (+/−)-N,N-di-Boc-5-((1R,3S)-3-methoxycyclohexyl)pyrazin-2-amine (184 mg, 0.452 mmol). LCMS (m/z): 408.3 (MH$^+$), 1.10 min.

Step 5. (+/−)-3-bromo-5-((1R,3S)-3-methoxycyclohexyl)pyrazin-2-amine (+/−)-N,N-di-Boc-5-((1R,3S)-3-methoxycyclohexyl)pyrazin-2-amine (184 mg, 0.452 mmol) in DCM (4.515 mL) was added HCl (4M in dioxane) (4.515 mL, 18.06 mmol). The reaction mixture was stirred at room temperature overnight. After the volatile material was removed in vacuo, the residue was dissolved in EtOAc. The organic layer was washed by NaHCO$_3$ solution, water and brine, dried over anhydrous Na$_2$SO$_4$, and concentrated affording (+/−)-5-((1R,3S)-3-methoxycyclohexyl)pyrazin-2-amine in quantitative yield. LCMS (m/z): 208 (MH$^+$), 0.43 min. To a solution of (+/−)-5-((1R,3S)-3-methoxycyclohexyl)pyrazin-2-amine (54 mg, 0.261 mmol) in acetonitrile (4.008 µL) was added NBS (48.7 mg, 0.274 mmol) at 0° C. The reaction mixture was stirred at 0° C. for 15 min. After quenched with NaHCO$_3$, extracted with EtOAc three times. The organic layer was washed by water and brine, dried over anhydrous Na$_2$SO$_4$, and concentrated to afford 75 mg of (+/−)-3-bromo-5-((1R,3S)-3-methoxycyclohexyl)pyrazin-2-amine in quantitative yield. LCMS (m/z): 286 (MH$^+$), 0.73 min.

Example 13

Synthesis of (+/−)-4-(3-amino-6-(3-(methylsulfonyl)cyclohexyl)pyrazin-2-yl)-N-benzyl-2-fluorobenzamide Scheme 31

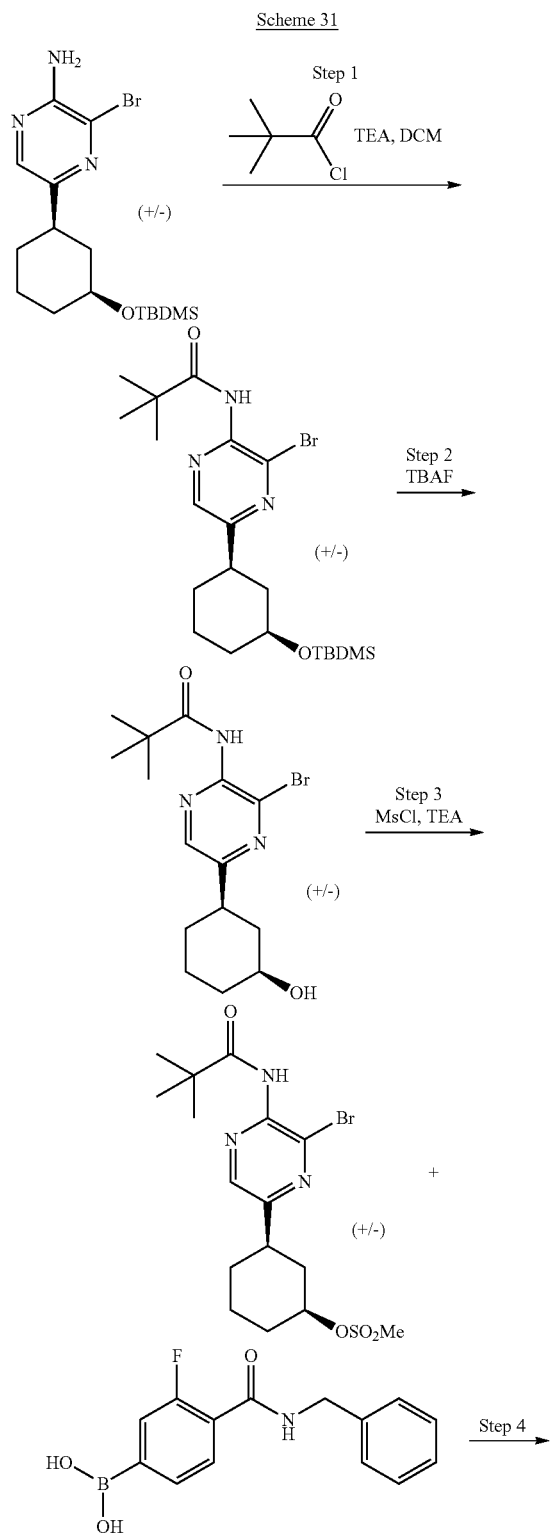

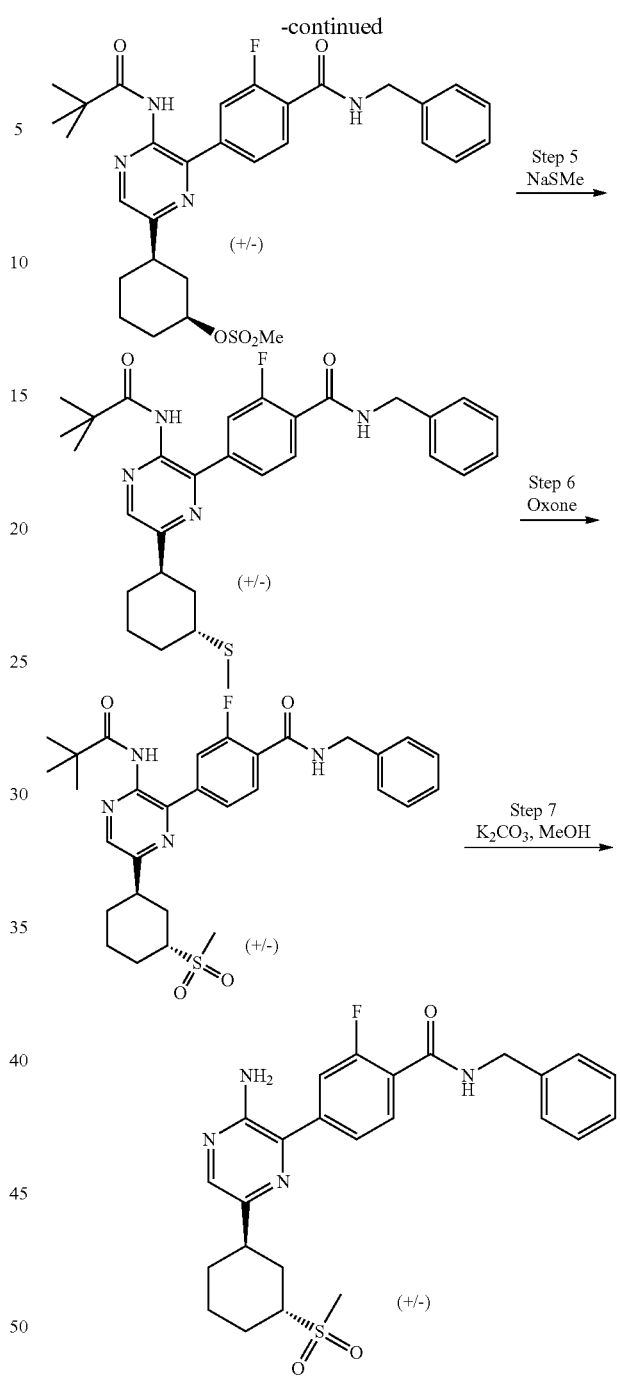

Step 1. (+/−)-N-(3-bromo-5-(3-((tert-butyldimethylsilyl)oxy)cyclohexyl)pyrazin-2-yl)pivalamide Pivaloyl chloride (71.5 μL, 0.569 mmol) was added dropwise to a stirred, cooled (0° C.) mixture of (+/−)-3-bromo-5-((1R,3S)-3-((tert-butyldimethylsilyl)oxy)cyclohexyl)pyrazin-2-amine (110 mg, 0.285 mmol) and TEA (159 μL, 1.139 mmol) in $CH_2Cl_2$ (949 μL). The red mixture was stirred at 0° C. for 1 h, then at room temperature for 2 h. EtOAc and Sat $NaHCO_3$ was added and stirred well. Organic layer was separated and the aqueous layer was extracted well with EtOAc. Combined EtOAc layers were washed with brine, dried over $Na_2SO_4$, filtered and concentrated. The residue was purified by flash chromatography on silica gel eluting with EtOAc/heptane to give (+/−)-N-(3-bromo-5-(3-((tert-butyldimethylsilyl)oxy)cyclohexyl)pyrazin-2-yl)pivalamide 97 mg in 72.4% yield. LCMS (m/z): 472.3 (MH+), 1.19 min.

Step 2. (+/−)-N-(3-bromo-5-((1R,3S)-3-((tert-butyldimethylsilyl)oxy)cyclohexyl)pyrazin-2-yl)pivalamide A mixture of (+/−)-N-(3-bromo-5-(3-((tert-butyldimethylsilyl)oxy)cyclohexyl)pyrazin-2-yl)pivalamide (97 mg, 0.206 mmol) in 6N HCl (687 μL), THF (687 μL) MeOH (687 μL) was stirred for 2 h. LCMS indicated that the reaction was completed. Solid sodium bicarbonate was added to neutralize the HCl. Dissolved in EtOAc and water. Organic layer was separated and washed with brine, dried over Na$_2$SO$_4$, filtered and concentrated to provide 72 mg of crude (+/−)-N-(3-bromo-5-((1R,3S)-3-((tert-butyldimethylsilyl)oxy)cyclohexyl)pyrazin-2-yl)pivalamide in 98% yield. LCMS (m/z): 358.6 (MH+), 0.70 min.

Step 3. (+/−)-(1S,3R)-3-(6-bromo-5-pivalamidopyrazin-2-yl)cyclohexyl methanesulfonate To a mixture of (+/−)-N-(3-bromo-5-((1R,3S)-3-((tert-butyldimethylsilyl)oxy)cyclohexyl)pyrazin-2-yl)pivalamide (72 mg, 0.202 mmol) in CH$_2$Cl$_2$ (2021 μL) at 0° C. was added TEA (56.3 μL, 0.404 mmol) and methanesulfonyl chloride (18.90 μL, 0.243 mmol). The resulting mixture was stirred at room temperature for 3 h. Another TEA (56.3 μL, 0.404 mmol) and Methanesulfonyl chloride (18.90 μL, 0.243 mmol) was added, and stirred for 6 h. Worked up the reaction by adding water. The organic phase was washed with brine, dried over sodium sulfate, filtered and concentrated. The crude product was purified with flash chromatography eluting with 0-100% EtOAc/heptane to provide 54 mg of (+/−)-(1S,3R)-3-(6-bromo-5-pivalamidopyrazin-2-yl)cyclohexyl methanesulfonate in 61.5% yield. LCMS (m/z): 436.1 (MH+), 0.75 min.

Step 4. (+/−)-(1S,3R)-3-(6-(4-(benzylcarbamoyl)-3-fluorophenyl)-5-pivalamidopyrazin-2-yl)cyclohexyl methanesulfonate To cis racemate (+/−)-3-(6-bromo-5-pivalamidopyrazin-2-yl)cyclohexyl methanesulfonate (54 mg, 0.124 mmol) in 2.0 mL MW vial was added (4-(benzylcarbamoyl)-3-fluorophenyl)boronic acid (50.9 mg, 0.186 mmol), PdCl$_2$(dppf) (9.10 mg, 0.012 mmol), DME (1166 μL) and 2M Na$_2$CO$_3$ solution (389 μL). The reaction mixture was heated at microwave synthesizer (12 min, 80° C.). The reaction mixture was diluted with EtOAc and washed with water three times, dried over Na$_2$SO$_4$, filtered and concentrated. The crude product was purified by flash chromatography eluting with 0-100% of EtOAc (containing 10% of MeOH) to provide 73 mg of (+/−)-(1S,3R)-3-(6-(4-(benzylcarbamoyl)-3-fluorophenyl)-5-pivalamidopyrazin-2-yl)cyclohexyl methanesulfonate which was taken to the next reaction without further purification. LCMS (m/z): 583.4 (MH+), 0.87 min.

Step 5. (+/−)-N-benzyl-2-fluoro-4-(6-((1R,3R)-3-(methylthio)cyclohexyl)-3-pivalamidopyrazin-2-yl)benzamide A mixture of (+/−)-(1S,3R)-3-(6-(4-(benzylcarbamoyl)-3-fluorophenyl)-5-pivalamidopyrazin-2-yl)cyclohexyl methanesulfonate (25 mg, 0.043 mmol) and sodium methanethiolate (24.09 mg, 0.344 mmol) in MeOH (430 μL) was heated at 80° C. for 2 h. Solvent was removed and the residue was purified with flash chromatography eluting with EtOAc (containing 10% of MeOH)/heptane to provide 25 mg of crude (+/−)-N-benzyl-2-fluoro-4-(6-((1R,3R)-3-(methylthio)cyclohexyl)-3-pivalamidopyrazin-2-yl)benzamide which was taken to the next step without further purification. LCMS (m/z): 535.3 (MH+), 1.09 min.

Step 6. (+/−)-N-benzyl-2-fluoro-4-(6-((1R,3R)-3-(methylsulfonyl)cyclohexyl)-3-pivalamidopyrazin-2-yl)benzamide To trans racemate (+/−)-N-benzyl-2-fluoro-4-(6-((1R,3R)-3-(methylthio)cyclohexyl)-3-pivalamidopyrazin-2-yl)benzamide (35 mg, 0.065 mmol) in MeOH (327 μL) at 0° C. was added oxone (52.3 mg, 0.085 mmol) in water (327 μL). The reaction mixture was stirred at 0° C. and room temperature thereafter for 3 h. The reaction mixture was quenched by 2 equiv. of sodium thiosulfate (20.70 mg, 0.131 mmol) in 2 mL water at 0° C. Stirred for 30 min, and then basified by adding 6N NaOH at 0° C. Diluted with EtOAc, and dried over sodium sulfate three times. Then filtered and concentrated to afford 25 mg of (+/−)-N-benzyl-2-fluoro-4-(6-((1R,3R)-3-(methylsulfonyl)cyclohexyl)-3-pivalamidopyrazin-2-yl)benzamide in 67.4% yield which was taken to the next step without further purification. LCMS (m/z): 567.4 (MH+), 0.90 min.

Step 7. (+/−)-4-(3-amino-6-((1R,3R)-3-(methylsulfonyl)cyclohexyl)pyrazin-2-yl)-N-benzyl-2-fluorobenzamide To (+/−)-N-benzyl-2-fluoro-4-(6-((1R,3R)-3-(methylsulfonyl)cyclohexyl)-3-pivalamidopyrazin-2-yl)benzamide (25 mg, 0.044 mmol) in MeOH (221 μL) was added potassium carbonate (61.0 mg, 0.441 mmol). The resulting mixture was heated at 80° C. for 4 h. The reaction mixture was filtered and concentrated. Purified with auto-prep to provide 5.4 mg of (+/−)-4-(3-amino-6-((1R,3R)-3-(methylsulfonyl)cyclohexyl)pyrazin-2-yl)-N-benzyl-2-fluorobenzamide in 20.11% yield. LCMS (m/z): 483.1 (MH+), 0.78 min. 1H NMR (400 MHz, MeOD-d4) δ ppm 8.00-7.81 (m, 2 H) 7.76-7.56 (m, 2 H) 7.43-7.16 (m, 5 H) 4.65-4.55 (m, 2 H) 3.61-3.51 (m, 1 H), 3.46-3.36 (m, 2 H) 2.87-2.97 (m, 3 H) 2.61-2.48 (m, 1 H) 2.19-1.95 (m, 3 H) 1.92-1.78 (m, 3 H).

Example 14

Synthesis of 4-(3-amino-6-((1r,4r)-4-hydroxycyclohexyl)pyrazin-2-yl)-N-benzyl-2-fluorobenzamide Scheme 32

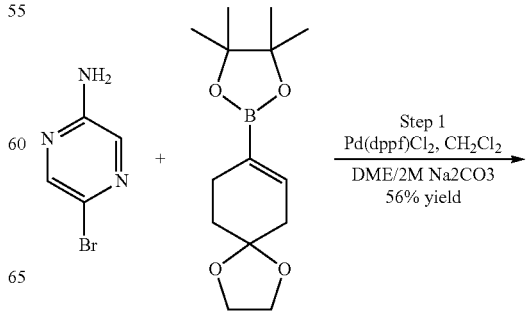

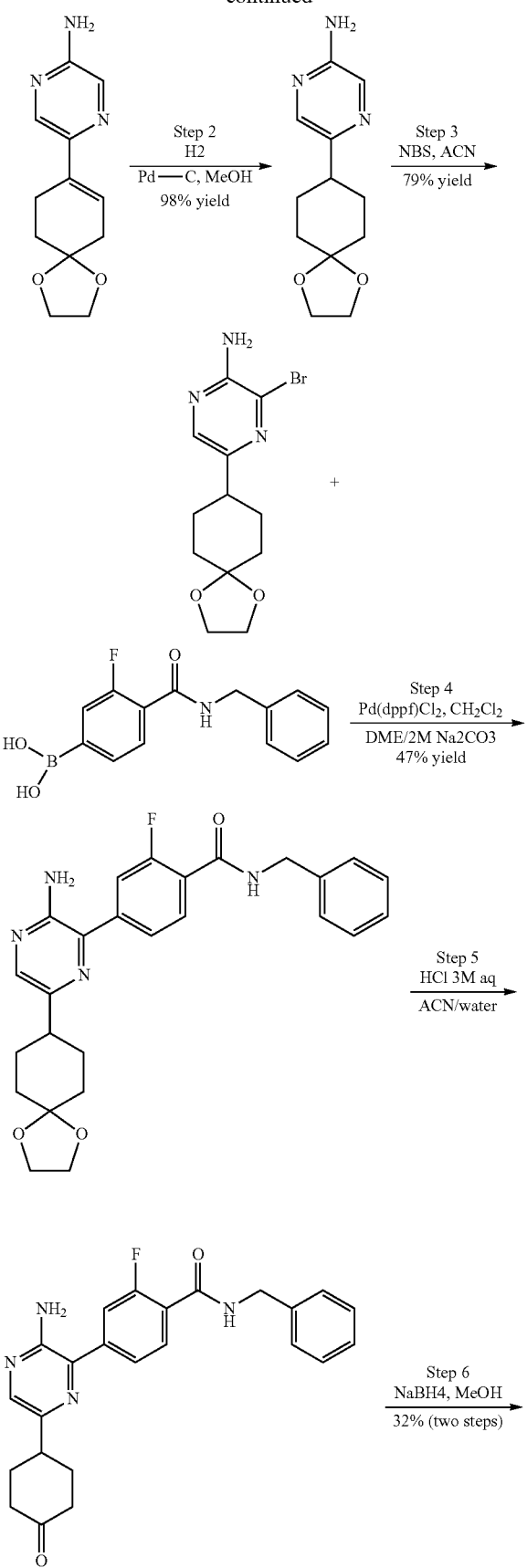

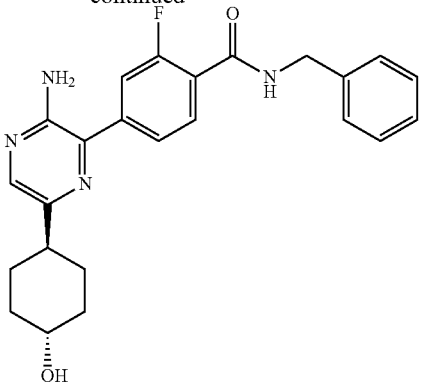

Step 1. 5-(1,4-dioxaspiro[4.5]dec-7-en-8-yl)pyrazin-2-amine

To 5-bromopyrazin-2-amine (225 mg, 1.293 mmol) was added 4,4,5,5-tetramethyl-2-(1,4-dioxaspiro[4.5]dec-7-en-8-yl)-1,3,2-dioxaborolane (482 mg, 1.810 mmol), $PdCl_2$ (dppf)-$CH_2Cl_2$ adduct (84 mg, 0.103 mmol), DME (3.5 mL) and then last sodium carbonate 2M (1.616 mL, 3.23 mmol). The reaction was microwaved at 120° C. for 15 min. To the reaction was added 80 mL of DCM, washed with water (1×), dried sodium sulfate, filtered and concentrated to residue. The crude was purified by silica gel chromatography using 12 gram column (solid load) eluting with 10-90% ethyl acetate and heptane. The desired fractions were concentrated to constant mass to give 173 mg of the desired product as free base used as is (56% yield). LCMS (m/z): 234.2 ($MH^+$), 0.43 min; $^1H$ NMR (400 MHz, DMSO-d6) δ ppm 8.01 (d, J=1.2 Hz, 1H), 7.80 (d, J=1.2 Hz, 1H), 6.33 (s, 2H), 6.27 (t, J=3.9 Hz, 1H), 3.89 (s, 4H), 2.52 (d, J=1.6 Hz, 2H), 2.33 (br. s., 2H), 1.76 (t, J=6.7 Hz, 2H).

Step 2. 5-(1,4-dioxaspiro[4.5]decan-8-yl)pyrazin-2-amine

To 5-(1,4-dioxaspiro[4.5]dec-7-en-8-yl)pyrazin-2-amine (645 mg, 2.77 mmol) in a round bottom flask that was flushed with argon was added PdC 10% degaussa (294 mg, 0.277 mmol). Then under argon with syringe was added MeOH (10 mL) and then last a hydrogen balloon was added. The flask was evacuated and refilled with hydrogen (6×). The reaction was stirred at room temperature for total of 16 h, under the hydrogen balloon, followed by LCMS. The reaction was flushed with argon and 25 mL of DCM was added. The crude mixture was filtered through a Celite plug, and concentrated to constant mass to give 635 mg of the desired product as free base, used as is (98% yield). LCMS (m/z): 236.2 ($MH^+$), 0.41 min; $^1H$ NMR (400 MHz, DMSO-d6) δ ppm 7.78 (d, J=1.2 Hz, 1H), 7.74 (d, J=1.2 Hz, 1H), 6.09 (s, 2H), 3.85 (s, 4H), 2.52-2.60 (m, 1H), 1.65-1.78 (m, 6H), 1.49-1.61 (m, 2H).

Step 3. 3-bromo-5-(1,4-dioxaspiro[4.5]decan-8-yl)pyrazin-2-amine

To 5-(1,4-dioxaspiro[4.5]decan-8-yl)pyrazin-2-amine (620 mg, 2.64 mmol) was added Acetonitrile (20 mL) and then was added NBS (469 mg, 2.64 mmol) in portions over 2 min. The reaction was stirred at room temperature for 20 min and quenched with saturated sodium bicarbonate solution, and 250 mL of ethyl acetate was added. The aqueous was extracted and the organic layer was washed with saturated sodium bicarbonate, water (2×), saturated salt solution, then dried with sodium sulfate, filtered and concentrated to residue to give 650 mg of the desired product, used as is, (79% yield). LCMS (m/z): 314.1/316.1 (MH+), 0.61 min.

Step 4. 4-(3-amino-6-(1,4-dioxaspiro[4.5]decan-8-yl)pyrazin-2-yl)-N-benzyl-2-fluorobenzamide To 3-bromo-5-(1,4-dioxaspiro[4.5]decan-8-yl)pyrazin-2-amine (630 mg, 2.005 mmol) was added (4-(benzylcarbamoyl)-3-fluorophenyl)boronic acid (767 mg, 2.81 mmol), PdCl$_2$(dppf)CH$_2$Cl$_2$ adduct (164 mg, 0.201 mmol), DME (9 mL) and then last sodium carbonate 2M (3.01 mL, 6.02 mmol). The reaction was microwaved at 115° C. for 12 min. To the reaction was added 400 mL of ethyl acetate washed with water (2×), dried with sodium sulfate, filtered and concentrated to residue. The crude was purified by silica gel chromatography using 40 gram column eluting with 20-100% ethyl acetate and heptane. The desired fractions were concentrated to constant mass to give 432 mg of the desired product as free base used as is, (47% yield). LCMS (m/z): 463.2 (MH+), 0.82 min; $^1$H NMR (400 MHz, DMSO-d6) δ ppm 8.94-8.81 (m, 1H), 7.89 (s, 1H), 7.80-7.69 (m, 1H), 7.67-7.52 (m, 2H), 7.33 (d, J=4.3 Hz, 4H), 7.27-7.18 (m, 1H), 6.09 (s, 2H), 4.49 (d, J=5.9 Hz, 2H), 3.85 (s, 4H), 2.70-2.61 (m, 1H), 1.84-1.67 (m, 6H), 1.65-1.48 (m, 2H).

Step 5. 4-(3-amino-6-(4-oxocyclohexyl)pyrazin-2-yl)-N-benzyl-2-fluorobenzamide

To 4-(3-amino-6-(1,4-dioxaspiro[4.5]decan-8-yl)pyrazin-2-yl)-N-benzyl-2-fluorobenzamide (170 mg, 0.368 mmol) was added acetonitrile (3 mL), water (2 mL) and then HCl 3M aqueous solution (0.613 mL, 1.838 mmol). The reaction was stirred at room temperature for 30 min followed by LCMS. To the reaction was added 200 mL of ethyl acetate, basified with excess 1M NaOH. The aqueous layer was extracted and the organic layer was washed with water (3×), filtered and concentrated to residue to give the desired product as free base. Assume quantitative yield (0.368 mmol). LCMS (m/z): 419.3 (MH+), 0.75 min.

Step 6. 4-(3-amino-6-((1r,4r)-4-hydroxycyclohexyl) pyrazin-2-yl)-N-benzyl-2-fluorobenzamide To 4-(3-amino-6-(4-oxocyclohexyl)pyrazin-2-yl)-N-benzyl-2-fluorobenzamide (77 mg, 0.184 mmol) was added MeOH (3 mL), cooled to 0° C. Then sodium borohydride (6.96 mg, 0.184 mmol) was added. The reaction was stirred for 20 min while allowing it to warm to room temperature, followed by LCMS. Crude LCMS shows about a 9:1 (trans\cis) isomers as expected. The reaction was quenched with excess saturated sodium chloride and stirred at room temperature for 1 hour. Then 150 mL of ethyl acetate was added and washed with saturated sodium bicarbonate, water (2×), saturated salt solution, dried with sodium sulfate, filtered and concentrated to residue to give 73 mg of crude product. To half (36.5 mg) of the crude product was dissolved in 2.0 mL of DMSO, filtered, purified by prep HPLC, and lyophilized to give 16.3 mg of the desired product 4-(3-amino-6-((1r,4r)-4-hydroxycyclohexyl)pyrazin-2-yl)-N-benzyl-2-fluorobenzamide as TFA salt, in (32 yield). LCMS (m/z): 421.3 (MH+), 0.69 min; $^1$H NMR (400 MHz, DMSO-d6) δ ppm 8.82 (br. s., 1H), 7.83 (s, 1H), 7.64-7.73 (m, 1H), 7.45-7.61 (m, 2H), 7.25-7.31 (m, 4H), 7.14-7.23 (m, 1H), 4.43 (d, J=5.9 Hz, 2H), 1.66-1.91 (m, 3H), 1.38-1.57 (m, 2H), 1.11-1.31 (m, 2H).

Example 15

Synthesis of 4-(3-amino-6-((1s,4s)-4-hydroxycyclohexyl)pyrazin-2-yl)-N-benzyl-2-fluorobenzamide Scheme 33

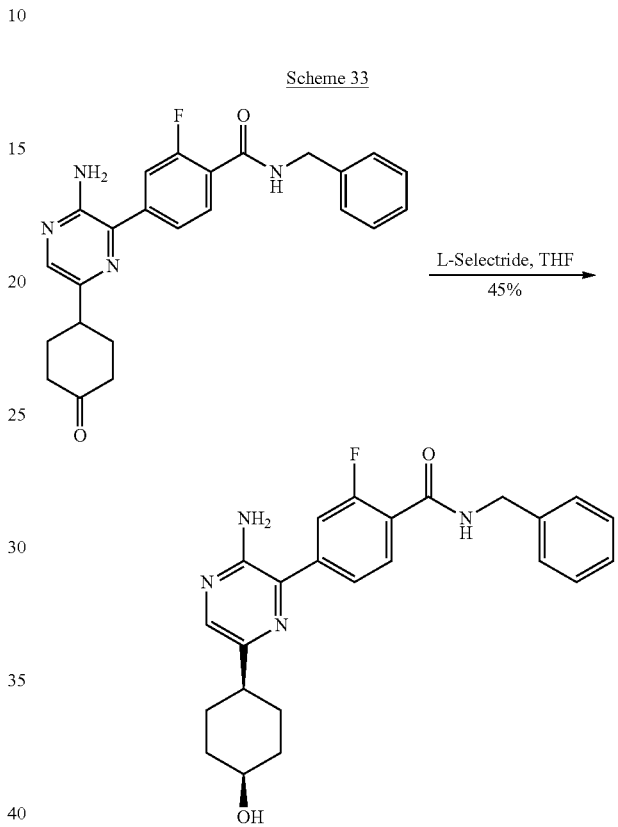

To 4-(3-amino-6-(4-oxocyclohexyl)pyrazin-2-yl)-N-benzyl-2-fluorobenzamide (77 mg, 0.184 mmol) was added THF (3 mL), cooled to 0° C. Then L-Selectride 1M THF (0.460 mL, 0.460 mmol) was added. The reaction was stirred for 20 min while allowing to warm to room temperature, followed by LCMS. The crude LCMS show about greater than 9:1 (cis/trans) isomers as expected. The reaction was basified with excess 5M NaOH and stirred at room temperature for 1 hour. Then 150 mL of ethyl acetate was added and washed with water (3×), saturated salt solution, dried with sodium sulfate, filtered and concentrated to residue to give 75 mg of product, used as is. To half (36.5 mg) of the crude product was dissolved in 2.0 mL of DMSO, filtered, purified by prep HPLC, and lyophilized to give 23 mg of the desired product 4-(3-amino-6-((1s,4s)-4-hydroxycyclohexyl)pyrazin-2-yl)-N-benzyl-2-fluorobenzamide as TFA salt, in (45% yield). LCMS (m/z): 421.3 (MH+), 0.72 min; $^1$H NMR (400 MHz, DMSO-d6) δ ppm 8.87 (br. s., 1H), 7.89 (s, 1H), 7.79-7.70 (m, 1H), 7.67-7.45 (m, 2H), 7.33 (d, J=4.3 Hz, 4H), 7.28-7.21 (m, 1H), 6.06 (s, 2H), 4.49 (d, J=5.9 Hz, 2H), 4.30 (br. s., 1H), 3.84 (br. s., 1H), 2.01-1.84 (m, 2H), 1.75-1.64 (m, 2H), 1.60-1.43 (m, 4H).

Example 16

Synthesis of 4-(3-amino-6-((1s,4s)-4-(methylsulfonyl)cyclohexyl)pyrazin-2-yl)-N-benzyl-2-fluorobenzamide Scheme 34

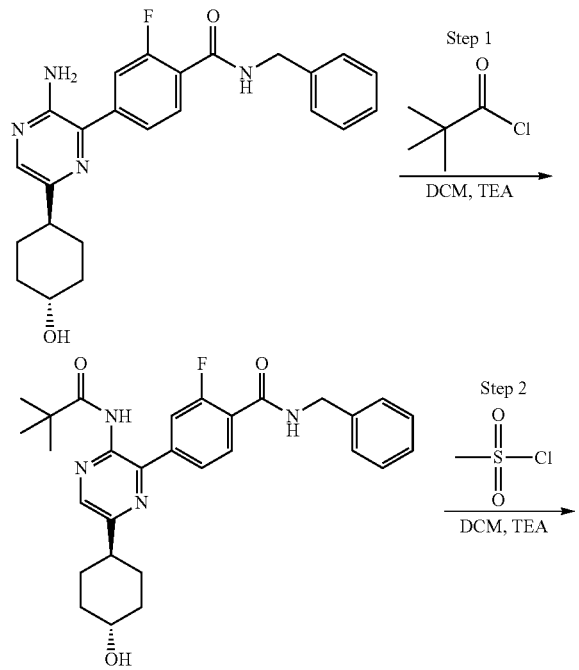

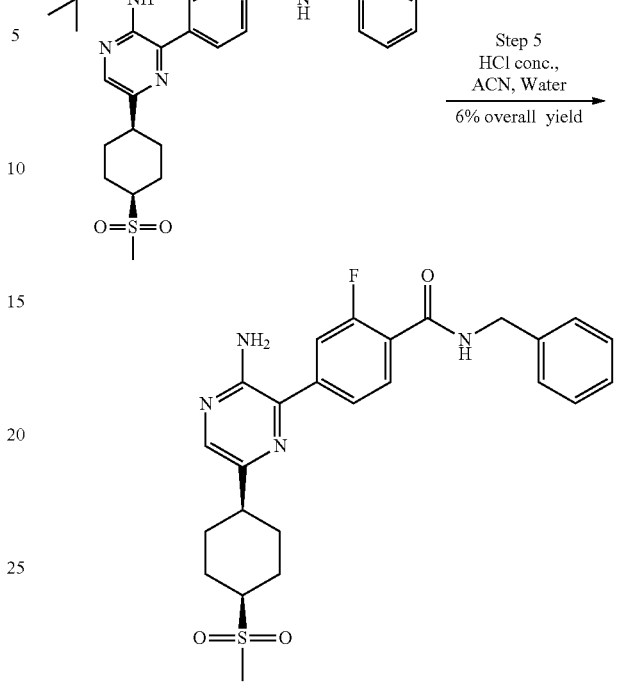

Step 1. N-benzyl-2-fluoro-4-(6-((1r,4r)-4-hydroxycyclohexyl)-3-pivalamidopyrazin-2-yl)benzamide To 4-(3-amino-6-((1r,4r)-4-hydroxycyclohexyl)pyrazin-2-yl)-N-benzyl-2-fluorobenzamide (0.105 g, 0.25 mmol) was added DCM (2.5 mL), TEA (0.105 mL, 0.750 mmol) and then pivaloyl chloride (0.045 g, 0.375 mmol). The reaction was stirred at room temperature for 3 h followed by LCMS. To the reaction was added 150 mL of ethyl acetate, basified with excess saturated bicarbonate. The organic layer was washed with water (3×), saturated salt solution, dried sodium sulfate, filtered and concentrated to residue to give the product as free base, used as is. Assume quantitative yield (0.25 mmol). LCMS (m/z): 505.4 (MH$^+$), 0.82 min.

Step 2. (1r,4r)-4-(6-(4-(benzylcarbamoyl)-3-fluorophenyl)-5-pivalamidopyrazin-2-yl)cyclohexyl methanesulfonate To N-benzyl-2-fluoro-4-(6-((1 r,4r)-4-hydroxycyclohexyl)-3-pivalamidopyrazin-2-yl)benzamide (125 mg, 0.248 mmol) was added DCM (2.5 mL), TEA (0.104 mL, 0.743 mmol) and cooled to 0° C. then methanesulfonyl chloride (42.6 mg, 0.372 mmol) was added. The reaction was allowed to warm to room temperature and stirred for 2 h, followed by LCMS. Then additional TEA (0.104 mL, 0.743 mmol) and methanesulfonyl chloride (42.6 mg, 0.372 mmol) was added and stirred at room temperature for 3 h more, for total of 5 h. To the reaction was added 150 mL of ethyl acetate, basified with excess saturated bicarbonate. The organic layer was washed water (3×), saturated salt solution, dried sodium sulfate, filtered and concentrated to residue to give product as free base, used as is. Assume quantitative yield (0.248 mmol). LCMS (m/z): 583.3 (MH$^+$), 0.90 min.

Step 3. N-benzyl-2-fluoro-4-(6-((1s,4s)-4-(methylthio)cyclohexyl)-3-pivalamidopyrazin-2-yl)benzamide To (1r,4r)-4-(6-(4-(benzylcarbamoyl)-3-fluorophenyl)-5-pivalamidopyrazin-2-yl)cyclohexyl methanesulfonate (130 mg, 0.223 mmol) was added t-butanol (3.5 mL), sodium thiomethoxide (235 mg, 3.35 mmol). The reaction was heated at 80° C. for 1 h followed by LCMS. The reaction was let cool. Then 75 mL of ethyl acetate was added, washed with saturated sodium bicarbonate, water (2×), saturated salt solution, dried sodium sulfate, filtered and concentrated to residue to give product as free base, used as is. Assume quantitative yield (0.223 mmol). LCMS (m/z): 535.3 (MH$^+$), 1.06 min.

Step 4. N-benzyl-2-fluoro-4-(6-((1s,4s)-4-(methylsulfonyl)cyclohexyl)-3-pivalamidopyrazin-2-yl)benzamide To N-benzyl-2-fluoro-4-(6-((1 s,4s)-4-(methylthio)cyclohexyl)-3-pivalamidopyrazin-2-yl)benzamide (118 mg, 0.221 mmol) was added DCM (4 mL). Then with stirring at room temperature a solution of mCPBA (118 mg, 0.527 mmol) in DCM (1 mL) was slowly titrated in until reaction was done, followed by LCMS. Then 75 mL of ethyl acetate was added, washed with saturated sodium bicarbonate, water (2×), saturated salt solution, dried sodium sulfate, filtered and concentrated to residue. The crude was dissolved in 5 mL of DMSO, filtered and purified by prep HPLC. The desired fractions were combined. The product as a 100 mL solution in acetonitrile/water with 0.1% TFA, was used as is in next step. Assume quantitative yield (0.221 mmol). LCMS (m/z): 567.4 (MH$^+$), 0.85 min.

Step 5. 4-(3-amino-6-((1s,4s)-4-(methylsulfonyl)cyclohexyl)pyrazin-2-yl)-N-benzyl-2-fluorobenzamide To N-benzyl-2-fluoro-4-(6-((1s,4s)-4-(methylsulfonyl)cyclohexyl)-3-pivalamidopyrazin-2-yl)benzamide (120 mg, 0.212 mmol) in a solution of water (60 mL) and Acetonitrile (40 mL) with 0.1% TFA was added HCl conc. (2 mL, 65.8 mmol). The reaction was stirred at 60° C. for 12 h, followed by LCMS. The crude was lyophilized to residue. The residue was dissolved in DMSO, purified by prep HPLC, and lyophilized to give 10.2 mg of the desired product 4-(3-amino-6-((1s,4s)-4-(methylsulfonyl)cyclohexyl)pyrazin-2-yl)-N-benzyl-2-fluorobenzamide as TFA salt, in 6% overall yield. LCMS (m/z): 483.2 (MH$^+$), 0.72 min; $^1$H NMR (CD$_3$OD) δ ppm 7.80 (s, 1H), 7.76 (t, J=7.6 Hz, 1H), 7.63 (dd, J=8.2, 1.6 Hz, 1H), 7.55 (dd, J=11.7, 1.2 Hz, 1H), 7.22-7.34 (m, 4H), 7.10-7.20 (m, 1H), 4.52 (s, 2H), 3.12 (dt, J=8.9, 4.4 Hz, 1H), 2.96 (t, J=4.9 Hz, 1H), 2.81 (s, 3H), 2.16-2.30 (m, 2H), 1.99-2.13 (m, 2H), 1.86-1.96 (m, 2H), 1.70-1.85 (m, 2H).

Example 17

Synthesis of 4-(3-amino-6-((1r,4r)-4-(methylsulfonyl)cyclohexyl)pyrazin-2-yl)-N-benzyl-2-fluorobenzamide Scheme 35

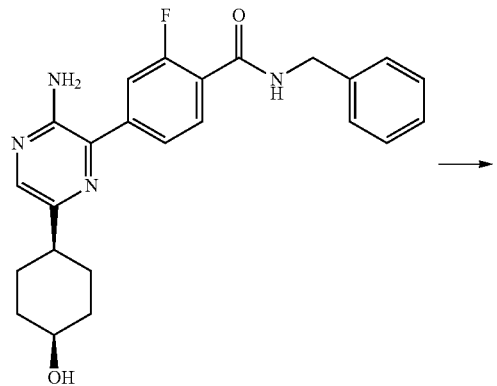

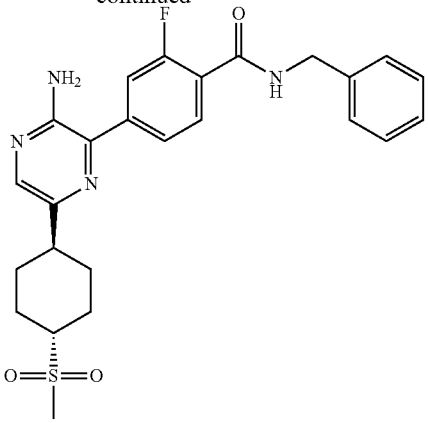

Following Scheme 35, using 4-(3-amino-6-((1s,4s)-4-hydroxycyclohexyl)pyrazin-2-yl)-N-benzyl-2-fluorobenzamide (Example 15), 4.5 mg of the desired product 4-(3-amino-6-((1r,4r)-4-(methylsulfonyl)cyclohexyl)pyrazin-2-yl)-N-benzyl-2-fluorobenzamide was obtained as TFA salt in 3% overall yield. LCMS (m/z): 483.2 (MH$^+$), 0.71 min; $^1$H NMR (CD$_3$OD) δ ppm 7.80-7.89 (m, 2H), 7.68 (dd, J=8.0, 1.4 Hz, 1H), 7.60 (dd, J=11.7, 1.6 Hz, 1H), 7.31-7.42 (m, 4H), 7.19-7.30 (m, 1H), 4.61 (s, 2H), 3.05-3.15 (m, 1H), 2.92 (s, 3H), 2.67-2.78 (m, 1H), 2.34 (br. s., 2H), 2.11 (br. s., 2H), 1.60-1.82 (m, 4H).

Example 18

Synthesis of N-((S)-2-amino-1-(3-chlorophenyl)ethyl)-4-(3-amino-6-((1r,4S)-4-methoxycyclohexyl)pyrazin-2-yl)-2-fluorobenzamide Scheme 36

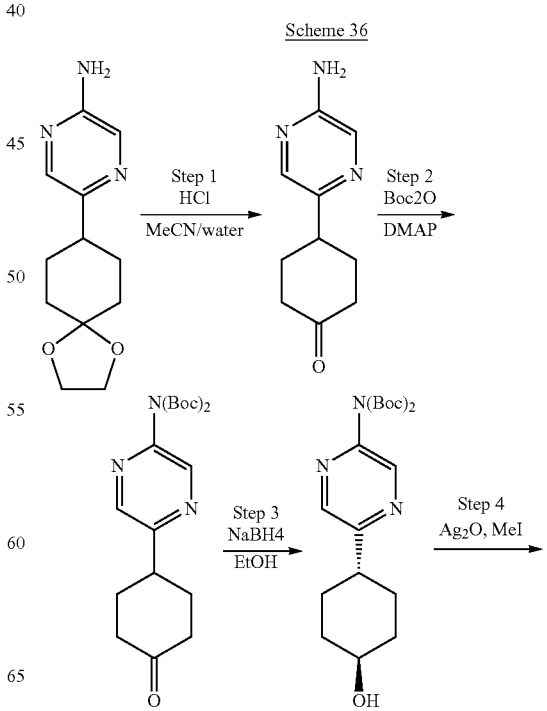

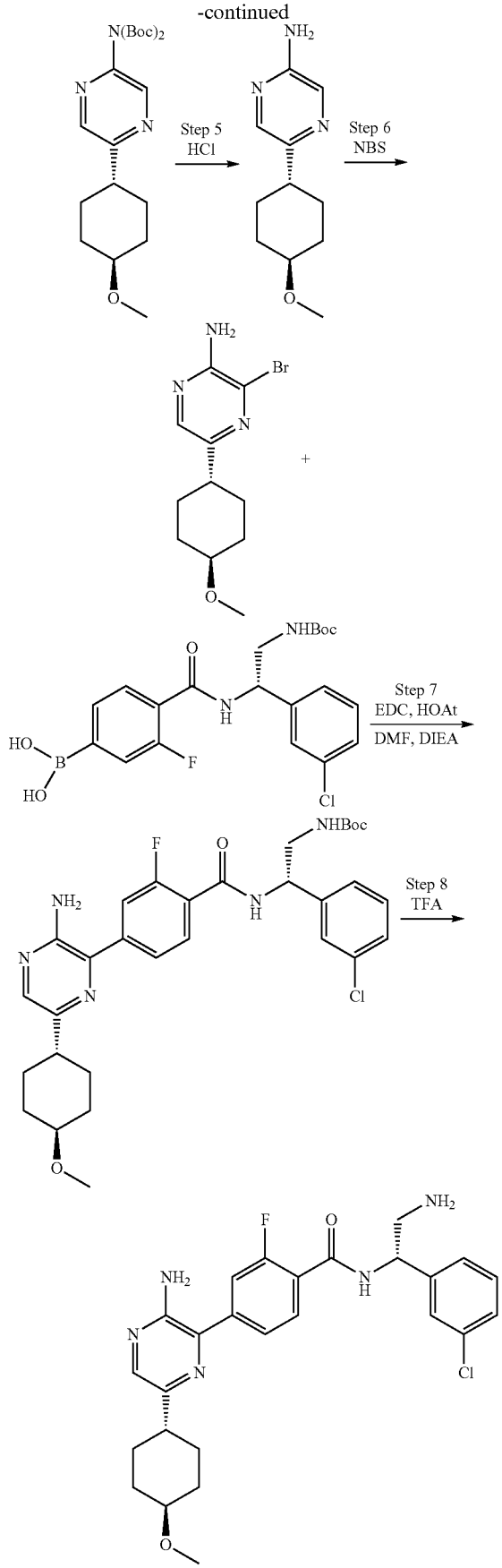

Step 1. 4-(5-aminopyrazin-2-yl)cyclohexanone

To 5-(1,4-dioxaspiro[4.5]decan-8-yl)pyrazin-2-amine (8.68 g, 45.4 mmol) was added acetonitrile (368 mL), water (245 mL) and 3M HCl (76 mL). The reaction was stirred at room temperature for 30 min. The reaction was basified with excess 1M NaOH, and then diluted with of ethyl acetate. The organic layer was separated. The aqueous layer was extracted well with EtOAc/2-methyl THF (1:1) three times. Organic layers were combined and dried over $Na_2SO_4$, filtered and concentrated to give 6.91 g of product as free base. LCMS (m/z): 192.12 (MH$^+$), 0.30 min.

Step 2. Imidodicarbonic acid, 2-(5-(4-oxocyclohexyl)pyrazin-2-yl)-, 1,3-bis(1,1-dimethylethyl) ester To 4-(5-aminopyrazin-2-yl)cyclohexanone (3.0 g, 15.69 mmol) in DCM (105 mL) was added di-tert-butyl dicarbonate (10.27 g, 47.1 mmol) and N,N-dimethylpyridin-4-amine (0.192 g, 1.569 mmol). The mixture was stirred at room temperature overnight. The reaction mixture was diluted with DCM and then washed with sat sodium bicarbonate solution. The separated organic layer was dried over sodium sulfate and concentrated. Purified on the flash chromatography and eluting with 0 to 50% ethyl acetate in heptane to provide 2.2 g of desired product. LCMS (m/z): 392.7 (MH$^+$), 0.91 min.

Step 3. Imidodicarbonic acid, 2-(5-(4-hydroxycyclohexyl)pyrazin-2-yl)-, 1,3-bis(1,1-dimethylethyl) ester Imidodicarbonic acid, 2-(5-(4-oxocyclohexyl)pyrazin-2-yl)-, 1,3-bis(1,1-dimethylethyl) ester (350 mg, 0.894 mmol) was dissolved in EtOH (10 mL), then NaBH$_4$ (50.7 mg, 1.341 mmol) was added. The reaction mixture was stirred at room temperature for 30 min. The trans and cis ratio is around 85:15 from TLC. Saturated NaHCO$_3$ solution was added to quench the reaction. The reaction mixture was then extracted by EtOAc/2-methyl THF (1:1). The organic layers were combined and dried over anhydrous Na$_2$SO$_4$, and concentrated to yield the crude product, which was taken to the next step without further purification. LCMS (m/z): 394.3 (MH$^+$), 0.89 min.

Step 4. Imidodicarbonic acid, 2-(5-(4-methoxycyclohexyl)pyrazin-2-yl)-, 1,3-bis(1,1-dimethylethyl) ester A mixture of imidodicarbonic acid, 2-(5-(4-hydroxycyclohexyl)pyrazin-2-yl)-, 1,3-bis(1,1-dimethylethyl) ester (350 mg, 0.890 mmol), silver oxide (1.649 g, 7.12 mmol), acetonitrile (2.22 mL) and methyl iodide (1.112 mL, 17.79 mmol) was stirred overnight. EtOAc was added, and the solid was filtered out. Solvent was evaporated and the residue was purified via flash chromatography eluting with 0-100% EtOAc/heptane to provide 168 mg of desired trans compound in 46.3% yield. LCMS (m/z): 408.3 (MH$^+$), 1.10 min.

Step 5. 5-((1r,4r)-4-methoxycyclohexyl)pyrazin-2-amine

Imidodicarbonic acid, 2-(5-(4-methoxycyclohexyl)pyrazin-2-yl)-, 1,3-bis(1,1-dimethylethyl) ester (168 mg, 0.412 mmol) in DCM (4.123 mL) was added HCl (4M in dioxane) (4.123 mL, 16.49 mmol), the reaction mixture was stirred at room temperature overnight. Concentrated, and EtOAc was added. Washed with sat NaHCO₃, and water. The aqueous layer was extracted with EtOAc and 2-methyl THF (1:1) three times. Dried over Na₂SO₄, filtered and concentrated to afford the desired trans product. LCMS (m/z): 208 (MH⁺), 0.42 min.

Step 6. 3-bromo-5-((1r,4r)-4-methoxycyclohexyl)pyrazin-2-amine

To a solution of 54(1r,4r)-4-methoxycyclohexyl)pyrazin-2-amine (92 mg, 0.444 mmol) in acetonitrile (8.877 mL) was added NBS (83 mg, 0.466 mmol) at 0° C. The reaction mixture was stirred at 0° C. for 15 min. After quenched with sat Na₂SO₃ and NaHCO₃, extracted with EtOAc and 2-methyl THF (1:1) three times. The organic layers were combined dried over Na₂SO₄, filtered and concentrated to afford 127 mg of desired trans compound in quantitative yield. LCMS (m/z): 288 (MH⁺), 0.72 min.

Step 7. tert-butyl ((S)-2-(4-(3-amino-6-((1r,4S)-4-methoxycyclohexyl)pyrazin-2-yl)-2-fluorobenzamido)-2-(3-chlorophenyl)ethyl)carbamate To 3-bromo-5-((1r,4r)-4-methoxycyclohexyl)pyrazin-2-amine (35 mg, 0.122 mmol) in 2 mL MW vial was added (S)-(4-((2-((tert-butoxycarbonyl)amino)-1-(3-chlorophenyl)ethyl)carbamoyl)-3-fluorophenyl)boronic acid (64.1 mg, 0.147 mmol), PdCl₂(dppf) (8.95 mg, 0.012 mmol), DME (917 μL) and 2M Na₂CO₃ solution (306 μL). The reaction mixture was heated at microwave synthesizer (12 min, 120° C.). The reaction mixture was diluted with EtOAc and washed with water three times, dried over Na₂SO₄, filtered and concentrated. The crude product was purified by flash chromatography to provide 28 mg of desired trans product in 38.3% yield.

Step 8. N-((S)-2-amino-1-(3-chlorophenyl)ethyl)-4-(3-amino-6-((1r,4S)-4-methoxycyclohexyl)pyrazin-2-yl)-2-fluorobenzamide A mixture of tert-butyl ((S)-2-(4-(3-amino-6-((1r,4S)-4-methoxycyclohexyl)pyrazin-2-yl)-2-fluorobenzamido)-2-(3-chlorophenyl)ethyl)carbamate (28 mg, 0.047 mmol), TFA (0.4 mL, 0.047 mmol) and CH₂Cl₂ (1 mL) was stirred at room temperature for 30 min. Solvent was evaporated and the residue was dissolved in DMSO, purified with auto-prep to provide 15 mg of desired trans product as a TFA salt in 51.3% yield. LCMS (m/z): 498.2 (MH⁺), 0.76 min; 1H NMR (400 MHz, CD₃OD) δ ppm 7.94-7.85 (m, 2 H) 7.70 (dd, J=8.22, 1.56 Hz, 1 H) 7.62 (dd, J=11.93, 1.37 Hz, 1 H) 7.55 (s, 1 H) 7.49-7.34 (m, 3 H) 5.49 (dd, J=9.00, 5.87 Hz, 1 H) 3.53-3.41 (m, 2 H) 3.38 (s, 3 H) 2.70-2.59 (m, 2 H) 2.20 (d, J=9.78 Hz, 2 H) 1.98 (d, J=12.91 Hz, 2 H) 1.65 (qd, J=13.04, 3.13 Hz, 2 H) 1.41-1.27 (m, 2 H).

Synthesis of (1s,4s)-4-(5-amino-6-bromopyrazin-2-yl)-1-methylcyclohexanol and (1r,4r)-4-(5-amino-6-bromopyrazin-2-yl)-1-methylcyclohexanol

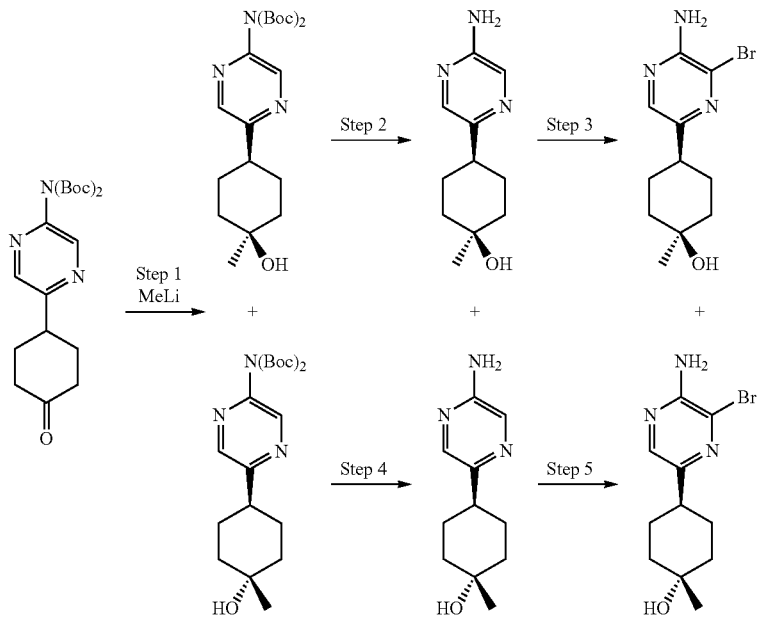

Scheme 37

Step 1. tert-butyl (5-((1s,4s)-4-hydroxy-4-methylcyclohexyl)pyrazin-2-yl)carbamate and tert-butyl (5-((1r,4r)-4-hydroxy-4-methylcyclohexyl)pyrazin-2-yl)carbamate N,N-di-Boc-4-(5-aminopyrazin-2-yl)cyclohexanone (657 mg, 1.678 mmol) in THF (11.8 mL) was treated with methyllithium (1.469 mL, 2.350 mmol) at −78° C. The reaction was stirred at −78° C. for 2 h. After methyllithium (1.469 mL, 2.350 mmol) was added more, the reaction mixture was stirred at −78° C. for another 2 h. This process repeated once more. Then, the reaction mixture was quenched with methanol and water. The resulting mixture was concentrated and the residue was suspended in ethyl acetate. The organic layer was washed with water and brine, dried over anhydrous $Na_2SO_4$, filtered off, and concentrated. The crude diastereomeric mixture was purified by chromatography (0-100% ethyl acetate in hexane). For tert-butyl (5-((1s,4s)-4-hydroxy-4-methylcyclohexyl)pyrazin-2-yl) carbamate (26.7% yield). LCMS (m/z): 308.7 (MH+), 0.79 min. For tert-butyl (5-((1r,4r)-4-hydroxy-4-methylcyclohexyl)pyrazin-2-yl)carbamate (23.3% yield), LCMS (m/z): 308.7 (MH+), 0.75 min.

Step 2. (1s,4s)-4-(5-aminopyrazin-2-yl)-1-methylcyclohexanol

Tert-butyl (5-((1s,4s)-4-hydroxy-4-methylcyclohexyl) pyrazin-2-yl)carbamate (138 mg, 0.449 mmol) in DCM was added HCl (4 M in dioxane) (4489 μL, 17.96 mmol). The reaction mixture was stirred at room temperature overnight. Diluted with EtOAc and washed with sat $NaHCO_3$. No separation, and dried with $Na_2SO_4$. Filtered and washed with EtOAc. Concentrated to provide 93 mg of desired product in quantitative yield. LCMS (m/z): 208 (MH+), 0.41 min.

Step 3. (1s,4s)-4-(5-amino-6-bromopyrazin-2-yl)-1-methylcyclohexanol

To a solution of (1s,4s)-4-(5-aminopyrazin-2-yl)-1-methylcyclohexanol (93 mg, 0.449 mmol) in acetonitrile (8974 μL) was added NBS (80 mg, 0.449 mmol) at 0° C. The reaction mixture was stirred at 0° C. for 15 min. After quenched with $NaHCO_3$. extracted with EtOAc three times. The organic layers were combined and washed with water, and brine. Dried over $Na_2SO_4$, filtered and concentrated to afford 100 mg of (1s,4s)-4-(5-amino-6-bromopyrazin-2-yl)-1-methylcyclohexanol in 78% yield. LCMS (m/z): 288 (MH+), 0.60 min.

Step 4. (1r,4r)-4-(5-aminopyrazin-2-yl)-1-methylcyclohexanol and Step 5. (1r,4r)-4-(5-amino-6-bromopyrazin-2-yl)-1-methylcyclohexanol Following Steps 2 and 3, using (1r,4r)-4-(5-aminopyrazin-2-yl)-1-methylcyclohexanol, (1r,4r)-4-(5-amino-6-bromopyrazin-2-yl)-1-methylcyclohexanol was obtained. LCMS (m/z): 288 (MH+), 0.57 min.

Examples 19 and 20

Synthesis of methyl 3-(5-amino-6-(4-(benzylcarbamoyl)-3-fluorophenyl)pyrazin-2-yl)propanoate and 4-(3-amino-6-(3-(methylamino)-3-oxopropyl) pyrazin-2-yl)-N-benzyl-2-fluorobenzamide Scheme 38

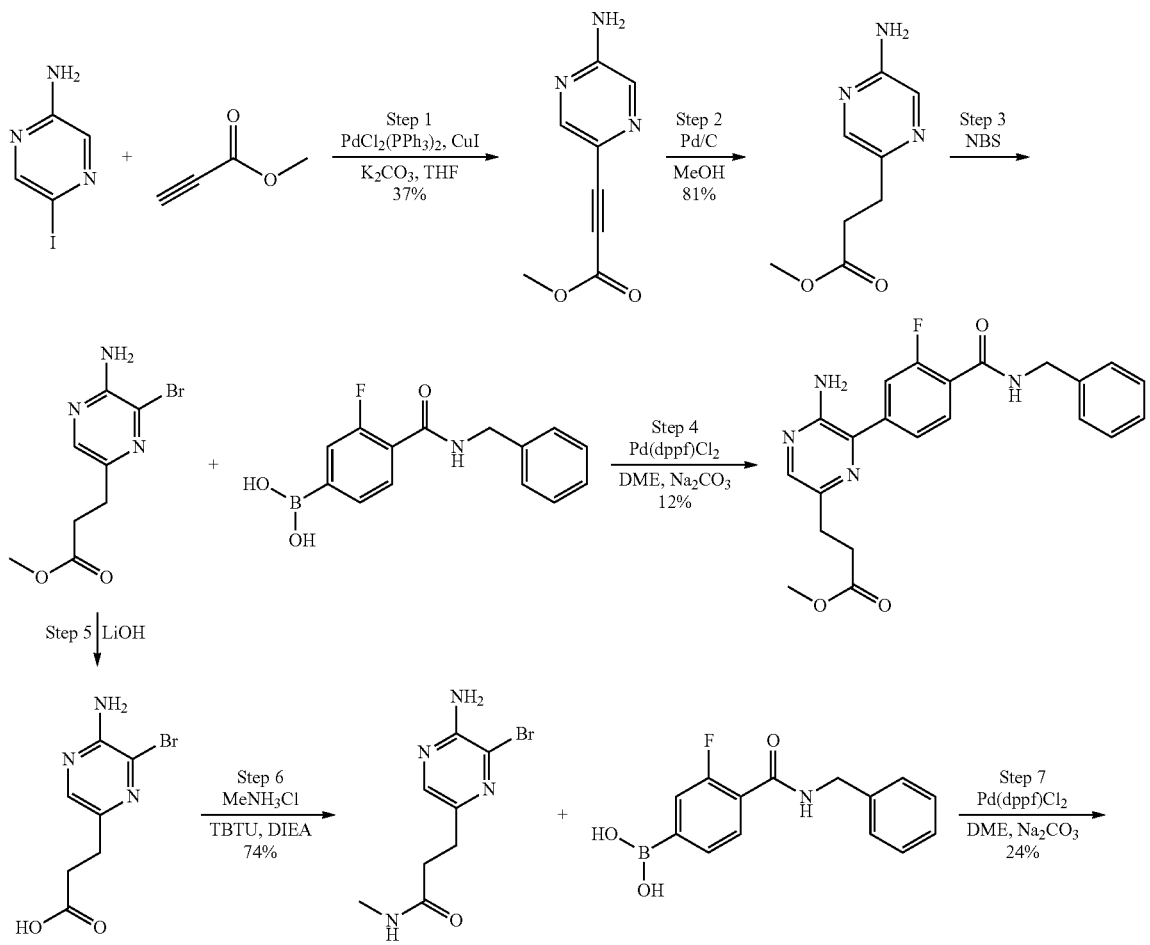

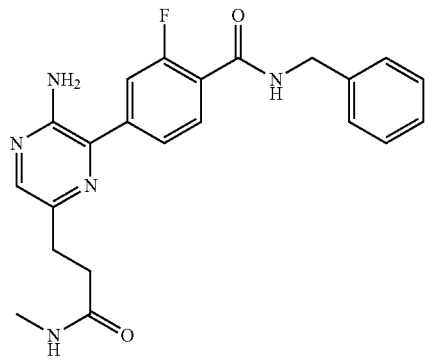

Step 1. methyl 3-(5-aminopyrazin-2-yl)propiolate

To a 5 mL of microwave vial was added 5-iodopyrazin-2-amine (100 mg, 0.452 mmol), methyl propiolate (161 μL, 1.810 mmol), potassium carbonate (125 mg, 0.905 mmol), copper (I) iodide (3.45 mg, 0.018 mmol), and THF (1508 μL). The reaction mixture was heated at 65° C. for 2 h. The reaction mixture was diluted with water and extracted with EtOAc. The organic layer was dried over anhydrous sodium sulfate, filtered, and evaporated in vacuo. The crude product was purified by flash chromatography (20% EtOAc in DCM) yielding methyl 3-(5-aminopyrazin-2-yl)propiolate (38%). LCMS (m/z): 178.4 (MH$^+$), 0.48 min.

Step 2. methyl 3-(5-aminopyrazin-2-yl)propanoate

To a solution of methyl 3-(5-aminopyrazin-2-yl)propiolate (30 mg, 0.169 mmol) in MeOH (847 μL) was added PdC (36.0 mg, 0.034 mmol). The solution was degassed by $N_2$ stream for 15 min. After flushed with hydrogen gas and equipped with a hydrogen balloon, the reaction mixture was stirred for 16 h. The reaction mixture was filtered through Celite. The volatile materials were removed in vacuo. The crude methyl 3-(5-aminopyrazin-2-yl)propanoate was obtained (81%) and used for the next step without further purification. LCMS (m/z): 182.1 (MH$^+$), 0.31 min.

Step 3. methyl 3-(5-amino-6-bromopyrazin-2-yl)propanoate

To a solution of methyl 3-(5-aminopyrazin-2-yl)propanoate (25 mg, 0.138 mmol) in $CH_3CN$ (690 μL) was added NBS (24.56 mg, 0.138 mmol). The reaction mixture was stirred for 1 h at room temperature. After quenched with $Na_2S_2O_3$ solution, the reaction mixture was stirred with $NaHCO_3$ solution for 20 min and extracted with EtOAc. The organic layer was washed with water and brine, dried over Na2SO4, filtered and concentrated in vacuo. The crude methyl 3-(5-amino-6-bromopyrazin-2-yl)propanoate was obtained (28%). LCMS (m/z): 260.2/262.2 (MH$^+$), 0.54 min.

Step 4. methyl 3-(5-amino-6-(4-(benzylcarbamoyl)-3-fluorophenyl)pyrazin-2-yl)propanoate To a solution of methyl 3-(5-amino-6-bromopyrazin-2-yl)propanoate (10 mg, 0.038 mmol), 4-(benzylcarbamoyl)-3-fluorophenylboronic acid (13.65 mg, 0.050 mmol) and PdCl2(dppf) (2.81 mg, 3.84 μmol) in DME (256 μL) was added 2M $Na_2CO_3$ (3.87 mL). The reaction mixture was heated at microwave synthesizer (120° C., 10 min). LCMS (m/z): 409.2 (MH$^+$ for ester), 0.75 min; 395.2 (MH$^+$ for very small amount of acid, but mixed with boronic ester), 0.66 min. To the reaction mixture, anhydrous sodium sulfate was added, filtered, and concentrated. The crude product was purified by prep HPLC, lyophilized yielding methyl 3-(5-amino-6-(4-(benzylcarbamoyl)-3-fluorophenyl)pyrazin-2-yl)propanoate as a TFA salt (12%). LCMS (m/z): 409.1 (MH$^+$), 0.73 min; 1H NMR (400 MHz, MeOH-$d_4$) δ ppm 7.89-7.76 (m, 2 H), 7.69-7.61 (m, 1 H), 7.60-7.51 (m, 1 H), 7.42-7.28 (m, 5 H), 7.28-7.20 (m, 1 H), 4.64-4.55 (m, 2 H), 3.62 (s, 3 H), 3.06-2.93 (m, 2 H), 2.79-2.67 (m, 2 H).

Step 5. 3-(5-amino-6-bromopyrazin-2-yl)propanoic acid

To a solution of methyl 3-(5-amino-6-bromopyrazin-2-yl)propanoate (55 mg, 0.211 mmol) in MeOH (961 μL) and $H_2O$ (96 μL) was added potassium carbonate (170 mg, 1.230 mmol). The reaction mixture was stirred for overnight. To the reaction mixture, anhydrous $Na_2SO_4$ was added. After diluted with EtOAc (3 mL) and filtered, the volatile materials were removed in vacuo. The crude 3-(5-amino-6-bromopyrazin-2-yl)propanoic acid was obtained and used for the next step without further purification. LCMS (m/z): 246.0/248.0 (MH$^+$, major), 0.26 min.

Step 6. 3-(5-amino-6-bromopyrazin-2-yl)-N-methylpropanamide

To a solution of 3-(5-amino-6-bromopyrazin-2-yl)propanoic acid (32 mg, 0.130 mmol) in DMF (1300 μL) was added TBTU (62.6 mg, 0.195 mmol), DIEA (68.1 μL, 0.390 mmol), and methanamine hydrochloride (9.66 mg, 0.143 mmol). The reaction mixture was stirred for 3 h. The reaction mixture was extracted with EtOAc. The organic layer was washed with water and brine, dried over $Na_2SO_4$, filtered and concentrated in vacuo. The crude 3-(5-amino-6-bromopyrazin-2-yl)-N-methylpropanamide (74%) was obtained and was used for the next step without further purification. LCMS (m/z): 259/261 (MH$^+$), 0.35 min.

Step 7. 4-(3-amino-6-(3-(methylamino)-3-oxopropyl)pyrazin-2-yl)-N-benzyl-2-fluorobenzamide Following Step 4 in Scheme 38, using 3-(5-amino-6-bromopyrazin-2-yl)-N-methylpropanamide, 4-(3-amino-6-(3-(methylamino)-3-oxopropyl)pyrazin-2-yl)-N-benzyl-2-fluorobenzamide was obtained (24%). LCMS (m/z): 408.1 (MH$^+$), 0.51 min; 1H NMR (400 MHz, MeOH-$d_4$) δ ppm 7.89-7.78 (m, 2 H), 7.68-7.51 (m, 2 H), 7.41-7.29 (m, 4 H), 7.26 (d, J=7.1 Hz, 1 H), 4.60 (s, 2 H), 2.98 (t, J=7.3 Hz, 2 H), 2.66 (s, 3 H), 2.57 (t, J=7.3 Hz, 2 H).

Synthesis of
2-(5-amino-6-bromopyrazin-2-yl)ethanol

Scheme 39

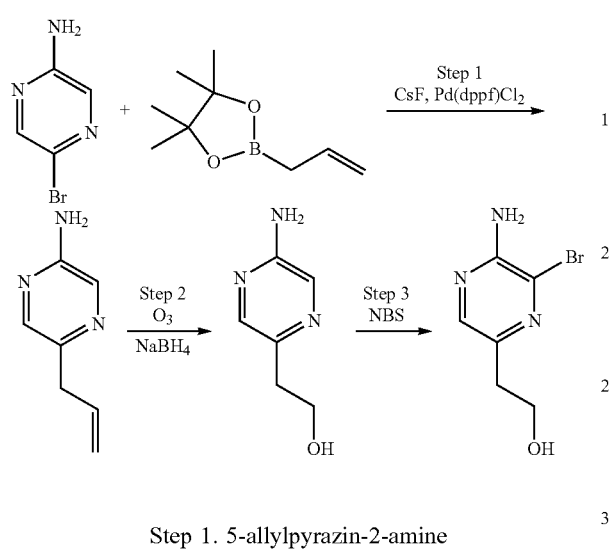

Step 1. 5-allylpyrazin-2-amine

To a solution of 5-bromopyrazin-2-amine (1.3 g, 7.47 mmol) in was added 2-allyl-,4,5,5-tetramethyl-1,3,2-dioxaborolane (1.883 g, 11.21 mmol), PdCl$_2$(dppf)CH$_2$Cl$_2$ adduct (0.610 g, 0.747 mmol) and CsF (3.40 g, 22.41 mmol), the reaction mixture was purge though Nitrogen. The reaction mixture was then heated at 100° C. in oil bath for 3 h. The reaction mixture was filtered through Celite, washed by EtOAc, the filtrated was partitioned between EtOAc and water. The organic was dried over anhydrous sodium sulfate and concentrated in vacuo, The crude material was purified by flash chromatography column to yield 5-allylpyrazin-2-amine in 37% yield. LCMS (m/z): 136.0 (MH$^+$), 0.30 min.

Step 2. 2-(5-aminopyrazin-2-yl)ethanol 5-allylpyrazin-2-amine (180 mg, 1.332 mmol) in DCM (26.6 mL) was cooled down to −78° C., then Ozone was bubbled through for 10 min until the solution turned to blue color. Then Nitrogen was purged through for 5 min. NaBH$_4$ (151 mg, 4.00 mmol) in ethanol (10 mL) was added slowly, The reaction mixture was allowed to return to room temperature. After 1 h, Sat. NH$_4$Cl was added slowly, the reaction mixture was then extracted by CHCl$_3$/IPA (7:3) (3 times), the organic was dried and concentrated to yield the crude product. The crude product is used in next step reaction without purification. LCMS (m/z): 140.0 (MH$^+$), 0.21 min.

Step 3. 2-(5-amino-6-bromopyrazin-2-yl)ethanol

To a solution of 2-(5-aminopyrazin-2-yl)ethanol (30 mg, 0.216 mmol) in CH$_3$CN (719 μL) was added NBS (38.4 mg, 0.216 mmol) at 0° C. The reaction mixture was stirred at 0° C. for 30 min. The reaction mixture was quenched by sat. NaHCO$_3$, then extracted by EtOAc, The combined organic layer was washed with water and brine, dried over anhydrous sodium sulfate. Filtered and concentrated in vacuo yielding crude 2-(5-amino-6-bromopyrazin-2-yl)ethanol which was used in next step reaction without purification. LCMS (m/z): 218.0/220.0 (MH$^+$), 0.33 min.

Synthesis of
3-bromo-5-(2-methoxyethyl)pyrazin-2-amine

Scheme 40

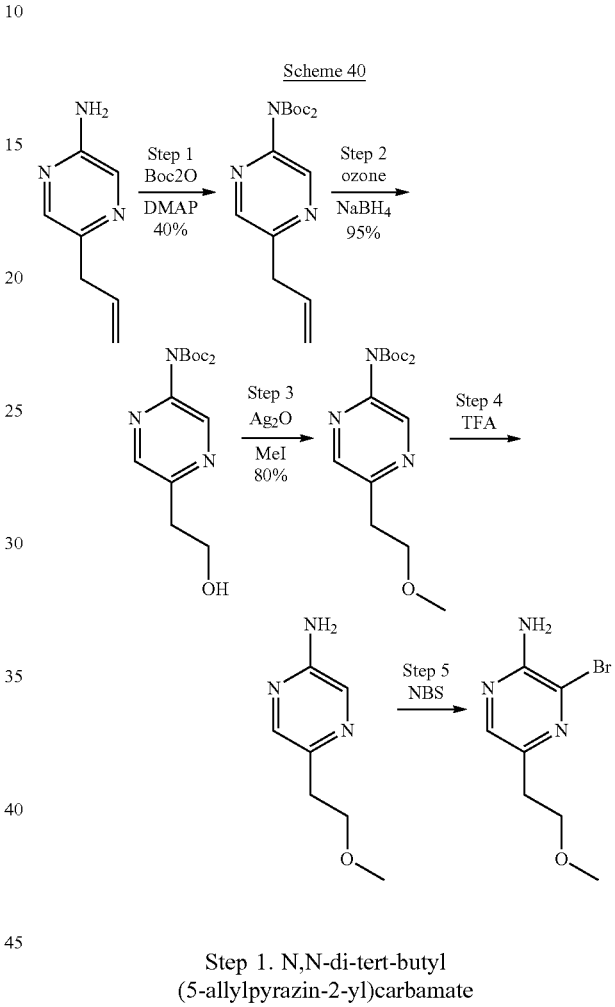

Step 1. N,N-di-tert-butyl (5-allylpyrazin-2-yl)carbamate

To a solution of 5-allylpyrazin-2-amine (1.2 g, 8.88 mmol) in CH$_2$Cl$_2$ (29.6 mL) was added Boc$_2$O (4.07 g, 18.64 mmol) and DMAP (1.627 g, 13.32 mmol) at room temperature. The reaction mixture was stirred at room temperature for overnight. After quenched with sat NaHCO$_3$, the reaction mixture was extracted with CH$_2$Cl$_2$ 3 times. The combined organic layer was washed with water and brine, dried over anhydrous sodium sulfate. Filtered and concentrated in vacuo. The desire was obtained as a white solid (1.1 g, 37% yield) by flash column chromatography. R$_f$ (TLC)=0.3 (20% EtOAc in hexanes). LCMS (m/z): 336.2 (MH$^+$), 1.04 min.

Step 2. N,N-di-tert-butyl (5-(2-hydroxyethyl)pyrazin-2-yl)carbamate

A solution of N,N-di-tert-butyl (5-allylpyrazin-2-yl)carbamate (1.1 g, 3.28 mmol) in DCM (32.8 mL) was cooled down to −78° C., ozone was bubbled through until blue color appears, then Nitrogen was purged through for 5 min. NaBH₄ (0.74 g, 19.6 mmol) in methanol (20 mL) was added slowly, The reaction mixture was allowed to return to room temperature. After 2 h, saturated NH₄Cl solution was added, the reaction mixture was partitioned between EtOAc and water. The organic was washed with NaHCO₃, water and brine, dried over anhydrous Na₂SO₄, filtered and concentrated. The crude product was used in next step reaction without purification. LCMS (m/z): 340.3 (MH⁺), 0.77 min.

Step 3. N,N-di-tert-butyl (5-(2-methoxyethyl) pyrazin-2-yl)carbamate

To a solution of N,N-di-tert-butyl (5-(2-hydroxyethyl) pyrazin-2-yl)carbamate (240 mg, 0.707 mmol) in MeI (7.7 mL) was added silver oxide (983 mg, 4.24 mmol). The reaction mixture was stirred at room temperature for overnight. The reaction mixture was filtered through Celite and washed with EtOAc and methanol, the organic was washed by sat. NaHCO₃, water and brine, dried and concentrated. The crude material was used in next step reaction without purification. LCMS (m/z): 354.2 (MH⁺), 0.92 min.

Step 4. 5-(2-methoxyethyl) pyrazin-2-amine

N,N-Di-tert-butyl (5-(2-methoxyethyl)pyrazin-2-yl)carbamate (200 mg, 0.566 mmol) in DCM (1.9 mL) was added TFA (872 μL, 11.32 mmol), the reaction mixture was stirred at room temperature for 1 h, the reaction mixture was added 5 mL toluene and concentrated to dryness. The crude material was used in next step reaction without purification. LCMS (m/z): 154.1 (MH⁺), 0.27 min.

Step 5. 3-bromo-5-(2-methoxyethyl) pyrazin-2-amine

To a solution of 5-(2-methoxyethyl)pyrazin-2-amine (80 mg, 0.522 mmol) in DCM (1.7 mL) was added NBS (93 mg, 0.522 mmol) at room temperature. The reaction mixture was stirred at room temperature for 1 h. After quenched with NaHCO₃, the reaction mixture was extracted with DCM 3 times. The combined organic layer was washed with water and brine, dried over anhydrous sodium sulfate. The crude material was used in next step reaction without purification. LCMS (m/z): 232.1/234.1 (MH⁺), 0.49 min.

Example 21

Synthesis of 4-(3-amino-6-(2-(methylsulfonyl)ethyl) pyrazin-2-yl)-N-benzyl-2-fluorobenzamide Scheme 41

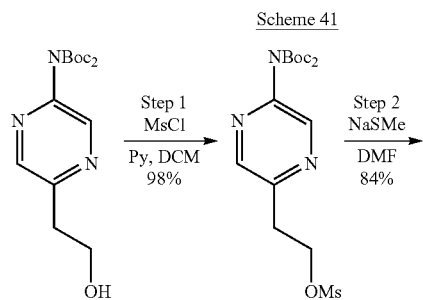

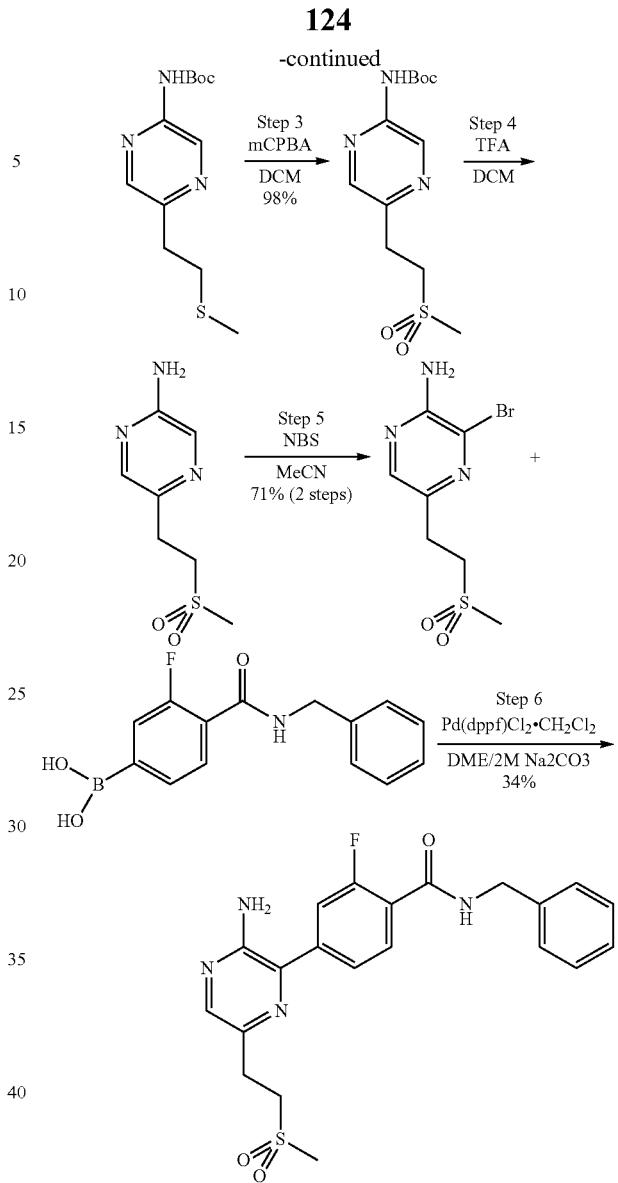

Step 1. 2-(5-(bis(tert-butoxycarbonyl)amino) pyrazin-2-yl)ethyl methanesulfonate To N,N-di-tert-butyl (5-(2-hydroxyethyl)pyrazin-2-yl) carbamate (450 mg, 1.326 mmol) in DCM (10 mL) was added pyridine (0.429 mL, 5.30 mmol) and cooled to 0° C. using ice bath. Then Mesyl-Cl (0.382 mL, 4.91 mmol) was added and the reaction was allowed to warm to room temperature and stirred for 16 h. To the reaction was added 150 mL of ethyl acetate and saturated sodium bicarbonate. The organic layer was extracted and washed again with saturated sodium bicarbonate, water (3×), filtered, dried with sodium sulfate and concentrated to constant mass to give 540 mg of desired product, used as is, (98% yield). LCMS (m/z): 418.3 (MH⁺), 0.89 min; ¹H NMR (400 MHz, CDCl₃) δ ppm 8.50 (s, 1H), 8.38 (s, 1H), 4.67 (t, J=6.3 Hz, 2H), 3.28 (t, J=6.3 Hz, 2H), 2.94 (s, 3H), 1.45 (s, 18H).

Step 2. tert-butyl 5-(2-(methylthio)ethyl)pyrazin-2-ylcarbamate

To 2-(5-(bis(tert-butoxycarbonyl)amino)pyrazin-2-yl) ethyl methanesulfonate (540 mg, 1.293 mmol) in DMF (7 mL) was added sodium thiomethoxide (408 mg, 5.82 mmol) and was stirred at 85° C. for 3 h, followed by LCMS. The reaction was let cool, 200 mL of ethyl acetate and saturated sodium bicarbonate was added. The organic layer was extracted and washed water (3×), saturated salt solution, dried sodium sulfate, filtered through 2 cm silica gel plug and flushed with ethyl acetate. The solvent was concentrated off to constant mass to give 294 mg of the desired product as free base used as is, (84% yield). LCMS (m/z): 270.4 (MH$^+$), 0.84 min. $^1$H NMR (400 MHz, CDCl$_3$) δ ppm 9.19 (s, 1H), 8.08 (d, J=1.2 Hz, 1H), 7.20 (br. s., 1H), 2.99-3.08 (m, 2H), 2.79-2.94 (m, 2H), 2.12 (s, 3H), 1.54 (s, 9H).

Step 3. tert-butyl 5-(2-(methylsulfonyl)ethyl)pyrazin-2-ylcarbamate

To tert-butyl 5-(2-(methylthio)ethyl)pyrazin-2-ylcarbamate (292 mg, 1.084 mmol) in DCM (10 mL) was added 40% (3.5 mL) of a freshly made solution of mCPBA (972 mg, 4.34 mmol) in DCM (8.7 mL) with stirring at room temperature, followed by LCMS. After 30 min another 15% (1.3 mL of the above mCPBA solution) was added and stirred for 30 min, followed by LCMS. Then another 5% (0.044 mL of the above mCPBA solution) was added and stirred for 30 min more. The reaction was followed by LCMS. To the reaction was added 200 mL of ethyl acetate and excess saturated sodium bicarbonate. The organic layer was extracted and washed again with saturate sodium bicarbonate, water (3×), filtered and concentrated to constant mass to give 320 mg of the desired product used as is, (98% yield). LCMS (m/z): 302.1 (MH$^+$), 0.62 min; $^1$H NMR (400 MHz, CDCl$_3$) δ ppm 9.20 (s, 1H), 8.14 (s, 1H), 7.23 (br. s., 1H), 3.47-3.57 (m, 2H), 3.26-3.36 (m, 2H), 2.86-2.93 (m, 3H), 1.55 (s, 9H).

Step 4. 5-(2-(methylsulfonyl)ethyl)pyrazin-2-amine

To tert-butyl 5-(2-(methylsulfonyl)ethyl)pyrazin-2-ylcarbamate (320 mg, 1.062 mmol) in DCM (6 mL) was added TFA (2.5 mL, 32.4 mmol) and stirred at room temperature for 1 hour. The solvent was concentrated off to constant mass. The product was free based by using solid supported carbonate 2.5 grams at 0.8 mmol/gram with 6 mL of acetonitrile and stirred for 5 min. The solid support was filtered off and flush with acetonitrile. The product was concentrated to constant mass to give the desired product used as is, assume quantitative yield (1.062 mmol). LCMS (m/z): 202.1 (MH$^+$), 0.20 min.

Step 5. 3-bromo-5-(2-(methylsulfonyl)ethyl)pyrazin-2-amine

To 5-(2-(methylsulfonyl)ethyl)pyrazin-2-amine (213 mg, 1.06 mmol) in acetonitrile (6 mL) was added NBS (179 mg, 1.007 mmol) and was stirred at room temperature for 1 h. The solvent was concentrated off to residue. To the crude was added ethyl acetate, washed with saturated sodium carbonate, water (2×), dried sodium sulfate, filtered and concentrated to constant mass to give 210 mg of the desired product as free base used as is, (71% yield). LCMS (m/z): 280.0/282.0 (MH$^+$), 0.38 min.

Step 6. 4-(3-amino-6-(2-(methylsulfonyl)ethyl) pyrazin-2-yl)-N-benzyl-2-fluorobenzamide To 3-bromo-5-(2-(methylsulfonyl)ethyl)pyrazin-2-amine (126 mg, 0.405 mmol) was added N-benzyl-2-fluoro-4-(4, 4,5,5-tetramethyl-1,3,2-dioxaborolan-2-yl)benzamide (144 mg, 0.405 mmol), PdCl$_2$(dppf)-CH$_2$Cl$_2$ adduct (33.1 mg, 0.040 mmol), DME (1.5 mL) and then sodium carbonate 2 M aqueous solution (0.607 mL, 1.214 mmol). The reaction was microwave at 125° C. for 12 min followed by LCMS. To the reaction was added 5 mL of DME and 5 mL of MeOH, filtered and concentrated to residue. The crude was dissolved in 2.5 mL of DMSO, filtered, purified by prep HPLC and lyophilized to TFA salt. To the TFA salt was added 200 mL of ethyl acetate, washed with saturated sodium carbonate (3×), water (3×), dried sodium sulfate, filtered and concentrated to constant mass to give 59 mg of the desired product 4-(3-amino-6-(2-(methylsulfonyl)ethyl) pyrazin-2-yl)-N-benzyl-2-fluorobenzamide as free base in 34% yield. LCMS (m/z): 429.2 (MH$^+$), 0.65 min; $^1$H NMR (400 MHz, CD$_3$OD) δ ppm 7.95 (s, 1H), 7.83 (t, J=7.6 Hz, 1H), 7.67 (dd, J=8.0, 1.4 Hz, 1H), 7.59 (dd, J=11.7, 1.2 Hz, 1H), 7.29-7.42 (m, 4H), 7.20-7.28 (m, 1H), 4.59 (s, 2H), 3.48-3.57 (m, 2H), 3.18 (dd, J=9.0, 6.7 Hz, 2H), 2.96 (s, 3H).

Examples 22, 23, and 24

Synthesis of (+/−)-4-(3-amino-6-(2-hydroxypropyl) pyrazin-2-yl)-N-benzyl-2-fluorobenzamide, (R)-4-(3-amino-6-(2-hydroxypropyl)pyrazin-2-yl)-N-benzyl-2-fluorobenzamide, and (S)-4-(3-amino-6-(2-hydroxypropyl) pyrazin-2-yl)-N-benzyl-2-fluorobenzamide

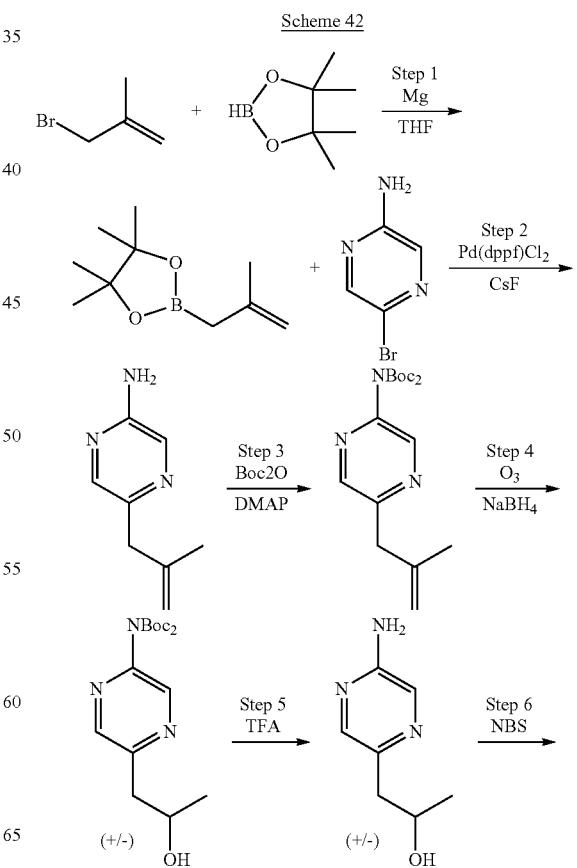

Scheme 42

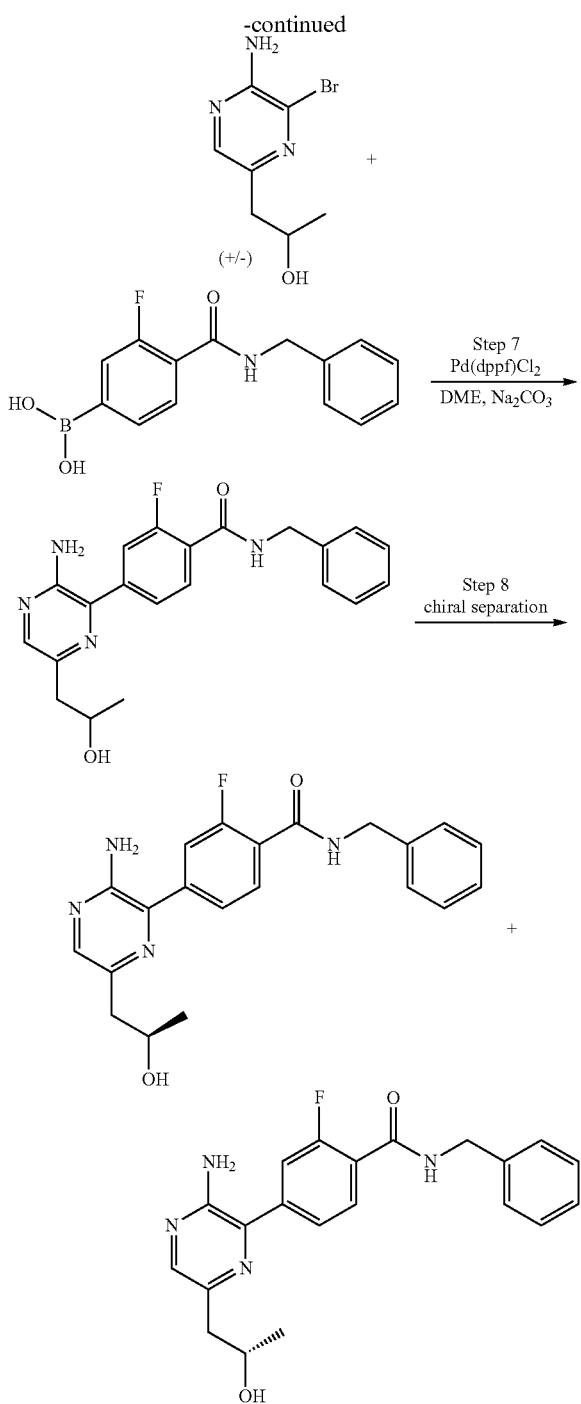

Step 1. 4,4,5,5-tetramethyl-2-(2-methylallyl)-1,3,2-dioxaborolane

To a suspension of magnesium turning (1.139 g, 46.9 mmol) in THF (65.1 mL) was added 4,4,5,5-tetramethyl-1,3,2-dioxaborolane (5.67 mL, 39.1 mmol) at room temperature under nitrogen. 3-bromo-2-methylprop-1-ene (3.97 mL, 39.1 mmol) was added slowly, after 30 min, more 3-bromo-2-methylprop-1-ene (3.97 mL, 39.1 mmol) was added, The reaction mixture was stirred at room temperature for 1 h. heptanes was added, followed by 1N HCl. The reaction mixture was then extracted by heptanes. The organic was washed by water and brine, dried and concentrated to yield 4,4,5,5-tetramethyl-2-(2-methylallyl)-1,3,2-dioxaborolane. The product was used in the next step without purification, $^1$H NMR (400 MHz, CDCl$_3$) δ ppm 4.67 (d, J=6.7 Hz, 2 H), 1.77 (s, 3 H), 1.34-1.20 (m, 12 H).

Step 2. 5-(2-methylallyl)pyrazin-2-amine

To a solution of 5-bromopyrazin-2-amine (1 g, 5.75 mmol) in was added 4,4,5,5-tetramethyl-2-(2-methylallyl)-1,3,2-dioxaborolane (1.360 g, 7.47 mmol), PdCl$_2$(dppf)-DCM adduct (0.469 g, 0.575 mmol), CsF (2.62 g, 17.24 mmol), purge though nitrogen. The reaction mixture was stirred at 100° C. in oil bath for 3 h. The reaction mixture was partitioned between EtOAc and water. The organic was washed with brine, dried and concentrated. The residue was dissolved in 1N HCl (10 mL) The aqueous layer was back extracted with EtOAc, The aqueous was then neutralized to pH=8, then extracted by EtOAc 3 times. The organic was then dried and concentrated. The crude product was used in next step reaction. LCMS (m/z): 150.5 (MH$^+$), 0.28 min.

Step 3. N,N-di-tert-butyl (5-(2-methylallyl)pyrazin-2-yl)carbamate

To a solution of 5-(2-methylallyl)pyrazin-2-amine (235 mg, 1.575 mmol) in DCM (5.2 mL), Boc$_2$O (731 μL, 3.15 mmol) was added, followed by DMAP (385 mg, 3.15 mmol). The reaction was stirred at room temperature for overnight. To the reaction was added 30 mL of DCM and washed with saturated sodium bicarbonate (2×) water (1×), dried sodium sulfate, filtered and concentrated to residue. The crude was purified by silica gel chromatography eluting with 0-30% ethyl acetate and heptane to yield 250 mg of product. LCMS (m/z): 350.1 (MH$^+$), 1.12 min; $^1$H NMR (400 MHz, CDCl$_3$) δ ppm 8.45 (d, J=1.2 Hz, 1 H), 8.41-8.33 (m, 1 H), 4.92 (s, 1 H), 4.75 (s, 1 H), 3.57 (s, 2 H), 1.73 (s, 3 H), 1.43 (s, 18 H).

Step 4. (+/−)-N,N-di-tert-butyl (5-(2-hydroxypropyl)pyrazin-2-yl)carbamate

N,N-Di-tert-butyl (5-(2-methylallyl)pyrazin-2-yl)carbamate (120 mg, 0.343 mmol) in methanol (6.8 mL) was cooled down to −78° C., the ozone was bubbled through for 6 min. Then nitrogen was purged through for 5 min. NaBH$_4$ (39.0 mg, 1.030 mmol) in methanol (5 mL) was added slowly. The reaction mixture was allowed to return to room temperature. After 1 h, Sat. NH$_4$Cl was added slowly. The reaction mixture was partitioned between EtOAc and water. The organic was washed with saturated NaHCO$_3$, water and brine, dried and concentrated. The crude product was used in next step reaction without purification. LCMS (m/z): 354.1 (MH$^+$), 0.84 min.

Step 5. (+/−)-1-(5-aminopyrazin-2-yl)propan-2-ol (+/−)-N,N-Di-tert-butyl (5-(2-hydroxypropyl)pyrazin-2-yl)carbamate (110 mg, 0.311 mmol) in DCM (3.11 mL) was added TFA (1 mL, 12.98 mmol), the reaction mixture was stirred at room temperature for 30 min, the reaction mixture was coevaporated with toluene. The crude product was used in next step reaction without purification. LCMS (m/z): 154.1 (MH$^+$), 0.24 min.

Step 6. (+/−)-1-(5-amino-6-bromopyrazin-2-yl)propan-2-ol

To a solution of (+/−)-1-(5-aminopyrazin-2-yl)propan-2-ol (47 mg, 0.307 mmol) in DCM (3.0 mL) was added NBS (49.1 mg, 0.276 mmol) at 0° C. The reaction mixture was stirred at 0° C. for 10 min. After quenched with sat NaHCO$_3$, the reaction mixture was extracted with EtOAc 3 times. The combined organic layer was washed with water and brine, dried over anhydrous sodium sulfate. Filtered and concentrated in vacuo. The crude product was used in next step reaction without purification. LCMS (m/z): 234.0 (MH$^+$), 0.40 min.

Step 7. (+/−)-4-(3-amino-6-(2-hydroxypropyl)pyrazin-2-yl)-N-benzyl-2-fluorobenzamide To a solution of (+/−)-1-(5-amino-6-bromopyrazin-2-yl)propan-2-ol (30 mg, 0.129 mmol) in DME (970 µL) was added 4-(benzylcarbamoyl)-3-fluorophenylboronic acid (31.8 mg, 0.116 mmol), PdCl$_2$(dppf)CH$_2$Cl$_2$ adduct (10.56 mg, 0.013 mmol), 2M Na$_2$CO$_3$ (323 µL). The reaction mixture was stirred at 120° C. for 10 min in microwave. The reaction mixture was partitioned between EtOAc and water. the organic was dried and concentrated. the crude product was purified by Prep HPLC. The pure fraction was combined and desalt to yield (+/−)-4-(3-amino-6-(2-hydroxypropyl)pyrazin-2-yl)-N-benzyl-2-fluorobenzamide. LCMS (m/z): 381.2 (MH$^+$), 0.67 min; $^1$H NMR (400 MHz, CD$_3$OD) δ ppm 7.95-7.81 (m, 2 H), 7.66 (dd, J=1.6, 8.2 Hz, 1 H), 7.58 (dd, J=1.6, 11.7 Hz, 1 H), 7.43-7.31 (m, 4 H), 7.31-7.19 (m, 1 H), 4.62 (s, 2 H), 4.16-4.04 (m, 1 H), 2.79 (d, J=6.3 Hz, 2 H), 1.23 (d, J=6.3 Hz, 3 H).

Step 7. (R)-4-(3-amino-6-(2-hydroxypropyl)pyrazin-2-yl)-N-benzyl-2-fluorobenzamide and (S)-4-(3-amino-6-(2-hydroxypropyl) pyrazin-2-yl)-N-benzyl-2-fluorobenzamide The racemic (+/−)-4-(3-amino-6-(2-hydroxypropyl)pyrazin-2-yl)-N-benzyl-2-fluorobenzamide was resolved by chiral SFC (ChiralPak 5mic AD column, 4.6×100 (mm), methanol+0.1% DEA=40%, 5 mL/min). The polar enantiomer, (R)-4-(3-amino-6-(2-hydroxypropyl)pyrazin-2-yl)-N-benzyl-2-fluorobenzamide, was obtained at Rt=1.39 min. LCMS (m/z): 381.2 (MH$^+$), 0.67 min. The less polar enantiomer, (S)-4-(3-amino-6-(2-hydroxypropyl)pyrazin-2-yl)-N-benzyl-2-fluorobenzamide was obtained at Rt=1.97 min. LCMS (m/z): 381.2 (MH$^+$), 0.67 min. The stereochemistry was assigned arbitrarily.

Synthesis of 3-bromo-5-(2-ethoxyethyl)pyrazin-2-amine

Scheme 43

Step 1

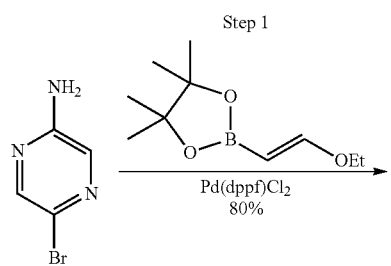

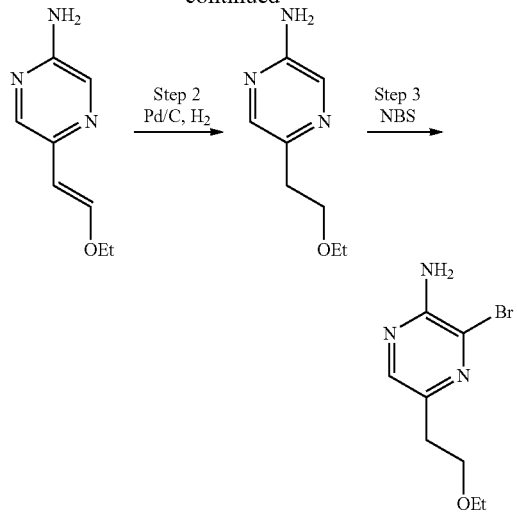

Step 1. (E)-5-(2-ethoxyvinyl)pyrazin-2-amine

To a solution of 5-bromopyrazin-2-amine (200 mg, 1.149 mmol) in DME (2874 µL) was added (E)-2-(2-ethoxyvinyl)-4,4,5,5-tetramethyl-1,3,2-dioxaborolane (341 mg, 1.724 mmol), PdCl$_2$(dppf)-CH$_2$Cl$_2$ adduct (94 mg, 0.115 mmol), and 2M Na$_2$CO$_3$ (958 µL). The reaction mixture was stirred at 130° C. in microwave reactor for 20 min. The reaction mixture was filtered through Celite and washed with EtOAc, the filtrate was partition between EtOAc and water. The aqueous was extracted by EtOAc three times, the combined organic was dried and concentrated. The crude material was purified by flash chromatography to give (E)-5-(2-ethoxyvinyl)pyrazin-2-amine. LCMS (m/z): 166.1 (MH$^+$), 0.41 min.

Step 2. 5-(2-ethoxyethyl)pyrazin-2-amine

To a solution of (E)-5-(2-ethoxyvinyl)pyrazin-2-amine (75 mg, 0.454 mmol) in ethanol (4.54 mL) was added Pd/C (48.3 mg, 0.454 mmol). The reaction mixture was purged by nitrogen for 10 min, and then stirred at room temperature for 2 h under hydrogen balloon. The reaction mixture was then filtered through Celite and washed with methanol and EtOAc, then concentrated. The crude product was used in next step reaction without purification. LCMS (m/z): 168.1 (MH$^+$), 0.33 min.

Step 3. 3-bromo-5-(2-ethoxyethyl)pyrazin-2-amine

To a solution of 5-(2-ethoxyethyl)pyrazin-2-amine (45 mg, 0.269 mmol) in DCM (897 µL) was added NBS (43.1 mg, 0.242 mmol) at 0° C. The reaction mixture was stirred at 0° C. for 10 min. After quenched with sat. NaHCO$_3$, the reaction mixture was extracted with EtOAc 3 times. The combined organic layer was washed with water and brine, dried over anhydrous sodium sulfate. Filtered and concentrated in vacuo. The crude product was used in next step reaction without purification. LCMS (m/z): 246.0 (MH$^+$), 0.59 min.

Synthesis of (+/−)-2-(5-amino-6-bromopyrazin-2-yl)propan-1-ol

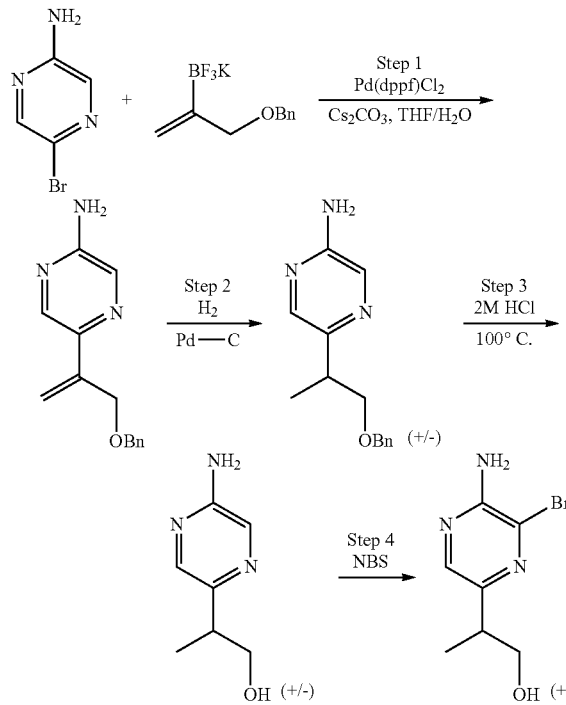

Step 1. 5-(3-(benzyloxy)prop-1-en-2-yl)pyrazin-2-amine

To a solution of 5-bromopyrazin-2-amine (200 mg, 1.149 mmol) in was added potassium (3-(benzyloxy)prop-1-en-2-yl)trifluoroborate (350 mg, 1.379 mmol), PdCl$_2$(dppf).CH$_2$Cl$_2$ adduct (94 mg, 0.115 mmol), Cs$_2$CO$_3$ (1124 mg, 3.45 mmol). Purged through Nitrogen. The reaction mixture was stirred at 100° C. in oil bath for 6 h. The reaction mixture was then partitioned between EtOAc and water, combined the organic layers and washed with water and brine, dried over anhydrous sodium sulfate and concentrated. The crude product was purified by flash chromatography to give 5-(3-(benzyloxy)prop-1-en-2-yl)pyrazin-2-amine in 61% yield. LCMS (m/z): 245.2 (MH$^+$), 0.67 min; $^1$H NMR (400 MHz, CD$_3$OD) δ ppm 8.26 (d, J=1.2 Hz, 1 H), 7.96 (d, J=1.2 Hz, 1 H), 7.34 (d, J=4.3 Hz, 5 H), 5.91 (s, 1 H), 5.44 (d, J=1.2 Hz, 1 H), 4.59 (s, 2 H), 4.49 (s, 2 H).

Step 2. (+/−)-5-(1-(benzyloxy)propan-2-yl)pyrazin-2-amine

To a solution of 5-(3-(benzyloxy)prop-1-en-2-yl)pyrazin-2-amine (91 mg, 0.377 mmol) in methanol (3771 μL) was added Pd/C (40.1 mg, 0.377 mmol) at room temperature. The reaction mixture was stirred at room temperature under hydrogen balloon for overnight. The reaction mixture was filtered through Celite, washed with methanol and EtOAc. The crude material was used in next step reaction without purification. LCMS (m/z): 244.2 (MH$^+$), 0.62 min.

Step 3. (+/−)-2-(5-aminopyrazin-2-yl)propan-1-ol

A solution of 5-(1-(benzyloxy)propan-2-yl)pyrazin-2-amine (80 mg, 0.329 mmol) in 1N HCl (1096 μL) was heat in oil bath for 7 h, cooling down, The reaction mixture was extracted by EtOAc, the aqueous was concentrated to dryness to yield the crude product as HCl salt and used in next step reaction. LCMS (m/z): 154.1 (MH$^+$), 0.26 min.

Step 4. (+/−)-2-(5-amino-6-bromopyrazin-2-yl)propan-1-ol

To a solution of 2-(5-aminopyrazin-2-yl)propan-1-ol (30 mg, 0.196 mmol) in DCM (653 μL) was added NBS (31.4 mg, 0.176 mmol) at 0° C. The reaction mixture was stirred at 0° C. for 10 min. After quenched with sat NaHCO$_3$, the reaction mixture was extracted with EtOAc 3 times. The combined organic layer was washed with water and brine, dried over anhydrous sodium sulfate. Filtered and concentrated in vacuo. The crude product was used in next step reaction without purification. LCMS (m/z): 234.0 (MH$^+$), 0.40 min.

Synthesis of 3-(5-amino-6-bromopyrazin-2-yl)propanenitrile

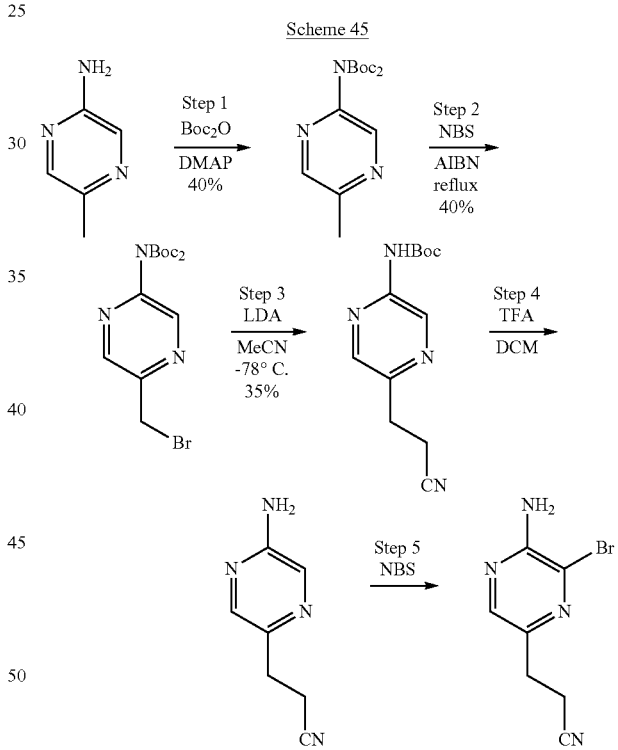

Step 1. N,N-di-tert-butyl (5-methylpyrazin-2-yl)carbamate

To a solution of 5-methylpyrazin-2-amine (1 g, 9.16 mmol) in CH$_2$Cl$_2$ (30 mL), Boc$_2$O (4.47 mL, 19.24 mmol) was added, followed by DMAP (1.679 g, 13.75 mmol) at room temperature. The reaction mixture was stirred at room temperature for overnight. After quenched with sat NaHCO$_3$, the reaction mixture was extracted with CH$_2$Cl$_2$ 3 times. The combined organic layer was washed with water and brine, dried over anhydrous sodium sulfate. Filtered and concentrated in vacuo. The desire product was obtained as a white solid by flash column chromatography (20% EtOAc in heptane). LCMS (m/z): 310.0 (MH+), 0.93 min.

Step 2. N,N-di-tert-butyl (5-(bromomethyl)pyrazin-2-yl)carbamate

To a solution of N,N-di-tert-butyl (5-methylpyrazin-2-yl) carbamate (1.37 g, 4.43 mmol) in CCl$_4$ (14.76 mL) was added NBS (0.828 g, 4.65 mmol), benzoyl peroxide (0.107 g, 0.443 mmol), AlBN (0.073 g, 0.443 mmol). The reaction mixture was stirred at reflux for 8 h. Work up, the solid was filtered, the organic was concentrated. The crude product was purified by flash chromatography to give the tile product in 36% yield. LCMS (m/z): 231.1 (MH+-Boc), 1.04 min.

Step 3. tert-butyl 5-(2-cyanoethyl)pyrazin-2-ylcarbamate n-Butyl lithium (2.5 M in hexanes 103 µL, 0.258 mmol) was added into diisopropylamine (39.3 µL, 0.276 mmol) in dry THF at 0° C. under argon, the mixture was then stirred at 0° C. for 1 h, then cooled down to −78° C., acetonitrile (14.12 µL, 0.270 mmol) was added slowly, the reaction mixture was allowed to return to room temperature and stirred at room temperature for 1 h, cooled down to −78° C. again, and N,N-di-tert-butyl (5-(bromomethyl)pyrazin-2-yl) carbamate (100 mg, 0.258 mmol) in THF (0.5 mL) was added slowly, the reaction mixture was stirred at −78° C. for 10 min, then allowed to return to room temperature, after 2 h, the reaction was quenched by sat. NH$_4$Cl solution, then extracted by EtOAc. The organic was washed by brine, dried and concentrated. The crude material was purified by flash chromatography (40% EtOAc/heptane) to give tert-butyl 5-(2-cyanoethyl)pyrazin-2-ylcarbamate in 40% yield. LCMS (m/z): 193.1 (MH+-tBu), 0.70 min; $^1$H NMR (400 MHz, CDCl$_3$) δ ppm 9.22 (s, 1 H), 8.12 (s, 1 H), 3.09 (t, J=7.2 Hz, 2 H), 2.83 (t, J=7.2 Hz, 2 H), 1.52-1.36 (m, 8 H).

Step 4. 3-(5-aminopyrazin-2-yl)propanenitrile

To a solution of tert-butyl 5-(2-cyanoethyl)pyrazin-2-ylcarbamate (25 mg, 0.101 mmol) in DCM (0.336 mL) was added TFA (0.1 mL, 1.298 mmol) at room temperature. The reaction mixture was stirred at room temperature for 1 h. After quenched with sat. NaHCO$_3$, the reaction mixture was extracted with DCM. The combined organic layer was washed with water and brine, dried over anhydrous sodium sulfate. Filtered and concentrated in vacuo. The crude product was used in next step reaction without purification. LCMS (m/z): 149.1 (MH+), 0.24 min.

Step 5. 3-(5-amino-6-bromopyrazin-2-yl)propanenitrile

To a solution of 3-(5-aminopyrazin-2-yl)propanenitrile (45 mg, 0.304 mmol) in DCM (1519 µL) was added NBS (48.7 mg, 0.273 mmol) at 0° C. The reaction mixture was stirred at 0° C. for 10 min. After quenched with NaHCO$_3$, the reaction mixture was extracted with EtOAc 3 times. The combined organic layer was washed with water and brine, dried over anhydrous sodium sulfate. Filtered and concentrated in vacuo. The crude product was used in next step reaction without purification. LCMS (m/z): 227/229.1 (MH+), 0.45 min.

Synthesis of 5-(5-amino-6-bromopyrazin-2-yl)piperidin-2-one

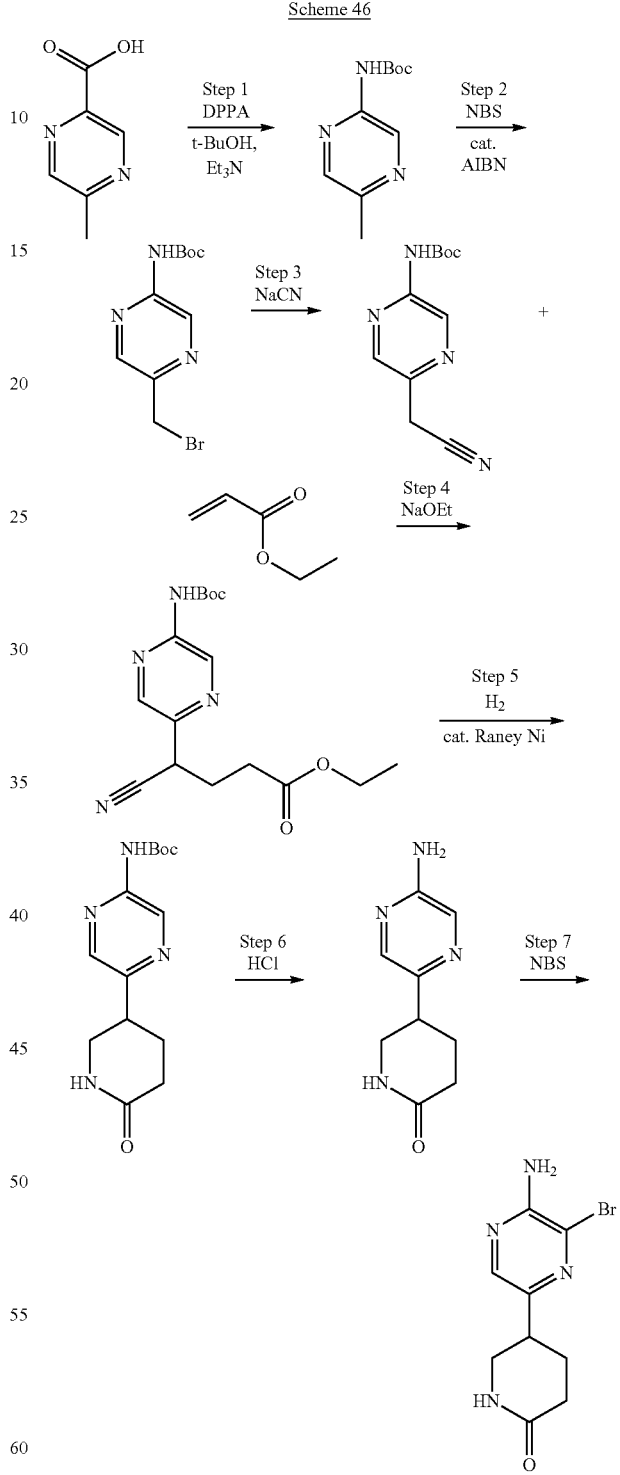

Scheme 46

Step 1. tert-butyl 5-methylpyrazin-2-ylcarbamate

To solution 5-methylpyrazine-2-carboxylic acid (2.5 g, 18.1 mmol), tert-butanol (6.92 mL, 72.4 mmol), Et$_3$N (3.78 mL, 27.1 mmol) in 1,4-dioxane (12.5 mL) at 95° C. was dropwise added diphenylphosphoryl azide (DPPA, 3.23 mL, 18.1 mmol), and the reaction was heated at 95° C. for 1.5 h, followed by a 2nd portion of DPPA (1 mL, 5.6 mmol) and heated for additional 1.5 h. The reaction mixture was cooled down, concentrated and the residue was diluted with EtOAc (50 mL), washed with water (30 mL), 3 M NaOH (30 mL), sat. NaHCO$_3$ (30 mL) and brine (30 mL), dried over Na$_2$SO$_4$, and concentrated. The residue was purified by flashed chromatography on silica gel eluting with gradient EtOAc/CH$_2$Cl$_2$ (0-20%) to afford tert-butyl 5-methyl-pyrazin-2-ylcarbamate as white solid. LCMS (m/z): 210.1 (MH$^+$), 0.69 min; 1H NMR (400 MHz, CDCl$_3$) δ ppm 9.17 (s, 1H), 8.09 (s, 1H), 7.75 (br. s., 1H), 2.51 (s, 3H), 1.56 (s, 9H).

Step 2. tert-butyl 5-(bromomethyl)pyrazin-2-ylcarbamate

A solution of tert-butyl 5-methylpyrazin-2-ylcarbamate (2.79 g, 13.33 mmol), NBS (2.61 g, 14.67 mmol) and AIBN (0.219 g, 1.33 mmol) in CCl$_4$ (45 mL) was purged with Argon, then the solution was heated with 85° C. oil bath for 4 h. The reaction mixture was cooled to room temperature, concentrated and the residue was redissolved in EtOAc (~50 mL), washed with dilute aqueous NaOH twice (10 mL 1 N NaOH diluted in 20 mL H$_2$O), brine (30 mL), dried (Na$_2$SO$_4$) and concentrated. The residue was further purified by flash chromatography on silica gel eluted with gradient EtOAc/CH$_2$Cl$_2$ (0-30%) and tert-butyl 5-(bromomethyl) pyrazin-2-ylcarbamate was obtained in off-white solid. LCMS (m/z): 288.1/290.1 (MH$^+$), 0.82 min; 1H NMR (400 MHz, CDCl$_3$) δ ppm 9.26 (s, 1H), 8.32 (d, J=1.2 Hz, 1H), 7.62 (br. s., 1H), 4.56 (s, 2H), 1.56 (s, 9H).

Step 3. tert-butyl 5-(cyanomethyl)pyrazin-2-ylcarbamate

A mixture of tert-butyl 5-(bromomethyl)pyrazin-2-ylcarbamate (0.75 g, 2.60 mmol) and NaCN (0.255 g, 5.21 mmol) in DMF (5 mL) was stirred at room temperature for 50 min. The reaction mixture was cooled down to room temperature, diluted with 0.5 N NaOH (10 mL) and extracted with EtOAc (2×20 mL), and EtOAc layers were combined, washed with 0.5 N NaOH (10 mL), dried (Na$_2$SO$_4$), concentrated and the crude residue was purified by flash chromatography on silica gel eluted with gradient EtOAc/CH$_2$Cl$_2$ (0-20%) to afford tert-butyl 5-(cyanomethyl)pyrazin-2-ylcarbamate (0.40 g, 65.6% yield). LCMS (MH$^+$-$^t$Bu): 179.0 (MH$^+$), 0.68 min; 1H NMR (400 MHz, CDCl$_3$) δ ppm 9.28 (s, 1H), 8.32 (s, 1H), 7.59 (br. s., 1H), 3.91 (s, 2H), 1.57 (s, 9H).

Step 4. ethyl 4-(5-(tert-butoxycarbonylamino) pyrazin-2-yl)-4-cyanobutanoate To tert-butyl 5-(cyanomethyl)pyrazin-2-ylcarbamate (0.32 g, 1.37 mmol) in a mixture solvent of ethanol/2-methyltetrahydrofuran (5 mL/5 mL) was added freshly prepared sodium ethoxide (1 M, 1.366 mL), and the mixture was stirred at 0° C. for 10 min, followed by addition of ethyl acrylate (145 ul, 1.366 mmol) and the mixture was stirred at 0° C. for 2 h. The reaction was quenched at this point by adding sat. NaHCO$_3$ (5 mL), and the reaction mixture was stirred for another 10 min, diluted with EtOAc (20 mL), filtered and the filtrate was concentrated. The residue was dissolved in EtOAc (20 mL), washed with pH 7.0 sodium phosphate buffer, and EtOAc layer was concentrated, and the light brown residual oil was purified by flash column eluted with gradient EtOAc/heptane (0-50%) to afford ethyl 4-(5-(tert-butoxycarbonylamino)pyrazin-2-yl)-4-cyanobutanoate (100 mg, 22% yield). LCMS (m/z): 279.2 (MH$^+$-$^t$Bu), 0.86 min.

Step 5. tert-butyl 5-(6-oxopiperidin-3-yl)pyrazin-2-ylcarbamate

Under Argon, to ethyl 4-(5-(tert-butoxycarbonylamino) pyrazin-2-yl)-4-cyanobutanoate in ethanol solution (94 mg, 0.281 mmol/8 mL) was added Raney Nickel catalyst ethanol suspension (Nickel in ~2 mL ethanol, the amount of Raney Nickel was not accurately measured), and the reaction mixture was stirred under H$_2$ balloon after 3 times air atmosphere exchange heated with external oil bath at 56° C. for overnight with H$_2$ balloon. The reaction mixture was cooled down to room temperature, and filtered through a pad of Celite, the filtrate was concentrated to afford tert-butyl 5-(6-oxopiperidin-3-yl)pyrazin-2-ylcarbamate in a yellow solid.

Step 6. 5-(5-aminopyrazin-2-yl)piperidin-2-one

A mixture of tert-butyl 5-(6-oxopiperidin-3-yl)pyrazin-2-ylcarbamate (60 mg, 0.205 mmol) and conc HCl (1 mL) in methanol (2 mL) was heated with 70° C. oil bath for 1 hour and the reaction mixture was cooled down, concentrated to dryness and the residue was redissolved in methanol (3 mL), and to it was added NaHCO$_3$ (200 mg), and the mixture was heated with 70° C. oil bath for 2 h. The solid suspension of reaction mixture was removed by filtration, and the filtrate was concentrated and a light yellow solid was obtained as crude 5-(5-aminopyrazin-2-yl)piperidin-2-one which was used directly in next step without further purification. LCMS (m/z): 193.1 (MH$^+$), 0.22 min.

Step 7. 5-(5-amino-6-bromopyrazin-2-yl)piperidin-2-one

To 5-(5-aminopyrazin-2-yl)piperidin-2-one (25 mg, 0.13 mmol) acetonitrile (10 mL) solution at 0° C. was added NBS (23.2 mg, 0.13 mmol) and the reaction mixture was stirred at 0° C. for 30 min, then at room temperature for 4 h. The reaction mixture was concentrated, and the residue was basified by 1 N NaOH (140 ul), diluted with methanol (2 mL), concentrated. The residue was triturated with EtOAc (3×1 mL), and the EtOAc supernatants were collected, combined and concentrated and a light solid was obtained as crude 5-(5-amino-6-bromopyrazin-2-yl)piperidin-2-one which was used in next step without further purification. LCMS (m/z): 241/243 (MH$^+$), 0.41 min.

Example 25

Synthesis of 4-(2-amino-5-(6-oxopiperidin-3-yl) pyridin-3-yl)-N-((S)-1-(3-chlorophenyl)-2-hydroxy-ethyl)-2-fluorobenzamide Scheme 47

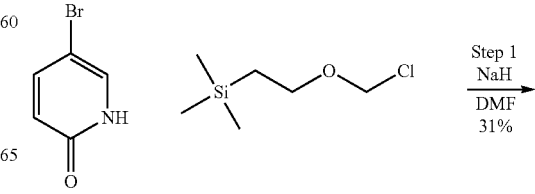

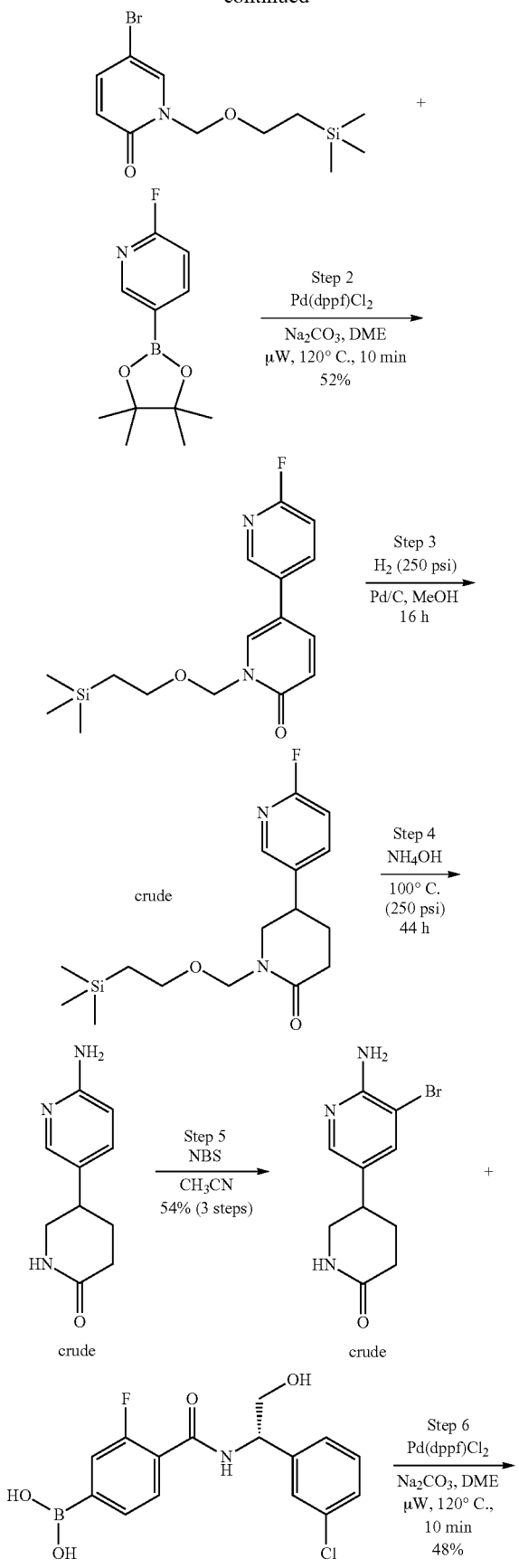

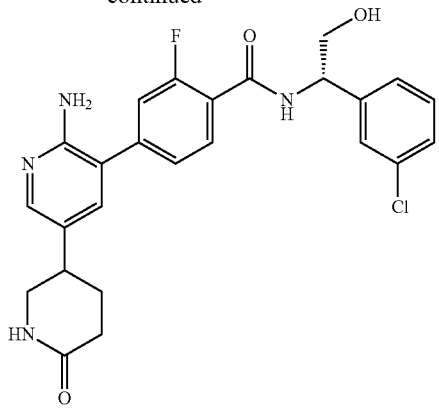

Step 1. 5-bromo-1-((2-(trimethylsilyl)ethoxy)methyl)pyridin-2(1H)-one

To a solution of 5-bromopyridin-2(1H)-one (2.01 g, 11.55 mmol) in DMF (30 mL) at 0° C. was added sodium hydride (0.924 g, 23.10 mmol). The reaction mixture was stirred for 1 h at room temperature. To this, (2-(chloromethoxy)ethyl)trimethylsilane (2.89 g, 17.33 mmol) was added slowly. The reaction mixture was stirred overnight. LCMS0.26 min, MH$^+$ 304.1 (non-polar method). The reaction was quenched with sat. aq. NH$_4$Cl, and then diluted with ethyl acetate. The reaction mixture was extracted with EtOAc. The combined organics were washed with water and brine, then dried over sodium sulfate, filtered off and concentrated in vacuo. The crude product was purified by flash chromatography column using 0-50% EtOAc/heptane. 5-bromo-1-((2-(trimethylsilyl)ethoxy)methyl)pyridin-2(1H)-one was obtained as a yellow viscous liquid. LCMS (m/z): 304/306 (MH$^+$), 0.95 min.

Step 2. 6'-fluoro-1-((2-(trimethylsilyl)ethoxy)methyl)-[3,3'-bipyridin]-6(1H)-one To a solution of 5-bromo-1-((2-(trimethylsilyl)ethoxy)methyl)pyridin-2(1H)-one (568 mg, 1.868 mmol) in DME (6227 µL, Ratio: 2.000) was added PdCl$_2$(dppf) (68.3 mg, 0.093 mmol), 2-fluoro-5-(4,4,5,5-tetramethyl-1,3,2-dioxaborolan-2-yl)pyridine (500 mg, 2.242 mmol), 2M Na$_2$CO$_3$ (3113 µl, Ratio: 1.000) at room temperature. The reaction mixture was heated at microwave synthesizer for 10 min at 120° C. To the reaction mixture, sodium sulfate and EtOAc were added. After filtered off, the volatile materials were removed in vacuo. The crude product was purified by flash chromatography (gradient EtOAc in heptane) yielding 6'-fluoro-1-((2-(trimethylsilyl)ethoxy)methyl)-[3,3'-bipyridin]-6(1H)-one (52%). LCMS (m/z): 321.3 (MH$^+$), 0.93 min.

Step 3. 5-(6-fluoropyridin-3-yl)-1-((2-(trimethylsilyl)ethoxy)methyl)piperidin-2-one To a steel bomb, a solution of 6'-fluoro-1-((2-(trimethylsilyl)ethoxy)methyl)-[3,3'-bipyridin]-6(1H)-one (311 mg, 0.971 mmol) in MeOH (remaining 60% head space) was added followed by addition of PdC (207 mg, 0.194 mmol). After degassing with nitrogen stream, the steel bomb was pressurized with hydrogen gas up to 250 psi. The reaction was stirred at room temperature for 20 h. LCMS0.9 min MH$^+$325.1 (single major). The reaction mixture was filtered off through Celite (washed with EtOAc). The volatile materials were concentrated in vacuo to give crude 5-(6-fluoropyridin-3-yl)-1-((2-(trimethylsilyl)ethoxy)methyl)piperidin-2-one (290 mg, 0.894 mmol, 92%), which was used for the next step without further purification.

Step 4. 5-(6-aminopyridin-3-yl)piperidin-2-one

To -(6-fluoropyridin-3-yl)-1-((2-(trimethylsilyl)ethoxy)methyl)piperidin-2-one (290 mg, 0.894 mmol) in a steel bomb, ammonium hydroxide (34.8 µl, 0.894 mmol) solution was added (40% head volume remained). The steel bomb reactor was heated at 150° C. for 44 h (250 psi on pressure gauge). LCMS-0.23 min, MH+ 192.1 (without SEM); 0.66 min, MH+ 322.1 (with SEM). After diluted with MeOH and toluene, volatile materials were completely removed in vacuo. 5-(6-aminopyridin-3-yl)piperidin-2-one was used for the next step.

Step 5.
5-(6-amino-5-bromopyridin-3-yl)piperidin-2-one

To a solution of 5-(6-aminopyridin-3-yl)piperidin-2-one (132 mg, 0.690 mmol) in Acetonitrile (8.00 mL) was added NBS (98 mg, 0.552 mmol) at 0° C. The reaction mixture was stirred for 30 min upon warming-up to room temperature. LCMS 0.28 min, MH+ 270/272; 0.7 min, MH+400.1/402.1 (SEM protected one). After quenched with Na$_2$S$_2$O$_3$ solution, the reaction mixture was extracted with EtOAc, which was washed with NaHCO$_3$ solution and brine. The organic layer was dried over anhydrous Na$_2$SO$_4$, filtered off, concentrated in vacuo. The crude 5-(6-amino-5-bromopyridin-3-yl)piperidin-2-one was used for the next step.

Step 6. 4-(2-amino-5-(6-oxopiperidin-3-yl)pyridin-3-yl)-N-((S)-1-(3-chlorophenyl)-2-hydroxyethyl)-2-fluorobenzamide To a microwave vial, 5-(6-amino-5-bromopyridin-3-yl)piperidin-2-one (45 mg, 0.167 mmol), (S)-(4-((1-(3-chlorophenyl)-2-hydroxyethyl)carbamoyl)-3-fluorophenyl)boronic acid (56.2 mg, 0.167 mmol), PdCl$_2$(dppf) (12.19 mg, 0.017 mmol), DME (1111 µl, Ratio: 2.000), and Na$_2$CO$_3$ (2M solution) (555 µL, Ratio: 1.000) were added. The reaction mixture was heated at microwave reactor for 10 min at 120° C. LCMS0.58 min, MH+ 483.2; 0.85 min, MH+ 613.3. After anhydrous sodium sulfate were added to remove water, the reaction mixture was filtered off and dried in vacuo. The small portion was purified by prep HPLC yielding 4-(2-amino-5-(6-oxopiperidin-3-yl)pyridin-3-yl)-N-((S)-1-(3-chlorophenyl)-2-hydroxyethyl)-2-fluorobenzamide as a diastereomeric mixture (12%). LCMS (m/z): 483.3 (MH+), 0.56 min; 1H NMR (400 MHz, CD$_3$OD) δ ppm 7.89 (m, 1H), 7.80 (m, 2H), 7.42-7.30 (m, 3H), 7.30-7.24 (m, 2H), 7.25-7.15 (m, 1H), 5.18-5.03 (m, 1H), 3.87-3.64 (m, 2H), 3.47-3.35 (m, 2H), 3.11-2.97 (m, 1H), 2.46-2.30 (m, 2H), 2.08-1.91 (m, 2H).

Synthesis of (+/−)-4-(6-amino-5-bromopyridin-3-yl)-1-methylpiperidin-2-one

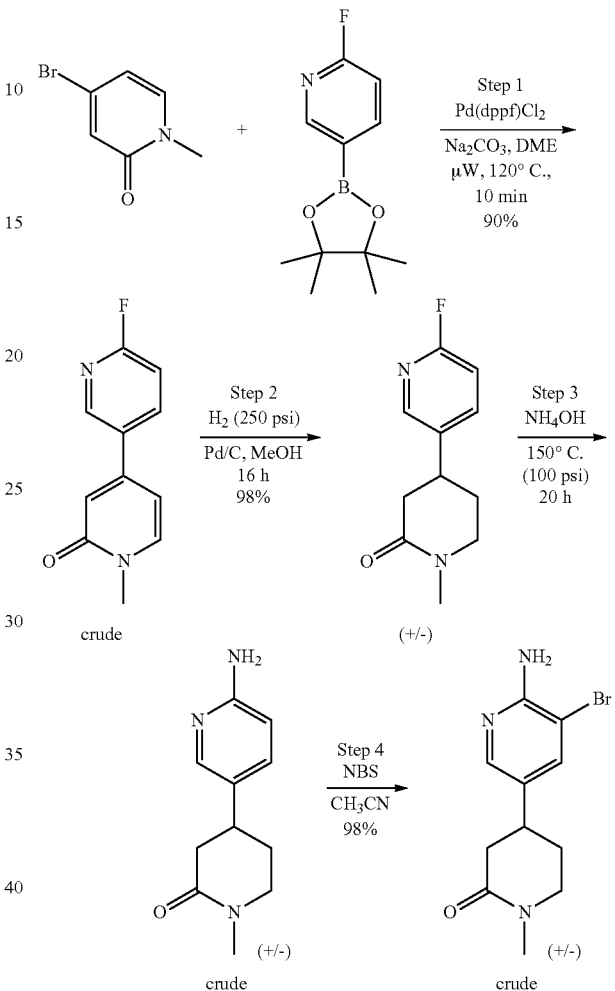

Scheme 48

Step 1. 6-fluoro-1'-methyl-[3,4'-bipyridin]-2'(1'H)-one

To a solution of 2-fluoro-5-(4,4,5,5-tetramethyl-1,3,2-dioxaborolan-2-yl)pyridine (500 mg, 2.242 mmol) was added PdCl$_2$(dppf) (68.3 mg, 0.093 mmol), 4-bromo-1-methylpyridin-2(1H)-one (351 mg, 1.868 mmol), 2M Na$_2$CO$_3$ (4.1 mL) and DME (8.3 mL) at room temperature. The reaction mixture was heated at microwave synthesizer for 10 min at 120° C. The reaction mixture was extracted with EtOAc. The organic layers were washed with water and brine, dried over anhydrous Na$_2$SO$_4$, filtered off, and concentrated in vacuo. The crude 6-fluoro-1'-methyl-[3,4'-bipyridin]-2'(1'H)-one was purified by flash chromatography (gradient EtOAc in DCM). LCMS (m/z): 205.2 (MH+), 0.47 min.

Step 2. (+/−)-4-(6-fluoropyridin-3-yl)-1-methylpiperidin-2-one

To a steel bomb, a solution of 6-fluoro-1'-methyl-[3,4'-bipyridin]-2'(1'H)-one (340 mg, 1.665 mmol) in MeOH (remaining 60% head space) was added followed by addition of PdC(Degussa) (354 mg, 0.333 mmol). After degassing with nitrogen stream, the steel bomb was filled with hydrogen (250 psi). The reaction mixture was stirred overnight. The reaction mixture was filtered off through Celite (washed with EtOAc/MeOH). The volatile materials were concentrated in vacuo to give crude (+/−)-4-(6-fluoropyridin-3-yl)-1-methylpiperidin-2-one (341 mg, 1.638 mmol, 98% yield) which was used for the next step without further purification. LCMS (m/z): 209.1 (MH+), 0.47 min.

Step 3. (+/−)-4-(6-aminopyridin-3-yl)-1-methylpiperidin-2-one

To a steel bomb, (+/−)-4-(6-fluoropyridin-3-yl)-1-methylpiperidin-2-one (341 mg, 1.638 mmol) was added followed by addition of ammonium hydroxide solution (0.00 mmol)remaining 40% head space. The reactor was heat at 150° C. for 20 hr (internal pressure built up to 100 psi upon heating). After cooling down, the reaction was completed. The whole solvent (transferred to a flask) was removed in vacuo. Toluene was added and co-evaporated to remove water. The crude product, (+/−)-4-(6-aminopyridin-3-yl)-1-methylpiperidin-2-one, was used for the next step without further purification (87%). LCMS (m/z): 206.1 (MH+), 0.24 min.

Step 4. (+/−)-4-(6-amino-5-bromopyridin-3-yl)-1-methylpiperidin-2-one

To a solution of (+/−)-4-(6-aminopyridin-3-yl)-1-methylpiperidin-2-one (291 mg, 1.418 mmol) in acetonitrile (14.200 mL) was added NBS (202 mg, 1.134 mmol) at 0° C. The reaction mixture was stirred for 30 min upon warming-up to room temperature. After quenched with Na2S2O3 solution, the reaction mixture was extracted with EtOAc, which was washed with NaHCO3 solution and brine. The organic layer was dried over anhydrous Na2SO4, filtered off, concentrated in vacuo. The crude product (+/−)-4-(6-amino-5-bromopyridin-3-yl)-1-methylpiperidin-2-one (98%) was used for the next step. LCMS (m/z): 284/286 (MH+), 0.34 min.

Examples 26, 27, and 28

4-(2-amino-5-(1-methyl-2-oxopiperidin-4-yl)pyridin-3-yl)-N-((S)-1-(3-chlorophenyl)-2-hydroxyethyl)-2-fluorobenzamide, 4-(2-amino-5-((R)-1-methyl-2-oxopiperidin-4-yl)pyridin-3-yl)-N-((S)-1-(3-chlorophenyl)-2-hydroxyethyl)-2-fluorobenzamide, and 4-(2-amino-5-((S)-1-methyl-2-oxopiperidin-4-yl)pyridin-3-yl)-N-((S)-1-(3-chlorophenyl)-2-hydroxyethyl)-2-fluorobenzamide

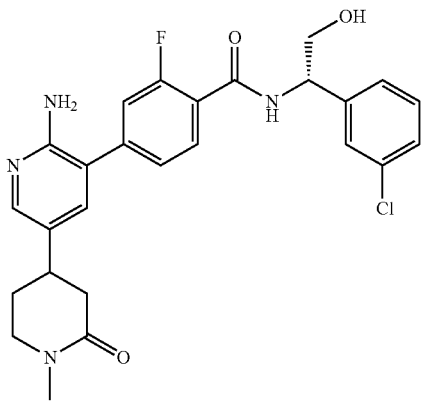

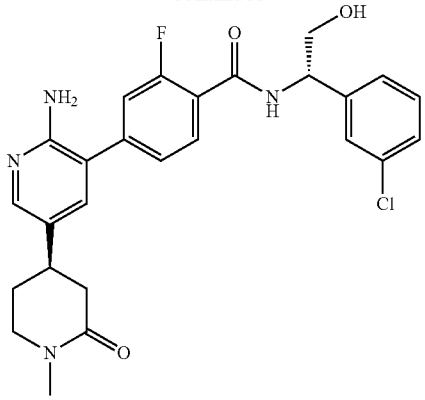

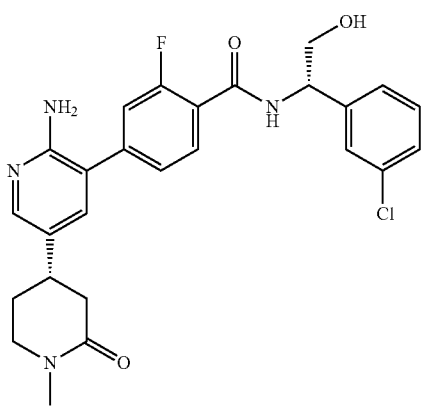

Following Step 6 in Scheme 47, using (+/−)-4-(6-amino-5-bromopyridin-3-yl)-1-methylpiperidin-2-one and (S)-(4-((1-(3-chlorophenyl)-2-hydroxyethyl)carbamoyl)-3-fluorophenyl)boronic acid, 4-(2-amino-5-(1-methyl-2-oxopiperidin-4-yl)pyridin-3-yl)-N-((S)-1-(3-chlorophenyl)-2-hydroxyethyl)-2-fluorobenzamide was obtained as a diastereomeric mixture (inseparable) (35%). LCMS (m/z): 497.3 (MH+), 0.59 min; 1H NMR (400 MHz, CD3OD) δ ppm 7.97 (m, 1H), 7.9 (m, 1H), 7.82 (m, 1H), 7.52-7.39 (m, 3H), 7.39-7.32 (m, 2H), 7.3 (m, 1H), 5.19 (m, 1H), 3.88 (m, 2H), 3.60-3.38 (m, 3H), 3.21-3.08 (m, 1H), 2.72-2.58 (m, 1H), 2.57-2.41 (m, 1H), 2.21-1.95 (m, 2H). The diastereomeric mixture was separated by chiral SFC (ChiralPak 5mic AD column, 4.6×100 (mm), 5 mL/min, EtOH+0.1%, DEA=45% in 5 min). The polar diastereomer, 4-(2-amino-5-((R)-1-methyl-2-oxopiperidin-4-yl)pyridin-3-yl)-N-((S)-1-(3-chlorophenyl)-2-hydroxyethyl)-2-fluorobenzamide was obtained at Rt=1.82 min. The less polar diastereomer, 4-(2-amino-5-((S)-1-methyl-2-oxopiperidin-4-yl)pyridin-3-yl)-N-((S)-1-(3-chlorophenyl)-2-hydroxyethyl)-2-fluorobenzamide was obtained at Rt=2.35 min. The absolute stereochemistry for both diastereomers was assigned arbitrarily.

Examples 29, 30, and 31

4-(2-amino-5-(1-methyl-2-oxopiperidin-4-yl)pyridin-3-yl)-2-fluoro-N-((R)-1-phenylethyl)benzamide, 4-(2-amino-5-((R)-1-methyl-2-oxopiperidin-4-yl)pyridin-3-yl)-2-fluoro-N-((R)-1-phenylethyl)benzamide, and 4-(2-amino-5-((S)-1-methyl-2-oxopiperidin-4-yl)pyridin-3-yl)-2-fluoro-N-((R)-1-phenylethyl)benzamide

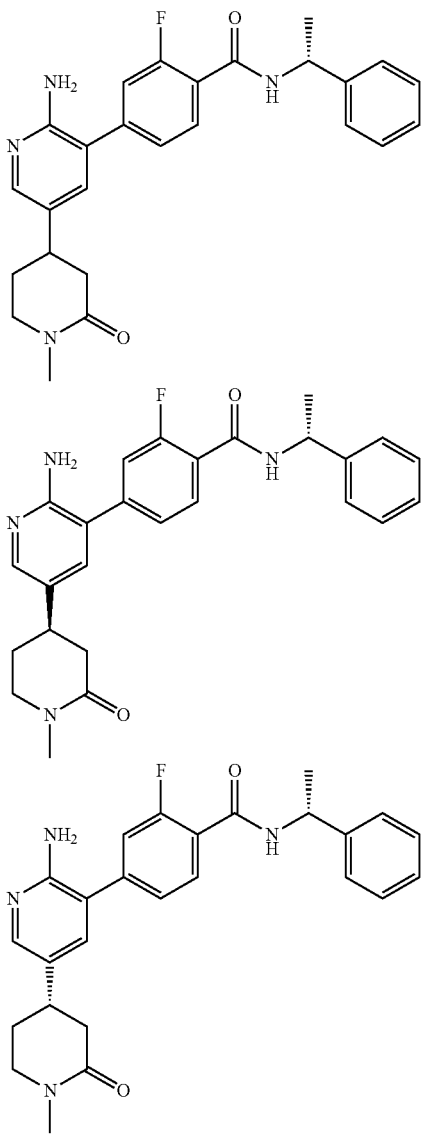

Following Step 6 in Scheme 47, using (+/−)-4-(6-amino-5-bromopyridin-3-yl)-1-methylpiperidin-2-one and (R)-(3-fluoro-4-((1-phenylethyl)carbamoyl)phenyl)boronic acid, 4-(2-amino-5-(1-methyl-2-oxopiperidin-4-yl)pyridin-3-yl)-2-fluoro-N-((R)-1-phenylethyl)benzamide was obtained as a diastereomeric mixture (inseparable) (34%). LCMS (m/z): 447.3 (MH+), 0.58 min; 1H NMR (400 MHz, CD3OD) δ ppm 7.85 (m, 1H), 7.72 (m, 2H), 7.41-7.20 (m, 6H), 7.18 (m, 1H), 5.17 (m, 1H), 3.51-3.29 (m, 3H), 3.13-2.98 (m, 1H), 2.88 (s, 3H), 2.60-2.48 (m, 1H), 2.48-2.30 (m, 1H), 2.10-1.85 (m, 2H), 1.58-1.38 (m, 3H). The diastereomeric mixture was separated by chiral SFC (ChiralPak 5mic AD column, 4.6×100 (mm), 100 mL/min, IPA+0.1%, DEA=40%, 5 ml/min). The polar diastereomer, 4-(2-amino-5-((R)-1-methyl-2-oxopiperidin-4-yl)pyridin-3-yl)-2-fluoro-N-((R)-1-phenylethyl)benzamide was obtained at Rt=1.67 min. LCMS (m/z): 447.3 (MH+), 0.64 min. The less polar diastereomer, 4-(2-amino-5-((S)-1-methyl-2-oxopiperidin-4-yl)pyridin-3-yl)-2-fluoro-N-((R)-1-phenylethyl)benzamide was obtained at Rt=2.37 min. LCMS (m/z): 447.2 (MH+), 0.64 min. The absolute stereochemistry for both diastereomers was assigned arbitrarily.

Examples 32, 33, and 34

4-(2-amino-5-(1-methyl-2-oxopiperidin-4-yl)pyridin-3-yl)-N-((R)-1-(3-chlorophenyl)ethyl)-2-fluorobenzamide, 4-(2-amino-5-((R)-1-methyl-2-oxopiperidin-4-yl)pyridin-3-yl)-N-((R)-1-(3-chlorophenyl)ethyl)-2-fluorobenzamide, and 4-(2-amino-5-((S)-1-methyl-2-oxopiperidin-4-yl)pyridin-3-yl)-N-((R)-1-(3-chlorophenyl)ethyl)-2-fluorobenzamide

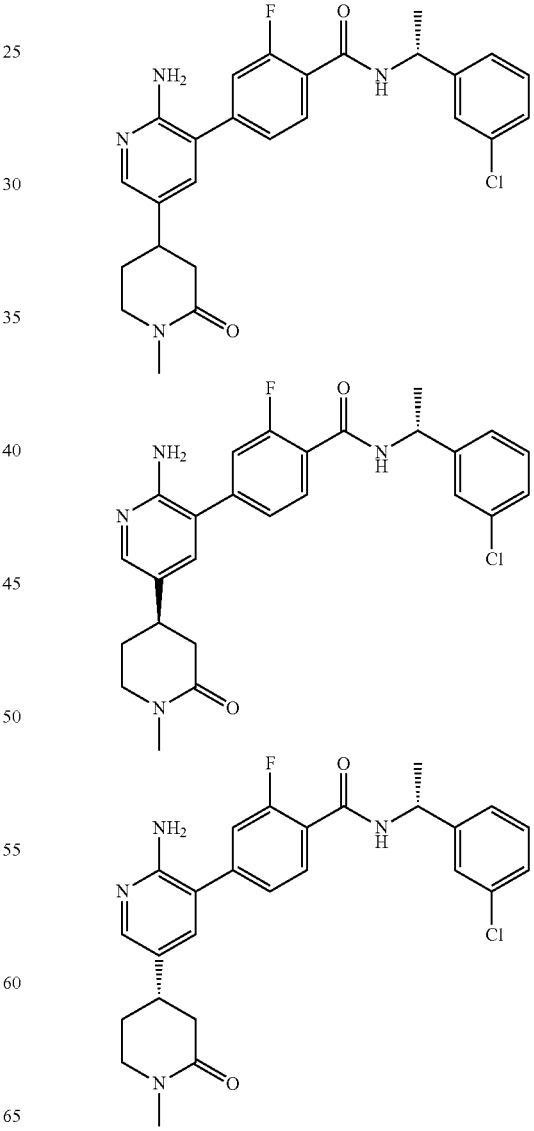

Following Step 6 in Scheme 47, using (R)-(4-((1-(3-chlorophenyl)ethyl)carbamoyl)-3-fluorophenyl)boronic acid, 4-(2-amino-5-(1-methyl-2-oxopiperidin-4-yl)pyridin-3-yl)-N-((R)-1-(3-chlorophenyl)ethyl)-2-fluorobenzamide was obtained as a diastereomeric mixture (inseparable) (33%). LCMS (m/z): 481.3 (MH$^+$), 0.70 min; 1H NMR (400 MHz, CD$_3$OD) δ ppm 7.86 (m, 1H), 7.73 (m, 2H), 7.39-7.20 (m, 5H), 7.19 (m, 1H), 5.14 (m, 1H), 3.52-3.28 (m, 3H), 3.14-2.98 (m, 1H), 2.88 (s, 3H), 2.62-2.48 (m, 1H), 2.46-2.30 (m, 1H), 2.12-1.84 (m, 2H), 1.48 (m, 3H). The diastereomeric mixture was separated by chiral SFC (ChiralPak 5mic AD column, 4.6×100 (mm), 5 ml/min, EtOH+0.1% DEA=35%). The polar diastereomer, 4-(2-amino-5-((R)-1-methyl-2-oxopiperidin-4-yl)pyridin-3-yl)-N-((R)-1-(3-chlorophenyl)ethyl)-2-fluorobenzamide was obtained at Rt=2.83 min. LCMS (m/z): 481.2 (MH$^+$), 0.71 min. The less polar diastereomer, 4-(2-amino-5-((S)-1-methyl-2-oxopiperidin-4-yl)pyridin-3-yl)-N-((R)-1-(3-chlorophenyl)ethyl)-2-fluorobenzamide was obtained at Rt=3.53 min. LCMS (m/z): 481.2 (MH$^+$), 0.72. The absolute stereochemistry for both diastereomers was assigned arbitrarily.

Synthesis of 5-(6-amino-5-bromopyridin-3-yl)-1-methylpiperidin-2-one

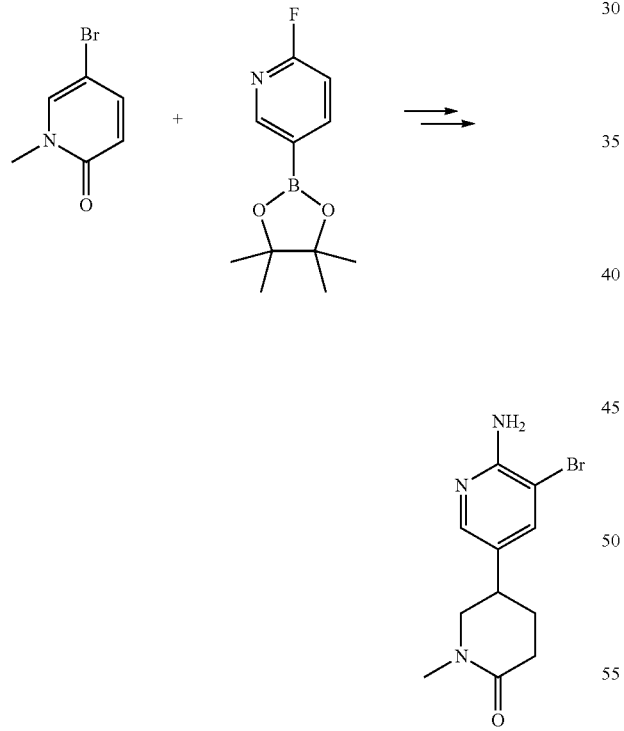

Following Scheme 48, using 5-bromo-1-methylpyridin-2(1H)-one, 5-(6-amino-5-bromopyridin-3-yl)-1-methylpiperidin-2-one was obtained. LCMS (m/z): 284/286 (MH$^+$), 0.34 min.

Examples 35, 36, and 37

4-(2-amino-5-(1-methyl-6-oxopiperidin-3-yl)pyridin-3-yl)-N-((S)-1-(3-chlorophenyl)-2-hydroxyethyl)-2-fluorobenzamide, 4-(2-amino-5-((R)-1-methyl-6-oxopiperidin-3-yl)pyridin-3-yl)-N-((S)-1-(3-chlorophenyl)-2-hydroxyethyl)-2-fluorobenzamide, and 4-(2-amino-5-((S)-1-methyl-6-oxopiperidin-3-yl)pyridin-3-yl)-N-((S)-1-(3-chlorophenyl)-2-hydroxyethyl)-2-fluorobenzamide

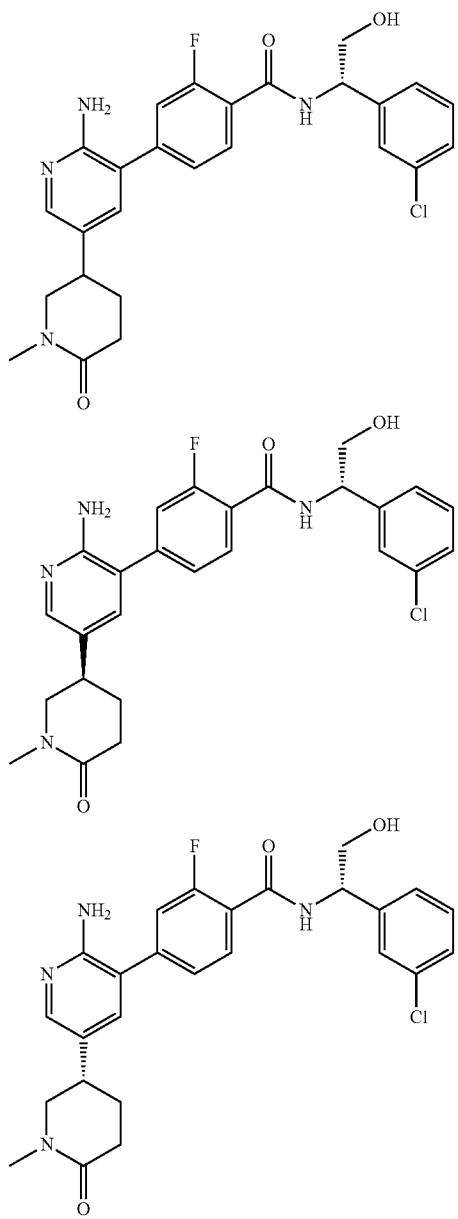

Following Step 6 in Scheme 47, using 5-(6-amino-5-bromopyridin-3-yl)-1-methylpiperidin-2-one and (S)-(4-((1-(3-chlorophenyl)-2-hydroxyethyl)carbamoyl)-3-fluorophenyl)boronic acid, 4-(2-amino-5-(1-methyl-6-oxopiperidin-3-yl)pyridin-3-yl)-N-((S)-1-(3-chlorophenyl)-2-hydroxyethyl)-2-fluorobenzamide was obtained (33%). LCMS (m/z): 497.2 (MH$^+$), 0.61 min; $^1$H NMR (400 MHz, CD₃OD) δ ppm 8.70 (m, 1H), 7.98 (m, 1H), 7.88 (m, 2H), 7.44 (m, 3H), 7.36 (m, 2H), 7.30 (m, 1H), 5.19 (m, 1H), 3.88 (m, 2H), 3.51 (m, 2H), 3.21 (m, 1H), 2.97 (s, 3H), 2.50 (m, 2H), 2.07 (m, 2H). The diastereomeric mixture was separated by chiral SFC (ChiralPak 5mic AD column, 4.6×100 (mm), EtOH+0.1% DEA=40%, 5 ml/min). The polar diastereomer, 4-(2-amino-5-((R)-1-methyl-6-oxopiperidin-3-yl)pyridin-3-yl)-N-((S)-1-(3-chlorophenyl)-2-hydroxyethyl)-2-fluorobenzamide was obtained at Rt=2.22 min. LCMS (m/z): 497.2 (MH⁺), 0.61 min. The less polar diastereomer, 4-(2-amino-5-((S)-1-methyl-6-oxopiperidin-3-yl)pyridin-3-yl)-N-((S)-1-(3-chlorophenyl)-2-hydroxyethyl)-2-fluorobenzamide was obtained at Rt=3.09 min. LCMS (m/z): 497.3 (MH⁺), 0.59 min.

Examples 38, 39, and 40

4-(2-amino-5-(1-methyl-6-oxopiperidin-3-yl)pyridin-3-yl)-N-((R)-1-(3-chlorophenyl)ethyl)-2-fluorobenzamide, 4-(2-amino-5-((R)-1-methyl-6-oxopiperidin-3-yl)pyridin-3-yl)-N-((R)-1-(3-chlorophenyl)ethyl)-2-fluorobenzamide, and 4-(2-amino-5-((S)-1-methyl-6-oxopiperidin-3-yl)pyridin-3-yl)-N-((R)-1-(3-chlorophenyl)ethyl)-2-fluorobenzamide

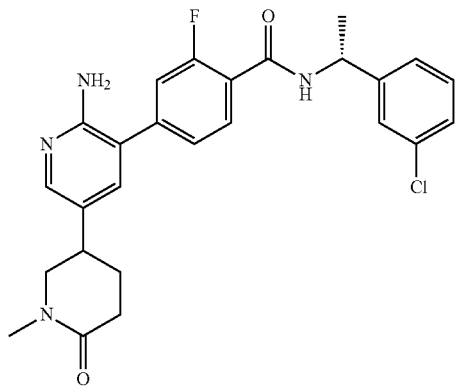

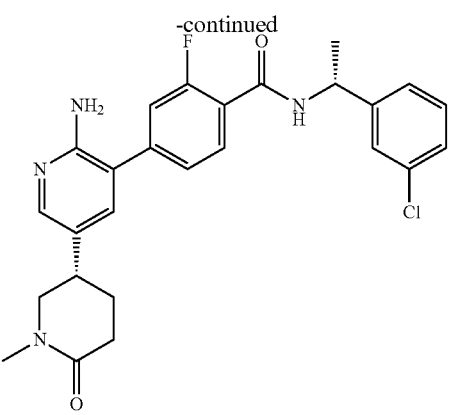

Following Step 6 in Scheme 47, using (R)-(4-((1-(3-chlorophenyl)ethyl)carbamoyl)-3-fluorophenyl)boronic acid and 5-(6-amino-5-bromopyridin-3-yl)-1-methylpiperidin-2-one, 4-(2-amino-5-(1-methyl-6-oxopiperidin-3-yl)pyridin-3-yl)-N-((S)-1-(3-chlorophenyl)-2-hydroxyethyl)-2-fluorobenzamide was obtained as a diastereomeric mixture (4%). LCMS (m/z): 481.3 (MH⁺), 0.69 min. ¹H NMR (400 MHz, CD₃OD) δ ppm 8.79-8.65 (m, 1H), 7.93-7.83 (m, 1H), 7.83-7.76 (m, 1H), 7.75-7.65 (m, 1H), 7.40-7.29 (m, 3H), 7.29-7.21 (m, 2H), 7.21-7.13 (m, 1H), 5.22-5.07 (m, 1H), 3.52-3.32 (m, 3H), 3.16-3.01 (m, 1H), 2.88 (s, 3H), 2.48-2.34 (m, 2H), 2.07-1.92 (m, 2H), 1.55-1.40 (m, 3H). The diastereomeric mixture was separated by chiral SFC (ChiralPak 5mic AD column, 4.6×100 (mm), 5 ml/min, MeOH+0.1% DEA=35%). The polar diastereomer, 4-(2-amino-5-((R)-1-methyl-6-oxopiperidin-3-yl)pyridin-3-yl)-N-((R)-1-(3-chlorophenyl)ethyl)-2-fluorobenzamide was obtained at Rt=2.98 min. LCMS (m/z): 481.2 (MH⁺), 0.71 min. The less polar diastereomer, 4-(2-amino-5-((S)-1-methyl-6-oxopiperidin-3-yl)pyridin-3-yl)-N-((R)-1-(3-chlorophenyl)ethyl)-2-fluorobenzamide was obtained at Rt=3.93 min. LCMS (m/z): 481.1 (MH⁺), 0.71 min.

Example 41

4-(2-amino-5-(5-oxopyrrolidin-3-yl)pyridin-3-yl)-2-fluoro-N-((S)-2-hydroxy-1-phenylethyl)benzamide Scheme 50

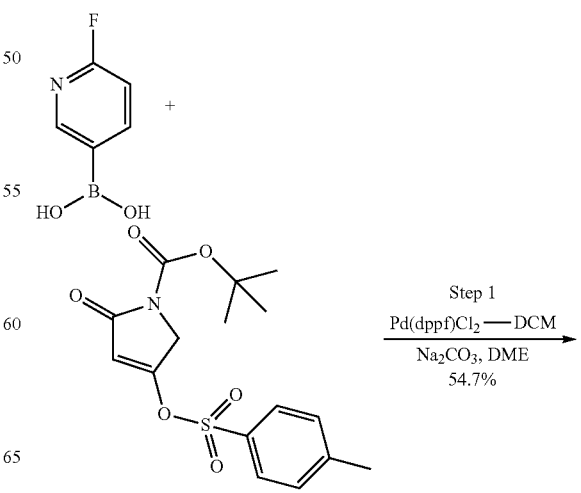

-continued

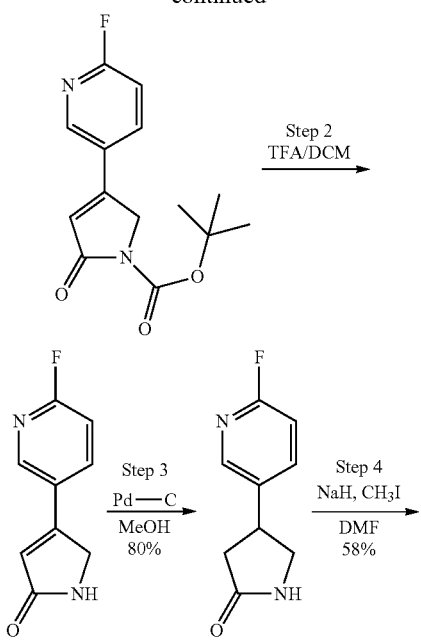

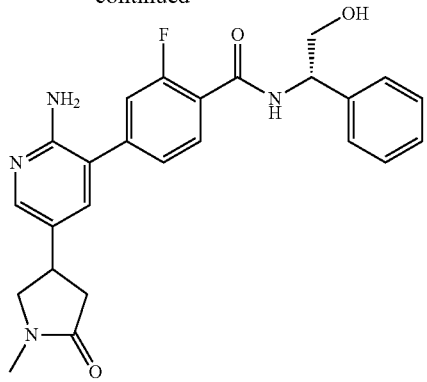

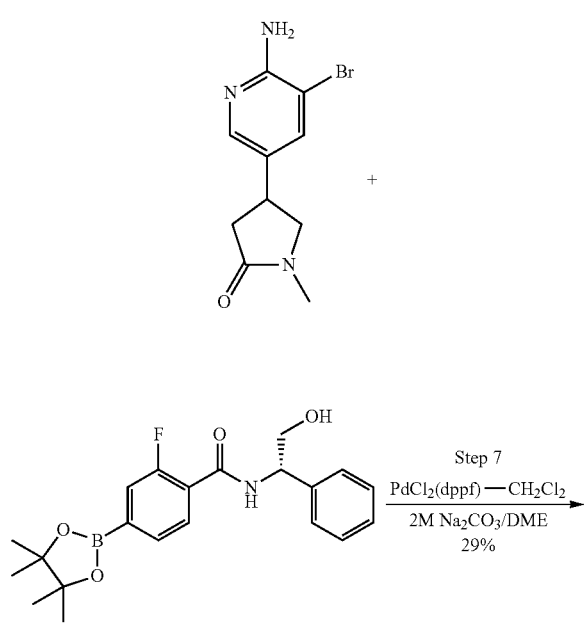

-continued

Step 1. tert-butyl 4-(6-fluoropyridin-3-yl)-2-oxo-2,5-dihydro-1H-pyrrole-1-carboxylate To tert-butyl 2-oxo-4-(tosyloxy)-2,5-dihydro-1H-pyrrole-1-carboxylate (0.8 g, 2.037 mmol) (See Example 24 for synthesis) in DME (27 mL) and sodium carbonate (7 mL, 14.00 mmol) (2M) was added (6-fluoropyridin-3-yl)boronic acid (0.431 g, 3.06 mmol) and $PdCl_2$(dppf).$CH_2Cl_2$ adduct (0.333 g, 0.407 mmol). Purge with $N_2$ for 5 min. The reaction mixture was heated in oil bath at 90° C. for 2 h. The reaction mixture was partitioned between ethylacetate and water. The organic layer was separated, washed with brine, dried over sodium sulfate, filtered and evaporated. Purified by flash chromatography column using 0-50% EtOAc/heptane. Fractions contains product were combined and evaporated to provide tert-butyl 4-(6-fluoropyridin-3-yl)-2-oxo-2,5-dihydro-1H-pyrrole-1-carboxylate as an off white solid (54.7%). LCMS (m/z): 223.2 ($MH^+$-$^t$Bu), 0.743 min.

Step 2. 4-(6-fluoropyridin-3-yl)-1H-pyrrol-2(5H)-one

To tert-butyl 4-(6-fluoropyridin-3-yl)-2-oxo-2,5-dihydro-1H-pyrrole-1-carboxylate (315 mg, 1.132 mmol) in DCM (4 mL) was added TFA (1 mL, 12.98 mmol). The reaction mixture was stirred at room temperature for 1 h. Reaction mixture was evaporated. Azeotrope with toluene (x=3) yielding 4-(6-fluoropyridin-3-yl)-1H-pyrrol-2(5H)-one. Proceed for next step. LCMS (m/z): 179.2 ($MH^+$), 0.373 min. The crude yield was quantitative.

Step 3. 4-(6-fluoropyridin-3-yl)pyrrolidin-2-one

To 4-(6-fluoropyridin-3-yl)-1H-pyrrol-2(5H)-one (190 mg, 1.066 mmol) in MeOH (10 mL) under $N_2$ atmosphere was added PdC (227 mg, 0.213 mmol). The reaction mixture was stirred under $H_2$ balloon at room temperature for overnight. Reaction mixture was filtered through Celite, washed with MeOH. Filtrate was evaporated. Azeotrope with toluene (x=3). Yield was 80%. Proceed for next step. LCMS (m/z): 181.0 ($MH^+$), 0.341 min.

Step 4. 4-(6-fluoropyridin-3-yl)-1-methylpyrrolidin-2-one

To 4-(6-fluoropyridin-3-yl)pyrrolidin-2-one (200 mg, 0.888 mmol) in DMF (4 mL) in ice bath was added NaH (42.6 mg, 1.066 mmol) and iodomethane (0.067 mL, 1.066 mmol). The reaction mixture was stirred in ice bath for 30 min and room temperature for 1 hour. LC-MS shows mixture of SM and product (1:1). Added again NaH (42.6 mg, 1.066 mmol) and iodomethane (0.067 mL, 1.066 mmol), stirred for 1 h at room temperature. Complete reaction by LC-MS. Reaction mixture was diluted with EtOAc and washed with water and bine. The organic layer was dried over sodium sulfate, filtered and evaporated. The crude was purified by flash chromatography [0-50-80% EtOAc (contains 10% MeOH)/heptane]. LCMS (m/z): 195.2 (MH$^+$), 0.492 min. Yield 58%

Step 5.
4-(6-aminopyridin-3-yl)-1-methylpyrrolidin-2-one

To 4-(6-fluoropyridin-3-yl)-1-methylpyrrolidin-2-one (100 mg, 0.515 mmol) was added ammonium hydroxide (2 mL, 15.41 mmol). The reaction mixture was heated in heating block at 140° C. for 48 h. LC-MS shows 80% product. Reaction mixture was evaporated. Azeotrope with Toluene (x=3) and proceed for next step. LCMS (m/z): 192.2 (MH$^+$), 0.256 min.

Step 6. 4-(6-amino-5-bromopyridin-3-yl)-1-methyl-pyrrolidin-2-one

To 4-(6-aminopyridin-3-yl)-1-methylpyrrolidin-2-one (90 mg, 0.377 mmol) in Acetonitrile (3 mL) in ice bath was added NBS (60.3 mg, 0.339 mmol). The reaction mixture was stirred in ice bath for 15 min and room temperature for 30 min. LC-MS shows mixture of SM and product. Added 0.1 equiv. more of NBS and stirred another 1 h at room temperature. Reaction mixture was diluted with EtOAc and added 2 mL of Satd sodium bicarbonate. Stirred 10 min. The organic layer was separated, dried over sodium sulfate, filtered and evaporated. Proceed for next step (73%). LCMS (m/z): 270.2/272.2 (MH$^+$), 0.302 min.

Step 7. 4-(2-amino-5-(1-methyl-5-oxopyrrolidin-3-yl)pyridin-3-yl)-2-fluoro-N-((S)-2-hydroxy-1-phenylethyl)benzamide To 4-(6-amino-5-bromopyridin-3-yl)-1-methylpyrrolidin-2-one (18 mg, 0.067 mmol) in DME (1.6 mL) and sodium carbonate (0.167 mL, 0.333 mmol) was added (S)-2-fluoro-N-(2-hydroxy-1-phenylethyl)-4-(4,4,5,5-tetramethyl-1,3,2-dioxaborolan-2-yl)benzamide (30.8 mg, 0.080 mmol) and PdCl$_2$(dppf).CH$_2$Cl$_2$ adduct (5.44 mg, 6.66 μmol). The reaction mixture was heated in microwave at 120° C. for 15 min. The reaction mixture was diluted with Ethylacetate. The organic layer was separated and evaporated. The crude was purified by prep HPLC to provide desired product as a TFA salt (29.3%). LCMS (m/z): 449.3 (MH$^+$), 0.52 min; 1H NMR (400 MHz, CD$_3$OD) δ ppm 8.65 (dd, J=7.24, 4.11 Hz, 1 H) 7.97 (d, J=2.35 Hz, 1 H) 7.94-7.83 (m, 2 H) 7.49-7.39 (m, 4 H) 7.36 (t, J=7.63 Hz, 2 H) 7.32-7.24 (m, 1 H) 5.30-5.13 (m, 1 H) 3.94-3.76 (m, 3 H) 3.69 (quin, J=8.31 Hz, 1 H) 3.50 (dd, J=9.59, 7.24 Hz, 1 H) 2.89 (s, 3 H) 2.79 (dd, J=16.82, 9.00 Hz, 1 H) 2.56 (dd, J=16.82, 8.22 Hz, 1 H).

Example 42, 43, and 44

4-(2-amino-5-(1-methyl-5-oxopyrrolidin-3-yl)pyridin-3-yl)-N-((S)-1-(3-chlorophenyl)-2-hydroxyethyl)-2-fluorobenzamide, 4-(2-amino-5-((R)-1-methyl-5-oxopyrrolidin-3-yl)pyridin-3-yl)-N-((S)-1-(3-chlorophenyl)-2-hydroxyethyl)-2-fluorobenzamide, and 4-(2-amino-5-((S)-1-methyl-5-oxopyrrolidin-3-yl)pyridin-3-yl)-N-((S)-1-(3-chlorophenyl)-2-hydroxyethyl)-2-fluorobenzamide

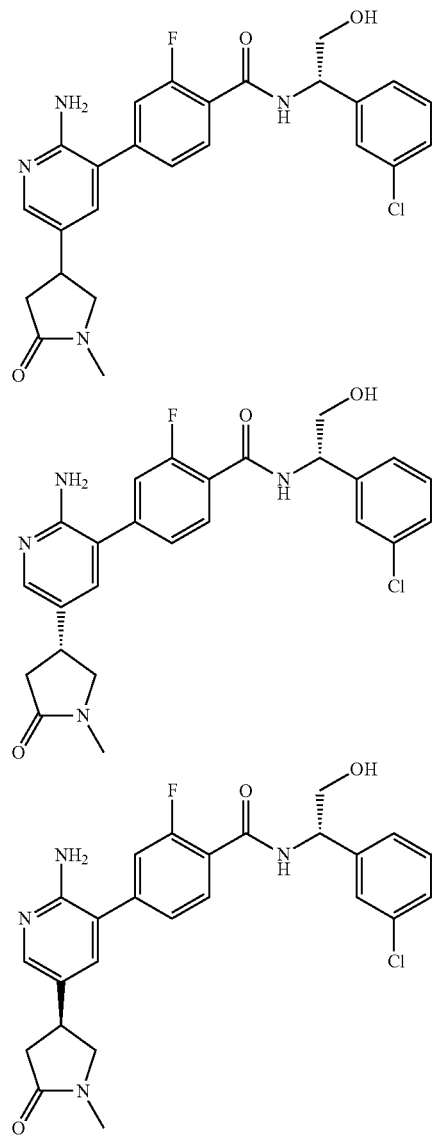

Following Step 6 in Scheme 50, using 4-(6-amino-5-bromopyridin-3-yl)-1-methylpyrrolidin-2-one and (S)N-(1-(3-chlorophenyl)-2-hydroxyethyl)-2-fluoro-4-(4,4,5,5-tetramethyl-1,3,2-dioxaborolan-2-yl)benzamide, 4-(2-amino-5-(1-methyl-5-oxopyrrolidin-3-yl)pyridin-3-yl)-N-((S)-1-(3-chlorophenyl)-2-hydroxyethyl)-2-fluorobenzamide was obtained as a diastereomeric mixture (33.3%). LCMS (m/z): 483.3 (MH$^+$), 0.59 min; $^1$H NMR (400 MHz, CD$_3$OD) δ ppm 8.79-8.61 (m, 1 H) 7.97 (d, J=1.96 Hz, 1 H) 7.93-7.82 (m, 2 H) 7.48-7.39 (m, 3 H) 7.39-7.25 (m, 3 H) 5.25-5.14 (m, 1 H) 3.95-3.76 (m, 3 H) 3.69 (quin, J=8.22 Hz, 1 H) 3.50 (dd, J=9.78, 7.43 Hz, 1 H) 2.89 (s, 3 H) 2.80 (dd, J=16.82, 9.00 Hz, 1 H) 2.56 (dd, J=16.82, 8.22 Hz, 1 H). The diastereomeric mixture was separated by chiral SFC (ChiralPak 5mic AD column, 4.6×100 (mm), IPA+0.1% DEA=40%, 5 mL/min). The polar diastereomer, 4-(2-amino-5-((R)-1-methyl-5-oxopyrrolidin-3-yl)pyridin-3-yl)-N-((S)-1-(3-chlorophenyl)-2-hydroxyethyl)-2-fluorobenzamide, was obtained at Rt=1.41 min. LCMS (m/z): 483.3 (MH+), 0.586 min; $^1$H NMR (400 MHz, CD$_3$OD) δ ppm 7.82 (d, J=1.56 Hz, 1 H) 7.74 (t, J=7.83 Hz, 1 H) 7.35 (d, J=2.35 Hz, 2 H) 7.33-7.15 (m, 5 H) 5.09 (t, J=5.87 Hz, 1 H) 4.48 (s, 1 H)) 3.83-3.63 (m, 3 H) 3.50 (quint, J=8.22 Hz, 1 H) 3.36 (dd, J=9.39, 7.43 Hz, 1 H) 2.78 (s, 3 H) 2.67 (dd, J=16.82, 9.00 Hz, 1 H) 2.42 (dd, J=16.63, 8.41 Hz, 1 H). The less polar diastereomer, 4-(2-amino-5-((S)-1-methyl-5-oxopyrrolidin-3-yl)pyridin-3-yl)-N-((S)-1-(3-chlorophenyl)-2-hydroxyethyl)-2-fluorobenzamide, was obtained at Rt=2.16 min. LCMS (m/z): 483.3 (MH+), 0.585 min; $^1$H NMR (400 MHz, CD$_3$OD) δ ppm 7.92 (d, J=2.35 Hz, 1 H) 7.84 (t, J=8.02 Hz, 1 H) 7.51-7.21 (m, 7 H) 5.18 (t, J=5.87 Hz, 1 H) 3.94-3.72 (m, 3 H) 3.59 (quin, J=8.22 Hz, 1 H) 3.50-3.42 (m, 1 H) 2.88 (s, 3 H) 2.82-2.70 (m, 1 H) 2.51 (dd, J=16.82, 8.61 Hz, 1 H).

Example 45

Synthesis of (S)-4-(2-Amino-5-(4-methyltetrahydro-2H-pyran-4-yl)pyridin-3-yl)-2-fluoro-N-(2-hydroxy-1-phenylethyl)benzamide Scheme 51

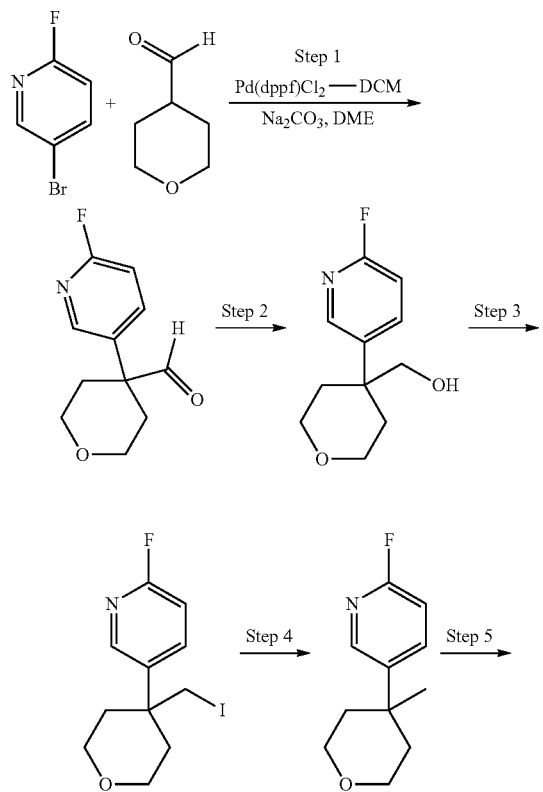

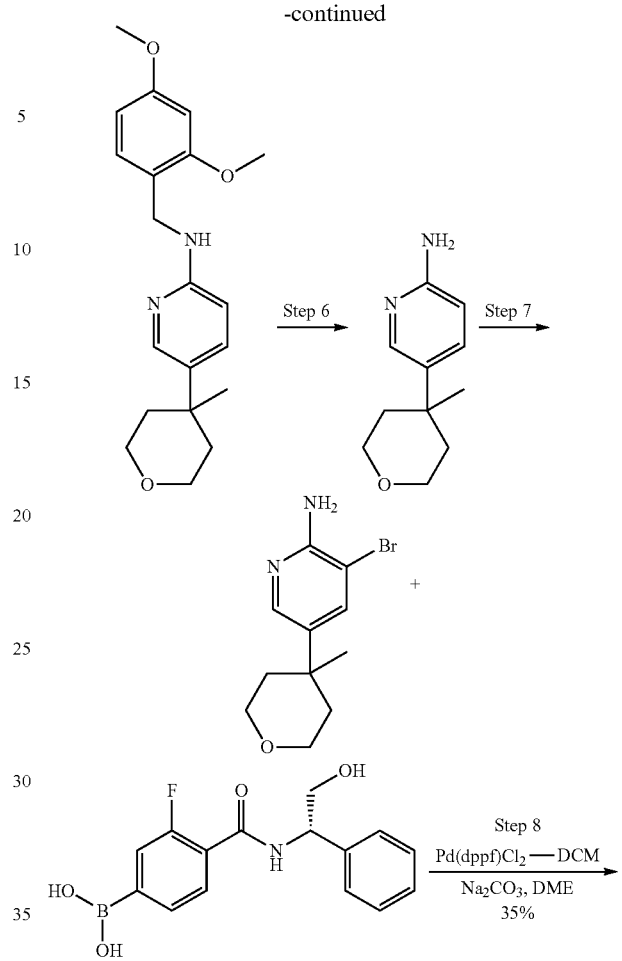

Step 1. 4-(6-Fluoropyridin-3-yl)tetrahydro-2H-pyran-4-carbaldehyde

To a solution of 5-bromo-2-fluoropyridine (2.0 g, 11.36 mmol) in dioxaane (35 mL) was added tetrahydro-2H-pyran-4-carbaldehyde (2.59 g, 22.73 mmol), Pd(OAc)$_2$ (0.25 g, 1.14 mmol), cesium carbonate (7.41 g, 22.73 mmol), and water (10.24 μL, 0.57 mmol), xantphos (0.98 g, 1.70 mmol). The mixture was purged with nitrogen for 5 min, the resulting mixture was heated to 110° C. in an oil bath for 15 h. The mixture was diluted with ethyl acetate, and was washed with water, brine, dried over sodium sulfate and concentrated. The residue was purified by flash column chromatography on silicagel (ISCO) eluting with 0-80% ethyl acetate in heptane to give 4-(6-fluoropyridin-3-yl)

tetrahydro-2H-pyran-4-carbaldehyde (560 mg, 2.68 mmol, 23.5% yield) as red color oil. LCMS (m/z): 210 (MH$^+$), 0.45 min.

Step 2. (4-(6-Fluoropyridin-3-yl)tetrahydro-2H-pyran-4-yl)methanol

To an ice cooled solution of 4-(6-fluoropyridin-3-yl)tetrahydro-2H-pyran-4-carbaldehyde (560 mg, 2.68 mmol) in methanol (18 mL) was added sodium borohydride (91 mg, 2.41 mmol). The reaction solution was stirred at ambient temperature for 30 min. The solvent was removed under vacuum. The residue was diluted with ethyl acetate, and was washed with water, brine, dried over sodium sulfate, filtered and concentrated to give (4-(6-fluoropyridin-3-yl)tetrahydro-2H-pyran-4-yl)methanol (550 mg, 2.60 mmol, 97%) as brown color oil. LCMS (m/z): 212 (MH$^+$), 0.42 min.

Step 3. 2-Fluoro-5-(4-(iodomethyl)tetrahydro-2H-pyran-4-yl)pyridine

To an ice cooled solution of triphenylphosphine (983 mg, 3.75 mmol), iodine (952 mg, 3.75 mmol) in dichloromethane (20 mL) was added imidazole (278 mg, 4.09 mmol). The solution was stirred at ambient temperature for 1 h, followed by the addition of (4-(6-fluoropyridin-3-yl)tetrahydro-2H-pyran-4-yl)methanol (360 mg, 1.70 mmol) in 10 mL dichloromethane. The reaction mixture was heated to 60° C. in an oil bath for 48 h. Solid was filtered off, the filtrate was purified by flash column chromatography on silicagel (ISCO) eluting with 0-80% ethyl acetate in heptane to give to give 2-fluoro-5-(4-(iodomethyl)tetrahydro-2H-pyran-4-yl)pyridine (330 mg, 1.03 mmol, 60.3% yield) as light yellow color oil. LCMS (m/z): 322 (MH$^+$), 0.77 min.

Step 4. 2-Fluoro-5-(4-methyltetrahydro-2H-pyran-4-yl)pyridine

To a solution of (2-fluoro-5-(4-(iodomethyl)tetrahydro-2H-pyran-4-yl)pyridine (330 mg, 1.03 mmol) in THF (5 mL) at −15° C., was added N-selectride (2.26 mL, 2.26 mmol) dropwise. The solution was stirred at ambient temperature for 16 h. The solution was recooled in an ice bath, and 0.3 mL of water was added. The resulting solution was stirred for 10 min. The solvent was removed under vacuum, and the residue was dissolved in DCM. Insoluble solid was filtered, and the filtrate was purified by flash column chromatography on silica gel (ISCO) eluting with 0-80% ethyl acetate in heptane to give to 2-fluoro-5-(4-methyltetrahydro-2H-pyran-4-yl)pyridine (110 mg, 0.56 mmol, 54.8 yield) as colorless oil with >90% purity. LCMS (m/z): 196 (MH$^+$), 0.64 min.

Step 5. N-(2,4-Dimethoxybenzyl)-5-(4-methyltetrahydro-2H-pyran-4-yl)pyridin-2-amine To a solution of 2-fluoro-5-(4-methyltetrahydro-2H-pyran-4-yl)pyridine (110 mg, 0.56 mmol) in (2,4-dimethoxyphenyl)methanamine (1016 µL, 6.76 mmol) and DIEA (246 µL, 1.41 mmol) was added potassium carbonate (156 mg, 1.12 mmol). The resulting mixture was heated to 160° C. in an oil bath for 16 h, The reaction mixture was diluted with ethyl acetate, washed with water, brine, dried over sodium sulfate and concentrated. The residue was purified by flash column chromatography on silicagel (ISCO) eluting with 0-100% ethyl acetate in heptane to give N-(2,4-dimethoxybenzyl)-5-(4-methyltetrahydro-2H-pyran-4-yl)pyridin-2-amine (100 mg, 0.29 mmol, 51.8% yield) as light yellow color solid. LCMS (m/z): 343 (MH$^+$), 0.63 min.

Step 6. 5-(4-Methyltetrahydro-2H-pyran-4-yl)pyridin-2-amine

To an ice cold solution of N-(2,4-dimethoxybenzyl)-5-(4-methyltetrahydro-2H-pyran-4-yl)pyridin-2-amine (100 mg, 0.29 mmol) in DCM (6 mL) was added 10 mL 30% TFA in DCM solution. The resulting solution was stirred at 0° C. for 15 min. The solvent was removed via vacuum. The resulting residue was redissolved in ethyl acetate, and the organic solution was washed with 1M NaOH, brine, dried over sodium sulfate and concentrated. The residue was purified by flash column chromatography on silicagel (ISCO) eluting with 0-100% ethyl acetate in heptane to give 5-(4-methyltetrahydro-2H-pyran-4-yl)pyridin-2-amine (50 mg, 0.26 mmol, 89% yield) as white color solid. LCMS (m/z): 193 (MH$^+$), 0.35 min.

Step 7. 3-Bromo-5-(4-methyltetrahydro-2H-pyran-4-yl)pyridin-2-amine

To an ice cold solution of 5-(4-methyltetrahydro-2H-pyran-4-yl)pyridin-2-amine (50 mg, 0.26 mmol) in DCM (5 mL) was added NBS (50.9 mg, 0.28 mmol) in two portions. The reaction mixture was stirred at ambient temperature for 40 min. The reaction solution was diluted with ethyl acetate, washed with water, aqueous sodium bicarbonate, brine, dried over sodium sulfate, filtered off, and concentrated to give 3-bromo-5-(4-methyltetrahydro-2H-pyran-4-yl)pyridin-2-amine (70 mg, 0.26 mmol, 99% yield) as yellow color residue. LCMS (m/z): 271/273 (MH$^+$), 0.41 min.

Step 8. (S)-4-(2-Amino-5-(4-methyltetrahydro-2H-pyran-4-yl)pyridin-3-yl)-2-fluoro-N-(2-hydroxy-1-phenylethyl)benzamide To a solution of 3-bromo-5-(4-methyltetrahydro-2H-pyran-4-yl)pyridin-2-amine (70 mg, 0.26 mmol) in DME (4 mL) was added (S)-2-fluoro-N-(2-hydroxy-1-phenylethyl)-4-(4,4,5,5-tetramethyl-1,3,2-dioxaborolan-2-yl)benzamide (298 mg, 0.77 mmol) and sodium carbonate (0.64 mL, 1.29 mmol). The mixture was purged with nitrogen for 10 min, then PdCl$_2$(dppf)-CH$_2$Cl$_2$ (31.6 mg, 0.039 mmol) was added. The reaction mixture was heated to 120° C. in an oil bath for 2 h. The reaction mixture was diluted with ethyl acetate, washed with water, brine, dried over sodium sulfate and concentrated. The resulting residue was purified by flash column chromatography on silicagel (ISCO) eluting with 0-100% ethyl acetate in heptane to give 70 mg crude product, which was purified by HPLC to give (S)-4-(2-amino-5-(4-methyltetrahydro-2H-pyran-4-yl)pyridin-3-yl)-2-fluoro-N-(2-hydroxy-1-phenylethyl)benzamide (40.8 mg, 0.089 mmol, 34.5% yield) as TFA salt. LCMS (m/z): 450 (MH$^+$), 0.61 min; 1H NMR (400 MHz, CDCl$_3$) δ ppm 8.22 (t, J=7.83 Hz, 1 H) 7.77-7.65 (m, 2 H) 7.50 (dd, J=11.74, 7.43 Hz, 1 H) 7.42-7.36 (m, 4 H) 7.33 (d, J=7.43 Hz, 2 H) 7.21 (d, J=11.74 Hz, 1 H) 5.33 (d, J=4.70 Hz, 1 H) 4.08-3.94 (m, 2 H) 3.83-3.65 (m, 4 H) 1.97 (ddd, J=13.40, 8.12, 5.09 Hz, 2 H) 1.72 (d, J=13.69 Hz, 2 H) 1.35 (s, 3 H)

Example 46

Synthesis of 4-(3-aminopyrazin-2-yl)-N-benzylbenzamide

Scheme 52

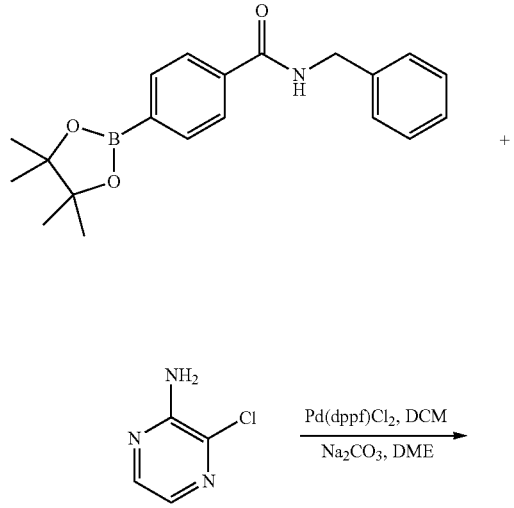

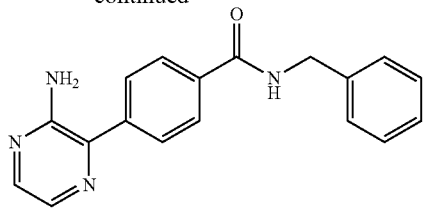

To a solution of N-benzyl-4-(4,4,5,5-tetramethyl-1,3,2-dioxaborolan-2-yl)benzamide (150 mg, 0.445 mmol), 3-chloropyrazin-2-amine (74.9 mg, 0.578 mmol), and PdCl$_2$(dppf)-CH$_2$Cl$_2$ adduct (36.3 mg, 0.044 mmol) in DME (3.3 mL) was added 2 M Na$_2$CO$_3$ (1.11 mL). The reaction mixture was heated at microwave synthesizer (120° C., 10 min). Diluted with EtOAc and washed with water twice. Then extracted with 1N HCl (3×15 mL). The acidic solution was washed with ether twice (2×15 mL), and then basified with Na$_2$CO$_3$. Followed by extracting with EtOAc (20 mL, 3 times) and then washed by sat NaHCO$_3$, water and brine, dried over Na$_2$SO$_4$ and filtered off, concentrated. The crude product was purified with flash chromatography eluting with 0-100% of EtOAc (containing 10% MeOH) in heptane, then concentrated on rotavap. The residue was triturated with ether to provide 80.2 mg of desired product. LCMS (m/z): 305.2 (MH$^+$), 0.59 min. 1H NMR (400 MHz, DMSO-d$_6$) δ ppm 8.74 (d, J=8.22 Hz, 1 H) 8.41 (s, 1 H) 8.06 (dd, J=9.39, 2.74 Hz, 1 H) 8.01 (d, J=8.61 Hz, 2 H) 7.94 (br. s., 1 H) 7.83 (d, J=8.22 Hz, 2 H) 7.40-7.34 (m, 2 H) 7.30 (t, J=7.63 Hz, 2 H) 7.22 (d, J=7.43 Hz, 1 H) 6.40 (d, J=9.39 Hz, 1 H) 5.12-5.03 (m, 1 H) 3.75-3.60 (m, 2 H).

TABLE 2

Compounds prepared from Method 1 described above

| Example | Structure | Name | MH$^+$ | R$_t$ (min) | NMR |
|---|---|---|---|---|---|
| 47 | 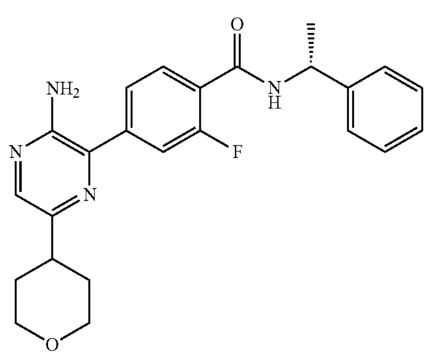 [SMILES: C[C@@H](NC(=O)c1ccc(-c2nc(C3CCOCC3)cnc2N)cc1F)c1ccccc1] | (R)-4-(3-amino-6-(tetrahydro-2H-pyran-4-yl)pyrazin-2-yl)-2-fluoro-N-(1-phenylethyl)benzamide | 421.3 | 0.8 | $^1$H NMR (400 MHz, CD$_3$OD) δ ppm 7.83 (s, 1H), 7.78 (t, J = 7.6 Hz, 1H), 7.66 (d, J = 7.8 Hz, 1H), 7.60 (d, J = 11.3 Hz, 1H), 7.46-7.39 (m, 2H), 7.35 (t, J = 7.6 Hz, 2H), 7.27 (d, J = 7.0 Hz, 1H), 5.26 (d, J = 7.0 Hz, 1H), 4.05 (d, J = 10.6 Hz, 2H), 3.57 (t, J = 10.4 Hz, 2H), 2.95 (d, J = 4.7 Hz, 1H), 1.96-1.78 (m, 4H), 1.58 (d, J = 7.0 Hz, 3H) |
| 48 | 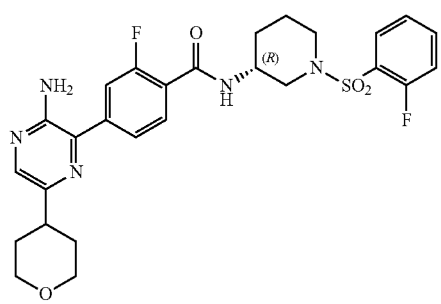 | (R)-4-(3-amino-6-(tetrahydro-2H-pyran-4-yl)pyrazin-2-yl)-2-fluoro-N-(1-((2-fluorophenyl)sulfonyl)piperidin-3-yl)benzamide | 558.3 | 0.8 | $^1$H NMR (400 MHz, CD$_3$OD) δ ppm 8.21 (br. s., 1H), 7.91-7.80 (m, 2H), 7.75-7.65 (m, 2 H), 7.60 (d, J = 11.7 Hz, 1H), 7.42-7.29 (m, 2H), 4.15 (d, J = 4.3 Hz, 1H), 4.10-4.00 (m, 2H), 3.68 (d, J = 8.6 Hz, 1H), 3.57 (dt, J = 2.3, 11.5 Hz, 2H), 3.50-3.40 (m, 1H), 3.03-2.88 (m, 2H), 1.99-1.78 (m, 5H), 1.76-1.65 (m, 1H), 1.65-1.54 (m, 1H) |

TABLE 2-continued

Compounds prepared from Method 1 described above

| Example | Structure | Name | MH+ | R$_t$ (min) | NMR |
|---|---|---|---|---|---|
| 49 | 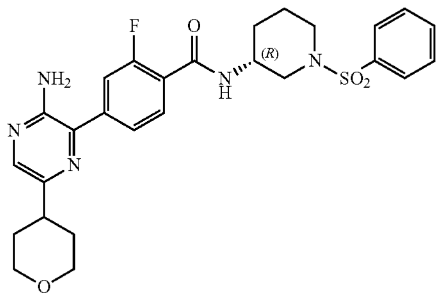 | (R)-4-(3-amino-6-(tetrahydro-2H-pyran-4-yl)pyrazin-2-yl)-2-fluoro-N-(1-(phenylsulfonyl)piperidin-3-yl)benzamide | 540.3 | 0.79 | $^1$H NMR (400 MHz, CD$_3$OD) δ ppm 7.89-7.75 (m, 4H), 7.74-7.65 (m, 2H), 7.65-7.56 (m, 3H), 4.16 (br. s., 1H), 4.11-4.00 (m, 2H), 3.57 (dt, J = 2.5, 11.4 Hz, 3H), 3.00-2.89 (m, 1H), 2.84-2.65 (m, 2H), 1.95-1.78 (m, 6H), 1.69 (dd, J = 3.5, 9.8 Hz, 1H), 1.58-1.43 (m, 1H) |
| 50 | 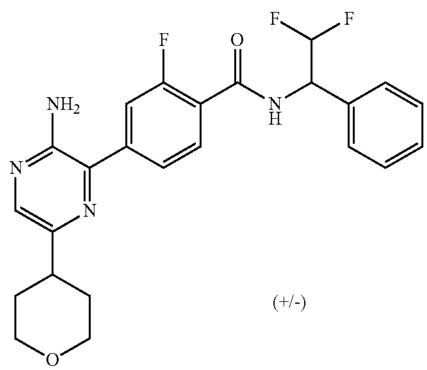 [SMILES: Nc1ncc(C2CCOCC2)nc1-c1ccc(C(=O)NC(c2ccccc2)C(F)F)c(F)c1] | (+/−)-4-(3-amino-6-(tetrahydro-2H-pyran-4-yl)pyrazin-2-yl)-N-(2,2-difluoro-1-phenylethyl)-2-fluorobenzamide | 457.1 | 0.8 | 1H NMR (400 MHz, CD$_3$OD) δ ppm 7.77 (s, 1H), 7.71 (m, 1H), 7.64-7.48 (m, 2H), 7.45-7.37 (m, 2H), 7.38-7.23 (m, 3H), 6.29-5.93 (m, 1H), 5.54-5.42 (m, 1H), 4.06-3.88 (m, 2H), 3.54-3.42 (m, 2H), 2.92-2.76 (m, 1H), 1.90-1.67 (m, 4H) |
| 51 | 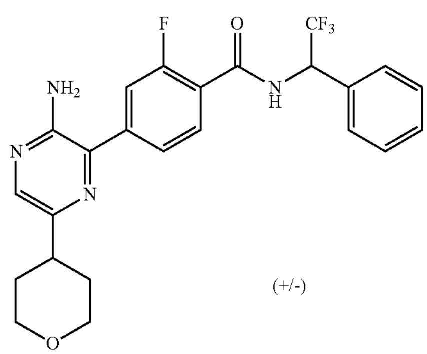 [SMILES: Nc1ncc(C2CCOCC2)nc1-c1ccc(C(=O)NC(c2ccccc2)C(F)(F)F)c(F)c1] | (+/−)-4-(3-amino-6-(tetrahydro-2H-pyran-4-yl)pyrazin-2-yl)-2-fluoro-N-(2,2,2-trifluoro-1-phenylethyl)benzamide | 475.3 | 0.89 | $^1$H NMR (400 MHz, DMSO-d6) δ ppm 9.67 (d, J = 9.39 Hz, 1H) 7.88 (s, 1H) 7.70-7.48 (m, 6H) 7.47-7.22 (m, 4H) 5.96 (t, J = 9.00 Hz, 1H) 3.87 (d, J = 10.96 Hz, 2H) 3.5 (m, 2H) 2.92-2.70 (m, 1H) 1.82-1.52 (m, 4H) |
| 52 | 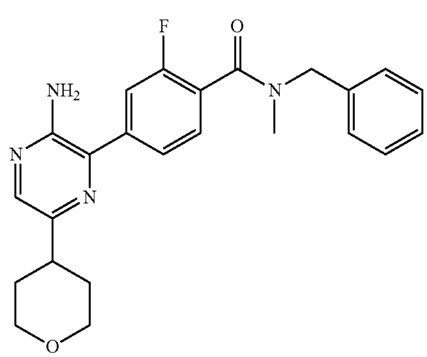 [SMILES: CN(Cc1ccccc1)C(=O)c1ccc(-c2nc(C3CCOCC3)cnc2N)cc1F] | 4-(3-amino-6-(tetrahydro-2H-pyran-4-yl)pyrazin-2-yl)-N-benzyl-2-fluoro-N-methylbenzamide | 421.3 | 0.77 | $^1$H NMR (400 MHz, DMSO-D6) δ ppm 7.92 (d, J = 7.0 Hz, 1H), 7.68-7.51 (m, 3H), 7.43-7.26 (m, 5H), 7.21 (d, J = 7.0 Hz, 1H), 4.73 (s, 1H), 4.49 (s, 1H), 3.97-3.88 (m, 2H), 3.44 (m, 2H hide inside of water peak) 2.90 (s, 1H), 2.88-2.80 (m, 3H), 1.78-1.69 (m, 4H) |

TABLE 2-continued

Compounds prepared from Method 1 described above

| Example | Structure | Name | MH+ | R$_t$ (min) | NMR |
|---|---|---|---|---|---|
| 53 | 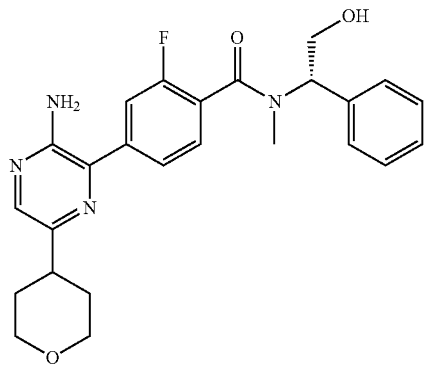 [SMILES: CN(C(=O)c1ccc(-c2nc(C3CCOCC3)cnc2N)cc1F)[C@H](CO)c1ccccc1] | (S)-4-(3-amino-6-(tetrahydro-2H-pyran-4-yl)pyrazin-2-yl)-2-fluoro-N-(2-hydroxy-1-phenylethyl)-N-methylbenzamide | 451.2 | 0.66 | $^1$H NMR (400 MHz, DMSO-d6) δ ppm 7.89 (d, J = 3.1 Hz, 1H), 7.63-7.52 (m, 2H), 7.45 (t, J = 7.6 Hz, 1H), 7.38-7.31 (m, 3H), 7.31-7.21 (m, 2H), 5.75 (dd, J = 6.3, 8.6 Hz, 1H), 4.76 (br. s., 1H), 4.03-3.93 (m, 1H), 3.90 (dd, J = 2.9, 11.2 Hz, 2H), 3.40-3.35 (m, 6H), 2.81 (td, J = 3.2, 6.6 Hz, 1H), 2.76 (s, 1H), 2.70 (s, 2H), 1.74-1.67 (m, 4H) |
| 54 | 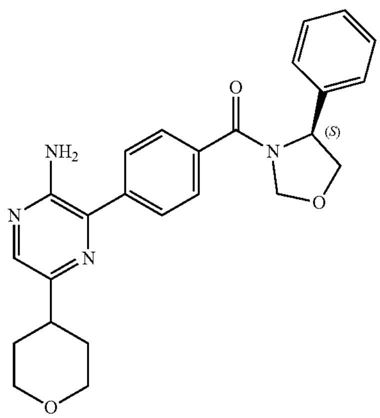 | (S)-(4-(3-amino-6-(tetrahydro-2H-pyran-4-yl)pyrazin-2-yl)phenyl)(4-phenyloxazolidin-3-yl)methanone | 431.3 | 0.69 | $^1$H NMR (400 MHz, DMSO-d6) δ ppm 7.78 (br. s., 1H), 7.70 (br. s., 1H), 7.40 (br. s., 1H), 7.34 (br. s., 1H). 7.26 (br. s., 1H), 6.02 (br. s., 1H), 5.31 (d, J = 4.3 Hz, 1H), 5.04 (br. s., 1H), 3.91 (d, J = 11.0 Hz. 1H). 2.82 (br. s., 1H), 2.04 (s, 1H), 1.71 (br. s., 2H), 1.20 (s, 2H) |
| 55 | 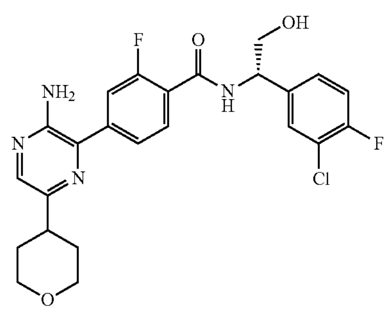 [SMILES: Nc1ncc(C2CCOCC2)nc1-c1ccc(C(=O)N[C@H](CO)c2ccc(F)c(Cl)c2)c(F)c1] | (S)-4-(3-amino-6-(tetrahydro-2H-pyran-4-yl)pyrazin-2-yl)-N-(1-(3-chloro-4-fluorophenyl)-2-hydroxyethyl)-2-fluorobenzamide | 489.1 | 0.76 | $^1$H NMR (400 MHz, CD$_3$OD) δ ppm 7.90-7.83 (m, 2H), 7.69 (d, J = 8.2 Hz, 1H), 7.64 (d, J = 11.7 Hz, 1H), 7.56 (dd, J = 2.0, 7.0 Hz, 1H), 7.45-7.35 (m, 1H), 7.32-7.18 (m, 1H), 5.18 (t, J = 5.9 Hz, 1H), 4.10-4.01 (m, 2H), 3.91-3.80 (m, 2H), 3.65-3.53 (m, 2H), 3.03-2.88 (m, 1H), 1.99-1.78 (m, 4H) |
| 56 | 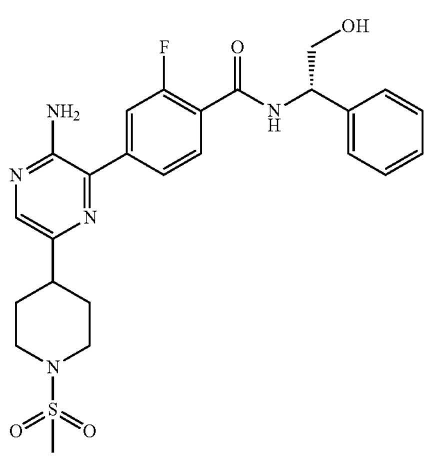 [SMILES: CS(=O)(=O)N1CCC(c2cnc(N)c(-c3ccc(C(=O)N[C@H](CO)c4ccccc4)c(F)c3)n2)CC1] | (S)-4-(3-amino-6-(1-(methylsulfonyl)piperidin-4-yl)pyrazin-2-yl)-2-fluoro-N-(2-hydroxy-1-phenylethyl)benzamide | 514.2 | 0.643 | $^1$H NMR (400 MHz, CD$_3$OD) δ ppm 8.56 (br. s., 1H) 7.89-7.70 (m, 2H) 7.66-7.46 (m, 2H) 7.41-7.07 (m, 5H) 5.23-5.01 (m, 1H) 3.90-3.60 (m, 4H) 2.91-2.62 (m, 6H) 2.06-1.61 (m, 4H) |

TABLE 2-continued

Compounds prepared from Method 1 described above

| Example | Structure | Name | MH+ | R$_t$ (min) | NMR |
|---|---|---|---|---|---|
| 57 | 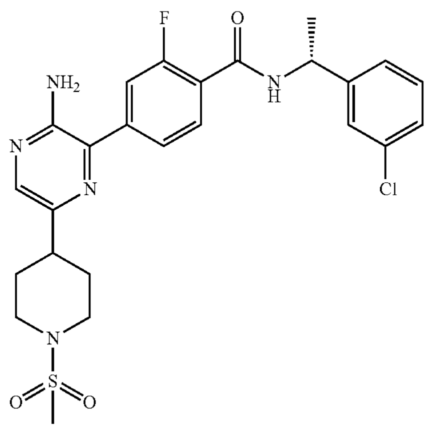 [SMILES: C[C@@H](NC(=O)c1ccc(-c2nc(C3CCN(S(C)(=O)=O)CC3)cnc2N)cc1F)c1cccc(Cl)c1] | (R)-4-(3-amino-6-(1-methylsulfonyl)piperidin-4-yl)pyrazin-2-yl)-N-(1-(3-chlorophenyl)ethyl)-2-fluorobenzamide | 532/534 | 0.85 | $^1$H NMR (400 MHz, CD$_3$OD) δ ppm 8.73 (d, J = 6.26 Hz, 1H) 7.78 (s, 1H) 7.63-7.71-7.63 (m, 1H) 7.60-7.47 (m, 2H) 7.35 (s, 1 H) 7.29-7.13 (m, 3H) 5.07-5.19-5.07 (m, 1H) 3.75 (d, J = 12.13 Hz, 2H)) 2.86-2.65 (m, 6H) 1.99-1.70 (m, 4H) 1.53-1.40 (m, 3H) |
| 58 | 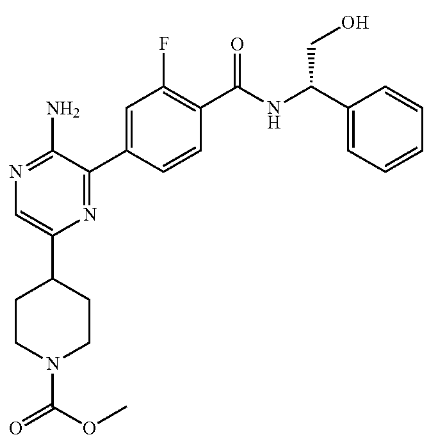 [SMILES: COC(=O)N1CCC(c2cnc(N)c(-c3ccc(C(=O)N[C@H](CO)c4ccccc4)c(F)c3)n2)CC1] | Synthesis of (S)-methyl 4-(5-amino-6-(3-fluoro-4-((2-hydroxy-1-phenylethyl)carbamoyl)phenyl)pyrazin-2-yl)piperidine-1-carboxylate | 494.2 | 0.709 | $^1$H NMR (400 MHz, CD$_3$OD) δ ppm 7.85-7.68 (m, 1H), 7.42-7.64-7.42 (m, 2H), 7.41-7.05 (m, 5H), 5.22-5.00 (m, 1H) 4.14 (d, J = 13.3 Hz, 2H), 3.83-3.69 (m, 2 H) 3.60 (s, 3H) 2.99-2.63 (m, 3 H), 1.80 (d, J = 12.52 Hz, 2H), 1.70-1.55 (m, 2H) |
| 59 | 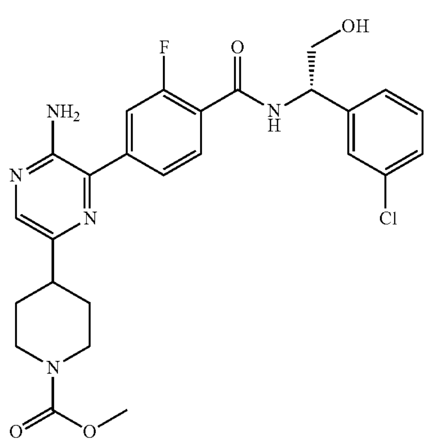 [SMILES: COC(=O)N1CCC(c2cnc(N)c(-c3ccc(C(=O)N[C@H](CO)c4cccc(Cl)c4)c(F)c3)n2)CC1] | (S)-methyl 4-(5-amino-6-(4-((1-(3-chlorophenyl)-2-hydroxyethyl)carbamoyl)-3-fluorophenyl)pyrazin-2-yl)piperidine-1-carboxylate | 528.2/530.2 | 0.777 | $^1$H NMR (400 MHz, CD$_3$OD) δ ppm 7.90-7.81 (m, 2H) 7.72-7.58 (m, 2H) 7.46 (s, 1H) 7.41-7.24 (m, 3H) 5.19 (t, J = 5.67 Hz, 1H) 4.23 (d, J = 12.91 Hz, 2H) 3.92-3.78 (m, 2H) 3.70 (s, 3H) 3.06-2.82 (m, 3H) 1.90 (d, J = 12.52 Hz, 2H) 1.72 (qd, J = 12.52, 4.30 Hz, 2H) |

TABLE 2-continued

Compounds prepared from Method 1 described above

| Example | Structure | Name | MH+ | R$_t$ (min) | NMR |
|---|---|---|---|---|---|
| 60 | 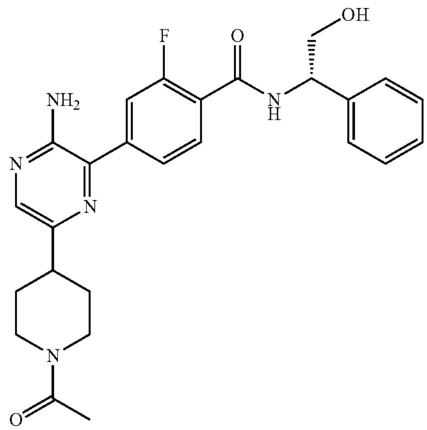 [SMILES: CC(=O)N1CCC(c2cnc(N)c(-c3ccc(C(=O)N[C@H](CO)c4ccccc4)c(F)c3)n2)CC1] | (S)-4-(6-(1-acetylpiperidin-4-yl)-3-aminopyrazin-2-yl)-2-fluoro-N-(2-hydroxy-1-phenylethyl)benzamide | 478.2 | 0.609 | $^1$H NMR (400 MHz, CD$_3$OD) δ ppm 7.81-7.69 (m, 2H), 7.62-7.45 (m, 2H), 7.09-7.37-7.09 (m, 6H), 6.5 (dd, J = 8.61, 2.35 Hz, 1H), 6.50 (dd, J = 13.50, 2.15 Hz, 1H), 5.17-5.01 (m, 1H), 4.55 (d, J = 13.30 Hz, 1H) 3.94 (d, J = 13.69 Hz, 1H) 3.83-3.63 (m, 2 H) 2.88 (tt, J = 11.84, 3.62 Hz, 1H) 2.67 (td, J = 12.91, 2.35 Hz, 1H) 2.03 (s, 3H) 1.96-1.79 (m, 2H) 1.78-1.50 (m, 2H) |
| 61 | 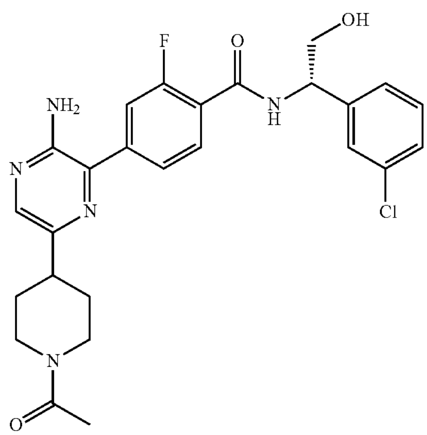 [SMILES: CC(=O)N1CCC(c2cnc(N)c(-c3ccc(C(=O)N[C@H](CO)c4cccc(Cl)c4)c(F)c3)n2)CC1] | (S)-4-(6-(1-acetylpiperidin-4-yl)-3-aminopyrazin-2-yl)-N-(1-(3-chlorophenyl)-2-hydroxyethyl)-2-fluorobenzamide | 512.2/514.2 | 0.68 | $^1$H NMR (400 MHz, CD$_3$OD) δ ppm 7.83-7.70 (m, 2H) 7.64-7.48 (m, 2H) 7.37 (s, 1H) 7.14-7.31-7.14 (m, 3H) 5.15-5.02 (m, 1H) 4.55 (d, J = 13.69 Hz, 1H) 4.01-3.88 (m, 1H) 3.84-3.67 (m, 2 H) 2.95-2.80 (m, 1H) 2.74-2.60 (m, 1H) 2.03 (s, 3H) 1.93-1.79 (m, 2H) 1.78-1.53 (m, 2H) |
| 62 | 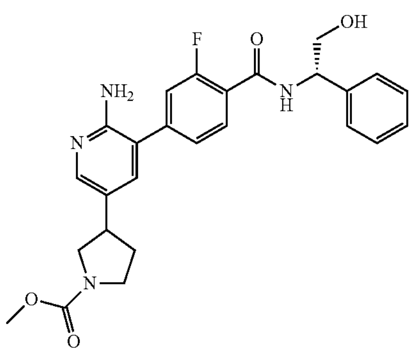 [SMILES: COC(=O)N1CCC(c2cnc(N)c(-c3ccc(C(=O)N[C@H](CO)c4ccccc4)c(F)c3)c2)C1] | methyl 3-(6-amino-5-(3-fluoro-4-(((S)-2-hydroxy-1-phenylethyl)carbamoyl)phenyl)pyridin-3-yl)pyrrolidine-1-carboxylate | 479.2 | 0.599 | $^1$H NMR (400 MHz, CD$_3$OD) δ ppm 8.66-8.41 (m, 1H) 7.98-7.61 (m, 3H) 7.51-7.00 (m, 7H) 5.26-5.02 (m, 1H) 3.87-3.67 (m, 3H) 3.61 (s, 3H) 3.59-3.49 (m, 1 H) 3.44-3.28 (m, 3H) 2.22 (br. s., 1H) 2.08-1.86 (m, 1H) |
| 63 | 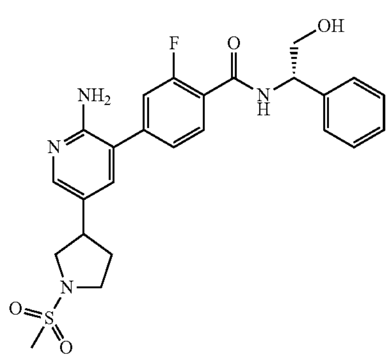 [SMILES: CS(=O)(=O)N1CCC(c2cnc(N)c(-c3ccc(C(=O)N[C@H](CO)c4ccccc4)c(F)c3)c2)C1] | 4-(2-amino-5-(1-(methylsulfonyl)pyrrolidin-3-yl)pyridin-3-yl)-2-fluoro-N-((S)-2-hydroxy-1-phenylethyl)benzamide | 499.2 | 0.565 | $^1$H NMR (400 MHz, CD$_3$OD) δ ppm 8.56 (dd, J = 7.24, 4.11 Hz, 1H) 7.87 (d, J = 1.96 Hz, 1H) 7.84-7.74 (m, 2H) 7.42-7.10 (m, 8H) 5.19-5.04 (m, 1H) 3.84-3.71 (m, 2H) 3.66 (dd, J = 9.78, 7.43 Hz, 1H) 3.54-3.28 (m, 3H) 2.84 (s, 3H) 2.37-2.22 (m, 1H) 2.11-1.93 (m, 1H) |

TABLE 2-continued

Compounds prepared from Method 1 described above

| Example | Structure | Name | MH+ | R_t (min) | NMR |
|---------|-----------|------|-----|-----------|-----|
| 64 | 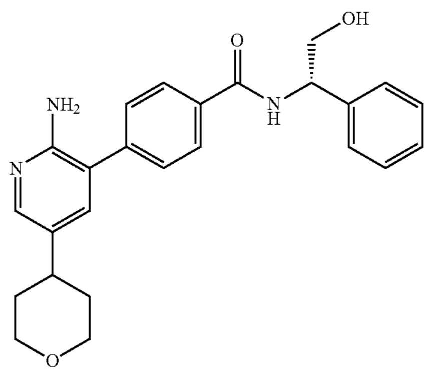 [SMILES: Nc1ncc(C2CCOCC2)cc1-c1ccc(C(=O)N[C@H](CO)c2ccccc2)cc1] | (S)-4-(2-amino-5-(tetrahydro-2H-pyran-4-yl)pyridin-3-yl)-N-(2-hydroxy-1-phenylethyl)benzamide | 418.2 | 0.56 | $^1$H NMR (400 MHz, DMSO-d$_6$) δ ppm 8.70 (d, J = 7.83 Hz, 1H), 7.97 (d, J = 8.61 Hz, 2H), 7.86 (d, J = 1.96 Hz, 1H), 7.53 (d, J = 8.22 Hz, 2H), 7.36-7.42 (m, 2H), 7.29 (t, J = 7.63 Hz, 2H), 7.15-7.25 (m, 2H), 5.38-5.51 (m, 2H), 5.00-5.14 (m, 1H), 4.91 (t, J = 5.87 Hz, 1H), 3.85-3.97 (m, 2H), 3.57-3.78 (m, 2H), 3.38 (dt, J = 3.72, 10.86 Hz, 2H), 2.56-2.72 (m, 1H), 1.49-1.71 (m, 4H) |
| 65 | 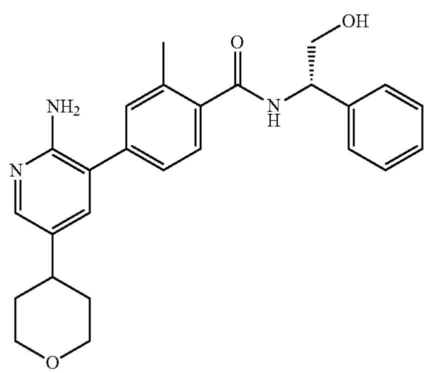 [SMILES: Cc1cc(-c2cc(C3CCOCC3)cnc2N)ccc1C(=O)N[C@H](CO)c1ccccc1] | (S)-4-(2-amino-5-(tetrahydro-2H-pyran-4-yl)pyridin-3-yl)-N-(2-hydroxy-1-phenylethyl)-2-methylbenzamide | 432.3 | 0.60 | $^1$H NMR (400 MHz, METHANOL-d$_4$) δ ppm 7.76 (d, J = 1.96 Hz, 1H), 7.66 (d, J = 1.96 Hz, 1H), 7.47 (d, J = 7.83 Hz, 1H), 7.31-7.36 (m, 2H), 7.23-7.31 (m, 4H), 7.15-7.22 (m, 1H), 5.04-5.20 (m, 1H), 3.95 (dd, J = 2.93, 11.54 Hz, 2H), 3.59-3.81 (m, 2H), 3.37-3.52 (m, 2H), 2.67-2.85 (m, 1H), 2.33 (s, 3H), 1.46-1.85 (m, 4H) |
| 66 | 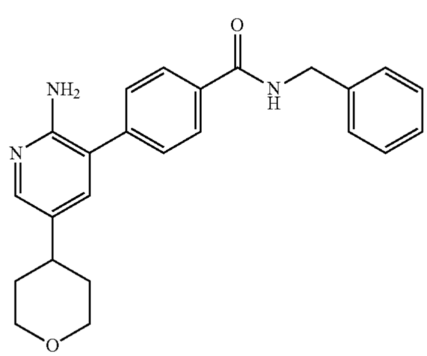 [SMILES: Nc1ncc(C2CCOCC2)cc1-c1ccc(C(=O)NCc2ccccc2)cc1] | 4-(2-amino-5-(tetrahydro-2H-pyran-4-yl)pyridin-3-yl)-N-benzylbenzamide | 388.1 | 0.64 | $^1$H NMR (400 MHz, DMSO-d$_6$) δ ppm 9.12 (t, J = 5.87 Hz, 1H), 8.00 (d, J = 8.61 Hz, 2H), 7.81 (s, 2H), 7.54 (d, J = 8.22 Hz, 2H), 7.08-7.44 (m, 6H), 4.46 (d, J= 5.87 Hz, 2H), 3.88 (dd, J = 2.35, 11.35 Hz, 2H), 2.66-2.80 (m, 1H), 1.46-1.77 (m, 4H) (two CH2 proton next to oxygen were under water) |
| 67 | 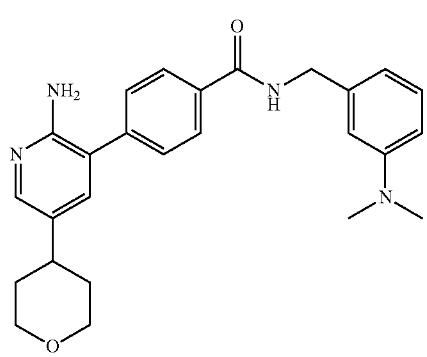 [SMILES: CN(C)c1cccc(CNC(=O)c2ccc(-c3cc(C4CCOCC4)cnc3N)cc2)c1] | 4-(2-amino-5-(tetrahydro-2H-pyran-4-yl)pyridin-3-yl)-N-(3-(dimethylamino)benzyl)benzamide | 431.2 | 0.47 | $^1$H NMR (400 MHz, DMSO-d$_6$) δ ppm 9.06 (t, J = 5.87 Hz, 1H), 8.00 (d, J = 8.61 Hz, 2H), 7.85 (d, J = 1.96 Hz, 1H), 7.81 (d, J = 1.57 Hz, 1H), 7.54 (d, J = 8.22 Hz, 3H), 7.09 (t, J = 7.83 Hz, 1H), 6.71 (br. s., 1H), 6.60 (d, J = 5.87 Hz, 2H), 4.40 (d, J = 5.87 Hz, 2H), 3.84-3.97 (m, 4H), 3.33 (dt, J = 2.35, 11.35 Hz, 2H), 2.83 (s, 6H), 2.74 (br. s., 1H), 1.50-1.75 (m, 4H) |

TABLE 2-continued

Compounds prepared from Method 1 described above

| Example | Structure | Name | MH+ | R_t (min) | NMR |
|---|---|---|---|---|---|
| 68 | 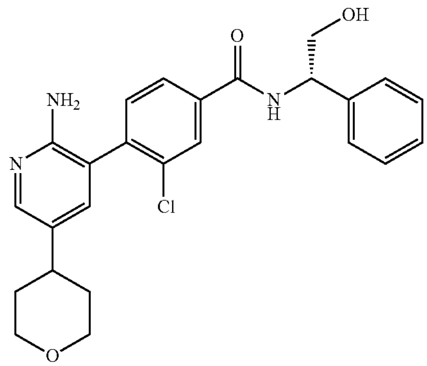 [SMILES: Nc1ncc(C2CCOCC2)cc1-c1ccc(C(=O)N[C@H](CO)c2ccccc2)cc1Cl] | (S)-4-(2-amino-5-(tetrahydro-2H-pyran-4-yl)pyridin-3-yl)-3-chloro-N-(2-hydroxy-1-phenylethyl)benzamide | 452.2 | 0.62 | 1H NMR (400 MHz, DMSO-d$_6$) δ ppm 8.92 (d, J = 7.83 Hz, 1H), 8.17 (d, J = 8.61 Hz, 1H), 7.99 (d, J = 7.83 Hz, 1H), 7.87 (d, J = 1.96 Hz, 1H), 7.80 (br. s., 1H), 7.52 (d, J = 7.83 Hz, 1H), 7.34-7.39 (m, 2H), 7.30 (t, J = 7.43 Hz, 2H), 7.22 (d, J = 7.04 Hz, 1H), 4.96-5.18 (m, 1H), 3.91 (dd, J = 10.96, 3.13 Hz, 2H), 3.58-3.79 (m, 2H), 3.43 (2H), 2.68-2.91 (m, 1H), 1.55-1.82 (m, 4H) |
| 69 | 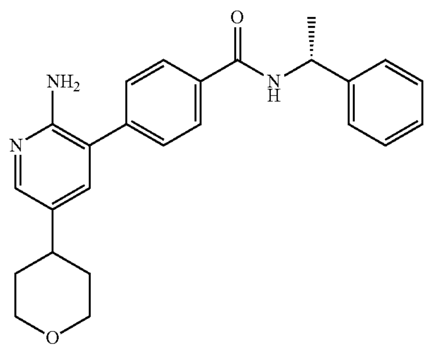 [SMILES: C[C@@H](NC(=O)c1ccc(-c2cc(C3CCOCC3)cnc2N)cc1)c1ccccc1] | (R)-4-(2-amino-5-(tetrahydro-2H-pyran-4-yl)pyridin-3-yl)-N-(1-phenylethyl)benzamide | 402.4 | 0.68 | 1H NMR (400 MHz, DMSO-d$_6$) δ ppm 8.85 (d, J = 8.22 Hz, 1H), 8.00 (d, J = 8.61Hz, 2H), 7.69-7.87 (m, 2H), 7.52 (d, J = 8.22 Hz, 2H), 7.31-7.36 (m, 2H), 7.27 (t, J = 7.63 Hz, 2H), 7.13-7.20 (m, 1H), 5.15 (t, J = 7.43 Hz, 1H), 3.75-3.99 (m, 2H), 3.36 (br. s., 2H), 2.66-2.84 (m, 1H), 1.53-1.75 (m, 4H), 1.44 (d, J = 7.04 Hz, 3H) |
| 70 | 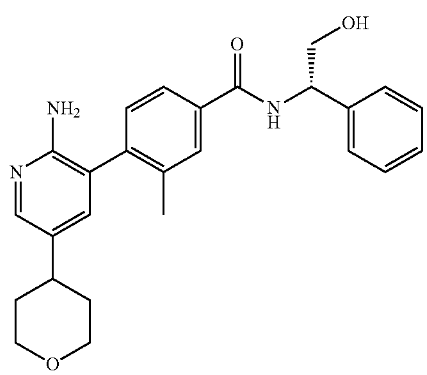 [SMILES: Cc1cc(C(=O)N[C@H](CO)c2ccccc2)ccc1-c1cc(C2CCOCC2)cnc1N] | (S)-4-(2-amino-5-(tetrahydro-2H-pyran-4-yl)pyridin-3-yl)-N-(2-hydroxy-1-phenylethyl)-3-methylbenzamide | 432.4 | 0.60 | 1H NMR (400 MHz, DMSO-d$_6$) δ ppm 8.67 (d, J = 7.83 Hz, 1H), 7.88 (br. s., 1H), 7.76-7.85 (m, 2H), 7.70 (br. s., 1H), 7.30-7.36 (m, 2H), 7.23-7.29 (m, 3H), 7.14-7.20 (m, 1H), 4.97-5.10 (m, 1H), 3.87 (dd, J = 10.76, 3.33 Hz, 2H), 3.53-3.74 (m, 2H), 3.33 (d, J = 1.96 Hz, 2H), 2.66-2.82 (m, 1H), 2.11 (s, 3H), 1.50-1.74 (m, 4H) |
| 71 | 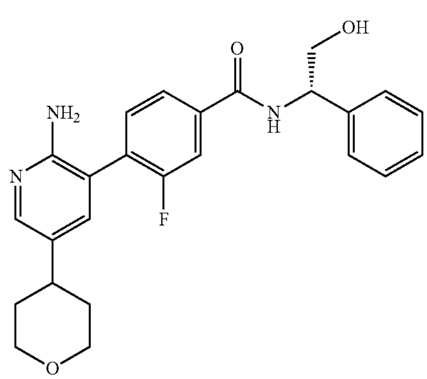 [SMILES: Nc1ncc(C2CCOCC2)cc1-c1ccc(C(=O)N[C@H](CO)c2ccccc2)cc1F] | (S)-4-(2-amino-5-(tetrahydro-2H-pyran-4-yl)pyridin-3-yl)-3-fluoro-N-(2-hydroxy-1-phenylethyl)benzamide | 436.5 | 0.59 | 1H NMR (400 MHz, DMSO-d$_6$) δ ppm 8.83 (d, J = 8.22 Hz, 1H), 7.78-7.93 (m, 4H), 7.52 (t, J = 7.63 Hz, 1H), 7.30-7.35 (m, 2H), 7.26 (t, J = 7.43 Hz, 2H), 7.14-7.22 (m, 1H), 4.99-5.08 (m, 1H), 3.88 (dd, J = 10.96, 3.13 Hz, 2H), 3.57-3.72 (m, 2H), 3.30 (2H), 2.67-2.79 (m, 1H), 1.53-1.71 (m, 4H), |

TABLE 2-continued

Compounds prepared from Method 1 described above

| Example | Structure | Name | MH+ | R$_t$ (min) | NMR |
|---|---|---|---|---|---|
| 72 | 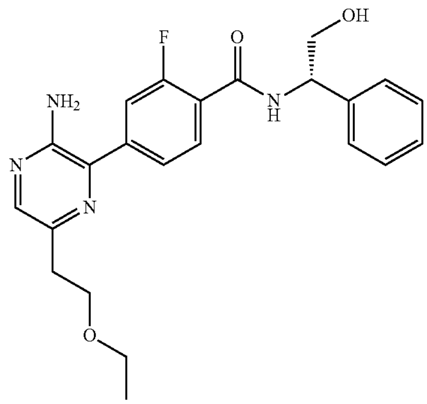 [SMILES: CCOCCc1cnc(N)c(-c2ccc(C(=O)N[C@H](CO)c3ccccc3)c(F)c2)n1] | (S)-4-(3-amino-6-(2-ethoxyethyl)pyrazin-2-yl)-2-fluoro-N-(2-hydroxy-1-phenylethyl)benzamide | 425.2 | 0.68 | $^1$H NMR (400 MHz, CD$_3$OD) δ ppm 7.79 (s, 1H), 7.78-7.74 (m, 1H), 7.56 (dd, J = 1.4, 8.0 Hz, 1 H), 7.51 (dd, J = 1.2, 11.7 Hz, 1 H), 7.36-7.31 (m, 2H), 7.27 (t, J = 7.6 Hz, 2H), 7.19 (d, J = 7.0 Hz, 1H), 5.12 (t, J = 6.1 Hz, 1H), 3.83-3.71 (m, 2H), 3.67 (t, J = 6.7 Hz, 2H), 3.42 (q, J = 7.0 Hz, 2H), 2.86 (t, J = 6.5 Hz, 2H), 1.06 (t, J = 7.0 Hz, 3H) |
| 73 | 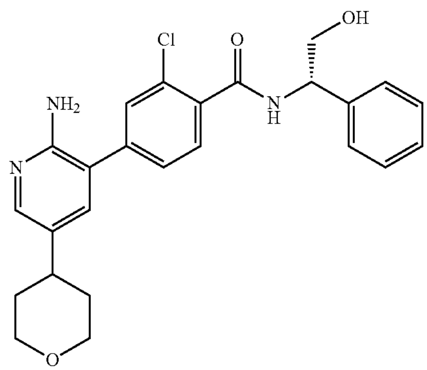 | (S)-4-(2-amino-5-(tetrahydro-2H-pyran-4-yl)pyridin-3-yl)-2-chloro-N-(2-hydroxy-1-phenylethyl)benzamide | 452.5 | 0.59 | 1H NMR (400 MHz, DMSO-d$_6$) δ ppm 8.77 (d, J = 8.22 Hz, 1H), 7.82 (d, J = 1.96 Hz, 1H), 7.76 (s, 1H), 7.59 (d, J = 1.57 Hz, 1H), 7.52-7.56 (m, 1H), 7.46 (dd, J = 8.02, 1.37 Hz, 1H), 7.32-7.37 (m, 2H), 7.28 (t, J = 7.43 Hz, 2H), 7.16-7.23 (m, 1H), 4.93-5.02 (m, 1H), 3.84-3.93 (m, 2H), 3.58 (d, J = 7.04 Hz, 2H), 3.30 (2 H), 2.68-2.79 (m, 1H), 1.55-1.70 (m, 4H) |
| 74 | 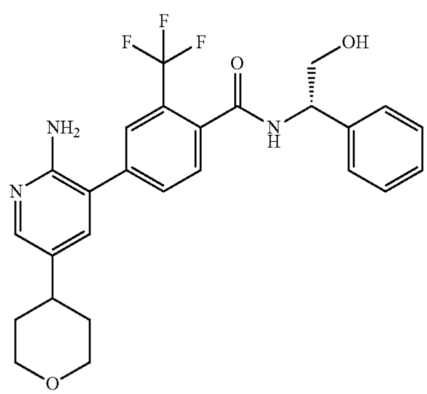 [SMILES: Nc1ncc(C2CCOCC2)cc1-c1ccc(C(=O)N[C@H](CO)c2ccccc2)c(C(F)(F)F)c1] | (S)-4-(2-amino-5-(tetrahydro-2H-pyran-4-yl)pyridin-3-yl)-N-(2-hydroxy-1-phenylethyl)-2-(trifluoromethyl)benzamide | 486.3 | 0.62 | 1H NMR (400 MHz, CD$_3$OD) δ ppm 8.87 (d, J = 8.22 Hz, 1H), 7.75-7.85 (m, 2H), 7.68-7.73 (m, 2H), 7.63-7.68 (m, 1 H), 7.31-7.36 (m, 2H), 7.28 (t, J = 7.43 Hz, 2H), 7.17-7.24 (m, 1 H), 5.02-5.20 (m, 1H), 3.95 (dd, J = 11.15, 3.33 Hz, 2H), 3.65-3.86 (m, 2H), 3.45 (td, J = 11.44, 2.54 Hz, 2H), 2.68- 2.90 (m, 1 H), 1.53-1.87 (m, 4H) |
| 75 | 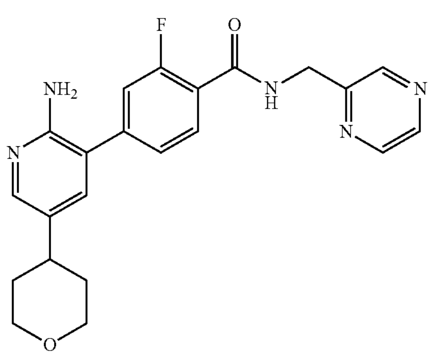 [SMILES: Nc1ncc(C2CCOCC2)cc1-c1ccc(C(=O)NCc2cnccn2)c(F)c1] | 4-(2-amino-5-(tetrahydro-2H-pyran-4-yl)pyridin-3-yl)-2-fluoro-N-(pyrazin-2-ylmethyl)benzamide | 408.1 | 0.47 | 1H NMR (400 MHz, DMSO-d$_6$) δ ppm 8.92 (m, 1H), 8.69-8.49 (m, 2H), 7.87 (m, 1H), 7.75 (m, 1H), 7.44-7.32 (m, 2H), 7.28 (m, 1H), 5.58 (m, 1H), 4.63 (m, 2H), 3.89 (m, 2H), 3.38 (m, 2 H), 2.64 (s, 1H), 1.64 (m, 4H). |

TABLE 2-continued

Compounds prepared from Method 1 described above

| Example | Structure | Name | MH+ | R_t (min) | NMR |
|---|---|---|---|---|---|
| 76 | 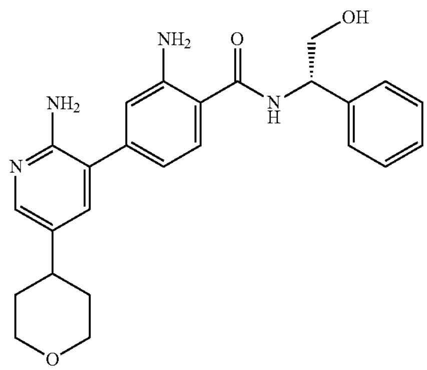 [SMILES: Nc1cc(-c2cc(C3CCOCC3)cnc2N)ccc1C(=O)N[C@H](CO)c1ccccc1] | (S)-2-amino-4-(2-amino-5-(tetrahydro-2H-pyran-4-yl)pyridin-3-yl)-N-(2-hydroxy-1-phenylethyl)benzamide | 419.3 | 0.57 | 1H NMR (400 MHz, CD$_3$OD) δ ppm 7.89 (d, J = 2.0 Hz, 1H) 7.76 (dd, J = 5.1, 3.1 Hz, 2H) 7.18-7.49 (m, 5H) 6.84 (d, J = 1.6 Hz, 1H) 6.74 (dd, J = 8.0, 1.8 Hz, 1H) 5.15-5.26 (m, 1H) 4.06 (dd, J = 11.0, 3.5 Hz, 2H) 3.78-3.95 (m, 2H) 3.57 (td, J = 11.5, 2.3 Hz, 2H) 2.77-2.97 (m, 1H) 1.68-1.91 (m, 4H) |
| 77 | 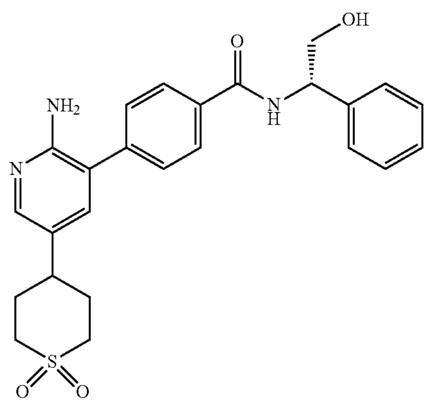 [SMILES: Nc1ncc(C2CCS(=O)(=O)CC2)cc1-c1ccc(C(=O)N[C@H](CO)c2ccccc2)cc1] | (S)-4-(2-amino-5-(1,1-dioxidotetrahydro-2H-thiopyran-4-yl)pyridin-3-yl)-N-(2-hydroxy-1-phenylethyl)benzamide | 466.3 | 0.53 | 1H NMR (400 MHz, CD$_3$OD) δ ppm 8.81 (d, J = 7.83 Hz, 1H), 8.05 (d, J = 8.61 Hz, 2H), 7.92 (d, J = 1.96 Hz, 1H), 7.84 (d, J = 1.57 Hz, 1H), 7.61 (d, J = 8.22 Hz, 2H), 7.39-7.45 (m, 2H), 7.35 (t, J = 7.43 Hz, 2H), 7.24-7.31 (m, 1H), 5.24 (q, J = 7.04 Hz, 1H), 3.89 (d, J = 6.65 Hz, 2H), 3.30 (2H), 3.07-3.22 (m, 2H), 2.99 (tt, J = 10.27, 5.38 Hz, 1H), 2.17-2.40 (m, 4H) |
| 78 | 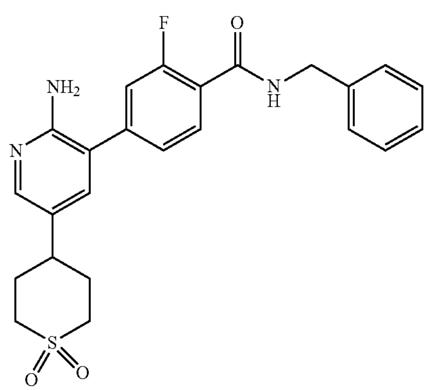 [SMILES: Nc1ncc(C2CCS(=O)(=O)CC2)cc1-c1ccc(C(=O)NCc2ccccc2)c(F)c1] | 4-(2-amino-5-(1,1-dioxidotetrahydro-2H-thiopyran-4-yl) pyridin-3-yl)-N-benzyl-2-fluorobenzamide | 454.2 | 0.59 | 1H NMR (400 MHz, DMSO-d6) δ ppm 8.89-8.74 (m, 1H), 7.94-7.79 (m, 1H), 7.72 (s, 1H), 7.47-7.28 (m, 6H), 7.25-7.14 (m, 1H), 4.47 (d, J = 6.1 Hz, 2H), 3.14-2.96 (m, 2H), 2.91-2.74 (m, 1H), 2.15-2.01 (m, 4H) |
| 79 | 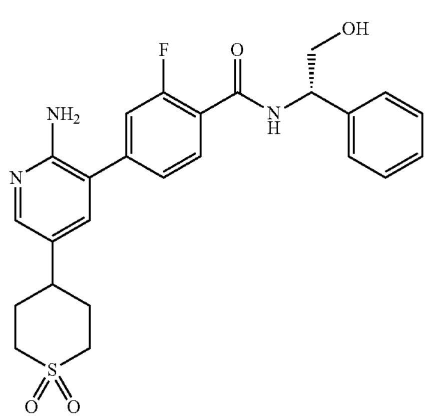 [SMILES: Nc1ncc(C2CCS(=O)(=O)CC2)cc1-c1ccc(C(=O)N[C@H](CO)c2ccccc2)c(F)c1] | (S)-4-(2-amino-5-(1,1-dioxidotetrahydro-2H-thiopyran-4-yl)pyridin-3-yl)-2-fluoro-N-(2-hydroxy-1-phenylethyl)benzamide | 484.1 | 0.5 | 1H NMR (400 MHz, CD$_3$OD) δ ppm 8.00-7.78 (m, 2H), 7.42 (m, 1H), 7.41-7.21 (m, 7H), 5.2 (m, 1H), 3.91-3.78 (m, 2H), 3.32 (m, 2H), 3.09 (m, 2H), 2.82 (m, 1H), 2.29-2.15 (m, 4H) |

TABLE 2-continued

Compounds prepared from Method 1 described above

| Example | Structure | Name | MH+ | R$_t$ (min) | NMR |
|---|---|---|---|---|---|
| 80 | 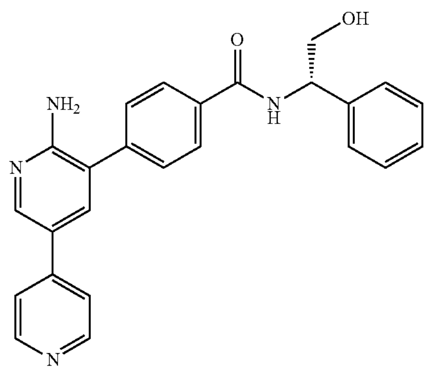 [SMILES: Nc1ncc(-c2ccncc2)cc1-c1ccc(C(=O)N[C@H](CO)c2ccccc2)cc1] | (S)-4-(6-amino-[3,4'-bipyridin]-5-yl)-N-(2-hydroxy-1-phenylethyl)benzamide | 411.3 | 0.43 | 1H NMR (400 MHz, CD$_3$OD) δ ppm 8.70 (d, J = 7.83 Hz, 1H), 8.61 (d, J = 6.65 Hz, 2H), 8.56 (d, J = 2.35 Hz, 1H), 8.11 (d, J = 6.65 Hz, 2H), 8.08 (d, J = 2.35 Hz, 1H), 7.96 (d, J = 8.22 Hz, 2H), 7.57 (d, J = 8.22 Hz, 2H), 7.30-7.36 (m, 2H), 7.26 (t, J = 7.43 Hz, 2H), 7.14-7.22 (m, 1H), 5.10-5.19 (m, 1H), 3.80 (d, J = 6.65 Hz, 2H) |
| 81 | 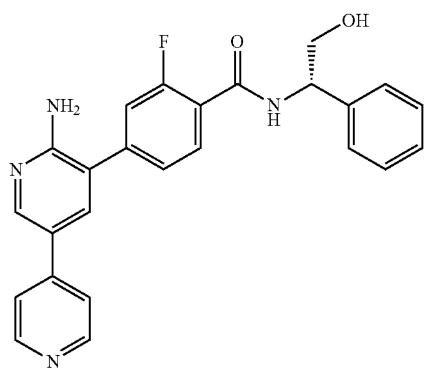 [SMILES: Nc1ncc(-c2ccncc2)cc1-c1ccc(C(=O)N[C@H](CO)c2ccccc2)c(F)c1] | (S)-4-(6-amino-[3,4'-bipyridin]-5-yl)-2-fluoro-N-(2-hydroxy-1-phenylethyl)benzamide | 429.3 | 0.45 | 1H NMR (400 MHz, CD$_3$OD) δ ppm 8.55-8.67 (m, 3H), 8.47-8.55 (m, 1H), 8.15 (d, J = 6.65 Hz, 2H), 8.07 (d, J = 2.35 Hz, 1H), 7.81 (t, J = 7.43 Hz, 1H), 7.31-7.42 (m, 4H), 7.27 (t, J = 7.63 Hz, 2H), 7.15-7.22 (m, 1H), 5.13 (t, J = 5.87 Hz, 1H), 3.70-3.85 (m, 2H) |
| 82 | 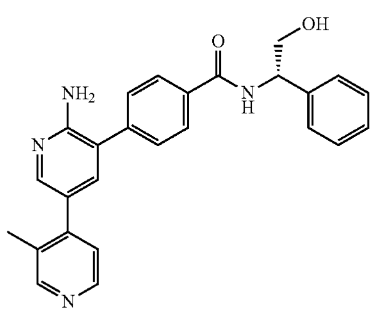 [SMILES: Cc1cnccc1-c1cnc(N)c(-c2ccc(C(=O)N[C@H](CO)c3ccccc3)cc2)c1] | (S)-4-(6-amino-3'-methyl-3,4'-bipyridin-5-yl)-N-(2-hydroxy-1-phenylethyl)benzamide | 425.1 | 0.44 | $^1$H NMR (400 MHz, DMSO-d6) δ ppm 8.78 (d, J = 7.8 Hz, 1H), 8.70 (s, 1H), 8.64 (d, J = 5.5 Hz, 1H), 8.24 (d, J = 2.0 Hz, 1H), 8.07 (d, J = 8.2 Hz, 2H), 7.75 (br. s., 2H), 7.64 (d, J = 8.2 Hz, 2H), 7.40 (d, J = 7.4 Hz, 2H), 7.33 (t, J = 7.6 Hz, 2H), 7.25 (d, J = 7.0 Hz, 1H), 5.11 (d, J = 5.5 Hz, 1H), 3.78-3.63 (m, 2H), 2.46 (s, 3H) |
| 83 | 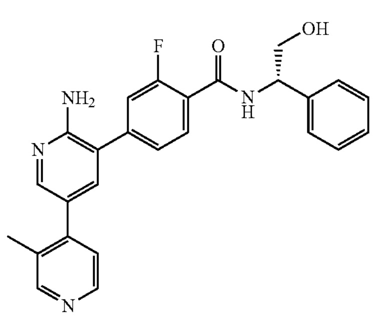 [SMILES: Cc1cnccc1-c1cnc(N)c(-c2ccc(C(=O)N[C@H](CO)c3ccccc3)c(F)c2)c1] | (S)-4-(6-amino-3'-methyl-3,4'-bipyridin-5-yl)-2-fluoro-N-(2-hydroxy-1-phenylethyl)benzamide | 443.3 | 0.44 | $^1$H NMR (300 MHz, DMSO-d6) δ ppm 8.68 (s, 1H), 8.62 (s, 2H), 8.23 (s, 1H), 7.83-7.66 (m, 2H), 7.55-7.21 (m, 7H), 5.06 (d, J = 7.3 Hz, 1H), 3.66 (d, J = 6.4 Hz, 2H), 2.44 (s, 3H) |

TABLE 2-continued

Compounds prepared from Method 1 described above

| Example | Structure | Name | MH+ | R$_t$ (min) | NMR |
|---|---|---|---|---|---|
| 84 | 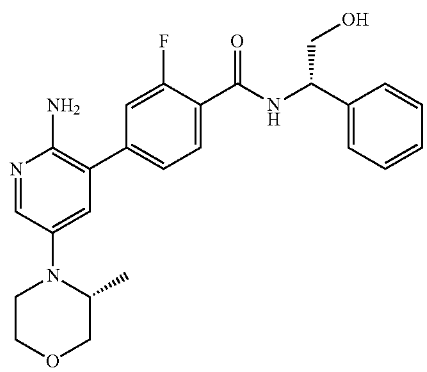 [SMILES: C[C@@H]1COCCN1c1cnc(N)c(-c2ccc(C(=O)N[C@H](CO)c3ccccc3)c(F)c2)c1] | 4-(2-amino-5-((R)-3-methylmorpholino)pyridin-3-yl)-2-fluoro-N-((S)-2-hydroxy-1-phenylethyl)benzamide | 451.3 | 0.58 | 1H NMR (400 MHz, CD$_3$OD) δ ppm 7.79-7.86 (m, 1H), 7.75 (d, J = 2.35 Hz, 1H), 7.31-7.44 (m, 6 H), 7.30 (d, J = 2.74 Hz, 1H), 7.27 (d, J = 7.43 Hz, 1H), 5.19 (t, J = 6.06 Hz, 1H), 3.72-3.90 (m, 4 H), 3.41-3.50 (m, 1H), 3.32-3.36 (m, 1H), 3.11 (t, J = 1.57 Hz, 1H), 2.96-3.02 (m, 2H), 0.91 (d, J = 6.65 Hz, 3H) |
| 85 | 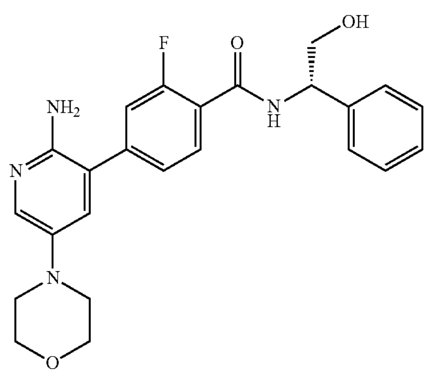 [SMILES: Nc1ncc(N2CCOCC2)cc1-c1ccc(C(=O)N[C@H](CO)c2ccccc2)c(F)c1] | (S)-4-(2-amino-5-morpholinopyridin-3-yl)-2-fluoro-N-(2-hydroxy-1-phenylethyl)benzamide | 419.3 | 0.54 | $^1$H NMR (400 MHz, CD$_3$OD) δ ppm 8.06 (d, J = 8.2 Hz, 2H) 7.87 (d, J = 2.7 Hz, 1H) 7.63 (d, J = 8.2 Hz, 2H) 7.24-7.48 (m, 6H) 5.19-5.30 (m, 1H) 3.90 (m, 2H)-3.85 (m, 4H) 3.12 (m, 4H) |
| 86 | 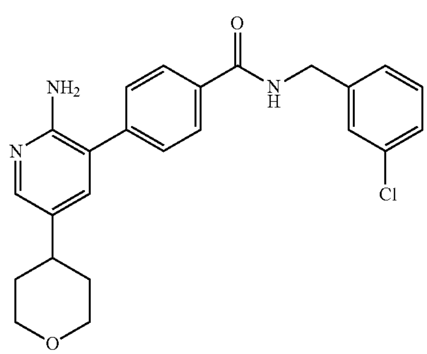 [SMILES: Nc1ncc(C2CCOCC2)cc1-c1ccc(C(=O)NCc2cccc(Cl)c2)cc1] | 4-(2-amino-5-(tetrahydro-2H-pyran-4-yl)pyridin-3-yl)-N-(3-chlorobenzyl)benzamide | 422.3 | 0.72 | 1H NMR (300 MHz, CD$_3$OD) δ ppm 8.04 (d, J = 8.20 Hz, 2H), 7.91 (d, J = 2.05 Hz, 1H) , 7.78 (d, J = 1.76 Hz, 1H), 7.61 (d, J = 8.20 Hz, 2H), 7.22-7.43 (m, 4H), 4.59 (s, 2H), 3.93-4.13 (m, 2 H), 3.54 (td, J = 11.43, 2.93 Hz, 2 H), 2.77-2.96 (m, 1H), 1.65-1.91 (m, 4H) |
| 87 | 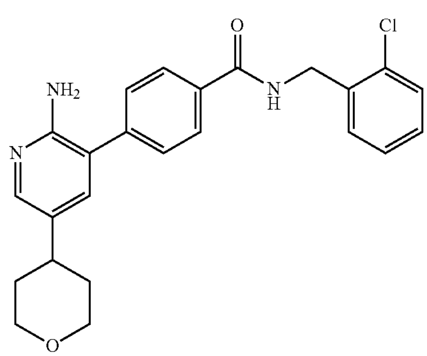 [SMILES: Nc1ncc(C2CCOCC2)cc1-c1ccc(C(=O)NCc2ccccc2Cl)cc1] | 4-(2-amino-5-(tetrahydro-2H-pyran-4-yl)pyridin-3-yl)-N-(2-chlorobenzyl)benzamide | 422.3 | 0.71 | 1H NMR (300 MHz, CD$_3$OD) δ ppm 7.95 (d, J = 8.20 Hz, 2H), 7.80 (d, J = 2.05 Hz, 1H), 7.69 (d, J = 1.76 Hz, 1H), 7.51 (d, J = 8.20 Hz, 2H), 7.28-7.38 (m, 2H), 7.13-7.26 (m, 2H), 4.61 (s, 2 H), 3.88-4.02 (m, 2H), 3.45 (td, J = 11.43, 2.93 Hz, 2H), 2.68-2.85 (m, 1H), 1.61-1.78 (m, 4 H) |

TABLE 2-continued

Compounds prepared from Method 1 described above

| Example | Structure | Name | MH+ | R$_t$ (min) | NMR |
|---|---|---|---|---|---|
| 88 | 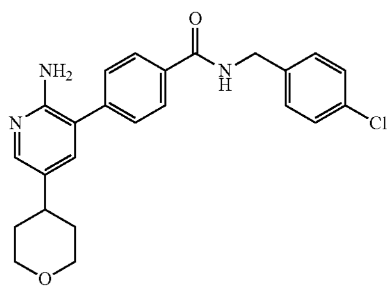 [SMILES: Nc1ncc(C2CCOCC2)cc1-c1ccc(C(=O)NCc2ccc(Cl)cc2)cc1] | 4-(2-amino-5-(tetrahydro-2H-pyran-4-yl)pyridin-3-yl)-N-(4-chlorobenzyl)benzamide | 422.3 | 0.71 | 1H NMR (300 MHz, CD$_3$OD) δ ppm 7.93 (d, J = 8.20 Hz, 2H), 7.81 (d, J = 2.05 Hz, 1H), 7.68 (d, J = 1.76 Hz, 1H), 7.51 (d, J = 8.50 Hz, 2H), 7.26 (d, J = 1.17 Hz, 4 H), 4.49 (s, 2H), 3.87-4.02 (m, 2H), 3.45 (td, J = 11.36, 2.78 Hz, 2H), 2.68-2.85 (m, 1H), 1.62-1.79 (m, 4H) |
| 89 | 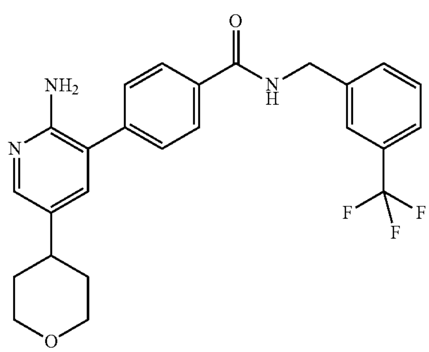 [SMILES: Nc1ncc(C2CCOCC2)cc1-c1ccc(C(=O)NCc2cccc(C(F)(F)F)c2)cc1] | 4-(2-amino-5-(tetrahydro-2H-pyran-4-yl)pyridin-3-yl)-N-(3-(trifluoromethyl)benzyl)benzamide | 456.3 | 0.74 | 1H NMR (300 MHz, CD$_3$OD) δ ppm 7.95 (d, J = 8.50 Hz, 2H), 7.82 (d, J = 2.05 Hz, 1H), 7.68 (d, J = 1.76 Hz, 1H), 7.40-7.61 (m, 6 H), 4.58 (s, 2H), 3.89-4.01 (m, 2H), 3.45 (td, J = 11.43, 2.93 Hz, 2H), 2.69-2.85 (m, 1H), 1.62-1.77 (m, 4H) |
| 90 | 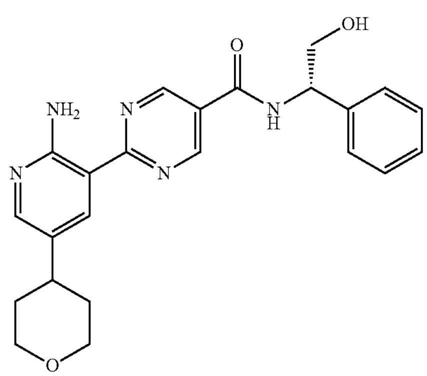 [SMILES: Nc1ncc(C2CCOCC2)cc1-c1ncc(C(=O)N[C@H](CO)c2ccccc2)cn1] | (S)-2-(2-amino-5-(tetrahydro-2H-pyran-4-yl)pyridin-3-yl)-N-(2-hydroxy-1-phenylethyl)pyrimidine-5-carboxamide | 420.3 | 0.56 | 1H NMR (300 MHz, CD$_3$OD) δ ppm 9.29-9.42 (m, 3H), 8.00 (d, J = 2.05 Hz, 1H), 7.21-7.52 (m, 5 H), 5.25 (t, J = 6.74 Hz, 1H), 3.98-4.16 (m, 2H), 3.81-3.96 (m, 2 H) 3.59 (td, J = 11.43, 2.93 Hz, 2 H), 2.85-3.05 (m, 1H), 1.76-1.91 (m, 4H) |
| 91 | 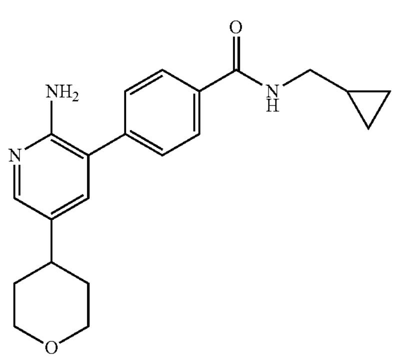 [SMILES: Nc1ncc(C2CCOCC2)cc1-c1ccc(C(=O)NCC2CC2)cc1] | 4-(2-amino-5-(tetrahydro-2H-pyran-4-yl)pyridin-3-yl)-N-(cyclopropylmethyl)benzamide | 352.2 | 0.56 | 1H NMR (400 MHz, CD$_3$OD) δ ppm 7.90 (d, J = 8.61 Hz, 2H), 7.82 (d, J = 1.96 Hz, 1H), 7.68 (d, J = 1.96 Hz, 1H), 7.50 (d, J = 8.22 Hz, 2H), 3.95 (dd, J = 10.96, 3.52 Hz, 2H), 3.45 (td, J = 11.64, 2.54 Hz, 2H), 3.18 (d, J = 7.43 Hz, 2 H), 2.71-2.84 (m, 1H), 1.58-1.78 (m, 4H), 0.96-1.10 (m, 1 H), 0.38-0.52 (m, 2H), 0.11-0.28 (m, 2H) |

TABLE 2-continued

Compounds prepared from Method 1 described above

| Example | Structure | Name | MH+ | R_t (min) | NMR |
|---|---|---|---|---|---|
| 92 | 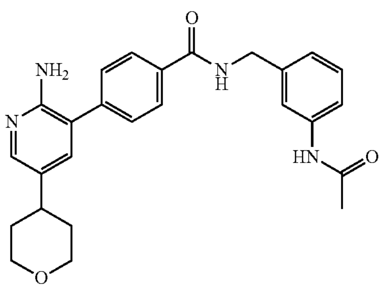 [SMILES: CC(=O)Nc1cccc(CNC(=O)c2ccc(-c3cc(C4CCOCC4)cnc3N)cc2)c1] | N-(3-acetamidobenzyl)-4-(2-amino-5-(tetrahydro-2H-pyran-4-yl)pyridin-3-yl)benzamide | 445.4 | 0.54 | 1H NMR (400 MHz, CD₃OD) δ ppm 8.02 (d, J = 8.22 Hz, 2H), 7.89 (d, J = 1.96 Hz, 1H), 7.76 (d, J = 1.57 Hz, 1H), 7.66 (s, 1 H), 7.58 (d, J = 8.61 Hz, 2H), 7.30-7.41 (m, 1H), 7.26 (t, J = 7.83 Hz, 1H), 7.06-7.13 (m, 1H), 4.53-4.63 (m, 2H), 4.02 (dd, J = 10.96, 3.52 Hz, 2H), 3.53 (td, J = 11.54, 2.35 Hz, 2H), 2.78-2.93 (m, 1H), 2.09 (s, 3H), 1.64-1.88 (m, 4H) |
| 93 | 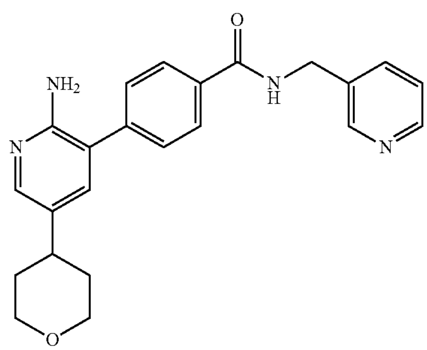 [SMILES: Nc1ncc(C2CCOCC2)cc1-c1ccc(C(=O)NCc2cccnc2)cc1] | 4-(2-amino-5-(tetrahydro-2H-pyran-4-yl)pyridin-3-yl)-N-(pyridin-3-ylmethyl)benzamide | 389.2 | 0.42 | 1H NMR (400 MHz, CD₃OD) δ ppm 8.71 (s, 1H), 8.59 (d, J = 5.09 Hz, 1H), 8.31 (d, J = 8.22 Hz, 1H), 7.95 (d, J = 8.22 Hz, 2 H), 7.74-7.86 (m, 2H), 7.69 (d, J = 1.96 Hz, 1H), 7.53 (d, J = 8.22 Hz, 2H), 4.59-4.68 (m, 2H), 3.94 (dd, J = 10.96, 3.52 Hz, 2H), 3.45 (td, J = 11.44, 2.54 Hz, 2 H), 2.70-2.84 (m, 1H), 1.58-1.80 (m, 4H) |
| 94 | 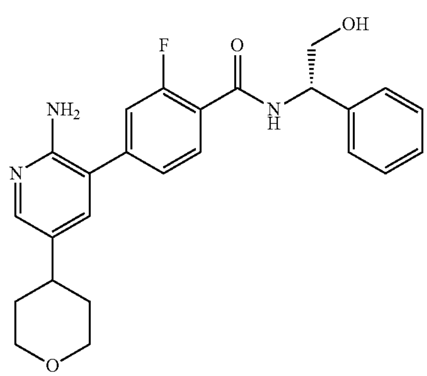 [SMILES: Nc1ncc(C2CCOCC2)cc1-c1ccc(C(=O)N[C@H](CO)c2ccccc2)c(F)c1] | (S)-4-(2-amino-5-(tetrahydro-2H-pyran-4-yl)pyridin-3-yl)-2-fluoro-N-(2-hydroxy-1-phenylethyl)benzamide | 436 | 0.58 | 1H NMR (400 MHz, CD₃OD) δ ppm 1.60-1.77 (m, 4H) 2.71-2.83 (m, 1H) 3.45 (td, J = 11.44, 2.54 Hz, 2H) 3.70-3.83 (m, 2H) 3.95 (dd, J = 11.35, 3.13 Hz, 2H) 5.09-5.17 (m, 1H) 7.15-7.22 (m, 1H) 7.27 (t, J = 7.43 Hz, 2H) 7.29-7.36 (m, 4H) 7.70 (d, J = 1.96 Hz, 1H) 7.80 (t, J = 8.02 Hz, 1H) 7.84 (d, J = 2.35 Hz, 1H). |
| 95 | 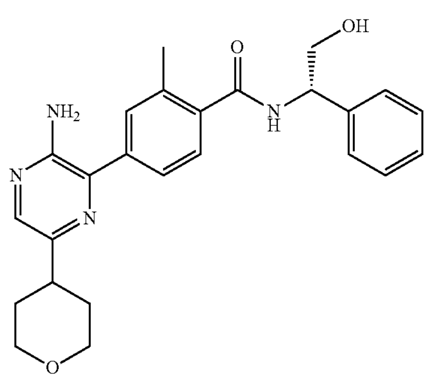 [SMILES: Cc1cc(-c2nc(C3CCOCC3)cnc2N)ccc1C(=O)N[C@H](CO)c1ccccc1] | (S)-4-(3-amino-6-(tetrahydro-2H-pyran-4-yl)pyrazin-2-yl)-N-(2-hydroxy-1-phenylethyl)-2-methylbenzamide | 433.2 | 0.59 | 1H NMR (400 MHz, DMSO-d6) δ ppm 8.59 (d, J = 8 Hz, 1H), 7.85 (s, 1H), 7.58-7.49 (m, 2H), 7.44 (d, J = 8 Hz, 1H), 7.39-7.27 (m, 4H), 7.25-7.18 (m, 1H), 5.02 (m, 1H), 3.93-3.87 (m, 2H), 3.64-3.57 (m, 2H), 3.43 (m, 2H, hidden behind DMSO), 2.81 (m, 1H), 2.33 (s, 3H), 1.74-1.66 (m, 4H). |

TABLE 2-continued

Compounds prepared from Method 1 described above

| Example | Structure | Name | MH+ | R$_t$ (min) | NMR |
|---|---|---|---|---|---|
| 96 | 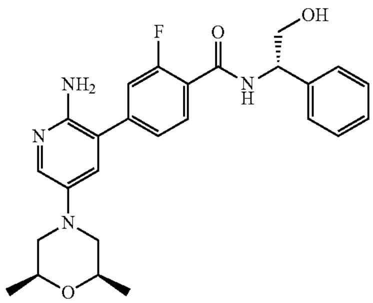 [SMILES: C[C@@H]1CN(c2cnc(N)c(-c3ccc(C(=O)N[C@H](CO)c4ccccc4)c(F)c3)c2)C[C@H](C)O1] | 4-(2-amino-5-((2S,6R)-2,6-dimethylmorpholino)pyridin-3-yl)-2-fluoro-N-((S)-2-hydroxy-1-phenylethyl)benzamide | 465.4 | 0.63 | 1H NMR (300 MHz, CD$_3$OD) δ ppm 7.83-7.95 (m, 2H), 7.24-7.51 (m, 8H), 5.22 (t, J = 6.01 Hz, 1H), 3.71-3.94 (m, 4H), 3.44 (d, J = 10.84 Hz, 2H), 2.34 (t, J = 10.99 Hz, 2H), 1.22 (d, J = 6.15 Hz, 6H) |
| 97 | 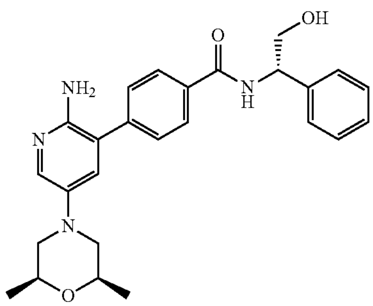 [SMILES: C[C@@H]1CN(c2cnc(N)c(-c3ccc(C(=O)N[C@H](CO)c4ccccc4)cc3)c2)C[C@H](C)O1] | 4-(2-amino-5-((2S,6R)-2,6-dimethylmorpholino)pyridin-3-yl)-N-((S)-2-hydroxy-1-phenylethyl)benzamide | 447.6 | 0.61 | 1H NMR (300 MHz, CD$_3$OD) δ ppm 8.23 (d, J = 7.33 Hz, 2H), 8.06 (br. s., 1H), 7.79 (d, J = 7.62 Hz, 2H), 7.41-7.68 (m, 6H), 5.41 (br. s., 1H), 3.87-4.18 (m, 4H), 3.62 (d, J = 12.31 Hz, 2H), 2.52 (t, J = 10.70 Hz, 2H), 1.31-1.52 (m, 6H) |
| 98 | 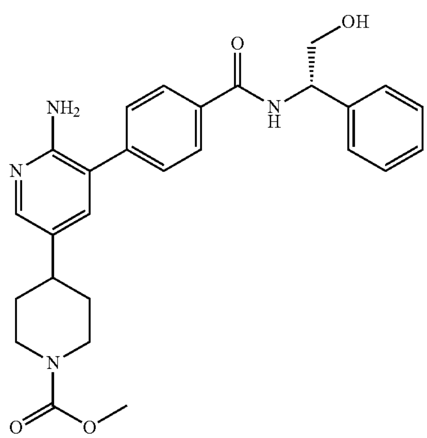 [SMILES: COC(=O)N1CCC(c2cnc(N)c(-c3ccc(C(=O)N[C@H](CO)c4ccccc4)cc3)c2)CC1] | (S)-methyl 4-(6-amino-5-(4-((2-hydroxy-1-phenylethyl)carbamoyl)phenyl)pyridin-3-yl)piperidine-1-carboxylate | 475.2 | 0.60 | 1H NMR (300 MHz, CD$_3$OD) δ ppm 7.98-8.12 (m, 2H), 7.91 (d, J = 1.76 Hz, 1H), 7.53-7.66 (m, 2H) 7.78 (s, 1H), 7.21-7.48 (m, 5H), 5.24 (d, J = 6.74 Hz, 1 H), 4.26 (d, J = 12.89 Hz, 2H), 3.89 (d, J = 6.74 Hz, 2H), 3.69 (d, J = 1.76 Hz, 3H), 2.73-3.03 (m, 3 H), 1.90 (d, J = 12.60 Hz, 2H), 1.51-1.72 (m, 2H) |
| 99 | 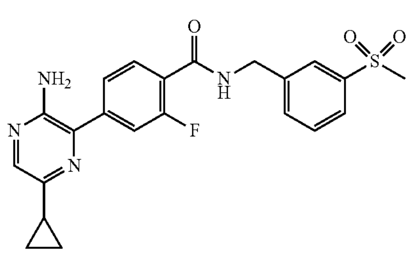 [SMILES: CS(=O)(=O)c1cccc(CNC(=O)c2ccc(-c3nc(C4CC4)cnc3N)cc2F)c1] | 4-(3-amino-6-cyclopropylpyrazin-2-yl)-2-fluoro-N-(3-(methylsulfonyl)benzyl)benzamide | 441.2 | 0.69 | 1H NMR (400 MHz, CD$_3$OD) δ ppm 8.00 (s, 1H), 7.82-7.91 (m, 3H), 7.76 (d, J = 7.8 Hz, 1H), 7.63-7.69 (m, 2H), 7.59 (dd, J = 11.5, 1.4 Hz, 1H), 4.72 (s, 2H), 3.12 (s, 3H), 2.06 (tt, J = 7.9, 5.0 Hz, 1H), 0.84-1.02 (m, 4H) |

TABLE 2-continued

Compounds prepared from Method 1 described above

| Example | Structure | Name | MH+ | R$_t$ (min) | NMR |
|---|---|---|---|---|---|
| 100 | 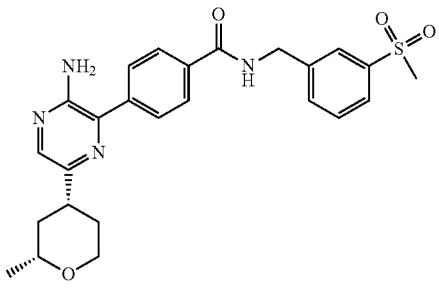 [SMILES: C[C@@H]1C[C@H](c2cnc(N)c(-c3ccc(C(=O)NCc4cccc(S(C)(=O)=O)c4)cc3)n2)CCO1] | 4-(3-amino-6-((2R,4R)-2-methyltetrahydro-2H-pyran-4-yl)pyrazin-2-yl)-N-(3-(methylsulfonyl)benzyl)benzamide | 481.2 | 0.64 | 1H NMR (400 MHz, CD$_3$OD) δ ppm 7.94-8.01 (m, 3H) 7.81-7.89 (m, 4H) 7.73 (d, J = 7.83 Hz, 1H) 7.58-7.65 (m, 1H) 4.69 (s, 2H) 4.00-4.09 (m, 1H) 3.53-3.65 (m, 2H) 3.10 (s, 3H) 2.87-2.98 (m, 1H) 1.74-1.92 (m, 3H) 1.44-1.56 (m, 1H) 1.24-1.39 (m, 1H) 1.19 (d, J = 6.26 Hz, 3H) |
| 101 | 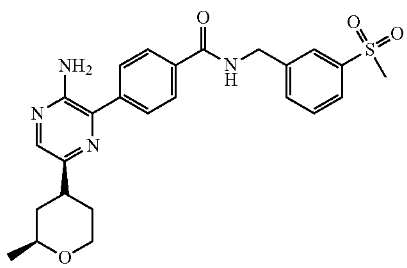 | 4-(3-amino-6-((2S,4S)-2-methyltetrahydro-2H-pyran-4-yl)pyrazin-2-yl)-N-(3-(methylsulfonyl)benzyl)benzamide | 481.2 | 0.65 | 1H NMR (400 MHz, DMSO-d6) δ 9.23 (t, J = 5.87 Hz, 1H) 7.99 (d, J = 8.22 Hz, 2H) 7.76-7.90 (m, 5 H) 7.57-7.69 (m, 2H) 4.59 (d, J = 5.87 Hz, 2H) 3.39-3.50 (m, 2 H) 3.18 (s, 3H) 2.79-2.91 (m, 1 H) 1.58-1.84 (m, 3H) 1.29-1.43 (m, 1H) 1.09 (d, J = 6.26 Hz, 3H) |
| 102 | 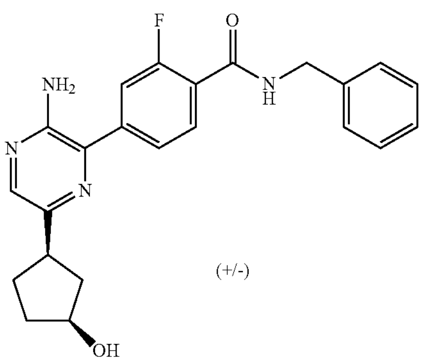 [SMILES: Nc1ncc([C@@H]2CC[C@H](O)C2)nc1-c1ccc(C(=O)NCc2ccccc2)c(F)c1] | (+/−)-4-(3-amino-6-((1R,3S)-3-hydroxycyclopentyl)pyrazin-2-yl)-N-benzyl-2-fluorobenzamide | 407.3 | 0.71 | 1H NMR (400 MHz, CD$_3$OD) δ ppm 7.91 (s, 1H), 7.87 (t, J = 7.6 Hz, 1H), 7.68 (dd, J = 1.6, 8.2 Hz, 1H), 7.64-7.56 (m, 1H), 7.44-7.31 (m, 4H), 7.28 (d, J = 7.0 Hz, 1H), 4.62 (s, 2H), 4.39-4.31 (m, 1H), 2.34 (ddd, J = 5.9, 8.6, 13.7 Hz, 1H), 2.10 (dd, J = 4.5, 8.0 Hz, 1H), 1.99-1.75 (m, 4H) |
| 103 | 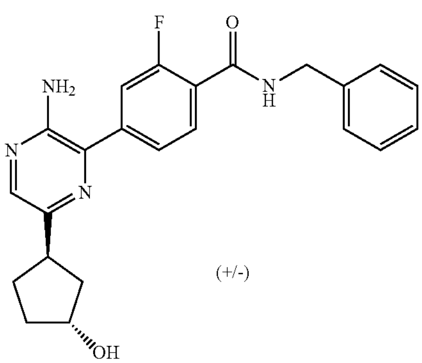 [SMILES: Nc1ncc([C@@H]2CC[C@@H](O)C2)nc1-c1ccc(C(=O)NCc2ccccc2)c(F)c1] | (+/−)-4-(3-amino-6-((1R,3R)-3-hydroxycyclopentyl)pyrazin-2-yl)-N-benzyl-2-fluorobenzamide | 407.3 | 0.69 | $^1$H NMR (400 MHz, CD$_3$OD) δ ppm 7.91 (s, 1H), 7.87 (t, J = 7.6 Hz, 1H), 7.68 (dd, J = 1.6, 8.2 Hz, 1H), 7.64-7.56 (m, 1H), 7.44-7.31 (m, 4H), 7.28 (d, J = 7.0 Hz, 1H), 4.62 (s, 2H), 4.39-4.31 (m, 1H), 2.34 (ddd, J = 5.9, 8.6, 13.7 Hz, 1H), 2.10 (dd, J = 4.5, 8.0 Hz, 1H), 1.99-1.75 (m, 4H) |

TABLE 2-continued

Compounds prepared from Method 1 described above

| Example | Structure | Name | MH+ | R_t (min) | NMR |
|---|---|---|---|---|---|
| 104 | (+/−) cis/trans mixture | 4-(3-amino-6-(3-methoxycyclopentyl)pyrazin-2-yl)-N-benzyl-2-fluorobenzamide | 421.3 | 0.84 | 1H NMR (400 MHz, CDCl$_3$) δ ppm 8.25 (t, J = 8.2 Hz, 1H), 7.98 (s, 1H), 7.92 (s, 1H), 7.77-7.71 (m, 2H), 7.57 (d, J = 7.8 Hz, 1H), 7.60 (d, J = 8.2 Hz, 1H), 7.38 (br. s., 2H), 7.37 (br. s., 3H), 7.34-7.28 (m, 2H), 7.13-7.04 (m, 2H), 4.72 (d, J = 5.5 Hz, 3H), 4.63 (br. s., 3H), 4.02-3.97 (m, 1H), 3.97-3.91 (m, 1H), 3.37 (d, J = 8.2 Hz, 1H), 3.33 (s, 3H), 3.32 (s, 2H), 3.16 (t, J = 8.8 Hz, 1H), 2.47-2.36 (m, 1H), 2.20-2.10 (m, 2H), 2.10-2.01 (m, 1H), 2.01-1.94 (m, 1H), 1.94-1.85 (m, 3H), 1.81-1.73 (m, 1H) |
| 105 | 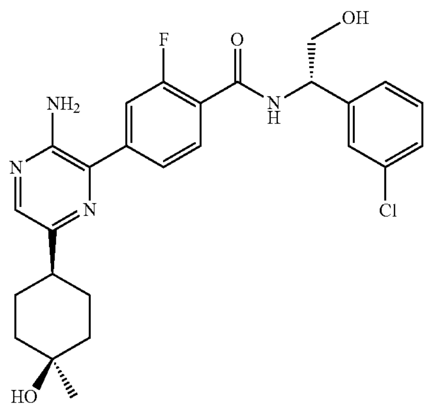 [SMILES: C[C@]1(O)CC[C@@H](c2cnc(N)c(-c3ccc(C(=O)N[C@H](CO)c4cccc(Cl)c4)c(F)c3)n2)CC1] | 4-(3-amino-6-((1s,4R)-4-hydroxy-4-methylcyclohexyl)pyrazin-2-yl)-N-((S)-1-(3-chlorophenyl)-2-hydroxyethyl)-2-fluorobenzamide | 499.2 | 0.76 | 1H NMR (500 MHz, METHANOL-d4)) δ ppm 7.91-7.84 (m, 2H) 7.71 (dd, J = 8.04, 0.79 Hz, 1H) 7.66 (d, J = 11.35 Hz, 1H) 7.49 (s, 1H) 7.42-7.35 (m, 2H) 7.34-7.28 (m, 1H) 5.26-5.18 (m, 1H) 3.88 (dd, J = 8.67, 6.15 Hz, 2H) 2.71-2.61 (m, 1H) 2.06-1.95 (m, 2H) 1.85-1.73 (m, 4H) 1.63-1.52 (m, 2H) 1.26 (s, 3H). |
| 106 | 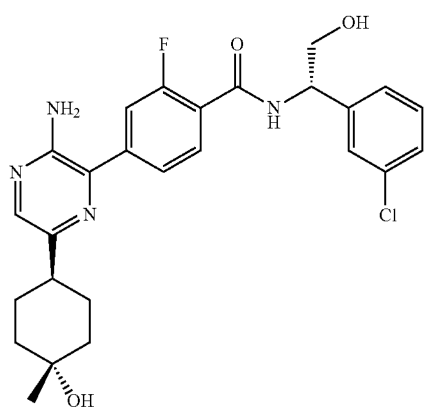 [SMILES: C[C@]1(O)CC[C@H](c2cnc(N)c(-c3ccc(C(=O)N[C@H](CO)c4cccc(Cl)c4)c(F)c3)n2)CC1] | 4-(3-amino-6-((1r,4S)-4-hydroxy-4-methylcyclohexyl)pyrazin-2-yl)-N-((S)-1-(3-chlorophenyl)-2-hydroxyethyl)-2-fluorobenzamide | 499.1 | 0.71 | 1H NMR (500 MHz, METHANOL-d4)) δ ppm 7.93-7.85 (m, 2H) 7.70 (dd, J = 8.04, 1.42 Hz, 1H) 7.65 (d, J = 11.66 Hz, 1H) 7.49 (s, 1H) 7.42-7.35 (m, 2H) 7.34-7.29 (m, 1H) 5.26-5.18 (m, 1H) 3.95-3.81 (m, 2H) 2.78-2.69 (m, 1H) 2.00-1.90 (m, 2H) 1.85-1.72 (m, 4H) 1.70-1.61 (m, 2H) 1.31 (s, 3H) |
| 107 | 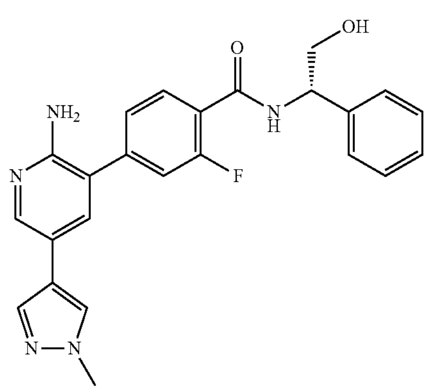 [SMILES: Cn1cc(-c2cnc(N)c(-c3ccc(C(=O)N[C@H](CO)c4ccccc4)c(F)c3)c2)cn1] | (S)-4-(2-amino-5-(1-methyl-1H-pyrazol-4-yl)pyridin-3-yl)-2-fluoro-N-(2-hydroxy-1-phenylethyl)benzamide | 432.2 | 0.58 | 1H NMR (400 MHz, CD$_3$OD) δ ppm 8.18 (d, J = 2.3 Hz, 1H), 7.98 (s, 1H), 7.85-7.93 (m, 2H), 7.83 (s, 1H), 7.40-7.48 (m, 4H), 7.37 (t, J = 7.4 Hz, 2H), 7.24-7.32 (m, 1H), 5.22 (t, J = 6.1 Hz, 1H), 3.92 (s, 3H), 3.81-3.91 (m, 2H) |

TABLE 2-continued

Compounds prepared from Method 1 described above

| Example | Structure | Name | MH+ | R_t (min) | NMR |
|---|---|---|---|---|---|
| 108 | 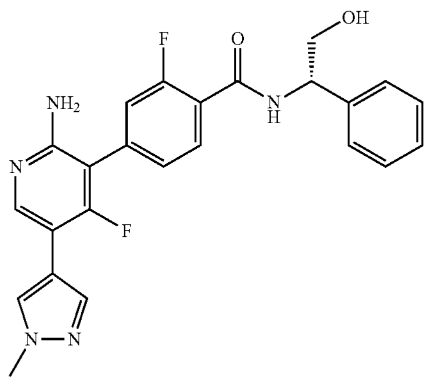 [SMILES: Cn1cc(-c2cnc(N)c(-c3ccc(C(=O)N[C@H](CO)c4ccccc4)c(F)c3)c2F)cn1] | (S)-4-(2-amino-4-fluoro-5-(1-methyl-1H-pyrazol-4-yl)pyridin-3-yl)-2-fluoro-N-(2-hydroxy-1-phenylethyl)benzamide | 323.4 | 0.60 | $^1$H NMR (400 MHz, MeOD-d4) δ ppm 8.22 (d, J = 7.83 Hz, 1H) 7.91 (d, J = 1.96 Hz, 1H) 7.86-7.72 (m, 2H) 7.38-7.26 (m, 6H) 7.20 (d, J = 7.43 Hz, 1H) 5.13 (t, J = 6.06 Hz, 1H) 3.85 (s, 3H) 3.82-3.69 (m, 2H) |
| 109 | 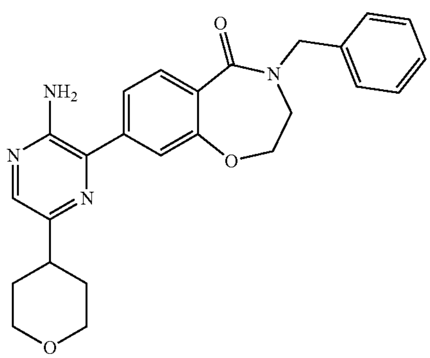 [SMILES: Nc1ncc(C2CCOCC2)nc1-c1ccc2c(c1)OCCN(Cc1ccccc1)C2=O] | 4-benzyl-8-(4,4,5,5-tetramethyl-1,3,2-dioxaborolan-2-yl)-3,4-dihydrobenzo[f][1,4]oxazepin-5(2H)-one, 8-(3-amino-6-(tetrahydro-2H-pyran-4-yl)pyrazin-2-yl)-4-benzyl-3,4-dihydrobenzo[f][1,4]oxazepin-5(2H)-one | 431.3 | 0.73 | $^1$H NMR (400 MHz, DMSO-d6) δ ppm 7.91 (s, 1H), 7.81 (d, J = 8.1 Hz, 1H), 7.55 (dd, J = 1.7, 8.1 Hz, 1H), 7.44-7.25 (m, 6H), 4.79 (s, 2H), 4.27 (t, J = 5.1 Hz, 2H), 3.94 (td, J = 3.1, 11.0 Hz, 2H), 3.57 (t, J = 5.1 Hz, 2H), 3.50-3.35 (m, 2H), 2.86 (s, 1H), 1.82-1.67 (m, 4H) |
| 110 | 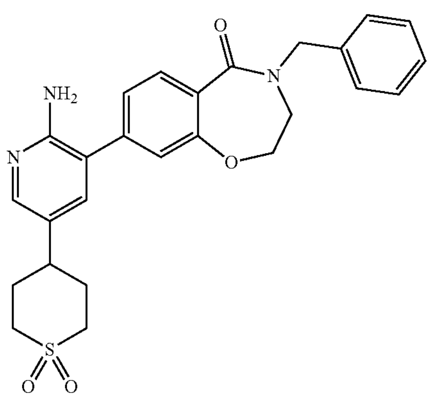 [SMILES: Nc1ncc(C2CCS(=O)(=O)CC2)cc1-c1ccc2c(c1)OCCN(Cc1ccccc1)C2=O] | 8-(2-amino-5-(1,1-dioxidotetrahydro-2H-thiopyran-4-yl)pyridin-3-yl)-4-benzyl-3,4-dihydrobenzo[f][1,4]oxazepin-5(2H)-one | 478.1 | 0.61 | $^1$H NMR (400 MHz, DMSO-d6) δ ppm 7.91 (d, J = 2.0 Hz, 1H), 7.86 (d, J = 7.9 Hz, 2H), 7.43-7.26 (m, 6H), 7.18 (d, J = 1.7 Hz, 1H), 4.80 (s, 2H), 4.27 (t, J = 5.0 Hz, 2H), 3.58 (t, J = 5.0 Hz, 2H), 3.34-3.22 (m, 2H), 3.19-3.07 (m, 2H), 2.94 (s, 1H), 2.21-2.07 (m, 4H) |
| 111 | 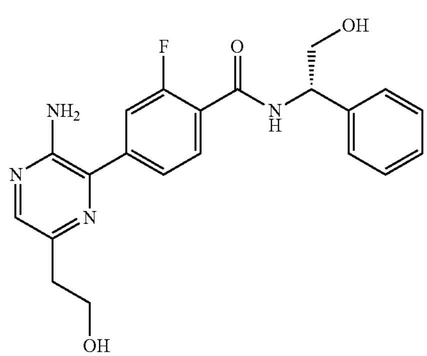 [SMILES: Nc1ncc(CCO)nc1-c1ccc(C(=O)N[C@H](CO)c2ccccc2)c(F)c1] | (S)-4-(3-amino-6-(2-hydroxyethyl)pyrazin-2-yl)-2-fluoro-N-(2-hydroxy-1-phenylethyl)benzamide | 397.2 | 0.53 | 1H NMR (400 MHz, CD$_3$OD) δ ppm 7.89 (s, 1H), 7.84 (t, J = 7.8 Hz, 1H), 7.64 (dd, J = 1.6, 7.8 Hz, 1H), 7.58 (dd, J = 1.2, 11.7 Hz, 1H), 7.44-7.31 (m, 4H), 7.27 (d, J = 7.0 Hz, 1H), 5.20 (s, 1H), 3.90-3.79 (m, 4H), 2.87 (t, J = 6.5 Hz, 2H). |

TABLE 2-continued

Compounds prepared from Method 1 described above

| Example | Structure | Name | MH+ | R$_t$ (min) | NMR |
|---|---|---|---|---|---|
| 112 | 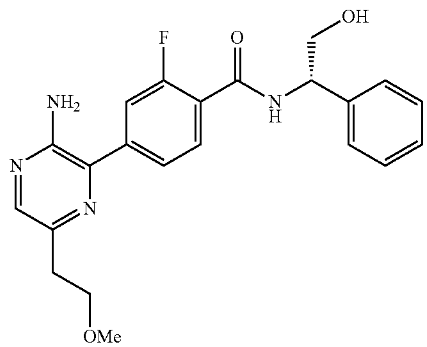 [SMILES: COCCc1cnc(N)c(-c2ccc(C(=O)N[C@H](CO)c3ccccc3)c(F)c2)n1] | (S)-4-(3-amino-6-(2-methoxyethyl)pyrazin-2-yl)-2-fluoro-N-(2-hydroxy-1-phenylethyl)benzamide | 411.3 | 0.62 | 1H NMR (400 MHz, CD$_3$OD) δ ppm 7.89 (s, 1H), 7.84 (t, J = 7.8 Hz, 1H), 7.64 (dd, J = 1.6, 7.8 Hz, 1H), 7.61-7.55 (m, 1H), 7.44-7.39 (m, 2H), 7.34 (t, J = 7.6 Hz, 2H), 7.27 (d, J = 7.4 Hz, 1H), 5.19 (d, J = 6.3 Hz, 1H), 3.87-3.82 (m, 2H), 3.70 (t, J = 6.5 Hz, 2H), 3.32 (s, 3H), 2.92 (t, J = 6.5 Hz, 2H). |
| 113 | 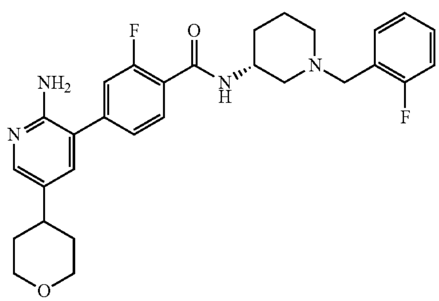 | (R)-4-(2-amino-5-(tetrahydro-2H-pyran-4-yl)pyridin-3-yl)-2-fluoro-N-(1-(2-fluorobenzyl)piperidin-3-yl)benzamide | 507.3 | 0.52 | 1H NMR (400 MHz, CD$_3$OD) δ ppm 7.92-7.87 (m, 1H), 7.86-7.76 (m, 2H), 7.64-7.51 (m, 2 H), 7.45-7.37 (m, 1H), 7.37-7.23 (m, 2H), 4.54-4.40 (m, 3 H), 4.09-3.95 (m, 2H), 3.59-3.44 (m, 2H), 2.92-2.78 (m, 1 H), 2.64 (s, 1H), 2.20-1.98 (m, 3H), 1.99-1.52 (m, 8H). |
| 114 | 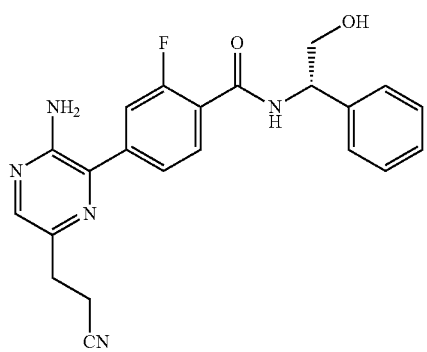 | (S)-4-(3-amino-6-(2-cyanoethyl)pyrazin-2-yl)-2-fluoro-N-(2-hydroxy-1-phenylethyl)benzamide | 406.3 | 0.63 | $^1$H NMR (400 MHz, CD$_3$OD) δ ppm 7.94 (s, 1H), 7.84 (t, J = 7.8 Hz, 1H), 7.69 (d, J = 8.2 Hz, 1 H), 7.63 (d, J = 12.1 Hz, 1H), 7.43-7.38 (m, 2H), 7.34 (t, J = 7.6 Hz, 2H), 7.27 (d, J = 7.4 Hz, 1H), 5.22-5.16 (m, 1H), 3.89-3.79 (m, 2H), 3.01 (t, J = 7.0 Hz, 2H), 2.84 (t, J = 7.2 Hz, 2H) |
| 115 | 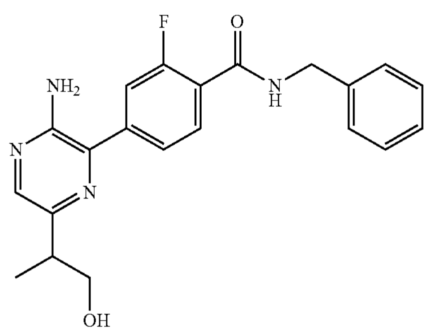 [SMILES: CC(CO)c1cnc(N)c(-c2ccc(C(=O)NCc3ccccc3)c(F)c2)n1] | (+/−)-4-(3-amino-6-(1-hydroxypropan-2-yl)pyrazin-2-yl)-N-benzyl-2-fluorobenzamide | 381.2 | 0.67 | 1H NMR (400 MHz, CD$_3$OD) δ ppm 7.90-7.77 (m, 2H), 7.67 (dd, J = 1.6, 8.2 Hz, 1H), 7.59 (dd, J = 1.4, 11.9 Hz, 1H), 7.40-7.29 (m, 4H), 7.28-7.21 (m, 1 H), 4.60 (s, 2H), 3.76 (dd, J = 7.4, 10.6 Hz, 1H), 3.67 (dd, J = 5.9, 10.6 Hz, 1H), 3.02-2.93 (m, 1H), 1.25 (d, J = 7.0 Hz, 3H) |

TABLE 2-continued

Compounds prepared from Method 1 described above

| Example | Structure | Name | MH+ | R$_t$ (min) | NMR |
|---|---|---|---|---|---|
| 116 | 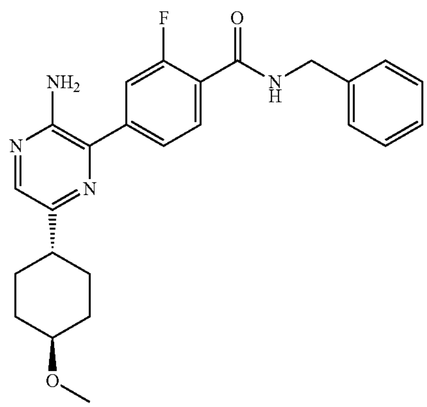 [SMILES: CO[C@H]1CC[C@H](c2cnc(N)c(-c3ccc(C(=O)NCc4ccccc4)c(F)c3)n2)CC1] | 4-(3-amino-6-((1r,4r)-4-methoxycyclohexyl)pyrazin-2-yl)-N-benzyl-2-fluorobenzamide | 435.2 | 0.85 | 1H NMR (400 MHz, CD$_3$OD) δ ppm 7.92-7.79 (m, 2H) 7.66 (dd, J = 8.02, 1.37 Hz, 1H) 7.59 (dd, J = 11.54, 1.37 Hz, 1H) 7.43-7.30 (m, 4H) 7.30-7.22 (m, 1H) 4.61 (s, 2H) 3.40-3.35 (m, 3H) 3.26 (t, J = 3.91 Hz, 1H) 2.74-2.61 (m, 1H) 2.20 (d, J = 9.39 Hz, 2H) 1.99 (d, J = 12.91 Hz, 2H) 1.65 (qd, J = 13.04, 3.13 Hz, 2H) 1.41-1.25 (m, 2H) |
| 117 | 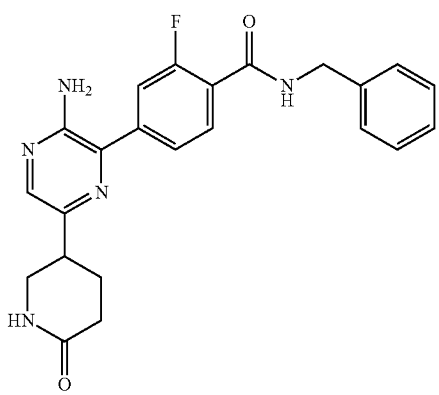 [SMILES: Nc1ncc(C2CCC(=O)NC2)nc1-c1ccc(C(=O)NCc2ccccc2)c(F)c1] | (+/−)-4-(3-amino-6-(6-oxopiperidin-3-yl)pyrazin-2-yl)-N-benzyl-2-fluorobenzamide | 420.2 | 0.61 | $^1$H NMR (400 MHz, CD$_3$OD) δ ppm 7.95 (s, 1H), 7.86 (t, J = 7.6 Hz, 1H), 7.69 (dd, J = 8.0, 1.4 Hz, 1H), 7.61 (dd, J = 11.7, 1.2 Hz, 1H), 7.31-7.45 (m, 4H), 7.22-7.30 (m, 1H), 4.62 (s, 2H), 3.53 (d, J = 7.8 Hz, 2H), 3.47 (q, J = 7.4 Hz, 1H), 3.15-3.26 (m, 1H), 2.40-2.57 (m, 2H), 2.06-2.24 (m, 2H), 1.36 (t, J = 7.2 Hz, 1H) |
| 118 | 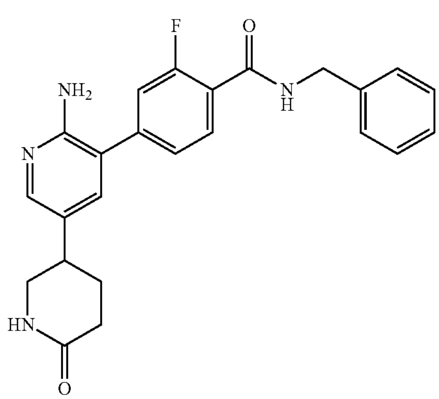 [SMILES: Nc1ncc(C2CCC(=O)NC2)cc1-c1ccc(C(=O)NCc2ccccc2)c(F)c1] | (+/−)-4-(2-amino-5-(6-oxopiperidin-3-yl)pyridin-3-yl)-N-benzyl-2-fluorobenzamide | 419.3 | 0.55 | 1H NMR (400 MHz, CD$_3$OD) δ ppm 8.88-8.77 (m, 1H), 8.03-7.95 (m, 2H), 7.92-7.83 (m, 4H), 7.48-7.30 (m, 2H), 7.28-7.21 (m, 1H), 4.69-4.54 (m, 2H), 3.56-3.42 (m, 1H), 3.20-3.05 (m, 1H), 2.55-2.39 (m, 2H), 2.16-1.99 (m, 2H) |

TABLE 2-continued

Compounds prepared from Method 1 described above

| Example | Structure | Name | MH+ | R$_t$ (min) | NMR |
|---|---|---|---|---|---|
| 119 | 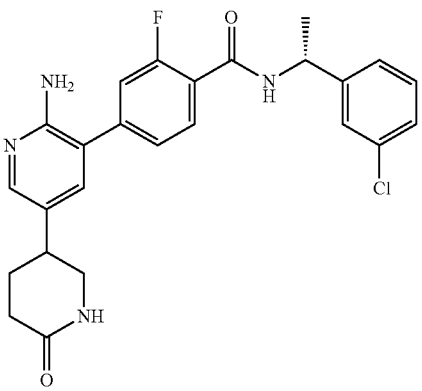 diastereomeric mixture | 4-(2-amino-5-(6-oxopiperidin-3-yl)pyridin-3-yl)-N-((R)-1-(3-chlorophenyl)ethyl)-2-fluorobenzamide | 467.3 | 0.66 | 1H NMR (400 MHz, CD$_3$OD) δ ppm 7.97 (m, 1H), 7.89 (m, 1H), 7.80 (m, 1H), 7.50-7.30 (m, 6H), 7.29-7.16 (m, 1H). 5.31-5.16 (m, 1H), 3.59-3.34 (m, 2H), 3.21-3.05 (m, 1H), 2.59-2.38 (m, 2H), 2.19-2.01 (m, 2H), 1.57 (m, 3H). |
| 120 | 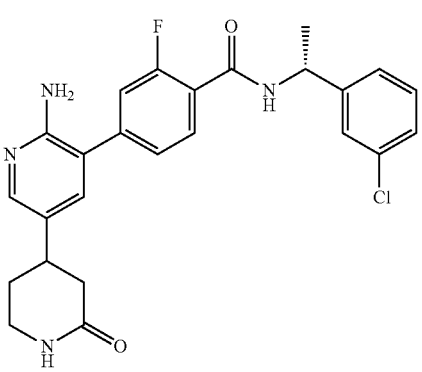 diastereomeric mixture | 4-(2-amino-5-(2-oxopiperidin-4-yl)pyridin-3-yl)-N-((R)-1-(3-chlorophenyl)ethyl)-2-fluorobenzamide | 467.2 | 0.66 | 1H NMR (400 MHz, CD$_3$OD) δ ppm 7.94 (m, 1H), 7.87-7.74 (m, 2H), 7.35 (s, 6H), 5.24 (m, 1H), 2.67-2.4 (m, 2H). 2.1-1.94 (m, 2H), 1.57 (m, 3H), 1.26 (m, 2H). |
| 121 | 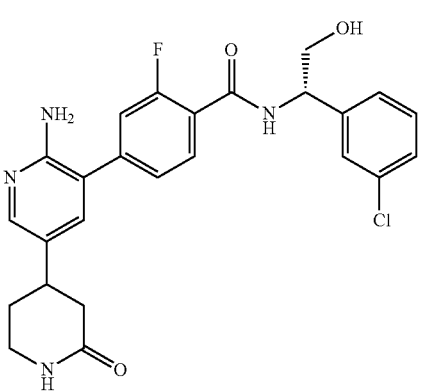 diastereomeric mixture | 4-(2-amino-5-(2-oxopiperidin-4-yl)pyridin-3-yl)-N-((S)-1-(3-chlorophenyl)-2-hydroxyethyl)-2-fluorobenzamide | 483.2 | 0.56 | 1H NMR (400 MHz, CD$_3$OD) δ ppm 7.89-7.69 (m, 2H), 7.27 (s, 7H), 5.17-5.01 (m, 1H), 3.87-3.64 (m, 2H), 3.44-3.31 (m, 3H), 2.62-2.24 (m, 2H), 2.12-1.74 (m, 2H). |

TABLE 2-continued

Compounds prepared from Method 1 described above

| Example | Structure | Name | MH+ | R_t (min) | NMR |
|---|---|---|---|---|---|
| 122 | 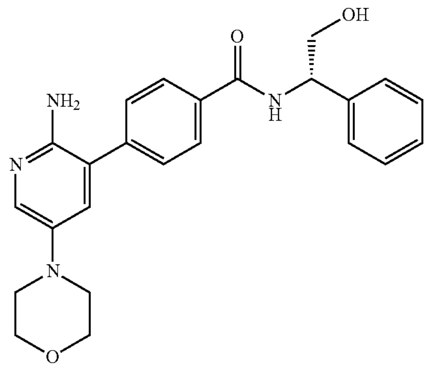 [SMILES: Nc1ncc(N2CCOCC2)cc1-c1ccc(C(=O)N[C@H](CO)c2ccccc2)cc1] | (S)-4-(2-amino-5-morpholinopyridin-3-yl)-N-(2-hydroxy-1-phenylethyl)benzamide | 419.3 | 0.54 | 1H NMR (400 MHz, CD$_3$OD) δ ppm 8.06 (d, J = 8.2 Hz, 2H) 7.87 (d, J = 2.7 Hz, 1H) 7.63 (d, J = 8.2 Hz, 2H) 7.24-7.48 (m, 6H) 5.19-5.30 (m, 1H) 3.90 (m, 2H)-3.85 (m, 4H) 3.12 (m, 4H) |
| 123 | diastereomeric mixture; cis on cyclohexane ring | cis-4-(3-amino-6-(3-methoxycyclohexyl)pyrazin-2-yl)-N-((S)-1-(3-chlorophenyl)-2-hydroxyethyl)-2-fluorobenzamide | 499.2 | 0.82 | 1H NMR (400 MHz, MeOD-d4) δ ppm 7.99-7.78 (m, 2H) 7.72-7.52 (m, 2H) 7.46 (s, 1H) 7.41-7.17 (m, 3H) 5.24-5.08 (m, 1H) 3.86 (t, J = 6.06 Hz, 2H) 3.43 (m, 1H) 3.38 (s, 3H) 2.75 (ddd, J = 12.03, 8.71, 3.52 Hz, 1H) 2.40-2.02 (m, 2H) 1.99-1.74 (m, 2H) 1.59-1.37 (m, 3H) 1.18 (dd, J = 11.35, 3.13 Hz, 1H) |
| 124 | 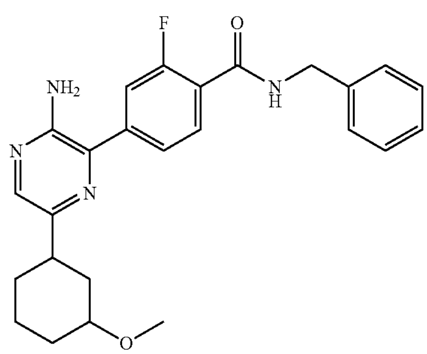 [SMILES: COC1CCCC(c2cnc(N)c(-c3ccc(C(=O)NCc4ccccc4)c(F)c3)n2)C1] | (+/-)-cis-4-(3-amino-6-(3-methoxycyclohexyl)pyrazin-2-yl)-N-benzyl-2-fluorobenzamide | 435.2 | 0.85 | 1H NMR (400 MHz, MeOD-d4) δ ppm 8.00-7.79 (m, 2H) 7.74-7.52 (m, 2H) 7.43-7.31 (m, 4H) 7.30-7.22 (m, 1H) 4.61 (s, 2H) 3.37 (s, 3H) 2.73 (t, J = 3.33 Hz, 1H) 2.27 (d, J = 11.74 Hz, 1H) 2.14 (d, J = 12.13 Hz, 1H) 1.99-1.82 (m, 2H) 1.52-1.39 (m, 3H) 1.24-1.10 (m, 1H) |
| 125 | 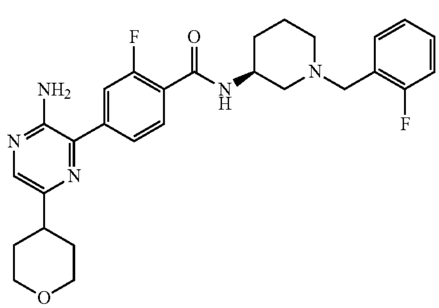 [SMILES: Nc1ncc(C2CCOCC2)nc1-c1ccc(C(=O)N[C@H]2CCCN(Cc3ccccc3F)C2)c(F)c1] | (S)-4-(3-amino-6-(tetrahydro-2H-pyran-4-yl)pyrazin-2-yl)-2-fluoro-N-(1-(2-fluorobenzyl)piperidin-3-yl)benzamide | 0.58 | 508.3 | 1H NMR (400 MHz, CD$_3$OD) δ ppm 7.80 (s, 1H), 7.71 (m, 1H), 7.61 (dd, J = 1.5, 8.0 Hz, 1H), 7.57-7.43 (m, 3H), 7.32-7.15 (m, 2H), 4.39 (s, 2H), 3.95 (dd, J = 2.6, 11.6 Hz, 2H), 3.48 (dt, J = 2.5, 11.7 Hz, 3H), 2.92-2.75 (m, 1H), 2.56 (s, 2H), 1.89-1.65 (m, 10 H). |

TABLE 2-continued

Compounds prepared from Method 1 described above

| Example | Structure | Name | MH+ | R$_t$ (min) | NMR |
|---|---|---|---|---|---|
| 126 | 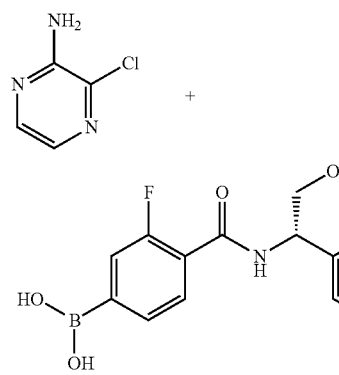 | (R)-4-(3-amino-6-(tetrahydro-2H-pyran-4-yl)pyrazin-2-yl)-2-fluoro-N-(1-(2-fluorobenzyl)piperidin-3-yl)benzamide | 508.4 | 0.63 | 1H NMR (400 MHz, CD$_3$OD) δ ppm 7.91 (s, 1H), 7.80 (t, J = 7.8 Hz, 1H), 7.71 (d, J = 9.4 Hz, 1 H), 7.67-7.55 (m, 3H), 7.41-7.27 (m, 2H), 4.49 (br. s., 2H), 4.34 (br. s., 1H), 4.10-4.01 (m, 2H), 3.75 (br. s., 1H), 3.64-3.51 (m, 4H), 3.02 (d, J = 13.7 Hz, 1H), 3.00-2.88 (m, 2H), 2.12 (br. s., 2H), 1.97-1.78 (m, 5H), 1.68 (d, J = 10.2 Hz, 1H) |

Method 2

Example 127

Synthesis of (S)-4-(3-amino-6-(1,3-dimethyl-1H-pyrazol-4-yl)pyrazin-2-yl)-N-(1-(3-chlorophenyl)-2-hydroxyethyl)-2-fluorobenzamide

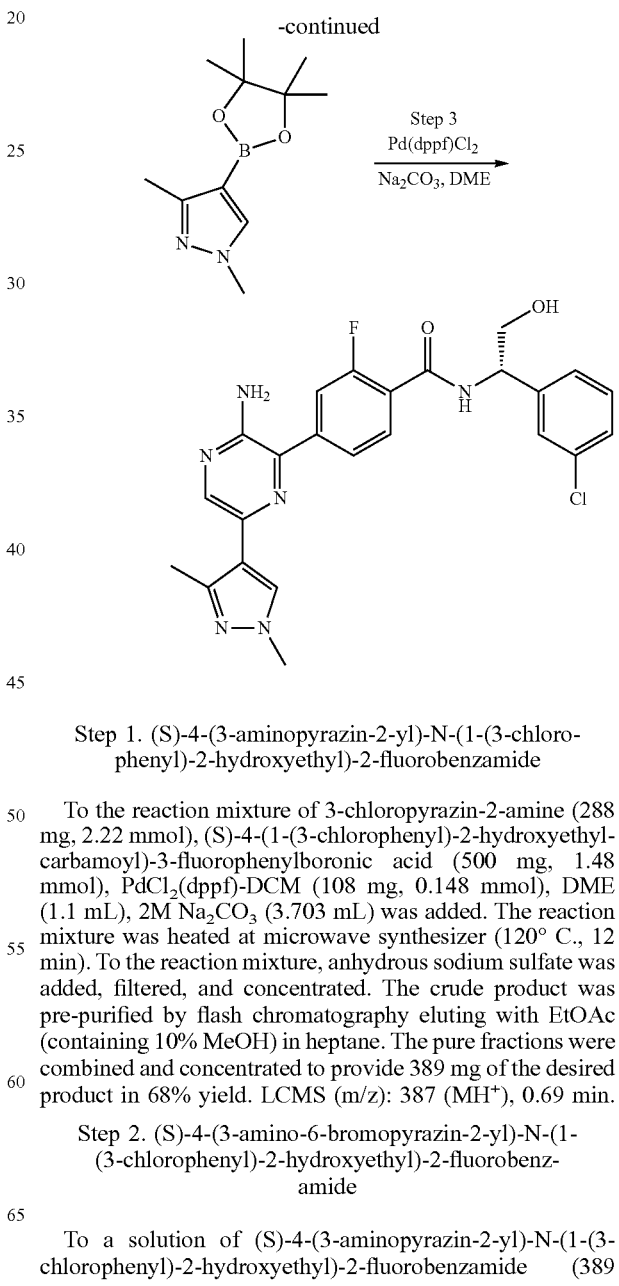

Step 1. (S)-4-(3-aminopyrazin-2-yl)-N-(1-(3-chlorophenyl)-2-hydroxyethyl)-2-fluorobenzamide To the reaction mixture of 3-chloropyrazin-2-amine (288 mg, 2.22 mmol), (S)-4-(1-(3-chlorophenyl)-2-hydroxyethylcarbamoyl)-3-fluorophenylboronic acid (500 mg, 1.48 mmol), PdCl$_2$(dppf)-DCM (108 mg, 0.148 mmol), DME (1.1 mL), 2M Na$_2$CO$_3$ (3.703 mL) was added. The reaction mixture was heated at microwave synthesizer (120° C., 12 min). To the reaction mixture, anhydrous sodium sulfate was added, filtered, and concentrated. The crude product was pre-purified by flash chromatography eluting with EtOAc (containing 10% MeOH) in heptane. The pure fractions were combined and concentrated to provide 389 mg of the desired product in 68% yield. LCMS (m/z): 387 (MH+), 0.69 min.

Step 2. (S)-4-(3-amino-6-bromopyrazin-2-yl)-N-(1-(3-chlorophenyl)-2-hydroxyethyl)-2-fluorobenzamide To a solution of (S)-4-(3-aminopyrazin-2-yl)-N-(1-(3-chlorophenyl)-2-hydroxyethyl)-2-fluorobenzamide (389 mg, 1.006 mmol) in acetonitrile (21 mL) was added NBS (171 mg, 0.961 mmol) at 0° C. The reaction mixture was stirred at 0° C. for 20 min. After quenched with sat NaHCO₃, and stir for 30 min. The reaction mixture was extracted with EtOAc 3 times, the organic was washed by sat NaHCO₃, water and brine, dried, filtered off, and concentrated. The crude material was taken to the next step without further purification. LCMS (m/z): 367 (MH⁺), 0.88 min.

Step 3. (S)-4-(3-amino-6-(1,3-dimethyl-1H-pyrazol-4-yl)pyrazin-2-yl)-N-(1-(3-chlorophenyl)-2-hydroxyethyl)-2-fluorobenzamide To the reaction mixture of (S)-4-(3-amino-6-bromopyrazin-2-yl)-N-(1-(3-chlorophenyl)-2-hydroxyethyl)-2-fluorobenzamide (40 mg, 0.086 mmol), 1,3-dimethyl-4-(4,4,5,5-tetramethyl-1,3,2-dioxaborolan-2-yl)-1H-pyrazole (38.2 mg, 0.172 mmol), PdCl₂(dppf)-DCM (6.28 mg, 8.59 μmol), and DME (644 μL), 2 M Na₂CO₃ (215 μL) were added. The reaction mixture was heated at microwave synthesizer (120° C., 12 min). To the reaction mixture, anhydrous sodium sulfate was added, filtered, and concentrated. The crude product was purified by auto-prep to provide 25 mg of desired product as a TFA salt. LCMS (m/z): 481.3 (MH⁺), 0.73 min; 1H NMR (500 MHz, CD₃OD) δ ppm 8.66 (d, J=6.26 Hz, 1 H) 8.17 (s, 1 H) 8.02 (s, 1 H) 7.76-7.51 (m, 3 H) 7.45-7.16 (m, 3 H) 5.07-4.09 (m, 1 H) 3.72 (s, 3 H) 3.62 (m, 2 H) 2.33 (s, 3 H).

Example 128

Synthesis of (S)-4-(2-amino-5-(1-methyl-1H-1,2,3-triazol-4-yl)pyridin-3-yl)-N-(1-(3-chlorophenyl)-2-hydroxyethyl)-2-fluorobenzamide

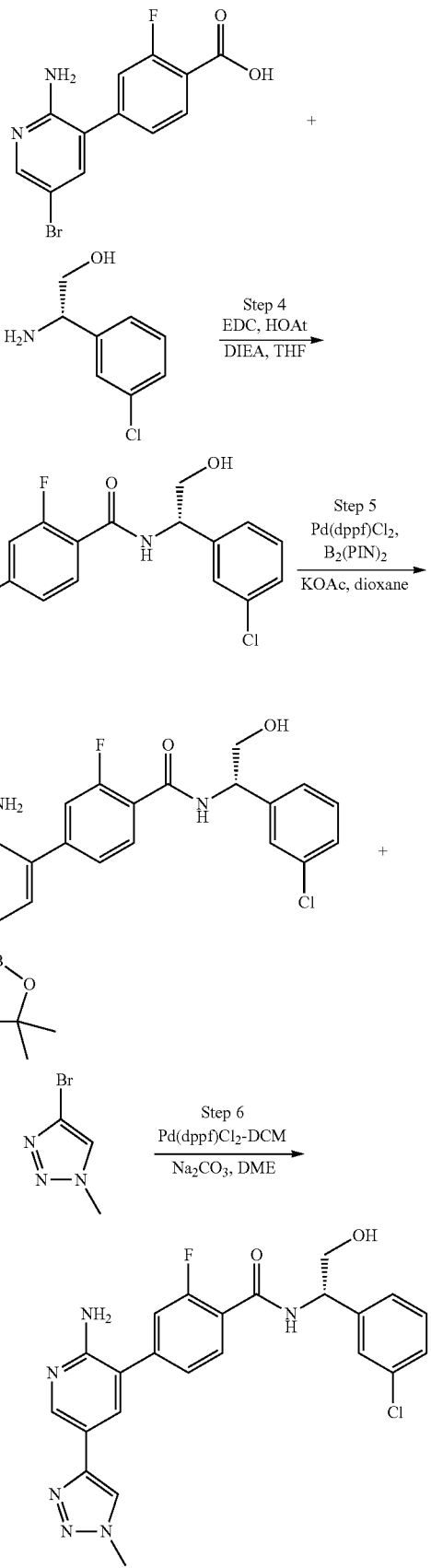

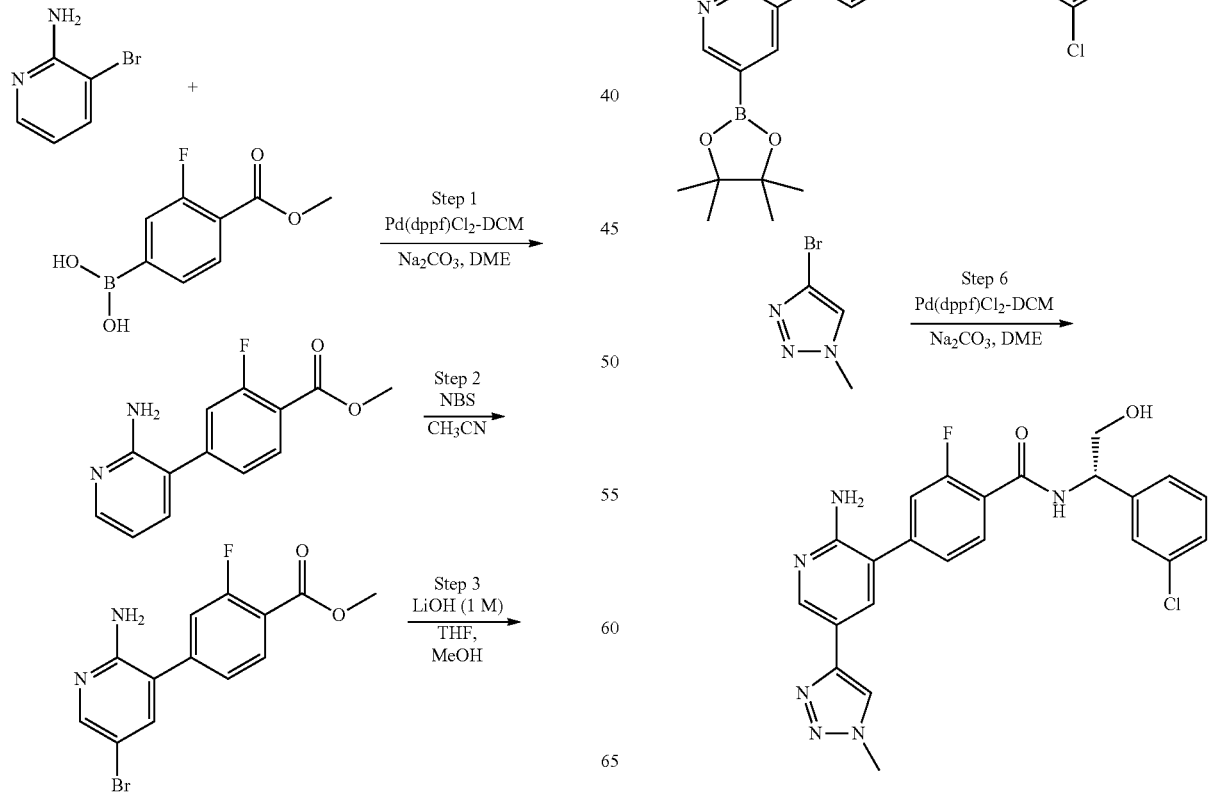

Step 1. methyl 4-(2-aminopyridin-3-yl)-2-fluorobenzoate

To 3-bromopyridin-2-amine (5 g, 28.9 mmol) in 500 mL round bottom flask was added (3-fluoro-4-(methoxycarbonyl)phenyl)boronic acid (7.44 g, 37.6 mmol), PdCl$_2$(dppf)-DCM (2.115 g, 2.89 mmol), DME (108 mL) and 2M Na$_2$CO$_3$ solution (36.1 mL). The reaction mixture was heated in an oil bath at 110° C. for 4 h. The reaction mixture was diluted with EtOAc and washed with water three times, dried over Na$_2$SO$_4$, filtered and concentrated. The crude product was purified by flash chromatography eluting with 0-100% of EtOAc (containing 10% of MeOH)/heptane yielding 5.6 g of methyl 4-(2-aminopyridin-3-yl)-2-fluorobenzoate in 79% yield. LCMS (m/z): 247.1 (MH$^+$), 0.50 min.

Step 2. methyl 4-(2-amino-5-bromopyridin-3-yl)-2-fluorobenzoate

To a solution of methyl 4-(2-aminopyridin-3-yl)-2-fluorobenzoate (5.64 g, 22.90 mmol) in acetonitrile (229 mL) was added NBS (4.16 g, 23.36 mmol) in two portions at 0° C. The reaction mixture was stirred at 0° C. for 20 min. After quenched with sat Na$_2$S$_2$O$_3$ and NaHCO$_3$, and stir for 30 min. The reaction mixture was extracted with EtOAc 3 times, the organic washed by sat NaHCO$_3$, water and brine. Dried and concentrated. The crude material was triturated with ether to provide 7.05 g of methyl 4-(2-amino-5-bromopyridin-3-yl)-2-fluorobenzoate in 95% yield. LCMS (m/z): 327.1 (MH$^+$), 0.66 min.

Step 3. 4-(2-amino-5-bromopyridin-3-yl)-2-fluorobenzoic acid

To a solution of methyl 4-(2-amino-5-bromopyridin-3-yl)-2-fluorobenzoate (1.9 g, 5.84 mmol) in THF (19.48 mL) and MeOH (9.74 mL, Ratio: 1.000) was added LiOH (1 M aqueous solutionueous solution) (10.52 mL, 10.52 mmol). The reaction mixture was stirred for 5 h. After 1N HCl (1.9 mL) was added up to pH 5, the reaction mixture was worked up with EtOAc, the organic layer was dried over Na$_2$SO$_4$, filtered off and concentrated in vacuo. The crude 4-(2-amino-5-bromopyridin-3-yl)-2-fluorobenzoic acid was used for the next step without further purification. LCMS (m/z): 311.1/313.1 (MH$^+$), 0.5 min.

Step 4. (S)-4-(2-amino-5-bromopyridin-3-yl)-N-(1-(3-chlorophenyl)-2-hydroxyethyl)-2-fluorobenzamide To a solution of 4-(2-amino-5-bromopyridin-3-yl)-2-fluorobenzoic acid (300 mg, 0.964 mmol) in THF (8.036 mL) was added (S)-2-amino-2-(3-chlorophenyl)ethanol (331 mg, 1.157 mmol). The reaction mixture was stirred for 15 h. After water was added, the reaction mixture was worked up with EtOAc, the organic layer was dried over anhydrous Na$_2$SO$_4$, filtered off and concentrated in vacuo. The crude (S)-4-(2-amino-5-bromopyridin-3-yl)-N-(1-(3-chlorophenyl)-2-hydroxyethyl)-2-fluorobenzamide was used for the next step without further purification. LCMS (m/z): 464.1/466.1 (MH$^+$), 0.69 min.

Step 5. (S)-4-(2-amino-5-(4,4,5,5-tetramethyl-1,3,2-dioxaborolan-2-yl)pyridin-3-yl)-N-(1-(3-chlorophenyl)-2-hydroxyethyl)-2-fluorobenzamide To a solution of (S)-4-(2-amino-5-bromopyridin-3-yl)-N-(1-(3-chlorophenyl)-2-hydroxyethyl)-2-fluorobenzamide (85 mg, 0.183 mmol), bis(pinacolato)diboron (93 mg, 0.366 mmol), and PdCl$_2$(dppf) (26.8 mg, 0.037 mmol) in dioxane (610 μL) was added potassium acetate (54 mg, 0.549 mmol). The reaction mixture was heated at microwave synthesizer (120° C. for 20 min). The reaction mixture was filtered through Celite pad. After the filtrate was almost concentrated, the crude (S)-4-(2-amino-5-(4,4,5,5-tetramethyl-1,3,2-dioxaborolan-2-yl)pyridin-3-yl)-N-(1-(3-chlorophenyl)-2-hydroxyethyl)-2-fluorobenzamide was used for the next step without further purification. LCMS (m/z): 430.2 (MH$^+$ for boronic acid), 0.57 min.

Step 6. (S)-4-(2-amino-5-(1-methyl-1H-1,2,3-triazol-4-yl)pyridin-3-yl)-N-(1-(3-chlorophenyl)-2-hydroxyethyl)-2-fluorobenzamide To a solution of the crude (S)-4-(2-amino-5-(4,4,5,5-tetramethyl-1,3,2-dioxaborolan-2-yl)pyridin-3-yl)-N-(1-(3-chlorophenyl)-2-hydroxyethyl)-2-fluorobenzamide (30 mg, 0.059 mmol) in residual dioxane was added 4-bromo-1-methyl-1H-1,2,3-triazole (14.24 mg, 0.088 mmol), PdCl$_2$(dppf) (42.9 mg, 0.059 mmol), DME (195 μl) and 2 M Na$_2$CO$_3$ (130 μl) at room temperature. The reaction mixture was stirred for 5 h. After water and EtOAc were added, the organic layer was extracted with EtOAc. The organic layer was washed with water and brine, dried over anhydrous Na$_2$SO$_4$, filtered off, and concentrated in vacuo. The crude product was purified by prep HPLC. The pure fractions were lyophilized yielding (S)-4-(2-amino-5-(1-methyl-1H-1,2,3-triazol-4-yl)pyridin-3-yl)-N-(1-(3-chlorophenyl)-2-hydroxyethyl)-2-fluorobenzamide as a TFA salt (25% over 2 steps).

LCMS (m/z): 467.3 (MH$^+$), 0.61 min; 1H NMR (400 MHz, CD$_3$OD) δ ppm 8.64 (m, 1 H), 8.31 (m, 1 H), 8.25 (m, 2 H), 8.2 (m, 1 H), 7.82 (m, 1 H), 7.4 (m, 3 H), 7.28 (m, 2 H), 7.22 (m, 1 H), 5.11 (m, 1 H), 4.07 (s, 3 H), 3.78 (m, 2 H).

Example 129

Synthesis of (S)-4-(3-amino-6-(6-oxo-1,6-dihydropyridin-3-yl)pyrazin-2-yl)-N-(2-hydroxy-1-phenylethyl)benzamide Scheme 55

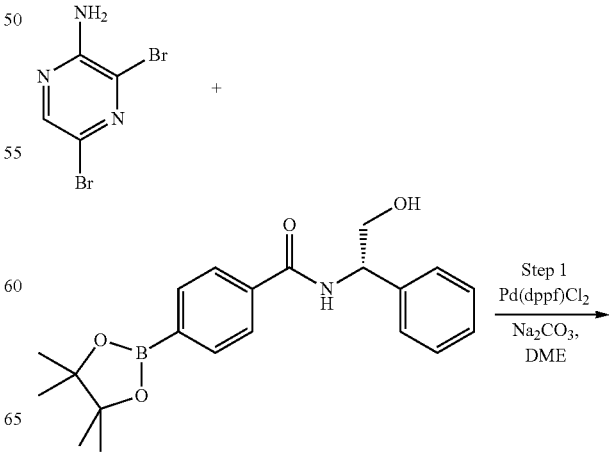

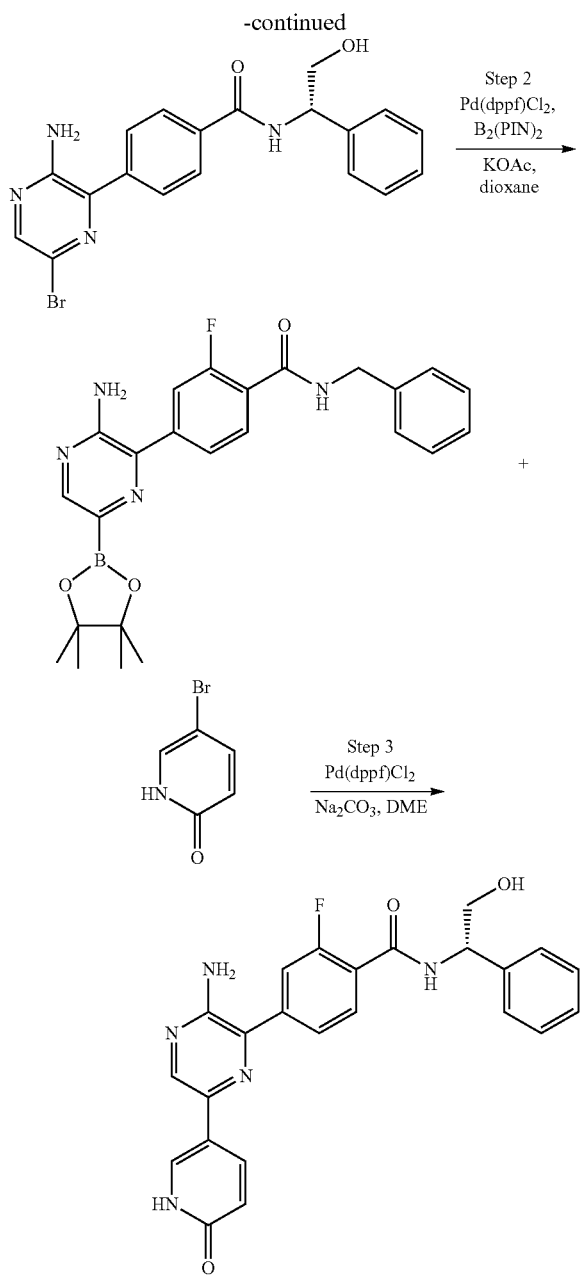

Step 1. (S)-4-(3-amino-6-bromopyrazin-2-yl)-N-(2-hydroxy-1-phenylethyl)benzamide To a solution of 3,5-dibromopyrazin-2-amine (826 mg, 3.27 mmol), (S)N-(2-hydroxy-1-phenylethyl)-4-(4,4,5,5-tetramethyl-1,3,2-dioxaborolan-2-yl)benzamide (600 mg, 1.634 mmol), and PdCl$_2$(dppf).CH$_2$Cl$_2$ adduct (133 mg, 0.163 mmol) in DME (12.3 mL) was added 2 M Na$_2$CO$_3$ (4.08 mL). The reaction mixture was heated at microwave synthesizer (120° C., 10 min). The reaction mixture was worked up with EtOAc. The organic layer was washed with sat NaHCO$_3$, water and brine, dried over Na$_2$SO$_4$, filtered off, concentrated in vacuo. The crude product was purified with silica flash chromatography eluting with 0-100% of EtOAc (containing 10% of MeOH) in heptane, and triturated with ether to provide 800 mg of (S)-4-(3-amino-6-bromopyrazin-2-yl)-N-(2-hydroxy-1-phenylethyl)benzamide. LCMS (m/z): 415 (MH$^+$), 0.73 min.

Step 2. (S)-4-(3-amino-6-(4,4,5,5-tetramethyl-1,3,2-dioxaborolan-2-yl)pyrazin-2-yl)-N-(2-hydroxy-1-phenylethyl)benzamide To a solution of (S)-4-(3-amino-6-(4,4,5,5-tetramethyl-1,3,2-dioxaborolan-2-yl)pyrazin-2-yl)-N-(2-hydroxy-1-phenylethyl)benzamide (50 mg, 0.121 mmol), bis(pinacolato)diboron (61.4 mg, 0.242 mmol), and PdCl$_2$(dppf)-CH$_2$Cl$_2$ adduct (9.88 mg, 0.012 mmol) in dioxane (302 µL) was added potassium acetate (35.6 mg, 0.363 mmol) just right after degassing. The reaction mixture was heated at microwave synthesizer (120° C. for 20 min). After diluted with EtOAc, the reaction mixture was filtered through Celite pad. After concentrated, the crude (S)-4-(3-amino-6-(4,4,5,5-tetramethyl-1,3,2-dioxaborolan-2-yl)pyrazin-2-yl)-N-(2-hydroxy-1-phenylethyl)benzamide was used for the next step without further purification. LCMS (m/z): 379 (MH$^+$ for boronic acid), 0.47 min.

Step 3. (S)-4-(3-amino-6-(6-oxo-1,6-dihydropyridin-3-yl)pyrazin-2-yl)-N-(2-hydroxy-1-phenylethyl)benzamide To a solution of (S)-5-amino-6-(4-(2-hydroxy-1-phenylethylcarbamoyl)phenyl)pyrazin-2-ylboronic acid (55 mg, 0.145 mmol), 5-bromopyridin-2(1H)-one (38.0 mg, 0.218 mmol), and PdCl$_2$(dppf)-CH$_2$Cl$_2$ (11.88 mg, 0.015 mmol) in DME (1091 µL) was added 2M Na$_2$CO$_3$ (364 µL). The reaction mixture was heated at microwave synthesizer (120° C., 10 min). The reaction mixture was worked up with EtOAc. The organic layer was washed with sat NaHCO$_3$, water and brine, dried over Na$_2$SO$_4$, filtered off, concentrated in vacuo. The crude product was purified by prep HPLC yielding 4.3 mg of (S)-4-(3-amino-6-(6-oxo-1,6-dihydropyridin-3-yl)pyrazin-2-yl)-N-(2-hydroxy-1-phenylethyl)benzamide as a TFA salt. LCMS (m/z): 428.2 (MH$^+$), 0.55 min; $^1$H NMR (400 MHz, DMSO-d6) 3.60-3.75 (m, 2 H)5.03-5.12 (m, 1 H) 6.40 (d, J=9.39 Hz, 1 H) 7.22 (d, J=7.43 Hz, 1 H) 7.30 (t, J=7.63 Hz, 2 H) 7.34-7.40 (m, 2 H) 7.83 (d, J=8.22 Hz, 2 H) 7.94 (br. s., 1 H) 8.01 (d, J=8.61 Hz, 2 H) 8.06 (dd, J=9.39, 2.74 Hz, 1 H) 8.41 (s, 1 H) 8.74 (d, J=8.22 Hz, 1 H).

Synthesis of (S)-4-(3-amino-6-bromopyrazin-2-yl)-N-(1-(3-chlorophenyl)-2-hydroxyethyl)-2,6-difluorobenzamide -continued

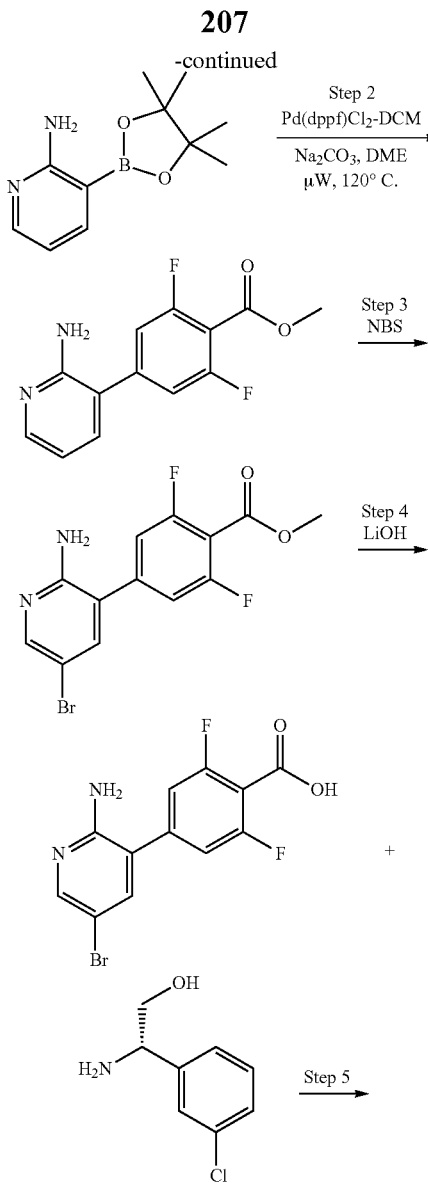

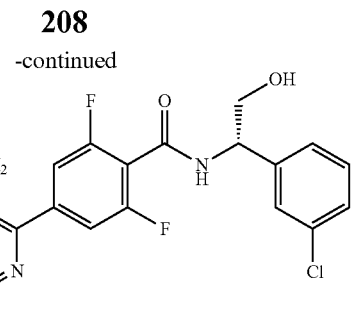

Step 1. methyl 4-bromo-2,6-difluorobenzoate

To a solution of 4-bromo-2,6-difluorobenzoic acid (800 mg, 3.38 mmol) in MeOH (11 mL) at room temperature, trimethylsilyldiazomethane (5.63 mL, 3.38 mmol) was slowly added until yellow solution was turned on. The small amount of AcOH was added until yellow color disappeared. All volatile materials were removed in vacuo yielding methyl 4-bromo-2,6-difluorobenzoate (47%). LCMS (m/z): 251.1 (MH$^+$), 0.86 min.

Step 2. methyl 4-(2-aminopyridin-3-yl)-2,6-difluorobenzoate

Followed by Step 1 in Scheme 54, methyl 4-(2-aminopyridin-3-yl)-2,6-difluorobenzoate was obtained (9%). LCMS (m/z): 485.2 (MH$^+$), 0.64 min; 1H NMR (400 MHz, CD$_3$OD) δ ppm 8.11 (m, 1 H), 7.76 (m, 2 H), 7.37 (m, 1 H), 7.27 (m, 2 H), 7.20 (m, 3 H), 5.09 (m, 1 H), 4.03 (s, 3 H), 3.73 (m, 2 H).

Step 3, 4, and 5. (S)-4-(3-amino-6-bromopyrazin-2-yl)-N-(1-(3-chlorophenyl)-2-hydroxyethyl)-2,6-difluorobenzamide Following Step 2, 3, and 4 in Scheme 54, (S)-4-(3-amino-6-(4,4,5,5-tetramethyl-1,3,2-dioxaborolan-2-yl)pyrazin-2-yl)-N-(1-(3-chlorophenyl)-2-hydroxyethyl)-2,6-difluorobenzamide was obtained. LCMS (m/z): 482/484 (MH$^+$), 0.68 min.

TABLE 3

Bromide or the corresponding boronic ester intermediates for Suzuki coupling

| Structure | Name | MH$^+$ | R$_t$ (min) | NMR |
|---|---|---|---|---|
| 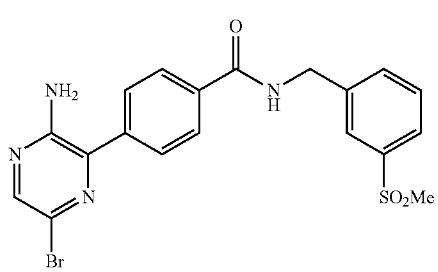 [SMILES: CS(=O)(=O)c1cccc(CNC(=O)c2ccc(-c3nc(Br)cnc3N)cc2)c1] | 4-(3-amino-6-bromopyrazin-2-yl)-N-(3-(methylsulfonyl)benzyl)benzamide | 461.1/463.0 | 0.72 | N/A |

TABLE 3-continued

Bromide or the corresponding boronic ester intermediates for Suzuki coupling

| Structure | Name | MH+ | R$_t$ (min) | NMR |
|---|---|---|---|---|
| 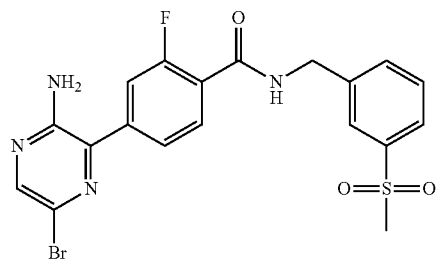 [SMILES: CS(=O)(=O)c1cccc(CNC(=O)c2ccc(-c3nc(Br)cnc3N)cc2F)c1] | 4-(3-amino-6-bromopyrazin-2-yl)-2-fluoro-N-(3-(methylsulfonyl)benzyl)benzamide | 479.2/481.2 | 0.782 | N/A |
| 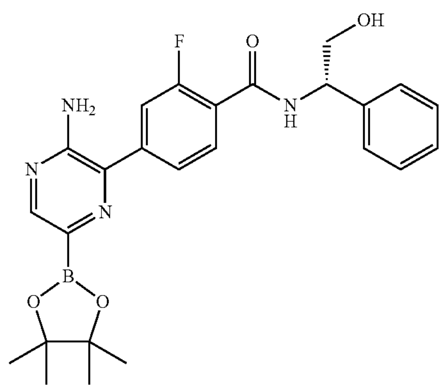 [SMILES: CC1(C)OB(c2cnc(N)c(-c3ccc(C(=O)N[C@H](CO)c4ccccc4)c(F)c3)n2)OC1(C)C] | (S)-4-(3-amino-6-(4,4,5,5-tetramethyl-1,3,2-dioxaborolan-2-yl)pyrazin-2-yl)-2-fluoro-N-(2-hydroxy-1-phenylethyl)benzamide | 397.1 (for boronic acid) | 0.49 | N/A |
| 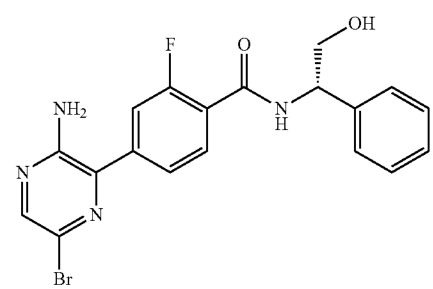 [SMILES: Nc1ncc(Br)nc1-c1ccc(C(=O)N[C@H](CO)c2ccccc2)c(F)c1] | (S)-4-(3-amino-6-bromopyrazin-2-yl)-2-fluoro-N-(2-hydroxy-1-phenylethyl)benzamide | 431.1/433.1 | 0.76 | N/A |
| 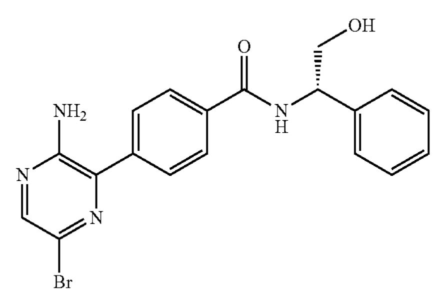 [SMILES: Nc1ncc(Br)nc1-c1ccc(C(=O)N[C@H](CO)c2ccccc2)cc1] | (S)-4-(3-amino-6-bromopyrazin-2-yl)-N-(2-hydroxy-1-phenylethyl)benzamide | 413/415 | 0.73 | 1H NMR (400 MHz, CD$_3$OD) δ ppm 8.05 (s, 1 H) 8.00 (d, J = 8.22 Hz, 3 H) 7.83 (d, J = 8.22 Hz, 3 H) 7.40-7.46 (m, 3H) 7.35 (t, J = 7.63 Hz, 2H) 7.23-7.31 (m, 1H) 5.23 (1, J = 6.65 Hz, 1H) 3.88 (d, J = 6.65 Hz, 2H) |
| 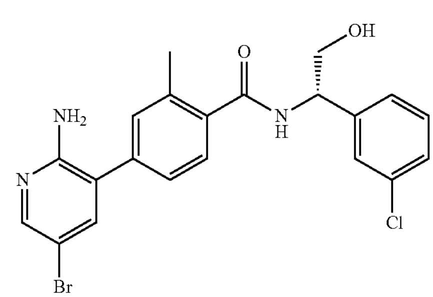 [SMILES: Cc1cc(-c2cc(Br)cnc2N)ccc1C(=O)N[C@H](CO)c1cccc(Cl)c1] | (S)-4-(2-amino-5-bromopyridin-3-yl)-N-(1-(3-chlorophenyl)-2-hydroxyethyl)-2-methylbenzamide | 462.1 | 0.69 | N/A |

TABLE 3-continued

Bromide or the corresponding boronic ester intermediates for Suzuki coupling

| Structure | Name | MH+ | R$_t$ (min) | NMR |
|---|---|---|---|---|
| 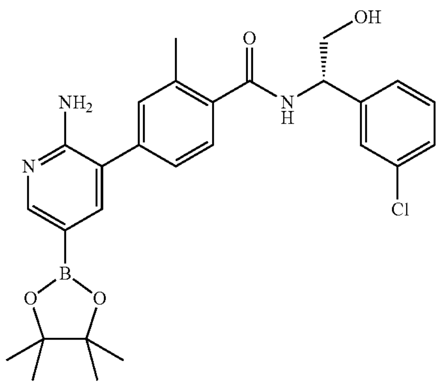 [SMILES: Cc1cc(-c2cc(B3OC(C)(C)C(C)(C)O3)cnc2N)ccc1C(=O)N[C@H](CO)c1cccc(Cl)c1] | (S)-4-(2-amino-5-(4,4,5,5-tetramethyl-1,3,2-dioxaborolan-2-yl)pyridin-3-yl)-N-(1-(3-chlorophenyl)-2-hydroxyethyl)-2-methylbenzamide | 426.2 | 0.57 | N/A |
| 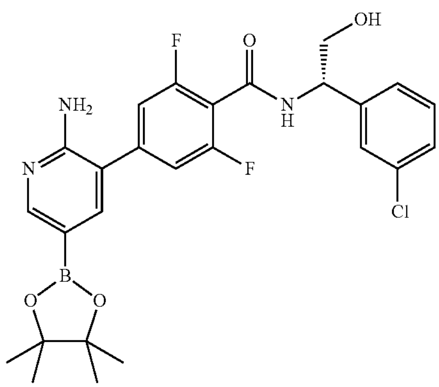 [SMILES: CC1(C)OB(c2cnc(N)c(-c3cc(F)c(C(=O)N[C@H](CO)c4cccc(Cl)c4)c(F)c3)c2)OC1(C)C] | (S)-4-(2-amino-5-(4,4,5,5-tetramethyl-1,3,2-diozaborolan-2-yl)pyridin-3-yl)-N-(1-(3-chlorophenyl)-2-hydroxyethyl)-2,6-difluorobenzamide | 448.2 (for boronic acid) | 0.65 | N/A |
| 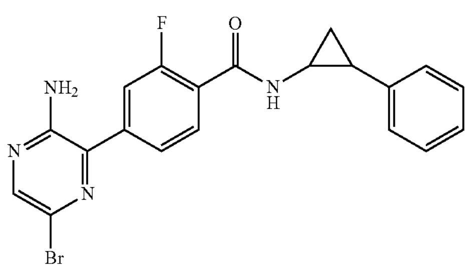 [SMILES: Nc1ncc(Br)nc1-c1ccc(C(=O)NC2CC2c2ccccc2)c(F)c1] | (+/−)-4-(3-amino-6-bromopyrazin-2-yl)-2-fluoro-N-(2-phenylcyclopropyl)benzamide | 427.1/429.1 | 0.95 | N/A |
| 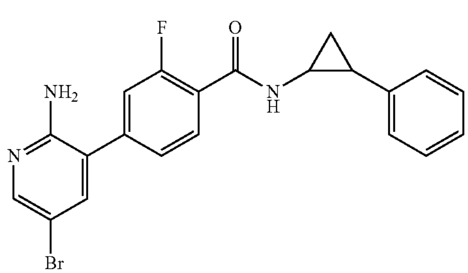 [SMILES: Nc1ncc(Br)cc1-c1ccc(C(=O)NC2CC2c2ccccc2)c(F)c1] | (+/−)-4-(2-amino-5-bromopyridin-3-yl)-2-fluoro-N-(2-phenylcyclopropyl)benzamide | 426.2/428.2 | 0.79 | N/A |

213

Chiral resolution of (+/−)-4-(2-amino-5-bromopyridin-3-yl)-2-fluoro-N-((1S,2R)-2-phenylcyclopropyl)benzamide Scheme 57

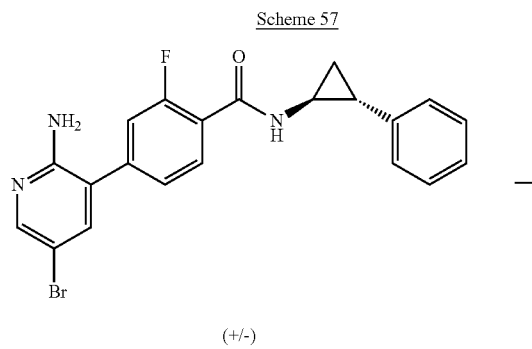

(+/−)

→

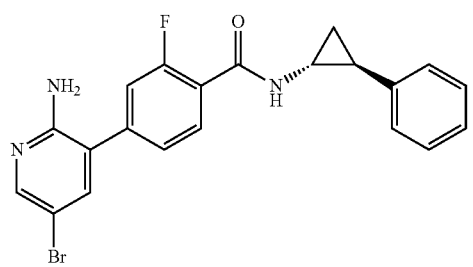

peak 1

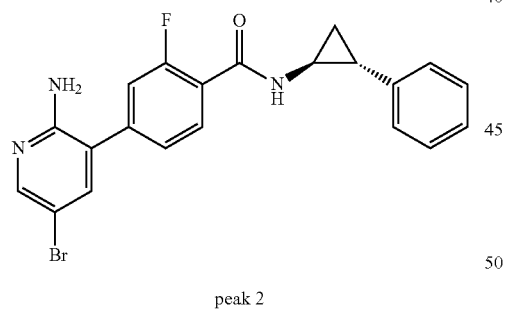

peak 2

(+/−)-4-(2-amino-5-bromopyridin-3-yl)-2-fluoro-N-((1S,2R)-2-phenylcyclopropyl)benzamide (121 mg) was resolved by chiral chromatography (AD-H column EtOH=60/40, 1 mL/min). The polar compound (Peak1), 4-(2-amino-5-bromopyridin-3-yl)-2-fluoro-N-((1R,2S)-2-phenylcyclopropyl)benzamide, was obtained at 7.41 min (50 mg, 41%) and the less polar compound (Peak2), 4-(2-amino-5-bromopyridin-3-yl)-2-fluoro-N-((1S,2R)-2-phenylcyclopropyl)benzamide, was obtained at 10.26 min (54 mg, 44%). The absolute stereochemistry was assigned based on biochemical data and docking model of the corresponding analogs.

214

Example 130

Synthesis of (+/−)-4-(2-amino-5-(1-methyl-1H-pyrazol-4-yl)pyridin-3-yl)-2-fluoro-N-((1R,2S)-2-phenylcyclopropyl)benzamide

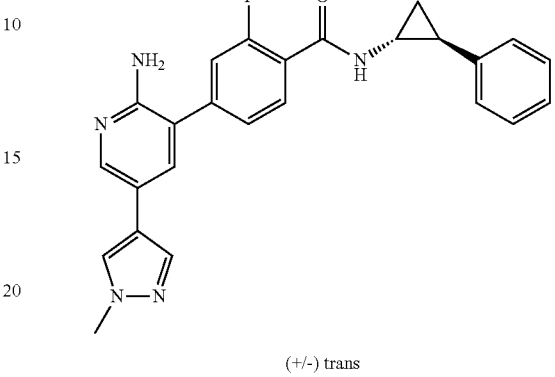

(+/−) trans

Followed Scheme 59, using (+/−)-4-(2-amino-5-bromopyridin-3-yl)-2-fluoro-N-((1S,2R)-2-phenylcyclopropyl)benzamide, (+/−)-4-(2-amino-5-(1-methyl-1H-pyrazol-4-yl)pyridin-3-yl)-2-fluoro-N-((1R,2S)-2-phenylcyclopropyl)benzamide was obtained (11%). LCMS (m/z): 428.2 (MH$^+$), 0.72 min; 1H NMR (400 MHz, CD$_3$OD) δ ppm 8.19 (m, 1 H), 7.91 (s, 1 H), 7.82 (m, 1 H), 7.77 (m, 1 H), 7.64 (m, 1 H), 7.48-7.33 (m, 2 H), 7.31-7.12 (m, 5 H), 3.91 (s, 3 H), 3.10 (m, 1 H), 2.20 (m, 1 H), 1.33 (m, 2 H).

Example 131

Synthesis of 4-(2-amino-5-(1-methyl-1H-pyrazol-4-yl)pyridin-3-yl)-2-fluoro-N-((1R,2S)-2-phenylcyclopropyl)benzamide

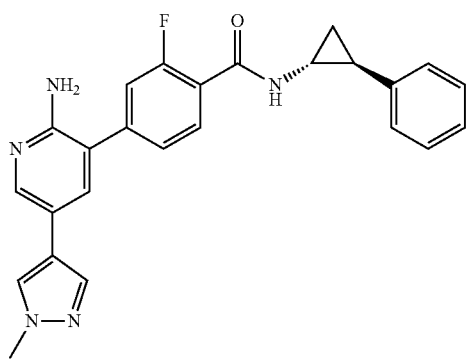 [SMILES: Cn1cc(-c2cnc(N)c(-c3ccc(C(=O)N[C@@H]4C[C@H]4c4ccccc4)c(F)c3)c2)cn1]

Followed by Scheme 59, using 4-(2-amino-5-bromopyridin-3-yl)-2-fluoro-N-((1R,2S)-2-phenylcyclopropyl)benzamide, 4-(2-amino-5-(1-methyl-1H-pyrazol-4-yl)pyridin-3-yl)-2-fluoro-N-((1R,2S)-2-phenylcyclopropyl)benzamide was obtained (53%). LCMS (m/z): 428.3 (MH$^+$), 0.69 min; 1H NMR (400 MHz, CD$_3$OD) δ ppm 8.11-8.02 (m, 1 H), 7.94 (m, 1 H), 7.97-7.88 (m, 2 H), 7.85-7.71 (m, 2 H), 7.43-7.30 (m, 2 H), 7.26-7.14 (m, 2H), 7.14-7.02 (m, 2 H), 3.83 (s, 3 H), 3.06-2.92 (m, 1 H), 2.19-2.02 (m, 1 H), 1.35-1.17 (m, 2 H). The absolute stereochemistry was assigned based on biochemical data and docking model.

Example 132

4-(2-amino-5-(1-methyl-1H-pyrazol-4-yl)pyridin-3-yl)-2-fluoro-N-((1S,2R)-2-phenylcyclopropyl)benzamide

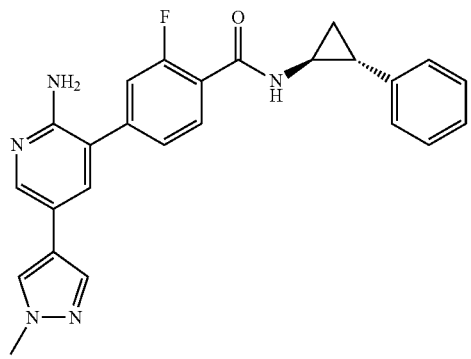 [SMILES: Cn1cc(-c2cnc(N)c(-c3ccc(C(=O)N[C@H]4C[C@@H]4c4ccccc4)c(F)c3)c2)cn1]

Followed by Scheme 59, using 4-(2-amino-5-bromopyridin-3-yl)-2-fluoro-N-((1S,2R)-2-phenylcyclopropyl)benzamide, 4-(2-amino-5-(1-methyl-1H-pyrazol-4-yl)pyridin-3-yl)-2-fluoro-N-((1S,2R)-2-phenylcyclopropyl)benzamide was obtained (42%). LCMS (m/z): 428.3 (MH+), 1H NMR (400 MHz, CD$_3$OD) δ ppm 8.09-8.02 (m, 1 H), 8.01-7.95 (m, 1 H), 7.96-7.88 (m, 2 H), 7.84-7.70 (m, 2 H), 7.42-7.29 (m, 2 H), 7.25-7.02 (m, 4 H), 3.83 (s, 3 H), 3.10-2.87 (m, 1 H), 2.24-2.00 (m, 1 H), 1.33-1.15 (m, 2 H). The absolute stereochemistry was assigned based on biochemical data and docking model.

Example 133

Synthesis of (S)-4-(2-amino-5-(1-deuterido-methyl, 5-methyl-1H-pyrazol-4-yl)pyridin-3-yl)-N-(1-(3-chlorophenyl)-2-hydroxyethyl)-2-fluorobenzamide Scheme 58

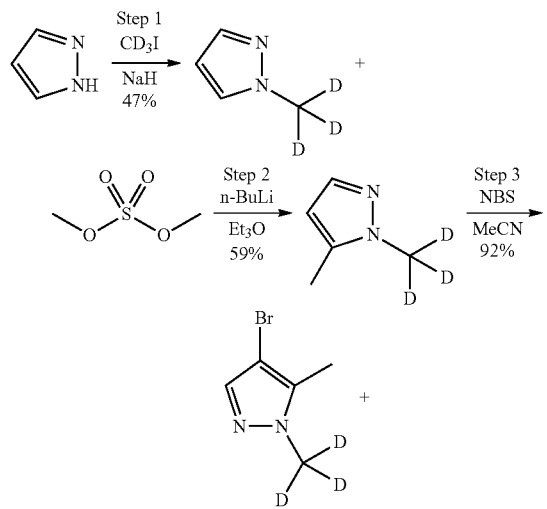

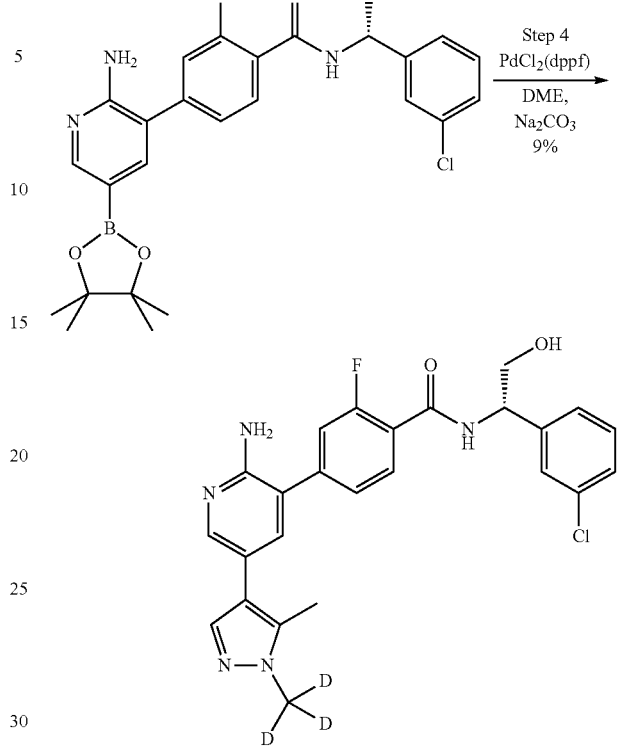

Step 1. 1-deuterido-methyl-1H-pyrazole

To a solution of NaH (1.851 g, 46.3 mmol) in 2-methyl THF (80 mL) was added 1H-pyrazole (3 g, 44.1 mmol) in 2-methyl THF (30 mL) at 0° C. The reaction mixture was warmed up to room temperature and stirred for 1 h. To this, CD$_3$I (3.02 mL, 48.5 mmol) was slowly added. The reaction mixture was stirred for overnight. After quenched with NH$_4$Cl solution, the reaction mixture extracted with EtOAc. The organic layer was washed with water and brine, filtered off, and concentrated in vacuo. The crude product was distilled off yielding 1-deuterido-methyl-1H-pyrazole (47%) (b.p.~130° C., bath temp was ~200° C.). LCMS (m/z): 86 (MH+), 0.24 min; 1H NMR (500 MHz, CDCl$_3$) δ ppm 7.55-7.42 (m, 1H), 7.39-7.28 (m, 1H), 6.28-6.15 (m, 1H).

Step 2. 1-deuterido-methyl,5-methyl-1H-pyrazole

To a solution of n-BuLi (2.5 M in hexanes) (4.14 mL, 10.34 mmol) in ether (20 mL) at −30° C. was slowly added a solution of 1-deuterido-methyl-1H-pyrazole (880 mg, 10.34 mmol) in ether (2 mL). The reaction mixture was allowed to warm up to room temperature and stirred for 2 h. After being cooled to 0° C., a solution of dimethyl sulfate (0.931 mL, 9.82 mmol) in ether (3 mL) was slowly added to the reaction mixture. The reaction mixture was stirred at room temperature for 3 h. After quenched with sat. NH$_4$Cl solution, the reaction mixture was extracted with ether (×2), but aqueous phase still contained product. Then, the aqueous phase was extracted with DCM (×2). The combined organic phase was dried over anhydrous Na$_2$SO$_4$, filtered off, and concentrated in vacuo. The crude product was purified by distillation yielding 1-deuterido-methyl,5-methyl-1H-pyrazole (59%). LCMS (m/z): 100.0 (MH+), 0.24 min; 1H NMR (400 MHz, CHLOROFORM-d) δ ppm 7.36 (m, 1H), 6.00 (m, 1H), 2.27 (s, 3H).

Step 3.
4-bromo-1-deuterido-methyl,5-methyl-1H-pyrazole

To a solution of 1-deuterido-methyl,5-methyl-1H-pyrazole (100 mg, 1.009 mmol) in MeCN (3.362 mL) was added NBS (171 mg, 0.958 mmol) slowly at 0° C. After the ice bath was removed, the reaction mixture was stirred for 30 min. After quenched with sodium sulfite solution, the reaction mixture was extracted with EtOAc. The organic layer was washed with sodium carbonate solution and brine, dried over sodium sulfate, filtered off and concentrated in vacuo. The crude 4-bromo-1-deuterido-methyl,5-methyl-1H-pyrazole was obtained and was used for the next step without further purification (92%). LCMS (m/z): 178, 180 (MH+), 0.61 min.

Step 4. (S)-4-(2-amino-5-(1-deuterido-methyl,5-methyl-1H-pyrazol-4-yl)pyridin-3-yl)-N-(1-(3-chlorophenyl)-2-hydroxyethyl)-2-fluorobenzamide Following Step 6 in Scheme 54, using 4-bromo-1-deuterido-methyl,5-methyl-1H-pyrazole, (S)-4-(2-amino-5-(1-deuterido-methyl,5-methyl-1H-pyrazol-4-yl)pyridin-3-yl)-N-(1-(3-chlorophenyl)-2-hydroxyethyl)-2-fluorobenzamide was obtained as a free base (9%). LCMS (m/z): 483.2 (MH+), 0.67 min; 1H NMR (500 MHz, CD3OD) δ ppm 8.00 (d, J=1.9 Hz, 1H), 7.86 (t, J=7.9 Hz, 1H), 7.58-7.23 (m, 8H), 5.19 (t, J=5.8 Hz, 1H), 3.93-3.77 (m, 2H), 2.37 (s, 1H).

Example 134

Synthesis of (S)-4-(2-amino-5-(cyanomethyl)pyridin-3-yl)-2-fluoro-N-(2-hydroxy-1-phenylethyl)benzamide Scheme 59

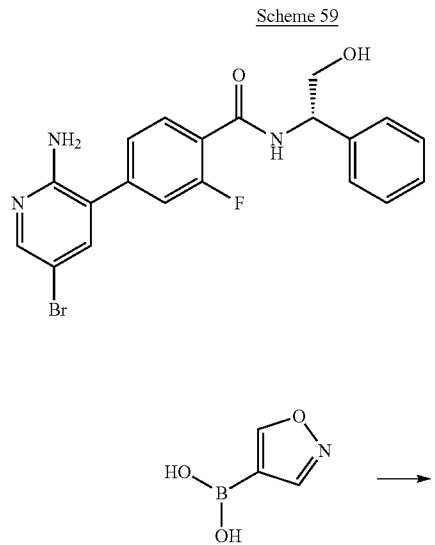

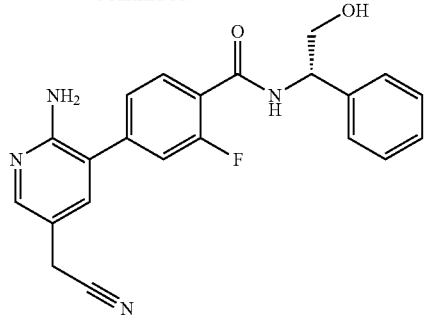

To a solution of (S)-4-(2-amino-5-bromopyridin-3-yl)-2-fluoro-N-(2-hydroxy-1-phenylethyl)benzamide (40 mg, 0.093 mmol) and isoxazol-4-ylboronic acid (20.99 mg, 0.186 mmol) in DME (697 µl) was added PdCl2(dppf)-CH2Cl2 (7.59 mg, 9.30 µmol) and 2 M Na2CO3 solution (232 µl). The reaction mixture was heated in microwave at 120° C. for 30 min. The reaction mixture was partitioned between EtOAc and water, The organic layer was dried over anhydrous sodium sulfate, filtered off, and concentrated in vacuo. The crude product was purified by prep HPLC. The pure fractions were collected and lyophilized yielding (S)-4-(2-amino-5-(cyanomethyl)pyridin-3-yl)-2-fluoro-N-(2-hydroxy-1-phenylethyl)benzamide as a TFA salt in 7% yield. LCMS (m/z): 391.2 (MH+), 0.51 min; 1H NMR (400 MHz, CD3OD) δ ppm 8.66 (br. s., 1 H), 7.99-7.95 (m, 1 H), 7.92-7.82 (m, 2 H), 7.44-7.39 (m, 4 H), 7.38-7.32 (m, 2 H), 7.31-7.25 (m, 1 H), 5.25-5.18 (m, 1 H), 3.92-3.90 (m, 2 H), 3.90-3.80 (m, 2 H).

Example 135

Synthesis of (S)-4-(3-amino-6-(2,2,6,6-tetradeuterido-tetrahydro-2H-pyran-4-yl)pyrazin-2-yl)-N-(2-hydroxy-1-phenylethyl)benzamide Scheme 60

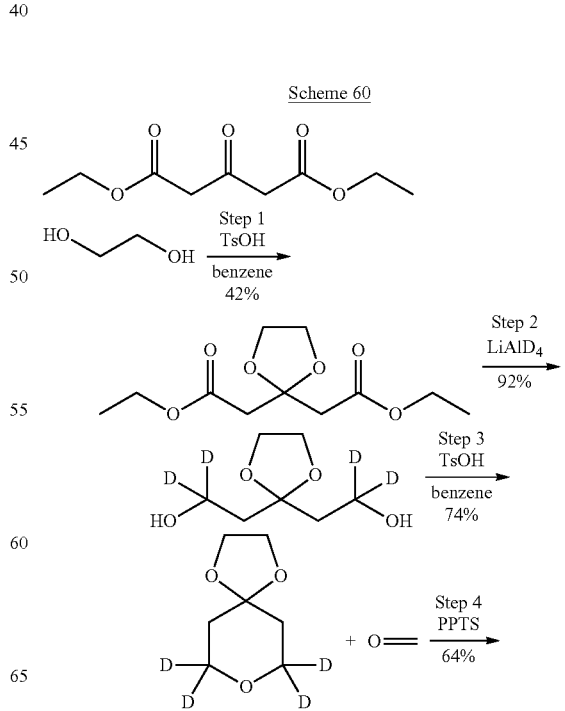

-continued

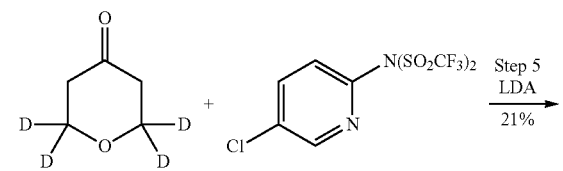

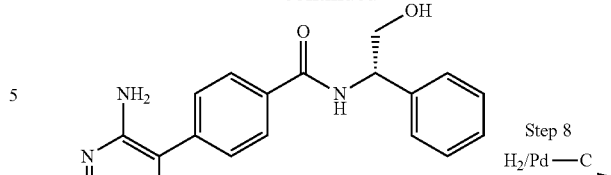

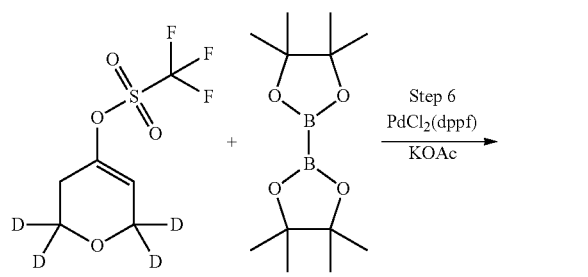

Step 5
LDA
21%

Step 6
PdCl₂(dppf)
KOAc

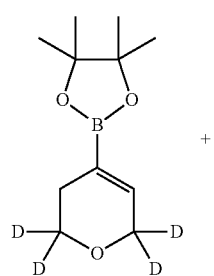

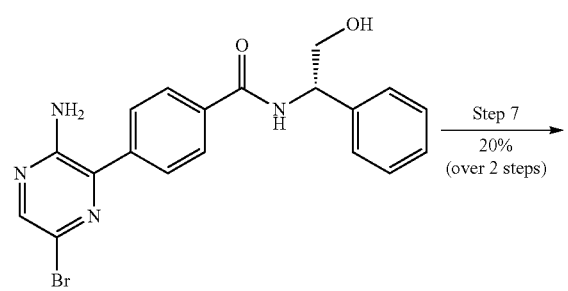

Step 7
20%
(over 2 steps)

Step 8
H₂/Pd—C
64%

Step 1. diethyl 2,2'-(1,3-dioxolane-2,2-diyl)diacetate

A solution of diethyl 1,3-acetonedicarboxylate (12 g, 59.3 mmol), ethyleneglycol (9.93 mL, 178 mmol), and p-toluenesulfonic acid monohydrate (564 mg, 2.97 mmol) in benzene (80 mL) was refluxed under heating removing water for 10 h by Dean-Stark trap. The benzene layer was washed with a saturated aqueous sodium bicarbonate solution and brine. The solvent was distilled away and the residue obtained was purified by flash chromatography (10 to 40% EtOAc in heptanes) yielding diethyl 2,2'-(1,3-dioxolane-2,2-diyl)diacetate (42%). LCMS (m/z): 247.2 (MH⁺), 0.65 min; $^1$H NMR (400 MHz, CDCl₃) δ ppm 4.17 (q, J=7.04 Hz, 4 H) 4.03 (s, 4 H) 2.95 (s, 4 H) 1.27 (t, J=7.24 Hz, 6 H).

Step 2. 2,2'-(1,3-dioxolane-2,2-diyl)diethanol-d4

To a suspension of LiAlD₄ in THF (2.46 g, 58.7 mmol in 40 mL) between −10 to 0° C. was added a solution of diethyl 2,2'-(1,3-dioxolane-2,2-diyl)diacetate (6.06 g) in THF (20 mL) over 10 min. The reaction mixture was stirred at 0° C. for 1 h and quenched by sequential addition of water (2.5 mL), 15 wt % NaOH (2.5 mL), and water (7.5 mL). The precipitates of the quenched mixture were removed by filtration and the filter cake was rinsed carefully with THF. The filtrate was concentrated and crude 2,2'-(1,3-dioxolane-2,2-diyl)diethanol-d4 was obtained (92%). $^1$H NMR (400 MHz, CDCl₃) δ ppm 4.06 (s, 4 H) 2.49 (s, 2 H) 1.98 (s, 4 H).

Step 3. 1,4,8-trioxaspiro[4.5]decane-d4

A mixture of 2,2'-(1,3-dioxolane-2,2-diyl)diethanol-d4 (3.57 g, 21.5 mmol) and 4-methylbenzenesulfonic acid hydrate (0.204 g, 1.07 mmol) and benzene (150 mL) were heated for 3 h at refluxing temperature with Dean-Stark apparatus to remove water. The reaction mixture was cooled down, washed with sat. NaHCO₃ (20 mL×2), and the aqueous layers were combined, extracted with Et₂O (2×20 mL), the organic layers were combined, washed with brine (30 mL), dried (Na₂SO₄), filtered off, and concentrated under 20 mbar via rotavap, and a light yellow oil was obtained as crude 1,4,8-trioxaspiro[4.5]decane-d4 (2.34 g, 73.5% yield). ¹H NMR (400 MHz, CDCl₃) δ ppm 3.98 (s, 4 H) 1.73 (s, 4 H).

Step 4. dihydro-2H-pyran-4(3H)-one-d4

The 1,4,8-trioxaspiro[4.5]decane-d4 (2.34 g, 15.8 mmol), formaldehyde (37%, 4.6 mL, 63.2 mmol) and pyridine 4-methylbenzenesulfonate (0.198 g, 0.79 mmol) were equally splitted into two microwave vials. Each vial was heated at 80° C. for 30 min and additional 15 min. The reaction mixtures were combined saturated with NaCl, extracted with Et₂O until no desired product found in aqueous layer by ¹H-NMR. The ether extracts were combined, concentrated and the residue was purified by flash column chromatography on silica gel (gradient Et₂O/n-pentane) twice yielding dihydro-2H-pyran-4(3H)-one-d4. ¹H NMR (400 MHz, CDCl₃) δ ppm 2.50 (s, 4 H).

Step 5. 3,6-dihydro-2H-pyran-4-yl trifluoromethanesulfonate-d4

To a freshly prepared LDA (10.6 mmol) in THF (10 mL) between −75 to −65° C. was dropwise added a solution of dihydro-2H-pyran-4(3H)-one-d4 (1.05 g) in THF (3.5 mL) over 10 min. The resulting reaction mixture was stirred at −75° C. for 3 h, followed by addition of N-(5-chloropyridin-2-yl)-1,1,1-trifluoro-N-((trifluoromethyl)sulfonyl)methanesulfonamide in THF (4.16 g/5 mL) over 10 min. The reaction mixture was stirred at −75° C. for 1 h, then with temperature gradually warming up to room temperature overnight. The reaction mixture was cooled to 0° C., quenched with D₂O (10 mL), and the two layers were separated, the organic layer was washed sequentially with D₂O (10 mL), citric acid (3×10 mL, 3 g citric acid in 30 mL water), 1M NaOH (2×10 mL), brine (30 mL), dried (Na₂SO₄), concentrated and the crude oily product was purified by flash chromatography on silica gel eluted with gradient Et₂O/n-pentane (0-60%). The purified product was further purified by distillation purification by Kugelrohr at 105° C./3 mbar yielding 3,6-dihydro-2H-pyran-4-yl trifluoromethanesulfonate-d4 (500 mg, 21% yield). ¹H NMR (400 MHz, CDCl₃) δ ppm 5.82 (s, 1 H) 2.45 (s, 2 H).

Step 6. 2-(3,6-dihydro-2H-pyran-4-yl)-4,4,5,5-tetramethyl-1,3,2-dioxaborolane-d4

A mixture of 3,6-dihydro-2H-pyran-4-yl trifluoromethanesulfonate-d4 (500 mg, 2.12 mmol), 4,4,4',4',5,5,5',5'-octamethyl-2,2'-bi(1,3,2-dioxaborolane) (806 mg, 3.18 mmol), potassium acetate (644 mg, 6.56 mmol), PdCl₂(dppf)-CH₂Cl₂ (86 mg, 0.106 mmol) and p-dioxane (5 mL) was charged into a microwave reactor vial, purged with argon for 5 min, sealed and heated at 80° C. overnight via oil bath. The reaction mixture was cooled down to room temperature, diluted with EtOAc (10 mL), filtered through a neutral alumina plug (1.25' H×0.75' D), and the filter cake was washed thoroughly with EtOAc. The filtrate was concentrated yielding crude 2-(3,6-dihydro-2H-pyran-4-yl)-4,4,5,5-tetramethyl-1,3,2-dioxaborolane-d4 in light brown solid (>99%). LCMS (m/z): 215.2 (MH⁺), 0.78 min.

Step 7. (S)-4-(3-amino-6-(3,6-dihydro-2H-pyran-4-yl)pyrazin-2-yl)-N-(2-hydroxy-1-phenylethyl)benzamide-d4

A mixture of 2-(3,6-dihydro-2H-pyran-4-yl)-4,4,5,5-tetramethyl-1,3,2-dioxaborolane-d4 (300 mg, 1.4 mmol), (S)-4-(3-amino-6-bromopyrazin-2-yl)-N-(2-hydroxy-1-phenylethyl)benzamide (694 mg, 1.68 mmol), aqueous Na₂CO₃ (2 M, 2.8 mL), and PdCl₂(dppf)-CH₂Cl₂ (57.2 mg, 0.07 mmol) and p-dioxane (6 mL) were charged into a microwave reactor vial, purged with argon for 5 min, sealed and heated at 115° C. for 30 min. The reaction mixture was diluted with EtOAc (15 mL), filtered and the filtrate was washed with 1M HCl (4×30 mL), and the aqueous layers were combined, basified by solid NaOH to pH 12, extracted with EtOAc (60 mL), dried (Na₂SO₄), concentrated and the first crop of product was obtained with some impurities. The EtOAc layer after aqueous HCl washes was concentrated and the residue was diluted with DMSO, purified by C18 reverse phase prep HPLC, and the product fractions were combined, saturated with Na₂CO₃, extracted with EtOAc (60 mL), and a second crop pure product was obtained in light yellow solid. The first crop product was purified by flash chromatography on silica gel eluted with gradient acetone/CH₂Cl₂ (0-60%). The two crops of product were combined and (S)-4-(3-amino-6-(3,6-dihydro-2H-pyran-4-yl)pyrazin-2-yl)-N-(2-hydroxy-1-phenylethyl)benzamide-d4 (179 mg, 27.9% yield) was obtained. LCMS (m/z): 421.2 (MH⁺), 0.65 min.

Step 8. (S)-4-(3-amino-6-(2,2,6,6-tetradeuterido-tetrahydro-2H-pyran-4-yl)pyrazin-2-yl)-N-(2-hydroxy-1-phenylethyl)benzamide A mixture of (S)-4-(3-amino-6-(3,6-dihydro-2H-pyran-4-yl)pyrazin-2-yl)-N-(2-hydroxy-1-phenylethyl)benzamide-d4 (175 mg) and Pd/C (10%, 22 mg) in methanol was stirred under hydrogen balloon at room temperature for 2 h. The reaction mixture was filtered through a thin layer of Celite pad, and the filtrate was concentrated to afford crude white solid. The crude product was purified by flash chromatography (0-60% acetone/CH₂Cl₂) and pure product was dissolved in acetonitrile/water (1:1, 10 mL), frozen and lyophilized to (S)-4-(3-amino-6-(2,2,6,6-tetradeuterido-tetrahydro-2H-pyran-4-yl)pyrazin-2-yl)-N-(2-hydroxy-1-phenylethyl)benzamide in a white powder (64%). LCMS (m/z): 423.2 (MH⁺), 0.60 min; ¹H NMR (400 MHz, CDCl₃) δ ppm 7.93-8.01 (m, 2 H), 7.92 (s, 1 H), 7.82-7.89 (m, 2 H), 7.38-7.47 (m, 4 H), 7.31-7.37 (m, 1 H), 6.90 (d, J=7.04 Hz, 1 H), 5.32 (dt, J=6.95, 4.55 Hz, 1 H), 4.68 (br. s., 2 H), 4.06 (d, J=4.30 Hz, 2 H), 2.93 (tt, J=11.44, 4.40 Hz, 1 H), 1.79-1.99 (m, 4 H).

Examples 136 and 137

Synthesis of 4-(3-amino-6-((S)-tetrahydrofuran-3-yl)pyrazin-2-yl)-N-((S)-2-hydroxy-1-phenylethyl)benzamide and 4-(3-amino-6-((R)-tetrahydrofuran-3-yl)pyrazin-2-yl)-N-((S)-2-hydroxy-1-phenylethyl)benzamide Scheme 61

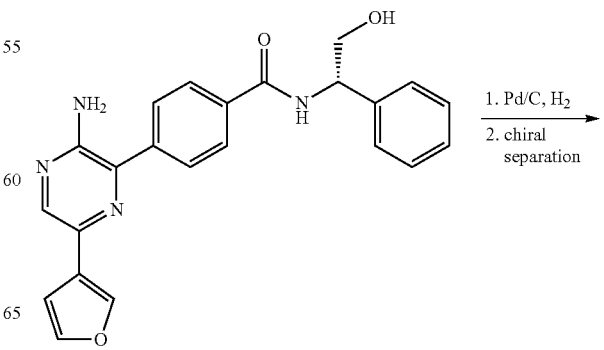

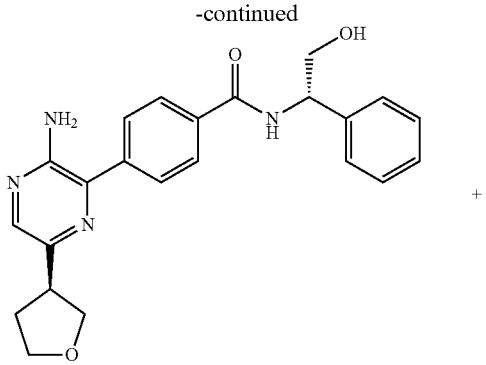

To a solution of (S)-4-(3-amino-6-(furan-3-yl)pyrazin-2-yl)-N-(2-hydroxy-1-phenylethyl)benzamide (75 mg, 0.187 mmol) in MeOH (1.873 mL) was added platinum (IV) oxide (12.76 mg, 0.056 mmol). The solution was degassed by $N_2$ stream for 15 min. After flushed with hydrogen gas and equipped with a hydrogen balloon, the reaction mixture was stirred for 24 h. The reaction mixture was filtered through Celite. After volatile materials were removed, the crude product was re-setup the reaction. The reaction mixture was stirred for another 24 h. LCMS (m/z): more side products were formed. The reaction mixture was filtered through Celite. After volatile materials were removed, to a solution of the crude product in MeOH (1.873 mL) was added PdC (100 mg, 0.094 mmol). The solution was degassed by N2 stream for 15 min. After flushed with hydrogen gas and equipped with a hydrogen balloon, the reaction mixture was stirred for 24 h. LCMS (m/z): all s.m. disappeared. The reaction mixture was filtered through Celite. After volatile materials were removed, the crude product was purified by flash chromatography (EtOAc in DCM) yielding 4-(3-amino-6-(tetrahydrofuran-3-yl)pyrazin-2-yl)-N-((S)-2-hydroxy-1-phenylethyl)benzamide (9 mg, 12%). LCMS (m/z): 405.2 (MH$^+$), 0.58 min; $^1$H NMR (400 MHz, CD$_3$OD) δ ppm 7.96-7.86 (m, 2 H), 7.80 (s, 1 H), 7.77-7.70 (m, 2 H), 7.38-7.32 (m, 2 H), 7.30-7.21 (m, 2 H), 7.21-7.12 (m, 1 H), 5.14 (m, 1 H), 4.08-3.97 (m, 1 H), 3.99-3.89 (m, 1 H), 3.89-3.67 (m, 4 H), 3.56-3.38 (m, 1 H), 2.33-2.04 (m, 2 H), 1.24-1.13 (m, 2 H). The racemic product was resolved in chiral HPLC (AD column, 5 mL/min, MeOH=30%, SFC) yielding 4-(3-amino-6-((S)-tetrahydrofuran-3-yl)pyrazin-2-yl)-N-((S)-2-hydroxy-1-phenylethyl)benzamide and 4-(3-amino-6-((R)-tetrahydrofuran-3-yl)pyrazin-2-yl)-N-((S)-2-hydroxy-1-phenylethyl)benzamide 3.4 mg of polar enantiomer (Rt=2.12 min) and 3.5 mg of less-polar enantiomer (Rt=2.66 min). The absolute stereochemistry was arbitrarily assigned.

TABLE 4

Compounds prepared using Method 2 described above.

| Example | Structure | Name | MH$^+$ | R$_t$ (min) | NMR |
|---|---|---|---|---|---|
| 138 | 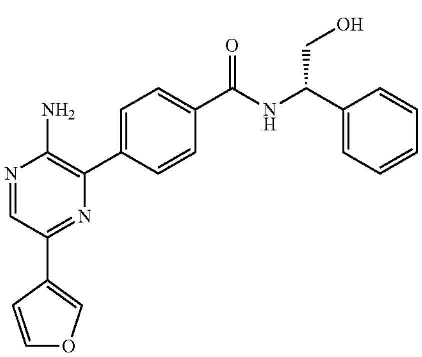 [SMILES: Nc1ncc(-c2ccoc2)nc1-c1ccc(C(=O)N[C@H](CO)c2ccccc2)cc1] | (S)-4-(3-amino-6-(furan-3-yl)pyrazin-2-yl)-N-(2-hydroxy-1-phenylethyl)benzamide | 401.2 | 2.84 | N/A |

TABLE 4-continued

Compounds prepared using Method 2 described above.

| Example | Structure | Name | MH+ | R$_t$ (min) | NMR |
|---|---|---|---|---|---|
| 139 | 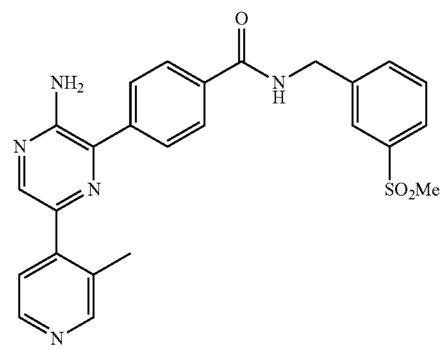 [SMILES: Cc1cnccc1-c1cnc(N)c(-c2ccc(C(=O)NCc3cccc(S(C)(=O)=O)c3)cc2)n1] | 4-(3-amino-6-(3-methylpyridin-4-yl)pyrazin-2-yl)-N-(3-(methylsulfonyl)benzyl)benzamide | 474.1 | 0.49 | $^1$H NMR (400 MHz, CD$_3$OD) δ ppm 8.43 (s, 1H), 8.40 (d, J = 5.1 Hz, 1H), 8.24 (s, 1H), 8.01 (d, J = 8.2 Hz, 2H), 7.96 (s, 1 H), 7.89 (d, J = 8.6 Hz, 2H), 7.84 (s, 1H), 7.72 (s, 1H), 7.63-7.58 (m 1H), 7.55 (d, J = 5.1 Hz, 1H), 4.69 (s, 2H), 3.10 (s, 3H), 2.48 (s, 3H) |
| 140 | 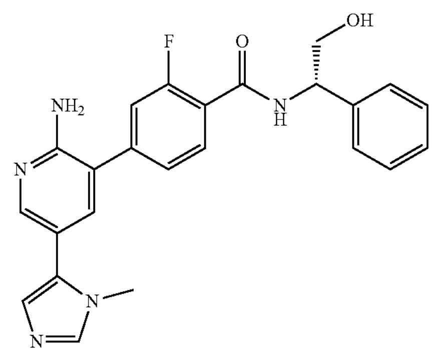 [SMILES: Cn1cncc1-c1cnc(N)c(-c2ccc(C(=O)N[C@H](CO)c3ccccc3)c(F)c2)c1] | (S)-4-(2-amino-5-(1-methyl-1H-imidazol-5-yl)pyrdin-3-yl)-2-fluoro-N-(2-hydroxy-1-phenylethyl)benzamide | 432.2 | 0.46 | $^1$H NMR (400 MHz, CD$_3$OD) δ ppm 8.97 (s, 1H), 8.65-8.53 (m, 1H), 8.18 (d, J = 2.3 Hz, 1 H), 7.88 (t, J = 7.4 Hz Hz, 1H), 7.74 (d, J = 2.3 Hz, 1H), 7.67 (d, J = 1.6 Hz, 1H), 7.47-7.39 (m, 4H), 7.36 (t, J = 7.6 Hz, 2 H), 7.31-7.25 (m, 1H), 5.34-5.17 (m, 1H), 3.98-3.78 (m, 5 H). |
| 141 | 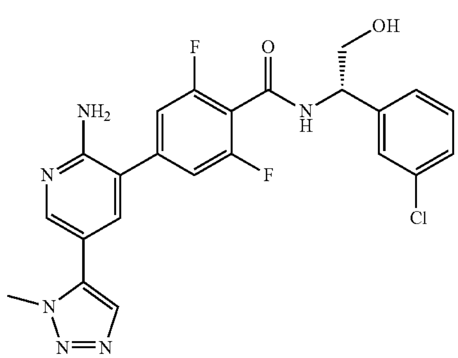 [SMILES: Cn1nncc1-c1cnc(N)c(-c2cc(F)c(C(=O)N[C@H](CO)c3cccc(Cl)c3)c(F)c2)c1] | Synthesis of (S)-4-(2-amino-5-(1-methyl-1H-1,2,3-triazol-5-yl)pyrdin-3-yl)-N-(1-(3-chlorophenyl)-2-hydroxyethyl)-2,6-difluorobenzamide | 485.2 | 0.64 | $^1$H NMR (400 MHz, CD$_3$OD) δ 8.11 (m, 1H), 7.76 (m, 2H), 7.37 (m, 1H), 7.27 (m, 2H), 7.20 (m, 3H), 5.09 (m, 1H), 4.03 (s, 3H), 3.73 (m, 2H) |
| 142 | 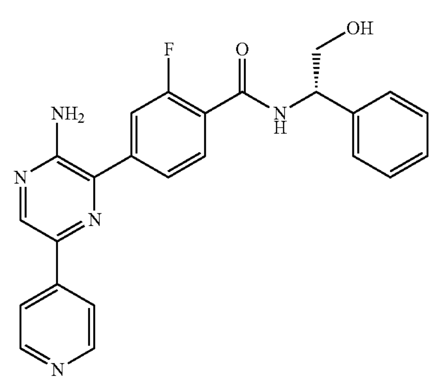 [SMILES: Nc1ncc(-c2ccncc2)nc1-c1ccc(C(=O)N[C@H](CO)c2ccccc2)c(F)c1] | (S)-4-(3-amino-6-(pyridin-4-yl)pyrazin-2-yl)-2-fluoro-N-(2-hydroxy-1-phenylethyl)benzamide | 430.1 | 0.53 | 1H NMR (400 MHz, DMSO-d6) δ 8.89 (s, 1H), 8.70 (m, 2H), 8.65 (m, 1H), 8.22 (m, 2H), 7.80-7.62 (, 3H), 7.49-7.20 (m, 5H), 7.08 (m, 1H), 5.03 (m, 1H), 3.65 (d, J = 4 Hz, 2H) |

TABLE 4-continued

Compounds prepared using Method 2 described above.

| Example | Structure | Name | MH+ | R<sub>t</sub> (min) | NMR |
|---|---|---|---|---|---|
| 143 | 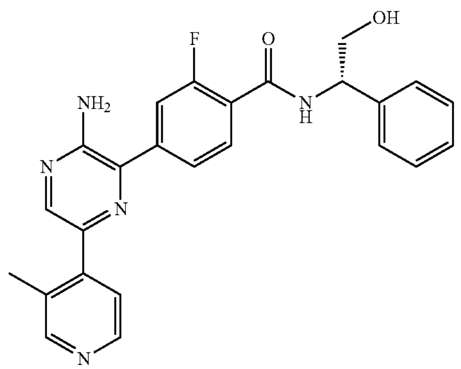 [SMILES: Cc1cnccc1-c1cnc(N)c(-c2ccc(C(=O)N[C@H](CO)c3ccccc3)c(F)c2)n1] | (S)-4-(3-amino-6-(3-methylpyridin-4-yl)pyrazin-2-yl)-2-fluoro-N-(2-hyddroxy-1-phenylethyl)benzamide | 444.3 | 0.52 | 1H NMR (400 MHz, DMSO-d6) δ 8.72-8.51 (m, 4H), 8.43 (s, 1H), 7.78-7.53 (m, 3H), 7.40-7.25 (m, 4H), 7.22 (m, 1H), 6.85 (m,, 1H), 5.02 (m, 1H), 3.65 (d, J = 8 Hz, 2H) |
| 144 | 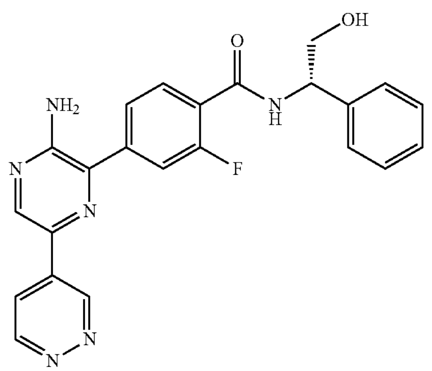 [SMILES: Nc1ncc(-c2ccnnc2)nc1-c1ccc(C(=O)N[C@H](CO)c2ccccc2)c(F)c1] | (S)-4-(3-amino-6-(pyridazin-4-yl)pyrazin-2-yl)-2-fluoro-N-(2-hyddroxy-1-phenylethyl)benzamide | 431.2 | 0.58 | 1H NMR (400 MHz, CD<sub>3</sub>OD) δ 9.86 (d, J = 1.2 Hz, 1H), 9.20 (d, J = 5.9 Hz, 1H), 8.82 (s, 1H), 8.49 (dd, J = 2.3, 5.9 Hz, 1H), 7.87-7.78 (m, 1H), 7.70-7.62 (m, 2H), 7.40-7.32 (m, 2H), 7.27 (t, J = 7.4 Hz, 2H), 7.20 (d, J = 7.4 Hz, 1H), 5.14 (t, J = 6.1 Hz, 1H), 3.85-3.72 (m, 2H) |
| 145 | 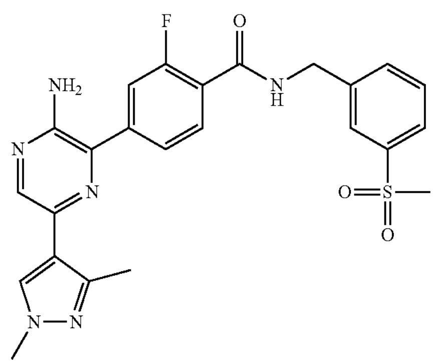 | 4-(3-amino-6-(1,3-dimethyl-1H-pyrazol-4-yl)pyrazin-2-yl)-2-fluoro-N-(3-(methylsulfonyl)benzyl)benzamide | 495.2 | 0.65 | 1H NMR (400 MHz, CD<sub>3</sub>OD) δ ppm 8.17 (s, 1H) 8.03-7.95 (m, 2H) 7.93-7.83 (m, 2H) 7.76 (d, J = 8.22 Hz, 2H) 7.72-7.59 (m, 2H) 4.72 (s, 2H) 3.86 (s, 4H) 3.12 (s, 3H) 2.47 (s, 3H) |
| 146 | 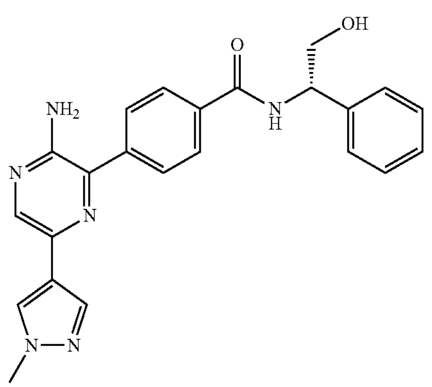 [SMILES: Cn1cc(-c2cnc(N)c(-c3ccc(C(=O)N[C@H](CO)c4ccccc4)cc3)n2)cn1] | (S)-4-(3-amino-6-(1-methyl-1H-pyrazol-4-yl)pyrazin-2-yl)-N-(2-hydroxy-1-phenylethyl)benzamide | 415.3 | 0.59 | 1H NMR (400 MHz, CD<sub>3</sub>OD) δ 8.17-8.09 (m, 1H), 8.03-7.90 (m, 3H), 7.88-7.73 (m, 3H), 7.38-7.30 (m, 2H), 7.31-7.23 (m, 2H), 7.21-7.14 (m, 1H), 5.21-5.10 (m, 1H), 3.84 (s, 3H), 3.82-3.75 (m, 2H) |

TABLE 4-continued

Compounds prepared using Method 2 described above.

| Example | Structure | Name | MH+ | R<sub>t</sub> (min) | NMR |
|---|---|---|---|---|---|
| 147 | 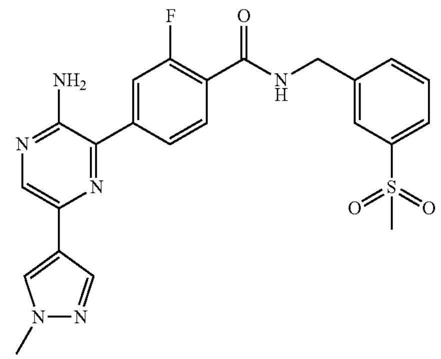 [SMILES: Cn1cc(-c2cnc(N)c(-c3ccc(C(=O)NCc4cccc(S(C)(=O)=O)c4)c(F)c3)n2)cn1] | 4-(3-amino-6-(1-methyl-1H-pyrazol-4-yl)pyrazin-2-yl)-2-fluoro-N-(3-(methylsulfonyl)benzyl)benzamide | 481.3 | 0.633 | 1H NMR (400 MHz, CD$_3$OD) δ ppm 8.30 (t, J = 8.02 Hz, 1H) 8.05 (s, 1H) 7.97-7.83 (m, 4H) 7.75-7.67 (m, 2H) 7.64-7.55 (m, 2H) 4.82 (d, J = 5.87 Hz, 2H) 3.99 (s, 3H) 3.07 (s, 3H) |
| 148 | 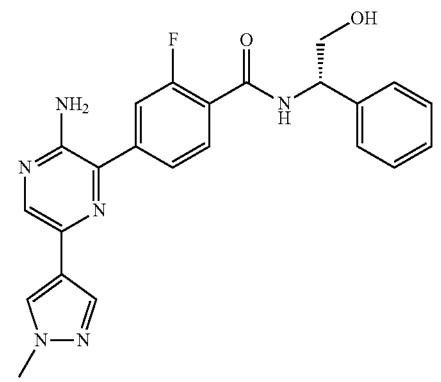 [SMILES: Cn1cc(-c2cnc(N)c(-c3ccc(C(=O)N[C@H](CO)c4ccccc4)c(F)c3)n2)cn1] | (S)-4-(3-amino-6-(1-methyl-1H-pyrazol-4-yl)pyrazin-2-yl)-2-fluoro-N-(2-hydroxy-1-phenylethyl)benzamide | 433.2 | 0.64 | $^1$H NMR (400 MHz, CD$_3$OD) δ 8.25 (s, 1H), 8.05 (s, 1H), 7.92 (s, 1H), 7.89-7.79 (m, 1H), 7.77-7.59 (m, 2H), 7.47-7.39 (m, 2H), 7.39-7.31 (m, 2H), 7.31-7.21 (m, 1H), 3.91 (s, 3H), 3.89-3.78 (m, 1H), 1.42-1.28 (m, 1H) |
| 149 | 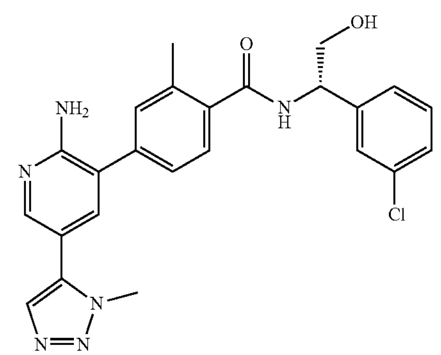 [SMILES: Cc1cc(-c2cc(-c3cnnn3C)cnc2N)ccc1C(=O)N[C@H](CO)c1cccc(Cl)c1] | (S)-4-(2-amino-5-(1-methyl-1H-1,2,3-triazol-5-yl)pyridin-3-yl)-N-(1-(3-chlorophenyl)-2-hydroxyethyl)-2-methylbenzamide | 463.3 | 0.61 | 1H NMR (400 MHz, CD$_3$OD) δ ppm 8.73 (d, J = 7.83 Hz, 1H) 8.08 (d, J = 2.35 Hz, 1H) 7.93-7.73 (m, 1H) 7.48 (d, J = 7.83 Hz, 1H) 7.41-7.07 (m, 6H) 5.22-5.01 (m, 1H) 4.04 (s, 3H) 3.86-3.57 (m, 2H) 2.44-2.24 (m, 3H) |
| 150 | 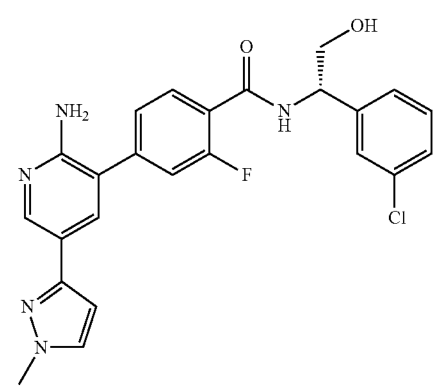 [SMILES: Cn1ccc(-c2cnc(N)c(-c3ccc(C(=O)N[C@H](CO)c4cccc(Cl)c4)c(F)c3)c2)n1] | (S)-4-(2-amino-5-(1-meethyl-1H-pyrazol-3-yl)pyridin-3-yl)-N-(1-(3-chlorophenyl)-2-hyddroxyethyl)-2-fluorobenzamide | 446 | 0.67 | 1H NMR (400 MHZ, METHANOL-d4) δ ppm 8.82-8.62 (m, 1H), 8.12 (d, J = 2.0 Hz, 1H), 8.00-7.76 (m, 2H), 7.58-7.17 (m, 7H), 6.49 (d, J = 2.0 Hz, 1H), 5.20 (d, J = 5.9 Hz, 1H), 3.95-3.69 (m, 5H) |

TABLE 4-continued

Compounds prepared using Method 2 described above.

| Example | Structure | Name | MH+ | R_t (min) | NMR |
|---|---|---|---|---|---|
| 151 | 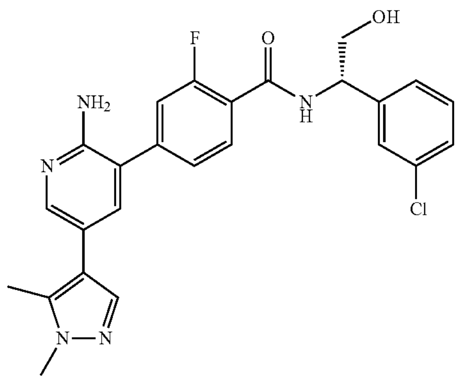 [SMILES: Cc1c(-c2cnc(N)c(-c3ccc(C(=O)N[C@H](CO)c4cccc(Cl)c4)c(F)c3)c2)cnn1C] | (S)-4-(2-amino-5-(1,5-dimethyl-1H-pyrazol-4-yl)pyridin-3-yl)-N-(1-(3-chlorophenyl)-2-hydroxyethyl)-2-fluorobenzamide | 480.2 | 0.69 | 1H NMR (400 MHZ, METHANOL-d4) δ ppm 7.90 (m, 1H), 7.85 (m, 1H), 7.81 (m, 1H), 7.55 (s, 1H), 7.42-7.34 (m, 3H), 7.30-7.24 (m, 2 H), 7.21 (m, 1H), 5.10 (m, 1 H), 3.82-3.71 (m, 2H), 3.75 (s, 3H), 2.31 (s, 3H) |
| 152 | 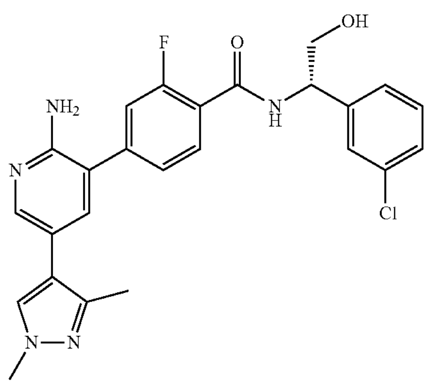 [SMILES: Cc1nn(C)cc1-c1cnc(N)c(-c2ccc(C(=O)N[C@H](CO)c3cccc(Cl)c3)c(F)c2)c1] | (S)-4-(2-amino-5-(1,3-dimethyl-1H-pyrazol-4-yl)pyridin-3-yl)-N-(1-(3-chlorophenyl)-2-hydroxyethyl)-2-fluorobenzamide | 480.2 | 0.69 | 1H NMR (400 MHZ, METHANOL-d4) δ ppm 7.92 (m, 1H), 7.87 (m, 1H), 7.81 (m, 1H), 7.76 (s, 1H), 7.41-7.34 (m, 3H), 7.30-7.24 (m, 2 H), 7.21 (m, 1H), 5.10 (m, 1 H), 3.85-3.67 (m, 2H), 3.76 (s, 3H), 2.26 (s, 3H) |
| 153 | 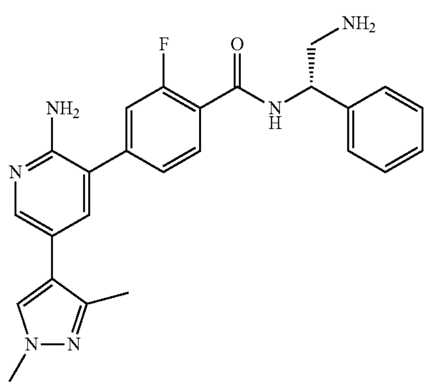 [SMILES: Cc1nn(C)cc1-c1cnc(N)c(-c2ccc(C(=O)N[C@H](CN)c3ccccc3)c(F)c2)c1] | (S)-N-(2-amino-1-phenylethyl)-4-(2-amino-5-(1,3-dimethyl-1H-pyrazol-4-yl)pyridin-3-yl)-2-fluorobenzamide | 445.3 | 0.56 | 1H NMR (400 MHZ, METHANOL-d4) δ ppm 7.88 (m, 2H), 7.84 (m, 1H), 7.74 (m, 1H), 7.44-7.33 (m, 6H), 7.33-7.27 (m, 1H), 5.40 (m, 1 H), 3.76 (s, 3H), 3.38 (m, 2H), 2.25 (s, 3H) |
| 154 | 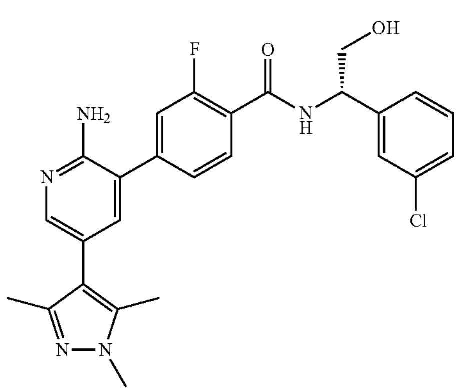 [SMILES: Cc1nn(C)c(C)c1-c1cnc(N)c(-c2ccc(C(=O)N[C@H](CO)c3cccc(Cl)c3)c(F)c2)c1] | (S)-4-(2-amino-5-(1,3,5-trimethyl-1H-pyrazol-4-yl)pyridin-3-yl)-N-(1-(3-chlorophenyl)-2-hydroxyethyl)-2-fluorobenzamide | 494.3 | 0.63 | 1H NMR (400 MHz, CD3OD) δ 7.77 (m, 3H), 7.37 (m, 2H), 7.27 (m, 1H), 5.1 (m, 1H), 3.76 (M, 2H), 3,67 (s, 3H), 2.18 (s, 3H), 2.11 (s, 3H) |

TABLE 4-continued

Compounds prepared using Method 2 described above.

| Example | Structure | Name | MH+ | R$_t$ (min) | NMR |
|---|---|---|---|---|---|
| 155 | 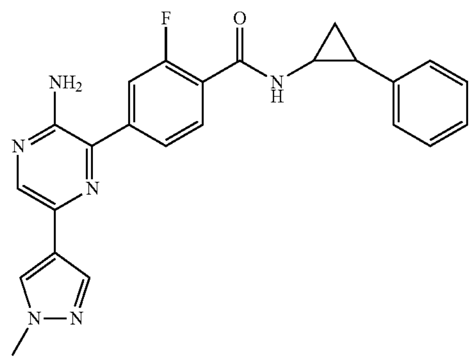 [SMILES: Cn1cc(-c2cnc(N)c(-c3ccc(C(=O)NC4CC4c4ccccc4)c(F)c3)n2)cn1] | 4-(3-amino-6-(1-methyl-1H-pyrazol-4-yl)pyrazin-2-yl)-2-fluoro-N-(2-phenylcyclopropyl)benzamide | 429.1 | 0.81 | 1H NMR (400 MHz, CD$_3$OD) δ 8.18 (s, 1H), 7.98 (s, 1H), 7.84 (s, 1H), 7.74 (m, 1H), 7.68-7-62 (m, 2H), 7.31-7.12 (m, 5H), 3.84 (s, 3H), 3.01 (m, 1H), 2.12 (m, 1H), 1.24 (m, 2H) |
| 156 | 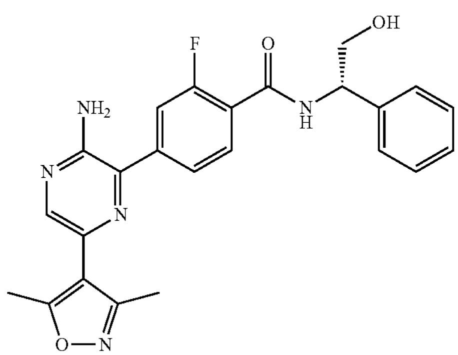 [SMILES: Cc1noc(C)c1-c1cnc(N)c(-c2ccc(C(=O)N[C@H](CO)c3ccccc3)c(F)c2)n1] | (S)-4-(3-amino-6-(3,5-dimethylisozazol-4-yl)pyrazin-2-yl)-2-fluoro-N-(2-hydroxy-1-phenylethyl)benzamide | 448.2 | 0.74 | H NMR (400 MHz, CD$_3$OD) δ 8.03 (s, 1H), 7.77 (m, 1H), 7.64 (m, 1H), 7.41 (m, 1H), 7.34 (m, 2H), 7.27 (m, 2H), 7.19 (m, 1H), 5.13 (m, 1H), 3.77 (m, 2H), 2.46 (s, 3H), 2.30 (s, 3H) |
| 157 | 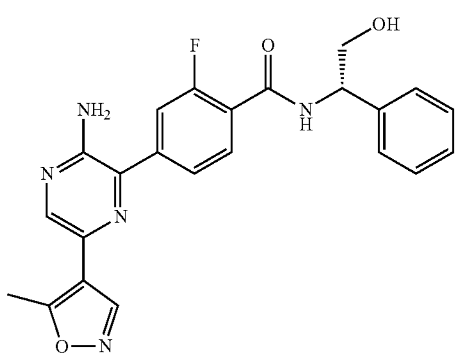 [SMILES: Cc1oncc1-c1cnc(N)c(-c2ccc(C(=O)N[C@H](CO)c3ccccc3)c(F)c2)n1] | (S)-4-(3-amino-6-(5-methylisoxazol-4-yl)pyrazin-2-yl)-2-fluoro-N-(2-hydroxy-1-phenylethyl)benzamide | 434.2 | 0.74 | 1H NMR (400 MHz, CD$_3$OD) δ 8.86 (m, 1H), 8.19 (m, 1H), 7.77 (m, 1H), 7.68-7.56 (m, 2H), 7.36-7.31 (m, 2H), 7.30-7.23 (m, 2H), 7.18 (m, 1H), 5.12 (m, 1H), 3.77 (m, 2H), 2.62 (s, 3H) |
| 158 | 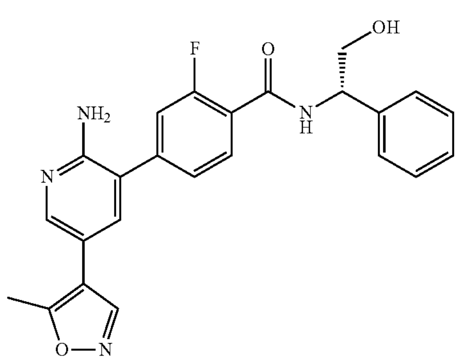 [SMILES: Cc1oncc1-c1cnc(N)c(-c2ccc(C(=O)N[C@H](CO)c3ccccc3)c(F)c2)c1] | (S)-4-(2-amino-5-(5-methylisoxazol-4-yl)pyridin-3-yl)-2-fluoro-N-(2-hyddroxy-1-phenylethyl)benzamide | 433.3 | 0.61 | 1H NMR (400 MHz, CD$_3$OD) δ 8.19 (d, J = 2.3 Hz, 1H), 7.91 (s, 1H), 7.85 (m, 1H), 7.77 (d, J = 0.7 Hz, 1H), 7.65 (d, J = 2.3 Hz, 1H), 7.51-7.23 (m, 6H), 5.29-5.11 (m, 1H), 3.99-3.77 (m, 5H) |

TABLE 4-continued

Compounds prepared using Method 2 described above.

| Example | Structure | Name | MH+ | R$_t$ (min) | NMR |
|---|---|---|---|---|---|
| 159 | 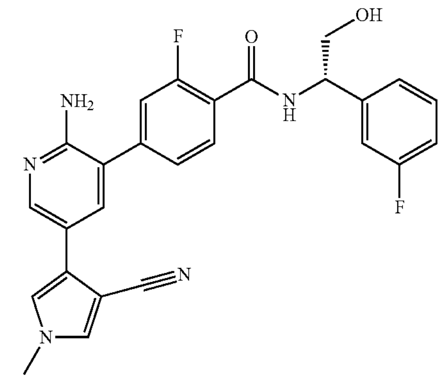 [SMILES: Cn1cc(C#N)c(-c2cnc(N)c(-c3ccc(C(=O)N[C@H](CO)c4cccc(F)c4)c(F)c3)c2)c1] | (S)-4-(2-amino-5-(3-cyano-1-methyl-1H-pyrazol-4-yl)pyridin-3-yl)-2-fluoro-N-(1-(3-fluorophenyl)-2-hydroxyethyl)benzamide | 475.3 | 0.64 | 1H NMR (400 MHz, CD$_3$OD) δ 8.3 (m, 1H), 8.06 (s, 1H), 7.86 (m, 1H), 7.73 (m, 1H), 7.48-7.733 (m, 3H), 7.26 (m, 1H), 7.17 (m, 1H), 7.01 (m, 1H), 5.21 (m, 1H), 3.99 (s, 3H), 3.88 (m, 2H) |
| 160 | 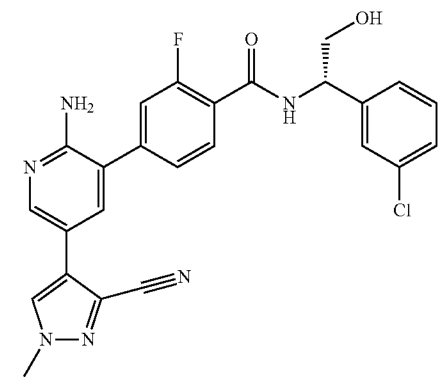 [SMILES: Cn1cc(-c2cnc(N)c(-c3ccc(C(=O)N[C@H](CO)c4cccc(Cl)c4)c(F)c3)c2)c(C#N)n1] | (S)-4-(2-amino-5-(3-cyano-1-methyl-1H-pyrazol-4-yl)pyridin-3-yl)-N-(1-(3-chlorophenyl)-2-hydroxyethyl)-2-fluorobenzamide | 491.1 | 0.68 | 1H NMR (400 MHz, CD$_3$OD) δ 8.62 (m, 1H), 8.17 (m, 1H), 8.07 (s, 1H), 7.95 (m, 1H), 7.80 (m, 1H), 7.38 (m, 3H), 7.27 (m, 3H), 7.21 (m, 1H), 5.10 (m, 1H), 3.92 (s, 3H), 3.78 (m, 2H) |
| 161 | 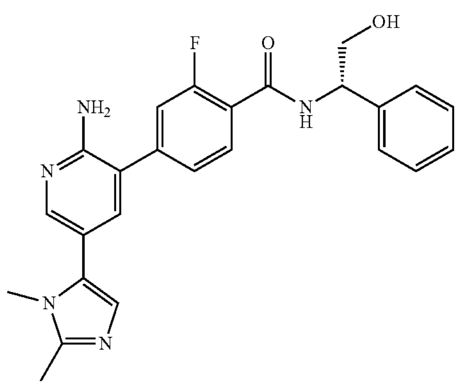 [SMILES: Cc1ncc(-c2cnc(N)c(-c3ccc(C(=O)N[C@H](CO)c4ccccc4)c(F)c3)c2)n1C] | (S)-4-(2-amino-5-(1,2-dimethyl-1H-imidazol-5-yl)pyridin-3-yl)-2-fluoro-N-(2-hydroxy-1-phenylethyl)benzamide | 446.2 | 0.45 | 1H NMR (400 MHz, CD$_3$OD) δ 8.59 (m, 1H), 8.12 (m, 1H), 7.88 (m, 1H), 7.68 (m, 1H), 7.53 (s, 1H), 7.48-7.38 (m, 5H), 7.41-7.31 (m, 1H), 7.31-7.23 (m, 1H), 5.23 (m, 1H), 3.95-3.77 (m, 2H), 3.70 (s, 3H), 2.68 (s, 3H). |
| 162 | 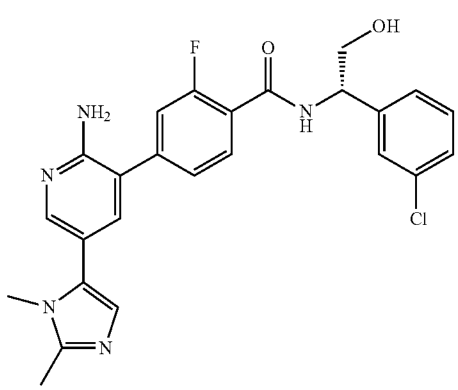 [SMILES: Cc1ncc(-c2cnc(N)c(-c3ccc(C(=O)N[C@H](CO)c4cccc(F)c4)c(F)c3)c2)n1C] | (S)-4-(2-amino-5-(1,2-dimethyl-1H-imidazol-5-yl)pyridin-3-yl)-N-(1-(3-chlorophenyl)-2-hydroxyethyl)-2-fluorobenzamide | 480.3 | 0.56 | 1H NMR (400 MHz, CD$_3$OD) δ 8.66 (m, 1H), 8.12 (m, 1H), 7.88 (m, 1H), 7.70 (m, 1H), 7.53 (s, 1H), 7.50-7.39 (m, 3H), 7.35 (m, 2H), 7.32 (, 2H), 5.26-5.11 (m, 1H), 3.90-3.76 (m, 2H), 3.70 (s, 3H), 2.68 (s, 3H) |

TABLE 4-continued

Compounds prepared using Method 2 described above.

| Example | Structure | Name | MH+ | R$_t$ (min) | NMR |
|---|---|---|---|---|---|
| 163 | 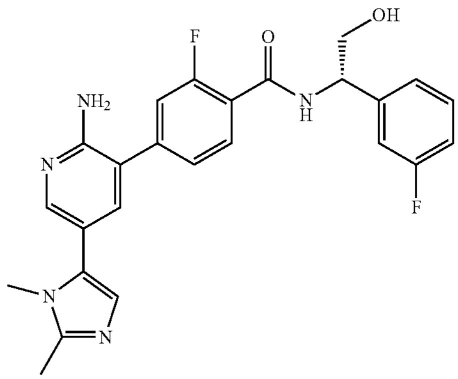 | (S)-4-(2-amino-5-(1,2-dimethyl-1H-imidazol-5-yl)pyridin-3-yl)-2-fluoro-N-(1-(3-fluorophenyl)-2-hydroxyethyl)benzamide | 464.2 | 0.46 | 1H NMR (400 MHz, CD$_3$OD) δ 8.64 (m, 1H), 8.12 (m, 1H), 7.88 (m, 1H), 7.66 (s, 1H), 7.52 (s, 1H), 7.45 (m, 1H), 7.43 (m, 1H), 7.38 (m 1H), 7.25 (m, 1H), 7.18 (m, 1H), 7.01 (m, 1H), 4.91 (m, 1H), 3.87 (m 2H), 3.7 (s, 3H), 2.68 (s, 3H) |
| 164 | 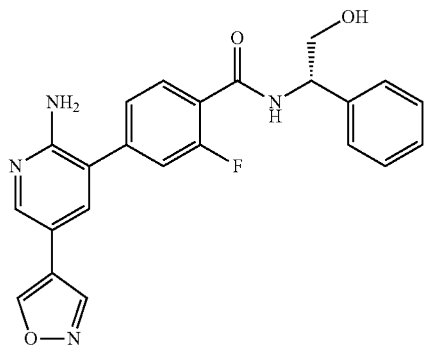 [SMILES: Nc1ncc(-c2cnoc2)cc1-c1ccc(C(=O)N[C@H](CO)c2ccccc2)c(F)c1] | (S)-4-(2-amino-5-(isoazol-4-yl)pyridin-3-yl)-2-fluoro-N-(2-hydroxy-1-phenylethyl)benzamide | 419.2 | 0.57 | 1H NMR (400 MHz, CD$_3$OD) δ 9.17 (s 1H), 8.90 (s, 1H), 8.65 (br. s., 1H), 8.28 (d, J = 2.0 Hz, 1H), 8.16 (d, J = 2.0 Hz, 1H), 7.91 (t, J = 7.8 Hz, 1 H), 7.55-7.25 (m, 6H), 5.23 (d, J = 5.1 Hz, 1H), 3.96-3.75 (m, 2H) |
| 165 | 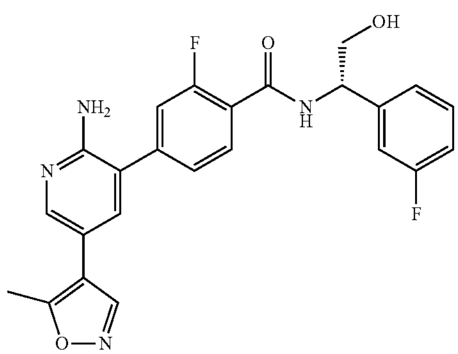 [SMILES: Cc1oncc1-c1cnc(N)c(-c2ccc(C(=O)N[C@H](CO)c3cccc(F)c3)c(F)c2)c1] | (S)-4-(2-amino-5-(5-methylisoxazol-4-yl)pyridin-3-yl)-2-fluoro-N-(1-(3-fluorophenyl)-2-hydroxyethyl)benzamide | 451.1 | 0.2 | 1H NMR (400 MHz, CD$_3$OD) δ 8.58 (m, 1H), 8.53 (s, 1H), 8.00 (m, 1H), 7.88 (m,, 1H), 7.81 (m, 1H), 7.38 (m, 2H), 7.29 (m, 1H), 7.15 (m, 1H), 5.13 (m, 1H), 3.78 (m, 2H), 2.49 (s, 3H) |
| 166 | 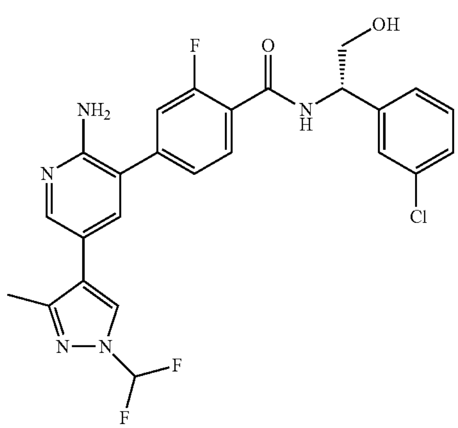 [SMILES: Cc1nn(C(F)F)cc1-c1cnc(N)c(-c2ccc(C(=O)N[C@H](CO)c3cccc(Cl)c3)c(F)c2)c1] | (S)-4-(2-amino-5-(1-(difluoromethyl)-3-methyl-1H-pyrazol-4-yl)pyridin-3-yl)-N-(1-(3-chlorophenyl)-2-hydroxyethyl)-2-fluorobenzamide | 516.9 | 0.7 | 1H NMR (400 MHz, CD$_3$OD) δ ppm 8.32 (s, 1H), 8.06 (m, 1 H), 8.02 (m, 1H), 7.91 (m, 1 H), 7.57-7.4 (m, 4H), 7.39-7.24 (m, 4H), 5.19 (m, 1H), 3.86 (m, 2H), 2.41 (s, 3H) |

TABLE 4-continued

Compounds prepared using Method 2 described above.

| Example | Structure | Name | MH+ | R$_t$ (min) | NMR |
|---|---|---|---|---|---|
| 167 | 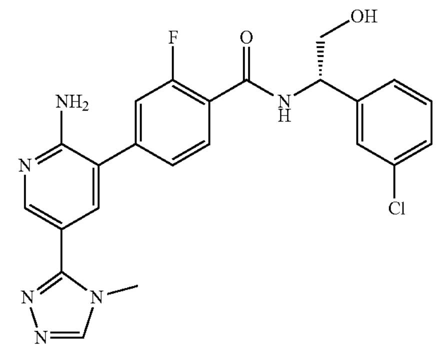 [SMILES: Cn1cnnc1-c1cnc(N)c(-c2ccc(C(=O)N[C@H](CO)c3cccc(Cl)c3)c(F)c2)c1] | (S)-4-(2-amino-5-(4-methyl-4H-1,2,4-triazol-3-yl)pyridin-3-yl)-N-(1-(3-chlorophenyl)-2-hydroxyethyl)-2-fluorobenzamide | 467.3 | 0.59 | 1H NMR (400 MHz, CD$_3$OD) δ 8.71-8.54 (m, 1H), 8.29 (d, J = 2.2 Hz, 1H), 7.94 (m, 2H), 7.81 (m, 1H), 7.38 (m, 3H), 7.28 (m,, 2H), 7.22 (m, 1H), 5.12 (m, 1H), 3.95 (s, 3H), 3.86-3.65 (m, 2H) |
| 168 | 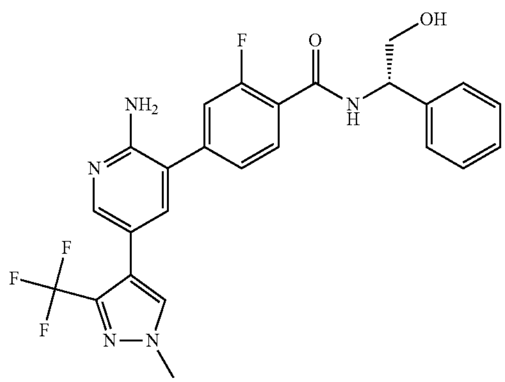 [SMILES: Cn1cc(-c2cnc(N)c(-c3ccc(C(=O)N[C@H](CO)c4ccccc4)c(F)c3)c2)c(C(F)(F)F)n1] | (S)-4-(2-amino-5-(1-methyl-3-(trifluoromethyl)-1H-pyrazol-4-yl)pyridin-3-yl)-2-fluoro-N-(2-hydroxy-1-phenylethyl) benzamide | 500.1 | 0.66 | 1H NMR (400 MHz, CD$_3$OD) δ ppm 8.54 (m, 1H), 7.94-7.84 (m, 1H), 7.83-7.74 (m, 1H), 7.75-7.68 (m, 1H), 7.63-7.54 (m, 1H), 7.41-7.30 (m, 4H), 7.29-7.22 (m, 2H), 7.21-7.11 (m, 1H), 5.21-5.06 (m, 1H), 4.02-3.93 (m, 3H), 3.86-3.65 (m, 2H) |
| 169 | 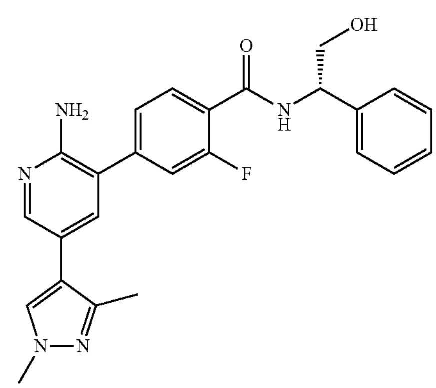 [SMILES: Cc1nn(C)cc1-c1cnc(N)c(-c2ccc(C(=O)N[C@H](CO)c3ccccc3)c(F)c2)c1] | (S)-4-(2-amino-5-(1,3-dimethyl-1H-pyrazol-4-yl)pyridin-3-yl)-2-fluoro-N-(2-hydroxy-1-phenylethyl) benzamide | 436.1 | 0.61 | 1H NMR (400 MHz, CD$_3$OD) δ 7.87 (d, J = 2.0 Hz, 1H), 7.91 (d, J = 2.3 Hz, 1H), 7.81 (t, J = 7.8 Hz, 1H), 7.75 (s, 1H), 7.41-7.30 (m,, 4H), 7.27 (t, J = 7.6 Hz, 2H), 7.20 (d, J = 7.0 Hz, 1 H), 5.13 (t, J = 5.9 Hz, 1H), 3.84-3.69 (m, 5H), 2.26 (s, 3 H) |
| 170 | 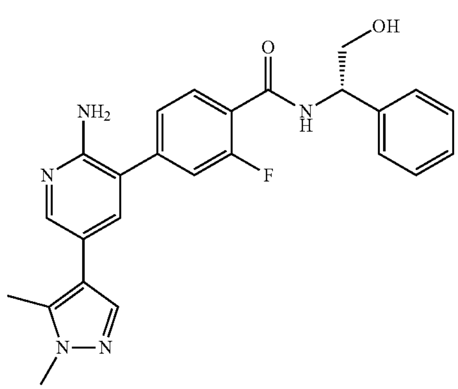 [SMILES: Cc1c(-c2cnc(N)c(-c3ccc(C(=O)N[C@H](CO)c4ccccc4)c(F)c3)c2)cnn1C] | (S)-4-(2-amino-5-(1,5-dimethyl-1H-pyrazol-4-yl)pyridin-3-yl)-2-fluoro-N-(2-hyrdroxy-1-phenylethyl) benzamide | 446.3 | 0.62 | 1H NMR (400 MHz, CD$_3$OD) δ 7.97 (d, J = 2.0 Hz, 1H), 7.93 (d, J = 2.0 Hz, 1H), 7.89 (t, J = 7.8 Hz, 1H), 7.63 (s, 1H), 7.48-7.31 (m, 6H), 7.27 (d, J = 7.0 Hz, 1H), 5.20 (t, J = 5.9 Hz, 1 H), 3.91-3.74 (m, 5H), 2.41-2.36 (m, 3H) |

TABLE 4-continued

Compounds prepared using Method 2 described above.

| Example | Structure | Name | MH+ | Rt (min) | NMR |
|---|---|---|---|---|---|
| 171 | 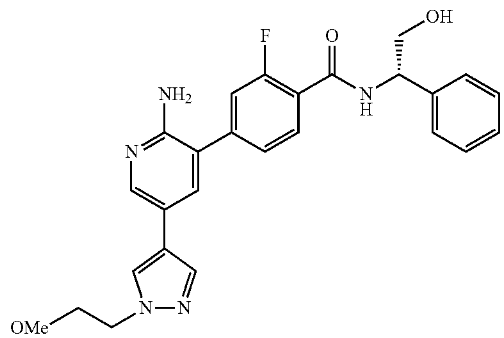 [SMILES: COCCn1cc(-c2cnc(N)c(-c3ccc(C(=O)N[C@H](CO)c4ccccc4)c(F)c3)c2)cn1] | (S)-4-(2-amino-5-(1-(2-methoxyethyl)-1H-pyrazol-4-yl)pyridin-3-yl)-2-fluoro-N-(2-hydroxy-1-phenylethyl)benzamide | 476.3 | 0.6 | 1H NMR (400 MHz, CD$_3$OD) δ 8.16 (d, J = 2.0 Hz, 1H), 8.13 (d, J = 2.3 Hz, 1H), 8.09 (s, 1 H), 7.94-7.88 (m, 2H), 7.51-7.40 (m, 4H), 7.37 (t, J = 7.6 Hz, 2H), 7.29 (d, J = 7.0 Hz, 1 H), 5.23 (d, J = 6.7 Hz, 1H), 4.33 (t, J = 5.1 Hz, 2H), 3.94-3.80 (m, 2H), 3.75 (t, J = 5.1 Hz, 2H) |
| 172 | 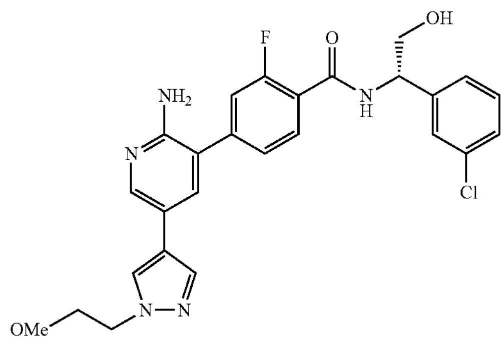 [SMILES: COCCn1cc(-c2cnc(N)c(-c3ccc(C(=O)N[C@H](CO)c4cccc(Cl)c4)c(F)c3)c2)cn1] | (s)-4-(2-amino-5-(1-(2-methoxyethyl)-1H-pyrazol-4-yl)pyridin-3-yl)-N-(1-(3-chlorophenyl)-2-hydroxyethyl)-2-fluorobenzamide | 510.3 | 0.67 | 1H NMR (400 MHz, CD$_3$OD) δ 8.17 (d, J = 2.3 Hz, 1H), 8.12 (d, J = 2.0 Hz, 1H), 8.09 (s, 1 H), 7.94-7.88 (m, 2H), 7.52-7.44 (m, 3H), 7.38-7.32 (m, 2 H), 7.31 (d, j = 2.3 Hz, 1H), 5.20 (s, 1H), 4.33 (t, J = 5.1 Hz, 2H), 3.93-3.80 (m, 2H), 3.75 (t, J = 5.1 Hz, 2H) |

Method 3

Example 173

Synthesis of 4-(3-amino-6-(tetrahydro-2H-pyran-4-yl)pyrazin-2-yl)-N-(3-chlorobenzyl)-2-fluorobenzamide Scheme 62

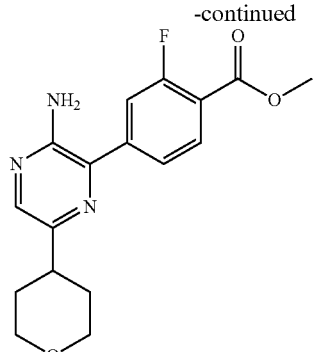

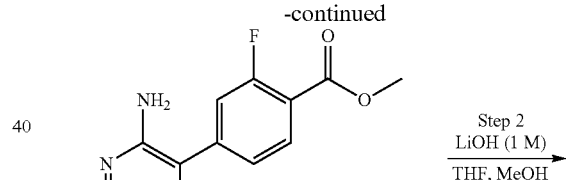

-continued

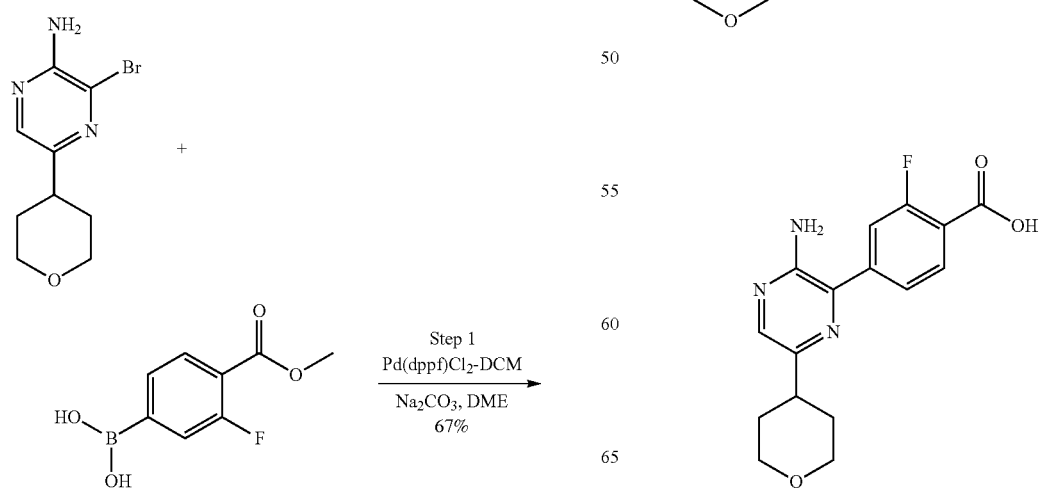

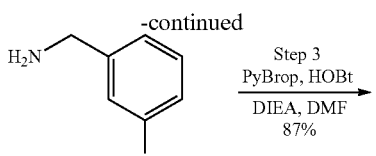

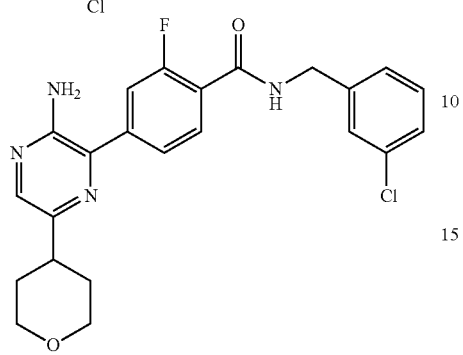

Step 1. methyl 4-(3-amino-6-(tetrahydro-2H-pyran-4-yl)pyrazin-2-yl)-2-fluorobenzoate To a solution of methyl 2-fluoro-4-(4,4,5,5-tetramethyl-1,3,2-dioxaborolan-2-yl)benzoate (259 mg, 1.308 mmol), 3-bromo-5-(tetrahydro-2H-pyran-4-yl)pyrazin-2-amine (225 mg, 0.872 mmol), and PdCl$_2$(dppf) (64 mg, 0.087 mmol) was added DME (6.5 mL) and 2 M Na$_2$CO$_3$ solution (3.2 mL). The reaction mixture was heated at the microwave synthesizer (120° C., 10 min). The reaction mixture was worked up with EtOAc. The organic layer was washed with water and brine, dried over anhydrous sodium sulfate, filtered off, and concentrated in vacuo. The crude product was purified by flash chromatography (gradient EtOAc in heptane) to yield the desired product (192 mg, 67%). LCMS (m/z): 332.2 (MH$^+$), 0.63 min.

Step 2. 4-(3-amino-6-(tetrahydro-2H-pyran-4-yl)pyrazin-2-yl)-2-fluorobenzoic acid To a solution of methyl 4-(3-amino-6-(tetrahydro-2H-pyran-4-yl)pyrazin-2-yl)-2-fluorobenzoate (104 mg, 0.314 mmol) in THF (698 μL) and MeOH (349 μL) was added LiOH (1 M solution) (565 μL, 0.565 mmol). The reaction mixture was stirred for 1 h at room temperature. The reaction mixture was quenched with 1N HCl solution up to pH 5, and worked up with EtOAc. The organic layer was washed with water and brine, dried over anhydrous sodium sulfate, filtered off, and concentrated in vacuo. The crude product was used for the next step. LCMS (m/z): 318.3 (MH$^+$), 0.5 min.

Step 3. 4-(3-amino-6-(tetrahydro-2H-pyran-4-yl)pyrazin-2-yl)-N-(3-chlorobenzyl)-2-fluorobenzamide To a solution of 4-(3-amino-6-(tetrahydro-2H-pyran-4-yl)pyrazin-2-yl)-2-fluorobenzoic acid (17 mg, 0.054 mmol) and (3-chlorophenyl)methanamine (8.34 mg, 0.059 mmol) in THF (268 μL) was added PyBroP (27.5 mg, 0.059 mmol), DIEA (28.1 μL, 0.161 mmol) and HOBT (9.02 mg, 0.059 mmol). The reaction mixture was stirred overnight at room temperature. All volatile material was removed in vacuo and dissolved in DCM. The crude product dissolved in DCM was loaded to flash chromatography column (gradient EtOAc in heptane) providing 4-(3-amino-6-(tetrahydro-2H-pyran-4-yl)pyrazin-2-yl)-N-(3-chlorobenzyl)-2-fluorobenzamide in 87% yield. LCMS (m/z): 441.1 (MH$^+$), 0.79 min. $^1$H NMR (400 MHz, DMSO-d$_6$) δ ppm 7.92 (s, 1 H), 7.74 (m, 1 H), 7.63 (m, 2 H), 7.35 (m, 4 H), 6.14 (s, 1 H), 4.48 (m, 2 H), 3.92 (m, 2 H), 3.43 (m, 2 H), 1.73 (m, 4 H).

Example 174

Synthesis of (S)-N-(2-amino-1-(3-chlorophenyl)ethyl)-4-(3-amino-6-(tetrahydro-2H-pyran-4-yl)pyrazin-2-yl)-2-fluorobenzamide Scheme 63

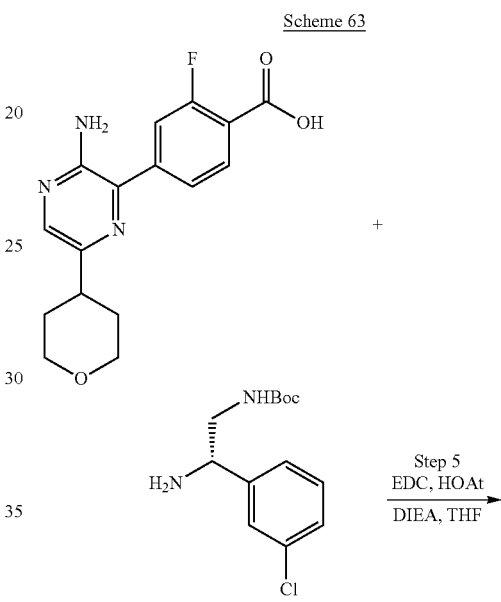

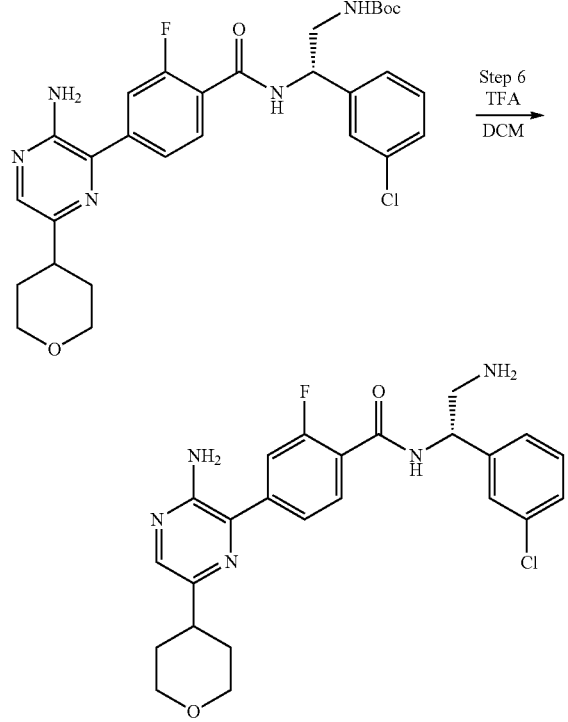

Step 1. (S)-tert-butyl (2-(4-(3-amino-6-(tetrahydro-2H-pyran-4-yl)pyrazin-2-yl)-2-fluorobenzamido)-2-(3-chlorophenyl)ethyl)carbamate To a solution of 4-(3-amino-6-(tetrahydro-2H-pyran-4-yl)pyrazin-2-yl)-2-fluorobenzoic acid (35 mg, 0.110 mmol) in DMF (368 μL) was add (S)-tert-butyl (2-amino-2-(3-chlorophenyl)ethyl)carbamate (33.9 mg, 0.110 mmol), aza-HOBt (22.52 mg, 0.165 mmol), EDC (31.7 mg, 0.165 mmol), and DIEA (57.8 μL, 0.331 mmol). The reaction mixture was stirred at room temperature for 3 h. The reaction mixture was partitioned between EtOAc and water. The organic layer was washed by NaHCO$_3$, water and brine, dried over anhydrous sodium sulfate, filtered off, and concentrated in vacuo yielding crude (S)-tert-butyl (2-(4-(3-amino-6-(tetrahydro-2H-pyran-4-yl)pyrazin-2-yl)-2-fluorobenzamido)-2-(3-chlorophenyl)ethyl)carbamate (>99%).

Step 2. (S)N-(2-amino-1-(3-chlorophenyl)ethyl)-4-(3-amino-6-(tetrahydro-2H-pyran-4-yl)pyrazin-2-yl)-2-fluorobenzamide The crude (S)-tert-butyl (2-(4-(3-amino-6-(tetrahydro-2H-pyran-4-yl)pyrazin-2-yl)-2-fluorobenzamido)-2-(3-chlorophenyl)ethyl)carbamate was dissolved in DCM (1.0 mL). After TFA (0.3 mL) was added, the reaction mixture was stirred at room temperature for 10 min. The reaction mixture was diluted with toluene and concentrated to dryness. The crude product was purified by reverse phase prep HPLC. The pure fractions were combined and lyophilized yielding (S)N-(2-amino-1-(3-chlorophenyl)ethyl)-4-(3-amino-6-(tetrahydro-2H-pyran-4-yl)pyrazin-2-yl)-2-fluorobenzamide as TFA salt (50% yield over 2 steps). LCMS (m/z): 470.1 (MH$^+$), 0.67 min; 1H NMR (400 MHz, CD$_3$OD) δ ppm 7.95-7.85 (m, 2H), 7.72 (d, J=8.2 Hz, 1H), 7.64 (d, J=12.1 Hz, 1H), 7.55 (s, 1H), 7.49-7.38 (m, 3H), 5.49 (dd, J=5.7, 8.8 Hz, 1H), 4.04 (dd, J=3.1, 11.3 Hz, 2H), 3.57 (dt, J=2.0, 11.5 Hz, 2H), 3.51-3.41 (m, 2H), 2.98-2.88 (m, 1H), 1.97-1.76 (m, 4H).

Example 175

Synthesis of 4-(3-amino-6-((1r,4S)-4-hydroxycyclohexyl)pyrazin-2-yl)-N-((S)-1-(3-bromo-5-fluorophenyl)-2-hydroxyethyl)-2-fluorobenzamide Scheme 64

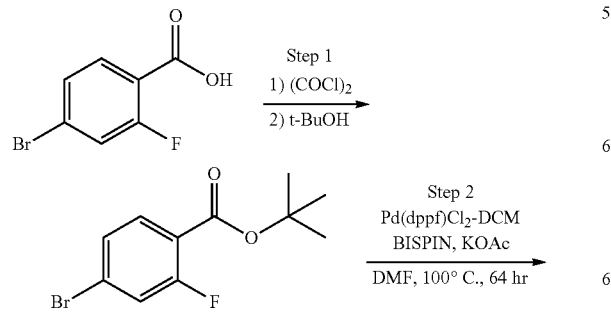

-continued

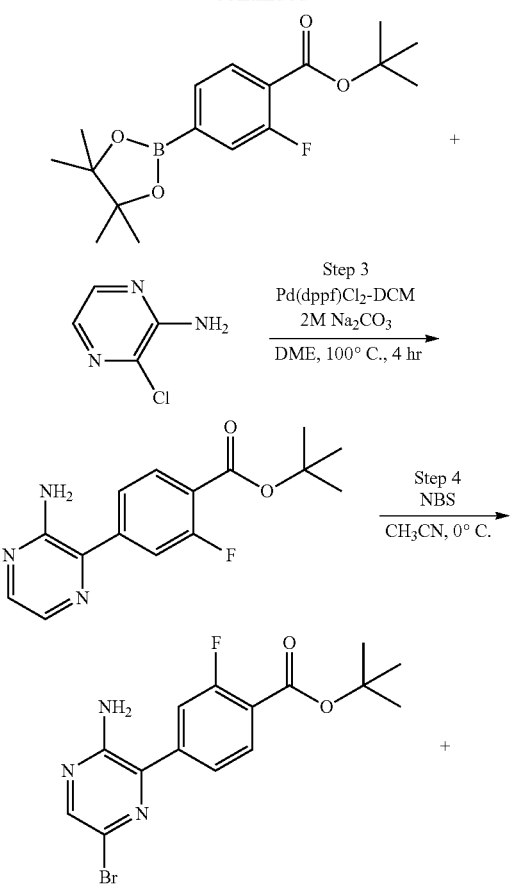

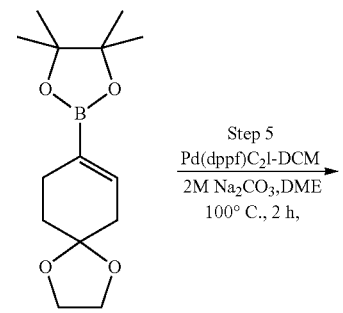

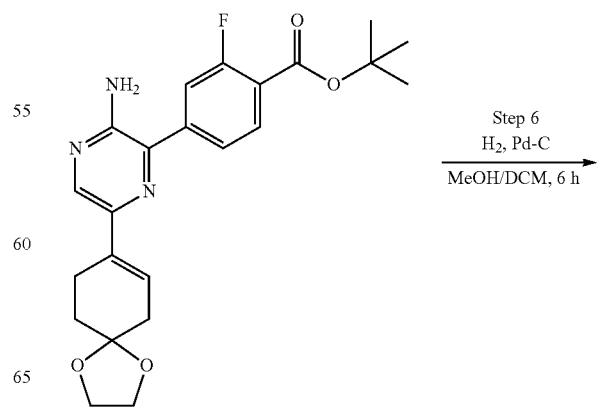

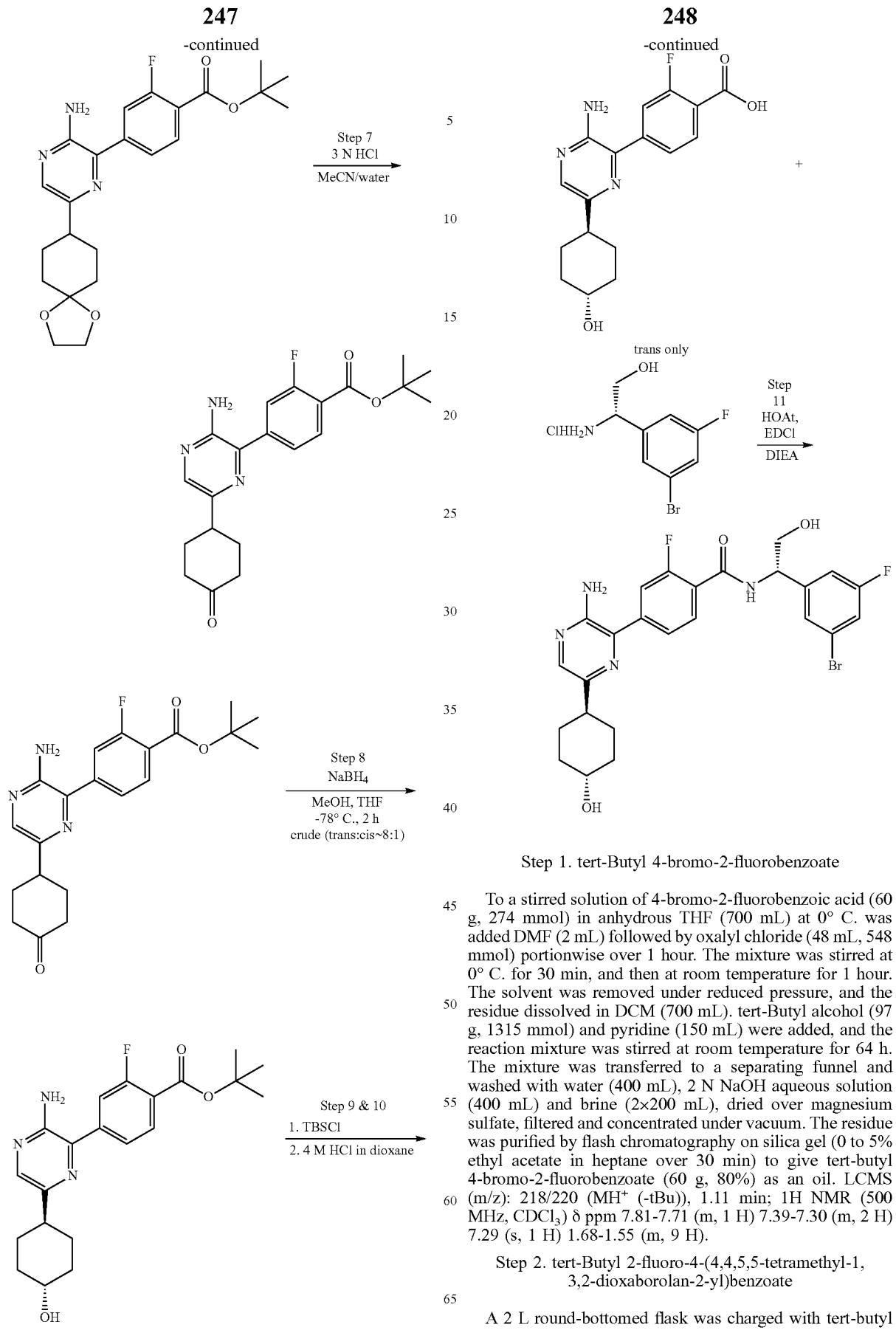

Step 1. tert-Butyl 4-bromo-2-fluorobenzoate

To a stirred solution of 4-bromo-2-fluorobenzoic acid (60 g, 274 mmol) in anhydrous THF (700 mL) at 0° C. was added DMF (2 mL) followed by oxalyl chloride (48 mL, 548 mmol) portionwise over 1 hour. The mixture was stirred at 0° C. for 30 min, and then at room temperature for 1 hour. The solvent was removed under reduced pressure, and the residue dissolved in DCM (700 mL). tert-Butyl alcohol (97 g, 1315 mmol) and pyridine (150 mL) were added, and the reaction mixture was stirred at room temperature for 64 h. The mixture was transferred to a separating funnel and washed with water (400 mL), 2 N NaOH aqueous solution (400 mL) and brine (2×200 mL), dried over magnesium sulfate, filtered and concentrated under vacuum. The residue was purified by flash chromatography on silica gel (0 to 5% ethyl acetate in heptane over 30 min) to give tert-butyl 4-bromo-2-fluorobenzoate (60 g, 80%) as an oil. LCMS (m/z): 218/220 (MH$^+$ (-tBu)), 1.11 min; 1H NMR (500 MHz, CDCl$_3$) δ ppm 7.81-7.71 (m, 1 H) 7.39-7.30 (m, 2 H) 7.29 (s, 1 H) 1.68-1.55 (m, 9 H).

Step 2. tert-Butyl 2-fluoro-4-(4,4,5,5-tetramethyl-1,3,2-dioxaborolan-2-yl)benzoate A 2 L round-bottomed flask was charged with tert-butyl 4-bromo-2-fluorobenzoate (30 g, 114 mmol), bis(pinocolato)diboron (41.5 g, 164 mmol), potassium acetate (32.1 g, 327 mmol), PdCl$_2$(dppf)-CH$_2$Cl$_2$ (2.67 g, 3.27 mmol) and 1,4-dioxane (500 mL). The reaction mixture was degassed with argon for 15 min, then heated to 95° C. and maintained at this temperature for 16 h. After cooling down, the reaction mixture was evaporated to dryness, dissolved in DCM (300 mL), and filtered over celite washing with DCM (3×100 mL). The filtrate was washed with water (200 mL) and brine (2×200 mL), dried over magnesium sulfate, filtered and concentrated. The residue was purified using flash chromatography on silica gel (0 to 10% EtOAc in heptane over 30 min), giving tert-butyl 2-fluoro-4-(4,4,5,5-tetramethyl-1,3,2-dioxaborolan-2-yl)benzoate (27 g, 90%) as a solid.

LCMS (m/z): 267 (MH$^+$ (-tBu)), 1.23 min; 1H NMR (500 MHz, DMSO-d$_6$) δ ppm 7.83 (t, 1 H) 7.57 (d, 1 H) 7.43 (d, 1 H) 1.62-1.46 (m, 9 H) 1.34-1.25 (m, 12 H).

Step 3. tert-Butyl 4-(3-aminopyrazin-2-yl)-2-fluorobenzoate

A 2 L round-bottomed flask was charged with tert-butyl 2-fluoro-4-(4,4,5,5-tetramethyl-1,3,2-dioxaborolan-2-yl) benzoate (54 g, 151 mmol), 2-amino-3-chloropyrazine (19.54 g, 151 mmol), 2 N sodium carbonate (158 mL, 317 mmol) and DME (600 mL). The reaction mixture was degassed for 10 min using argon, and then PdCl$_2$(dppf)-CH$_2$Cl$_2$ (6.16 g, 7.54 mmol) was added. The reaction mixture was heated to 100° C. and maintained at this temperature for 4 h. After cooling down, the reaction mixture was poured into water (400 mL) and extracted with EtOAc (3×200 mL). The combined organics were washed with brine (3×200 mL), dried over magnesium sulfate, filtered and concentrated. The crude material was purified using flash chromatography on silica gel (0 to 70% EtOAc in heptane over 50 min), giving tert-butyl 4-(3-aminopyrazin-2-yl)-2-fluorobenzoate (37.7 g, 86%) as a solid. LCMS (m/z): 290 (MH$^+$), 0.80 min; 1H NMR (400 MHz, DMSO-d$_6$) δ ppm 7.98 (d, 1 H) 7.91-7.81 (m, 2 H) 7.65-7.46 (m, 2 H) 6.35 (br. s., 2 H) 1.54 (s, 9 H).

Step 4. tert-butyl 4-(3-amino-6-bromopyrazin-2-yl)-2-fluorobenzoate

To a stirred solution of tert-butyl 4-(3-aminopyrazin-2-yl)-2-fluorobenzoate (37.7 g, 130 mmol) in acetonitrile (800 mL) at 0° C. was added N-bromosuccinimide (23.19 g, 130 mmol) in one portion. The reaction was stirred at 0° C. for 2 h, then quenched with saturated NaHCO$_3$ solution (200 mL) and stirred at 0° C. for 30 min. The mixture was diluted with water (300 mL) and extracted with EtOAc (3×250 mL). The combined organics were washed with water (200 mL) and brine (2×200 mL), dried over magnesium sulfate, filtered and concentrated. The crude material was purified using flash chromatography on silica gel (0 to 40% EtOAc in heptane over 40 min), giving tart-butyl 4-(3-amino-6-bromopyrazin-2-yl)-2-fluorobenzoate (30.9 g, 64%) as a solid. LCMS (m/z): 368/370 (MH$^+$), 1.03 min; 1H NMR (400 MHz, DMSO-d$_6$) δ ppm 8.14 (s, 1 H) 7.97-7.74 (m, 1 H) 7.62-7.39 (m, 2 H) 6.64 (s, 2 H) 1.54 (s, 9 H).

Step 5. Tert-butyl 4-(3-amino-6-(1,4-dioxaspiro[4.5]dec-7-en-8-yl)pyrazin-2-yl)-2-fluorobenzoate To tert-butyl 4-(3-amino-6-bromopyrazin-2-yl)-2-fluorobenzoate (5.17 g, 46.2 mmol) in DME (115 mL) were added 4,4,5,5-tetramethyl-2-(1,4-dioxaspiro[4.5]dec-7-en-8-yl)-1,3,2-dioxaborolane (15.36 g, 57.7 mmol), PdCl$_2$(dppf).CH$_2$Cl$_2$ adduct (1.885 g, 2.309 mmol), and then 2 M aqueous solution sodium carbonate (19.57 g, 185 mmol). The reaction mixture was heated at 100° C. overnight. LCMS indicated the reaction was completed. The reaction was cooled down. To the mixture was added 1000 mL of EtOAc and 300 mL of water. The resulting mixture was stirred for 30 min, and the organic layer was separated. The aqueous layer was extracted with EtOAc (3×200 mL). The organic layers were combined, washed with water three times and brine, dried over sodium sulfate, filtered off, and concentrated in vacuo. The crude product was triturated by ether to provide tert-butyl 4-(3-amino-6-(1,4-dioxaspiro [4.5]dec-7-en-8-yl)pyrazin-2-yl)-2-fluorobenzoate (19.5 g, 45.6 mmol, 99%) as a light yellow solid. LCMS (m/z): 428.1 (MH$^+$), 1.02 min.

Step 6. Tert-butyl 4-(3-amino-6-(1,4-dioxaspiro[4.5]decan-8-yl)pyrazin-2-yl)-2-fluorobenzoate To a solution of tert-butyl 4-(3-amino-6-(1,4-dioxaspiro [4.5]dec-7-en-8-yl)pyrazin-2-yl)-2-fluorobenzoate (11 g, 25.7 mmol) in DCM (100 mL) and MeOH (100 mL) at room temperature was added Pd/C (5 g, 25.7 mmol) (10% in carbon, wet). The resulting mixture was vacuumed, and then refilled with hydrogen. The process was repeated three times. Then the reaction was stirred at room temperature under H$_2$ atmosphere for 6 h. Catalyst was filtered out through Celite®, and washed with DCM. The filtrate was concentrated, and the residue was dissolved in DCM (60 mL), filtered and concentrated. The crude product was purified by flash chromatography eluting with 0-100% of EtOAc/heptane to provide tert-butyl 4-(3-amino-6-(1,4-dioxaspiro[4.5]decan-8-yl)pyrazin-2-yl)-2-fluorobenzoate (8.18 g, 19.04 mmol, 74%) as a light yellow solid. LCMS (m/z): 430.2 (MH$^+$), 0.99 min; 1H NMR (400 MHz, DMSO-d6) δ ppm 7.98-7.82 (m, 2 H), 7.71-7.49 (m, 2 H), 6.13 (s, 2 H), 3.85 (s, 4 H), 3.30 (s, 1 H), 2.77-2.55 (m, 1 H), 2.48 (dt, J=3.62, 1.91 Hz, 2 H), 1.88-1.65 (m, 6 H), 1.63-1.46 (m, 10 H).

Step 7. Tert-butyl 4-(3-amino-6-(4-oxocyclohexyl) pyrazin-2-yl)-2-fluorobenzoate To tert-butyl 4-(3-amino-6-(1,4-dioxaspiro[4.5]decan-8-yl)pyrazin-2-yl)-2-fluorobenzoate (14.34 g, 33.4 mmol) were added acetonitrile (250 mL), water (160 mL) and then 3 M aqueous solutionueous HCl (55.6 mL, 167 mmol). The reaction mixture was stirred at 25° C. for 30 min which was monitored by LCMS. The mixture was basified with 2 M NaOH aqueous solution under stirring to pH 9. Light yellow solid was precipitated out. Acetonitrile was removed under reduced pressure at room temperature. The solid was filtered and washed with water (2×30 mL), and dried under high vacuum overnight to afford tert-butyl 4-(3-amino-6-(4-oxocyclohexyl)pyrazin-2-yl)-2-fluorobenzoate (12 g, 31.1 mmol, 93%) as a light yellow solid. LCMS (m/z): 386.1 (MH$^+$), 0.89 min; 1H NMR (400 MHz, ACETONITRILE-d3) δ ppm 8.05-7.89 (m, 2 H) 7.73-7.51 (m, 2 H), 5.14 (br. s., 2 H), 3.30-3.08 (m, 1 H), 2.64-2.48 (m, 2 H), 2.40 (br. s., 2 H), 2.30-2.17 (m, 2 H), 2.12-1.99 (m, 2 H), 1.96 (dt, J=4.99, 2.40 Hz, 4 H), 1.61 (s, 9 H).

Step 8. Tert-butyl 4-(3-amino-6-(4-hydroxycyclohexyl)pyrazin-2-yl)-2-fluorobenzoate A solution of tert-butyl 4-(3-amino-6-(4-oxocyclohexyl) pyrazin-2-yl)-2-fluorobenzoate (9 g, 23.35 mmol) in methanol (125 mL) and THF (125 mL) was cooled down to −78° C., and then NaBH$_4$ (2.297 g, 60.7 mmol) was added portion wise. The reaction mixture was then stirred at −78° C. for 40 min, and LCMS indicated the reaction was completed. Some over-reduction product was observed. The ratio of trans to cis was about 8:1. 100 mL of sat. NH$_4$Cl was added slowly at −78° C., and then the mixture was warmed up gradually to room temperature. The reaction mixture was quenched by sat. NaHCO$_3$, and extracted by EtOAc (2×200 mL). The organic layers were combined, dried over Na$_2$SO$_4$, filtered off, concentrated and dried under high vacuum to provide tert-butyl 4-(3-amino-6-(4-hydroxycyclohexyl)pyrazin-2-yl)-2-fluorobenzoate (8.9 g, 22.97 mmol, 98%), which was used in next step without further purification. LCMS (m/z): 388.2 (MH$^+$), 0.86 min.

Step 9 &10. 4-(3-amino-6-((1r,4r)-4-hydroxycyclohexyl)pyrazin-2-yl)-2-fluorobenzoic acid Tert-butyl 4-(3-amino-6-(4-hydroxycyclohexyl)pyrazin-2-yl)-2-fluorobenzoate (8.8 g, 22.71 mmol) was dissolved in THF (100 mL), and then TBDMSCI (8.22 g, 54.5 mmol) and imidazole (5.57 g, 82 mmol) were added. The reaction mixture was stirred at room temperature for 3 h. The reaction mixture was diluted by EtOAc (150 mL), washed by water and brine, dried over Na$_2$SO$_4$, filtered off, and concentrated. The crude material was purified by flash chromatography eluting with 0-100% of acetone/DCM (10% acetone/DCM in DCM, 10 to 50%, 40 min duration, 320 g silica gel column) to afford tert-butyl 4-(3-amino-6-((1s,4s)-4-((tert-butyldimethylsilyl)oxy)cyclohexyl)pyrazin-2-yl)-2-fluorobenzoate (7.7 g, 15.35 mmol, 67.6%). LCMS (m/z): 502.3 (MH$^+$), 0.96 min. To a solution of tert-butyl 4-(3-amino-6-((1s,4s)-4-((tert-butyldimethylsilyl)oxy)cyclohexyl)pyrazin-2-yl)-2-fluorobenzoate (7.789 g, 15.52 mmol) in 4 N HCl in dioxane was stirred at room temperature for 48 h. The reaction mixture was concentrated. To the light yellow residue was added 50 mL of Et$_2$O, sonicated for 15 min, filtered, washed with 15 mL of Et$_2$O twice, and dried under vacuum suction for 2 h to provide 4-(3-amino-6-((1r,4r)-4-hydroxycyclohexyl)pyrazin-2-yl)-2-fluorobenzoic acid (11, 6.0 g, 15.99 mmol, 100% yield) as a light yellow solid. LCMS (m/z): 332.0 (MH$^+$, acid), 0.48 min; 1H NMR (400 MHz, DMSO-d6) δ ppm 8.06-7.79 (m, 2 H). 7.69-7.50 (m, 2 H), 3.63-3.30 (m, 3 H) 2.62-2.50 (m, 1 H), 1.97-1.71 (m, 4 H), 1.34-1.11 (m, 2 H), 1.63-1.42 (m, 2 H),

Step 11. 4-(3-amino-6-((1r,4S)-4-hydroxycyclohexyl)pyrazin-2-yl)-N-((S)-1-(3-bromo-5-fluorophenyl)-2-hydroxyethyl)-2-fluorobenzamide 4-(3-amino-6-((1r,4r)-4-hydroxycyclohexyl)pyrazin-2-yl)-2-fluorobenzoic acid (670 mg, 2.022 mmol) in DMF (16.80 mL) was added aza-HOBt (413 mg, 3.03 mmol), EDC (581 mg, 3.03 mmol), DIEA (1.059 mL, 6.07 mmol) and (S)-2-amino-2-(3-bromo-5-fluorophenyl)ethanol hydrochloride (547 mg, 2.022 mmol). The reaction mixture was stirred at room temperature for 3 h. LCMS indicated the product. The reaction mixture was diluted with EtOAc, washed with sat NaHCO$_3$, water and brine, dried over Na$_2$SO$_4$, filtered off, and concentrated. The residue was purified with flash chromatography eluting with 0-100% of EtOAc (containing 10% MeOH)/heptane to provide 4-(3-amino-6-((1r,4S)-4-hydroxycyclohexyl)pyrazin-2-yl)-N-((S)-1-(3-bromo-5-fluorophenyl)-2-hydroxyethyl)-2-fluorobenzamide (920 mg, 1.66 mmol, 82%). LCMS (m/z): 547/549 (MH$^+$), 0.72 min; 1H NMR (500 MHz, DMSO-d6) δ ppm 8.74 (dd, J=1.9, 7.9 Hz, 1H), 7.92 (s, 1H), 7.81-7.70 (m, 1H), 7.68-7.55 (m, 2H), 7.52-7.39 (m, 2H), 7.30 (d, J=9.5 Hz, 1H), 6.11 (s, 2H), 5.09 (t, J=5.7 Hz, 2H), 4.58 (d, J=4.4 Hz, 1H), 3.69 (dt, J=2.4, 5.8 Hz, 2H), 3.49-3.40 (m, 1H), 2.55 (t, J=3.5 Hz, 1H), 1.98-1.76 (m, 4H), 1.55 (dd, J=2.8, 12.6 Hz, 2H), 1.29 (d, J=13.6 Hz, 2H).

Synthesis of (S)N-(2-amino-2-(3-chlorophenyl)ethyl)-N-methyl-2-nitrobenzenesulfonamide Scheme 65

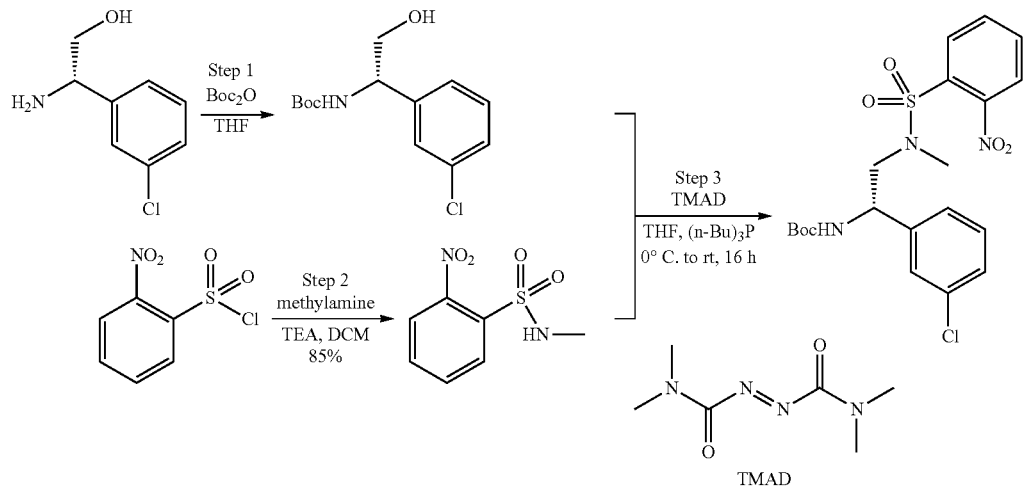

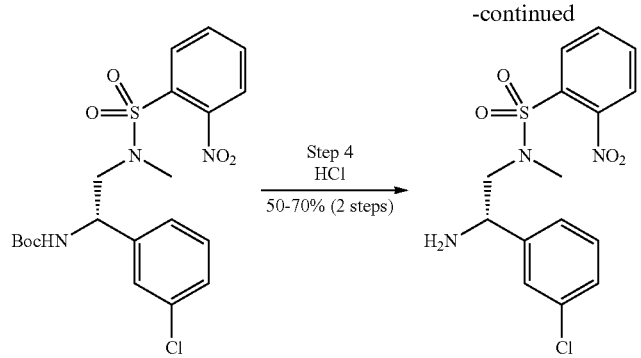

Step 1. (S)-tert-butyl (1-(3-chlorophenyl)-2-hydroxyethyl)carbamate

To a mixture of (s)-2-amino-2-(3-chlorophenyl)ethanol (4 g, 19.22 mmol) in THF (64.1 mL) was added NaHCO$_3$ (1.776 g, 21.15 mmol), followed by Boc$_2$O (4.91 mL, 21.15 mmol) and DMAP (0.235 g, 1.922 mmol). The reaction mixture was then stirred at room temperature overnight. LCMS indicated the reaction was not completed. TEA (5.36 mL, 38.4 mmol) was added, and the reaction mixture was stirred at room temperature for 5 h. Water was added, and the reaction mixture was extracted by EtOAc. The organic layer was washed with brine, dried over sodium sulfate, filtered and concentrated. The crude material was purified by flash chromtography eluting with 0-100% of EtOAc/heptane to afford (S)-tert-butyl (1-(3-chlorophenyl)-2-hydroxyethyl) carbamate (4.0 g, 14.72 mmol, 77%). LCMS (m/z): 216.1 (MH$^+$-56), 0.75 min.

Step 2. N-methyl-2-nitrobenzenesulfonamide

A solution of 2-nitrobenzene-1-sulfonyl chloride (4 g, 18.05 mmol) in DCM (60.2 mL) was cooled down to 0° C. with an ice water bath. TEA (7.55 mL, 54.1 mmol) and 2 M methylamine in tetrahydrofuran (13.54 mL, 27.1 mmol) were added. The resulting solution was stirred at room temperature for 6 h. The reaction mixture was diluted with DCM, washed with sat. NaHCO$_3$ (2×100 mL), brine (100 mL) and then dried over magnesium sulphate. The solution was filtered before concentrating under reduced pressure, and triturated in ether to afford N-methyl-2-nitrobenzenesulfonamide (3.12 g, 14.44 mmol, 80 yield). LCMS (m/z): 217.1 (MH$^+$), 0.53 min.

Step 3. (S)-tert-butyl (1-(3-chlorophenyl)-2-(N-methyl-2-nitrophenylsulfonamido)ethyl)-carbamate N-methyl-2-nitrobenzenesulfonamide (3.50 g, 16.19 mmol) in THF (56.6 mL) was added (S)-tert-butyl (1-(3-chlorophenyl)-2-hydroxyethyl)carbamate (4 g, 14.72 mmol) and tributylphosphine (3.87 g, 19.14 mmol). Then (E)-di-tert-butyl diazene-1,2-dicarboxylate (3.29 g, 19.14 mmol) in THF (56.6 mL) was added slowly at 0° C. The reaction mixture was stirred at room temperature overnight. LCMS indicated there was slightly starting material left. The reaction was diluted with EtOAc, washed with sat. NaHCO$_3$, water and brine, dried over Na$_2$SO$_4$, filtered off, and concentrated. The crude product was purified by flash chromatography eluting with 0-100% of EtOAc/heptane to afford (S)-tert-butyl (1-(3-chlorophenyl)-2-(N-methyl-2-itrophenylsulfonamido)ethyl)carbamate (7 g, 14.9 mmol, 100%). LCMS (m/z): 370.1 (MH$^+$-100), 1.05 min.

Step 4. (S)N-(2-amino-2-(3-chlorophenyl)ethyl)-N-methyl-2-nitrobenzenesulfonamide (S)-tert-butyl (1-(3-chlorophenyl)-2-(N-methyl-2-itrophenylsulfonamido)ethyl)carbamate (7 g, 14.9 mmol) in DCM (149 mL) was added HCl (4 M in dioxane) (14.90 mL, 59.6 mmol). The reaction mixture was stirred at room temperature for 4 h. LCMS indicated that the reaction was completed. White precipitate was filtered out and washed well with DCM to provide 2.8 g of (S)N-(2-amino-2-(3-chlorophenyl)ethyl)-N-methyl-2-nitrobenzenesulfonamide as a HCl salt. The residue was evaporated to dryness, and stirred in DCM (20 mL) for 30 min. Solid was filtered and washed well with DCM to provide another 400 mg of (S)N-(2-amino-2-(3-chlorophenyl)ethyl)-N-methyl-2-nitrobenzenesulfonamide which brought total yield to 52.9% with 95% purity. LCMS (m/z): 370.1 (MH$^+$-100), 0.67 min; $^1$H NMR (500 MHz, METHANOL-d$_4$) δ ppm 8.09-7.99 (m, 1H), 7.92-7.77 (m, 3H), 7.60 (s, 1H), 7.53-7.35 (m, 3H), 4.74-4.62 (m, 1H), 3.93 (dd, J=9.0, 14.7 Hz, 1H), 3.53 (dd, J=5.4, 14.8 Hz, 1H), 2.98 (s, 3H).

Example 176

Synthesis of (S)-4-(3-amino-6-(tetrahydro-2H-pyran-4-yl)pyrazin-2-yl)-N-(1-(3-chlorophenyl)-2-(methylamino)ethyl)-2-fluorobenzamide Scheme 66

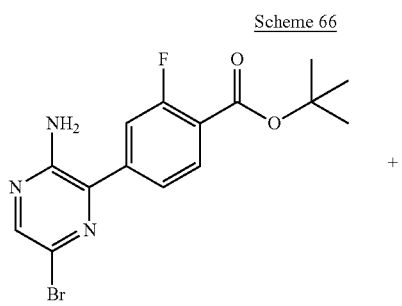

+

-continued

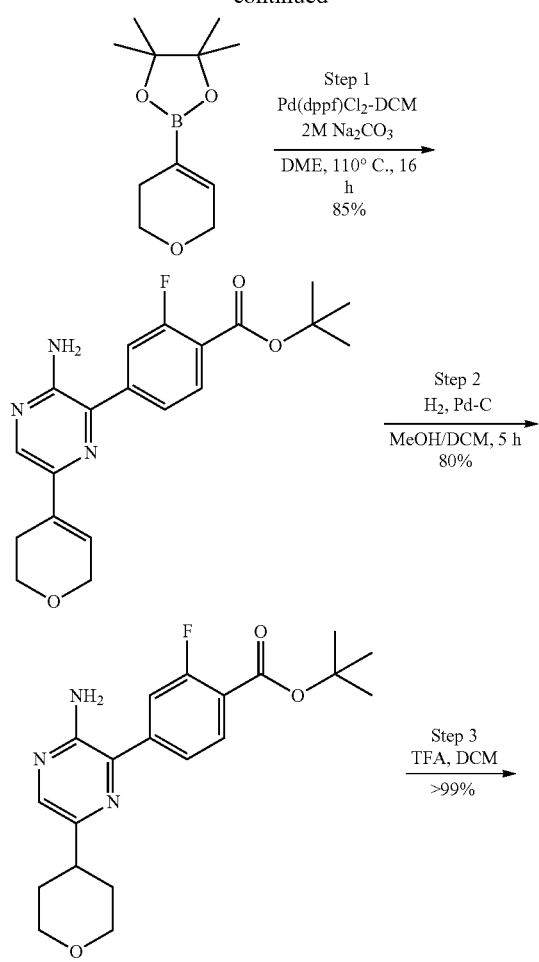

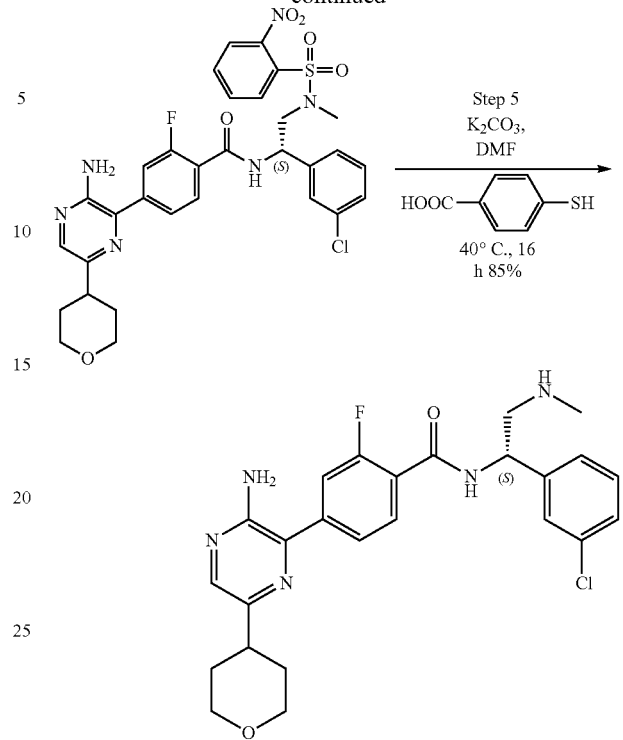

Step 1. Tert-butyl 4-(3-amino-6-(3,6-dihydro-2H-pyran-4-yl)pyrazin-2-yl)-2-fluorobenzoate To a solution of tert-butyl 4-(3-amino-6-bromopyrazin-2-yl)-2-fluorobenzoate (21 g, 57.0 mmol) in DME (127 mL) was added PdCl$_2$(dppf).CH$_2$Cl$_2$ adduct (2.329 g, 2.85 mmol), 2-(cyclohex-1-en-1-yl)-4,4,5,5-tetramethyl-1,3,2-dioxaborolane (13.18 g, 62.7 mmol), and 2 M Na$_2$CO$_3$ aqueous solution (63.4 mL). The reaction was heated at 110° C. for 16 h. To the reaction mixture was added 200 mL of ethyl acetate, washed with water (2×100 mL), brine, dried over sodium sulfate, filtered and concentrated. The residue was purified by flash chromatography eluting with 0-100% of EtOAc/DCM to provide tert-butyl 4-(3-amino-6-(3,6-dihydro-2H-pyran-4-yl)pyrazin-2-yl)-2-fluorobenzoate (18 g, 48.5 mmol, 85%). LCMS (m/z): 372.3 (MH$^+$), 0.95 min.

Step 2. Tert-butyl 4-(3-amino-6-(tetrahydro-2H-pyran-4-yl)pyrazin-2-yl)-2-fluorobenzoate To a suspension of tert-butyl 4-(3-amino-6-(3,6-dihydro-2H-pyran-4-yl)pyrazin-2-yl)-2-fluorobenzoate (15 g, 40.4 mmol) in MeOH (800 mL) was added DCM (100 mL) until the suspension turned to a homogeneous solution. After degassed by N$_2$ stream for 15 min, Pd/C (10 g, 9.40 mmol) was added to the reaction mixture. To this mixture, hydrogen balloon was equipped after flushed with hydrogen gas three times. The reaction mixture was stirred for 6 h. After the reaction mixture was filtered through Celite® pad, the volatile materials were removed in vacuo. The residue was dissolved in MeOH (200 mL) by heating and cooling down to room temperature and standing overnight. The brown precipitate was filtered off, which afforded 4.5 g of tert-butyl 4-(3-amino-6-(tetrahydro-2H-pyran-4-yl)pyrazin-2-yl)-2-fluorobenzoate. The filtrate was concentrated and dissolved in EtOH (200 mL) by heating. The second brown precipitate was filtered off to afford 3.9 g of tert-butyl 4-(3-amino-6-(tetrahydro-2H-pyran-4-yl)pyrazin-2-yl)-2-fluorobenzoate (55.7% combined yield). LCMS (m/z): 374.7 (MH+), 0.90 min.

Step 3. 4-(3-Amino-6-(tetrahydro-2H-pyran-4-yl)pyrazin-2-yl)-2-fluorobenzoic acid To a solution of tert-butyl 4-(3-amino-6-(tetrahydro-2H-pyran-4-yl)pyrazin-2-yl)-2-fluorobenzoate (4.5 g, 12.05 mmol) in DCM (60.3 mL) was added TFA (60.3 mL). The reaction mixture was stirred for 2 h. After diluted with toluene (30 mL), the volatile materials were removed in vacuo twice to provide 4-(3-amino-6-(tetrahydro-2H-pyran-4-yl)pyrazin-2-yl)-2-fluorobenzoic acid (5.2 g, 12.06 mmol, 100%) as a TFA salt. The crude product was used for the next step without further purification. LCMS (m/z): 318.5 (MH+), 0.55 min.

Step 4. (S)-4-(3-amino-6-(tetrahydro-2H-pyran-4-yl)pyrazin-2-yl)-N-(1-(3-chlorophenyl)-2-(N-methyl-2-nitrophenylsulfonamido)ethyl)-2-fluorobenzamide To a solution of 4-(3-amino-6-(tetrahydro-2H-pyran-4-yl)pyrazin-2-yl)-2-fluorobenzoic acid (1.55 g, 4.88 mmol) in DMF (16.28 mL) was added HOAt (0.997 g, 7.33 mmol), EDC (1.498 g, 7.82 mmol), DIEA (2.61 ml, 14.65 mmol) and (S)N-(2-amino-2-(3-chlorophenyl)ethyl)-N-methyl-2-nitrobenzenesulfonamide (2.084 g, 5.13 mmol). The reaction mixture was stirred at room temperature for 3 h, and LCMS indicated the reaction was completed. The reaction mixture was diluted with EtOAc, and the organic was washed by sat. Na$_2$CO$_3$, water and brine, dried over Na$_2$SO$_4$, filtered off, and concentrated. The crude material was purified by flash chromatography eluting with 50% DCM/EtOAc (10% methanol) to provide (S)-4-(3-amino-6-(tetrahydro-2H-pyran-4-yl)pyrazin-2-yl)-N-(1-(3-chlorophenyl)-2-(N-methyl-2-nitrophenylsulfonamido)ethyl)-2-fluorobenzamide (2.68 g, 4.01 mmol, 82%). LCMS: 669.1 (MH+), 0.95 min.

Step 5. (S)-4-(3-amino-6-(tetrahydro-2H-pyran-4-yl)pyrazin-2-yl)-N-(1-(3-chlorophenyl)-2-(methylamino)ethyl)-2-fluorobenzamide To a solution of (S)-4-(3-amino-6-(tetrahydro-2H-pyran-4-yl)pyrazin-2-yl)-N-(1-(3-chlorophenyl)-2-(N-methyl-2-nitrophenylsulfonamido)ethyl)-2-fluorobenzamide (2.68 g, 4.01 mmol) in DMF (20 mL) was added 4-mercaptobenzoic acid (1.235 g, 8.01 mmol) and K$_2$CO$_3$ (2.214 g, 16.02 mmol). The reaction mixture was heated at 40° C. overnight under nitrogen. Water (50 mL) was added, and the mixture turned into homogenous. The reaction was stirred at room temperature for 30 min, and then water (150 mL) was added slowly. Light yellow solid was precipitated out. The mixture was stirred for another 30 min, and the suspension was filtered out. The solid was washed well with water, followed by heptane, and air dried for 1 h. The solid was suspended in water and stirred at room temperature for 1 h, and then filtered. To the solid was added EtOAc, and slowly rotated on rotavap to remove excess ethyl acetate until about 20 mL of EtOAc left, the white solid was filtered, and redissolved in acetonitrile and water, lyophilized. The solution was dried on lyophilizer to afford (S)-4-(3-amino-6-(tetrahydro-2H-pyran-4-yl)pyrazin-2-yl)-N-(1-(3-chlorophenyl)-2-(methylamino)ethyl)-2-fluorobenzamide (1.31 g, 2.69 mmol, 67.2%). LCMS (m/z): 484.3 (MH+), 0.66 min; $^1$H NMR (500 MHz, METHANOL-d$_4$) δ ppm 7.90 (s, 1H), 7.83 (t, J=7.7 Hz, 1H), 7.70 (dd, J=1.1, 8.0 Hz, 1H), 7.63 (d, J=10.7 Hz, 1H), 7.48 (s, 1H), 7.38 (d, J=5.4 Hz, 2H), 7.32 (dt, J=1.9, 4.6 Hz, 1H), 5.33 (dd, J=5.2, 9.0 Hz, 1H), 4.05 (dd, J=3.5, 11.0 Hz, 2H), 3.57 (dt, J=1.9, 11.8 Hz, 2H), 3.12-3.04 (m, 1H), 3.04-2.88 (m, 2H), 2.48 (s, 3H), 1.89-1.88 (m, 1H), 1.96-1.76 (m, 4H).

Synthesis of (S)-tert-butyl 2-amino-2-phenylethylcarbamate

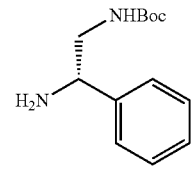

Following Scheme 9, using (R)-2-amino-1-phenylethanol, (S)-tert-butyl 2-amino-2-phenylethylcarbamate was obtained in 47% yield. LCMS (m/z): 237.5 (MH+), 0.54 min. $^1$H NMR (400 MHz, CDCl$_3$) δ ppm 7.42-7.32 (m, 5 H), 4.81 (br. s., 1 H), 4.11-4.00 (m, 1 H), 3.44-3.28 (m, 1 H), 3.28-3.13 (m, 1 H), 1.49-1.35 (m, 9 H).

Synthesis of (S)-2-fluoro-1-phenylethanamine

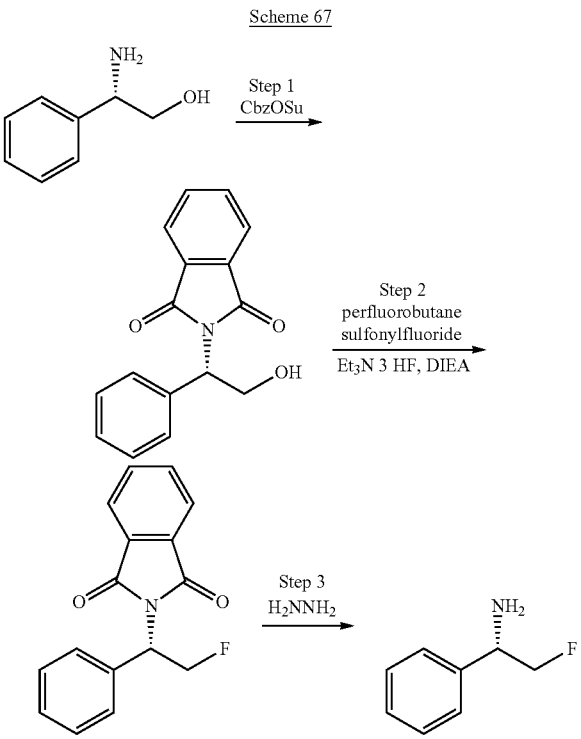

Step 1. (S)-2-(2-hydroxy-1-phenylethyl)isoindoline-1,3-dione

To a solution of (S)-2-amino-2-phenylethanol (3 g, 21.87 mmol) in water (26.5 mL), and acetonitrile (46.4 mL) was added 2,5-dioxopyrrolidin-1-yl methyl phthalate (5.76 g, 20.78 mmol) at room temperature. The reaction mixture was stirred at room temperature for overnight. After acetonitrile was removed in vacuo, the reaction mixture was then extracted with EtOAc. The organic was washed by water and brine, dried over anhydrous sodium sulfate, filtered off, and concentrated in vacuo yielding (S)-2-(2-hydroxy-1-phenylethyl)isoindoline-1,3-dione (2.2 g, 40%). LCMS (m/z): 268 (MH+), 0.79 min.

Step 2. (S)-2-(2-fluoro-1-phenylethyl)isoindoline-1,3-dione

To a solution of (S)-2-(2-hydroxy-1-phenylethyl)isoindoline-1,3-dione (1.5 g, 5.61 mmol) in PhCF$_3$ (18.71 mL) was added triethylamine trihydrofluoride (5.48 mL, 33.7 mmol), perfluorobutanesulfonyl fluoride (1.019 mL, 5.67 mmol), DIEA (14.70 mL, 84 mmol) at room temperature. The reaction mixture was stirred at room temperature for 1 h, then more perfluorobutanesulfonyl fluoride (1.019 mL, 5.67 mmol) was added. After 5 h, the reaction mixture was quenched with NaHCO$_3$ and extracted with EtOAc. The combined organic layers were washed with water and brine, dried over anhydrous sodium sulfate, filtered off, and concentrated in vacuo. The crude product was purified by flash chromatography (0-10% EtOAC in heptane) yielding (S)-2-(2-fluoro-1-phenylethyl)isoindoline-1,3-dione (30% yield). LCMS (m/z): 270.1 (MH+), 0.96 min.

Step 3. (S)-2-fluoro-1-phenylethanamine

To a solution of (S)-2-(2-fluoro-1-phenylethyl)isoindoline-1,3-dione (290 mg, 1.077 mmol) in MeOH (3.59 mL) was added hydrazine (0.507 mL, 16.15 mmol). The reaction mixture was stirred at 80° C. for 3 h. The white precipitate was filtered off. The filtrate was concentrated to yield the crude (S)-2-fluoro-1-phenylethanamine, which was used in next step without further purification. LCMS (m/z): 140.1 (MH+), 0.28 min; 1H NMR (400 MHz, CDCl$_3$) δ ppm 7.43-7.34 (m, 4 H), 7.34-7.27 (m, 1 H), 4.57 (dd, J=3.7, 8.8 Hz, 1 H), 4.49-4.38 (m, 1 H), 4.38-4.32 (m, 1 H), 4.32-4.25 (m, 1 H).

Synthesis of (S)-2-azido-1-(3-bromo-5-fluorophenyl)ethanamine

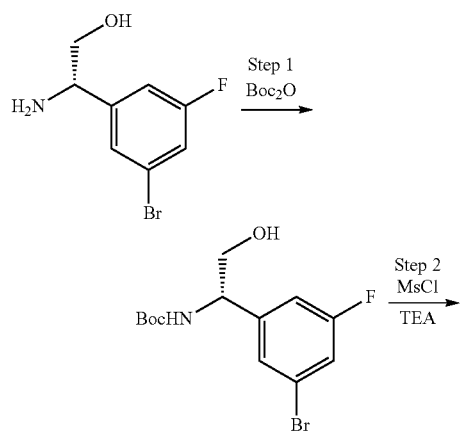

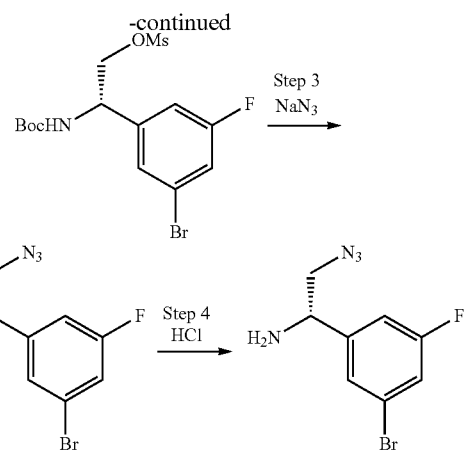

Step 1. (S)-tert-butyl (1-(3-bromo-5-fluorophenyl)-2-hydroxyethyl)carbamate

To a solution of (S)-2-amino-2-(3-bromo-5-fluorophenyl)ethanol (4.4 g, 16.26 mmol) in DCM (80 mL) was added TEA (6.80 mL, 48.8 mmol) followed by Boc anhydride (5.32 g, 24.4 mmol) at room temperature. The reaction mixture was stirred at room temperature for 16 h. The reaction mixture was extracted with EtOAc. The organic layer was washed with sat NaHCO$_3$, water and brine, dried over anhydrous Na$_2$SO$_4$, filtered off, and concentrated. The crude product was purified by flash chromatography (gradient EtOAc in heptane) to provide (S)-tert-butyl (1-(3-bromo-5-fluorophenyl)-2-hydroxyethyl)carbamate (4.8 g, 88%). LCMS (m/z): 280 (MH+-$^t$Bu), 0.79 min.

Step 2. (S)-2-((tert-butoxycarbonyl)amino)-2-(3-bromo-5-fluorophenyl)ethyl methanesulfonate To a stirred solution of (S)-tert-butyl (1-(3-bromo-5-fluorophenyl)-2-hydroxyethyl)carbamate (4.8 g, 14.36 mmol) in anhydrous DCM (100 mL) at 0° C. was added triethylamine (4.00 mL, 28.7 mmol) followed by methanesulfonyl chloride (1.343 mL, 17.24 mmol). The reaction was stirred at 0° C. for 1 hr, by which time the LCMS indicated the reaction had gone to completion. The reaction mixture was poured into saturated NaHCO$_3$ solution (100 mL). The mixture was shaken, the layers separated and the aqueous layer was extracted with DCM (2×50 mL). The combined organics were washed with NaHCO$_3$ solution (50 mL) and brine (50 mL), dried (MgSO$_4$), filtered and concentrated, giving (S)-2-((tert-butoxycarbonyl)amino)-2-(3-bromo-5-fluorophenyl)ethyl methanesulfonate (5.92 g, 14.36 mmol, 100% yield) as a very pale orange solid. 1H NMR (500 MHz, DMSO-d6) δ ppm 7.75 (d, J=8.83 Hz, 1 H), 7.43-7.55 (m, 2 H), 7.31 (d, J=9.46 Hz, 1 H), 4.86-5.00 (m, 1 H), 4.30 (dd, J=10.09, 5.04 Hz, 1 H), 4.24 (t, J=9.30 Hz, 1 H), 3.16-3.23 (m, 3 H), 1.36-1.44 (m, 9 H).

Step 3. (S)-tert-butyl (2-azido-1-(3-bromo-5-fluorophenyl)ethyl)carbamate (S)-2-((tert-butoxycarbonyl)amino)-2-(3-bromo-5-fluorophenyl)ethyl methanesulfonate (5.92 g, 14.36 mmol) was dissolved in anhydrous DMF (60 mL). Sodium azide (2.80 g, 43.1 mmol) was added, and the reaction heated to 70° C. and maintained at this temperature for 2 h. After cooling, the reaction mixture was poured into water (100 mL) and extracted with EtOAc (3×80 mL). The combined organics were washed with water (50 mL) and brine (3×50 mL), dried (MgSO₄), filtered and concentrated. Flash chromatography (AnaLogix, 80 g column, loaded in DCM, 0 to 40% EtOAc in heptane over 30 min) gave (S)-tert-butyl (2-azido-1-(3-bromo-5-fluorophenyl)ethyl)carbamate (4.29 g, 11.94 mmol, 83% yield) as a white solid. 1H NMR (500 MHz, DMSO-d6) δ ppm 7.73 (d, J=8.83 Hz, 1 H), 7.48 (t, J=4.26 Hz, 2 H), 7.29 (d, J=9.77 Hz, 1 H), 4.80 (d, J=8.20 Hz, 1 H), 3.47 (d, J=7.88 Hz, 2 H), 1.44-1.38 (m, 9 H), 1.36 (br. s., 1 H).

Step 4. (S)-2-azido-1-(3-bromo-5-fluorophenyl) ethanamine

To a stirred solution of (S)-tert-butyl (2-azido-1-(3-bromo-5-fluorophenyl)ethyl)carbamate (3.15 g, 8.77 mmol) in dioxane (40 mL) was added hydrochloric acid (10.96 mL, 43.8 mmol) (4N solution in dioxane). The reaction was heated to 40° C. and maintained at this temperature for 2 h. After cooling the reaction mixture was evaporated to dryness, giving (S)-2-azido-1-(3-bromo-5-fluorophenyl)ethanamine hydrochloride (2.59 g, 8.76 mmol, 100% yield) as a white solid.

Synthesis of (S)-2-azido-1-(3-chloro-5-fluorophenyl)ethanamine

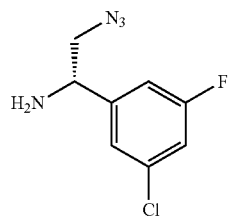 [SMILES: [N-]=[N+]=NC[C@@H](N)c1cc(F)cc(Cl)c1]

Following Scheme 68, using (S)-2-amino-2-(3-chloro-5-fluorophenyl)ethanol, (S)-2-azido-1-(3-chloro-5-fluorophenyl)ethanamine was obtained. LCMS (m/z): 215.1 (MH⁺), 0.48 min.

Synthesis of (S)-2-azido-1-(3-chlorophenyl)ethanamine

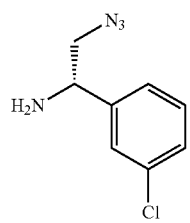 [SMILES: [N-]=[N+]=NC[C@@H](N)c1cccc(Cl)c1]

Following Scheme 68, using (S)-2-amino-2-(3-chlorophenyl)ethanol, (S)-2-azido-1-(3-chloro-5-fluorophenyl) ethanamine was obtained. LCMS (m/z): 197 (MH⁺), 0.5 min.

Synthesis of (S)-3-phenylmorpholine

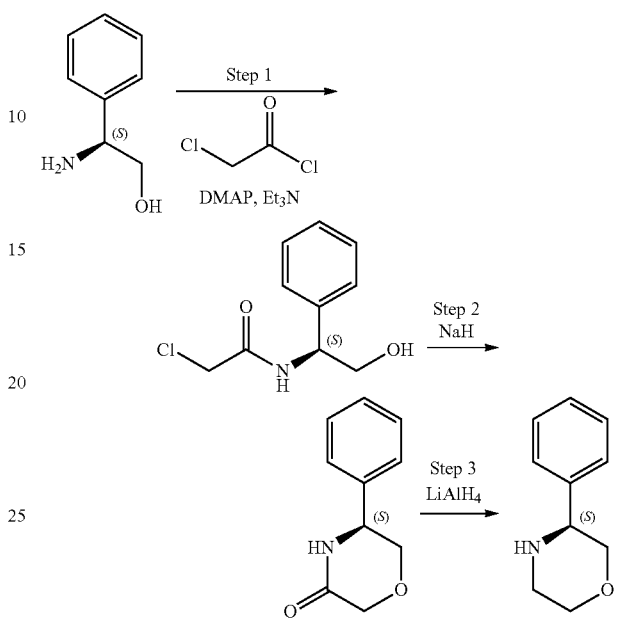

Scheme 69

Step 1. (S)-2-chloro-N-(2-hydroxy-1-phenylethyl) acetamide

To a solution of (S)-2-amino-2-phenylethanol (0.852 g, 6.21 mmol), Et₃N (0.952 mL, 6.83 mmol), DMAP (76 mg, 0.621 mmol) in CH₂Cl₂ (10 mL) at 0° C. was added 2-chloroacetyl chloride (0519 mL, 6.52 mmol), and the resulting mixture was stirred at 0° C. for 15 min. The reaction mixture was washed with aqueous HCl (1 M, 20 mL), then sat. NaHCO₃ (20 mL), dried (Na₂SO₄), concentrated, further dried under high vacuum and (S)-2-chloro-N-(2-hydroxy-1-phenylethyl)acetamide (0.60 g, 45.2% yield) was obtained as white solid. LCMS (m/z): 214 (MH⁺), 0.44 min.

Step 2. (S)-5-phenylmorpholin-3-one

To a solution of (S)-2-chloro-N-(2-hydroxy-1-phenylethyl)acetamide (600 mg, 2.8 mmol) in anhydrous THF solution at 0° C. was added NaH mineral oil suspension (247 mg, 6.18 mmol). The resulting mixture was stirred overnight at room temperature. The reaction mixture was concentrated to dryness, and the residue was partitioned between CH₂Cl₂/brine/H₂O (20 mL/18 mL/2 mL). CH₂Cl₂ layer was dried over anhydrous Na₂SO₄, filtered off, concentrated in vacuo. The crude product, (S)-5-phenylmorpholin-3-one, was obtained as a white solid (498 mg, 97%). The crude product was used directly in next step without further purification. LCMS (m/z): 178.2 (MH⁺), 0.47 min.

Step 3. (S)-3-phenylmorpholine

To a LiAlH₄/THF slurry (0.47 g/2 mL) was added dropwise (S)-5-phenylmorpholin-3-one in THF solution (481 mg in 6 mL) at room temperature over 5 min. The resulting mixture was stirred at room temperature thereafter for 1 hour, then was heated with 72° C. oil bath overnight, then was cooled down to 0° C., quenched by sequential addition of H$_2$O (0.47 mL), 3M aqueous solutionueous NaOH (0.47 mL) and H$_2$O (1.4 mL), and the quenched residue was diluted with Et$_2$O (30 mL), stirred for 10 min and the ethereal solution was separated by filtration. The filtrate was concentrated, further dried under vacuum and (S)-3-phenylmorpholine (424 mg, 96% yield) was obtained as colorless solid. LCMS (m/z): 164.2 (MH$^+$), 0.33 min.

Synthesis of (S)-tert-butyl (2-amino-2-(3-chlorophenyl)ethyl)(methyl)carbamate

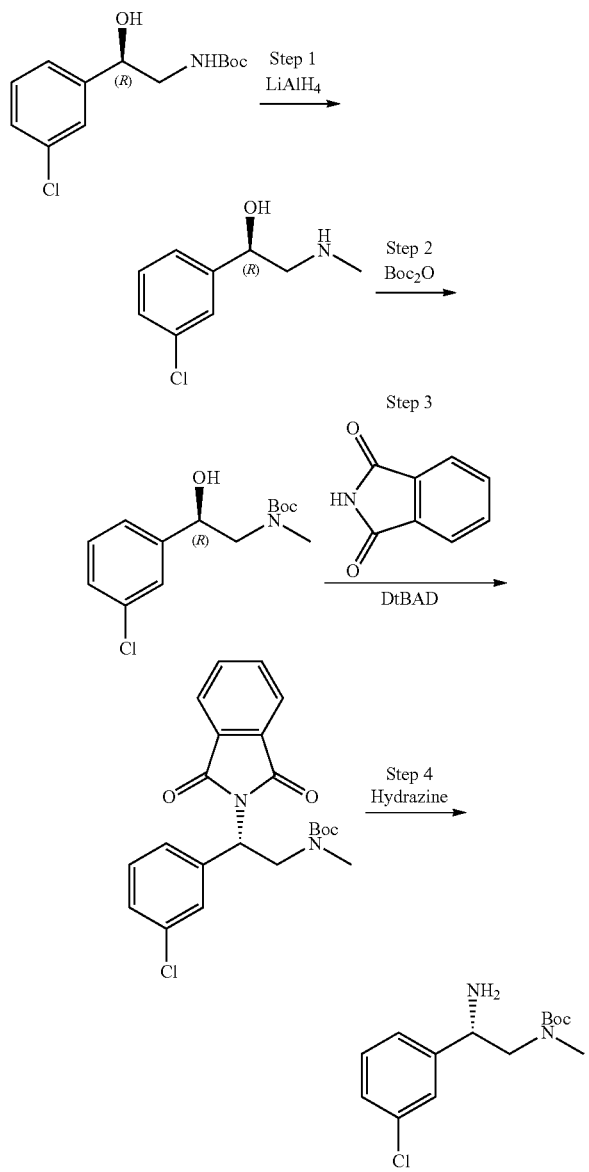

Step 1. (R)-1-(3-chlorophenyl)-2-(methylamino)ethanol (R)-tert-butyl (2-(3-chlorophenyl)-2-hydroxyethyl)carbamate (2.48 g, 9.13 mmol), prepared in Scheme 9, was dissolved THF (30.4 mL), and LiAlH$_4$ (1.039 g, 27.4 mmol) was added. The reaction mixture was heated at reflux for 6 h and then cooled down. Water (1.06 mL) was added, followed by aqueous NaOH (15%, 3 mL), and water (1.06 mL). The reaction mixture was stirred at room temperature for 1 h. Solid precipitate was filtered through Celite® and rinsed well with EtOAc. The filtrate was concentrated. The crude product (R)-1-(3-chlorophenyl)-2-(methylamino) ethanol (1.75 g, 9.43 mmol, 100%) was used in next step reaction without further purification. LCMS (m/z): 186.1 (MH$^+$), 0.43 min.

Step 2. (R)-tert-butyl (2-(3-chlorophenyl)-2-hydroxyethyl)(methyl)carbamate (R)-1-(3-chlorophenyl)-2-(methylamino)ethanol (1.75 g, 9.43 mmol) was dissolved in THF (31.4 mL), and then Boc anhydride (2.298 mL, 9.90 mmol) was added. The reaction mixture was stirred at room temperature for 2 h. LCMS indicated that the reaction was completed. The reaction mixture was concentrated, and purified by flash chromatography to afford (R)-tert-butyl (2-(3-chlorophenyl)-2-hydroxyethyl)(methyl)carbamate (2.0 g, 7.00 mmol, 74.3%). LCMS (m/z): 212.1 (MH$^+$-56), 0.94 min.

Step 3. (S)-tert-butyl (2-(3-chlorophenyl)-2-(1,3-dioxoisoindolin-2-yl)ethyl)(methyl)carbamate To a mixture of (R)-tert-butyl (2-(3-chlorophenyl)-2-hydroxyethyl)(methyl)carbamate (2.0 g, 7.00 mmol) in THF (23.33 mL) was added phthalimide (1.339 g, 9.10 mmol) and PPh$_3$ (3 mmol of PPh$_3$/1 g of resin, 2.34 g, 7.02 mmol). Then DTBAD (1.660 g, 7.21 mmol) in THF was slowly added at room temperature, and the reaction mixture was stirred at room temperature overnight. The reaction mixture was filtered through Celite® and washed with EtOAc. The filtrate was concentrated, redissolved in EtOAc, washed with sat. Na$_2$CO$_3$, water and brine, dried over sodium sulfate, filtered off, and concentrated. The crude product was purified by flash chromatography to afford (S)-tert-butyl (2-(3-chlorophenyl)-2-(1,3-dioxoisoindolin-2-yl)ethyl) (methyl)carbamate (1.96 g, 4.72 mmol, 67.5%). LCMS (m/z): 315.1 (MH$^+$-100), 1.19 min.

Step 4. (S)-tert-butyl (2-amino-2-(3-chlorophenyl)ethyl)(methyl)carbamate

To a solution of (S)-tert-butyl (2-(3-chlorophenyl)-2-(1,3-dioxoisoindolin-2-yl)ethyl)(methyl)carbamate (1.96 g, 4.72 mmol) in ethanol (15.75 mL) was added hydrazine hydrate (2.296 mL, 47.2 mmol). The reaction mixture was heated at 60° C. for 2 h. The reaction mixture was then filtered through Celite pad and the filtrate was concentrated. The residue was re-dissolved in ethanol and filtered through Celite® pad to remove extra white solid. NMR showed there was impurity in crude material. The crude product was filtered through a plug of silica, washed by DCM/EtOAc (2:1 ratio) and flashed with DCM/EtOAc (20% methanol, 0.5% NH$_3$ in methanol) (1:1 ratio) to provide (s)-tert-butyl (2-amino-2-(3-chlorophenyl)ethyl)(methyl)carbamate (1.2 g, 89% yield). LCMS (m/z): 285.1 (MH$^+$), 0.65 min; $^1$H NMR (400 MHz, CDCl$_3$) δ ppm 7.37 (s, 1H) 7.26 (3H), 4.20 (br. s., 1H), 2.85-2.77 (m, 3H), 1.51-1.38 (m, 9H).

Synthesis of (S)-2-amino-4-cyclopropylbut-3-yn-1-ol

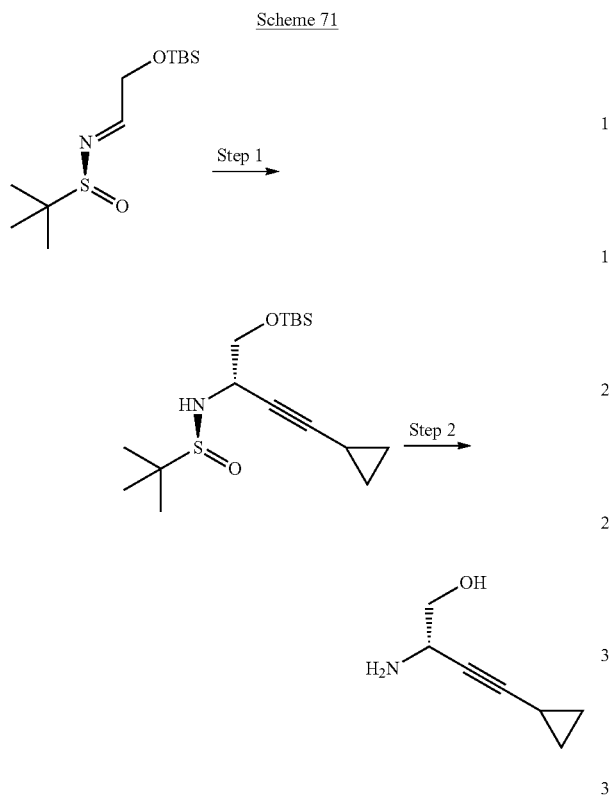

Step 1. (S)N-((S)-1-((tert-butyldimethylsilyl)oxy)-4-cyclopropylbut-3-yn-2-yl)-2-methylpropane-2-sulfinamide 3.0 M ethyl magnesium bromide in Et$_2$O (0.360 mL, 1.081 mmol) was added to a solution of ethynylcyclopropane (71.5 mg, 1.081 mmol) in THF (4 mL). The solution was heated to 50° C. for 1 h, then the resulting Grignard was added to a −78° C. solution of (S,E)-N-(2-((tert-butyldimethylsilyl)oxy)ethylidene)-2-methylpropane-2-sulfinamide (100 mg, 0.360 mmol) in DCM (4.00 mL), and the reaction was allowed to warm to room temperature. After 3 h, the reaction was quenched with sat. aq. NH$_4$Cl. The layers were separated and the organics were dried over magnesium sulfate and concentrated to provide (S)N-((S)-1-((tert-butyldimethylsilyl)oxy)-4-cyclopropylbut-3-yn-2-yl)-2-methylpropane-2-sulfinamide, which was used directly. LCMS (m/z): 344.1 (MH$^+$), 1.23 min.

Step 2. (S)-2-amino-4-cyclopropylbut-3-yn-1-ol 4.0 N HCl in dioxane (0.873 mL, 3.49 mmol) was added to a room temperature solution of (S)N-((S)-1-((tert-butyldimethylsilyl)oxy)-4-cyclopropylbut-3-yn-2-yl)-2-methylpropane-2-sulfinamide (120 mg, 0.349 mmol) in MeOH (4 mL). After 30 min, the reaction was concentrated, then azeotroped with benzene to provide (S)-2-amino-4-cyclopropylbut-3-yn-1-ol as the HCl salt. LCMS (m/z): 126.2 (MH$^+$), 0.50 min.

Synthesis of (S)-2-amino-2-(3-fluoro-5-(methylthio)phenyl)ethanol

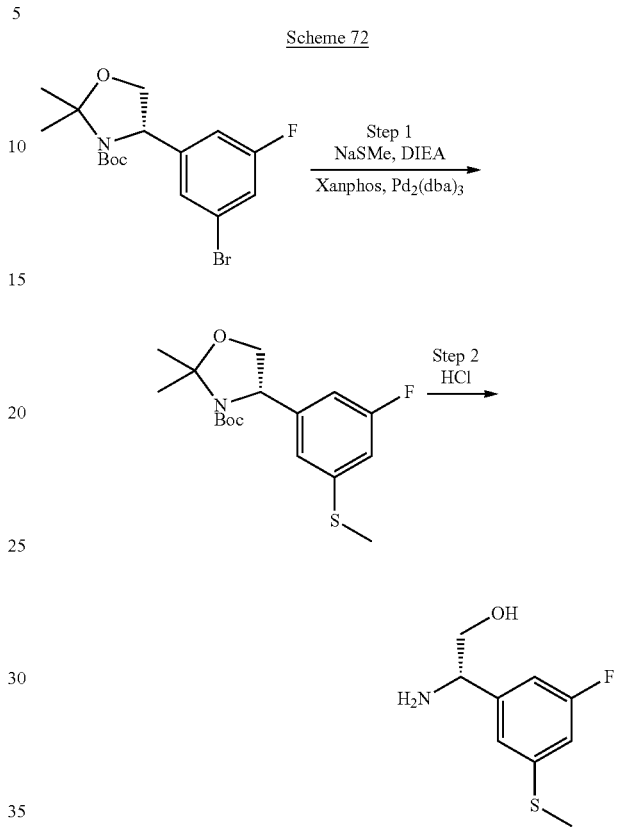

Step 1: (S)-tert-butyl 4-(3-fluoro-5-(methylthio)phenyl)-2,2-dimethyloxazolidine-3-carboxylate A mixture of Xantphos (13.91 mg, 0.024 mmol), Pd$_2$(dba)$_3$ (22.02 mg, 0.024 mmol), (S)-tert-butyl 4-(3-bromo-5-fluorophenyl)-2,2-dimethyloxazolidine-3-carboxylate (300 mg, 0.802 mmol), DIEA (700 µl, 4.01 mmol) and sodium methanethiolate (112 mg, 1.603 mmol) in toluene (2.6 mL) was microwave heated at 110° C. for 18 min. EtOAc was added, and washed with sat NaHCO$_3$, water, and brine. The mixture was filtered off, concentrated and purified with flash chromatography eluting with 0-60% of EtOAc/heptane to provide (S)-tert-butyl 4-(3-fluoro-5-(methylthio)phenyl)-2,2-dimethyloxazolidine-3-carboxylate (278 mg, 102%) as an oil. LCMS (m/z): 286.1 (MH$^+$-56), 1.14 min.

Step 2: (S)-2-amino-2-(3-fluoro-5-(methylthio)phenyl)ethanol

A solution of (S)-tert-butyl 4-(3-fluoro-5-(methylthio)phenyl)-2,2-dimethyloxazolidine-3-carboxylate (278 mg, 0.814 mmol) in 4 M HCl in dioxane (2.4 mL) was heated to 80° C. overnight. There was still some starting material left. More 4 M HCl in dioxane (2.035 mL, 8.14 mmol) was added, and heated at 80° C. for another 10 h. Solvent was removed under reduced vacuum to provide (S)-2-amino-2-(3-fluoro-5-(methylthio)phenyl)ethanol (194 mg, 0.814 mmol, 100%). LCMS (m/z): 170.1 (MH$^+$-56), 0.26 min.

267

Synthesis of (S)-2-amino-2-(3-(methylthio)phenyl)ethanol

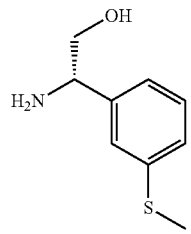

Following Scheme 72, using (S)-tert-butyl 4-(3-bromophenyl)-2,2-dimethyloxazolidine-3-carboxylate, (S)-2-amino-2-(3-(methylthio)phenyl)ethanol was obtained. LCMS (m/z): 184 (MH$^+$), 0.41 min.

Synthesis of (S)-2-amino-2-(3-(chloromethyl)-5-fluorophenyl)ethanol

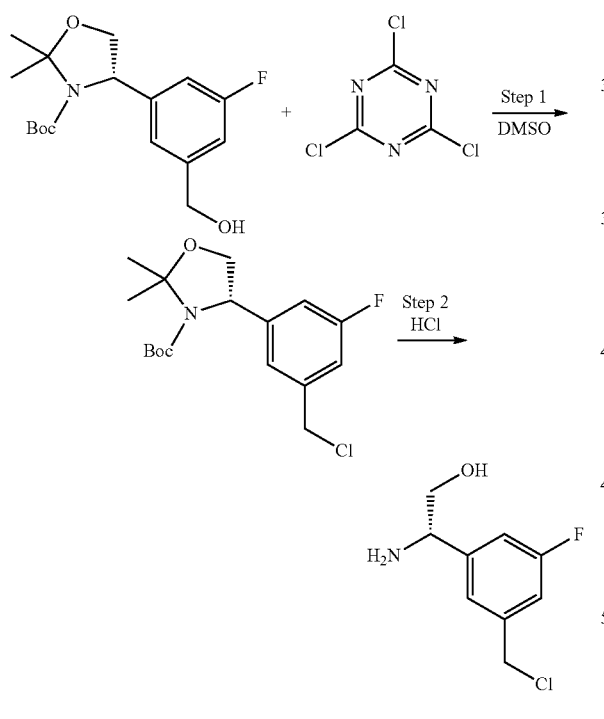

Step 1. (S)-tert-butyl 4-(3-(chloromethyl)-5-fluorophenyl)-2,2-dimethyloxazolidine-3-carboxylate To a solution of (S)-tert-butyl 4-(3-fluoro-5-(hydroxymethyl)phenyl)-2,2-dimethyloxazolidine-3-carboxylate (330 mg, 1.014 mmol) in anhydrous DMSO (2.028 mL) was added 2,4,6-trichloro-1,3,5-triazine (112 mg, 0.609 mmol) portionwise. The mixture was stirred at room temperature for 30 min. The mixture was diluted with EtOAc, and separated. The organic phase was washed with H$_2$O (5×30 mL), dried over anhydrous Na$_2$SO$_4$, filtered off and concentrated under reduced pressure. The residue was purified with flash chromatography eluting with 0-100% EtOAc/heptane to provide (S)-tert-butyl 4-(3-(chloromethyl)-5-fluorophenyl)-2,2-dimethyloxazolidine-3-carboxylate (329 mg, 94%). LCMS (m/z): 288.1 (MH$^+$-56), 1.12 min.

Step 2: (S)-2-amino-2-(3-(chloromethyl)-5-fluorophenyl)ethanol

To a solution of (S)-tert-butyl 4-(3-(chloromethyl)-5-fluorophenyl)-2,2-dimethyloxazolidine-3-carboxylate (140 mg, 0.407 mmol) in anhyd DCM (1.357 mL) was added 4 N HCl in Dioxane (1.018 mL, 4.07 mmol) portionwise. The mixture was refluxed at 80° C. overnight. The reaction was not completed. More 4N HCl in dioxane (1.018 mL, 4.07 mmol) was added, and refluxed for another 24 h. Solvent was removed under reduced vacuum to provide (S)-2-amino-2-(3-(chloromethyl)-5-fluorophenyl)ethanol (70 mg, 84%). LCMS (m/z): 204 (MH$^+$), 0.41 min.

Synthesis of (S)-2-amino-2-(3-fluoro-5-(fluoromethyl)phenyl)ethanol

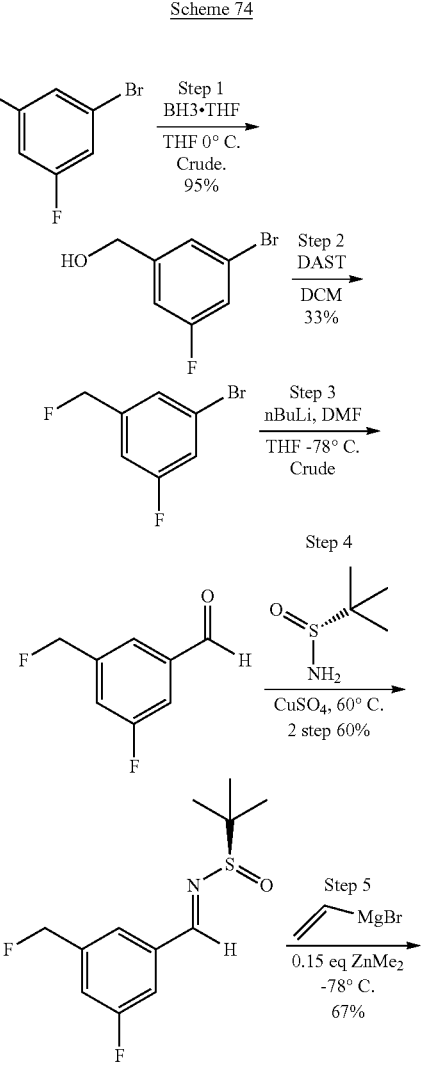

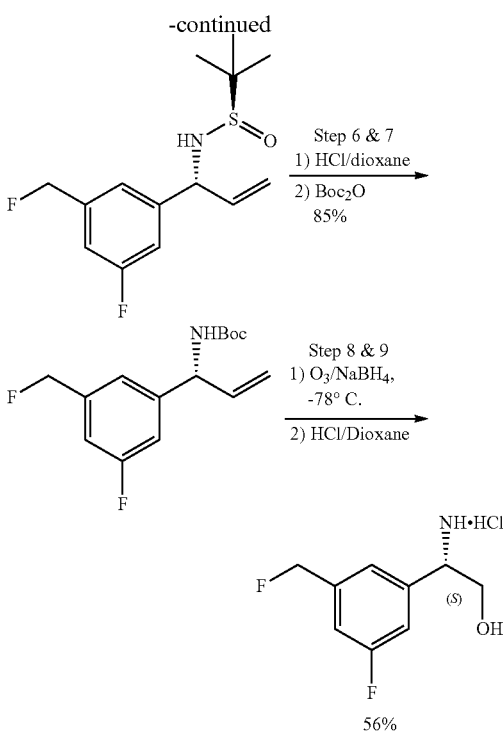

Step 1. (3-bromo-5-fluorophenyl)methanol

To a suspension of 3-bromo-5-fluorobenzoic acid (4.51 g, 20.59 mmol) in THF (41.2 mL) at 0° C., BH₃.THF (41.2 mL, 41.2 mmol) was added dropwise over 30 min, the reaction mixture was then allowed to return to room temperature and stirred at room temperature ovenight. Methanol (40 mL) was added slowly and stirred at room temperature for 1 h. THF and Methanol was removed in vacuo. The residue was then extracted by EtOAc, and washed with sat. NaHCO₃, The organic was dried and concentrated. The crude product was used in next step reaction without purification. LCMS (m/z): 187.2 (MH⁺-18), 0.66 min. ¹H NMR (400 MHz, CDCl₃) δ ppm 7.32 (s, 1H), 7.19-7.14 (m, 1H), 7.05 (tdd, J=0.7, 1.5, 9.1 Hz, 1H), 4.70 (br. s., 2H), 1.78 (br. s., 1H).

Step 2. 1-bromo-3-fluoro-5-(fluoromethyl)benzene

To a solution of (3-bromo-5-fluorophenyl)methanol (4 g, 19.51 mmol) in DCM (39.0 mL) at 0° C., DAST (3.35 mL, 25.4 mmol) was added. The reaction mixture was allowed to return to room temperature and stirred at room temperation overnight. Sat. NaHCO₃ was added, the reaction mixture was then extracted by DCM. The organic was dried and concentrated. The crude material was purified by flash chromatography (0-10% EtOAc/heptanes) to yield the final product as colorless oil. LCMS (m/z): no mass (MH⁺), 0.86 min. ¹H NMR (400 MHz, CDCl₃) δ ppm 7.30 (s, 1H), 7.23 (d, J=8.2 Hz, 1H), 7.03 (d, J=8.6 Hz, 1H), 5.41 (s, 1H), 5.29 (s, 1H).

Step 3. 3-fluoro-5-(fluoromethyl)benzaldehyde 1-bromo-3-fluoro-5-(fluoromethyl)benzene (1.30 g, 6.28 mmol) was dissolved in THF (31.4 mL), then cooling down to −78° C., butyllithium (2.5M in Hexanes) (2.76 mL, 6.91 mmol) was added at −78° C., the reaction mixture was then stirred at −78° C. for 30 min. DMF (0.972 mL, 12.56 mmol) was added, after stirred at −78° C. for 1 h, The reaction mixture was quenched by HCl and the reaction mixture was then extracted by EtOAc, the organic was dried and concentrated to yield the crude product. The crude material was used in next step reaction without purification. LCMS (m/z): no mass (MH⁺), 0.60 min. ¹H NMR (400 MHz, CDCl₃) δ ppm 10.08-9.93 (m, 1H), 7.68 (s, 1H), 7.56 (d, J=8.2 Hz, 1H), 7.37 (d, J=7.8 Hz, 1H), 5.53 (s, 1H), 5.42 (s, 1H)

Step 4. (R,E)-N-(3-fluoro-5-(fluoromethyl)benzylidene)-2-methylpropane-2-sulfinamide To a solution of 3-fluoro-5-(fluoromethyl)benzaldehyde (890 mg, 5.70 mmol) and (R)-2-methylpropane-2-sulfinamide (760 mg, 6.27 mmol) in DCE (19.0 mL) was added copper(II) sulfate (anhydrous) (1.820 g, 11.40 mmol), the suspension was stirred under nitrogen at 60° C. in an oil bath for overnight. The suspension turned to light blue color. Cooling down, the reaction mixture was filtered though a plug of Celite and rinsed with DCM, the filtrate was concentrated to yield the crude product. The crude product was purified by flash chromatograph (0-30% EtOAc in heptane) to yield the (R,E)-N-(3-fluoro-5-(fluoromethyl)benzylidene)-2-methylpropane-2-sulfinamide (900 mg, 60.9% yield) as light yellow color oil. LCMS (m/z): 260.1 (MH⁺), 0.88 min. ¹H NMR (400 MHz, CDCl₃) δ ppm 8.57 (s, 1H), 7.60 (s, 1H), 7.56 (d, J=8.8 Hz, 1H), 7.26-7.22 (m, 1H), 5.50 (s, 1H), 5.38 (s, 1H), 1.29-1.23 (m, 9H)

Step 5. (R)N-((R)-1-(3-fluoro-5-(fluoromethyl)phenyl)allyl)-2-methylpropane-2-sulfinamide Dimethyl Zinc (2M in Tolune) (0.434 mL, 0.868 mmol) and vinylmagnesium bromide (1M in THF) (4.51 mL, 4.51 mmol) was mixed at room temperature for 20 min under argon before cooling down to −78° C., then (R,E)-N-(3-fluoro-5-(fluoromethyl)benzylidene)-2-methylpropane-2-sulfinamide (0.900 g, 3.47 mmol) in dry THF (11.57 mL) as added dropwise, maintain the internal temperature between −74° C. to −72° C., after addition the reaction mixture was stirred at −78° C. for 1 h, the reaction was quenched by sat. NH₄Cl, THF was removed in vacuo, then extracted by EtOAc. The organic was washed by water and brine, dried over anhydrous Na₂SO₄, filtered and concentrated. The crude product was purified by flash chromatography (0-30% EtOAc/heptaneatane) to yield product 660 mg, LCMS (m/z): 288.0 (MH⁺), 0.83 min. ¹H NMR (400 MHz, CDCl₃) δ ppm 7.14 (s, 1H), 7.03 (d, J=9.0 Hz, 1H), 7.07 (d, J=9.4 Hz, 1H), 5.90 (ddd, J=7.4, 10.1, 17.3 Hz, 1H), 5.45-5.35 (m, 2H), 5.35-5.25 (m, 2H), 5.01-4.94 (m, 1H), 3.45 (br. s., 1H), 1.30-1.22 (m, 9H)

Step 6. (R)-1-(3-fluoro-5-(fluoromethyl)phenyl)prop-2-en-1-amine (R)N-((R)-1-(3-fluoro-5-(fluoromethyl)phenyl)allyl)-2-methylpropane-2-sulfinamide (660 mg, 2.297 mmol) in MeOH (7.66 mL), was added HCl (4 M in dioxane) (5.742 mL, 22.97 mmol) at 0° C., the reaction mixture was stirred at room temperature for 2 h, The reaction mixture was concentrated to dryness. Sat. Na₂CO₃ was added, the reaction mixture was then extracted by EtOAc. The organic was dried and concentrated to yield the crude product. The crude product was used in next step reaction without purification. LCMS (m/z): 184.1 (MH⁺), 0.40 min.

Step 7. (R)-tert-butyl (1-(3-fluoro-5-(fluoromethyl)phenyl)allyl)carbamate

To a solution of (R)-1-(3-fluoro-5-(fluoromethyl)phenyl)prop-2-en-1-amine (421 mg, 2.30 mmol) in DCM (7.6 mL) was added Boc₂O (640 µl, 2.76 mmol), the reaction mixture was stirred at room temperature overnight, concentrated. The crude product was purified by flash chromatography (0-20% EtOAc/heptane) to yield (R)-tert-butyl (1-(3-fluoro-5-(fluoromethyl)phenyl)allyl)carbamate. LCMS (m/z): 228.1 (MH⁺-56)), 0.91 min. 1H NMR (400 MHz, CDCl₃) δ ppm 7.08 (s, 1H), 6.99 (d, J=9.0 Hz, 2H), 5.95 (ddd, J=5.5, 10.6, 16.8 Hz, 1H), 5.42 (s, 1H), 5.30 (s, 1H), 5.30-5.13 (m, 3H), 4.86 (br. s., 1H), 1.44 (s, 9H).

Step 8. (S)-tert-butyl (1-(3-fluoro-5-(fluoromethyl)phenyl)-2-hydroxyethyl)carbamate (R)-tert-butyl (1-(3-fluoro-5-(fluoromethyl)phenyl)allyl)carbamate (410 mg, 1.447 mmol) in DCM (14.5 mL) was cooled down to −78° C., The reaction mixture was bubbled by O₃ (from ozone generator) for 5 min. The reaction mixture is light blue color, N₂ was bubbled through to get rid of O₃, then NaBH₄ (547 mg, 14.47 mmol) in ethanol (10 mL) was added, the reaction mixture was stirred at −78° C. for 10 min, then allowed to return to room temperature. After 30 min, sat. NH₄Cl was added followed methanol, the reaction mixture was concentrated, then extracted by EtOAc. The organic was washed by sat. NaHCO₃, water and brine, dried and concentrated to yield crude product. The crude product was purified by flash chromatography to give the (S)-tert-butyl (1-(3-fluoro-5-(fluoromethyl)phenyl)-2-hydroxyethyl)carbamate (223 mg, 54% yield). LCMS (m/z): 232.2 (MH⁺-56), 0.73 min. ¹H NMR (400 MHz, CDCl₃) δ ppm 7.10 (s, 1H), 7.02 (d, J=9.4 Hz, 2H), 5.43 (s, 1H), 5.35-5.28 (m, 1H), 4.78 (br. s., 1H), 3.95-3.78 (m, 2H), 1.44 (br. s., 9H).

Step 9. (S)-2-amino-2-(3-fluoro-5-(fluoromethyl)phenyl)ethanol

To a solution of (S)-tert-butyl (1-(3-fluoro-5-(fluoromethyl)phenyl)-2-hydroxyethyl)carbamate (220 mg, 0.766 mmol) in DCM (2.5 mL), HCl (4M in dioxane) (1.9 mL 7.66 mmol) was added at room temperature, the reaction mixture was stirred at room temperature for 1 h. The reaction mixture was then concentrated to dryness. The residue was recrystallized from DCM and heptane. The solid was filtered and air dry to yield (S)-2-amino-2-(3-fluoro-5-(fluoromethyl)phenyl)ethanol (145 mg, 0.908 mmol, 100% yield) HCl salt as white solid. LCMS (m/z): 188.2 (MH⁺), 0.32 min.

Examples 177 and 178

Synthesis of 4-(3-amino-6-((1r,4S)-4-hydroxycyclohexyl)pyrazin-2-yl)-2-fluoro-N-((S)-1-(3-fluoro-5-(fluoromethyl)phenyl)-2-hydroxyethyl)benzamide and 4-(3-amino-6-((1s,4R)-4-hydroxycyclohexyl)pyrazin-2-yl)-2-fluoro-N-((S)-1-(3-fluoro-5-(fluoromethyl)phenyl)-2-hydroxyethyl)benzamide Scheme 75

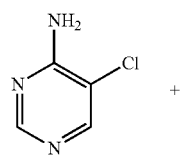

+

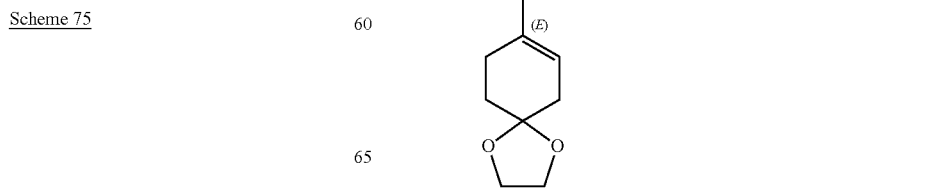

273
-continued

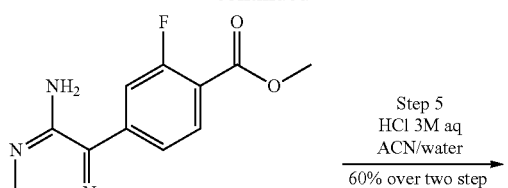

Step 5
HCl 3M aq
ACN/water
60% over two step

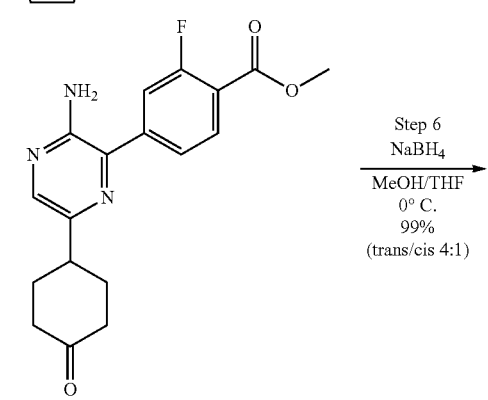

Step 6
NaBH₄
MeOH/THF
0° C.
99%
(trans/cis 4:1)

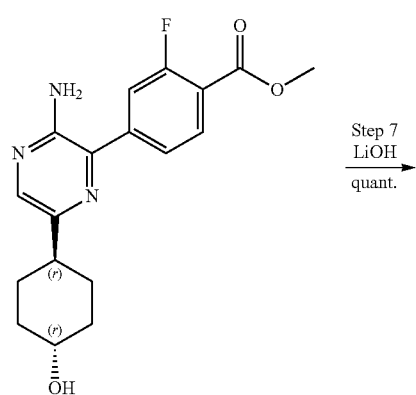

Step 7
LiOH
quant.

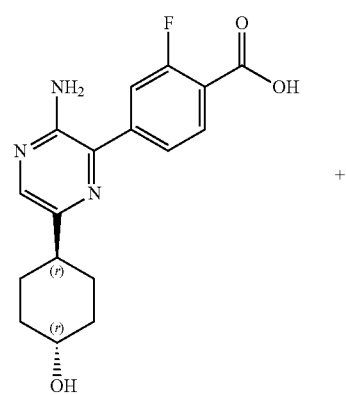

+

274
-continued

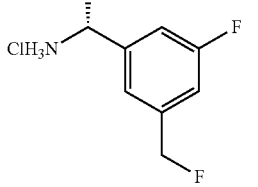

Step 8
HATU, DIEA
NMP

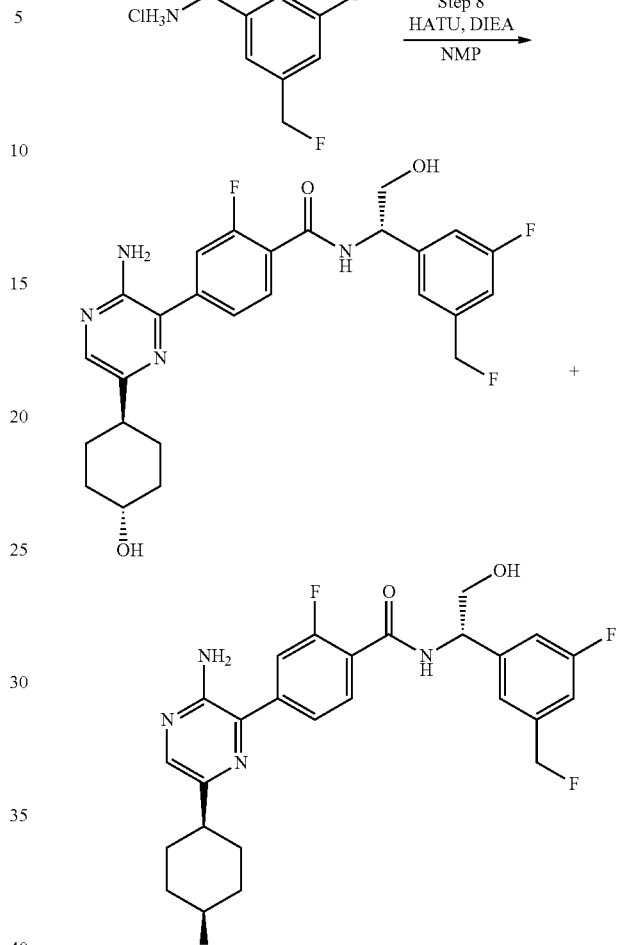

Step 1. Methyl 4-(3-aminopyrazin-2-yl)-2-fluorobenzoate

To 3-chloropyrazin-2-amine (27 g, 208 mmol) in DME (391 mL) and sodium carbonate (66.3 g, 625 mmol) was added methyl 2-fluoro-4-(4,4,5,5-tetramethyl-1,3,2-dioxaborolan-2-yl)benzoate (64.2 g, 229 mmol) and PdCl₂(dppf).CH₂Cl₂ adduct (8.51 g, 10.42 mmol). The reaction mixture was purged with N₂ and heated in oil bath at 100° C. for 3 h. The reaction mixture was partitioned between EtOAc and water. The organic layer was separated, washed with brine, dried over sodium sulfate, filtered and evaporated. The crude product was recrystallized by EtOAc and heptane (2:3) to give methyl 4-(3-aminopyrazin-2-yl)-2-fluorobenzoate in 84% yield. LCMS (m/z): 248.1 (MH⁺), 0.58 min.

Step 2. Methyl 4-(3-amino-6-bromopyrazin-2-yl)-2-fluorobenzoate

To a suspension of methyl 4-(3-aminopyrazin-2-yl)-2-fluorobenzoate (31.5 g, 127 mmol) in acetonitrile (430 mL) at 0° C. was added NBS (23.9 g, 134 mmol). The reaction mixture was stirred in ice bath for 1 h, sat. sodium bicarbonate was added, stirred 30 min and product was extracted with ethylacetate. The organic extracts were combined, washed with brine, dried over sodium sulfate, filtered and evaporated. The crude product was recrystallized in EtOAc and heptane to give methyl 4-(3-amino-6-bromopyrazin-2-yl)-2-fluorobenzoate as brown color solid in 96% yield. LCMS (m/z): 326.0/328.0 (MH$^+$), 0.87 min.

Step 3. Methyl 4-(3-amino-6-(1,4-dioxaspiro[4.5]dec-7-en-8-yl)pyrazin-2-yl)-2-fluorobenzoate To a solution of methyl 4-(3-amino-6-bromopyrazin-2-yl)-2-fluorobenzoate (10 g, 30.7 mmol) in DME (77 mL) was added 4,4,5,5-tetramethyl-2-(1,4-dioxaspiro[4.5]dec-7-en-8-yl)-1,3,2-dioxaborolane (9.79 g, 36.8 mmol), PdCl$_2$(dppf).CH$_2$Cl$_2$ adduct (1.252 g, 1.533 mmol), H$_2$O (25.6 mL) and then last sodium carbonate (9.75 g, 92 mmol). The reaction was heat at 100° C. in oil bath for 2 h. Cooled down. The reaction mixture was extracted by EtOAc 3 times, the organic was washed with water and brine, dried and concentrated. The crude material was recrystallized in DCM and heptane (1:1) to give product methyl 4-(3-amino-6-(1,4-dioxaspiro[4.5]dec-7-en-8-yl)pyrazin-2-yl)-2-fluorobenzoate in 75% yield. LCMS (m/z): 382.2 (MH$^+$), 0.82 min.

Step 4. Methyl 4-(3-amino-6-(1,4-dioxaspiro[4.5]decan-8-yl)pyrazin-2-yl)-2-fluorobenzoate Methyl 4-(3-amino-6-(1,4-dioxaspiro[4.5]dec-7-en-8-yl)pyrazin-2-yl)-2-fluorobenzoate (6.1 g, 15.83 mmol) was dissolved in MeOH (150 mL) and EtOAc (80 mL) the reaction mixture was flushed with N$_2$ for 15 min, Then PdC(DEGASSA) (6 g, 5.64 mmol) was added, the reaction mixture was then charged with hydrogen balloon and stirred at room temperature overnight. The reaction mixture was filtered through Celite, which was washed with EtOAc and methanol. The filtrate was concentrated to yield the crude product, which was used in the next step reaction without purification. LCMS (m/z): 388.0 (MH$^+$), 0.79 min.

Step 5. Methyl 4-(3-amino-6-(4-oxocyclohexyl)pyrazin-2-yl)-2-fluorobenzoate

To a solution of methyl 4-(3-amino-6-(1,4-dioxaspiro[4.5]decan-8-yl)pyrazin-2-yl)-2-fluorobenzoate (6.2 g, 16.00 mmol) in Acetonitrile (100 mL), Water (40 mL), was added 3M aqueous solution HCl (13.34 mL, 80 mmol). The reaction was stirred at room temperature for 30 min. The reaction mixture was basified with 6M NaOH (10 mL), then use sat. NaHCO$_3$ to adjust to pH 8. After acetonitrile was removed in vacuo, the solid suspension residue was filtered and washed with water and heptane, air-dried to give methyl 4-(3-amino-6-(4-oxocyclohexyl)pyrazin-2-yl)-2-fluorobenzoate as light yellow solid in 67% yield. LCMS (m/z): 344.0 (MH$^+$), 0.70 min.

Step 6. Methyl 4-(3-amino-6-((1r,4r)-4-hydroxycyclohexyl)pyrazin-2-yl)-2-fluorobenzoate To a solution of methyl 4-(3-amino-6-(4-oxocyclohexyl)pyrazin-2-yl)-2-fluorobenzoate (3.25 g, 9.47 mmol) in Methanol (100 mL) and THF (20 mL) at 0° C., NaBH$_4$ was added (0.358 g, 9.47 mmol). After 30 min, saturated NH$_4$Cl was added slowly, then stirred at room temperature for 1 h. Methanol and THF was removed in vacuo. The residue was extracted by EtOAc 3 times, the combined organic was washed with NaHCO$_3$ and water, dried and concentrated. The crude product was used in next step reaction without purification. LCMS (m/z): 346.4 (MH$^+$), 0.63 min (trans) and 0.66 min (cis); trans/cis (~4:1).

Step 7. 4-(3-amino-6-((1r,4r)-4-hydroxycyclohexyl)pyrazin-2-yl)-2-fluorobenzoic acid and 4-(3-amino-6-((1s,4s)-4-hydroxycyclohexyl)pyrazin-2-yl)-2-fluorobenzoic acid To a solution of methyl 4-(3-amino-6-((1r,4r)-4-hydroxycyclohexyl)pyrazin-2-yl)-2-fluorobenzoate (3.25 g, 9.41 mmol) in MeOH (15.68 mL) and THF (15.68 mL) and then LiOH 1M aqueous solution (23.53 mL, 23.53 mmol). The reaction was stirred at room temperature for 2 h, 6 M HCl (3.9 mL) was added slowly. Methanol and THF was removed in vacuo, the residue (yellow solid suspension) was filtered. The solid was washed with water and heptane, air dry to yield the crude product. The crude product was used in next step reaction without purification. LCMS (m/z): 332.1 (MH$^+$), 0.49 min (trans) and 0.53 min (cis).

Step 8. 4-(3-amino-6-((1r,4S)-4-hydroxycyclohexyl)pyrazin-2-yl)-2-fluoro-N-((S)-1-(3-fluoro-5-(fluoromethyl)phenyl)-2-hydroxyethyl)benzamide and 4-(3-amino-6-((1s,4R)-4-hydroxycyclohexyl)pyrazin-2-yl)-2-fluoro-N-((S)-1-(3-fluoro-5-(fluoromethyl)phenyl)-2-hydroxyethyl)benzamide To a mixture of 4-(3-amino-6-((1r,4r)-4-hydroxycyclohexyl)pyrazin-2-yl)-2-fluorobenzoic acid and 4-(3-amino-6-((1s,4s)-4-hydroxycyclohexyl)pyrazin-2-yl)-2-fluorobenzoic acid (19.45 mg, 0.053 mmol) was added NMP (0.5 mL), Hünig's base (0.042 mL, 0.240 mmol) and (S)-2-amino-2-(3-fluoro-5-(fluoromethyl)phenyl)ethanol-HCl (9 mg, 0.048 mmol). Then HATU (36.6 mg, 0.096 mmol) was added. The reaction was stirred for 1 h at room temperature, followed by LCMS. To the crude reaction was added 0.5 mL of NMP, filtered, purified by prep HPLC with both isomers isolated 4-(3-amino-6-((1r,4S)-4-hydroxycyclohexyl)pyrazin-2-yl)-2-fluoro-N-((S)-1-(3-fluoro-5-(fluoromethyl)phenyl)-2-hydroxyethyl)benzamide as trans and minor 4-(3-amino-6-((1s,4R)-4-hydroxycyclohexyl)pyrazin-2-yl)-2-fluoro-N-((S)-1-(3-fluoro-5-(fluoromethyl)phenyl)-2-hydroxyethyl)benzamide as cis. Both products were lyophilized to TFA salts. For trans diastereomer, 1H NMR (400 MHz, CD$_3$OD) δ ppm 7.84-7.70 (m, 2 H), 7.64-7.47 (m, 2 H), 7.19 (s, 1 H), 7.09 (d, J=9.78 Hz, 1 H), 6.98 (d, J=9.00 Hz, 1 H), 5.36 (s, 1 H), 5.24 (s, 1 H), 5.13 (t, J=5.87 Hz, 1 H), 3.87-3.70 (m, 2 H), 3.59-3.45 (m, 1 H), 2.62-2.49 (m, 1 H), 2.05-1.92 (m, 2 H), 1.91-1.79 (m, 2 H), 1.57 (qd, J=12.98 Hz, 2.93 Hz, 2 H), 1.39-1.24 For cis diastereomer, 1H NMR (400 MHz, CD$_3$OD) δ ppm 7.93-7.81 (m, 2H) 7.75-7.58 (m, 2H) 7.29 (d, J=9.78 Hz, 1 H), 7.19 (d, J=9.78 Hz, 1H), 7.07 (d, J=9.00 Hz, 1H), 5.45 (s, 1 H), 5.33 (s, 1 H), 5.22 (t, J=5.67 Hz, 1H), 4.01 (br. s., 1 H), 3.94-3.77 (m, 2 H), 2.80-2.68 (m, 1 H), 2.12-1.96 (m, 2 H) 1.91-1.80 (m, 2 H), 1.77-1.60 (m, 4 H).

Synthesis of (S)N-(2-amino-2-(3-fluoro-5-iodophenyl)ethyl)-N-methyl-2-nitrobenzenesulfonamide Scheme 76

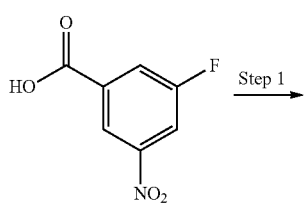

277

-continued

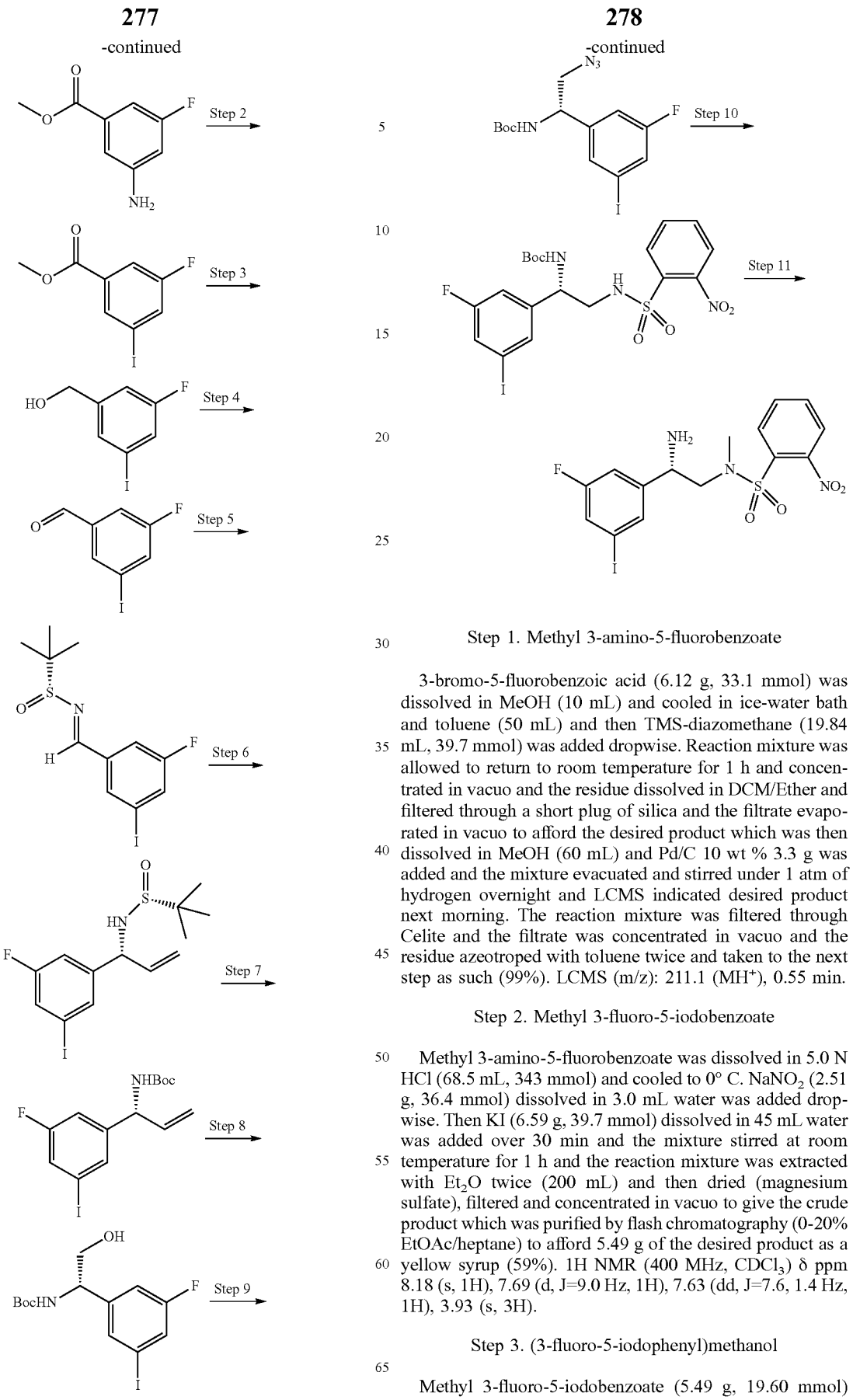

278

-continued

Step 1. Methyl 3-amino-5-fluorobenzoate 3-bromo-5-fluorobenzoic acid (6.12 g, 33.1 mmol) was dissolved in MeOH (10 mL) and cooled in ice-water bath and toluene (50 mL) and then TMS-diazomethane (19.84 mL, 39.7 mmol) was added dropwise. Reaction mixture was allowed to return to room temperature for 1 h and concentrated in vacuo and the residue dissolved in DCM/Ether and filtered through a short plug of silica and the filtrate evaporated in vacuo to afford the desired product which was then dissolved in MeOH (60 mL) and Pd/C 10 wt % 3.3 g was added and the mixture evacuated and stirred under 1 atm of hydrogen overnight and LCMS indicated desired product next morning. The reaction mixture was filtered through Celite and the filtrate was concentrated in vacuo and the residue azeotroped with toluene twice and taken to the next step as such (99%). LCMS (m/z): 211.1 (MH$^+$), 0.55 min.

Step 2. Methyl 3-fluoro-5-iodobenzoate

Methyl 3-amino-5-fluorobenzoate was dissolved in 5.0 N HCl (68.5 mL, 343 mmol) and cooled to 0° C. NaNO$_2$ (2.51 g, 36.4 mmol) dissolved in 3.0 mL water was added dropwise. Then KI (6.59 g, 39.7 mmol) dissolved in 45 mL water was added over 30 min and the mixture stirred at room temperature for 1 h and the reaction mixture was extracted with Et$_2$O twice (200 mL) and then dried (magnesium sulfate), filtered and concentrated in vacuo to give the crude product which was purified by flash chromatography (0-20% EtOAc/heptane) to afford 5.49 g of the desired product as a yellow syrup (59%). 1H NMR (400 MHz, CDCl$_3$) δ ppm 8.18 (s, 1H), 7.69 (d, J=9.0 Hz, 1H), 7.63 (dd, J=7.6, 1.4 Hz, 1H), 3.93 (s, 3H).

Step 3. (3-fluoro-5-iodophenyl)methanol

Methyl 3-fluoro-5-iodobenzoate (5.49 g, 19.60 mmol) was dissolved in DCM (100 mL) and cooled to −78° C.

DIBAL-H (49.0 mL, 49.0 mmol) was added dropwise over 30 min and then after 1 h another portion of DIBAL-H (49.0 mL, 49.0 mmol) was added. Reaction mixture agitated at −78° C. for 4 h and poured carefully onto ice-cold 1N HCl. The mixture was agitated for 10 min and the layers separated and the aq. layer extracted with DCM and the combined organic extract was dried (magnesium sulfate), filtered and concentrated in vacuo to afford the desired product in quantitative yield. LCMS not conclusive.

Step 4. 3-fluoro-5-iodobenzaldehyde (3-fluoro-5-iodophenyl)methanol (9.79 g, 35.0 mmol) was dissolved in DCM (94 mL) and then silica gel (18.0 g) was added. To the mixture at room temperature was added PCC (18.3 g, 45.0 mmol) portion-wise and the mixture agitated at room temperature for 1 h and followed by TLC. After 1 h, TLC indicated complete conversion of the SM to a non-polar (presumably aldehyde). The reaction mixture was filtered over 1-inch plug of silica pad and eluted with 30% Ether in DCM (200 mL). The filtrate was concentrated in vacuo to afford the crude product, which was taken to the next step without further purification.

Step 5. (R,E)-N-(3-fluoro-5-iodobenzylidene)-2-methylpropane-2-sulfinamide

To a solution of 3-fluoro-5-iodobenzaldehyde (8.75 g, 35 mmol) and (R)-(+)-t-Butylsulfinamide (4.67 g, 38.5 mmol) in DCE (117 mL) was added copper(II) sulfate (anhydrous) (16.76 g, 105 mmol) and the resulting suspension was heated at 60° C. overnight. LCMS indicated desired product formation. Reaction mixture was filtered through Celite and the filtrate concentrate in vacuo and then taken to the next step as such. LCMS (m/z): 354.1 (MH$^+$), 1.08 min.

Step 6. (R)-N-((R)-1-(3-fluoro-5-iodophenyl)allyl)-2-methylpropane-2-sulfinamide Dimethyl zinc (1.2M in toluene) (7.29 mL, 8.75 mmol) and vinylmagnesium bromide (45.5 mL, 45.5 mmol) was mixed at room temperature for 20 min under argon before cooling down to −78° C., then (R,E)-N-(3-fluoro-5-iodobenzylidene)-2-methylpropane-2-sulfinamide in dry THF (117 mL) as added dropwise about 30 min. The internal temperature between −74 C to −72° C., after addition the reaction mixture was stirred at −78° C. for 1 h, sample was taken quenched by Water, LCMS showed the desired product along with unreacted starting material. More vinylmagnesium bromide (12 mL, 12.0 mmol)) was added and reaction monitored by LCMS and after 30 min, reaction was deemed complete. The reaction mixture was poured over ice-cold by sat. NH$_4$Cl and water, THF was removed in vacuo and the product extracted by EtOAc. The organic layer was washed by water and Brine, dried over anhydrous Na$_2$SO$_4$, filtered and concentrated and the crude product was purified by flash chromatography (0-70% EtOAc/heptane) to provide 8.99 g of (R)-N-((R)-1-(3-fluoro-5-iodophenyl)allyl)-2-methylpropane-2-sulfinamide as the desired product as a colorless yellow syrup. Yield (67.4%). The yield is for the 4 step sequence. Note: The major side-product corresponds to de-iodinated desired product. LCMS (m/z): 382.5 (MH$^+$), 0.96 min; 1H NMR (400 MHz, CDCl$_3$)) δ ppm 7.48 (s, 1H), 7.37 (dt, J=7.6, 1.9 Hz, 1H), 7.06 (d, J=9.0 Hz, 1H), 5.85 (ddd, J=17.0, 10.0, 7.4 Hz, 1H), 5.25-5.47 (m, 3H), 4.90 (d, J=7.0 Hz, 1H), 3.23-3.66 (m, 1H), 1.26 (s, 9H).

Step 7. (R)-tert-butyl (1-(3-fluoro-5-iodophenyl)allyl)carbamate (R)-N-((R)-1-(3-fluoro-5-iodophenyl)allyl)-2-methylpropane-2-sulfinamide (8.99 g, 23.58 mmol) was dissolved in MeOH (40 mL) and treated with 4 N HCl (11.79 mL, 47.2 mmol) and the mixture agitated at room temperature for 1 h and concentrated in vacuo. The residue was dissolved water and Sat'd Na2CO3 was added. The product was extracted with 3:1 CHCl$_3$:IPA and the organic layer was dried (magnesium sulfate), filtered and concentrated in vacuo. The residue was dissolved in DCM (60 mL) and Boc-anhydride (6.79 mL, 29.2 mmol) was added. The mixture was agitated overnight at room temperature and the next morning, the reaction mixture was concentrated in vacuo and the crude product (R)-tert-butyl (1-(3-fluoro-5-iodophenyl)allyl)carbamate taken to the next step without any further purification. LCMS (m/z): 322.1 (MH$^+$-56), 1.11 min.

Step 8. (S)-tert-butyl (1-(3-fluoro-5-iodophenyl)-2-hydroxyethyl)carbamate (R)-tert-butyl (1-(3-fluoro-5-iodophenyl)allyl)carbamate (8.89 g, 23.58 mmol) was dissolved in DCM (236 mL) and cooled to −78° C. Ozone was purged through the mixture until blue color persisted. Reaction mixture was then purged with nitrogen and NaBH$_4$ (8.92 g, 236 mmol) was added in one portion followed by addition of MeOH (120 mL) and the mixture was agitated at same temperature for 2 h and then acetone 20 mL was added. Reaction mixture was agitated for another 1 h and then poured over saturated NH$_4$Cl and then extracted with DCM (500 mL) and then with 3:1 CHCl$_3$/IPA (200 mL) and the organic extracts were combined and dried (magnesium sulfate), and the solvent concentrated in vacuo and the residue purified by flash chromatography to afford 6.74 g (17.7 mmol) of (S)-tert-butyl (1-(3-fluoro-5-iodophenyl)-2-hydroxyethyl)carbamate (75%). LCMS (m/z): 326.1 (MH$^+$-56), 0.90 min.

Step 9. (S)-tert-butyl (2-azido-1-(3-fluoro-5-iodophenyl)ethyl)carbamate (S)-tert-butyl (1-(3-fluoro-5-iodophenyl)-2-hydroxyethyl)carbamate (4.8112 g, 12.62 mmol) was dissolved in DCM (100 mL) and cooled to 0° C. Et$_3$N (2.62 mL, 18.93 mmol) was added next and then MsCl (1.180 mL, 15.15 mmol) was added dropwise. The reaction mixture was agitated at same temperature for 30 min after which RM quenched with Sat'd NaHCO$_3$ and water. The product was extracted with DCM and the combined organic layer was dried (magnesium sulfate), filtered and concentrated in vacuo to afford the crude product which was dissolved in DMF (25 mL, ca 0.5 M). NaN$_3$ (2.462 g, 37.9 mmol) was added next and the mixture heated at 70° C. After 6 h, the reaction mixture was cooled to room temperature and diluted with EtOAc and water and the product extracted with EtOAc. The combined organic extract was washed with water thrice and dried (magnesium sulfate), filtered and concentrated in vacuo and the residue purified by flash chromatography (0-50%) EtOAc/heptane to afford 4.03 g of (S)-tert-butyl (2-azido-1-(3-fluoro-5-iodophenyl)ethyl)carbamate as desired product. LCMS (m/z): 351.0 (MH$^+$-56), 1.05 min.

Step 10. (S)-tert-butyl (1-(3-fluoro-5-iodophenyl)-2-(2-nitrophenylsulfonamido)ethyl)carbamate (S)-tert-butyl (2-azido-1-(3-fluoro-5-iodophenyl)ethyl)carbamate (288 mg, 0.709 mmol) was dissolved in MeOH (7.09 mL) and then polymer-bound PPh₃ (7.09 mmol) was added. RM agitated at 70° C. overnight. The next morning, LCMS indicated formation of desired product. RM filtered through Celite and the filter-cake washed with DCM and MeOH and the filtrate concentrated in vacuo to afford the crude amine which was taken to the next step without any further purification. The crude amine was dissolved in DCM (7 mL) and cooled to 0° C. and then Triethylamine (0.198 mL, 1.418 mmol) was added. Then 2-nitrobenzene-1-sulfonyl chloride (189 mg, 0.851 mmol) was added in one portion. The reaction mixture was agitated at room temperature for 1 h and quenched with water and the product extracted with DCM. The organic layer was washed with brine and dried (magnesium sulfate), filtered and concentrated in vacuo and the residue purified by flash chromatography (0-40% EtOAc/heptane) to afford 290 mg of (S)-tert-butyl (1-(3-fluoro-5-iodophenyl)-2-(2-nitrophenylsulfonamido)ethyl)carbamate as the desired product. LCMS (m/z): 524.0 (MH⁺-56), 1.10 min.

Step 11. (S)-N-(2-amino-2-(3-fluoro-5-iodophenyl)ethyl)-N-methyl-2-nitrobenzenesulfonamide (S)-tert-butyl (1-(3-fluoro-5-iodophenyl)-2-(2-nitrophenylsulfonamido)ethyl)carbamate (290 mg, 0.513 mmol) was dissolved in DMF (5.1 mL) and K₂CO₃ (142 mg, 1.026 mmol) followed by iodomethane (48.1 µl, 0.769 mmol) were added. The mixture was agitated at room temperature for 1 h upon which complete reaction observed. RM diluted with water and EtOAc. The organic layer was washed with water twice and dried (magnesium sulfate), filtered and concentrated in vacuo to give relatively pure product which was dissolved in DCM (5 mL) and treated with 4N HCl in dioxane (2 mL) and the mixture agitated at room temperature overnight and the mixture concentrated in vacuo to afford the desired product (S)-N-(2-amino-2-(3-fluoro-5-iodophenyl)ethyl)-N-methyl-2-nitrobenzenesulfonamide as the hydrochloride salt. LCMS (m/z): 480.4 (MH⁺), 0.72 min.

Example 179

Synthesis of (S)-N-(2-amino-1-(3-fluoro-5-iodophenyl)ethyl)-4-(3-amino-6-(tetrahydro-2H-pyran-4-yl)pyrazin-2-yl)-2-fluorobenzamide Scheme 77

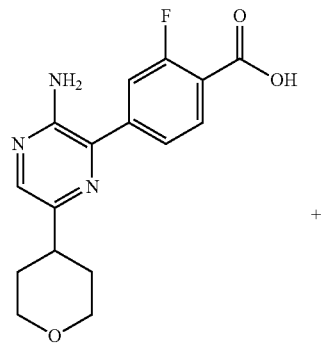

+

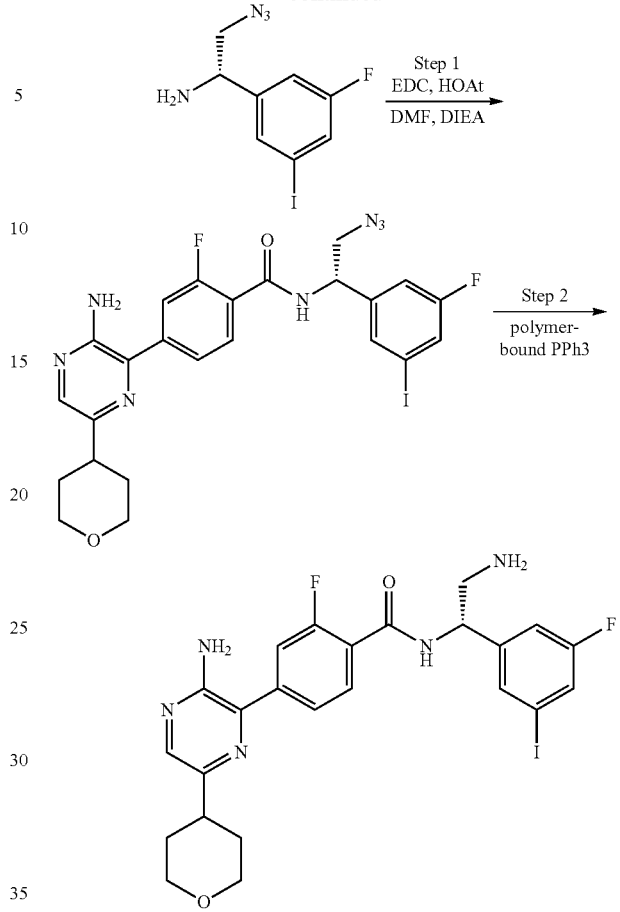

Step 1. (S)-4-(3-amino-6-(tetrahydro-2H-pyran-4-yl)pyrazin-2-yl)-N-(2-azido-1-(3-fluoro-5-iodophenyl)ethyl)-2-fluorobenzamide 4-(3-Amino-6-(tetrahydro-2H-pyran-4-yl)pyrazin-2-yl)-2-fluorobenzoic acid TFA adduct (126 mg, 0.292 mmol) and HOAt (0.060 g, 0.438 mmol) was dissolved in DMF (1 mL) and DIEA (0.156 mL, 0.876 mmol). (S)-2-azido-1-(3-fluoro-5-iodophenyl)ethanamine hydrochloride salt (100 mg, 292 mmol), obtained from the reaction of (S)-tert-butyl (2-azido-1-(3-fluoro-5-iodophenyl)ethyl)carbamate with 4M HCl in dioxane (Step 9 in Scheme 76), was added, followed by EDC (0.090 g, 0.467 mmol). The reaction mixture was stirred at room temperature overnight. The reaction mixture was diluted with EtOAc and water, and the organic layer was washed with water twice and then with saturated Na₂CO₃. The organic layer was dried over magnesium sulfate, filtered and concentrated in vacuo providing crude (S)-4-(3-amino-6-(tetrahydro-2H-pyran-4-yl)pyrazin-2-yl)-N-(2-azido-1-(3-fluoro-5-iodophenyl)ethyl)-2-fluorobenzamide without further purification.

Step 2. (S)-N-(2-amino-1-(3-fluoro-5-iodophenyl)ethyl)-4-(3-amino-6-(tetrahydro-2H-pyran-4-yl)pyrazin-2-yl)-2-fluorobenzamide The crude (S)-4-(3-amino-6-(tetrahydro-2H-pyran-4-yl)pyrazin-2-yl)-N-(2-azido-1-(3-fluoro-5-iodophenyl)ethyl)-2-fluorobenzamide was dissolved in THF (5 mL), and triphenylphosphine (polymer bound, 3 mmol/g) (0.97 g, 3.70 mmol) was added dropwise. The mixture was heated at 70° C. for 3 h. LCMS indicated absence of starting material (at this stage, the phosphorylimine intermediate is likely present in solid phase). Water (4.5 mL) and THF (5 mL) were added, and the mixture was heated at 80° C. for 3 h and then filtered. The filter cake was washed with DCM and then filtrate was concentrated in vacuo. The residue was dissolved in DCM and washed with water and the organic layer dried over magnesium sulfate, filtered and concentrated in vacuo to afford the residue which was purified by flash chromatography (0-60% DCM/10% MeOH in EtOAc containing 0.5% NH₄OH), and the product fractions were collected and concentrated. The residue was dissolved in acetonitrile and water, and lyophillized to obtain 101.2 mg of (S)-N-(2-amino-1-(3-fluoro-5-iodophenyl)ethyl)-4-(3-amino-6-(tetrahydro-2H-pyran-4-yl)pyrazin-2-yl)-2-fluorobenzamide as the desired product. LCMS (m/z): 580.1 (MH⁺), 0.70 min. ¹H NMR (CD₃OD) δ (ppm): 7.92 (s, 1H), 7.85-7.79 (m, 1H), 7.73 (dd, J=8.0, 1.4 Hz, 1H), 7.68-7.61 (m, 2H), 7.50-7.43 (m, 1H), 7.23 (d, J=9.5 Hz, 1H), 5.12 (t, J=6.9 Hz, 1H), 4.07 (dd, J=11.2, 3.3 Hz, 2H), 3.60 (td, J=11.7, 2.0 Hz, 2H), 3.09-2.83 (m, 3H), 2.02-1.76 (m, 4H).

Synthesis of (S)-tert-butyl (2-amino-2-(3-bromo-5-fluorophenyl)ethyl)carbamate

Scheme 78

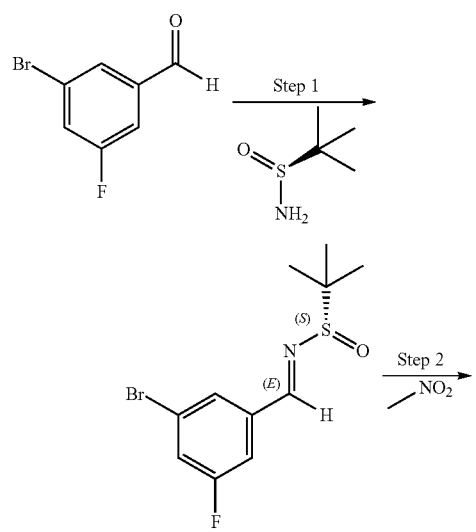

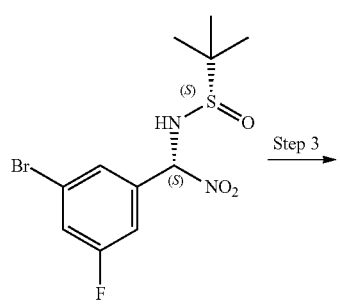

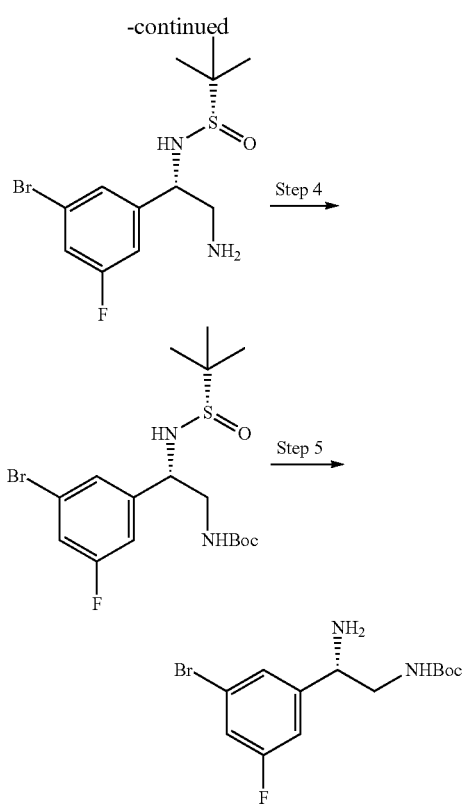

Step 1. (S,E)-N-(3-bromo-5-fluorobenzylidene)-2-methylpropane-2-sulfinamide

To a solution of 3-bromo-5-fluorobenzaldehyde (5 g, 24.63 mmol) and (S)-2-methylpropane-2-sulfinamide (3.28 g, 27.1 mmol) in DCE (82 mL) was added copper(II) sulfate (anhydrous) (7.86 g, 49.3 mmol). The suspension was stirred under nitrogen at 60° C. overnight. The reaction mixture was cooled down, filtered through a plug of celite, and rinsed with DCM. The filtrate was concentrated to yield the crude product. The crude product was purified by flash chromatograph eluting with 0-30% EtOAc in heptane to yield the product (S,E)-N-(3-bromo-5-fluorobenzylidene)-2-methylpropane-2-sulfinamide (7.5 g, 24.49 mmol, 99% yield) as a light yellow color oil. LCMS (m/z): 306.1/308.1 (MH⁺), 1.04 min.

Step 2. (S) N-((S)-1-(3-bromo-5-fluorophenyl)-2-nitroethyl)-2-methylpropane-2-sulfinamide Nitromethane (1.0 mL, 17.20 mmol) was dissolved in THF (34.4 mL), then BuLi (2.5 M in hexanes) (7.22 mL, 18.06 mmol) was added at −78° C. The reaction mixture was stirred at −78° C. for 10 min, then warmed up to room temperature for 20 min. After cooling down to −78° C., (S,E)-N-(3-bromo-5-fluorobenzylidene)-2-methylpropane-2-sulfinamide (4.74 g, 15.48 mmol) in THF (6 mL) was added dropwise. The reaction mixture was stirred at −78° C. for 20 min, warmed up to room temperature, and stirred at room temperature for 5 h. The reaction mixture was quenched by sat NH₄Cl, and extracted by EtOAc. The organic was dried over Na₂SO₄, filtered and concentrated. The crude product was purified by flash chromatography (0-40%-100% EtOAC/heptane). Pure fractions were combined to yield (S) N-((S)-1-(3-bromo-5-fluorophenyl)-2-ni-troethyl)-2-methylpropane-2-sulfinamide (2.2 g, 5.99 mmol, 38.7% yield). LCMS (m/z): 367.1/369.1 (MH$^+$), 0.89 min; $^1$H NMR (400 MHz, CDCl$_3$) δ ppm 7.31 (s, 1H), 7.03 (d, J=9.0 Hz, 1H), 5.03 (q, J=5.7 Hz, 1H), 4.87-4.78 (m, 2H), 4.48 (d, J=5.1 Hz, 1H), 1.33-1.25 (m, 9H).

Step 3. (S) N-((S)-2-amino-1-(3-bromo-5-fluoro-phenyl)ethyl)-2-methylpropane-2-sulfinamide (S) N-((S)-1-(3-bromo-5-fluorophenyl)-2-nitroethyl)-2-methylpropane-2-sulfinamide (2.2 g, 5.99 mmol) was dissolved in MeOH (19.97 mL), flushed with N$_2$ for 10 min, and then PtO$_2$ (0.408 g, 1.797 mmol) was added. The reaction mixture was charged with hydrogen balloon and stirred at room temperature overnight. The reaction mixture was filtered through celite and washed by methanol and EtOAc. The filtrate was dried over Na$_2$SO$_4$, filtered and concentrated. The crude material was used in next step reaction without further purification. LCMS (m/z): 337.1/339.1 (MH$^+$), 0.64 min.

Step 4. tert-butyl ((S)-2-(3-bromo-5-fluorophenyl)-2-((S)-1,1-dimethylethylsulfinamido)ethyl)carbamate (S) N-((S)-2-amino-1-(3-bromo-5-fluorophenyl)ethyl)-2-methylpropane-2-sulfinamide (1.75 g, 5.19 mmol) was dissolved in DCM (17.30 mL), and then Boc$_2$O (1.325 mL, 5.71 mmol) was added. The reaction mixture was stirred at room temperature for 3 h, and then concentrated. The crude product was purified to yield the product tert-butyl ((S)-2-(3-bromo-5-fluorophenyl)-2-((S)-1,1-dimethylethylsulfinamido)ethyl)carbamate (1.78 g, 78%). LCMS (m/z): 437.1/439.1 (MH$^+$), 0.99 min.

Step 5. (S)-tert-butyl (2-amino-2-(3-bromo-5-fluorophenyl)ethyl)carbamate

To a solution of tert-butyl ((S)-2-(3-bromo-5-fluorophenyl)-2-((R)-1,1-dimethylethylsulfinamido)ethyl)carbamate (1.78 g, 4.07 mmol) in DCM (13.57 mL) was added HCl (4M in dioxane) (4.07 mL, 16.28 mmol) at room temperature. The reaction mixture was stirred at room temperature for 1 h. The reaction mixture was neutralized to pH=7, then extracted by EtOAc to give the desired (S)-tert-butyl (2-amino-2-(3-bromo-5-fluorophenyl)ethyl)carbamate (300 mg) as a free base. LCMS (m/z): 317.1/319.1 (MH$^+$), 0.66 min.

Synthesis of (S)-tert-butyl (2-amino-2-(3-bromophenyl)ethyl)carbamate

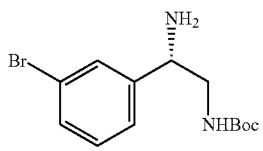

Following Scheme 78, using 3-bromobenzaldehyde, (S)-tert-butyl (2-amino-2-(3-bromophenyl)ethyl)carbamate was obtained as a HCl salt. LCMS (m/z): 315.1/317.1 (MH$^+$), 0.66 min.

Synthesis of (S)-methyl (2-amino-2-(3-bromo-5-fluorophenyl)ethyl)carbamate

Scheme 79

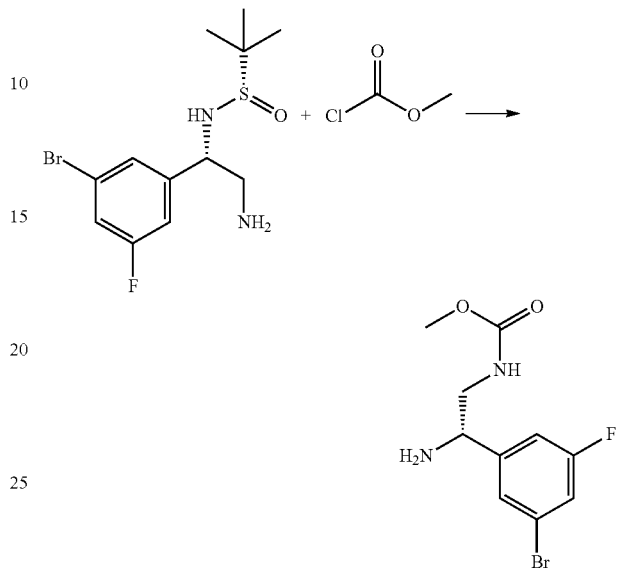

To a solution of (S) N-((S)-2-amino-1-(3-bromo-5-fluorophenyl)ethyl)-2-methylpropane-2-sulfinamide (100 mg, 0.297 mmol) in DCM (988 µl) was added TEA (124 µl, 0.890 mmol) and methyl chloroformate (24.12 µl, 0.311 mmol). The reaction mixture was stirred at room temperature for 1 h. The reaction mixture was extracted by EtOAc and the organics were washed with water and brine, dried over sodium sulfate, filtered off, and concentrated in vacuo. The residue was dissolved in Et$_2$O (1 mL), then HCl (4M in dioxane) (148 µl, 0.593 mmol) was added. The reaction mixture was stirred at room temperature for 30 min. After the solvent was decant out, the residue solid was used in next step without further purification. LCMS (m/z): 291.2/293 (MH$^+$), 0.49 min.

(S)-methyl (2-amino-2-(3-bromophenyl)ethyl)car-bamate

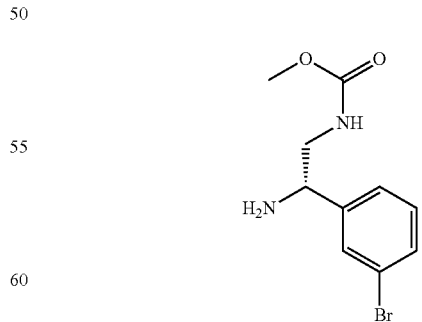

Following Scheme 79, using (S)-N-((S)-2-amino-1-(3-bromophenyl)ethyl)-2-methylpropane-2-sulfinamide, (S)-methyl (2-amino-2-(3-bromophenyl)ethyl)carbamate was obtained. LCMS (m/z): 273.0/275.0 (MH$^+$), 0.46 min.

287

(S)-methyl (2-amino-2-(3-chlorophenyl)ethyl)carbamate

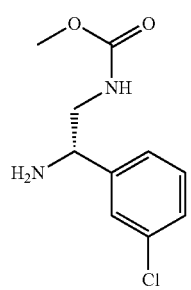

Following Scheme 79, using (S)-N-((S)-2-amino-1-(3-chlorophenyl)ethyl)-2-methylpropane-2-sulfinamide, (S)-methyl (2-amino-2-(3-chlorophenyl)ethyl)carbamate was obtained. LCMS (m/z): 229.2 (MH$^+$), 0.42 min.

Synthesis of (S)N-(2-amino-2-(3-bromo-5-fluorophenyl)ethyl)acetamide

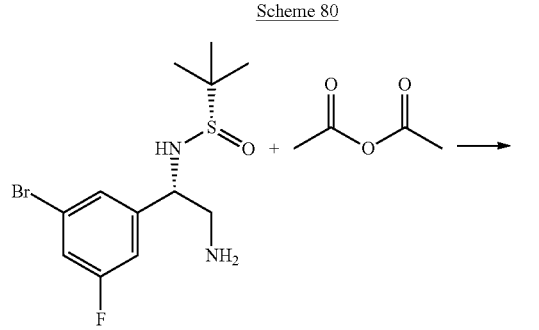

Scheme 80

(S)-N-((S)-2-amino-1-(3-bromo-5-fluorophenyl)ethyl)-2-methylpropane-2-sulfinamide (100 mg, 0.297 mmol) was dissolved in DCM (988 μl), followed by pyridine (71.9 μl, 0.890 mmol) and acetic anhydride (28.0 μl, 0.297 mmol). The reaction mixture was stirred at room temperature for 1 h, extracted by EtOAc, washed by water and brine, dried over Na$_2$SO$_4$ and concentrated. The residue was dissolved in Et$_2$O (1 mL), then HCl (4 M in dioxane) (148 μl, 0.593 mmol) was added. The reaction mixture was stirred at room temperature for 30 min. After the solvent was decant out, the residue solid was used in next step reaction without purification. LCMS (m/z): 275.1/277.1 (MH$^+$), 0.41 min.

288

Synthesis of (S)-N-(2-amino-2-(3-bromophenyl)ethyl)acetamide

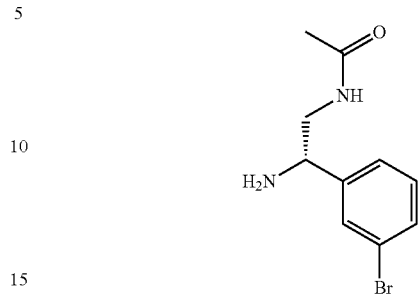

Following scheme 80, using (S)-N-((S)-2-amino-1-(3-bromophenyl)ethyl)-2-methylpropane-2-sulfinamide, (S)-N-(2-amino-2-(3-bromophenyl)ethyl)acetamide was obtained. LCMS (m/z): 257.1/259.1 (MH$^+$), 0.40 min.

Example 180

Synthesis of (S)-N-(2-amino-1-(3-bromo-5-fluorophenyl)ethyl)-4-(3-amino-6-(tetrahydro-2H-pyran-4-yl)pyrazin-2-yl)-2-fluorobenzamide

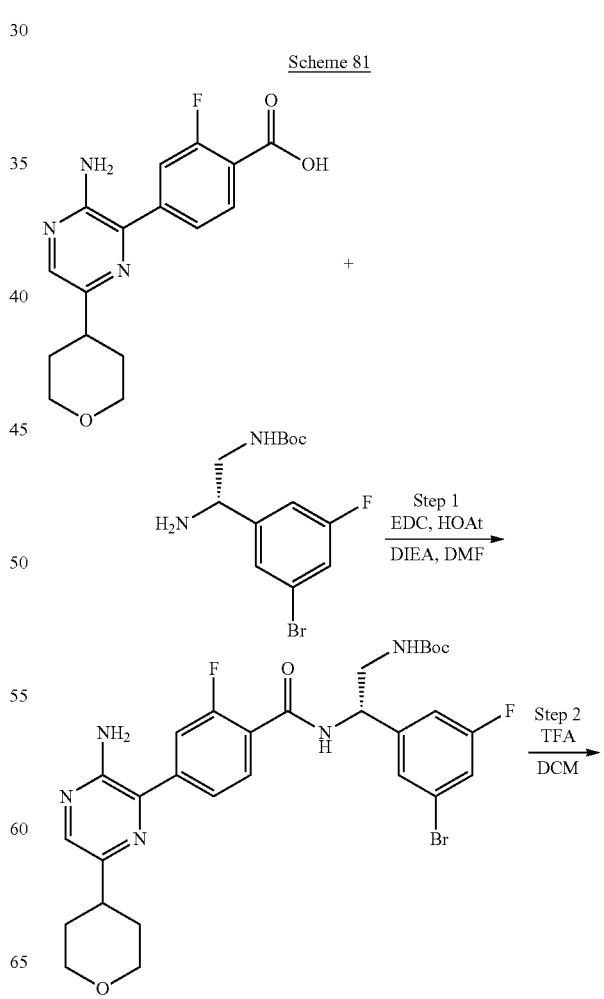

Scheme 81

-continued

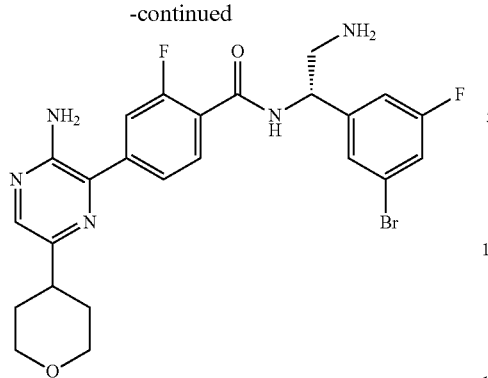

Step 1. (S)-tert-butyl (2-(4-(3-amino-6-(tetrahydro-2H-pyran-4-yl)pyrazin-2-yl)-2-fluorobenzamido)-2-(3-bromo-5-fluorophenyl)ethyl)carbamate To a solution of 4-(3-amino-6-(tetrahydro-2H-pyran-4-yl)pyrazin-2-yl)-2-fluorobenzoic acid (35 mg, 0.110 mmol) in DMF (368 µl) was added (S)-tert-butyl (2-amino-2-(3-bromo-5-fluorophenyl)ethyl)carbamate (40.8 mg, 0.110 mmol), aza-HOBt (22.52 mg, 0.165 mmol), EDC (31.7 mg, 0.165 mmol), and DIEA (57.8 µl, 0.331 mmol). The reaction mixture was stirred at room temperature for 3 h, and then partitioned between EtOAc and water. The organic was washed by $NaHCO_3$, water and brine, dried over $Na_2SO_4$ and concentrated. The crude (S)-tert-butyl (2-(4-(3-amino-6-(tetrahydro-2H-pyran-4-yl)pyrazin-2-yl)-2-fluorobenzamido)-2-(3-bromo-5-fluorophenyl)ethyl)carbamate was used in next step reaction without further purification. LCMS (m/z): 632.1/634.1 (MH+), 0.97 min.

Step 2. (S)-N-(2-amino-1-(3-bromo-5-fluorophenyl)ethyl)-4-(3-amino-6-(tetrahydro-2H-pyran-4-yl)pyrazin-2-yl)-2-fluorobenzamide To a solution of (S)-tert-butyl (2-(4-(3-amino-6-(tetrahydro-2H-pyran-4-yl)pyrazin-2-yl)-2-fluorobenzamido)-2-(3-bromo-5-fluorophenyl)ethyl)carbamate (69 mg, 0.110 mmol) in DCM (1.0 mL) was added TFA (0.5 mL) and stirred at room temperature for 1 h. The reaction mixture was concentrated to dryness, then dissolved in DMSO and subject to prep HPLC. Pure fraction was combined and lyophilized to yield final product as a TFA salt. LCMS (m/z): 532.1/534.1 (MH+), 0.69 min; $^1$H NMR (400 MHz, Methanol-$d_4$) δ ppm 7.94-7.84 (m, 2H), 7.73 (dd, J=1.4, 8.0 Hz, 1H), 7.66 (dd, J=1.4, 11.9 Hz, 1H), 7.55 (s, 1H), 7.49-7.39 (m, 1H), 7.29 (d, J=9.4 Hz, 1H), 5.48 (t, J=7.2 Hz, 1H), 4.04 (dd, J=2.9, 11.5 Hz, 2H), 3.57 (dt, J=2.2, 11.6 Hz, 2H), 3.51-3.41 (m, 2H), 3.01-2.85 (m, 1H), 1.97-1.76 (m, 4H).

Example 181

Synthesis of (S)-N-(2-amino-1-(3-chloro-5-fluorophenyl)ethyl)-4-(3-amino-6-(tetrahydro-2H-pyran-4-yl)pyrazin-2-yl)-2-fluorobenzamide Scheme 82

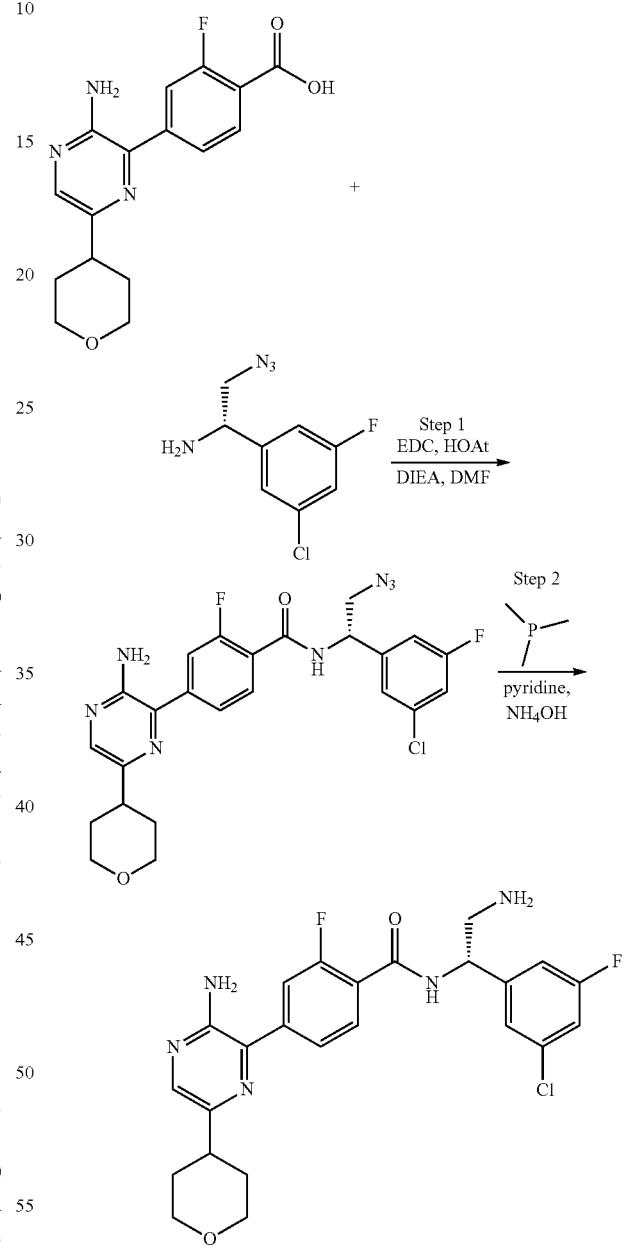

Step 1. (S)-4-(3-amino-6-(tetrahydro-2H-pyran-4-yl)pyrazin-2-yl)-N-(2-azido-1-(3-chloro-5-fluorophenyl)ethyl)-2-fluorobenzamide To a solution of 4-(3-amino-6-(tetrahydro-2H-pyran-4-yl)pyrazin-2-yl)-2-fluorobenzoic acid (126 mg, 0.398 mmol) in DMF (1328 µl) was added (S)-2-azido-1-(3-chloro-5-fluorophenyl)ethanamine (100.0 mg, 0.398 mmol), DIEA (348

µl, 1.991 mmol), EDC (153 mg, 0.797 mmol), and aza-HOBt (81 mg, 0.597 mmol). The reaction mixture was stirred for 15 h. After water was added, the reaction mixture was worked up with EtOAc. The organic layer was dried over $Na_2SO_4$, filtered off, and concentrated in vacuo. The crude product was purified by flash chromatography (gradient EtOAc in heptane) to provide (S)-4-(3-amino-6-(tetrahydro-2H-pyran-4-yl)pyrazin-2-yl)-N-(2-azido-1-(3-chloro-5-fluorophenyl)ethyl)-2-fluorobenzamide (118 mg, 58%). LCMS (m/z): 514.2 (MH+), 0.91 min.

Step 2. (S)-N-(2-amino-1-(3-chloro-5-fluorophenyl)ethyl)-4-(3-amino-6-(tetrahydro-2H-pyran-4-yl)pyrazin-2-yl)-2-fluorobenzamide To a solution of (S)-4-(3-amino-6-(tetrahydro-2H-pyran-4-yl)pyrazin-2-yl)-N-(2-azido-1-(3-chloro-5-fluorophenyl)ethyl)-2-fluorobenzamide (118 mg, 0.230 mmol) in pyridine (2 mL) was added $NH_4OH$ (200 µl) and trimethylphosphine (344 µl, 0.344 mmol) sequentially at room temperature. The reaction mixture was stirred for 2 h. After EtOH (1 mL) was added, the reaction mixture was concentrated in vacuo. The crude product was purified by flash chromatography (20% MeOH in DCM containing 0.5% $NH_3$/DCM) to provide 89.6 mg of (S)-N-(2-amino-1-(3-chloro-5-fluorophenyl)ethyl)-4-(3-amino-6-(tetrahydro-2H-pyran-4-yl)pyrazin-2-yl)-2-fluorobenzamide (79%). LCMS (m/z): 488.2 (MH+), 0.66 min. 1H NMR (500 MHz, METHANOL-$d_4$) δ ppm 7.98-7.89 (m, 1H), 7.89-7.79 (m, 1H), 7.74 (td, J=1.4, 8.0 Hz, 1H), 7.69-7.61 (m, 1H), 7.41-7.28 (m, 1H), 7.27-7.08 (m, 2H), 5.27-5.12 (m, 1H), 4.07 (dd, J=3.8, 11.0 Hz, 2H), 3.69-3.52 (m, 2H), 3.14-3.03 (m, 2H), 2.96 (tt, J=3.9, 11.7 Hz, 1H), 2.02-1.77 (m, 4H).

Synthesis of (S)-N-(2-amino-2-(3-bromo-5-fluorophenyl)ethyl)-N-methyl-2-nitrobenzenesulfonamide Scheme 83

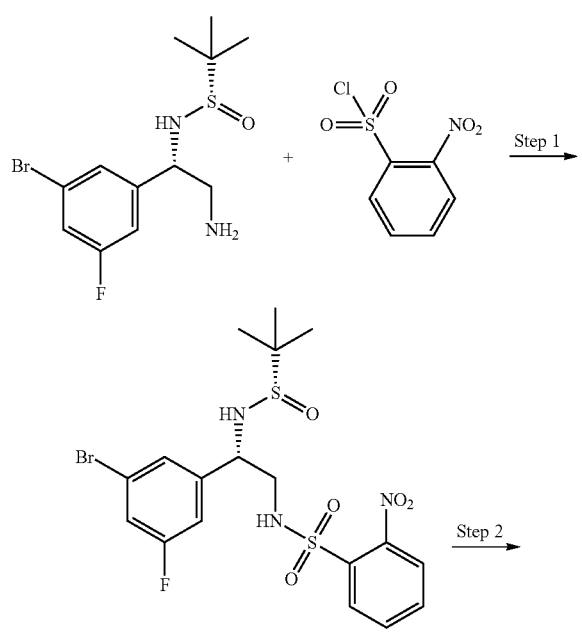

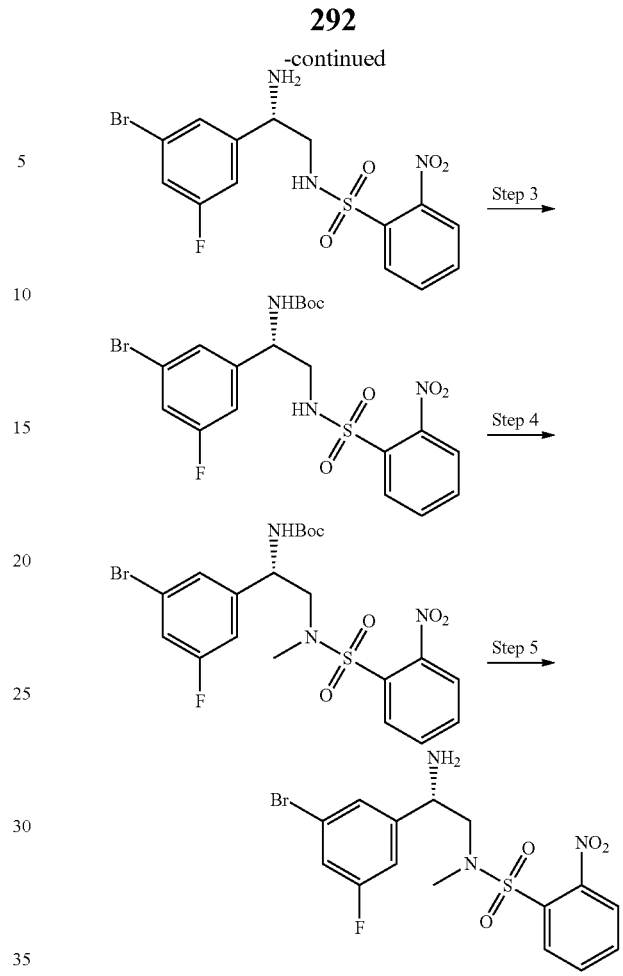

Step 1. N-((S)-2-(3-bromo-5-fluorophenyl)-2-((S)-1,1-dimethylethylsulfinamido)ethyl)-2-nitrobenzenesulfonamide (S)-N-((S)-2-amino-1-(3-bromo-5-fluorophenyl)ethyl)-2-methylpropane-2-sulfinamide (3.3 g, 9.78 mmol) was dissolved in DCM (32.6 mL) at 0° C., then TEA (1.405 mL, 10.08 mmol), and 2-nitrobenzene-1-sulfonyl chloride (2.169 g, 9.78 mmol) were added. The reaction mixture was stirred at room temperature for 3 h. The reaction mixture was concentrated in vacuo and the crude product was purified to yield N-((S)-2-(3-bromo-5-fluorophenyl)-2-((S)-1,1-dimethylethylsulfinamido)ethyl)-2-nitrobenzenesulfonamide. LCMS (m/z): 522.1/524.1 (MH+), 0.94 min.

Step 2. (S)-N-(2-amino-2-(3-bromo-5-fluorophenyl)ethyl)-2-nitrobenzenesulfonamide N-((S)-2-(3-bromo-5-fluorophenyl)-2-((R)-1,1-dimethylethylsulfinamido)ethyl)-2-nitrobenzenesulfonamide (3.55 g, 6.80 mmol) in $Et_2O$ (22.65 mL), and HCl (4 M in dioxane) (3.40 mL, 13.59 mmol) was added. The reaction mixture was stirred at room temperature for 1 h. The reaction mixture was neutralized by $Na_2CO_3$ solution and extracted by EtOAc. The organic layer was washed with water, dried, filtered off, and concentrated in vacuo providing the crude (S)-N-(2-amino-2-(3-bromo-5-fluorophenyl)ethyl)-2-nitrobenzenesulfonamide, which was used in next step reaction without further purification. LCMS (m/z): 418.2/420.2 (MH+), 0.62 min.

Step 3. (S)-tert-butyl (1-(3-bromo-5-fluorophenyl)-2-(2-nitrophenyl)sulfonamido)ethyl)carbamate (S)-N-(2-amino-2-(3-bromo-5-fluorophenyl)ethyl)-2-nitrobenzenesulfonamide (1.55 g, 3.71 mmol) was dissolved in CH$_2$Cl$_2$ (12.35 mL), and then TEA (0.517 mL, 3.71 mmol) and Boc-anhydride (1.119 mL, 4.82 mmol) were added. The reaction mixture was stirred at room temperature for 1 h, and concentrated. The crude product was purified by flash chromatography to yield (S)-tert-butyl (1-(3-bromo-5-fluorophenyl)-2-(2-nitrophenylsulfonamido)ethyl)carbamate. LCMS (m/z): 462.0/464.0 (MH$^+$-56), 0.99 min.

Step 4. (S)-tert-butyl (1-(3-bromo-5-fluorophenyl)-2-(N-methyl-2-nitrophenylsulfonamido)ethyl)carbamate (S)-tert-butyl (1-(3-bromo-5-fluorophenyl)-2-(2-nitrophenylsulfonamido)ethyl)carbamate (2.3 g, 4.44 mmol) was dissolved in DMF (14.79 mL). K$_2$CO$_3$ (1.226 g, 8.87 mmol) and MeI (0.416 mL, 6.66 mmol) were added. The reaction mixture was stirred at room temperature for 2 h, and then water was added. The reaction mixture was extracted by EtOAc. The organic was washed by water and brine, dried and concentrated. The crude product was purified by flash chromatography to yield (S)-tert-butyl (1-(3-bromo-5-fluorophenyl)-2-(N-methyl-2-nitrophenylsulfonamido)ethyl)carbamate (2.3 g, 4.32 mmol, 97% yield).

Step 5. (S)-N-(2-amino-2-(3-bromo-5-fluorophenyl)ethyl)-N-methyl-2-nitrobenzenesulfonamide (S)-tert-butyl (1-(3-bromo-5-fluorophenyl)-2-(N-methyl-2-nitrophenylsulfonamido)ethyl) carbamate (2.3 g, 4.32 mmol, 97% yield) was dissolved in CH$_2$Cl$_2$ and HCl (4 M in dioxane, 4.44 mL, 17.75 mmol) wad added. The reaction mixture was stirred at room temperature overnight. Heptane was added. The solid was filtered, and dried by air to yield (S)-N-(2-amino-2-(3-bromo-5-fluorophenyl)ethyl)-N-methyl-2-nitrobenzenesulfonamide (1.8 g, 3.84 mmol, 87% yield). LCMS (m/z): 432.2/434.1 (MH$^+$), 0.69 min.

(S)-N-(2-amino-2-(3-bromo-5-fluorophenyl)ethyl)-N-methyl-2-nitrobenzenesulfonamide hydrochloride salt was prepared as follows:

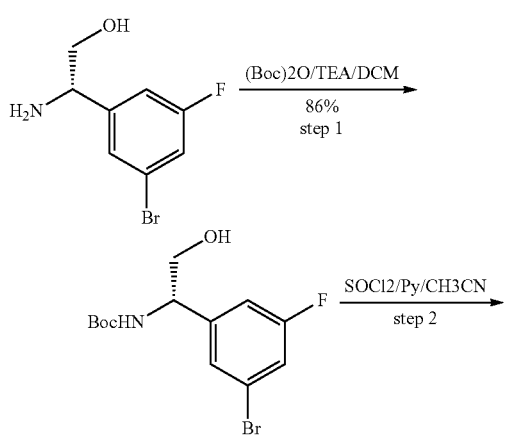

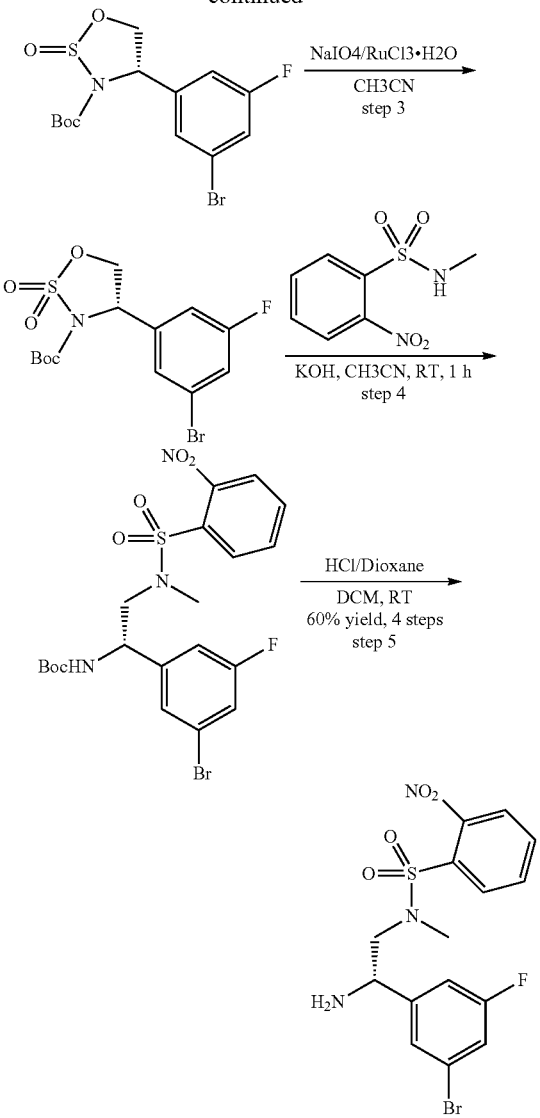

Step 1: (S)-tert-butyl (1-(3-bromo-5-fluorophenyl)-2-hydroxyethyl)carbamate

To an ice water cooled solution of (S)-2-amino-2-(3-bromo-5-fluorophenyl)ethanol (30 g, 111 mmol) (HCl salt) in DCM (390 mL) was added TEA (46.5 mL, 333 mmol) followed by Boc-anhydride (26.4 mL, 114 mmol in 50 ml of DCM). The addition was completed in 15 minutes. The ice water bath was removed and the reaction mixture was stirred at room temperature for 16 hours. The reaction mixture was concentrated, (the water bath temperature was kept below 30° C.), the residue was diluted with 500 ml of EtOAc, washed with 100 ml of 1N NaOH, 100 ml of water and 100 ml of brine, dried over Na$_2$SO$_4$, filtered and concentrated to afford the crude product as an viscous liquid, (in smaller scales, it was a semi-solid). To this viscous (or semi-solid) product was added 120 ml of Et$_2$O and the resultant mixture was sonicated for 5 minutes. The mixture was concentrated to about 60 ml of total volume. After 1 hour at room temperature, a white crystalline solid precipitated out. (if no crystal formed, ~2 mg of the seed was added). After 4 hours, the white solid was filtered, washed with a minimal amount of ether and dried (over house vacuum for at least 1 hour) to afford a total of 30.5 g of the white solid as the desired product. Recovery was improved if the filtrate was concentrated and the above procedure was repeated. (S)-tert-butyl (1-(3-bromo-5-fluorophenyl)-2-hydroxyethyl)carbamate: 30.5 g, 82% yield. LC-MS: (MW-56): 279.8 m/z at 0.84 min. 1 H NMR (400 MHz, DMSO) ppm 1.29-1.43 (m, 8 H) 3.38-3.55 (m, 2 H) 4.39-4.61 (m, 1 H) 4.84 (t, J=5.67 Hz, 1 H) 7.15 (d, J=9.39 Hz, 1 H) 7.24-7.44 (m, 3 H).

Step 2: (4S)-tert-butyl 4-(3-bromo-5-fluorophenyl)-1,2,3-oxathiazolidine-3-carboxylate 2-oxide To a solution of $SOCl_2$ (19.98 mL, 274 mmol) in acetonitrile (280 ml) at −40-45° C. (inner temperature, dry ice-acetone bath temperature around −55C) under nitrogen atmosphere was added (S)-tert-butyl (1-(3-bromo-5-fluorophenyl)-2-hydroxyethyl)carbamate (30.5 g, 91 mmol) in $CH_3CN$ (175 ml). The addition was completed in about 30 minutes. After about 20 minutes stirring at −40-45° C., pyridine (40.6 mL, 502 mmol) was added (in about 10 minutes). After stirring for 10 minutes at −40° C., the cooling bath was removed, the mixture was warmed to room temperature and stirred for 2 hours. LC-MS shown two diastereomeric products, and some amount of dimer by-product. The mixture was diluted with 400 ml of EtOAc, washed with brine (200 ml) three times, dried over $Na_2SO_4$, filtered and concentrated (water bath around 40° C., about 2 hours) to afford 35.7 grams of the crude product as a light yellow viscous liquid, which was used immediately in the next step or stored at 4° C. (4S)-tert-butyl 4-(3-bromo-5-fluorophenyl)-1,2,3-oxathiazolidine-3-carboxylate 2-oxide: LC-MS: (MW-100): 281.8 at 1.02 min.

Step 3: (S)-tert-butyl 4-(3-bromo-5-fluorophenyl)-1,2,3-oxathiazolidine-3-carboxylate 2,2-dioxide To an ice water cooled solution of (4S)-tert-butyl 4-(3-bromo-5-fluorophenyl)-1,2,3-oxathiazolidine-3-carboxylate 2-oxide (34.6 g, 91 mmol) in acetonitrile (420 mL) under stirring was added $NaIO_4$ (29.2 g, 137 mmol), and ruthenium trichloride hydrate (0.359 g, 1.729 mmol), followed by water (320 ml). The reaction mixture was stirred at 0° C. for 2 hours. The mixture was diluted with EtOAc (500 ml), washed with brine (200 ml) twice, dried over $Na_2SO_4$, filtered and concentrated to afford the crude product, which was used directly at the next step. 40.3 grams of the crude product was obtained. LC-MS: (MW+Na): 419.9 m/z at 1.01 min.

Step 4: (S)-tert-butyl (1-(3-bromo-5-fluorophenyl)-2-(N-methyl-2-nitrophenylsulfonamido)ethyl)carbamate To a solution of N-methyl-2-nitrobenzenesulfonamide (18.69 g, 86 mmol) in acetonitrile (400 ml) at room temperature was added KOH (10.21 g, 182 mmol, commercial, powder form). The resultant mixture was stirred at room temperature for about 15 minutes before (S)-tert-butyl 4-(3-bromo-5-fluorophenyl)-1,2,3-oxathiazolidine-3-carboxylate 2,2-dioxide (36.1 g, 91 mmol) in 180 ml of $CH_3CN$ was added (addition was finished in 15-20 minutes). The resultant mixture was stirred at room temperature for 1-2 hours. The reaction mixture was concentrated to about 200 ml of total volume. To the residue was added 600 ml of EtOAc, followed by washing with 180 ml of 3N HCl, 200 ml of 1N NaOH, and brine (200 ml), twice. The solution was dried by $Na_2SO_4$, filtered through a filter funnel with celite (~30 g) and silica gel (20 g). The filtered solution was concentrated to afford 40.3 grams of the product as a viscous liquid, which was used at the next step directly. (S)-tert-butyl (1-(3-bromo-5-fluorophenyl)-2-(N-methyl-2-nitrophenylsulfonamido)ethyl)carbamate: LC-MS: (MW+Na): 555.8 m/z at 1.07 min. (40.3 g, 76 mmol, 83% yield).

Step 5: (S)-N-(2-amino-2-(3-bromo-5-fluorophenyl)ethyl)-N-methyl-2-nitrobenzenesulfonamide hydrochloride salt To a solution of (S)-tert-butyl (1-(3-bromo-5-fluorophenyl)-2-(N-methyl-2-nitrophenylsulfonamido)ethyl)carbamate (40 g, 75 mmol) in DCM (420 ml) at room temperature was added HCl (4M in dioxane, 150 ml, 601 mmol). The resultant solution was stirred at room temperature for 4 hours during which time a white solid precipitated out. The reaction mixture was filtered, the white solid was washed with DCM (50 ml×2), and vacuum dried to afford 23.8 grams of the desired product as a white solid. (HCl salt). (S)N-(2-amino-2-(3-bromo-5-fluorophenyl)ethyl)-N-methyl-2-nitrobenzenesulfonamide (23.8 g, 68% yield over four steps). LC-MS: (M+1): 433.9 m/z at 0.66 min. 1H NMR (400 MHz, <dmso>) ppm 2.86 (s, 3 H) 3.56-3.82 (m, 2 H) 4.61 (t, J=7.24 Hz, 1 H) 7.42-7.61 (m, 2 H) 7.68 (d, J=1.57 Hz, 1 H) 7.75-8.05 (m, 4 H).

Synthesis of (S)-N-(2-amino-2-(3-bromo-5-fluorophenyl)ethyl)-N-(2-fluoroethyl)-2-nitrobenzenesulfonamide

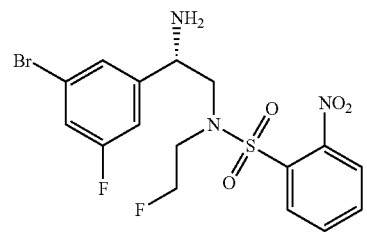 [SMILES: N[C@H](CN(CCF)S(=O)(=O)c1ccccc1[N+](=O)[O-])c1cc(F)cc(Br)c1]

Following steps 4 and 5 in scheme 83, using 1-bromo-2-fluoroethane, (S)N-(2-amino-2-(3-bromo-5-fluorophenyl)ethyl)-N-(2-fluoroethyl)-2-nitrobenzenesulfonamide was obtained. LCMS (m/z): 464.1/466.1 (MH+), 0.71 min.

Example 182
Synthesis of 4-(3-amino-6-((1S,3S,4S)-3-fluoro-4-hydroxycyclohexyl)pyrazin-2-yl)-N-((S)-1-(3-bromo-5-fluorophenyl)-2-hydroxyethyl)-2-fluorobenzamide
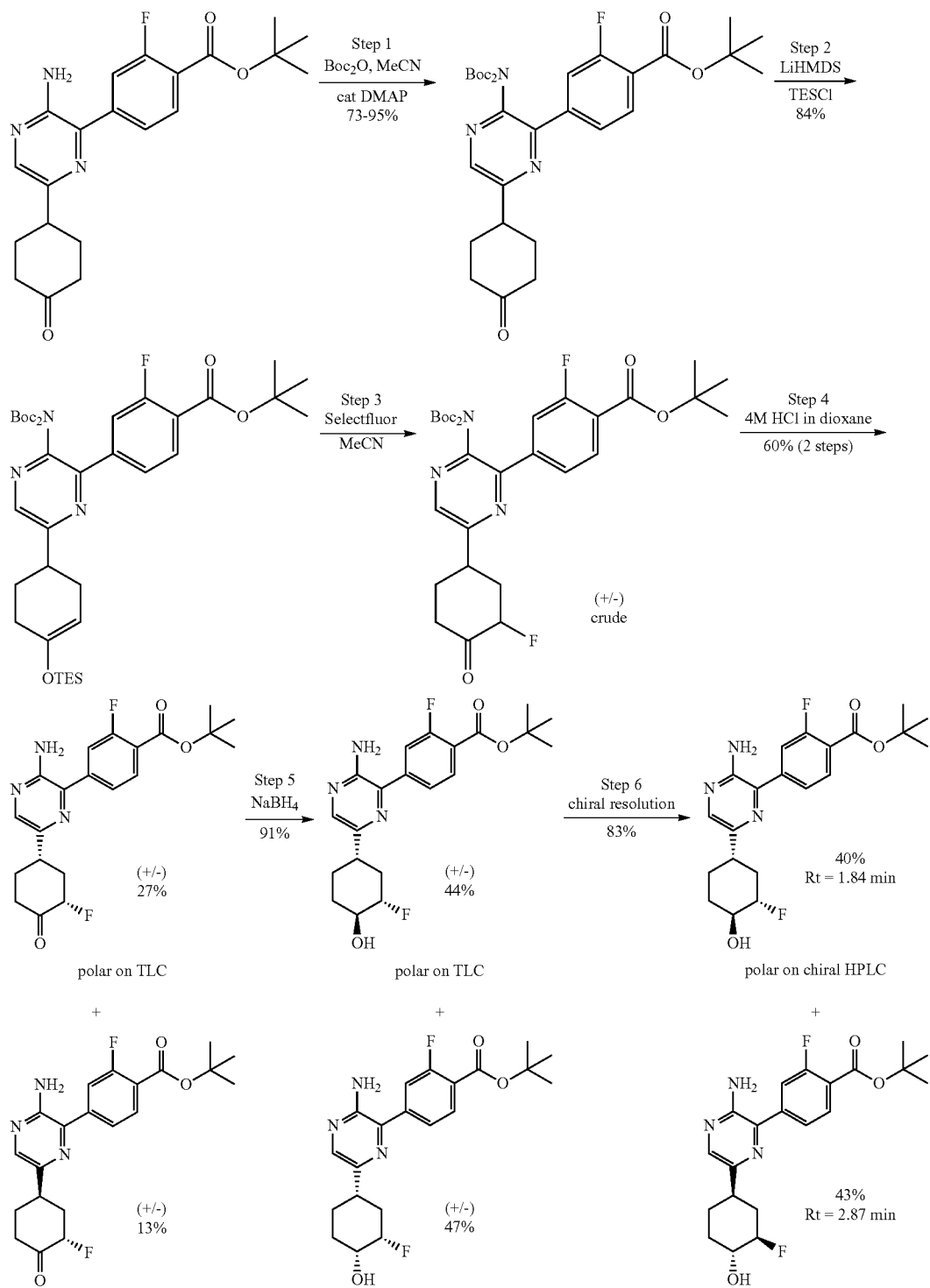
Scheme 84

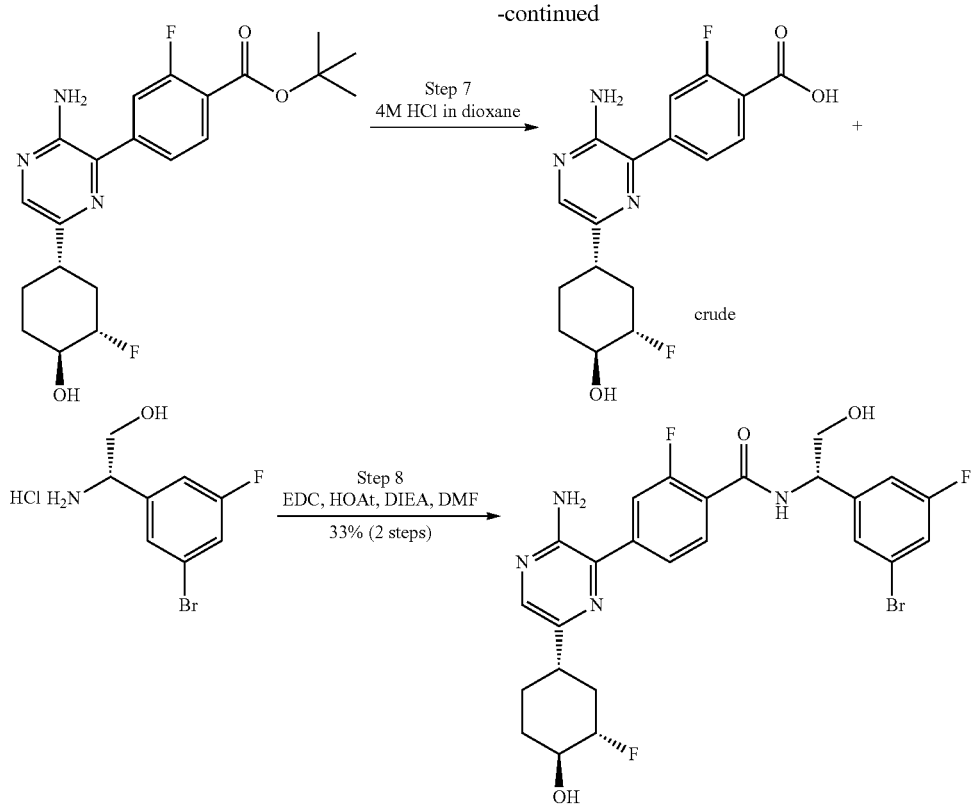

Step 1. Imidodicarbonic acid, 4-(3-((tert-butoxycarbonyl)amino)-6-(4-oxocyclohexyl)pyrazin-2-yl)-2-fluorobenzoate, 1,3-bis(1,1-dimethylethyl) ester To a solution of tert-butyl 4-(3-amino-6-(4-oxocyclohexyl)pyrazin-2-yl)-2-fluorobenzoate (3 g, 7.78 mmol) in acetonitrile (130 mL) was added Boc$_2$O (6.33 mL, 27.2 mmol) and DMAP (0.048 g, 0.389 mmol). The reaction mixture was stirred overnight at room temperature. After volatile materials were removed on rotavap under reduced pressure, the crude product was purified by flash chromatography eluting with 0-50% of EtOAc/heptane to provide imidodicarbonic acid, 4-(3-((tert-butoxycarbonyl)amino)-6-(4-oxocyclohexyl)pyrazin-2-yl)-2-fluorobenzoate, 1,3-bis(1,1-dimethylethyl) ester (4.34 g, 7.41 mmol, 95%). LCMS (m/z): 586.5 (MH$^+$), 1.24 min; $^1$H NMR (500 MHz, CHLOROFORM-d) δ ppm 8.52-8.41 (m, 1H), 7.97 (t, J=7.7 Hz, 1H), 7.61-7.44 (m, 2H), 3.46-3.30 (m, 1H), 2.68-2.52 (m, 4H), 2.38 (dd, J=3.0, 13.7 Hz, 2H), 2.28-2.10 (m, 2H), 1.69-1.61 (m, 9H), 1.42-1.29 (m, 18H).

Step 2. Imidodicarbonic acid, 4-(3-((tert-butoxycarbonyl)amino)-6-(4-((triethylsilyl)oxy)cyclohex-3-en-1-yl)pyrazin-2-yl)-2-fluorobenzoate, 1,3-bis(1,1-dimethylethyl) ester To a solution of imidodicarbonic acid, 4-(3-((tert-butoxycarbonyl)amino)-6-(4-oxocyclohexyl)pyrazin-2-yl)-2-fluorobenzoate, 1,3-bis(1,1-dimethylethyl) ester (12.1 g, 20.66 mmol) in THF (68.9 mL) was slowly added LiHMDS (1 M in THF) (22.73 mL, 22.73 mmol) at −78° C. After stirring for 30 min, triethylchlorosilane (3.67 mL, 21.69 mmol) was added. The reaction mixture was warmed to room temperature and stirred for 1 h. Saturated sodium bicarbonate solution was added, and the mixture was extracted with EtOAc. The organic layer was washed well with water and brine, dried over anhydrous NaHCO$_3$, filtered off, and concentrated in vacuo. The crude product was purified by flash chromatography eluting with 5% of EtOAc/heptane to provide imidodicarbonic acid, 4-(3-((tert-butoxycarbonyl)amino)-6-(4-((triethylsilyl)oxy)cyclohex-3-en-1-yl)pyrazin-2-yl)-2-fluorobenzoate, 1,3-bis(1,1-dimethylethyl) ester (12.1 g, 17.29 mmol). LCMS (m/z, neutral-nonpolar method): 701.8 (MH$^+$), 1.14 min; $^1$H NMR (400 MHz, CDCl$_3$) δ ppm 8.41 (s, 1H), 8.00-7.88 (m, 1H), 7.57-7.46 (m, 2H), 4.97 (br. s., 1H), 3.16-3.00 (m, 1H), 2.49-2.38 (m, 2H), 2.38-2.23 (m, 1H), 2.19-1.94 (m, 3H), 1.61 (s, 9H), 1.33 (s, 18H), 1.06-0.94 (m, 8H), 0.77-0.64 (m, 6H).

Step 3. Imidodicarbonic acid, 4-(3-((tert-butoxycarbonyl)amino)-6-(3-fluoro-4-oxocyclohexyl)pyrazin-2-yl)-2-fluorobenzoate, 1,3-bis(1,1-dimethylethyl) ester To a solution of imidodicarbonic acid, 4-(3-((tert-butoxycarbonyl)amino)-6-(4-((triethylsilyl)oxy)cyclohex-3-en-1-yl)pyrazin-2-yl)-2-fluorobenzoate, 1,3-bis(1,1-dimethylethyl) ester (12.1 g, 17.29 mmol) in acetonitrile (57.6 mL) was added Selectfluor® (7.96 g, 22.47 mmol) at 0° C. The reaction mixture was warmed up to room temperature and stirred overnight. After quenched with sat. NaHCO$_3$ solution, the reaction mixture was extracted with EtOAc. The organic layer was washed with water and brine, dried over Na$_2$SO$_4$, filtered and concentrated in vacuo to provide imidodicarbonic acid, 4-(3-((tert-butoxycarbonyl)amino)-6-(3-fluoro-4-oxocyclohexyl)pyrazin-2-yl)-2-fluorobenzoate, 1,3-bis(1,1-dimethylethyl) ester (10.44 g, 17.29, 100%), which was used for the next step without further purification. LCMS (m/z, neutral-nonpolar method): 604.3 (MH+), 1.12 min.

Step 4. (+/−)-tert-butyl 4-(3-amino-6-((1R,3R)-3-fluoro-4-oxocyclohexyl)pyrazin-2-yl)-2-fluorobenzoate To a solution of Imidodicarbonic acid, 4-(3-((tert-butoxycarbonyl)amino)-6-(3-fluoro-4-oxocyclohexyl)pyrazin-2-yl)-2-fluorobenzoate, 1,3-bis(1,1-dimethylethyl) ester (10.44 g, 17.29 mmol) in THF (57.6 mL) was added 4 M HCl in dioxane (130 mL, 519 mmol) at room temperature. The reaction mixture was stirred for 3-4 h, which was monitored by LCMS to prevent more of the t-butyl ester from hydrolyzing to carboxylic acid. The reaction was cooled in water bath, and neutralized with saturated sodium carbonate. The resulting mixture was extracted with EtOAc three times. The combined organic layers were washed with brine, dried over Na$_2$SO$_4$, filtered and concentrated. The residue was purified by flash chromatography eluting with 0-100% of EtOAc/heptane to provide (+/−)-tert-butyl 4-(3-amino-6-((1R,3R)-3-fluoro-4-oxocyclohexyl)pyrazin-2-yl)-2-fluorobenzoate (1.9 g, 4.71 mmol, 27.2%) and (+/−)-tert-butyl 4-(3-amino-6-((1S,3S)-3-fluoro-4-oxocyclohexyl)pyrazin-2-yl)-2-fluorobenzoate (926 mg, 2.295 mmol, 13.3%). LCMS (m/z): 404.3 (MH+), 0.84 min and 404.3 (MH+), 0.84 min respectively.

Step 5. (+/−)-Tert-butyl 4-(3-amino-6-((1S,3S,4S)-3-fluoro-4-hydroxycyclohexyl)pyrazin-2-yl)-2-fluorobenzoate To a solution of (+/−)-tert-butyl 4-(3-amino-6-((1R,3R)-3-fluoro-4-oxocyclohexyl)pyrazin-2-yl)-2-fluorobenzoate (1.9 g, 4.71 mmol) in MeOH (47.1 mL) was added NaBH$_4$ (0.267 g, 7.06 mmol) at 0° C. The reaction mixture was stirred for 2 h. After quenched with sat. NaHCO$_3$ solution, the reaction mixture was extracted with EtOAc. The organic layer was washed with water and brine, dried over sodium sulfate, filtered and concentrated in vacuo. The crude product was purified by flash chromatography eluting with flat 35% of EtOAc in heptane to provide (+/−)-tert-butyl 4-(3-amino-6-((1S,3S,4S)-3-fluoro-4-hydroxycyclohexyl)pyrazin-2-yl)-2-fluorobenzoate (839 mg, 2.07 mmol, 43.9%) and (+/−)-tert-butyl 4-(3-amino-6-((1R,3R,4R)-3-fluoro-4-hydroxycyclohexyl)pyrazin-2-yl)-2-fluorobenzoate (900 mg, 2.22 mmol, 47%). LCMS (m/z): 406.3 (MH+), 0.85 min and 406.3 (MH+), 0.85 min respectively.

Step 6. Tert-butyl 4-(3-amino-6-((1S,3S,4S)-3-fluoro-4-hydroxycyclohexyl)pyrazin-2-yl)-2-fluorobenzoate Tert-butyl 4-(3-amino-6-((1S,3S,4S)-3-fluoro-4-hydroxycyclohexyl)pyrazin-2-yl)-2-fluorobenzoate (839 mg, 2.07 mmol) was subjected to chiral separation (ChiralPak 5mic AD column, 4.6×100 (mm), CO2/EtOH+0.1% DEA=70/30, SFC=5 ml/min) to provide single enantiomer tert-butyl 4-(3-amino-6-((1S,3S,4S)-3-fluoro-4-hydroxycyclohexyl)pyrazin-2-yl)-2-fluorobenzoate (Rt=1.61 min, 336 mg, 0.829 mmol, 40%) and the less polar enantiomer (Rt=2.45 min, 43%).

Step 7. 4-(3-amino-6-((1S,3S,4S)-3-fluoro-4-hydroxycyclohexyl)pyrazin-2-yl)-2-fluorobenzoic acid To a solution of tert-butyl 4-(3-amino-6-((1S,3S,4S)-3-fluoro-4-hydroxycyclohexyl)pyrazin-2-yl)-2-fluorobenzoate (90 mg, 0.22 mmol) in DCM (0.444 mL) was added 4 M HCl in dioxane (3.7 mL, 14.80 mmol). The reaction mixture was stirred overnight at room temperature. After the volatile materials were evaporated in vacuo, the reaction mixture was triturated with Et$_2$O, and filtered off to provide 4-(3-amino-6-((1S,3S,4S)-3-fluoro-4-hydroxycyclohexyl)pyrazin-2-yl)-2-fluorobenzoic acid (86 mg, 0.22 mmol, 100%) as a HCl salt, which was used for the next step without any further purification. LCMS (m/z): 350.2 (MH+), 0.51 min.

Step 8. 4-(3-amino-6-((1S,3S,4S)-3-fluoro-4-hydroxycyclohexyl)pyrazin-2-yl)-N-((S)-1-(3-bromo-5-fluorophenyl)-2-hydroxyethyl)-2-fluorobenzamide To a solution of 4-(3-amino-6-((1S,3S,4S)-3-fluoro-4-hydroxycyclohexyl)pyrazin-2-yl)-2-fluorobenzoic acid (20 mg, 0.057 mmol) in DMF (573 µL) was added (S)-2-amino-2-(3-bromo-5-fluorophenyl)ethanol HCl salt (18.59 mg, 0.069 mmol), aza-HOBt (11.69 mg, 0.086 mmol), EDC (21.95 mg, 0.115 mmol), and DIEA (30.0 µl, 0.172 mmol). The reaction mixture was stirred for 15 h. Water was added, and the reaction mixture was extracted with EtOAc three times. The organic layers were dried over Na$_2$SO$_4$, filtered and concentrated in vacuo. The crude product was purified by HPLC. Pure fractions were lyophilized to provide 4-(3-amino-6-((1S,3S,4S)-3-fluoro-4-hydroxycyclohexyl)pyrazin-2-yl)-N-((S)-1-(3-bromo-5-fluorophenyl)-2-hydroxyethyl)-2-fluorobenzamide (12.9 mg, 0.019 mmol, 32.8%) as a TFA salt. LCMS (m/z): 565.1/567.1 (MH+), 0.72 min; $^1$H NMR (400 MHz, CD$_3$OD) δ ppm 7.78 (s, 2H), 7.63-7.47 (m, 2H), 7.37 (s, 1H), 7.22-7.02 (m, 2H), 5.15-5.03 (m, 1H), 4.43-4.15 (m, 1H), 3.77 (t, J=5.7 Hz, 2H), 3.62-3.47 (m, 1H), 2.76 (br. s., 1H), 2.19 (dd, J=3.1, 6.3 Hz, 1H), 2.02-1.92 (m, 1H), 1.89-1.66 (m, 2H), 1.56 (dd, J=3.3, 12.3 Hz, 1H), 1.42 (br. s., 1H). The absolute stereochemistry was determined based on the information of X-ray co-structure of 4-(3-amino-6-((1S,3S,4S)-3-fluoro-4-hydroxycyclohexyl)pyrazin-2-yl)-N-((S)-1-(3-bromo-5-fluorophenyl)-2-hydroxyethyl)-2-fluorobenzamide.

Example 183

Synthesis of 4-(3-amino-6-((1R,3R,4R)-3-fluoro-4-hydroxycyclohexyl)pyrazin-2-yl)-N-((S)-1-(3-bromo-5-fluorophenyl)-2-hydroxyethyl)-2-fluorobenzamide Scheme 85

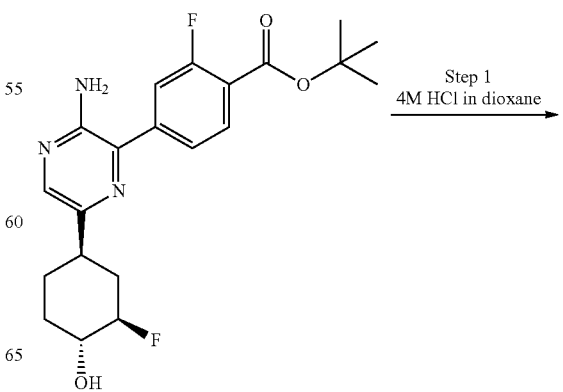

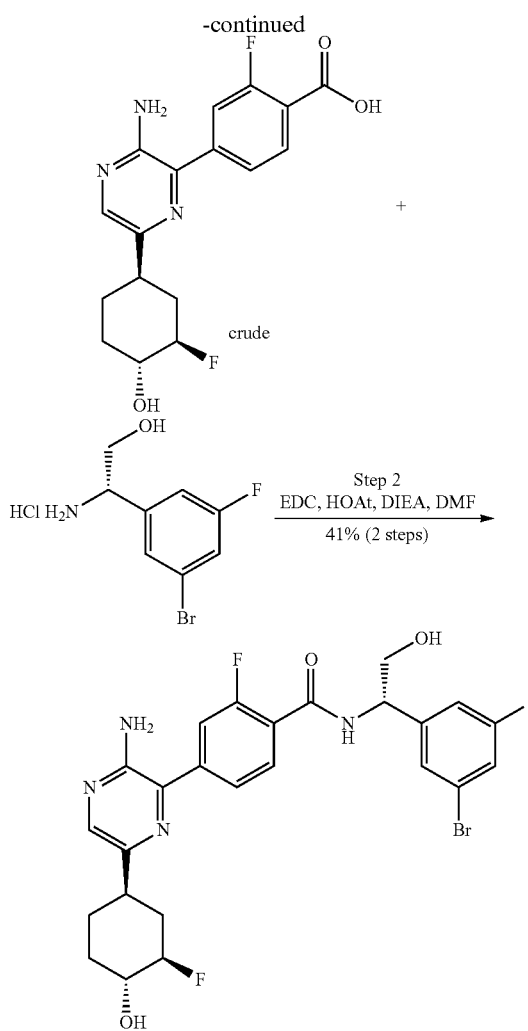

Step 1. 4-(3-amino-6-((1R,3R,4R)-3-fluoro-4-hydroxycyclohexyl)pyrazin-2-yl)-2-fluorobenzoic acid To a solution of tert-butyl 4-(3-amino-6-((1R,3R,4R)-3-fluoro-4-hydroxycyclohexyl)pyrazin-2-yl)-2-fluorobenzoate (Scheme 84: 365 mg, 0.9 mmol) in DCM (2 mL) was added 4 M HCl in dioxane (8 mL, 32.0 mmol). The reaction mixture was stirred for 3 days at room temperature. After the volatile materials were evaporated in vacuo to yield 4-(3-amino-6-((1R,3R,4R)-3-fluoro-4-hydroxycyclohexyl)pyrazin-2-yl)-2-fluorobenzoic acid, which was used for the next step without further purification. LCMS (m/z): 350.3 (MH$^+$), 0.48 min.

Step 2. 4-(3-amino-6-((1R,3R,4R)-3-fluoro-4-hydroxycyclohexyl)pyrazin-2-yl)-N-((S)-1-(3-bromo-5-fluorophenyl)-2-hydroxyethyl)-2-fluorobenzamide To a solution of 4-(3-amino-6-((1R,3R,4R)-3-fluoro-4-hydroxycyclohexyl)pyrazin-2-yl)-2-fluorobenzoic acid (20 mg, 0.057 mmol) in DMF (573 μL) was added (S)-2-amino-2-(3-bromo-5-fluorophenyl)ethanol HCl salt (18.59 mg, 0.069 mmol), aza-HOBt (11.69 mg, 0.086 mmol), EDC (21.95 mg, 0.115 mmol), and DIEA (30.0 μl, 0.172 mmol). The reaction mixture was stirred for 15 h. Water was added, and the reaction mixture was extracted with EtOAc three times. The organic layers were dried over Na$_2$SO$_4$, filtered and concentrated in vacuo. The crude product was purified by HPLC. Pure fractions were lyophilized to provide 4-(3-amino-6-((1R,3R,4R)-3-fluoro-4-hydroxycyclohexyl)pyrazin-2-yl)-N-((S)-1-(3-bromo-5-fluorophenyl)-2-hydroxyethyl)-2-fluorobenzamide (16.1 mg, 0.023 mmol, 41%) as a TFA salt. LCMS (m/z): 565.1/567.1 (MH$^+$), 0.72 min; $^1$H NMR (400 MHz, CD$_3$OD) δ ppm 7.86-7.69 (m, 2H), 7.65-7.47 (m, 2H), 7.40-7.30 (m, 1H), 7.22-7.06 (m, 2H), 5.08 (t, J=5.7 Hz, 1H), 4.41-4.14 (m, 1H), 3.85-3.67 (m, 2H), 3.63-3.48 (m, 1H), 2.74 (t, J=11.5 Hz, 1H), 2.17 (td, J=3.1, 6.3 Hz, 1H), 2.04-1.89 (m, 1H), 1.84-1.66 (m, 2H), 1.65-1.30 (m, 2H). The absolute stereochemistry was determined based on the information of X-ray co-structure in ERK2 of 4-(3-amino-6-((1R,3R,4R)-3-fluoro-4-hydroxycyclohexyl)pyrazin-2-yl)-N-((S)-1-(3-bromo-5-fluorophenyl)-2-hydroxyethyl)-2-fluorobenzamide.

Example 184

Synthesis of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide Scheme 86

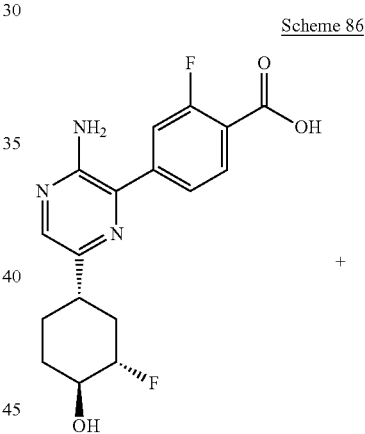

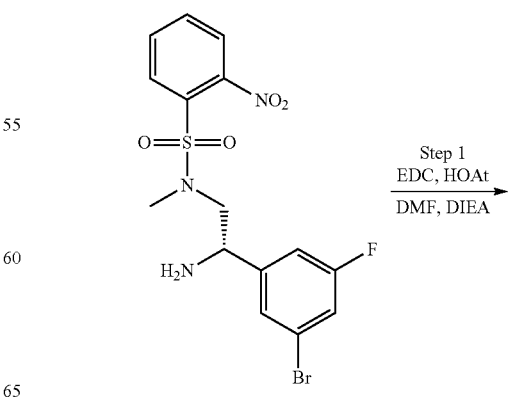

Step 1
EDC, HOAt
DMF, DIEA

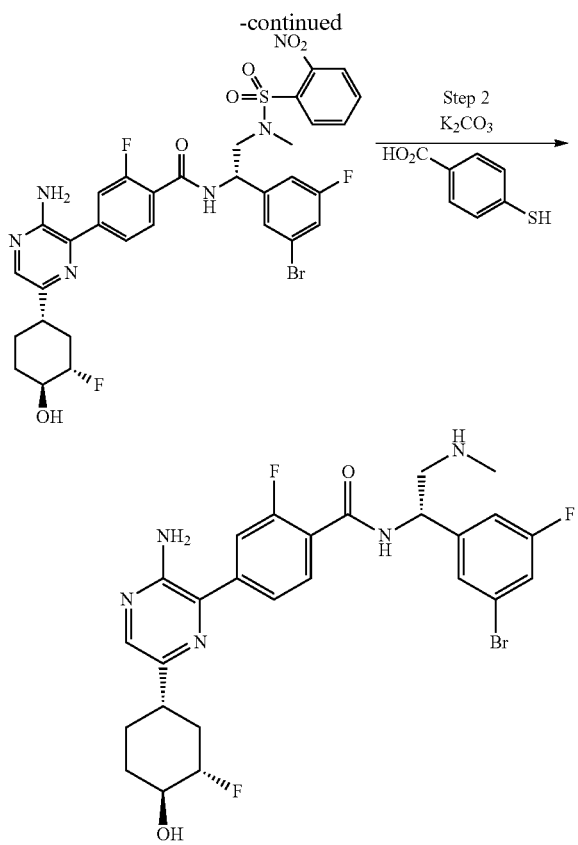

Step 1. 4-(3-amino-6-((1S,3S,4S)-3-fluoro-4-hydroxycyclohexyl)pyrazin-2-yl)-N-((S)-1-(3-bromo-5-fluorophenyl)-2-(N-methyl-2-nitrophenylsulfonamido)ethyl)-2-fluorobenzamide To a solution of 4-(3-amino-6-((1S,3S,4S)-3-fluoro-4-hydroxycyclohexyl)pyrazin-2-yl)-2-fluorobenzoic acid (156 mg, 0.403 mmol) in DMF (1.28 mL) was added (S)-N-(2-amino-2-(3-bromo-5-fluorophenyl)ethyl)-N-methyl-2-nitrobenzenesulfonamide (180 mg, 0.384 mmol), HOAt (105 mg, 0.768 mmol), DIEA (402 μl, 2.8 mmol), and EDC.HCl (147 mg, 0.768 mmol). The reaction mixture was stirred at room temperature for 15 h, LCMS indicated the product. The mixture was diluted with EtOAc and washed with water and once with saturated $Na_2CO_3$ and the organic layer was dried (magnesium sulfate), filtered and concentrated in vacuo providing 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide. The crude product was purified by ISCO column chromatography (0-100% EtOAc in heptane) leading to 4-(3-amino-6-((1S,3S,4S)-3-fluoro-4-hydroxycyclohexyl)pyrazin-2-yl)-N-((S)-1-(3-bromo-5-fluorophenyl)-2-(N-methyl-2-nitrophenylsulfonamido)ethyl)-2-fluorobenzamide (99%).

Step 2. 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide To a solution of 4-(3-amino-6-((1S,3S,4S)-3-fluoro-4-hydroxycyclohexyl)pyrazin-2-yl)-N-((S)-1-(3-bromo-5-fluorophenyl)-2-(N-methyl-2-nitrophenylsulfonamido)ethyl)-2-fluorobenzamide (293 mg, 0.38 mmol) in DMF (3.8 mL) was added $K_2CO_3$ (371 mg, 2.69 mmol) and 4-mercaptobenzoic acid (207 mg, 1.34 mmol). The reaction mixture was heated in microwave synthesizer at 45° C. for 55 min. After the reaction, water was added, and the mixture was extracted with EtOAc three times. The organic layers were combined and washed with water three times. The combined organic layer was dried over sodium sulfate, filtered off, and concentrated in vacuo. The residue was purified with flash chromatography eluting with EtOAc (containing 20% MeOH and 0.5% ammonia in water)/DCM to provide 150 mg of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide. LCMS (m/z): 578, 580 (MH$^+$), 0.64 min. $^1$H NMR (400 MHz, $CD_3OD$) δ ppm 7.80 (s, 1H), 7.76-7.68 (m, 1H), 7.59 (dd, J=1.6, 7.8 Hz, 1H), 7.53 (dd, J=1.2, 11.7 Hz, 1H), 7.37 (s, 1H), 7.18 (d, J=8.2 Hz, 1H), 7.11 (d, J=9.4 Hz, 1H), 5.27-5.10 (m, 1H), 4.42-4.13 (m, 1H), 3.65-3.49 (m, 1H), 2.97-2.88 (m, 1H), 2.87-2.79 (m, 1H), 2.74 (t, J=11.7 Hz, 1H), 2.35 (s, 3H), 2.22-2.11 (m, 1H), 2.04-1.92 (m, 1H), 1.85-1.68 (m, 2H), 1.55 (dq, J=3.1, 12.9 Hz, 1H), 1.46-1.33 (m, 1H).

Alternatively, 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide can be synthesized as follows:

(1R,3S,4S)-ethyl 4-((tert-butyldimethylsilyl)oxy)-3-fluorocyclohexanecarboxylate

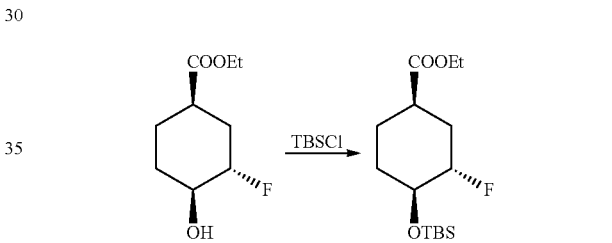

To a 500 mL flask was added (1R,3S,4S)-ethyl 3-fluoro-4-hydroxycyclohexane-carboxylate (17 g, 89.3 mmol, 97.9% ee), TBSCI (17.5 g, 116.1 mmol) and DCM (200 mL). Imidazole (12.1 g, 178 mmol) was added to the resultant clear solution and the reaction mixture was stirred for 16 hours. Water (100 mL) was added and the mixture was stirred for a further 10 minutes. The phases were separated and the organic layer was washed with water (100 mL) and concentrated under reduced pressure (40±5° C., 50~250 mbar). Purification by flash chromatography on silica eluting with a mixture of heptane and ethyl acetate (100:1) gave (1R,3S,4S)-ethyl 4-((tert-butyldimethylsilyl)oxy)-3-fluorocyclohexanecarboxylate as a colorless oil (20.6 g, yield 75.7%). $^1$H NMR (400 MHz, DMSO-$d_6$): 4.38~4.52 (m, 1 H), 4.03~4.08 (dd, J=12 Hz, J=8 Hz, 2H), 3.77~3.81 (m, 1 H), 2.54~2.60 (m, 1 H), 1.93~2.06 (m, 1 H), 1.58~1.86 (m, 4 H), 1.46~1.50 (m, 1 H), 1.17~1.20 (t, J=12 Hz, J=6 Hz, 3 H), 0.85 (s, 9 H), 0.03~0.04 (d, J=4 Hz, 8 H), [M+H]$^+$=305.1 via GC-MS (Instrument: Agilent Technologies, GC 6890N, MS 5975C. GC conditions: Column: HP-5 MS, Capillary: 30.0 m×250 μm×0.25 μm, Detecor parameters: Temperature: 350° C., Flow $H_2$: 40 mL/min, Air flow: 400 mL/min, Makeup (He): 40 mL/min. Injector parameters: temperature: 200° C. Split ratio: 100:1. Carrier gas: He, Flow: 2.0 mL/min, Mode: Constant flow. Oven parameters: 0 min, 50° C.; 2.0 min, 50° C.; 5.33 min, 100° C.; 15.83 min, 270° C. Injection volume: 1 μL, Syringe wash solvent: acetonitrile. MS conditions: Volt: 70 EV, Scan range: m/z=50~550)

2-((1S,3S,4S)-4-((tert-butyldimethylsilyl)oxy)-3-fluorocyclohexyl)-5-(2,5-dimethyl-1H-pyrrol-1-yl)pyrazine

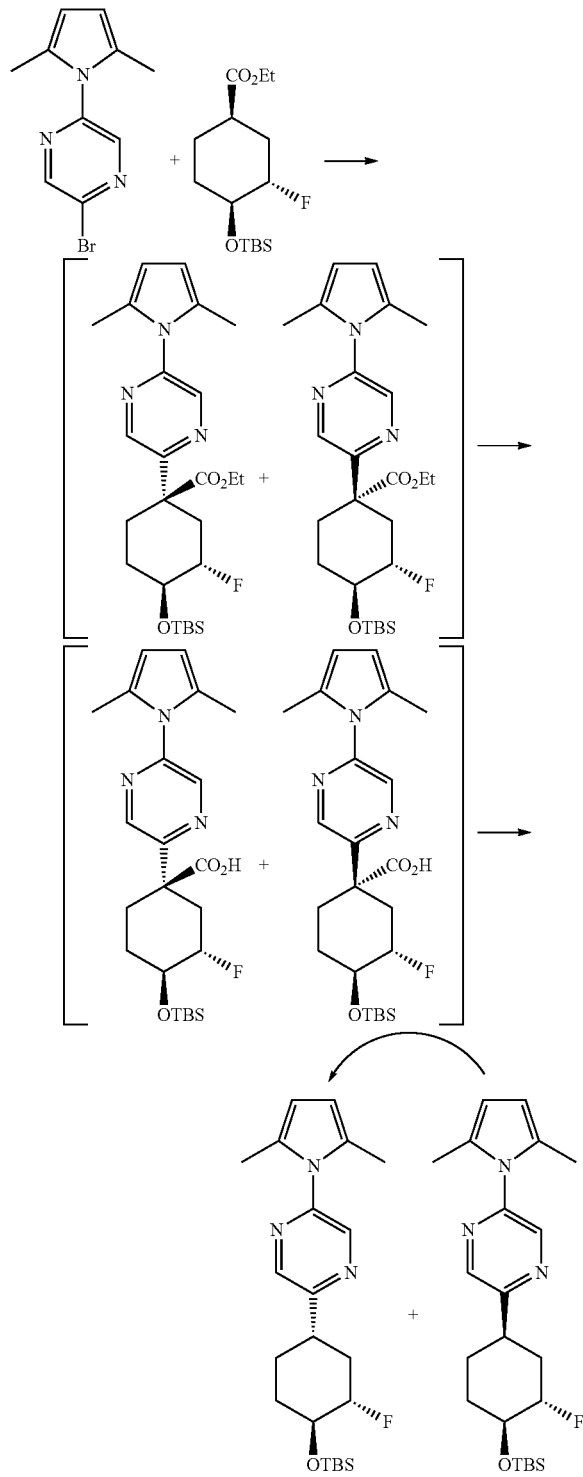

overall yield of 4 steps = 51.8%

To a 1 flask was added 2-bromo-5-(2,5-dimethyl-1H-pyrrol-1-yl)pyrazine (23 g, 67 mmol), (1R,3S,4S)-ethyl 4-((tert-butyldimethylsilyl)oxy)-3-fluorocyclohexanecarboxylate (28 g, 83 mmol), $\{[P(t\text{-}Bu)_3]PdBr\}_2$ (800 mg, 1 mmol) followed by toluene (250 mL). The reaction mixture was degassed three times by purging with nitrogen and then cooled to −35±5° C. To the reaction mixture was added NaHMDS (47 mL, 2 M in THF, 94 mmol), dropwise. The temperature was raised to room temperature over a one hour period and stirred for a further 30 minutes. The reaction mixture was quenched with 8% aqueous ammonium chloride (200 mL), the phases separated, and the aqueous layer extracted with heptane (300 mL). The combined organic layer was washed with 10% brine (400 mL), concentrated under reduced pressure (45±5° C., 50~100 mbar) to give 48 g of (1RS,3S,4S)-ethyl 4-((tert-butyldimethylsilyl)oxy)-1-(5-(2,5-dimethyl-1H-pyrrol-1-yl)pyrazin-2-yl)-3-fluorocyclohexanecarboxylate as a mixture of 1R and 1S diastereomers. This material was used for next step without further purification. HPLC retention time=8.274 min HPLC method d: Instrument: Agilent Technologies 1200 series. Column: Waters Xbridge C18, 150*3.0 mm, 3 um. Column temperature: 35° C. Flow rate: 0.70 mL/min. Detection: 210 nm/DAD. Mobile phase composition: A: 0.1% $H_3PO_4$ in water; B: acetonitrile. Gradient: 0 min: 90% A, 10% B; 5 min: 100% B; 11 min 100% B. LC-MS method: $[M+H]^+$=476.2706, $^1$H NMR (400 MHz, DMSO-$d_6$): 8.47 (s. 1 H), 8.43 (s, 1 H), 5.85 (s, 2 H), 4.39~4.52 (m, 1 H), 4.14 (dd, J=12 Hz, J=8 Hz, 2 H), 3.59~3.66 (m, 1 H), 2.28~2.94 (m, 1H), 2.06 (s, 6 H), 1.84~1.97 (m, 3 H), 1.46~1.52 (m, 3 H), 1.14~1.17 (t, J=12 Hz, J=8 Hz, 2H), 0.81 (s, 9 H), 0.01 (d, J=4 Hz, 6 H).

To a 1 flask was added (1R,3S,4S)-ethyl 4-((tert-butyldimethylsilyl)oxy)-1-(5-(2,5-dimethyl-1H-pyrrol-1-yl)pyrazin-2-yl)-3-fluorocyclohexanecarboxylate (48 g, 67 mmol), ethanol (250 mL) followed by 11% aqueous NaOH solution (112 g, 300 mmol). The reaction mixture was stirred at 30±5° C. for 16 hours, and then was quenched with 10% aqueous HCl (70 mL) to pH=6~7. After distillation of ethanol under reduced pressure (50±5° C., 50~100 mbar), the pH of the resulting mixture was adjusted to between 4 and 5 with 10% HCl. The aqueous solution was extracted twice with IPAc (200 mL×2). The combined organic layers were washed with 10% brine (200 mL) and concentrated under reduced pressure (50±5° C., 50~100 mbar) to give 46 g of (1RS,3S,4S)-4-((tert-butyldimethylsilyl)oxy)-1-(5-(2,5-dimethyl-1H-pyrrol-1-yl)pyrazin-2-yl)-3-fluorocyclohexanecarboxylic acid which was used for next step without further purifications. HPLC retention time=7.390 min (Instrument: Agilent Technologies 1200 series. Column: Waters Xbridge C18, 150*3.0 mm, 3 um. Column temperature: 35° C. Flow rate: 0.70 mL/min. Detection: 210 nm/DAD. Mobile phase composition: A: 0.1% $H_3PO_4$ in water; B: acetonitrile. Gradient: 0 min: 90% A, 10% B; 5 min: 100% B; 11 min 100% B), LC-MS: $[M+H]^+$=448.2415.

To a 500 mL flask was added (1RS,3S,4S)-4-((tert-butyldimethylsilyl)oxy)-1-(5-(2,5-dimethyl-1H-pyrrol-1-yl)pyrazin-2-yl)-3-fluorocyclohexanecarboxylic acid (46 g), toluene (250 mL) and HOAc (0.8 g, 13.3 mmol) under nitrogen. The reaction mixture was refluxed for 1 hour and then cooled to room temperature before adding 6% aqueous $NaHCO_3$ (200 mL). The phases were separated and the aqueous layer was extracted with heptane (250 mL). The combined organic layer was washed with 10% brine (200 mL) and concentrated under reduced pressure (50±5° C., 50~100 mbar) to give an oil. After the addition of 80 mL methanol to the residue, the mixture was heated to 55±5° C. and stirred for 1 hour. The temperature was cooled to 25±5° C. over a 2 hour period and stirred for a further 2-3 hours. The resulting suspension was filtered and the wet cake was dried under reduced pressure (50±5° C., 50~100 mbar) for 3 hours to give 8.6 g of 2-((1S,3S,4S)-4-((tert-butyldimethylsilyl)oxy)-3-fluorocyclohexyl)-5-(2,5-dimethyl-1H-pyrrol-1-yl)pyrazine as a crystalline solid (dr>99:1). The mother liquor was concentrated under reduced pressure (50±5° C., 50~100 mbar) to give 34.5 g (71 mmol) dark oil. To this residue was added ᵗBuOH (200 mL), followed by ᵗBuOK (8.0 g, 71 mmol). The reaction mixture was heated to 90±5° C. and stirred for 3 hours. After the temperature was cooled to room temperature, 10% aqueous NaHCO$_3$ (150 mL) was added followed by heptane (200 mL) and the mixture was stirred for a further 10 minutes. The phases were separated and the aqueous layer was washed with heptane (200 mL). The combined organic layers were washed with 10% brine (150 mL) and concentrated under reduced pressure (50±5° C., 50~100 mbar) to give an oil residue. To this residue was added methanol (60 mL), and the mixture was heated to 55±5° C. After stirring for 1 hour, the temperature was cooled to 25±5° C. over a 2 hour period followed by stirring for a further 2 hours. The suspension was filtered and the resulting wet cake was dried under reduced pressure (50±5° C., 50~100 mbar) for 3 hours to give the second batch of 2-((1S,3S,4S)-4-((tert-butyldimethylsilyl)oxy)-3-fluorocyclohexyl)-5-(2,5-dimethyl-1H-pyrrol-1-yl)pyrazine as a crystalline solid (5.6 g, dr=98:2). The overall yield of the 4 steps starting from 2-bromo-5-(2,5-dimethyl-1H-pyrrol-1-yl)pyrazine is 51.8%. mp=100.6° C.~102.9° C. LC/MS: [M+H]$^+$=404.2459, $^1$H NMR (400 MHz, DMSO-d$_6$): 8.53 (s, 1 H), 8.50 (s, 1 H), 5.75 (s, 2 H), 4.25~4.43 (m, 1 H), 3.60~3.69 (m, 1 H), 3.25 (s, 6 H), 2.93~3.00 (m, 1 H), 2.19~2.27 (m, 1 H), 1.98 (s, 6 H), 1.72~1.90 (m, 3 H), 1.39~1.61 (m, 2 H), 0.80 (s, 9 H), 0.01 (d, J=4 Hz, 6 H). HPLC (Instrument: Agilent Technologies 1200 series. Column: Waters Xbridge C18, 150*3.0 mm, 3 um. Column temperature: 35° C. Flow rate: 0.70 mL/min. Detection: 210 nm/DAD. Mobile phase composition: A: 0.1% H$_3$PO$_4$ in water; B: acetonitrile. Gradient: 0 min: 90% A, 10% B; 5 min: 100% B; 11 min 100% B) retention time: 8.084 min for 2-((1S,3S,4S)-4-((tert-butyldimethylsilyl)oxy)-3-fluorocyclohexyl)-5-(2,5-dimethyl-1H-pyrrol-1-yl)pyrazine, 8.324 min for 2-((1R,3S,4S)-4-((tert-butyldimethylsilyl)oxy)-3-fluorocyclohexyl)-5-(2,5-dimethyl-1H-pyrrol-1-yl)pyrazine.

2-bromo-5-(2,5-dimethyl-1H-pyrrol-1-yl)pyrazine

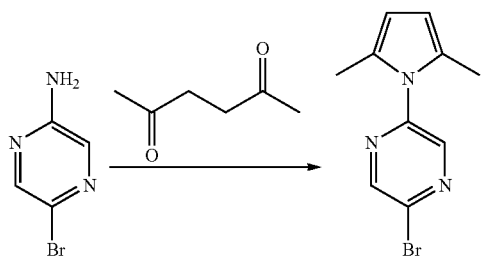

To a 250 mL flask was added 5-bromopyrazin-2-amine (18 g, 10.35 mmol), hexane-2,5-dione (14.5 g, 12.41 mmol) and PPTS (0.9 g, 0.36 mmol) in toluene (60 mL). The reaction mixture was heated to reflux in a Dean-Stark trap for 16 hours. The reaction mixture was cooled to room temperature and then concentrated under reduced pressure (55±5° C., 50~100 mbar) to give 2-bromo-5-(2,5-dimethyl-1H-pyrrol-1-yl)pyrazine as an oil (28 g, containing ~10% toluene, assay yield: 95%). This material was used without further purification. LC/MS: [M+H]$^+$=252.0139, $^1$H NMR (400 MHz, DMSO-d$_6$): 8.87 (s, 1H), 8.63 (s, 1 H), 5.86 (s, 2 H), 2.10 (s, 6 H). HPLC retention time=6.21 min, Instrument: Agilent Technologies 1200 series. Column: Waters Xbridge C18, 150*3.0 mm, 3 um. Column temperature: 35° C. Flow rate: 0.70 mL/min. Detection: 210 nm/DAD. Mobile phase composition: A: 0.1% H$_3$PO$_4$ in water; B: acetonitrile. Gradient: 0 min: 90% A, 10% B; 5 min: 100% B; 11 min 100% B.

5-((1S,3S,4S)-4-((tert-butyldimethylsilyl)oxy)-3-fluorocyclohexyl)pyrazin-2-amine

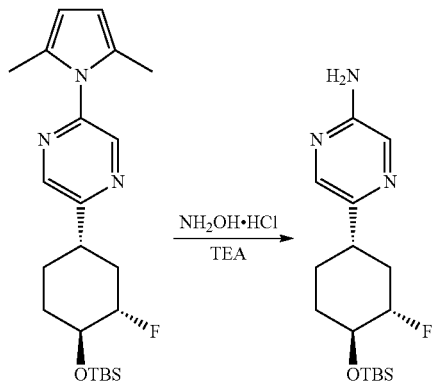 [SMILES: Cc1ccc(C)n1-c1cnc([C@H]2CC[C@H](O[Si](C)(C)C(C)(C)C)[C@@H](F)C2)cn1 ; "NH2OH·HCl" ; CC(C)(C)[Si](C)(C)O[C@H]1CC[C@H](c2cnc(N)cn2)C[C@@H]1F]

To a stirred suspension of 2-((1S,3S,4S)-4-((tert-butyldimethylsilyl)oxy)-3-fluorocyclohexyl)-5-(2,5-dimethyl-1H-pyrrol-1-yl)pyrazine (1250 g, 3097 mmol) in ethanol (7.5 kg) was added hydroxylamine hydrochloride (860.9 g, 12388.2 mmol) followed by triethylamine (642.5 g, 6349.0 mmol). The reaction mixture was heated to reflux (77-78° C.) for 42 hours, and then cooled to about 40° C. After distillation of 6 kg of ethanol under vacuum (<100 mbar) at 40° C., the mixture was cooled to room temperature, diluted with MTBE (7.0 kg) and water (8.0 kg). After stirring for 10 minutes, the organic layer was separated and the aqueous layer was extracted with MTBE (6.0 Kg). The combined organic layers were washed successively with 2×12 kg of water and 8 kg of 10% brine. The MTBE layer was concentrated under vacuum (<100 mbar) to give 1.2 kg yellow solid as crude product. The crude product was dissolved in 2 kg DCM and further purified via silica column chromatography eluting with EtOAc and heptane (1/6, v/v) to recover 2-((1S,3S,4S)-4-((tert-butyldimethylsilyl)oxy)-3-fluorocyclohexyl)-5-(2,5-dimethyl-1H-pyrrol-1-yl)pyrazine (310 g), then eluting with EtOAc and heptane (1/3, v/v) to give 5-((1S,3S,4S)-4-((tert-butyldimethylsilyl)oxy)-3-fluorocyclohexyl)pyrazin-2-amine (650 g, 64.5% yield) as light yellow solid, mp 113-116° C. ESI-MS (m/z): 326.1940 ([M+H]$^+$, 100). HPLC (method A), retention time 12.26 min. $^1$H NMR (400 MHz, CDCl$_3$): 7.93 (s, 1H), 7.86 (s, 1H), 4.50 (br. s, 2H), 4.41-4.46, 4.27-4.31 (m, 1H), 3.65-3.74 (m, 1H), 2.68-2.74 (m, 1H), 2.24-2.30 (m, 1H), 1.97-2.02 (m, 1H), 1.74-1.87 (m, 2H), 1.44-1.63 (m, 2H), 0.91 (s, 9H), 0.10 (d, J=8 Hz, 6H).

tert-butyl 4-(3-amino-6-((1S, 3S, 4S)-4-((tert-butyldimethylsilyl)oxy)-3-fluorocyclohexyl)pyrazin-2-yl)-2-fluorobenzoate

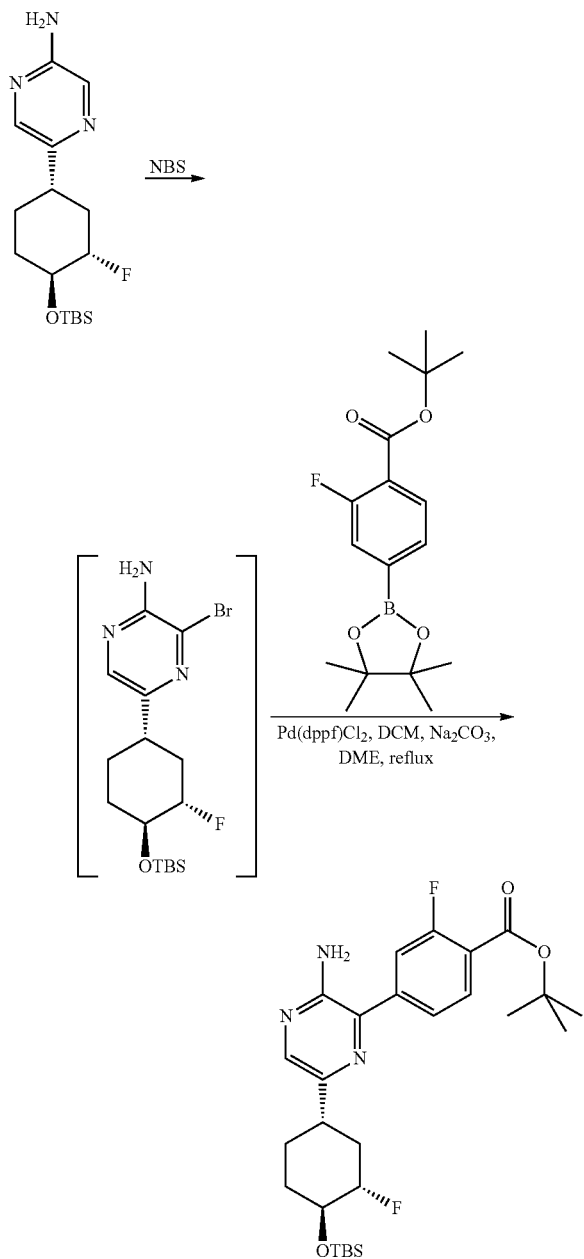

A solution of 5-((1S,3S,4S)-4-((tert-butyldimethylsilyl)oxy)-3-fluorocyclohexyl)pyrazin-2-amine (620.0 g, 1904.8 mmol) in DMSO (5 L) and water (400 mL) was cooled to ~4° C. NBS (389.8 g, 2190.5 mmol) was added in 10 portions within 1 hour and the reaction temperature was controlled under 5° C. with continuous stirring for 30 minutes. After addition of 0.3 M aqueous Na$_2$CO$_3$ (8.5 kg), the reaction temperature was increased to 35° C. MTBE (4.5 kg) was added and the mixture was stirred for a further 10 minutes. After phase separation, the aqueous layer was extracted with MTBE (4 kg). The combined organic layers were washed successively with 0.3 M aqueous Na$_2$CO$_3$ (8.5 kg) and water (8 kg), and concentrated under vacuum at 30-40° C. to give crude product 3-bromo-5-((1 S,3S,4S)-4-((tert-butyldimethylsilyl)oxy)-3-fluorocyclohexyl)pyrazin-2-amine as a foam (770 g). This crude product was used in next step without further purification. ESI-MS (m/z): 404.1105, 406.1093 ([M+H]$^+$, 100). HPLC (method A), retention time=14.38 min. $^1$H NMR (400 MHz, CDCl3): 7.81 (s, 1H), 4.99 (br. s, 2H), 4.37-4.42, 4.25-4.30 (m, 1H), 3.66-3.72 (m, 1H), 2.67-2.73 (m, 1H), 2.26-2.29 (m, 1H), 1.97-2.02 (m, 1H), 1.74-1.87 (m, 2H), 1.44-1.63 (m, 2H), 0.91 (s, 9H), 0.10 (d, J=8 Hz, 6H).

To a solution of 3-bromo-5-((1S, 3S, 4S)-4-((tert-butyldimethylsilyl)oxy)-3-fluorocyclohexyl)pyrazin-2-amine (760.0 g, 1879.4 mmol) and tert-butyl 2-fluoro-4-(4,4,5,5-tetramethyl-1,3,2-dioxaborolan-2-yl)benzoate (605.5 g, 1879.4 mmol) in DME (3.0 kg) was added 2.0 M aqueous Na$_2$CO$_3$ (1880 mL, 3760 mmol) and Pd(dppf)Cl$_2$.DCM (38.4 g, 47.0 mmol). After degassing with N$_2$ three times, the reaction mixture was heated to reflux (79-80° C.) and stirred at this temperature for 3 hours. The reaction temperature was cooled to room temperature and MTBE (2.5 kg) was added followed by water (4.0 kg). The mixture was stirred for 10 minutes before phase separation, and the aqueous layer was extracted with MTBE (1.8 kg). The combined organic layers were washed with water (2×4 kg), and concentrated under vacuum at 30-40° C. to give crude product tert-butyl 4-(3-amino-6-((1S, 3S, 4S)-4-((tert-butyldimethylsilyl)oxy)-3-fluorocyclohexyl)pyrazin-2-yl)-2-fluorobenzoate (ca. 1 kg). The mixture of this crude product and EtOH (95%, 3.2 kg) was heated to reflux (78-80° C.) for 30 minutes to give a solution. The temperature was cooled to 40° C. within 100 minutes followed by addition of water (800 g) within 30 minutes. The temperature was cooled to ~5° C. within 100 minutes and stirring at this temperature was continued for a further 60 minutes. The solid precipitation was filtered and the wet cake was washed with EtOH/water (1.2 L, 5/1, vol/vol). After drying under vacuum at 50° C. for 5 hours, tert-butyl 4-(3-amino-6-((1 S, 3S, 4S)-4-((tert-butyldimethylsilyl)oxy)-3-fluorocyclohexyl)pyrazin-2-yl)-2-fluorobenzoate was obtained as a brown powder (755 g, 76.4% yield over 2 steps, assay purity is 98.8%). mp 169-172° C. ESI-MS (m/z): 520.2739 ([M+H]$^+$, 100). HPLC (method A) retention time 15.76 min. $^1$H NMR (400 MHz, CDCl3): 7.98 (t, J=8 Hz, 1H), 7.91 (s, 1H), 7.61 (d, J=8 Hz, 1H), 7.55 (d, J=8 Hz, 1H), 4.68 (br. s, 2H), 4.42-4.48, 4.30-4.36 (m, 1H), 3.67-3.76 (m, 1H), 2.75-2.83 (m, 1H), 2.28-2.36 (m, 1H), 1.98-2.05 (m, 1H), 1.83-1.92 (m, 2H), 1.46-1.68 (m, 2H), 1.62 (s, 9H), 0.92 (s, 9H), 0.11 (d, J=8 Hz, 6H).

4-(3-amino-6-((1S,3S,4S)-3-fluoro-4-hydroxycyclohexyl)pyrazin-2-yl)-2-fluorobenzoic acid

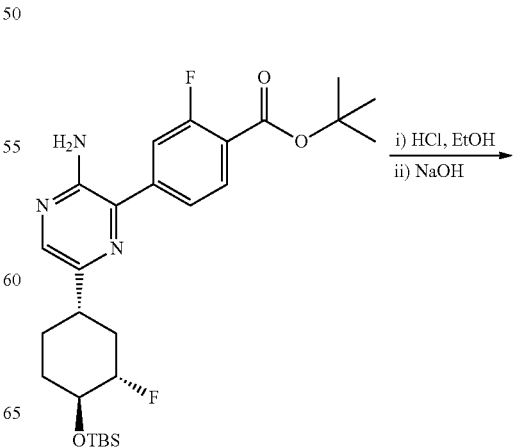

-continued

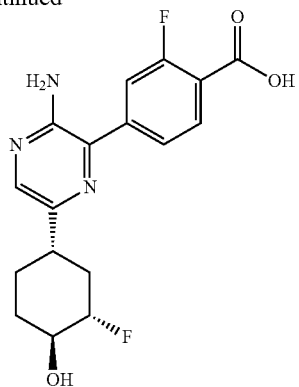

To a suspension of tert-butyl 4-(3-amino-6-((1S, 3S, 4S)-4-((tert-butyldimethylsilyl)oxy)-3-fluorocyclohexyl)pyrazin-2-yl)-2-fluorobenzoate (685.0 g, 1318.0 mmol) in EtOH (3.6 kg) was added aqueous HCl (36%, 400.5 g, 3954.2 mmol). The reaction mixture was heated to 30° C. and stirred for 4 hours. The reaction temperature was lowered to 5° C. and a solution of NaOH (342.7 g, 8567.5 mmol) in water (1.6 kg) was added. The reaction mixture was heated to 30° C. and stirred at this temperature for 18 hours. The pH of the reaction mixture was adjusted to 5 using 4 N aqueous HCl to form a solid precipitation. After distillation of EtOH under vacuum at 40-50° C., water (2.5 kg) was added to the residue and the temperature was cooled to 5° C. within 1 hour. The suspension was filtered, the solid was collected and dried under vacuum (<100 mbar) at 50-60° C. for 24 hours to give 4-(3-amino-6-((1S,3S,4S)-3-fluoro-4-hydroxycyclohexyl)pyrazin-2-yl)-2-fluorobenzoic acid as a brown powder (460 g, HPLC purity at 230 nm was 98.2%, quantitative yield). Mp 226-228° C. ESI-MS (m/z): 350.1282 ([M+H]$^+$, 100). HPLC (method A), retention time 5.93 min. $^1$H NMR (400 MHz, DMSO-D6): 13.32 (br. s, 1H), 8.00 (t, J=8 Hz, 1H), 7.99 (s, 1H), 7.70 (d, J=8 Hz, 1H), 7.65 (d, J=8 Hz, 1H), 6.24 (br. s, 2H), 5.16 (br. s, 1H), 4.44-4.49, 4.30-4.35 (m, 1H), 3.50-3.60 (m, 1H), 2.79-2.84 (m, 1H), 2.20-2.25 (m, 1H), 1.92-1.99 (m, 1H), 1.72-1.83 (m, 2H), 1.50-1.60 (m, 1H), 1.36-1.46 (m, 1H).

4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide

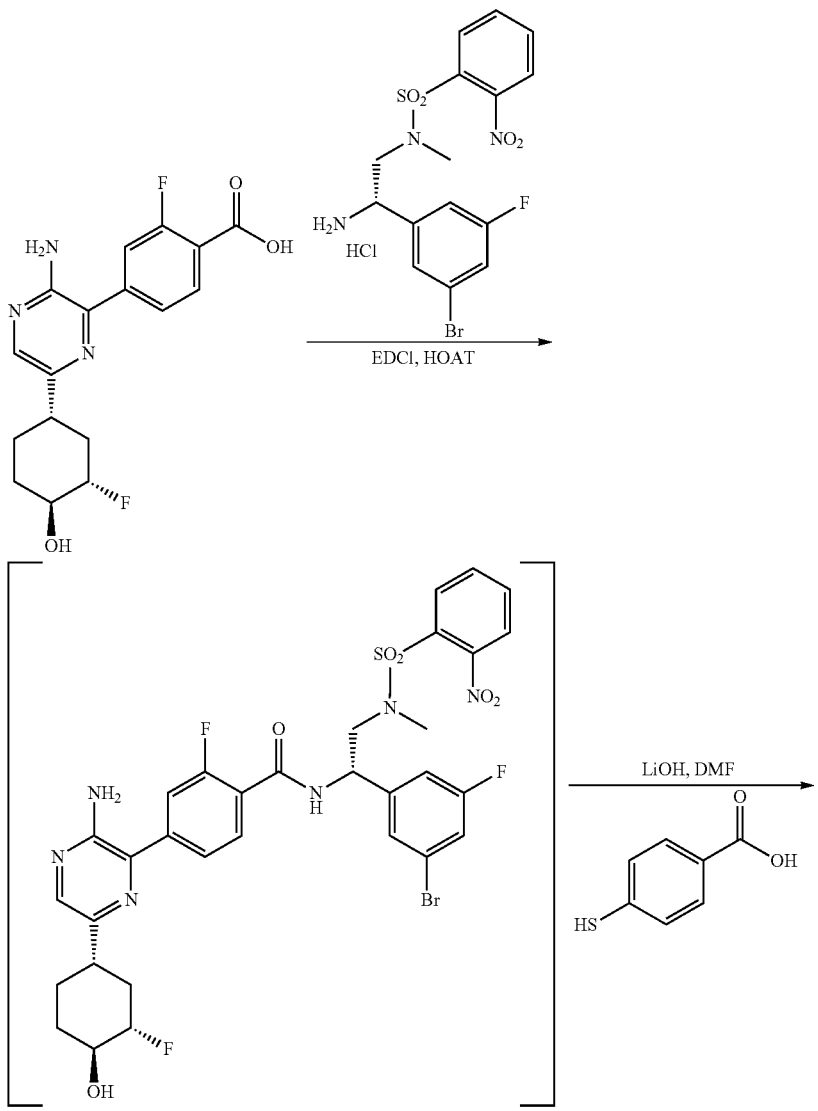

-continued

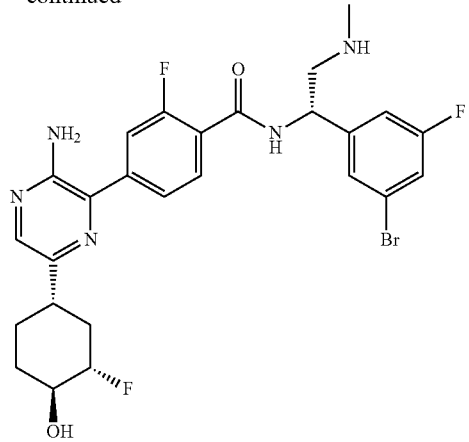

To a solution of 4-(3-amino-6-((1S,3S,4S)-3-fluoro-4-hydroxycyclohexyl)pyrazin-2-yl)-2-fluorobenzoic acid (300 g, 95% assay, 815.8 mmol) and (S)N-(2-amino-2-(3-bromo-5-fluorophenyl)ethyl)-N-methyl-2-nitrobenzenesulfonamide hydrochloride (397.7 g, 848.5 mmol) in DMF (2.5 kg) was added DIPEA (421.8 g, 3263.4 mmol), followed by EDCI (312.8 g, 1631.7 mmol) and HOAt (222.1 g, 1631.7 mmol). After the reaction mixture was stirred at 25° C. for 18 hours, the reaction temperature was lowered to 10° C. before IPAC (3.5 kg) and water (4.0 kg) was added. The mixture was stirred for 10 minutes and then the layers were separated. The aqueous layer was extracted with IPAC (2.5 kg). The combined organic layers were washed successively with 10% aqueous $Na_2CO_3$ (4.5 kg) and water (2×4 kg), and then concentrated under vacuum (<100 mbar) at 40-45° C. to give 4-(3-amino-6-((1S,3S,4S)-3-fluoro-4-hydroxycyclohexyl)pyrazin-2-yl)-N-((S)-1-(3-bromo-5-fluorophenyl)-2-(N-methyl-2-nitrophenylsulfonamido)ethyl)-2-fluorobenzamide as a foam (670 g, assay purity is 93%), which was used in next step without further purification. ESI-MS (m/z): 763.1216, 765.1161 ([M+H]+, 100). Mp=115-117° C. HPLC (method A), retention time=10.57 min. $^1$H NMR (400 MHz, CDCl$_3$): 8.11 (t, J=8 Hz, 1H), 7.99 (m, 1H), 7.91 (s, 1H), 7.59-7.72 (m, 5H), 7.35 (s, 1H), 7.19 (d, J=8 Hz, 1H), 7.09 (d, J=8 Hz, 1H), 5.46 (br. s, 1H), 4.77 (br. s, 2H), 4.48-4.55, 4.35-4.42 (m, 1H), 3.93 (q, $J_1$=12 Hz, $J_1$=16 Hz, 1H), 3.73-3.82 (m, 1H), 3.33 (q, $J_1$=4 Hz, $J_1$=12 Hz, 1H), 3.00 (s, 3H), 2.78-2.85 (m, 1H), 2.31-2.37 (m, 1H), 2.12-2.20 (m, 1H), 1.84-1.96 (m, 2H), 1.60-1.71 (m, 1H), 1.47-1.56 (m, 1H).

To a suspension of 4-(3-amino-6-((1S,3S,4S)-3-fluoro-4-hydroxycyclohexyl)-pyrazin-2-yl)-N-((S)-1-(3-bromo-5-fluorophenyl)-2-(N-methyl-2-nitrophenyl-sulfonamido)ethyl)-2-fluorobenzamide (500 g crude product from previous step) in DMF (2.0 kg) was added 4-mercaptobenzoic acid (161.5 g, 1047.7 mmol). The reaction mixture became a solution after 5 minutes and then was cooled to 10° C. After addition of LiOH.H$_2$O (137.3 g, 3274.0 mmol) in one portion, the mixture was stirred at 25° C. for 3 hours before the temperature was cooled to 10° C. The reaction mixture was diluted with water (3.0 kg) and extracted with IPAC (3*2.5 kg). The IPAC layers was first washed with 15% aqueous $Na_2CO_3$ (2*3.0 kg) followed by water (2*3.0 kg), and then concentrated under vacuum (<100 mbar) at 40-45° C. To the resulting residue was added MeCN (1.8 kg) to give a clear solution, which was heated to 50° C. and stirred for 30 minutes. The mixture was further cooled to 10° C. in 2 hours and stirred at this temperature for a further 1 hour. After filtration of the resulting suspension, the solid cake was washed with pre-cooled MeCN (400 g, 5° C.). The wet cake was dried under vacuum (<100 mbar) at 80° C. for 18 hours to give 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide as a crystalline solid (245 g, overall yield for 2 steps is 66%, HPLC purity=98.3%, chiral purity=99.0%). Mp 115-117° C. ESI-MS (m/z): 578.1381, 580.1381 ([M+H]+, 100). HPLC (method A), retention time=7.24 min. $^1$H NMR (400 MHz, DMSO-D6): 8.82 (d, J=8 Hz, 1H), 8.0 (s, 1H), 8.82 (t, J=8 Hz, 1H), 7.70 (d, J=8 Hz, 1H), 7.67 (d, J=8 Hz, 1H), 7.53 (s, 1H), 7.48 (d, J=8 Hz, 1H), 7.34 (d, J=8 Hz, 1H), 6.21 (br. s, 2H), 5.18 (m, 2H), 4.46-4.52, 4.32-4.37 (m, 1H), 3.52-3.60 (m, 1H), 2.80-2.94 (m, 3H), 2.36 (s, 3H), 2.23-2.25 (m, 1H), 1.95-1.98 (m, 1H), 1.76-1.86 (m, 3H), 1.51-1.62 (m, 1H), 1.39-1.48 (m, 1H).

Figure 1:
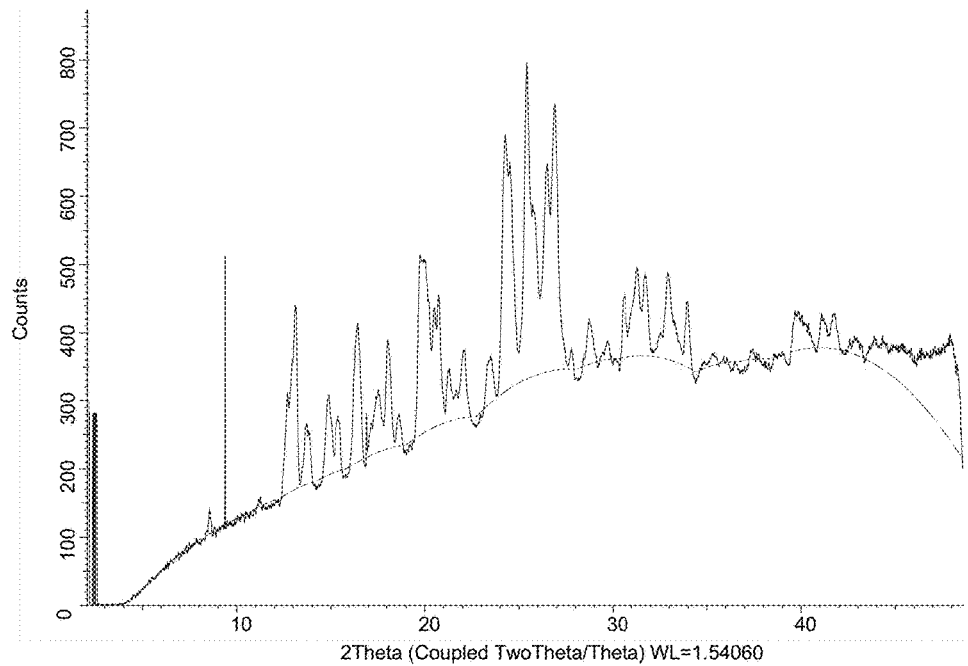
FIG. 1 shows the X-ray powder diffraction pattern of the free base of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide.
Figure 2:
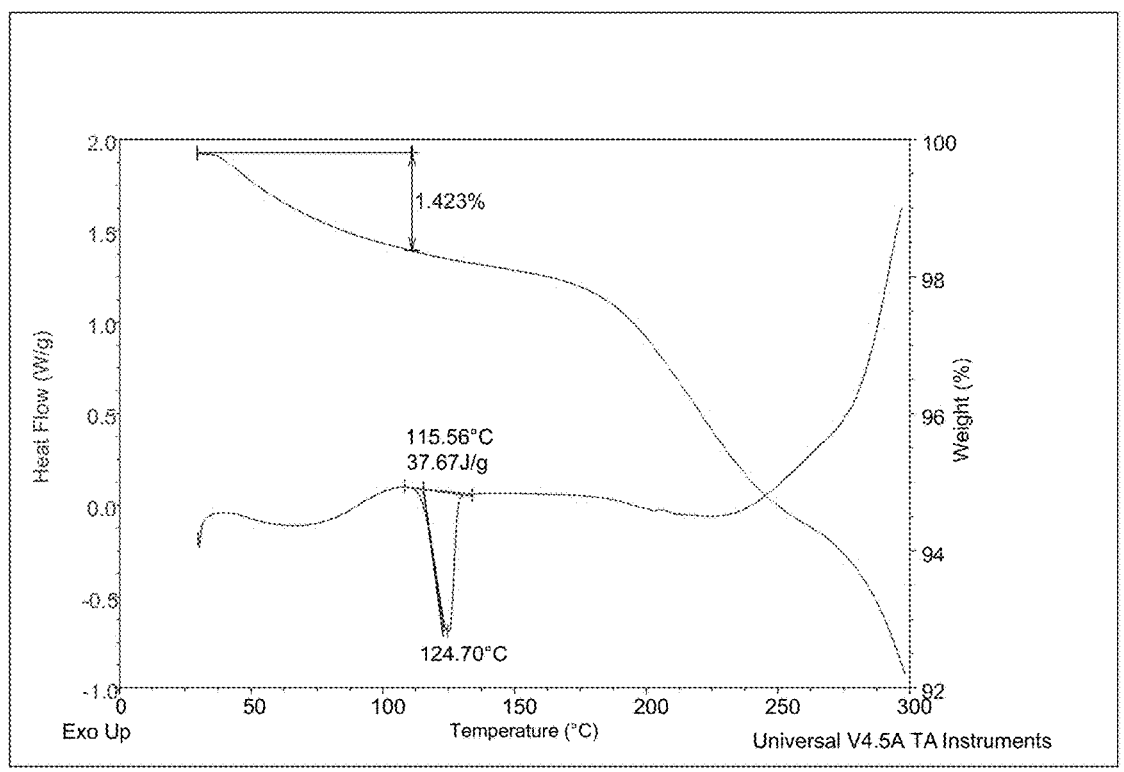
FIG. 2 is a DSC/TGA thermograph of the free base of 4-(3-amino-6-((1S,3S,4S)-3-fluoro-4-hydroxycyclohexyl)

The free base form of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide was prepared by suspending 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide (200 mg) was suspended in 4 ml of nitromethane at room temperature. The suspension was heated to 55° C. until the solution was clear. Eight heat-cool cycles were conducted in the temperature range 55° C. to 5° C. The solid was generated by filtration and dried under vacuum at 40° C. overnight. An X-ray powder diffraction pattern of the free base form was determined in FIG. 1. A DSC/TGA thermograph of the free base of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide is provided in FIG. 2.

The HCl salt form of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide was prepared by dissolving amorphous 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide (120 mg) in 0.5N HCl ethanol solution (414 μL) with stirring at room temperature. A precipitate is observed after 5 minutes of stirring. A DSC/TGA thermograph of the highly crystalline HCl salt form of 4-(3-amino-6-((1S, 3S,4S)-3-fluoro-4-hydroxycyclohexyl)pyrazin-2-yl)-N-((S)-1-(3-bromo-5-fluorophenyl)-2-(methylamino) ethyl)-2-fluorobenzamide is provided in FIG. 4. An X-ray powder diffraction pattern of the free base form was determined in FIG. 3. The most significant peaks in the XRPD of FIG. 3 are shown in the table:

| Angle 2-theta | Intensity % |
|---|---|
| 12.346 | 9.9 |
| 15.57 | 10.8 |
| 16.195 | 15.3 |
| 16.652 | 59.3 |
| 18.245 | 4.5 |
| 19.118 | 47.7 |
| 19.26 | 100 |
| 19.642 | 39.3 |
| 20.029 | 5.4 |
| 21.509 | 22.2 |
| 21.777 | 22.2 |
| 22.568 | 68.9 |
| 23.611 | 36.3 |
| 24.334 | 88 |
| 24.733 | 18.9 |
| 25.748 | 10.9 |
| 26.826 | 16 |
| 27.421 | 13.6 |
| 28.46 | 15.5 |
| 28.837 | 13.6 |
| 29.177 | 17.3 |
| 29.382 | 10.1 |

-continued

| Angle 2-theta | Intensity % |
|---|---|
| 29.88 | 19.1 |
| 30.14 | 20.5 |
| 31.361 | 7.8 |
| 31.424 | 7.8 |
| 32.751 | 21.2 |
| 33.787 | 12.3 |
| 34.649 | 17 |
| 35.391 | 26.9 |
| 37.057 | 11.4 |
| 38.005 | 6.1 |
| 40.657 | 6.2 |
| 40.954 | 5.1 |
| 41.658 | 5.1 |
| 42.926 | 5.8 |
| 44.201 | 17.7 |

Examples 185 and 186

Synthesis of 4-(3-amino-6-((1R,3R,4S)-3-fluoro-4-hydroxycyclohexyl)pyrazin-2-yl)-N-((S)-1-(3-bromo-5-fluorophenyl)-2-hydroxyethyl)-2-fluorobenzamide and 4-(3-amino-6-((1S,3S,4R)-3-fluoro-4-hydroxycyclohexyl)pyrazin-2-yl)-N-((S)-1-(3-bromo-5-fluorophenyl)-2-hydroxyethyl)-2-fluorobenzamide

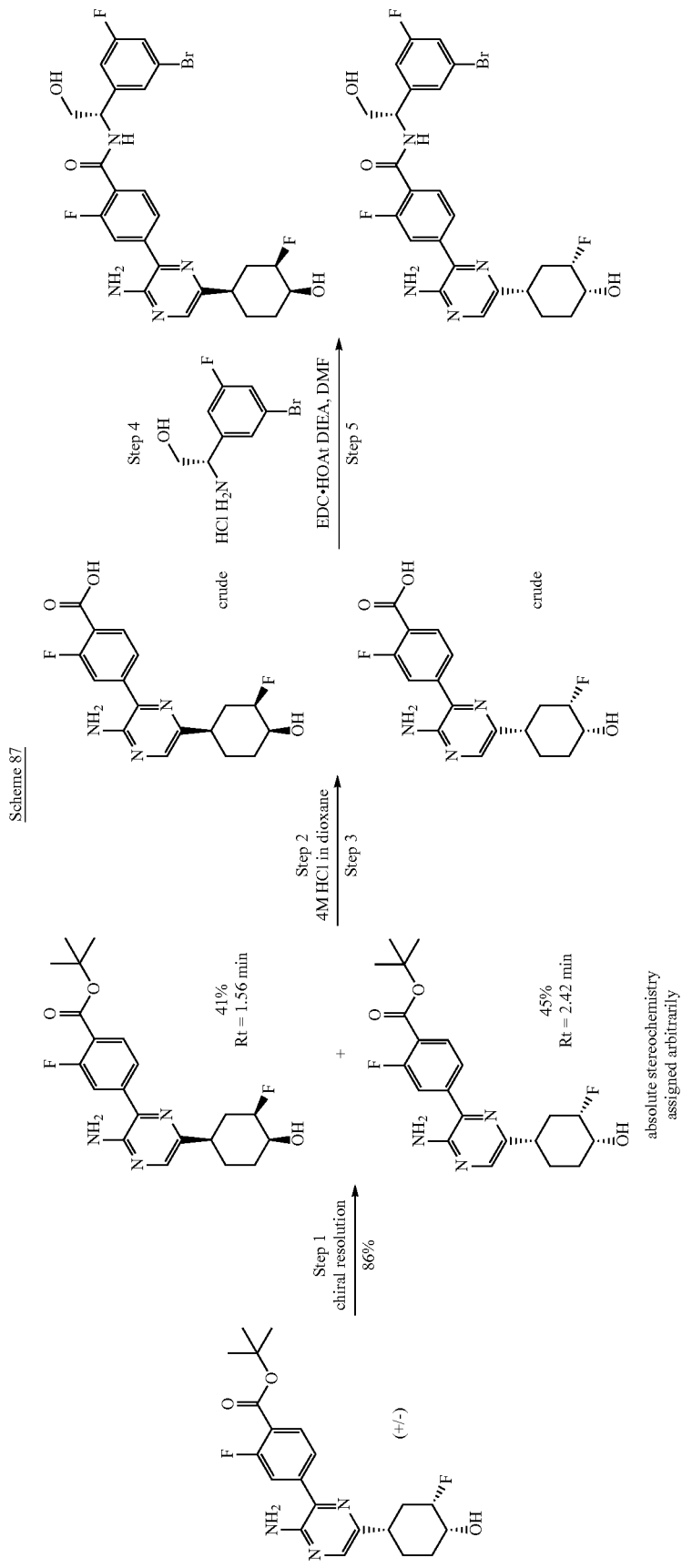
Scheme 87

Step 1. Tert-butyl 4-(3-amino-6-((1S,3S,4S)-3-fluoro-4-hydroxycyclohexyl)pyrazin-2-yl)-2-fluorobenzoate tert-butyl 4-(3-amino-6-((1R,3R,4S)-3-fluoro-4-hydroxycyclohexyl)pyrazin-2-yl)-2-fluorobenzoate (154 mg, 0.38 mmol) was subjected to chiral separation (ChiralPak 5mic AD column, 4.6×100 (mm), CO2/IPA+0.1% DEA=75/25, SFC=5 ml/min) to provide polar enantiomer, tert-butyl 4-(3-amino-6-((1R,3R,4S)-3-fluoro-4-hydroxycyclohexyl)pyrazin-2-yl)-2-fluorobenzoate (Rt=1.86 min, 63 mg, 0.155 mmol, 41%) and the less polar enantiomer, tert-butyl 4-(3-amino-6-((1S,3S,4R)-3-fluoro-4-hydroxycyclohexyl)pyrazin-2-yl)-2-fluorobenzoate (Rt=2.91, 70 mg, 0.173 mmol, 46%). The absolute stereochemistry was assigned arbitrarily.

Step 2 and 3. 4-(3-amino-6-((1R,3R,4S)-3-fluoro-4-hydroxycyclohexyl)pyrazin-2-yl)-2-fluorobenzoic acid and 4-(3-amino-6-((1S,3S,4S)-3-fluoro-4-hydroxycyclohexyl)pyrazin-2-yl)-2-fluorobenzoic acid To a solution of each ester (1 mmol) in DCM (2 mL) was added 4 M HCl in dioxane (30 mL). The reaction mixture was stirred at room temperature for 2 days. After the volatile materials were evaporated in vacuo, the reaction mixture was triturated with Et$_2$O and filtered off to provide 4-(3-amino-6-((1R,3R,4S)-3-fluoro-4-hydroxycyclohexyl)pyrazin-2-yl)-2-fluorobenzoic acid (60 mg from 63 mg of the ester) and 4-(3-amino-6-((1S,3S,4R)-3-fluoro-4-hydroxycyclohexyl)pyrazin-2-yl)-2-fluorobenzoic acid (59 mg from 70 mg of the ester) as a HCl salt respectively, which was used for the next step without any further purification. LCMS (m/z): 350.2 (MH$^+$), 0.5 min (for each acid).

Step 4 and 5. 4-(3-amino-6-((1R,3R,4S)-3-fluoro-4-hydroxycyclohexyl)pyrazin-2-yl)-N-((S)-1-(3-bromo-5-fluorophenyl)-2-hydroxyethyl)-2-fluorobenzamide and 4-(3-amino-6-((1S,3S,4R)-3-fluoro-4-hydroxycyclohexyl)pyrazin-2-yl)-N-((S)-1-(3-bromo-5-fluorophenyl)-2-hydroxyethyl)-2-fluorobenzamide To a solution of each acid (20 mg, 0.057 mmol) in DMF (573 μL) was added (S)-2-amino-2-(3-bromo-5-fluorophenyl)ethanol HCl salt (18.59 mg, 0.069 mmol), aza-HOBt (11.69 mg, 0.086 mmol), EDC (21.95 mg, 0.115 mmol), and DIEA (30.0 μl, 0.172 mmol). The reaction mixture was stirred for 15 h. Water was added, and the reaction mixture was extracted with EtOAc three times. The organic layers were dried over Na$_2$SO$_4$, filtered and concentrated in vacuo. The crude product was purified by HPLC. Pure fractions were lyophilized to provide the desired product (11 mg, 0.016 mmol, 28%) as a TFA salt respectively. For 4-(3-amino-6-((1R,3R,4S)-3-fluoro-4-hydroxycyclohexyl)pyrazin-2-yl)-N-((S)-1-(3-bromo-5-fluorophenyl)-2-hydroxyethyl)-2-fluorobenzamide, LCMS (m/z): 565.1/567 (MH$^+$), 0.74 min; $^1$H NMR (400 MHz, CD$_3$OD) δ ppm 7.95-7.79 (m, 1H), 7.76-7.59 (m, 1H), 7.46 (s, 1H), 7.33-7.14 (m, 2H), 5.24-5.10 (m, 1H), 4.75-4.49 (m, 1H), 4.16 (br. s., 2H), 3.96-3.77 (m, 4H), 2.80 (t, J=12.5 Hz, 2H), 2.25 (dq, J=7.6, 11.9 Hz, 2H), 2.08-1.78 (m, 7H), 1.76-1.55 (m, 4H). For 4-(3-amino-6-((1S,3S,4R)-3-fluoro-4-hydroxycyclohexyl)pyrazin-2-yl)-N-((S)-1-(3-bromo-5-fluorophenyl)-2-hydroxyethyl)-2-fluorobenzamide, LCMS (m/z): 565.1/567.1 (MH$^+$), 0.74 min; $^1$H NMR (400 MHz, CD$_3$OD) δ ppm 7.84-7.70 (m, 2H), 7.66-7.49 (m, 2H), 7.37 (s, 1H), 7.24-7.05 (m, 2H), 5.09 (d, J=5.5 Hz, 1H), 4.66-4.41 (m, 1H), 4.07 (br. s., 1H), 3.88-3.65 (m, 2H), 2.71 (t, J=12.9 Hz, 1H), 2.16 (dq, J=7.4, 12.0 Hz, 1H), 1.99-1.70 (m, 3H), 1.66-1.47 (m, 2H). The absolute stereochemistry was not determined yet.

Examples 187 and 188

Synthesis of 4-(3-amino-6-((1R,3S,4R)-3-fluoro-4-hydroxycyclohexyl)pyrazin-2-yl)-N-((S)-1-(3-bromo-5-fluorophenyl)-2-hydroxyethyl)-2-fluorobenzamide and 4-(3-amino-6-((1S,3R,4S)-3-fluoro-4-hydroxycyclohexyl)pyrazin-2-yl)-N-((S)-1-(3-bromo-5-fluorophenyl)-2-hydroxyethyl)-2-fluorobenzamide Scheme 88

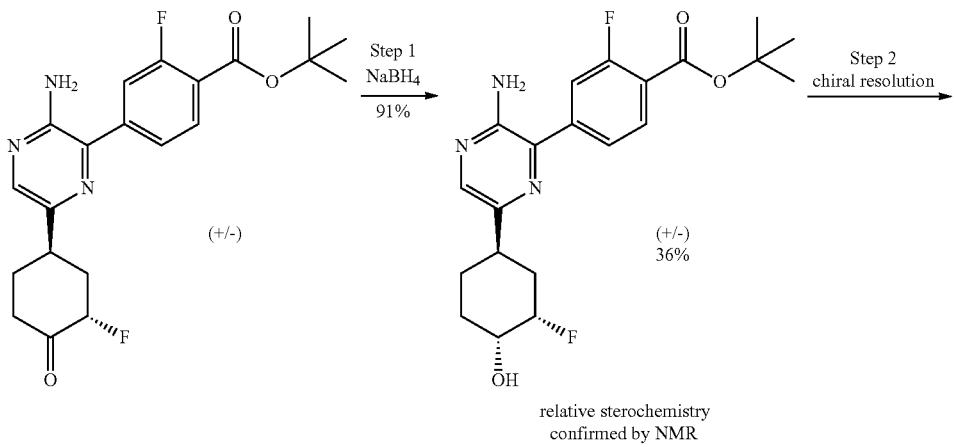

relative stereochemistry confirmed by NMR

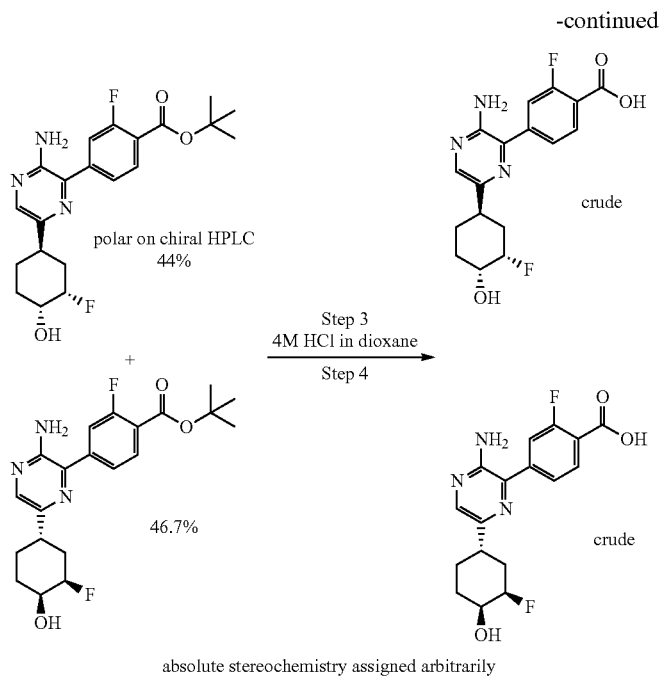
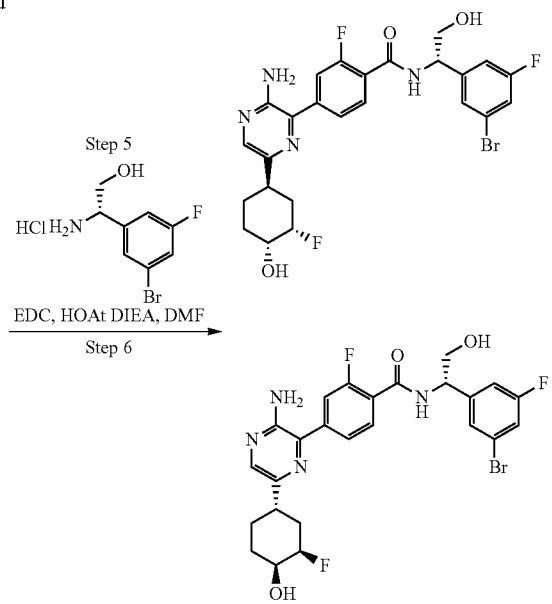

absolute stereochemistry assigned arbitrarily

Step 1. (+/−)-tert-butyl 4-(3-amino-6-((1R,3S,4R)-3-fluoro-4-hydroxycyclohexyl)pyrazin-2-yl)-2-fluorobenzoate To a solution of (+/−)-tert-butyl 4-(3-amino-6-((1R,3S)-3-fluoro-4-oxocyclohexyl)pyrazin-2-yl)-2-fluorobenzoate (208 mg, 0.516 mmol) in MeOH (3.017 mL) was added NaBH₄ (29.3 mg, 0.773 mmol) at 0° C. The reaction mixture was stirred for 2 h. LCMS showed ~4:1 ratio of two diastereomers. After quenched with NaHCO₃ solution, the reaction mixture was extracted with EtOAc. The organic layer was washed with water and brine, dried over sodium sulfate, filtered off and concentrated in vacuo. The major diastereomer was separated by neutral prep HPLC. After lyophilzation, (+/−)-tert-butyl 4-(3-amino-6-((1R,3S,4R)-3-fluoro-4-hydroxycyclohexyl)pyrazin-2-yl)-2-fluorobenzoate was obtained in 35.8% yield. (74.9 mg). LCMS (m/z): 406.3 (MH⁺), 0.80 min. The relative stereochemistry of (+/−)-tert-butyl 4-(3-amino-6-((1R,3S,4R)-3-fluoro-4-hydroxycyclohexyl)pyrazin-2-yl)-2-fluorobenzoate was confirmed by NMR.

Step 2. tert-butyl 4-(3-amino-6-((1R,3S,4R)-3-fluoro-4-hydroxycyclohexyl)pyrazin-2-yl)-2-fluorobenzoate and tert-butyl 4-(3-amino-6-((1S,3R,4S)-3-fluoro-4-hydroxycyclohexyl)pyrazin-2-yl)-2-fluorobenzoate (+/−)-Tert-butyl 4-(3-amino-6-((1R,3S,4R)-3-fluoro-4-hydroxycyclohexyl)pyrazin-2-yl)-2-fluorobenzoate (74.9 mg, 0.185 mmol) was subjected to chiral SFC (ChiralPak 5mic AD column, 4.6×100 (mm), CO₂/EtOH+0.1%, DEA=80/20, SFC=5 mL/min) to provide polar enantiomer, tert-butyl 4-(3-amino-6-((1R,3S,4R)-3-fluoro-4-hydroxycyclohexyl)pyrazin-2-yl)-2-fluorobenzoate (Rt=1.95 min, 33 mg, 44%) and the less polar enantiomer, tert-butyl 4-(3-amino-6-((1S,3R,4S)-3-fluoro-4-hydroxycyclohexyl)pyrazin-2-yl)-2-fluorobenzoate (Rt=3.17, 35 mg, 46%). The absolute stereochemistry was assigned arbitrarily.

Step 3 and 4. 4-(3-amino-6-((1R,3S,4R)-3-fluoro-4-hydroxycyclohexyl)pyrazin-2-yl)-2-fluorobenzoic acid and 4-(3-amino-6-((1S,3R,4S)-3-fluoro-4-hydroxycyclohexyl)pyrazin-2-yl)-2-fluorobenzoic acid To a solution of each ester (1 mmol) was added 4 M HCl in dioxane (111 mL). The reaction mixture was stirred at room temperature for 2 days. After the volatile materials were evaporated in vacuo, the reaction mixture was triturated with Et₂O and filtered off to provide 4-(3-amino-6-((1R,3S,4R)-3-fluoro-4-hydroxycyclohexyl)pyrazin-2-yl)-2-fluorobenzoic acid (31 mg from 33 mg of the ester), LCMS (m/z): 350.2 (MH⁺), 0.47 min, and 4-(3-amino-6-((1S,3R,4S)-3-fluoro-4-hydroxycyclohexyl)pyrazin-2-yl)-2-fluorobenzoic acid (33 mg from 35 mg of the ester), LCMS (m/z): 350.2 (MH⁺), 0.48 min, as a HCl salt respectively, which was used for the next step without any further purification.

Step 5 and 6. 4-(3-amino-6-((1R,3S,4R)-3-fluoro-4-hydroxycyclohexyl)pyrazin-2-yl)-N-((S)-1-(3-bromo-5-fluorophenyl)-2-hydroxyethyl)-2-fluorobenzamide and 4-(3-amino-6-((1S,3R,4S)-3-fluoro-4-hydroxycyclohexyl)pyrazin-2-yl)-N-((S)-1-(3-bromo-5-fluorophenyl)-2-hydroxyethyl)-2-fluorobenzamide Following Step 8 in Scheme 85, using 4-(3-amino-6-((1R,3S,4R)-3-fluoro-4-hydroxycyclohexyl)pyrazin-2-yl)-2-fluorobenzoic acid, 4-(3-amino-6-((1R,3S,4R)-3-fluoro-4-hydroxycyclohexyl)pyrazin-2-yl)-N-((S)-1-(3-bromo-5-fluorophenyl)-2-hydroxyethyl)-2-fluorobenzamide was obtained. LCMS (m/z): 565.0/567.1 (MH⁺), 0.71 min; 1H NMR (400 MHz, CD₃OD) δ ppm 7.93-7.78 (m, 2H), 7.73-7.55 (m, 2H), 7.46 (s, 1H), 7.33-7.13 (m, 2H), 5.17 (t, J=5.9 Hz, 1H), 3.95-3.78 (m, 2H), 3.75-3.42 (m, 1H), 3.09-2.93 (m, 1H), 2.32-2.14 (m, 1H), 2.05-1.79 (m, 5H), 1.80-1.59 (m, 1H). Using 4-(3-amino-6-((1S,3R,4S)-3-fluoro-4-hydroxycyclohexyl)pyrazin-2-yl)-2-fluorobenzoic acid, 4-(3-amino-6-((1S,3R,4S)-3-fluoro-4-hydroxycyclohexyl)pyrazin-2-yl)-N-((S)-1-(3-bromo-5-fluorophenyl)-2-hydroxyethyl)-2-fluorobenzamide was obtained. LCMS (m/z): 565.0/567.1 (MH+), 0.71 min; 1H NMR (400 MHz, CD3OD) δ ppm 7.95-7.80 (m, 2H), 7.75-7.56 (m, 2H), 7.46 (s, 1H), 7.33-7.12 (m, 2H), 5.17 (t, J=5.9 Hz, 1H), 3.96-3.78 (m, 2H), 3.76-3.55 (m, 1H), 3.10-2.95 (m, 1H), 2.31-2.12 (m, 1H), 2.08-1.82 (m, 5H), 1.79-1.62 (m, 1H).

Example 189

Synthesis of 4-(3-amino-6-((1S,3S,4S)-3-fluoro-4-hydroxycyclohexyl)pyrazin-2-yl)-2-fluoro-N-((S)-1-(3-fluoro-5-iodophenyl)-2-hydroxyethyl)benzamide

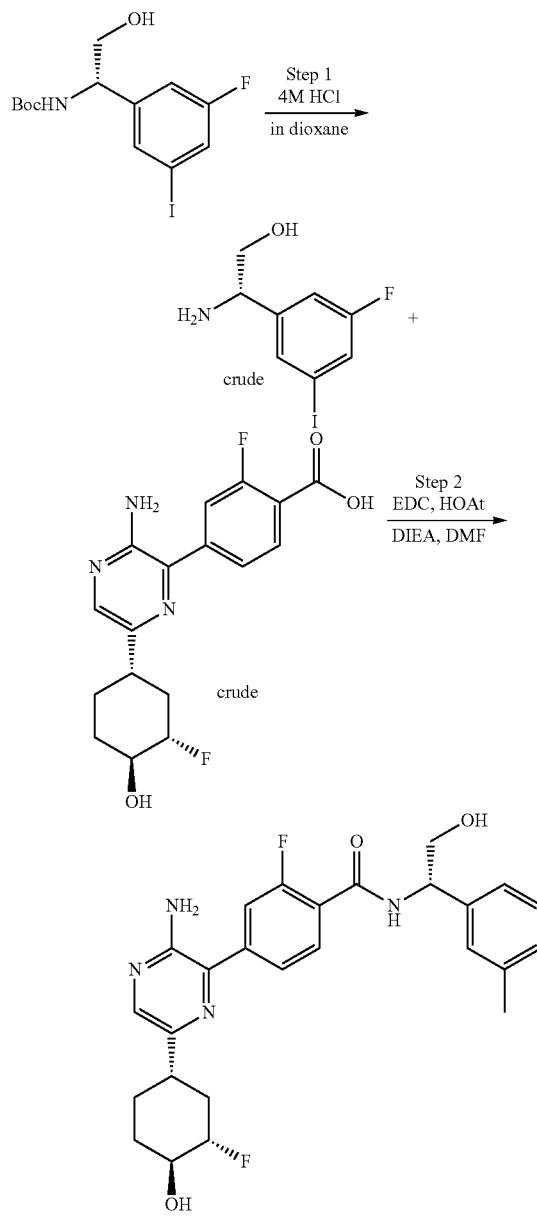

Step 1. (S)-2-amino-2-(3-fluoro-5-iodophenyl)ethanol hydrochloride (S)-tert-butyl (1-(3-fluoro-5-iodophenyl)-2-hydroxyethyl)carbamate (2.507 g, 6.58 mmol) was dissolved in DCM (60 mL) and treated with 4 N HCl in dioxane (4.93 mL, 19.73 mmol). The mixture was stirred overnight at room temperature. After the majority of the solvent was evaporated carefully in vacuo, the slurry was titrated with Et2O to afford 1.525 g of a fine white HCl salt of (S)-2-amino-2-(3-fluoro-5-iodophenyl)ethanol (72%), which was isolated by suction filtration. LCMS (m/z): 282.4 (MH+), 0.46 min.

Step 2. 4-(3-amino-6-((1S,3S,4S)-3-fluoro-4-hydroxycyclohexyl)pyrazin-2-yl)-2-fluoro-N-((S)-1-(3-fluoro-5-iodophenyl)-2-hydroxyethyl)benzamide To a solution of 4-(3-amino-6-((1S,3S,4S)-3-fluoro-4-hydroxycyclohexyl)pyrazin-2-yl)-2-fluorobenzoic acid (16 mg, 0.046 mmol) in DMF (0.46 mL) was added (S)-2-amino-2-(3-fluoro-5-iodophenyl)ethanol hydrochloride (17.5 mg, 0.055 mmol), HOAt (9.35 mg, 0.069 mmol), EDC (17.6 mg, 0.092 mmol), and DIEA (24 µl, 0.137 mmol). The reaction mixture was stirred for 15 h. After water was added, the reaction mixture was extracted with EtOAc and the organic layer was washed with water twice. The organic layer was separated and dried over Na2SO4, filtered off and concentrated in vacuo. The crude product was purified by flash chromtography eluting with 0-100% EtOAc/heptane to provide crude product, which was triturated with 70% of DCM/ether to provide 9.3 mg of 4-(3-amino-6-((1S,3S,4S)-3-fluoro-4-hydroxycyclohexyl)pyrazin-2-yl)-2-fluoro-N-((S)-1-(3-fluoro-5-iodophenyl)-2-hydroxyethyl)benzamide as a TFA salt (28%). LCMS (m/z): 613.1 (MH+), 0.74 min; 1H NMR (400 MHz, CD3OD) δ ppm 7.93-7.78 (m, 2H), 7.76-7.57 (m, 3H), 7.73-7.56 (m, 3H), 7.43 (d, J=7.8 Hz, 1H), 7.21 (d, J=9.4 Hz, 1H), 5.15 (t, J=5.9 Hz, 1H), 4.37 (m, 1H), 3.83 (m, 2H), 3.63 (m, 1H), 2.84 (t, J=11.7 Hz, 1H), 2.27 (dd, J=2.9, 9.2 Hz, 1H), 2.14-1.98 (m, 1H), 1.96-1.75 (m, 2H), 1.65 (dq, J=3.3, 13.0 Hz, 1H), 1.56-1.34 (m, 1H).

Synthesis of (S)-2-(4-(3-amino-6-((1S,3S,4S)-3-fluoro-4-hydroxycyclohexyl)pyrazin-2-yl)-2-fluorobenzamido)-2-(3-fluoro-5-iodophenyl)ethyl dihydrogen phosphate

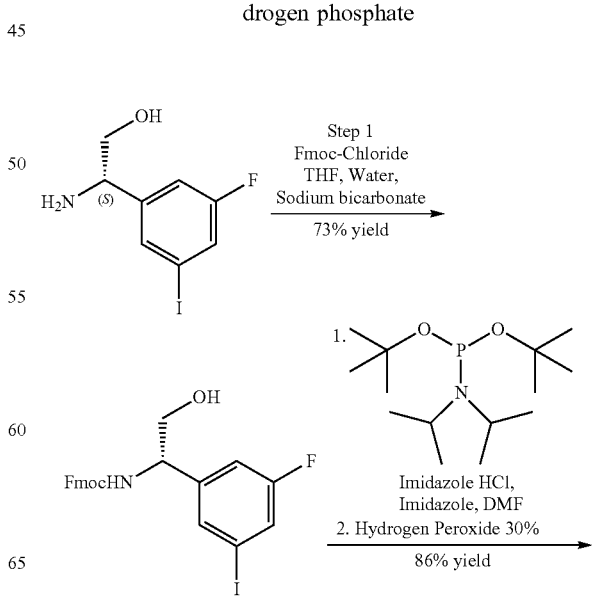

327
-continued

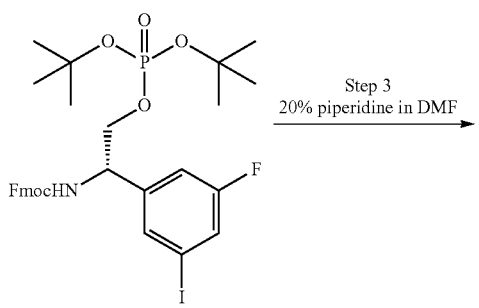

Step 3
20% piperidine in DMF

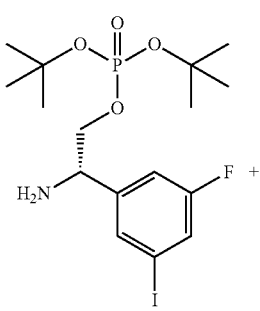

+

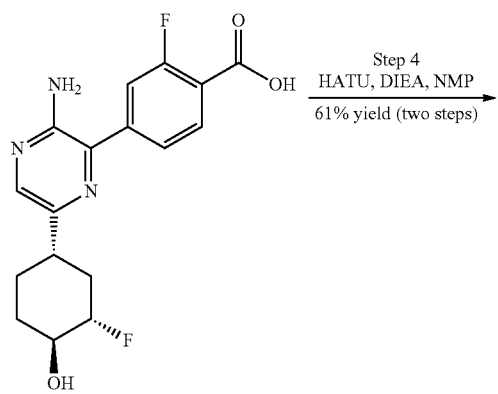

Step 4
HATU, DIEA, NMP
61% yield (two steps)

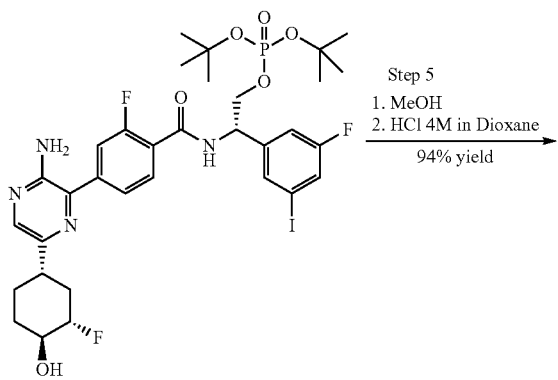

Step 5
1. MeOH
2. HCl 4M in Dioxane
94% yield

328
-continued

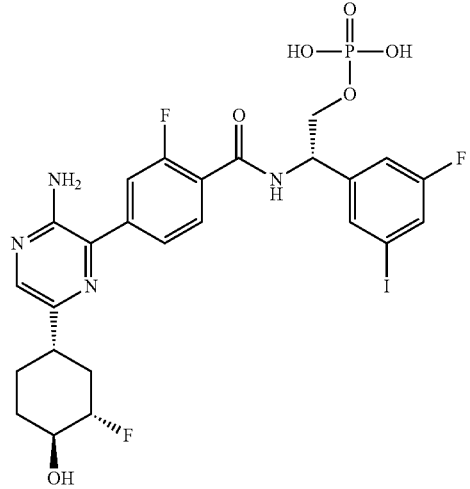

Step 1. (S)-(9H-fluoren-9-yl)methyl (1-(3-fluoro-5-iodophenyl)-2-hydroxyethyl)carbamate To (S)-2-amino-2-(3-fluoro-5-iodophenyl)ethanol (4500 mg, 14.17 mmol) was added THF (Volume: 40 mL, Ratio: 2.67) and water (Volume: 15 mL, Ratio: 1.000), followed by NaHCO$_3$ (4762 mg, 56.7 mmol). The mixture was stirred for 2 minutes then cooled to 0° C. in an ice bath. To the reaction was added (9H-fluoren-9-yl)methyl carbonochloridate (5499 mg, 21.26 mmol) and the reaction was stirred at 0° C. for 30 minutes, allowed to warm to room temperature and stirred for a further 60 minutes, before conducting LCMS. Ethyl acetate was added to the crude reaction mixture. The mixture was washed with water (2×), saturated salt solution, dried sodium sulfate, filtered and concentrated to residue. The crude product was purified by silica gel chromatography using a 300 g column (solid load) eluting from 0-60% ethyl acetate in heptane. The desired fractions were concentrated to constant mass to give as white solid 5375 mg of the desired product as free base used as is, (73% yield). LCMS (m/z): 504.1 (MH$^+$), 1.05 min. 1H NMR (<cd3od>) d: 7.78 (d, J=7.4 Hz, 2H), 7.64 (d, J=7.2 Hz, 2H), 7.53 (s, 1H), 7.33-7.43 (m, 3H), 7.25-7.33 (m, 2H), 7.07 (d, J=9.2 Hz, 1H), 4.64 (t, J=5.9 Hz, 1H), 4.31-4.46 (m, 2H), 4.21 (t, J=6.3 Hz, 1H), 3.66 (d, J=3.1 Hz, 2H).

Step 2. (S)-(9H-fluoren-9-yl)methyl (2-((di-tert-butoxyphosphoryl)oxy)-1-(3-fluoro-5-iodophenyl)ethyl)carbamate To (S)-(9H-fluoren-9-yl)methyl (1-(3-fluoro-5-iodophenyl)-2-hydroxyethyl)carbamate (5260 mg, 10.45 mmol) was added imidazole (818 mg, 12.02 mmol), imidazole HCl (1857 mg, 17.77 mmol), and DMF (Volume: 50 mL). The reaction was stirred to dissolve under argon for 2-3 minutes. Then di-tert-butyl diisopropylphosphoramidite (4928 mg, 17.77 mmol) was added drop wise over 2-3 minutes and stirred at room temperature for 2 hours. The reaction was followed by neutral LCMS and by TLC eluting with 1:1 ethyl acetate/heptane. The crude reaction was placed in a water bath, hydrogen peroxide 30% (5.34 mL, 52.3 mmol) was added slowly, and the mixture was stirred at room temperature for 30 minutes, followed by LCMS. The crude reaction was placed in an ice bath and excess saturated sodium thiosulphate was added (carefully) drop wise over 5-10 minutes. To the crude reaction mixture was added 800 ml of ethyl acetate washed with water (3×), saturated salt solution, dried sodium sulfate, filtered and concentrated to residue. The crude was purified by silica gel chromatography using 300 g column eluting from 0-55% ethyl acetate in heptane. The desired peak was concentrated to constant mass to give 6560 mg of the desired product as free base used as is, (86% yield). LCMS (m/z): 696.3 (MH$^+$) weak, 1.25 min. Note: −112 fragment at 584.2 is major ion in LCMS as expected from loss of two t-butyl protecting groups. 1H NMR (<cd3od>) d: 7.79 (d, J=7.3 Hz, 2H), 7.64 (d, J=7.3 Hz, 2H), 7.58 (s, 1H), 7.45 (d, J=7.6 Hz, 1H), 7.34-7.42 (m, 2H), 7.22-7.32 (m, 2H), 7.12 (d, J=9.1 Hz, 1H), 4.90 (t, J=6.0 Hz, 1H), 4.41-4.48 (m, 1H), 4.31-4.40 (m, 1H), 4.21 (t, J=6.6 Hz, 1H), 4.08 (t, J=6.3 Hz, 2H), 1.42 (s, 9H), 1.40 (s, 9H).

Step 3. (S)-2-amino-2-(3-fluoro-5-iodophenyl)ethyl di-tert-butyl phosphate

To (S)-(9H-fluoren-9-yl)methyl (2-((di-tert-butoxyphosphoryl)oxy)-1-(3-fluoro-5-iodophenyl)ethyl)carbamate (6450 mg, 9.27 mmol) was added DMF (Volume: 90 mL) followed by piperidine (25 mL, 253 mmol) and stirred at room temperature for 30 minutes, followed by LCMS. To the crude reaction mixture was added 750 ml of ethyl acetate, washed with saturated sodium bicarbonate (2×), water (5×), saturated salt solution, dried sodium sulfate, and filtered. The solvent was concentrated off to constant mass under high vacuum to give the desire crude product which includes FMOC piperidine impurity, used as is. LCMS (m/z): 474.2 (MH$^+$), 0.80 min.

Step 4. (S)-2-(4-(3-amino-6-((1S,3S,4S)-3-fluoro-4-hydroxycyclohexyl)pyrazin-2-yl)-2-fluorobenzamido)-2-(3-fluoro-5-iodophenyl)ethyl di-tert-butyl phosphate To a solution of 4-(3-amino-6-((1S,3S,4S)-3-fluoro-4-hydroxycyclohexyl)pyrazin-2-yl)-2-fluorobenzoic acid (3927 mg, 9.3 mmol) in NMP (Volume: 60 mL) was added (S)-2-amino-2-(3-fluoro-5-iodophenyl)ethyl di-tert-butyl phosphate (4740 mg, 9.30 mmol), DIEA (9.75 mL, 55.8 mmol), and then HATU (5304 mg, 13.95 mmol). The reaction mixture was stirred at room temperature for 2 hours followed by LCMS. To the crude reaction was added 850 ml of ethyl acetate washed with saturated bicarbonate (2×), water (3×), saturated salt solution, dried sodium sulfate, filtered and dried to residue. The crude product was purified by silica gel chromatograph 330 g column eluting with 0-70% (EtOAc with 10% MeOH)/heptane. The desired peak was concentrated to constant mass to give 5.75 grams of crude product. The material was re-purified by silica gel chromatograph 330 g column eluting with 0-60% (EtOAc with 10% MeOH)/heptane to give 5.03 grams of crude product. The material was further purified by adding 1200 ml of ethyl acetate to dissolve and 200 ml of heptane, washed with 200 ml of 0.5 N HCl (5×), water, saturated sodium bicarbonate, water (3×), saturated salt solution, dried sodium sulfate, filtered and concentrated to constant mass to give 4.70 grams of desired product, yield used as is. (61% yield over two steps). LCMS (m/z): 805.4 (MH$^+$), 0.99 min. 1H NMR (<cd3od>) d: 7.90 (s, 1H), 7.77-7.86 (m, 1H), 7.68-7.73 (m, 2H), 7.63 (dd, J=11.8, 1.2 Hz, 1H), 7.42-7.52 (m, 1H), 7.26 (d, J=9.5 Hz, 1H), 5.43 (t, J=5.7 Hz, 1H), 4.30-4.49 (m, 1H), 4.28 (t, J=6.3 Hz, 2H), 3.58-3.72 (m, 1H), 2.83 (t, J=11.6 Hz, 1H), 2.27 (dt, J=6.2, 3.1 Hz, 1H), 2.02-2.13 (m, 1H), 1.77-1.94 (m, 2H), 1.58-1.74 (m, 1H), 1.48-1.55 (m, 1H), 1.45 (d, J=5.8 Hz, 18H).

Step 5. (S)-2-(4-(3-amino-6-((1S,3S,4S)-3-fluoro-4-hydroxycyclohexyl)pyrazin-2-yl)-2-fluorobenzamido)-2-(3-fluoro-5-iodophenyl)ethyl dihydrogen phosphate (S)-2-(4-(3-amino-6-((1S,3S,4S)-3-fluoro-4-hydroxycyclohexyl)pyrazin-2-yl)-2-fluorobenzamido)-2-(3-fluoro-5-iodophenyl)ethyl di-tert-butyl phosphate (4600 mg, 5.72 mmol) was fully dissolved in MeOH (Volume: 70 mL). Then HCl 4M in Dioxane (14.29 mL, 57.2 mmol) was added and stirred at room temperature for 3 hours, followed by LCMS. The solvent was concentrated mostly off. Then MeOH (Volume: 70 mL) was added and the solvent was concentrated off to residue, additional MeOH (Volume: 70 mL) was added and the residue concentrated to constant mass. The product was dissolved in 90 ml of 1:1 ACN/water and lyophilized to give 3.99 grams of the desired product as HCl salt. (94% yield). LCMS (m/z): 692.9 (MH$^+$), 0.63 min. 1H NMR (<cd3od>) d: 7.84-7.93 (m, 1H), 7.75 (s, 1H), 7.60-7.71 (m, 3H), 7.45-7.51 (m, 1H), 7.26 (dt, J=9.7, 1.6 Hz, 1H), 5.40 (t, J=5.9 Hz, 1H), 4.31-4.50 (m, 1H), 4.22-4.30 (m, 2H), 3.64 (tdd, J=11.7, 8.6, 5.1 Hz, 1H), 2.82-2.98 (m, 1H), 2.32 (ddt, J=11.7, 5.8, 2.8 Hz, 1H), 2.01-2.15 (m, 1H), 1.89-1.97 (m, 1H), 1.75-1.89 (m, 1H), 1.58-1.72 (m, 1H), 1.42-1.55 (m, 1H). 31P NMR (<cd3od>) d: 0.00 (s, 1P).

Conversion of HCl salt to di-sodium salt: To the above desired product as HCl salt (24 mg, 0.035 mmol) was added water (Volume: 17 mL) then titrated with 2M sodium carbonate to pH10-11 and then extracted with 15 ml of DCM (4×). The basic water was directly loaded on to a 12 gram Grace Reveleris C18 reverse phase column, eluted with 0-20% ACN/water over 18 minutes at flow rate of 15 ml/minute, with no buffers. The desired fractions were lyophilized to give 18 mg of the desire product (S)-2-(4-(3-amino-6-((1S,3S,4S)-3-fluoro-4-hydroxycyclohexyl)pyrazin-2-yl)-2-fluorobenzamido)-2-(3-fluoro-5-iodophenyl)ethyl dihydrogen phosphate as the di-sodium salt, determined by counterion analysis. (70% yield). LCMS (m/z): 692.9 (MH+), 0.64 min. 1H NMR (<cd3od>) d: 7.82-7.92 (m, 2H), 7.64-7.72 (m, 2H), 7.58 (dd, J=11.4, 1.2 Hz, 1H), 7.39 (d, J=7.6 Hz, 1H), 7.28 (d, J=9.5 Hz, 1H), 5.17 (dd, J=6.9, 4.1 Hz, 1H), 4.25-4.49 (m, 1H), 4.02-4.20 (m, 2H), 3.57-3.73 (m, 1H), 2.83 (t, J=11.6 Hz, 1H), 2.27 (dd, J=6.1, 3.6 Hz, 1H), 1.98-2.14 (m, 1H), 1.78-1.94 (m, 2H), 1.59-1.73 (m, 1H), 1.40-1.55 (m, 1H).

Example 190

Synthesis of 4-(3-amino-6-((1R,3R,4R)-3-fluoro-4-hydroxycyclohexyl)pyrazin-2-yl)-2-fluoro-N-((S)-1-(3-fluoro-5-iodophenyl)-2-hydroxyethyl)benzamide

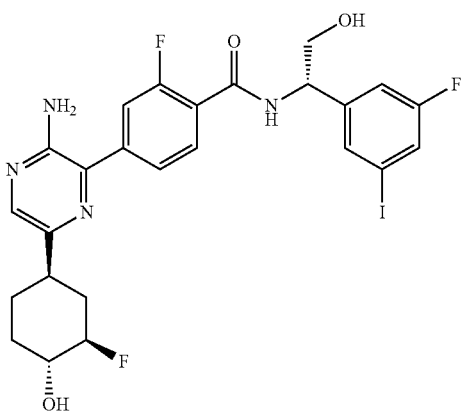 [SMILES: Nc1ncc([C@@H]2CC[C@@H](O)[C@H](F)C2)nc1-c1ccc(C(=O)N[C@H](CO)c2cc(F)cc(I)c2)c(F)c1]

To a solution of 4-(3-amino-6-((1R,3R,4R)-3-fluoro-4-hydroxycyclohexyl)pyrazin-2-yl)-2-fluorobenzoic acid (18 mg, 0.052 mmol) in DMF (0.52 mL) was added (S)-2-amino-2-(3-fluoro-5-iodophenyl)ethanol hydrochloride (19.6 mg, 0.062 mmol), HOAt (10.52 mg, 0.077 mmol), EDC (19.76 mg, 0.103 mmol), and DIEA (27 µl, 0.155 mmol). The reaction mixture was stirred for 15 h. After water was added, the reaction mixture was extracted with EtOAc and the organic layer was washed with water twice. The organic layer was separated and dried over Na₂SO₄, filtered off and concentrated in vacuo. The crude product was purified by flash chromtography eluting with 0-100% EtOAc/heptane to provide 15.8 mg of 4-(3-amino-6-((1R,3R,4R)-3-fluoro-4-hydroxycyclohexyl)pyrazin-2-yl)-2-fluoro-N-((S)-1-(3-fluoro-5-iodophenyl)-2-hydroxyethyl)benzamide as a free base (50%). LCMS (m/z): 613.1 (MH⁺), 0.74 min; 1H NMR (400 MHz, CD₃OD) δ ppm 7.89-7.69 (m, 2H), 7.66-7.47 (m, 3H), 7.39-7.26 (m, 1H), 7.12 (d, J=9.4 Hz, 1H), 5.05 (t, J=5.9 Hz, 1H), 4.43-4.14 (m, 1H), 3.84-3.66 (m, 2H), 3.64-3.45 (m, 1H), 2.74 (t, J=11.7 Hz, 1H), 2.17 (td, J=3.1, 6.0 Hz, 1H), 2.05-1.87 (m, 1H), 1.84-1.66 (m, 2H), 1.65-1.47 (m, 1H), 1.47-1.27 (m, 1H).

Synthesis of (S)-2-(4-(3-amino-6-((1R,3R,4R)-3-fluoro-4-hydroxycyclohexyl)pyrazin-2-yl)-2-fluorobenzamido)-2-(3-fluoro-5-iodophenyl)ethyl dihydrogen phosphate

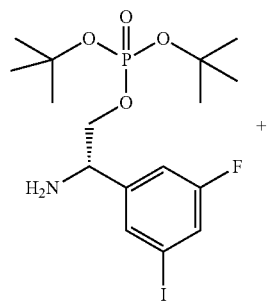

+

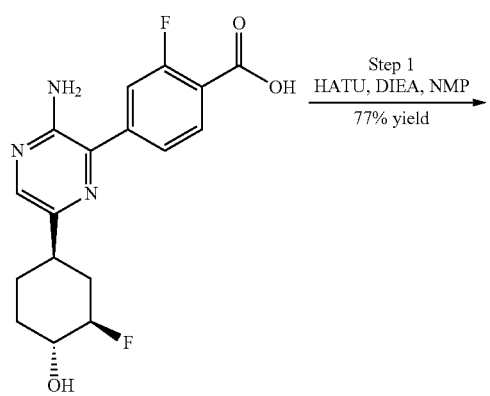

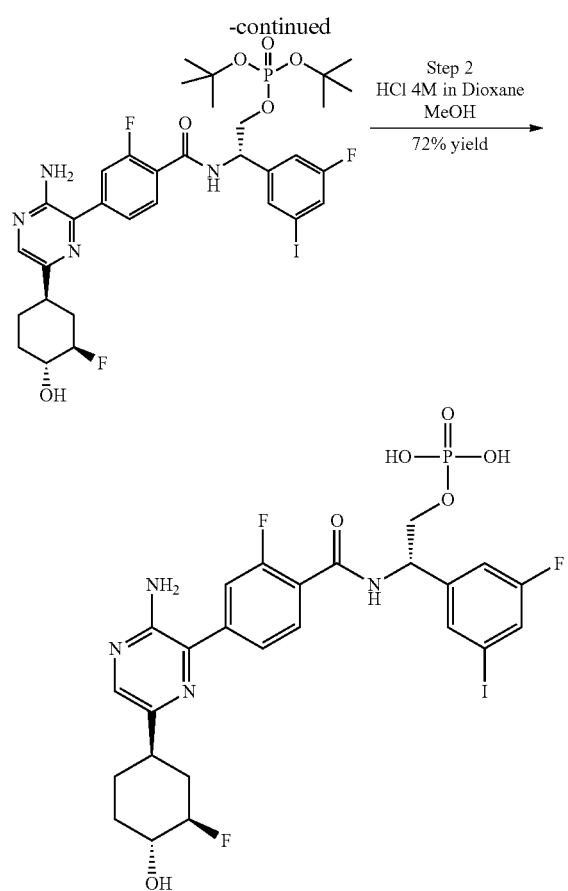

Step 1. (S)-2-(4-(3-amino-6-((1R,3R,4R)-3-fluoro-4-hydroxycyclohexyl)pyrazin-2-yl)-2-fluorobenzamido)-2-(3-fluoro-5-iodophenyl)ethyl di-tert-butyl phosphate To a solution of 4-(3-amino-6-((1R,3R,4R)-3-fluoro-4-hydroxycyclohexyl)pyrazin-2-yl)-2-fluorobenzoic acid (215 mg, 0.509 mmol) in NMP (Volume: 4 mL) was added (S)-2-amino-2-(3-fluoro-5-iodophenyl)ethyl di-tert-butyl phosphate (260 mg, 0.509 mmol), DIEA (0.534 mL, 3.06 mmol) and then HATU (290 mg, 0.764 mmol). The reaction mixture was stirred at room temperature for 1 hour, followed by LCMS. To the crude reaction was added 150 ml of ethyl acetate washed with saturated bicarbonate (2×), water (3×), saturated salt solution, dried sodium sulfate, filtered and dried to residue. The crude product was purified by silica gel chromatograph 24 g column (DCM loading) eluting with 0-80% (EtOAc with 10% MeOH)/heptane. The desired fractions were concentrated to constant mass to give 315 mg of desired product as free base. (77% yield). LCMS (m/z): 805.3 (MH⁺), 1.01 min.

Step 2. (S)-2-(4-(3-amino-6-((1R,3R,4R)-3-fluoro-4-hydroxycyclohexyl)pyrazin-2-yl)-2-fluorobenzamido)-2-(3-fluoro-5-iodophenyl)ethyl dihydrogen phosphate:

To a solution of (S)-2-(4-(3-amino-6-((1R,3R,4R)-3-fluoro-4-hydroxycyclohexyl)pyrazin-2-yl)-2-fluorobenzamido)-2-(3-fluoro-5-iodophenyl)ethyl di-tert-butyl phosphate (315 mg, 0.392 mmol) was added HCl 4M in dioxane (5 mL, 20.00 mmol) and methanol (Volume: 0.5 mL). The reaction mixture was stirred at room temperature for 1 hour followed by LCMS. The solvent was concentrated off. The crude material was basified and dissolved with 3M NaOH solution with minimal MeOH added. The material was purified by 12 gram Grace Reveleris C18 reverse phase column eluted with 0-15% ACN/water over 18 minutes at a flow rate of 15 ml/minute, without buffers. The desired fractions were collected, acidified with 1 M HCl to pH of 1 and extracted with ethyl acetate (5×). The combined organic layer (800 ml) was washed with minimal water (3×25 ml) to remove salts. The solvent was concentrated off, dissolved in 1:1 ACN/water and lyophilized to give 207 mg of the desired product as HCL salt. (72% yield). LCMS (m/z): 693.2 (MH+), 0.64 min. 1H NMR (<cd3od>) d: 7.87 (s, 1H), 7.81-7.86 (m, 1H), 7.65-7.72 (m, 2H), 7.61 (dd, J=11.7, 1.6 Hz, 1H), 7.46 (ddd, J=8.0, 2.3, 1.4 Hz, 1H), 7.26 (dt, J=9.5, 1.9 Hz, 1H), 5.38 (t, J=5.7 Hz, 1H), 4.29-4.49 (m, 1H), 4.18-4.29 (m, 2H), 3.64 (tdd, J=11.6, 8.6, 4.9 Hz, 1H), 2.76-2.92 (m, 1H), 2.27 (ddd, J=8.8, 5.9, 2.5 Hz, 1H), 2.01-2.13 (m, 1H), 1.76-1.94 (m, 2H), 1.58-1.71 (m, 1H), 1.39-1.55 (m, 1H). 31P NMR (<cd3od>) d: 0.16 (br. s., 1P).

Examples 191 and 192

Synthesis of 4-(3-amino-6-((1r,4S)-4-aminocyclohexyl)pyrazin-2-yl)-N-((S)-1-(3-chlorophenyl)-2-hydroxyethyl)-2-fluorobenzamide and 4-(3-amino-6-((1s,4R)-4-aminocyclohexyl)pyrazin-2-yl)-N-((S)-1-(3-chlorophenyl)-2-hydroxyethyl)-2-fluorobenzamide

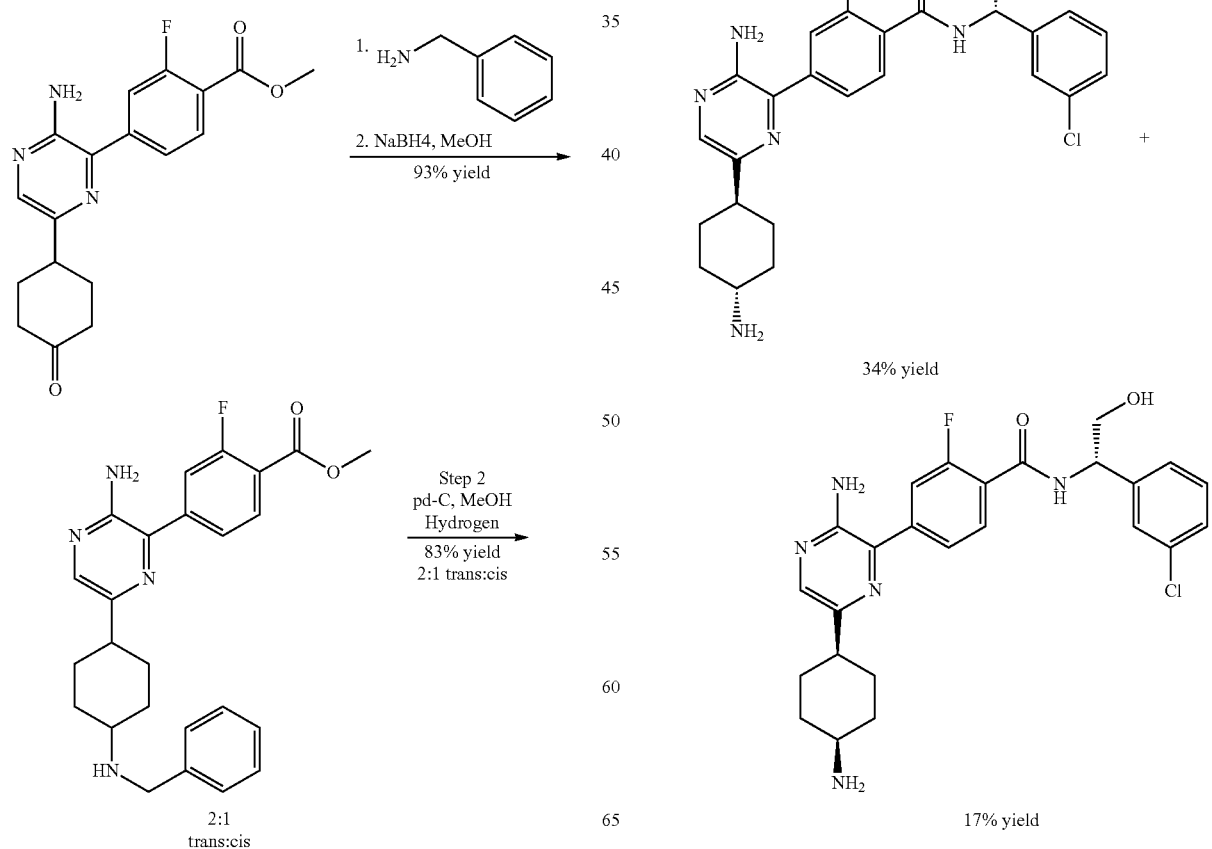

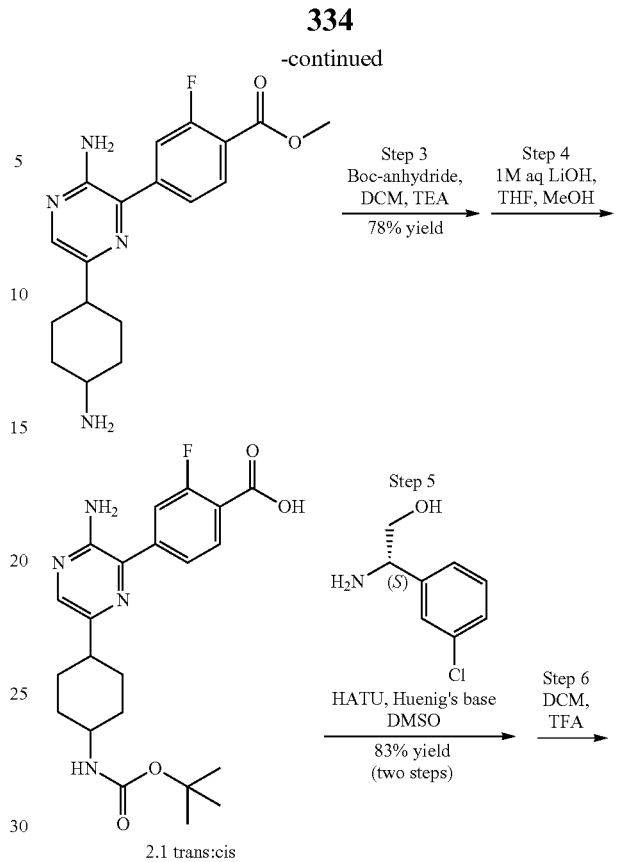

Step 1. methyl 4-(3-amino-6-(4-(benzylamino)cyclohexyl)pyrazin-2-yl)-2-fluorobenzoate To methyl 4-(3-amino-6-(4-oxocyclohexyl)pyrazin-2-yl)-2-fluorobenzoate (300 mg, 0.874 mmol) was added MeOH (4 mL), phenylmethanamine (112 mg, 1.048 mmol) and last dry 4 Å molecular sieves. The reaction was stirred at room temperature for 16 h. Then NaBH$_4$ (165 mg, 4.37 mmol) was added and stirred at room temperature for 2 h followed by LCMS. To the reaction was added 150 mL of ethyl acetate, washed with saturated sodium bicarbonate, water (2×), saturated salt solution, dried over sodium sulfate, filtered and concentrated to residue to give 352 mg of the desired product in 2:1 trans to cis ratio, used as is (93%). LCMS (m/z): 435.3 (MH$^+$), 0.68 min and 0.72 min.

Step 2. methyl 4-(3-amino-6-(4-aminocyclohexyl)pyrazin-2-yl)-2-fluorobenzoate To methyl 4-(3-amino-6-(4-(benzylamino)cyclohexyl)pyrazin-2-yl)-2-fluorobenzoate (350 mg, 0.806 mmol) in a round bottom flask that was flushed with argon was added PdC 10% degaussa, wet (171 mg, 0.161 mmol). Then under argon with syringe, was added MeOH (5 mL) and last a hydrogen balloon. The flask was evacuated and refilled with hydrogen six times. The reaction was stirred at room temperature for 14 h. The reaction was purged with argon, then PdC 10% degaussa, wet (171 mg, 0.161 mmol) was carefully added. Then a hydrogen balloon was added, and the flask was evacuated and refilled with hydrogen six times. The reaction was stirred for additional 10 h to give a total of 24 h, followed by LCMS. The reaction was flushed with argon and 35 mL of DCM was added. The crude mixture was filtered through a Celite plug, and concentrated to constant mass to give 230 mg of desired product (which is 2:1 trans to cis ratio), used as is (83%). LCMS (m/z): 345.2 (MH$^+$), 0.48 min and 0.51 min.

Step 3. methyl 4-(3-amino-6-(4-((tert-butoxycarbonyl)amino)cyclohexyl)pyrazin-2-yl)-2-fluorobenzoate To methyl 4-(3-amino-6-(4-aminocyclohexyl)pyrazin-2-yl)-2-fluorobenzoate (230 mg, 0.668 mmol) was added DCM (5 mL), TEA (0.233 mL, 1.670 mmol), and Boc-anhydride (0.186 mL, 0.801 mmol). The reaction was stirred at room temperature for 1 h, followed by LCMS. To the reaction was added 150 mL of ethyl acetate, washed with saturated sodium bicarbonate, water twice, saturated salt solution, dried over sodium sulfate, filtered and concentrated to constant mass to give 233 mg of the desired product (which is 2:1 trans to cis ratio), used as is (78%). LCMS (m/z): 445.2 (MH$^+$), 0.92 min for both.

Step 4. 4-(3-amino-6-(4-((tert-butoxycarbonyl)amino)cyclohexyl)pyrazin-2-yl)-2-fluorobenzoic acid To methyl 4-(3-amino-6-(4-((tert-butoxycarbonyl)amino)cyclohexyl)pyrazin-2-yl)-2-fluorobenzoate (230 mg, 0.517 mmol) was added MeOH (2 mL), THF (2 mL) and then lithium hydroxide 1M aqueous solution (1.552 mL, 1.552 mmol). The reaction was stirred at room temperature for 1 h. The solvent was concentrated to residue, then THF (20 mL) was added and concentrated to residue. Then THF (20 mL) was added again and re-concentrated to residue to constant mass to give the desired product (which is 2:1 trans to cis ratio), used as is. Assume quantitative yield (0.517 mmol). LCMS (m/z): 431.2 (MH$^+$), 0.78 min for both.

Step 5. (S)-tert-butyl (4-(5-amino-6-(4-((1-(3-chlorophenyl)-2-hydroxyethyl)carbamoyl)-3-fluorophenyl)pyrazin-2-yl)cyclohexyl)carbamate To 4-(3-amino-6-(4-((tert-butoxycarbonyl)amino)cyclohexyl)pyrazin-2-yl)-2-fluorobenzoic acid (222 mg, 0.516 mmol) was added DMSO (4 mL), Hünig's base (0.450 mL, 2.58 mmol), (S)-2-amino-2-(3-chlorophenyl)ethanol (133 mg, 0.774 mmol) and then HATU (392 mg, 1.031 mmol). The reaction was stirred for 1 h at room temperature. To the reaction was added 50 mL of ethyl acetate, washed with water twice, saturated salt solution, dried over sodium sulfate, filtered and concentrated to residue. The crude was purified by flash chromatography using 12 gram column (solid load) eluting with 10-95% ethyl acetate in heptane. The desired fractions were concentrated to constant mass to give 252 mg of product (which is 2:1 trans to cis ratio), used as is (83% over two steps). LCMS (m/z): 584.3 (MH$^+$), 0.91 min for both.

Step 6. 4-(3-amino-6-((1r,4S)-4-aminocyclohexyl)pyrazin-2-yl)-N-((S)-1-(3-chlorophenyl)-2-hydroxyethyl)-2-fluorobenzamide and 4-(3-amino-6-((1s,4R)-4-aminocyclohexyl)pyrazin-2-yl)-N-((S)-1-(3-chlorophenyl)-2-hydroxyethyl)-2-fluorobenzamide To (S)-tert-butyl (4-(5-amino-6-(4-((1-(3-chlorophenyl)-2-hydroxyethyl)carbamoyl)-3-fluorophenyl)pyrazin-2-yl)cyclohexyl)carbamate (252 mg, 0.431 mmol) was added DCM (8 mL) and then TFA (2 mL, 26.0 mmol). The reaction was stirred for 1 h at room temperature. The solvent was concentrated, redissolved in DMSO, filtered, and purified by prep HPLC with both isomer collected. With major isomer, trans eluted out first and mior, cis isomers eluted out second. After lypholization, 87 mg of trans product 4-(3-amino-6-((1r,4S)-4-aminocyclohexyl)pyrazin-2-yl)-N-((S)-1-(3-chlorophenyl)-2-hydroxyethyl)-2-fluorobenzamide was obtained as TFA salt in 34% yield. LCMS (m/z): 484.2 (MH$^+$), 0.58 min; $^1$H NMR (CD3OD) δ ppm 7.79 (s, 1H), 7.76 (t, J=7.8 Hz, 1H), 7.58 (dd, J=7.8, 1.6 Hz, 1H), 7.52 (dd, J=11.9, 1.4 Hz, 1H), 7.36 (s, 1H), 7.30-7.23 (m, 2H), 7.22-7.16 (m, 1H), 5.10 (t, J=5.9 Hz, 1H), 3.83-3.70 (m, 2H), 3.08 (tt, J=11.7, 3.9 Hz, 1H), 2.69-2.49 (m, 1H), 2.06 (d, J=10.6 Hz, 2H), 1.97 (d, J=12.9 Hz, 2H), 1.75-1.57 (m, 2H), 1.55-1.31 (m, 2H).

In addition, after lypholization 43 mg of the cis product 4-(3-amino-6-((1s,4R)-4-aminocyclohexyl)pyrazin-2-yl)-N-((S)-1-(3-chlorophenyl)-2-hydroxyethyl)-2-fluorobenzamide was obtained as TFA salt, in 17% yield. LCMS (m/z): 484.2 (MH$^+$), 0.61 min; $^1$H NMR (CD$_3$OD) δ ppm 7.87 (s, 1H), 7.81-7.72 (m, 1H), 7.60 (dd, J=8.0, 1.4 Hz, 1H), 7.55 (d, J=11.7 Hz, 1H), 7.36 (s, 1H), 7.26 (d, J=5.9 Hz, 2H), 7.22-7.16 (m, 1H), 5.10 (t, J=5.7 Hz, 1H), 3.87-3.67 (m, 2H), 2.91-2.80 (m, 1H), 1.98 (q, J=8.9 Hz, 2H), 1.90-1.71 (m, 6H).

Example 193

Synthesis of 4-(6-((1r,4S)-4-acetamidocyclohexyl)-3-aminopyrazin-2-yl)-N-((S)-1-(3-chlorophenyl)-2-hydroxyethyl)-2-fluorobenzamide

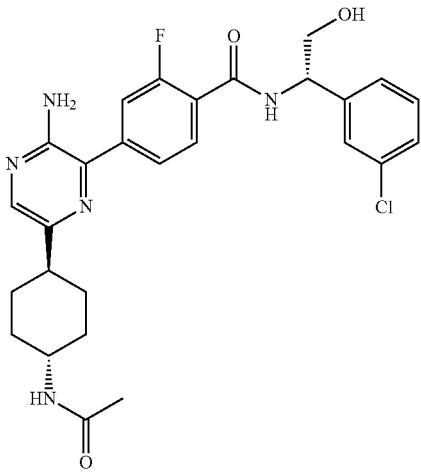 [SMILES: CC(=O)N[C@H]1CC[C@H](c2cnc(N)c(-c3ccc(C(=O)N[C@H](CO)c4cccc(Cl)c4)c(F)c3)n2)CC1]

To 4-(3-amino-6-((1r,4S)-4-aminocyclohexyl)pyrazin-2-yl)-N-((S)-1-(3-chlorophenyl)-2-hydroxyethyl)-2-fluorobenzamide (15 mg, 0.025 mmol) were added DCM (0.25 mL), THF (0.75 mL) and TEA (10.49 µl, 0.075 mmol) at 0° C. Then acetic anhydride (2.367 µl, 0.025 mmol) was added. The reaction was stirred for 30 min at 0° C. The reaction was concentrated, dissolved in 1 mL of DMSO, filtered, purified by prep HPLC, and lyophilized to give 5.4 mg of the desired product 4-(6-((1r,4S)-4-acetamidocyclohexyl)-3-aminopyrazin-2-yl)-N-((S)-1-(3-chlorophenyl)-2-hydroxyethyl)-2-fluorobenzamide as a TFA salt (33% yield). LCMS (m/z): 526.3 (MH$^+$), 0.67 min; $^1$H NMR (CD$_3$OD) δ ppm 7.71-7.82 (m, 2H), 7.58 (dd, J=8.0, 1.4 Hz, 1H), 7.53 (d, J=11.7 Hz, 1H), 7.37 (s, 1H), 7.22-7.29 (m, 2H), 7.15-7.22 (m, 1H), 5.10 (t, J=5.9 Hz, 1H), 3.71-3.84 (m, 2H), 3.52-3.66 (m, 1H), 2.51-2.65 (m, 1H), 1.86-2.02 (m, 4H), 1.83 (s, 3H), 1.53-1.69 (m, 2H), 1.22-1.39 (m, 2H).

Example 194

Synthesis of 4-(3-amino-6-((1r,4S)-4-(methylsulfonamido)cyclohexyl)pyrazin-2-yl)-N-((S)-1-(3-chlorophenyl)-2-hydroxyethyl)-2-fluorobenzamide

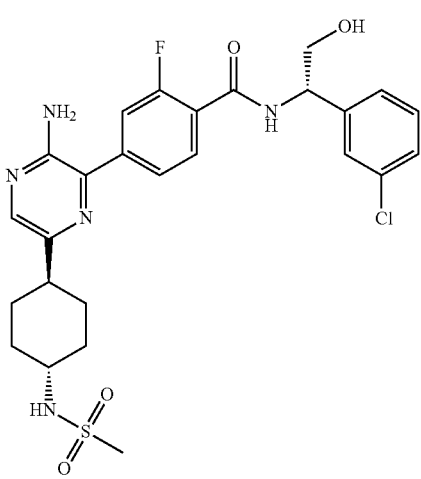 [SMILES: CS(=O)(=O)N[C@H]1CC[C@H](c2cnc(N)c(-c3ccc(C(=O)N[C@H](CO)c4cccc(Cl)c4)c(F)c3)n2)CC1]

To 4-(3-amino-6-((1r,4S)-4-aminocyclohexyl)pyrazin-2-yl)-N-((S)-1-(3-chlorophenyl)-2-hydroxyethyl)-2-fluorobenzamide (15 mg, 0.025 mmol) was added DCM (0.25 mL, Ratio: 1.000), THF (0.250 mL), TEA (10.49 µl, 0.075 mmol) stirred to dissolve and cooled to 0° C., and then methanesulfonyl chloride (1.955 µl, 0.025 mmol) was added. The reaction was stirred for 30 min at 0° C., followed by LCMS. The reaction was concentrated dissolved in 1 mL of DMSO, filtered, purified by prep HPLC, and lyophilized to give 1.6 mg of the desired product 4-(3-amino-6-((1r,4S)-4-(methylsulfonamido)cyclohexyl)pyrazin-2-yl)-N-((S)-1-(3-chlorophenyl)-2-hydroxyethyl)-2-fluorobenzamide as TFA salt (9% yield). LCMS (m/z): 562.2 (MH$^+$), 0.69 min. $^1$H NMR (CD$_3$OD) δ ppm 7.70-7.82 (m, 2H), 7.59 (d, J=7.8 Hz, 1H), 7.53 (d, J=11.7 Hz, 1H), 7.37 (s, 1H), 7.22-7.30 (m, 2H), 7.13-7.21 (m, 1H), 5.09 (t, J=5.9 Hz, 1H), 3.68-3.89 (m, 2H), 2.87 (s, 3H), 2.48-2.60 (m, 1H), 2.05 (d, J=14.9 Hz, 2H), 1.84-1.95 (m, 2H), 1.54-1.74 (m, 2H), 1.38 (q, J=12.9 Hz, 2H).

Example 195

Synthesis of methyl ((1S,4r)-4-(5-amino-6-(4-(((S)-1-(3-chlorophenyl)-2-hydroxyethyl)carbamoyl)-3-fluorophenyl)pyrazin-2-yl)cyclohexyl)carbamate

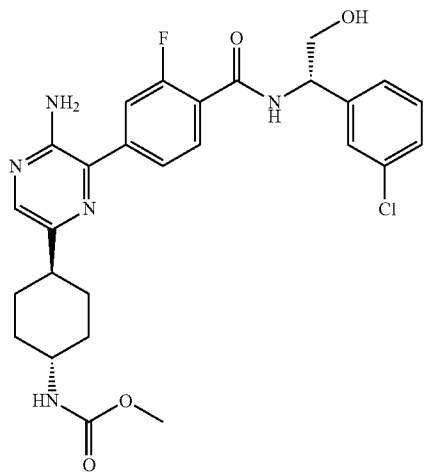

To 4-(3-amino-6-((1r,4S)-4-aminocyclohexyl)pyrazin-2-yl)-N-((S)-1-(3-chlorophenyl)-2-hydroxyethyl)-2-fluorobenzamide (15 mg, 0.025 mmol) was added DCM (0.25 mL), THF (0.250 mL), TEA (10.49 µl, 0.075 mmol) stirred to dissolve and cooled to 0° C., and then methyl chloroformate (1.943 µl, 0.025 mmol) was added. The reaction was stirred for 30 min at 0° C., followed by LCMS. The reaction was concentrated dissolved in 1 mL of DMSO, filtered, purified by prep HPLC, and lyophilized to give 4.5 mg of the desired product methyl ((1S,4r)-4-(5-amino-6-(4-(((S)-1-(3-chlorophenyl)-2-hydroxyethyl)carbamoyl)-3-fluorophenyl)pyrazin-2-yl)cyclohexyl)carbamate as TFA salt (27% yield). LCMS (m/z): 542.3 (MH$^+$), 0.75 min. $^1$H NMR (CD$_3$OD) δ: 7.73-7.81 (m, 2H), 7.58 (dd, J=8.0, 1.4 Hz, 1H), 7.48-7.55 (m, 1H), 7.37 (s, 1H), 7.23-7.30 (m, 2H), 7.15-7.22 (m, 1H), 5.10 (t, J=5.9 Hz, 1H), 3.69-3.84 (m, 2H), 3.53 (s, 3H), 3.31-3.36 (m, 1H), 2.48-2.62 (m, 1H), 1.84-2.00 (m, 4H), 1.51-1.68 (m, 2H), 1.21-1.44 (m, 2H)

Example 196

Synthesis of 4-(3-amino-6-((1r,4S)-4-(2-hydroxyacetamido)cyclohexyl)pyrazin-2-yl)-N-((S)-1-(3-chlorophenyl)-2-hydroxyethyl)-2-fluorobenzamide

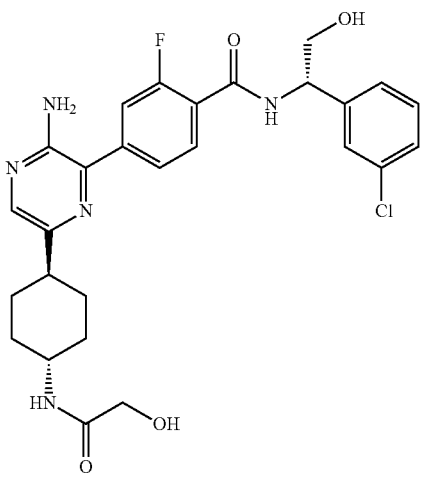 [SMILES: Nc1ncc([C@H]2CC[C@H](NC(=O)CO)CC2)nc1-c1ccc(C(=O)N[C@H](CO)c2cccc(Cl)c2)c(F)c1]

To 4-(3-amino-6-((1r,4S)-4-aminocyclohexyl)pyrazin-2-yl)-N-((S)-1-(3-chlorophenyl)-2-hydroxyethyl)-2-fluorobenzamide (11 mg, 0.018 mmol) were added NMP (0.4 mL), 2-hydroxyacetic acid (2.80 mg, 0.037 mmol), Hünig's base (0.013 mL, 0.074 mmol) and then HATU (17.49 mg, 0.046 mmol). The reaction was stirred for 30 min at room temperature. The reaction was concentrated, dissolved in 0.75 mL of DMSO, filtered, purified by prep HPLC, and lyophilized to give 3.6 mg of the desired product 4-(3-amino-6-((1r,4S)-4-(2-hydroxyacetamido)cyclohexyl)pyrazin-2-yl)-N-((S)-1-(3-chlorophenyl)-2-hydroxyethyl)-2-fluorobenzamide as TFA salt (29%). LCMS (m/z): 542.2 (MH$^+$), 0.63 min. $^1$H NMR (CD$_3$OD) δ ppm 7.83-7.72 (m, 2H), 7.59 (dd, J=8.0, 1.4 Hz, 1H), 7.53 (d, J=11.7 Hz, 1H), 7.37 (s, 1H), 7.32-7.23 (m, 2H), 7.22-7.16 (m, 1H), 5.10 (t, J=5.9 Hz, 1H), 3.86 (s, 2H), 3.82-3.63 (m, 3H), 2.65-2.50 (m, 1H), 2.02-1.86 (m, 4H), 1.72-1.56 (m, 2H), 1.48-1.33 (m, 2H).

Example 197

Synthesis of (S)-N-(2-amino-1-(3-chlorophenyl)ethyl)-4-(3-amino-6-(4,4-difluorocyclohexyl)pyrazin-2-yl)-2-fluorobenzamide Scheme 91

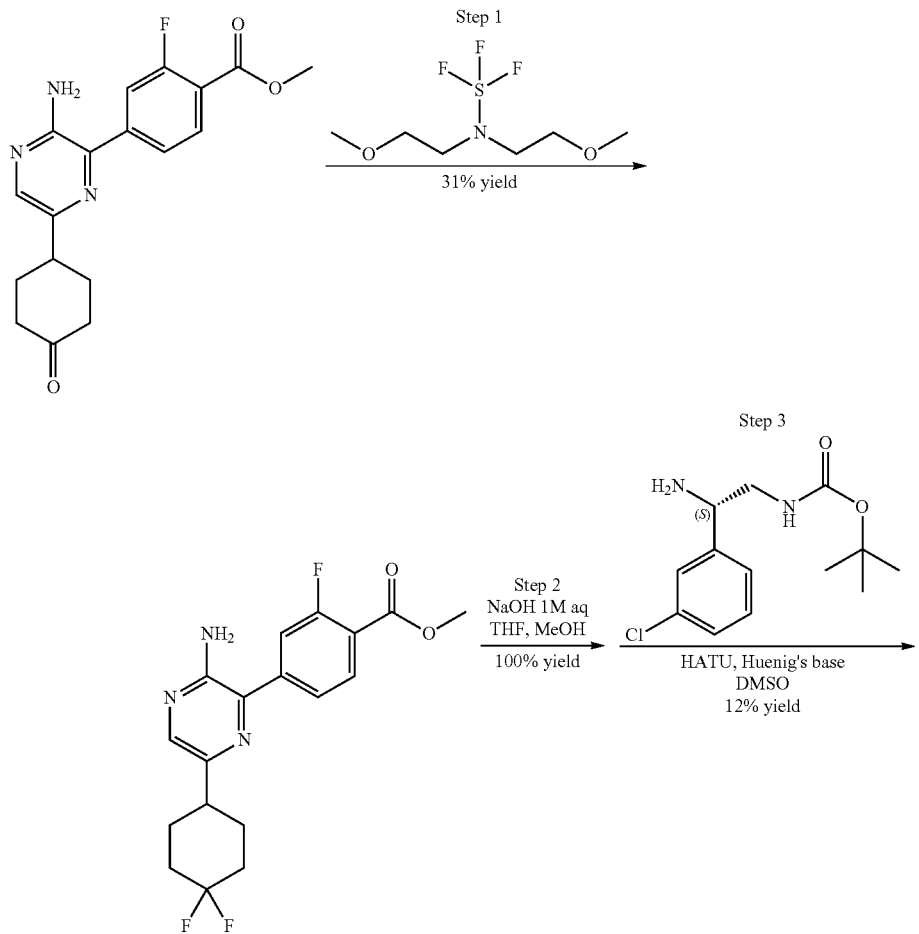

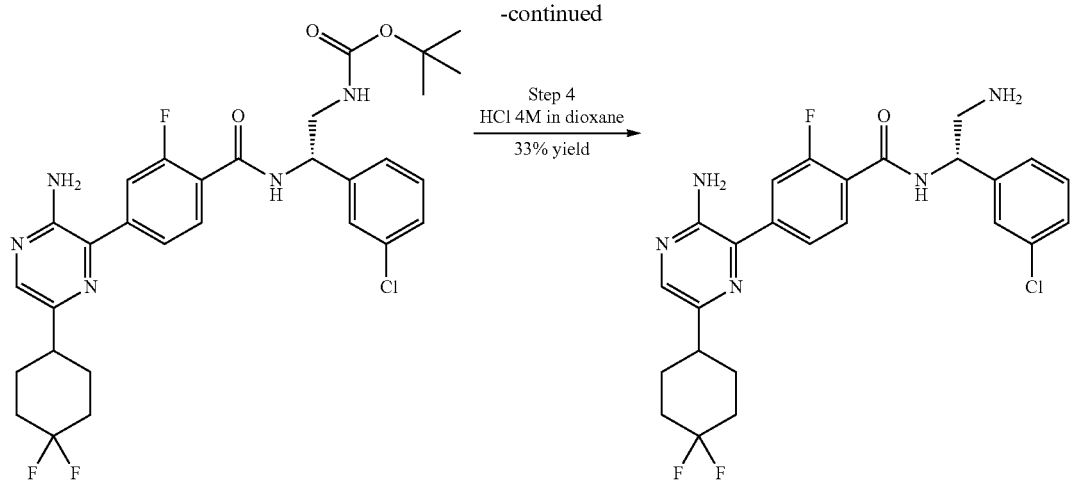

Step 1. methyl 4-(3-amino-6-(4,4-difluorocyclohexyl)pyrazin-2-yl)-2-fluorobenzoate To methyl 4-(3-amino-6-(4-oxocyclohexyl)pyrazin-2-yl)-2-fluorobenzoate (250 mg, 0.728 mmol) was added DCM (10 mL) and the solution was cooled to 0° C. in ice bath. Then Deoxo-fluoro solution in toluene 50% (805 mg, 1.820 mmol) was added at 0° C. The reaction was allowed to warm up to room temperature and stirred for 2 h. To quench the reaction, TEA (1.522 mL, 10.92 mmol) was added and stirred for 1 h at room temperature. The solvent was concentrated off to residue and the crude was purified by flash chromatography (dry load) using 12 gram column eluting with 5-75% ethyl acetate in heptane. The desired fractions were concentrated to constant mass to give 83 mg of the desired product as a free base, used as is (31% yield). LCMS (m/z): 366.2 (MH+), 0.87 min.

Step 2. 4-(3-amino-6-(4,4-difluorocyclohexyl)pyrazin-2-yl)-2-fluorobenzoic acid To methyl 4-(3-amino-6-(4,4-difluorocyclohexyl)pyrazin-2-yl)-2-fluorobenzoate (83 mg, 0.227 mmol) was added MeOH (1.5 mL), THF (1.5 mL) and then 1 M aqueous solution NaOH (0.909 mL, 0.909 mmol). The reaction was stirred at room temperature for 6 h. The reaction was concentrated to residue. THF was added and concentrated to residue again. Then the mixture was dissolved in 1:1 ACN/water, acidified with 6 M HCl and lyophilized to give desired product as HCl salt used as is. Assume quantitative yield, (0.227 mmol). LCMS (m/z): 352.1 (MH+), 0.71 min.

Step 3. (S)-tert-butyl (2-(4-(3-amino-6-(4,4-difluorocyclohexyl)pyrazin-2-yl)-2-fluorobenzamido)-2-(3-chlorophenyl)ethyl)carbamate To 4-(3-amino-6-(4,4-difluorocyclohexyl)pyrazin-2-yl)-2-fluorobenzoic acid (48 mg, 0.124 mmol) were added DMSO (1 mL), Hünig's base (0.108 mL, 0.619 mmol), (S)-tert-butyl (2-amino-2-(3-chlorophenyl)ethyl)carbamate (50.3 mg, 0.186 mmol) and then HATU (94 mg, 0.248 mmol). The reaction was stirred for 1 h at room temperature. To the reaction was added 0.5 mL of DMSO, filtered, purified by prep HPLC, and lyophilized to give 11 mg of the desired product used as is (12% yield). LCMS (m/z): 604.2 (MH+), 1.05 min.

Step 4. (S)-N-(2-amino-1-(3-chlorophenyl)ethyl)-4-(3-amino-6-(4,4-difluorocyclohexyl)pyrazin-2-yl)-2-fluorobenzamide To (S)-tert-butyl (2-(4-(3-amino-6-(4,4-difluorocyclohexyl)pyrazin-2-yl)-2-fluorobenzamido)-2-(3-chlorophenyl)ethyl)carbamate (11 mg, 0.018 mmol) was added HCl 4M in dioxane (1 mL, 4.00 mmol). The reaction was stirred for 1 h at room temperature. The solvent was removed and concentrated to residue, which was dissolved in 1:1 acetonitrile/water, filtered and lyophilized to HCl salt. The crude salt residue was dissolved in 1 mL of DMSO, purified by prep HPLC and lyophilized to give 3.8 mg of the desired product (S)-N-(2-amino-1-(3-chlorophenyl)ethyl)-4-(3-amino-6-(4,4-difluorocyclohexyl)pyrazin-2-yl)-2-fluorobenzamide as a TFA salt (33%). LCMS (m/z): 504.2 (MH+), 0.74 min; $^1$H NMR (CD$_3$OD) δ ppm 7.85-7.73 (m, 2H), 7.62 (dd, J=8.0, 1.4 Hz, 1H), 7.54 (dd, J=12.1, 1.2 Hz, 1H), 7.46 (s, 1H), 7.38-7.28 (m, 3H), 5.39 (dd, J=9.0, 5.9 Hz, 1H), 3.40-3.33 (m, 2H), 2.72 (br. s., 1H), 2.12-1.98 (m, 2H), 1.96-1.73 (m, 6H).

Examples 198 and 199

Synthesis of enantiomerically enriched diastereomers of cis-4-(3-amino-6-(3-hydroxycyclohexyl)pyrazin-2-yl)-N-((S)-1-(3-chlorophenyl)-2-hydroxyethyl)-2-fluorobenzamide Scheme 92

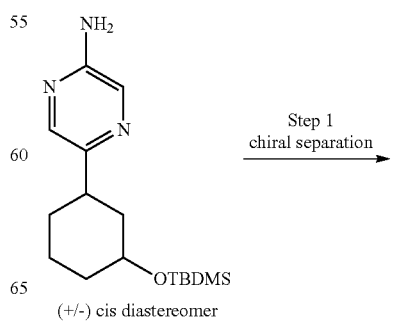

(+/-) cis diastereomer

Step 1
chiral separation →

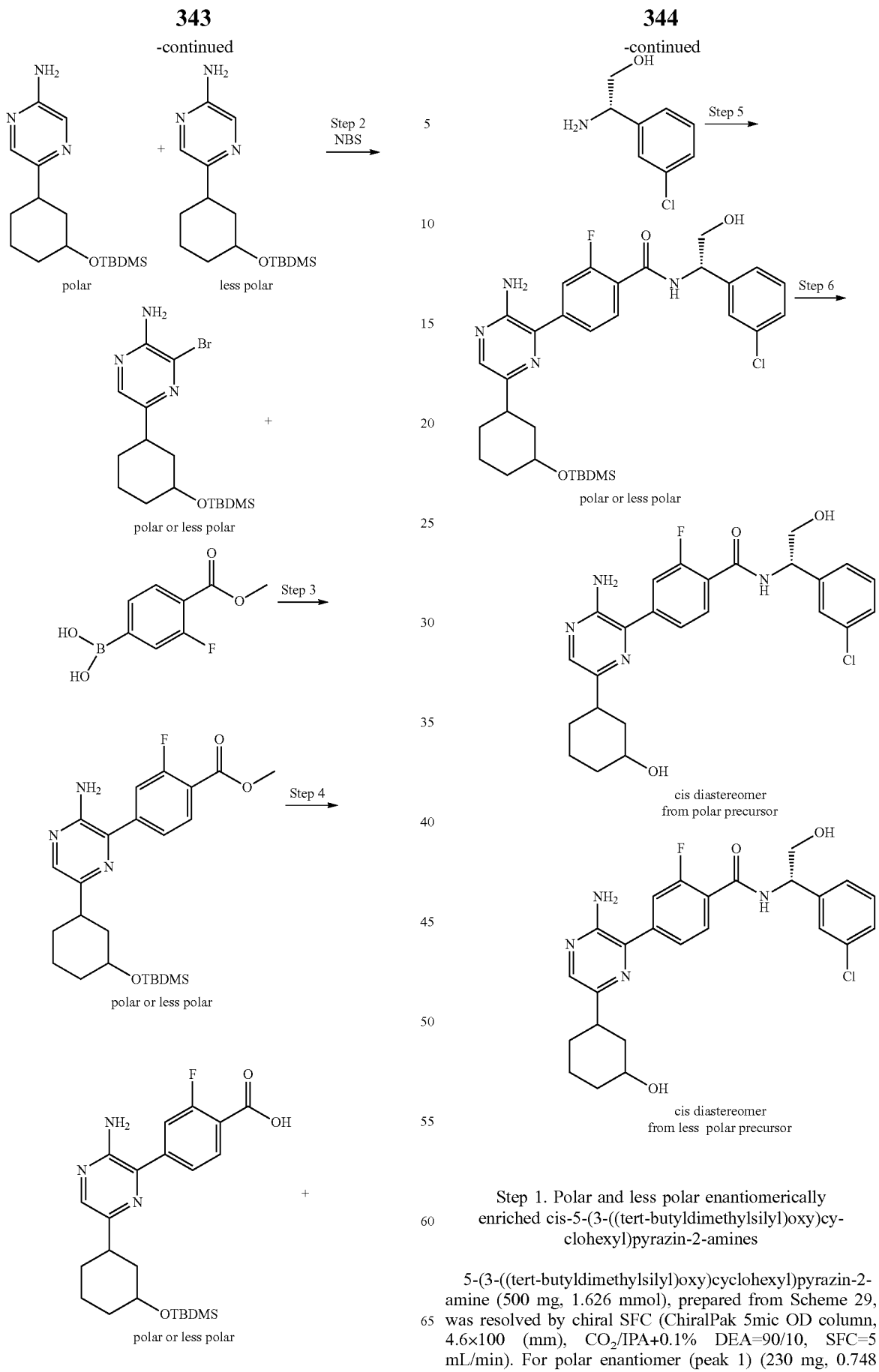
Step 1. Polar and less polar enantiomerically enriched cis-5-(3-(((tert-butyldimethylsilyl)oxy)cyclohexyl)pyrazin-2-amines
5-(3-((tert-butyldimethylsilyl)oxy)cyclohexyl)pyrazin-2-amine (500 mg, 1.626 mmol), prepared from Scheme 29, was resolved by chiral SFC (ChiralPak 5mic OD column, 4.6×100 (mm), CO$_2$/IPA+0.1% DEA=90/10, SFC=5 mL/min). For polar enantiomer (peak 1) (230 mg, 0.748 mmol, 46.0% yield), Rt=1.58 min. For less polar enantiomer (peak 2) (230 mg, 0.748 mmol, 46.0% yield), Rt=2.36 min.

Step 2, 3, 4, 5 and 6. cis-4-(3-amino-6-(3-hydroxy-cyclohexyl)pyrazin-2-yl)-N-((S)-1-(3-chlorophenyl)-2-hydroxyethyl)-2-fluorobenzamide diastereomers Following Steps 2, 3, and 7 in Scheme 75, each enantiomeric enriched cis-5-(3-((tert-butyldimethylsilyl)oxy)cyclohexyl)pyrazin-2-amine underwent bromination followed by Suzuki coupling with 3-fluoro-4-(methoxycarbonyl)phenyl)boronic acid. After hydrolysis, following Step 8 in Scheme 75, using (S)-2-amino-2-(3-chlorophenyl)ethanol and each enantiomer, each diastereomer of cis-4-(3-amino-6-(3-hydroxycyclohexyl)pyrazin-2-yl)-N-((S)-1-(3-chlorophenyl)-2-hydroxyethyl)-2-fluorobenzamide was obtained respectively. For cis diastereomer from polar precursor, LCMS (m/z): 485.0 (MH$^+$), 0.70 min; 1H NMR (400 MHz, METHANOL-d$_4$) δ ppm 7.90-7.69 (m, 2 H) 7.64-7.48 (m, 2 H) 7.37 (s, 1 H) 7.30-7.09 (m, 3 H) 5.10 (t, J=6.06 Hz, 1 H) 3.89-3.69 (m, 2 H) 3.66-3.47 (m, 1 H) 2.79-2.60 (m, 1 H) 2.06 (d, J=11.74 Hz, 1 H) 1.97-1.68 (m, 3 H) 1.52-1.26 (m, 3 H) 1.24-0.99 (m, 1 H). For cis diastereomer from less polar precursor, LCMS (m/z): 485.0 (MH$^+$), 0.70 min. 1H NMR (400 MHz, METHANOL-d$_4$) δ ppm 7.88-7.70 (m, 2 H) 7.65-7.49 (m, 2 H) 7.37 (s, 1 H) 7.32-6.98 (m, 3 H) 5.10 (s, 1 H) 3.76 (t, J=6.06 Hz, 2 H) 3.58 (s, 1 H) 2.79-2.59 (m, 1 H) 2.06 (d, J=12.13 Hz, 1 H) 1.97-1.61 (m, 3 H) 1.54-1.30 (m, 3 H) 1.25-0.96 (m, 1 H).

Absolute stereochemistry on cyclohexane ring for both diastereomers has not been determined.

Examples 200 and 201

Synthesis of 4-(3-amino-6-(tetrahydro-2H-pyran-4-yl)pyrazin-2-yl)-2-fluoro-N-((1S,2R)-2-phenylcyclopropyl)benzamide and 4-(3-amino-6-(tetrahydro-2H-pyran-4-yl)pyrazin-2-yl)-2-fluoro-N-((1R,2S)-2-phenylcyclopropyl)benzamide Scheme 93

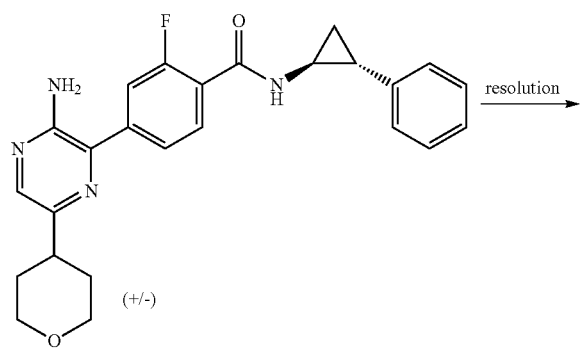

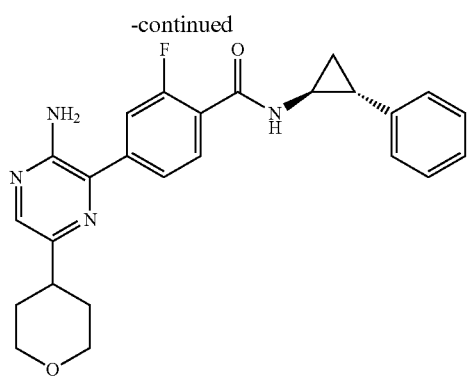

Peak 1

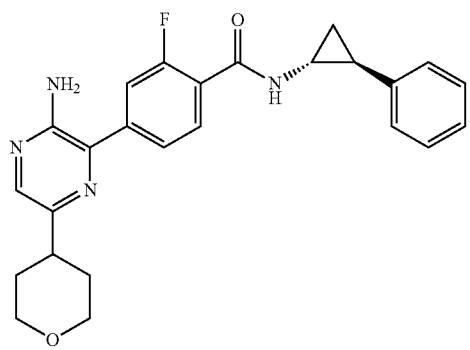

Peak 2

Following Step 2 in Scheme 89, using (+/−)-trans-2-phenylcyclopropanamine, EDC (30.2 mg, 0.158 mmol), HOAt (17.2 mg, 0.126 mmol), and DIEA (0.033 mL, 0.189 mmol), (+/−)-trans-4-(3-amino-6-(tetrahydro-2H-pyran-4-yl) pyrazin-2-yl)-2-fluoro-N-(2-phenylcyclopropyl)benzamide was obtained (19 mg, 70%). LCMS (m/z): 433.2 (MH$^+$), 0.82 min; $^1$H NMR (400 MHz, CDCl$_3$) δ ppm 8.29-8.22 (m, 1 H), 7.94 (s, 1 H), 7.76-7.71 (m, 1 H), 7.63-7.56 (m, 1 H), 7.35-7.18 (m, 4 H), 7.04-6.94 (m, 1 H), 4.67 (s, 2 H), 4.09 (m, 2 H), 3.35 (m, 2 H), 3.15 (m, 1 H), 2.93 (m, 1 H), 2.22 (m, 1 H), 2.90-1.8 (m, 4 H), 1.43-1.23 (m, 3 H).

The racemic product was resolved by chiral SFC (ChiralPak 5mic AD-H column, 4.6×100 (mm), heptane: EtOH=50/50, 1 mL/min). For polar 4-(3-amino-6-(tetrahydro-2H-pyran-4-yl)pyrazin-2-yl)-2-fluoro-N-((1S,2R)-2-phenylcyclopropyl)benzamide (27%) at Rt=11.0 min, LCMS (m/z): 433.2 (MH$^+$), 0.81 min. For less polar 4-(3-amino-6-(tetrahydro-2H-pyran-4-yl)pyrazin-2-yl)-2-fluoro-N-((1R,2S)-2-phenylcyclopropyl)benzamide (+/−)-trans-4-(3-amino-6-(tetrahydro-2H-pyran-4-yl)pyrazin-2-yl)-2-fluoro-N-(2-phenylcyclopropyl)benzamide (27%) at Rt=15.8 min, LCMS (m/z): 433.2 (MH$^+$), 0.81 min. The absolute stereochemistry was assigned based on biochemical data and docking model.

Examples 202 and 203

Synthesis of 4-(3-amino-6-((1r,4S)-4-hydroxycyclohexyl)pyrazin-2-yl)-2-fluoro-N-((1S,2R)-2-phenylcyclopropyl)benzamide and 4-(3-amino-6-((1r,4R)-4-hydroxycyclohexyl)pyrazin-2-yl)-2-fluoro-N-((1R,2S)-2-phenylcyclopropyl)benzamide

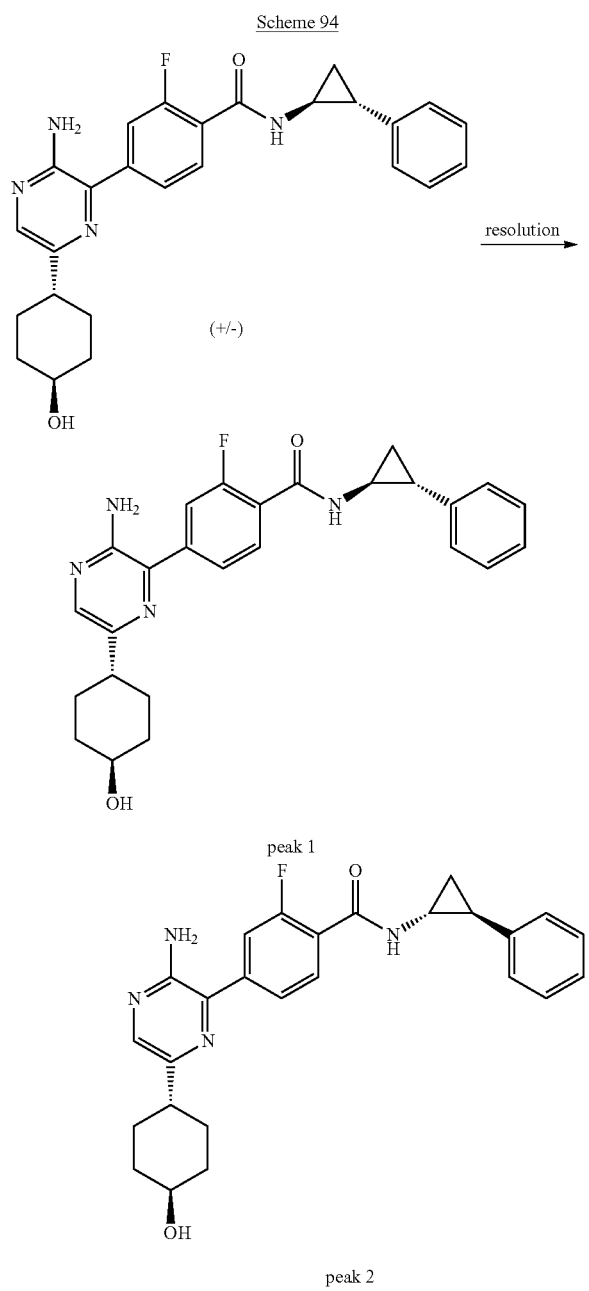 [SMILES: Nc1ncc([C@H]2CC[C@H](O)CC2)nc1-c1ccc(C(=O)N[C@H]2C[C@@H]2c2ccccc2)c(F)c1 ; Nc1ncc([C@H]2CC[C@H](O)CC2)nc1-c1ccc(C(=O)N[C@H]2C[C@@H]2c2ccccc2)c(F)c1 ; Nc1ncc([C@H]2CC[C@H](O)CC2)nc1-c1ccc(C(=O)N[C@@H]2C[C@H]2c2ccccc2)c(F)c1]

Following Step 2 in Scheme 89, using (+/−)-trans-2-phenylcyclopropanamine (48.6 mg, 0.37 mmol), EDC (127 mg, 0.66 mmol), HOAt (67.8 mg, 0.498 mmol), and DIEA (0.174 mL, 0.996 mmol), (+/−)-trans-4-(3-amino-6-(tetrahydro-2H-pyran-4-yl)pyrazin-2-yl)-2-fluoro-N-(2-phenylcyclopropyl)benzamide was obtained (40 mg, 97%), which was separated by chiral SFC (ChiralPak 5mic OJ column, 4.6×100 (mm), $CO_2$/IPA+0.1% DEA=60/40, SFC=5 ml/min). The polar diastereomer was 4-(3-amino-6-((1r,4S)-4-hydroxycyclohexyl)pyrazin-2-yl)-2-fluoro-N-((1S,2R)-2-phenylcyclopropyl)benzamide (Rt=1.38 min). LCMS (m/z): 447.3 (MH$^+$), 0.76 min; 1H NMR (500 MHz, CD$_3$OD) δ ppm 7.89-7.78 (m, 2H), 7.72-7.53 (m, 2H), 7.33-7.23 (m, 2H), 7.24-7.10 (m, 3H), 3.68-3.53 (m, 1H), 3.14-3.03 (m, 1H), 2.74-2.56 (m, 1H), 2.27-2.13 (m, 1H), 2.12-1.88 (m, 4H), 1.77-1.57 (m, 2H), 1.52-1.29 (m, 4H). The less polar diastereomer was 4-(3-amino-6-((1r,4R)-4-hydroxycyclohexyl)pyrazin-2-yl)-2-fluoro-N-((1R,2S)-2-phenylcyclopropyl)benzamide (Rt=1.82 min). LCMS (m/z): 447.3 (MH$^+$), 0.75 min; 1H NMR (500 MHz, CD$_3$OD) δ ppm 7.89-7.78 (m, 2H), 7.72-7.53 (m, 2H), 7.33-7.23 (m, 2H), 7.24-7.10 (m, 3H), 3.68-3.53 (m, 1H), 3.14-3.03 (m, 1H), 2.74-2.56 (m, 1H), 2.27-2.13 (m, 1H), 2.12-1.88 (m, 4H), 1.77-1.57 (m, 2H), 1.52-1.29 (m, 4H). The absolute stereochemistry was assigned based on biochemical data and docking model.

Example 204

Synthesis of 4-(2-amino-5-(tetrahydro-2H-pyran-4-yl)pyridin-3-yl)-N-benzyl-2-cyano-6-fluorobenzamide

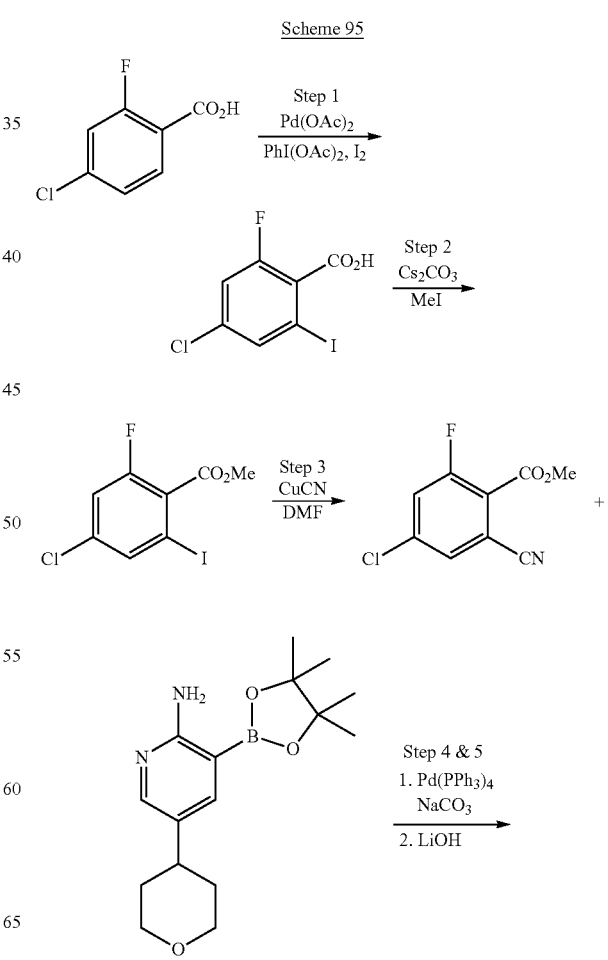

Step 3. Methyl 4-chloro-2-cyano-6-fluorobenzoate

Methyl 4-chloro-2-fluoro-6-iodobenzoate (1.99 g, 10.6 mmol) was dissolved in DMF (12 mL). CuCN (2.84 g, 31.7 mmol) was added and the suspension was heated under microwave at 110° C. for 18 min. EtOAc was added and the suspension was filtered through a piece of filter paper. The filtrate was washed three times with water. The aqueous layers were combined and extracted once with EtOAc. The organic layers were combined, dried over $Na_2SO_4$ and concentrated. The residue was purified on a silica gel column (heptane:EtOAc 1:0 to 9:1) to give the product as a colorless solid (505 mg). $^1$H NMR (400 MHz, $CDCl_3$) δ ppm 7.56 (s, 1H), 7.40 (d, 1H, J=8 Hz), 4.00 (s, 3H); $^{13}$C NMR (100 MHz, $CDCl_3$) δ ppm 161.78 (d, J=58 Hz), 159.44, 139.16 (d, J=11 Hz), 129.96, 121.99, 121.74, 115.48, 114.72, 53.04.

Step 4. Methyl 4-(2-amino-5-(tetrahydro-2H-pyran-4-yl)pyridin-3-yl)-2-cyano-6-fluorobenzoate To a 2 mL microwave vial were added 5-(tetrahydro-2H-pyran-4-yl)-3-(4,4,5,5-tetramethyl-1,3,2-dioxaborolan-2-yl)pyridin-2-amine (638 mg, 1.049 mmol), methyl 4-chloro-2-cyano-6-fluorobenzoate (140 mg, 0.655 mmol), $Pd_2(dba)_3$ (30.0 mg, 0.033 mmol), XPhos (31.2 mg, 0.066 mmol), $NaHCO_3$ (275 mg, 3.28 mmol), DME (3 mL) and $H_2O$ (1.5 mL). The solution was heated under microwave at 100° C. for 15 min. Water and EtOAc were added and the aqueous layer was extracted three times with EtOAc. The organic layers were combined, dried over $Na_2SO_4$ and concentrated. The residue was purified on a silica gel column (heptane:EtOAc 1:0 to 1:4) to give the product as a yellow foam (85 mg). LCMS (m/z) 356.1 ($MH^+$), 0.58 min.

Step 5. 4-(2-amino-5-(tetrahydro-2H-pyran-4-yl)pyridin-3-yl)-2-cyano-6-fluorobenzoic acid To methyl 4-(2-amino-5-(tetrahydro-2H-pyran-4-yl)pyridin-3-yl)-2-cyano-6-fluorobenzoate (85 mg, 0.239 mmol) and lithium hydroxide monohydrate (11.04 mg, 0.263 mmol) were added THF (1 mL) and $H_2O$ (1.000 mL). The solution was stirred at room temperature for 3 h. All solvents were evaporated to give the crude product's lithium salt as a yellow solid (92 mg) which was used in the next step without purification. LCMS (m/z) 342.0 ($MH^+$), 0.42 min,

Step 6. 4-(2-amino-5-(tetrahydro-2H-pyran-4-yl)pyridin-3-yl)-N-benzyl-2-cyano-6-fluorobenzamide To 4-(2-amino-5-(tetrahydro-2H-pyran-4-yl)pyridin-3-yl)-2-cyano-6-fluorobenzoic acid were added DCM (1 mL), followed by benzylamine (0.017 mL, 0.153 mmol), triethylamine (0.053 mL, 0.383 mmol) and T3P (50% in EtOAc, 0.084 mL, 0.141 mmol). After 1 h more benzylamine (0.017 mL, 0.153 mmol) and T3P (50% in EtOAc, 0.084 mL, 0.141 mmol) were added and at 2 h the reaction was completed. Saturated NaHCO3 solution was added and extracted twice with EtOAc. The organic layers were combined, dried over $Na_2SO_4$ and concentrated. The residue was purified on a silica gel column (heptane:EtOAc 1:0 to 0:1) to give the product as a colorless solid (17 mg). LCMS (m/z) 431.1 ($MH^+$), 0.65 min. 1H NMR (400 MHz, $CDCl_3$)) δ ppm 8.03 (s, 1 H), 7.74 (s, 1 H), 7.54 (d, 1 H, J 12 Hz), 7.43-7.30 (m, 4 H) 7.26 (s, 1 H), 7.23 (s, 1 H) 6.57 (br s, 1 H), 4.74 (d, J

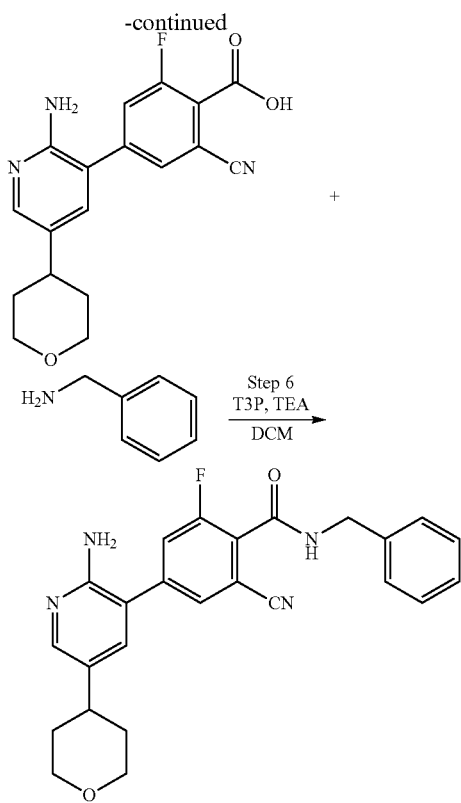

Step 1. 4-chloro-2-fluoro-6-iodobenzoic acid

To a 250 mL flask were added 4-chloro-2-fluorobenzoic acid (4 g, 22.92 mmol), $Pd(OAc)_2$ (0.257 g, 1.146 mmol), iodobenzene diacetate (8.12 g, 25.2 mmol), iodine (6.40 g, 25.2 mmol) and DMF (60 mL). The solution was heated under a nitrogen atmosphere at 100° C. for 20 h. LCMS showed about half of 4-chloro-2-fluorobenzoic acid was converted to the product (LCMS retention time 0.98 min, no $MH^+$ peak). After cooling to room temperature, the solution was diluted with EtOAc and washed three times with 1 N HCl. The aqueous layers were combined and extracted once with EtOAc. The organic layers were combined, dried over $Na_2SO_4$ and concentrated to give a dark brown oil (16.4 g, 42% pure), which was taken to the next step without purification.

Step 2. Methyl 4-chloro-2-fluoro-6-iodobenzoate

4-Chloro-2-fluoro-6-iodobenzoic acid (16.4 g, 22.93 mmol, along with 4-chloro-2-fluorobenzoic acid) were dissolved in DMF (30 mL). $Cs_2CO_3$ (8.96 g, 27.5 mmol) was added, followed by MeI (1.577 mL, 25.2 mmol). After 90 min at room temperature. LCMS showed the reaction was completed (retention time 1.06 min, no $MH^+$ peak). It was diluted with EtOAc and filtered through a piece of filter paper. The filtrate was washed three times with water. The aqueous layers were combined and extracted once with EtOAc. The organic layers were combined, dried over $Na_2SO_4$ and concentrated. The residue was purified on a silica gel column (heptane:EtOAc 1:0 to 9:1) to give a mixture of methyl 4-chloro-2-fluoro-6-iodobenzoate and methyl 4-chloro-2-fluorobenzoate in approximately 1:1 ratio (1.99 g).

5.53 Hz, 2 H), 4.10-4.06 (m, 2 H), 3.55-3.46 (m, 2 H), 2.77-2.67 (m, 1H), 1.80-1.70 (m, 4 H).
Example 205
Synthesis of 4-(2-amino-5-(tetrahydro-2H-pyran-4-yl)pyridin-3-yl)-2-fluoro-N-((6-methylpyridin-2-yl)methyl)benzamide
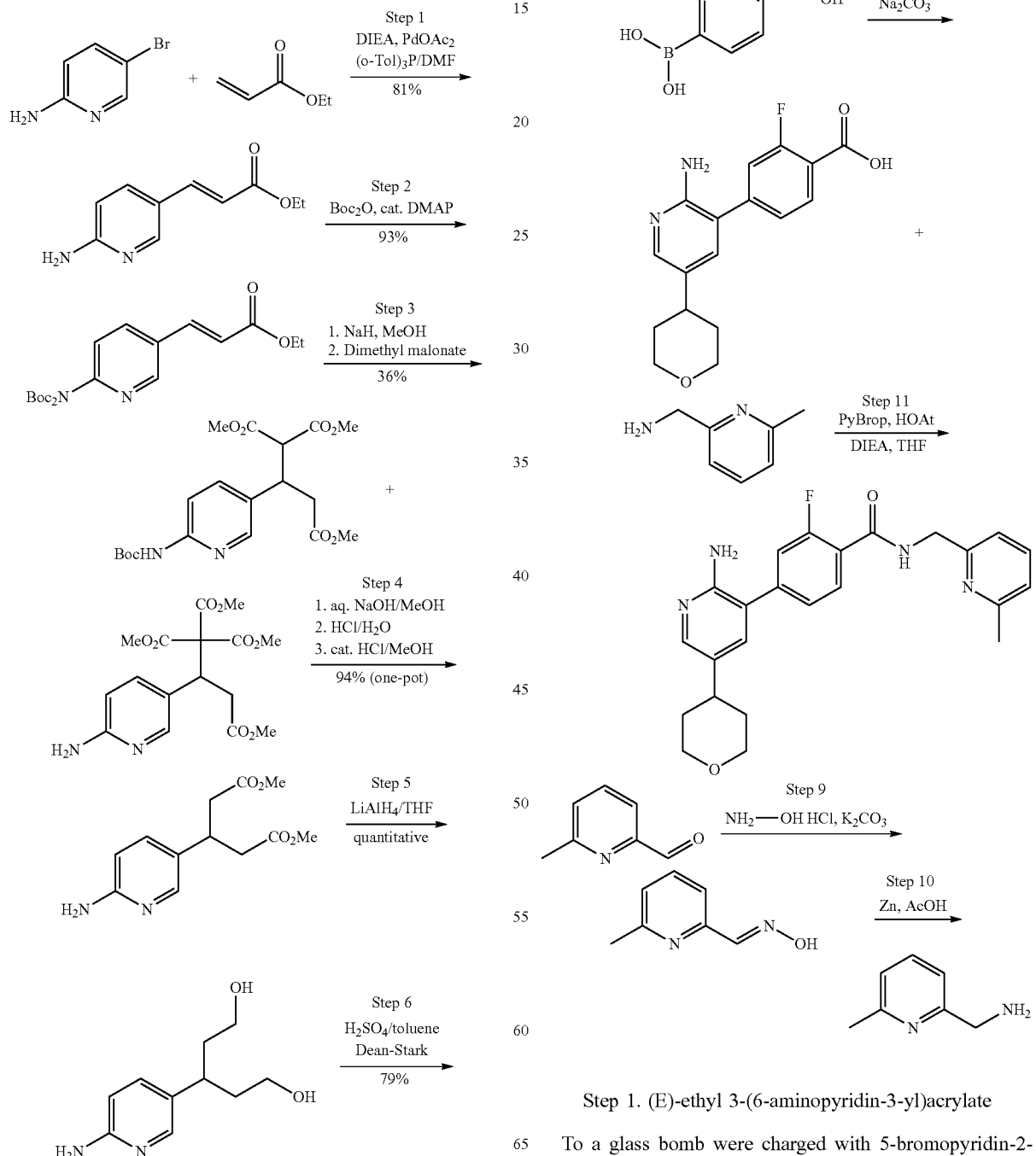
Step 1. (E)-ethyl 3-(6-aminopyridin-3-yl)acrylate
To a glass bomb were charged with 5-bromopyridin-2-amine (10.0 g, 57.8 mmol), ethyl acrylate (8.14 mL, 75 mmol) and DIEA (25.2 mL, 144 mmol) in DMF (40 mL).

The mixture was purged with argon, followed by addition of Pd(OAc)$_2$ (0.649 g, 2.89 mmol) and (o-Tol)$_3$P (3.87 g, 12.72 mmol), and finally purged thoroughly with argon. The mixture was sealed, and heated with 100° C. oil bath overnight. The reaction mixture was cooled down to room temperature, and the precipitates were removed by filtering through a thin layer of Celite. The filtrate was concentrated as much as possible via rotavap, and the residue was partitioned between EtOAc/water (150 mL/100 mL). EtOAc layer was washed with water (2×100 mL), dried over Na$_2$SO$_4$, and concentrated. A brown slid was obtained as crude product. The crude product was triturated with EtOAc (40 mL) and the yellow solid was collected via filtration. The filter cake was rinsed with small amount of EtOAc and dried under vacuum as the first crop of product (5.0 g). The mother liquor from trituration was stripped by dilute aqueous 1 N HCl (30 mL) and water (70 mL). Aqueous layer was transferred to a clean separative funnel, basicified with 20 mL sat. Na$_2$CO$_3$, and extracted with EtOAc (60 mL). EtOAc layer was dried over Na$_2$SO$_4$, concentrated and provided the second portion of product (4.0 g). The two crops of product were combined to afford 81% yield. LCMS (m/z) 193.2 (MH$^+$), 0.39 min.

Step 2. (E)-ethyl 3-(6-(bis(tert-butoxycarbonyl)amino)pyridin-3-yl)acrylate

To solution of (E)-ethyl 3-(6-aminopyridin-3-yl)acrylate (6.6 g, 34.3 mmol) and DMAP (0.21 g, 1.7 mmol) in THF (150 mL) was added di-tert-butyl dicarbonate (15.7 g, 71.9 mmol). The mixture was stirred overnight at room temperature. The reaction was concentrated and a brown solid was obtained as crude (E)-ethyl 3-(6-(bis(tert-butoxycarbonyl)amino)pyridin-3-yl)acrylate (12.5 g, 93%). LCMS (m/z) 237.4 (MH$^+$) 0.98 min.

Step 3. trimethyl 2-(6-(tert-butoxycarbonylamino)pyridin-3-yl)propane-1,1,3-tricarboxylate and tetramethyl 2-(6-aminopyridin-3-yl)propane-1,1,1,3-tetracarboxylate To a flame flask was charged with anhydrous MeOH (50 mL), and the content was cooled down to 0° C. To the flask was added sodium hydride (3.18 g, 60% in dispersion mineral oil, 80 mmol) with gas evolution under control. The reaction mixture was stirred at room temperature until gas evolution ceased. To this freshly prepared NaOMe/MeOH solution was added dimethyl malonate (10.52 g, 80 mmol), and the mixture was stirred at room temperature for 20 min. The mixture turned into a milky slurry. The milky slurry was diluted with 25 mL anhydrous MeOH, and decanted to a flask with sodium hydride (12.5 g, 31.9 mmol). The reaction mixture slurry was stirred at room temperature for 15 min, and then heated to reflux overnight. The reaction mixture was cooled down to room temperature, and concentrated. The residue was partitioned between EtOAc/H$_2$O (100 mL/100 mL). The EtOAc layer was washed with 1 N NaOH (3×30 mL), brine (30 mL), dried over Na$_2$SO$_4$, and concentrated. A light brown oil was obtained as crude product. The crude product was purified by flash chromatography eluting with gradient EtOAc/CH$_2$Cl$_2$. Two major peaks were isolated and collected as trimethyl 2-(6-(tert-butoxycarbonylamino)pyridin-3-yl)propane-1,1,3-tricarboxylate (2.65 g, 20.3% yield) and tetramethyl 2-(6-aminopyridin-3-yl)propane-1,1,1,3-tetracarboxylate (1.89 g, 16% yield). The two products were characterized and confirmed by LCMS and 1H NMR. For trimethyl 2-(6-(tert-butoxycarbonylamino)pyridin-3-yl)propane-1,1,3-tricarboxylate. LCMS (m/z) 411.5 (MH$^+$), 0.64 min; $^1$H NMR (CDCl$_3$) δ ppm 8.15 (d, J=2.0 Hz, 1H), 7.88 (d, J=8.6 Hz, 1H), 7.60-7.52 (m, 2H), 3.90 (td, J=9.8, 4.7 Hz, 1H), 3.76 (s, 3H), 3.56 (s, 3H), 3.55 (s, 3H), 2.92-2.81 (m, 1H), 2.80-2.69 (m, 1H), 1.53 (s, 9H). For tetramethyl 2-(6-aminopyridin-3-yl)propane-1,1,1,3-tetracarboxylate: LCMS (m/z) 369.5 (MH$^+$) 0.47 min; $^1$H NMR (CDCl$_3$) δ ppm 8.31 (s, 1H), 8.19 (d, J=2.3 Hz, 1H), 7.93 (d, J=8.6 Hz, 1H), 7.60 (dd, J=8.6, 2.3 Hz, 1H), 3.92 (td, J=9.7, 4.9 Hz, 1H), 3.82 (s, 3H), 3.76 (s, 3H), 3.57 (s, 3H), 3.55 (s, 3H), 2.93-2.82 (m, 1H), 2.81-2.70 (m, 1H).

Step 4. dimethyl 3-(6-aminopyridin-3-yl)pentanedioate

To a mixture of trimethyl 2-(6-(tert-butoxycarbonylamino)pyridin-3-yl)propane-1,1,3-tricarboxylate (2.5 g, 6.1 mmol) and tetramethyl 2-(6-aminopyridin-3-yl)propane-1,1,1,3-tetracarboxylate (1.8 g, 4.9 mmol) in MeOH (30 mL) was added aqueous NaOH solution (2.44 g NaOH in 5 mL water, 60.9 mmol). The resulting mixture was heated to relux by oil bath for 1 hour. The reaction mixture was cooled down to room temperature, and concentrated under reduced pressure via rotavap. To the concentrated residue were added water (15 mL) and conc. HCl (3 mL). The resulting mixture was heated to reflux overnight. The reaction mixture was cooled down, and concentrated under reduced pressure via rotavap, and a solid was obtained. The obtained solid residue was triturated with methanol (100 mL) and the precipitates was removed by filtration, and a light color filtrate was obtained. To the filtrate was added conc. HCl (200 µL) and the resulting mixture was heated to reflux via external oil bath for 1 h. The reaction mixture was cooled down, and concentrated. The residue was partitioned between EtOAc/sat. NaHCO$_3$ (50 mL/50 mL). Aqueous layer was extracted with EtOAc (50 mL). The EtOAc extracts were combined, washed with brine (50 mL), dried over Na$_2$SO$_4$, and concentrated. A white solid was obtained as desired dimethyl 3-(6-aminopyridin-3-yl)pentanedioate (2.6 g, 10.31 mmol, 93.9% yield). LCMS (m/z) 253.2 (MH$^+$) 0.38 min; $^1$H NMR (CDCl$_3$) δ ppm 7.95 (d, J=2.3 Hz, 1H), 7.32 (dd, J=8.2, 2.3 Hz, 1H), 6.46 (d, J=8.6 Hz, 1H), 4.37 (br. s., 2H), 3.61 (s, 6H), 3.55 (quin, J=7.5 Hz, 1H), 2.80-2.66 (m, 2H), 2.65-2.51 (m, 2H).

Step 5. 3-(6-aminopyridin-3-yl)pentane-1,5-diol

To aluminum (III) lithium hydride/THF slurry (0.94 g in 60 mL THF, 25 mmol) at 0° C. was added dimethyl 3-(6-aminopyridin-3-yl)pentanedioate/THF solution (2.5 g, 9.9 mmol in 30 mL THF) over ~10 min. The slurry was stirred at 0° C. for 40 min, and then at room temperature for 45 min. The mixture was cooled down to 0° C., and quenched by sequential addition of water (0.96 mL) with gas evolution under control, then 15% aqueous NaOH (0.96 mL), and water (2.9 mL). The quenched mixture was stirred at room temperature for 30 min. The precipitates were removed via filtration. The filtrate was concentrated, and a light yellow solid (1.97 g, quantitative yield) was obtained as 3-(6-aminopyridin-3-yl)pentane-1,5-diol. LCMS (m/z) 197.2 (MH$^+$) 0.22 min.

Step 6. 5-(tetrahydro-2H-pyran-4-yl)pyridin-2-amine

To 3-(6-aminopyridin-3-yl)pentane-1,5-diol/toluene mixture (1.96 g, 10 mmol in 40 mL) were added 1 mL water to help dissolving, and then conc. H$_2$SO$_4$ (98%, 1.6 mL, 30 mmol). The resulting mixture was heated to reflux with Dean-Stark to remove water from reaction mixture for 1 h 20 min. The reaction mixture was cooled down to room temperature, and concentrated. The residue was diluted with ice cold water (15 mL), neutralized by solid Na$_2$CO$_3$ (4 g), and extracted with EtOAc (3×30 mL). The EtOAc extracts were combined, washed with brine (30 mL), dried over Na$_2$SO$_4$, and concentrated. A light yellow solid was obtained as crude 5-(tetrahydro-2H-pyran-4-yl)pyridin-2-amine. LCMS (m/z) 179.2 (MH$^+$) 0.33 min; $^1$H NMR (CDCl$_3$) δ ppm 7.95 (d, J=2.0 Hz, 1H), 7.32 (dd, J=8.2, 2.3 Hz, 1H), 6.49 (d, J=8.2 Hz, 1H), 4.34 (br. s., 2H), 4.11-3.99 (m, 2H), 3.51 (td, J=11.2, 3.3 Hz, 2H), 2.73-2.56 (m, 1H), 1.75-1.69 (m, 4H).

Step 7. 3-bromo-5-(tetrahydro-2H-pyran-4-yl)pyridin-2-amine

To 5-(tetrahydro-2H-pyran-4-yl)pyridin-2-amine/acetonitrile solution (1.4 g, 7.85 mmol/30 mL) at 0-5° C. was added portionwise NBS (1.4 g, 7.85 mmol) with internal temperature controlled below 5° C. The resulting mixture was stirred at 0° C. for 1 hour 40 min. The reaction mixture was concentrated under reduced pressure, and the residue was triturated with dilute aqueous NaOH/H$_2$O (1 g/30 mL). The solid suspension was collected via filtration. The filtercake was washed with ice cold water (~10 mL), and the filtrates were combined, and extracted with EtOAc (20 mL). The EtOAc extract was washed with brine (20 mL), dried over Na$_2$SO$_4$, and concentrated. A light yellow solid was combined with the filter cake, and dried under high vacuum as crude 3-bromo-5-(tetrahydro-2H-pyran-4-yl)pyridin-2-amine. LCMS (m/z) 257.1/259.1 (MH$^+$) 0.39 min. $^1$H NMR (CDCl$_3$) δ ppm 7.90 (d, J=1.6 Hz, 1H), 7.54 (d, J=2.0 Hz, 1H), 4.80 (br. s., 1H), 4.12-4.02 (m, 2H), 3.54-3.44 (m, 2H), 2.71-2.61 (m, 1H), 1.78-1.68 (m, 4H).

Step 8. 4-(2-amino-5-(tetrahydro-2H-pyran-4-yl)pyridin-3-yl)-2-fluorobenzoic acid To a microwave vial were charged with 3-bromo-5-(tetrahydro-2H-pyran-4-yl)pyridin-2-amine (500 mg, 1.95 mmol), 4-borono-2-fluorobenzoic acid (1.07 g, 5.83 mmol), aqueous Na$_2$CO$_3$ (2 M, 4.86 mL) and DME (10 mL). The mixture was purged with argon, then followed by addition of Pd(PPh$_3$)$_4$ (225 mg, 0.194 mmol). The mixture was purged with argon, sealed and heated via microwave reactor at 125° C. for 20 min, and then at 130° C. for another 40 min. The DME layer of the reaction mixture was collected, and the solid precipitates were triturated with methanol (2×10 mL). Methanol supernatants were combined with DME layer, and concentrated. The obtained residue was stirred with Et$_2$O (2×60 mL), and the Et$_2$O supernatants were discarded. The solid residue was partitioned between EtOAc (20 mL) and aq. HCl (1N, 20 mL). The EtOAc layer was stripped with 1N HCl (2×5 mL), and the aqueous layers were combined. The aqueous layer was concentrated under reduced pressure, and the obtained light yellow solid was triturated with methanol (8 mL). The supernant was isolated via filtration and concentrated. 4-(2-Amino-5-(tetrahydro-2H-pyran-4-yl)pyridin-3-yl)-2-fluorobenzoic acid (0.844 g, 2.67 mmol, 137% yield) was obtained as light yellow foam. LCMS (m/z) 317.2 (MH$^+$) 0.46 min.

Step 9. (E)-6-methylpicolinaldehyde oxime

To 6-methylpicolinaldehyde ethanol solution (642 mg, 5.3 mmol/2.1 mL) was added hydroxyamine hydrochloride (368 mg, 5.3 mmol) and K$_2$CO$_3$ aqueous solution (0.88 g/4.2 mL). The resulting solution was then heated to reflux via external oil bath for 30 min. The reaction mixture was cooled down to 0° C., and stirred for 30 min. The white solid suspension was collected via filtration, and the filter cake was washed with some ice-cold water. The filter cake was air dried, and further dried under high vacuum as the first crop product (0.565 g). The filtrates were combined, and concentrated to dryness. The residue was redissolved in water (2 mL), cooled to 0° C. and stirred for 20 min. The solid product was collected via filtration as the second crop of product (70 mg) as light yellow solid. The two crops of product were combined to provide (E)-6-methylpicolinaldehyde oxime (88%). LCMS (m/z) 136.9 (MH$^+$) 0.21 min.

Step 10. (6-methylpyridin-2-yl)methanamine

To (E)-6-methylpicolinaldehyde oxime (0.635 g, 4.66 mmol)/acetic acid (267 μL, 4.66 mmol)/ethanol (10 mL) solution was added portionwise zinc dust (5.19 g, 79 mmol) over 30 min. The resulting mixture was stirred for additional 30 min. LCMS of reaction aliquot indicated reaction was completed. The zinc precipitates in reaction mixture was removed by filtration, and the filtrate was concentrated. The residue was basified to pH>12 with excess sat. KOH (~7 mL), and stirred with Et$_2$O (30 mL). The Et$_2$O layer was collected, dried over Na$_2$SO$_4$, and concentrated. The residue was redissolved in EtOAc (15 mL), dried over Na$_2$SO$_4$, and concentrated. (6-Methylpyridin-2-yl)methanamine was obtained as a colorless oil (385 mg, 3.15 mmol, 67.6%). LCMS (m/z) 123.2 (MH$^+$) 0.15 min.

Step 11. 4-(2-amino-5-(tetrahydro-2H-pyran-4-yl)pyridin-3-yl)-2-fluoro-N-((6-methylpyridin-2-yl)methyl)benzamide To a vial were charged with 4-(2-amino-5-(tetrahydro-2H-pyran-4-yl)pyridin-3-yl)-2-fluorobenzoic acid (20 mg, 0.063 mmol), (6-methylpyridin-2-yl)methanamine (11.6 mg, 0.095 mmol), DIEA (28 μL, 0.158 mmol), PyBOP (65.8, 0.126 mmol) and DMF (0.5 mL). The mixture was stirred at room temperature for 10 min. The reaction mixture was then purified by preparative HPLC, and product fractions were combined, frozen and lyophilized to afford 4-(2-amino-5-(tetrahydro-2H-pyran-4-yl)pyridin-3-yl)-2-fluoro-N-((6-methylpyridin-2-yl)methyl)benzamide as a white powder. LCMS (m/z) 421.3 (MH$^+$) 0.41 min. $^1$H NMR (DMSO-d6) δ ppm 8.99 (d, J=3.1 Hz, 1H), 7.95-7.83 (m, 3H), 7.79 (t, J=7.6 Hz, 1H), 7.53 (d, J=11.7 Hz, 2H), 7.44 (dd, J=8.0, 1.4 Hz, 1H), 7.24 (d, J=7.4 Hz, 2H), 4.60 (d, J=5.5 Hz, 2H), 4.02-3.88 (m, 2H), 3.40 (td, J=11.2, 2.7 Hz, 3H), 2.88-2.71 (m, 1H), 2.51 (br. s., 3H), 1.82-1.58 (m, 4H).

Example 206

Synthesis of (S)-4-(2-amino-5-(1-(difluoromethyl)-3-methyl-1H-pyrazol-4-yl)pyridin-3-yl)-2-fluoro-N-(1-(3-fluoro-5-(fluoromethyl)phenyl)-2-hydroxyethyl)benzamide Scheme 97

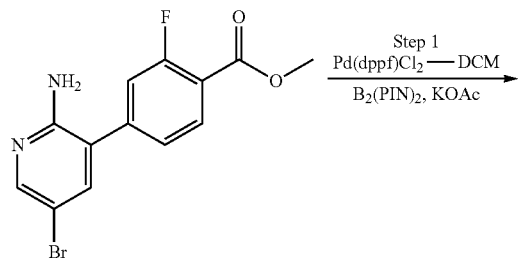

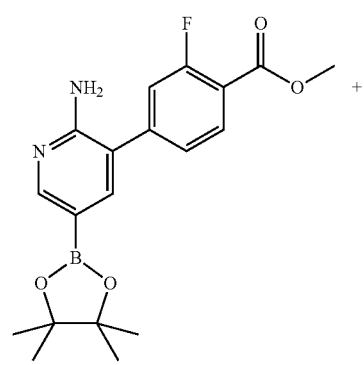

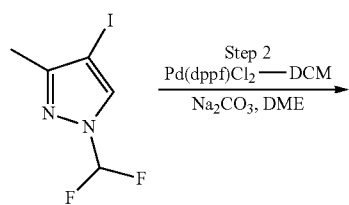

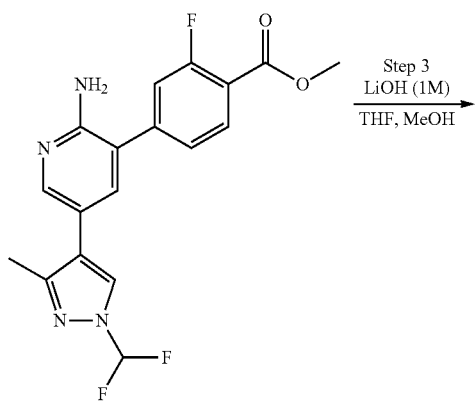

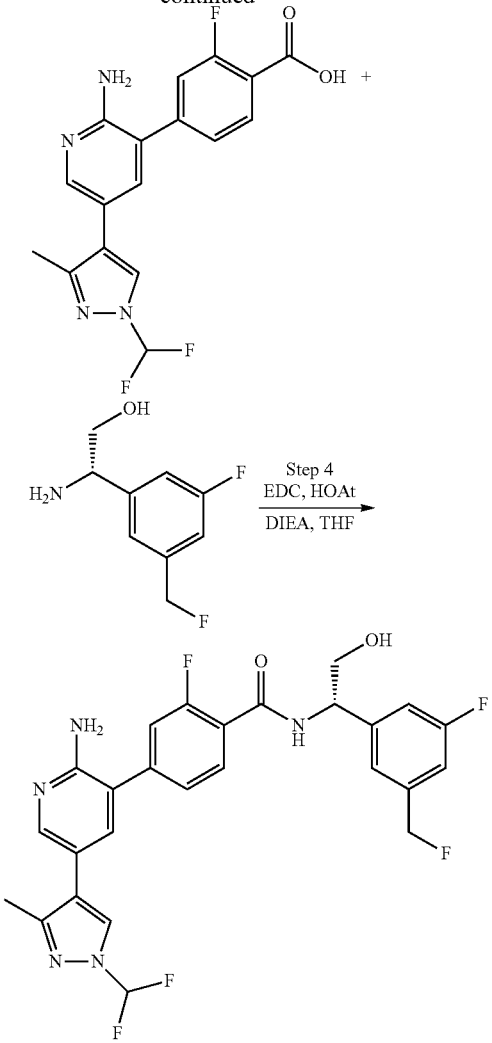

Step 1. methyl 4-(2-amino-5-(4,4,5,5-tetramethyl-1,3,2-dioxaborolan-2-yl)pyridin-3-yl)-2-fluorobenzoate A mixture of methyl 4-(2-amino-5-bromopyridin-3-yl)-2-fluorobenzoate (2 g, 6.15 mmol), B₂(PIN)₂ (3.12 g, 12.30 mmol), PdCl₂(dppf) (0.225 g, 0.308 mmol), KOAc (1.811 g, 18.45 mmol) and dioxane (30.8 mL) was heated at oil bath overnight at 100° C. The reaction mixture was extracted with EtOAc. The organic layer was washed with water and brine, dried over Na₂SO₄, filtered off and concentrated in vacuo. To the crude product, ether was added. The insoluble material was filtered off to provide methyl 4-(2-amino-5-(4,4,5,5-tetramethyl-1,3,2-dioxaborolan-2-yl)pyridin-3-yl)-2-fluorobenzoate as a brown solid (79%). LCMS (m/z): 291.2 (MH⁺), 0.44 min (for boronic acid).

Step 2. methyl 4-(2-amino-5-(1-methyl-1H-pyrazol-4-yl)pyridin-3-yl)-2-fluorobenzoate A mixture of crude methyl 4-(2-amino-5-(4,4,5,5-tetramethyl-1,3,2-dioxaborolan-2-yl)pyridin-3-yl)-2-fluorobenzoate (712 mg, 1.912 mmol), 1-(difluoromethyl)-4-iodo-3-methyl-1H-pyrazole (740 mg, 2.87 mmol), PdCl₂(dppf)

(70.0 mg, 0.096 mmol), DME (7.899 mL), and 2M Na₂CO₃ (3.95 mL) was heated at 100° C. overnight. After adding Na₂SO₄ followed by dilution with EtOAc, the reaction mixture was filtered off and the resulting volatile materials were concentrated in vacuo. The crude product was purified by flash chromatography eluting with 0-100% of EtOAc in DCM. LCMS (m/z): 491.1 (MH⁺), 0.64 min Step 3. 4-(2-amino-5-(1-methyl-1H-pyrazol-4-yl)pyridin-3-yl)-2-fluorobenzoic acid To a solution of methyl 4-(2-amino-5-(1-(difluoromethyl)-3-methyl-1H-pyrazol-4-yl)pyridin-3-yl)-2-fluorobenzoate (352 mg, 0.935 mmol) in THF (6236 µL) and MeOH (3118 µL) was added LiOH (1 M solution) (1684 µL, 1.684 mmol). The reaction mixture was stirred at room temperature. To the reaction mixture, 1 N HCl was added up to pH 5. The reaction mixture was extracted with EtOAc. The organic layer was dried over anhydrous sodium sulfate, filtered off, and concentrated in vacuo to provide crude 4-(2-amino-5-(1-(difluoromethyl)-3-methyl-1H-pyrazol-4-yl)pyridin-3-yl)-2-fluorobenzoic acid (88%). LCMS (m/z): 363.3 (MH⁺), 0.51 min.

Step 4. (S)-4-(2-amino-5-(1-methyl-1H-pyrazol-4-yl)pyridin-3-yl)-N-(1-(3-chlorophenyl)-2-hydroxyethyl)-2-fluorobenzamide To a solution of 4-(2-amino-5-(1-(difluoromethyl)-3-methyl-1H-pyrazol-4-yl)pyridin-3-yl)-2-fluorobenzoic acid (25 mg, 0.069 mmol) in DMF were added (S)-2-amino-2-(3-fluoro-5-(fluoromethyl)phenyl)ethanol (15.50 mg, 0.083 mmol), EDC, HOAt, and DIEA. The reaction mixture was stirred for 15 h. After water was added, the reaction mixture was worked up with EtOAc. The organic layer was dried over Na₂SO₄, filtered off and concentrated in vacuo. The crude product was purified by reverse phase prep HPLC. The pure fractions were lyophilized to provide (S)-4-(2-amino-5-(1-(difluoromethyl)-3-methyl-1H-pyrazol-4-yl)pyridin-3-yl)-2-fluoro-N-(1-(3-fluoro-5-(fluoromethyl)phenyl)-2-hydroxyethyl)benzamide as a TFA salt (50%). LCMS (m/z): 532.2 (MH⁺), 0.65 min; 1H NMR (400 MHz, CD₃OD) δ ppm 8.23 (m, 1H), 7.97 (m, 1H), 7.93 (m, 1H), 7.82 (m, 1H), 7.51-7.30 (m, 3H), 7.2 (m, 1H), 7.09 (d, J=8 Hz, 1H), 6.98 (d, J=12 Hz, 1H), 5.30 (d, J=44 Hz, 2H), 5.14 (m, 1H), 3.8 (m, 2H), 2.32 (s, 3H).

Synthesis of 4-(2-amino-5-(1-(difluoromethyl)-5-methyl-1H-pyrazol-4-yl)pyridin-3-yl)-2-fluorobenzoic acid

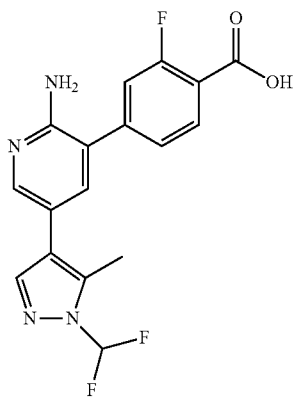 [SMILES: Cc1c(-c2cnc(N)c(-c3ccc(C(=O)O)c(F)c3)c2)cnn1C(F)F]

Following Steps 2 and 3 in Scheme 97, using 1,5-dimethyl-4-(4,4,5,5-tetramethyl-1,3,2-dioxaborolan-2-yl)-1H-pyrazole, 4-(2-amino-5-(1-(difluoromethyl)-5-methyl-1H-pyrazol-4-yl)pyridin-3-yl)-2-fluorobenzoic acid was obtained. LCMS (m/z): 363.1 (MH⁺), 0.53 min.

Synthesis of 4-(2-amino-5-(1-methyl-1H-1,2,3-triazol-5-yl)pyridin-3-yl)-2-fluorobenzoic acid

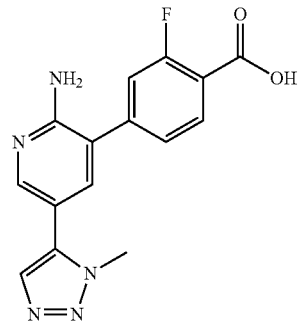

Following Steps 2 and 3 in Scheme 97, using 5-iodo-1-methyl-1H-1,2,3-triazole, 4-(2-amino-5-(1-methyl-1H-1,2,3-triazol-5-yl)pyridin-3-yl)-2-fluorobenzoic acid was obtained. LCMS (m/z): 314.3 (MH⁺), 0.38 min.

Synthesis of 4-(2-amino-5-(1,5-dimethyl-1H-pyrazol-4-yl)pyridin-3-yl)-2-fluorobenzoic acid

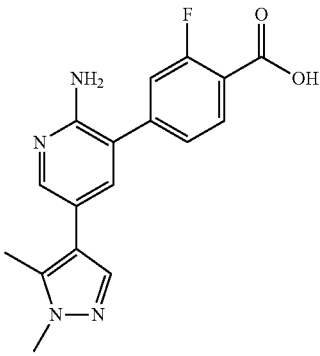 [SMILES: Cc1c(-c2cnc(N)c(-c3ccc(C(=O)O)c(F)c3)c2)cnn1C]

Following Steps 1 and 2 in Scheme 97, using methyl 4-(2-amino-5-bromopyridin-3-yl)-2-fluorobenzoate and 1,5-dimethyl-4-(4,4,5,5-tetramethyl-1,3,2-dioxaborolan-2-yl)-1H-pyrazole, 4-(2-amino-5-(1,5-dimethyl-1H-pyrazol-4-yl)pyridin-3-yl)-2-fluorobenzoic acid was obtained. LCMS (m/z): 327.1 (MH⁺), 0.45 min.

Synthesis of 4-(2-amino-5-(1,5-dimethyl-1H-pyrazol-4-yl)pyridin-3-yl)-2-fluorobenzoic acid

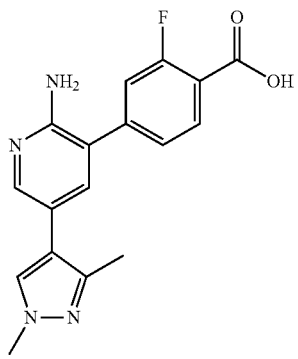 [SMILES: Cc1nn(C)cc1-c1cnc(N)c(-c2ccc(C(=O)O)c(F)c2)c1]

Following Steps 2 and 3 in Scheme 97, using methyl 4-(2-amino-5-bromopyridin-3-yl)-2-fluorobenzoate and 1,3-dimethyl-4-(4,4,5,5-tetramethyl-1,3,2-dioxaborolan-2-yl)-1H-pyrazole, 4-(2-amino-5-(1,3-dimethyl-1H-pyrazol-4-yl)pyridin-3-yl)-2-fluorobenzoic acid was obtained. LCMS (m/z): 327.2 (MH$^+$), 0.47 min.

Synthesis of 4-(2-amino-5-(1,5-dimethyl-1H-pyrazol-4-yl)pyridin-3-yl)-2-fluorobenzoic acid

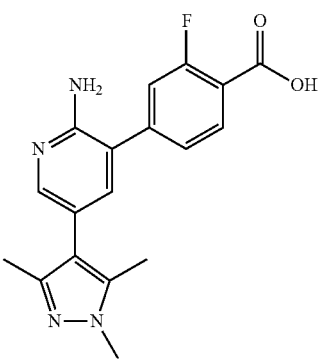 [SMILES: Cc1nn(C)c(C)c1-c1cnc(N)c(-c2ccc(C(=O)O)c(F)c2)c1]

Following Steps 2 and 3 in Scheme 97, using methyl 4-(2-amino-5-bromopyridin-3-yl)-2-fluorobenzoate and 4-bromo-1-(difluoromethyl)-5-methyl-1H-pyrazole, 4-(2-amino-5-(1,3-dimethyl-1H-pyrazol-4-yl)pyridin-3-yl)-2-fluorobenzoic acid was obtained. LCMS (m/z): 341.2 (MH$^+$), 0.47 min.

Synthesis of (3S,4R)-4-(4-chloro-3-fluorophenyl)-1-methylpyrrolidin-3-amine

Scheme 97b

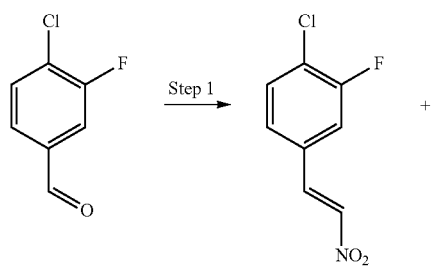

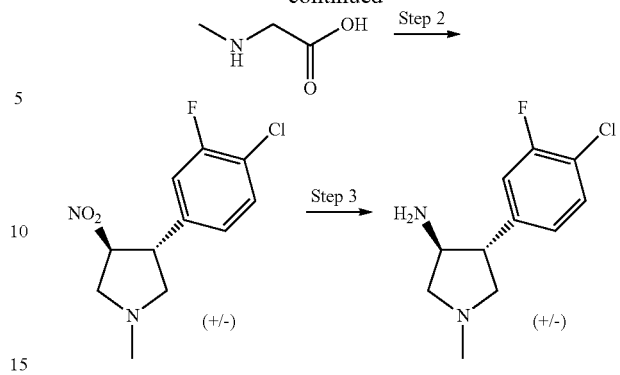

Step 1. (E)-1-chloro-2-fluoro-4-(2-nitrovinyl)benzene

To a solution of 4-chloro-3-fluorobenzaldehyde (8 g, 50.5 mmol) and ammonium acetate (9.72 g, 126 mmol) in acetic acid (168 mL) was added nitromethane (8.16 mL, 151 mmol). The reaction mixture was heated at reflux for 5 h and cooled down. Water (100 mL) was added, and the mixture was stirred at room temperature for 1 h. The solid was filtered, washed by water, and dried under vacuum. The solid was purified by flash chromatography (0-20% EtOAc/heptane) to yield clean product 4.2 g in 41% yield. $^1$H NMR (400 MHz, CDCl$_3$) δ ppm 7.92 (d, J=13.7 Hz, 1H), 7.54 (d, J=13.8 Hz, 1H), 7.49 (d, J=7.5 Hz, 1H), 7.33 (dd, J=2.0, 9.3 Hz, 1H), 7.31-7.28 (m, 1H).

Step 2. (+/−)-(3R,4S)-3-(4-chloro-3-fluorophenyl)-1-methyl-4-nitropyrrolidine (E)-1-chloro-2-fluoro-4-(2-nitrovinyl)benzene (4.2 g, 20.84 mmol), 2-(methylamino)acetic acid (4.64 g, 52.1 mmol), paraformaldehyde (3.75 g, 125 mmol) were mixed in dry toluene (104 mL). The reaction mixture was heated at reflux using Dean-stark overnight. The reaction mixture was partitioned between EtOAc and water. The organic was washed by sat. NaCl, dried over Na$_2$SO$_4$ and concentrated. The crude material was purified by flash chromatography to yield (+/−)-(3R,4S)-3-(4-chloro-3-fluorophenyl)-1-methyl-4-nitropyrrolidine in 45% yield. LCMS (m/z): 259.2 (MH$^+$), 0.52 min; $^1$H NMR (400 MHz, CDCl$_3$) δ ppm 7.37 (t, J=8.0 Hz, 1H), 7.15 (dd, J=2.0, 10.2 Hz, 1H), 7.09-7.01 (m, 1H), 4.91-4.82 (m, 1H), 3.98 (d, J=5.1 Hz, 1H), 3.34 (dd, J=4.1, 10.8 Hz, 1H), 3.23 (t, J=8.6 Hz, 1H), 3.10 (dd, J=7.8, 10.6 Hz, 1H), 2.63 (dd, J=7.0, 9.4 Hz, 1H), 2.44 (s, 3H).

Step 3. (+/−)-(3S,4R)-4-(4-chloro-3-fluorophenyl)-1-methylpyrrolidin-3-amine

Zinc dust (5.76 g, 88 mmol) was added into a mixture of (+/−)-(3R,4S)-3-(4-chloro-3-fluorophenyl)-1-methyl-4-nitropyrrolidine (2.28 g, 8.81 mmol) in MeOH (29.4 mL) and acetic acid (30 mL, 524 mmol). The reaction mixture was stirred at room temperature for 5 h and filtered. Solvent was removed under vacuum. The residue was neutralized to pH 9, then extracted by IPA:CHCl$_3$ (3:7). The organic was dried over Na$_2$SO$_4$, filtered and concentrated. The crude product was purified by flash chromatography (DCM/Methanol/NH$_3$ 90:9:1) to obtain (+/−)-(3S,4R)-4-(4-chloro-3-fluorophenyl)-1-methylpyrrolidin-3-amine in 40% yield. LCMS (m/z): 229.2 (MH$^+$), 0.25 min.

363

Synthesis of (+/−)-(3S,4R)-4-(3-chloro-4-fluorophenyl)-1-methylpyrrolidin-3-amine

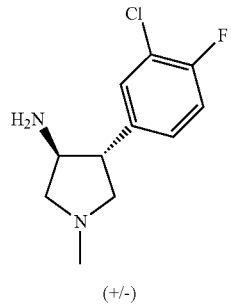

(+/−)

Following Scheme 97b, using 3-chloro-4-fluorobenzaldehyde (3.92 g, 24.72 mmol), (+/−)-(3S,4R)-4-(3-chloro-4-fluorophenyl)-1-methylpyrrolidin-3-amine was obtained. LCMS (m/z): 229.0 (MH+), 0.32 min.

Examples 207 and 208

Synthesis of trans-4-(2-amino-5-(1-methyl-1H-pyrazol-4-yl)pyridin-3-yl)-N-((3S,4R)-4-(3-chloro-4-fluorophenyl)-1-methylpyrrolidin-3-yl)-2-fluorobenzamide and trans-4-(2-amino-5-(1-methyl-1H-pyrazol-4-yl)pyridin-3-yl)-N-((3R,4S)-4-(3-chloro-4-fluorophenyl)-1-methylpyrrolidin-3-yl)-2-fluorobenzamide Scheme 98

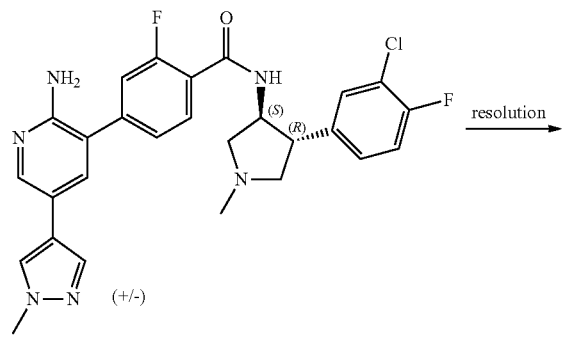

(+/−)

resolution

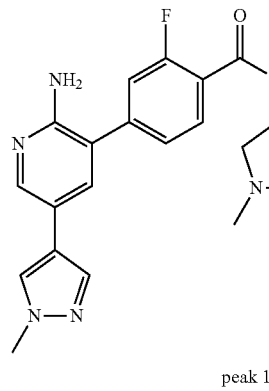

peak 1

364

-continued

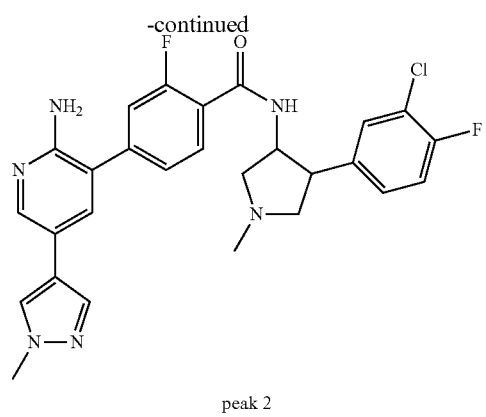

peak 2

Followed Step 2 in Scheme 89, using (+/−)-(3S,4R)-4-(3-chloro-4-fluorophenyl)-1-methylpyrrolidin-3-amine, 4-(2-amino-5-(1-methyl-1H-pyrazol-4-yl)pyridin-3-yl)-N-((3S,4R)-4-(3-chloro-4-fluorophenyl)-1-methylpyrrolidin-3-yl)-2-fluorobenzamide was obtained in 70% yield. LCMS (m/z): 523.3 (MH+), 0.56 min. The crude racemic mixture was resolved by chiral SFC (ChiralPak 5mic OD column, 4.6×100 (mm), IPA+0.1% DEA=30%, 5 mL/min). For polar diastereomer (Rt=2.37 min), LCMS (m/z): 523.2 (MH+), 0.57 min; $^1$H NMR (400 MHz, CD$_3$OD) δ ppm 8.19 (d, J=2.0 Hz, 1H), 7.91 (s, 1H), 7.79-7.73 (m, 2H), 7.63 (d, J=2.3 Hz, 1H), 7.52 (dd, J=2.3, 7.0 Hz, 1H), 7.46-7.29 (m, 3H), 7.26-7.13 (m, 1H), 4.66 (d, J=6.3 Hz, 1H), 3.45-3.37 (m, 1H), 3.21 (t, J=9.0 Hz, 1H), 3.16-3.08 (m, 1H), 2.82 (dd, J=5.7, 10.0 Hz, 1H), 2.70 (t, J=9.2 Hz, 1H), 2.54-2.41 (m, 3H), 1.27 (d, J=17.6 Hz, 1H). For less polar diastereomer (Rt=3.96 min), LCMS (m/z): 523.2 (MH+), 0.58 min; $^1$H NMR (400 MHz, CD$_3$OD) δ ppm 8.19 (d, J=2.0 Hz, 1H), 7.91 (s, 1H), 7.79-7.73 (m, 2H), 7.63 (d, J=2.3 Hz, 1H), 7.52 (dd, J=2.3, 7.0 Hz, 1H), 7.46-7.29 (m, 3H), 7.26-7.13 (m, 1H), 4.66 (d, J=6.3 Hz, 1H), 3.45-3.37 (m, 1H), 3.21 (t, J=9.0 Hz, 1H), 3.16-3.08 (m, 1H), 2.82 (dd, J=5.7, 10.0 Hz, 1H), 2.70 (t, J=9.2 Hz, 1H), 2.54-2.41 (m, 3H), 1.27 (d, J=17.6 Hz, 1H).

Examples 209 and 210

Synthesis of trans-4-(2-amino-5-(1-methyl-1H-pyrazol-4-yl)pyridin-3-yl)-N-((3S,4R)-4-(4-chloro-3-fluorophenyl)-1-methylpyrrolidin-3-yl)-2-fluorobenzamide and trans-4-(2-amino-5-(1-methyl-1H-pyrazol-4-yl)pyridin-3-yl)-N-((3R,4S)-4-(4-chloro-3-fluorophenyl)-1-methylpyrrolidin-3-yl)-2-fluorobenzamide Scheme 99

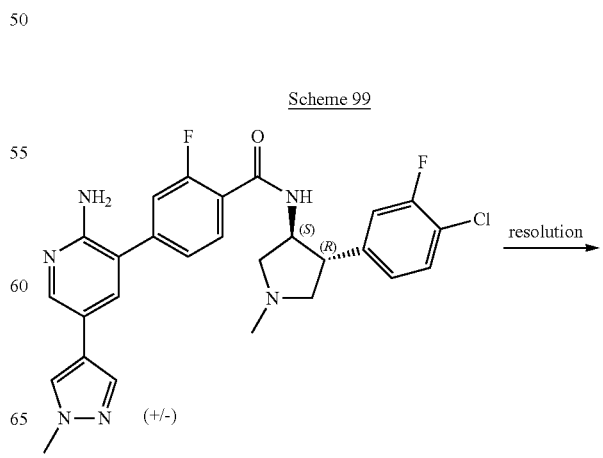

(+/−)

resolution

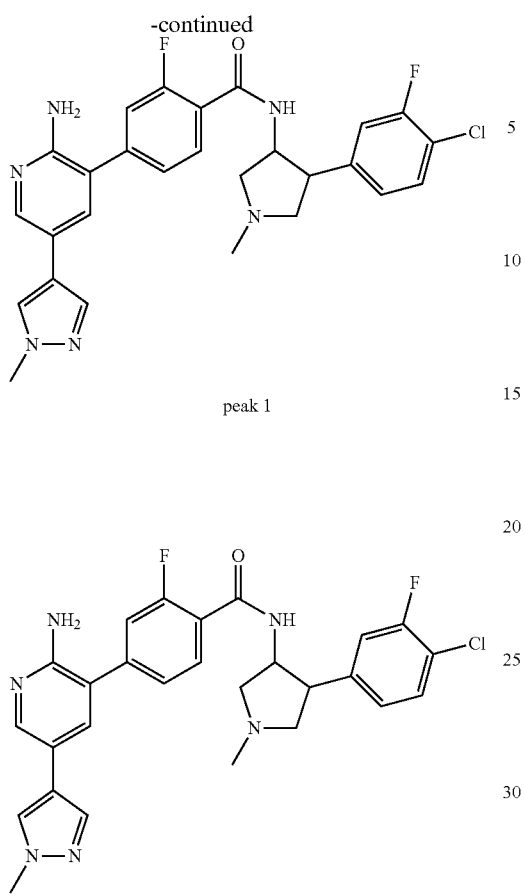

peak 1 peak 2

Following Step 2 in Scheme 86, using (3S,4R)-4-(4-chloro-3-fluorophenyl)-1-methylpyrrolidin-3-amine, (+/−)-4-(2-amino-5-(1-methyl-1H-pyrazol-4-yl)pyridin-3-yl)-N-((3S,4R)-4-(4-chloro-3-fluorophenyl)-1-methylpyrrolidin-3-yl)-2-fluorobenzamide was obtained in 79% yield. LCMS (m/z): 523.2 (MH+), 0.57 min. The crude racemic mixture was resolved by chiral SFC (ChiralPak 5mic OD column, 4.6×100 (mm), IPA+0.1% DEA=30%, 5 mL/min). For polar diastereomer (Rt=2.45 min), LCMS (m/z): 523.2 (MH+), 0.58 min; $^1$H NMR (400 MHz, CD$_3$OD) δ ppm 8.18 (d, J=2.2 Hz, 1H), 7.90 (s, 1H), 7.80-7.72 (m, 2H), 7.66-7.61 (m, 1H), 7.44-7.36 (m, 3H), 7.33-7.29 (m, 1H), 7.19 (dd, J=1.8, 8.3 Hz, 1H), 4.71-4.62 (m, 1H), 3.90 (s, 3H), 3.44-3.37 (m, 1H), 3.22 (d, J=9.6 Hz, 1H), 3.12 (dd, J=7.9, 10.0 Hz, 1H), 2.86-2.80 (m, 1H), 2.74-2.67 (m, 1H), 2.51-2.44 (m, 3H). For less polar diastereomer (Rt=3.92 min), LCMS (m/z): 523.2 (MH+), 0.58 min; 1H NMR (400 MHz, CD$_3$OD) δ ppm 8.19 (d, J=2.2 Hz, 1H), 7.90 (s, 1H), 7.80-7.70 (m, 2H), 7.63 (d, J=2.2 Hz, 1H), 7.46-7.36 (m, 3H), 7.30 (dd, J=2.0, 10.6 Hz, 1H), 7.19 (dd, J=1.8, 8.4 Hz, 1H), 4.66 (d, J=5.9 Hz, 1H), 3.91 (s, 3H), 3.44-3.36 (m, 1H), 3.19 (t, J=9.0 Hz, 1H), 3.11 (dd, J=7.8, 10.0 Hz, 1H), 2.83-2.78 (m, 1H), 2.69 (dd, J=8.4, 9.5 Hz, 1H), 2.45 (s, 3H).

Synthesis of 4-(3-amino-6-cyclopropylpyrazin-2-yl)-2-fluorobenzoic acid

Scheme 100

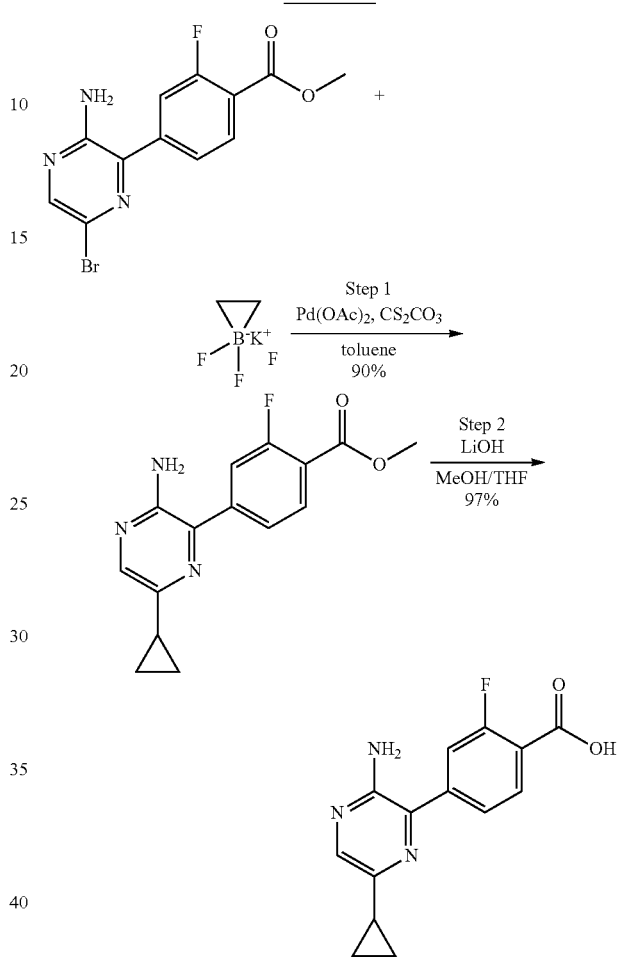

Step 1. methyl 4-(3-amino-6-cyclopropylpyrazin-2-yl)-2-fluorobenzoate

To methyl 4-(3-amino-6-bromopyrazin-2-yl)-2-fluorobenzoate (for synthesis see Example 34, Step 2) (300 mg, 0.920 mmol) in toluene (10 mL) and water (1 mL) was added potassium cyclopropyl trifluoroborate (408 mg, 2.76 mmol), di(1-adamantyl)-n-butylphosphine (66.0 mg, 0.184 mmol), cesium carbonate (1499 mg, 4.60 mmol), and palladium(II) acetate (20.65 mg, 0.092 mmol). The reaction mixture was heated in heating block at 100° C. overnight. The reaction mixture was quenched with sat. NH$_4$Cl and extracted with ethyl acetate. The organic extracts were combined, washed with brine, dried over sodium sulfate, filtered and evaporated. The crude was purified by flash chromatography (0 to 80% EtOAc in heptane) yielding methyl 4-(3-amino-6-cyclopropylpyrazin-2-yl)-2-fluorobenzoate (250 mg, 90%). LCMS (m/z): 288.2 (MH+), 0.756 min.

Step 2. 4-(3-amino-6-cyclopropylpyrazin-2-yl)-2-fluorobenzoic acid

To methyl 4-(3-amino-6-cyclopropylpyrazin-2-yl)-2-fluorobenzoate (250 mg, 0.870 mmol) in THF (6 mL) and MeOH (3 mL) was added 1M LiOH (1.740 mL, 1.740 mmol). The reaction mixture was stirred at room temperature for 2 h. The pH of reaction mixtures was adjusted to ~4 by aqueous. 2N HCl. The reaction mixture was partitioned between EtOAc and water. The organic layer was separated, washed with brine, dried over sodium sulfate, filtered and evaporated to yield 4-(3-amino-6-cyclopropylpyrazin-2-yl)-2-fluorobenzoic acid (230 mg, 97%) as a light yellow solid. LCMS (m/z): 274.2 (MH$^+$), 0.621 min.

Synthesis of 4-(2-amino-5-cyclopropylpyridin-3-yl)-2-fluorobenzoic acid

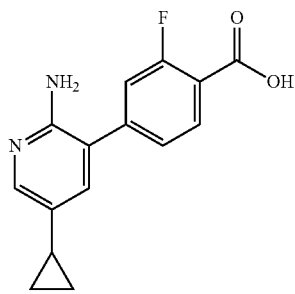 [SMILES: Nc1ncc(C2CC2)cc1-c1ccc(C(=O)O)c(F)c1]

Following Scheme 100, using methyl 4-(2-amino-5-bromopyridin-3-yl)-2-fluorobenzoate, 4-(2-amino-5-cyclopropylpyridin-3-yl)-2-fluorobenzoic acid was obtained (80%). LCMS (m/z): 273.0 (MH$^+$), 0.515 min.

Synthesis of 4-(3-amino-6-cyclohexylpyrazin-2-yl)-2-fluorobenzoic acid

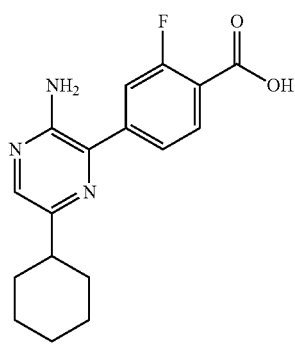 [SMILES: Nc1ncc(C2CCCCC2)nc1-c1ccc(C(=O)O)c(F)c1]

Following Steps 1, 2 and 3 in Scheme 66, using 2-(cyclohex-1-en-1-yl)-4,4,5,5-tetramethyl-1,3,2-dioxaborolane, 4-(3-amino-6-cyclohexylpyrazin-2-yl)-2-fluorobenzoic acid was obtained. LCMS (m/z): 316.3 (MH$^+$), 0.79 min.

Example 211

Synthesis of 4-(2-amino-5-((1S,4r)-1-oxidotetrahydro-2H-thiopyran-4-yl)pyridin-3-yl)-N-((S)-1-(3-chlorophenyl)-2-hydroxyethyl)-2-fluorobenzamide Scheme 101

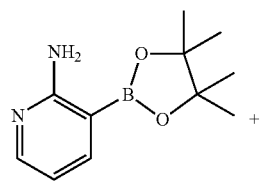

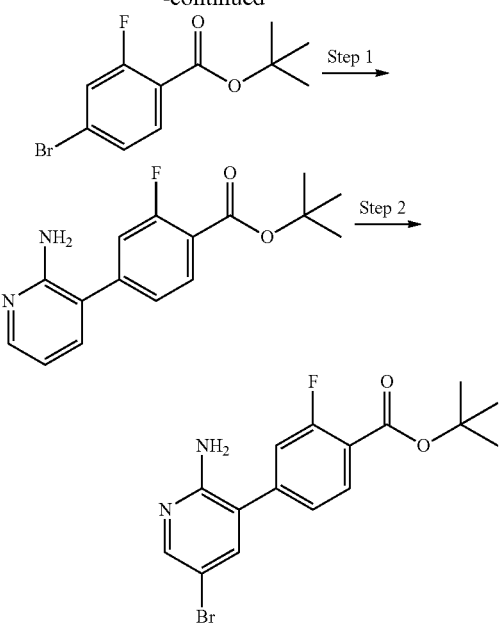

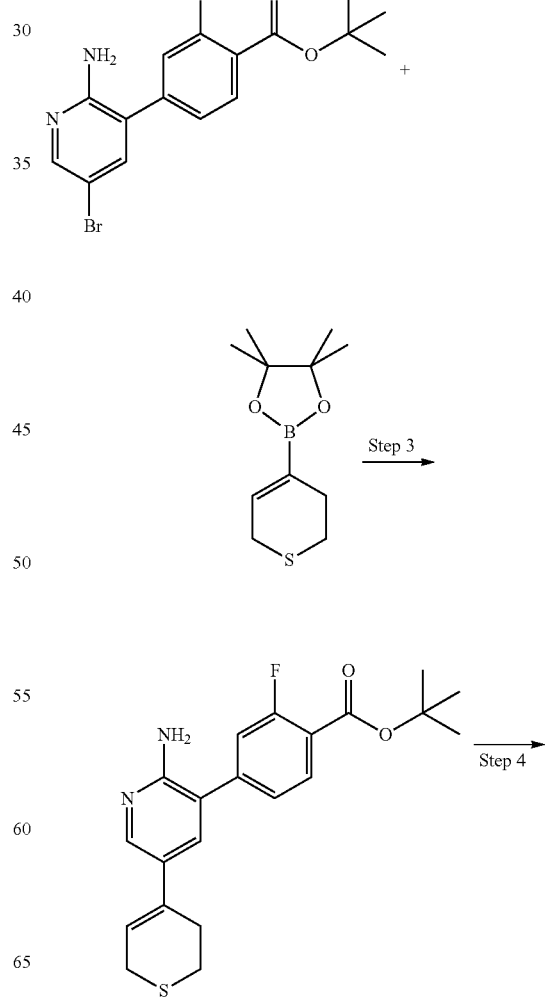

369

-continued

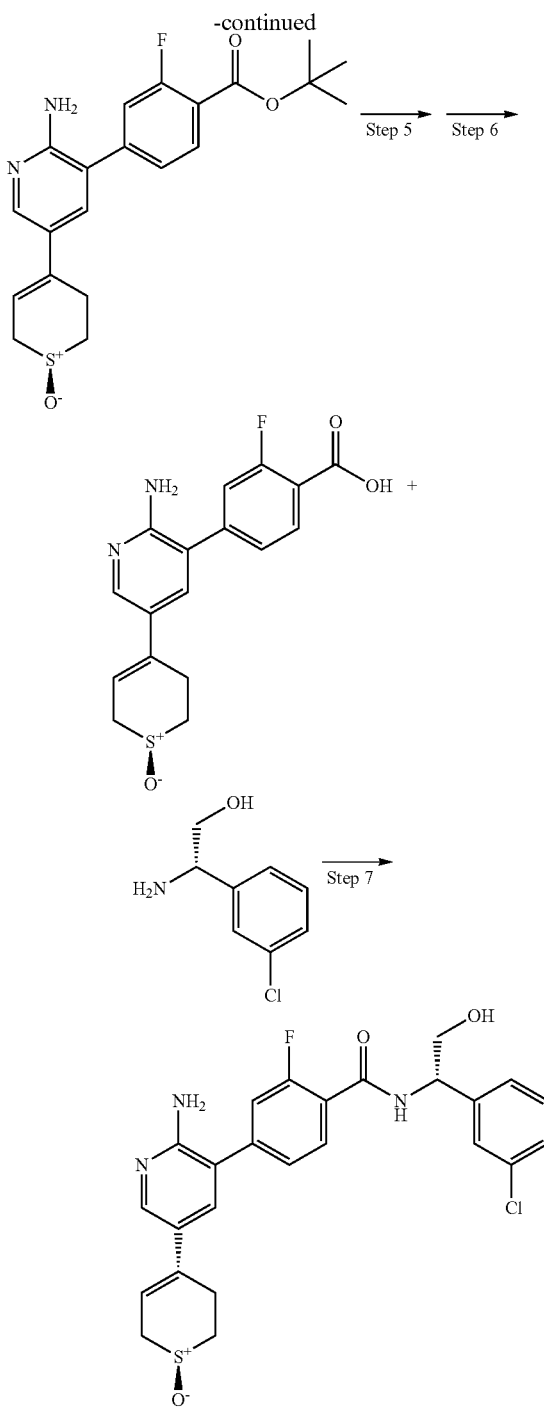

Step 1. tert-butyl 4-(2-aminopyridin-3-yl)-2-fluorobenzoate

A degassed mixture of 3-(4,4,5,5-tetramethyl-1,3,2-dioxaborolan-2-yl)pyridin-2-amine (2.4 g, 10.91 mmol), tert-butyl 4-bromo-2-fluorobenzoate (3.30 g, 12.00 mmol), Pd(PPh₃)₄ (0.63 mg, 0.0545 mmol), 2.0 M Na₂CO₃ aqueous solution (10.91 mL) in n-butanol (26 mL) was microwave heated to 130° C. for 10 min. The reaction was diluted with ethyl acetate (30 mL), and then washed with water (10 mL) and brine (10 mL). The organics were dried over sodium sulfate, filtered, concentrated, and then purified by flash

370 chromatography (10-60% ethyl acetate/heptane eluent) to provide tert-butyl 4-(2-aminopyridin-3-yl)-2-fluorobenzoate (1.35 g, 43% yield). LCMS (m/z): 289.4 (MH⁺), 0.67 min.

Step 2. tert-butyl 4-(2-amino-5-bromopyridin-3-yl)-2-fluorobenzoate

A solution of tert-butyl 4-(2-aminopyridin-3-yl)-2-fluorobenzoate (700 mg, 2.43 mmol) in acetonitrile (10 mL) was treated with NBS (453 mg, 2.55 mmol). After 10 min, the reaction was completed. The reaction was treated with 1:1 sat. aq. NaHCO₃: sat.aq. Na₂S₂O₃ (10 mL). The mixture was stirred vigorously for 10 min. The mixture was diluted with ethyl acetate (30 mL) and the layers were separated. The organics were washed with brine, dried over magnesium sulfate, filtered and concentrated to provide tert-butyl 4-(2-amino-5-bromopyridin-3-yl)-2-fluorobenzoate (803 mg, 90% yield). LCMS (m/z): 367.2, 369.2 (MH⁺), 0.75 min.

Step 3. tert-butyl 4-(2-amino-5-(3,6-dihydro-2H-thiopyran-4-yl)pyridin-3-yl)-2-fluorobenzoate A degassed mixture of tert-butyl 4-(2-amino-5-bromopyridin-3-yl)-2-fluorobenzoate (400 mg, 1.09 mmol), 2-(3,6-dihydro-2H-thiopyran-4-yl)-4,4,5,5-tetramethyl-1,3,2-dioxaborolane (296 mg, 1.31 mmol), Pd(PPh₃)₄ (126 mg, 0.109 mmol) in 2.0 M Na₂CO₃ aqueous solution (1.63 mL) and n-butanol (5 mL) was microwave heated to 130° C. for 15 min. The reaction was diluted with ethyl acetate (20 mL), and then washed with water (10 mL) and brine (10 mL). The organics were dried over sodium sulfate, filtered, concentrated, and then purified by flash chromatography (10-60% ethyl acetate/heptane eluent) to provide tert-butyl 4-(2-amino-5-(3,6-dihydro-2H-thiopyran-4-yl)pyridin-3-yl)-2-fluorobenzoate (400 mg, 95% yield). LCMS (m/z): 387.1 (MH⁺), 0.87 min; 1H NMR (400 MHz, CD₃OD) δ ppm 7.83-7.76 (m, 2H), 7.68 (d, J=1.96 Hz, 1H), 7.37-7.34 (m, 1H), 7.33-7.29 (m, 2H), 7.28-7.24 (m, 2H), 7.24-7.18 (m, 1H), 5.10 (t, J=5.87 Hz, 1H), 3.83-3.69 (m, 2H), 2.81-2.70 (m, 2H), 2.63-2.49 (m, 3H), 2.08 (dd, J=2.74, 13.30 Hz, 2H), 1.72 (dq, J=2.93, 12.59 Hz, 2H).

Step 4. tert-butyl 4-(2-amino-5-(1-oxido-3,6-dihydro-2H-thiopyran-4-yl)pyridin-3-yl)-2-fluorobenzoate A 0° C. solution of 4-(2-amino-5-(3,6-dihydro-2H-thiopyran-4-yl)pyridin-3-yl)-2-fluorobenzoate in acetone (20 mL) was treated with a solution of oxone (227 mg, 0.369 mmol) in water (5 mL). After 20 min, the reaction was diluted with ethyl acetate (50 mL) and water (50 mL). The layers were separated and the aqueous layer was washed with ethyl acetate (50 mL). The combined organics were washed with water (30 mL) and brine (30 mL), dried over magnesium sulfate, filtered and concentrated to provide tert-butyl 4-(2-amino-5-(1-oxido-3,6-dihydro-2H-thiopyran-4-yl)pyridin-3-yl)-2-fluorobenzoate (220 mg, 74% yield). LCMS (m/z): 403.5 (MH⁺), 0.66 min.

Step 5. tert-butyl 4-(2-amino-5-((1r,4r)-1-oxidotetrahydro-2H-thiopyran-4-yl)pyridin-3-yl)-2-fluorobenzoate A degassed slurry of tert-butyl 4-(2-amino-5-(1-oxido-3,6-dihydro-2H-thiopyran-4-yl)pyridin-3-yl)-2-fluorobenzoate (220 mg, 0.547 mmol) in methanol (15 mL) was treated with 1.0 N HCl aqueous solution (0.82 mL) and 10%

371

Pd(OH)$_2$. The vessel was charged with hydrogen to 250 PSI. After 2 h, the reaction was completed. The slurry was degassed, filtered over celite and concentrated to provide tert-butyl 4-(2-amino-5-((1r,4r)-1-oxidotetrahydro-2H-thiopyran-4-yl)pyridin-3-yl)-2-fluorobenzoate (150 mg, 68% yield). LCMS (m/z): 405.6 (MH$^+$), 0.63 min.

Step 6. 4-(2-amino-5-((1r,4r)-1-oxidotetrahydro-2H-thiopyran-4-yl)pyridin-3-yl)-2-fluorobenzoic acid-TFA A room temperature solution of tert-butyl 4-(2-amino-5-((1r,4r)-1-oxidotetrahydro-2H-thiopyran-4-yl)pyridin-3-yl)-2-fluorobenzoate (50 mg, 0.124 mmol) in DCM (2 mL) was treated with TFA (1 mL). After 1 h, the reaction was concentrated. The resulting material was slurried in benzene with sonication, and then concentrated again to provide 4-(2-amino-5-((1r,4r)-1-oxidotetrahydro-2H-thiopyran-4-yl)pyridin-3-yl)-2-fluorobenzoic acid-TFA (57 mg, 100% yield). LCMS (m/z): 349.2 (MH$^+$), 0.37 min.

Step 7. 4-(2-amino-5-((1S,4r)-1-oxidotetrahydro-2H-thiopyran-4-yl)pyridin-3-yl)-N-((S)-1-(3-chlorophenyl)-2-hydroxyethyl)-2-fluorobenzamide A solution of 4-(2-amino-5-((1r,4r)-1-oxidotetrahydro-2H-thiopyran-4-yl)pyridin-3-yl)-2-fluorobenzoic acid-TFA (57 mg, 0.123 mmol) and (S)-2-amino-2-(3-chlorophenyl)ethanol (25 mg, 0.148 mmol) in DMF (1 mL) was treated with HATU (61 mg, 0.160 mmol) and DIEA (129 µL, 0.738 mmol). After 1 h, the reaction was diluted with water (5 mL) and extracted into ethyl acetate (2×10 mL). The product was present in both layers. Therefore both the aqueous and organic layers were concentrated and purified by reverse phase prep HPLC to provide 4-(2-amino-5-((1S,4r)-1-oxidotetrahydro-2H-thiopyran-4-yl)pyridin-3-yl)-N-((S)-1-(3-chlorophenyl)-2-hydroxyethyl)-2-fluorobenzamide as a TFA salt (20 mg, 26% yield). LCMS (m/z): 502.1, 504.1 (MH$^+$), 0.57 min. 1H NMR (400 MHz, CD$_3$OD) δ ppm 8.63 (dd, J=4.11, 7.24 Hz, 1H), 7.90 (d, J=1.96 Hz, 1H), 7.80 (t, J=7.83 Hz, 1H), 7.76 (d, J=1.57 Hz, 1H), 7.38-7.31 (m, 3H), 7.29-7.25 (m, 2H), 7.24-7.17 (m, 1H), 5.14-5.06 (m, 1H), 3.83-3.70 (m, 2H), 3.06 (d, J=12.91 Hz, 2H), 2.85-2.70 (m, 3H), 2.38-2.24 (m, 2H), 1.83 (d, J=12.13 Hz, 2H).

Example 212

Synthesis of (S)-4-(2-amino-5-(tetrahydro-2H-thiopyran-4-yl)pyridin-3-yl)-N-(1-(3-chlorophenyl)-2-hydroxyethyl)-2-fluorobenzamide

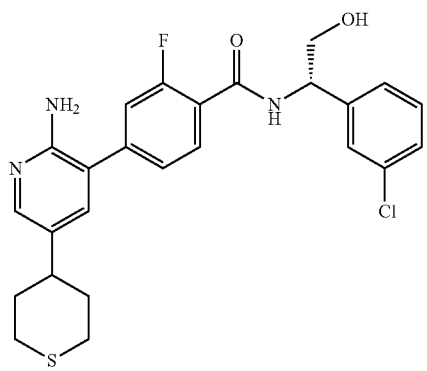 [SMILES: Nc1ncc(C2CCSCC2)cc1-c1ccc(C(=O)N[C@H](CO)c2cccc(Cl)c2)c(F)c1]

The reaction sequence depicted in Scheme 101, steps 5, 6, and 7 was applied to tert-butyl 4-(2-amino-5-(3,6-dihydro-2H-thiopyran-4-yl)pyridin-3-yl)-2-fluorobenzoate to obtain (S)-4-(2-amino-5-(tetrahydro-2H-thiopyran-4-yl)pyridin-3-yl)-N-(1-(3-chlorophenyl)-2-hydroxyethyl)-2-fluorobenzamide. LCMS (m/z): 486.0, 488.0 (MH$^+$), 0.73 min; 1H NMR (400 MHz, CD$_3$OD) δ ppm 7.83-7.76 (m, 2H), 7.68 (d, J=1.96 Hz, 1H), 7.37-7.34 (m, 1H), 7.33-7.29 (m, 2H), 7.28-7.24 (m, 2H), 7.24-7.18 (m, 1H), 5.10 (t, J=5.87 Hz, 1H), 3.83-3.69 (m, 2H), 2.81-2.70 (m, 2H), 2.63-2.49 (m, 3H), 2.08 (dd, J=2.74, 13.30 Hz, 2H), 1.72 (dq, J=2.93, 12.59 Hz, 2H).

Synthesis of 4-(2-amino-5-(1-methyl-1H-pyrazol-4-yl)pyridin-3-yl)-2-methylbenzoic acid Scheme 102

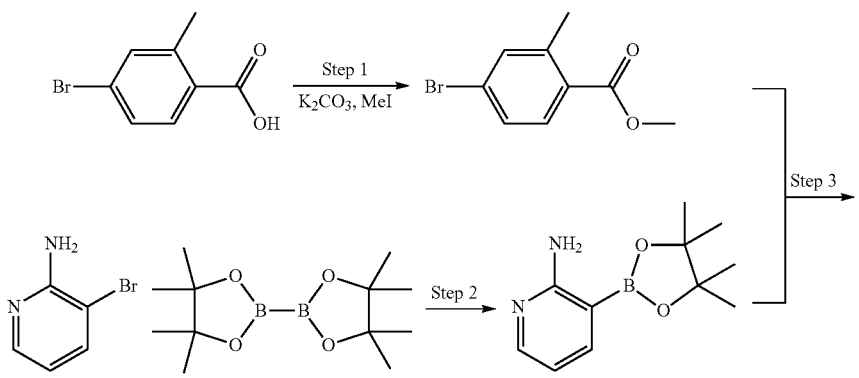

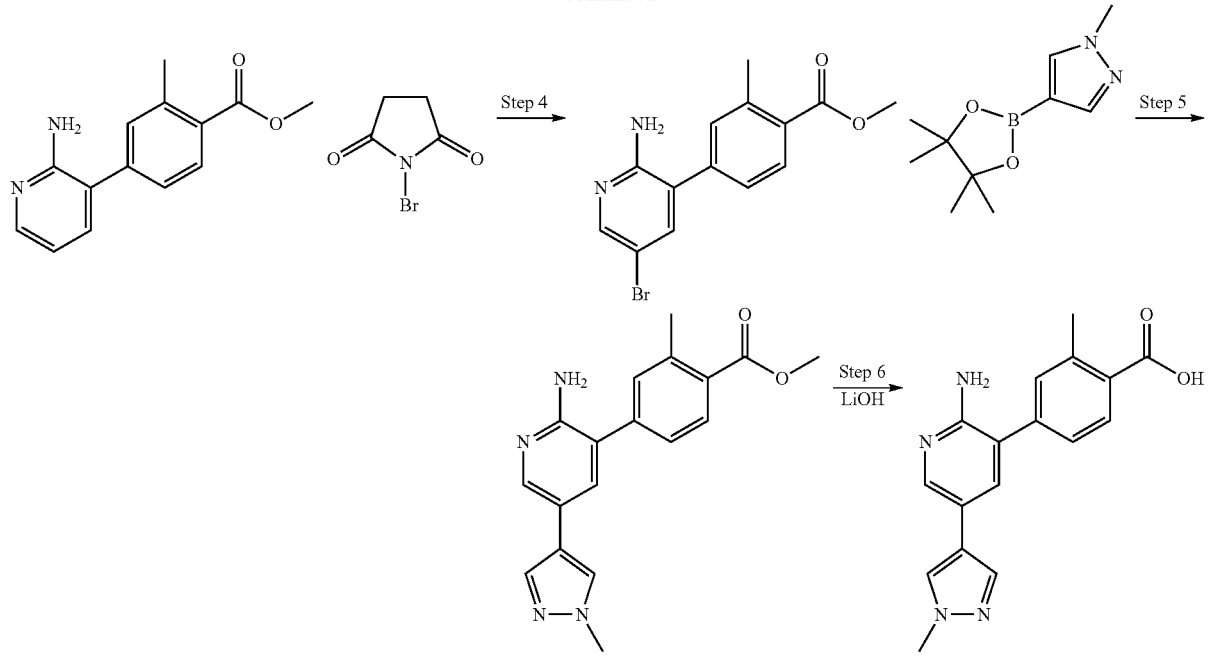

Step 1. methyl 4-bromo-2-methylbenzoate

A stirred mixture of 4-bromo-2-methylbenzoic acid (6 g, 27.9 mmol), iodomethane (5.21 mL, 84 mmol) and potassium carbonate (11.57 g, 84 mmol) in DMF (60 mL) was stirred at room temperature overnight. The reaction mixture was partitioned between water (250 mL) and 4:1 hexanes:ethyl acetate (650 mL). The organic layer was washed with water and dried over $Na_2SO_4$. The solvent was removed under vacuum to give 6.39 g of desired product as an oil in 100% yield. 1H NMR (400 MHz, $CD_3OD$) δ ppm 7.86-7.65 (m, 7 H) 7.50 (br. s., 2 H) 3.88 (s, 3H) 2.56 (s, 3 H).

Step 2. 3-(4,4,5,5-tetramethyl-1,3,2-dioxaborolan-2-yl)pyridin-2-amine

To a suspension of 3-bromopyridin-2-amine (6 g, 34.7 mmol) in 1,4-dioxane (87 mL) was added Bispin (13.21 g, 52.0 mmol) and potassium acetate (10.21 g, 104 mmol). The mixture was purged with nitrogen for 10 min, and then $PdCl_2$(dppf)-$CH_2Cl_2$ adduct (2.83 g, 3.47 mmol) was added. The reaction mixture was heated to 108° C. in an oil bath for 2-3 h. The reaction mixture was diluted with ethyl acetate, filtered through celite and concentrated. The residue was used in next step Suzuki coupling without further purification. LCMS (m/z): 139 (MH$^+$) 0.22 min (for boronic acid).

Step 3. methyl 4-(2-aminopyridin-3-yl)-2-methylbenzoate

To 3-(4,4,5,5-tetramethyl-1,3,2-dioxaborolan-2-yl)pyridin-2-amine (7.37 g, 33.5 mmol) in 500 mL round bottom flask were added methyl 4-bromo-2-methylbenzoate (6.390 g, 27.9 mmol), $PdCl_2$(dppf)-DCM (2.041 g, 2.79 mmol), DME (209 mL) and 2 M $Na_2CO_3$ solution (69.7 mL). The reaction mixture was bubbled through $N_2$ for 20 min and heated in an oil bath at 108° C. for 1.5 h. The reaction mixture was diluted with EtOAc, washed with water three times, dried over $Na_2SO_4$, filtered and concentrated. The crude product was purified by flash chromatography eluting with 0-100% of EtOAc (containing 10% of MeOH)/heptane to provide crude product around 8 g which contained fair amount of $B_2$(PIN)$_2$ from previous experiment. Ether was added to dissolve the crude mixture, and then heptane was added to crush out the desired product. Solid was filtered out to provide 4.2 g of desired product with high purity in 62.1% yield. LCMS (m/z): 243.5 (MH$^+$), 0.56 min.

Step 4. methyl 4-(2-amino-5-bromopyridin-3-yl)-2-methylbenzoate

To a solution of methyl 4-(2-aminopyridin-3-yl)-2-methylbenzoate (4.2 g, 17.34 mmol) in acetonitrile (173 mL) was added NBS (3.15 g, 17.68 mmol) in two portions at 0° C. The reaction mixture was stirred at 0° C. for 20 min. LCMS showed the reaction completed. After quenched with sat. $Na_2SO_3$ and $NaHCO_3$, the reaction mixture was stirred for 30 min. The reaction mixture was extracted with EtOAc 3 times, washed by sat $NaHCO_3$, water and brine. The organics was dried over $Na_2SO_4$, filtered and concentrated. The crude material was triturated with ether and taken to the next step without further purification. LCMS (m/z): 323.1 (MH$^+$), 0.68 min.

Step 5. methyl 4-(2-amino-5-(1-methyl-1H-pyrazol-4-yl)pyridin-3-yl)-2-methylbenzoate To methyl 4-(2-amino-5-bromopyridin-3-yl)-2-methylbenzoate (500 mg, 1.557 mmol) in 20 mL MW vial was added 1-methyl-4-(4,4,5,5-tetramethyl-1,3,2-dioxaborolan-2-yl)-1H-pyrazole (421 mg, 2.024 mmol), $PdCl_2$(dppf)DCM (114 mg, 0.156 mmol), DME (11.7 mL) and 2 M $Na_2CO_3$ solution (3.892 mL). The reaction mixture was heated at microwave synthesizer (12 min, 120° C.). The reaction mixture was diluted with EtOAc and washed with water three times, dried over $Na_2SO_4$, filtered and concentrated. The crude product was purified by flash chromatography eluting with 0-100% of EtOAc (containing 10% of MeOH)/ heptane to provide crude product which was triturated with ether to provide 400 mg of pure product in 80% yield. LCMS (m/z): 323.4 (MH+), 0.60 min.

Step 6. 4-(2-amino-5-(1-methyl-1H-pyrazol-4-yl)pyridin-3-yl)-2-methylbenzoic acid To a solution of methyl 4-(2-amino-5-(1-methyl-1H-pyrazol-4-yl)pyridin-3-yl)-2-methylbenzoate (1.20 g, 3.72 mmol) in THF/MeOH/H$_2$O (1:1:1, 36 mL) was added LiOH·H$_2$O (0.234 g, 5.58 mmol). The solution was stirred at room temperature overnight. The pH was adjusted to 3-5, optimally 4. All the organic solvents were removed by reduced pressure. EtOAc was added to triturate out all the impurities. Water was added and the mixture was stirred for 30 min. Solid was filtered and washed well with 50% of ether and water. The solid was then azotropied on rotovap with toluene to provide about 800 mg of desired acid in 69.7% yield. LCMS (m/z): 309.2 (MH+), 0.50 min.

Synthesis of 4-(2-amino-5-(1-ethyl-1H-pyrazol-4-yl)pyridin-3-yl)-2-fluorobenzoic acid

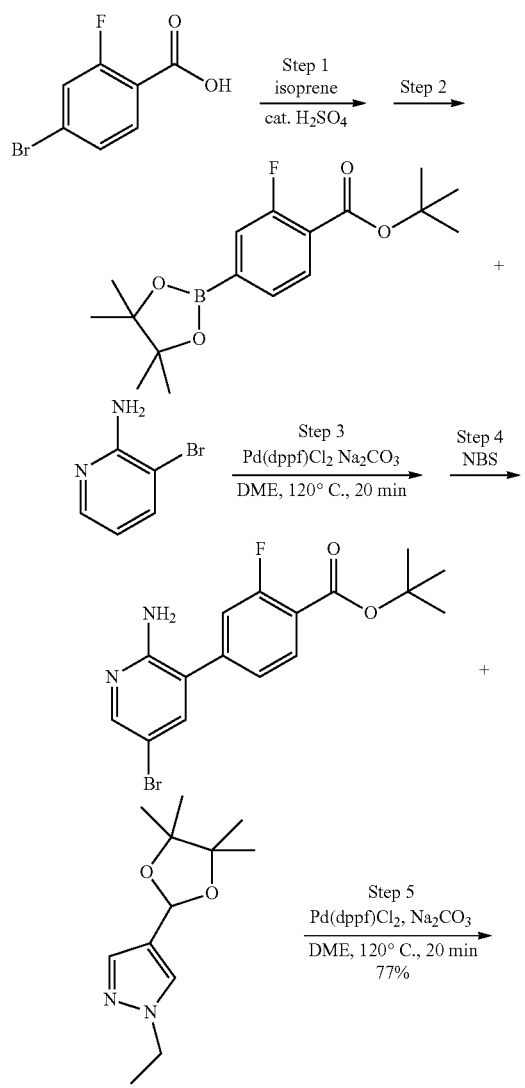

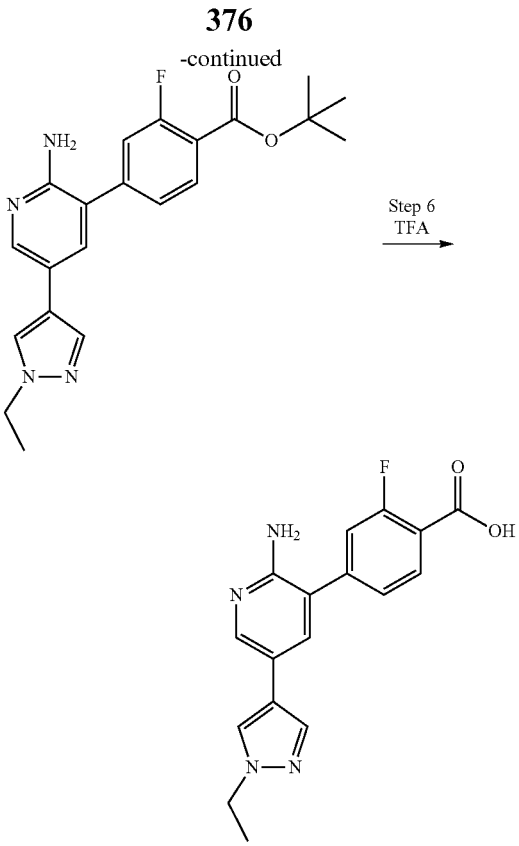

Step 1. tert-butyl 4-bromo-2-fluorobenzoate

A slurry of 4-bromo-2-fluorobenzoic acid (20.16 g, 92 mmol) in dioxane (90 mL) and conc. H$_2$SO$_4$ (5 mL) was cooled to 0° C., and then bubbled through with isobutene for 2 h. The reaction was allowed to gradually warm up to room temperature overnight. Solid NaHCO$_3$ (40 g) was carefully added to the reaction and the mixture was stirred for 1 h. The mixture was concentrated, and then redissolved in water and ethyl acetate. The layers were separated. The aqueous phase was washed with ethyl acetate. The combined organics were washed with sat aq NaHCO$_3$ and brine, then dried over Na$_2$SO$_4$, filtered and concentrated. The resulting oily tert-butyl 4-bromo-2-fluorobenzoate was used without further purification. $^1$H NMR (400 MHz, MeOH-d$_4$) δ ppm 7.79-7.70 (m, 1H), 7.42-7.23 (m, 3H), 1.59 (s, 11H).

Step 2. tert-butyl 2-fluoro-4-(4,4,5,5-tetramethyl-1,3,2-dioxaborolan-2-yl)benzoate A slurry of tert-butyl 4-bromo-2-fluorobenzoate (5.55 g, 20.17 mmol), BISPIN (7.68 g, 30.3 mmol), PdCl$_2$(dppf)-CH$_2$Cl$_2$ adduct (1.153 g, 1.412 mmol) and potassium acetate (5.94 g, 60.5 mmol) in DMF (75 mL) was degassed, and then heated to 100° C. overnight. The reaction was concentrated, then dissolved in DCM, filtered over celite, and then washed with water and brine. The organics were filtered over celite, concentrated, and then purified by flash chromatography eluting with 0-20% ethyl acetate/heptane to provide 5.2 g of tert-butyl 2-fluoro-4-(4,4,5,5-tetramethyl-1,3,2-dioxaborolan-2-yl)benzoate in 80% yield.

Step 3. tert-butyl 4-(2-aminopyridin-3-yl)-2-fluorobenzoate

A slurry of tert-butyl 2-fluoro-4-(4,4,5,5-tetramethyl-1,3,2-dioxaborolan-2-yl)benzoate (5.1 g, 15.83 mmol), 3-bromoaminopyridine (3.01 g, 17.41 mmol) and Pd(PPh₃)₄ (0.732 g, 0.633 mmol) in n-butanol (50 mL) and 2.0 M Na₂CO₃ aqueous solution (19.79 mL, 39.6 mmol) was degassed, and then heated to 100° C. overnight. The reaction was cooled, and diluted with ethyl acetate. The layers were separated, and the organics were washed with brine, filtered over celite and concentrated. The crude was purified by flash chromatography eluting with 10-50% ethyl acetate/heptane to provide 3.41 g of tert-butyl 4-(2-aminopyridin-3-yl)-2-fluorobenzoate in 75% yield.

Step 4. tert-butyl 4-(2-amino-5-bromopyridin-3-yl)-2-fluorobenzoate

NBS (2.145 g, 12.05 mmol) was added to a room temperature solution of tert-butyl 4-(2-aminopyridin-3-yl)-2-fluorobenzoate (3.31 g, 11.48 mmol) in MeCN (60 mL). The resulting mixture was stirred for 10 min. The reaction was quenched with 1:1 of sat. aq. Na₂S₂O₃:sat. aq. NaHCO₃ solution, and then extracted into ethyl acetate. The combined organics were washed with brine, dried over sodium sulfate and concentrated in vacuo yielding tert-butyl 4-(2-amino-5-bromopyridin-3-yl)-2-fluorobenzoate. The material was used without further purification. LCMS (m/z): 369.0 (MH⁺), 0.85 min.

Step 5. tert-butyl 4-(2-amino-5-(1-ethyl-1H-pyrazol-4-yl)pyridin-3-yl)-2-fluorobenzoate To tert-butyl 4-(2-amino-5-bromopyridin-3-yl)-2-fluorobenzoate (200 mg, 0.544 mmol) (See Scheme 101, Step 2 for synthesis) in DME (3 mL) and 2 M sodium carbonate (1.5 mL, 3.0 mmol) was added 1-ethyl-4-(4,4,5,5-tetramethyl-1,3,2-dioxaborolan-2-yl)-1H-pyrazole (182 mg, 0.816 mmol) followed by PdCl₂(dppf)-CH₂Cl₂ adduct (44.5 mg, 0.054 mmol). The reaction mixture was microwave heated at 120° C. for 20 min. The reaction mixture was partitioned between ethylacetate and water. The organic layer was separated, washed with brine, dried over sodium sulfate, filtered and evaporated. The crude was purified by flash chromatography eluting with 0-50% of EtOAc (contains 10% MeOH)/heptane yielding tert-butyl 4-(2-amino-5-(1-ethyl-1H-pyrazol-4-yl)pyridin-3-yl)-2-fluorobenzoate (160 mg, 77%). LCMS (m/z): 383.2 (MH⁺), 0.782 min.

Step 6. 4-(2-amino-5-(1-ethyl-1H-pyrazol-4-yl)pyridin-3-yl)-2-fluorobenzoic acid To tert-butyl 4-(2-amino-5-(1-ethyl-1H-pyrazol-4-yl) pyridin-3-yl)-2-fluorobenzoate (160 mg, 0.418 mmol) in DCM (0.5 mL) was added TFA (2 mL, 26 mmol). The reaction mixture was stirred at room temperature for 1 h. The reaction mixture was co-evaporated with toluene in vacuo. The crude 4-(2-amino-5-(1-ethyl-1H-pyrazol-4-yl)pyridin-3-yl)-2-fluorobenzoic acid was used for next step. LCMS (m/z): 327.2 (MH⁺), 0.509 min.

Example 213

4-(2-amino-5-(1-(methylsulfonyl)pyrrolidin-3-yl) pyridin-3-yl)-2-fluoro-N-((S)-2-hydroxy-1-phenyl-ethyl)benzamide Scheme 104

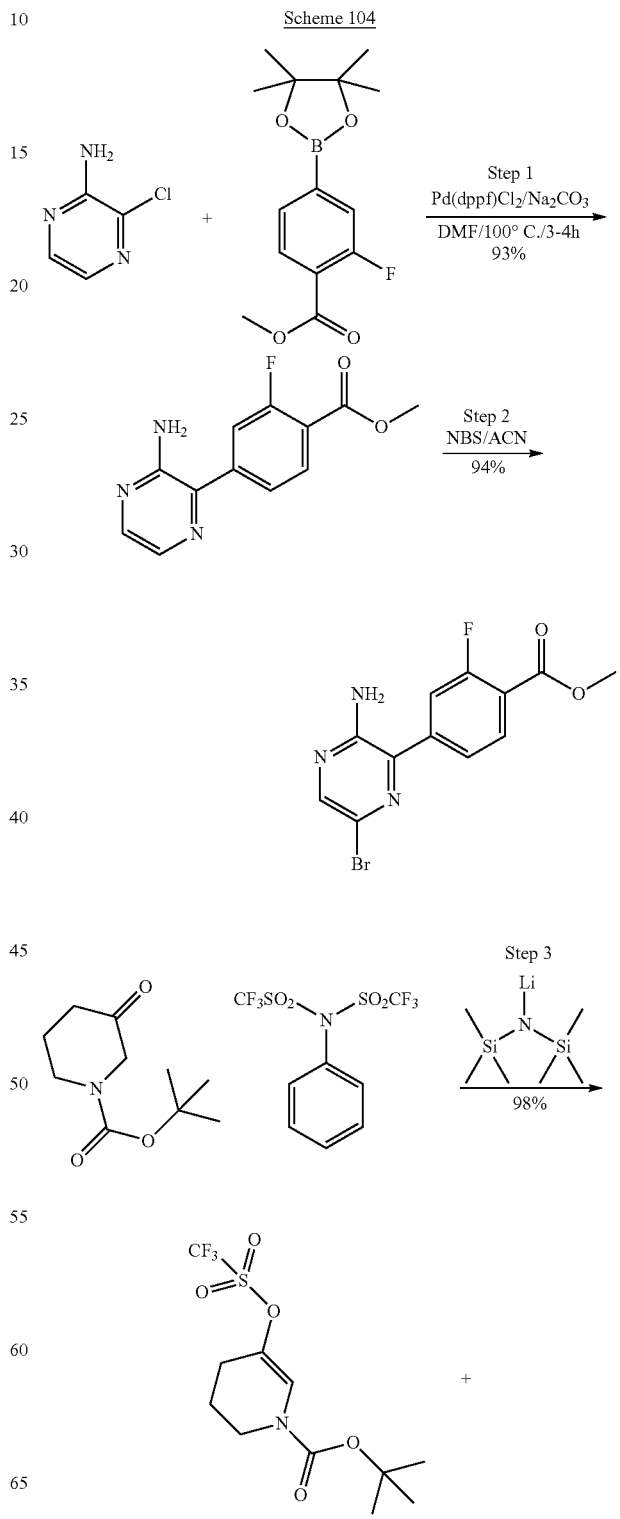

379
-continued
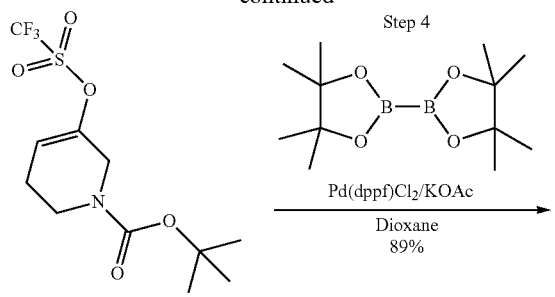
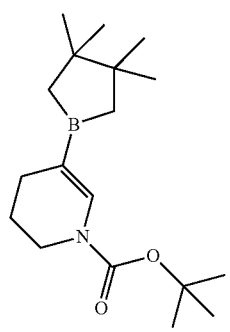
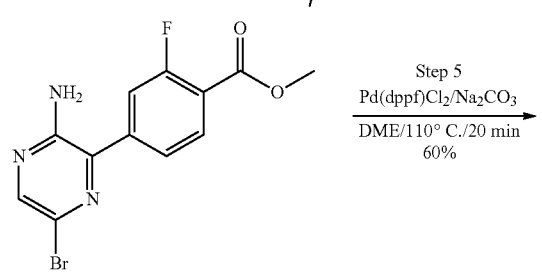
380
-continued
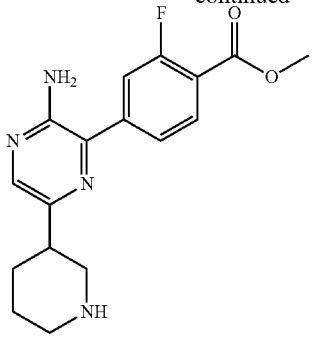
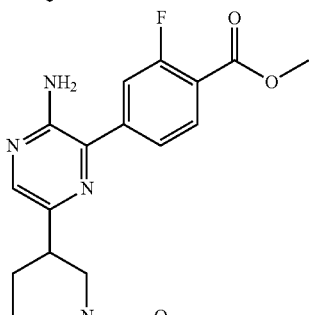
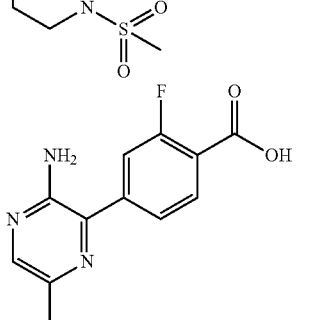
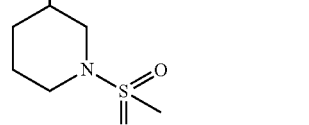
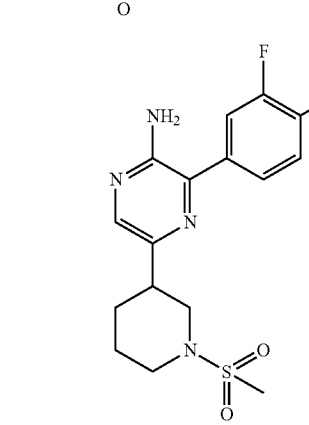
Step 1. methyl 4-(3-aminopyrazin-2-yl)-2-fluorobenzoate
To a mixture of 3-chloropyrazin-2-amine (5 g, 38.6 mmol) in DME (160 mL) and aq. 2 M sodium carbonate (40 mL, 80 mmol) was added methyl 2-fluoro-4-(4,4,5,5-tetramethyl-1,3,2-dioxaborolan-2-yl)benzoate (12.97 g, 46.3 mmol) followed by PdCl$_2$(dppf)-CH$_2$Cl$_2$ adduct (3.15 g, 3.86 mmol). The reaction mixture was purged with N$_2$ and heated in an oil bath at 100° C. for 3-4 h. The reaction mixture was partitioned between ethylacetate and water. The organic layer was separated, washed with brine, dried over sodium sulfate, filtered and evaporated. The crude was triturated with DCM. Solid observed was filtered, washed with ether and dried under reduced pressure to provide product as an off white solid. Filtrate was purified by flash chromatography eluting with 0-50-80% EtOAc/heptane to provide 10.6 g of product in 93% yield. LCMS (m/z): 248.1 (MH$^+$), 0.563 min.

Step 2. methyl 4-(3-aminopyrazin-2-yl)-2-fluorobenzoate

To a mixture of methyl 4-(3-aminopyrazin-2-yl)-2-fluorobenzoate (8.9 g, 36.0 mmol) in acetonitrile (300 mL) in an ice bath was added NBS (5.77 g, 32.4 mmol). The reaction mixture was stirred at 0° C. for 1 h. NBS (0.05 equiv.) was added and the resulting mixture was stirred for another 30 min. To the reaction mixture was added saturated sodium bicarbonate solution. The mixture was stirred for 30 min and product was extracted with EtOAc. The organic extracts were combined, washed with brine, dried over sodium sulfate, filtered and evaporated. The residue was dried under high vacuum to provide a brown solid (12.2 g, 94%). LCMS (m/z): 326.0/328.0 (MH$^+$), 0.846 min.

Step 3. tert-butyl 5-(((trifluoromethyl)sulfonyl)oxy)-3,4-dihydropyridine-1(2H)-carboxylate Tert-butyl 3-oxopiperidine-1-carboxylate (1.1 g, 5.52 mmol) was taken in THF (10 mL) and cooled to −78° C. To that was added lithium bis(trimethylsilyl)amide (6.07 mL, 6.07 mmol) (1 M solution in THF). The reaction mixture was stirred at −78° C. for 20 min, and then a solution of 1,1,1-trifluoro-N-phenyl-N-((trifluoromethyl)sulfonyl)methanesulfonamide (2.071 g, 5.80 mmol) in THF (10 mL) was added dropwise. The reaction mixture was stirred at −78° C. for 15 min, then warmed to and stirred at 0° C. for 3 h. The reaction mixture was quenched with sat. sodium bicarbonate solution and then extracted with ethyl acetate. The combined extracts were washed with brine, dried over sodium sulfate, filtered and evaporated. The crude was purified through a plug of neutral alumina with 10% EtOAc in heptane. Solvent was evaporated and the residue was dried to provide the desired product as a yellow liquid (2 g, 98%).

Step 4. tert-butyl 5-(4,4,5,5-tetramethyl-1,3,2-dioxaborolan-2-yl)-3,4-dihydropyridine-1(2H)-carboxylate A mixture of 4,4,4',4',5,5,5',5'-octamethyl-2,2'-bi(1,3,2-dioxaborolane) (1.223 g, 4.81 mmol), potassium acetate (1.289 g, 13.13 mmol) and PdCl$_2$(dppf)-CH$_2$Cl$_2$ adduct (0.107 g, 0.131 mmol) in flask was flushed with N$_2$, and then dioxane (12 mL) was added, followed by a solution of tert-butyl 5-(((trifluoromethyl)sulfonyl)oxy)-3,4-dihydropyridine-1(2H)-carboxylate (1.45 g, 4.38 mmol) in dioxane (12 mL). The reaction mixture was purged with N$_2$ for 5 min, and then heated in oil bath at 80° C. overnight. The reaction mixture was partitioned between ethyl acetate and water. The organic layer was separated, washed with brine, dried over sodium sulfate, filtered and evaporated. The residue was purified by flash chromatography eluting with 0-30% of EtOAc/heptane to yield the desired product as a highly viscous liquid (1.2 g, 89%). LCMS (m/z): 254.1 (MH$^+$-tBu), 1.21 min.

Step 5. tert-butyl 5-(5-amino-6-(3-fluoro-4-(methoxycarbonyl)phenyl)pyrazin-2-yl)-3,4-dihydropyridine-1(2H)-carboxylate To a mixture of methyl 4-(3-amino-6-bromopyrazin-2-yl)-2-fluorobenzoate (240 mg, 0.70 mmol) in DME (6 mL) and 2 M sodium carbonate (1.0 mL, 2.0 mmol) was added tert-butyl 5-(4,4,5,5-tetramethyl-1,3,2-dioxaborolan-2-yl)-3,4-dihydropyridine-1(2H)-carboxylate (180 mg, 0.582 mmol) followed by PdCl$_2$(dppf).CH$_2$Cl$_2$ adduct (14.4 mg, 17.5 µmol). The reaction mixture was heated in microwave at 110° C. for 20 min. The reaction mixture was partitioned between ethylacetate and water. The organic layer was separated, and washed with water and brine. The organic was dried over sodium sulfate, filtered and evaporated. The residue was purified by flash chromatography eluting with 0-50-80% EtOAc in heptane to yield the desired product as a yellow solid (150 mg, 60%). LCMS (m/z): 429.2 (MH$^+$), 1.03 min.

Step 6. methyl 4-(3-amino-6-(1,4,5,6-tetrahydropyridin-3-yl)pyrazin-2-yl)-2-fluorobenzoate To tert-butyl 5-(5-amino-6-(3-fluoro-4-(methoxycarbonyl)phenyl)pyrazin-2-yl)-3,4-dihydropyridine-1(2H)-carboxylate (150 mg, 0.350 mmol) (inseparable mixture) in DCM (4 mL) was added TFA (1 mL, 12.98 mmol). The reaction mixture was stirred at room temperature for 30-45 min. The reaction mixture was evaporated on rotovap, and azeotroped with toluene. The crude product was proceeded to next step without purification. LCMS (m/z): 329.2 (MH$^+$), 0.502 min.

Step 7. methyl 4-(3-amino-6-(piperidin-3-yl)pyrazin-2-yl)-2-fluorobenzoate

To methyl 4-(3-amino-6-(1,4,5,6-tetrahydropyridin-3-yl)pyrazin-2-yl)-2-fluorobenzoate (115 mg, 0.350 mmol) in MeOH (10 mL) was added Pd/C (93 mg, 0.088 mmol). The reaction mixture was stirred at room temperature for 24 h under H$_2$ balloon. The reaction mixture was filtered through Celite and washed with DCM. The filtrate was evaporated and dried to yield the desired product. The crude product was proceeded for the next step (115 mg, 95%). LCMS (m/z): 331.2 (MH$^+$), 0.492 min.

Step 8. methyl 4-(3-amino-6-(1-(methylsulfonyl)piperidin-3-yl)pyrazin-2-yl)-2-fluorobenzoate To a mixture of crude methyl 4-(3-amino-6-(piperidin-3-yl)pyrazin-2-yl)-2-fluorobenzoate (38 mg, 0.114 mmol) in DCM (2 mL) in an ice bath was added DIEA (79 µL, 0.454 mmol) followed by methanesulfonyl chloride (9.73 µL, 0.125 mmol). The reaction mixture was stirred at 0° C. for 30 min. The reaction mixture was partitioned between DCM and water. The DCM layer was separated and washed with brine. The organic layer was dried over sodium sulfate, filtered and evaporated. The crude product (50% purity) was proceeded to next step. LCMS (m/z): 409.1 (MH$^+$), 0.721 min.

Step 9. 4-(3-amino-6-(1-(methylsulfonyl)piperidin-3-yl)pyrazin-2-yl)-2-fluorobenzoic acid To methyl 4-(3-amino-6-(1-(methylsulfonyl)piperidin-3-yl)pyrazin-2-yl)-2-fluorobenzoate (60 mg, 0.147 mmol) in THF (4 mL) and MeOH (2 mL) was added 1 M LiOH (400 µL, 0.400 mmol). The reaction mixture was stirred at room temperature overnight. The pH of the reaction mixture was adjusted to ~3 to 4 with 2 N HCl, and the product was extracted with ethyl acetate. The organic layer was separated from water and washed with brine, dried over sodium sulfate, filtered off, and evaporated to provide the crude product, which was taken to the next step without further purification. LCMS (m/z): 395.1 (MH+), 0.573 min.

Step 10. 4-(3-amino-6-(1-(methylsulfonyl)piperidin-3-yl)pyrazin-2-yl)-2-fluoro-N-((S)-2-hydroxy-1-phenylethyl)benzamide To a mixture of 4-(3-amino-6-(1-(methylsulfonyl)piperidin-3-yl)pyrazin-2-yl)-2-fluorobenzoic acid (40 mg, 0.101 mmol) in DMF (1 mL) was added (S)-2-amino-2-phenylethanol (13.91 mg, 0.101 mmol) followed by HATU (57.8 mg, 0.152 mmol) and DIEA (0.089 mL, 0.507 mmol). The reaction mixture was stirred at room temperature overnight. The reaction mixture was diluted with DMF and filtered through syringe filter, which was then purified by prep HPLC to yield the desired product as a TFA salt (33.4%). LCMS (m/z): 514.2 (MH+), 0.687 min; 1H NMR (400 MHz, CD$_3$OD) δ ppm 7.95 (s, 1 H) 7.85 (t, J=7.83 Hz, 1 H) 7.73-7.57 (m, 2 H) 7.49-7.21 (m, 5 H) 5.22 (d, J=6.65 Hz, 1 H) 3.94-3.78 (m, 3 H) 3.71 (d, J=11.74 Hz, 1 H) 3.03-2.93 (m, 2 H) 2.87-2.74 (m, 4 H) 2.07-1.97 (m, 1 H) 1.92 (d, J=12.13 Hz, 1 H) 1.85-1.68 (m, 1 H) 1.37-1.25 (m, 1 H).

Example 214 methyl 3-(5-amino-6-(3-fluoro-4-(((S)-2-hydroxy-1-phenylethyl)carbamoyl)phenyl)pyrazin-2-yl)piperidine-1-carboxylate

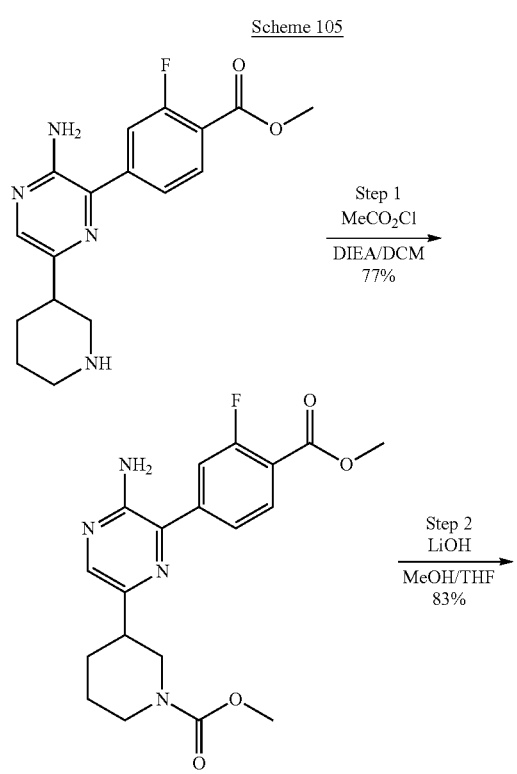

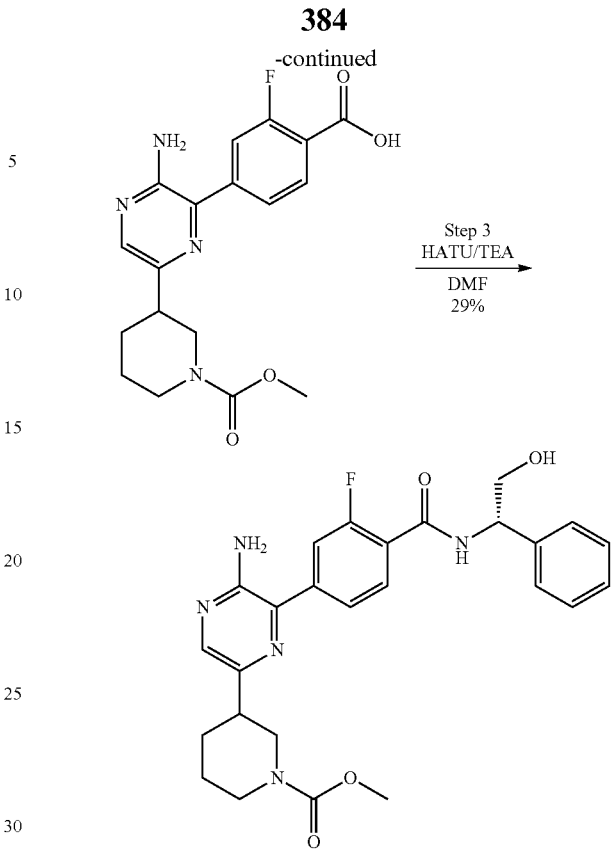

Step 1. methyl 3-(5-amino-6-(3-fluoro-4-(methoxycarbonyl)phenyl)pyrazin-2-yl)piperidine-1-carboxylate To methyl 4-(3-amino-6-(piperidin-3-yl)pyrazin-2-yl)-2-fluorobenzoate (55 mg, 0.166 mmol) (for synthesis, see Example 34, Step 7) in DCM (3 mL) in ice bath was added DIEA (0.116 mL, 0.666 mmol) and methyl chloroformate (0.013 mL, 0.166 mmol). The reaction mixture was stirred at in ice bath for 30 min. The reaction mixture was partitioned between DCM and water. The DCM layer was separated, washed with brine, dried over sodium sulfate, filtered and evaporated. The residue (50 mg, 77%) was taken to the next step without further purification. LCMS (m/z): 389.2 (MH+), 0.785 min.

Step 2. 4-(3-amino-6-(1-(methoxycarbonyl)piperidin-3-yl)pyrazin-2-yl)-2-fluorobenzoic acid To methyl 3-(5-amino-6-(3-fluoro-4-(methoxycarbonyl)phenyl)pyrazin-2-yl)piperidine-1-carboxylate (50 mg, 0.129 mmol) in THF (4 mL) and MeOH (2 mL) was added 1 M LiOH (0.500 mL, 0.500 mmol). The reaction mixture was stirred at room temperature for 4 h. The reaction mixture pH was adjusted to ~3 with 2 N HCl, and product was extracted with ethyl acetate. The EtOAc layer was separated, washed with brine, dried over sodium sulfate, filtered and evaporated. The residue was proceeded to next step without purification (40 mg, 83%). LCMS (m/z): 375.2 (MH+), 0.637 min.

Step 3. methyl 3-(5-amino-6-(3-fluoro-4-(((S)-2-hydroxy-1-phenylethyl)carbamoyl)phenyl)pyrazin-2-yl)piperidine-1-carboxylate To a mixture of 4-(3-amino-6-(1-(methoxycarbonyl)piperidin-3-yl)pyrazin-2-yl)-2-fluorobenzoic acid (28 mg, 0.06 mmol) in DMF (1 mL) was added (S)-2-amino-2-phenylethanol (12.31 mg, 0.090 mmol) followed by HATU (34.1 mg, 0.090 mmol) and DIEA (0.052 mL, 0.299 mmol). The reaction mixture was stirred at room temperature overnight. The reaction mixture was diluted with DMF, filtered through syringe filter and purified by prep HPLC to yield the desired product as a TFA salt (10.9 mg, 29.4%) LCMS (m/z): 494.2 (MH$^+$), 0.733 min. 1H NMR (400 MHz, CD$_3$OD) δ ppm 7.82-7.72 (m, 2 H) 7.63-7.48 (m, 2 H) 7.38-7.11 (m, 5 H) 5.12 (t, J=6.06 Hz, 1 H) 4.09 (d, J=12.91 Hz, 1 H) 3.97 (d, J=12.13 Hz, 1 H) 3.87-3.68 (m, 2 H) 3.59 (s, 3 H) 3.11-2.66 (m, 3 H) 2.00-1.88 (m, 1 H)) 1.85-1.65 (m, 2 H) 1.58-1.40 (m, 1 H)

Example 215

4-(6-(1-acetylpiperidin-3-yl)-3-aminopyrazin-2-yl)-2-fluoro-N-((S)-2-hydroxy-1-phenylethyl)benzamide Scheme 106

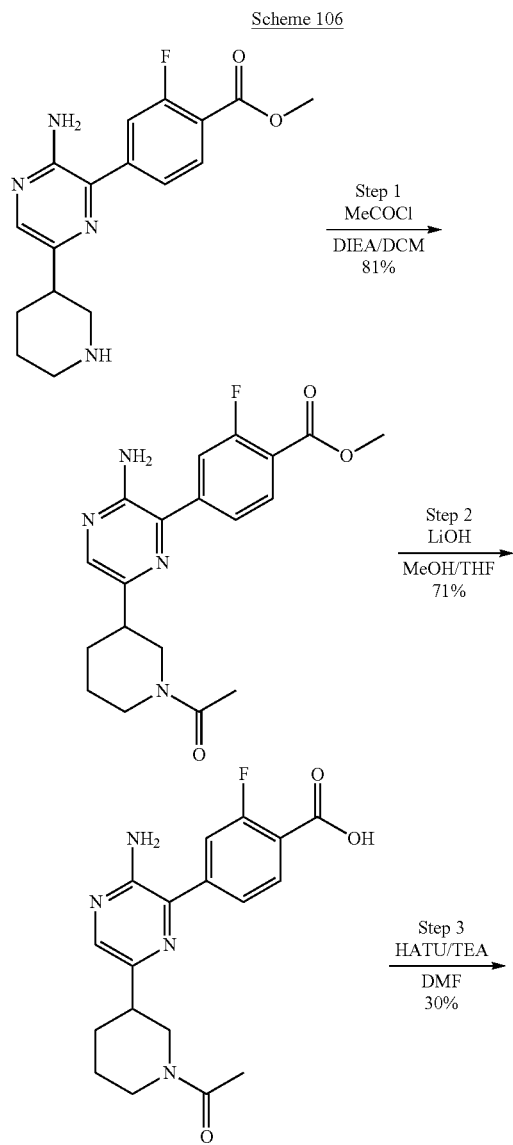

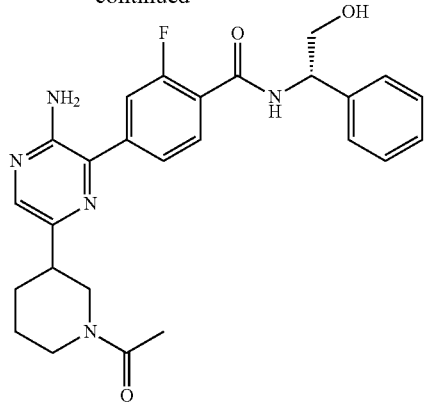

Step 1. methyl 4-(6-(1-acetylpiperidin-3-yl)-3-aminopyrazin-2-yl)-2-fluorobenzoate To a mixture of methyl 4-(3-amino-6-(piperidin-3-yl)pyrazin-2-yl)-2-fluorobenzoate (55 mg, 0.166 mmol) (for synthesis, see example 34, Step 7) in DCM (3 mL) in ice bath was added DIEA (0.116 mL, 0.666 mmol) followed by acetyl chloride (0.012 mL, 0.166 mmol). The reaction mixture was stirred at 0° C. for 30 min. The reaction mixture was partitioned between DCM and water. The DCM layer was separated, washed with brine, dried over sodium sulfate, filtered and evaporated. The residue was proceeded to next step without purification (50 mg, 81%). LCMS (m/z): 373.3 (MH$^+$), 0.666 min.

Step 2. 4-(6-(1-acetylpiperidin-3-yl)-3-aminopyrazin-2-yl)-2-fluorobenzoic acid

To a mixture of methyl 4-(6-(1-acetylpiperidin-3-yl)-3-aminopyrazin-2-yl)-2-fluorobenzoate (50 mg, 0.134 mmol) in THF (4 mL) and MeOH (2 mL) was added 1 M LiOH (0.500 mL, 0.500 mmol). The reaction mixture was stirred at room temperature for 4 h. The pH of reaction mixture was adjusted to ~3 with 2 N HCl, and the product was extracted with ethyl acetate. The organic layer was separated, washed with brine, dried over sodium sulfate, filtered and evaporated. The residue was proceeded for next step without purification (34 mg, 70.7%). LCMS (m/z): 359.1 (MH$^+$), 0.534 min.

Step 3. 4-(6-(1-acetylpiperidin-3-yl)-3-aminopyrazin-2-yl)-2-fluoro-N-((S)-2-hydroxy-1-phenylethyl)benzamide To a mixture of 4-(6-(1-acetylpiperidin-3-yl)-3-aminopyrazin-2-yl)-2-fluorobenzoic acid (34 mg, 0.076 mmol) in DMF (1.5 mL) was added (S)-2-amino-2-phenylethanol (15.62 mg, 0.114 mmol), followed by HATU (43.3 mg, 0.114 mmol) and DIEA (0.066 mL, 0.379 mmol). The reaction mixture was stirred at room temperature overnight. The reaction mixture was diluted with DMF, filtered through syringe filter and purified by prep HPLC to yield the desired product as a TFA salt (13.9 mg, 30%). LCMS (m/z): 478.2 (MH$^+$), 0.641 min. 1H NMR (400 MHz, CD$_3$OD) δ ppm 7.98-7.97 (m, 2 H) 7.73-7.58 (m, 2 H) 7.47-7.23 (m, 5 H) 5.22 (t, J=6.06 Hz, 1 H) 4.62-4.37 (m, 1 H) 4.08-3.75 (m, 3

H) 3.27-3.08 (m, 1 H) 3.03-2.71 (m, 2 H) 2.11 (d, J=11.35 Hz, 3 H) 2.04 (d, J=8.22 Hz, 1 H) 2.00-1.75 (m, 2 H) 1.73-1.46 (m, 1 H)

Example 216 methyl 3-(5-amino-6-(4-(((S)-1-(3-chlorophenyl)-2-hydroxyethyl)carbamoyl)-3-fluorophenyl)pyrazin-2-yl)piperidine-1-carboxylate

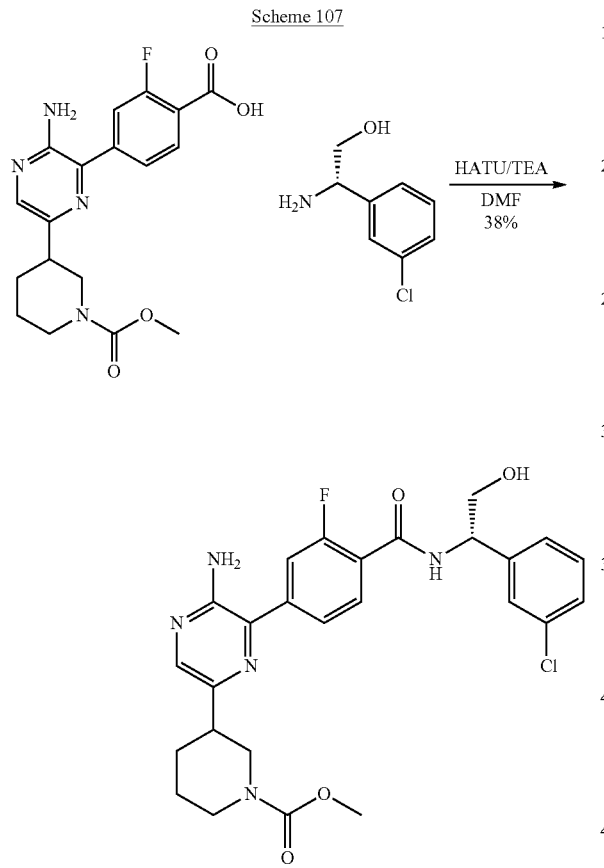

To 4-(3-amino-6-(1-(methoxycarbonyl)piperidin-3-yl)pyrazin-2-yl)-2-fluorobenzoic acid (12 mg, 0.026 mmol) (for synthesis, see Example 35, Step 2) in DMF (1 mL) was added (S)-2-amino-2-(3-chlorophenyl)ethanol (6.60 mg, 0.038 mmol), followed by HATU (14.63 mg, 0.038 mmol) and DIEA (0.022 mL, 0.128 mmol). The reaction mixture was stirred at room temperature overnight. The reaction mixture was diluted with DMF, filtered through syringe filter and purified by prep HPLC to yield desired product as a TFA salt (6.5 mg, 38%). LCMS (m/z): 528.1/530.1 (MH$^+$), 0.798 min. 1H NMR (400 MHz, CD$_3$OD) δ ppm 7.96-7.80 (m, 2 H) 7.75-7.58 (m, 2 H) 7.50-7.23 (m, 4 H) 5.19 (t, J=5.87 Hz, 1 H) 4.25-4.01 (m, 2 H) 3.92-3.79 (m, 2 H) 3.68 (s, 3 H) 3.20-2.74 (m, 3 H) 2.08-1.97 (m, 1 H) 1.91-1.73 (m, 2 H) 1.67-1.51 (m, 1 H)

Example 217

(S)-4-(3-amino-6-(1-ethyl-1H-pyrazol-4-yl)pyrazin-2-yl)-2-fluoro-N-(2-hydroxy-1-phenylethyl)benzamide Scheme 108

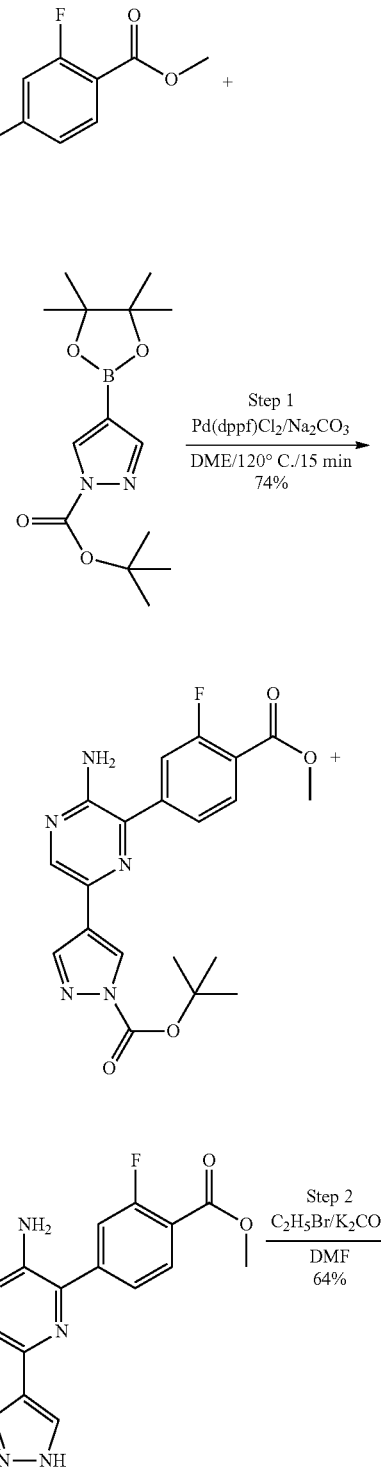

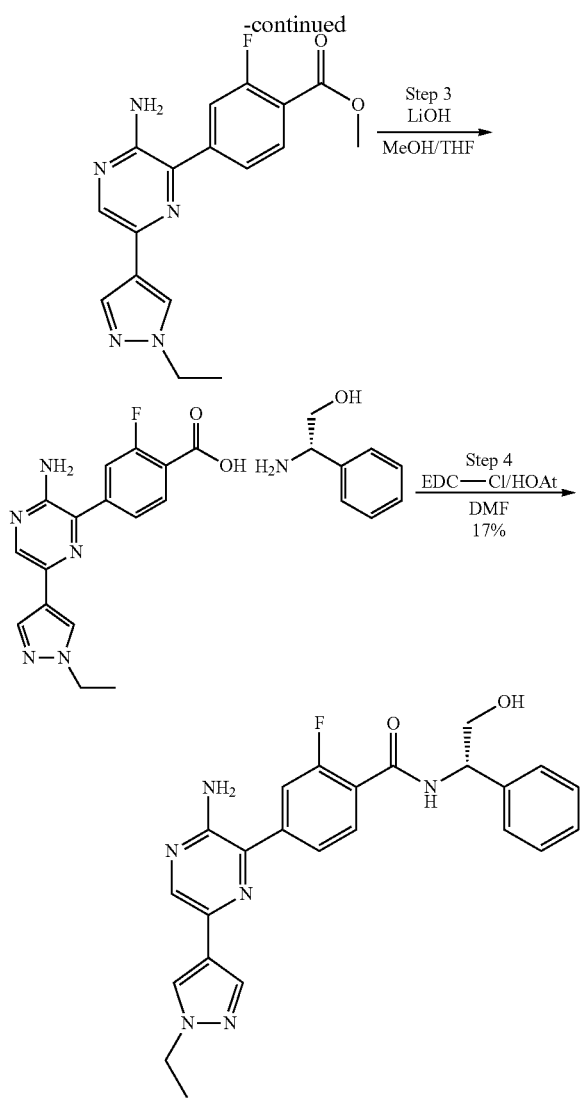

Step 1. methyl 4-(3-amino-6-(1H-pyrazol-4-yl) pyrazin-2-yl)-2-fluorobenzoate)

To methyl 4-(3-amino-6-bromopyrazin-2-yl)-2-fluorobenzoate (For Synthesis see Example 34, Step 2) (100 mg, 0.307 mmol) in DME (3 mL) and 2 M sodium carbonate (0.75 mL, 1.5 mmol) was added tert-butyl 4-(4,4,5,5-tetramethyl-1,3,2-dioxaborolan-2-yl)-1H-pyrazole-1-carboxylate (90 mg, 0.307 mmol) followed by $PdCl_2(dppf)\text{-}CH_2Cl_2$ adduct (25.04 mg, 0.031 mmol). The reaction mixture was heated in microwave at 120° C. for 15 min. The reaction mixture was partitioned between ethyl acetate and water. The organic layer was separated, washed with water and brine, dried over sodium sulfate, filtered and evaporated. The residue was proceeded to next step without purification (90 mg, 74%, 80% purity). LCMS (m/z): 314.1 (MH+), 0.595 min.

Step 2. methyl 4-(3-amino-6-(1-ethyl-1H-pyrazol-4-yl)pyrazin-2-yl)-2-fluorobenzoate To methyl 4-(3-amino-6-(1H-pyrazol-4-yl) pyrazin-2-yl)-2-fluorobenzoate (45 mg, 0.115 mmol) in DMF (2 mL) was added potassium carbonate (47.6 mg, 0.345 mmol), followed by bromoethane (0.017 mL, 0.230 mmol). The reaction mixture was stirred at room temperature for 48 h. The reaction mixtures was partitioned between ethylacetate and water. The organic layer was separated, washed with brine, dried over sodium sulfate, filtered, evaporated and purified by flash chromatography eluting with 0-60% of EtOAc (contains 10% of MeOH)/heptane to yield the desired product (25 mg, 64%, 80% purity). LCMS (m/z): 342.0 (MH+), 0.73 min.

Step 3. 4-(3-amino-6-(1-ethyl-1H-pyrazol-4-yl) pyrazin-2-yl)-2-fluorobenzoic acid To methyl 4-(3-amino-6-(1-ethyl-1H-pyrazol-4-yl) pyrazin-2-yl)-2-fluorobenzoate (25 mg, 0.073 mmol) in MeOH (1 mL) and THF (2 mL) was added 1 M LiOH (0.220 mL, 0.220 mmol). The reaction mixture was stirred at room temperature for 4 h. The pH of reaction mixture was adjusted to ~4 by 2 N HCl. The product was extracted with ethyl acetate twice. The combined organics extracts were washed with brine, dried over sodium sulfate, filtered, and evaporated. The residue was proceeded to next step without further purification. LCMS (m/z): 328.1 (MH+), 0.607 min.

Step 4. (S)-4-(3-amino-6-(1-ethyl-1H-pyrazol-4-yl) pyrazin-2-yl)-2-fluoro-N-(2-hydroxy-1-phenylethyl) benzamide To 4-(3-amino-6-(1-ethyl-1H-pyrazol-4-yl)pyrazin-2-yl)-2-fluorobenzoic acid (25 mg, 0.076 mmol) in DMF (1 mL) was added EDC.HCl (21.96 mg, 0.115 mmol), followed by HOAt (15.60 mg, 0.115 mmol), (S)-2-amino-2-phenylethanol (15.92 mg, 0.092 mmol) and DIEA (0.040 mL, 0.229 mmol). The reaction mixture was stirred at room temperature for 6 h. The reaction mixture was diluted with DMF and filtered through syringe filter. The crude was purified by prep HPLC to yield the desired product as a TFA salt (9.1 mg, 17%). LCMS (m/z): 447.2 (MH+), 0.699 min. 1H NMR (400 MHz, $CD_3OD$) δ ppm 8.67-8.41 (m, 1 H), 8.17 (s, 1 H), 8.03 (s, 1 H), 7.86 (s, 1 H), 7.78 (t, J=7.63 Hz, 1 H), 7.67-7.53 (m, 2 H), 7.40-7.09 (m, 5 H), 5.21-5.03 (m, 1 H), 4.13 (q, J=7.30 Hz, 2 H), 3.86-3.65 (m, 2 H), 1.39 (t, J=7.24 Hz, 3 H).

Example 218

Synthesis of 4-(2-amino-5-(5-oxopyrrolidin-3-yl) pyridin-3-yl)-2-fluoro-N-((S)-2-hydroxy-1-phenylethyl)benzamide Scheme 109

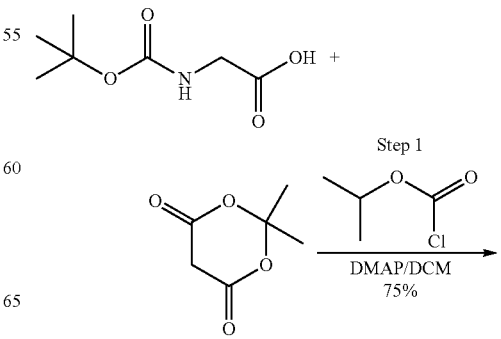

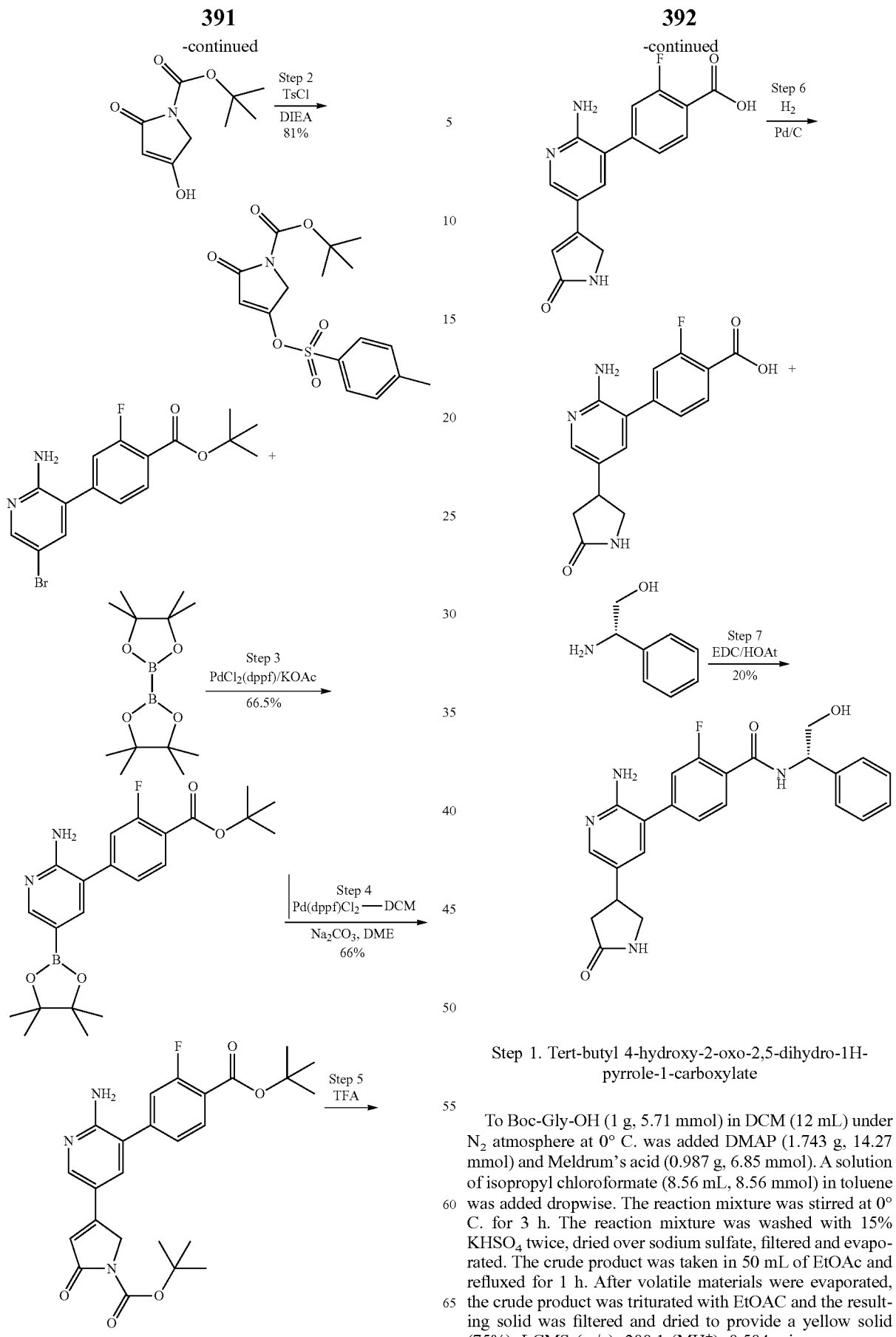

Step 1. Tert-butyl 4-hydroxy-2-oxo-2,5-dihydro-1H-pyrrole-1-carboxylate

To Boc-Gly-OH (1 g, 5.71 mmol) in DCM (12 mL) under N$_2$ atmosphere at 0° C. was added DMAP (1.743 g, 14.27 mmol) and Meldrum's acid (0.987 g, 6.85 mmol). A solution of isopropyl chloroformate (8.56 mL, 8.56 mmol) in toluene was added dropwise. The reaction mixture was stirred at 0° C. for 3 h. The reaction mixture was washed with 15% KHSO$_4$ twice, dried over sodium sulfate, filtered and evaporated. The crude product was taken in 50 mL of EtOAc and refluxed for 1 h. After volatile materials were evaporated, the crude product was triturated with EtOAC and the resulting solid was filtered and dried to provide a yellow solid (75%). LCMS (m/z): 200.1 (MH$^+$), 0.504 min.

Step 2. Tert-butyl 2-oxo-4-(tosyloxy)-2,5-dihydro-1H-pyrrole-1-carboxylate

To tert-butyl 4-hydroxy-2-oxo-2,5-dihydro-1H-pyrrole-1-carboxylate (680 mg, 3.41 mmol) in DCM (12 mL) was added DIEA (1.192 mL, 6.83 mmol) and tosyl chloride (651 mg, 3.41 mmol). The reaction mixture was stirred at room temperature for 6 h. The reaction mixture was diluted with DCM and washed with saturated sodium bicarbonate. The organic layer was separated, washed with brine, dried over sodium sulfate, filtered and evaporated. The crude product was purified by flash chromatography (0 to 50% EtOAc/heptane). Pure fractions were combined, evaporated and dried to give desired product as a white solid (0.98 g, 81%). LCMS (m/z): 354.1 (MH$^+$), 0.97 min; 1H NMR (400 MHz, DMSO-d6) δ ppm 7.99 (d, J=8.22 Hz, 2 H) 7.54 (d, J=7.83 Hz, 2 H) 5.77 (s, 1 H) 4.33 (s, 2 H) 2.43 (s, 3H) 1.41 (s, 9 H).

Step 3. Tert-butyl 4-(2-amino-5-(4,4,5,5-tetramethyl-1,3,2-dioxaborolan-2-yl)pyridin-3-yl)-2-fluorobenzoate To tert-butyl 4-(2-amino-5-bromopyridin-3-yl)-2-fluorobenzoate (400 mg, 1.089 mmol) in DME (12 mL) was added 4,4,4',4',5,5,5'-heptamethyl-2,2'-bi(1,3,2-dioxaborolane) (523 mg, 2.179 mmol), potassium acetate (321 mg, 3.27 mmol) and PdCl$_2$(dppf)-CH$_2$Cl$_2$ (89 mg, 0.109 mmol). The reaction mixture was purged with N$_2$ and heated in microwave vial in heating block at 110° C. for overnight. The reaction mixture was partitioned between ethyl acetate and water. The organic layer was separated, washed with brine, dried over sodium sulfate, filtered and evaporated. The crude was taken in ether and sonicated for 10 min and black solid was filtered off. The filtrate was evaporated to provide product as a light yellow solid (300 mg, 66.5%). LCMS (m/z): 333.2 (MH$^+$), 0.672 min (for boronic acid).

Step 4. Tert-butyl 4-(6-amino-5-(4-(tert-butoxycarbonyl)-3-fluorophenyl)pyridin-3-yl)-2-oxo-2,5-dihydro-1H-pyrrole-1-carboxylate To tert-butyl 4-(2-amino-5-(4,4,5,5-tetramethyl-1,3,2-dioxaborolan-2-yl)pyridin-3-yl)-2-fluorobenzoate (158 mg, 0.382 mmol) in DME (3 mL) and sodium carbonate (0.509 mL, 1.019 mmol) was added tert-butyl 2-oxo-4-(tosyloxy)-2,5-dihydro-1H-pyrrole-1-carboxylate (90 mg, 0.255 mmol) and PdCl$_2$(dppf)-CH$_2$Cl$_2$ (41.6 mg, 0.051 mmol). The reaction mixture was heated in microwave at 90° C. for 30 min. LCMS showed starting material remained. More catalysts were added and heated again at 90° C. for 20 min. The reaction mixture was partitioned between ethylacetate and water. The organic layer was separated, washed with brine, dried over sodium sulfate, filtered and evaporated. The crude product was purified by flash chromatography using 0-50% EtOAc (contains 10% MeOH)/heptane to provide product as a yellow solid (66%). LCMS (m/z): 470.2 (MH$^+$), 0.846 min.

Step 5. 4-(2-amino-5-(5-oxo-2,5-dihydro-1H-pyrrol-3-yl)pyridin-3-yl)-2-fluorobenzoic acid To tert-butyl 4-(6-amino-5-(4-(tert-butoxycarbonyl)-3-fluorophenyl)pyridin-3-yl)-2-oxo-2,5-dihydro-1H-pyrrole-1-carboxylate (158 mg, 0.337 mmol) was added TFA (2 mL, 26.0 mmol). The reaction mixture was stirred at room temperature for 1 h. After toluene was added, the volatile solvents were evaporated. The crude product was used for the next step. LCMS (m/z): 314.2 (MH$^+$), 0.382 min.

Step 6. 4-(2-amino-5-(5-oxopyrrolidin-3-yl)pyridin-3-yl)-2-fluorobenzoic acid To 4-(2-amino-5-(5-oxo-2,5-dihydro-1H-pyrrol-3-yl)pyridin-3-yl)-2-fluorobenzoic acid (100 mg, 0.319 mmol) in MeOH (15 mL) under N$_2$ atmosphere was added PdC (67.9 mg, 0.064 mmol). The reaction mixture was stirred at room temperature for 24 h under H$_2$ balloon. The reaction mixture was filter through Celite and washed with methanol. The filtrate was evaporated. The crude was proceed for next step. LCMS (m/z): 316.2 (MH$^+$), 0.338 min.

Step 7. (+/−)-4-(2-amino-5-(5-oxopyrrolidin-3-yl)pyridin-3-yl)-2-fluoro-N-((S)-2-hydroxy-1-phenylethyl)benzamide To 4-(2-amino-5-(5-oxopyrrolidin-3-yl)pyridin-3-yl)-2-fluorobenzoic acid (30 mg, 0.076 mmol) in DMF (1 mL) was added (S)-2-amino-2-phenylethanol (12.53 mg, 0.091 mmol), EDC-HCl (21.89 mg, 0.114 mmol), HOAt (15.54 mg, 0.114 mmol) and DIEA (0.040 mL, 0.228 mmol). The reaction mixture was stirred at room temperature for 5 h. The reaction mixture was diluted with DMF and directly purified by prep HPLC to provide (+/−)-4-(2-amino-5-(5-oxopyrrolidin-3-yl)pyridin-3-yl)-2-fluoro-N-((S)-2-hydroxy-1-phenylethyl)benzamide as a TFA salt (20.2%). LCMS (m/z): 435.2 (MH$^+$), 0.476 min; 1H NMR (400 MHz, CD$_3$OD) δ ppm 7.88 (s, 1 H), 7.84-7.74 (m, 2 H), 7.38-7.30 (m, 4 H), 7.27 (t, J=7.43 Hz, 2 H), 7.22-7.13 (m, 1 H), 5.18-5.05 (m, 1 H), 3.85-3.56 (m, 4 H), 3.39-3.26 (m, 1 H), 2.62 (dd, J=16.82, 8.61 Hz, 1 H), 2.48-2.33 (m, 1 H).

Examples 219 and 220

Synthesis of 4-(2-amino-5-((R)-5-oxopyrrolidin-3-yl)pyridin-3-yl)-2-fluoro-N-((S)-2-hydroxy-1-phenylethyl)benzamide and 4-(2-amino-5-((S)-5-oxopyrrolidin-3-yl)pyridin-3-yl)-2-fluoro-N-((S)-2-hydroxy-1-phenylethyl)benzamide Scheme 110

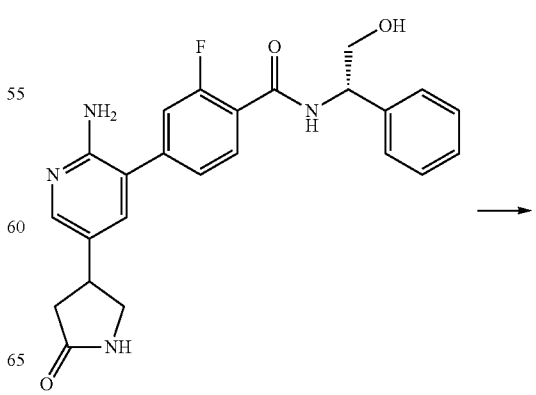

395

-continued

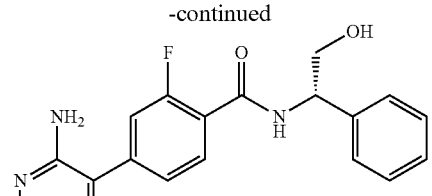

peak 1

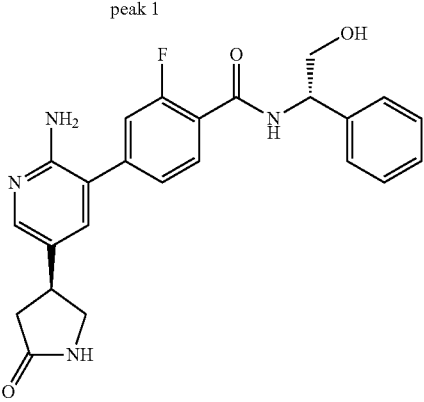

peak 2

(+/−)-4-(2-amino-5-(5-oxopyrrolidin-3-yl)pyridin-3-yl)-2-fluoro-N-((S)-2-hydroxy-1-phenylethyl)benzamide was resolved by chiral SFC (Chiral Pak 5mic C10=AD-H column, 4.6×100 (mm), 5 mL/min, MeOH=50%). The polar compound (peak 1) was obtained at Rt=1.36 min (24.5%). LCMS (m/z): 435.2 (MH$^+$), 0.485 min. The less polar compound (peak 2) was obtained at Rt=2.20 min (22%). LCMS (m/z): 435.2 (MH$^+$), 0.482 min. The absolute stereochemistry on cyclic lactam was arbitrarily assigned.

Example 221

Synthesis of (2S,4R)-methyl 4-(6-amino-5-(4-(((S)-1-(3-chlorophenyl)-2-hydroxyethyl)carbamoyl)-3-fluorophenyl)pyridin-3-yl)pyrrolidine-2-carboxylate Scheme 111

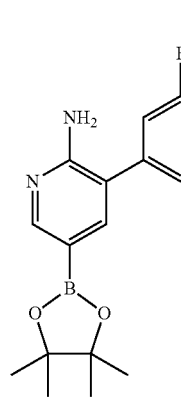

+

396

-continued

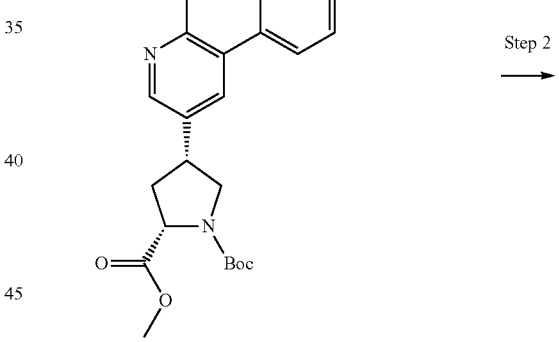

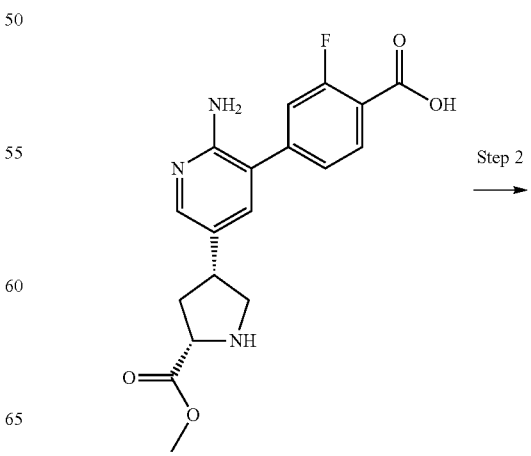

397
-continued

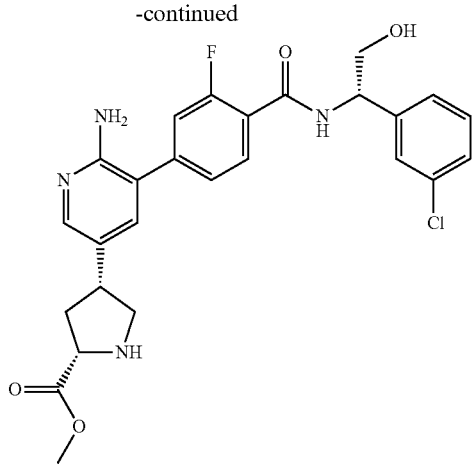

Step 1. (S)-1-tert-butyl 2-methyl 4-(6-amino-5-(4-(tert-butoxycarbonyl)-3-fluorophenyl)pyridin-3-yl)-1H-pyrrole-1,2(2H,5H)-dicarboxylate A mixture of tert-butyl 4-(2-amino-5-(4,4,5,5-tetramethyl-1,3,2-dioxaborolan-2-yl)pyridin-3-yl)-2-fluorobenzoate (400 mg, 0.966 mmol), (S)-1-tert-butyl 2-methyl 4-(((trifluoromethyl)sulfonyl)oxy)-1H-pyrrole-1,2(2H,5H)-dicarboxylate (1.087 g, 2.90 mmol, Pd(PPh$_3$)$_4$ (112 mg, 0.097 mmol) and cesium carbonate (1.258 g, 3.86 mmol) in THF (10 mL) and water (2 mL) was degassed, then microwave heated to 90° C. for 10 min. At completion, the reaction was diluted with ethyl acetate. The organics were washed with brine, dried over magnesium sulfate and concentrated. The crude mixture was purified by flash chromatography over silica gel (20-90% ethyl acetate/heptane) to provide (S)-1-tert-butyl 2-methyl 4-(6-amino-5-(4-(tert-butoxycarbonyl)-3-fluorophenyl)pyridin-3-yl)-1H-pyrrole-1,2(2H,5H)-dicarboxylate (470 mg, 95%). LCMS (m/z): 514.3 (MH$^+$), 0.92 min.

Step 2. (2S,4R)-1-tert-butyl 2-methyl 4-(6-amino-5-(4-(tert-butoxycarbonyl)-3-fluorophenyl)pyridin-3-yl)pyrrolidine-1,2-dicarboxylate A degassed solution of (S)-1-tert-butyl 2-methyl 4-(6-amino-5-(4-(tert-butoxycarbonyl)-3-fluorophenyl)pyridin-3-yl)-1H-pyrrole-1,2(2H,5H)-dicarboxylate (470 mg, 0.915 mmol) in methanol (40 mL) was treated with 10 wt. % Pd/C (3.214 g, 3.02 mmol). The system was degassed again, then charged with 1 atm hydrogen overnight. At completion, the reaction degassed, then treated ammonia gas then filtered over Celite. The cake was reslurried in methanol, treated with ammonia gas, and filtered to retrieve additional product. The process was repeated until no further product eluted from filter cake. The combined organics were concentrated to provide (2S,4R)-1-tert-butyl 2-methyl 4-(6-amino-5-(4-(tert-butoxycarbonyl)-3-fluorophenyl)pyridin-3-yl)pyrrolidine-1,2-dicarboxylate (300 mg, 64%). LCMS (m/z): 516.1 (MH$^+$), 0.89 min.

Step 3. 4-(2-amino-5-((3R,5S)-5-(methoxycarbonyl)pyrrolidin-3-yl)pyridin-3-yl)-2-fluorobenzoic acid-2TFA A solution of (2S,4R)-1-tert-butyl 2-methyl 4-(6-amino-5-(4-(tert-butoxycarbonyl)-3-fluorophenyl)pyridin-3-yl)pyrrolidine-1,2-dicarboxylate (300 mg, 0.58 mmol) in DCM (6 mL) was treated with TFA (3 mL). After 1 h, the reaction was concentrated, then the residue was slurried in benzene, sonicated, then concentrated to provide 4-(2-amino-5-((3R,5S)-5-(methoxycarbonyl)pyrrolidin-3-yl)pyridin-3-yl)-2-fluorobenzoic acid-2TFA (345 mg, 100% yield). LCMS (m/z): 360.2 (MH$^+$), 0.34 min.

Step 4. (2S,4R)-methyl 4-(6-amino-5-(4-(((S)-1-(3-chlorophenyl)-2-hydroxyethyl)carbamoyl)-3-fluorophenyl)pyridin-3-yl)pyrrolidine-2-carboxylate A mixture of 4-(2-amino-5-((3R,5S)-5-(methoxycarbonyl)pyrrolidin-3-yl)pyridin-3-yl)-2-fluorobenzoic acid-2TFA (35 mg, 0.060 mmol), HATU (34 mg, 0.089 mmol), and DIEA (0.104 mL, 0.596 mmol) in DMF (2 mL) was treated with (S)-2-amino-2-(3-chlorophenyl)ethanol (51 mg, 0.348 mmol). At completion, the reaction was washed with water and brine, then dried over MgSO$_4$ and concentrated. The crude material was purified by reverse phase prep HPLC to provide (2S,4R)-methyl 4-(6-amino-5-(4-(((S)-1-(3-chlorophenyl)-2-hydroxyethyl)carbamoyl)-3-fluorophenyl)pyridin-3-yl)pyrrolidine-2-carboxylate (4.2 mg, 9%). LCMS (m/z): 513.2, 515.2 (MH$^+$), 0.58 min; 1H NMR (400 MHz, CD$_3$OD) δ ppm 7.97-7.86 (m, 3H), 7.49-7.40 (m, 3H), 7.39-7.34 (m, 2H), 7.33-7.26 (m, 1H), 5.19 (t, J=5.87 Hz, 1H), 4.62 (dd, J=7.63, 10.76 Hz, 1H), 3.93-3.77 (m, 6H), 3.74-3.61 (m, 1H), 2.87 (td, J=6.90, 13.21 Hz, 1H), 2.33-2.21 (m, 1H).

Examples 222 and 223

Synthesis of (2S,4R)-4-(6-amino-5-(4-(((S)-1-(3-chlorophenyl)-2-hydroxyethyl)carbamoyl)-3-fluorophenyl)pyridin-3-yl)pyrrolidine-2-carboxylic acid and (2S,4R)-methyl 4-(6-amino-5-(4-(((S)-1-(3-chlorophenyl)-2-hydroxyethyl)carbamoyl)-3-fluorophenyl)pyridin-3-yl)pyrrolidine-2-carboxylate Scheme 112

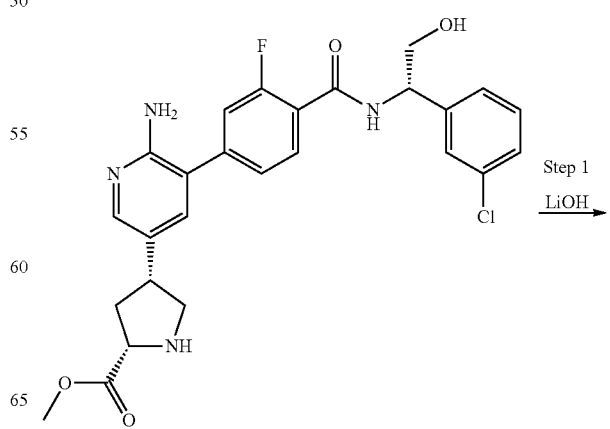

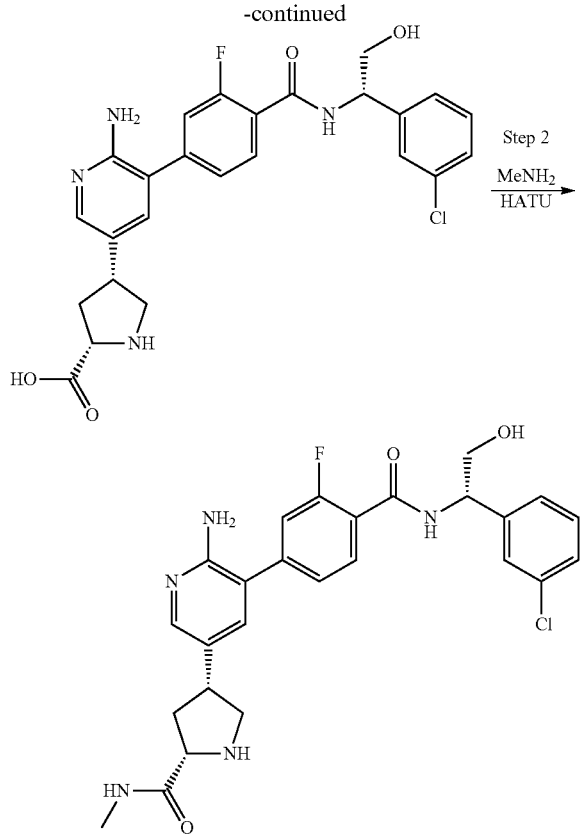

Step 1. (2S,4R)-4-(6-amino-5-(4-(((S)-1-(3-chlorophenyl)-2-hydroxyethyl)carbamoyl)-3-fluorophenyl)pyridin-3-yl)pyrrolidine-2-carboxylic acid A solution of (2S,4R)-methyl 4-(6-amino-5-(4-(((S)-1-(3-chlorophenyl)-2-hydroxyethyl)carbamoyl)-3-fluorophenyl)pyridin-3-yl)pyrrolidine-2-carboxylate (120 mg, 0.234 mmol) in MeOH (4 mL) was treated with 1.0 M LiOH aqueous solution (0.468 mL), then heated to 70° C. After 1 h, the reaction was concentrated then dissolved in water (2 mL) and treated with 1.0 N aqueous HCl (0.468 mL). The reaction mixture was extracted with ethyl acetate (20 mL). The organic layer was washed with water and brine, then dried over MgSO₄ and concentrated to provide the crude product (97 mg, 57%). A portion of this material was purified by reverse phase prep HPLC yielding (2S,4R)-4-(6-amino-5-(4-(((S)-1-(3-chlorophenyl)-2-hydroxyethyl)carbamoyl)-3-fluorophenyl)pyridin-3-yl)pyrrolidine-2-carboxylic acid. LCMS (m/z): 499.1/501.1 (MH⁺), 0.49 min; ¹H NMR (400 MHz, CD₃OD) δ ppm 8.56-8.64 (m, 1H), 7.75-7.87 (m, 4H), 7.31-7.38 (m, 4H), 7.24-7.29 (m, 3H), 7.17-7.24 (m, 1H), 5.07-5.14 (m, 1H), 4.36 (dd, J=7.63, 9.98 Hz, 1H), 3.64-3.83 (m, 4H), 3.52-3.62 (m, 1H), 3.27-3.34 (m, 1H), 2.72-2.81 (m, 1H), 2.56 (s, 1H), 2.15 (td, J=10.42, 13.21 Hz, 1H).

Step 2. (2S,4R)-methyl 4-(6-amino-5-(4-(((S)-1-(3-chlorophenyl)carbamoyl)-3-fluorophenyl)pyridin-3-yl)pyrrolidine-2-carboxylate A solution of (2S,4R)-4-(6-amino-5-(4-(((S)-1-(3-chlorophenyl)-2-hydroxyethyl)carbamoyl)-3-fluorophenyl)pyridin-3-yl)pyrrolidine-2-carboxylic acid (25 mg, 0.050 mmol) in THF (2 mL) and DMF (2 mL) was treated sequentially treated with a 2.0 M solution of methylamine in THF (1.25 mL, 2.5 mmol), and HATU (95 mg, 0.25 mmol). After 2 h, the reaction was diluted with ethyl acetate and washed with water and brine. The organics were dried over magnesium sulfate and concentrated to provide (2S,4R)-methyl 4-(6-amino-5-(4-(((S)-1-(3-chlorophenyl)-2-hydroxyethyl)carbamoyl)-3-fluorophenyl)pyridin-3-yl)pyrrolidine-2-carboxylate after purification by reverse phase prep HPLC (1.8 mg, 5%). LCMS (m/z): 512.2, 514.2 (MH⁺), 0.54 min; ¹H NMR (400 MHz, CD₃OD) δ ppm 8.64-8.73 (m, 1H), 7.84-7.96 (m, 2H), 7.45 (s, 1H), 7.40-7.44 (m, 1H), 7.35-7.38 (m, 1H), 7.27-7.34 (m, 1H), 5.16-5.24 (m, 1H), 4.38 (dd, J=7.83, 10.17 Hz, 1H), 3.75-3.92 (m, 2H), 3.60-3.72 (m, 1H), 2.78-2.89 (m, 3H).

Synthesis of 4-(2-amino-5-(1-methyl-1H-imidazol-5-yl)pyridin-3-yl)-2-fluorobenzoic acid

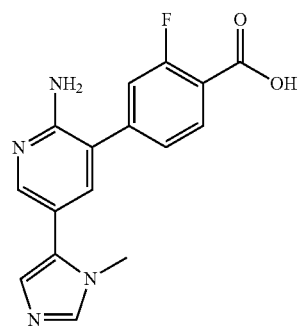 [SMILES: Cn1cncc1-c1cnc(N)c(-c2ccc(C(=O)O)c(F)c2)c1]

Following Steps 4 and 5 in Scheme 109, using 5-bromo-1-methyl-1H-imidazole, 4-(2-amino-5-(1-methyl-1H-imidazol-5-yl)pyridin-3-yl)-2-fluorobenzoic acid was obtained. LCMS (m/z): 313.1 (MH⁺), 0.3 min.

Synthesis of 4-(2-amino-5-(1-methyl-1H-pyrazol-5-yl)pyridin-3-yl)-2-fluorobenzoic acid

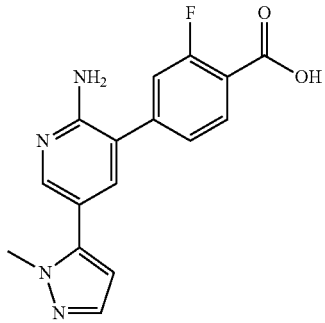 [SMILES: Cn1nccc1-c1cnc(N)c(-c2ccc(C(=O)O)c(F)c2)c1]

Following Steps 4 and 5 in Scheme 109, using 1-methyl-5-(4,4,5,5-tetramethyl-1,3,2-dioxaborolan-2-yl)-1H-pyrazole, 4-(2-amino-5-(1-methyl-1H-pyrazol-5-yl)pyridin-3-yl)-2-fluorobenzoic acid was obtained. LCMS (m/z): 313.4 (MH⁺), 0.44 min.

401

Synthesis of 4-(2-amino-5-(1-isopropyl-1H-pyrazol-4-yl)pyridin-3-yl)-2-fluorobenzoic acid

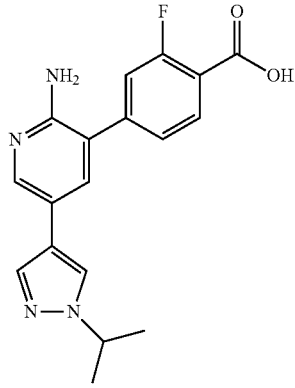 [SMILES: CC(C)n1cc(-c2cnc(N)c(-c3ccc(C(=O)O)c(F)c3)c2)cn1]

Following Steps 4 and 5 in Scheme 109, using 1-isopropyl-4-(4,4,5,5-tetramethyl-1,3,2-dioxaborolan-2-yl)-1H-pyrazole, 4-(2-amino-5-(1-isopropyl-1H-pyrazol-4-yl)pyridin-3-yl)-2-fluorobenzoic acid was obtained. LCMS (m/z): 341 (MH$^+$), 0.56 min.

Example 224

Synthesis of (S)-4-(3-amino-6-(oxetan-3-yl)pyrazin-2-yl)-2-fluoro-N-(2-hydroxy-1-phenylethyl)benzamide Scheme 113

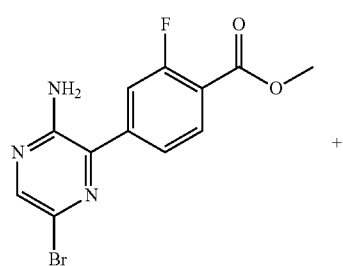

+

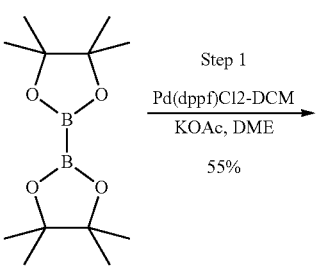

Step 1
Pd(dppf)Cl2-DCM
KOAc, DME
55%

-continued

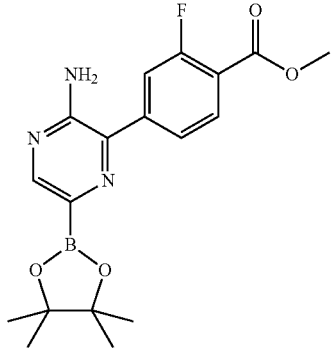

+

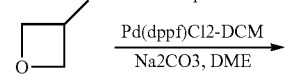

Step 2
Pd(dppf)Cl2-DCM
Na2CO3, DME
11%

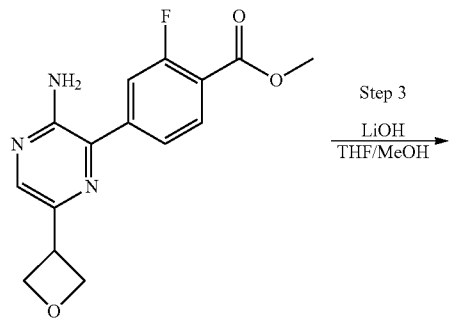

Step 3
LiOH
THF/MeOH

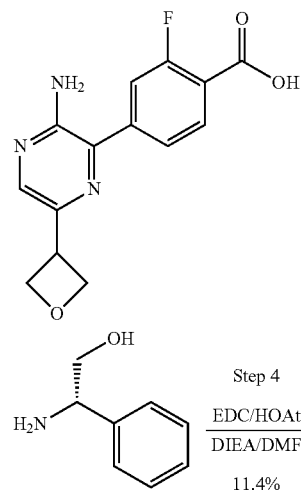

+

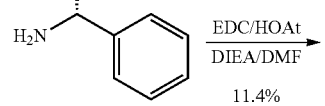

Step 4
EDC/HOAt
DIEA/DMF
11.4%

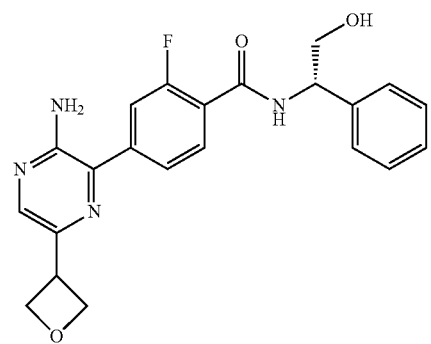

Step 1. Methyl 4-(3-amino-6-(4,4,5,5-tetramethyl-1,3,2-dioxaborolan-2-yl)pyrazin-2-yl)-2-fluorobenzoate To methyl 4-(3-amino-6-bromopyrazin-2-yl)-2-fluorobenzoate (400 mg, 1.227 mmol) in DME (12 mL) was added 4,4,4',4',5,5,5'-heptamethyl-2,2'-bi(1,3,2-dioxaborolane (589 mg, 2.453 mmol), potassium acetate (361 mg, 3.68 mmol) and PdCl$_2$(dppf)-CH$_2$Cl$_2$ (100 mg, 0.123 mmol). The reaction mixture was purged with N$_2$ and heated in microwave at 120° C. for 15 min. The reaction mixtures was partitioned between ethylacetate and water. The organic layer was separated, washed with brine, dried over sodium sulfate, filtered and evaporated. The crude product was taken in ether and sonicate for 20 min. The black solid was filtered off. To the filtrate was added heptane. The precipitate was filtered and dried to provide a light yellow solid. (250 mg, 54.6%). LCMS (m/z): 292.2 (MH$^+$), 0.47 min (for boronic acid).

Step 2. Methyl 4-(3-amino-6-(oxetan-3-yl)pyrazin-2-yl)-2-fluorobenzoate

To methyl 4-(3-amino-6-(4,4,5,5-tetramethyl-1,3,2-dioxaborolan-2-yl)pyrazin-2-yl)-2-fluorobenzoate (150 mg, 0.402 mmol) in DME (6 mL) and sodium carbonate (1.5 mL, 3.0 mmol) was added 3-iodooxetane (370 mg, 2.01 mmol) and PdCl$_2$(dppf)-CH$_2$Cl$_2$ (32.8 mg, 0.042 mmol). The reaction mixture was heated in microwave at 100° C. for 15 min. The reaction mixture was partitioned between ethylacetate and water. The organic layer was separated, washed with brine, dried over sodium sulfate, filtered and evaporated. The crude product was purified by prep HPLC to isolate the product (13.5 mg, 11.0%). LCMS (m/z): 304.2 (MH$^+$), 0.61 min.

Step 3. 4-(3-amino-6-(oxetan-3-yl)pyrazin-2-yl)-2-fluorobenzoic acid

To methyl 4-(3-amino-6-(oxetan-3-yl)pyrazin-2-yl)-2-fluorobenzoate (13 mg, 0.043 mmol) in MeOH (1 mL) and THF (2 mL) was added LiOH (0.128 mL, 0.128 mmol). The reaction mixture was stirred 2 h at room temperature. The reaction mixtures was adjusted to acidic (pH ~3) and solvent was evaporated on rotovap. The crude was azeotrope with toluene and proceed for next step. LCMS (m/z): 290.1 (MH$^+$), 0.46 min.

Step 4. (S)-4-(3-amino-6-(oxetan-3-yl)pyrazin-2-yl)-2-fluoro-N-(2-hydroxy-1-phenylethyl)benzamide To 4-(3-amino-6-(oxetan-3-yl)pyrazin-2-yl)-2-fluorobenzoic acid-crude (10 mg, 0.035 mmol) in DMF (1 mL) was added (S)-2-amino-2-phenylethanol (14.22 mg, 0.104 mmol), DIEA (0.030 mL, 0.173 mmol), EDC (13.25 mg, 0.069 mmol) and aza-HOBt (7.06 mg, 0.052 mmol). The reaction mixture was stirred at room temperature for overnight. The crude was purified by prep HPLC to provide desired product as a TFA salt (11.5%). LCMS (m/z): 409.2 (MH$^+$), 0.597 min; 1H NMR (400 MHz, CD$_3$OD) δ ppm 7.92-7.82 (m, 2H) 7.78-7.64 (m, 2 H) 7.48-7.32 (m, 5 H) 7.23-7.31-7.23 (m, 1 H) 5.28-5.17 (m, 1 H) 5.03-4.90 (m, 5 H) 4.47-4.34 (m, 1 H) 3.96-3.76 (m, 3 H).

Examples 225, 226, and 227

Synthesis of (+/−)-N-(2-amino-1-(3-chlorophenyl)ethyl)-4-(2-amino-5-(1,3-dimethyl-1H-pyrazol-4-yl)pyridin-3-yl)-2-fluorobenzamide

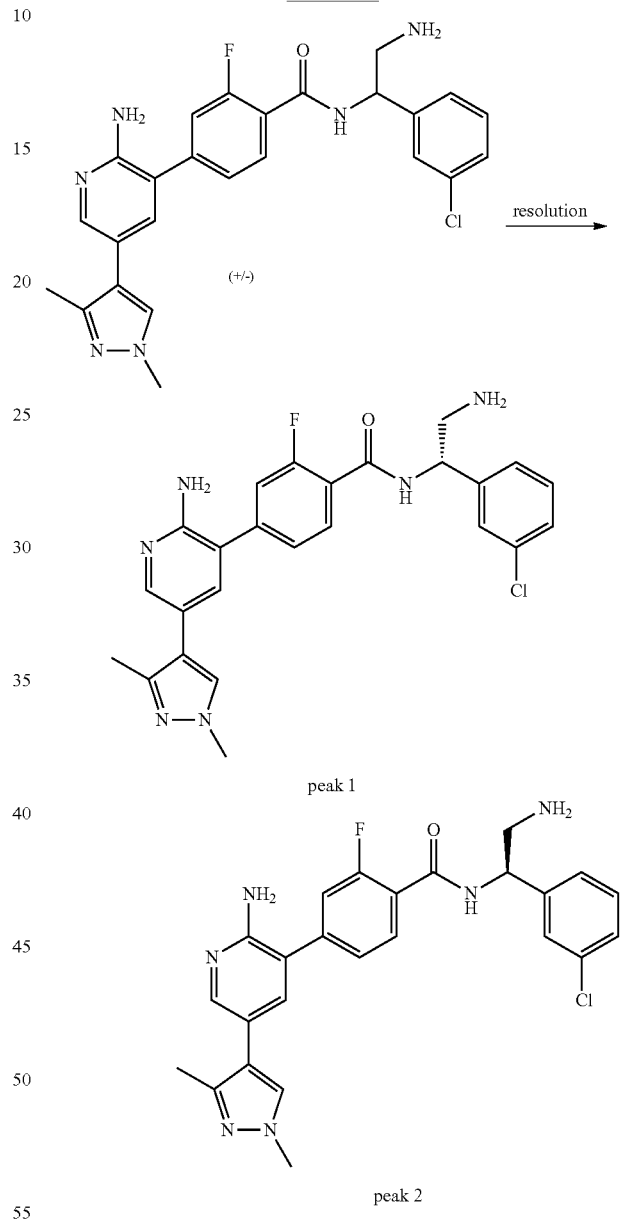

Following Steps 1 and 2 in Scheme 82, Steps 5 and 6 in Scheme 102, using (+/−)-tert-butyl (2-amino-2-(3-chlorophenyl)ethyl)carbamate, (+/−)-N-(2-amino-1-(3-chlorophenyl)ethyl)-4-(2-amino-5-(1,3-dimethyl-1H-pyrazol-4-yl)pyridin-3-yl)-2-fluorobenzamide was obtained. LCMS (m/z): 479.3 (MH$^+$), 0.54 min. 1H NMR (400 MHz, CDCl3) δ ppm 8.16 (m, 2H), 7.87 (m, 1H), 7.47-7.18 (m, 7H), 5.23 (m, 1H), 4.58 (bs, 2H), 3.88 (s, 3H), 3.19 (m, 2H), 2.36 (s, 3H). The racemic mixture was resolved by chiral SFC (ChiralPak 5mic AD column, 4.6×100 (mm), 5 mL/min, EtOH+0.1%, DEA=30%). The polar enantiomer, (S)-N-(2- amino-1-(3-chlorophenyl)ethyl)-4-(2-amino-5-(1,3-dimethyl-1H-pyrazol-4-yl)pyridin-3-yl)-2-fluorobenzamide, was obtained at Rt=2.6 min. LCMS (m/z): 479.1 (MH$^+$), 0.57 min. The less polar enantiomer, (R)-N-(2-amino-1-(3-chlorophenyl)ethyl)-4-(2-amino-5-(1,3-dimethyl-1H-pyrazol-4-yl)pyridin-3-yl)-2-fluorobenzamide, was obtained at Rt=3.22 min. LCMS (m/z): 479.1 (MH$^+$), 0.57 min. The absolute stereomchemisty was assigned based on biochemical data and docking model.

Synthesis of 4-(3-amino-6-((1r,4r)-4-deuterido-4-hydroxycyclohexyl)pyrazin-2-yl)-2-fluorobenzoic acid

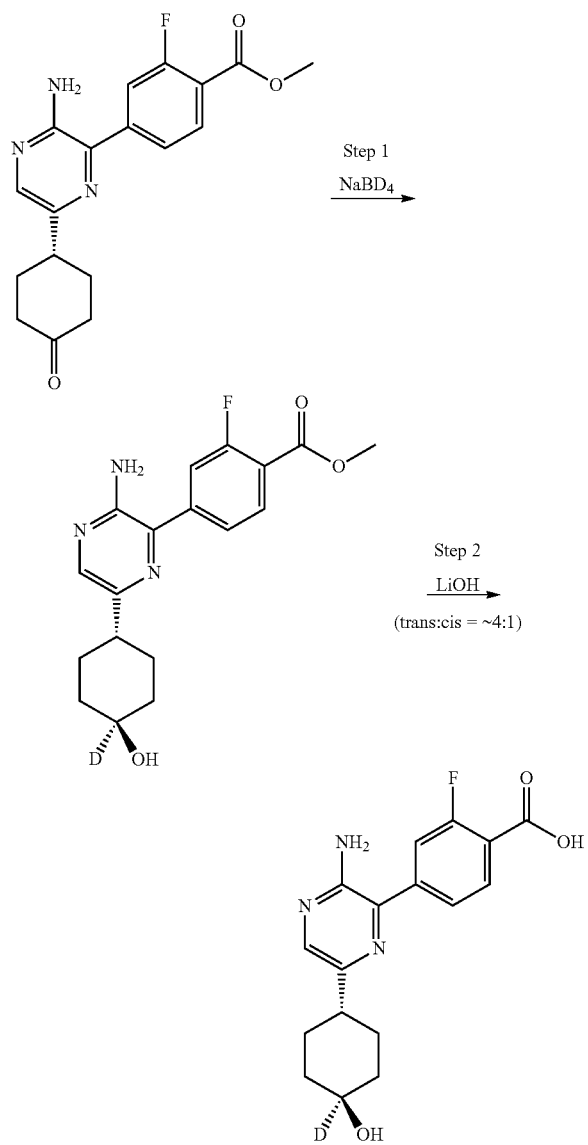

Scheme 115

Step 1. methyl 4-(3-amino-6-((1r,4r)-4-deuterido-4-hydroxycyclohexyl)pyrazin-2-yl)-2-fluorobenzoate A solution of ethyl 4-(3-amino-6-(4-oxocyclohexyl) pyrazin-2-yl)-2-fluorobenzoate (98 mg, 0.285 mmol) in methanol (1.903 mL), THF (0.952 mL) was cooled down to −78° C. To this, NaBD$_4$ (32.4 mg, 0.856 mmol) was slowly added by a portion. The reaction mixture was allowed to warm up to room temperature for 1 h. The reaction mixture was quenched with NH$_4$Cl solution, then followed by Na$_2$CO$_3$ solution and stirred for 1 h. The reaction mixture was extracted by EtOAc. The combined organic layer was washed with water and brine, dried over anhydrous Na$_2$SO$_4$, filtered off, and concentrated in vacuo to provide crude methyl 4-(3-amino-6-((1r,4r)-4-deuterido-4-hydroxycyclohexyl)pyrazin-2-yl)-2-fluorobenzoate (81.4 mg, trans:cis=~4:1, 82%), which was used for the next step. LCMS (m/z): 347.1 (MH$^+$), 0.61 min (major, trans) and 0.64 min (cis).

Step 2. 4-(3-amino-6-((1r,4r)-4-deuterido-4-hydroxycyclohexyl)pyrazin-2-yl)-2-fluorobenzoic acid To a solution of methyl 4-(3-amino-6-((1r,4r)-4-deuterido-4-hydroxycyclohexyl)pyrazin-2-yl)-2-fluorobenzoate (81 mg, 0.234 mmol) in THF (1559 μl,) and MeOH (780 μl) was added LiOH (1M solution) (421 μl, 0.421 mmol). The reaction mixture was stirred at room temperature for 1 h. After pH was adjusted to 5, the reaction mixture was extracted with EtOAc. The combined organic layer was washed with water and brine, filtered off, and concentrated in vacuo. The crude 4-(3-amino-6-((1r,4r)-4-deuterido-4-hydroxycyclohexyl)pyrazin-2-yl)-2-fluorobenzoic acid (99%) was used for the next step without further purification. LCMS (m/z): 333.1 (MH$^+$), 0.47 min (major, trans) and 0.51 min (cis).

Synthesis of (S)-2-amino-2-deuterido-2-(3-bromo-5-fluorophenyl)ethanol

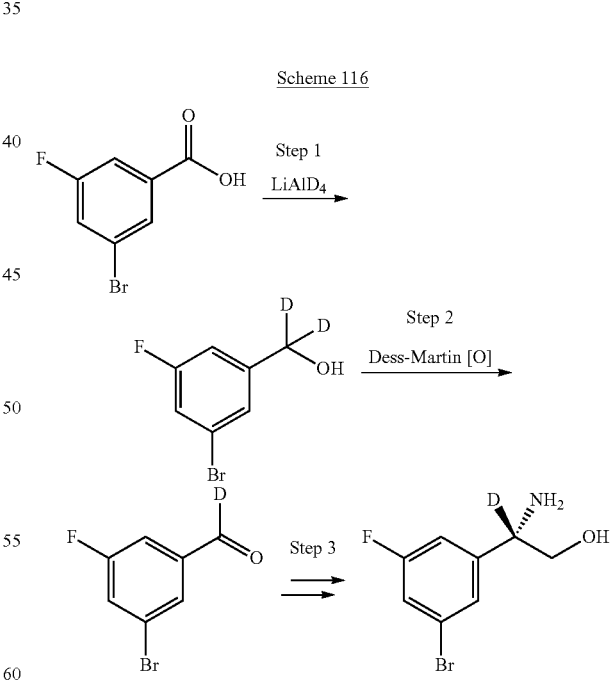

Scheme 116

Step 1. (3-bromo-5-fluorophenyl)-1,1-di-deuterido-methanol

3-Bromo-5-fluorobenzoic acid (5.3 g, 24.20 mmol) was dissolved in THF (81 mL). To this, LiAlD$_4$ (1.102 g, 29.0 mmol) was added at 0° C. The reaction mixture was stirred at room temperature overnight. After the reaction mixture was cooled down to 0° C., 1.1 mL of water was added, followed by 1.1 mL of 15% NaOH and 3.2 mL of water. The suspension was stirred at room temperature for 2 h, then filtered through Celite and rinsed with $Et_2O$, the filtrate was concentrated to yield the crude product, which was purified by flash chromatography (0-30% EtOAc/heptane) to yield (3-bromo-5-fluorophenyl)-1,1-di-deuterido-methanol in 64% yield. LCMS (m/z): 232.0 (MNa+), 0.69 min.

Step 2. 3-bromo-5-fluorobenzaldehyde-d1

(3-Bromo-5-fluorophenyl)-1,1-di-deuterido-methanol (3.2 g, 15.4 mmol) was dissolved in DCM (51.5 mL) and cooled down to 0° C. Dess-Martin periodinane (9.83 g, 23.18 mmol) was added to the reaction mixture, which was stirred at 0° C. for 3 h. Saturated $Na_2S_2O_3$/$NaHCO_3$ (8:1) solution was added to the mixture, which was stirred at room temperature for 1 h. The reaction mixture was then extracted with DCM. The combined organic layer was washed with water and brine, filtered off, and concentrated in vacuo. The crude material was purified by flash chromatography to yield 3-bromo-5-fluorobenzaldehyde-d1 as white solid (2.6 g, 82%). 1H NMR (400 MHz, $CDCl_3$) δ ppm 7.83 (s, 1H), 7.57-7.50 (m, 2H).

Step 3. (S)-2-amino-2-deuterido-2-(3-bromo-5-fluorophenyl)ethanol

Following Steps 4 to 9 in Scheme 74, using 3-bromo-5-fluorobenzaldehyde-d1, (S)-2-amino-2-deuterido-2-(3-bromo-5-fluorophenyl)ethanol was obtained as a HCl salt. LCMS (m/z): 235.0/237.0 (MH+), 0.40 min.

Synthesis of (R)-2-amino-2-(3-bromo-5-fluorophenyl)-2,2-di-deuterido-ethanol hydrochloride Scheme 117

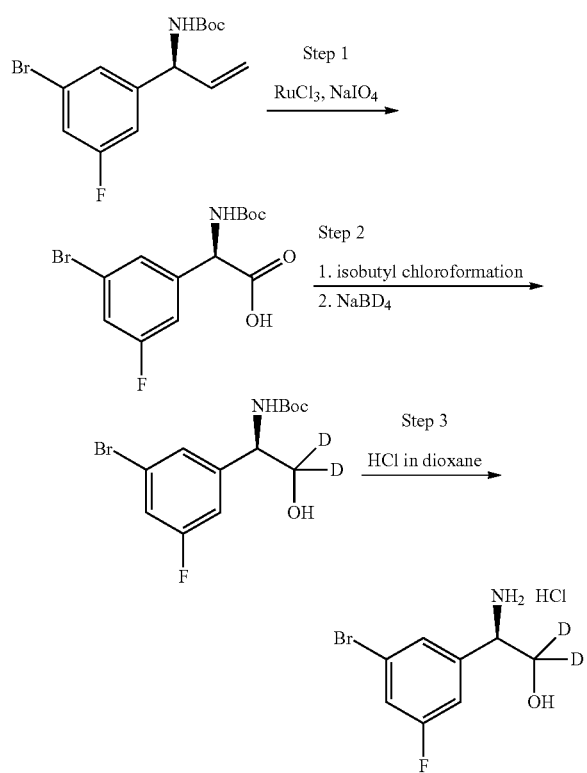

Step 1. (R)-2-(3-bromo-5-fluorophenyl)-2-((tert-butoxycarbonyl)amino)acetic acid A solution of (S)-tert-butyl (1-(3-bromo-5-fluorophenyl)allyl)carbamate (1.235 g, 3.74 mmol) in $CCl_4$ (4 mL), acetonitrile (4 mL) and water (6 mL) was treated with sodium periodate (1.680 g, 7.85 mmol) and $RuCl_3$ (16 mg, 0.075 mmol). After 1 h, the reaction was complete. The reaction was partitioned between ethyl acetate and water. The organics were washed with brine, then filtered over celite and concentrated. The crude was redissolved in benzene, then filtered and concentrated again to provide crude (R)-2-(3-bromo-5-fluorophenyl)-2-((tert-butoxycarbonyl)amino)acetic acid (1.30 g, 99% yield) which was used directly. LCMS (m/z): 348.2 (MH+), 0.52 min.

Step 2. (R)-tert-butyl (1-(3-bromo-5-fluorophenyl)-2-hydroxy-2,2-deuterido-ethyl)carbamate A −10° C. solution of (R)-2-(3-bromo-5-fluorophenyl)-2-((tert-butoxycarbonyl)amino)acetic acid (1.30 g, 3.73 mmol) in DME (6 mL) was treated with N-methyl morpholine (0.431 mL, 3.92 mmol). After 5 min, the reaction was treated with isobutyl chloroformate (0.515 mL, 3.92 mmol). After an additional 5 min, the reaction was filtered and the cake was washed with DME (4 mL). The combined organics were treated with a solution of $NaBD_4$ (0.251 g, 5.97 mmol) in water (1 mL). At completion, the reaction was partitioned between ethyl acetate and water. The organics were washed with brine, then dried over sodium sulfate and concentrated. The crude material was purified by prep HPLC to provide the title compound, (R)-tert-butyl (1-(3-bromo-5-fluorophenyl)-2-hydroxy-2,2-deuterido-ethyl)carbamate (55 mg, 4.4% yield). LCMS (m/z): 337.3 (MH+), 1.03 min.

Step 3. (R)-2-amino-2-(3-bromo-5-fluorophenyl)-2,2-di-deuterido-ethanol hydrochloride A solution of (R)-tert-butyl (1-(3-bromo-5-fluorophenyl)-2-hydroxy-2,2-deuterido-ethyl)carbamate (46 mg, 0.137 mmol) in 4 M HCl in dioxane (1368 μl) was stirred for overnight. The volatile materials were removed in vacuo. The crude product was used for the next step without further purification. LCMS (m/z): 236/238 (MH+), 0.4 min.

Synthesis of 4-(3-amino-6-(4-(hydroxymethyl)cyclohexyl)pyrazin-2-yl)-2-fluorobenzoic acid Scheme 118

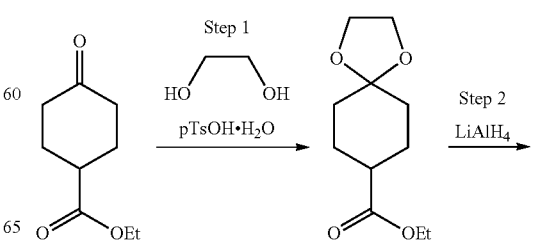

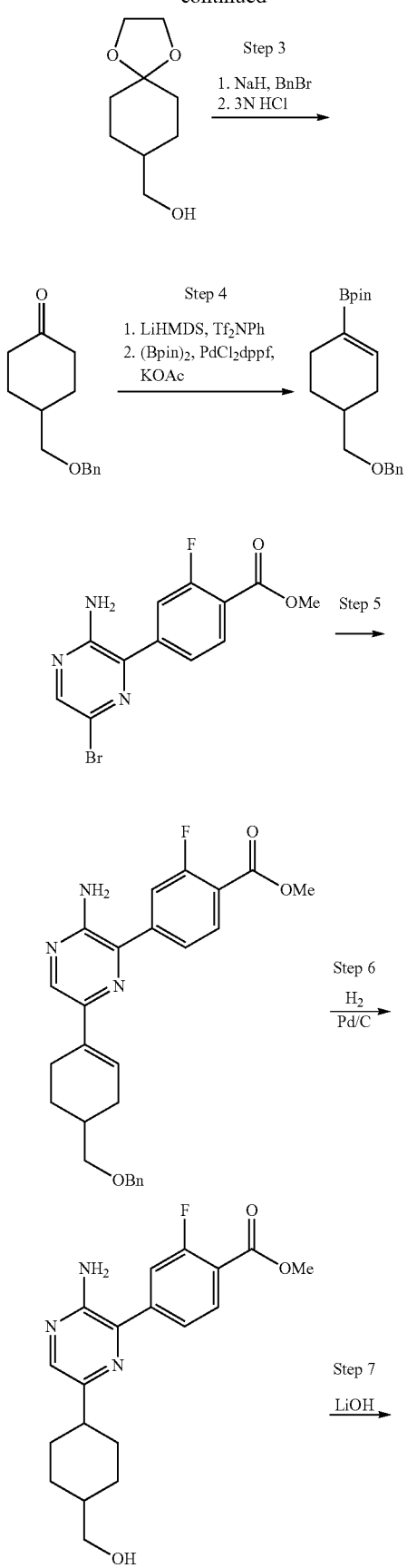

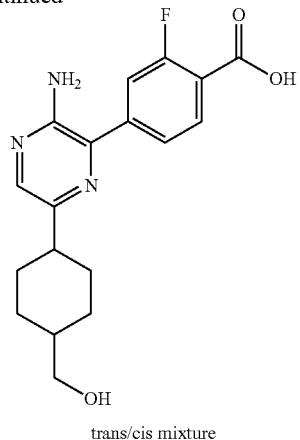

trans/cis mixture

Step 1. Ethyl 1,4-dioxaspiro[4.5]decane-8-carboxylate

Ethyl 4-oxocyclohexanecarboxylate (15.01 g, 88.16 mmol) was combined with ethylene glycol (21 mL, 4.27 equiv.) and p-toluenesulfonic acid monohydrate (0.2 g, 0.012 equiv.) in anhydrous toluene (50 mL), and the mixture was stirred 14 h at room temperature. The reaction was diluted with ether (200 mL) and was washed with $H_2O$ (2×200 mL), saturated sodium bicarbonate (100 mL) and brine (80 mL). The organic layer was dried ($Na_2SO_4$), filtered and concentrated under reduced pressure to yield 18.15 g ethyl 4-oxocyclohexanecarboxylate ethylene ketal (96% yield). LCMS (m/z): 214.8 ($MH^+$), 0.74 min.

Step 2. 1,4-dioxaspiro[4.5]decan-8-ylmethanol $LiAlH_4$ (2.51 g, 66.3 mmol) was suspended in THF (60 mL) and then cooled in an ice-bath. To the suspension was added Ethyl 1,4-dioxaspiro[4.5]decane-8-carboxylate (11.357 g, 53.0 mmol) dissolved in THF (40 mL) dropwise and the reaction mixture was gradually warmed to room temperature over 1 h upon which LCMS indicated complete reduction of SM. The reaction mixture was diluted with ether (200 mL) and quenched with 2.5 mL water and then 5 mL (10% NaOH) and then 7.5 mL water. To this, anhydrous $MgSO_4$ was added, which was then agitated for 30 min and filtered over Celite. The filtrate was concentrated in vacuo to afford the desired product in quantitative yield. LCMS (m/z): 173.1 ($MH^+$), 0.41 min.

Step 3. 4-((benzyloxy)methyl)cyclohexanone 1,4-dioxaspiro[4.5]decan-8-ylmethanol (1.33 g, 7.72 mmol) was dissolved in DMF (14 mL) and then cooled to 0° C. To the solution was added NaH (0.402 g, 10.04 mmol) in portions and the mixture agitated at 10° C. for 1 h and then benzyl bromide (1.194 mL, 10.04 mmol) was added and the mixture agitated over 72 h. The reaction mixture was quenched with water and extracted with ether and the combined organic extracts dried ($MgSO_4$), filtered and concentrated in vacuo and the crude product 8-((benzyloxy)methyl)-1,4-dioxaspiro[4.5]decane dissolved in acetonitrile (35 mL) and water (25 mL) and treated with 3N HCl (13 mL) and agitated at room temperature for 20 min upon which LCMS indicated desired product. The reaction mixture was quenched with 40 mmol aqueous NaOH and then extracted with EtOAc (200 mL) and the organic layer was washed with water and dried (MgSO$_4$), filtered and concentrated in vacuo and the residue purified by flash chromatography (0-50% EtOAc/heptane) to afford 1.23 g of the desired product as a colorless syrup (73%). LCMS (m/z): 329.2 (MH$^+$), 1.33 min.

Step 4. 2-(4-((benzyloxy)methyl)cyclohex-1-en-1-yl)-4,4,5,5-tetramethyl-1,3,2-dioxaborolane 1,4-dioxaspiro[4.5]decan-8-ylmethanol (1.23 g, 5.63 mmol) was dissolved in THF (22.5 mL) and cooled to −78° C. Then LiHMDS (6.20 mL, 6.20 mmol) was added dropwise and the mixture stirred at this temperature for 1 h upon which 1,1,1-trifluoro-N-phenyl-N-((trifluoromethyl)sulfonyl)methanesulfonamide (2.214 g, 6.20 mmol) was added in one portion and the reaction mixture was let to warm to room temperature and stir overnight. The next morning, the reaction mixture was quenched with 1.0 M NaHSO$_4$ and the solvent evaporated in vacuo. The residue was partitioned between NaOH/ether and the organic layer was separated and washed with 1.0 M NaOH twice, and dried with brine and then MgSO$_4$, filtered and concentrated in vacuo to afford the desired product 4-((benzyloxy)methyl)cyclohex-1-en-1-yl trifluoromethanesulfonate in quantitative yield which was taken to the next step without any further purification. The intermediate 4-((benzyloxy)methyl)cyclohex-1-en-1-yl (1000 mg, 2.85 mmol), B$_2$(PIN)$_2$ (1087 mg, 4.28 mmol), PdCl$_2$(dppf)-CH$_2$Cl$_2$ (233 mg, 0.285 mmol) and KOAc (560 mg, 5.71 mmol) were charged in a microwave vial and then dioxane (9.5 mL) was added. The mixture was evacuated and purged with N$_2$ and then heated to 100° C. for 22 min in microwave. The crude mixture was diluted with ether and water and the organic layer was separated and dried (MgSO$_4$), filtered and concentrated in vacuo and the residue purified by flash chromatography (0-10% EtOAc/heptanes) to afford the desired product (51%). LCMS (m/z): 219.2 (MH$^+$), 0.88 min.

Step 5. Methyl 4-(3-amino-6-(4-((benzyloxy)methyl)cyclohex-1-en-1-yl)pyrazin-2-yl)-2-fluorobenzoate Methyl 4-(3-amino-6-bromopyrazin-2-yl)-2-fluorobenzoate (343 mg, 1.051 mmol), 2-(4-((benzyloxy)methyl)cyclohex-1-en-1-yl)-4,4,5,5-tetramethyl-1,3,2-dioxaborolane (414 mg, 1.261 mmol) PdCl$_2$(dppf)-CH$_2$Cl$_2$ adduct (86 mg, 0.105 mmol) were placed in a microwave vial and then DME (3.5 mL) was added. Then 2.0 M Na$_2$CO$_3$ (1261 µL, 2.52 mmol) was added and the mixture was degassed and purged with nitrogen and then heated at 115° C. for 30 min upon which the reaction was complete. The reaction mixture was diluted with EtOAc and washed with water and the organic layer was separated and dried (MgSO$_4$), filtered and concentrated and the residue purified by flash chromatography (0-100% EtOAc/heptane) to afford 381 mg the desired product as a yellow solid (81%). LCMS (m/z): 448.2 (MH$^+$), 1.16 min.

Step 6. Methyl 4-(3-amino-6-(4-(hydroxymethyl)cyclohexyl)pyrazin-2-yl)-2-fluorobenzoate Methyl 4-(3-amino-6-(4-((benzyloxy)methyl)cyclohex-1-en-1-yl)pyrazin-2-yl)-2-fluorobenzoate (381 mg, 0.851 mmol) was dissolved in THF (5 mL) and then MeOH (15 mL) was added and then PdC (10% wet) (550 mg, 0.517 mmol) was added. The mixture was put under vacuum and purged with hydrogen and this cycle was repeated thrice and then finally under hydrogen overnight. After 14 h, LCMS indicated alkene saturation but only partial benzyl deprotection, and therefore another PdC (10% wet) (700 mg) was added and the mixture stirred at room temperature for another 5 h after which complete benzyl deprotection observed. The reaction mixture was filtered and concentrated in vacuo to afford 215.6 mg of the desired product as a mixture of diasteromers (cis/trans unspecified) (70%). LCMS (m/z): 360.2 (MH$^+$), 0.71, 0.72 min.

Step 7. (S)-4-(3-amino-6-(4-(hydroxymethyl)cyclohexyl)pyrazin-2-yl)-N-(1-(3-chlorophenyl)-2-hydroxyethyl)-2-fluorobenzamide Methyl 4-(3-amino-6-(4-(hydroxymethyl)cyclohexyl)pyrazin-2-yl)-2-fluorobenzoate (215.6 mg, 0.600 mmol) was dissolved in THF (3 mL) and then MeOH (3 mL) was added and then 1.0 M LiOH (2400 µL, 2.400 mmol) was added. The reaction mixture was agitated overnight and the next morning, LCMS indicated formation of desired product. The reaction mixture was concentrated in vacuo and then azeotroped with THF twice (10 mL each) and then acidified with 1.5 mL of 4.0 N HCl in dioxane and concentrated in vacuo. The residue was dissolved in DMSO (5 mL) and taken to the next step as such. LCMS (m/z): 346.2 (MH$^+$), 0.57, 0.58 min.

Synthesis of 4-(3-amino-6-((1s,4s)-4-fluorocyclohexyl)pyrazin-2-yl)-2-fluorobenzoic acid

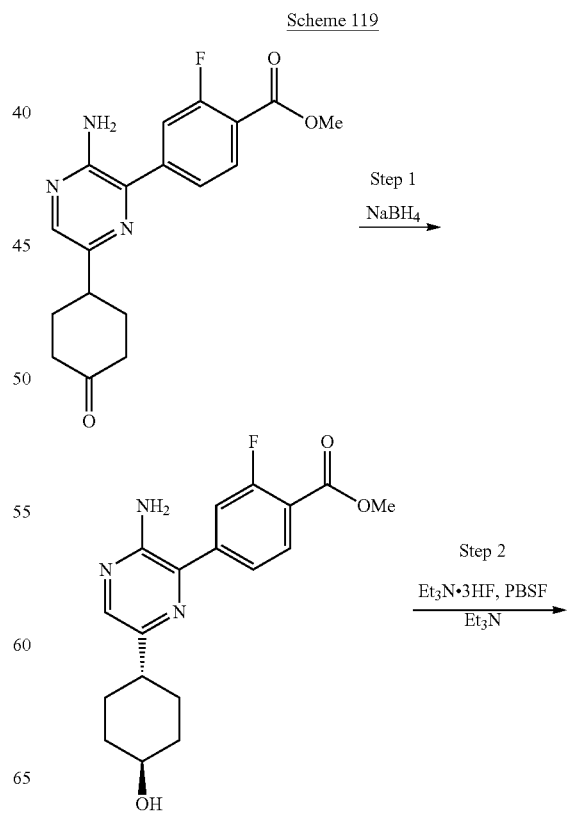

Scheme 119

-continued

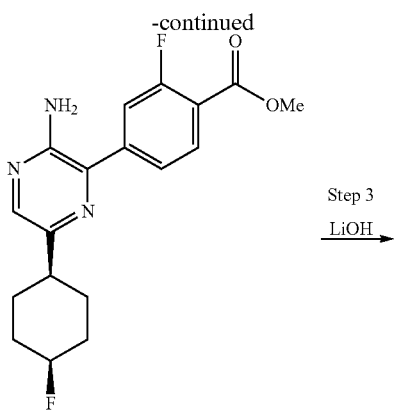

Step 3
LiOH

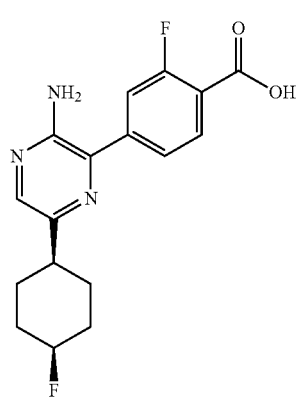

Step 1. methyl 4-(3-amino-6-((1r,4r)-4-hydroxycyclohexyl)pyrazin-2-yl)-2-fluorobenzoate Methyl 4-(3-amino-6-(4-oxocyclohexyl)pyrazin-2-yl)-2-fluorobenzoate (401.4 mg, 1.169 mmol) was suspended in MeOH and cooled to 0° C. To the mixture was added NaBH$_4$ (133 mg, 3.51 mmol) dissolved in MeOH (5 mL) and the mixture was gradually warmed to room temperature and stirred for 30 min upon which reaction was complete. The reaction mixture was diluted with EtOAc and saturated NaHCO$_3$ and the organic layer washed with water twice and dried (MgSO$_4$), filtered and concentrated in vacuo to afford 339.4 mg of the desired product (84%). LCMS (m/z): 346.2 (MH$^+$), 0.63 min.

Step 2. Methyl 4-(3-amino-6-((1s,4s)-4-fluorocyclohexyl)pyrazin-2-yl)-2-fluorobenzoate A flask containing a solution of methyl 4-(3-amino-6-((1r,4r)-4-hydroxycyclohexyl)pyrazin-2-yl)-2-fluorobenzoate (339.4 mg, 0.983 mmol) in acetonitrile (3.2 mL) was cooled to 0° C. in a ice/brine bath and perfluorobutanesulfonyl fluoride (530 µl, 2.95 mmol) followed by triethylamine trihydrofluoride (480 µl, 2.95 mmol) and triethylamine (1233 µl, 8.84 mmol) was added and the resulting reaction mixture was allowed to stir at 0° C. for 90 min. After the elapsed time, LCMS indicated a 2.5:1 ratio of elimination vs. desired product. The reaction mixture was quenched with water and extracted with EtOAc and the organic extract washed with water twice and dried (MgSO$_4$), filtered and concentrated in vacuo to afford the crude product mixture which was carefully chromatographed (0-60% EtOAc/heptane) to afford 67.5 mg of the desired product. (19.8%). LCMS (m/z): 348.2 (MH$^+$), 0.86 min.

Step 3. 4-(3-amino-6-((1s,4s)-4-fluorocyclohexyl)pyrazin-2-yl)-2-fluorobenzoic acid Methyl 4-(3-amino-6-((1s,4s)-4-fluorocyclohexyl)pyrazin-2-yl)-2-fluorobenzoate (67.5 mg, 0.194 mmol) was dissolved in THF (1 mL) and MeOH (1 mL) and then 1.0 M LiOH (0.777 mL, 0.777 mmol) was added. The reaction mixture was agitated at room temperature. After 1 h, LCMS indicated formation of desired acid. LCMS (m/z): 334.2 (MH$^+$), 0.70 min.

Synthesis of 3-bromo-5-((1r,4r)-4-fluorocyclohexyl)pyrazin-2-amine

Scheme 120

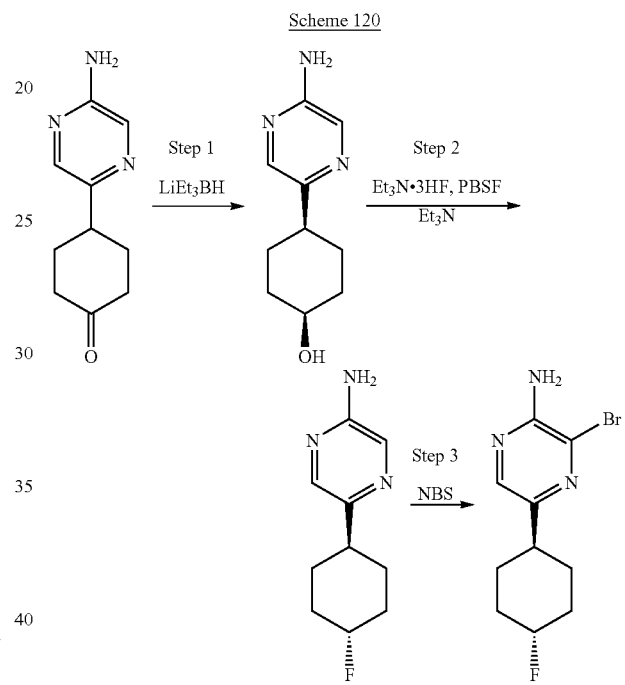

Step 1. (1s,4s)-4-(5-aminopyrazin-2-yl)cyclohexanol 4-(5-aminopyrazin-2-yl)cyclohexanone (1.049 g, 5.48 mmol) was dissolved in THF (10 mL) and cooled to 0° C. L-Selectride (12.06 mL, 12.06 mmol) was added dropwise and the mixture stirred for 20 min upon which reaction complete. The reaction mixture was quenched with 5 N NaOH (40 mmol) and then MeOH (5 mL). The reaction mixture was diluted with 2-methyl THF and the aqueous layer separated and the organic layer washed with brine and dried (MgSO$_4$), filtered and concentrated in vacuo to afford the desired product in a 95:5 cis/trans ratio which was then triturated with ether to obtain 586.3 mg of a faint yellow precipitate as the desired product (55%). LCMS (m/z): 194.1 (MH$^+$), 0.32 min.

Step 2 and 3. 3-bromo-5-((1r,4r)-4-fluorocyclohexyl)pyrazin-2-amine

Following Step 2 and 3 in Scheme 119, 3-bromo-5-((1r,4r)-4-fluorocyclohexyl)pyrazin-2-amine was obtained. LCMS (m/z): 276.0 (MH$^+$), 0.81 min.

Synthesis of 4-(3-amino-6-(4-cyanocyclohexyl)pyrazin-2-yl)-2-fluorobenzoic acid

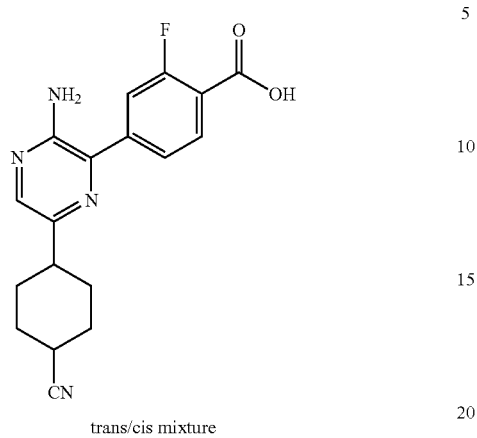

trans/cis mixture

Following Steps 4 to 7 in Scheme 118, 4-(3-amino-6-(4-cyanocyclohexyl)pyrazin-2-yl)-2-fluorobenzoic acid was obtained. LCMS (m/z): 341.2 (MH$^+$), 0.64, 0.66 min (trans, cis).

TABLE 5

Compounds prepared using Method 3 described above.

| Example | Structure | Name | MH$^+$ | R$_t$ (min) | NMR |
|---|---|---|---|---|---|
| 228 | 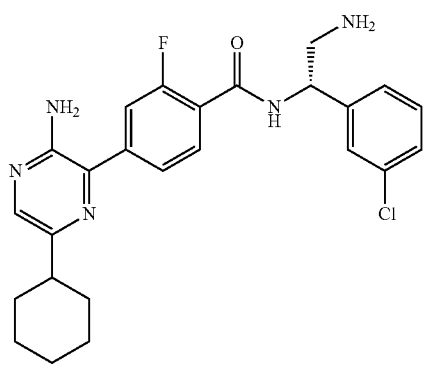 [SMILES: NC[C@@H](NC(=O)c1ccc(-c2nc(C3CCCCC3)cnc2N)cc1F)c1cccc(Cl)c1] | (S)-N-(2-amino-1-(3-chlorophenyl)ethyl)-4-(3-amino-6-cyclohexylpyrazin-2-yl)-2-fluorobenzamide | 468.2 | 0.8 | 1H NMR (400MHz, CD$_3$OD) δ 7.88-7.7 (m, 2H), 7.62 (m, 1H), 7.52 (m, 1H), 7.46 (s, 1H), 7.36 (m, 3 H), 5.4 (m, 1H), 3.38 (m, 2H), 2.56 (m, 1H), 1.79 (m, 4H), 1.64 (m, 1 H), 1.48-1.33 (m, 4H), 1.33 (m, 1H). |
| 229 | 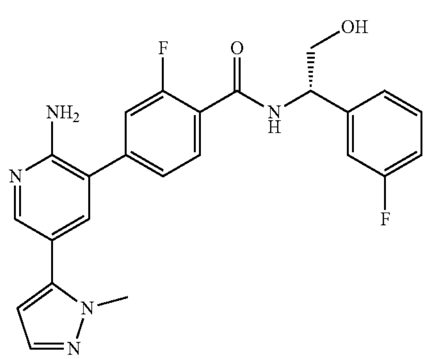 [SMILES: Cn1nccc1-c1cnc(N)c(-c2ccc(C(=O)N[C@H](CO)c3cccc(F)c3)c(F)c2)c1] | (S)-4-(2-amino-5-(1-methyl-1H-pyrazol-5-yl)pyridin-3-yl)-2-fluoro-N-(1-(3-fluorophenyl)-2-hydroxyethyl)benzamide | 450.2 | 0.62 | 1H NMR (400 MHz ,CD$_3$OD) δ 8.13 (d, J = 2.0 Hz, 1H), 8.01 (d, J = 2.0 Hz, 1H), 7.91 (t, J = 7.6 Hz, 1H), 7.54 (d, J = 2.0 Hz, 1H), 7.53-7.43 (m, 2H), 7.43-7.34 (m, 1H), 7.25 (d, J = 7.8 Hz. 1H), 7.17 (d, J = 10.2 Hz, 1H), 7.02 (dt, J = 2.2, 8.5 Hz, 1H), 6.51 (d, J = 2.0 Hz, 1 H), 5.23 (d, J = 6.3 Hz, 1H), 3.96-3.89 (m, 3H), 3.90-3.80 (m, 2H) |

TABLE 5-continued

Compounds prepared using Method 3 described above.

| Example | Structure | Name | MH+ | R$_t$ (min) | NMR |
|---|---|---|---|---|---|
| 230 | 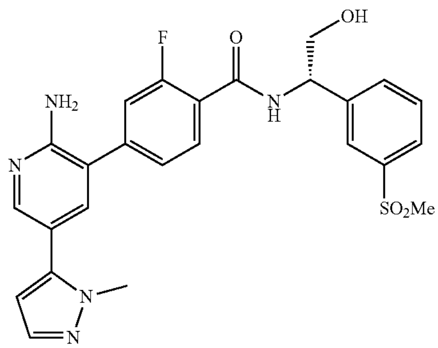 [SMILES: Cn1nccc1-c1cnc(N)c(-c2ccc(C(=O)N[C@H](CO)c3cccc(S(C)(=O)=O)c3)c(F)c2)c1] | (S)-4-(2-amino-5-(1-methyl-1H-pyrazol-5-yl)pyridin-3-yl)-2-fluoro-N-(2-hydroxy-1-(3-(methylsulfonyl)phenyl)ethyl)benzamide | 510.3 | 0.51 | 1H NMR (400 MHz, CD$_3$OD) δ 8.13 (d, J = 2.0 Hz. 1H), 8.04 (s, 1H), 7.98 (d, J = 2.0 Hz. 1H), 7.95-7.87 (m, 2H), 7.80 (d, J = 7.8 Hz, 1H), 7.65 (t, J = 7.8 Hz, 1H), 7.53 (d, J = 2.0 Hz, 1H), 7.52-7.44 (m, 2H), 6.50 (s, 1H), 5.31 (d, J = 5.5 Hz, 1H), 4.00-3.86 (m, 5H), 3.12 (s, 3H) |
| 231 | 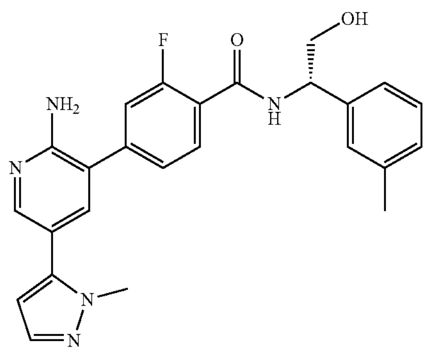 [SMILES: Cc1cccc([C@@H](CO)NC(=O)c2ccc(-c3cc(-c4ccnn4C)cnc3N)cc2F)c1] | (S)-4-(2-amino-5-(1-methyl-1H-pyrazol-5-yl)pyridin-3-yl)-2-fluoro-N-(2-hydroxy-1-(m-tolyl)ethyl)benzamide | 446.3 | 0.64 | 1H NMR (400 MHz, CD$_3$OD) δ ppm 8.13 (d, J = 2.0 Hz, 1H), 8.03 (d, J = 2.3 Hz, 1H), 7.91 (t, J = 7.8 Hz, 1H), 7.54 (d, J = 2.0 Hz, 1H), 7.52-7.40 (m, 2H), 7.28-7.13 (m, 3H), 7.10 (d, J = 6.7 Hz, 1H), 6.51 (d, J = 2.0 Hz, 1H), 5.24-5.15 (m, 1H), 3.95-3.89 (m, 3H), 3.89-3.74 (m, 2H) |
| 232 | 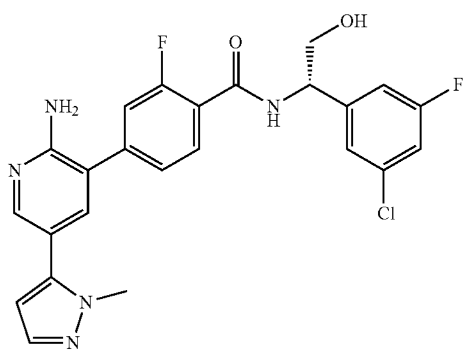 [SMILES: Cn1nccc1-c1cnc(N)c(-c2ccc(C(=O)N[C@H](CO)c3cc(F)cc(Cl)c3)c(F)c2)c1] | (S)-4-(2-amino-5-(1-methyl-1H-pyrazol-5-yl)pyridin-3-yl)-N-(1-(3-chloro-5-fluorophenyl)-2-hydroxyethyl)-2-fluorobenzamide | 484.2 | 0.66 | $^1$H NMR (400 MHz, CD$_3$OD) δ 8.13 (d, J = 2.3 Hz, 1H), 8.00 (d, J = 2.0 Hz, 1H), 7.91 (t, J = 7.8 Hz, 1H), 7.56-7.45 (m, 3H), 7.30 (s, 1H), 7.18-7.10 (m, 2H), 6.50 (d, J = 2.0 Hz, 1H), 5.18 (t, J = 5.7 Hz, 1H), 3.91 (s, 3H), 3.90-3.81 (m, 2H). |
| 233 | 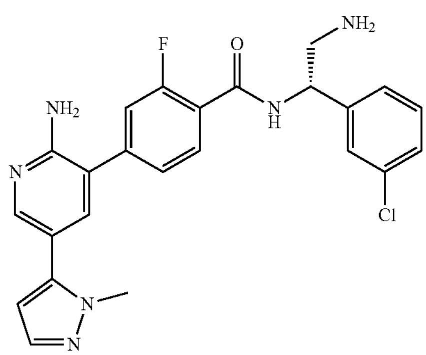 [SMILES: Cn1nccc1-c1cnc(N)c(-c2ccc(C(=O)N[C@H](CN)c3cccc(Cl)c3)c(F)c2)c1] | (S)-N-(2-amino-1-(3-chlorophenyl)ethyl)-4-(2-amino-5-(1-methyl-1H-pyrazol-5-yl)pyridin-3-yl)-2-fluorobenzamide | 465.2 | 0.55 | 1H NMR (400 MHz, CD$_3$OD) δ 8.10-7.98 (m, 1H), 7.90-7.75 (m, 2H), 7.50-7.25 (m, 7H), 6.45-6.32 (m, 1H), 5.46-5.30 (m, 1H), 3.81 (s, 3H), 3.48-3.28 (m, 2H) |

TABLE 5-continued

Compounds prepared using Method 3 described above.

| Example | Structure | Name | MH+ | R$_t$ (min) | NMR |
|---|---|---|---|---|---|
| 234 | 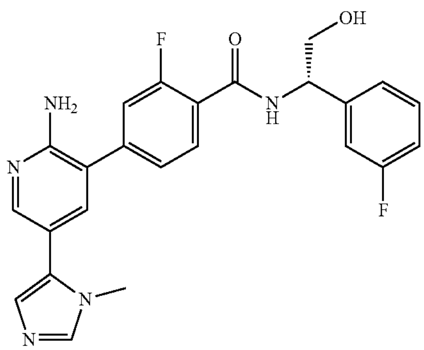 [SMILES: Cn1cncc1-c1cnc(N)c(-c2ccc(C(=O)N[C@H](CO)c3cccc(F)c3)c(F)c2)c1] | (S)-4-(2-amino-5-(1-methyl-1H-imidazol-5-yl)pyridin-3-yl)-2-fluoro-N-(1-(3-fluorophenyl)-2-hydroxyethyl)benzamide | 450.3 | 0.49 | 1H NMR (400 MHz, CD$_3$OD) δ 8.87 (s, 1H), 8.54 (d, J = 4.7 Hz, 1H), 8.08 (d, J = 2.0 Hz, 1H), 7.79 (t, J = 7.6 Hz, 1H), 7.64 (d, J = 2.3 Hz, 1H), 7.57 (d, J = 1.6 Hz, 1H), 7.43-7.32 (m, 3H), 7.32-7.23 (m, 1H), 7.19-7.12 (m, 2H), 7.08 (d, J = 9.8 Hz, 1H), 6.92 (dt, J = 2.0, 8.4 Hz, 1H), 5.15-5.09 (m, 1H), 3.83-3.71 (m, 5H) |
| 235 | 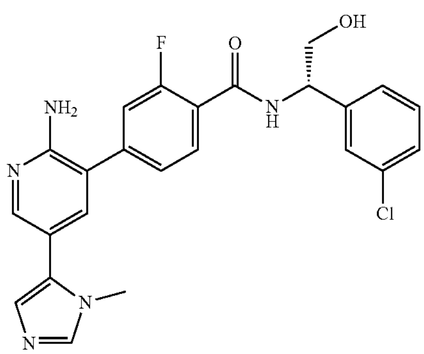 [SMILES: Cn1cncc1-c1cnc(N)c(-c2ccc(C(=O)N[C@H](CO)c3cccc(Cl)c3)c(F)c2)c1] | (S)-4-(2-amino-5-(1-methyl-1H-imidazol-5-yl)pyridin-3-yl)-N-(1-(3-chlorophenyl)-2-hydroxyethyl)-2-fluorobenzamide | 466.4 | 0.55 | $^1$H NMR (400 MHz, CD$_3$OD) δ 8.97 (s, 1H), 8.66 (br. s., 1H), 8.18 (d, J = 2.0 Hz, 1H), 7.88 (t, J = 7.8 Hz, 1H), 7.72 (d, J = 2.0 Hz, 1H), 7.67 (d, J = 1.6 Hz, 1H), 7.50-7.40 (m, 3H), 7.40-7.25 (m, 3H), 5.20 (d, J = 5.9 Hz, 1H), 3.95-3.81 (m, 5H) |
| 236 | 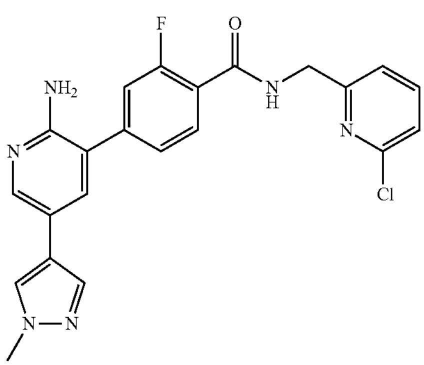 [SMILES: Cn1cc(-c2cnc(N)c(-c3ccc(C(=O)NCc4cccc(Cl)n4)c(F)c3)c2)cn1] | 4-(2-amino-5-(1-methyl-1H-pyrazol-4-yl)pyridin-3-yl)-N-((6-chloropyridin-2-yl)methyl)-2-fluorobenzamide | 437.2 | 0.62 | 1H NMR (400 MHz, CD$_3$OD) δ 8.21-8.12 (m, 2H), 8.05 (s, 1H), 7.99(t, J = 7.8 Hz, 1H), 7.88 (s, 1H), 7.81 (t, J = 7.6 Hz, 1H), 7.54-7.44(m, 2H), 7.41 (d, J = 7.8 Hz, 1H), 7.37 (d, J = 7.8 Hz, 1H), 4.71 (s, 2H), 3.94 (s, 3H). |
| 237 | 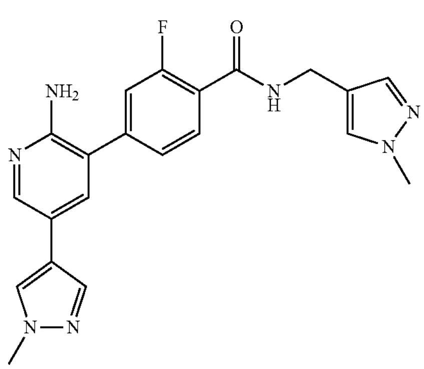 [SMILES: Cn1cc(CNC(=O)c2ccc(-c3cc(-c4cnn(C)c4)cnc3N)cc2F)cn1] | 4-(2-amino-5-(1-methyl-1H-pyrazol-4-yl)pyridin-3-yl)-2-fluoro-N-((1-methyl-1H-pyrazol-4-yl)methyl)benzamide | 406.3 | 0.47 | $^1$H NMR (400 MHz, CD$_3$OD) δ = 8.15 (q, J = 2.2 Hz, 2H), 8.05 (s, 1H), 7.94-7.87 (m, 2H), 7.62 (s, 1H), 7.53-7.42 (m, 3H), 4.46 (s, 2H), 3.93 (s, 3H), 3.87 (s, 3H) |

TABLE 5-continued

Compounds prepared using Method 3 described above.

| Example | Structure | Name | MH+ | R$_t$ (min) | NMR |
|---|---|---|---|---|---|
| 238 | 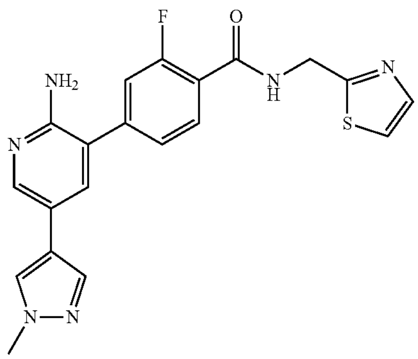 [SMILES: Cn1cc(-c2cnc(N)c(-c3ccc(C(=O)NCc4nccs4)c(F)c3)c2)cn1] | 4-(2-amino-5-(1-methyl-1H-pyrazol-4-yl)pyridin-3-yl)-2-fluoro-N-(thiazol-2-ylmethyl)benzamide | 409.2 | 0.49 | $^1$H NMR (400 MHz, CD$_3$OD) δ = 8.15 (d, J = 2.0 Hz, 1H), 8.17 (d, J = 2.3 Hz, 1H), 8.05 (s, 1H), 7.98 (t, J = 7.8 Hz, 1H), 7.88 (s, 1H), 7.75 (d, J = 3.5 Hz, 1H), 7.56 (d, J = 3.5 Hz, 1H), 7.52-7.43 (m, 2H), 4.92 (s, 2H), 3.93 (s, 3H) |
| 239 | 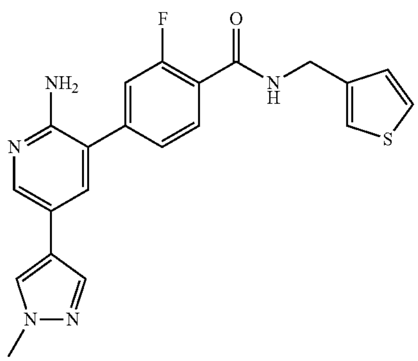 [SMILES: Cn1cc(-c2cnc(N)c(-c3ccc(C(=O)NCc4ccsc4)c(F)c3)c2)cn1] | 4-(2-amino-5-(1-methyl-1H-pyrazol-4-yl)pyridin-3-yl)-2-fluoro-N-(thiophen-3-ylmethyl)benzamide | 408.2 | 0.64 | $^1$H NMR (400 MHz, CD$_3$OD) δ 8.15(d, J = 2.3 Hz, 1H), 8.09 (s, 1H), 8.03 (s, 1H), 7.94-7.84 (m, 2H), 7.48-7.37 (m, 3H). 7.31 (br. s, 1H), 7.13 (d, J = 3.9 Hz, 1H), 4.62(s, 2H), 3.93 (s, 3H) |
| 240 | 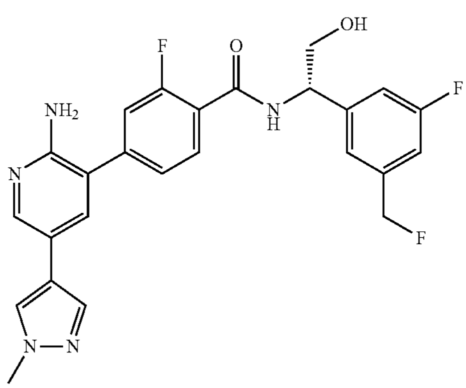 [SMILES: Cn1cc(-c2cnc(N)c(-c3ccc(C(=O)N[C@H](CO)c4cc(F)cc(CF)c4)c(F)c3)c2)cn1] | (S)-4-(2-amino-5-(1-methyl-1H-pyrazol-4-yl)pyridin-3-yl)-2-fluoro-N-(1-(3-fluoro-5-(fluoromethyl)phenyl)-2-hydroxyethyl)benzamide | 482.2 | 0.6 | $^1$H NMR (400 MHz, CD$_3$OD) δ 8.16(q, J = 2.1 Hz, 2H), 8.05 (s, 1H), 7.92(t, J = 7.8 Hz, 1H), 7.88 (s, 1H), 7.51-7.44 (m, 2H), 7.29 (s, 1H), 7.18 (d,J = 9.8 Hz, 1H), 7.07 (d, J = 9.0 Hz,1H), 5.45 (s, 1H), 5.34 (s, 1H), 5.23(t, J = 5.9 Hz, 1H), 3.93 (s, 3H), 3.92-3.82 (m, 2H) |
| 241 | 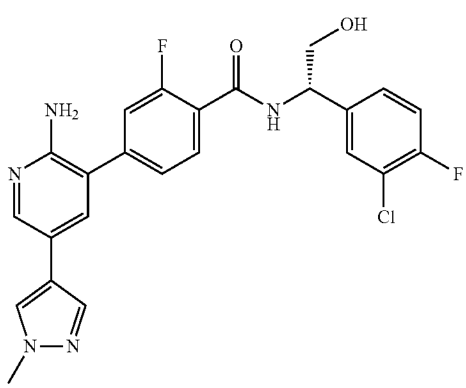 [SMILES: Cn1cc(-c2cnc(N)c(-c3ccc(C(=O)N[C@H](CO)c4ccc(F)c(Cl)c4)c(F)c3)c2)cn1] | (S)-4-(2-amino-5-(1-methyl-1H-pyrazol-4-yl)pyridin-3-yl)-N-(1-(3-chloro-4-fluorophenyl)-2-hydroxyethyl)-2-fluorobenzamide | 484.1 | 0.67 | $^1$H NMR (400 MHz, CD$_3$OD) δ 8.16(s, 2H), 8.06 (s, 1H), 7.96-7.90 (m,1H), 7.89 (s, 1H), 7.56 (dd, J = 2.0,7.0 Hz, 1H), 7.53-7.45 (m, 2H),7.44-7.37 (m, 1H), 7.25 (t, J = 8.8Hz, 1H), 5.23-5.15 (m, 1H), 3.94(s, 2H), 3.92-3.80 (m, 2H) |

TABLE 5-continued

Compounds prepared using Method 3 described above.

| Example | Structure | Name | MH+ | R$_t$ (min) | NMR |
|---|---|---|---|---|---|
| 242 | 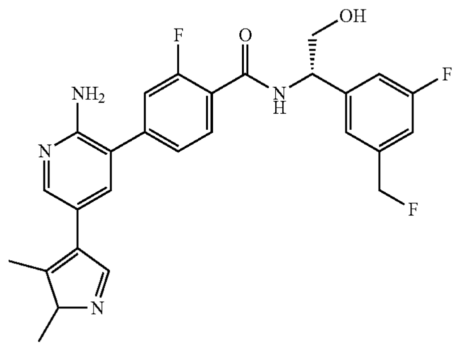 [SMILES: CC1=C(c2cnc(N)c(-c3ccc(C(=O)N[C@H](CO)c4cc(F)cc(CF)c4)c(F)c3)c2)C=NC1C] | (S)-4-(2-amino-5-(1,5-dimethyl-1H-pyrazol-4-yl)pyridin-3-yl)-2-fluoro-N-(1-(3-fluoro-5-(fluoromethyl)phenyl)-2-hydroxyethyl)benzamide | 496.2 | 0.60 | $^1$H NMR (400 MHz, CD$_3$OD) δ 8.01(d, J = 2.2 Hz, 1H), 7.96 (d, J = 2.1Hz, 1H), 7.95-7.90 (m, 1H), 7.66(s, 1H), 7.52 (d, J = 1.5 Hz, 0.5H), 7.49 (s, 1H), 7.47 (d, J = 1.7 Hz,0.5H), 7.30 (d, J = 0.9 Hz, 1H), 7.19(d, J = 9.8 Hz, 1H), 7.09 (d, J = 8.5Hz, 1H), 5.46 (s, 1H), 5.35 (s, 1H),5.24 (t, J = 5.8 Hz, 1H), 3.95-3.86 (m, 2H), 3.86 (s, 3H), 2.42 (s, 3H) |
| 243 | 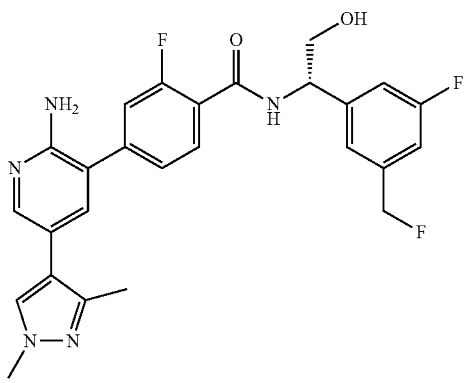 [SMILES: Cc1nn(C)cc1-c1cnc(N)c(-c2ccc(C(=O)N[C@H](CO)c3cc(F)cc(CF)c3)c(F)c2)c1] | (S)-4-(2-amino-5-(1,3-dimethyl-1H-pyrazol-4-yl)pyridin-3-yl)-2-fluoro-N-(1-(3-fluoro-5-(fluoromethyl)phenyl)-2-hydroxyethyl)benzamide | 496.2 | 0.61 | $^1$H NMR (400 MHz, CD$_3$OD) δ 8.02(d, J = 2.2 Hz, 1H), 7.97 (d, J = 2.2Hz, 1), 7.94-7.88 (m, 1H), 7.85(s, 1H), 7.51-7.44 (m, 2H), 7.29 (d,J = 0.9 Hz, 1H), 7.18 (d, J = 9.8 Hz,1H), 7.07 (d, J = 8.5 Hz, 1H), 5.45 (s,1H), 5.33 (s, 1H), 5.23 (t, J = 5.9 Hz,1H), 3.93-3.86 (m, 2H), 3.86-3.84(m, 3H), 2.36 (s, 3H) |
| 244 | 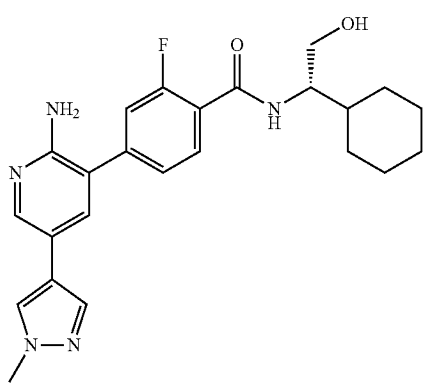 [SMILES: Cn1cc(-c2cnc(N)c(-c3ccc(C(=O)N[C@H](CO)C4CCCCC4)c(F)c3)c2)cn1] | (S)-4-(2-amino-5-(1-methyl-1H-pyrazol-4-yl)pyridin-3-yl)-N-(1-cyclohexyl-2-hydroxyethyl)-2-fluorobenzamide | 438.6 | 0.65 | $^1$H NMR (400 MHz, CD$_3$OD) δ 8.15(s, 2H), 8.06 (s, 1H), 7.93-7.85 (m,2H), 7.50-7.41 (m, 2H), 4.03-3.97(m, 1H), 3.93 (s, 3H), 3.72 (d, J = 5.1Hz, 2H), 1.94-1.74 (m, 4H), 1.74-1.64 (m, 2H), 1.38-1.08 (m, 5H) |
| 245 | 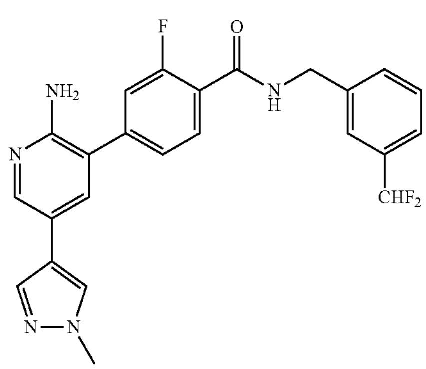 [SMILES: Cn1cc(-c2cnc(N)c(-c3ccc(C(=O)NCc4cccc(C(F)F)c4)c(F)c3)c2)cn1] | 4-(2-amino-5-(1-methyl-1H-pyrazol-4-yl)pyridin-3-yl)-N-(3-(difluoromethyl)benzyl)-2-fluorobenzamide | 452.1 | 0.67 | 1H NMR (400 MHz, CD$_3$OD) δ 8.19(d, J = 2.35 Hz, 1H), 7.91 (s, 1H),7.87 (t, J = 7.83 Hz, 1H), 7.77 (s,1H), 7.66 (d, J = 2.35 Hz, 1H), 7.58(s, 1H), 7.55 (d, J = 7.04 Hz, 1H),7.38-7.51 (m, 4H), 6.59-6.92 (m,1H), 4.67 (s, 2H), 3.91 (s, 3H) |

TABLE 5-continued

Compounds prepared using Method 3 described above.

| Example | Structure | Name | MH+ | R_t (min) | NMR |
|---|---|---|---|---|---|
| 246 | 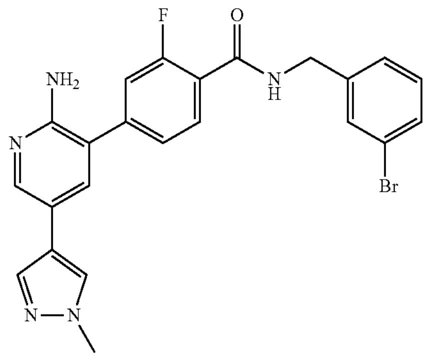 [SMILES: Cn1cc(-c2cnc(N)c(-c3ccc(C(=O)NCc4cccc(Br)c4)c(F)c3)c2)cn1] | 4-(2-amino-5-(1-methyl-1H-pyrazol-4-yl)pyridin-3-yl)-N-(3-bromobenzyl)-2-fluorobenzamide | 480/482 | 0.72 | 1H NMR (400 MHz, CD$_3$OD) δ 8.92(d, J = 3.52 Hz, 1H), 8.15 (s, 2H),8.05 (s, 1H), 7.92 (t, J = 7.83 Hz,1H), 7.88 (s, 1H), 7.57 (s, 1H), 7.41-7.51 (m, 3H), 7.37 (d, J = 7.43 Hz,1H), 7.21-7.31 (m, 1H), 4.60 (d, J =5.87 Hz, 2H), 3.93 (s, 3H) |
| 247 | 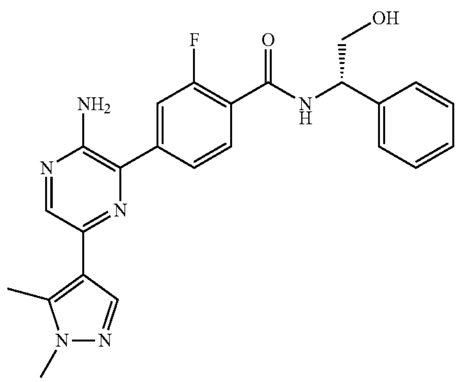 [SMILES: Cc1c(-c2cnc(N)c(-c3ccc(C(=O)N[C@H](CO)c4ccccc4)c(F)c3)n2)cnn1C] | (S)-4-(3-amino-6-(1,5-dimethyl-1H-pyrazol-4-yl)pyrazin-2-yl)-2-fluoro-N-(2-hydroxy-1-phenylethyl) benzamide | 447.1 | 0.67 | N/A |
| 248 | 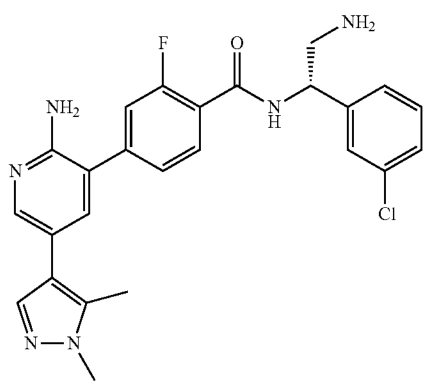 [SMILES: Cc1c(-c2cnc(N)c(-c3ccc(C(=O)N[C@H](CN)c4cccc(Cl)c4)c(F)c3)c2)cnn1C] | (S)-N-(2-amino-1-(3-chlorophenyl)ethyl)-4-(2-amino-5-(1,5-dimethyl-1H-pyrazol-4-yl) pyrid i n-3-yl)-2-fluoro-benzamide | 478.95 | 0.58 | 1H NMR (400 MHz, CD$_3$OD) d 7.93-7.77 (m, 3H), 7.60-7.43 (m, 2H),7.43-7.28 (m, 5H), 5.47-5.33 (m,1H), 3.82-3.68 (m, 3H), 3.47-3.30(m, 2H), 2.39-2.24 (m, 3H) |
| 249 | 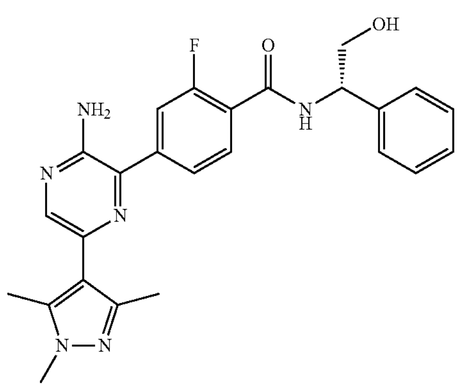 [SMILES: Cc1nn(C)c(C)c1-c1cnc(N)c(-c2ccc(C(=O)N[C@H](CO)c3ccccc3)c(F)c2)n1] | (S)-4-(3-amino-6-(1,3,5-trimethyl-1 H-pyrazol-4-yl)pyrazin-2-yl)-2-fluoro-N-(2-hydroxy-1-phenylethyl) benzamide | 461.1 | 0.63 | 1H NMR (400 MHz, CD$_3$OD) d 8.01(s, 1H), 7.85 (m, 1H), 7.70 (m, 1H), 7.63 (m, 1H), 7.41 (m, 2H),7.34 (m, 2H), 7.27 (m, 1H), 5.20(m, 1H), 3.84 (m, 2H), 3.79 (s, 3H), 2.39 (s, 3H), 0.32 (s, 3H) |

TABLE 5-continued

Compounds prepared using Method 3 described above.

| Example | Structure | Name | MH+ | R$_f$ (min) | NMR |
|---|---|---|---|---|---|
| 250 | 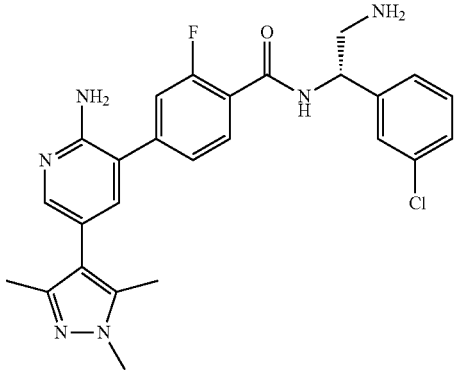 [SMILES: Cc1nn(C)c(C)c1-c1cnc(N)c(-c2ccc(C(=O)N[C@H](CN)c3cccc(Cl)c3)c(F)c2)c1] | (S)-N-(2-amino-1-(3-chlorophenyl)ethyl)-4-(2-amino-5-(1,3,5-trimethyl-1H-pyrazol-4-yl)pyridin-3-yl)-2-fluorobenzamide | 493.3 | 0.56 | 1H NMR (400 MHz, CD$_3$OD) δ 7.91-7.80 (m, 1H), 7.79-7.67 (m, 2H), 7.49-7.43 (m, 1H), 7.42-7.25 (m, 6H), 5.45-5.30 (m, 1H), 3.67(s, 3H), 3.46-3.30 (m, 2H), 2.17 (s, 3H), 2.10 (s, 3H) |
| 251 | 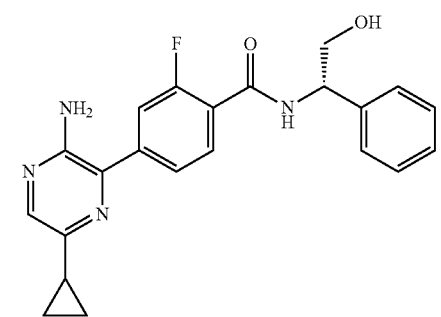 | (S)-4-(3-amino-6-cyclopropyl-pyrazin-2-yl)-2-fluoro-N-(2-hydroxy-1-phenylethyl)benzamide | 393.1 | 0.71 | 1H NMR (400 MHz, CD$_3$OD) δ 7.80-7.71 (m, 2H), 7.56 (m, 1H), 7.49 (m, 1H), 7.36-7.15 (m, 5H), 5.11 (m, 1H), 3.76 (m, 2H), 1.94 (m, 1H), 0.82 (m, 4H) |
| 252 | 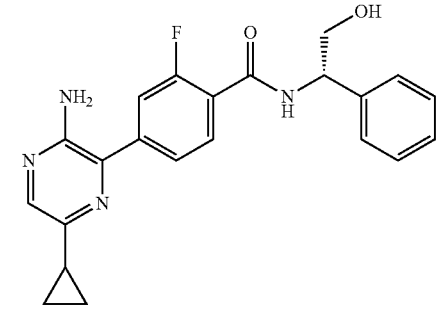 [SMILES: Nc1ncc(C2CC2)nc1-c1ccc(C(=O)N[C@H](CO)c2ccccc2)c(F)c1] | (S)-N-(2-amino-1-phenylethyl)-4-(3-amino-6-cyclopropyl-pyrazin-2-yl)-2-fluorobenzamide | 392.2 | 0.63 | 1H NMR (400 MHz, CD$_3$OD) δ 7.82-7.75 (m, 2H), 7.58 (m, 1H), 7.49 (m, 1H), 7.43-7.26 (m, 5H), 5.39 (m, 1H), 3.36 (m, 2H), 1.94 (m, 1H), 0.81 (m, 4H) |
| 253 | 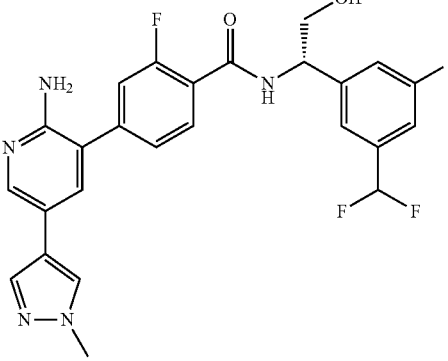 | (S)-4-(2-amino-5-(1-methyl-1H-pyrazol-4-yl)pyridin-3-yl)-N-(1-(3-(difluoromethyl)-5-fluorophenyl)-2-hydroxyethyl)-2-fluorobenzamide | 500.1 | 0.65 | 1H NMR (400 MHz, CD$_3$OD) δ ppm 8.06 (m, 1H), 7.99 (m, 1H), 7.90 (m, 1H), 7.79 (m, 1H), 7.38 (m, 2H), 7.26 (d, J = 9.0 Hz, 1H), 7.13 (d, J = 8.6 Hz, 1H), 6.88-6.49 (t, J = 56 Hz, 1H), 5.39 (s, 2H), 5.17 (t, J = 5.7 Hz, 1H), 3.83 (s, 3H), 3.82 (m, 2H) |

TABLE 5-continued

Compounds prepared using Method 3 described above.

| Example | Structure | Name | MH+ | R_t (min) | NMR |
|---|---|---|---|---|---|
| 254 | 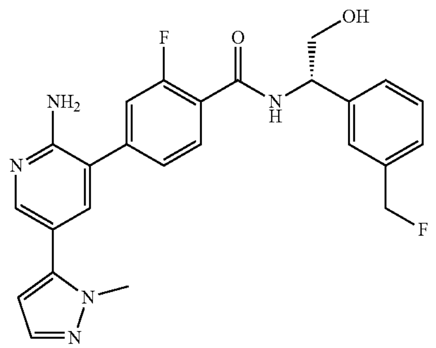 [SMILES: Cn1nccc1-c1cnc(N)c(-c2ccc(C(=O)N[C@H](CO)c3cccc(CF)c3)c(F)c2)c1] | (S)-4-(2-amino-5-(1-methyl-1H-pyrazol-5-yl)pyridin-3-yl)-2-fluoro-N-(1-(3-(fluoromethyl)phenyl)-2-hydroxyethyl)benzamide | 464.2 | 0.56 | 1H NMR (400 MHz, CD$_3$OD) δ ppm 8.77-8.61 (m, 1H), 8.17-8.08 (m, 1H), 8.03-7.95 (m, 1H), 7.95-7.83 (m, 1H), 7.57-7.35 (m, 6H), 7.35-7.26 (m, 1H), 6.54-6.43 (m, 1H), 5.43 (s, 1H), 5.32 (s, 1H), 5.28-5.19 (m, 1H), 3.91 (s, 1H), 3.91-3.79 (m, 2H) |
| 255 | 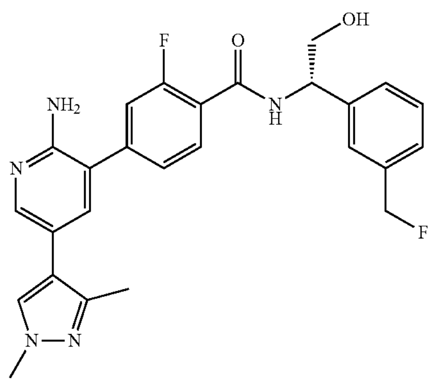 [SMILES: Cc1nn(C)cc1-c1cnc(N)c(-c2ccc(C(=O)N[C@H](CO)c3cccc(CF)c3)c(F)c2)c1] | (S)-4-(2-amino-5-(1,3-dimethyl-1H-pyrazol-4-yl)pyridin-3-yl)-2-fluoro-N-(1-(3-(fluoromethyl)phenyl)-2-hydroxyethyl)benzamide | 478.3 | 0.58 | 1H NMR (400 MHz, CD$_3$OD) δ ppm 8.69 (m, 1H), 8.02 (m, 7H), 7.97 (m,7H), 7.56-7.38 (m, 6H), 7.33 (m,1H), 5.44 (s, 1H), 5.32 (s, 1H), 5.25 (m, 1H), 3.96-3.82 (m, 2H), 3.86(s, 3H), 2.36 (s, 3H) |
| 256 | 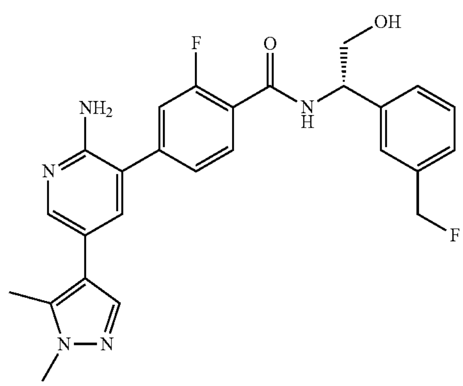 [SMILES: Cc1c(-c2cnc(N)c(-c3ccc(C(=O)N[C@H](CO)c4cccc(CF)c4)c(F)c3)c2)cnn1C] | (S)-4-(2-amino-5-(1,5-dimethyl-1H-pyrazol-4-yl)pyridin-3-yl)-2-fluoro-N-(1-(3-(fluoromethyl)phenyl)-2-hydroxyethyl)benzamide | 478.2 | 0.58 | 1H NMR (400 MHz, CD$_3$OD) δ ppm 8.60 (m, 1H), 7.9 (m, 1H), 7.86 (m,1H), 7.82 (m, 1H), 7.56 (m, 1H), 7.43-7.27 (m, 5H), 7.24 (m, 1H), 5.35 (s, 1H), 5.23 (s, 1H), 5.16 (m,1H), 3.85-3.72 (m, 2H), 3.76 (s,3H), 2.32 (s, 3H) |
| 257 | 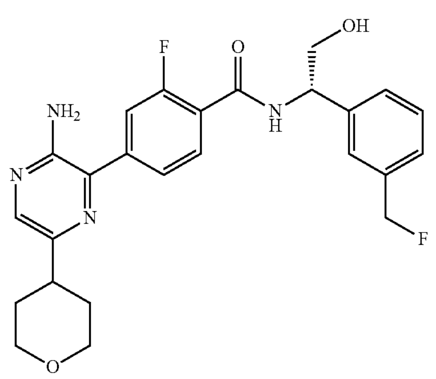 [SMILES: Nc1ncc(C2CCOCC2)nc1-c1ccc(C(=O)N[C@H](CO)c2cccc(CF)c2)c(F)c1] | (S)-4-(3-amino-6-(tetrahydro-2H-pyran-4-yl)pyrazin-2-yl)-2-fluoro-N-(1-(3-(fluoromethyl)phenyl)-2-hydroxyethyl)benzamide | 469.2 | 0.63 | 1H NMR (400 MHz, CD3OD) δ ppm 8.69 (m, 1H), 7.86 (m, 2H), 7.73-7.58 (m, 2H), 7.56-7.38 (m, 3H), 7.33 (m, 1H), 5.44 (s, 1H), 5.32 (s, 1H), 5.24 (m, 1H), 4.04 (m, 2H), 3.94-3.78 (m, 2H), 3.57 (m, 2H), 2.94 (m, 1H), 1.97-1.78 (m, 4H) |

TABLE 5-continued

Compounds prepared using Method 3 described above.

| Example | Structure | Name | MH+ | R$_f$ (min) | NMR |
|---|---|---|---|---|---|
| 258 | 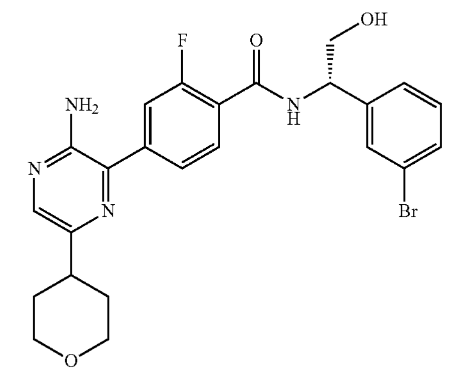 [SMILES: Nc1ncc(C2CCOCC2)nc1-c1ccc(C(=O)N[C@H](CO)c2cccc(Br)c2)c(F)c1] | (S)-4-(3-amino-6-(tetrahydro-2H-pyran-4-yl)pyrazin-2-yl)-N-(1-(3-bromophenyl)-2-hydroxyethyl)-2-fluorobenzamide | 515.2/ 517.1 | 0.71 | 1H NMR (400 MHz, CD$_3$OD) δ ppm 7.86 (m, 2H), 7.72-7.58 (m, 2H), 7.56-7.38 (m, 3H), 7.48-7.38 (m, 2H), 7.29 (m, 1H), 5.44 (s, 1H), 5.32 (s, 1H), 5.18 (m, 1H), 4.05 (m, 2H), 3.85 (m, 2H), 3.57 (m, 2H), 2.95 (m, 1H), 1.97-1.78 (m, 4H) |
| 259 | 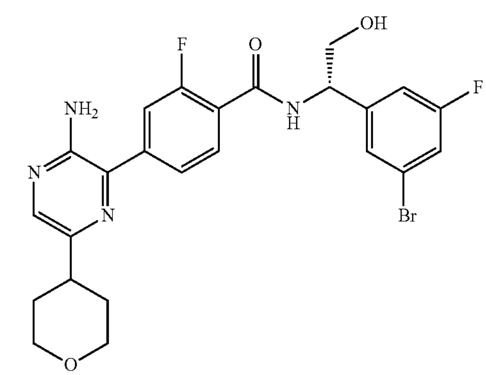 [SMILES: Nc1ncc(C2CCOCC2)nc1-c1ccc(C(=O)N[C@H](CO)c2cc(F)cc(Br)c2)c(F)c1] | (S)-4-(3-amino-6-(tetrahydro-2H-pyran-4-yl)pyrazin-2-yl)-N-(1-(3-bromo-5-fluorophenyl)-2-hydroxyethyl)-2-fluorobenzamide | 533.2/ 535.1 | 0.74 | 1H NMR (400 MHz, CD$_3$OD) δ ppm 7.86 (m, 2H), 7.73-7.60 (m, 2H), 7.56-7.38 (m, 3H), 7.46 (s, 1H), 7.30-7.17 (m, 2H), 5.17 (m, 1H), 4.04 (m, 2H), 3.86 (m, 2H), 3.57 (m, 2H), 2.95 (m, 1H), 1.97-1.79 (m, 4H) |
| 260 | 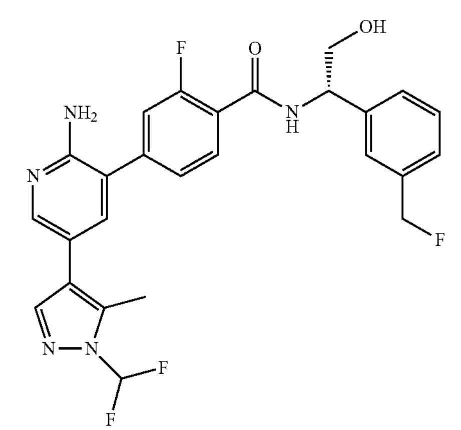 [SMILES: Cc1c(-c2cnc(N)c(-c3ccc(C(=O)N[C@H](CO)c4cccc(CF)c4)c(F)c3)c2)cnn1C(F)F] | (S)-4-(2-amino-5-(1-(difluoromethyl)-5-methyl-1H-pyrazol-4-yl)pyridin-3-yl)-2-fluoro-N-(1-(3-(fluoromethyl)phenyl)-2-hydroxyethyl)benzamide | 514.03 | 0.63 | 1H NMR (400 MHz, CD3OD) δ ppm 7.93 (m, 1H), 7.87-7.77 (m, 2H), 7.74 (s, 1H), 7.45 (t, J = 60 Hz, 1H), 7.41-7.28 (m, 5H), 7.23 (m, 1H), 5.28 (d, J = 48 Hz, 1H), 5.15 (m, 1H), 3.78 (m, 2H), 2.46 (s, 3H) |

TABLE 5-continued

Compounds prepared using Method 3 described above.

| Example | Structure | Name | MH+ | R*f* (min) | NMR |
|---|---|---|---|---|---|
| 261 | 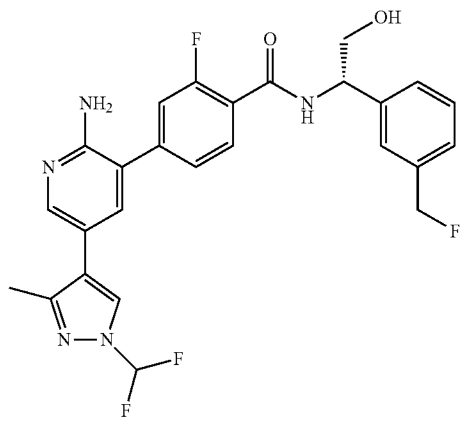 [SMILES: Cc1nn(C(F)F)cc1-c1cnc(N)c(-c2ccc(C(=O)N[C@H](CO)c3cccc(CF)c3)c(F)c2)c1] | (S)-4-(2-amino-5-(1-(difluoromethyl)-3-methyl-1H-pyrazol-4-yl)pyridin-3-yl)-2-fluoro-N-(1-(3-(fluoromethyl)phenyl)-2-hydroxyethyl)benzamide | 514.2 | 0.63 | 1H NMR (400 MHz, CD$_3$OD) δ ppm 8.2 (m, 1H), 7.97 (m, 1H), 7.87-7.77 (m, 2H), 7.4-7.28 (m, 5H), 7.32 (t, J = 60, 1H), 7.23 (m, 1H), 5.28 (d, J = 48 Hz, 2H), 5.15 (m, 1H), 3.78 (m, 2H), 2.31 (s, 3H) |
| 262 | 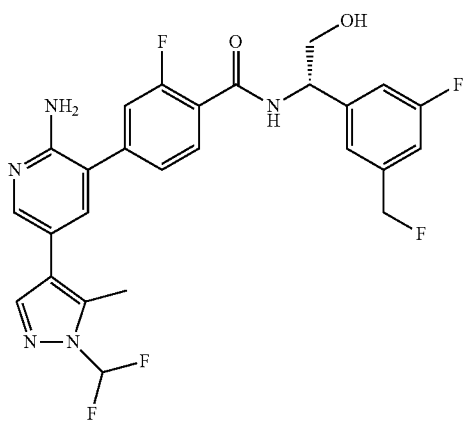 [SMILES: Cc1c(-c2cnc(N)c(-c3ccc(C(=O)N[C@H](CO)c4cc(F)cc(CF)c4)c(F)c3)c2)cnn1C(F)F] | (S)-4-(2-amino-5-(1-(difluoromethyl)-5-methyl-1H-pyrazol--4-yl)pyridin-3-yl)-2-fluoro-N-(1-(3-fluoro-5-(fluoromethyl)phenyl)-2-hydroxyethyl)benzamide | 532.3 | 0.66 | 1H NMR (400 MHz, CD$_3$OD) δ ppm 7.93 (m, 1H), 7.87 (m, 1H), 7.81 (m, 1H), 7.75 (s, 1H), 7.46 (t, J = 56 Hz, m), 7.38 (m, 2H), 7.19 (m, 1H), 7.9 (d, J = 12 Hz, 1H), 6.98 (d, J = 8 Hz, 1H), 5.3 (d, J = 48 Hz, 2H), 5.14 (m, 1H), 3.78 (m, 2H), 2.46 (s, 3H) |
| 263 | 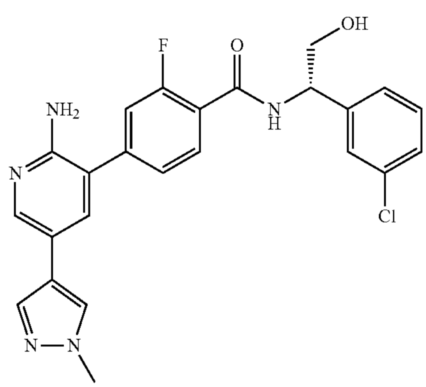 [SMILES: Cn1cc(-c2cnc(N)c(-c3ccc(C(=O)N[C@H](CO)c4cccc(Cl)c4)c(F)c3)c2)cn1] | (S)-4-(2-amino-5-(1-methyl-1H-pyrazol-4-yl)pyridin-3-yl)-N-(1-(3-chlorophenyl)-2-hydroxyethyl)-2-fluorobenzamide | 466.1 | 0.64 | 1H NMR (500 MHz, METHANOL-d4) δ 8.19 (d, J = 2.35 Hz, 1H) 7.91 (s, 1H) 7.86 (t, J = 7.83 Hz, 1H) 7.77 (s, 1H) 7.67 (d, J = 2.35 Hz, 1H) 7.49-7.39 (m, 3H) 7.39-7.25 (m, 3H) 5.19 (t, J = 5.87 Hz, 1H) 4.02-3.78 (m, 5H). |

TABLE 5-continued

Compounds prepared using Method 3 described above.

| Example | Structure | Name | MH+ | R_t (min) | NMR |
|---|---|---|---|---|---|
| 264 | 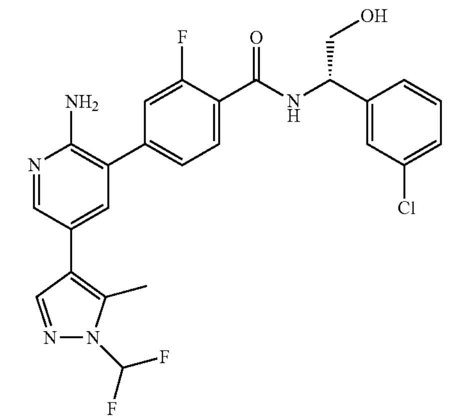 [SMILES: Cc1c(-c2cnc(N)c(-c3ccc(C(=O)N[C@H](CO)c4cccc(Cl)c4)c(F)c3)c2)cnn1C(F)F] | (S)-4-(2-amino-5-(1-(difluoromethyl)-5-methyl-1H-pyrazol-4-yl)pyridin-3-yl)-N-(1-(3-chlorophenyl)-2-hydroxyethyl)-2-fluorobenzamide | 516.1 | 0.72 | 1H NMR (400 MHz, CD$_3$OD) δ ppm 8.2 (m, 1H), 8.1 (m, 1H), 7.6 (m,1H), 7.55 (m, 1H), 7.48-7.20 (m,7H), 5.32 (m, 1H), 4.03 (m, 2H), 2.54 (s, 3H) |
| 265 | 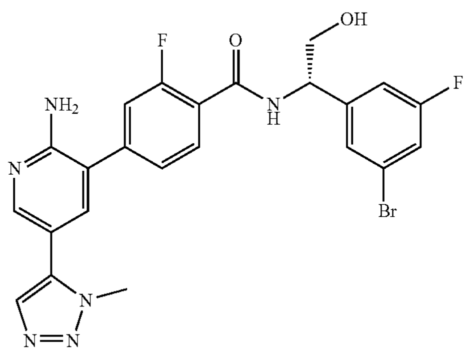 [SMILES: Cn1nncc1-c1cnc(N)c(-c2ccc(C(=O)N[C@H](CO)c3cc(F)cc(Br)c3)c(F)c2)c1] | (S)-4-(2-amino-5-(1-methyl-1H-1,2,3-triazol-5-yl)pyridin-3-yl)-N-(1-(3-chlorophenyl)-2-hydroxyethyl)-2-fluorobenzamide | 529/531 | 0.64 | 1H NMR (400 MHz. CD$_3$OD) δ ppm 8.20 (d, J = 2.0 Hz, 1H), 7.96-7.83 (m, 3H), 7.53-7.39 (m, 3H), 7.27 (d, J = 8.2 Hz, 1H), 7.19 (d, J = 9.8Hz, 1H), 5.17 (s, 1H), 4.13 (s, 3H), 3.86 (dd, J = 6.1, 8.0 Hz, 2H) |
| 266 | 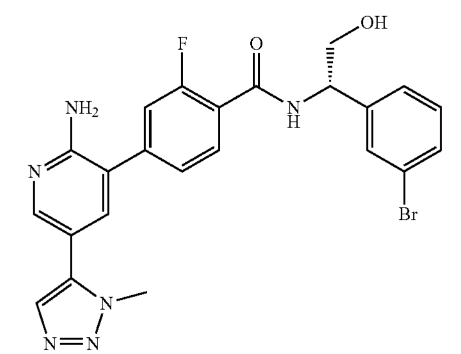 [SMILES: Cn1nncc1-c1cnc(N)c(-c2ccc(C(=O)N[C@H](CO)c3cccc(Br)c3)c(F)c2)c1] | (S)-4-(2-amino-5-(1-methyl-1H-1,2,3-triazol-5-yl)pyridin-3-yl)-N-(1-(3-bromophenyl)-2-hydroxyethyl)-2-fluorobenzamide | 511/513 | 0.61 | 1H NMR (400 MHz, CD$_3$OD) δ ppm 8.19 (m, 1H), 7.91 (m, 1H), 7.89 (m,2H), 7.61 (s, 1H), 7.53-7.36 (m,4H), 7.36-7.21 (m, 1H), 5.48 (s,2H), 5.18 (t, J = 5.9 Hz, 1H), 4.13 (s,3H), 3.86 (dd, J = 5.9, 8.6 Hz, 2H) |
| 267 | 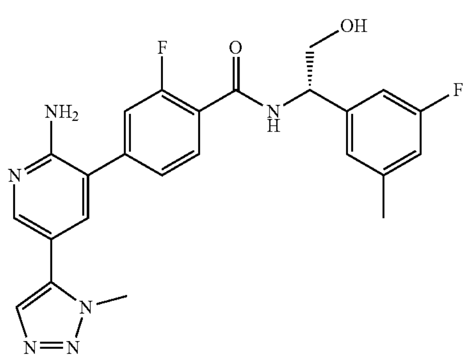 [SMILES: Cc1cc(F)cc([C@@H](CO)NC(=O)c2ccc(-c3cc(-c4cnnn4C)cnc3N)cc2F)c1] | (S)-4-(2-amino-5-(1-methyl-1H-1,2,3-triazol-5-yl)pyridin-3-yl)-2-fluoro-N-(1-(3-fluoro-5-iodophenyl)-2-hydroxyethyl)benzamide | 577.1 | 0.67 | 1H NMR (400 MHz, CD$_3$OD) δ ppm 8.20 (d, J = 2.0 Hz, 1H), 7.96-7.83 (m, 3H), 7.53-7.39 (m, 3H), 7.27 (d, J = 8.2 Hz, 1H), 7.19 (d, J = 9.8Hz, 1H), 5.17 (s, 1H), 4.13 (s, 3H), 3.86 (dd, J = 6.1, 8.0 Hz, 2H). |

TABLE 5-continued

Compounds prepared using Method 3 described above.

| Example | Structure | Name | MH+ | R_t (min) | NMR |
|---|---|---|---|---|---|
| 268 | 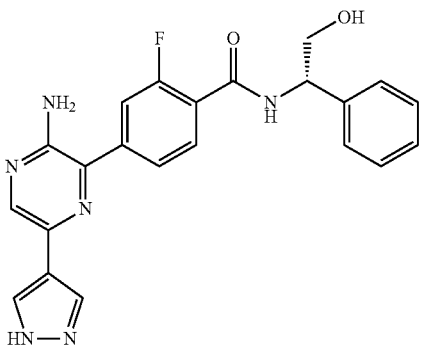 [SMILES: Nc1ncc(-c2cn[nH]c2)nc1-c1ccc(C(=O)N[C@H](CO)c2ccccc2)c(F)c1] | (S)-4-(3-amino-5-(1H-pyrazol-4-yl)pyrazin-2-yl)-2-(luoro-N-(2-hydroxy-1-phenylethyl) benzamide | 419.2 | 0.585 | 1H NMR (400 MHz, CD3OD) δ ppm8.64 (br. s., 1H) 8.35-8.27 (m, 1H)8.09 (s, 2H) 7.92-7.82 (m, 1H)7.78-7.61 (m, 2H) 7.50-7.21 (m, 5H) 5.29-5.14 (m, 1H) 3.92-3.76 (m,2H) |
| 269 | 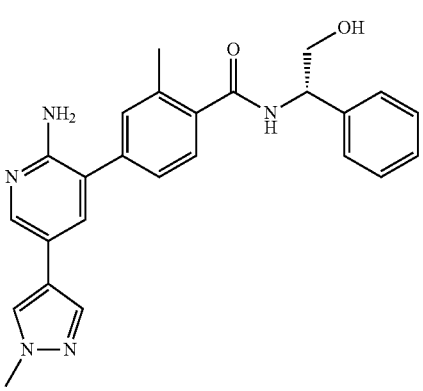 [SMILES: Cc1cc(-c2cc(-c3cnn(C)c3)cnc2N)ccc1C(=O)N[C@H](CO)c1ccccc1] | (S)-4-(2-amino-5-(1-methyl-1H-pyrazol-4-yl) pyrid i n-3-yl)-N-(2-hydroxy-1-phenylethyl)-2-methylbenzamide | 428.2 | 0.57 | 1H NMR (400 MHz, CD3OD) δ ppm8.23-7.96 (m, 3H), 7.88 (s, 1H), 7.58 (d, J = 7.83 Hz, 1H), 7.51-7.01 (m, 7H), 5.23 (dd, J = 7.83,5.09 Hz, 1H), 4.07-3.53 (m, 5H),2.44 (s, 3H) |
| 270 | 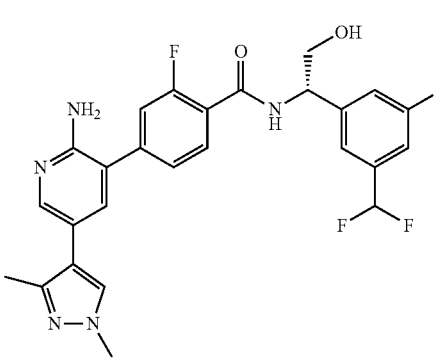 | (S)-4-(2-amino-5-(1,3-dimethyl-1H-pyrazol-4-yl) pyrid I n-3-yl)-N-(1-(3-(difluoromethyl)-5-fluorophenyl)-2-hydroxyethyl)-2-fluorobenzamide | 514.1 | 0.65 | 1H NMR (400 MHz, CD3OD) δ 8.06-7.78 (m, 4H), 7.53-7.42 (m, 3H), 7.35 (d, J = 9.8 Hz, 1H), 7.23 (d, J = 8.6 Hz, 1H), 6.97-6.58 (t, J = 56 Hz, 1H), 5.48 (s, 2H), 5.26 (t, J = 5.7 Hz, 1H), 3.89 (m, 2H), 3.85 (s, 3H), 2.36 (s, 3H) |
| 271 | 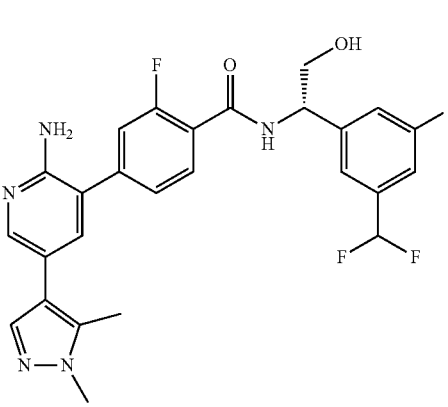 | (S)-4-(2-amino-5-(1,5-dimethyl-1H-pyrazol-4-yl)pyridin-3-yl)-N-(1-(3-(difluoromethyl)-5-fluorophenyl)-2-hydroxyethyl)-2-fluorobenzamide | 514.2 | 0.66 | 1H NMR (400 MHz, CD3OD) δ ppm8.03-7.85 (m, 3H), 7.64 (s, 1H), 7.55-7.41 (m, 3H), 7.35 (d, J = 9.4Hz, 1H), 7.23 (d, J = 8.6 Hz, 1H),6.99-6.56 (t, J = 56 Hz, 1H), 5.48(s, 2H), 5.26 (t, J = 5.7 Hz, 1H), 3.91(m, 2H), 3.84 (s, 3H), 2.40 (s, 3H) |

TABLE 5-continued

Compounds prepared using Method 3 described above.

| Example | Structure | Name | MH+ | R$_t$ (min) | NMR |
|---|---|---|---|---|---|
| 272 | 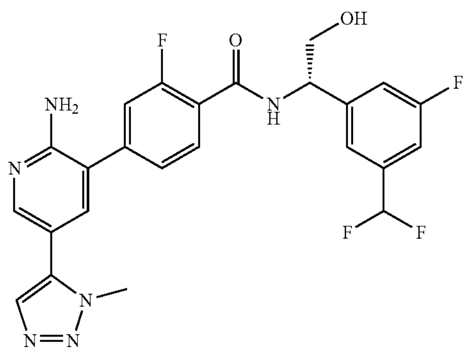 [SMILES: Cn1nncc1-c1cnc(N)c(-c2ccc(C(=O)N[C@H](CO)c3cc(F)cc(C(F)F)c3)c(F)c2)c1] | (S)-4-(2-amino-5-(1-methyl-1H-1,2,3-triazol-5-yl)pyridin-3-yl)-N-(1-(3-(difluoromethyl)-5-fluorophenyl)-2-hydroxyethyl)-2-fluorobenzamide | 501.1 | 0.61 | 1H NMR (400 MHz, CD$_3$OD) δ 8.20(d, J = 2.0 Hz, 1H), 7.95-7.82 (m,3H), 7.54-7.42 (m, 3H), 7.34 (d,J = 9.4 Hz, 1H), 7.22 (d, J = 8.6 Hz,1H), 5.25 (t, J = 5.9 Hz, 1H), 4.13 (s,3H), 3.97-3.80 (m, 2H) |
| 273 | 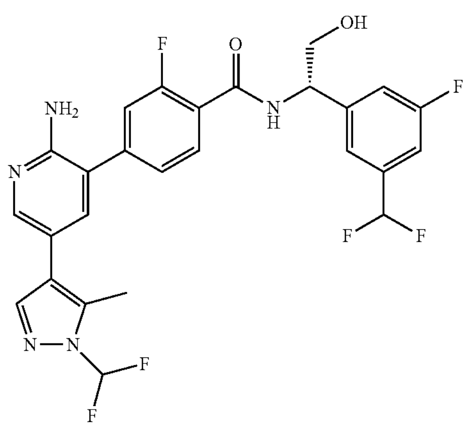 [SMILES: Cc1c(-c2cnc(N)c(-c3ccc(C(=O)N[C@H](CO)c4cc(F)cc(C(F)F)c4)c(F)c3)c2)cnn1C(F)F] | (S)-4-(2-amino-5-(1-(difluoromethyl)-5-methyl-1H-pyrazol-4-yl)pyridin-3-yl)-N-(1-(3-(difluoromethyl)-5-fluorophenyl)-2-hydroxyethyl)-2-fluorobenzamide | 550.1 | 0.73 | 1H NMR (400 MHz, CD$_3$OD) δ ppm7.94 (m, 1H), 7.85-7.76 (m, 2H), 7.74 (s, 1H), 7.65-7.25 (t, J = 60Hz, 1H), 7.45-7.34 (m, 3H), 7.25(d, J = 9.8 Hz, 1H), 7.13 (d, J = 8.6Hz, 1H), 6.89-6.49 (t, J = 56 Hz, 1H), 5.21-5.08 (m, 1H), 3.89-3.70 (m, 2H), 2.46 (s, 3H) |
| 274 | 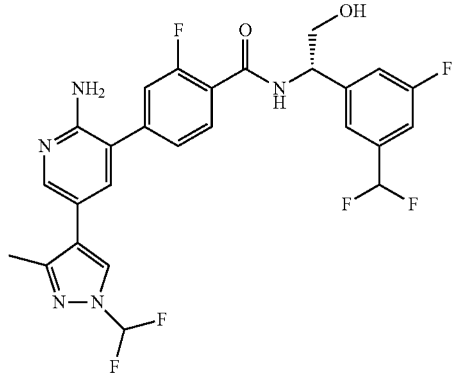 [SMILES: Cc1nn(C(F)F)cc1-c1cnc(N)c(-c2ccc(C(=O)N[C@H](CO)c3cc(F)cc(C(F)F)c3)c(F)c2)c1] | (S)-4-(2-amino-5-(1-(difluoromethyl)-3-methyl-1H-pyrazol-4-yl)pyridin-3-yl)-N-(1-(3-(difluoromethyl)-5-fluorophenyl)-2-hydroxyethyl)-2-fluorobenzamide | 550.1 | 0.73 | 1H NMR (400 MHz, CD$_3$OD) δ ppm8.28 (s, 1H), 8.07 (d, J = 2.0 Hz, 1H),7.98-7.81 (m, 2H), 7.61-7.45 (m,4H), 7.36 (m, 1H), 7.26 (m, 1H), 5.97-6.60 (t, J = 56 Hz, 1H), 5.25 (t,J = 5.7 Hz, 1H), 4.01-3.77 (m, 2H),2.40 (s, 3H) |

TABLE 5-continued

Compounds prepared using Method 3 described above.

| Example | Structure | Name | MH+ | R_f (min) | NMR |
|---|---|---|---|---|---|
| 275 | 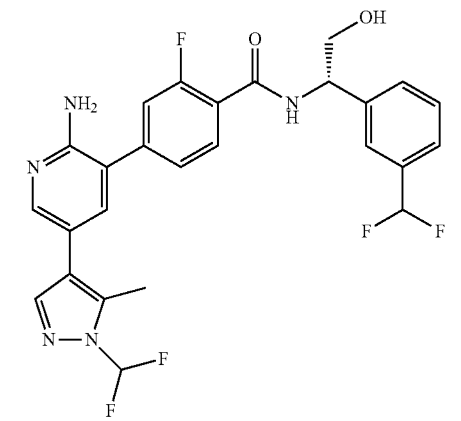 [SMILES: Cc1c(-c2cnc(N)c(-c3ccc(C(=O)N[C@H](CO)c4cccc(C(F)F)c4)c(F)c3)c2)cnn1C(F)F] | (S)-4-(2-amino-5-(1-(difluoromethyl)-5-methyl-1H-pyrazol-4-yl)pyridin-3-yl)-N-(1-(3-(difluoromethyl)phenyl)-2-hydroxyethyl)-2-(fluorobenzamide | 532.2 | 0.7 | 1H NMR (400 MHz, CD$_3$OD) δ ppm 8.86-8.73 (m, 1H), 8.10-7.98 (m, 2H), 7.96-7.83 (m, 2H), 7.73-7.55 (m, 3H), 7.55-7.41 (m, 5H), 6.98-5.61 (m, 1H), 5.36-5.22 (m, 1H), 4.01-3.77 (m, 2H), 2.65-2.51 (m, 3H) |
| 276 | 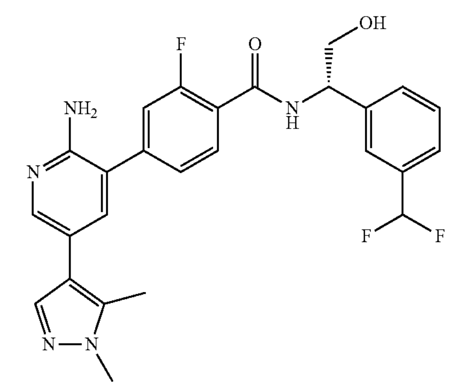 [SMILES: Cc1c(-c2cnc(N)c(-c3ccc(C(=O)N[C@H](CO)c4cccc(C(F)F)c4)c(F)c3)c2)cnn1C] | (S)-4-(2-amino-5-(1,5-dimethyl-1H-pyrazol-4-yl)pyridin-3-yl)-N-(1-(3-(difluoromethyl)phenyl)-2-hydroxyethyl)-2-fluorobenzamide | 496.2 | 0.63 | 1H NMR (400 MHz, CD$_3$OD) δ ppm 8.85-8.74 (m, 1H), 8.06-7.87 (m, 3H), 7.73-7.57 (m, 3H), 7.55-7.42 (m, 4H), 6.98-6.62 (m, 1H), 5.39-5.22 (m, 1H), 4.00-3.81 (m, 5H), 2.48-2.36 (m, 3H) |
| 277 | 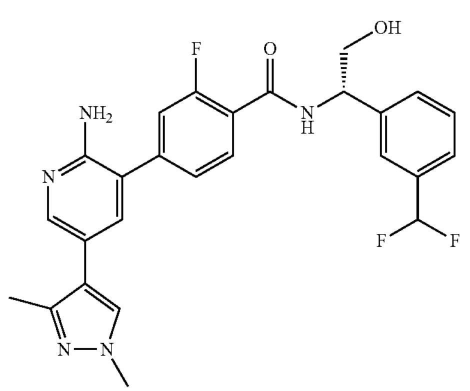 [SMILES: Cc1nn(C)cc1-c1cnc(N)c(-c2ccc(C(=O)N[C@H](CO)c3cccc(C(F)F)c3)c(F)c2)c1] | (S)-4-(2-amino-5-(1,3-dimethyl-1H-pyrazol-4-yl)pyridin-3-yl)-N-(1-(3-(difluoromethyl)phenyl)-2-hydroxyethyl)-2-fluorobenzamide | 496.1 | 0.63 | 1H NMR (400 MHz, CD$_3$OD) δ ppm 8.81 (d, J = 4.1 Hz, 1H), 8.10-7.97 (m, 2H), 7.97-7.83 (m, 2H), 7.70-7.57 (m, 2H), 7.56-7.43 (m, 3H), 5.98-6.63 (m, 1H), 5.37-5.23 (m, 1H), 3.99-3.80 (m, 5H), 2.44-2.33 (m, 3H) |

TABLE 5-continued

Compounds prepared using Method 3 described above.

| Example | Structure | Name | MH+ | R$_t$ (min) | NMR |
|---|---|---|---|---|---|
| 278 | 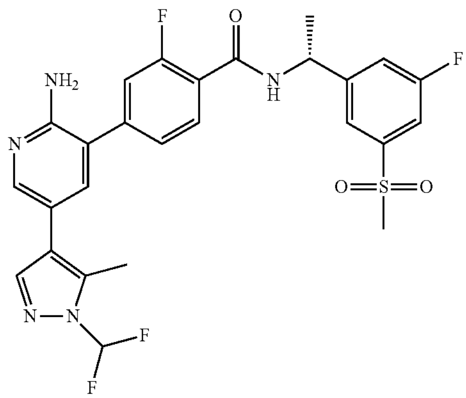 [SMILES: Cc1c(-c2cnc(N)c(-c3ccc(C(=O)N[C@H](C)c4cc(F)cc(S(C)(=O)=O)c4)c(F)c3)c2)cnn1C(F)F] | (R)-4-(2-amino-5-(1-(difluoromethyl)-5-methyl-1H-pyrazol-4-yl)pyridin-3-yl)-2-fluoro-N-(1-(3-fluoro-5-(methylsulfonyl)phenyl)ethyl)benzamide | 562.1 | 0.7 | 1H NMR (400 MHz, CD$_3$OD) δ ppm 9.03 (d, J = 6.3 Hz, 1H), 8.11-7.94 (m, 2H), 7.93-7.77 (m, 3H), 7.74-7.64 (m, 1H), 7.61-7.54 (m, 1H), 7.53-7.42 (m, 2H), 5.36 (t, J = 6.9Hz, 1H), 3.19 (s, 3H), 2.65-2.51(m, 3H), 1.64 (d, J = 6.9 Hz, 3H) |
| 279 | 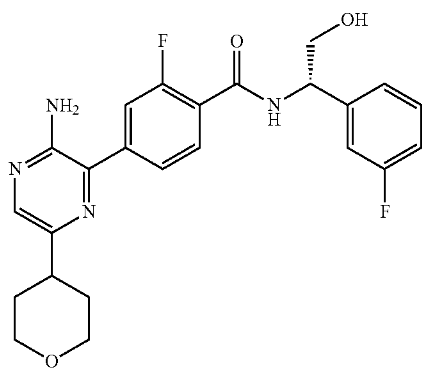 [SMILES: Nc1ncc(C2CCOCC2)nc1-c1ccc(C(=O)N[C@H](CO)c2cccc(F)c2)c(F)c1] | (S)-4-(3-amino-6-(tetrahydro-2H-pyran-4-yl)pyrazin-2-yl)-2-fluoro-N-(1-(3-fluorophenyl)-2-hydroxyethyl)benzamide | 455.2 | 0.6 | 1H-NMR (400 MHz, CD$_3$OD) δ 7.85-7.70 (m, 2H), 7.66-7.50 (m, 2 H), 7.34-7.22 (m, 1H), 7.19-7.12 (m, 1H), 7.12-7.04 (m, 1H), 6.98-6.83 (m, 1H), 5.18-5.04 (m, 1 H), 4.03-3.87 (m, 2H), 3.83-3.67 (m, 2H), 3.54-3.40 (m, 2H), 2.92-2.78 (m, 1H), 1.89-1.66 (m, 4H) |
| 280 | 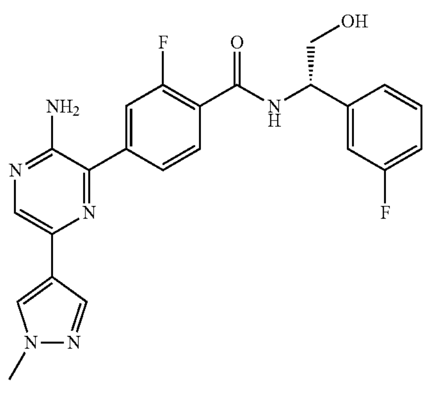 [SMILES: Cn1cc(-c2cnc(N)c(-c3ccc(C(=O)N[C@H](CO)c4cccc(F)c4)c(F)c3)n2)cn1] | (S)-4-(3-amino-6-(1-methyl-1H-pyrazol-4-yl)pyrazin-2-yl)-2-fluoro-N-(1-(3-fluorophenyl)-2-hydroxyethyl)benzamide | 451.1 | 0.66 | N/A |
| 281 | 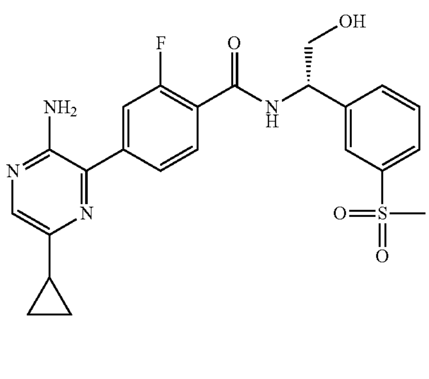 [SMILES: CS(=O)(=O)c1cccc([C@@H](CO)NC(=O)c2ccc(-c3nc(C4CC4)cnc3N)cc2F)c1] | (S)-4-(3-amino-6-cyclopropylpyrazin-2-yl)-2-fluoro-N-(2-hydroxy-1-(3-(methylsulfonyl)phenyl)ethyl)benzamide | 471.2 | 0.63 | 1H NMR (400 MHz, CD$_3$OD) δ 8.05(m, 1H), 7.91-7.87 (m, 2H), 7.87-7.78 (m, 2H), 7.68-7.64 (m, 2H), 7.64-7.57 (m, 1H), 5.30 (m, 1H), 3.91 (m, 2H), 3.12 (s, 3H), 2.05 (m, 1H), 0.93 (m, 2H). |

TABLE 5-continued

Compounds prepared using Method 3 described above.

| Example | Structure | Name | MH+ | R$_t$ (min) | NMR |
|---|---|---|---|---|---|
| 282 | 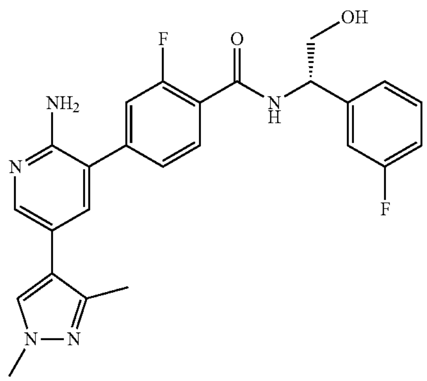 [SMILES: Cc1nn(C)cc1-c1cnc(N)c(-c2ccc(C(=O)N[C@H](CO)c3cccc(F)c3)c(F)c2)c1] | (S)-4-(2-amino-5-(1,3-dimethyl-1H-pyrazol-4-yl)pyridin-3-yl)-2-fluoro-N-(1-(3-fluorophenyl)-2-hydroxyethyl)benzamide | 464.1 | 0.60 | 1H NMR (400 MHz, CD$_3$OD) δ 8.60(m, 1H), 7.92 (m, 1H), 7.87 (m, 1H), 7.81 (m 1H), 7.76 (m, 2H),7.37 (m, 2H), 7.28 (m, 1H), 7.15(m, 1H), 7.08 (m, 1H), 6.92 (m, 1H), 5.12 (m, 1H), 3.84-3.69 (m, 2H), 3.76 (s, 3H), 2.26 (s, 3H) |
| 283 | 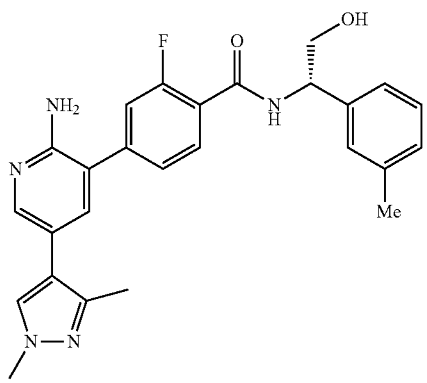 [SMILES: Cc1cccc([C@@H](CO)NC(=O)c2ccc(-c3cc(-c4cn(C)nc4C)cnc3N)cc2F)c1] | (S)-4-(2-amino-5-(1,3-dimethyl-1H-pyrazol-4-yl)pyridin-3-yl)-2-fluoro-N-(2-hydroxy-1-(m-tolyl)ethyl)benzamide | 460.1 | 0.63 | 1H NMR (400 MHz, CD$_3$OD) δ 8.52(m, 1H), 7.92 (m, 1H). 7.87 (m 1H), 7.81 (m, 1H), 7.76 (m, 1H),7.36 (m, 2H), 7.22-7.08 (m, 3H),7.01 (m, 1H), 5.1 (m, 1H), 3.82-3.68 (m, 2H). 3.76 (s, 3H), 2.26 (s,3H), 2.25 (s, 3H). |
| 284 | 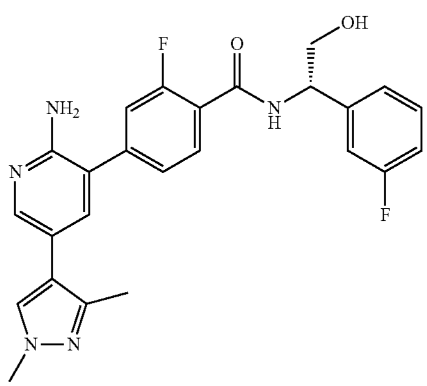 [SMILES: Cc1nn(C)cc1-c1cnc(N)c(-c2ccc(C(=O)N[C@H](CO)c3cccc(F)c3)c(F)c2)c1] | (S)-4-(2-amino-5-(1,3-dimethyl-1H-pyrazol-4-yl)pyridin-3-yl)-2-fluoro-N-(2-hydroxy-1-(3-(methylsulfonyl)phenyl)ethyl)benzamide | 524.3 | 0.51 | 1H NMR (400 MHz, CD$_3$OD) δ 8.74(m, 1H), 7.95 (m, 1H), 7.92 (m, 1H), 7.87 (m 1H), 7.81 (m, 2H),7.76 (m, 1H), 7.71 (m, 1H), 7.56(m, 1H), 7.38 (m, 2H), 5.21 (m, 1H), 3.84 (m, 2H), 3.76 (s, 3H),3.03 (s, 3H), 2.26 (s, 3H). |
| 285 | 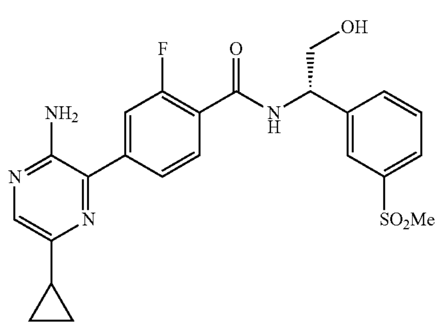 [SMILES: CS(=O)(=O)c1cccc([C@@H](CO)NC(=O)c2ccc(-c3nc(C4CC4)cnc3N)cc2F)c1] | 4-(3-amino-6-cyclopropylpyrazin-2-yl)-N-(3-chloro-5-(methylsulfonyl)benzyl)-2-fluorobenzamide | 475.0 | 0.78 | 1H NMR (400 MHz, CD$_3$OD) δ 7.93-7.84 (m, 3H), 7.87 (m 1H), 7.76(m, 1H), 7.67 (m, 1H), 7.59 (m, 1H), 4.09 (m, 2H), 3.15 (s, 3H),2.05 (m, 1H), 0.92 (s, 4H). |

TABLE 5-continued

Compounds prepared using Method 3 described above.

| Example | Structure | Name | MH+ | R_f (min) | NMR |
|---|---|---|---|---|---|
| 286 | 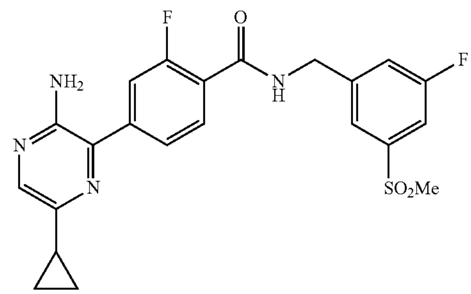 [SMILES: CS(=O)(=O)c1cc(F)cc(CNC(=O)c2ccc(-c3nc(C4CC4)cnc3N)cc2F)c1] | 4-(3-amino-6-cyclopropylpyrazin-2-yl)-2-fluoro-N-(3-fluoro-5-(methylsulfonyl)benzyl)benzamide | 459.2 | 0.75 | 1H NMR (400 MHz, CD$_3$OD) δ 7.91-7.84 (m, 2H), 7.83 (m 1H), 7.70-7.57 (m, 3H), 7.51 (m, 1H), 4.71(m, 2H), 3.16 (s, 3H), 2.04 (m, 1H), 0.91 (s, 4H) |
| 287 | 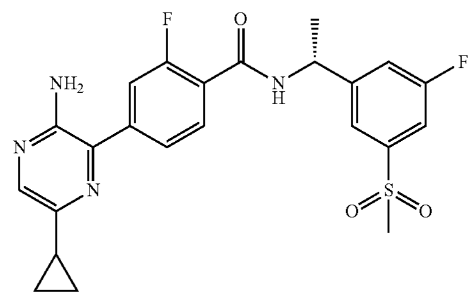 [SMILES: C[C@@H](NC(=O)c1ccc(-c2nc(C3CC3)cnc2N)cc1F)c1cc(F)cc(S(C)(=O)=O)c1] | (R)-4-(3-amino-6-cyclopropylpyrazin-2-yl)-2-fluoro-N-(1-(3-fluoro-5-(methylsulfonyl)phenyl)ethyl)benzamide | 473.3 | 0.775 | 1H NMR (400 MHz, CD$_3$OD) δ 7.90-7.82 (m, 2H) 7.80-7.72 (m, 1H) 7.68-7.51 (m, 4H) 5.32 (q, J = 7.04 Hz, 1H) 3.16 (s, 3H) 2.13-1.99 (m, 1H) 1.61 (d, J = 7.04 Hz, 3H) 1.00-0.87 (m, 4H) |
| 288 | 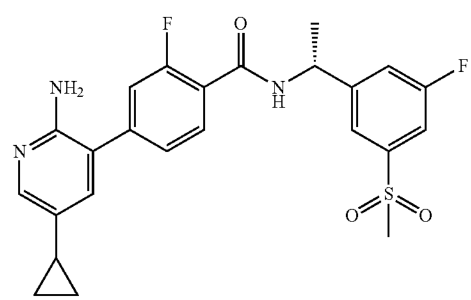 [SMILES: C[C@@H](NC(=O)c1ccc(-c2cc(C3CC3)cnc2N)cc1F)c1cc(F)cc(S(C)(=O)=O)c1] | (R)-4-(2-amino-5-cyclopropylpyridin-3-yl)-2-fluoro-N-(1-(3-fluoro-5-(methylsulfonyl)phenyl)ethyl)benzamide | 472.3 | 0.682 | 1H NMR (400 MHz, CD$_3$OD) δ ppm 8.97 (d, J = 6.26 Hz, 1H), 7.87 (s, 1H), 7.80 (t, J = 7.63 Hz, 1H), 7.72 (dd, J = 11.93, 2.15 Hz, 2H) 7.63(dt, J = 7.83, 1.76 Hz, 1H), 7.55 (d, J = 9.39 Hz, 1H), 7.45-7.35 (m, 2H), 5.40-5.25 (m, 1H), 3.16 (s, 3H), 2.03-1.88 (m, 1H), 1.61 (d, J = 7.04 Hz, 3H), 1.07-0.97 (m, 2H), 0.80-0.69 (m, 2H) |
| 289 | 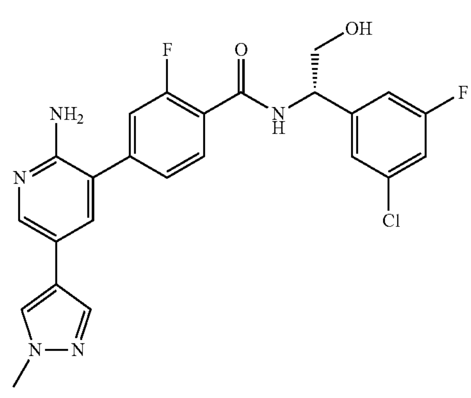 [SMILES: Cn1cc(-c2cnc(N)c(-c3ccc(C(=O)N[C@H](CO)c4cc(F)cc(Cl)c4)c(F)c3)c2)cn1] | (S)-4-(2-amino-5-(1-methyl-1H-pyrazol-4-yl)pyridin-3-yl)-N-(1-(3-chloro-5-fluorophenyl)-2-hydroxyethyl)-2-fluorobenzamide | 484.2 | 0.68 | 1H NMR (400 MHz, CD$_3$OD) δ 8.16(m, 2H), 8.05 (s, 1H), 7.88 (m 2H), 7.48 (m, 2H), 7.31 (s, 1H),7.14 (m, 2H), 5.12 (m, 1H), 3.93(s, 3H), 3.87 (m, 2H). |

TABLE 5-continued

Compounds prepared using Method 3 described above.

| Example | Structure | Name | MH+ | R_t (min) | NMR |
|---|---|---|---|---|---|
| 290 | 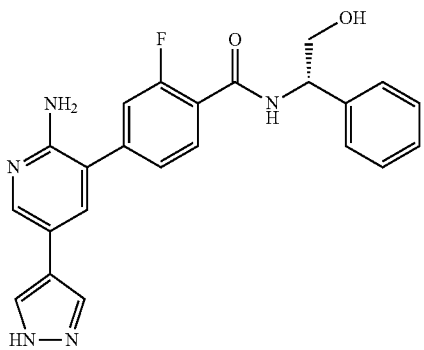 [SMILES: Nc1ncc(-c2cn[nH]c2)cc1-c1ccc(C(=O)N[C@H](CO)c2ccccc2)c(F)c1] | (S)-4-(2-amino-5-(1H-pyrazol-4-yl)pyridin-3-yl)-2-fluoro-N-(2-hydroxy-1-phenylethyl)benzamide | 418.2 | 0.53 | 1H NMR (400 MHz, CD$_3$OD) δ ppm 8.24-8.15 (m, 2H) 8.06 (s, 2H) 7.91 (t, J = 7.83 Hz, 1H) 7.54-7.22(m, 7H) 5.22 (t, J = 6.06 Hz, 1H) 3.96-3.77 (m, 2H) |
| 291 | 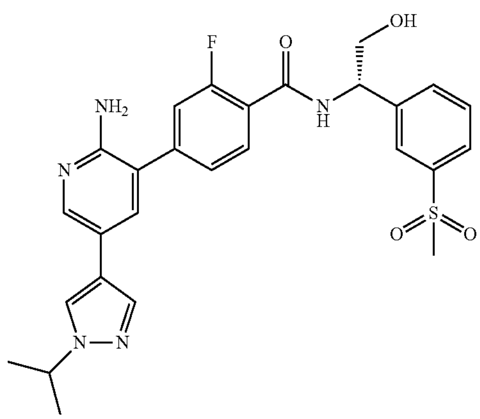 [SMILES: CC(C)n1cc(-c2cnc(N)c(-c3ccc(C(=O)N[C@H](CO)c4cccc(S(C)(=O)=O)c4)c(F)c3)c2)cn1] | (S)-4-(2-amino-5-(1-isopropyl-1H-pyrazol-4-yl)pyridin-3-yl)-2-fluoro-N-(2-hydroxy-1-(3-(methylsulfonyl)phenyl)ethyl)benzamide | 538.3 | 0.601 | 1H NMR (400 MHz, CD$_3$OD) δ ppm 8.17 (s, 3H) 8.04 (s, 1H) 7.96-7.86 (m, 3H) 7.80 (d, J = 7.83 Hz, 1H) 7.70-7.61 (m, 1H) 7.54-7.42 (m, 2H) 5.31 (t, J = 5.67 Hz, 1H) 4.56 (dt, J = 13.30, 6.65 Hz, 1H) 4.08-3.74(m, 2H) 3.12 (s, 4H) 1.52 (d, J = 6.65 Hz, 6H) |
| 292 | 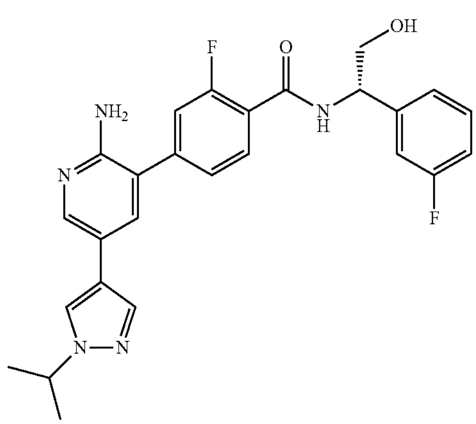 [SMILES: CC(C)n1cc(-c2cnc(N)c(-c3ccc(C(=O)N[C@H](CO)c4cccc(F)c4)c(F)c3)c2)cn1] | (S)-4-(2-amino-5-(1-isopropyl-1H-pyrazol-4-yl)pyridin-3-yl)-2-fluoro-N-(1-(3-fluorophenyl)-2-hydroxyethyl)benzamide | 478.2 | 0.698 | 1H NMR (400 MHz, CD$_3$OD) δ ppm 8.08 (d, J = 2.35 Hz, 1H) 8.05 (s, 1H) 8.00 (br. s., 1H) 7.87-7.72 (m, 2H) 7.42-7.35 (m, 2H) 7.33-7.23 (m,1H) 7.16 (d, J = 7.43 Hz, 1H) 7.09(d, J = 10.17 Hz, 1H) 6.93 (t, J = 8.41Hz, 1H) 4.46 (quin. J = 6.65 Hz, 1H) 5.13 (t, J = 5.87 Hz, 1H) 3.92-3.58(m, 2H) 1.42 (d, J = 6.65 Hz, 6 H |

TABLE 5-continued

Compounds prepared using Method 3 described above.

| Example | Structure | Name | MH+ | R_f (min) | NMR |
|---|---|---|---|---|---|
| 293 | 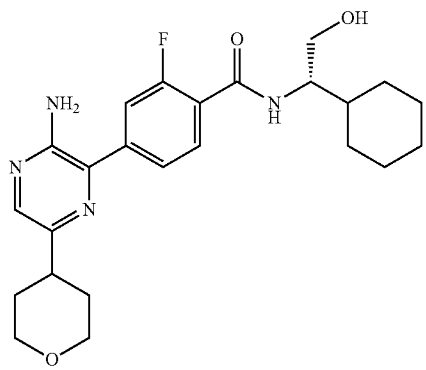 [SMILES: Nc1ncc(C2CCOCC2)nc1-c1ccc(C(=O)N[C@H](CO)C2CCCCC2)c(F)c1] | (S)-4-(3-amino-6-(tetrahydro-2H-pyran-4-yl)pyrazin-2-yl)-N-(1-cyclohexyl-2-hydroxyethyl)-2-fluorobenzamide | 444.1 | 0.74 | $^1$H NMR (400 MHz, CD$_3$OD) δ ppm 7.88-7.82 (m, 2H), 7.71-7.65 (m,1H), 7.63-7.58 (m, 1H). 4.10-4.01 (m, 2H), 4.01-3.94 (m, 1H), 3.72(d, J = 5.1 Hz, 2H), 3.58 (dt, J = 2.5,11.4 Hz, 2H), 3.01-2.90 (m, 1H),1.97-1.75 (m, 9H), 1.75-1.64 (m,2H), 1.38-1.09 (m, 5H) |
| 294 | 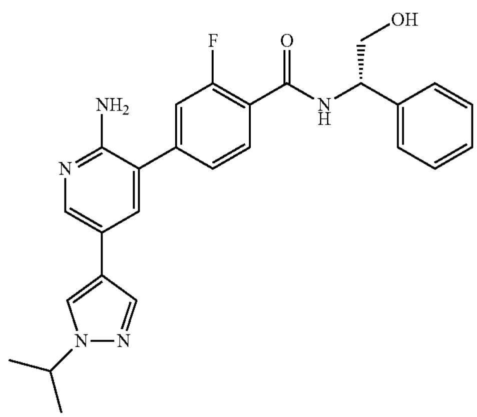 [SMILES: CC(C)n1cc(-c2cnc(N)c(-c3ccc(C(=O)N[C@H](CO)c4ccccc4)c(F)c3)c2)cn1] | (S)-4-(2-amino-5-(1-isopropyl-1H-pyrazol-4-yl)pyridin-3-yl)-2-fluoro-N-(2-hydroxy-1-phenylethyl)benzamide | 466.2 | 0.655 | 1H NMR (400 MHz, CD$_3$OD) δ ppm 8.65-8.47 (m, 1H) 8.13-8.02 (m, 3H) 7.89-7.71 (m, 2H) 7.47-7.10 (m,7H) 5.23-5.05 (m, 1H) 4.47 (spt,J = 6.65 Hz, 1H) 3.92-3.68 (m, 2H)1.43 (d, J = 6.65 Hz, 6H) |
| 295 | 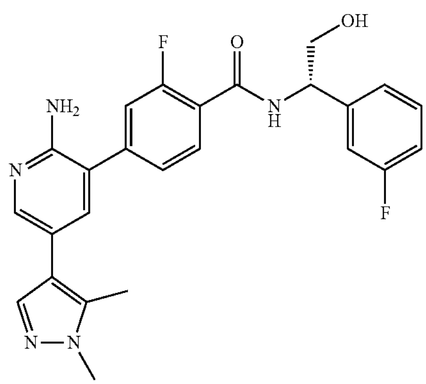 [SMILES: Cc1c(-c2cnc(N)c(-c3ccc(C(=O)N[C@H](CO)c4cccc(F)c4)c(F)c3)c2)cnn1C] | (S)-4-(2-amino-5-(1,5-dimethyl-1H-pyrazol-4-yl)pyridin-3-yl)-2-fluoro-N-(1-(3-fluorophenyl)-2-hydroxyethyl)benzamide | 464.1 | 0.59 | 1H NMR (400 MHz, CD$_3$OD) δ ppm 8.00 (d, J = 2.35 Hz, 1H) 7.96-7.86 (m, 2H) 7.65 (s, 1H) 7.53-7.43(m, 2H) 7.42-7.33 (m, 1H) 7.25(d, J = 7.83 Hz, 1H) 7.17 (d, J = 10.17 Hz, 1H) 7.02 (td, J = 8.41, 1.96 Hz, 1H) 5.22 (t, J = 5.87 Hz, 1H) 3.84 (s, 5H) 2.40 (s, 3H) |

TABLE 5-continued

Compounds prepared using Method 3 described above.

| Example | Structure | Name | MH+ | R<sub>f</sub> (min) | NMR |
|---|---|---|---|---|---|
| 296 | 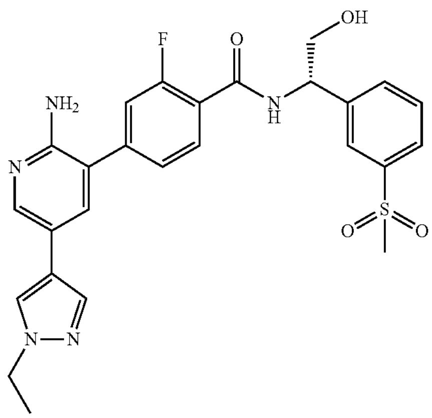 [SMILES: CCn1cc(-c2cnc(N)c(-c3ccc(C(=O)N[C@H](CO)c4cccc(S(C)(=O)=O)c4)c(F)c3)c2)cn1] | (S)-4-(2-amino-5-(1-ethyl-1H-pyrazol-4-yl)pyridin-3-yl)-2-fluoro-N-(2-hydroxy-1-(3-(methylsulfonyl)phenyl)ethyl)benzamide | 524.3 | 0.55 | 1H NMR (400 MHz, CD$_3$OD) δ ppm 8.20-8.15 (m, 2H) 8.12 (s, 1H) 8.04 (s, 1H) 7.96-7.87 (m, 3H) 7.80 (d, J = 7.83 Hz, 1H) 7.70-7.60 (m, 1H) 7.54-7.42 (m, 2H) 5.31 (t, J = 5.48 Hz, 1H)) 4.22 (q, J = 7.30 Hz, 2H) 4.05-3.77 (m, 2H) 3.12 (s, 3H) 1.48 (t, J = 7.24 Hz, 3H) |
| 297 | 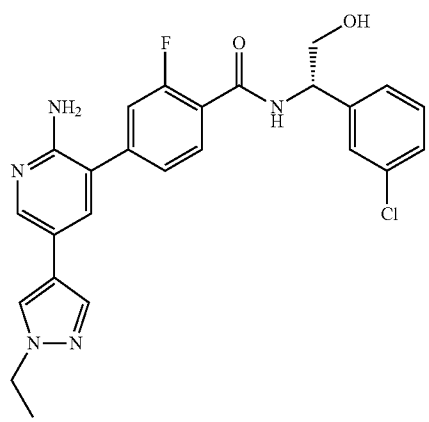 [SMILES: CCn1cc(-c2cnc(N)c(-c3ccc(C(=O)N[C@H](CO)c4cccc(Cl)c4)c(F)c3)c2)cn1] | (S)-4-(2-amino-5-(1-ethyl-1H-pyrazol-4-yl)pyridin-3-yl)-N-(1-(3-chlorophenyl)-2-hydroxyethyl)-2-fluorobenzamide | 480.3/ 482.3 | 0.687 | 1H NMR (400 MHz, CD3OD) δ ppm 8.08 (s, 2H) 8.03 (s, 1H) 7.89-7.76 (m, 2H) 7.47-7.33 (m, 3H) 7.31-7.13 (m, 3H) 5.11 (t, J = 5.87 Hz, 1 H) 4.14 (q, J = 7.30 Hz, 2H) 3.93-3.58 (m, 2H) 1.40 (t, J = 7.43 Hz, 3 H) |
| 298 | 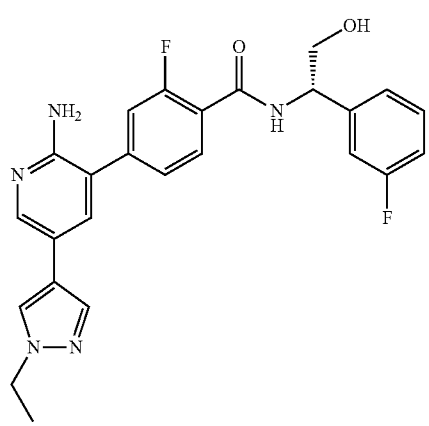 [SMILES: CCn1cc(-c2cnc(N)c(-c3ccc(C(=O)N[C@H](CO)c4cccc(F)c4)c(F)c3)c2)cn1] | (S)-4-(2-amino-5-(1-ethyl-1H-pyrazol-4-yl)pyridin-3-yl)-2-fluoro-N-(1-(3-fluorophenyl)-2-hydroxyethyl)benzamide | 464.3 | 0.64 | 1H NMR (400 MHz, CD$_3$OD) δ ppm 8.19-8.14 (m, 2H) 8.12 (s, 1H) 7.95-7.87 (m, 2H) 7.52-7.44 (m, 2H) 7.38 (td, J = 7.83, 5.87 Hz, 1H) 7.25 (d, J = 7.83 Hz, 1H) 7.18 (d, J = 10.17 Hz, 1H) 7.02 (td, J = 8.41, 1.96 Hz, 1H) 5.22 (t, J = 5.87 Hz, 1 H) 4.22 (q, J = 7.43 Hz, 2H) 4.01-3.67 (m, 2H) 1 48 (t, J = 7.43 Hz, 3 H) |

TABLE 5-continued

Compounds prepared using Method 3 described above.

| Example | Structure | Name | MH+ | R_f (min) | NMR |
|---|---|---|---|---|---|
| 299 | 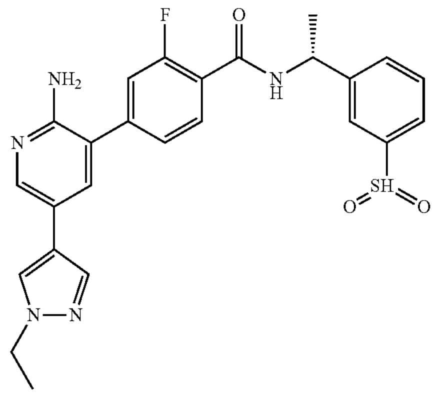 | (R)-4-(2-amino-5-(1-ethyl-1H-pyrazol-4-yl)pyridin-3-yl)-2-fluoro-N-(1-(3-(methylsulfonyl)phenyl)ethyl)benzamide | 508.3 | 0.624 | 1H NMR (400MHz, CD$_3$OD) δ ppm 8.06 (s, 2H) 8.02 (s, 1H) 7.94 (s, 1H) 7.83-7.65 (m, 4H) 7.60-7.50 (m, 1H) 7.42-7.32 (m, 2H) 5.26 (q, J = 6.52 Hz, 1H) 4.12 (q, J = 7.04 Hz, 2H) 3.03 (s, 3H) 1.59-1.47 (m, 3H) 1.43-1.32 (m, 3H) |
| 300 | 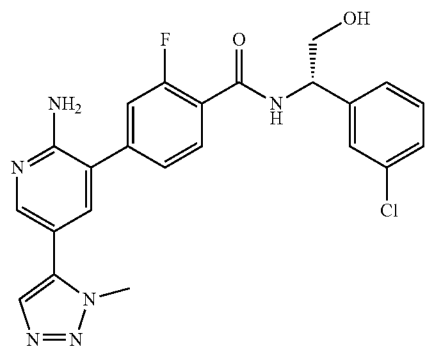 [SMILES: Cn1nncc1-c1cnc(N)c(-c2ccc(C(=O)N[C@H](CO)c3cccc(Cl)c3)c(F)c2)c1] | (S)-4-(2-amino-5-(1-methy-1H-1,2,3-triazol-5-yl)pyridin-3-yl)-N-(1-(3-chlorophenyl)-2-hydroxyethyl)-2-fluoro benzamide | 467.2 | 0.61 | 1H NMR (400 MHz, CD$_3$OD) δ ppm 8.2 (m, 1H), 7.95-7.81 (m, 3H), 7.48 (m, 3H), 7.35-7.25 (m, 3H), 5.19 (m, 1H), 4.13 (s, 3H), 3.86 (m, 2H) |
| 301 | 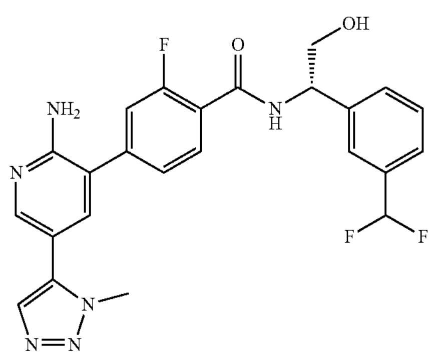 [SMILES: Cn1nncc1-c1cnc(N)c(-c2ccc(C(=O)N[C@H](CO)c3cccc(C(F)F)c3)c(F)c2)c1] | 4-(3-amino-6-((1 r,4S)-4-hydroxycyclohexyl)pyrazin-2-yl)-N-((S)-1-(3-(difluoromethyl)-5-fluorophenyl)-2-hydroxyethyl)-2-fluorobenzamide | 483.2 | 0.58 | 1H NMR (400 MHz, CD$_3$OD) δ ppm 8.85-8.72 (m, 1H), 8.23 (d, J = 1.6Hz, 1H), 7.99 (d, J = 1.6 Hz, 1H), 7.96-7.87 (m, 3H), 7.71-7.57 (m, 2H), 7.57-7.43 (m, 4H), 6.97-6.62 (m, 1H), 5.35-5.22 (m, 1H), 4.22-4.10 (m, 3H), 4.01-3.82 (m, 2H) |
| 302 | 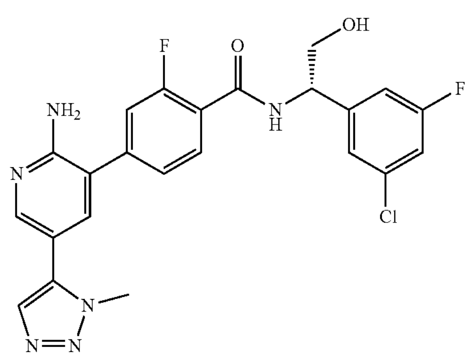 [SMILES: Cn1nncc1-c1cnc(N)c(-c2ccc(C(=O)N[C@H](CO)c3cc(F)cc(Cl)c3)c(F)c2)c1] | (S)-4-(2-amino-5-(1-methyHH-1,2,3-triazol-5-yl)pyridin-3-yl)-N-(1-(3-chloro-5-fluorophenyl)-2-hydroxyethyl)-2-fluorobenzamide | 485.2 | 0.62 | 1H NMR (400 MHz, CD$_3$OD) δ 8.72 (m, 1H), 8.21 (m, 1H), 7.80 (m, 3H), 7.48 (m, 2H), 7.3 (s, 1H), 7.15 (m, 2H), 5.19 (m, 1H), 7.41 (s, 3H), 3.87 (m, 2H). |

TABLE 5-continued

Compounds prepared using Method 3 described above.

| Example | Structure | Name | MH+ | R$_t$ (min) | NMR |
|---|---|---|---|---|---|
| 303 | 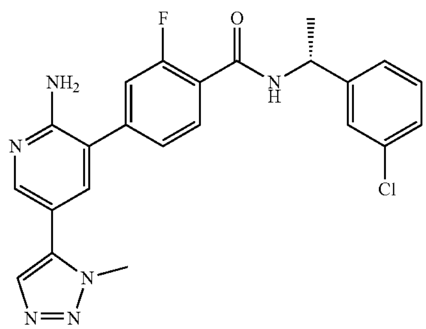 [SMILES: C[C@@H](NC(=O)c1ccc(-c2cc(-c3cnnn3C)cnc2N)cc1F)c1cccc(Cl)c1] | (R)-4-(2-amino-5-(1-methyl-1H-1,2,3-triazol-5-yl)pyridin-3-yl)-N-(1-(3-chlorophenyl)ethyl)-2-fluorobenzamide | 451.2 | 0.71 | 1H NMR (400 MHz, CD$_3$OD) δ 8.7(m, 1H), 8.11 (m, 1H), 7.79 (m, 2H), 7.71 (m, 1H), 7.35 (m, 3H), 7.29-7.12 (m, 3H), 5.15 (m, 1H), 4.03 (s, 3H), 1.47 (m, 3H). |
| 304 | 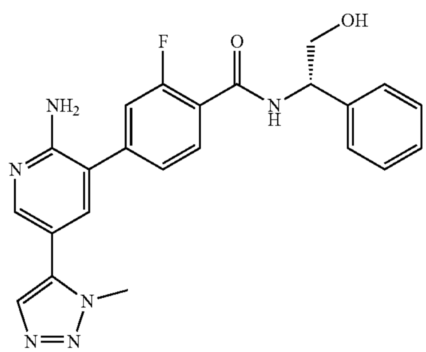 [SMILES: Cn1nncc1-c1cnc(N)c(-c2ccc(C(=O)N[C@H](CO)c3ccccc3)c(F)c2)c1] | (S)-4-(2-amino-5-(1-methyl-1H-1,2,3-triazol-5-yl)pyridin-3-yl)-2-fluoro-N-(2-hydroxy-1-phenylethyl)benzamide | 433.3 | 1.642 | 1H NMR (400 MHz, CD$_3$OD) δ 8.62(m, 1H), 8.2 (m, 1H), 7.89 (m, 3H), 7.5-7.39 (m 4H), 7.39-7.22(m, 2H), 5.23 (m, 1H), 4.13 (s, 3H), 3.87 (m, 2H) |
| 305 | 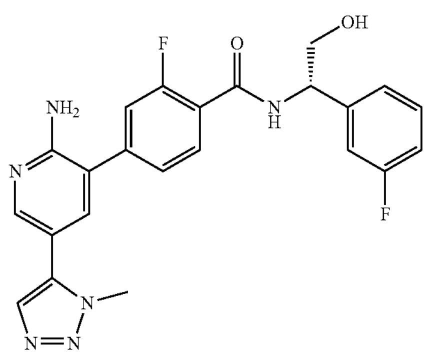 [SMILES: Cn1nncc1-c1cnc(N)c(-c2ccc(C(=O)N[C@H](CO)c3cccc(F)c3)c(F)c2)c1] | (S)-4-(2-amino-5-(1-methyl-1H-1,2,3-triazol-5-yl)pyridin-3-yl)-2-fluoro-N-(1-(3-fluorophenyl)-2-hydroxyethyl)benzamide | 451.1 | 0.45 | 1H NMR (400 MHz, CD$_3$OD) δ 8.67(m, 1H), 8.2 (m, 1H), 7.87 (m, 3H), 7.45 (m, 2H), 7.38 (m, 1H), 7.30-7.20 (m, 2H), 7.02 (m, 1H), 5.22 (m, 1H), 4.12 (s, 3H), 3.86 (m, 2 H |
| 306 | 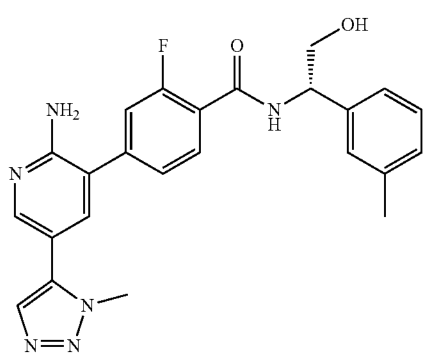 [SMILES: Cc1cccc([C@@H](CO)NC(=O)c2ccc(-c3cc(-c4cnnn4C)cnc3N)cc2F)c1] | (S)-4-(2-amino-5-(1-methyl-1H-1,2,3-triazol-5-yl)pyridin-3-yl)-2-fluoro-N-(2-hydroxy-1-(m-tolyl)ethyl)benzamide | 447.1 | 0.58 | 1H NMR (400 MHz, CD$_3$OD) δ 8.58(m, 1H), 8.19 (m, 1H), 7.85 (m, 3H), 7.46 (m, 2H), 7.24 (m, 3H),7.21 (m, 1H), 5.19 (m, 1H), 4.12(s, 3H), 3.84 (m, 2H), 2.35 (s, 3H) |

TABLE 5-continued

Compounds prepared using Method 3 described above.

| Example | Structure | Name | MH+ | R$_t$ (min) | NMR |
|---|---|---|---|---|---|
| 307 | 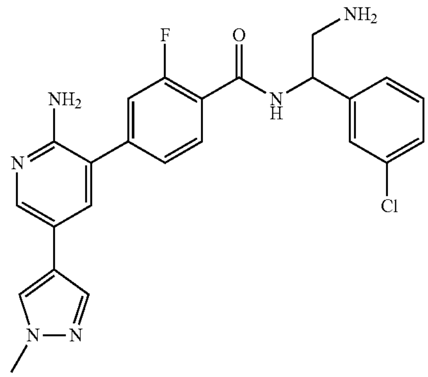 [SMILES: Cn1cc(-c2cnc(N)c(-c3ccc(C(=O)NC(CN)c4cccc(Cl)c4)c(F)c3)c2)cn1] | N-(2-amino-1-(3-chlorophenyl)ethyl)-4-(2-amino-5-(1-methyl-1H-pyrazol-4-yl)pyridin-3-yl)-2-fluorobenzamide | 465.2 | 0.63 | 1H NMR (400 MHz, CD$_3$OD) δ 8.07(m, 1H), 8.02 (s, 1H), 7.95 (s, 1H), 7.85 (m, 1H), 7.78 (s, 1H), 7.47 (m, 1H), 7.35 (m, 5H), 5.4 (m, 1H), 3.84 (s, 3H), 3.38 (m, 2H) |
| 308 | 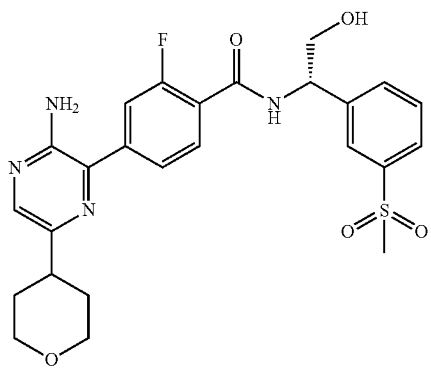 [SMILES: CS(=O)(=O)c1cccc([C@@H](CO)NC(=O)c2ccc(-c3nc(C4CCOCC4)cnc3N)cc2F)c1] | (S)-4-(3-amino-6-(tetrahydro-2H-pyran-4-yl)pyrazin-2-yl)-2-fluoro-N-(2-hydroxy-1-(3-(methylsulfonyl)phenyl)ethyl)benzamide | 515.3 | 0.575 | 1H NMR (400 MHz, CD$_3$OD) δ ppm8.05 (s, 1H) 7.94-7.76 (m, 4H)7.73-7.58 (m, 3H) 5.35-5.25 (m, 1H) 4.05 (dd, J = 11.54, 2.15 Hz, 2H) 3.97-3.84 (m, 2H) 3.64-3.49 (m, 2 H) 3.13 (s, 3H) 3.01-2.88 (m, 1H) 1.97-1.75 (m, 4H) 1.15 (d, J = 5.87 Hz, 1H) |
| 309 | 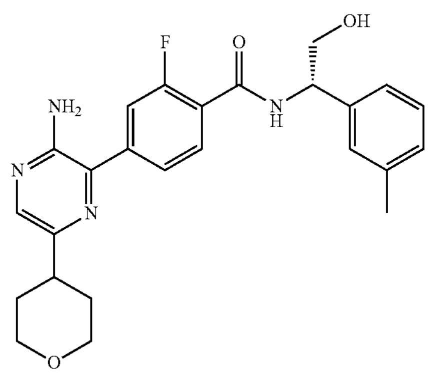 [SMILES: Cc1cccc([C@@H](CO)NC(=O)c2ccc(-c3nc(C4CCOCC4)cnc3N)cc2F)c1] | (S)-4-(3-amino-6-(tetra hydro-2H-pyran-4-yl)pyrazin-2-yl)-2-fluoro-N-(2-hydroxy-1-(m-tolyl)ethyl)benzamide | 451.1 | 0.695 | 1H NMR (400 MHz, CD$_3$OD)) δppm 7.83-7.68 (m, 2H) 7.63-7.42(m, 2H) 7.20-7.07 (m, 3H) 7.00 (d,J = 7.04 Hz. 1H) 5.08 (t, J = 6.06 Hz, 1H) 4.07-3.88 (m, 2H) 3.83-3.64 (m, 2H) 3.48 (td, J = 11.44, 2.54 Hz, 2H) 2.96-2.74 (m, 1H) 2.25 (s, 3 H) 1.89-1.63 (m, 4H) |
| 310 | 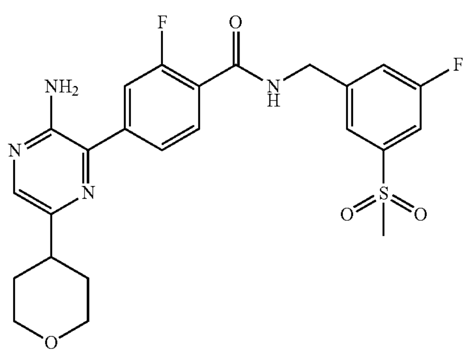 [SMILES: CS(=O)(=O)c1cc(F)cc(CNC(=O)c2ccc(-c3nc(C4CCOCC4)cnc3N)cc2F)c1] | 4-(3-amino-6-(tetrahydro-2H-pyran-4-yl)pyrazin-2-yl)-2-fluoro-N-(3-fluoro-5-(methylsulfonyl)benzyl)benzamide | 503.2 | 0.682 | 1H NMR (400MHz, CD$_3$OD)) δppm 7.98-7.80 (m, 3H) 7.71 (dd,J = 8.02, 1.37 Hz, 1H) 7.67-7.59 (m,2H) 7.51 (d, J = 9.00 Hz, 1H) 4.71(s, 2H) 4.10-3.99 (m, 2H) 3.57 (td,J = 11.44, 2.54 Hz, 2H) 3.15 (s, 3H)3.01-2.87 (m, 1H) 1.98-1.74 (m, 5H) |

TABLE 5-continued

Compounds prepared using Method 3 described above.

| Example | Structure | Name | MH+ | R$_t$ (min) | NMR |
|---|---|---|---|---|---|
| 311 | 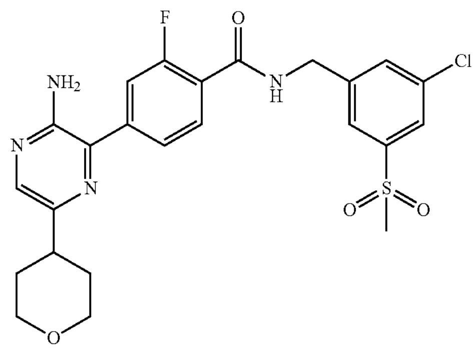 [SMILES: CS(=O)(=O)c1cc(Cl)cc(CNC(=O)c2ccc(-c3nc(C4CCOCC4)cnc3N)cc2F)c1] | 4-(3-amino-6-(tetrahydro-2H-pyran-4-yl)pyrazin-2-yl)-N-(3-chloro-5-(methylsulfonyl)benzyl)-2-fluorobenzamide | 519.3 | 0.736 | 1H NMR (400 MHz, CD$_3$OD) δ ppm 7.95-7.84 (m, 4H) 7.79-7.57 (m, 3H) 4.70 (s, 2H) 4.09-3.98 (m, 2H) 3.57 (td, J = 11.64, 2.54 Hz, 2H) 3.15 (s, 3H) 3.00-2.87 (m, 1H) 1.97-1.76 (m, 4H) |
| 312 | 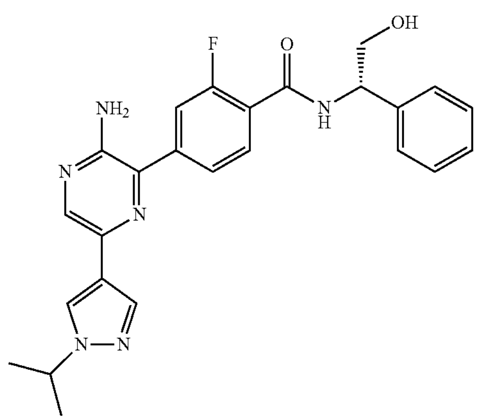 [SMILES: CC(C)n1cc(-c2cnc(N)c(-c3ccc(C(=O)N[C@H](CO)c4ccccc4)c(F)c3)n2)cn1] | (S)-4-(3-amino-6-(1-isopropyl-1H-pyrazol-4-yl)pyrazin-2-yl)-2-fluoro-N-(2-hydroxy-1-phenylethyl)benzamide | 461.3 | 0.75 | 1H NMR (400 MHz, CD$_3$OD) δ ppm 8.17 (s, 1H) 8.07 (s, 1H) 7.87 (s, 1H) 7.83-7.75 (m, 1H) 7.67-7.54 (m, 2H) 7.38-7.31 (m, 2H) 7.27 (t, J = 7.63 Hz, 2H) 7.22-7.14 (m, 1H) 5.13 (t, J = 6.06 Hz, 1H) 4.47 (spt, J = 6.72 Hz, 1H) 3.85-3.69 (m, 2H) 1.43 (d, J = 6.65 Hz, 6H) |
| 313 | 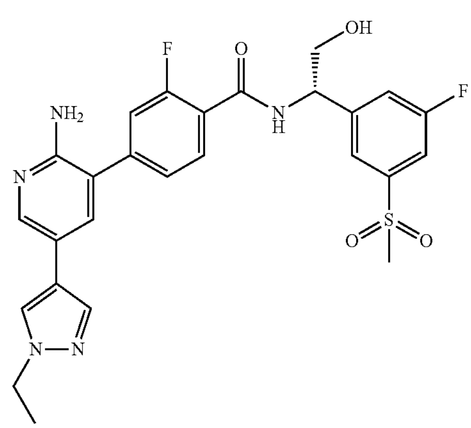 [SMILES: CCn1cc(-c2cnc(N)c(-c3ccc(C(=O)N[C@H](CO)c4cc(F)cc(S(C)(=O)=O)c4)c(F)c3)c2)cn1] | (R)-4-(2-amino-5-(1-ethyl-1H-pyrazol-4-yl)pyridin-3-yl)-2-fluoro-N-(1-(3-fluoro-5-(methylsulfonyl)phenyl)ethyl)benzamide | 526.3 | 0.653 | 1H NMR (400 MHz, CD$_3$OD) δ ppm 8.99 (d, J = 6.26 Hz, 1H), 8.16 (s, 2H) 8.12 (s, 1H) 7.94-7.78 (m, 3H) 7.63 (dt, J = 7.83, 1.76 Hz, 1H) 7.56 (d, J = 9.39 Hz, 1H) 7.51-7.42 (m, 2H) 5.40-5.26 (m, 1H) 4.22 (q, J = 7.17 Hz, 2H) 3.16 (s, 3H) 1.62 (d, J = 7.04 Hz, 3H) 1.52-1.41 (m, 3H) |

TABLE 5-continued

Compounds prepared using Method 3 described above.

| Example | Structure | Name | MH+ | R_t (min) | NMR |
|---|---|---|---|---|---|
| 314 | 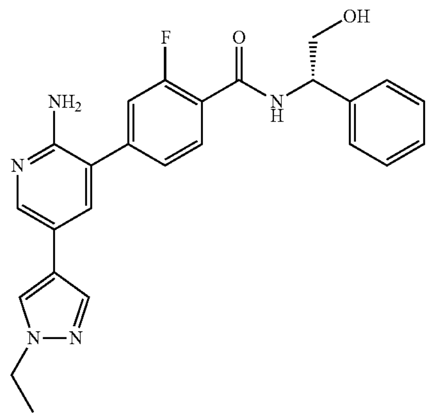 [SMILES: CCn1cc(-c2cnc(N)c(-c3ccc(C(=O)N[C@H](CO)c4ccccc4)c(F)c3)c2)cn1] | (S)-4-(2-amino-5-(1-ethyl-1H-pyrazol-4-yl)pyridin-3-yl)-2-fluoro-N-(2-hydroxy-1-phenylethyl)benzamide | 446.3 | 0.616 | 1H NMR (400 MHz, CD$_3$OD) δ ppm 8.10-8.05 (m, 2H) 8.03 (s, 1H) 7.87-7.73 (m, 2H) 7.44-7.10 (m, 7H) 5.30-4.94 (m, 1H) 4.13 (q, J = 7.17 Hz, 2H) 3.89-3.54 (m, 2H) 1.39 (t, J = 7.24 Hz, 3H) |
| 315 | 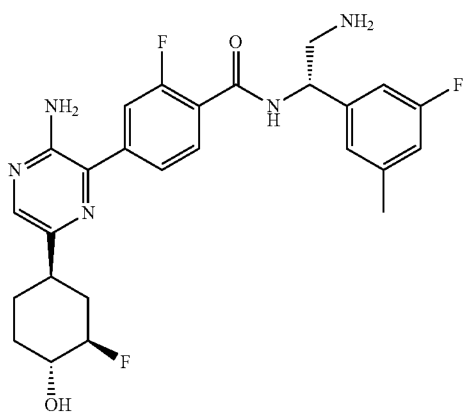 [SMILES: Cc1cc(F)cc([C@@H](CN)NC(=O)c2ccc(-c3nc([C@@H]4CC[C@@H](O)[C@H](F)C4)cnc3N)cc2F)c1] | N-((S)-2-amino-1-(3-fluoro-5-iodophenyl)ethyl)-4-(3-amino-6-((1R,3R,4R)-3-fluoro-4-hydroxycyclohexyl)pyrazin-2-yl)-2-fluorobenzamide | 612.1 | 0.66 | 1H NMR (400 MHz, METHANOL-d4) δ ppm 7.81 (s, 1H), 7.77-7.65 (m, 1H), 7.65-7.46 (m, 3H), 7.36 (d, J = 7.8 Hz, 1H), 7.11 (d, J = 9.8 Hz, 1H), 5.02 (t, J = 6.8 Hz, 1H), 4.44-4.09 (m, 1H), 3.67-3.45 (m, 1H), 2.99-2.85 (m, 2H), 2.75 (t, J = 11.5 Hz, 1H), 2.28-2.08 (m, 1H), 2.06-1.88 (m, 1H), 1.87-1.64 (m, 2H), 1.56 (dq, J = 3.3, 13.0 Hz, 1H), 1.46-1.29 (m, 1H) |
| 316 | 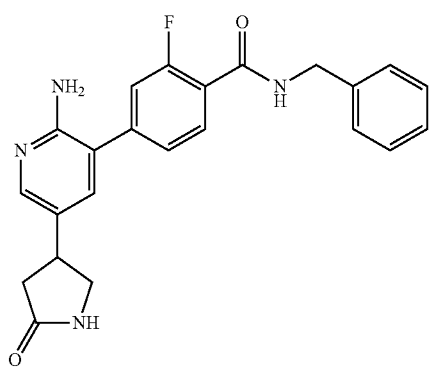 [SMILES: Nc1ncc(C2CNC(=O)C2)cc1-c1ccc(C(=O)NCc2ccccc2)c(F)c1] | 4-(2-amino-5-(5-oxopyrrolidin-3-yl)pyridin-3-yl)-N-benzyl-2-fluorobenzamide | 405.2 | 0.54 | 1H NMR (400 MHz, CD$_3$OD) δ 7.97 (d, J = 2.35 Hz, 1H), 7.93-7.83 (m, 2H), 7.49-7.31 (m, 6H), 7.30-7.22 (m, 1H), 4.64-4.57 (m, 2H), 3.82-3.68 (m, 2H), 3.46-3.38 (m, 1H), 2.76-2.65 (m, 1H), 2.56-2.44 (m, 1H) |
| 317 | 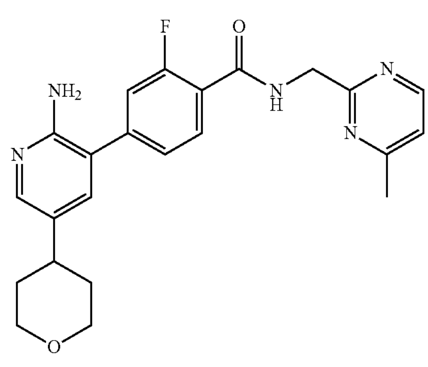 [SMILES: Cc1ccnc(CNC(=O)c2ccc(-c3cc(C4CCOCC4)cnc3N)cc2F)n1] | 4-(2-amino-5-(tetrahydro-2H-pyran-4-yl)pyridin-3-yl)-2-fluoro-N-((4-methylpyrimidin-2-yl)methyl)benzamide | 422.3 | 0.51 | 1H NMR (400 MHz, CD$_3$OD) δ 8.61 (d, J = 5.1 Hz, 1H), 8.06 (t, J = 7.8 Hz, 1H), 7.96 (d, J = 2.0 Hz, 1H), 7.80 (d, J = 2.0 Hz, 1H), 7.41-7.50 (m, 2H), 7.30 (d, J = 5.1 Hz, 1H), 4.78-4.82 (m, 2H), 4.05 (dd, J = 11.2, 2.9 Hz, 2H), 3.55 (td, J = 11.4, 2.5 Hz, 2H), 2.81-2.95 (m, 1H), 2.55 (s, 3H), 1.69-1.89 (m, 4H) |

TABLE 5-continued

Compounds prepared using Method 3 described above.

| Example | Structure | Name | MH+ | R_f (min) | NMR |
|---|---|---|---|---|---|
| 318 | 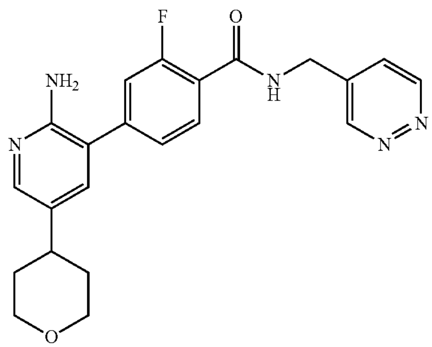 [SMILES: Nc1ncc(C2CCOCC2)cc1-c1ccc(C(=O)NCc2ccnnc2)c(F)c1] | 4-(2-amino-5-(tetrahydro-2H-pyran-4-yl)pyridin-3-yl)-2-fluoro-N-(pyridazin-4-ylmethyl)benzamide | 408.2 | 0.42 | 1H NMR (400 MHz, DMSO-d6) δ 9.26-9.11 (m, 2H), 9.08-8.98 (m, 1H), 7.96-7.76 (m, 3H), 7.69-7.44 (m, 3H), 7.40 (dd, J = 1.4, 8.0 Hz, 1H), 4.54 (d, J = 5.9 Hz, 2H), 4.02-3.77 (m, 3H), 3.37 (dt, J = 2.7, 11.3 Hz, 2H), 2.77 (s, 1H), 1.78-1.54 (m, 4H) |
| 319 | 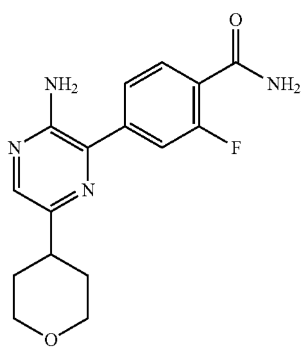 [SMILES: NC(=O)c1ccc(-c2nc(C3CCOCC3)cnc2N)cc1F] | 4-(3-amino-6-(tetrahydro-2H-pyran-4-yl)pyrazin-2-yl)-2-fluorobenzamide | 317.2 | 0.45 | 1H NMR (400MHz, CD3OD) δ 7.95(t, J = 7.8 Hz, 1H), 7.87 (s, 1H),7.70 (dd, J = 7.8, 1.6 Hz, 1H), 7.61(dd, J = 11.9, 1.4 Hz, 1H), 4.05 (dd,J = 11.3, 2.3 Hz, 3H), 3.57 (td, J = 11.5, 2.7 Hz, 3H), 2.89-3.01 (m, 1H), 1.77-1.97 (m, 6H) |
| 320 | 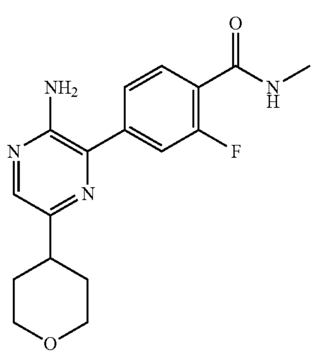 [SMILES: CNC(=O)c1ccc(-c2nc(C3CCOCC3)cnc2N)cc1F] | 4-(3-amino-6-(tetrahydro-2H-pyran-4-yl)pyrazin-2-yl)-2-fluoro-N-methylbenzamide | 331.2 | 0.49 | 1H NMR (400MHz, CD3OD) δ 7.83-7.91 (m, 2H), 7.68 (dd, J = 8.0, 1.4Hz, 1H), 7.60 (dd, J = 11.7, 1.6 Hz, 1H), 4.05 (dd, J = 11.3, 2.3 Hz, 2H), 3.57 (td, J = 11.5, 2.7 Hz, 2H), 2.88-3.01 (m, 4H), 1.74-1.96 (m, 4H) |
| 321 | 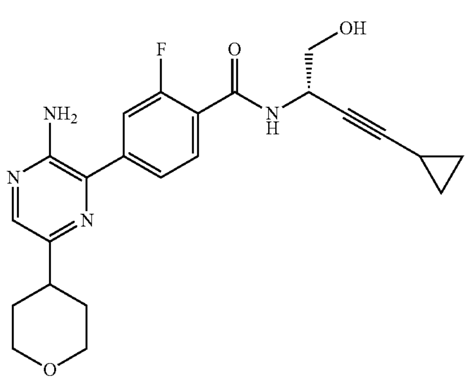 [SMILES: Nc1ncc(C2CCOCC2)nc1-c1ccc(C(=O)N[C@@H](C#CC2CC2)CO)c(F)c1] | (S)-4-(3-amino-6-(tetrahydro-2H-pyran-4-yl)pyrazin-2-yl)-N-(4-cyclopropyl-1-hydroxybut-3-yn-2-yl)-2-fluorobenzamide | 425.1 | 0.64 | 1H NMR (400 MHz, d6-DMSO)) δ ppm 0.47-0.55 (m, 2H) 0.64-0.73 (m, 2H) 1.21-1.30 (m, 1H) 1.62-1.73 (m, 4H) 2.72-2.86 (m, 1H) 3.30-3.41 (m, 2H) 3.45 (d, J = 6.26 Hz, 3H) 3.87 (d, J = 10.96 Hz, 2H) 4.66 (q, J = 6.65 Hz, 1H) 7.52 (d, J = 11.74 Hz, 1H) 7.55-7.59 (m, 1H) 7.61-7.68 (m, 1H) 7.87 (s, 1H) 8.35-8.42 (m, 1H) |

TABLE 5-continued

Compounds prepared using Method 3 described above.

| Example | Structure | Name | MH⁺ | R$_t$ (min) | NMR |
|---|---|---|---|---|---|
| 322 | 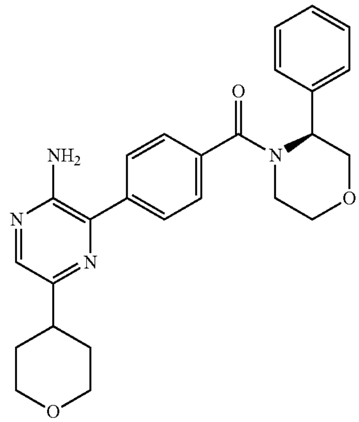 [SMILES: Nc1ncc(C2CCOCC2)nc1-c1ccc(C(=O)N2CCOC[C@@H]2c2ccccc2)cc1] | (S)-(4-(3-amino-6-(tetrahydro-2H-pyran-4-yl)pyrazin-2-yl)phenyl)(3-phenylmorpholino) methanone | 445.3 | 0.7 | 1H NMR (400 MHz, CD$_3$OD) δ 7.77-7.88 (m, 3H), 7.59 (d, J = 8.2 Hz, 2H), 7.54 (br. s., 1H), 7.41 (t, J = 7.6 Hz, 2H), 7.28-7.36 (m, 1H), 4.54 (d, J = 11.3 Hz, 1H), 3.95-4.11 (m, 3H), 3.88 (br. s., 1H), 3.68 (t. J = 11.5 Hz, 1H), 3.56 (td, J = 11.4, 2.5 Hz, 2H), 3.34-3.41 (m, 1H), 2.85-3.01 (m, 1H), 1.73-1.99 (m, 4H) |
| 323 | 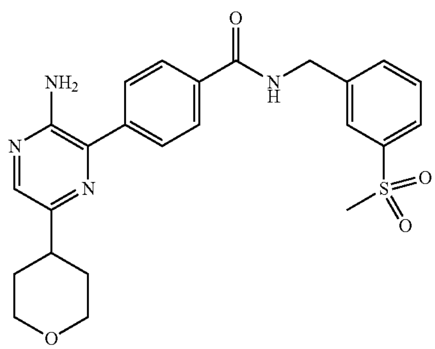 [SMILES: CS(=O)(=O)c1cccc(CNC(=O)c2ccc(-c3nc(C4CCOCC4)cnc3N)cc2)c1] | 4-(3-amino-6-(tetrahydro-2H-pyran-4-yl)pyrazin-2-yl)-N-(3-(methylsulfonyl) benzyl)benzamide | 467.3 | 0.58 | 1H NMR (400 MHz, CD$_3$OD) δ 8.03(d, J = 8.2 Hz, 2H), 7.98 (s, 1H),7.83-7.91 (m, 3H), 7.80 (s, 1H), 7.75 (d, J = 7.8 Hz, 1H), 7.59-7.67(m, 1H), 4.71 (s, 2H), 3.99-4.10(m, 2H), 3.57 (td, J = 11.3, 2.7 Hz, 2H), 3.12 (s, 3H), 2.90-3.03 (m, 1H), 1.78-1.99 (m, 4H) |
| 324 | 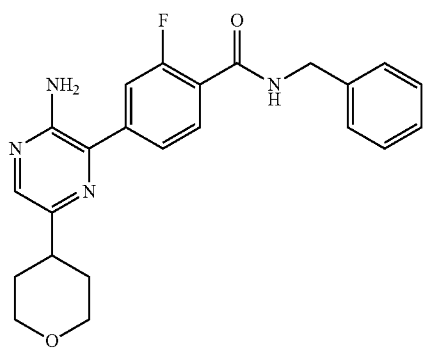 [SMILES: Nc1ncc(C2CCOCC2)nc1-c1ccc(C(=O)NCc2ccccc2)c(F)c1] | 4-(3-amino-6-(tetrahydro-2H-pyran-4-yl)pyrazin-2-yl)-N-benzyl-2-fluorobenzamide | 407.2 | 0.73 | 1H NMR (400 MHz, DMSO-d6) δ 8.86 (s, 1H), 7.90 (s, 1H), 7.76-7.51 (m, 2H), 7.32 (m, 4H), 7.23 (m, 1H), 6.11 (s, 1H), 4.47 (m, 1 H), 3.91 (m, 2H), 3.40 (m, 2H), 3.26 (m, 1H), 2.78 (m, 1H), 1.71 (m, 4H) |
| 325 | 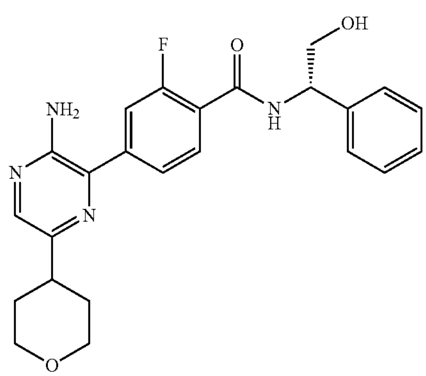 [SMILES: Nc1ncc(C2CCOCC2)nc1-c1ccc(C(=O)N[C@H](CO)c2ccccc2)c(F)c1] | (S)-4-(3-amino-6-(tetrahydro-2H-pyran-4-yl)pyrazin-2-yl)-2-fluoro-N-(2-hydroxy-1-phenylethyl) benzamide | 473.2 | 0.61 | 1H NMR (400 MHz, DMSO-d6) δ 8.61 (s, 1H), 7.92 (s, 1H), 7.78-7.51 (m, 5H), 6.12 (s, 1H), 4.95 (m, 1H), 3.92 (m, 2H), 3.66 (m, 2 H), 3.4 (m, 2H), 1.73 (m, 4H) |

TABLE 5-continued

Compounds prepared using Method 3 described above.

| Example | Structure | Name | MH+ | R_t (min) | NMR |
|---|---|---|---|---|---|
| 326 | 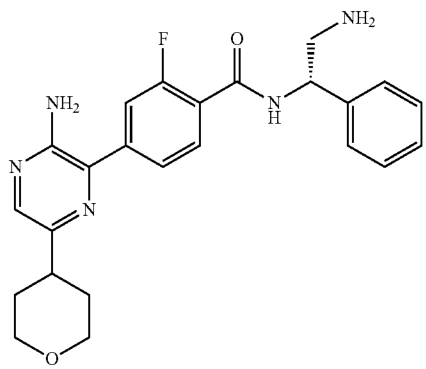 [SMILES: NC[C@@H](NC(=O)c1ccc(-c2nc(C3CCOCC3)cnc2N)cc1F)c1ccccc1] | (S)-N-(2-amino-1-phenylethyl)-4-(3-amino-6-(tetrahydro-2H-pyran-4-yl)pyrazin-2-yl)-2-fluorobenzamide | 436.3 | 0.59 | 1H NMR (400 MHz, CD₃OD) δ 7.90(s, 1H), 7.82 (t, J = 7.6 Hz, 1H),7.70 (dd, J = 1.4, 8.0 Hz, 1H), 7.63(dd, J = 1.2, 11.7 Hz, 1H), 7.49-7.36 (m, 4H), 7.32 (d, J = 7.4 Hz, 1H), 5.20 (t, J = 6.8 Hz, 1H), 4.05(dd, J = 2.9, 11.2 Hz, 2H), 3.58 (dt,J = 2.3, 11.7 Hz, 2H), 3.08 (d, J =7.4 Hz, 2H), 2.94 (s, 1H), 2.00-1.77 (m, 4H). |
| 327 | 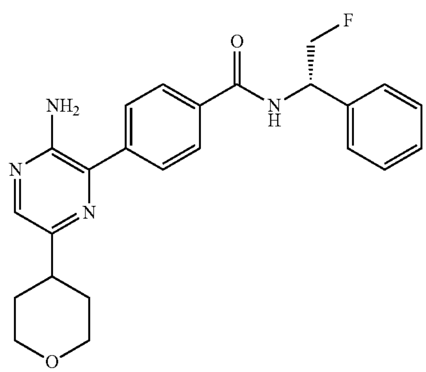 [SMILES: Nc1ncc(C2CCOCC2)nc1-c1ccc(C(=O)N[C@H](CF)c2ccccc2)cc1] | (S)-4-(3-amino-6-(tetrahydro-2H-pyran-4-yl)pyrazin-2-yl)-N-(2-fluoro-1-phenylethyl) benzamide | 421.1 | 0.72 | 1H NMR (400 MHz, CD₃OD) δ 7.92(d, J = 8.6 Hz, 2H), 7.75 (d, J = 9.8Hz, 3H), 7.40-7.32 (m, 2H), 7.29(t, J = 7.4 Hz, 2H), 7.26-7.18 (m, 1H), 5.41 (dd, J = 7.4, 15.7 Hz, 1 H), 4.71-4.66 (m, 1H), 4.62-4.53 (m, 1H), 4.00-3.89 (m, 2H), 3.48 (dt, J = 2.7, 11.5 Hz, 2H), 2.92-2.74 (m, 1H), 1.88-1.68 (m, 4H). |
| 328 | 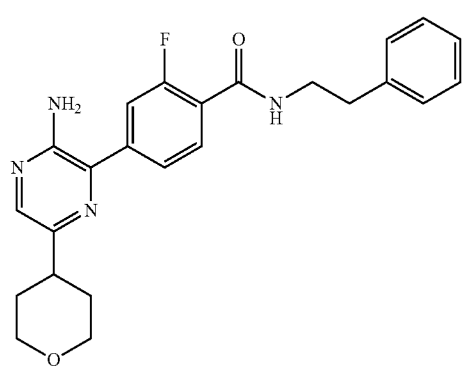 [SMILES: Nc1ncc(C2CCOCC2)nc1-c1ccc(C(=O)NCCc2ccccc2)c(F)c1] | 4-(3-amino-6-(tetrahydro-2H-pyran-4-yl)pyrazin-2-yl)-2-fluoro-N-phenethyl-benzamide | 421.2 | 0.77 | 1H NMR (400 MHz, DMSO-d6) δ 8.35 (m, 1H), 7.90 (s, 1H), 7.70-7.51 (m, 3H), 7.35-7.12 (m, 4H), 6.10 (s, 1H), 3.92 (m, 2H), 3.53-3.35 (m, 4H), 2.82 (m, 2H), 1.72 (m, 4H) |
| 329 | 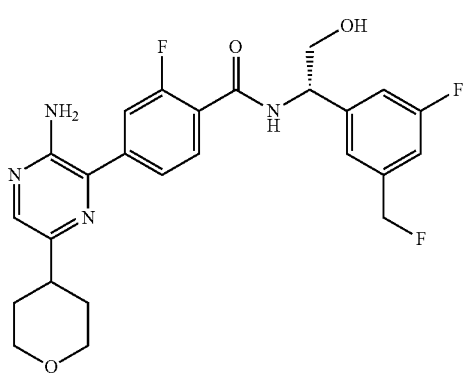 [SMILES: Nc1ncc(C2CCOCC2)nc1-c1ccc(C(=O)N[C@H](CO)c2cc(F)cc(CF)c2)c(F)c1] | (S)-4-(3-amino-6-(tetrahydro-2H-pyran-4-yl)pyrazin-2-yl)-2-fluoro-N-(1-(3-fluoro-5-(fluoromethyl)phenyl)-2-hydroxyethyl) benzamide | 487.2 | 0.67 | 1H NMR (400 MHz, CD₃OD) δ 7.91-7.84 (m, 2H), 7.70 (dd, J = 1.6, 7.8Hz, 1H), 7.65 (dd, J = 1.2, 11.7 Hz,1H), 7.30 (s, 1H), 7.20 (d, J = 9.8 Hz,1H), 7.08 (d, J = 9.0 Hz, 1H), 5.46 (s,1H), 5.35 (s, 1H), 5.23 (t, J = 5.7 Hz,1H), 4.06 (dd, J = 2.3, 11.3 Hz, 2H),3.93-3.82 (m, 2H), 3.58 (dt, J = 2.5,11.4 Hz, 2H), 3.00-2.90 (m, 1H),1.98-1.79 (m, 4H). |

TABLE 5-continued

Compounds prepared using Method 3 described above.

| Example | Structure | Name | MH+ | R_t (min) | NMR |
|---|---|---|---|---|---|
| 330 | 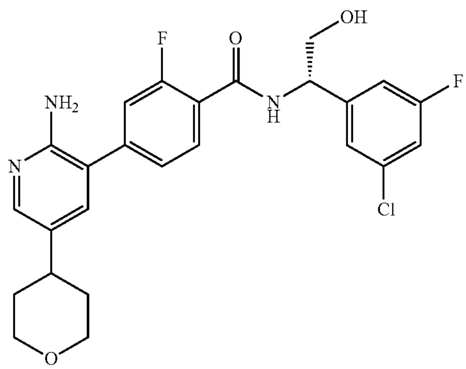 [SMILES: Nc1ncc(C2CCOCC2)cc1-c1ccc(C(=O)N[C@H](CO)c2cc(F)cc(Cl)c2)c(F)c1] | (S)-4-(3-amino-6-(tetrahydro-2H-pyran-4-yl)pyrazin-2-yl)-N-(1-(3-chloro-5-(fluorophenyl)-2-hydroxyethyl)-2-fluorobenzamide | 489.1 | 0.74 | 1H NMR (400 MHz, CD$_3$OD) δ 8.21(m, 1H), 7.94 (m, 1H), 7.75 (m, 1H),7.63 (m, 2H), 7.21 (m, 1H), 7.05 (m,2H), 5.20 (m, 1H), 4.09 (m, 4H),3.56 (m, 2H), 2.93 (m, 1H), 1.88 (m, 4H) |
| 331 | 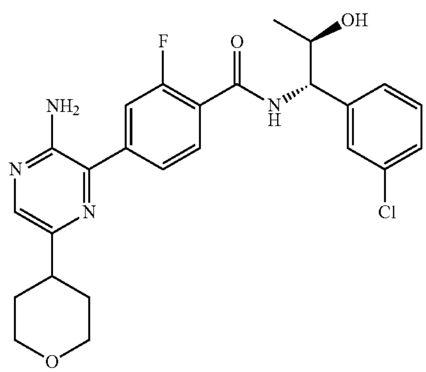 [SMILES: C[C@@H](O)[C@@H](NC(=O)c1ccc(-c2nc(C3CCOCC3)cnc2N)cc1F)c1cccc(Cl)c1] | 4-(3-amino-6-(tetrahydro-2H-pyran-4-yl)pyrazin-2-yl)-N-((1S,2R)-1-(3-chlorophenyl)-2-hydroxypropyl)-2-fluorobenzamide | 485.1 | 0.76 | 1H NMR (400 MHz, CD$_3$OD) δ ppm 8.72 (br. s., 1H), 7.94-7.77 (m, 2H), 7.74-7.59 (m, 2H), 7.48 (s, 1H), 7.42-7.23 (m, 3H), 5.06-4.95 (m, 1H), 4.14 (quin, J = 6.2 Hz, 1H), 4.05 (dd, J = 3.6, 11.5 Hz, 2H), 3.66-3.51 (m, 2H), 2.95 (ddd, J = 3.5, 7.9, 15.4 Hz, 1H), 2.02-1.75 (m, 4H), 1.30-1.13 (m, 3H) |
| 332 | 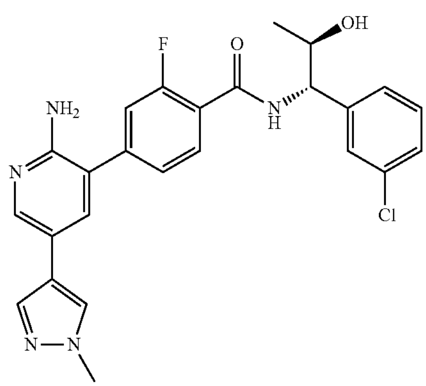 [SMILES: C[C@@H](O)[C@@H](NC(=O)c1ccc(-c2cc(-c3cnn(C)c3)cnc2N)cc1F)c1cccc(Cl)c1] | 4-(2-amino-5-(1-methyl-1H-pyrazol-4-yl)pyridin-3-yl)-N-((1S,2R)-1-(3-chlorophenyl)-2-hydroxypropyl)-2-fluorobenzamide | 480.1 | 0.66 | 1H NMR (400 MHz, CD$_3$OD) δ ppm 8.14 (d, J = 1.6 Hz, 2H), 8.05 (s, 1H),7.94-7.80 (m, 2H), 7.55-7.40 (m,3H), 7.39-7.23 (m, 3H), 5.48 (s, 1H), 4.99 (d, J = 5.9 Hz, 1H), 4.21-4.07 (m, 1H), 3.93 (s, 3H), 1.29-1.11 (m, 3H) |
| 333 | 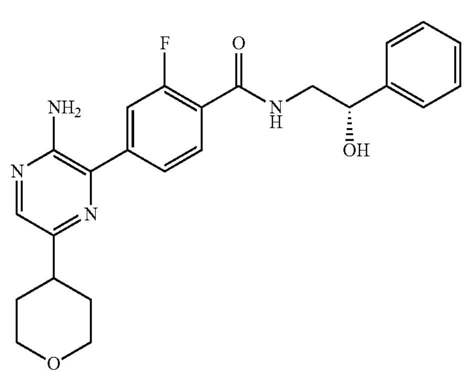 [SMILES: Nc1ncc(C2CCOCC2)nc1-c1ccc(C(=O)NC[C@@H](O)c2ccccc2)c(F)c1] | (S)-4-(3-amino-6-(tetrahydro-2H-pyran-4-yl)pyrazin-2-yl)-2-fluoro-N-(2-hydroxy-2-phenylethyl)benzamide | 437.2 | 0.61 | 1H NMR (400 MHz, DMSO-d6) δ 8.16 (m, 1H), 7.90 (s, 1H), 7.76-7.53 (m, 3H). 7.48-7.20 (m, 6H), 6.11 (s, 2H), 5.54 (d, J = 4 Hz, 1H), 4.75 (m, 1H), 3.92 (m, 2 H), 3.58-3.28 (m, 4H), 2.82 (m, 1 H), 1.71 (m, 4H) |

TABLE 5-continued

Compounds prepared using Method 3 described above.

| Example | Structure | Name | MH+ | R$_t$ (min) | NMR |
|---|---|---|---|---|---|
| 334 | 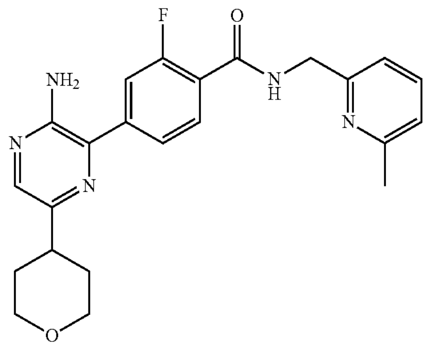 [SMILES: Cc1cccc(CNC(=O)c2ccc(-c3nc(C4CCOCC4)cnc3N)cc2F)n1] | 4-(3-amino-6-(tetrahydro-2H-pyran-4-yl)pyrazin-2-yl)-2-fluoro-N-((6-methylpyridin-2-yl)methyl)benzamide | 422.2 | 0.46 | 1H NMR (400 MHz, DMSO-d6) δ 7.96 (m, 1H), 7.91 (S, 1H), 7.79 (m, 1H), 7.70-7.57 (m, 2H), 7.38 (m, 2H), 4.62 (m, 2H), 3.90 (m, 2H), 3.4 (m, 2H), 2.55 (s, 3H), 1.72 (m, 4H) |
| 335 | 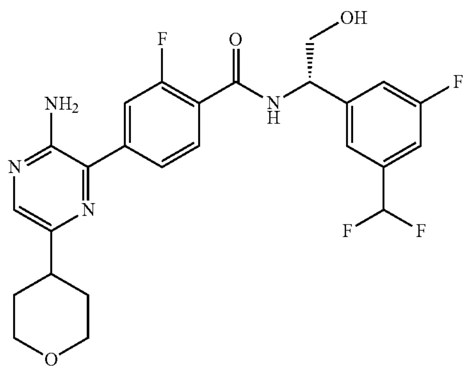 [SMILES: Nc1ncc(C2CCOCC2)nc1-c1ccc(C(=O)N[C@H](CO)c2cc(F)cc(C(F)F)c2)c(F)c1] | (S)-4-(3-amino-6-(tetrahydro-2H-pyran-4-yl)pyrazin-2-yl)-N-(1-(3-(difluoromethyl)-5-fluorophenyl)-2-hydroxyethyl)-2-fluorobenzamide | 505.1 | 0.73 | 1H NMR (400 MHz, CD$_3$OD) δ ppm 7.95-7.79 (m, 2H), 7.77-7.58 (m, 2H), 7.47 (s, 1H), 7.35 (d, J = 9.8 Hz, 1H), 7.22 (d, J = 8.6 Hz, 1H), 6.98-5.58 (t, J = 56 Hz, 1H), 5.48 (s, 2H), 5.25 (t, J = 5.9 Hz, 1H), 4.12-3.97 (m, 2H), 3.95-3.76 (m, 2H), 3.57 (dt, J = 2.3, 11.5 Hz. 2H), 2.94 (m, 1H), 2.00-1.75 (m, 4H) |
| 336 | 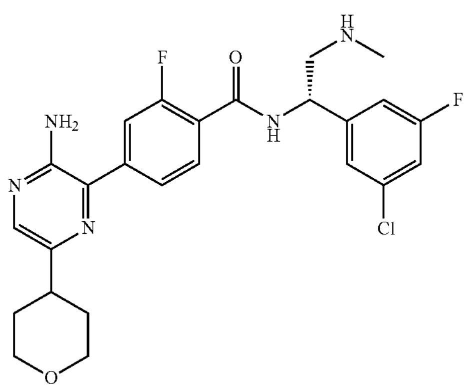 [SMILES: CNC[C@@H](NC(=O)c1ccc(-c2nc(C3CCOCC3)cnc2N)cc1F)c1cc(F)cc(Cl)c1] | (S)-4-(3-amino-6-(tetrahydro-2H-pyran-4-yl)pyrazin-2-yl)-N-(1-(3-chloro-5-fluorophenyl)-2-(methylamino)ethyl)-2-fluorobenzamide | 502.2 | 0.69 | 1H NMR (400 MHz, CD$_3$OD) δ ppm 7.98-7.90 (m, 1H), 7.89-7.80 (m, 1H), 7.73 (d, J = 8.2 Hz, 1H), 7.66 (d, J = 11.7 Hz, 1H), 7.39-7.31 (m, 1H), 7.26-7.11 (m, 2H), 5.33 (dd, J = 5.2, 9.0 Hz, 1H), 4.15-4.01 (m, 2H), 3.60 (dt, J = 2.2, 11.7 Hz, 2H), 3.14-2.86 (m, 3H), 2.54-2.43 (m, 3H), 1.99-1.79 (m, 4H) |
| 337 | 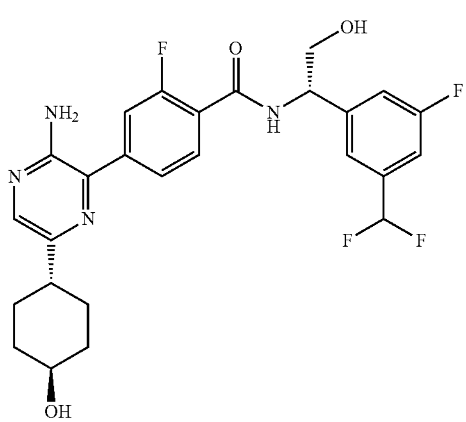 [SMILES: Nc1ncc([C@H]2CC[C@H](O)CC2)nc1-c1ccc(C(=O)N[C@H](CO)c2cc(F)cc(C(F)F)c2)c(F)c1] | 4-(3-amino-6-((1r,4S)-4-hydroxycyclohexyl)pyrazin-2-yl)-N-((S)-1-(3-(difluoromethyl)-5-fluorophenyl)-2-hydroxyethyl)-2-fluorobenzamide | 519.2 | 0.67 | 1H NMR (400 MHz, CD$_3$OD) δ ppm 8.76 (br. s., 1H), 7.92-7.78 (m,2H), 7.74-7.56 (m, 2H), 7.47 (s,1H), 7.35 (d, J = 9.0 Hz, 1H), 7.22 (dJ = 8.6 Hz, 1H), 6.99-6.59 (t, J = 56Hz, 1H), 5.26 (m, 2H), 4.10 (q,J = 7.0 Hz, 8H), 3.89 (m, 2H), 3.63(m, 1H), 2.64 (t, J = 12.1 Hz, 1H), 2.12-1.88 (m, 4H), 1.75-1.56 (m, 2H), 1.50-1.32 (m, 2H). |

TABLE 5-continued

Compounds prepared using Method 3 described above.

| Example | Structure | Name | MH+ | R_t (min) | NMR |
|---|---|---|---|---|---|
| 338 | 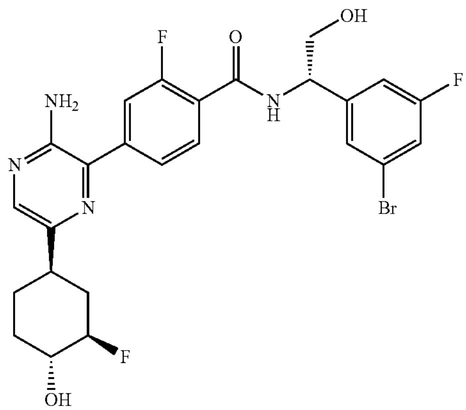 [SMILES: Nc1ncc([C@@H]2CC[C@@H](O)[C@H](F)C2)nc1-c1ccc(C(=O)N[C@H](CO)c2cc(F)cc(Br)c2)c(F)c1] | N-((S)-2-amino-1-(3-bromo-5-fluorophenyl)ethyl)-4-(3-amino-6-((1R,3R,4R)-3-fluoro-4-hydroxycyclohexyl)pyrazin-2-yl)-2-fluorobenzamide | 564.0/566.1 | 0.62 | 1H NMR (400MHz, CD$_3$OD) d = 7.96-7.82 (m, 2H), 7.76-7.59 (m, 2H), 7.59-7.48 (m, 1H), 7.41 (d, J = 8.2 Hz, 1H), 7.29 (d, J = 9.4 Hz, 1H), 5.48 (t, J = 7.2 Hz, 1H), 4.51-4.24 (m, 1H). 3.74-3.55 (m, 1H), 3.53-3.38 (m, 2H), 2.84 (t, J = 11.9 Hz, 1H), 2.27 (td, J = 3.1, 6.0 Hz, 1H), 2.14-1.96 (m, 1H), 1 96-1.73 (m, 2H), 1.64 (dq, J = 2.9, 13.0 Hz, 1H), 1.56-1.39 (m, 1H) |
| 339 | 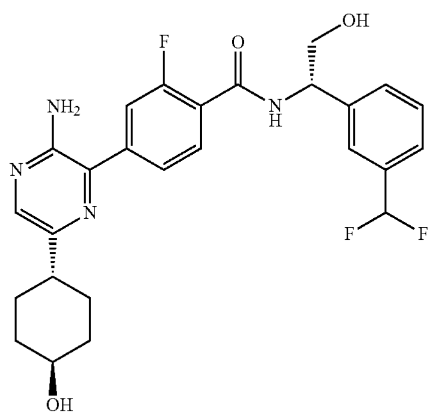 [SMILES: Nc1ncc([C@H]2CC[C@H](O)CC2)nc1-c1ccc(C(=O)N[C@H](CO)c2cccc(C(F)F)c2)c(F)c1] | 4-(3-amino-6-((1r,4S)-4-hydroxycyclohexyl)pyrazin-2-yl)-N-((S)-1-(3-(difluoromethyl)phenyl)-2-hydroxyethyl)-2-fluorobenzamide | 501.1 | 0.65 | 1H NMR (400 MHz, CD$_3$OD) δ ppm 7.84-7.69 (m, 1H), 7.63-7.44 (m,2H), 7.43-7.31 (m, 1H), 6.91-6.44(t, J = 56 Hz, 1H), 5.25-5.10 (m,1H), 3.88-3.68 (m, 2H), 3.60-3.42(m, 1H), 2.67-2.43 (m, 1H), 2.03-1.78 (m, 4H), 1.68-1.44 (m, 2H),1.42-1.25 (m, 2H) |
| 340 | 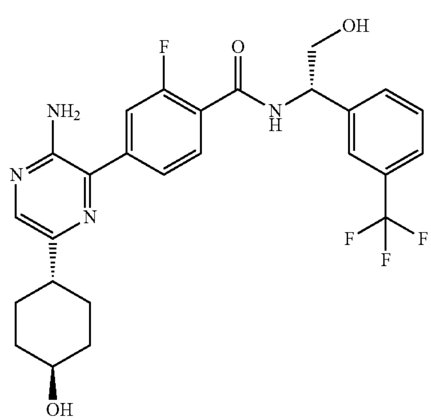 [SMILES: Nc1ncc([C@H]2CC[C@H](O)CC2)nc1-c1ccc(C(=O)N[C@H](CO)c2cccc(C(F)(F)F)c2)c(F)c1] | 4-(3-amino-6-((1r,4S)-4-hydroxycyclohexyl)pyrazin-2-yl)-2-fluoro-N-((S)-2-hydroxy-1-(3-(trifluoromethyl)phenyl)ethyl)benzamide | 519.2 | 0.71 | 1H NMR (400 MHz, CD$_3$OD) δ ppm 8.86 (br. s., 1H), 7.93-7.83 (m, 2H), 7.79 (s, 1H), 7.74-7.67 (m, 2H), 7.66-7.54 (m, 3H), 5.30 (t, J = 5.8 Hz, 1H), 4.01-3.82 (m, 2H), 3.71-3.55 (m, 1H), 2.77-2.60 (m, 1H), 2.18-2.05 (m, 2H), 2.02-1.89 (m, 2H), 1.80-1.60 (m, 2H), 1.51-1.34 (m, 2H) |

TABLE 5-continued

Compounds prepared using Method 3 described above.

| Example | Structure | Name | MH+ | R$_t$ (min) | NMR |
|---|---|---|---|---|---|
| 341 | 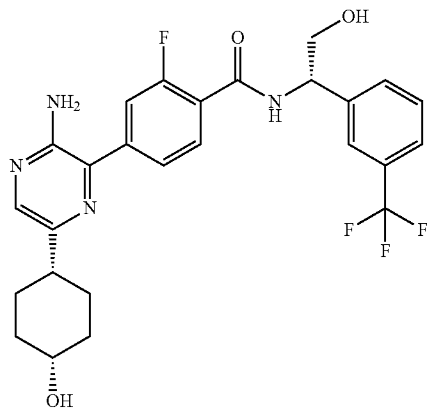 [SMILES: Nc1ncc([C@H]2CC[C@@H](O)CC2)nc1-c1ccc(C(=O)N[C@H](CO)c2cccc(C(F)(F)F)c2)c(F)c1] | 4-(3-amino-6-((1s,4R)-4-hydroxycyclohexyl)pyrazin-2-yl)-2-fluoro-N-((S)-2-hydroxy-1-(3-(trifluoromethyl)phenyl)ethyl)benzamide | 519.2 | 0.74 | 1H NMR (400MHz, CD$_3$OD) δ ppm 8.86 (br. s. 1H), 7.93-7.83 (m, 2H), 7.82-7.71 (m, 2H), 7.70-7.56 (m, 3H), 5.36-5.24 (m, 1H), 4.04 (br. s., 2H), 3.96-3.81 (m, 1H), 2.80-2.66 (m, 1H), 2.14-2.00 (m, 2H), 1.90 (d, J = 10.7 Hz, 2H), 1.77-1.65 (m, 4H) |
| 342 | 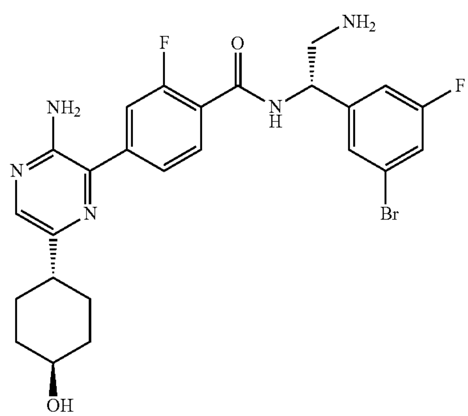 [SMILES: NC[C@@H](NC(=O)c1ccc(-c2nc([C@H]3CC[C@H](O)CC3)cnc2N)cc1F)c1cc(F)cc(Br)c1] | N-((S)-2-amino-1-(3-bromo-5-fluorophenyl)ethyl)-4-(3-amino-6-((1r,4S)-4-hydroxycyclohexyl)pyrazin-2-yl)-2-fluorobenzamide | 546.1/ 548.1 | 0.66 | 1H NMR (400 MHz, CD$_3$OD) δ ppm7.95-7.84 (m, 2H), 7.71 (dd, J = 1.6,8.0 Hz, 1H), 7.63 (dd, J = 1.5, 12.0Hz, 1H), 7.55 (s, 1H), 7.41 (td, J = 2.1, 8.2 Hz, 1H), 7.33-7.23 (m, 1H), 5.55-5.40 (m, 1H), 3.67-3.53 (m, 1H), 3.52-3.39 (m, 2H), 2.72-2.54 (m, 2H), 2.06 (d, J = 9.7 Hz, 2H), 1.99-1.87 (m, 2H), 1.76-1.56 (m, 2H), 1.49-1.31 (m, 2H) |
| 343 | 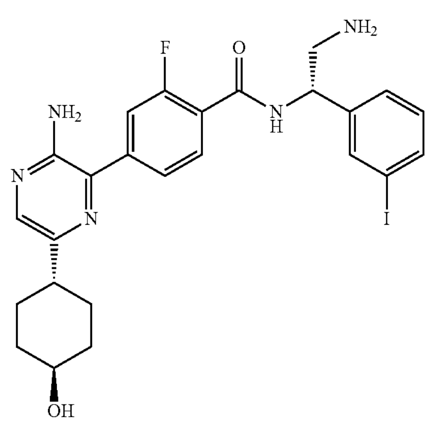 | N-((S)-2-amino-1-(3-iodophenyl)ethyl)4-(3-amino-6-((1r,4S)-4-hydroxycyclohexyl)pyrazin-2-yl)-2-fluorobenzamide | 576.2 | 0.65 | N/A |

TABLE 5-continued

Compounds prepared using Method 3 described above.

| Example | Structure | Name | MH+ | R_t (min) | NMR |
|---|---|---|---|---|---|
| 344 | 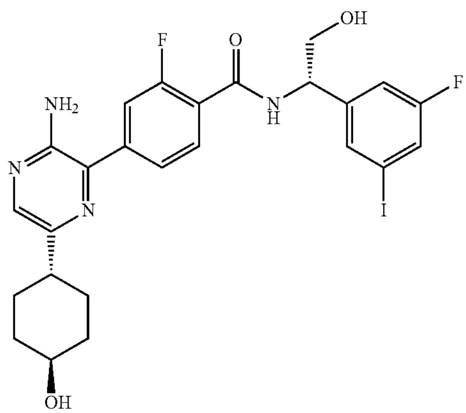 [SMILES: Nc1ncc([C@H]2CC[C@H](O)CC2)nc1-c1ccc(C(=O)N[C@H](CO)c2cc(F)cc(I)c2)c(F)c1] | 4-(3-amino-6-((1r,4S)-4-hydroxycyclohexyl)pyrazin-2-yl)-2-fluoro-N-((S)-1-(3-fluoro-5-iodophenyl)-2-hydroxyethyl)benzamide | 595.1 | 0.73 | 1H NMR (400 MHz, CD3OD) δ ppm8.76 (br. s., 1H), 7.92-7.80 (m, 2H), 7.73-7.55 (m, 3H), 7.45 (d, J = 7.9 Hz, 1H), 7.22 (d, J = 9.5 Hz, 1H), 5.49 (m, 1H), 5.23-5.11 (m, 1H), 3.94-3.76 (m, 2H), 3.69-3.53 (m, 1H), 2.72-2.57 (m, 1H), 2.07 (m, 2H), 1.97 (m, 2H), 1.97 (m, 2H), 1.44 (m, 2H). |
| 345 | 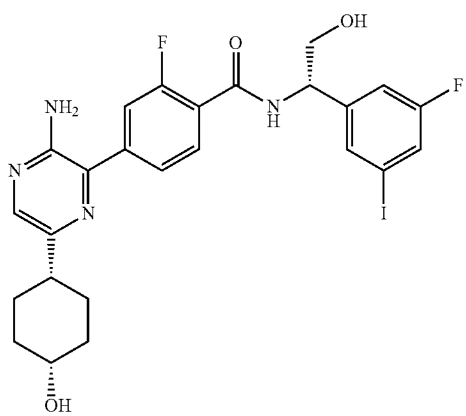 [SMILES: Nc1ncc([C@H]2CC[C@@H](O)CC2)nc1-c1ccc(C(=O)N[C@H](CO)c2cc(F)cc(I)c2)c(F)c1] | 4-(3-amino-6-((1s,4R)-4-hydroxycyclohexyl)pyrazin-2-yl)-2-fluoro-N-((S)-1-(3-fluoro-5-iodophenyl)-2-hydroxyethyl)benzamide | 595.2 | 0.76 | 1H NMR (400 MHz, CD3OD) δ ppm8.75 (br. s., 1H), 7.95-7.79 (m, 2H), 7.77-7.58 (m, 3H), 7.44 (d, J = 6.9 Hz, 1H), 7.22 (d, J = 9.5 Hz, 1H), 5.49 (m, 1H), 5.15 (m, 1H), 4.02 (br. s., 1H), 3.85 (m, 2H), 2.71 (m, 1H). 2.03 (m, 2H), 1.88 (m, 2H), 1.77-1.59 (m, 4H) |
| 346 | 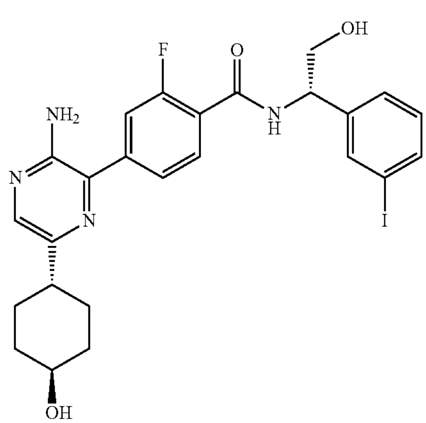 [SMILES: Nc1ncc([C@H]2CC[C@H](O)CC2)nc1-c1ccc(C(=O)N[C@H](CO)c2cccc(I)c2)c(F)c1] | 4-(3-amino-6-((1r,4S)-4-hydroxycyclohexyl)pyrazin-2-yl)-2-fluoro-N-((S)-2-hydroxy-1-(3-iodophenyl)ethyl)benzamide | 577.1 | 0.7 | 1H NMR (400 MHz, CD3OD) δ ppm8.73 (br. s., 1H), 7.92-7.77 (m, 3H), 7.71-7.56 (m, 3H), 7.44 (d, J = 7.6 Hz, 1H), 7.15 (t, J = 7.7 Hz, 1H), 5.5 (m, 1H), 5.15 (m, 1H), 3.85 (m, 2H), 3.61 (m, 1H), 2.65 (m, 1H). 2.07 (m, 2H), 1.97 (m, 2H), 1.68 (m, 2H), 1.46 (m, 2H). |

TABLE 5-continued

Compounds prepared using Method 3 described above.

| Example | Structure | Name | MH+ | R_f (min) | NMR |
|---|---|---|---|---|---|
| 347 | 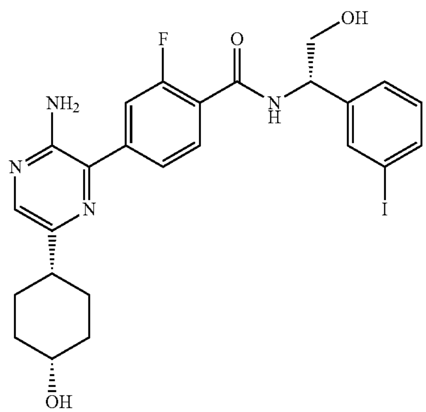 [SMILES: Nc1ncc([C@H]2CC[C@@H](O)CC2)nc1-c1ccc(C(=O)N[C@H](CO)c2cccc(I)c2)c(F)c1] | 4-(3-amino-6-((1s,4R)-4-hydroxycyclohexyl)pyrazin-2-yl)-2-fluoro-N-((S)-2-hydroxy-1-(3-iodophenyl)ethyl)benzamide | 577.4 | 0.76 | 1H NMR (400 MHz, CD3OD) δ ppm 8.74 (br. s., 1H), 7.91-7.76 (m, 3H), 7.76-7.56 (m, 3H), 7.44 (d, J = 7.6 Hz, 1H), 7.15 (t, J = 7.9 Hz, 1H), 5.49 (m, 1H), 5.15 (m, 1H), 4.02 (br. s., 1H), 3.84 (m, 2H), 2.74 (m, 1H), 1.99 (m, 2H), 1.88 (m, 2H), 1.72 (m, 4H) |
| 348 | 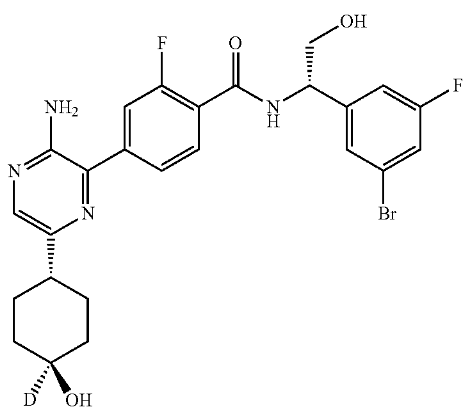 [SMILES: [2H][C@]1(O)CC[C@H](c2cnc(N)c(-c3ccc(C(=O)N[C@H](CO)c4cc(F)cc(Br)c4)c(F)c3)n2)CC1] | 4-(3-amino-6-((1r,4S)-4-deuterido-4-hydroxycyclohexyl)pyrazin-2-yl)-N-((S)-1-(3-bromo-5-fluorophenyl)-2-hydroxyethyl)-2-fluorobenzamide | 548.1 | 0.71 | 1H NMR (500 MHz, CD3OD) δ ppm 7.93-7.79 (m, 2H), 7.73-7.57 (m, 2H), 7.47 (s, 1H), 7.34-7.14 (m, 2H), 5.18 (t, J = 5.7 Hz, 1H), 3.93-3.78 (m, 2H), 2.70-2.55 (m, 1H), 2.06 (d, J = 12.3 Hz, 2H), 1.95 (d, J = 12.3 Hz, 2H), 1.76-1.58 (m, 2H), 1.48-1.35 (m, 2H) |
| 349 | 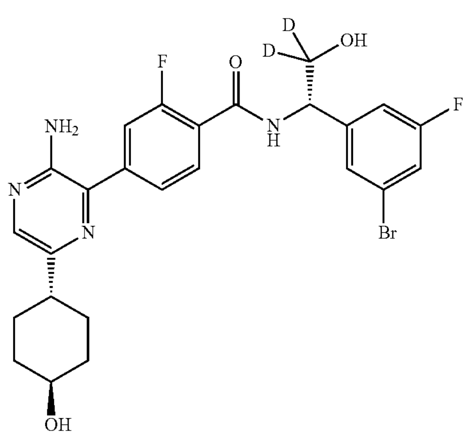 [SMILES: [2H]C([2H])(O)[C@@H](NC(=O)c1ccc(-c2nc([C@H]3CC[C@H](O)CC3)cnc2N)cc1F)c1cc(F)cc(Br)c1] | 4-(3-amino-6-((1r,4S)-4-hydroxycyclohexyl)pyrazin-2-yl)-N-((S)-1-(3-bromo-5-fluorophenyl)-2-hydroxy,2,2-dideuteridoethyl)-2-fluorobenzamide | 549.1/ 551.0 | 0.71 | 1H NMR (400 MHz, CD3OD) δ ppm 8.72-8.56 (m, 1H), 7.84-7.67 (m, 2H), 7.67-7.45 (m, 2H), 7.37 (s, 1H), 7.23-7.03 (m, 2H), 5.07 (d, J = 5.1 Hz, 1H), 3.82-3.68 (m, 0.15H), 3.59-3.41 (m, 1H), 2.67-2.44 (m, 1H), 2.05-1.79 (m, 2H), 1.57 (dq, J = 2.7, 13.0 Hz, 2H), 1.39-1.24 (m, 2H) |

TABLE 5-continued

Compounds prepared using Method 3 described above.

| Example | Structure | Name | MH+ | R$_t$ (min) | NMR |
|---|---|---|---|---|---|
| 350 | 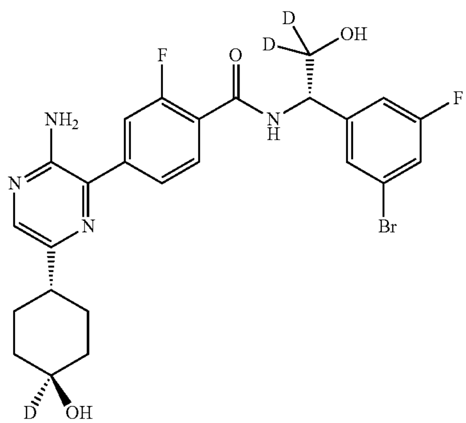 [SMILES: [2H]C([2H])(O)[C@@H](NC(=O)c1ccc(-c2nc([C@H]3CC[C@]([2H])(O)CC3)cnc2N)cc1F)c1cc(F)cc(Br)c1] | 4-(3-amino-6-((1r,4S)-4-deuterido-4-hydroxycyclohexyl)pyrazin-2-yl)-N-((S)-1-(3-bromo-5-fluorophenyl)-2-hydroxy-2,2-dideuteridoethyl)-2-fluorobenzamide | 550.0/ 552.1 | 0.71 | 1H NMR (400 MHz, CD$_3$OD) δ ppm 8.64 (br. s., 1H), 7.82-7.68 (m, 2H), 7.63-7.47 (m, 2H), 7.37 (s, 1H), 7.22-7.03 (m, 2H), 5.07 (d, J = 7.4 Hz, 1H), 3.81-3.66 (m, 0.15H), 2.63-2.45 (m, 1H), 2.05-1.78 (m, 2H), 1.66-1.46 (m, 2H), 1.39-1.20 (m, 2H) |
| 351 | 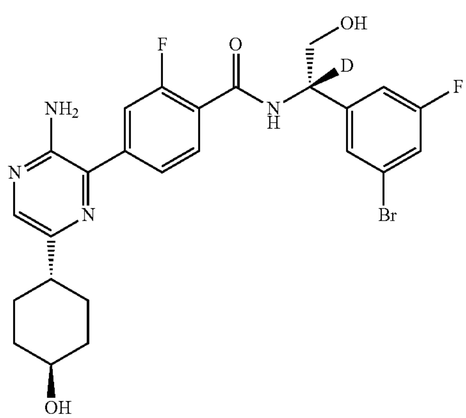 [SMILES: [2H][C@](CO)(NC(=O)c1ccc(-c2nc([C@H]3CC[C@H](O)CC3)cnc2N)cc1F)c1cc(F)cc(Br)c1] | 4-(3-amino-6-((1r,4S)-4-hydroxycyclohexyl)pyrazin-2-yl)-N-((S)-1-(3-bromo-5-fluorophenyl)-2-hydroxy-1-deuteridoethyl)-2-fluorobenzamide | 548.1/ 550.1 | 0.72 | 1H NMR (400 MHz, CD$_3$OD) δ ppm 7.87 (s, 1H), 7.84 (t, J = 7.8 Hz, 1H), 7.68 (d, J = 8.2 Hz, 1H), 7.62 (d, J = 11.7 Hz, 1H), 7.46 (s, 1H), 7.27 (d, J = 8.2 Hz, 1H), 7.20 (d, J = 9.4 Hz, 1H), 3.85 (d, J = 5.1 Hz, 2H), 3.60 (t, J = 11.2 Hz, 1H), 2.63 (t, J = 11.9 Hz, 1H), 2.06 (d, J = 12.1 Hz, 2H), 1.95 (d, J = 12.9 Hz, 2H), 1.73-1.60 (m, 2H), 1.48-1.36 (m, 2H) |
| 352 | 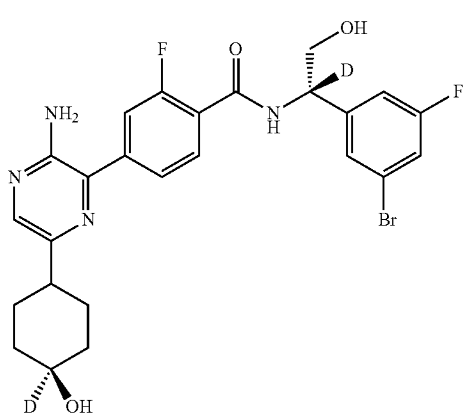 | 4-(3-amino-6-((1r,4S)-4-deuterido-4-hydroxycyclohexyl)pyrazin-2-yl)-N-((S)-1-(3-bromo-5-fluorophenyl)-2-hydroxy-1-deuteridoethyl)-2-fluorobenzamide | 549.1/ 551.0 | 0.72 | 1H NMR (400 MHz, CD$_3$OD) δ ppm 8.76 (br. s., 1H), 7.92-7.80 (m, 2H), 7.73-7.55 (m, 3H), 7.45 (d, J = 7.9 Hz, 1H), 7.22 (d, J = 9.5 Hz, 1H), 5.49 (m, 1H), 5.23-5.11 (m, 1H), 3.94-3.76 (m, 2H), 3.69-3.53 (m, 1H), 2.72-2.57 (m, 1H), 2.07 (m, 2H), 1.97 (m, 2H), 1.97 (m, 2H), 1.44 (m, 2H). |

TABLE 5-continued

Compounds prepared using Method 3 described above.

| Example | Structure | Name | MH+ | R$_t$ (min) | NMR |
|---|---|---|---|---|---|
| 353 | absolute stereochemistry assigned aritrarily | N-((S)-2-amino-1-(3-bromo-5-fluorophenyl)ethyl)-4-(3-amino-6-((1R,3S,4R)-3-fluoro-4-hydroxycyclohexyl)pyrazin-2-yl)-2-fluorobenzamide | 564.1/ 566.3 | 0.61 | 1H NMR (400 MHz, CD$_3$OD) δ ppm 7.97-7.82 (m, 2H), 7.77-7.58 (m, 2H), 7.59-7.47 (m, 1H), 7.44-7.35 (m, 1H), 7.29 (d, J = 9.4 Hz, 1H), 5.48 (t, J = 7.2 Hz, 1H), 3.77-3.56 (m, 1H), 3.53-3.38 (m, 3H), 3.10-2.94 (m, 1H), 2.31-2.14 (m, 1H), 2.09-1.78 (m, 4H), 1.77-1.60 (m, 1H) |
| 354 | absolute stereochemistry assigned aritrarily | N-((S)-2-amino-1-(3-bromo-5-fluorophenyl)ethyl)-4-(3-amino-6-((1S,3R,4S)-3-fluoro-4-hydroxycyclohexyl)pyrazin-2-yl)-2-fluorobenzamide | 564.2.1/ 562.2 | 0.62 | 1H NMR (400 MHz, CD$_3$OD) δ ppm 7.85-7.74 (m, 2H), 7.62 (dd, J = 1.4, 8.0 Hz, 1H), 7.55 (dd, J = 1.2, 11.7 Hz, 1H), 7.45 (s, 1H), 7.36-7.26 (m, 1H), 7.20 (d, J = 9.4 Hz, 1H), 5.39 (t, J = 7.2 Hz, 1H), 3.66-3.46 (m, 1H), 3.44-3.32 (m, 2H), 2.98-2.82 (m, 1H), 2.21-2.05 (m, 1H), 1.97-1.70 (m, 4H), 1.69-1.49 (m, 1H) |
| 355 | absolute stereochemistry assigned aritrarily | 4-(3-amino-6-((1R,3S,4R)-3-fluoro-4-hydroxycyclohexyl)pyrazin-2-yl)-N-((S)-1-(3-bromo-5-fluorophenyl)-2-(methylamino)ethyl)-2-fluorobenzamide | 578/ 580.1 | 0.63 | 1H NMR (400 MHz, CD$_3$OD) δ ppm 7.88-7.69 (m, 3H), 7.62 (dd, J = 1.6, 8.2 Hz, 1H), 7.59-7.50 (m, 1H), 7.47 (s, 1H), 7.36-7.28 (m, 1H), 7.23 (dd, J = 9.0, 14.9 Hz, 2H), 5.48 (t, J = 7.2 Hz, 1H), 3.67-3.49 (m, 1H), 3.49-3.39 (m, 2H), 3.00-2.85 (m, 1H), 2.72 (s, 3H), 2.14 (dt, J = 3.9, 10.8 Hz, 1H), 1.99-1.71 (m, 4H), 1.70-1.49 (m, 1H) |

TABLE 5-continued

Compounds prepared using Method 3 described above.

| Example | Structure | Name | MH+ | R$_f$ (min) | NMR |
|---|---|---|---|---|---|
| 356 | 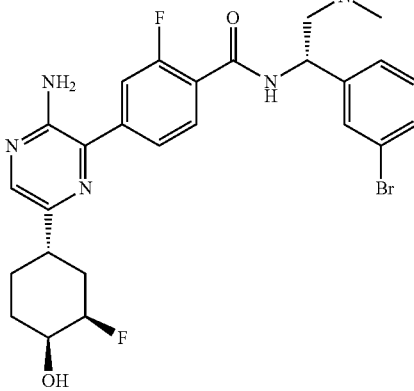<br>absolute stereochemistry assigned aritrarily | 4-(3-amino-6-((1S,3R,4S)-3-fluoro-4-hydroxycyclohexyl)pyrazin-2-yl)-N-((S)-1-(3-bromo-5-fluorophenyl)-2-(methylamino)ethyl)-2-fluorobenzamide | 578/ 580.2 | 0.63 | 1H NMR (400 MHz, CD$_3$OD) δ ppm 7.87-7.74 (m, 2H), 7.62 (dd, J = 1.6, 8.2 Hz, 1H), 7.55 (dd, J = 1.2, 12.1 Hz, 1H), 7.47 (s, 1H), 7.32 (td, J = 1.8, 8.2 Hz, 1H), 7.21 (d, J = 9.4 Hz, 1H), 5.55-5.40 (m, 1H), 3.67-3.50 (m, 1H), 3.48-3.37 (m, 2H), 2.99-2.84 (m, 1H), 2.72 (s, 3H), 2.20-2.06 (m, 1H), 1.97-1.69 (m, 5H), 1.68-1.50 (m, 1H) |
| 357 | 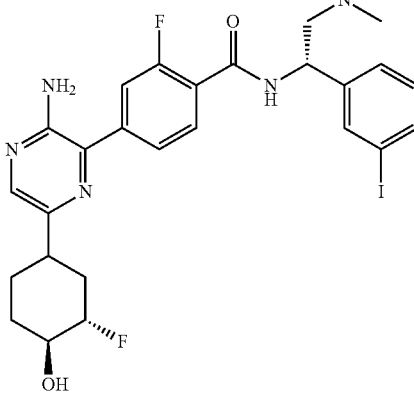 | 4-(3-amino-6-((1S,3S,4S)-3-fluoro-4-hydroxycyclohexyl)pyrazin-2-yl)-2-fluoro-N-((S)-1-(3-fluoro-5-iodophenyl)-2-(methylamino)ethyl)benzamide | 626.1 | 0.68 | 1H NMR (400 MHz, CD$_3$OD) δ ppm 7.87-7.76 (m, 2H), 7.69-7.60 (m, 2H), 7.59-7.51 (m, 1H), 7.49 (d, J = 7.4 Hz, 1H), 7.22 (d, J = 9.4 Hz, 1H), 5.45 (t, J = 7.2 Hz, 1H), 4.43-4.14 (m, 1H), 3.62-3.49 (m, 1H), 3.45 (d, J = 7.4 Hz, 2H), 2.81-2.66 (m, 4H), 2.25-2.09 (m, 1H), 2.04-1.88 (m, 1H), 1.87-1.63 (m, 2H), 1.64-1.30 (m, 2H) |
| 358 | 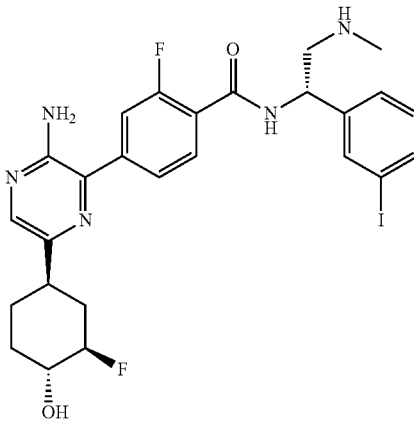 | 4-(3-amino-6-((1R,3R,4R)-3-fluoro-4-hydroxycyclohexyl)pyrazin-2-yl)-2-fluoro-N-((S)-1-(3-fluoro-5-iodophenyl)-2-(methylamino)ethyl)benzamide | 626.1 | 0.67 | 1H NMR (400 MHz, CD$_3$OD) δ ppm7.98-7.84 (m, 2H), 7.77-7.68 (m,2H), 7.68-7.53 (m, 2H), 7.49 (d,J = 8.2 Hz, 1H), 7.43-7.33 (m, 1H), 5.56 (dd, J = 5.5, 9.0 Hz, 1H), 4.50-4.25 (m, 1H), 3.72-3.59 (m, 1H), 3.60-3.48 (m, 2H), 2.89-2.74 (m, 4H), 2.33-2.19 (m, 1H), 2.05 (br. s., 1H), 1.96-1.73 (m, 2H), 1.73-1.56 (m, 1H), 1.55-1.40 (m, 1H) |

TABLE 5-continued

Compounds prepared using Method 3 described above.

| Example | Structure | Name | MH+ | R$_t$ (min) | NMR |
|---|---|---|---|---|---|
| 359 | 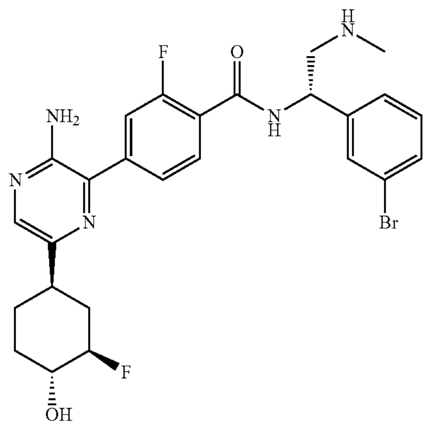 [SMILES: CNC[C@@H](NC(=O)c1ccc(-c2nc([C@@H]3CC[C@@H](O)[C@H](F)C3)cnc2N)cc1F)c1cccc(Br)c1] | 4-(3-amino-6-((1R,3R,4R)-3-fluoro-4-hydroxycyclohexyl)pyrazin-2-yl)-N-((S)-1-(3-bromophenyl)-2-(methylamino)ethyl)-2-fluorobenzamide | 560.2/ 562.2 | 0.64 | 1H NMR (400 MHz, CD$_3$OD) δ ppm8.00-7.85 (m, 2H), 7.78-7.68 (m,2H), 7.68-7.53 (m, 2H), 7.49 (d,J = 8.2 Hz, 1H), 7.43-7.32 (m, 1H), 5.56 (dd, J = 5.5, 9.0 Hz, 1H), 4.51-4.24 (m, 1H), 3.74-3.60 (m, 1H), 3.59-3.49 (m, 2H), 2.87-2.74 (m, 4H), 2.34-2.19 (m, 1H), 2.14-1.97 (m, 1H), 1.96-1.75 (m, 2H), 1.73-1.40 (m, 2H) |
| 360 | 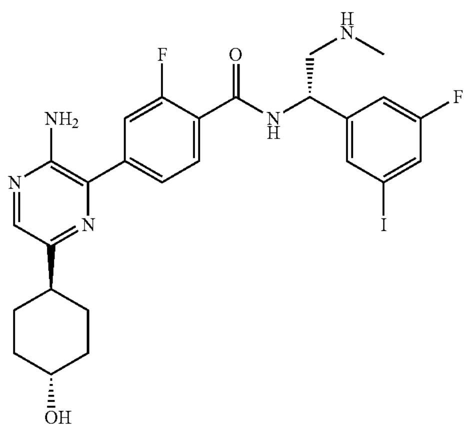 [SMILES: CNC[C@@H](NC(=O)c1ccc(-c2nc([C@H]3CC[C@H](O)CC3)cnc2N)cc1F)c1cc(F)cc(I)c1] | 4-(3-amino-6-((1r,4S)-4-hydroxycyclohexyl)pyrazin-2-yl)-2-fluoro-N-((S)-1-(3-fluoro-5-iodophenyl)-2-(methylamino)ethyl)benzamide | 608.1 | 0.68 | 1H NMR (400 MHz, CD$_3$OD) δ ppm7.87 (s, 1H), 7.81 (t, J = 7.8 Hz, 1H),7.58-7.71 (m, 3H), 7.42-7.49 (m,1H), 7.21 (d, J = 9.4 Hz, 1H), 5.25 (dd, J = 8.6, 5.1 Hz, 1H), 3.52-3.71(m, 1H), 2.88-3.08 (m, 2H), 2.62 (tt,J = 12.1, 3.4 Hz, 1H), 2.44 (s, 3H),2.06 (d, J = 9.8 Hz, 2H), 1.95 (d,J = 12.9 Hz. 2H), 1.66 (qd, J = 13.0,2.9 Hz, 2H), 1.32-1.50 (m, 2H) |
| 361 | 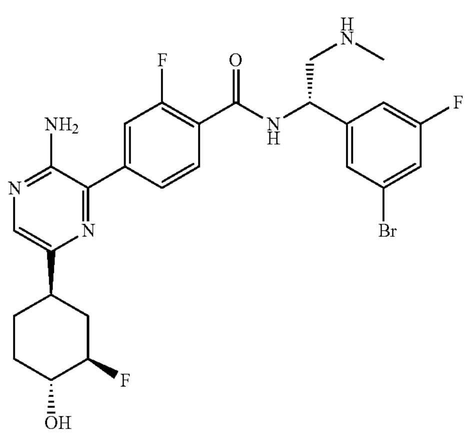 [SMILES: CNC[C@@H](NC(=O)c1ccc(-c2nc([C@@H]3CC[C@@H](O)[C@H](F)C3)cnc2N)cc1F)c1cc(F)cc(Br)c1] | 4-(3-amino-6-((1R,3R,4R)-3-fluoro-4-hydroxycyclohexyl)pyrazin-2-yl)-N-((S)-1-(3-bromo-5-fluorophenyl)-2-(methylamino)ethyl)-2-fluorobenzamide | 578.2/ 580.1 | 0.65 | 1H NMR (400 MHz, METHANOL-d4) d = 7.88-7.75 (m, 2H), 7.69-7.51 (m, 2H), 7.47 (s, 1H), 7.37-7.27 (m, 1H), 7.21 (d, J = 9.0 Hz, 1H), 5.48 (t, J = 7.2 Hz, 1H), 4.43-4.13 (m, 1H), 3.64-3.50 (m, 1H), 3.46 (d, J = 7.4 Hz, 2H), 2.80-2.65 (m, 4H), 2.17 (br. s, 1H), 2.05-1.89 (m, 1H), 1 86-1.64 (m, 2H), 1.65-1.46 (m, 1H), 1.46-1.29 (m, 1H) |

TABLE 5-continued

Compounds prepared using Method 3 described above.

| Example | Structure | Name | MH+ | R$_t$ (min) | NMR |
|---|---|---|---|---|---|
| 362 | 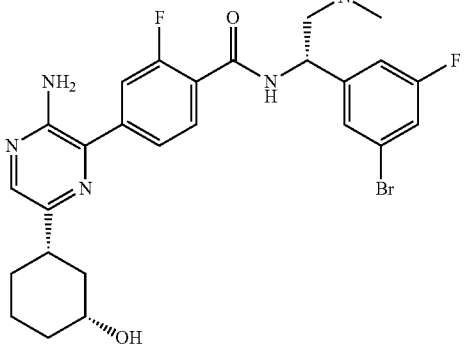<br>single enantiomer; cis on cyclohexyl group; absolute stereochemistry assigned arbitrarily | 4-(3-amino-6-((1S,3R)-3-hydroxycyclohexyl)pyrazin-2-yl)-N-((S)-1-(3-bromo-5-fluorophenyl)-2-(methylamino)ethyl)-2-fluorobenzamide | 560/562 | 0.68 | 1H NMR (500 MHz, METHANOL-d4) δ ppm 8.01-7.88 (m, 2H), 7.84-7.65 (m, 2H), 7.59 (s, 1H), 7.45 (d, J = 8.2 Hz, 1H), 7.34 (d, J = 9.1 Hz, 1H), 5.73-5.49 (m, 1H), 3.81-3.64 (m, 1H), 3.57 (s, 2H), 2.84 (s, 3H), 2.80-2.71 (m, 1H), 2.24-2.09 (m, 1H), 2.08-1.76 (m, 3H), 1.63-1.39 (m, 3H), 1.39-1.16 (m, 1H) |
| 363 | 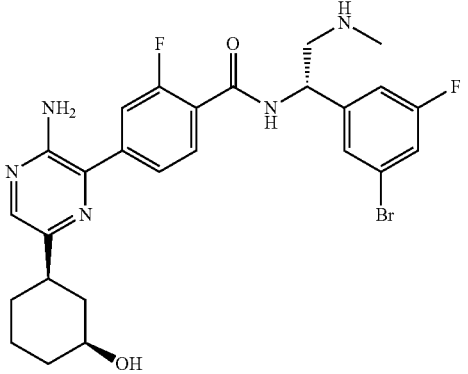<br>single enantiomer; cis on cyclohexyl group; absolute stereochemistry assigned arbitrarily | 4-(3-amino-6-((1R,3S)-3-hydroxycyclohexyl)pyrazin-2-yl)-N-((S)-1-(3-bromo-5-fluorophenyl)-2-(methylamino)ethyl)-2-fluorobenzamide | 560/562 | 0.67 | 1H NMR (500 MHz, METHANOL-d4) δ ppm 8.01-7.86 (m, 2H), 7.81-7.55 (m, 3H), 7.44 (d, J = 8.2 Hz, 1H), 7.38-7.25 (m, 1H), 5.71-5.51 (m, 1H), 3.80-3.46 (m, 3H), 2.84 (s, 4H), 1.91 (br. s., 4H), 1.63-1.37 (m, 3H), 1.35-1.13 (m, 1H) |
| 364 | 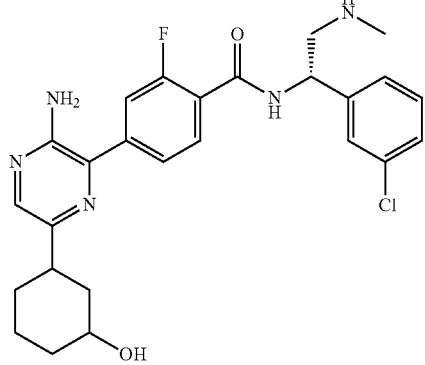<br>single enantiomer; cis on cyclohexyl group; absolute stereochemistry unknown | 4-(3-amino-6-(3-hydroxycyclohexyl)pyrazin-2-yl)-N-((S)-1-(3-chlorophenyl)-2-(methylamino)ethyl)-2-fluorobenzamide | 498.2 | 0.64 | 1H NMR (500 MHz, METHANOL-d4) δ ppm 8.01-7.86 (m, 2H), 7.60 (s, 3H), 7.48 (s, 3H), 5.72-5.46 (m, 1H), 3.79-3.64 (m, 1H), 3.65-3.49 (m, 2H), 2.84 (s, 4H), 2.16 (d, J = 12.0 Hz, 1H), 2.08-1.80 (m, 3H), 1.63-1.39 (m, 3H), 1.33-1.19 (m, 1H) |

TABLE 5-continued

Compounds prepared using Method 3 described above.

| Example | Structure | Name | MH+ | R$_f$ (min) | NMR |
|---|---|---|---|---|---|
| 365 | 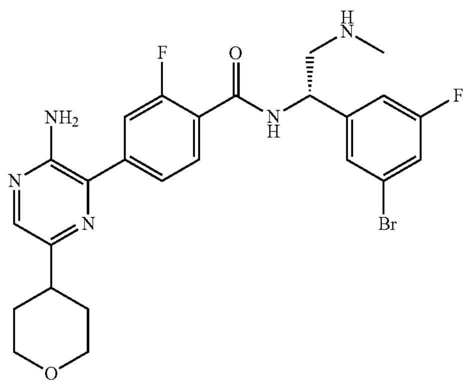 [SMILES: CNC[C@@H](NC(=O)c1ccc(-c2nc(C3CCOCC3)cnc2N)cc1F)c1cc(F)cc(Br)c1] | (S)-4-(3-amino-6-(tetrahydro-2H-pyran-4-yl)pyrazin-2-yl)-N-(1-(3-bromo-5-fluorophenyl)-2-(methylamino)ethyl)-2-fluorobenzamide | 564/548 | 0.69 | 1H NMR (500 MHz, METHANOL-d4) δ ppm 7.99-7.79 (m, 2H), 7.77-7.57 (m, 2H), 7.50 (s, 1H), 7.37-7.07 (m, 2H), 5.41-5.21 (m, 1H), 4.07 (dd, J = 3.8, 11.0 Hz. 2H), 3.68-3.54 (m, 2H), 2.98 (d, J = 5.4 Hz, 3H), 2.48 (s, 3H), 1.99-1.66 (m, 4H) |
| 366 | single enantiomer; cis on cyclohexyl group; absolute stereochemistry unknown | 4-(3-amino-6-(3-hydroxycyclohexyl)pyrazin-2-yl)-N-((S)-1-(3-chlorophenyl)-2-(methylamino)ethyl)-2-fluorobenzamide | 496.2 | 0.67 | 1H NMR (500 MHz, METHANOL-d4) δ ppm 7.90 (s, 2H), 7.74 (dd, J = 1.4, 8.0 Hz, 1H), 7.67 (dd, J = 1.4, 11.8 Hz, 1H), 7.60 (s, 1H), 7.50-7.41 (m, 3H), 5.69-5.47 (m, 1H), 3.70 (tt, J = 4.2, 11.0 Hz. 1H), 3.64-3.51 (m, 2H), 2.84 (s, 3H), 2.81-2.72 (m, 1H), 2.20-2.11 (m, 1H), 2.03 (d, J = 12.6 Hz, 1H), 1.96-1.79 (m, 2H), 1.61-1.42 (m, 3H), 1.34-1.24 (m, 1H) |
| 367 | single enantiomer; cis on cyclohexyl group; absolute stereochemistry unknown | N-((S)-2-amino-1-(3-chlorophenyl)ethyl)-4-(3-amino-6-(3-hydroxycyclohexyl)pyrazin-2-yl)-2-fluorobenzamide | 484.3 | 0.61 | 1H NMR (500 MHz, ETHANOL-d4) δ ppm 8.01-7.82 (m, 2H), 7.78-7.64 (m, 2H), 7.61-7.56 (m, 1H), 7.52-7.35 (m, 3H), 5.65-5.42 (m, 1H), 3.77-3.66 (m, 1H), 3.55-3.42 (m, 2H), 2.84-2.73 (m, 1H), 2.16 (d, J = 12.0 Hz, 1H), 2.03 (d, J = 12.0 Hz, 1H), 1.97-1.83 (m, 2H), 1.62-1.41 (m, 3H), 1.34-1.22 (m, 1H) |

TABLE 5-continued

Compounds prepared using Method 3 described above.

| Example | Structure | Name | MH+ | R$_t$ (min) | NMR |
|---|---|---|---|---|---|
| 368 | 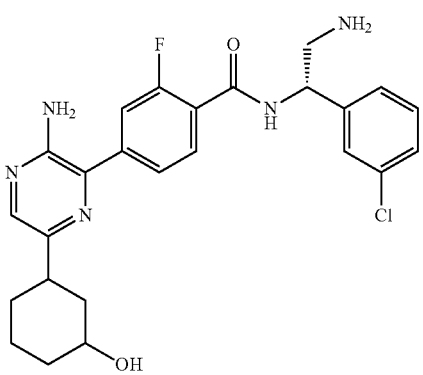<br>single enantiomer;<br>cis on cyclohexyl group;<br>absoulte stereochemistry unknown | N-((S)-2-amino-1-(3-chlorophenyl)ethyl)-4-(3-amino-6-(3-hydroxycyclohexyl)pyrazin-2-yl)-2-fluorobenzamide | 484 | 0.67 | 1H NMR (500 MHz, METHANOL-d4) δ ppm 7.89 (s, 2H), 7.80-7.70 (m, 1H), 7.58 (s, 2H), 7.47 (s, 3H), 5.62-5.43 (m, 1H), 3.80-3.64 (m, 1H), 3.59-3.40 (m, 2H), 2.77 (br. s., 1H), 2.16 (d, J = 12.0 Hz, 1H), 2.07-1.77 (m, 3H), 1.65-1.40 (m, 3H), 1.36-1.16 (m, 1H) |
| 369 | 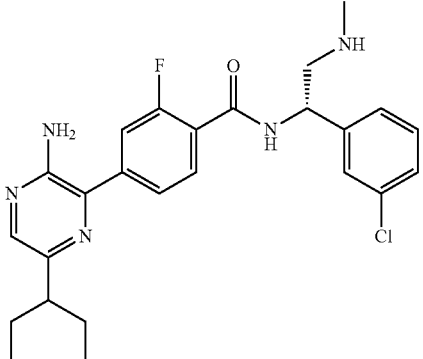<br>single enantiomer;<br>trans on cyclohexyl group;<br>absolute stereochemistry unknown | 4-(3-amino-6-(3-hydroxycyclohexyl)pyrazin-2-yl)-N-((S)-1-(3-chlorophenyl)-2-(methylamino)ethyl)-2-fluorobenzamide | 498 | 0.69 | 1H NMR (500 MHz, METHANOL-d4) δ ppm 7.89 (s, 2H), 7.80-7.71 (m, 1H), 7.70-7.62 (m, 1H), 7.61-7.54 (m, 1H), 7.48 (s, 3H), 5.67-5.50 (m, 1H), 4.18 (br. s, 1H), 3.65-3.51 (m, 2H), 3.21-3.07 (m, 1H), 2.84 (s, 3H), 2.02-1.74 (m, 5H), 1.70-1.46 (m, 3H) |
| 370 | 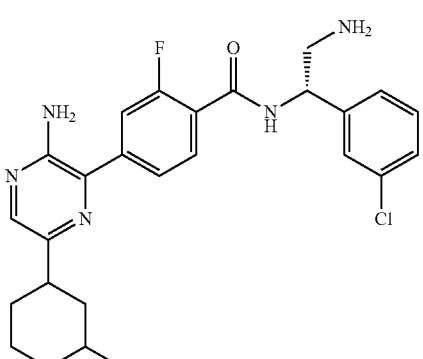<br>single enantiomer;<br>trans on cyclohexyl group;<br>absolute stereochemistry unknown | N-((S)-2-amino-1-(3-chlorophenyl)ethyl)-4-(3-amino-6-(3-hydroxycyclohexyl)pyrazin-2-yl)-2-fluorobenzamide | 484.2 | 0.68 | 1H NMR (500 MHz, METHANOL-d4) δ ppm 7.97-7.84 (m, 2H), 7.74 (d, J = 0.9 Hz, 1H), 7.68-7.62 (m, 1H), 7.58 (s, 1H), 7.50-7.37 (m, 3H), 5.62-5.44 (m, 1H), 4.27-4.13 (m, 1H), 3.57-3.42 (m, 2H), 3.17 (br. s., 1H), 2.05-1.72 (m, 5H), 1.68-1.53 (m, 3H) |

TABLE 5-continued

Compounds prepared using Method 3 described above.

| Example | Structure | Name | MH+ | R$_f$ (min) | NMR |
|---|---|---|---|---|---|
| 371 | 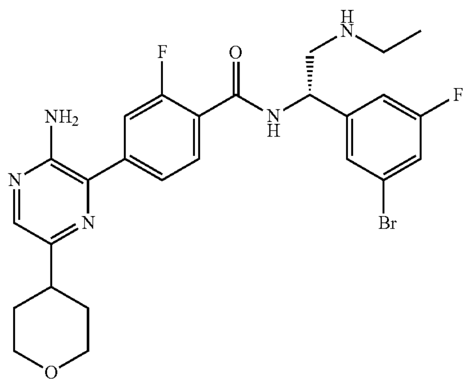 [SMILES: CCNC[C@@H](NC(=O)c1ccc(-c2nc(C3CCOCC3)cnc2N)cc1F)c1cc(F)cc(Br)c1] | (S)-4-(3-amino-6-(tetrahydro-2H-pyran-4-yl)pyrazin-2-yl)-N-(1-(3-bromo-5-fluorophenyl)-2-(ethylamino)ethyl)-2-fluorobenzamide | 560, 562 | 0.72 | 1H NMR (400 MHz, METHANOL-d4) δ ppm 7.87-7.71 (m, 2H), 7.67-7.53 (m, 1H), 7.46 (d, J = 7.8 Hz, 1H), 7.40-7.27 (m, 2H), 7.25-7.15 (m, 1H), 5.52-5.36 (m, 1H), 4.01-3.82 (m, 2H), 3.54-3.36 (m, 4H), 3.36-3.27 (m, 1H), 3.13-3.00 (m, 2H), 2.84 (s, 1H), 1.73 (br. s., 3H), 1.31-1.18 (m, 3H) |
| 372 | single enantiomer; trans on cyclohexyl group; absolute stereochemistry unknown | N-((S)-2-amino-1-(3-chlorophenyl)ethyl)-4-(3-amino-6-(3-hydroxycyclohexyl)pyrazin-2-yl)-2-fluorobenzamide | 484.2 | 0.66 | 1H NMR (500 MHz, METHANOL-d4) δ ppm 7.88 (s, 2H), 7.74 (s, 1H), 7.66 (dd, J = 1.3, 11.7 Hz, 1H), 7.58 (s, 1H), 7.49-7.40 (m, 3H), 5.59-5.43 (m, 1H), 4.18 (d, J = 2.8 Hz, 1H), 3.56-3.42 (m, 2H), 3.22-3.12 (m, 1H), 2.00-1.76 (m, 5H), 1.69-1.55 (m, 3H) |
| 373 | 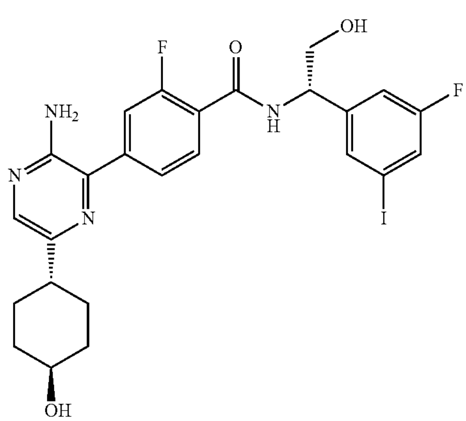 [SMILES: Nc1ncc([C@H]2CC[C@H](O)CC2)nc1-c1ccc(C(=O)N[C@H](CO)c2cc(F)cc(I)c2)c(F)c1] | N-((S)-2-amino-1-(3-fluoro-5-iodophenyl)ethyl)-4-(3-amino-6-((1r,4S)-4-hydroxycyclohexyl)pyrazin-2-yl)-2-fluorobenzamide | 594 | 0.66 | 1H NMR (400 MHz, METHANOL-d4) δ ppm 7.92-7.81 (m, 2H), 7.78-7.67 (m, 2H), 7.66-7.47 (m, 2H), 7.30 (d, J = 9.4 Hz, 1H), 5.50-5.38 (m, 1H), 3.68-3.53 (m, 1H), 3.50-3.40 (m, 2H), 2.69-2.54 (m, 1H), 2.14-1.86 (m, 4H), 1.66 (dq, J = 2.9, 13.0 Hz. 2H). 1.50-1.33 (m, 2H) |

TABLE 5-continued

Compounds prepared using Method 3 described above.

| Example | Structure | Name | MH+ | R$_f$ (min) | NMR |
|---|---|---|---|---|---|
| 374 | 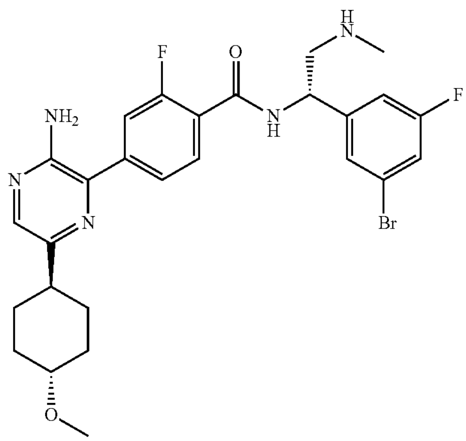 [SMILES: CNC[C@@H](NC(=O)c1ccc(-c2nc([C@H]3CC[C@H](OC)CC3)cnc2N)cc1F)c1cc(F)cc(Br)c1] | 4-(3-amino-6-((1r,4S)-4-methoxy-cyclohexyl)pyrazin-2-yl)-N-((S)-1-(3-bromo-5-fluorophenyl)-2-(methylamino)ethyl)-2-fluorobenzamide | 574/576 | 0.76 | 1H NMR (500 MHz, METHANOL-d4) δ ppm 7.91 (s, 2H), 7.76-7.58 (m, 2H), 7.54-7.47 (m, 1H), 7.36-7.27 (m, 1H), 7.27-7.13 (m, 1H), 5.36-5.25 (m, 1H), 3.41 (s, 3H), 3.12-2.89 (m, 2H), 2.76-2.59 (m, 1H), 2.49 (s, 3H), 2.32-2.14 (m, 2H), 2.06-1.96 (m, 2H), 1.79-1.61 (m, 2H), 1.44-1.23 (m, 2H) |
| 375 | 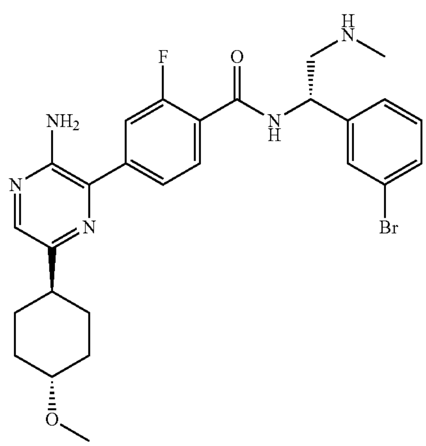 [SMILES: CNC[C@@H](NC(=O)c1ccc(-c2nc([C@H]3CC[C@H](OC)CC3)cnc2N)cc1F)c1cccc(Br)c1] | 4-(3-amino-6-((1r,4S)-4-methoxy-cyclohexyl)pyrazin-2-yl)-N-((S)-1-(3-bromophenyl)-2-(methylamino)ethyl)-2-fluorobenzamide | 556/558 | 0.76 | 1H NMR (400 MHz, METHANOL-d4) δ ppm 7.99-7.83 (m, 2H), 7.78-7.67 (m, 2H), 7.65-7.44 (m, 3H), 7.42-7.32 (m, 1H), 5.63-5.49 (m, 1H), 3.64-3.48 (m, 2H), 3.37 (s, 3H), 3.26 (s, 1H), 2.81 (s, 3H), 2.71-2.57 (m, 1H), 2.20 (d, J = 9.8 Hz, 2H), 2.05-1.94 (m, 2H), 1.65 (dq, J = 2.9, 13.0 Hz, 2H), 1.44-1.25 (m, 2H) |
| 376 | 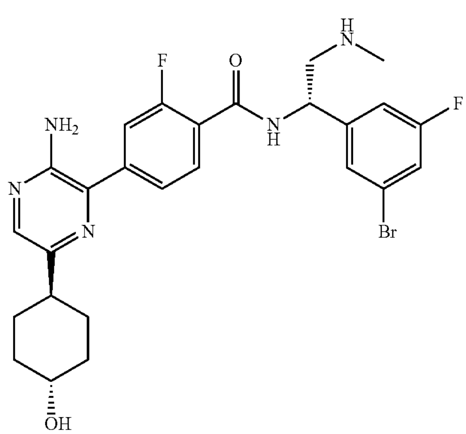 [SMILES: CNC[C@@H](NC(=O)c1ccc(-c2nc([C@H]3CC[C@H](O)CC3)cnc2N)cc1F)c1cc(F)cc(Br)c1] | 4-(3-amino-6-((1r,4S)-4-hydroxy-cyclohexyl)pyrazin-2-yl)-N-((S)-1-(3-bromo-5-fluorophenyl)-2-(methylamino)ethyl)-2-fluorobenzamide | 560/562 | 0.64 | 1H NMR (500 MHz, METHANOL-d4) δ ppm 7.97-7.83 (m, 2H), 7.79-7.57 (m, 2H), 7.50 (s, 1H), 7.38-7.29 (m, 1H), 7.27-7.16 (m, 1H), 5.39-5.28 (m, 1H), 3.63 (s, 1H), 3.13-2.91 (m, 2H), 2.66 (s, 1H), 2.49 (s, 3H), 2.15-1.88 (m, 4H), 1.69 (d, J = 12.6 Hz, 2H), 1.44 (d, J = 13.6 Hz, 2H) |

TABLE 5-continued

Compounds prepared using Method 3 described above.

| Example | Structure | Name | MH+ | R_f (min) | NMR |
|---|---|---|---|---|---|
| 377 | 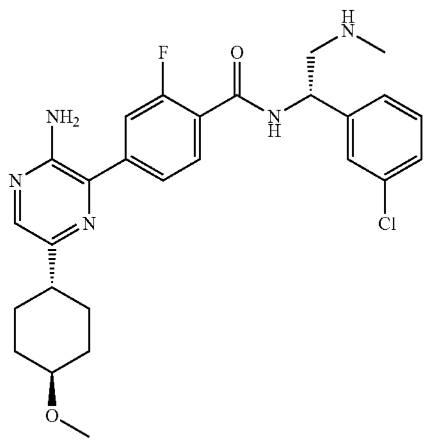 [SMILES: CNC[C@@H](NC(=O)c1ccc(-c2nc([C@H]3CC[C@H](OC)CC3)cnc2N)cc1F)c1cccc(Cl)c1] | 4-(3-amino-6-((1r,4S)-4-methoxy-cyclohexyl)pyrazine-2-yl)-N-((S)-1-(3-chlorophenyl)-2-(methylamino)ethyl)-2-fluorobenzamide | 512.4 | 0.74 | 1H NMR (400 MHz, METHANOL-d4) δ ppm 7.93-7.90 (m, 1H), 7.88 (s, 1H), 7.71 (d, J = 7.8 Hz, 1H), 7.63 (d, J = 12.1 Hz, 1H), 7.57 (s, 1H), 7.49-7.39 (m, 3H), 5.57 (dd, J = 5.3, 9.2 Hz, 1H), 3.61-3.50 (m, 2H), 3.37 (s, 3H), 3.28-3.22 (m, 1H), 2.81 (s, 3H), 2.70-2.60 (m, 1H), 2.20 (d, J = 10.2 Hz, 2H), 1.98 (d, J = 12.9 Hz, 2H), 1.65 (d, J = 14.9 Hz, 2H), 1.47-1.23 (m, 2H) |
| 378 | 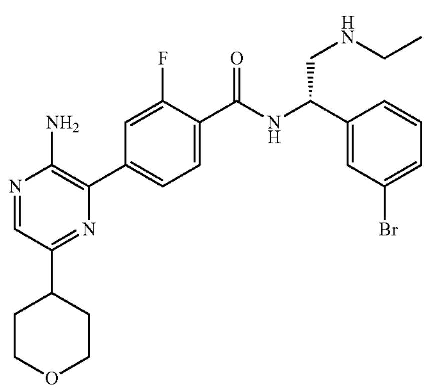 [SMILES: CCNC[C@@H](NC(=O)c1ccc(-c2nc(C3CCOCC3)cnc2N)cc1F)c1cccc(Br)c1] | (S)-4-(3-amino-6-(tetrahydro-2H-pyran-4-yl)pyrazin-2-yl)-N-(1-(3-bromophenyl)-2-(ethylamino)ethyl)-2-fluorobenzamide | 542/544 | 0.69 | 1H NMR (500 MHz, METHANOL-d4) δ ppm 7.98-7.90 (m, 2H), 7.75 (d, J = 1.6 Hz, 2H), 7.71-7.65 (m, 1H), 7.62-7.57 (m, 1H), 7.52 (s, 1H), 7.42 (s, 1H), 5.65-5.45 (m, 1H), 4.11-3.99 (m, 2H), 3.69-3.50 (m, 4H), 3.26-3.16 (m, 3H), 3.05-2.87 (m, 1H), 1.85 (br. s., 4H), 1.38 (t, J = 7.3 Hz, 3H) |
| 379 | 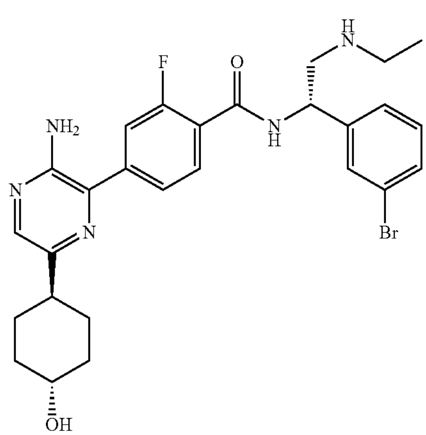 [SMILES: CCNC[C@@H](NC(=O)c1ccc(-c2nc([C@H]3CC[C@H](O)CC3)cnc2N)cc1F)c1cccc(Br)c1] | 4-(3-amino-6-((1r,4S)-4-hydroxy-cyclohexyl)pyrazin-2-yl)-N-((S)-1-(3-bromophenyl)-2-(ethylamino)ethyl)-2-fluorobenzamide | 556/558 | 0.65 | 1H NMR (500 MHz, METHANOL-d4) δ ppm 7.90 (s, 2H), 7.77-7.72 (m, 2H), 7.69-7.63 (m, 1H), 7.62-7.58 (m, 1H), 7.55-7.51 (m, 1H), 7.42 (s, 1H), 5.67-5.49 (m, 1H), 3.68-3.52 (m, 3H), 3.47 (t, J = 1.6 Hz, 1H), 3.23-3.16 (m, 3H), 2.71-2.62 (m, 1H), 2.09 (d, J = 9.1 Hz, 2H), 1.97 (d, J = 13.6 Hz, 2H), 1.68 (d, J = 15.4 Hz, 2H), 1.44 (d, J = 12.6 Hz, 2H), 1.38 (t, J = 7.4 Hz, 3H) |

TABLE 5-continued

Compounds prepared using Method 3 described above.

| Example | Structure | Name | MH+ | R$_f$ (min) | NMR |
|---|---|---|---|---|---|
| 380 | 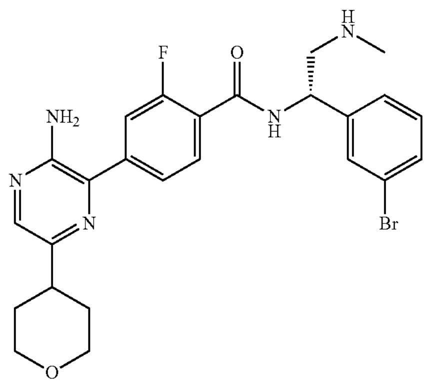 [SMILES: CNC[C@@H](NC(=O)c1ccc(-c2nc(C3CCOCC3)cnc2N)cc1F)c1cccc(Br)c1] | (S)-4-(3-amino-6-(tetrahydro-2H-pyran-4-yl)pyrazin-2-yl)-N-(1-(3-bromophenyl)-2-(methylamino)ethyl)-2-fluorobenzamide | 528/530 | 0.69 | 1H NMR (400 MHz, METHANOL-d4) δ ppm 7.88 (s, 2H), 7.77-7.45 (m, 5H), 7.43-7.29 (m, 1H), 5.63-5.47 (m, 1H), 4.04 (dd, J = 2.7, 11.3 Hz, 2H), 3.66-3.48 (m, 4H), 3.04-2.88 (m, 1H), 2.81 (s, 3H), 1.97-1.74 (m, 4H) |
| 381 | 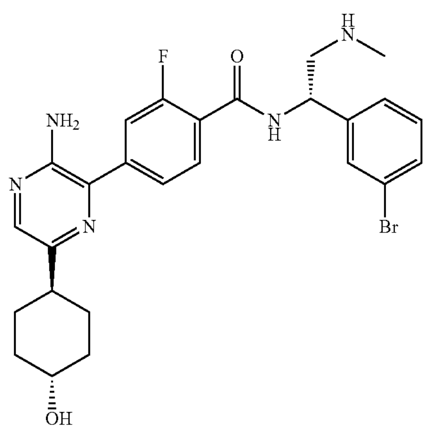 [SMILES: CNC[C@@H](NC(=O)c1ccc(-c2nc([C@H]3CC[C@H](O)CC3)cnc2N)cc1F)c1cccc(Br)c1] | 4-(3-amino-6-((1r,4S)-4-hydroxycyclohexyl)pyrazin-2-yl)-N-((S)-1-(3-bromophenyl)-2-(methylamino)ethyl)-2-fluorobenzamide | 542/544 | 0.65 | 1H NMR (400 MHz, METHANOL-d4) δ ppm 7.89-7.74 (m, 2H), 7.64 (d, J = 1.6 Hz, 2H), 7.58-7.45 (m, 2H), 7.40 (s, 1H), 7.31 (d, J = 7.8 Hz, 1H), 5.48 (dd, J = 5.1, 9.4 Hz, 1H), 3.60-3.41 (m, 3H), 2.73 (s, 3H), 2.61-2.43 (m, 1H), 2.05-1.76 (m, 4H), 1.57 (dq, J = 2.9, 13.0 Hz, 2H), 1.33 (d, J = 13.7 Hz, 2H) |
| 382 | 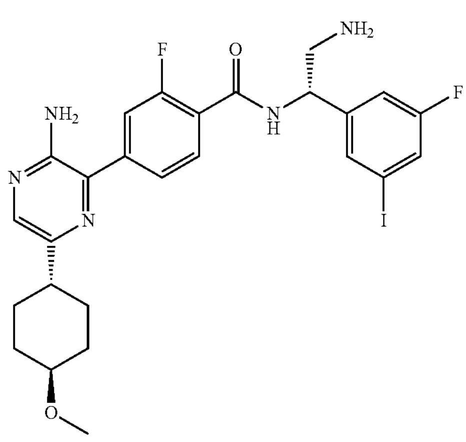 [SMILES: CO[C@H]1CC[C@H](c2cnc(N)c(-c3ccc(C(=O)N[C@H](CN)c4cc(F)cc(I)c4)c(F)c3)n2)CC1] | N-((S)-2-amino-1-(3-fluoro-5-iodophenyl)ethyl)-4-(3-amino-6-((1r,4S)-4-methoxycyclohexyl)pyrazin-2-yl)-2-fluorobenzamide | 608 | 0.77 | 1H NMR (400 MHz, METHANOL-d4) δ ppm 7.94-7.81 (m, 2H), 7.77-7.51 (m, 4H), 7.37-7.21 (m, 1H), 5.59-5.32 (m, 1H), 3.49-3.40 (m, 2H), 3.37 (s, 3H), 3.27-3.20 (m, 1H), 2.73-2.55 (m, 1H), 2.20 (d, J = 9.4 Hz, 2H), 2.04-1.89 (m, 2H), 1.65 (dd, J = 2.7, 12.5 Hz, 2H), 1.33 (d, J = 13.7 Hz, 2H) |

TABLE 5-continued

Compounds prepared using Method 3 described above.

| Example | Structure | Name | MH+ | R<sub>f</sub> (min) | NMR |
|---|---|---|---|---|---|
| 383 | 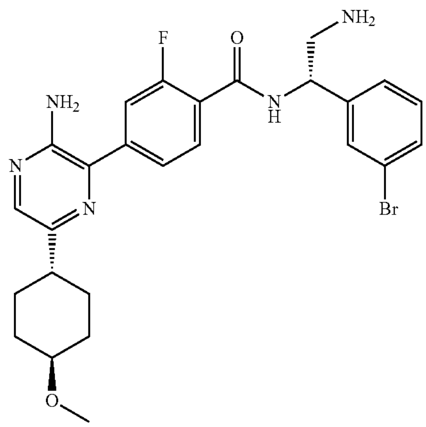 [SMILES: CO[C@H]1CC[C@H](c2cnc(N)c(-c3ccc(C(=O)N[C@H](CN)c4cccc(Br)c4)c(F)c3)n2)CC1] | N-((S)-2-amino-1-(3-bromophenyl)ethyl)-4-(3-amino-6-((1r,4S)-4-methoxycyclohexyl)pyrazin-2-yl)-2-fluorobenzamide | 542/544 | 0.73 | NA |
| 384 | single enantiomer; cis on cyclohexane ring; absolute stereochemistry unknown | 4-(3-amino-6-(3-hydroxycyclohexyl)pyrazin-2-yl)-N-((S)-1-(3-bromo-5-fluorophenyl)-2-hydroxyethyl)-2-fluorobenzamide | 547/549 | 0.77 | 1H NMR (400MHz, DMSO-d6) δ ppm 8.76-8.55 (m, 1H), 7.88 (S, 1H), 7.77-7.53 (m, 3H), 7.47 (s, 2H), 7.27 (d, J=9.8 Hz, 1H), 5.05 (q, J=6.5 Hz,1H), 3.58-3.37 (m, 3H), 2.72-2.56 (m, 1H), 1.98 (d, J=11.7 Hz, 1H), 1.90-1.64 (m, 3H), 1.49-1.24 (m, 3H), 1.17-0.97 (m, 1H) |
| 385 | single enantiomer; cis on cyclohexane ring; absolute stereochemistry unknown | 4-(3-amino-6-(3-hydroxycyclohexyl)pyrazin-2-yl)-N-((S)-1-(3-bromophenyl)-2-hydroxyethyl)-2-fluorobenzamide | 529/531 | 0.74 | 1H NMR (400 MHz, DMSO-d6) δ ppm 8.76-8.59 (m, 1H), 7.88 (s, 1H), 7.76-7.53 (m, 4H), 7.50-7.21 (m, 3H), 5.03 (q, J = 6.7 Hz, 1H), 3.80-3.68 (m, 4H), 2.75-2.57 (m, 1H), 1.98 (d, J = 11.7 Hz, 1H), 1.89-1.62 (m, 3H), 1.47-1.21 (m, 3H), 1.16-0.96 (m, 1H) |

TABLE 5-continued

Compounds prepared using Method 3 described above.

| Example | Structure | Name | MH+ | R_f (min) | NMR |
|---|---|---|---|---|---|
| 386 | single enantiomer; cis on cyclohexane ring; absolute stereochemistry unknown | 4-(3-amino-6-(3-hydroxy-cyclohexyl)pyrazin-2-yl)-N-((S)-1-(3-bromo-5-fluorophenyl)-2-hydroxyethyl)-2-fluorobenzamide | 547/549 | 0.77 | H NMR (400 MHz, DMSO-d6) δ ppm 8.76-8.55 (m, 1H), 7.83 (s, 1H), 7.73-7.50 (m, 3H), 7.45-7.32 (m, 2H), 7.22 (d, J = 9.4 Hz, 1H), 5.00 (q, J = 6.5 Hz, 1H), 3.48-3.35 (m, 2H), 2.68-2.52 (m, 1H), 1.93 (d, J = 11.7 Hz. 1H), 1.86-1.60 (m, 3H), 1.41-1.18 (m, 3H), 1.12-0.93 (m, 1H) |
| 387 | 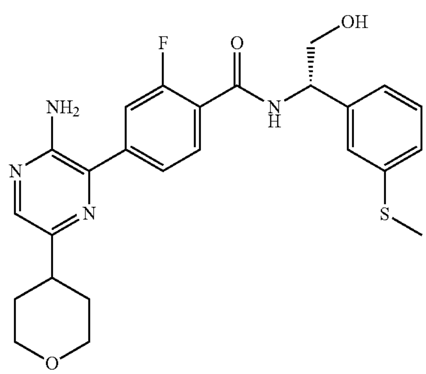 [SMILES: CSc1cccc([C@@H](CO)NC(=O)c2ccc(-c3nc(C4CCOCC4)cnc3N)cc2F)c1] | (S)-4-(3-amino-6-(tetrahydro-2H-pyran-4-yl)pyrazin-2-yl)-2-fluoro-N-(2-hydroxy-1-(3-(methylthio)phenyl)ethyl)benzamide | 483 | 0.75 | 1H NMR (400 MHz, DMSO-d6) δ ppm 8.70-8.58 (m, 1H), 7.92 (s, 1H), 7.76-7.52 (m, 3H), 7.37-7.21 (m, 2H), 7.18-7.04 (m, 2H), 5.09-4.92 (m, 1H), 3.99-3.87 (m, 2H), 3.64 (d, J = 6.7 Hz, 2H), 3.50-3.29 (m, 2H), 2.94-2.75 (m, 1H), 1.83-1.62 (m, 4H) |
| 388 | 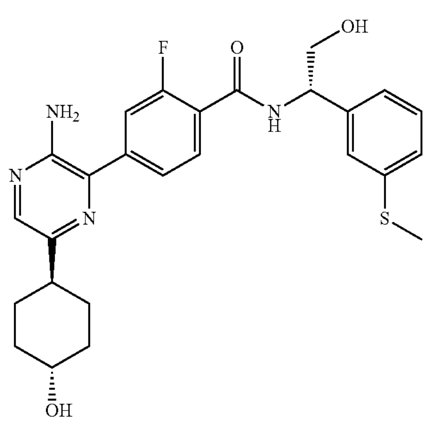 [SMILES: CSc1cccc([C@@H](CO)NC(=O)c2ccc(-c3nc([C@H]4CC[C@H](O)CC4)cnc3N)cc2F)c1] | 4-(3-amino-6-((1r,4S)-4-hydroxy-cyclohexyl)pyrazin-2-yl)-2-fluoro-N-((S)-2-hydroxy-1-(3-(methylthio)phenyl)ethyl)benzamide | 497 | 0.69 | 1H NMR (400 MHz, DMSO-d6) δ ppm 8.69-8.56 (m, 1H), 7.88 (s, 1H), 7.76-7.49 (m, 3H), 7.34-7.20 (m, 2H), 7.18-7.02 (m, 2H), 5.02 (q, J = 6.7 Hz, 1H), 3.64 (d, J = 6.3 Hz, 2H), 3.49-3.29 (m, 1H), 2.46 (s, 3H), 2.02-1.76 (m, 4H), 1.59-1.43 (m, 2H), 1.35-1.12 (m, 2H) |

TABLE 5-continued

Compounds prepared using Method 3 described above.

| Example | Structure | Name | MH+ | R_f (min) | NMR |
|---|---|---|---|---|---|
| 389 | single enantiomer; cis on cyclohexane ring; absolute sterochemistry unknown | 4-(3-amino-6-(3-hydroxy-cyclohexyl)pyrazin-2-yl)-N-((S)-1-(3-bromophenyl)-2-hydroxyethyl)-2-fluorobenzamide | 529/531 | 0.74 | 1H NMR (400 MHz, DMSO-d6) δ ppm 8.78-8.55 (m, 1H), 7.88 (s, 1H), 7.76-7.67 (m, 1H), 7.66-7.55 (m, 3H), 7.48-7.35 (m, 2H), 7.34-7.24 (m, 1H), 5.03 (d, J = 7.4 Hz, 1H), 3.55-3.24 (m, 1H), 2.79-2.56 (m, 1H), 1.98 (d, J = 12.1 Hz, 1H), 1.85 (d, J = 12.1 Hz, 1H), 1.79-1.65 (m, 2H), 1.48-1.22 (m, 3H), 1.09 (d, J = 11.3 Hz, 1H) |
| 390 | 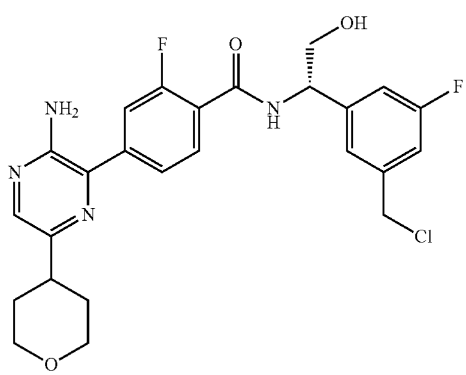 [SMILES: Nc1ncc(C2CCOCC2)nc1-c1ccc(C(=O)N[C@H](CO)c2cc(F)cc(CCl)c2)c(F)c1] | (S)-4-(3-amino-6-(tetrahydro-2H-pyran-4-yl)pyrazin-2-yl)-(N-1-(3-(chloromethyl)-5-fluorophenyl)-2-hydroxyethyl)-2-fluorobenzamide | 503 | 0.76 | 1H NMR (400 MHz, DMSO-d6) δ ppm 8.79-8.55 (m, 1H), 7.92 (s, 1H), 7.78-7.48 (m, 3H), 7.31 (s, 1H), 7.19 (t, J = 10.0 Hz, 2H), 6.13 (s, 1H), 5.13-4.95 (m, 1H), 4.82-4.66 (m, 1H), 3.92 (d, J = 11.0 Hz, 2H), 3.66 (t, J = 5.9 Hz, 2H), 3.42 (dd, J = 2.7, 5.9 Hz, 2H), 2.84 (s, 1H), 1.78-1.64 (m, 4H) |
| 391 | single enantiomer; trans on cyclohexane ring; absolute stereochemistry unknown | 4-(3-amino-6-(3-hydroxy-cyclohexyl)pyrazin-2-yl)-N-((S)-1-(3-chlorophenyl)-2-hydroxyethyl)-2-fluorobenzamide | 485.3 | 0.73 | 1H NMR (500 MHz, METHANOL-d4) δ ppm 8.06-7.82 (m, 2H) 7.77-7.58 (m, 2H) 7.49 (s, 1H) 7.46-7.13 (m, 3H) 5.30-5.13 (m, 1H) 4.19 (br. s., 1H) 3.88 (dd, J = 8.98, 5.15 Hz, 2H) 3.18 (d, J = 4.41 Hz, 1H) 2.08-1.74 (m, 5H) 1.71-1.50 (m, 3H) |

TABLE 5-continued

Compounds prepared using Method 3 described above.

| Example | Structure | Name | MH+ | R$_t$ (min) | NMR |
|---|---|---|---|---|---|
| 392 | 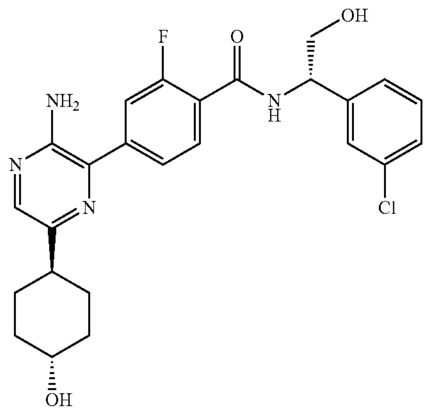 [SMILES: Nc1ncc([C@H]2CC[C@H](O)CC2)nc1-c1ccc(C(=O)N[C@H](CO)c2cccc(Cl)c2)c(F)c1] | N-((S)-2-amino-1-(3-chlorophenyl)ethyl)-4-(3-amino-6-((1r,4S)-4-hydroxycyclohexyl)pyrazin-2-yl)-2-fluorobenzamide | 484.3 | 0.62 | 1H NMR (500 MHz, METHANOL-d4) δ ppm 7.90 (s, 2H) 7.75-7.71 (m, 1H) 7.65 (dd, J = 11.98, 1.26 Hz, 1H) 7.58 (s, 1H) 7.47 (s, 3H) 5.63-5.42 (m, 1H) 3.67-3.58 (m, 1H) 3.54-3.42 (m, 2H) 2.70-2.62 (m, 1H) 2.09 (d, J = 9.46 Hz, 2H) 1.97 (d, J = 14.82 Hz, 2H) 1.74-1.63 (m, 2H) 1.50-1.39 (m, 2H) |
| 393 | single enantiomer; trans on cyclohexane ring; absolute stereochemistry unknown | 4-(3-amino-6-(3-hydroxycyclohexyl)pyrazin-2-yl)-N-((S)-1-(3-chlorophenyl)-2-hydroxyethyl)-2-fluorobenzamide | 485.3 | 0.73 | 1H NMR (500 MHz, METHANOL-d4) δ ppm 8.00-7.81 (m, 2H) 7.75-7.57 (m, 2H) 7.57-7.47 (m, 1H) 7.42-7.13 (m, 3H) 5.22 (s, 1H) 4.19 (br. s., 1H) 3.88 (dd, J = 8.83, 5.99 Hz, 2H) 3.23-3.07 (m, 1H) 2.12-1.75 (m, 5H) 1.71-1.49 (m, 3H) |
| 394 | 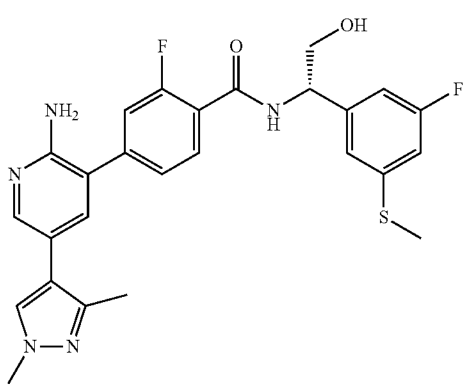 [SMILES: CSc1cc(F)cc([C@@H](CO)NC(=O)c2ccc(-c3cc(-c4cn(C)nc4C)cnc3N)cc2F)c1] | (S)-4-(2-amino-5-(1,3-dimethyl-1H-pyrazol-4-yl)pyridin-3-yl)-2-fluoro-N-(1-(3-fluoro-5-(methylthio)phenyl)-2-hydroxyethyl)benzamide | 510.3 | 0.72 | 1H NMR (500 MHz, DMSO-d6) δ ppm 8.74 (d, J = 7.88 Hz, 1H) 8.16-7.74 (m, 4H) 7.61-7.33 (m, 2H) 7.19-6.86 (m, 3H) 5.19-4.97 (m, 1H) 3.79 (s, 3H) 3.71-3.64 (m, 2H) 2.29 (s, 3H) |

TABLE 5-continued

Compounds prepared using Method 3 described above.

| Example | Structure | Name | MH+ | R_f (min) | NMR |
|---|---|---|---|---|---|
| 395 | 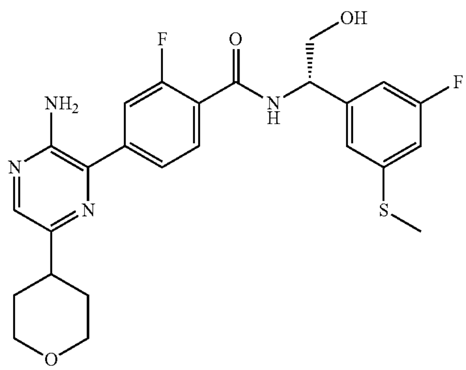 [SMILES: CSc1cc(F)cc([C@@H](CO)NC(=O)c2ccc(-c3nc(C4CCOCC4)cnc3N)cc2F)c1] | (S)-4-(3-amino-6-(tetrahydro-2H-pyran-4-yl)pyrazin-2-yl)-2-fluoro-N-(1-(3-fluoro-5-(methylthio)phenyl)-2-hydroxyethyl)benzamide | 501.2 | 0.77 | 1H NMR (500 MHz, DMSO-d6) δ ppm 8.71 (d, J = 7.88 Hz, 1H) 7.95 (s, 1H) 7.79-7.44 (m, 3H) 7.17-6.91 (m, 3H) 5.05 (q, J = 6.83 Hz, 1H) 3.97-3.87 (m, 4H) 3.67 (d, J = 6.31 Hz, 3H) 3.44 (br. s., 2H) 2.95-2.75 (m, 1H) 1.80-1.68 (m, 4H) |
| 396 | 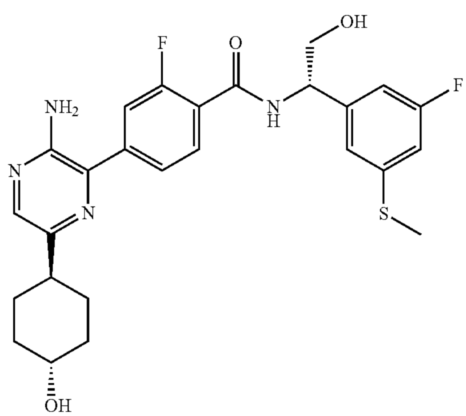 [SMILES: CSc1cc(F)cc([C@@H](CO)NC(=O)c2ccc(-c3nc([C@H]4CC[C@H](O)CC4)cnc3N)cc2F)c1] | 4-(3-amino-6-((1r,4S)-4-hydroxy-cyclohexyl)pyrazin-2-yl)-2-fluoro-N-((S)-1-(3-fluoro-5-(methylthio)phenyl)-2-hydroxyethyl)benzamide | 515 | 0.72 | 1H NMR (500 MHz, DMSO-d6) δ ppm 8.70 (d, J = 8.20 Hz, 1H) 7.91 (s, 1H) 7.77-7.46 (m, 3H) 7.14 (s, 1H) 7.01 (t, J = 10.25 Hz, 2H) 5.05 (d, J = 7.57 Hz, 1H) 3.50-3.33 (m, 1H) 2.60-2.53 (m, 1H) 2.47-2.42 (m, 1H) 2.02-1.80 (m, 4H) 1.5 5 (d, J = 15.13 Hz, 2H) 1.28 (d, J = 13.24 Hz, 2H) |
| 397 | 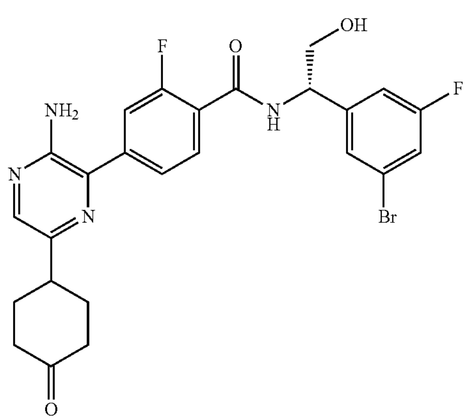 [SMILES: Nc1ncc(C2CCC(=O)CC2)nc1-c1ccc(C(=O)N[C@H](CO)c2cc(F)cc(Br)c2)c(F)c1] | (S)-4-(3-amino-6-(4-oxocyclohexyl)pyrazin-2-yl)-N-(1-(3-bromo-5-fluorophenyl)-2-hydroxyethyl)-2-fluorobenzamide | 545/547 | 0.77 | 1H NMR (400 MHz, METHANOL-d4) δ ppm 7.83-7.70 (m, 2H) 7.65-7.45 (m, 2H) 7.37 (s, 1H) 7.22-7.00 (m, 2H) 5.08 (t, J = 5.67 Hz, 1H) 3.76 (t, J = 5.67 Hz, 2H) 2.74-2.58 (m, 1H) 2.04 (d, J = 12.13 Hz, 2H)) 1.80-1.58 (m, 4H) 1.41 (td, J = 13.11, 4.30 Hz, 2H) |

TABLE 5-continued

Compounds prepared using Method 3 described above.

| Example | Structure | Name | MH+ | R$_t$ (min) | NMR |
|---|---|---|---|---|---|
| 398 | 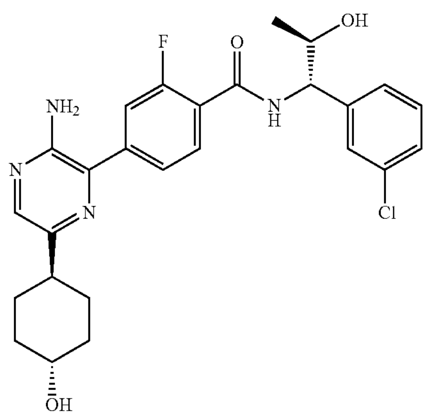 [SMILES: C[C@@H](O)[C@@H](NC(=O)c1ccc(-c2nc([C@H]3CC[C@H](O)CC3)cnc2N)cc1F)c1cccc(Cl)c1] | 4-(3-amino-6-((1r,4S)-4-hydroxy-cyclohexyl)pyrazin-2-yl)-N-((1S,2R)-1-(3-chlorophenyl)-2-hydroxypropyl)-2-fluorobenzamide | 499.1 | 0.69 | 1H NMR (400 MHz, METHANOL-d4) δ ppm 8.73-8.63 (m, 1H) 7.88-7.77 (m, 2H) 7.70-7.56 (m, 2H) 7.47 (s, 1H) 7.40-7.23 (m, 3H) 5.03-4.94 (m, 1H) 4 13 (quin, J = 6.26 Hz, 1H) 3.66-3.54 (m, 1 H) 2.74-2.57 (m, 1H) 2.06 (d, J = 9.78 Hz, 2H) 1.96 (d, J = 12.91 Hz, 2H) 1.74-1.58 (m, 2H) 1.51-1.35 (m, 2H) 1.20 (d, J = 6.26 Hz, 3 H) |
| 399 | 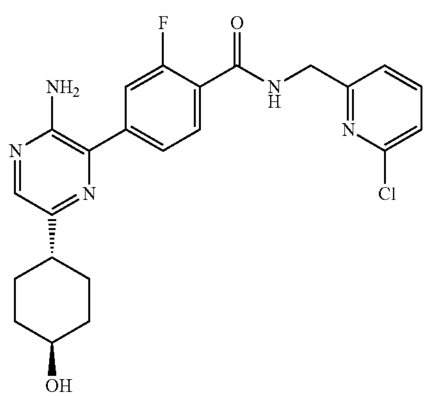 [SMILES: Nc1ncc([C@H]2CC[C@H](O)CC2)nc1-c1ccc(C(=O)NCc2cccc(Cl)n2)c(F)c1] | 4-(3-amino-6-((1r,4r)-4-hydroxy-cyclohexyl)pyrazin-2-yl)-N-((6-chloropyridin-2-yl)methyl)-2-fluorobenzamide | 498.2 | 0.63 | 1H NMR (400 MHz, CD$_3$OD) δ 7.94(t, J = 7.6 Hz, 1H), 7.85-7.76 (m,2H), 7.69 (dd, J = 1.6, 8.2 Hz, 1H),7.62 (dd, J = 1.2, 11.7 Hz, 1H), 7.42(s, 1H), 7.35 (d, J = 8.2 Hz, 1H), 4.69(s, 2H), 3.67-3.54 (m, 1H), 2.72-2.58 (m, 1H), 2.07 (d, J = 9.4 Hz, 2H), 1.96 (d, J = 12.9 Hz, 2H), 1.74-1.56 (m, 2H), 1.50-1.35 (m, 2H) |
| 400 | 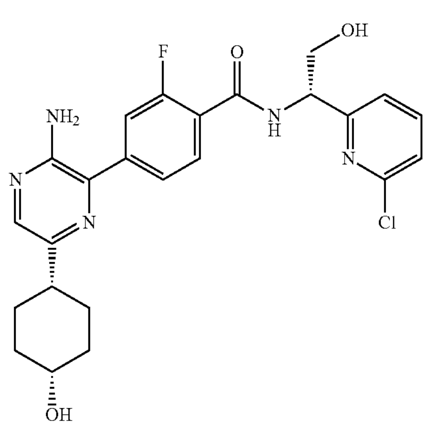 [SMILES: Nc1ncc([C@H]2CC[C@@H](O)CC2)nc1-c1ccc(C(=O)N[C@H](CO)c2cccc(Cl)n2)c(F)c1] | 4-(3-amino-6-((1s,4s)-4-hydroxy-cyclohexyl)pyrazin-2-yl)-N-((6-chloropyridin-2-yl)methyl)-2-fluorobenzamide | 498.2 | 0.65 | 1H NMR (400 MHz, CD$_3$OD) δ 7.93(t, J = 7.8 Hz, 1H), 7.85 (s, 1H), 7.80(t, J = 7.8 Hz, 1H), 7.71 (dd, J = 1.6,8.2 Hz, 1H), 7.65 (dd, J = 1.4, 11.9Hz, 1H), 7.41 (d, J = 7.4 Hz, 1H), 7.35 (d, J = 8.2 Hz, 1H), 4.69 (s, 2H), 4 01 (br. s., 1H), 2.79-2.68 (m, 1H), 2.11-1.96 (m, 2H), 1.93-1.83 (m, 2H), 1.77-1.64 (m, 4H) |

TABLE 5-continued

Compounds prepared using Method 3 described above.

| Example | Structure | Name | MH+ | R_f (min) | NMR |
|---|---|---|---|---|---|
| 401 | 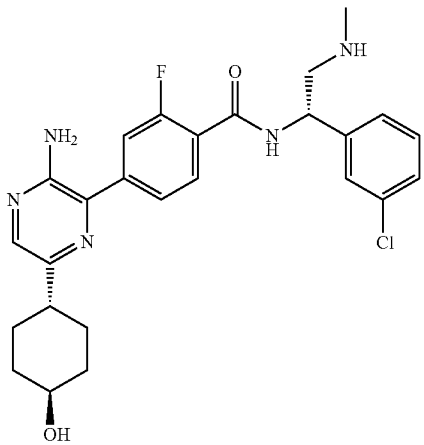 [SMILES: CNC[C@@H](NC(=O)c1ccc(-c2nc([C@H]3CC[C@H](O)CC3)cnc2N)cc1F)c1cccc(Cl)c1] | 4-(3-amino-6-((1r,4S)-4-hydroxy-cyclohexyl)pyrazin-2-yl)-N-((S)-1-(3-chlorophenyl)-2-(methylamino)ethyl)-2-fluorobenzamide | 498.3 | 0.60 | 1H NMR (500 MHz, METHANOL-d4) δ ppm 7.90 (s, 1H), 7.84 (t, J = 7.7 Hz, 1H), 7.70 (dd, J = 1.4, 8.0 Hz, 1H), 7.63 (dd, J = 1.3, 11.7 Hz, 1H), 7.49 (s, 1H), 7.40 (d, J = 5.0 Hz, 2H), 7.38-7.29 (m, 1H), 5.34 (dd, J = 5.4, 8.8 Hz, 1H), 3.68-3.57 (m, 1H), 3.07 (dd, J = 9.0, 12.8 Hz, 1H), 2.97 (dd, J = 5.4, 12.6 Hz, 1H), 2.71-2.59 (m, 1H), 2.48 (s, 3H), 2.13-2.04 (m, 2H), 2.03-1.90 (m, 2H), 1.76-1.61 (m, 2H), 1.51-1.37 (m, 2H) |
| 402 | 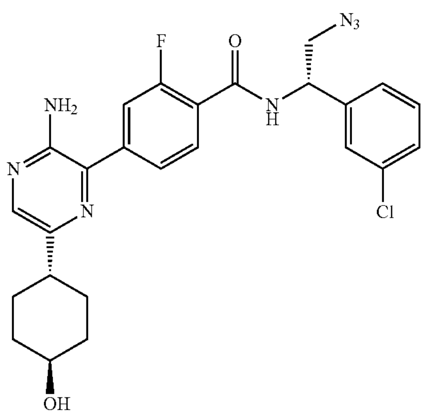 [SMILES: [N-]=[N+]=NC[C@@H](NC(=O)c1ccc(-c2nc([C@H]3CC[C@H](O)CC3)cnc2N)cc1F)c1cccc(Cl)c1] | 4-(3-amino-6-((1r,4S)-4-hydroxy-cyclohexyl)pyrazin-2-yl)-N-((S)-2-azido-1-(3-chlorophenyl)ethyl)-2-(fluorobenzamide | 510.2 | 0.83 | 1H NMR (400 MHz, CD3OD) δ ppm 7.89-7.75 (m, 2H), 7.71-7.64 (m,1H), 7.61 (d, J = 12.6 Hz, 1H), 7.53-7.45 (m, 1H), 7.46-7.27 (m, 3H), 5.43-5.28 (m, 1H), 3.74 (d, J = 6.7Hz, 2H), 3.68-3.50 (m, 1H), 2.64(tt, J = 3.6, 12.2 Hz, 1H), 2.14-1.99(m, 2H), 1.96 (d, J = 12.9 Hz, 2H), 1.77-1.56 (m, 2H), 1.51-1.31 (m, 2H) |
| 403 | 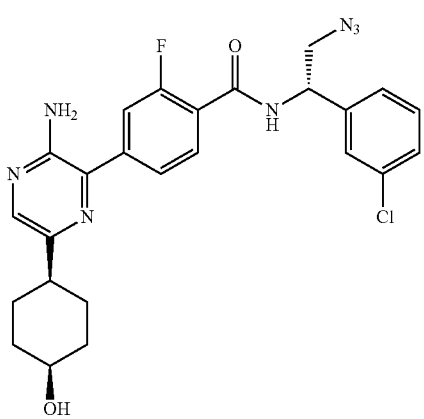 [SMILES: [N-]=[N+]=NC[C@@H](NC(=O)c1ccc(-c2nc([C@H]3CC[C@@H](O)CC3)cnc2N)cc1F)c1cccc(Cl)c1] | 4-(3-amino-6-((1s,4R)-4-hydroxy-cyclohexyl)pyrazin-2-yl)-N-((S)-2-azido-1-(3-chlorophenyl)ethyl)-2-fluorobenzamide | 510.2 | 0.86 | 1H NMR (400 MHz, CD3OD) δ ppm7.88 (s, 1H), 7.83-7.74 (m, 1H), 7.73-7.66 (m, 1H), 7.64 (d, J = 11.4Hz, 1H), 7.50 (s, 1H), 7.43-7.27(m, 3H), 5.44-5.30 (m, 1H), 3.80-3.67 (m, 4H), 2.79-2.64 (m, 1H),2.11-1.93 (m, 2H), 1.76-1.61 (m,5H) |

TABLE 5-continued

Compounds prepared using Method 3 described above.

| Example | Structure | Name | MH+ | R_f (min) | NMR |
|---|---|---|---|---|---|
| 404 | 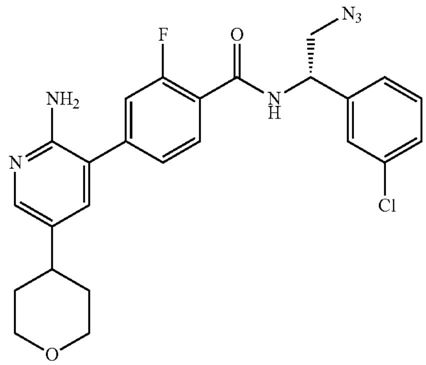 [SMILES: [N-]=[N+]=NC[C@@H](NC(=O)c1ccc(-c2cc(C3CCOCC3)cnc2N)cc1F)c1cccc(Cl)c1] | (S)-4-(3-amino-6-(tetrahydro-2H-pyran-4-yl)pyrazin-2-yl)-N-(2-azido-1-(3-chlorophenyl)ethyl)-2-fluorobenzamide | 496.2 | 0.93 | 1H NMR (400 MHz, CD$_3$OD) δ ppm 7.94-7.75 (m, 2H), 7.75-7.58 (m, 2H), 7.50 (s, 1H), 7.43-7.26 (m, 3H), 5.35 (t, J = 6.5 Hz, 1H), 4.13-3.96 (m, 2H), 3.74 (d, J = 6.7 Hz, 2H), 3.57 (dt, J = 2.3, 11.5 Hz, 2H), 3.02-2.85 (m, 1H), 2.00-1.71 (m, 4H) |
| 405 | 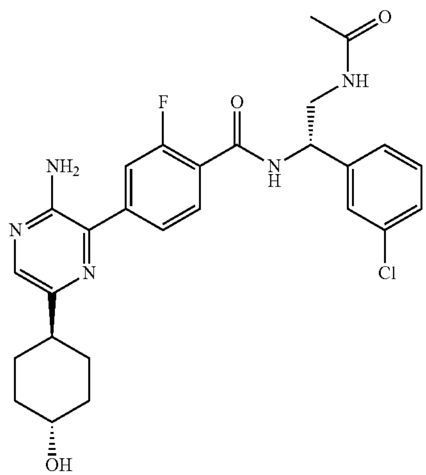 [SMILES: CC(=O)NC[C@@H](NC(=O)c1ccc(-c2nc([C@H]3CC[C@H](O)CC3)cnc2N)cc1F)c1cccc(Cl)c1] | N-((S)-2-acetamido-1-(3-chlorophenyl)ethyl)-4-(3-amino-6-((1r,4S)-4-hydroxycyclohexyl)pyrazin-2-yl)-2-fluorobenzamide | 526.2 | 0.67 | 1H NMR (400 MHz, CD$_3$OD) δ ppm 8.85 (br. s., 1H), 7.89-7.76 (m, 2H), 7.71-7.55 (m, 2H), 7.45 (s, 1H), 7.40-7.24 (m, 3H), 5.26 (br. s., 1H), 3.71-3.51 (m, 3H), 2.75-2.53 (m, 1H), 2.06 (d, J = 9.8 Hz, 2H), 2.00-1.86 (m, 5H), 1.78-1.56 (m, 2H), 1.53-1.31 (m, 2H) |
| 406 | 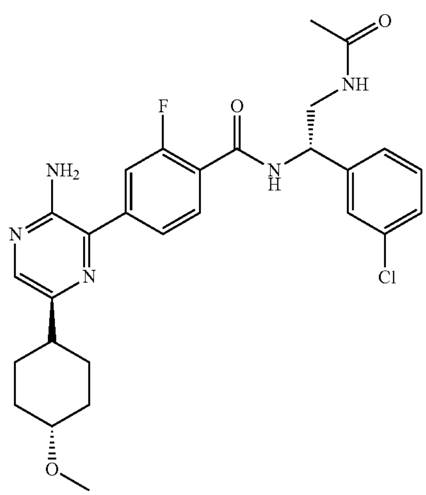 | N-((S)-2-acetamido-1-(3-chlorophenyl)ethyl)-4-(3-amino-6-((1r,4S)-4-methoxycyclohexyl)pyrazin-2-yl)-2-fluorobenzamide | 540.3 | 0.81 | 1H NMR (400 MHz, CD$_3$OD) δ ppm 7.93-7.79 (m, 2H), 7.73-7.57 (m, 2H), 7.47 (s, 1H), 7.34-7.14 (m, 2H), 5.18 (t, J = 5.7 Hz, 1H), 3.93-3.78 (m, 2H), 2.70-2.55 (m, 1H), 2.06 (d, J = 12.3 Hz, 2H), 1.95 (d, J = 12.3 Hz, 2H), 1.76-1.58 (m, 2H), 1.48-1.35 (m, 2H) |

TABLE 5-continued

Compounds prepared using Method 3 described above.

| Example | Structure | Name | MH+ | R_f (min) | NMR |
|---|---|---|---|---|---|
| 407 | 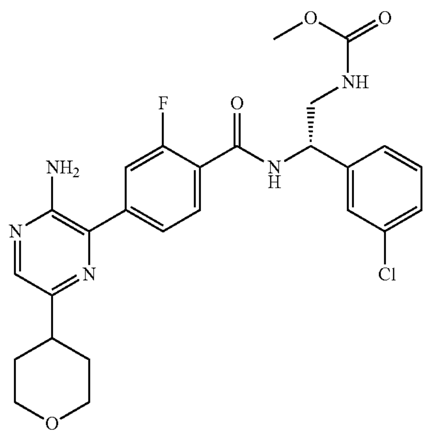 [SMILES: COC(=O)NC[C@@H](NC(=O)c1ccc(-c2nc(C3CCOCC3)cnc2N)cc1F)c1cccc(Cl)c1] | (S)-methyl (2-(4-(3-amino-6-(tetrahydro-2H-pyran-4-yl)pyrazin-2-yl)-2-fluorobenzamido)-2-(3-chlorophenyl)ethyl)carbamate | 528.2 | 0.76 | 1H NMR (500 MHz, METHANOL-d4) δ ppm 7.90 (s, 1H), 7.85 (t, J = 7.7 Hz, 1H), 7.72 (d, J = 7.9 Hz, 1H), 7.66 (d, J = 11.3 Hz, 1H), 7.48 (s, 1H), 7.44-7.36 (m, 2H), 7.36-7.22 (m, 1H), 5.28 (d, J = 7.3 Hz, 1H), 4.07 (dd, J = 3.8, 11.0 Hz, 2H), 3.67 (s, 3H), 3.60 (dt, J = 2.0, 11.7 Hz, 2H), 3.54 (d, J = 6.9 Hz, 2H), 2.97 (s, 1H), 2.02-1.81 (m, 4H) |
| 408 | 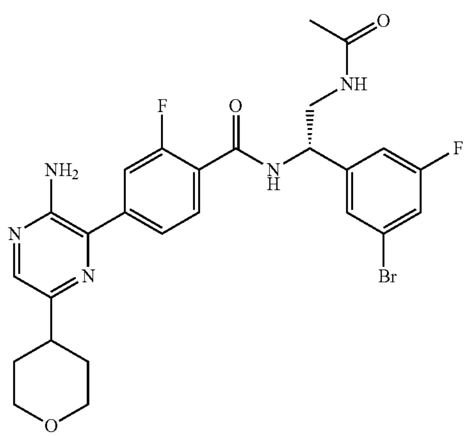 [SMILES: CC(=O)NC[C@@H](NC(=O)c1ccc(-c2nc(C3CCOCC3)cnc2N)cc1F)c1cc(F)cc(Br)c1] | (S)-N-(2-acetamido-1-(3-bromo-5-fluorophenyl)ethyl)-4-(3-amino-6-(tetrahydro-2H-pyran-4-yl)pyrazin-2-yl)-2-fluorobenzamide | 574.2/ 576.2 | 0.76 | 1H NMR (500 MHz, METHANOL-d4) δ 8.92 (br. s., 1H), 8.31 (br. s., 1H), 7.88 (s, 1H), 7.83 (t, J = 7.7 Hz, 1H), 7.70 (d, J = 7.9 Hz, 1H), 7.65 (d, J = 12.9 Hz, 1H), 7.46 (s, 1H), 7.30 (d, J = 8.2 Hz, 1H), 7.20 (d, J = 10.1 Hz, 1H), 5.26 (d, J = 6.6 Hz, 1H), 4.05 (dd, J = 3.5, 11.0 Hz, 2H), 3.66-3.53 (m, 4H), 3.01-2.88 (m, 1H), 1.95 (s, 3H), 1.94-1.80 (m, 4H) |
| 409 | 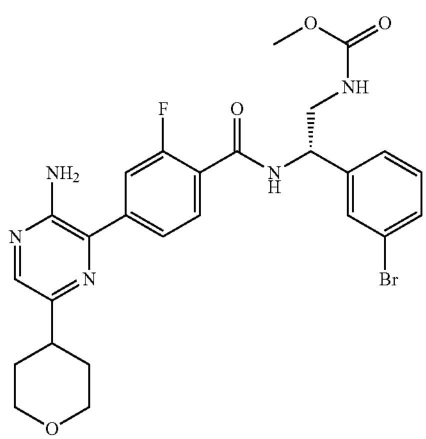 [SMILES: COC(=O)NC[C@@H](NC(=O)c1ccc(-c2nc(C3CCOCC3)cnc2N)cc1F)c1cccc(Br)c1] | (S)-methyl (2-(4-(3-amino-6-(tetrahydro-2H-pyran-4-yl)pyrazin-2-yl)-2-fluorobenzamido)-2-(3-bromophenyl)ethyl)carbamate | 572.1/ 574.1 | 0.79 | 1H NMR (400 MHz, CD3OD) δ ppm 7.89 (s, 1H), 7.86-7.78 (m, 1H), 7.74-7.67 (m, 1H), 7.67-7.57 (m, 2H), 7.49-7.38 (m, 2H), 7.34-7.25 (m, 1H), 5.25 (d, J = 7.4 Hz, 1H), 4.12-3.98 (m, 2H), 3.65 (s, 3H), 3.62-3.49 (m, 4H), 2.99-2.89 (m, 1H), 1.97-1.78 (m, 4H) |

TABLE 5-continued

Compounds prepared using Method 3 described above.

| Example | Structure | Name | MH+ | R$_t$ (min) | NMR |
|---|---|---|---|---|---|
| 410 | 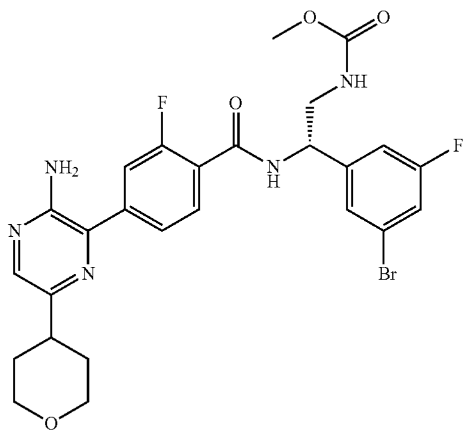 [SMILES: COC(=O)NC[C@@H](NC(=O)c1ccc(-c2nc(C3CCOCC3)cnc2N)cc1F)c1cc(F)cc(Br)c1] | (S)-methyl (2-(4-(3-amino-6-(tetrahydro-2H-pyran-4-yl)pyrazin-2-yl)-2-fluorobenzamido)-2-(3-bromo-5-fluorophenyl)ethyl) carbamate | 590.1/ 592.1 | 0.83 | 1H NMR (400 MHz, CD$_3$OD) δ ppm 7.89 (s, 1H), 7.88-7.80 (m, 1H), 7.76-7.68 (m, 1H), 7.64 (d, J = 11.7 Hz, 1H), 7.45 (s, 1H), 7.29 (d, J = 8.2 Hz, 1H), 7.19 (d, J = 9.4 Hz, 1H), 5.31-5.19 (m, 1H), 4.13-4.01 (m, 2H), 3.65 (s, 3H), 3.62-3.46 (m, 4H), 3.01-2.87 (m, 1H), 1.98-1.77 (m, 4H) |
| 411 | 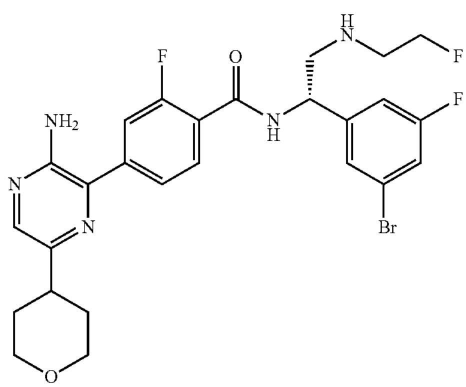 [SMILES: Nc1ncc(C2CCOCC2)nc1-c1ccc(C(=O)N[C@H](CNCCF)c2cc(F)cc(Br)c2)c(F)c1] | (S)-4-(3-amino-6-(tetrahydro-2H-pyran-4-yl)pyrazin-2-yl)-N-(1-(3-bromo-5-fluorophenyl)-2-((2-fluoroethyl)amino)ethyl)-2-fluorobenzamide | 578.2/ 580.2 | 0.72 | 1H NMR (400 MHz, CD$_3$OD) δ ppm 7.99-7.88 (m, 2H), 7.75 (dd, J = 1.4, 8.0 Hz, 1H), 7.72-7.63 (m, 1H), 7.58 (s, 1H), 7.43 (d, J = 8.2 Hz, 1H), 7.32 (d, J = 9.4 Hz, 1H), 5.61 (dd, J = 5.5, 9.0 Hz, 1H), 4.74 (t, J = 4.3 Hz, 1H), 4.05 (dd, J = 3.1, 11.0 Hz, 2H), 3.72-3.53 (m, 5H), 3.53-3.45 (m, 1H), 3.04-2.86 (m, 1H), 2.01-1.72 (m, 4H) |
| 412 | 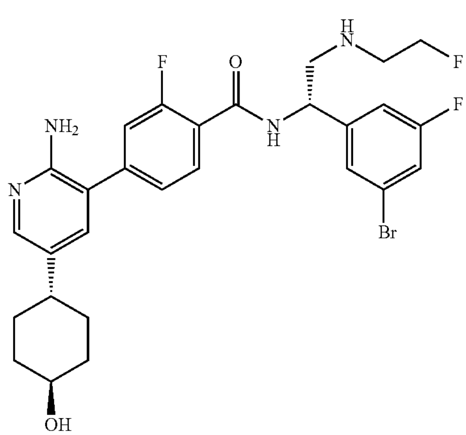 [SMILES: Nc1ncc([C@H]2CC[C@H](O)CC2)cc1-c1ccc(C(=O)N[C@H](CNCCF)c2cc(F)cc(Br)c2)c(F)c1] | 4-(3-amino-6-((1r,4S)-4-hydroxy-cyclohexyl)pyrazin-2-yl)-N-((S)-1-(3-bromo-5-fluorophenyl)-2-((2-fluoroethyl)amino)ethyl)-2-fluorobenzamide | 592.2/ 594.5 | 0.67 | 1H NMR (400 MHz, CD$_3$OD) δ ppm 7.99-7.87 (m, 2H), 7.77-7.70 (m, 1H), 7.65 (d, J = 12.1 Hz, 1H), 7.58 (s, 1H), 7.43 (d, J = 8.2 Hz, 1H), 7.32 (d, J = 9.4 Hz, 1H), 5.61 (dd, J = 5.9, 8.6 Hz, 1H), 4.74 (t, J = 4.3 Hz, 1H), 3.73-3.49 (m, 6H), 2.70-2.53 (m, 1H), 2.07 (d, J = 9.8 Hz, 2H), 1.95 (d, J = 12.9 Hz, 2H), 1.76-1.58 (m, 2H), 1.52-1.34 (m, 2H) |

TABLE 5-continued

Compounds prepared using Method 3 described above.

| Example | Structure | Name | MH+ | R$_f$ (min) | NMR |
|---|---|---|---|---|---|
| 413 | 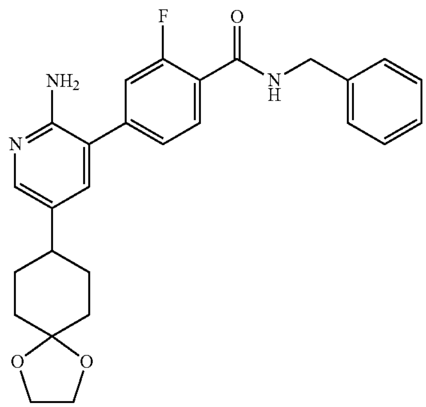 [SMILES: Nc1ncc(C2CCC3(CC2)OCCO3)cc1-c1ccc(C(=O)NCc2ccccc2)c(F)c1] | 4-(3-amino-6-(1,4-dioxaspiro[4.5]decan-8-yl)pyrazin-2-yl)-N-benzyl-2-fluorobenzamide | 463.3 | 0.82 | 1H NMR (400 MHz, DMSO-d6) δ 8.81-8.94 (m, 1H), 7.89 (s, 1H), 7.69-7.80 (m, 1H), 7.52-7.67 (m, 2H), 7.33 (d, J = 4.3 Hz, 4H), 7.18-7.27 (m, 1H), 6 09 (s, 2H), 4 49 (d, J = 5.9 Hz, 2H), 3.85 (s, 4H), 2.61-2.70 (m, 1H), 1.67-1.84 (m, 6H), 1.48-1.65 (m, 2H) |
| 414 | 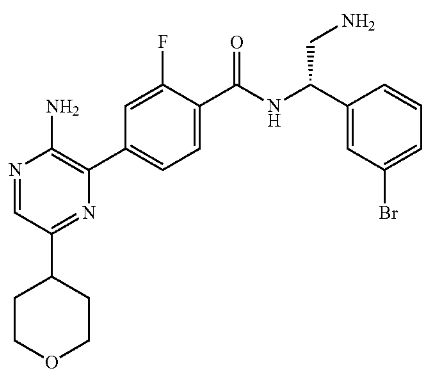 [SMILES: NC[C@@H](NC(=O)c1ccc(-c2nc(C3CCOCC3)cnc2N)cc1F)c1cccc(Br)c1] | (S)-N-(2-amino-1-(3-bromophenyl)ethyl)-4-(3-amino-6-(tetrahydro-2H-pyran-4-yl)pyrazin-2-yl)-2-fluorobenzamide | 514, 516 | 0.64 | 1H NMR (400 MHz. CD$_3$OD) δ 7.97-7.85 (m, 2H), 7.75-7.69 (m, 2H), 7.65 (dd, J = 1.2, 11.7 Hz, 1H), 7.57 (d, J = 8.2 Hz, 1H), 7.48 (d, J = 7.8 Hz, 1H), 7.38 (t, J = 7.8 Hz, 1H), 5.48 (dd, J = 5.9, 8.6 Hz, 1H), 4.04 (dd, J = 3.1, 11.3 Hz, 2H), 3.57 (dt, J = 2.2, 11.6 Hz, 2H), 3.52-3.39 (m, 3H), 2.99-2.87 (m, 1H), 1.97-1.76 (m, 4H) |
| 415 | 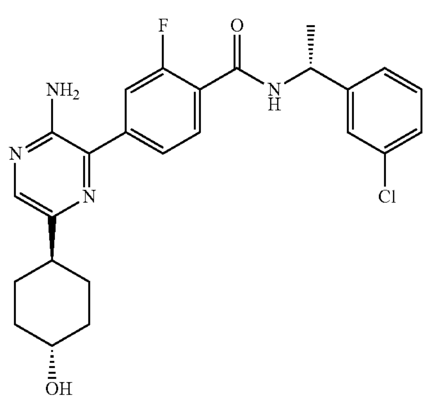 [SMILES: C[C@@H](NC(=O)c1ccc(-c2nc([C@H]3CC[C@H](O)CC3)cnc2N)cc1F)c1cccc(Cl)c1] | 4-(3-amino-6-((1r,4R)-4-hydroxy-cyclohexyl)pyrazin-2-yl)-N-((R)-1-(3-chlorophenyl)ethyl)-2-fluorobenzamide | 469.2 | 0.79 | 1H NMR (400 MHz, CD$_3$OD) δ 7.81 (s, 1H), 7.71-7.79 (m, 1H), 7.65 (dd, J = 8.0, 1.4 Hz, 1H), 7.59 (dd, J = 11.3. 1.2 Hz, 1H), 7.45 (s, 1H), 7.31-7.38 (m, 2H), 7.23-7.29 (m, 1H), 5.23 (q, J = 6.8 Hz, 1H), 3.54-3.67 (m, 1H), 2.65 (tt, J = 12.1, 3.5 Hz, 1H), 2.07 (d, J = 9.4 Hz, 2H), 1.97 (d, J = 12.9 Hz, 2H), 1.66 (qd, J = 13.0. 2.9 Hz, 2H), 1.56 (d, J = 7.0 Hz, 3H), 1.32-1.49 (m, 2H) |

TABLE 5-continued

Compounds prepared using Method 3 described above.

| Example | Structure | Name | MH+ | R$_f$ (min) | NMR |
|---|---|---|---|---|---|
| 416 | 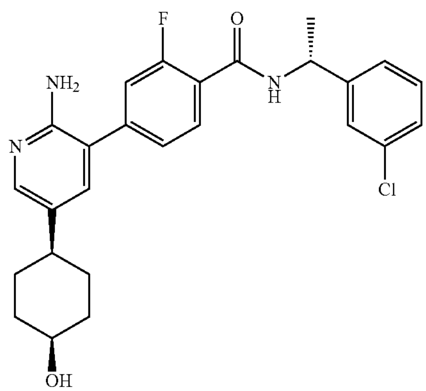 [SMILES: C[C@@H](NC(=O)c1ccc(-c2cc([C@H]3CC[C@@H](O)CC3)cnc2N)cc1F)c1cccc(Cl)c1] | 4-(3-amino-6-((1s,4S)-4-hydroxycyclohexyl)pyrazin-2-yl)-N-((R)-1-(3-chlorophenyl)ethyl)-2-fluorobenzamide | 469.3 | 0.82 | 1H NMR (400 MHz, CD$_3$OD) δ 7.75(s, 1H), 7.64-7.71 (m, 1H), 7.55-7.60 (m, 1H), 7.47-7.54 (m, 1H), 7.35 (s, 1H), 7.21-7.28 (m, 2H), 7.13-7.19 (m, 1H), 5.09-5.19 (m, 1H), 3.92 (br. s., 1H), 2.59-2.70 (m, 1H), 1.86-2.00 (m, 2H), 1.71-1.82 (m, 2H), 1.61 (d, J = 12.1 Hz, 4H), 1.47 (d, J = 7.0 Hz, 3H) |
| 417 | 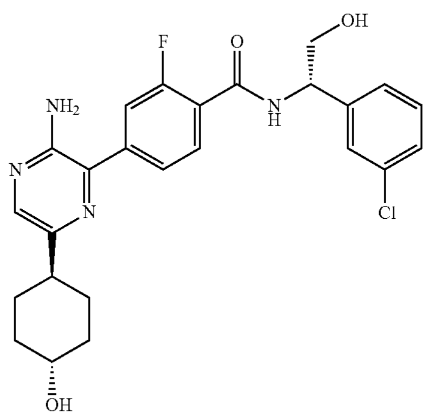 [SMILES: Nc1ncc([C@H]2CC[C@H](O)CC2)nc1-c1ccc(C(=O)N[C@H](CO)c2cccc(Cl)c2)c(F)c1] | 4-(3-amino-6-((1r,4S)-4-hydroxycyclohexyl)pyrazin-2-yl)-N-((S)-1-(3-chlorophenyl)-2-hydroxyethyl)-2-fluorobenzamide | 485.3 | 0.66 | 1H NMR (400 MHz, CD$_3$OD) δ 7.77(t, J = 7.8 Hz, 1H), 7.72 (s, 1H), 7.48-7.61 (m, 2H), 7.37 (s, 1H), 7.23-7.30 (m, 2H), 7.15-7.22 (m, 1H), 5.10 (t, J = 6.1 Hz, 1H), 3.69-3.85 (m, 2H), 3.45-3.58 (m, 1H), 2.56 (tt, J = 12.1, 3.4 Hz, 1H), 1.97 (d, J = 9.4 Hz, 2H), 1.82-1.92 (m, 2H), 1.57 (qd, J = 12.9, 2.7 Hz, 2H), 1.25-1.41 (m, 2H) |
| 418 | 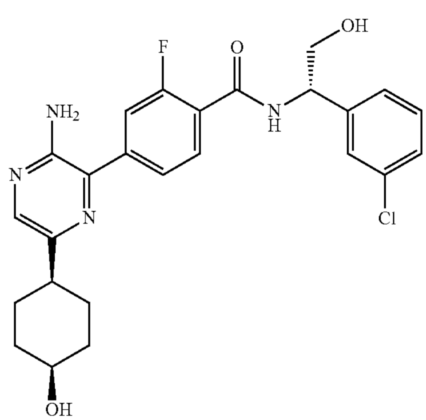 [SMILES: Nc1ncc([C@H]2CC[C@@H](O)CC2)nc1-c1ccc(C(=O)N[C@H](CO)c2cccc(Cl)c2)c(F)c1] | 4-(3-amino-6-((1s,4R)-4-hydroxycyclohexyl)pyrazin-2-yl)-N-((S)-1-(3-chlorophenyl)-2-hydroxyethyl)-2-fluorobenzamide | 485.3 | 0.69 | 1H NMR (400 MHz, CD$_3$OD) δ7.70-7.85 (m, 2H), 7.50-7.64 (m,2H), 7.37 (s, 1H), 7.22-7.30 (m,2H), 7.15-7.22 (m, 1H), 5.10 (t,J = 5.9 Hz. 1H), 3.92 (br. s., 1H).3.65-3.83 (m, 2H), 2.59-2.75 (m,1H), 1.86-2.07 (m, 2H), 1.72-1.82 (m, 2H), 1.62 (d, J = 12.1 Hz, 4H) |

TABLE 5-continued

Compounds prepared using Method 3 described above.

| Example | Structure | Name | MH+ | R_r (min) | NMR |
|---|---|---|---|---|---|
| 419 | 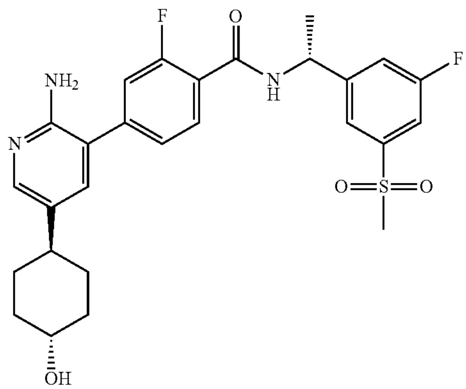 [SMILES: C[C@@H](NC(=O)c1ccc(-c2cc([C@H]3CC[C@H](O)CC3)cnc2N)cc1F)c1cc(F)cc(S(C)(=O)=O)c1] | 4-(3-amino-6-((1r,4R)-4-hydroxy-cyclohexyl)pyrazin-2-yl)-2-(fluoro-N-((R)-1-(3-fluoro-5-(methylsulfonyl)phenyl)ethyl)benzamide | 531.3 | 0.64 | 1H NMR (400 MHz, CD$_3$OD) δ 7.88(s, 1H), 7.83 (s, 1H), 7.74-7.81 (m,1H), 7.52-7.69 (m, 4H), 5.33 (q,J = 7.0 Hz, 1H), 3.54-3.67 (m, 1H),3.16 (s, 3H), 2.59-2.71 (m, 1H),2.07 (d, J = 9.4 Hz, 2H), 1.91-2.01(m, 2H), 1.63-1.74 (m, 2H), 1.61 (d,J = 7.0 Hz, 3H), 1.33-1.50 (m, 2H) |
| 420 | 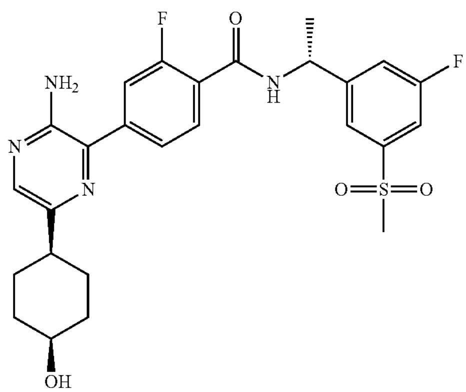 [SMILES: C[C@@H](NC(=O)c1ccc(-c2nc([C@H]3CC[C@@H](O)CC3)cnc2N)cc1F)c1cc(F)cc(S(C)(=O)=O)c1] | 4-(3-amino-6-((1s,4S)-4-hydroxy-cyclohexyl)pyrazin-2-yl)-2-fluoro-N-((R)-1-(3-fluoro-5-(methylsulfonyl)phenyl)ethyl)benzamide | 531.3 | 0.67 | 1H NMR (400 MHz, CD$_3$OD) δ7.82-7.90 (m, 2H), 7.74-7.81 (m,1H), 7.68 (dd, J = 8.0, 1.4 Hz, 1H),7.59-7.66 (m, 2H), 7.56 (d, J = 9.4Hz, 1H), 5.33 (t, J = 7.0 Hz, 1H), 4.01 (br. s., 1H), 3.16 (s, 3H), 2.73 (tt, J = 11.2, 3.3 Hz, 1H), 1.96-2.10 (m, 2H), 1.81-1.93 (m, 2H), 1.64-1.78 (m, 4H), 1.61 (d, J = 7.0 Hz, 3H) |
| 421 | 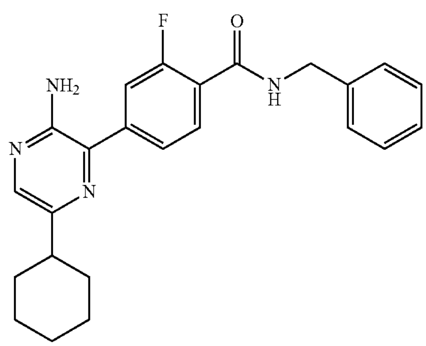 [SMILES: Nc1ncc(C2CCCCC2)nc1-c1ccc(C(=O)NCc2ccccc2)c(F)c1] | 4-(3-amino-6-cyclohexylpyrazin-2-yl)-N-benzyl-2-fluorobenzamide | 405.3 | 0.97 | 1H NMR (400 MHz, CD$_3$OD) δ 7.76(t, J = 7.6 Hz, 1H), 7.71 (s, 1H), 7.57(dd, J = 8.0, 1.4 Hz, 1H), 7.49 (dd,J = 11.5, 1.4 Hz, 1H), 7.21-7.32 (m,4H), 7.12-7.20 (m, 1H), 4.52 (s, 2H), 2.50-2.67 (m, 1H), 1.73-1.89 (m, 4H), 1.66 (d, J = 12.5 Hz, 1H), 1.27-1.55 (m, 4H), 1.12-1.27 (m, 1H) |
| 422 | 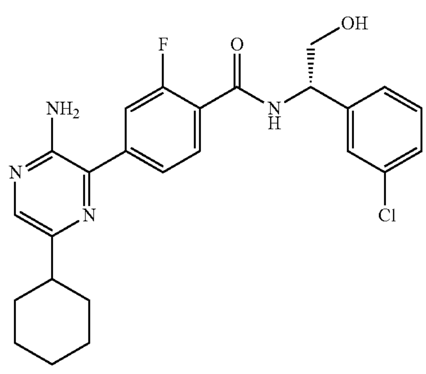 [SMILES: Nc1ncc(C2CCCCC2)nc1-c1ccc(C(=O)N[C@H](CO)c2cccc(Cl)c2)c(F)c1] | (S)-4-(3-amino-6-cyclohexylpyrazin-2-yl)-N-(1-(3-chlorophenyl)-2-hydroxyethyl)-2-fluorobenzamide | 469.2 | 0.93 | 1H NMR (400 MHz, CD$_3$OD) δ 7.77(t, J = 7.6 Hz. 1H), 7.72 (s, 1H), 7.58(dd, J = 8.0, 1.4 Hz, 1H), 7.47-7.55(m, 1H), 7.37 (s, 1H), 7.23-7.30 (m,2H), 7.15-7.22 (m, 1H), 5.10 (t,J = 5.9 Hz, 1H), 3.69-3.86 (m, 2H),2.51-2.65 (m, 1H), 1.73-1.93 (m,4H), 1.67 (d, J = 12.5 Hz, 1H), 1.28-1.57 (m, 4H), 1.12-1.27 (m, 1H) |

TABLE 5-continued

Compounds prepared using Method 3 described above.

| Example | Structure | Name | MH+ | R_f (min) | NMR |
|---|---|---|---|---|---|
| 423 | 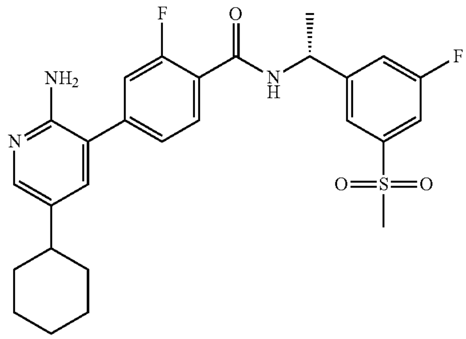 [SMILES: C[C@@H](NC(=O)c1ccc(-c2cc(C3CCCCC3)cnc2N)cc1F)c1cc(F)cc(S(C)(=O)=O)c1] | (R)-4-(3-amino-6-cyclohexylpyrazin-2-yl)-2-fluoro-N-(1-(3-fluoro-5-(methylsulfonyl)phenyl)ethyl)benzamide | 515.3 | 0.92 | 1H NMR (400 MHz, CD$_3$OD) δ 7.87(s, 1H), 7.83 (s, 1H), 7.74-7.80 (m,1H), 7.67 (dd, J = 8.0, 1.4 Hz, 1H),7.50-7.65 (m, 3H), 5.27-5.38 (m,1H), 3.16 (s, 3H), 2.60-2.71 (m, 1H), 1.82-1.97 (m, 4H), 1.76 (d, J = 12.5 Hz. 1H), 1.61 (d, J = 7.0 Hz, 3H), 1.37-1.58 (m, 4H), 1.23-1.37 (m, 1H) |
| 424 | 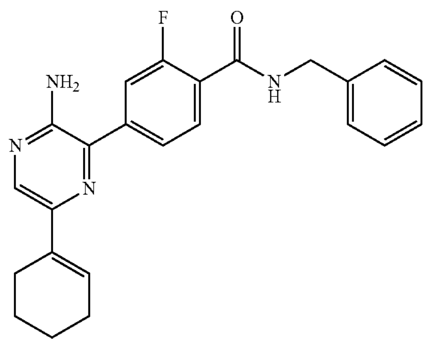 [SMILES: Nc1ncc(C2=CCCCC2)nc1-c1ccc(C(=O)NCc2ccccc2)c(F)c1] | 4-(3-amino-6-(cyclohex-1-en-1-yl)pyrazin-2-yl)-N-benzyl-2-fluorobenzamide | 403.2 | 0.98 | 1H NMR (400 MHz, CD$_3$OD) δ 7.98(s, 1H), 7.70-7.79 (m, 1H), 7.61 (dd,J = 8.2, 1.6 Hz, 1H), 7.53 (dd, J = 11.9, 1.4 Hz, 1H), 7.21-7.35 (m, 4H), 7.08-7.20 (m, 1H), 6.36-6.48 (m, 1H), 4.52 (s, 2H), 2.39 (d, J = 2.0 Hz, 2H), 2.10-2.19 (m, 2H), 1.65-1.74 (m, 2H), 1.54-1.63 (m, 2H) |
| 425 | 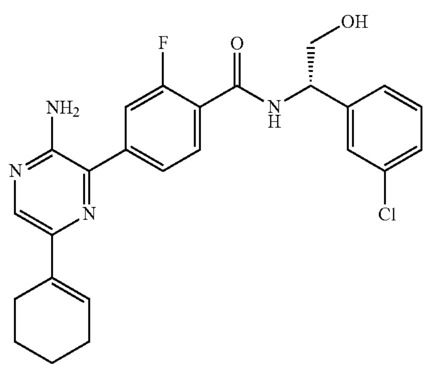 [SMILES: Nc1ncc(C2=CCCCC2)nc1-c1ccc(C(=O)N[C@H](CO)c2cccc(Cl)c2)c(F)c1] | (S)-4-(3-amino-6-(cyclohex-1-en-1-yl)pyrazin-2-yl)-N-(1-(3-chlorophenyl)-2-hydroxyethyl)-2-fluorobenzamide | 467.2 | 0.94 | 1H NMR (400 MHz, CD$_3$OD) δ 7.98(s, 1H), 7.71-7.80 (m, 1H), 7.62 (dd,J = 8.0, 1.4 Hz, 1H), 7.55 (d, J = 11.7Hz, 1H), 7.37 (s, 1H), 7.26 (d, J = 6.7Hz, 2H), 7.14-7.21 (m, 1H), 6.44(br. s., 1H), 5.09 (t, J = 6.1 Hz, 1H),3.76 (t, J = 5.9 Hz, 2H), 2.39 (d, J = 2.0 Hz, 2H), 2.08-2.21 (m, 2H), 1.65-1.76 (m, 3H), 1.54-1.64 (m, 2H) |
| 426 | 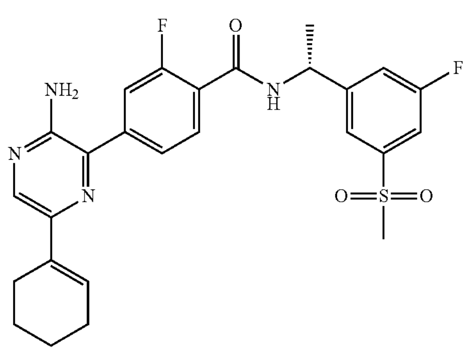 [SMILES: C[C@@H](NC(=O)c1ccc(-c2nc(C3=CCCCC3)cnc2N)cc1F)c1cc(F)cc(S(C)(=O)=O)c1] | (R)-4-(3-amino-6-(cyclohex-1-en-1-yl)pyrazin-2-yl)-2-fluoro-N-(1-(3-fluoro-5-(methylsulfonyl)phenyl)ethyl)benzamide | 513.2 | 0.92 | 1H NMR (400 MHz, CD$_3$OD) δ 7.98(s, 1H), 7.78 (s, 1H), 7.64-7.70 (m,1H), 7.58-7.63 (m, 1H). 7.50-7.57(m, 2H), 7.46 (d, J = 9.4 Hz, 1H), 6.41-6.48 (m, 1H), 5.23 (q, J = 7.0 Hz, 1H), 3.06 (s, 3H), 2.34-2.44 (m, 2H), 2.15 (dd, J = 6.3, 2.3 Hz, 2H), 1.66-1.75 (m, 2H), 1.54-1.64 (m, 3H), 1.51 (d, J = 7.0 Hz, 3H) |

TABLE 5-continued

Compounds prepared using Method 3 described above.

| Example | Structure | Name | MH+ | R_t (min) | NMR |
|---|---|---|---|---|---|
| 427 | 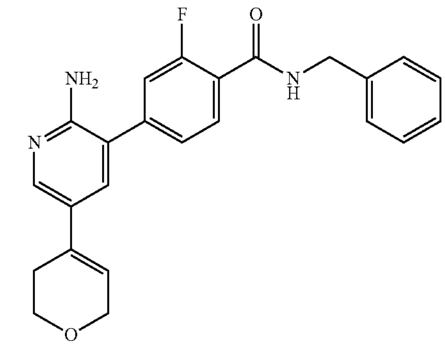 [SMILES: Nc1ncc(C2=CCOCC2)cc1-c1ccc(C(=O)NCc2ccccc2)c(F)c1] | 4-(3-amino-6-(3,6-dihydro-2H-pyran-4-yl)pyrazin-2-yl)-N-benzyl-2-fluorobenzamide | 405.2 | 0.79 | 1H NMR (400 MHz, CD$_3$OD) δ 7.99(s, 1H), 7.73-7.79 (m, 1H), 7.61 (dd, J = 8.0, 1.4 Hz, 1H), 7.53 (dd, J = 11.7, 1.2 Hz, 1H), 7.21-7.34 (m, 4H), 7.10-7.19 (m, 1H), 6.49 (br. s., 1H), 4.52 (s, 2H), 4.23 (d, J = 2.7 Hz, 2H), 3.82 (t, J = 5.5 Hz, 2H), 2.49 (d, J = 1.6 Hz, 2H) |
| 428 | 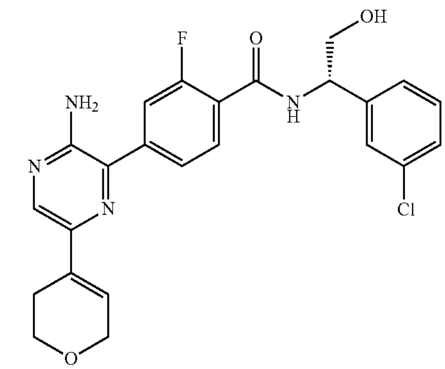 [SMILES: Nc1ncc(C2=CCOCC2)nc1-c1ccc(C(=O)N[C@H](CO)c2cccc(Cl)c2)c(F)c1] | (S)-4-(3-amino-6-(3,6-dihydro-2H-pyran-4-yl)pyrazin-2-yl)-N-(1-(3-chlorophenyl)-2-hydroxyethyl)-2-fluorobenzamide | 469.1 | 0.77 | 1H NMR (400 MHz, CD$_3$OD) δ 8.01(s, 1H), 7.76 (t, J = 7.6 Hz, 1H), 7.62(dd, J = 8.2, 1.6 Hz, 1H), 7.53-7.58(m, 1H), 7.37 (s, 1H), 7.23-7.29 (m,2H), 7.14-7.22 (m, 1H), 6.49 (br. s.,1H), 5.10 (t, J = 5.9 Hz, 1H), 4.23 (d,J = 2.7 Hz, 2H), 3.83 (t, J = 5.5 Hz,2H), 3.76 (t, J = 6.3 Hz, 2H), 2.50 (d,J=2.0 Hz, 2H) |
| 429 | 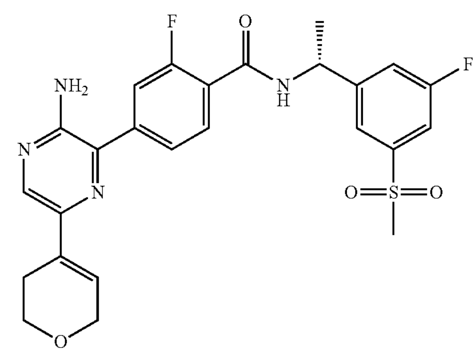 [SMILES: C[C@@H](NC(=O)c1ccc(-c2nc(C3=CCOCC3)cnc2N)cc1F)c1cc(F)cc(S(C)(=O)=O)c1] | (R)-4-(3-amino-6-(3,6-dihydro-2H-pyran-4-yl)pyrazin-2-yl)-2-fluoro-N-(1-(3-fluoro-5-(methylsulfonyl)phenyl)ethyl)benzamide | 515.1 | 0.75 | 1H NMR (400 MHz, CD$_3$OD) δ 8.09(s, 1H), 7.87 (s, 1H), 7.74-7.81 (m,1H), 7.68-7.73 (m, 1H), 7.59-7.67(m, 2H), 7.56 (d, J = 9.4 Hz, 1H), 5.59 (br. s., 1H), 5.33 (q, J = 7.0 Hz, 1H), 4.32 (d, J = 2.7 Hz, 2H), 3.92 (t, J = 5.5 Hz, 2H), 3.16 (s, 3H), 2.59 (d, J = 2.0 Hz, 2H), 1.61 (d, J =7.0 Hz, 3H) |
| 430 | 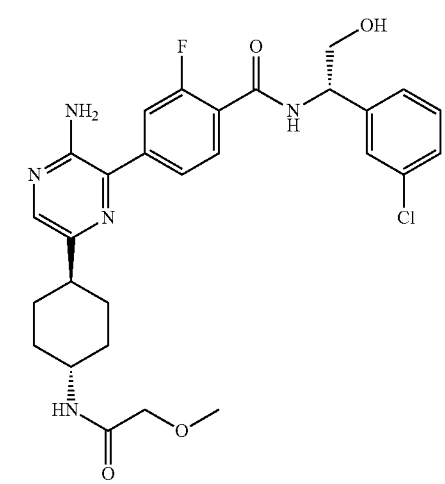 [SMILES: COCC(=O)N[C@H]1CC[C@H](c2cnc(N)c(-c3ccc(C(=O)N[C@H](CO)c4cccc(Cl)c4)c(F)c3)n2)CC1] | 4-(3-amino-6-((1r,4S)-4-(2-methoxyacetamido)cyclohexyl)pyrazin-2-yl)-N-((S)-1-(3-chlorophenyl)-2-hydroxyethyl)-2-fluorobenzamide | 556.3 | 0.71 | 1H NMR (400 MHz, CD$_3$OD) δ7.70-7.82 (m, 2H), 7.59 (dd, J = 8.0,1.4 Hz, 1H), 7.53 (d, J = 11.7 Hz,1H), 7.37 (s, 1H), 7.22-7.30 (m,2H), 7.14-7.22 (m, 1H), 5.10 (t,J = 5.9 Hz, 1H), 3.62-3.85 (m, 5H),3.32 (s, 3H), 2.52-2.65 (m, 1H), 1.91 (d, J = 11.3 Hz, 4H), 1.55-1.70(m, 2H), 1.33-1.48 (m, 2H) |

TABLE 5-continued

Compounds prepared using Method 3 described above.

| Example | Structure | Name | MH+ | R_t (min) | NMR |
|---|---|---|---|---|---|
| 431 | 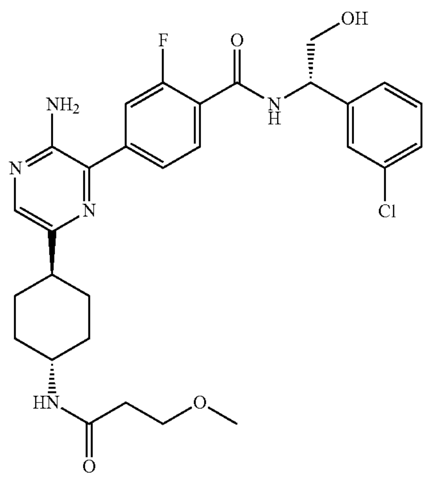 [SMILES: COCCC(=O)N[C@H]1CC[C@H](c2cnc(N)c(-c3ccc(C(=O)N[C@H](CO)c4cccc(Cl)c4)c(F)c3)n2)CC1] | 4-(3-amino-6-((1r,4S)-4-(3-methoxypropanamido)cyclohexyl)pyrazin-2-yl)-N-((S)-1-(3-chlorophenyl)-2-hydroxyethyl)-2-fluorobenzamide | 570.3 | 0.70 | 1H NMR (400 MHz, CD$_3$OD) δ7.79-7.91 (m, 2H), 7.68 (dd, J=8.0,1.4 Hz, 1H), 7.62 (d, J = 11.7 Hz,1H), 7.46 (s, 1H), 7.33-7.40 (m,2H), 7.26-7.31 (m, 1H), 5.19 (t,J = 5.9 Hz, 1H), 3.80-3.92 (m, 2H),3.67-3.78 (m, 1H), 3.63 (t, J = 6.1Hz, 2H), 3.33 (s, 3H), 2.66 (t,J = 12.1 Hz, 1H), 2.41 (t, J = 6.1 Hz,2H), 2.01 (t, J = 15.1 Hz, 4H), 1.62-1.80 (m, 2H), 1.33-1.48 (m, 2H) |
| 432 | 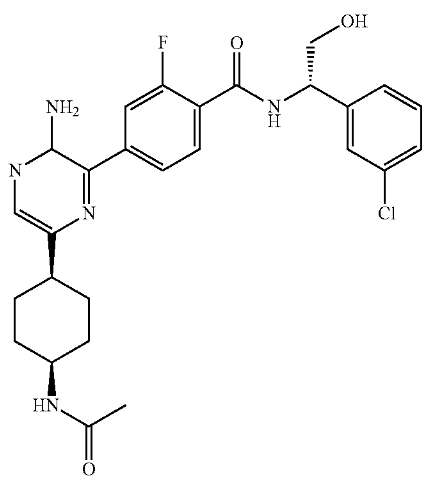 [SMILES: CC(=O)N[C@H]1CC[C@@H](C2=CNC(N)C(c3ccc(C(=O)N[C@H](CO)c4cccc(Cl)c4)c(F)c3)=N2)CC1] | 4-(6-((1s,4R)-4-acetamidocyclohexyl)-3-aminopyrazin-2-yl)-N-((S)-1-(3-chlorophenyl)-2-hydroxyethyl)-2-fluorobenzamide | 526.3 | 0.69 | 1H NMR (400 MHz, CD$_3$OD) δ7.75-7.83 (m, 2H), 7.58 (d, J = 7.8Hz, 1H), 7.54 (d, J = 11.7 Hz, 1H),7.37 (s, 1H), 7.23-7.31 (m, 2H),7.16-7.22 (m, 1H), 5.10 (t, J = 5.9Hz, 1H), 3.93 (d, J = 3.5 Hz. 1H),3.69-3.84 (m, 2H), 2.64-2.76 (m,1H), 1.86 (s, 3H), 1.78-1.85 (m,2H), 1.68-1.77 (m, 4H), 1.55-1.67(m, 2H) |
| 433 | 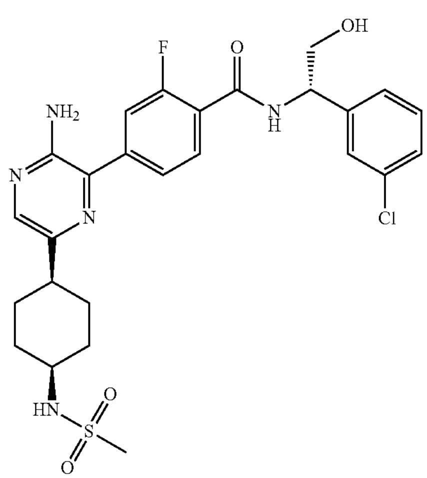 [SMILES: CS(=O)(=O)N[C@H]1CC[C@@H](c2cnc(N)c(-c3ccc(C(=O)N[C@H](CO)c4cccc(Cl)c4)c(F)c3)n2)CC1] | 4-(3-amino-6-((1s,4R)-4-(methylsulfonamido)cyclohexyl)pyrazin-2-yl)-N-((S)-1-(3-dilorophenyl)-2-hydroxyethyl)-2-fluorobenzamide | 562.3 | 0.72 | 1H NMR (400 MHz, CD$_3$OD) δ7.72-7.84 (m, 2H), 7.49-7.64 (m,2H), 7.37 (s, 1H), 7.22-7.30 (m,2H), 7.15-7.22 (m, 1H), 5.04-5.15(m, 1H), 3.70-3.84 (m, 2H), 3.57(br. s., 1H), 2.86 (s, 3H), 2.62-2.76(m, 1H), 1.78-1.96 (m, 4H), 1.55-1.75 (m, 4H) |

TABLE 5-continued

Compounds prepared using Method 3 described above.

| Example | Structure | Name | MH+ | R_f (min) | NMR |
|---|---|---|---|---|---|
| 434 | 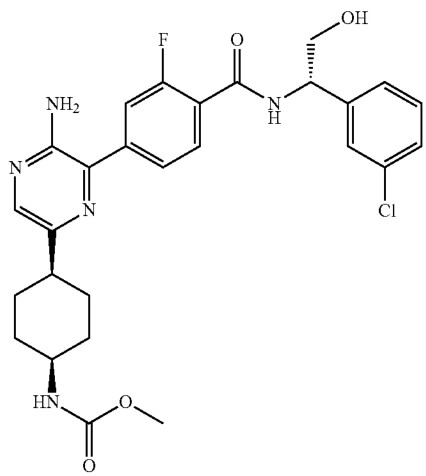 [SMILES: COC(=O)N[C@H]1CC[C@@H](c2cnc(N)c(-c3ccc(C(=O)N[C@H](CO)c4cccc(Cl)c4)c(F)c3)n2)CC1] | methyl ((1R,4s)-4-(5-amino-6-(4-(((S)-1-(3-chlorophenyl)-2-hydroxyethyl)carbamoyl)-3-fluorophenyl)pyrazin-2-yl)cyclohexyl)carbamate | 542.3 | 0.76 | 1H NMR (400 MHz, CD$_3$OD) δ 7.81(s, 1H), 7.77 (t, J = 7.6 Hz, 1H), 7.47-7.63 (m, 2H), 7.37 (s, 1H), 7.22-7.31 (m, 2H), 7.12-7.22 (m, 1H), 5.04-5.15 (m, 1H), 3.74-3.82 (m,2H), 3.71 (d, J = 5.5 Hz, 1H), 3.53 (s,3H), 2.62-2.74 (m, 1H), 1.53-1.92(m, 8H) |
| 435 | 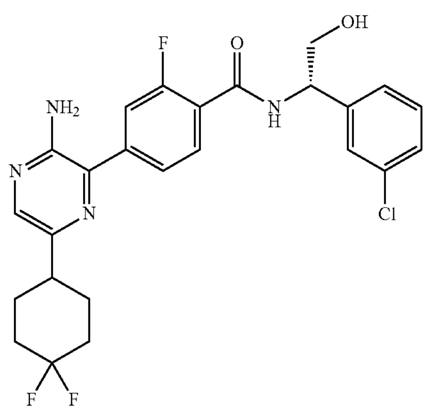 [SMILES: Nc1ncc(C2CCC(F)(F)CC2)nc1-c1ccc(C(=O)N[C@H](CO)c2cccc(Cl)c2)c(F)c1] | (S)-4-(3-amino-6-(4,4-difluorocyclohexyl)pyrazin-2-yl)-N-(1-(3-chlorophenyl)-2-hydroxyethyl)-2-fluorobenzamide | 505.2 | 0.87 | 1H NMR (400 MHz, CD$_3$OD) δ7.79-7.92 (m, 2H), 7.68 (dd, J = 8.0,1.4 Hz, 1H), 7.58-7.65 (m, 1H),7.46 (s, 1H), 7.32-7.40 (m, 2H),7.25-7.32 (m, 1H), 5.19 (t, J = 5.9Hz, 1H), 3.78-3.94 (m, 2H), 2.77-2.88 (m, 1H), 2.08-2.23 (m, 2H), 1.78-2.05 (m, 6H) |
| 436 | 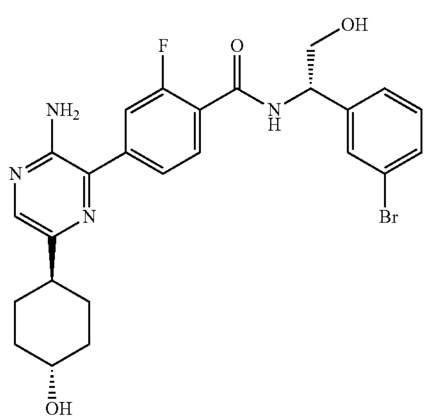 [SMILES: Nc1ncc([C@H]2CC[C@H](O)CC2)nc1-c1ccc(C(=O)N[C@H](CO)c2cccc(Br)c2)c(F)c1] | 4-(3-amino-6-((1r,4S)-4-hydroxycyclohexyl)pyrazin-2-yl)-N-((S)-1-(3-bromophenyl)-2-hydroxyethyl)-2-fluorobenzamide | 529.2/ 531.1 | 0.66 | 1H NMR (400 MHz, CD$_3$OD) δ7.68-7.82 (m, 2H), 7.47-7.62 (m,3H), 7.34 (dd, J = 12.9, 7.8 Hz, 2H),7.10-7.27 (m, 1H), 5.09 (t, J = 5.7Hz, 1H), 3.69-3.80 (m, 2H), 3.44-3.57 (m, 1H), 2.50-2.62 (m, 1H),1.97 (d, J = 9.8 Hz, 2H), 1.87 (d, J = 12.5 Hz, 2H), 1.48-1.66 (m, 2H), 1.21-1.41 (m, 2H) |

TABLE 5-continued

Compounds prepared using Method 3 described above.

| Example | Structure | Name | MH+ | R$_t$ (min) | NMR |
|---|---|---|---|---|---|
| 437 | 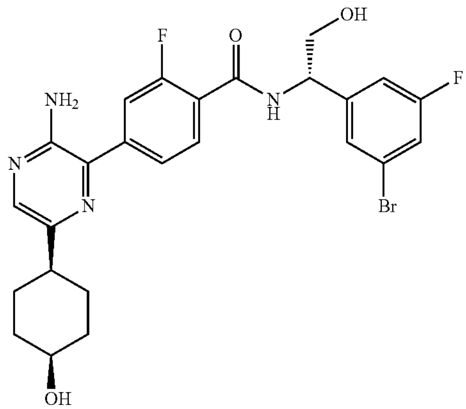 [SMILES: Nc1ncc([C@H]2CC[C@@H](O)CC2)nc1-c1ccc(C(=O)N[C@H](CO)c2cc(F)cc(Br)c2)c(F)c1] | 4-(3-amino-6-((1s,4R)-4-hydroxy-cyclohexyl)pyrazin-2-yl)-N-((S)-1-(3-bromo-5-fluorophenyl)-2-hydroxyethyl)-2-fluorobenzamide | 547.1/ 549.1 | 0.71 | 1H NMR (400 MHz, CD$_3$OD) δ 7.79-7.91 (m, 2H), 7.60-7.75 (m, 2H), 7.46 (s, 1H), 7.27 (d, J = 8.2 Hz, 1H), 7.20 (d, J = 9.4 Hz, 1H), 5.18 (d, J = 5.1 Hz, 1H), 4.01 (br. s., 1H), 3.86 (t, J = 5.5 Hz, 2H), 2.68-2.80 (m, 1H), 1.95-2.11 (m, 2H), 1.79-1.92 (m, 2H), 1.61-1.76 (m, 4H) |
| 438 | 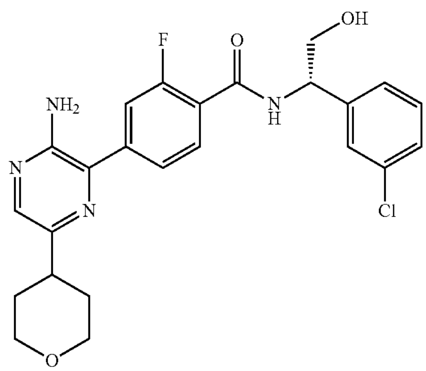 [SMILES: Nc1ncc(C2CCOCC2)nc1-c1ccc(C(=O)N[C@H](CO)c2cccc(Cl)c2)c(F)c1] | (S)-4-(3-amino-6-(tetrahydro-2H-pyran-4-yl)pyrazin-2-yl)-N-(1-(3-chlorophenyl)-2-hydroxyethyl)-2-fluorobenzamide | 471.1 | 0.7 | 1H NMR (400 MHz, DMSO-d6) δ 8.69 (m, 1H), 7.92 (s, 1H), 7.78-7.54 (m, 3H), 7.45 (s, 1H), 7.44-7.21 (m, 3H), 6.13 (m, 1H), 5.01 (m, 1H), 3.92 (m, 2H), 3.65 (m, 2H), 3.43 (m, 2H), 1.74 (m, 4H) |
| 439 | 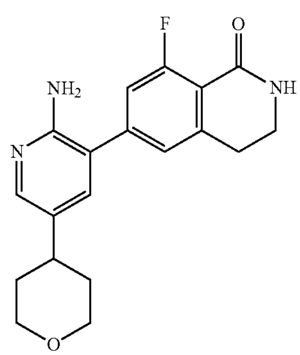 [SMILES: Nc1ncc(C2CCOCC2)cc1-c1cc(F)c2c(c1)CCNC2=O] | S-(2-amino-5-(tetrahydro-2H-pyran-4-yl)pyridin-3-yl)-3,4-dihydro-isoquinolin-1(2H)-one | 324.1 | 0.47 | 1H NMR (400 MHz, CD$_3$OD) δ ppm1.59-1.80 (m, 4H) 2.70-2.85 (m,1H) 2.98 (t, J = 6.65 Hz, 2H) 3.40-3.54 (m, 4H) 3.95 (dd, J = 11.15, 3.33 Hz, 2H) 7.35 (s, 1H) 7.36-7.42 (m, 1H) 7.68 (d, J = 1.96 Hz, 1H) 7.82 (d, J = 2.35 Hz, 1H) 7.99 (d, J = 7.83 Hz, 1H) |
| 440 | 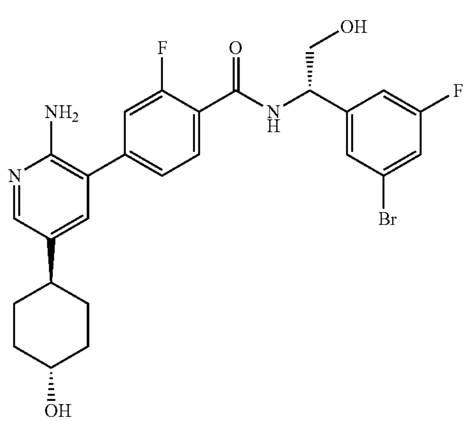 [SMILES: Nc1ncc([C@H]2CC[C@H](O)CC2)cc1-c1ccc(C(=O)N[C@H](CO)c2cc(F)cc(Br)c2)c(F)c1] | 4-(2-amino-5-((1s,4R)-4-hydroxy-cyclohexyl)pyridin-3-yl)-N-((S)-1-(3-chlorophenyl)-2-hydroxyethyl)-2-fluorobenzamide | 484.2 | 0.67 | 1H NMR (400 MHz, CD$_3$OD) δ ppm7 7.75-7.86 (m, 2H) 7.68 (d, J = 1.96 Hz, 1H) 7.14-7.40 (m, 6H) 5.10 (t, J = 5.87 Hz, 1H) 3.95 (br. s., 1H) 3.65-3.83 (m, 2H) 2.34-2.65 (m, 1H) 1.49-1.91 (m, 8H) |

TABLE 5-continued

Compounds prepared using Method 3 described above.

| Example | Structure | Name | MH+ | R$_t$ (min) | NMR |
|---|---|---|---|---|---|
| 441 | 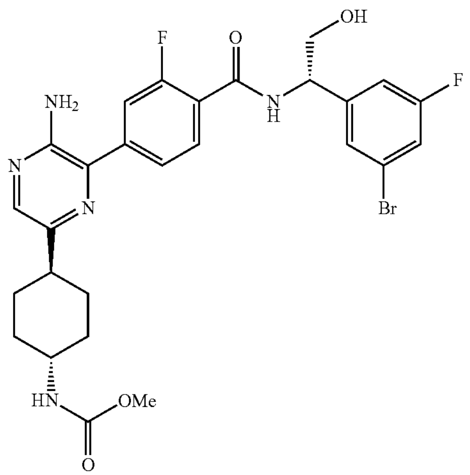 [SMILES: COC(=O)N[C@H]1CC[C@H](c2cnc(N)c(-c3ccc(C(=O)N[C@H](CO)c4cc(F)cc(Br)c4)c(F)c3)n2)CC1] | Methyl ((1S,4r)-4-(5-amino-6-(4-(((S)-1-(3-bromo-5-fluorophenyl)-2-hydroxyethyl)carbamoyl)-3-fluorophenyl)pyrazin-2-yl)cyclohexyl)carbamate | 606.1 | 0.83 | 1H NMR (400 MHz, CD$_3$OD) δ ppm7.79-7.92 (m, 1H) 7.57-7.71 (m,1H) 7.46 (s, 1H) 7.14-7.31 (m, 2H) 5.17 (t, J = 5.87 Hz, 1H) 3.83-3.98 (m, 2H) 3.62 (s, 3H) 3.39-3.50 (m, 1H) 2.65 (t, J = 12.13 Hz, 1H) 1.90-2.14 (m, 4H) 1.61-1.79(m, 2H) 1.25-1.52 (m, 2H). |
| 442 | 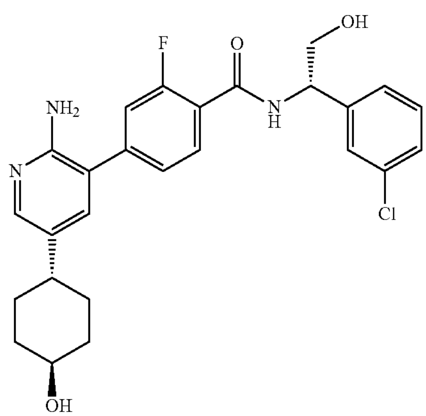 [SMILES: Nc1ncc([C@H]2CC[C@H](O)CC2)cc1-c1ccc(C(=O)N[C@H](CO)c2cccc(Cl)c2)c(F)c1] | 4-(2-amino-5-((1r,4S)-4-hydroxycyclohexyl)pyridin-3-yl)-N-((S)-1-(3-chlorophenyl)-2-hydroxyethyl)-2-fluorobenzamide | 484.2 | 0.63 | 1H NMR (400 MHz, CD$_3$OD) δ ppm7.77-7.85 (m, 2H) 7.69 (d, J = 1.96Hz, 1H) 7.18-7.38 (m, 6H) 5.10(t, J = 5.87 Hz, 1H) 3.70-3.86 (m,2H) 3.45-3.60 (m, 1H) 2.40-2.54(m, 1H) 1.97 (d, J = 9.78 Hz, 2H) 1.85 (d, J = 12.52 Hz, 2H) 1.40-1.57 (m, 2H) 1.23-1.39 (m, 2H) |
| 443 | 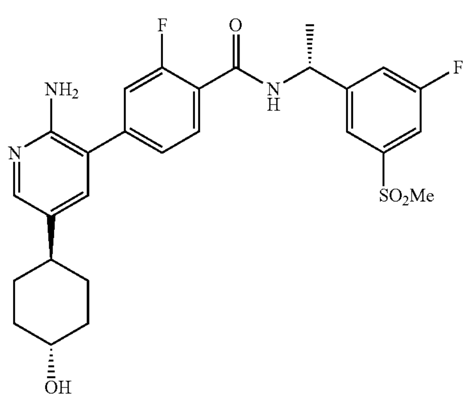 [SMILES: C[C@@H](NC(=O)c1ccc(-c2cc([C@H]3CC[C@H](O)CC3)cnc2N)cc1F)c1cc(F)cc(S(C)(=O)=O)c1] | 4-(2-amino-5-((1r,4R)-4-hydroxycyclohexyl)pyridin-3-yl)-2-fluoro-N-((R)-1-(3-fluoro-5-(methylsulfonyl)phenyl)ethyl)benzamide | 530.2 | 0.61 | 1H NMR (400 MHz, CD$_3$OD) δ ppm 7.85-7.91 (m, 2H) 7.81 (t, J = 7.83 Hz, 1H) 7.77 (d, J = 1.96 Hz, 1H) 7.63 (d, J = 7.83 Hz, 1H) 7.55 (d, J = 9.39 Hz, 1H) 7.37-7.45 (m, 2 H) 5.33 (q, J = 7.04 Hz, 1H) 3.54-3.74 (m, 1H) 3.16 (s, 3H) 2.48-2.63 (m, 1H) 2.06 (d, J = 9.78 Hz, 2 H) 1.94 (d, J = 12.52 Hz, 2H) 1.61 (d, J = 7.43 Hz, 3H) 1.49-1.58 (m, 2H) 1.34-1.48 (m, 2H). |

TABLE 5-continued

Compounds prepared using Method 3 described above.

| Example | Structure | Name | MH+ | R$_t$ (min) | NMR |
|---|---|---|---|---|---|
| 444 | single diastereomer; trans or cis | (S)-4-(3-amino-6-(4-(hydroxymethyl)cyclohexyl)pyrazin-2-yl)-N-(1-(3-chlorophenyl)-2-hydroxyethyl)-2-fluorobenzamide | 499.1 | 0.74 | 1H NMR (400 MHz, CD$_3$OD) δ ppm 7.79-7.91 (m, 2H) 7.58-7.71 (m, 2H) 7.46 (s, 1H) 7.24-7.40 (m, 3H) 5.19 (t, J = 5.87 Hz, 1H) 3.76-3.98 (m, 2H) 3.41 (d, J = 6.26 Hz, 2H) 2.56-2.75 (m, 1H) 1.88-2.14 (m, 4H) 0.99-1.81 (m, 6H) |
| 445 | single diastereomer; trans or cis | (S)-4-(3-amino-6-(4-(hydroxymethyl)cyclohexyl)pyrazin-2-yl)-N-(1-(3-chlorophenyl)-2-hydroxyethyl)-2-fluorobenzamide | 499.1 | 0.75 | 1H NMR (400 MHz, CD$_3$OD) δ ppm 7.69-7.82 (m, 1H) 7.50-7.62 (m, 1H) 7.37 (s, 1H) 7.15-7.31 (m, 3H) 5.10 (t, J = 5.87 Hz, 1H) 3.68-3.86 (m, 2H) 3.47 (d, J = 7.04 Hz, 1H) 2.74 (td, J = 8.71, 4.50 Hz, 1H) 1.46-1.97 (m, 11H). |
| 446 | single diastereomer; trans or cis | (S)-4-(3-amino-6-(4-(hydroxymethyl)cyclohexyl)pyrazin-2-yl)-N-(1-(3-bromo-5-fluorophenyl)-2-hydroxyethyl)-2-fluorobenzamide | 561/563 | 0.76 | 1H NMR (400 MHz, CD$_3$OD) δ ppm 7.79-7.91 (m, 2H) 7.58-7.71 (m, 2H) 7.46 (s, 1H) 7.24-7.40 (m, 3H) 5.19 (t, J = 5.87 Hz, 1H) 3.76-3.98 (m, 2H) 3.41 (d, J = 6.26 Hz, 2H) 2.56-2.75 (m, 1H) 1.88-2.14 (m, 4H) 0.99-1.81 (m, 6H) |

TABLE 5-continued

Compounds prepared using Method 3 described above.

| Example | Structure | Name | MH+ | R$_t$ (min) | NMR |
|---|---|---|---|---|---|
| 447 | 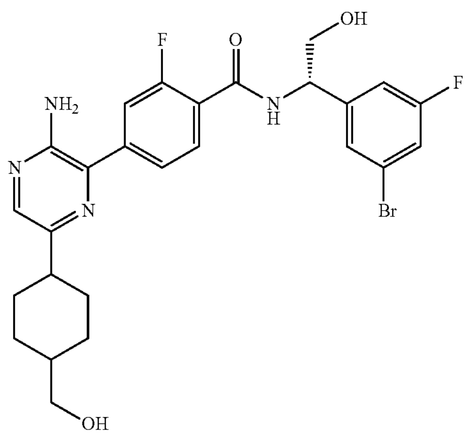 | (S)-4-(3-amino-6-(4-(hydroxymethyl)cyclohexyl)pyrazin-2-yl)-N-(1-(3-bromo-5-fluorophenyl)-2-hydroxyethyl)-2-fluorobenzamide<br><br>single diastereomer; trans or cis | 561/563 | 0.77 | 1H NMR (400 MHz, CD$_3$OD) δ ppm 7.69-7.82 (m, 1H) 7.50-7.62 (m, 1H) 7.37 (s, 1H) 7.15-7.31 (m, 3H) 5.10 (t, J = 5.87 Hz, 1H) 3.68-3.86 (m, 2H) 3.47 (d, J = 7.04 Hz, 1H) 2.74 (td, J = 8.71, 4.50 Hz, 1H) 1.46-1.97 (m, 11H). |
| 448 | 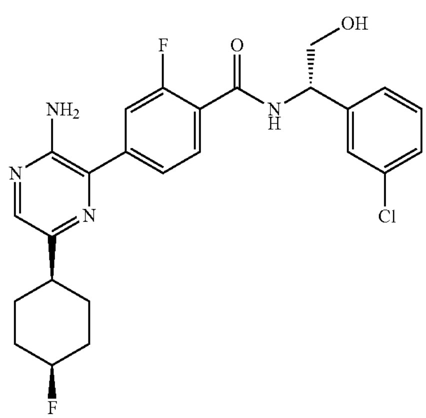 [SMILES: Nc1ncc([C@H]2CC[C@@H](F)CC2)nc1-c1ccc(C(=O)N[C@H](CO)c2cccc(Cl)c2)c(F)c1] | 4-(3-amino-6-((1s,4R)-4-fluorocyclohexyl)pyrazin-2-yl)-N-((S)-1-(3-chlorophenyl)-2-hydroxyethyl)-2-fluorobenzamide | 487.2 | 0.86 | 1H NMR (400 MHz, CD$_3$OD) δ ppm 7.77 (t, J = 7.63 Hz, 1H) 7.72 (s, 1H) 7.50-7.63 (m, 2H) 7.37 (s, 1H) 7.17-7.33 (m, 3H) 5.10 (t, J = 5.87 Hz, 1H) 3.65-3.85 (m, 2H) 2.68 (t, J = 11.74 Hz, 1H) 1.96-2.13 (m, 2H) 1.46-1.90 (m, 7H). |
| 449 | 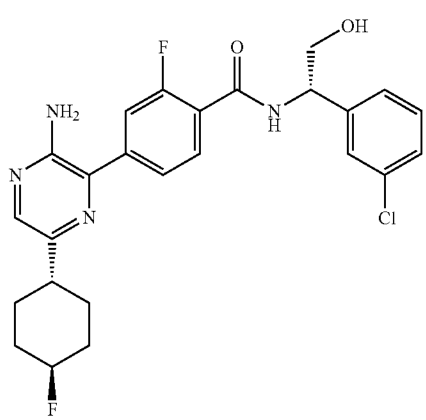 [SMILES: Nc1ncc([C@H]2CC[C@H](F)CC2)nc1-c1ccc(C(=O)N[C@H](CO)c2cccc(Cl)c2)c(F)c1] | 4-(3-amino-6-((1r,4S)-4-fluorocyclohexyl)pyrazin-2-yl)-N-((S)-1-(3-chlorophenyl)-2-hydroxyethyl)-2-fluorobenzamide | 487.2 | 0.88 | 1H NMR (400 MHz, CD$_3$OD) δ ppm 7.80-7.90 (m, 2H) 7.55-7.71 (m, 2H) 7.46 (s, 1H) 7.20-7.41 (m, 3H) 5.19 (t, J = 5.87 Hz, 1H) 4.42-4.71 (m, 1H) 3.76-3.96 (m, 2H) 2.57-2.82 (m, 1H) 2.19 (d, J = 5.87 Hz, 2H) 2.00 (d, J = 11.74 Hz, 2H) 1.50-1.79 (m, 4H) |

TABLE 5-continued

Compounds prepared using Method 3 described above.

| Example | Structure | Name | MH+ | R$_t$ (min) | NMR |
|---|---|---|---|---|---|
| 450 | (trans/cis mixture) | (S)-4-(3-amino-6-(4-cyanocyclohexyl)pyrazin-2-yl)-N-(1-(3-bromo-5-fluorophenyl)-2-hydroxyethyl)-2-fluorobenzamide | 556/558.0 | 0.85 | 1H NMR (400 MHz, CD$_3$OD) δ ppm 7.80-7.95 (m, 2H) 7.59-7.72 (m, 2H) 7.46 (s, 1H) 7.14-7.30 (m, 2H) 5.17 (t, J = 5.87 Hz, 1H) 3.74-3.97 (m, 2H) 3.14 (d, J = 3.13 Hz, 1H) 2.67-2.85 (m, 1H) 1.68-2.18 (m, 9H) |
| 451 | (trans/cis mixture) | (S)-4-(3-amino-6-(4-cyanocyclohexyl)pyrazin-2-yl)-N-(1-(3-bromo-5-fluorophenyl)-2-hydroxyethyl)-2-fluorobenzamide | 556/558.0 | 0.84 | 1H NMR (400 MHz, CD$_3$OD) δ ppm 7.80-7.95 (m, 2H) 7.59-7.72 (m, 2H) 7.46 (s, 1H) 7.14-7.30 (m, 2H) 5.17 (t, J = 5.87 Hz, 1H) 3.74-3.97 (m, 2H) 3.14 (d, J = 3.13 Hz, 1H) 2.67-2.85 (m, 1H) 1.68-2.18 (m, 9H) |
| 452 | 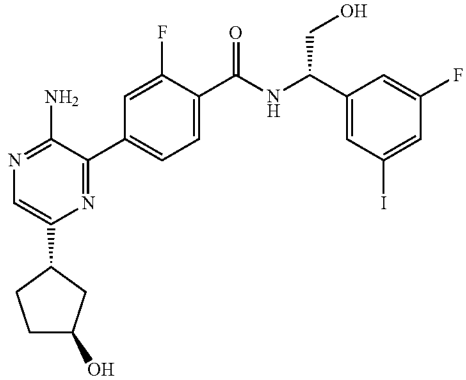 [SMILES: Nc1ncc([C@H]2CC[C@H](O)C2)nc1-c1ccc(C(=O)N[C@H](CO)c2cc(F)cc(I)c2)c(F)c1] | 4-(3-amino-6-((1S,3S)-3-hydroxycyclopentyl)pyrazin-2-yl)-2-fluoro-N-((S)-1-(3-fluoro-5-iodophenyl)-2-hydroxyethyl)benzamide | 581.0 | 0.73 | 1H NMR (400 MHz, CD$_3$CN), δ ppm 1.76 (s, 2H) 2.15 (s, 3H) 3 34-3.57 (m, 3H) 3.74-3.96 (m, 4H) 4.39 (d, J = 5.48 Hz, 2H) 5.12 (d, J = 6.65 Hz, 1H) 7.22 (dd, J = 9.78, 1.96 Hz, 1H) 7.48 (dd, J = 8.22, 1.56 Hz, 1H) 7.56-7.72 (m, 4H) 7.81 (s, 1H) 7.96 (t, J = 7.82 Hz, 1H) |

TABLE 5-continued

Compounds prepared using Method 3 described above.

| Example | Structure | Name | MH+ | R_t (min) | NMR |
|---|---|---|---|---|---|
| 453 | 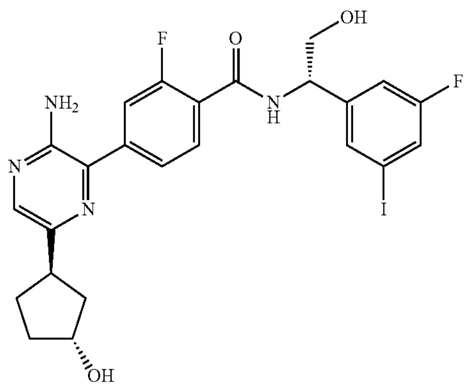 [SMILES: Nc1ncc([C@@H]2CC[C@@H](O)C2)nc1-c1ccc(C(=O)N[C@H](CO)c2cc(F)cc(I)c2)c(F)c1] | 4-(3-amino-6-((1R,3R)-3-hydroxy-cyclopentyl)pyrazin-2-yl)-2-fluoro-N-((S)-1-(3-fluoro-5-iodophenyl)-2-hydroxyethyl)benzamide | 581.1 | 0.73 | 1H NMR (400 MHz, CD₃CN), δ ppm 1.56-1.82 (m, 2H) 2.01-2.30 (m, 3H) 3.47 (t, J = 8.61 Hz, 1H) 3.73-3.92 (m, 3H) 4.32-4.45 (m, 2H) 5.05-5.19 (m, 1H) 7.16-7.27 (m, 1H) 7.48 (dt, J = 8.12, 1.81 Hz, 1H) 7.56-7.71 (m, 4H) 7.74-7.81 (m, 1H) 7.97 (t, J = 7.83 Hz, 1 H |
| 454 | 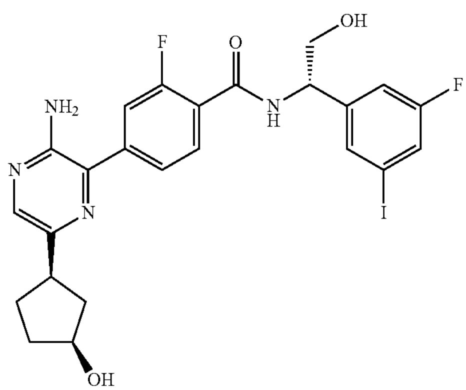 [SMILES: Nc1ncc([C@@H]2CC[C@H](O)C2)nc1-c1ccc(C(=O)N[C@H](CO)c2cc(F)cc(I)c2)c(F)c1] | 4-(3-amino-6-((1R,3S)-3-hydroxy-cyclopentyl)pyrazin-2-yl)-2-fluoro-N-((S)-1-(3-fluoro-5-iodophenyl)-2-hydroxyethyl)benzamide | 581.0 | 0.73 | 1H NMR (400 MHz. CD₃CN), δ ppm1.65-1.91 (m, 4H) 2.03-2.39 (m, 3H) 3.33 (t, J = 7.24 Hz, 1H) 3.70-3.92 (m, 2H) 4.30 (br. s., 1H) 5.03-5.19 (m, 2H) 7.22 (d, J = 9.78 Hz, 1 H) 7.40-7.71 (m, 5H) 7.81-7.90 (m, 1H) 7.97 (td, J = 7.83, 1.96 Hz, 1H) |
| 455 | 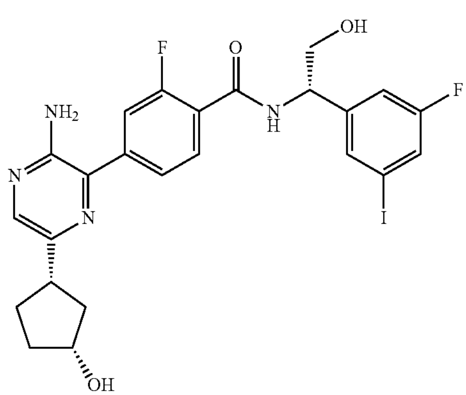 [SMILES: Nc1ncc([C@H]2CC[C@@H](O)C2)nc1-c1ccc(C(=O)N[C@H](CO)c2cc(F)cc(I)c2)c(F)c1] | 4-(3-amino-6-((1S,3R)-3-hydroxy-cyclopentyl)pyrazin-2-yl)-2-fluoro-N-((S)-1-(3-fluoro-5-iodophenyl)-2-hydroxyethyl)benzamide | 581.0 | 0.74 | 1H NMR (400 MHz, CD₃CN) δ ppm1.67-1.92 (m, 4H) 2.02-2.17 (m, 2H) 2.22-2.43 (m, 1H) 3.33 (t, J = 7.63 Hz, 1H) 3.69-3.92 (m, 2 H) 4.24-4.34 (m, 1H) 5.03-5.18 (m, 3H) 7.22 (dt, J = 9.78, 1.96 Hz, 1H) 7.44-7.53 (m, 1H) 7.57-7.70 (m, 4H) 7.84 (s, 1H) 7.92-8.04 (m, 1H) |

TABLE 5-continued

Compounds prepared using Method 3 described above.

| Example | Structure | Name | MH+ | R$_f$ (min) | NMR |
|---|---|---|---|---|---|
| 456 | 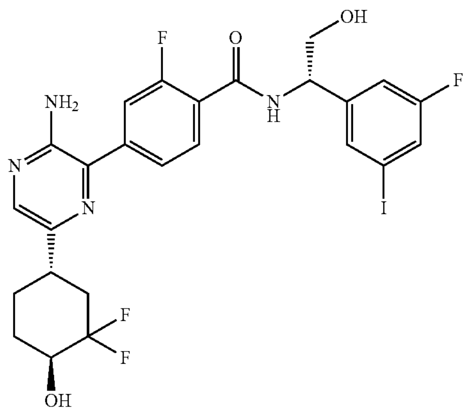 [SMILES: Nc1ncc([C@H]2CC[C@H](O)C(F)(F)C2)nc1-c1ccc(C(=O)N[C@H](CO)c2cc(F)cc(I)c2)c(F)c1] | 4-(3-amino-6-((1S,4S)-3,3-difluoro-4-hydroxy-cyclohexyl)pyrazin-2-yl)-2-fluoro-N-((S)-1-(3-fluoro-5-iodophenyl)-2-hydroxyethyl)benzamide | 631.1 | 0.77 | 1H NMR (400 MHz, DMSO), δ ppm 1.46-1.69 (m, 2H) 1.71-2.26 (m, 4H) 2.79-3.02 (m, 1H) 3.58-3.83 (m, 2H) 4.94-5.15 (m, 2H) 5.25-5.45 (m, 1H) 6.11-6.26 (m, 1H) 7.19-7.34 (m, 1H) 7.46-7.56 (m, 1H) 7.56-7.66 (m, 2H) 7.66-7.77 (m, 1H) 7.95 (s, 1H) 8.66-8.79 (m, 1H) |
| 457 | 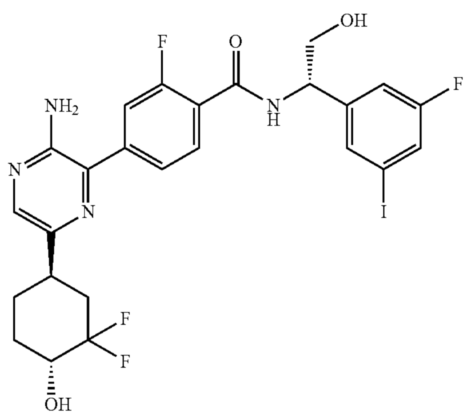 [SMILES: Nc1ncc([C@@H]2CC[C@@H](O)C(F)(F)C2)nc1-c1ccc(C(=O)N[C@H](CO)c2cc(F)cc(I)c2)c(F)c1] | 4-(3-amino-6-((1R,4R)-3,3-difluoro-4-hydroxy-cyclohexyl)pyrazin-2-yl)-2-fluoro-N-((S)-1-(3-fluoro-5-iodophenyl)-2-hydroxyethyl)benzamide | 631.1 | 0.77 | 1H NMR (400 MHz, DMSO), δ ppm 1.15-1.30 (m, 1H) 1.48-1.69 (m, 2H) 1.72-2.25 (m, 5H) 2.77-2.97 (m, 2H) 3.57-3.84 (m, 3H) 4.92-5.14 (m, 2H) 5.27-5.42 (m, 1H) 8.10-6.24 (m, 2H) 7.16-7.34 (m, 1H) 7.46-7.57 (m, 1H) 7.57-7.67 (m, 2H) 7.67-7.77 (m, 1H) 7.95 (s, 1H) 8.63-8.80 (m, 1H) |
| 458 | 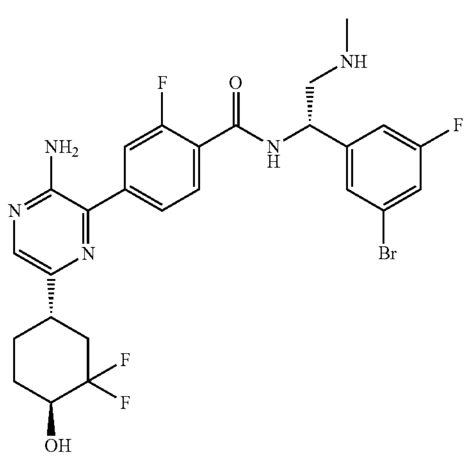 [SMILES: CNC[C@@H](NC(=O)c1ccc(-c2nc([C@H]3CC[C@H](O)C(F)(F)C3)cnc2N)cc1F)c1cc(F)cc(Br)c1] | 4-(3-amino-6-((1S,4S)-3,3-difluoro-4-hydroxy-cyclohexyl)pyrazin-2-yl)-2-fluoro-N-((S)-1-(3-fluoro-5-iodophenyl)-2-methylaminoethyl)benzamide | 598.0 | 0.66 | 1H NMR (400 MHz, DMSO) δ ppm 1.56 (d, J = 10.56 Hz, 2H) 1.76-1.94 (m, 2H) 1.96-2.28 (m, 2H) 2.63 (t, J = 5.28 Hz, 3H) 2.88 (br. s., 1H) 3.33-3.41 (m, 4H) 3.66 (d, J = 4.30 Hz, 3H) 5.44 (d, J = 7.82 Hz, 1H) 6.07-6.30 (m, 2H) 7.26-7.40 (m, 1H) 7.50-7.84 (m, 5H) 7.97 (s, 1H) 8.45-8.70 (m, 2H) 8.98 (d, J = 8.22 Hz, 1H) |

TABLE 5-continued

Compounds prepared using Method 3 described above.

| Example | Structure | Name | MH+ | R$_t$ (min) | NMR |
|---|---|---|---|---|---|
| 459 | 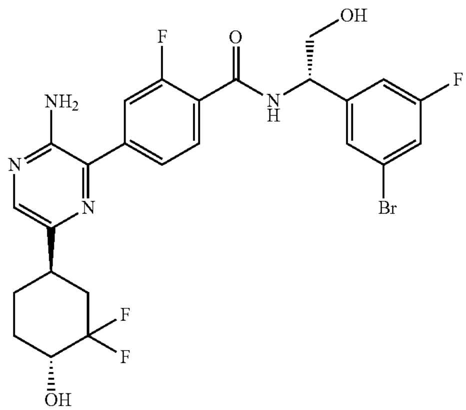 [SMILES: Nc1ncc([C@@H]2CC[C@@H](O)C(F)(F)C2)nc1-c1ccc(C(=O)N[C@H](CO)c2cc(F)cc(Br)c2)c(F)c1] | 4-(3-amino-6-((1R,4R)-3,3-difluoro-4-hydroxycyclohexyl)pyrazin-2-yl)-2-fluoro-N-((S)-1-(3-fluoro-5-bromophenyl)-2-hydroxyethyl)benzamide | 585.0 | 0.73 | 1H NMR (400 MHz. CD$_3$CN) δ ppm1.58-1.77 (m, 2H) 1.85-2.12 (m, 3H) 2.27-2.37 (m, 1H) 2.88-3.05 (m, 1H) 3.40 (br. s., 2H) 3.70-3.94 (m, 3H) 5.08-5.22 (m, 2H) 7.21 (d, J = 9.78 Hz, 1H) 7.30 (d, J = 8.61 Hz, 1H) 7.46 (s, 1H) 7.59-7.76 (m, 3H) 7.86-8.00 (m, 2H). |
| 460 | 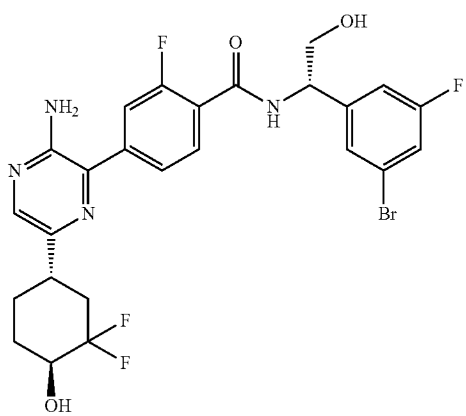 [SMILES: Nc1ncc([C@H]2CC[C@H](O)C(F)(F)C2)nc1-c1ccc(C(=O)N[C@H](CO)c2cc(F)cc(Br)c2)c(F)c1] | 4-(3-amino-6-((1S,4S)-3,3-difluoro-4-hydroxycyclohexyl)pyrazin-2-yl)-2-fluoro-N-((S)-1-(3-fluoro-5-bromophenyl)-2-hydroxyethyl)benzamide | 585.0 | 0.73 | 1H NMR (400 MHz, CD$_3$CN) δ ppm1 45-1.66 (m, 2H) 1.71-1.87 (m,3H) 1.87-1.97 (m, 2H) 2.13-2.30(m, 2H) 2.89 (t, J = 11.35 Hz, 1H) 3.11-3.37 (m, 2H) 3.61-3.83 (m, 3H) 4.96-5.14 (m, 3H) 7.10 (d, J = 9.78 Hz, 1H) 7.20 (dt, J = 8.31, 1.71 Hz, 1H) 7.36 (s, 1H) 7.46-7.64 (m, 3H) 7.78-7.92 (m, 2H) |
| 461 | 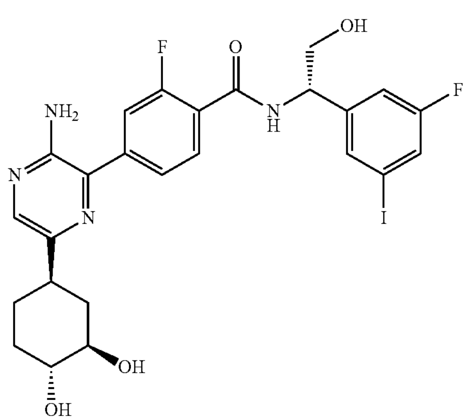 [SMILES: Nc1ncc([C@@H]2CC[C@@H](O)[C@H](O)C2)nc1-c1ccc(C(=O)N[C@H](CO)c2cc(F)cc(I)c2)c(F)c1] | 4-(3-amino-6-((1R,3R,4R)-3,4-dihydroxycyclohexyl)pyrazin-2-yl)-2-fluoro-N-((S)-1-(3-fluoro-5-iodophenyl)-2-hydroxyethyl)benzamide | 611.1 | 0.67 | 1H NMR (400 MHz, CD$_3$OD) δ ppm1.35-1.55 (m, 1H) 1.57-1.74 (m, 2H) 1.84-1.98 (m, 1H) 1.98-2.23 (m, 2H) 2.72-2.91 (m, 1H) 3.34-3.54 (m, 3H) 3.74-3.93 (m, 2H) 5.06-5.23 (m, 1H) 7.10-7.30 (m, 1H) 7.36-7.52 (m, 1H) 7.64 (s, 3 H) 7.78-7.95 (m, 2H) |

TABLE 5-continued

Compounds prepared using Method 3 described above.

| Example | Structure | Name | MH+ | R$_f$ (min) | NMR |
|---|---|---|---|---|---|
| 462 | 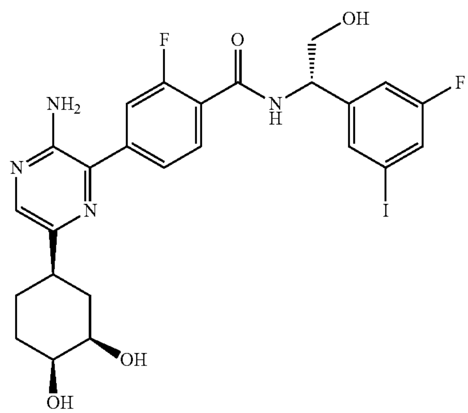 [SMILES: Nc1ncc([C@@H]2CC[C@H](O)[C@H](O)C2)nc1-c1ccc(C(=O)N[C@H](CO)c2cc(F)cc(I)c2)c(F)c1] | 4-(3-amino-6-((1R,3R,4S)-3,4-dihydroxy-cyclohexyl)pyrazin-2-yl)-2-fluoro-N-((S)-1-(3-fluoro-5-iodophenyl)-2-hydroxyethyl)benzamide | 611.1 | 0.67 | 1H NMR (400 MHz, CD$_3$OD) δ ppm 1.53-1.75 (m, 2H) 1.78-2.09 (m, 5H) 2.71-2.89 (m, 1H) 3.64-3.77 (m, 1H) 3.84 (s, 2H) 3.91-4.04 (m, 1H) 5.06-5.23 (m, 1H) 7.10-7.27 (m, 1H) 7.36-7.51 (m, 1H) 7.57-7.74 (m, 3H) 7.84 (s, 2H) |
| 463 | 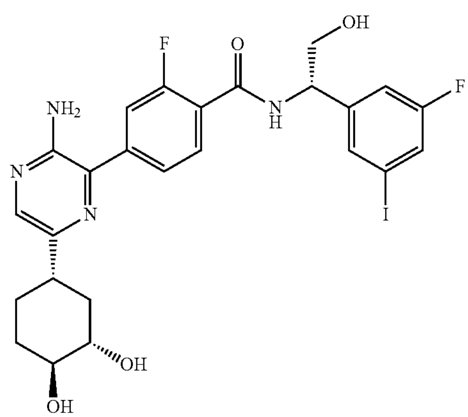 [SMILES: Nc1ncc([C@H]2CC[C@H](O)[C@@H](O)C2)nc1-c1ccc(C(=O)N[C@H](CO)c2cc(F)cc(I)c2)c(F)c1] | 4-(3-amino-6-((1S,3S,4S)-3,4-dihydroxy-cyclohexyl)pyrazin-2-yl)-2-fluoro-N-((S)-1-(3-fluoro-5-iodophenyl)-2-hydroxyethyl)benzamide | 611.1 | 0.67 | 1H NMR (400 MHz, CD$_3$OD) δ ppm 1.37-1.73 (m, 4H) 1.83-1.96 (m, 1H) 1.98-2.21 (m, 2H) 2.71-2.91 (m, 1H) 3.34-3.55 (m, 3H) 3.85 (s, 2H) 5.05-5.26 (m, 1H) 7.08-7.28 (m, 1H) 7.34-7.51 (m, 1H) 7.64 (s, 3H) 7.84 (s, 2H) |
| 464 | 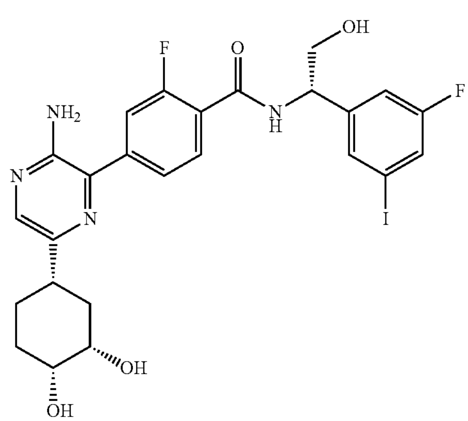 [SMILES: Nc1ncc([C@H]2CC[C@@H](O)[C@@H](O)C2)nc1-c1ccc(C(=O)N[C@H](CO)c2cc(F)cc(I)c2)c(F)c1] | 4-(3-amino-6-((1S,3S,4R)-3,4-dihydroxy-cyclohexyl)pyrazin-2-yl)-2-fluoro-N-((S)-1-(3-fluoro-5-iodophenyl)-2-hydroxyethyl)benzamide | 611.1 | 0.67 | 1H NMR (400 MHz, DMSO) δ ppm 0.72-0.91 (m, 2H) 0.96-1.25 (m, 5H) 1.89-2.05 (m, 1H) 2.81-2.95 (m, 1H) 3.03 (s, 2H) 3.09-3.21 (m, 1H) 4.25-4.42 (m, 1H) 6.30-8.47 (m, 1H) 6.55-6.69 (m, 1H) 8.77-6.94 (m, 3H) 7.03 (s, 2H) |

TABLE 5-continued

Compounds prepared using Method 3 described above.

| Example | Structure | Name | MH+ | R_f (min) | NMR |
|---|---|---|---|---|---|
| 465 | 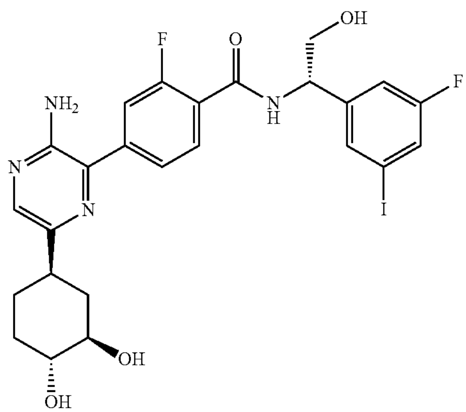 [SMILES: Nc1ncc([C@@H]2CC[C@@H](O)[C@H](O)C2)nc1-c1ccc(C(=O)N[C@H](CO)c2cc(F)cc(I)c2)c(F)c1] | 4-(3-amino-6-((1R,3R,4R)-3,4-dihydroxycyclohexyl)pyrazin-2-yl)-2-fluoro-N-((S)-1-(3-fluoro-5-bromophenyl)-2-hydroxyethyl)benzamide | 563..0 | 0.64 | 1H NMR (400 MHz, CD$_3$CN) δ ppm1.19-1.59 (m, 3H) 1.68-2.07 (m,4H) 3.13-3.39 (m, 4H) 3.62-3.88(m, 3H) 4.95-5.14 (m, 1H) 7.10(d, J = 9.78 Hz, 1H) 7.20 (dt, J = 8.31, 1.91 Hz, 1H) 7.29-7.74 (m, 5H) 7.86 (t, J = 8.02 Hz, 1H) |
| 466 | 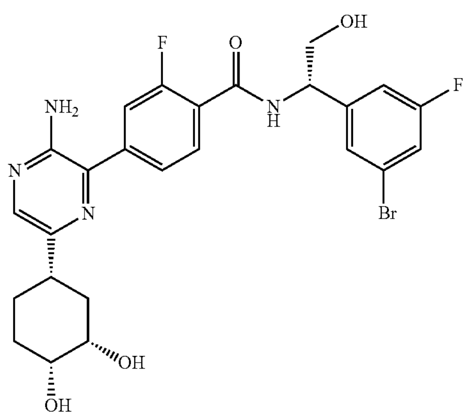 [SMILES: Nc1ncc([C@H]2CC[C@@H](O)[C@@H](O)C2)nc1-c1ccc(C(=O)N[C@H](CO)c2cc(F)cc(Br)c2)c(F)c1] | 4-(3-amino-6-((1S,3S,4R)-3,4-dihydroxycyclohexyl)pyrazin-2-yl)-2-fluoro-N-((S)-1-(3-fluoro-5-bromophenyl)-2-hydroxyethyl)benzamide | 563.0 | 0.64 | 1H NMR (400 MHz, CD$_3$CN) δ ppm 1.42-1.95 (m, 7H) 3.48-3.86 (m, 5H) 4.97-5.12 (m, 1H) 7.10 (d, J = 9.78 Hz, 1H) 7.20 (d, J = 8.22 Hz, 1H) 7.36 (s, 1H) 7.44-7.60 (m, 3 H) 7.68 (d, J = 5.09 Hz, 1H) 7.86 (t, J = 7.83 Hz, 1H) |
| 467 | 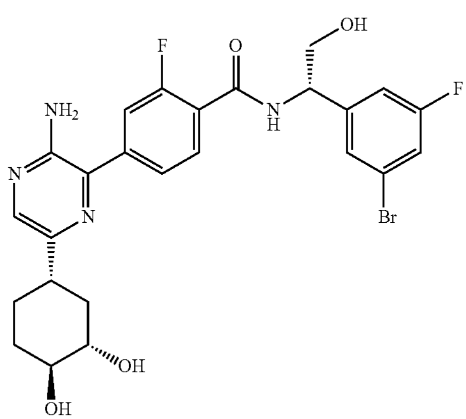 [SMILES: Nc1ncc([C@H]2CC[C@H](O)[C@@H](O)C2)nc1-c1ccc(C(=O)N[C@H](CO)c2cc(F)cc(Br)c2)c(F)c1] | 4-(3-amino-6-((1S,3S,4S)-3,4-dihydroxycyclohexyl)pyrazin-2-yl)-2-fluoro-N-((S)-1-(3-fluoro-5-bromophenyl)-2-hydroxyethyl)benzamide | 563.0 | 0.64 | 1H NMR (400 MHz, CD$_3$CN) δ ppm1 19-1.58 (m, 4H) 1.69-2.08 (m,5H) 2.65-2.79 (m, 5H) 3.12-3.36(m, 5H) 3.63-3.87 (m, 3H) 4.94-5.14 (m, 1H) 7.10 (d, J = 9.39 Hz, 1H) 7.15-7.26 (m, 1H) 7.36 (s, 1H) 7.42-7.70 (m, 3H) 7.79-7.95 (m, 1H) |

TABLE 5-continued

Compounds prepared using Method 3 described above.

| Example | Structure | Name | MH+ | R_f (min) | NMR |
|---|---|---|---|---|---|
| 468 | 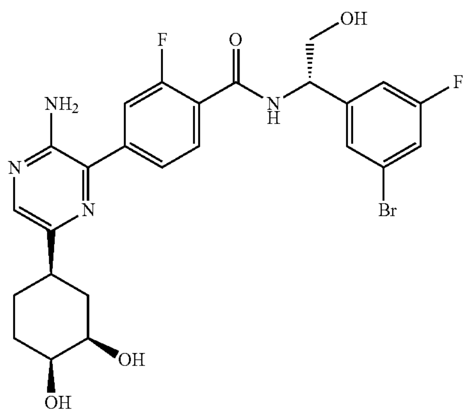 [SMILES: Nc1ncc([C@@H]2CC[C@H](O)[C@H](O)C2)nc1-c1ccc(C(=O)N[C@H](CO)c2cc(F)cc(Br)c2)c(F)c1] | 4-(3-amino-6-((1R,3R,4S)-3,4-dihydroxy-cyclohexyl)pyrazin-2-yl)-2-fluoro-N-((S)-1-(3-fluoro-5-bromophenyl)-2-hydroxyethyl)benzamide | 565.0 | 0.65 | 1H NMR (400 MHz, CD3CN) δ ppm 1.49-2.02 (m, 7H) 3.55-3.94 (m, 4H) 5.04-5.26 (m, 1H) 7.21 (d, J = 9.00 Hz, 1H) 7.30 (d, J = 7.83 Hz, 1H) 7.46 (s, 1H) 7.54-8.03 (m, 4H) |
| 469 | 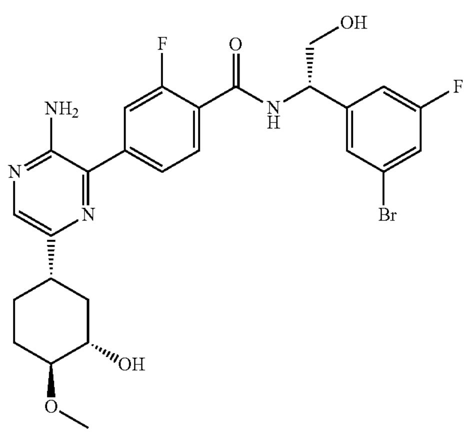 [SMILES: CO[C@H]1CC[C@H](c2cnc(N)c(-c3ccc(C(=O)N[C@H](CO)c4cc(F)cc(Br)c4)c(F)c3)n2)C[C@@H]1O] | 4-(3-amino-6-((1S,3S,4S)-3-hydroxy,4-methoxyl-cyclohexyl)pyrazin-2-yl)-2-fluoro-N-((S)-1-(3-fluoro-5-bromophenyl)-2-hydroxyethyl)benzamide | 579.0 | 0.71 | 1H NMR (400 MHz, CD3CN) δ ppm 1.18-1.35 (m, 2H) 1.49-1.68 (m, 3H) 1.86-2.00 (m, 5H) 2.04-2.15 (m, 3H) 2.17-2.25 (m, 3H) 2.72-2.89 (m, 2H) 2.94-3.08 (m, 2H) 3.41 (d, J = 1.17 Hz, 3H) 3.46-3.60 (m, 1H) 3.72-3.91 (m, 2H) 4.01-4.14 (m, 1H) 4.70 (t, J = 8.22 Hz, 1H) 5.03-5.24 (m, 2H) 7.14-7.26 (m, 1H) 7.27-7.35 (m, 1H) 7.47 (s, 1H) 7.56-7.74 (m, 2H) 7.82-8.03 (m, 2H) |
| 470 | 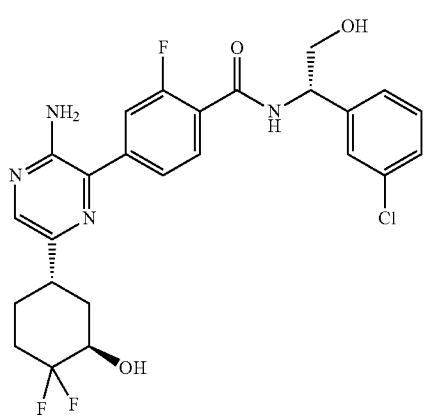 [SMILES: Nc1ncc([C@H]2CCC(F)(F)[C@H](O)C2)nc1-c1ccc(C(=O)N[C@H](CO)c2cccc(Cl)c2)c(F)c1] | 4-(3-amino-6-((1S,3R)-4,4-difluoro-3-hydroxy-cyclohexyl)pyrazin-2-yl)-N-((S)-1-(3-chlorophenyl)-2-hydroxyethyl)-2-fluorobenzamide | 521.1 | 0.76 | 1H NMR (400 MHz, CD3OD) δ ppm 1.16-1.28 (m, 1H) 1.75-1.98 (m, 4H) 2.07-2.28 (m, 2H) 2.83-3.06 (m, 2H) 3.86 (s, 3H) 4.03-4.19 (m, 1H) 5.11-5.27 (m, 1H) 7.21-7.32 (m, 1H) 7.35 (d, J = 6.26 Hz, 2H) 7.42-7.49 (m, 1H) 7.57-7.65 (m, 1H) 7.66-7.73 (m, 1H) 7.79-7.88 (m, 1H) 7.90 (s, 1H) |

TABLE 5-continued

Compounds prepared using Method 3 described above.

| Example | Structure | Name | MH+ | R$_t$ (min) | NMR |
|---|---|---|---|---|---|
| 471 | 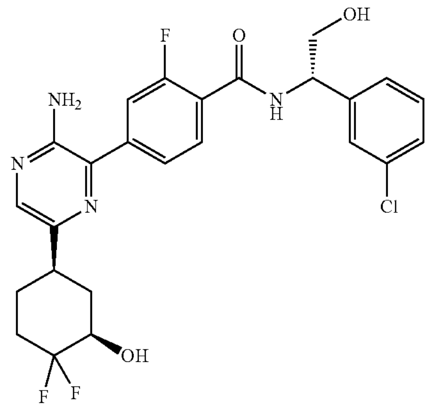 [SMILES: Nc1ncc([C@@H]2CCC(F)(F)[C@H](O)C2)nc1-c1ccc(C(=O)N[C@H](CO)c2cccc(Cl)c2)c(F)c1] | 4-(3-amino-6-((1R,3R)-4,4-difluoro-3-hydroxy-cyclohexyl)pyrazin-2-yl)-N-((S)-1-(3-chlorophenyl)-2-hydroxyethyl)-2-fluorobenzamide | 521.1 | 0.76 | 1H NMR (400 MHz, CD$_3$OD) δ ppm 1.07-1.37 (m, 3H) 1.74-2.12 (m, 5H) 2.12-2.41 (m, 3H) 3.04-3.24 (m, 3H) 3.75-3.90 (m, 2H) 3.92-4.05 (m, 2H) 5.10-5.27 (m, 2H) 7.35 (d, J = 6.65 Hz, 3H) 7.40-7.52 (m, 1H) 7.56-7.75 (m, 2H) 7.78-7.99 (m, 2H) |
| 472 | 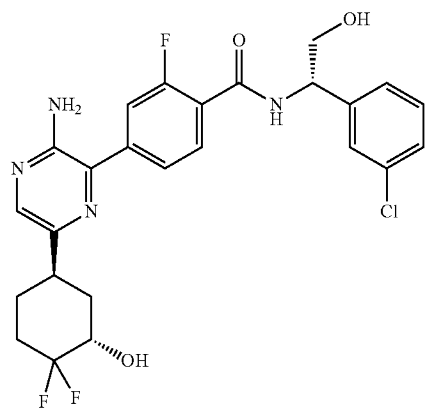 [SMILES: Nc1ncc([C@@H]2CCC(F)(F)[C@@H](O)C2)nc1-c1ccc(C(=O)N[C@H](CO)c2cccc(Cl)c2)c(F)c1] | 4-(3-amino-6-((1R,3S)-4,4-difluoro-3-hydroxy-cyclohexyl)pyrazin-2-yl)-N-((S)-1-(3-chlorophenyl)-2-hydroxyethyl)-2-fluorobenzamide | 521.1 | 0.76 | 1H NMR (400 MHz, CD$_3$OD) δ ppm 1.23 (s, 2H) 1.71-2.04 (m, 5H) 2.06-2.24 (m, 2H) 2.26-2.46 (m, 1H) 2.82-3.05 (m, 2H) 3.86 (t, J = 5.67 Hz, 3H) 4.01-4.18 (m, 1H) 5.19 (s, 2H) 7.18-7.41 (m, 3H) 7.46 (s, 1H) 7.70 (d, J = 0.78 Hz, 2H) 7.77-7.99 (m, 2H) |
| 473 | 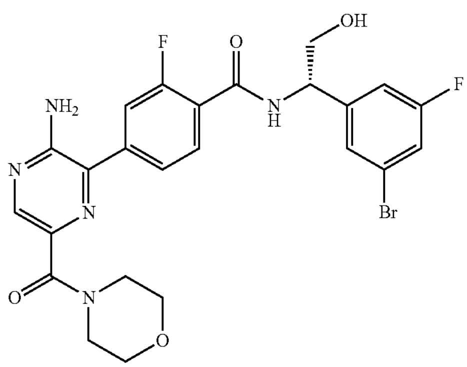 [SMILES: Nc1ncc(C(=O)N2CCOCC2)cc1-c1ccc(C(=O)N[C@H](CO)c2cc(F)cc(Br)c2)c(F)c1] | (S)-4-(3-amino-6-(morpholine-4-carbonyl)pyrazin-2-yl)-N-(1-(3-bromo-5-fluorophenyl)-2-hydroxyethyl)-2-fluorobenzamide | 563.9 | 0.71 | 1H NMR (500 MHz, ACETONITRILE-d3) δ ppm 3.56-3.99 (m, 13H) 5.06-5.23 (m, 1H) 5.78-6.13 (m, 2H) 7.22 (d, J = 8.20 Hz, 1H) 7.27-7.36 (m, 1H) 7.41-7.79 (m, 5H) 7.89-8.05 (m, 1H) 8.25-8.43 (m, 1H) |
| 474 | 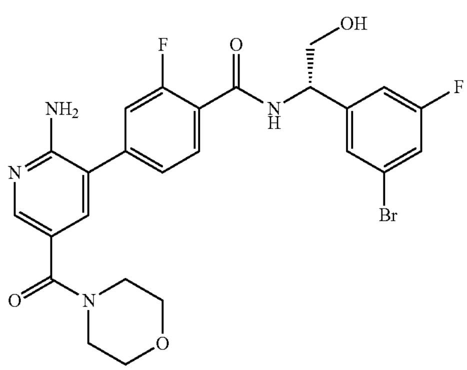 | (S)-4-(2-amino-5-(morpholine-4-carbonyl)pyridin-3-yl)-N-(1-(3-bromo-5-fluorophenyl)-2-hydroxyethyl)-2-fluorobenzamide | 562.9 | 0.63 | 1HNMR (500 MHz, ACETONITRILE-d3) δ ppm 3.49-3.74 (m, 7H) 3.77-3.94 (m, 2H) 5.15 (br. s., 1H) 7.15-7.52 (m, 5H) 7.62-7.83 (m, 2H) 7.92-8.07 (m, 2H) |

TABLE 5-continued

Compounds prepared using Method 3 described above.

| Example | Structure | Name | MH+ | R$_f$ (min) | NMR |
|---|---|---|---|---|---|
| 475 | 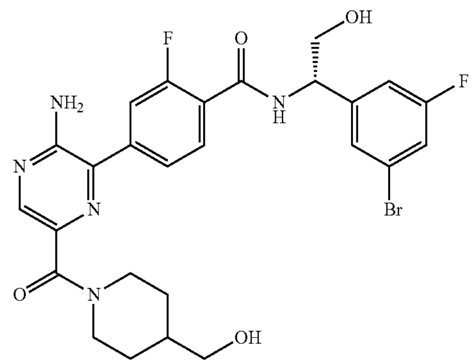 [SMILES: Nc1ncc(C(=O)N2CCC(CO)CC2)nc1-c1ccc(C(=O)N[C@H](CO)c2cc(F)cc(Br)c2)c(F)c1] | (S)-4-(3-amino-6-(4-(hydroxymethyl)piperidine-1-carbonyl)pyrazin-2-yl)-N-(1-(3-bromo-5-fluorophenyl)-2-hydroxyethyl)-2-fluorobenzamide | 592.0 | 0.68 | 1H NMR (500 MHz, ACETONITRILE-d3) δ ppm 1.12-1.36 (m, 2H) 1.60-1.87 (m, 4H) 2.71-2.92 (m, 2H) 2.98-3.22 (m, 1H) 3.39 (d, J = 5.99 Hz, 2H) 3.85 (dd, J = 18.29, 5.36 Hz, 2H) 4.12-4.36 (m, 1H) 4 48-4.68 (m, 1H) 5.04-5.25 (m, 1H) 5.58-5.82 (m, 2H) 7.15-7.26 (m, 1H) 7.31 (s, 1H) 7.47 (S, 1H) 7.54-7.73 (m. 3H) 7.97 (S, 1H) 8.23-8.38 (m, 1H) |
| 476 | 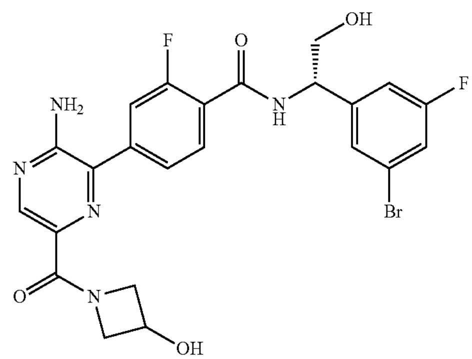 [SMILES: Nc1ncc(C(=O)N2CC(O)C2)nc1-c1ccc(C(=O)N[C@H](CO)c2cc(F)cc(Br)c2)c(F)c1] | (S)-4-(3-amino-6-(3-hydroxy-azetidine-1-carbonyl)pyrazin-2-yl)-N-(1-(3-bromo-5-fluorophenyl)-2-hydroxyethyl)-2-fluorobenzamide | 549.9 | 0.66 | 1H NMR (500 MHz, ACETONITRILE-d3) δ ppm 3.74-3.99 (m, 3H) 4.25-4.44 (m, 2H) 4.58 (ddd, J = 6.62, 4.10, 2.52 Hz, 1H) 4.81 (d, J = 7.25 Hz, 1H) 5.16 (d, J = 5.04 Hz, 1H) 5.89 (br. s., 2H) 7.22 (d, J = 9.77 Hz, 1H) 7.32 (dt, J = 8.20, 2.05 Hz, 1H) 7.48 (d, J = 1.26 Hz. 1H) 7.58-7.77 (m, 3H) 7.91-8.05 (m, 1H) 8.49-8.74 (m, 1H) |
| 477 | 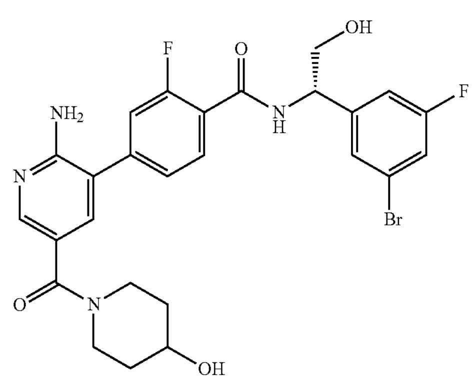 [SMILES: Nc1ncc(C(=O)N2CCC(O)CC2)cc1-c1ccc(C(=O)N[C@H](CO)c2cc(F)cc(Br)c2)c(F)c1] | (S)-4-(2-amino-5-(4-hydroxy-piperidine-1-carbonyl)pyridin-3-yl)-N-(1-(3-bromo-5-fluorophenyl)-2-hydroxyethyl)-2-fluorobenzamide | 577.0 | 0.59 | 1H NMR (500 MHz, ACETONITRILE-d3) δ ppm 1.32-1.57 (m, 2H) 1.74-1.89 (m, 3H) 3.29 (ddd, J = 13.16, 9.54, 3.15 Hz, 2H) 3.73-3.91 (m, 3H) 3.91-4.17 (m, 1H) 5.15 (d, J = 5.67 Hz, 1H) 7.12-7.52 (m, 4H) 7.68 (br. s., 1H) 7.80 (d, J = 1.89 Hz, 1H) 7.91-8.08 (m, 2H) |

Example 453
Synthesis of 4-(3-amino-6-((1R,3R)-3-hydroxycyclopentyl)pyrazin-2-yl)-2-fluoro-N-((S)-1-(3-fluoro-5-iodophenyl)-2-hydroxyethyl)benzamide
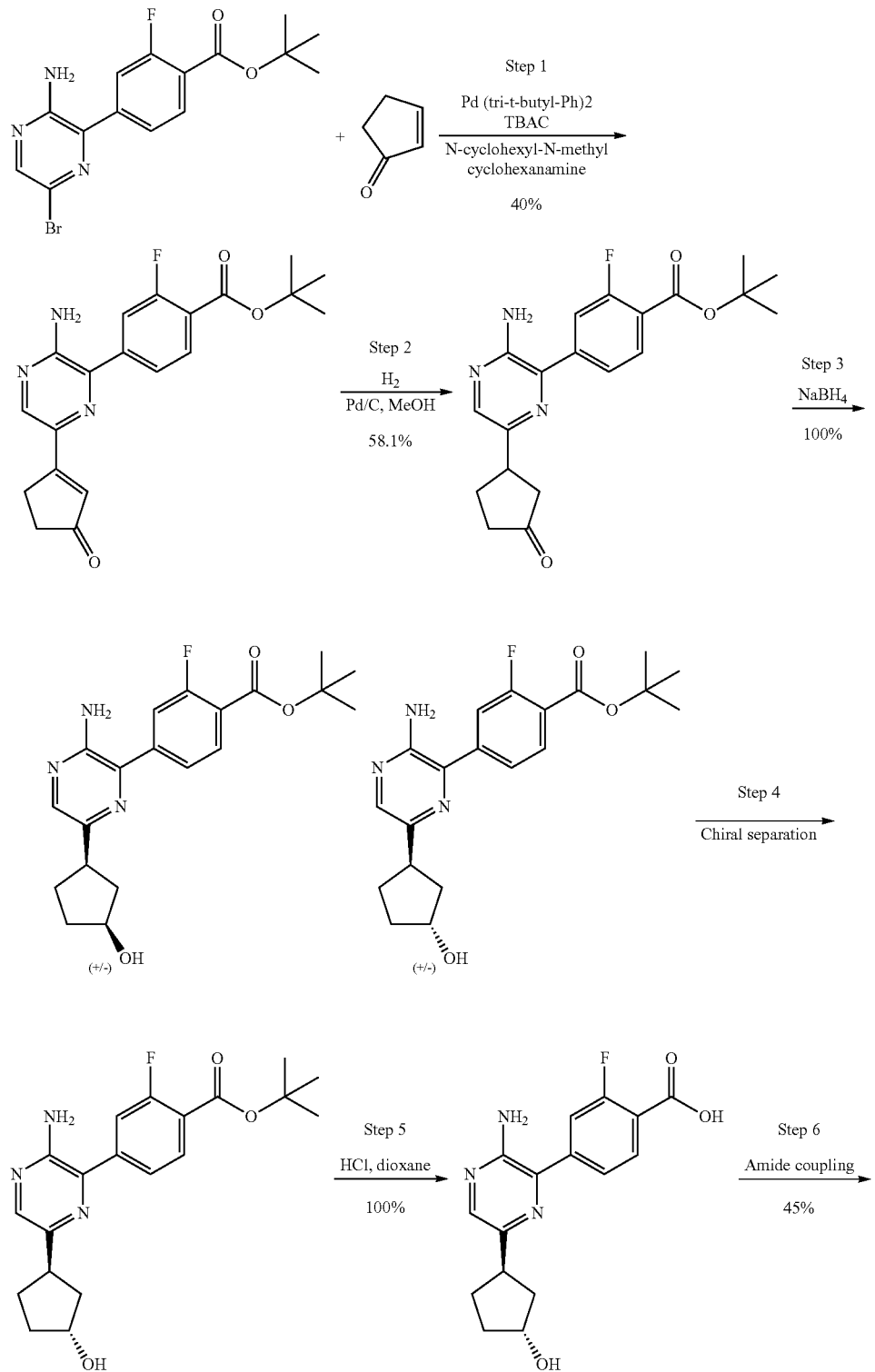

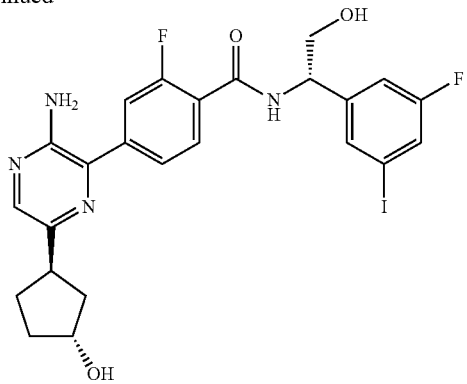

Step 1. tert-butyl 4-(3-amino-6-(3-oxocyclopent-1-en-1-yl)pyrazin-2-yl)-2-fluorobenzoate A mixture of tert-butyl 4-(3-amino-6-bromopyrazin-2-yl)-2-fluorobenzoate (1 g, 2.72 mmol), cyclopent-2-enone (0.892 g, 10.86 mmol), N-cyclohexyl-N-methylcyclohexanamine (1.061 g, 5.43 mmol), bis(tri-t-butylphosphine)palladium(0) (0.069 g, 0.136 mmol), TBAC (0.075 g, 0.272 mmol) in dioxane (7 mL) was microwaved at 135° C. for 25 min. After cooling, the mixture was concentrated and the residue was diluted with 10 ml of DCM, sonicated for 5 min, filtered and the solid was washed with 3 ml of DCM. The combined DCM solution was directly applied for ISCO silica column separation. (40 gram column, 10 to 90% EtOAc in Heptane). 400 mg of the desired product was obtained as a light yellow solid. LCMS (m/z): (MH$^+$) 370.0, 0.903 min. 1H NMR (400 MHz, DMSO) δ ppm 1.12-1.26 (m, 5 H) 1.55 (s, 10 H) 1.59-1.72 (m, 5 H) 2.41 (dt, J=5.09, 2.15 Hz, 3 H) 2.48 (dt, J=3.62, 1.91 Hz, 3 H) 3.00 (dd, J=5.09, 2.35 Hz, 2 H) 3.30 (s, 3 H) 6.66 (t, J=1.76 Hz, 1 H) 7.09 (s, H) 7.55-7.69 (m, H) 7.83-7.95 (m, 1 H) 8.57 (s, 1H).

Step 2: tert-butyl 4-(3-amino-6-(3-oxocyclopentyl)pyrazin-2-yl)-2-fluorobenzoate To tert-butyl 4-(3-amino-6-(3-oxocyclopent-1-en-1-yl)pyrazin-2-yl)-2-fluorobenzoate (650 mg, 1.760 mmol) in MeOH (15 ml) was added 15 ml of DCM under stirring until a clear solution was obtained. The solution was purged by nitrogen for 5 min, then Pd/C (300 mg, 10%, Degussa type) was added, and the resultant mixture was degassed by N$_2$ stream for 15 min. After equipped with hydrogen gas balloon, the reaction mixture was stirred at room temperature for 16 h. The reaction mixture was filtered, and the filtrated solution was concentrated, and the crude material was purified by ISCO. (24 g silica gel, 20 to 80% EtOAc in heptane) to afford 380 mg of the desired product as a light yellow solid. 58.1% yield. LC-MS (m/z): (MH$^+$) 372.1, 0.829 min.

Step 3: (+/−) tert-butyl 4-(3-amino-6-((1R,3R)-3-hydroxycyclopentyl)pyrazin-2-yl)-2-fluorobenzoate and (+/−)tert-butyl 4-(3-amino-6-((1R,3S)-3-hydroxycyclopentyl)pyrazin-2-yl)-2-fluorobenzoate To a solution of tert-butyl 4-(3-amino-6-(3-oxocyclopentyl)pyrazin-2-yl)-2-fluorobenzoate (200 mg, 0.538 mmol) in MeOH (4 mL) at −78° C. was added NaBH$_4$ (61.1 mg, 1.615 mmol). The reaction mixture was stirred at −78° C. for 1 hr. At −78° C., the reaction mixture was quenched with sat NH$_4$Cl (4 ml), and the cooling bath was removed, and the mixture was gradually warmed to RT, then sat NaHCO$_3$ solution (4 ml) was added. The reaction mixture was extracted with EtOAc (30 ml×2). The organic layer was washed with water and brine, dried over sodium sulfate, filtered off and concentrated in vacuo. About 210 mg of the crude product was obtained. The crude product was dissolved into 4 ml of DMSO, filtered and purified by prep HPLC. The more polar compound is trans (desired, came out earlier), the less polar compound is cis, came out later. After neutralized with 1N NaOH, tran and cis compound were obtained as free base compounds.

(+/−) tert-butyl 4-(3-amino-6-((1R,3R)-3-hydroxycyclopentyl)pyrazin-2-yl)-2-fluorobenzoate: 40 mg, 19.9% yield), trans. LC-MS (m/z): (MH$^+$) 374.1, 0.81 min, NMR (400 MHz, CD$_3$CN) δ ppm 1.61 (s, 9 H) 1.69-1.82 (m, 1 H) 1.88-2.25 (m, 6 H) 2.59-2.77 (m, 1 H) 3.32-3.56 (m, 1 H) 4.31-4.48 (m, 1 H) 5.07 (br. s., 2 H) 7.59 (dd, J=12.13, 1.56 Hz, 1 H) 7.66 (dd, J=8.02, 1.76 Hz, 1 H) 7.88-8.03 (m, 2 H).

(+/−) tert-butyl 4-(3-amino-6-((1R,3R)-3-hydroxycyclopentyl)pyrazin-2-yl)-2-fluorobenzoate: 150 mg, 74.6% yield, cis. LC-MS (m/z): (MH$^+$) 374.1, 0.81 min. 1H NMR (400 MHz, CD$_3$CN) δ ppm: 1.55-1.67 (m, 9 H) 1.69-1.89 (m, 2 H) 1.91-2.03 (m, 4 H) 2.05-2.13 (m, 1 H) 2.21-2.33 (m, 1 H) 3.21-3.41 (m, 1 H) 3.99 (s, 1 H) 4.20-4.34 (m, 1 H) 5.04-5.23 (m, 2 H) 7.50-7.58 (m, 1 H) 7.58-7.67 (m, 1 H) 7.90-8.05 (m, 2 H).

Step 4: tert-butyl 4-(3-amino-6-((1R,3R)-3-hydroxycyclopentyl)pyrazin-2-yl)-2-fluorobenzoate and tert-butyl 4-(3-amino-6-((1S,3S)-3-hydroxycyclopentyl)pyrazin-2-yl)-2-fluorobenzoate The two trans isomers (160 mg total) were separated by chiral column: OJ column (21×250 mm), SFC=100 ml/min, CO$_2$/EtOH=85/15, loading: 70 mg/7 ml EtOH, 274 bar. 80 mg of each enantiomer was obtained.

tert-butyl 4-(3-amino-6-((1R,3R)-3-hydroxycyclopentyl)pyrazin-2-yl)-2-fluorobenzoate: NMR (400 MHz, DMSO) δ ppm: 1.04 (t, J=6.85 Hz, 1 H) 1.47-1.73 (m, 11 H) 1.75-1.86 (m, 2 H) 1.89-2.18 (m, 2 H) 3.15 (s, 1 H) 3.30 (s, 4H) 3.97-4.16 (m, 1 H) 4.19-4.39 (m, 1 H) 4.44-4.59 (m, 1 H) 6.10 (s, 2 H) 7.57 (d, J=12.13 Hz, 1 H) 7.63 (dd, J=8.02, 1.76 Hz, 1 H) 7.77-8.01 (m, 2 H).

tert-butyl 4-(3-amino-6-((1S,3S)-3-hydroxycyclopentyl)pyrazin-2-yl)-2-fluorobenzoate: NMR (400 MHz, DMSO) δ ppm: 1.04 (t, J=6.85 Hz, 1 H) 1.14-1.28 (m, 1 H) 1.50-1.57 (m, 10 H) 1.59-1.71 (m, 1 H) 1.75-1.87 (m, 2 H) 1.89-2.14

(m, 2 H) 3.15 (s, 1 H) 3.30 (s, 4 H) 4.18-4.37 (m, 1 H) 4.42-4.55 (m, 1 H) 6.10 (s, 2 H) 7.51-7.60 (m, 1 H) 7.63 (dd, J=8.02, 1.76 Hz, 1 H) 7.81-7.95 (m, 2 H).

Step 5. 4-(3-amino-6-((1R,3R)-3-hydroxycyclopentyl)pyrazin-2-yl)-2-fluorobenzoic acid Procedure: To a solution of tert-butyl 4-(3-amino-6-((1R, 3R)-3-hydroxycyclopentyl)-pyrazin-2-yl)-2-fluorobenzoate (7 mg, 0.019 mmol) in DCM (2 mL) at RT was added TFA (0.361 mL, 4.69 mmol). The resultant solution was stirred at RT for 2 h. The solution was concentrated, and further dried by high vacuum to afford the desired product as a TFA slat, which was used at the next step directly. (6 mg, 100% yield) LC-MS (m/z): 318.1 (MH+), 0.46 min.

Step 6: 4-(3-amino-6-((1R,3R)-3-hydroxycyclopentyl)pyrazin-2-yl)-2-fluoro-N-((S)-1-(3-fluoro-5-iodophenyl)-2-hydroxyethyl)benzamide To a mixture of (4-(3-amino-6-((1R,3R)-3-hydroxycyclopentyl)pyrazin-2-yl)-2-fluorobenzoic acid) (6 mg, 0.019 mmol), (S)-2-amino-2-(3-fluoro-5-iodophenyl)ethanol (8.96 mg, 0.028 mmol), HOAt (5.15 mg, 0.038 mmol) and EDC (7.25 mg, 0.038 mmol) in DMF (1 ml) was added DIEA (0.036 ml, 0.208 mmol). The resultant mixture was stirred over night at RT. The mixture was diluted with EtOAc, washed with water three times and brine, dried with Na₂SO₄, filtered and concentrated to afford the crude product as a light yellow viscous liquid. This crude was purified by prep HPLC to afford desired product (6 mg, 45.2% yield) as a light yellow solid, a TFA salt. LC-MS: (MH+) 581.0 at 0.726 min. 1H NMR (400 MHz, CD₃CN) δ ppm 1.56-1.82 (m, 2 H) 2.01-2.30 (m, 3 H) 3.47 (t, J=8.61 Hz, 1 H) 3.73-3.92 (m, 3 H) 4.32-4.45 (m, 2 H) 5.05-5.19 (m, 1 H) 7.16-7.27 (m, 1 H) 7.48 (dt, J=8.12, 1.81 Hz, 1 H) 7.56-7.71 (m, 4 H) 7.74-7.81 (m, 1 H) 7.97 (t, J=7.83 Hz, 1 H).

Example 456

Synthesis of 4-(3-amino-6-((1S,4S)-3,3-difluoro-4-hydroxycyclohexyl)pyrazin-2-yl)-2-fluoro-N-((S)-1-(3-fluoro-5-iodophenyl)-2-hydroxyethyl)benzamide

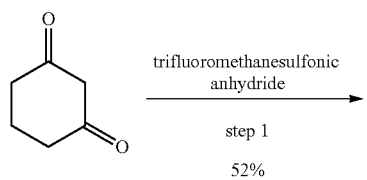

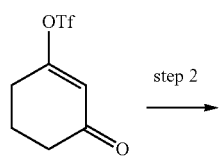

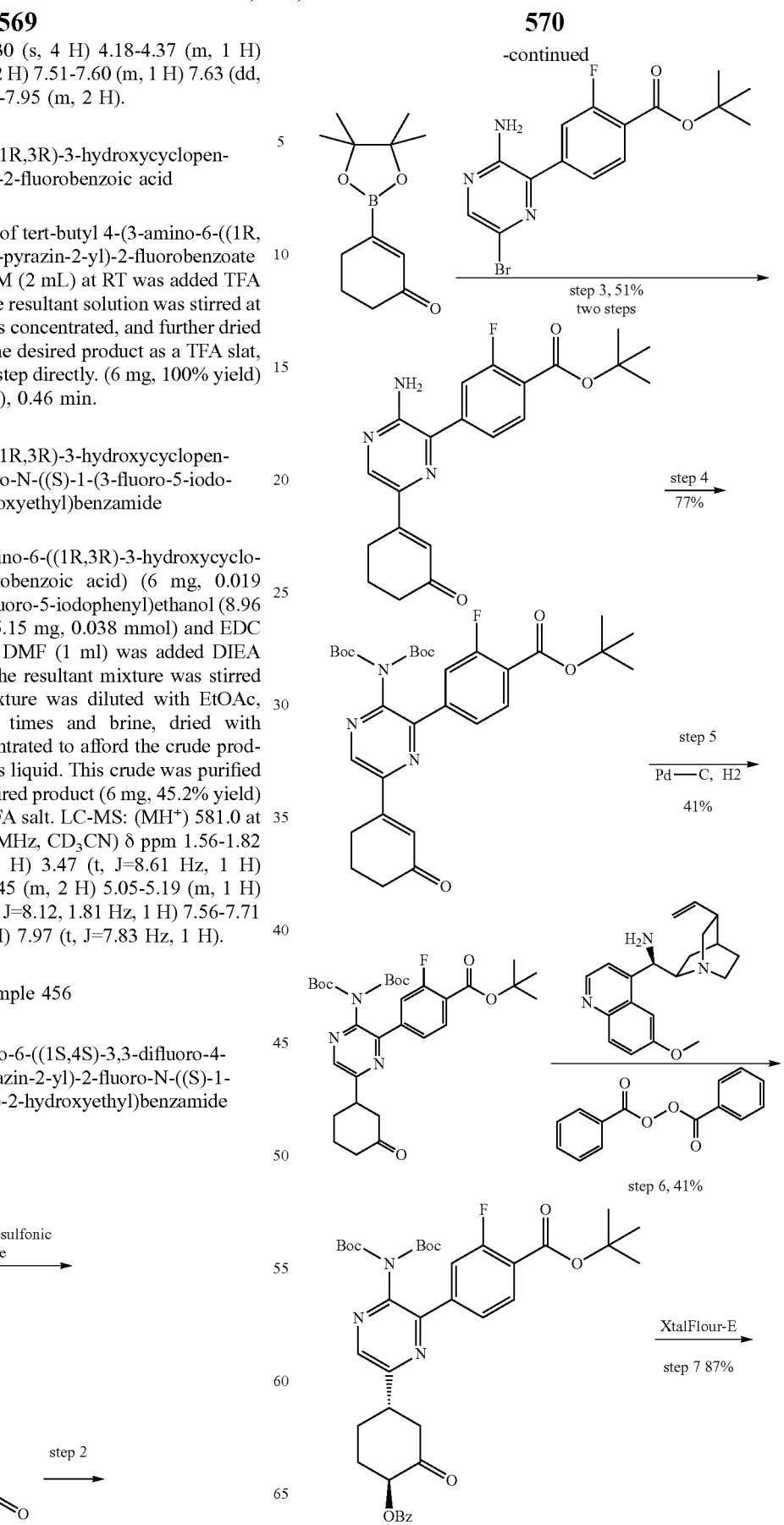

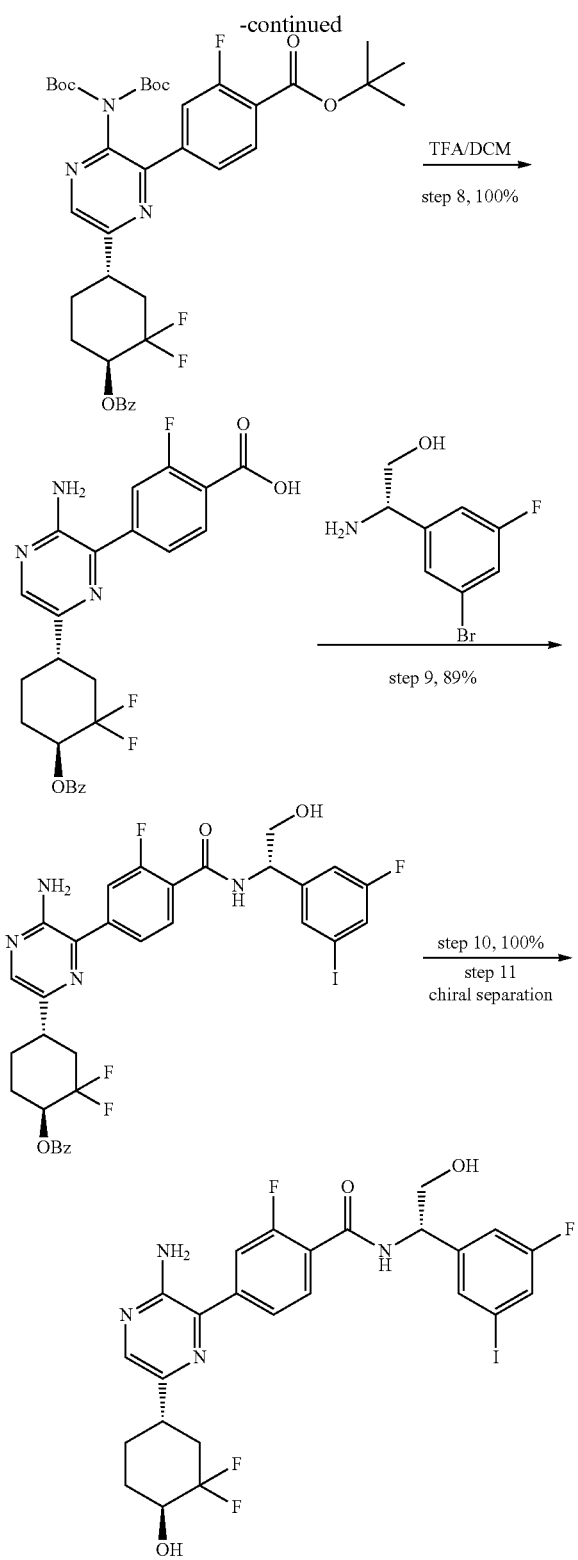

Step 1: 3-oxocyclohex-1-en-1-yl trifluoromethanesulfonate

To a solution of cyclohexane-1,3-dione (8 g, 71.3 mmol) in CH₂Cl₂ (120 ml) at 0° C. (ice water bath) under nitrogen was added sodium carbonate (8.32 g, 78 mmol). The resultant mixture was stirred at 0° C. for 10 min. A solution of trifluoromethanesulfonic anhydride (12.05 ml, 71.3 mmol) in 35 ml of DCM was added dropwise over 1 h. The mixture was stirred at 0° C. for 1.5 h. The mixture was filtered through fritted glass funnel, and 60 ml of saturated NaHCO₃ was added slowly. Organic layer was then separated and washed with 40 ml of brine, dried over Na₂SO₄, filtered and concentrated to provide 9 g (52% yield) of desired product as a light yellow liquid. LC-MS (m/z): (MH⁺) 244.9, 0.72 min.

Step 2: 3-(4,4,5,5-tetramethyl-1,3,2-dioxaborolan-2-yl)cyclohex-2-enone, (3-oxocyclohex-1-en-1-yl) boronic acid A mixture of 3-oxocyclohex-1-en-1-yl trifluoromethanesulfonate (9 g, 36.9 mmol), 4,4,4',4',5,5,5',5'-octamethyl-2,2'-bi(1,3,2-dioxaborolane) (14.04 g, 55.3 mmol), potassium acetate (10.85 g, 111 mmol) and Pd(dppf)Cl₂.DCM (0.808 g, 1.106 mmol) in dioxane (80 mL) was flushed with nitrogen for 5 min and then heated at 90° C. overnight. After cooling, the mixture was filtered, and the solid was washed with 3×20 mL warm dioxane. The combined solution was concentrated until about 70 ml of dioxan was left. This product (in dioxane) was used directly at the next step. LCMS (m/z): MH+=140.8 (Boronic acid), 0.284 min.

Step 3: Tert-butyl 4-(3-amino-6-(3-oxocyclohex-1-en-1-yl)pyrazin-2-yl)-2-fluorobenzoate A 250 ml RB was charged with 3-(4,4,5,5-tetramethyl-1,3,2-dioxaborolan-2-yl)cyclohex-2-enone (7.00 g, 31.5 mmol) (in about 70 ml dioxane), tert-butyl 4-(3-amino-6-bromopyrazin-2-yl)-2-fluorobenzoate (5.8 g, 15.75 mmol)), Pd(dppf)Cl₂.DCM (0.576 g, 0.788 mmol), and then Saturated Na₂CO₃ (25 mL). The resultant mixture was flushed with nitrogen for 15 min. DME (10 mL) was then added. The mixture was stirred at 100° C. overnight. Ethyl acetate (150 ml) and water (50 ml) were added, and the resultant mixture was stirred for 30 min. Organics was separated and the aqueous layer was extracted with ethyl acetate (30 ml×3). Organic layers were combined and dried over Na₂SO₄, filtered and evaporated to provide crude desired material as a sticky dark color semi solid. This solid was taken to about 30 ml of ether, sonicated for 10 min, and the precipitated yellow solid was filtered, and washed with cold ether (5 ml×3), dried under high vacuum to afford the desired product (3.1 g, 51.3%) as a yellow solid. LC-MS (m/z): (MH⁺) 384.2, 0.92 min.

Step 4: tert-butyl 4-(3-(bis(tert-butoxycarbonyl)amino)-6-(3-oxocyclohex-1-en-1-yl)pyrazin-2-yl)-2-fluorobenzoate To a suspension of tert-butyl 4-(3-amino-6-(3-oxocyclohex-1-en-1-yl)pyrazin-2-yl)-2-fluorobenzoate (3 g, 7.82 mmol) in acetonitrile (25 mL) at RT was added DMAP (0.048 g, 0.391 mmol) followed by Boc-anhydride (6.36 mL, 27.4 mmol). The resultant mixture was stirred at RT for 25 min. The solution was diluted with EtOAc, washed with sat NaHCO₃ and water, dried and concentrated. The crude product was purified by ISCO separation (80 g silica, 30 min, 5 to 60% EtOAc in Heptane). The desired product was obtained as a light yellow sticky liquid, which solidified upon standing over night. (3.5 g, 6.00 mmol, 77% yield). LC-MS (m/z): (MH⁺) 584.2, 1.286 min. 1 H NMR (400 MHz, ACETONITRILE-d3) δ ppm 0.91 (s, 1 H) 1.31 (s, 16

H) 1.61 (s, 7 H) 1.88-2.03 (m, 1 H) 2.16 (s, 2 H) 2.50 (d, J=7.04 Hz, 2H) 2.85-3.09 (m, 2 H) 6.90 (s, 1 H) 7.51-7.71 (m, 2 H) 7.91-8.11 (m, 1 H) 8.92 (s, 1 H).

Step 5: tert-butyl 4-(3-(bis-(tert-butoxycarbonyl)amino)-6-(3-oxocyclohexyl)pyrazin-2-yl)-2-fluorobenzoate To a solution of tert-butyl 4-(3-(bis(tert-butoxycarbonyl)amino)-6-(3-oxocyclohex-1-en-1-yl)pyrazin-2-yl)-2-fluorobenzoate (3 g, 5.14 mmol) in MeOH (15 mL) and DCM (10 mL) at RT was added PdC (10%, degauss, 1.094 g, 1.028 mmol). The resultant mixture was flushed with hydrogen for 10 min, then stirred at RT for 5 hours under hydrogen atmosphere. The suspension was filtered and the solution was concentrated. ISCO silica column separation (80 g silica, 30 min, 5 to 60% EtOAc in Heptane) afforded the desired product as a light yellow sticky liquid, which solidified upon standing over night. (1.485 g, 2.54 mmol, 49.3% yield). LC-MS (m/z): (MH$^+$) 586.3, 1.17 min.

Step 6: tert-butyl 4-(6-((1S,4S)-4-(benzoyloxy)-3-oxocyclohexyl)-3-(bis(tert-butoxycarbonyl)amino)pyrazin-2-yl)-2-fluorobenzoate and tert-butyl 4-(6-((1R,4R)-4-(benzoyloxy)-3-oxocyclohexyl)-3-(bis(tert-butoxycarbonyl)amino)pyrazin-2-yl)-2-fluorobenzoate A: Prep of the free base catalyst: 300 mg of (S)-(6-methoxyquinolin-4-yl)((1S,2R,4S,5R)-5-vinylquinuclidin-2-yl)methanamine (tri.HCl salt) was dissolved into 20 ml of DCM, then neutralized with 1N NaOH (5 ml), the organic layer was separated, washed with brine (5 ml×2) and water (5 ml×2), dried, filtered and concentrated to afford the product as a free base. (200 mg free base amine in 4 ml of dioxane).
B: A 10 mL microwave vial, equipped with a magnetic stirring bar, was charged with tert-butyl 4-(3-(bis-(tert-butoxycarbonyl)amino)-6-(3-oxocyclohexyl) pyrazin-2-yl)-2-fluorobenzoate (1.485 g, 2.54 mmol), BHT (Butylated hydroxyltoluene, 0.067 g, 0.304 mmol), (S)-(6-methoxyquinolin-4-yl)((1S,2R,4S,5R)-5-vinylquinuclidin-2-yl)methanamine (0.098 g, 0.304 mmol) (in 2 ml of Dioxane) and trichloroacetic acid (0.050 g, 0.304 mmol). Dioxane (1 ml) was then added, and the resultant mixture was stirred for 5 min before benzoic peroxyanhydride (0.983 g, 4.06 mmol) was added. The reaction mixture was stirred at 30° C. for 16 h. The reaction mixture was diluted with dichloromethane, treated with a saturated aqueous solution of NaHCO$_3$, washed with brine, dried over Na$_2$SO$_4$, filtered, concentrated to approx. 3 ml of DCM. The crude (in 3 ml of DCM) was purified by ISCO flash column chromatography eluting with a EtOAc in Heptane (10 to 45% EtOAc in Heptane, 120 g silica gel column, 35 min). The enantioselectivity could not be determined at this stage by chiral-phase HPLC analysis. No separations were observed by all the columns/methods available. This product was directly used in the next step reaction. (730 mg, 40.8% yield) LC-MS (m/z): (MH$^+$) 706.3 at 1.38 min. 1H NMR (400 MHz, CDCl$_3$) δ ppm 1.26-1.41 (m, 19 H) 1.46-1.67 (m, 11 H) 2.08-2.22 (m, 1 H) 2.26-2.42 (m, 2 H) 2.50-2.67 (m, 1 H) 2.70-2.91 (m, 1 H) 3.08 (s, 1 H) 3.26-3.49 (m, 1 H) 4.03-4.19 (m, 1 H) 5.49-5.67 (m, 1 H) 7.26 (d, J=0.78 Hz, 2 H) 7.40-7.66 (m, 5 H) 7.97 (t, J=7.83 Hz, 1 H) 8.07-8.19 (m, 2 H) 8.41 (s, 1 H).

Step 7: tert-butyl 4-(6-(4-(benzoyloxy)-3,3-difluorocyclohexyl)-3-(bis(tert-butoxycarbonyl)amino)pyrazin-2-yl)-2-fluorobenzoate To a solution of tert-butyl 4-(6-((1S,4S)-4-(benzoyloxy)-3-oxocyclohexyl)-3-(bis(tert-butoxycarbonyl)amino)pyrazin-2-yl)-2-fluorobenzoate (730 mg, 1.034 mmol) in DCM (7 mL) at RT was added XtalFlour-E (939 mg, 4.14 mmol) followed by triethylamine trihydrofluoride (0.674 mL, 4.14 mmol). The resultant mixture was stirred at RT for 5 hours. The mixture was filtered and the filtered solution was directly applied for ISCO separation: 24 g silica gel, 0 to 70% EtOAc in Heptane, 30 min. A light yellow solid (670 mg, 0.902 mmol, 87% yield) was obtained. LC-MS (m/z): (MH$^+$) 728.0 at 0.95 min (non-polar MS method). 1H NMR (400 MHz, CDCl$_3$) δ ppm 0.88 (s, 2 H) 1.19-1.39 (m, 21 H) 1.48-1.68 (m, 11 H) 1.86-2.08 (m, 2 H) 2.08-2.21 (m, 1 H) 2.26-2.47 (m, 2 H) 2.47-2.63 (m, 1 H) 3.21-3.44 (m, 1 H) 5.22-5.51 (m, 1 H) 7.41-7.55 (m, 4 H) 7.60 (s, 1 H) 7.96 (d, J=7.82 Hz, 1 H) 8.06-8.19 (m, 2H) 8.42 (s, 1 H).

Step 8: 4-(3-amino-6-(4-(benzoyloxy)-3,3-difluorocyclohexyl)pyrazin-2-yl)-2-fluorobenzoic acid To a solution of tert-butyl 4-(6-(4-(benzoyloxy)-3,3-difluorocyclohexyl)-3-(bis(tert-butoxycarbonyl)amino)pyrazin-2-yl)-2-fluorobenzoate (670 mg, 0.921 mmol) in DCM (12 mL) at RT was added TFA (4.96 mL, 64.4 mmol). The resultant mixture was stirred at RT for 2 hours. The mixture was concentrated, diluted with EtOAc, neutralized with NaHCO$_3$ twice, then brine, the organic layer was separated, dried and concentrated to afford the crude product, which was used at the next step directly. (434 mg, 0.921 mmol, 100% yield). LC-MS (m/z): (MH$^+$) 472.1, at 0.942 min. 1H NMR (400 MHz, DMSO) δ ppm: 1.07 (t, J=7.04 Hz, 2 H) 1.83 (t, J=10.17 Hz, 2 H) 2.16 (d, J=5.09 Hz, 1 H) 2.29-2.45 (m, 2 H) 3.02 (br. s., 1H) 3.16-3.44 (m, 9 H) 5.22-5.52 (m, 1 H) 5.73 (s, 1 H) 6.24 (s, 2 H) 7.44-7.75 (m, 5 H) 7.89 (t, J=7.83 Hz, 1 H) 7.94-8.07 (m, 3 H).

Step 9: 4-(5-amino-6-(3-fluoro-4-(((S)-1-(3-fluoro-5-iodophenyl)-2-hydroxyethyl)carbamoyl)phenyl)pyrazin-2-yl)-2,2-difluorocyclohexyl benzoate, 4-(5-amino-6-(3-fluoro-4-(((S)-1-(3-fluoro-5-iodophenyl)-2-hydroxyethyl)carbamoyl)phenyl)pyrazin-2-yl)-2,2-difluorocyclohexyl benzoate To a mixture of 4-(3-amino-6-(4-(benzoyloxy)-3,3-difluorocyclohexyl)pyrazin-2-yl)-2-fluorobenzoic acid (434 mg, 0.92 mmol) (4-(3-amino-6-((4R)-4-(benzoyloxy)-3,3-difluorocyclohexyl)pyrazin-2-yl)-2-fluorobenzoic acid), (S)-2-amino-2-(3-fluoro-5-iodophenyl)ethanol (320 mg, 1.012 mmol), HOAt (250 mg, 1.840 mmol) and EDC (353 mg, 1.840 mmol) in DMF (5 mL) was added DIEA (1.607 mL, 9.20 mmol). The resultant mixture was stirred over night at RT. The mixture was diluted with EtOAc, washed with water three times and brine, dried, concentrated to afford the crude product as a light yellow viscous liquid.
After ISCO purification (24 g silica, 10 to 80% EtOAc in heptane, 35 min), the desired product was obtained as a light yellow liquid, which contains two possible isomers. (601 mg, 0.818 mmol, 89% yield) LC-MS (m/z): (MH$^+$) 735.0 at 1.09 min. 1H NMR (400 MHz, CDCl$_3$) δ ppm 1.71 (br. s., 1 H) 1.80-2.00 (m, 2 H) 2.18-2.39 (m, 2 H) 2.39-2.52 (m, 1 H) 2.53-2.70 (m, 1 H) 3.13 (br. s., 1 H) 3.82-4.07 (m, 2 H) 4.78 (s, 2 H) 5.23 (d, J=5.09 Hz, 2 H) 7.02-7.16 (m, 1 H)

7.31-7.39 (m, 1 H) 7.41-7.50 (m, 2 H) 7.50-7.76 (m, 5 H) 7.87-8.03 (m, 2H) 8.07-8.23 (m, 3H).

Step 10: 4-(3-amino-6-(3,3-difluoro-4-hydroxycyclohexyl)pyrazin-2-yl)-2-fluoro-N-((S)-1-(3-fluoro-5-iodophenyl)-2-hydroxyethyl)benzamide To 4-(5-amino-6-(3-fluoro-4-(((S)-1-(3-fluoro-5-iodophenyl)-2-hydroxyethyl)carbamoyl)phenyl)pyrazin-2-yl)-2,2-difluorocyclohexyl benzoate (600 mg, 0.817 mmol) in MeOH (8 ml), THF (8 ml) and Water (8 ml) at RT was added LiOH.H$_2$O (206 mg, 4.90 mmol). The resultant mixture was stirred at 25° C. for 2 hours. The reaction mixture was concentrated and to the residue was added 30 ml of EtOAc, washed with water (10 ml×3), dried, filtered, and concentrated to afford the crude product as a light yellow sticky liquid, which became an off white solid after overnight standing. (515 mg, 100% yield). LC-MS (m/z): (MH$^+$) 631.1 at 0.771 min.

Step 11: 4-(3-amino-6-((1S,4S)-3,3-difluoro-4-hydroxycyclohexyl)pyrazin-2-yl)-2-fluoro-N-((S)-1-(3-fluoro-5-iodophenyl)-2-hydroxyethyl)benzamide The compound obtained from step 10 was purified by chiral separation column (OJ column (21×250 mm), SFC=100 ml/min, CO$_2$/EtOH=85/15, loading: 70 mg/7 ml EtOH, 274 bar) to afford two chiral pure compounds: 4-(3-amino-6-((1S,4S)-3,3-difluoro-4-hydroxycyclohexyl)pyrazin-2-yl)-2-fluoro-N-((S)-1-(3-fluoro-5-iodophenyl)-2-hydroxyethyl)benzamide (255 mg, 27.8% yield). 1H NMR (400 MHz, DMSO) δ ppm 1.46-1.69 (m, 2 H) 1.71-2.26 (m, 4 H) 2.79-3.02 (m, 1 H) 3.58-3.83 (m, 2 H) 4.94-5.15 (m, 2 H) 5.25-5.45 (m, 1 H) 6.11-6.26 (m, 1 H) 7.19-7.34 (m, 1 H) 7.46-7.56 (m, 1 H) 7.56-7.66 (m, 2 H) 7.66-7.77 (m, 1 H) 7.95 (s, 1 H) 8.66-8.79 (m, 1H).

4-(3-amino-6-((1R,4R)-3,3-difluoro-4-hydroxycyclohexyl)pyrazin-2-yl)-2-fluoro-N-((S)-1-(3-fluoro-5-iodophenyl)-2-hydroxyethyl)benzamide (53 mg, 5.77% yield). 1H NMR (400 MHz, DMSO) δ ppm 1.15-1.30 (m, 1 H) 1.48-1.69 (m, 2 H) 1.72-2.25 (m, 5 H) 2.77-2.97 (m, 2 H) 3.57-3.84 (m, 3 H) 4.92-5.14 (m, 2 H) 5.27-5.42 (m, 1 H) 6.10-6.24 (m, 2 H) 7.16-7.34 (m, 1 H) 7.46-7.57 (m, 1 H) 7.57-7.67 (m, 2 H) 7.67-7.77 (m, 1 H) 7.95 (s, 1H) 8.63-8.80 (m, 1 H).

Example 473

Synthesis of (S)-4-(3-amino-6-(morpholine-4-carbonyl)pyrazin-2-yl)-N-(1-(3-bromo-5-fluorophenyl)-2-hydroxyethyl)-2-fluorobenzamide

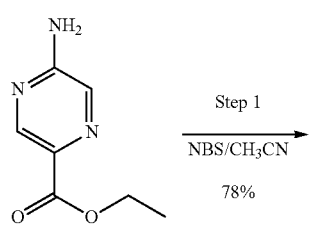

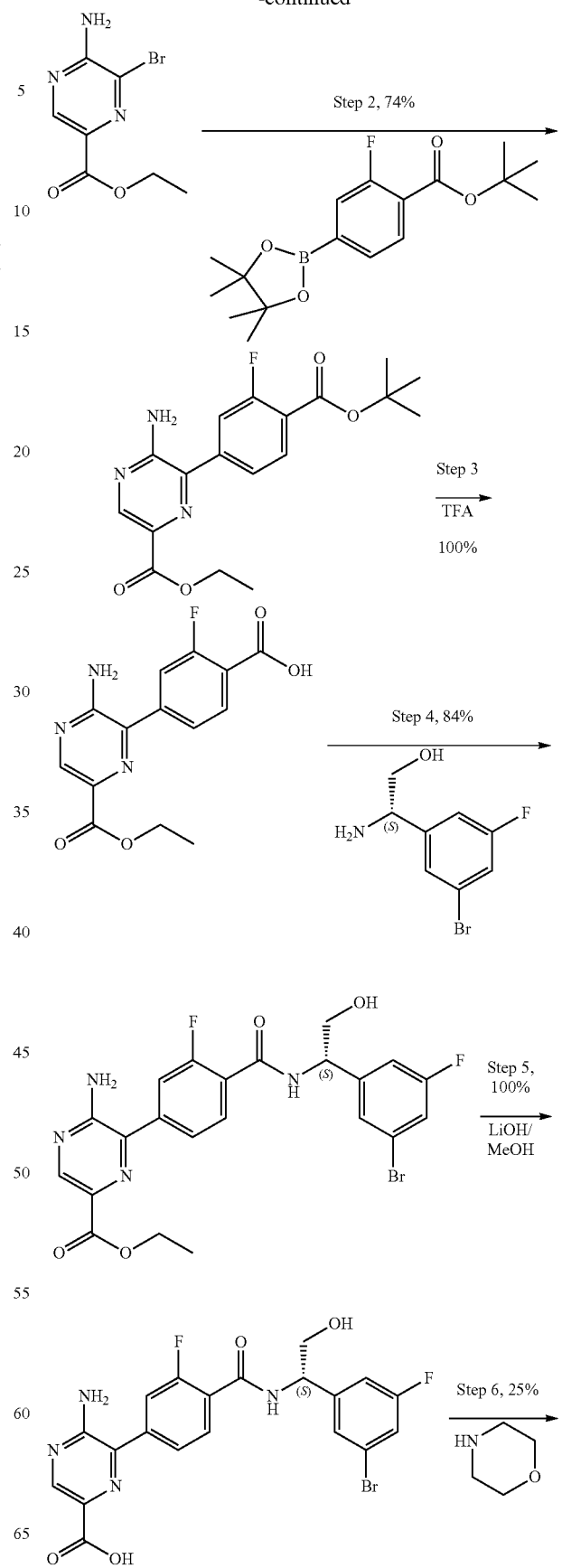

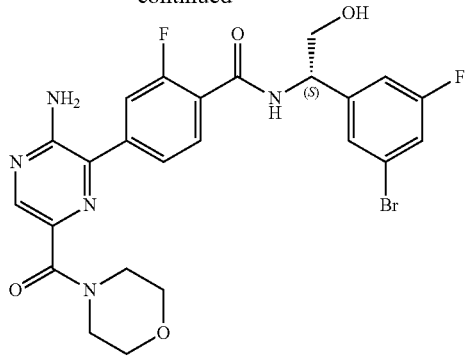

Step 1: Ethyl 5-amino-6-bromopyrazine-2-carboxylate

To a solution of ethyl 5-aminopyrazine-2-carboxylate (880 mg, 5.26 mmol) in acetonitrile (20 mL) at RT was added NBS (984 mg, 5.53 mmol), the resultant solution was stirred at RT for 1 hour. The reaction mixture was diluted with EtOAc, washed with sat NaHCO$_3$, brine and water, dried, filtered, and concentrated to afford the crude product, which was purified by ISCO (24 g silica gel column, 0 to 50% EtOAc in Heptane, 30 min). 1.01 g, 78% yield. LC-MS (m/z): 247.9 (MH$^+$), 0.51 min.

Step 2: Ethyl 5-amino-6-(4-(tert-butoxycarbonyl)-3-fluorophenyl)pyrazine-2-carboxylate A mixture of ethyl 5-amino-6-bromopyrazine-2-carboxylate (210 mg, 0.853 mmol), tert-butyl 2-fluoro-4-(4,4,5,5-tetramethyl-1,3,2-dioxaborolan-2-yl)benzoate (357 mg, 1.109 mmol), PdCl$_2$(dppf).CH$_2$Cl$_2$ adduct (69.7 mg, 0.085 mmol) and Na$_2$CO$_3$ (362 mg, 3.41 mmol) (2M solution was used) in DME (5 mL) was placed into a 20 ml vial and sealed. The mixture was microwaved for 15 min at 110° C. The mixture was diluted with EtOAc, washed with water twice and brine, dried, filtered, and concentrated to afford the crude as a light yellow solid. The crude product was purified by ISCO (12 g, 10-55% EtOAc in heptane, 30 min) to afford 228 mg (74% yield) of light yellow solid. LC-MS (m/z): 362.1 (MH$^+$), 0.89 min.

Step 3: 4-(3-amino-6-(ethoxycarbonyl)pyrazin-2-yl)-2-fluorobenzoic acid

To a solution of ethyl 5-amino-6-(4-(tert-butoxycarbonyl)-3-fluorophenyl)pyrazine-2-carboxylate (0.253 g, 0.7 mmol) in DCM (4 mL) at RT was added TFA (2.157 mL, 28.0 mmol). The resultant solution was stirred at RT for 2 hours. The reaction solution was concentrated and further dried to afford the crude desired product as a TFA salt. This product was directly used at the next step. 0.214 g (100% yield) of light sticky liquid was obtained. LC-MS (m/z): 306.1 (MH$^+$), 0.563 min.

Step 4: (S)-ethyl 5-amino-6-(4-((1-(3-bromo-5-fluorophenyl)-2-hydroxyethyl)carbamoyl)-3-fluorophenyl)pyrazine-2-carboxylate To a mixture of 4-(3-amino-6-(ethoxycarbonyl)pyrazin-2-yl)-2-fluorobenzoic acid (0.214 g, 0.7 mmol), (S)-2-amino-2-(3-bromo-5-fluorophenyl)ethanol (272 mg, 1.009 mmol), HOAt (187 mg, 1.376 mmol) and EDC (264 mg, 1.376 mmol) in DMF (2.5 mL) was added DIEA (0.961 mL, 5.50 mmol). The resultant mixture was stirred over night at RT. The mixture was diluted with EtOAc, washed with water three times and brine, dried, concentrated to afford the crude product as a light yellow viscous liquid. ISCO purification (12 g silica, 10 to 90% EtOAc in heptane, 30 min) provided the desired product (200 mg, 84% yield) as a light yellow liquid. LC-MS (m/z): 522.9 (MH$^+$), 0.787 min.

Step 5: (S)-5-amino-6-(4-((1-(3-bromo-5-fluorophenyl)-2-hydroxyethyl)carbamoyl)-3-fluorophenyl)pyrazine-2-carboxylic acid A mixture of (S)-ethyl 5-amino-6-(4-((1-(3-bromo-5-fluorophenyl)-2-hydroxyethyl)carbamoyl)-3-fluorophenyl)pyrazine-2-carboxylate (220 mg, 0.422 mmol) and LiOH.H2O (142 mg, 3.38 mmol) in MeOH (2 ml), THF (2 mL) and Water (2 mL) was stirred for 3 hours at RT. The mixture was concentrated, to the residue was added 2 ml of water, 3N HCl was then added under stirring until the final pH was about 4. The resultant mixture was then concentrated and further dried to afford the crude product was a light yellow solid. (208 mg, 0.422 mmol, 100% yield). LC-MS (m/z): 494.9 (MH$^+$), 0.653 min.

Step 6: (S)-4-(3-amino-6-(morpholine-4-carbonyl)pyrazin-2-yl)-N-(1-(3-bromo-5-fluorophenyl)-2-hydroxyethyl)-2-fluorobenzamide To a mixture of (S)-5-amino-6-(4-((1-(3-bromo-5-fluorophenyl)-2-hydroxyethyl)carbamoyl)-3-fluorophenyl)pyrazine-2-carboxylic acid (40 mg, 0.081 mmol), morpholine (28.3 mg, 0.324 mmol), HOAt (33.1 mg, 0.243 mmol) and EDC (46.6 mg, 0.243 mmol) in DMF (0.5 mL) was added DIEA (0.170 mL, 0.973 mmol). The resultant mixture was stirred over night at RT. The mixture was diluted with EtOAc, washed with water three times and brine, dried, concentrated to afford the crude product as a light yellow viscous liquid. The crude product was dissolved into 1.5 ml of DMSO, filtered, and was purified by prep HPLC. (14 mg, 25.3% yield). LC-MS (m/z): 563.9 (MH$^+$), 0.707 min. 1H NMR (500 MHz, ACETONITRILE-d3) δ ppm 3.56-3.99 (m, 13 H) 5.06-5.23 (m, 1 H) 5.78-6.13 (m, 2 H) 7.22 (d, J=8.20 Hz, 1 H) 7.27-7.36 (m, 1 H) 7.41-7.79 (m, 5 H) 7.89-8.05 (m, 1 H) 8.25-8.43 (m, 1 H).

Example 478a and 478b 4-(3-amino-6-((R)-6-oxopiperidin-3-yl)pyrazin-2-yl)-2-fluoro-N-((S)-1-(3-fluoro-5-iodophenyl)-2-hydroxyethyl)benzamide (Example 478a) and 4-(3-amino-6-((S)-6-oxopiperidin-3-yl) pyrazin-2-yl)-2-fluoro-N-((S)-1-(3-fluoro-5-iodophenyl)-2-hydroxyethyl)benzamide (Example 478b)

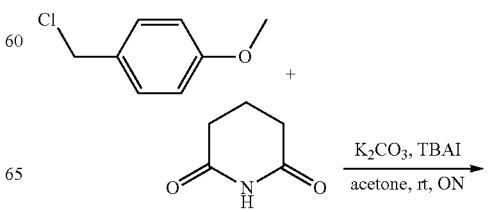

-continued

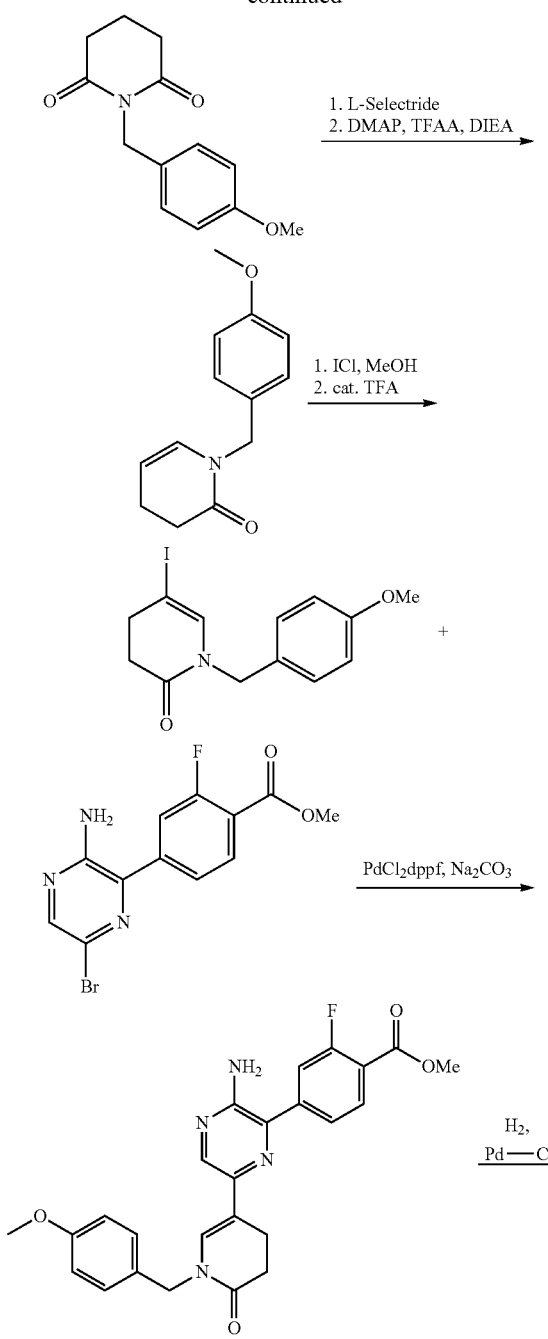

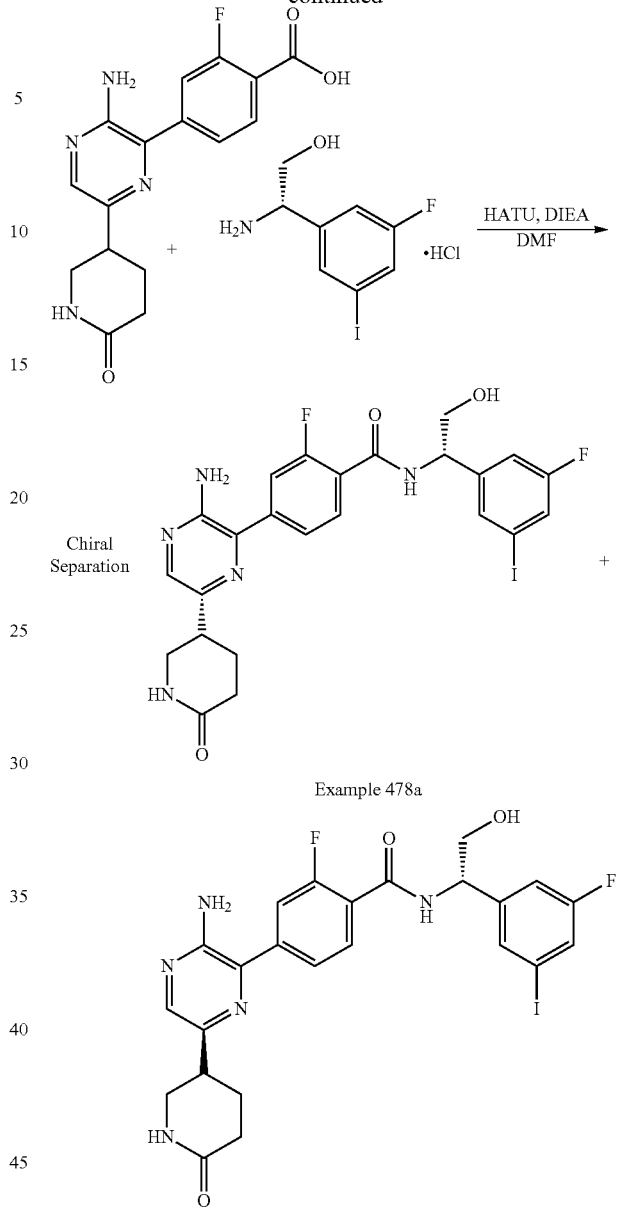

Example 478a

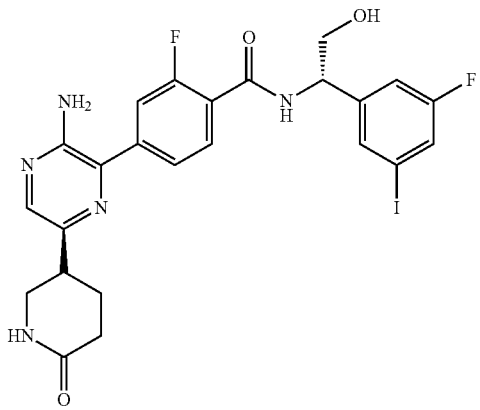

Example 478b 1-(4-methoxybenzyl)piperidine-2,6-dione: Glutarimide (5 g, 44.2 mmol) was suspended in acetone (Volume: 100 mL) and then K₂CO₃ (12.22 g, 88 mmol), Bu₄NI (3.27 g, 8.84 mmol) and 4-methoxybenzyl chloride (6.02 mL, 44.2 mmol) were added. The mixture was agitated at room temperature overnight and filtered through celite and then concentrated in vacuo and the residue purified by flash chromatography (0-50% EtOAc/heptane) to afford 8.99 g of the desired product as a colorless solid. LCMS (m/z): (MH⁺), 234.2, 0.66 min.

1-(4-methoxybenzyl)-3,4-dihydropyridin-2(1H)-one:
1-(4-methoxybenzyl)piperidine-2,6-dione (8.99 g, 38.5 mmol) was dissolved in Toluene (Volume: 128 ml) and cooled to −78° C. L-Selectride (42.4 ml, 42.4 mmol) was added dropwise and the mixture agitated for 1 h. After 1 h, thick slurry along with precipitate observed. Reaction mixture was briefly pulled outside cooling bath to homogenize the mixture. Then DMAP (0.047 g, 0.385 mmol) was added in one portion and then DIEA (38.4 ml, 220 mmol) was added and then TFAA (6.53 ml, 46.2 mmol) was added. Then the cooling flask was removed and the mixture agitated at room temperature for 2 h and then quenched with water and the product extracted with EtOAc. The combined organic layer was dried (MgSO$_4$), filtered and concentrated in vacuo to afford crude residue which was purified by flash chromatography to afford 7.66 g of the desired product as a yellow syrup. LCMS (m/z): (MH$^+$), 234.2, 0.73 min.

5-iodo-1-(4-methoxybenzyl)-3,4-dihydropyridin-2(1H)-one: 1-(4-methoxybenzyl)-3,4-dihydropyridin-2(1H)-one (2 g, 9.21 mmol) was dissolved in MeOH (90 mL) and cooled to −78° C. ICl (13.81 ml, 13.81 mmol) was added slowly and the mixture agitated for 1 h and then Sat'd Na$_2$S$_2$O$_3$ was added and the mixture was agitated until room temperature was observed. The solvent was evaporated in vacuo. The residue was dissolved in DCM and washed with Sat'd Na$_2$S$_2$O$_3$ and then with water and dried (MgSO$_4$), filtered and concentrated in vacuo. The residue was dissolved in toluene (40 mL) and treated with Trifluoroacetic acid (100 uL) and heated immediately to 145° C. for 15 min and then cooled to 0° C. and ET$_3$N (5 mL) was added. The mixture was agitated for 1 h and concentrated in vacuo and then the residue purified by flash chromatography (0-20% EtOAc/heptane) to afford the desired product as a gummy syrup. LCMS (m/z): (MH$^+$), 344.1, 0.88 min.

Methyl 4-(3-amino-6-(1-(4-methoxybenzyl)-6-oxo-1,4,5,6-tetrahydropyridin-3-yl)pyrazin-2-yl)-2-fluorobenzoate: 5-iodo-1-(4-methoxybenzyl)-3,4-dihydropyridin-2(1H)-one (630 mg, 1.836 mmol), PdCl$_2$(dppf).CH$_2$Cl$_2$ adduct (150 mg, 0.184 mmol), methyl 4-(3-amino-6-bromopyrazin-2-yl)-2-fluorobenzoate (1028 mg, 2.75 mmol) and Na$_2$CO$_3$ (2754 μl, 5.51 mmol) were combined in a flask and then DME (Volume: 6120 μl) was added. The mixture was degassed and purged with nitrogen and then finally heated at 90° C. for 2 h upon which complete consumption of starting material was observed. The reaction mixture was diluted with EtOAc and water and the organic layer was separated and dried (MgSO$_4$), filtered and concentrated in vacuo and the residue purified by flash chromatography (0-60% EtOAc/DCM) to afford 361 mg of the desired product as a yellow solid. LCMS (m/z): (MH$^+$), 463.1, 0.88 min.

Methyl 4-(3-amino-6-(6-oxopiperidin-3-yl)pyrazin-2-yl)-2-fluorobenzoate: Methyl 4-(3-amino-6-(1-(4-methoxybenzyl)-6-oxo-1,4,5,6-tetrahydropyridin-3-yl)pyrazin-2-yl)-2-fluorobenzoate (361 mg, 0.781 mmol) was dissolved in MeOH (Volume: 7 mL) and then PdC (400 mg, 3.76 mmol) was added. The mixture was evacuated and purged with hydrogen thrice and finally, the mixture was agitated under 1 atm of hydrogen overnight. The next morning, desired product along with over-reduced amino-pyrazine was obtained. The mixture was filter over celite and the filtrate concentrated in vacuo and the residue dissolved in DCM and agitated under air for 1 day and then concentrated and purified by flash chromatography (0-50% DCM/EtOAc) to afford 144 mg the desired product as a yellow solid. LCMS (m/z): (MH$^+$), 465.1, 0.81 min.

4-(3-Amino-6-(6-oxopiperidin-3-yl)pyrazin-2-yl)-2-fluorobenzoic acid: Methyl 4-(3-amino-6-(6-oxopiperidin-3-yl)pyrazin-2-yl)-2-fluorobenzoate (144 mg, 0.310 mmol) was dissolved in TFA (Volume: 3 mL) and heated at 150° C. for 30 min in microwave The solvent was evaporated in vacuo and the residue was azeotroped with toluene thrice to afford the crude debenzylated lactam. This crude product was dissolved in THF (Volume: 3 mL, Ratio: 3) and MeOH (Volume: 1.500 mL, Ratio: 1.5) and to the mixture was added LiOH (0.037 g, 1.550 mmol) dissolved in Water (Volume: 1.500 mL, Ratio: 1.5). The mixture was agitated at room temperature for 30 min and concentrated in vacuo and the residue neutralized with 2 mL (4.0 N HCl) and the solvent evaporated. The residue was azeotroped once with THF and once with toluene to afford the crude acid which was taken to the next step (assuming quantitative yield) without any further purification.

LCMS (m/z): (MH$^+$), 331.2, 0.44 min.

4-(3-Amino-6-(6-oxopiperidin-3-yl)pyrazin-2-yl)-2-fluoro-N-((S)-1-(3-fluoro-5-iodophenyl)-2-hydroxyethyl)benzamide: 4-(3-Amino-6-(6-oxopiperidin-3-yl) pyrazin-2-yl)-2-fluorobenzoic acid (41.0 mg, 0.124 mmol), DIEA (0.108 mL, 0.620 mmol) and HATU (94 mg, 0.248 mmol) were combined in DMF (1.0 mL) and then (S)-2-amino-2-(3-fluoro-5-iodophenyl)ethanol (39.4 mg, 0.124 mmol) was added. The mixture was agitated at room temperature for 1 h and then subjected directly to purification by reverse-phase HPLC to afford the title compound as TFA adduct. The solid obtained upon lyophilization was dissolved in MeOH and passed through basic carbonate containing silica cartridge and the filtrate was concentrated in vacuo to afford 28.5 mg of the mixture of diastereomer. The residue was purified by chiral SFC to provide the two diastereomers:

Diastereomer 1 (Example 478a): 4-(3-amino-6-((R)-6-oxopiperidin-3-yl)pyrazin-2-yl)-2-fluoro-N-((S)-1-(3-fluoro-5-iodophenyl)-2-hydroxyethyl)benzamide (8.8 mg). $^1$H NMR (CD$_3$OD): 7.88 (s, 1H), 7.75 (t, J=7.8 Hz, 1H), 7.48-7.64 (m, 3H), 7.34 (d, J=7.4 Hz, 1H), 7.11 (d, J=9.8 Hz, 1H), 5.05 (t, J=5.7 Hz, 1H), 3.67-3.83 (m, 2H), 3.43 (d, J=7.8 Hz, 2H), 3.00-3.15 (m, 1H), 2.28-2.46 (m, 2H), 1.88-2.16 (m, 2H); LCMS (m/z): (MH$^+$), 594.1, 0.71 min.

Diastereomer 2 (Example 478b): 4-(3-amino-6-((R)-6-oxopiperidin-3-yl)pyrazin-2-yl)-2-fluoro-N-((S)-1-(3-fluoro-5-iodophenyl)-2-hydroxyethyl)benzamide (8.2 mg)$^1$H NMR (CD$_3$OD): 7.89 (s, 1H), 7.75 (t, J=7.6 Hz, 1H), 7.50-7.65 (m, 3H), 7.35 (d, J=7.8 Hz, 1H), 7.12 (d, J=9.8 Hz, 1H), 5.06 (t, J=5.7 Hz, 1H), 3.65-3.89 (m, 2H), 3.37-3.53 (m, 2H), 2.96-3.16 (m, 1H), 2.31-2.59 (m, 2H), 1.88-2.20 (m, 2H); LCMS (m/z): (MH$^+$), 594.1, 0.71 min.

Biological Activity

Inhibition of ERK1 and ERK2 was measured using the following methods.

Activated ERK2 (20 pM) Kinase Assay:

Compound potency against activated ERK2 was determined using a kinase assay that measures ERK2-catalyzed phosphorylation of biotinylated ERKtide peptide substrate ([Biotin]-AHA-K-R-E-L-V-E-P-L-T-P-S-G-E-A-P-N-Q-A-L-L-R-[NH2], the peptide sequence derived from EGF receptor: SEQ ID NO:1). The assay was carried out in 20 mM HEPES [pH 7.5], 5 mM MgCl2, 1 mM DTT, 0.01% Tween-20, 0.05% BSA using 0.02 nM ERK2, 400 nM ERKtide peptide and 35 μM ATP (all concentrations are final in the reaction) in a total volume of 10.25 μL. A 16-point, half-log dilution series of compounds at 41× final concentration was used for generating IC50 curves. Compound dilution series were prepared in 100% DMSO. ERK2 was preincubated with compounds for 30 minutes at ambient temperature. Reaction was initiated by addition of a substrate cocktail of ERKtide peptide and ATP and was allowed to proceed for 4 hours at ambient temperature. Reaction was terminated by addition of 10 μL of a 2× stop buffer consisting of 100 mM Tris-Cl [pH 7.5], 25 mM EDTA, 0.01% Tween 20, 20 μg/mL of AlphaScreen Protein A Acceptor Beads, 20 μg/mL of Streptavidin Donor Beads (PerkinElmer, Waltham, Mass.), and 1:1000 dilution phospho- EGF Receptor (Thr669) antibody (Cat #8808, Cell Signaling Technology, Danvers, Mass.). Terminated reactions were read, after overnight incubation in the dark, on an EnVision Multilabel Plate Reader (PerkinElmer, Waltham, Mass.), with excitation and emission wavelengths set to 680 nm and 570 nm, respectively. IC50 values were determined using a four-parameter fit.

The following assay conditions (ERK2 New) were used for some compounds in the following Table, and provide substantially similar IC50s to the assay described above, for IC50 about 0.1 µM or above. When the limitation of this assay was reached, the assay described above was used.

Compound potency against activated ERK2 is determined using a kinase assay that measures ERK2-catalyzed phosphorylation of biotinylated ERKtide peptide substrate ([Biotin]-AHA-K-R-E-L-V-E-P-L-T-P-S-G-E-A-P-N-Q-A-L-L-R- [NH2], the peptide sequence derived from EGF receptor: SEQ ID NO:1). The assay is carried out in 50 mM HEPES [pH 7.5], 5 mM MgCl2, 1 mM DTT, 0.01% Tween-20, 0.05% BSA using 0.25 nM ERK2, 200 nM ERKtide peptide and 35 µM ATP (all concentrations are final in the reaction) in a total volume of 10.25 µL. A 16-point, half-log dilution series of compounds at 41× final concentration is used for generating IC50 curves. Compound dilution series are prepared in 100% DMSO. ERK2 is preincubated with compounds for 30 minutes at ambient temperature. Reaction is initiated by addition of a substrate cocktail of ERKtide peptide and ATP and is allowed to proceed for 2-3 hours at ambient temperature. Reaction is terminated by addition of 10 µL of a 2× stop buffer consisting of 100 mM Tris-Cl [pH 7.5], 25 mM EDTA, 0.01% Tween 20, 10 µg/mL of AlphaScreen Protein A Acceptor Beads, 10 µg/mL of Streptavidin Donor Beads (PerkinElmer, Waltham, Mass.), and 1.4 µg/mL phospho-EGF Receptor (Thr669) antibody (Cat #3056, Cell Signaling Technology, Danvers, Mass.). Terminated reactions are read, after overnight incubation in the dark, on an EnVision Multilabel Plate Reader (PerkinElmer, Waltham, Mass.), with excitation and emission wavelengths set to 680 nm and 570 nm, respectively. IC50 values are determined using a four-parameter fit.

Activated ERK1 Kinase Assay:

Compound potency against activated ERK1 was determined using a kinase assay that measures ERK1-catalyzed phosphorylation of biotinylated ERKtide peptide substrate ([Biotin] -AHA-K-R-E-L-V-E-P-L-T-P-S-G-E-A-P-N-Q-A-L-L-R- [NH2], the peptide sequence derived from EGF receptor: SEQ ID NO:1). The assay was carried out in 20 mM HEPES [pH 7.5], 5 mM MgCl2, 1 mM DTT, 0.01% Tween-20, 0.05% BSA using 0.2 nM ERK1, 200 nM ERKtide peptide and 45 µM ATP (all concentrations are final in the reaction) in a total volume of 10.25 µL. A 16-point, half-log dilution series of compounds at 41× final concentration was used for generating IC50 curves. Compound dilution series were prepared in 100% DMSO. ERK1 was preincubated with compounds for 30 minutes at ambient temperature. Reaction was initiated by addition of a substrate cocktail of ERKtide peptide and ATP and was allowed to proceed for 4 hours at ambient temperature. Reaction was terminated by addition of 10 µL of a 2× stop buffer consisting of 100 mM Tris-Cl [pH 7.5], 25 mM EDTA, 0.01% Tween 20, 10 µg/mL of AlphaScreen Protein A Acceptor Beads, 10 µg/mL of Streptavidin Donor Beads (PerkinElmer, Waltham, Mass.), and 1.4 µg/mL phospho-EGF Receptor (Thr669) antibody (Cat #3056, Cell Signaling Technology, Danvers, Mass.). Terminated reactions were read, after overnight incubation in the dark, on an EnVision Multilabel Plate Reader (PerkinElmer, Waltham, Mass.), with excitation and emission wavelengths set to 680 nm and 570 nm, respectively. IC50 values were determined using a four-parameter fit.

All IC50s are presented in scientific notation where 'E' indicates the power of 10; for example, 1.63E-03 represents $1.63 \times 10^{-3}$, or 0.00163.

| Example | ERK2 New (µM) | ERK2 (20 pM) (µM) | ERK2 Alphascreen (µM) |
|---|---|---|---|
| 1 | 1.63E-03 | | 1.06E-03 |
| 2 | | | 1.92E-01 |
| 3 | 1.23E+01 | | |
| 4 | 3.15E-01 | | |
| 5 | 2.78E-01 | | |
| 6 | 3.54E-01 | | |
| 7 | 6.52E-02 | | |
| 8 | 4.12E-03 | | |
| 9 | 3.57E-03 | | |
| 10 | 1.21E-02 | | |
| 11 | 3.77E-03 | | |
| 12 | 3.96E-02 | | |
| 13 | 3.61E-01 | | |
| 14 | 1.27E-02 | | |
| 15 | 2.35E-01 | | |
| 16 | 2.06E-01 | 1.97E-01 | |
| 17 | 6.44E-02 | 2.97E-02 | |
| 18 | | 3.96E-05 | |
| 19 | 6.03E+00 | | |
| 20 | 1.09E+00 | | |
| 21 | 2.67E+00 | | |
| 22 | 5.81E-01 | | |
| 23 | 3.93E-01 | | |
| 24 | 4.53E-01 | | |
| 25 | 3.43E-04 | | |
| 26 | 3.27E-03 | | |
| 27 | 4.10E-03 | 1.87E-03 | |
| 28 | 2.55E-03 | 1.20E-03 | |
| 29 | 7.52E-02 | | |
| 30 | 6.95E-02 | 2.25E-02 | |
| 31 | 7.40E-02 | 3.20E-02 | |
| 32 | 2.43E-02 | | |
| 33 | 1.82E-02 | 1.32E-02 | |
| 34 | 7.13E-03 | 3.98E-03 | |
| 35 | 1.09E-03 | | |
| 36 | 1.60E-03 | | |
| 37 | 1.05E-03 | | |
| 38 | 8.09E-03 | | |
| 39 | 2.48E-03 | 1.30E-03 | |
| 40 | 2.46E-03 | 1.26E-03 | |
| 41 | 5.10E-02 | | |
| 42 | 5.44E-03 | | |
| 43 | 5.32E-03 | | |
| 44 | 4.77E-03 | | |
| 45 | 3.61E-03 | | |
| 46 | 4.79E+00 | | |
| 47 | 8.18E-04 | | |
| 48 | 1.22E-01 | | |
| 49 | 4.59E-02 | | |
| 50 | 8.39E-03 | | |
| 51 | 2.70E-02 | | |
| 52 | 3.03E-02 | | 3.12E-02 |
| 53 | 1.23E-02 | | |
| 54 | 1.07E-01 | | |
| 55 | | 1.39E-04 | |
| 56 | 3.89E-03 | | |
| 57 | 1.14E-03 | | |
| 58 | 3.61E-03 | | |
| 59 | 3.50E-04 | | |
| 60 | 1.24E-02 | | |
| 61 | 1.24E-03 | | |
| 62 | 6.41E-02 | | |
| 63 | 2.33E-02 | | |
| 64 | | 4.36E-03 | 3.64E-03 |
| 65 | | 6.84E-04 | 1.84E-03 |
| 66 | | 4.18E-02 | 5.53E-02 |
| 67 | | 6.77E-02 | 8.55E-02 |
| 68 | 3.14E-01 | | 2.14E-01 |

| Example | ERK2 New (μM) | ERK2 (20 pM) (μM) | ERK2 Alphascreen (μM) |
|---|---|---|---|
| 69 | | 1.00E−02 | 1.60E−02 |
| 70 | | 3.31E−01 | 5.74E−01 |
| 71 | | 8.78E−03 | 1.72E−02 |
| 72 | 1.77E−01 | | |
| 73 | | 1.29E−03 | 3.08E−03 |
| 74 | | 2.03E−02 | 3.76E−02 |
| 75 | 1.22E+00 | | 1.16E+00 |
| 76 | | 3.04E−03 | 5.24E−03 |
| 77 | | 5.08E−02 | 9.76E−02 |
| 78 | 1.72E−01 | | |
| 79 | 3.24E−02 | | 3.33E−02 |
| 80 | | 5.10E−04 | 5.84E−04 |
| 81 | 4.87E−04 | 1.63E−04 | 1.66E−04 |
| 82 | | 9.00E−04 | 2.13E−03 |
| 83 | 7.52E−04 | | 5.74E−04 |
| 84 | | 2.05E−03 | 9.64E−03 |
| 85 | | 1.31E−03 | 2.06E−02 |
| 86 | | 3.75E−03 | 4.78E−03 |
| 87 | | 2.09E−01 | 2.66E−01 |
| 88 | | 7.05E−02 | 8.14E−02 |
| 89 | | 2.02E−02 | 9.80E−03 |
| 90 | | 3.30E−02 | 4.90E−02 |
| 91 | | 2.84E−01 | 5.59E−01 |
| 92 | | 1.35E−01 | 2.67E−01 |
| 93 | | 5.05E−01 | 8.87E−01 |
| 94 | | 8.79E−04 | 9.14E−04 |
| 95 | | 1.36E−04 | 5.33E−04 |
| 96 | | 8.46E−02 | 9.13E−02 |
| 97 | 2.33E−01 | | 1.10E−01 |
| 98 | | 1.58E−02 | 2.63E−02 |
| 99 | 1.21E−02 | | |
| 100 | 7.76E−03 | | |
| 101 | 7.69E−02 | | |
| 102 | 9.17E−02 | | |
| 103 | 3.16E−02 | | |
| 104 | 1.91E−01 | | |
| 105 | | 2.56E−03 | |
| 106 | | 1.28E−03 | |
| 107 | 1.16E−03 | | |
| 108 | 9.77E−03 | | |
| 109 | 5.81E−03 | | |
| 110 | 1.00E+00 | | |
| 111 | 3.08E−02 | | |
| 112 | 1.41E−01 | | |
| 113 | 7.80E−01 | | |
| 114 | 1.24E−01 | | |
| 115 | 2.74E−01 | | |
| 116 | 1.89E−02 | 9.42E−03 | |
| 117 | 4.79E−03 | | |
| 118 | 1.76E−02 | | |
| 119 | 5.49E−04 | | |
| 120 | 1.35E−03 | 5.36E−04 | |
| 121 | 3.40E−04 | 2.17E−04 | |
| 122 | | 7.38E−03 | 1.10E−02 |
| 123 | 5.93E−04 | | |
| 124 | 6.26E−02 | | |
| 125 | 2.23E+00 | | |
| 126 | 1.69E−01 | | |
| 127 | 2.43E−04 | 6.04E−05 | |
| 128 | 8.35E−04 | | |
| 129 | 2.02E−03 | | |
| 130 | 1.66E−03 | | |
| 131 | 9.92E−02 | | |
| 132 | 8.13E−04 | | |
| 133 | | 1.87E−05 | |
| 134 | 2.02E−01 | | |
| 135 | | 6.31E−04 | |
| 136 | 4.51E−03 | | |
| 137 | 3.10E−02 | | |
| 138 | 1.33E−02 | | |
| 139 | 7.95E−03 | | |
| 140 | 1.41E−03 | | |
| 141 | 1.83E−04 | | |
| 142 | | 2.10E−04 | 2.01E−04 |
| 143 | | 3.64E−04 | 2.65E−04 |
| 144 | 1.18E−03 | | |
| 145 | 7.33E−03 | | |
| 146 | 3.39E−03 | | |
| 147 | 4.54E−02 | | |
| 148 | 1.90E−03 | | |
| 149 | 1.49E−04 | | |
| 150 | | 9.37E−05 | |
| 151 | 1.15E−04 | 2.33E−05 | |
| 152 | 1.45E−04 | 4.10E−05 | |
| 153 | 3.80E−04 | | |
| 154 | 2.88E−04 | | |
| 155 | 1.89E−03 | | |
| 156 | 3.32E−03 | | |
| 157 | 4.16E−04 | | |
| 158 | 6.34E−04 | | |
| 159 | 3.14E−03 | | |
| 160 | 6.53E−04 | | |
| 161 | 5.78E−03 | | |
| 162 | 4.87E−04 | | |
| 163 | 5.14E−03 | | |
| 164 | 1.40E−03 | | |
| 165 | 3.90E−01 | | |
| 166 | | 2.45E−05 | |
| 167 | 9.98E−04 | | |
| 168 | 5.13E−03 | | |
| 169 | 1.41E−03 | | |
| 170 | 1.58E−03 | | |
| 171 | 1.09E−03 | | |
| 172 | 1.58E−04 | 7.85E−05 | |
| 173 | | | 7.58E−04 |
| 174 | | 2.10E−05 | |
| 175 | | 2.85E−05 | |
| 176 | | 2.82E−05 | |
| 177 | | 2.29E−05 | |
| 178 | | 2.11E−04 | |
| 179 | | 6.12E−06 | |
| 180 | | 6.71E−06 | |
| 181 | | 1.19E−05 | |
| 182 | | 5.10E−05 | |
| 183 | | 5.71E−05 | |
| 184 | | 2.61E−05 | |
| 185 | | 9.24E−04 | |
| 186 | | 6.53E−04 | |
| 187 | | 3.63E−05 | |
| 188 | | 4.69E−05 | |
| 189 | | 1.39E−05 | |
| 190 | | 1.76E−05 | |
| 191 | 4.53E−03 | 1.49E−03 | |
| 192 | 8.04E−03 | 4.93E−03 | |
| 193 | 1.19E−03 | 5.61E−04 | |
| 194 | 2.60E−04 | 9.55E−05 | |
| 195 | 2.82E−04 | 1.02E−04 | |
| 196 | 9.29E−04 | 3.63E−04 | |
| 197 | 2.10E−03 | 7.51E−04 | |
| 197 | | 4.00E−05 | |
| 198 | | 2.23E−04 | |
| 199 | | 3.00E−04 | |
| 200 | 2.07E−04 | 8.42E−05 | 1.83E−04 |
| 201 | | | 6.42E−02 |
| 202 | | 1.52E−04 | |
| 203 | | 7.33E−03 | |
| 204 | | 5.46E−02 | |
| 205 | | | 8.02E−02 |
| 206 | | 1.04E−05 | |
| 207 | | 4.30E−01 | |
| 208 | | 7.44E+00 | |
| 209 | | 3.28E+00 | |
| 210 | | 1.03E+01 | |
| 211 | 5.44E−03 | | |
| 212 | 3.97E−04 | | |
| 213 | 1.19E−02 | | |
| 214 | 1.34E−02 | | |
| 215 | 2.85E−02 | | |
| 216 | 1.81E−03 | | |
| 217 | 1.13E−03 | | |

| Example | ERK2 New (μM) | ERK2 (20 pM) (μM) | ERK2 Alphascreen (μM) |
|---|---|---|---|
| 218 | 2.42E−02 | | |
| 219 | 3.27E−02 | | |
| 220 | 7.23E−02 | | |
| 221 | 3.06E−02 | | |
| 222 | 2.48E−02 | | |
| 223 | 1.04E−02 | | |
| 224 | 1.88E−02 | | |
| 225 | 9.01E−05 | | |
| 226 | 4.97E−05 | | |
| 227 | 8.11E−04 | | |
| 228 | | 5.05E−05 | |
| 229 | 1.07E−03 | | |
| 230 | 8.99E−04 | | |
| 231 | 2.17E−04 | | |
| 232 | 2.57E−04 | | |
| 233 | | 2.09E−05 | |
| 234 | 1.47E−03 | | |
| 235 | 3.26E−04 | | |
| 236 | 5.66E−02 | | |
| 237 | 2.61E+00 | | |
| 238 | 3.52E−01 | | |
| 239 | 2.85E−02 | | |
| 240 | | 1.99E−05 | |
| 241 | | 9.44E−04 | |
| 242 | | 8.75E−06 | |
| 243 | | 1.21E−05 | |
| 244 | | 1.57E−01 | |
| 245 | 2.67E−03 | | |
| 246 | 1.52E−03 | | |
| 247 | 7.30E−04 | | |
| 248 | | 3.64E−05 | |
| 249 | 3.71E−03 | | |
| 250 | | 3.64E−05 | |
| 251 | 7.04E−03 | | |
| 252 | 2.60E−03 | | |
| 253 | | 1.06E−04 | |
| 254 | | 5.99E−05 | |
| 255 | | 2.87E−05 | |
| 256 | | 2.58E−05 | |
| 257 | | 1.97E−05 | |
| 258 | | 3.43E−05 | |
| 259 | | 1.27E−05 | |
| 260 | | 2.08E−05 | |
| 261 | | 1.68E−05 | |
| 262 | | 1.40E−05 | |
| 263 | 1.91E−04 | 9.23E−05 | |
| 264 | | 4.31E−05 | |
| 265 | | 3.10E−05 | |
| 266 | | 4.87E−05 | |
| 267 | | 1.58E−05 | |
| 268 | 4.80E−03 | | |
| 269 | 1.08E−03 | | |
| 270 | | 4.67E−05 | |
| 271 | | 3.08E−05 | |
| 272 | | 6.19E−05 | |
| 273 | | 4.82E−05 | |
| 274 | | 3.12E−05 | |
| 275 | | 7.45E−05 | |
| 276 | | 3.71E−05 | |
| 277 | | 7.07E−05 | |
| 278 | | 1.46E−04 | |
| 279 | 5.18E−04 | 4.29E−04 | |
| 280 | 1.66E−03 | | |
| 281 | 1.79E−03 | | |
| 282 | 1.20E−03 | | |
| 283 | 1.69E−04 | 3.78E−05 | |
| 284 | 2.96E−04 | | |
| 285 | 2.66E−02 | | |
| 286 | 3.90E−03 | | |
| 287 | 7.94E−04 | | |
| 288 | 2.03E−03 | | |
| 289 | 1.92E−04 | 8.14E−05 | |
| 290 | 1.74E−03 | | |
| 291 | 1.48E−03 | | |
| 292 | 2.82E−03 | | |
| 293 | 2.65E−02 | | |
| 294 | 2.06E−03 | | |
| 295 | 5.95E−04 | | |
| 296 | 1.08E−03 | | |
| 297 | 1.53E−04 | 7.15E−05 | |
| 298 | 1.95E−03 | | |
| 299 | 3.57E−03 | | |
| 300 | 2.28E−04 | 6.55E−05 | |
| 301 | | 9.33E−05 | |
| 302 | 1.69E−04 | 5.47E−05 | |
| 303 | 2.21E−04 | | |
| 304 | 2.50E−03 | | |
| 305 | 1.91E−03 | | |
| 306 | 3.78E−04 | | |
| 307 | 2.00E−04 | | |
| 308 | 1.29E−04 | 3.45E−05 | |
| 309 | 1.04E−04 | 2.63E−05 | |
| 310 | 2.42E−04 | | |
| 311 | 1.19E−03 | | |
| 312 | 3.74E−03 | | |
| 313 | 6.17E−04 | | |
| 314 | 1.48E−03 | | |
| 315 | | 5.00E−06 | |
| 316 | 3.30E−01 | | |
| 317 | 1.34E+00 | | |
| 318 | | 3.81E−01 | 3.11E−01 |
| 319 | 1.51E−01 | | |
| 320 | 3.54E−01 | | |
| 321 | | 8.49E−02 | |
| 322 | 9.12E−02 | | |
| 323 | 3.29E−03 | | |
| 324 | 6.83E−03 | | 6.17E−03 |
| 325 | | 5.93E−04 | 5.44E−04 |
| 326 | 2.53E−04 | | |
| 327 | 5.42E−02 | | |
| 328 | 8.29E−03 | | 7.64E−03 |
| 329 | | 1.00E−05 | |
| 330 | | 2.22E−05 | |
| 331 | | 6.45E−05 | |
| 332 | | 8.15E−04 | |
| 333 | 3.46E−02 | | 3.38E−02 |
| 334 | 2.52E−02 | | 1.94E−02 |
| 335 | | 2.08E−05 | |
| 336 | | 1.43E−05 | |
| 337 | | 4.35E−05 | |
| 338 | | 1.39E−05 | |
| 339 | | 1.05E−04 | |
| 340 | | 1.87E−01 | |
| 341 | | 1.05E+00 | |
| 342 | | 1.73E−05 | |
| 343 | | 1.10E−05 | |
| 344 | | 9.77E−06 | |
| 345 | | 9.56E−05 | |
| 346 | | 1.75E−05 | |
| 347 | | 1.93E−04 | |
| 348 | | 3.94E−05 | |
| 349 | | 2.34E−05 | |
| 350 | | 2.17E−05 | |
| 351 | | 2.25E−05 | |
| 352 | | 2.39E−05 | |
| 353 | | 1.03E−05 | |
| 354 | | 1.94E−05 | |
| 355 | | 2.30E−05 | |
| 356 | | 3.17E−05 | |
| 357 | | 1.43E−05 | |
| 358 | | 2.05E−05 | |
| 359 | | 7.60E−05 | |
| 360 | | 6.65E−06 | |
| 361 | | 1.04E−04 | |
| 362 | | 2.91E−05 | |
| 363 | | 5.57E−05 | |
| 364 | | 2.05E−04 | |
| 365 | | 2.08E−05 | |
| 366 | | 1.27E−04 | |
| 367 | | 1.50E−04 | |

| Example | ERK2 New (μM) | ERK2 (20 pM) (μM) | ERK2 Alphascreen (μM) |
|---|---|---|---|
| 368 |  | 8.95E−05 |  |
| 369 |  | 2.13E−04 |  |
| 370 |  | 1.38E−04 |  |
| 371 |  | 3.00E−05 |  |
| 372 |  | 4.00E−05 |  |
| 373 |  | 8.37E−06 |  |
| 374 |  | 2.05E−05 |  |
| 375 |  | 4.01E−05 |  |
| 376 |  | 1.83E−05 |  |
| 377 |  | 7.00E−05 |  |
| 378 |  | 2.48E−05 |  |
| 379 |  | 6.17E−05 |  |
| 380 |  | 9.70E−06 |  |
| 381 |  | 2.09E−05 |  |
| 382 |  | 1.07E−05 |  |
| 383 |  | 6.89E−05 |  |
| 384 |  | 6.14E−05 |  |
| 385 |  | 1.22E−04 |  |
| 386 |  | 3.33E−05 |  |
| 387 |  | 1.00E−05 |  |
| 388 |  | 2.69E−05 |  |
| 389 |  | 3.08E−05 |  |
| 390 |  | 2.42E−05 |  |
| 391 |  | 1.15E−04 |  |
| 392 |  | 4.52E−05 |  |
| 393 |  | 7.52E−05 |  |
| 394 |  | 1.53E−05 |  |
| 395 |  | 8.27E−06 |  |
| 396 |  | 1.98E−05 |  |
| 397 |  | 3.60E−05 |  |
| 398 |  | 2.81E−04 |  |
| 399 |  | 2.10E−02 |  |
| 400 |  | 1.59E−01 |  |
| 401 |  | 4.63E−05 |  |
| 402 |  | 4.36E−04 |  |
| 403 |  | 5.81E−03 |  |
| 404 |  | 1.15E−04 |  |
| 405 |  | 2.38E−04 |  |
| 406 |  | 2.49E−04 |  |
| 407 |  | 3.33E−04 |  |
| 408 |  | 2.01E−05 |  |
| 409 |  | 2.25E−04 |  |
| 410 |  | 9.43E−05 |  |
| 411 |  | 7.43E−05 |  |
| 412 |  | 3.74E−04 |  |
| 413 | 2.04E−01 |  |  |
| 414 |  | 2.00E−05 |  |
| 415 | 1.68E−03 |  |  |
| 416 | 5.68E−03 |  |  |
| 417 | 6.90E−04 | 9.28E−05 |  |
| 418 | 1.28E−03 |  |  |
| 419 | 8.53E−04 |  |  |
| 420 | 1.95E−03 |  |  |
| 421 | 1.26E−02 | 6.38E−03 |  |
| 422 | 1.87E−04 | 6.51E−05 |  |
| 423 | 1.47E−04 | 6.14E−05 |  |
| 424 | 1.55E−01 | 1.13E−01 |  |
| 425 | 9.07E−04 | 3.59E−04 |  |
| 426 | 1.36E−03 | 5.85E−04 |  |
| 427 | 1.67E−02 | 6.41E−03 |  |
| 428 | 2.19E−04 | 7.59E−05 |  |
| 429 | 5.03E−04 | 2.21E−04 |  |
| 430 | 7.87E−04 | 3.43E−04 |  |
| 432 |  | 1.11E−03 |  |
| 433 |  | 2.90E−03 |  |
| 434 |  | 1.57E−03 |  |
| 435 |  | 1.05E−04 |  |
| 436 |  | 4.85E−05 |  |
| 437 |  | 5.40E−04 |  |
| 438 | 9.14E−05 | 2.52E−05 | 1.13E−04 |
| 439 |  | 6.09E−02 | 9.85E−02 |
| 440 |  | 7.01E−05 |  |
| 441 |  | 5.59E−05 |  |
| 442 |  | 3.39E−04 |  |
| 443 |  | 3.45E−04 |  |
| 444 |  | 2.15E−04 |  |
| 445 |  | 5.31E−04 |  |
| 446 |  | 4.64E−05 |  |
| 447 |  | 1.63E−04 |  |
| 448 |  | 3.71E−04 |  |
| 449 |  | 1.84E−04 |  |
| 450 |  | 1.50E−03 |  |
| 451 |  | 4.42E−05 |  |
| 452 |  | 0.00003 |  |
| 453 |  | 0.0000684 |  |
| 454 |  | 0.0000403 |  |
| 455 |  | 0.000144 |  |
| 456 |  | 0.0000872 |  |
| 457 |  | 0.0000581 |  |
| 458 |  | 0.0000823 |  |
| 459 |  | 0.0000261 |  |
| 460 |  | 0.0000397 |  |
| 461 |  | 0.00000431 |  |
| 462 |  | 0.000135 |  |
| 463 |  | 0.0000055 |  |
| 464 |  | 0.000137 |  |
| 465 |  | 0.0000187 |  |
| 466 |  | 0.000218 |  |
| 467 |  | 0.0000446 |  |
| 468 |  | 0.000251 |  |
| 469 |  | 0.000136 |  |
| 470 |  | 0.000221 |  |
| 471 |  | 0.000483 |  |
| 472 |  | 0.000179 |  |
| 473 |  | 0.0105 |  |
| 474 |  | 0.00156 |  |
| 475 |  | 0.00968 |  |
| 476 |  | 0.00202 |  |
| 477 |  | 0.00859 |  |
| 478a |  | 0.000009 |  |
| 478b |  | 0.000039 |  |

The invention claimed is:

1. A method of treating non-small cell lung cancer comprising administering to a subject in need of such treatment a therapeutically effective amount of 4-(3-amino-6-((1S,3S,4R)-3-fluoro-4-hydroxycyclohexyl)pyrazin-2-yl)-N-((S)-1-(3-bromo-5-fluorophenyl)-2-(methylamino)ethyl)-2-fluorobenzamide, or a pharmaceutically acceptable salt thereof.

2. A method of treating ovarian cancer comprising administering to a subject in need of such treatment a therapeutically effective amount of N-((S)-2-amino-1-(3-bromo-5-fluorophenyl)ethyl)-4-(3-amino-6-((1R,3S,4R)-3-fluoro-4-hydroxycyclohexyl)pyrazin-2-yl)-2-fluorobenzamide, or a pharmaceutically acceptable salt thereof.

3. A method of treating ovarian cancer comprising administering to a subject in need of such treatment a therapeutically effective amount of 4-(3-amino-6-((1S,3S,4R)-3-fluoro-4-hydroxycyclohexyl)pyrazin-2-yl)-N-((S)-1-(3-bromo-5-fluorophenyl)-2-(methylamino)ethyl)-2-fluorobenzamide, or a pharmaceutically acceptable salt thereof.

4. A method of treating non-small cell lung cancer comprising administering to a subject in need of such treatment a therapeutically effective amount of N-((S)-2-amino-1-(3-bromo-5-fluorophenyl)ethyl)-4-(3-amino-6-((1R,3S,4R)-3-fluoro-4-hydroxycyclohexyl)pyrazin-2-yl)-2-fluorobenzamide, or a pharmaceutically acceptable salt thereof.

* * * * *

SEQUENCE LISTING

<160> NUMBER OF SEQ ID NOS: 1

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Biotin-amino hexanoic acid

```
<220> FEATURE:
<221> NAME/KEY: MOD_RES
<222> LOCATION: (22)..(22)
<223> OTHER INFORMATION: Arg-NH2

<400> SEQUENCE: 1

Xaa Lys Arg Glu Leu Val Glu Pro Leu Thr Pro Ser Gly Glu Ala Pro
1               5                   10                  15

Asn Gln Ala Leu Leu Arg
            20
```